(12) United States Patent
Braun et al.

(10) Patent No.: US 10,968,203 B2
(45) Date of Patent: Apr. 6, 2021

(54) PYRIMIDINYL-PYRIDYLOXY-NAPHTHYL COMPOUNDS AND METHODS OF TREATING IRE1-RELATED DISEASES AND DISORDERS

(71) Applicants: Genentech, Inc., South San Francisco, CA (US); The Regents of the University of California, Oakland, CA (US)

(72) Inventors: Marie-Gabrielle Braun, South San Francisco, CA (US); Paul Gibbons, San Francisco, CA (US); Wendy Lee, San Ramon, CA (US); Cuong Ly, Burlingame, CA (US); Joachim Rudolph, Burlingame, CA (US); Jacob Schwarz, San Ramon, CA (US); Avi Ashkenazi, San Mateo, CA (US); Leo Fu, Shanghai (CN); Tommy Lai, Shanghai (CN); Fei Wang, Shanghai (CN); Ramsay Beveridge, Quebec (CA); Liang Zhao, Montreal (CA)

(73) Assignees: Genentech, Inc., South San Francisco, CA (US); The Regents of the University of California, Oakland, CA (US)

( * ) Notice: Subject to any disclaimer, the term of this patent is extended or adjusted under 35 U.S.C. 154(b) by 0 days.

(21) Appl. No.: 15/989,008

(22) Filed: May 24, 2018

(65) Prior Publication Data

US 2018/0265497 A1    Sep. 20, 2018

Related U.S. Application Data

(63) Continuation of application No. PCT/CN2018/079292, filed on Mar. 16, 2018.

(30) Foreign Application Priority Data

Mar. 17, 2017    (WO) ............... PCT/CN2017/077059

(51) Int. Cl.
| | |
|---|---|
| *A61K 31/506* | (2006.01) |
| *A61K 45/06* | (2006.01) |
| *C07D 401/04* | (2006.01) |
| *C07D 401/14* | (2006.01) |
| *C07D 405/14* | (2006.01) |
| *C07D 413/14* | (2006.01) |
| *C07D 417/14* | (2006.01) |
| *A61P 35/00* | (2006.01) |

(52) U.S. Cl.
CPC .......... *C07D 401/14* (2013.01); *A61K 31/506* (2013.01); *A61P 35/00* (2018.01); *C07D 401/04* (2013.01); *C07D 405/14* (2013.01); *C07D 413/14* (2013.01); *C07D 417/14* (2013.01); *A61K 45/06* (2013.01)

(58) Field of Classification Search
CPC .... A61K 31/506; A61K 45/06; C07D 401/14; C07D 401/04; C07D 405/14; C07D 417/14; C07D 413/14
See application file for complete search history.

(56) References Cited

U.S. PATENT DOCUMENTS

| | | | |
|---|---|---|---|
| 7,868,177 | B2 | 1/2011 | Cee |
| 7,880,000 | B2 | 2/2011 | Geuns-Meyer |
| | | (Continued) | |

FOREIGN PATENT DOCUMENTS

| | | |
|---|---|---|
| EA | 201591904 A1 | 2/2016 |
| WO | 2005/113494 A2 | 1/2005 |
| | (Continued) | |

OTHER PUBLICATIONS

Ni et al., The Role of IRE1 Signaling in the Central Nervous System Diseases, Current Neuropharmacology, vol. 6, No. 9, pp. 1340-1347 (Year: 2018).*

(Continued)

*Primary Examiner* — Brenda L Coleman
(74) *Attorney, Agent, or Firm* — Alston & Bird LLP

(57) ABSTRACT

Described herein are pyrimidinyl-pyridyloxy-naphthyl compounds with inositol requiring enzyme 1 (IRE1) modulation activity or function having the Formula I or I' structure:

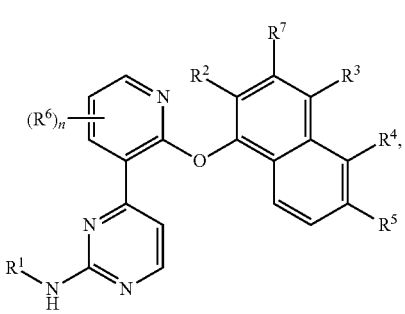

I or stereoisomers, tautomers, or pharmaceutically acceptable salts thereof, and with the substituents and structural features described herein. Also described are pharmaceutical compositions and medicaments that include the Formula I or I' compounds, as well as methods of using such IRE1 modulators, alone and in combination with other therapeutic agents, for treating diseases or conditions that are mediated or dependent upon estrogen receptors.

41 Claims, No Drawings

(56) References Cited

U.S. PATENT DOCUMENTS

| | | |
|---|---|---|
| 8,476,434 B2 | 7/2013 | Geuns-Meyer |
| 8,815,885 B2 | 8/2014 | Walter |
| 9,382,230 B2 | 7/2016 | Walter |
| 2006/0009453 A1 | 1/2006 | Geuns-Meyer et al. |

FOREIGN PATENT DOCUMENTS

| | | |
|---|---|---|
| WO | 2007/100646 A1 | 7/2007 |
| WO | WO 2014/161808 A1 | 10/2014 |

OTHER PUBLICATIONS

Adams et al., Structure and Molecular Mechanism of ER Stress Signaling by the Unfolded Protein Response Signal Activator IRE1, Frontiers in Molecular Biosciences, vol. 6, Article 11, pp. 1-12 (Year: 2019).*

Ni et al., The Role of IRE1 Signaling in the Central Nervous System Diseases, Current Neuropharmacology, vol. 16, pp. 1340-1347 (Year: 2018).*

Cee et al., "Pyridyl-pyrimidine benzimidazole derivatives as potent, selective, and orally bioavailable inhibitors of Tie-2 kinase" Bioorg Med Chem Lett. 19(2):424-7 (Jan. 15, 2009)

Cheng et al., "Analysis of kinase inhibitor selectivity using a thermodynamics-based partition index" J Med Chem. 53(11):4502-10 (Jun. 10, 2010).

Cross et al., "The molecular basis for selective inhibition of unconventional mRNA splicing by an IRE1-binding small molecule" Proc Natl Acad Sci U S A. (Proc Natl Acad Sci U S A. Apr. 10, 2012;109(15):E869-78), 109(15):E869-78 (Apr. 10, 2012).

Ghosh et al., "Allosteric inhibition of the IRE1α RNase preserves cell viability and function during endoplasmic reticulum stress" Cell 158(3):534-48 (Jul. 31, 2014).

Harrington et al., "Unfolded Protein Response in Cancer: IRE1α Inhibition by Selective Kinase Ligands Does Not Impair Tumor Cell Viability" ACS Med Chem Lett. 6(1):68-72 (Sep. 24, 2014).

Hetz et al., "Targeting the unfolded protein response in disease" Nat Rev Drug Discov. 12(9):703-19 (Sep. 2013).

Korennykh et al., "The unfolded protein response signals through high-order assembly of Ire1" Nature. 457(7230):687-93 (Feb. 5, 2009).

Lu et al., "Opposing unfolded-protein-response signals converge on death receptor 5 to control apoptosis" Science 345(6192):98-101 ( 2014).

PCT ISR and Written Opinion for PCT/CN2018/079292

Ranatunga et al., "Synthesis of novel tricyclic chromenone-based inhibitors of IRE-1 RNase activity" J Med Chem. 57(10):4289-301 (May 22, 2014).

Sanches et al., "Structure and mechanism of action of the hydroxy-aryl-aldehyde class of IRE1 endoribonuclease inhibitors" Nat Commun. 5:4202 (16 pages) (Aug. 28, 2014).

Vincenz et al., "Endoplasmic reticulum stress and the unfolded protein response: targeting the Achilles heel of multiple myeloma" Send to Mol Cancer Ther. 12(6):831-43 (Jul. 2013).

Volkmann et al., "Potent and selective inhibitors of the inositol-requiring enzyme 1 endoribonuclease" J Biol Chem. 286(14):12743-55 (Apr. 8, 2011).

Waller et al., "A Covalent Cysteine-Targeting Kinase Inhibitor of Ire1 Permits Allosteric Control of Endoribonuclease Activity" Chembiochem. 17(9):843-51 (May 3, 2016).

Wang and Kaufman et al., "Protein misfolding in the endoplasmic reticulum as a conduit to human disease" Nature 529(7586):326-35 (Jan. 21, 2016).

Wang et al., "Divergent allosteric control of the IRE1α endoribonuclease using kinase inhibitors" Nat Chem Biol. 8(12):982-9 (Dec. 2012).

Wiseman et al., "Flavonol activation defines an unanticipated ligand-binding site in the kinase-RNase domain of IRE1" Mol Cell. 38(2):291-304 (Apr. 23, 2010).

Indian Application No. 201947041989, Examination Report dated Mar. 19, 2020.

Russian Application No. 2019129411, Office Action dated Mar. 27, 2020.

Jiang et al., "Targeting the IRE1α-XBP1 branch of the unfolded protein response in human diseases," Seminars in Cancer Biology, 33:48-56, (2015).

European Application No. 18768363.6, Extended European Search Report dated Nov. 26, 2020.

* cited by examiner

PYRIMIDINYL-PYRIDYLOXY-NAPHTHYL COMPOUNDS AND METHODS OF TREATING IRE1-RELATED DISEASES AND DISORDERS

CROSS-REFERENCE TO RELATED APPLICATIONS

This application is a continuation of International Patent Application No. PCT/CN2018/079292 filed 16 Mar. 2018, which claims the benefit of priority to International Patent Application No. PCT/CN2017/077059 filed 17 Mar. 2017, the contents of which applications are hereby incorporated by reference in their entirety.

FIELD OF THE INVENTION

Described herein are compounds that target inositol requiring enzyme 1 (IRE1 alpha,α), including pharmaceutically acceptable salts, solvates, metabolites, prodrugs thereof, pharmaceutical compositions comprising such compounds, and methods of using such compounds to treat, prevent or diagnose diseases.

BACKGROUND OF THE INVENTION

The kinase/endoribonuclease inositol requiring enzyme 1 (IRE1 a, alpha,α), one of the key sensors of misfolded protein accumulation in the endoplasmic reticulum that triggers the unfolded protein response (UPR), is a potential therapeutic target for diverse diseases including cancer for inhibitors that bind to the ATP-binding site on the kinase moiety of IRE1α and block its endoribonuclease activity. IRE1α is a transmembrane, bifunctional protein with a luminal domain that binds to misfolded proteins, a transmembrane segment, and a cytoplasmic portion consisting of a kinase moiety and a tandem endoribonuclease domain. Structure-activity relationship (SAR) studies led to compounds selective in recombinant IRE1α kinase screens and potent against endoribonuclease activity of recombinant IRE1α as well as cellular IRE1α. IRE1α activity mediates certain cytoprotective and pro-survival functions of the UPR, increases viability and growth in certain tumor cell lines, and may be an effective therapeutic target for specific small molecule inhibitors that block malignant tumor growth, contrary to an earlier report (Harrington, P. E. et al (2015) ACS Med. Chem. Lett. 6:68-72). In addition, inhibitors of IRE1α may be therapeutically useful for other types of diseases besides cancer including certain autoimmune, neurodegenerative, fibrotic and metabolic disorders (Wang M. and Kaufman, R. J. (2016) Nature 529:326-335).

Homeostatic regulation of protein folding in the endoplasmic reticulum (ER) is under the control of three key intracellular signaling pathways: IRE1α, PERK, and ATF6, which together orchestrate the unfolded protein response (UPR) (Schroder, et al (2005) Mutat Res-Fund Mol Mech Metagenesis 569:29-63). An increase in demand for protein folding in the ER or certain types of cellular injury or stress lead to the accumulation of unfolded proteins in the ER—a condition called ER stress. Cells respond to ER stress by activating the UPR to help adjust or maintain their high-fidelity protein synthetic capacity (Walter, P. and Ron, D. (2011) Science, 334:1081-1086). IRE1α is the most evolutionarily conserved of the three branches of the UPR. Importantly, the UPR makes life/death decisions for the cell, depending on the severity and duration of ER stress, and the final outcome is either cell survival and recovery or programmed cell death (apoptosis) (Sovolyova et al, (2014) Biol Chem 395: 1-13). All three pathways of the UPR form a coordinated reaction to the accumulation of unfolded proteins; and several studies have demonstrated that there is cross talk between the different pathways (Yamamoto et al, J. Biochem. (2004) 136:343-350); Arai et al, FEBS Letts. (2006) 580:184-190; Adachi et al, Cell Struct. Func. (2008) 33:75-89). ER stress and activation of the UPR can be caused by mechanical injury, inflammation, genetic mutations, infections, oxidative stress, metabolic stress, and other types of cellular stress associated with malignancy. ER stress has also been implicated in diseases that result in fibrotic remodeling of internal organs, such as chronic liver diseases (Galligan et al, J. Toxicol. (2012) Vol. 2012, Article ID 207594, 12 pgs.; Shin et al, Cell Reports (2013) 5:654-665; Ji, Int. J. Hepatol. (2014) Vol. 2014, Article ID 513787, 11 pages), pulmonary fibrosis (Baek et al, Am. J. Resp. Cell Mol. Bio. (2012) 46:731-739); Tanjore et al, Biochim Biophys Acta (2012, online), (2013) 1832:940-947), kidney fibrosis (Chiang et al, Mol. Med. (2011) 17:1295-1305), cardiovascular disease (Spitler & Webb, Hypertension (2014) 63:e40-e45), and inflammatory bowel disease (Bogaert et al, PLoS One (2011) 6(10) e25589; Cao et al, Gastroent (2013) 144:989-1000).

IRE1α (alpha) is a transmembrane, bifunctional protein with cytoplasmic kinase and endoribonuclease activity. The N-terminal domain of IRE1α is proposed to sense the presence of unfolded proteins in the ER lumen, triggering activation of the cytoplasmic kinase domain, which, in turn, activates the C-terminal endoribonuclease. IRE1α transmits information across the ER lipid bilayer (Tirasophon et al, Genes & Develop. (2000) 14:2725-2736). Increased ER protein load and presence of unfolded proteins leads to the dissociation of the ER chaperone GRP78/BiP from IRE1α molecules, which bind to misfolded proteins and then undergo dimerization and trans-autophosphorylation in the cytoplasmic kinase domain. This leads to activation of the IRE1α endoribonuclease moiety in the cytosol. The IRE1α endoribonuclease has the ability to cleave the mRNA that encodes unspliced X box protein 1 (XBP1u); this excises a 26-nucleotide intron and leads to formation of spliced XBP1 (XBP1s) mRNA, which encodes a potent transcription factor. After transport into the nucleus, the XBP1s protein binds to UPR promoter elements to initiate transcription of genes that enhance the ability of the ER to cope with unfolded proteins, for example, through enhanced ER-associated degradation of misfolded proteins, and through elevated levels of chaperones and disulfide isomerases that support protein folding in the ER. IRE1α activation is also associated with enlargement of the ER volume, which has been interpreted as an adaptive mechanism to increase protein folding capacity (Sriburi et al, J. Cell. Bio. (2004) 167:35-41); (Chen, Y. (2013) Trends Cell Biol., 23, 547-555). In addition, the IRE1α endoribonuclease cleaves various mRNAs in a process called regulated IRE1α-dependent decay of mRNA (RIDD), which reduces both protein translation and import of proteins into the ER to help reestablish homeostasis (Hollien & Weissman, Science (2006) 313:104-107). In cancer cells, IRE1α suppresses ER-stress-induced apoptosis by reducing the mRNA levels of death receptor 5 (DR5) through RIDD (Lu et al., Science (2014) 345:98-101).

Besides degrading mRNA (Binet et al, Cell Metabol. (2013) 17:353-371), it was recently shown that IRE1α also has the ability to degrade microRNAs (miRs) (Upton et al, Science (2012) 338:818-822). miRs are short noncoding RNA oligonucleotides consisting of 17-25 nucleotides that generally act to inhibit gene expression by binding to complementary sequences in the 30-untranslated region of target mRNAs, either to repress mRNA translation or to induce mRNA cleavage. A number of cellular functions such as proliferation, differentiation, and apoptosis are regulated by miRs, and aberrant miR expression is observed in a variety of human diseases including fibrosis (Bowen et al, J. Pathol (2013) 229:274-285). Inhibitors that specifically target individual components of the UPR have recently been described. The inhibitor 4μ8C that stably binds to lysine 907 in the IRE1α endoribonuclease domain has been shown to inhibit both RIDD activity and XBP-1 splicing (Cross et al, Proc Natl. Acad. Sci. (2012) 109:E869-E878). High levels of 4μ8C cause no measurable toxicity in cells and concentrations ranging from 80 to 128 lM of 4μ8C completely block XBP1 splicing without affecting IRE1α (alpha) kinase activity (Cross et al, 2012). The inhibitor 4μ8C thus represents an important tool to delineate the functions of IRE1α in vivo as IRE1α-knockout mice die during embryonic development. Inhibition of IRE1α prevents activation of myofibroblasts and reduces fibrosis in animal models of liver and skin fibrosis. Pharmacological inhibition of IRE1α could revert the profibrotic phenotype of activated myofibroblasts isolated from patients with scleroderma and indicates that ER stress inhibitors should be taken into consideration when developing new strategies for the treatment of fibrotic diseases (Heindryckx, F. et al (2016) EMBO Molecular Medicine Vol 8(7):729-744).

Activation of the UPR has been shown to be an important survival pathway for tumors of secretory cell origin like multiple myeloma that have a very high protein synthesis burden. Therefore, efforts to disrupt the UPR by blocking the IRE1α endoribonuclease cleavage and activation of XBP1 have been an active area of cancer research. As a specific IRE1α RNase product, XBP1s is a direct indicator of functional IRE1 inhibition. A potent and selective IRE1α inhibitor would serve as an important tool to test the hypothesis that, without full UPR activation, tumor cells would be driven to apoptosis. IRE1α inhibitors and activating compounds have been reported (Harrington, P. E. et al (2015) ACS Med. Chem. Lett. 6:68-72; Volkmann, K., et al (2011) J. Biol. Chem., 286:12743-12755; Cross, B. C. S., et al (2012) Proc. Natl. Acad. Sci. U.S.A., 109:E869-E878; Wang, L., et al (2012) Nat. Chem. Biol., 8:982-989; Ghosh, R., et al (2014) Cell, 158:534-548; Ranatunga, S., et al (2014) J. Med. Chem., 57, 4289-4301; U.S. Pat. Nos. 9,382,230; 8,815,885).

SUMMARY OF THE INVENTION

The invention relates generally to heteroaryl compounds with IRE1 modulation activity or function having the Formula I structure:

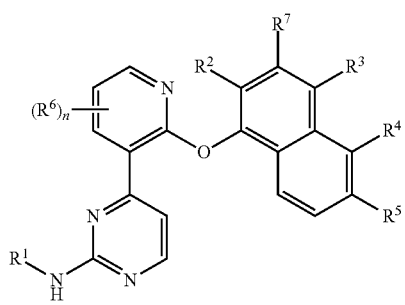

I or stereoisomers, tautomers, or pharmaceutically acceptable salts thereof, and with the substituents and structural features described herein.

An aspect of the invention is a pharmaceutical composition of a Formula I compound and a pharmaceutically acceptable carrier, glidant, diluent, or excipient.

An aspect of the invention is a process for making a Formula I compound or a pharmaceutical composition comprising a Formula I compound.

An aspect of the invention is a method of treating an IRE1-related disease or disorder in a patient comprising administering a therapeutically effective amount of the pharmaceutical composition to a patient with an IRE1-related disease or disorder.

An aspect of the invention is a kit for treating a condition mediated by an IRE1 receptor, comprising:
a) a pharmaceutical composition comprising a Formula I compound; and
b) instructions for use.

DETAILED DESCRIPTION OF EXEMPLARY EMBODIMENTS

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents which may be included within the scope of the present invention as defined by the claims. One skilled in the art will recognize many methods and materials similar or equivalent to those described herein, which could be used in the practice of the present invention. The present invention is in no way limited to the methods and materials described. In the event that one or more of the incorporated literature, patents, and similar materials differs from or contradicts this application, including but not limited to defined terms, term usage, described techniques, or the like, this application controls. Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below. All publications, patent applications, patents, and other references mentioned herein are incorporated by reference in their entirety. The nomenclature used in this Application is based on IUPAC systematic nomenclature, unless indicated otherwise.

Definitions

The term "substituent" denotes an atom or a group of atoms replacing a hydrogen atom on the parent molecule. The term "substituted" denotes that a specified group bears one or more substituents. Where any group may carry multiple substituents and a variety of possible substituents is provided, the substituents are independently selected and need not to be the same. The term "unsubstituted" means that the specified group bears no substituents. The term "optionally substituted" means that the specified group is unsubstituted or substituted by one or more substituents, independently chosen from the group of possible substituents. When indicating the number of substituents, the term "one or more" means from one substituent to the highest possible number of substitution, i.e. replacement of one hydrogen up to replacement of all hydrogens by substituents.

The term "alkyl" as used herein refers to a saturated linear or branched-chain monovalent hydrocarbon radical of one to twelve carbon atoms ($C_1$-$C_{12}$), wherein the alkyl radical may be optionally substituted independently with one or more substituents described below. In another embodiment, an alkyl radical is one to eight carbon atoms ($C_1$-$C_8$), or one to six carbon atoms ($C_1$-$C_6$). Examples of alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$, 1-heptyl, 1-octyl, and the like.

The term "alkyldiyl" as used herein refers to a saturated linear or branched-chain divalent hydrocarbon radical of about one to twelve carbon atoms ($C_1$-$C_{12}$), wherein the alkyldiyl radical may be optionally substituted independently with one or more substituents described below. In another embodiment, an alkyldiyl radical is one to eight carbon atoms ($C_1$-$C_8$), or one to six carbon atoms ($C_1$-$C_6$). Examples of alkyldiyl groups include, but are not limited to, methylene (—$CH_2$—), ethylene (—$CH_2CH_2$—), propylene (—$CH_2CH_2CH_2$—), and the like. An alkyldiyl group may also be referred to as an "alkylene" group.

The term "alkenyl" refers to linear or branched-chain monovalent hydrocarbon radical of two to eight carbon atoms ($C_2$-$C_8$) with at least one site of unsaturation, i.e., a carbon-carbon, $sp^2$ double bond, wherein the alkenyl radical may be optionally substituted independently with one or more substituents described herein, and includes radicals having "cis" and "trans" orientations, or alternatively, "E" and "Z" orientations. Examples include, but are not limited to, ethenyl or vinyl (—CH=$CH_2$), allyl (—$CH_2$CH=$CH_2$), and the like.

The terms "alkenylene" or "alkenyldiyl" refer to a linear or branched-chain divalent hydrocarbon radical of two to eight carbon atoms ($C_2$-$C_8$) with at least one site of unsaturation, i.e., a carbon-carbon, $sp^2$ double bond, wherein the alkenylene radical may be optionally substituted independently with one or more substituents described herein, and includes radicals having "cis" and "trans" orientations, or alternatively, "E" and "Z" orientations. Examples include, but are not limited to, ethenylene or vinylene (—CH=CH—), allyl (—$CH_2$CH=CH—), and the like.

The term "alkynyl" refers to a linear or branched monovalent hydrocarbon radical of two to eight carbon atoms ($C_2$-$C_8$) with at least one site of unsaturation, i.e., a carbon-carbon, sp triple bond, wherein the alkynyl radical may be optionally substituted independently with one or more substituents described herein. Examples include, but are not limited to, ethynyl (—C≡CH), 1-propynyl (—C≡$CCH_3$), propargyl (—$CH_2$C≡CH), and the like.

The term "alkynylene" or "alkynyldiyl" refer to a linear or branched divalent hydrocarbon radical of two to eight carbon atoms ($C_2$-$C_8$) with at least one site of unsaturation, i.e., a carbon-carbon, sp triple bond, wherein the alkynylene radical may be optionally substituted independently with one or more substituents described herein. Examples include, but are not limited to, ethynylene (—C≡C—), propynylene (propargylene, —$CH_2$C≡C—), and the like.

The terms "carbocycle", "carbocyclyl", "carbocyclic ring" and "cycloalkyl" refer to a monovalent non-aromatic, saturated or partially unsaturated ring having 3 to 12 carbon atoms ($C_3$-$C_{12}$) as a monocyclic ring or 7 to 12 carbon atoms as a bicyclic ring. Bicyclic carbocycles having 7 to 12 atoms can be arranged, for example, as a bicyclo [4,5], [5,5], [5,6] or [6,6] system, and bicyclic carbocycles having 9 or 10 ring atoms can be arranged as a bicyclo [5,6] or [6,6] system, or as bridged systems such as bicyclo[2.2.1]heptane, bicyclo[2.2.2]octane and bicyclo[3.2.2]nonane. Spiro carbocyclyl moieties are also included within the scope of this definition. Examples of spiro carbocyclyl moieties include [2.2]pentanyl, [2.3]hexanyl, and [2.4]heptanyl. Examples of monocyclic carbocycles include, but are not limited to, cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, and the like. Carbocyclyl groups are optionally substituted independently with one or more substituents described herein.

The term "carbocyclyldiyl" refers to a divalent non-aromatic, saturated or partially unsaturated ring having 3 to 12 carbon atoms ($C_3$-$C_{12}$) as a monocyclic ring or 7 to 12 carbon atoms as a bicyclic ring.

"Aryl" means a monovalent aromatic hydrocarbon radical of 6-20 carbon atoms ($C_6$-$C_{20}$) derived by the removal of one hydrogen atom from a single carbon atom of a parent aromatic ring system. Some aryl groups are represented in the exemplary structures as "Ar". Aryl includes bicyclic radicals comprising an aromatic ring fused to a saturated, partially unsaturated ring, or aromatic carbocyclic ring. Typical aryl groups include, but are not limited to, radicals derived from benzene (phenyl), substituted benzenes, naphthalene, anthracene, biphenyl, indenyl, indanyl, 1,2-dihydronaphthalene, 1,2,3,4-tetrahydronaphthyl, and the like. Aryl groups are optionally substituted independently with one or more substituents described herein.

The terms "arylene" or "aryldiyl" mean a divalent aromatic hydrocarbon radical of 6-20 carbon atoms ($C_6$-$C_{20}$) derived by the removal of two hydrogen atom from a two carbon atoms of a parent aromatic ring system. Some aryldiyl groups are represented in the exemplary structures as "Ar". Aryldiyl includes bicyclic radicals comprising an aromatic ring fused to a saturated, partially unsaturated ring, or aromatic carbocyclic ring. Typical aryldiyl groups include, but are not limited to, radicals derived from benzene (phenyldiyl), substituted benzenes, naphthalene, anthracene, biphenylene, indenylene, indanylene, 1,2-dihydronaphthalene, 1,2,3,4-tetrahydronaphthyl, and the like. Aryldiyl groups are also referred to as "arylene", and are optionally substituted with one or more substituents described herein.

The terms "heterocycle," "heterocyclyl" and "heterocyclic ring" are used interchangeably herein and refer to a saturated or a partially unsaturated (i.e., having one or more double and/or triple bonds within the ring) carbocyclic radical of 3 to about 20 ring atoms in which at least one ring atom is a heteroatom selected from nitrogen, oxygen, phosphorus and sulfur, the remaining ring atoms being C, where one or more ring atoms is optionally substituted independently with one or more substituents described below. A heterocycle may be a monocycle having 3 to 7 ring members (2 to 6 carbon atoms and 1 to 4 heteroatoms selected from N, O, P, and S) or a bicycle having 7 to 10 ring members (4 to 9 carbon atoms and 1 to 6 heteroatoms selected from N, O, P, and S), for example: a bicyclo [4,5], [5,5], [5,6], or [6,6] system. Heterocycles are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566. "Heterocyclyl" also includes radicals where heterocycle radicals are fused with a saturated, partially unsaturated ring, or aromatic carbocyclic or heterocyclic ring. Examples of heterocyclic rings include, but are not limited to, morpholin-4-yl, piperidin-1-yl, piperazinyl, piperazin-4-yl-2-one, piperazin-4-yl-3-one, pyrrolidin-1-yl, thiomorpholin-4-yl, S-dioxothiomorpholin-4-yl, azocan-1-yl, azetidin-1-yl, octahydropyrido[1,2-a]pyrazin-2-yl, [1,4]diazepan-1-yl, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 3-azabicyco[3.1.0]hexanyl, 3-azabicyclo[4.1.0]heptanyl, azabicyclo[2.2.2]hexanyl, 3H-indolyl quinolizinyl and N-pyridyl ureas. Spiro heterocyclyl moieties are also included within the scope of this definition. Examples of spiro heterocyclyl moieties include azaspiro[2.5]octanyl and azaspiro[2.4]heptanyl. Examples of a heterocyclic group wherein 2 ring atoms are substituted with oxo (=O) moieties are pyrimidinonyl and 1,1-dioxo-thiomorpholinyl. The heterocycle groups herein are optionally substituted independently with one or more substituents described herein.

The term "heterocyclyldiyl" refers to a divalent, saturated or a partially unsaturated (i.e., having one or more double and/or triple bonds within the ring) carbocyclic radical of 3 to about 20 ring atoms in which at least one ring atom is a heteroatom selected from nitrogen, oxygen, phosphorus and sulfur, the remaining ring atoms being C, where one or more ring atoms is optionally substituted independently with one or more substituents as described.

The term "heteroaryl" refers to a monovalent aromatic radical of 5-, 6-, or 7-membered rings, and includes fused ring systems (at least one of which is aromatic) of 5-20 atoms, containing one or more heteroatoms independently selected from nitrogen, oxygen, and sulfur. Examples of heteroaryl groups are pyridinyl (including, for example, 2-hydroxypyridinyl), imidazolyl, imidazopyridinyl, pyrimidinyl (including, for example, 4-hydroxypyrimidinyl), pyrazolyl, triazolyl, pyrazinyl, tetrazolyl, furyl, thienyl, isoxazolyl, thiazolyl, oxadiazolyl, oxazolyl, isothiazolyl, pyrrolyl, quinolinyl, isoquinolinyl, tetrahydroisoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. Heteroaryl groups are optionally substituted independently with one or more substituents described herein.

The term "heteroaryldiyl" refers to a divalent aromatic radical of 5-, 6-, or 7-membered rings, and includes fused ring systems (at least one of which is aromatic) of 5-20 atoms, containing one or more heteroatoms independently selected from nitrogen, oxygen, and sulfur.

The heterocycle or heteroaryl groups may be carbon (carbon-linked), or nitrogen (nitrogen-linked) bonded where such is possible. By way of example and not limitation, carbon bonded heterocycles or heteroaryls are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline.

By way of example and not limitation, nitrogen bonded heterocycles or heteroaryls are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or 3-carboline.

The terms "treat" and "treatment" refer to therapeutic treatment, wherein the object is to slow down (lessen) an undesired physiological change or disorder, such as the development or spread of arthritis or cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those with the condition or disorder.

The phrase "therapeutically effective amount" means an amount of a compound of the present invention that (i) treats the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can be measured, for example, by assessing the time to disease progression (TTP) and/or determining the response rate (RR).

The terms "cancer" refers to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

"Hematological malignancies" (British spelling "Haematological" malignancies) are the types of cancer that affect blood, bone marrow, and lymph nodes. As the three are intimately connected through the immune system, a disease affecting one of the three will often affect the others as well: although lymphoma is a disease of the lymph nodes, it often spreads to the bone marrow, affecting the blood. Hematological malignancies are malignant neoplasms ("cancer"), and they are generally treated by specialists in hematology and/or oncology. In some centers "Hematology/oncology" is a single subspecialty of internal medicine while in others they are considered separate divisions (there are also surgical and radiation oncologists). Not all hematological disorders are malignant ("cancerous"); these other blood conditions may also be managed by a hematologist. Hematological malignancies may derive from either of the two major blood cell lineages: myeloid and lymphoid cell lines. The myeloid cell line normally produces granulocytes, erythrocytes, thrombocytes, macrophages and mast cells; the lymphoid cell line produces B, T, NK and plasma cells. Lymphomas, lymphocytic leukemias, and myeloma are from the lymphoid line, while acute and chronic myelogenous leukemia, myelodysplastic syndromes and myeloproliferative diseases are myeloid in origin. Leukemias include Acute lymphoblastic leukemia (ALL), Acute myelogenous leukemia (AML), Chronic lymphocytic leukemia (CLL), Chronic myelogenous leukemia (CML), Acute monocytic leukemia (AMOL) and small lymphocytic lymphoma (SLL). Lymphomas include Hodgkin's lymphomas (all four subtypes) and Non-Hodgkin's lymphomas (NHL, all subtypes).

A "chemotherapeutic agent" is a chemical compound useful in the treatment of cancer, regardless of mechanism of action. Classes of chemotherapeutic agents include, but are not limited to: alkylating agents, antimetabolites, spindle poison plant alkaloids, cytotoxic/antitumor antibiotics, topoisomerase inhibitors, antibodies, photosensitizers, and kinase inhibitors. Chemotherapeutic agents include compounds used in "targeted therapy" and conventional chemotherapy. Examples of chemotherapeutic agents include proteasome inhibitors such as bortezomib (VELCADE®, Millennium Pharm., CAS Reg. No. 179324-69-7), carfilzomib (KYPROLIS®, Amgen, CAS Reg. No. 868540-17-4) and ixazomib (NINLARO®, Takeda, CAS Reg. No. 1072833-77-2); lenalidomide (REVLIMID®, Celgene, CAS Reg. No. 191732-72-6); pomalidomide (POMALYST®, Celgene, CAS Reg. No. 19171-19-8); venetoclax (VENCLEXTA®, GDC-0199, ABT-199, AbbVie/Genentech, CAS Reg. No. 1257044-40-8); ibrutinib (IMBRUVICA™, APCI-32765, Pharmacyclics Inc./Janssen Biotech Inc.; CAS Reg. No. 936563-96-1, U.S. Pat. No. 7,514,444), idelalisib (ZYDELIG®, CAL-101, GS 1101, GS-1101, Gilead Sciences Inc.; CAS Reg. No. 1146702-54-6), erlotinib (TARCEVA®, Genentech/OSI Pharm.), docetaxel (TAXOTERE®, Sanofi-Aventis), 5-FU (fluorouracil, 5-fluorouracil, CAS Reg. No. 51-21-8), gemcitabine (GEMZAR®, Lilly), PD-0325901 (CAS No. 391210-10-9, Pfizer), cisplatin (Platinol®, (SP-4-2)-diamminedichloroplatinum(II), cis-diamine, dichloroplatinum(II), CAS No. 15663-27-1), carboplatin (CAS No. 41575-94-4), paclitaxel (TAXOL®, Bristol-Myers Squibb Oncology, Princeton, N.J.), trastuzumab (HERCEPTIN®, Genentech), temozolomide (4-methyl-5-oxo-2,3,4,6,8-pentazabicyclo [4.3.0]nona-2,7,9-triene-9-carboxamide, CAS No. 85622-93-1, TEMODAR®, TEMODAL®, Schering Plough), tamoxifen ((Z)-2-[4-(1,2-diphenylbut-1-enyl)phenoxy]-N,N-dimethylethanamine, NOLVADEX®, ISTUBAL®, VALODEX®), and doxorubicin (ADRIAMYCIN®, CAS No. 23214-92-8), Akti-1/2, HPPD, and rapamycin.

Chemotherapeutic agents include inhibitors of B-cell receptor targets such as BTK, Bcl-2 and JAK inhibitors.

More examples of chemotherapeutic agents include: oxaliplatin (ELOXATIN®, Sanofi), sutent (SUNITINIB®, SU11248, Pfizer), letrozole (FEMARA®, Novartis), palbociclib, (IBRANCE®, Pfizer), imatinib mesylate (GLEEVEC®, Novartis), cobimetinib (COTELLIC™, GDC-0973, XL-518, Exelixis, WO 2007/044515, CAS Reg. No. 934660-93-2), ARRY-886 (Mek inhibitor, AZD6244, Array BioPharma, Astra Zeneca), SF-1126 (PI3K inhibitor, Semafore Pharmaceuticals), BEZ-235 (PI3K inhibitor, Novartis), XL-147 (PI3K inhibitor, Exelixis), PTK787/ZK 222584 (Novartis), fulvestrant (FASLODEX®, AstraZeneca), leucovorin (folinic acid), rapamycin (sirolimus, RAPAMUNE®, Wyeth), lapatinib (TYKERB®, GSK572016, Glaxo Smith Kline), lonafarnib (SARASAR™, SCH 66336, Schering Plough), sorafenib (NEXAVAR®, BAY43-9006, Bayer Labs), gefitinib (IRESSA®, AstraZeneca), irinotecan (CAMPTOSAR®, CPT-11, Pfizer), tipifarnib (ZARNESTRA™ Johnson & Johnson), ABRAXANE™ (Cremophor-free), albumin-engineered nanoparticle formulations of paclitaxel (American Pharmaceutical Partners, Schaumberg, Ill.), vandetanib (rINN, ZD6474, ZACTIMA®, AstraZeneca), chlorambucil, AG1478, AG1571 (SU 5271; Sugen), temsirolimus (TORISEL®, Wyeth), pazopanib (GlaxoSmithKline), canfosfamide (TELCYTA®, Telik), thiotepa and cyclosphosphamide (CYTOXAN®, NEOSAR®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, calicheamicin gamma1I, calicheamicin omega1I (Angew Chem. Intl. Ed. Engl. (1994) 33:183-186); dynemicin, dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, morpholino-doxorubicin, cyanomorpholino-doxorubicin, 2-pyrrolino-doxorubicin and deoxydoxorubicin), epirubicin, esorubicin, idarubicin, nemorubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; 6-thioguanine; mercaptopurine; methotrexate; platinum analogs such as cisplatin and carboplatin; vinblastine; etoposide (VP-16); ifosfamide; mitoxantrone; vincristine; vinorelbine (NAVELBINE®); novantrone; teniposide; edatrexate; daunomycin; aminopterin; capecitabine (XELODA®, Roche); ibandronate; CPT-11; topoisomerase inhibitor RFS 2000; difluoromethylornithine (DMFO); retinoids such as retinoic acid; and pharmaceutically acceptable salts, acids and derivatives of any of the above.

Also included in the definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, ketoxifene, LY117018, onapristone, and FARESTON® (toremifine citrate) and selective estrogen receptor modulators (SERDs) such as brilanestrant (GDC-0810, AR810, Genentech, Seragon), GDC-0927 (Genentech, Seragon), fulvestrant (FASLODEX®, Astra Zeneca); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors such as MEK inhibitors, such as cobimetinib (WO 2007/044515); (v) lipid kinase inhibitors, such as taselisib (GDC-0032, Genentech Inc.); (vi) antisense oligonucleotides, particularly those which inhibit expression of genes in signaling pathways implicated in aberrant cell proliferation, for example, PKC-alpha, Raf and H-Ras, such as oblimersen (GENASENSE®, Genta Inc.); (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN® rIL-2; topoisomerase 1 inhibitors such as LURTOTECAN®; ABARELIX® rmRH; (ix) anti-angiogenic agents such as bevacizumab (AVASTIN®, Genentech); and pharmaceutically acceptable salts, acids and derivatives of any of the above.

Also included in the definition of "chemotherapeutic agent" are therapeutic antibodies such as atezolizumab (TECENTRIQ®, anti-PDL-1, Genentech, CAS Reg. No. 1380723-44-3), nivolumab (OPDIVO®, Bristol-Myers Squib, CAS Reg. No. 946414-94-4), daratumumab (DARZALEX®, anti-CD38, Janssen Biotech, CAS Reg. No. 945721-28-8), pembrolizumab (KEYTRUDA®, MK-3475, lambrolizumab, Merck, anti-PD 1, CAS Reg. No. 1374853-91-4), alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), pertuzumab (PERJETA™, 2C4, Genentech), trastuzumab (HERCEPTIN®, Genentech), trastuzumab emtansine (KADCYLA®, Genentech Inc.), and tositumomab (BEXXAR, Corixia).

A "metabolite" is a product produced through metabolism in the body of a specified compound or salt thereof. Metabolites of a compound may be identified using routine techniques known in the art and their activities determined using tests such as those described herein. Such products may result for example from the oxidation, reduction, hydrolysis, amidation, deamidation, esterification, deesterification, enzymatic cleavage, and the like, of the administered compound. Accordingly, the invention includes metabolites of compounds of the invention, including compounds produced by a process comprising contacting a Formula I compound of this invention with a mammal for a period of time sufficient to yield a metabolic product thereof.

The term "package insert" is used to refer to instructions customarily included in commercial packages of therapeutic products, that contain information about the indications, usage, dosage, administration, contraindications and/or warnings concerning the use of such therapeutic products.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., "Stereochemistry of Organic Compounds", John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity. Enantiomers may be separated from a racemic mixture by a chiral separation method, such as supercritical fluid chromatography (SFC). Assignment of configuration at chiral centers in separated stereoisomers may be tentative, and depicted in Table 1 structures for illustrative purposes, before stereochemistry is definitively established, such as from x-ray crystallographic data.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The term "pharmaceutically acceptable salts" denotes salts which are not biologically or otherwise undesirable. Pharmaceutically acceptable salts include both acid and base addition salts. The phrase "pharmaceutically acceptable" indicates that the substance or composition must be compatible chemically and/or toxicologically, with the other ingredients comprising a formulation, and/or the mammal being treated therewith.

The term "pharmaceutically acceptable acid addition salt" denotes those pharmaceutically acceptable salts formed with inorganic acids such as hydrochloric acid, hydrobromic acid, sulfuric acid, nitric acid, carbonic acid, phosphoric acid, and organic acids selected from aliphatic, cycloaliphatic, aromatic, aryl-aliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, malonic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid "mesylate", ethanesulfonic acid, p-toluenesulfonic acid, and salicyclic acid.

The term "pharmaceutically acceptable base addition salt" denotes those pharmaceutically acceptable salts formed with an organic or inorganic base. Examples of acceptable inorganic bases include sodium, potassium, ammonium, calcium, magnesium, iron, zinc, copper, manganese, and aluminum salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, and polyamine resins.

A "solvate" refers to an association or complex of one or more solvent molecules and a compound of the invention. Examples of solvents that form solvates include, but are not limited to, water (i.e., "hydrate"), isopropanol, ethanol, methanol, DMSO, ethylacetate (EtOAc), acetic acid (AcOH), and ethanolamine.

The term "$EC_{50}$" is the half maximal effective concentration" and denotes the plasma concentration of a particular compound required for obtaining 50% of the maximum of a particular effect in vivo.

The term "Ki" is the inhibition constant and denotes the absolute binding affinity of a particular inhibitor to a receptor. It is measured using competition binding assays and is equal to the concentration where the particular inhibitor would occupy 50% of the receptors if no competing ligand (e.g. a radioligand) was present. Ki values can be converted logarithmically to pKi values (−log Ki), in which higher values indicate exponentially greater potency.

The term "$IC_{50}$" is the half maximal inhibitory concentration and denotes the concentration of a particular compound required for obtaining 50% inhibition of a biological process in vitro. $IC_{50}$ values can be converted logarithmically to $pIC_{50}$ values (−log $IC_{50}$), in which higher values indicate exponentially greater potency. The $IC_{50}$ value is not an absolute value but depends on experimental conditions e.g. concentrations employed, and can be converted to an absolute inhibition constant (Ki) using the Cheng-Prusoff equation (Biochem. Pharmacol. (1973) 22:3099). Other percent inhibition parameters, such as $IC_{70}$, $IC_{90}$, etc., may be calculated.

The terms "compound of this invention," and "compounds of the present invention" and "compounds of Formula I" include compounds of Formula I, and stereoisomers, geometric isomers, tautomers, solvates, metabolites, and pharmaceutically acceptable salts and prodrugs thereof.

Any formula or structure given herein, including Formula I compounds, is also intended to represent hydrates, solvates, and polymorphs of such compounds, and mixtures thereof.

Any formula or structure given herein, including Formula I compounds, is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as, but not limited to $^2H$ (deuterium, D), $^3H$ (tritium), $^{11}C$, $^{13}C$, $^{14}C$, $^{15}N$, $^{18}F$, $^{31}P$, $^{32}P$, $^{35}S$, $^{36}Cl$, and $^{125}I$. Various isotopically labeled compounds of the present invention, for example those into which radioactive isotopes such as $^3$H and $^{14}$C are incorporated. Such isotopically labeled compounds may be useful in metabolic studies, reaction kinetic studies, detection or imaging techniques, such as positron emission tomography (PET) or single-photon emission computed tomography (SPECT) including drug or substrate tissue distribution assays, or in radioactive treatment of patients. Deuterium labeled or substituted therapeutic compounds of the invention may have improved DMPK (drug metabolism and pharmacokinetics) properties, relating to distribution, metabolism, and excretion (ADME). Substitution with heavier isotopes such as deuterium may afford certain therapeutic advantages resulting from greater metabolic stability, for example increased in vivo half-life or reduced dosage requirements. An 18F labeled compound may be useful for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent. Further, substitution with heavier isotopes, particularly deuterium (i.e., $^2$H or D) may afford certain therapeutic advantages resulting from greater metabolic stability, for example increased in vivo half-life or reduced dosage requirements or an improvement in therapeutic index. It is understood that deuterium in this context is regarded as a substituent in the compound of the formula (I). The concentration of such a heavier isotope, specifically deuterium, may be defined by an isotopic enrichment factor. In the compounds of this invention any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this invention any atom specifically designated as a deuterium (D) is meant to represent deuterium.

IRE1 Assays

Inhibition of IRE1α RNase activity was determined in an enzyme assay that measured cleavage of the XBP1 stem loop by autophosphorylated IRE1α. This assay format was chosen to ensure that inhibitors of either the IRE1α kinase or the RNase domains would be identified. Binding to the ATP pocket and inhibition of IRE1α kinase activity are not necessarily required to inhibit the RNase activity. Compounds were also profiled in cellular assays by direct measurement of XBP s (B-DNA assay) or by quantification of the luciferase signal in HT1080 XBP1-Luc, which carries a luciferase fusion that is only in frame and expressed from the spliced XBP1 transcript. In the IRE1α enzyme and XPB1-Luc assays, pyrimidinyl-pyridyloxy-naphthyl compounds described herein (e.g., compounds in Tables 1 and 2) demonstrated activity.

Pyrimidinyl-Pyridyloxy-Naphthyl Compounds

The present invention provides pyrimidinyl-pyridyloxy-naphthyl compounds of Formula I including subgeneric formulas and pharmaceutical formulations thereof, which are potentially useful in the treatment of diseases, conditions and/or disorders modulated by inositol requiring enzyme 1 (IRE1).

Compounds of the invention include salt forms of Formula I compounds.

In an effort to probe this pathway and identify suitable therapeutic compounds, IRE1α inhibitors were designed and prepared.

Formula I compounds have the structure:

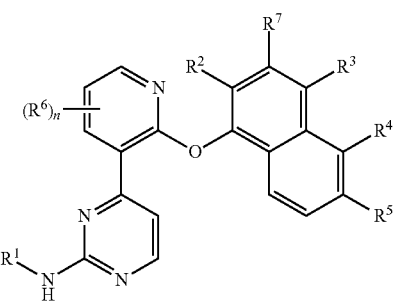

I or stereoisomers, tautomers, or pharmaceutically acceptable salts thereof, wherein:

$R^1$ is selected from $C_3$-$C_{12}$ cycloalkyl, $C_3$-$C_{12}$ heterocyclyl, $C_1$-$C_{12}$ heteroaryl, $C_6$-$C_{20}$ aryl, —($C_1$-$C_6$ alkyldiyl)-($C_3$-$C_{12}$ cycloalkyl), and —($C_1$-$C_6$ alkyldiyl)-($C_3$-$C_{12}$ heterocyclyl);

$R^2$ is selected from H, F, Cl, —CN, —OCH$_3$, —OCH$_2$CH$_3$, and $C_1$-$C_6$ alkyl;

$R^3$ and $R^4$ are independently selected from H, —CN, $C_3$-$C_{12}$ cycloalkyl, $C_3$-$C_{12}$ heterocyclyl, $C_1$-$C_{12}$ heteroaryl, $C_6$-$C_{20}$ aryl, —O—($C_1$-$C_{12}$ heteroaryl), —O—($C_1$-$C_6$ alkyldiyl)-($C_6$-$C_{20}$ aryl), —NR$^8$R$^9$, —NR$^8$C(O)R$^9$, —NR$^8$C(O)OR$^9$, —NR$^8$C(O)NHR$^9$, —NR$^8$SO$_2$—($C_1$-$C_6$ alkyl), —NR$^8$SO$_2$—($C_1$-$C_6$ alkenyl), —NR$^8$SO$_2$—($C_1$-$C_{12}$ heteroaryl), —NR$^8$SO$_2$—($C_1$-$C_6$ alkyldiyl)-($C_3$-$C_{12}$ cycloalkyl), —NR$^8$SO$_2$—($C_1$-$C_6$ alkyldiyl)-($C_3$-$C_{12}$ heterocyclyl), —NR$^8$SO$_2$—($C_1$-$C_6$ alkyldiyl)-($C_1$-$C_{12}$ heteroaryl), —NR$^8$SO$_2$—($C_1$-$C_6$ alkyldiyl)-($C_6$-$C_{20}$ aryl), —NR$^8$SO$_2$NR$^8$R$^9$, and —SO$_2$NR$^8$R$^9$;

$R^5$ and $R^7$ are independently selected from H, F, Cl, —CN, —CH$_2$OH, —C(O)NH$_2$, —OH, —OCH$_3$, —OCH$_2$CH$_3$, and $C_1$-$C_6$ alkyl;

$R^6$ are independently selected from H, F, Cl, Br, I, —CN, —NO$_2$, and $C_1$-$C_6$ alkyl;

$R^8$ is independently selected from H, and $C_1$-$C_6$ alkyl;

$R^9$ is independently selected from $C_1$-$C_6$ alkyl, $C_2$-$C_6$ alkenyl, $C_3$-$C_{12}$ cycloalkyl, $C_3$-$C_{12}$ heterocyclyl, $C_1$-$C_{12}$ heteroaryl, $C_6$-$C_{20}$ aryl; —($C_1$-$C_6$ alkyldiyl)-($C_3$-$C_{12}$ cycloalkyl), —($C_1$-$C_6$ alkyldiyl)-($C_3$-$C_{12}$ heterocyclyl), —($C_1$-$C_6$ alkyldiyl)-($C_1$-$C_6$ heteroaryl), —($C_1$-$C_6$ alkyldiyl)-($C_6$-$C_{20}$ aryl), and —($C_1$-$C_6$ alkyldiyl)-O—($C_6$-$C_{20}$ aryl); and n is 0, 1, 2, or 3;

wherein cycloalkyl, heterocyclyl, heteroaryl, aryl, alkyl, alkyldiyl, and alkenyl are optionally and independently substituted with one or more groups selected from F, Cl, Br, I, —CN, —CH$_3$, —CH$_2$CH$_3$, —CH$_2$CH$_2$CH$_3$, —CH(CH$_3$)$_2$, —CH$_2$CH(CH$_3$)$_2$, —CH(CH$_3$)CH$_2$CH$_3$, —CH$_2$C(CH$_3$)$_3$, —CH$_2$OH, —CH$_2$OCH$_3$, —CH$_2$CH$_2$OH, —C(CH$_3$)$_2$OH, —CH(OH)CH(CH$_3$)$_2$, —C(CH$_3$)$_2$CH$_2$OH, —CH$_2$CH$_2$CH$_2$OH, —CH$_2$CH$_2$C(CH$_3$)$_2$OH, —CH$_2$CH$_2$OCH$_3$, —CH$_2$CH(CH$_3$)OCH$_3$, —CH$_2$CH$_2$CH$_2$OCH$_3$, —CH$_2$CH$_2$C(CH$_3$)$_2$OCH$_3$, —CH$_2$CH$_2$SO$_2$CH$_3$, —CH$_2$OP(O)(OH)$_2$, —CH$_2$F, —CHF$_2$, —CH$_2$NH$_2$, —CH$_2$NHSO$_2$CH$_3$, —CH$_2$NHCH$_3$, —CH$_2$N(CH$_3$)$_2$, —CF$_3$, —CH$_2$CF$_3$, —CH$_2$CHF$_2$, —CH$_2$CHF$_2$, —CH$_2$CH$_2$CF$_3$, —CH(CH$_3$)CN, —C(CH$_3$)$_2$CN, —CH$_2$CN, —CO$_2$H, —COCH$_3$, —CO$_2$CH$_3$, —CO$_2$C(CH$_3$)$_3$, —COCH(OH)CH$_3$, —CONH$_2$, —CONHCH$_3$, —CONHCH$_2$CH$_3$, —CONHCH (CH₃)₂, —CON(CH₃)₂, —C(CH₃)₂CONH₂, —NH₂, —NHCH₃, —N(CH₃)₂, —N(CH₃)CH₂CH₃, —NHCOCH₃, —N(CH₃)COCH₃, —NHS(O)₂CH₃, —N(CH₃)C(CH₃)₂CONH₂, —N(CH₃)CH₂CH₂S(O)₂CH₃, —NO₂, =O, —OH, —OCH₃, —OCH₂CH₃, —OCH₂CH₂OCH₃, —OCH₂CH₂OH, —OCH₂CH₂N(CH₃)₂, —OP(O)(OH)₂, —S(O)₂N(CH₃)₂, —SCH₃, —S(O)₂CH₃, —S(O)₃H, cyclopropyl, cyclopropylamide, cyclobutyl, oxetanyl, azetidinyl, 1-methylazetidin-3-yl)oxy, N-methyl-N-oxetan-3-ylamino, azetidin-1-ylmethyl, benzyloxyphenyl, pyrrolidin-1-yl, pyrrolidin-1-yl-methanone, phenyl, piperazin-1-yl, piperidin-1-yl, morpholinomethyl, morpholino-methanone, and morpholino.

In some embodiments of the compound of the Formula I, or stereoisomers, tautomers, or pharmaceutically acceptable salts thereof, the compound is other than Compound Nos. 1x-17x of Table 1X. In some embodiments of the Formula I, or stereoisomers, tautomers, or pharmaceutically acceptable salts thereof, wherein $R^3$ is other than —NH-(heteroaryl).

TABLE 1X

| No. | Name |
|---|---|
| 1x | 1,4-Cyclohexanediamine, N1-[4-[2-[[4-(2-benzoxazolylamino)-2-methyl-1-naphthalenyl]oxy]-3-pyridinyl]-2-pyrimidinyl]-, trans- |
| 2x | 1H-Benzimidazol-2-amine, N-[3-methyl-4-[[3-[2-[(3S)-3-piperidinylamino]-4-pyrimidinyl]-2-pyridinyl]oxy]-1-naphthalenyl]- |
| 3x | 1,4-Cyclohexanediamine, N1-[4-[2-[[4-(1H-benzimidazol-2-ylamino)-2-methyl-1-naphthalenyl]oxy]-3-pyridinyl]-2-pyrimidinyl]-, trans- |
| 4x | 1,4-Cyclohexanediamine, N1-[4-[2-[[4-(1H-benzimidazol-2-ylamino)-1-naphthalenyl]oxy]-3-pyridinyl]-2-pyrimidinyl]-, cis- |
| 5x | 1,4-Cyclohexanediamine, N1-[4-[2-[[4-(1H-benzimidazol-2-ylamino)-1-naphthalenyl]oxy]-3-pyridinyl]-2-pyrimidinyl]-, trans- |
| 6x | 1H-Benzimidazol-2-amine, N-[4-[[3-[2-[(3S)-3-piperidinylamino]-4-pyrimidinyl]-2-pyridinyl]oxy]-1-naphthalenyl]- |
| 7x | 1H-Benzimidazol-2-amine, N-[4-[[3-[2-[(3R)-3-piperidinylamino]-4-pyrimidinyl]-2-pyridinyl]oxy]-1-naphthalenyl]- |
| 8x | 1H-Benzimidazol-2-amine, N-[4-[[3-[2-[(1-methyl-3-piperidinyl)amino]-4-pyrimidinyl]-2-pyridinyl]oxy]-1-naphthalenyl]- |
| 9x | Ethanol, 2-[[4-[2-[[4-(1H-benzimidazol-2-ylamino)-1-naphthalenyl]oxy]-3-pyridinyl]-2-pyrimidinyl]amino]- |
| 10x | 1H-Benzimidazol-2-amine, N-[4-[[3-[2-[(3-methylbutyl)amino]-4-pyrimidinyl]-2-pyridinyl]oxy]-1-naphthalenyl]- |
| 11x | 1,2-Ethanediamine, N2-[4-[2-[[4-(1H-benzimidazol-2-ylamino)-2-methyl-1-naphthalenyl]oxy]-3-pyridinyl]-2-pyrimidinyl]-N1,N1-dimethyl- |
| 12x | 1H-Benzimidazol-2-amine, N-[4-[[3-[2-[[3-(1-piperidinyl)propyl]amino]-4-pyrimidinyl]-2-pyridinyl]oxy]-1-naphthalenyl]- |
| 13x | 1H-Benzimidazol-2-amine, N-[4-[[3-[2-[(1-methyl-4-piperidinyl)amino]-4-pyrimidinyl]-2-pyridinyl]oxy]-1-naphthalenyl]- |
| 14x | 1H-Benzimidazol-2-amine, N-[4-[[3-[2-[[(1-ethyl-4-piperidinyl)methyl]amino]-4-pyrimidinyl]-2-pyridinyl]oxy]-1-naphthalenyl]- |
| 15x | 1H-Benzimidazol-2-amine, N-[4-[[3-[2-[[2-(1-methyl-2-pyrrolidinyl)ethyl]amino]-4-pyrimidinyl]-2-pyridinyl]oxy]-1-naphthalenyl]- |
| 16x | 1H-Benzimidazol-2-amine, N-[4-[[3-[2-[[3-(1-pyrrolidinyl)propyl]amino]-4-pyrimidinyl]-2-pyridinyl]oxy]-1-naphthalenyl]- |
| 17x | 1H-Benzimidazol-2-amine, N-[4-[[3-[2-[[2-(4-morpholinyl)ethyl]amino]-4-pyrimidinyl]-2-pyridinyl]oxy]-1-naphthalenyl]- |

In some embodiments, provided is a compound of the Formula I':

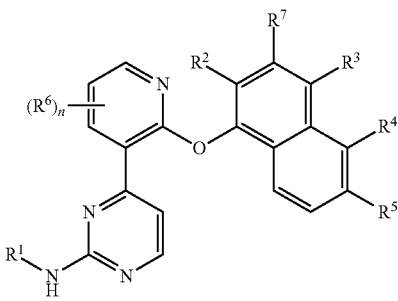

I' or a stereoisomer, tautomer, or pharmaceutically acceptable salt thereof, wherein:

$R^1$ is $C_3$-$C_{12}$ cycloalkyl, $C_3$-$C_{12}$ heterocyclyl, $C_1$-$C_{12}$ heteroaryl, $C_6$-$C_{20}$ aryl, —($C_1$-$C_6$ alkyldiyl)-($C_3$-$C_{12}$ cycloalkyl), or —($C_1$-$C_6$ alkyldiyl)-($C_3$-$C_{12}$ heterocyclyl);

$R^2$ is H, F, Cl, —CN, —OCH$_3$, —OCH$_2$CH$_3$, or $C_1$-$C_6$ alkyl;

$R^3$ is H, —CN, $C_3$-$C_{12}$ cycloalkyl, $C_3$-$C_{12}$ heterocyclyl, $C_1$-$C_{12}$ heteroaryl, $C_6$-$C_{20}$ aryl, —O—($C_1$-$C_{12}$ heteroaryl), —O—($C_1$-$C_6$ alkyldiyl)-($C_6$-$C_{20}$ aryl), —N($R^8$)($C_1$-$C_6$ alkyl), —NR$^8$C(O)R$^9$, —NR$^8$C(O)OR$^9$, —NR$^8$C(O)NHR$^9$, —NR$^8$SO$_2$—($C_1$-$C_6$ alkyl), —NR$^8$SO$_2$—($C_1$-$C_6$ alkenyl), —NR$^8$SO$_2$—($C_3$-$C_{12}$ cycloalkyl), —NR$^8$SO$_2$—($C_1$-$C_{12}$ heteroaryl), —NR$^8$SO$_2$—($C_1$-$C_6$ alkyldiyl)-($C_3$-$C_{12}$ cycloalkyl), —NR$^8$SO$_2$—($C_1$-$C_6$ alkyldiyl)-($C_3$-$C_{12}$ heterocyclyl), —NR$^8$SO$_2$—($C_1$-$C_6$ alkyldiyl)-($C_1$-$C_{12}$ heteroaryl), —NR$^8$SO$_2$—($C_1$-$C_6$ alkyldiyl)-($C_6$-$C_{20}$ aryl), —NR$^8$SO$_2$NR$^8$R$^9$, or —SO$_2$NR$^8$R$^9$;

$R^4$ is H, —CN, $C_3$-$C_{12}$ cycloalkyl, $C_3$-$C_{12}$ heterocyclyl, $C_1$-$C_{12}$ heteroaryl, $C_6$-$C_{20}$ aryl, —O—($C_1$-$C_{12}$ heteroaryl), —O—($C_1$-$C_6$ alkyldiyl)-($C_6$-$C_{20}$ aryl), —NR$^8$R$^9$, —NR$^8$C(O)R$^9$, —NR$^8$C(O)OR$^9$, —NR$^8$C(O)NHR$^9$, —NR$^8$SO$_2$—($C_1$-$C_6$ alkyl), —NR$^8$SO$_2$—($C_1$-$C_6$ alkenyl), —NR$^8$SO$_2$—($C_1$-$C_{12}$ heteroaryl), —NR$^8$SO$_2$—($C_3$-$C_{12}$ cycloalkyl), —NR$^8$SO$_2$—($C_3$-$C_{12}$ heterocyclyl), —NR$^8$SO$_2$—($C_1$-$C_6$ alkyldiyl)-($C_3$-$C_{12}$ cycloalkyl), —NR$^8$SO$_2$—($C_1$-$C_6$ alkyldiyl)-($C_3$-$C_{12}$ heterocyclyl), —NR$^8$SO$_2$—($C_1$-$C_6$ alkyldiyl)-($C_1$-$C_{12}$ heteroaryl), —NR$^8$SO$_2$—($C_1$-$C_6$ alkyldiyl)-($C_6$-$C_{20}$ aryl), —NR$^8$SO$_2$NR$^8$R$^9$, or —SO$_2$NR$^8$R$^9$;

each $R^5$ and $R^7$ are independently H, F, Cl, —CN, —CH$_2$OH, —C(O)NH$_2$, —OH, —OCH$_3$, —OCH$_2$CH$_3$, or $C_1$-$C_6$ alkyl;

n is 0, 1, 2, or 3;

each $R^6$ is independently H, F, Cl, Br, I, —CN, —NO$_2$, —O—($C_1$-$C_6$ alkyl) or $C_1$-$C_6$ alkyl;

each $R^8$ is independently H, or $C_1$-$C_6$ alkyl;

each $R^9$ is independently $C_1$-$C_6$ alkyl, $C_2$-$C_6$ alkenyl, $C_3$-$C_{12}$ cycloalkyl, $C_3$-$C_{12}$ heterocyclyl, $C_1$-$C_{12}$ heteroaryl, $C_6$-$C_{20}$ aryl; —($C_1$-$C_6$ alkyldiyl)-($C_3$-$C_{12}$ cycloalkyl), —($C_1$-$C_6$ alkyldiyl)-($C_3$-$C_{12}$ heterocyclyl), —($C_1$-$C_6$ alkyldiyl)-($C_1$-$C_6$ heterocyclyl), —($C_1$-$C_6$ alkyldiyl)-($C_6$-$C_{20}$ aryl), or —($C_1$-$C_6$ alkyldiyl)-O—($C_6$-$C_{20}$ aryl); and wherein cycloalkyl, heterocyclyl, heteroaryl, aryl, alkyl, alkyldiyl, and alkenyl are optionally and independently substituted with one or more (e.g., 1 to 2, 1 to 3, 1 to 4, or 1 to 5) substituents selected from the group consisting of F, Cl, Br, I, —CN, —CH$_3$, —CH$_2$CH$_3$, —CH$_2$CH$_2$CH$_3$, —CH(CH$_3$)$_2$, —CH$_2$CH(CH$_3$)$_2$, —CH(CH$_3$)CH$_2$CH$_3$, —CH$_2$C(CH$_3$)$_3$, —CH$_2$OH, —CH$_2$OCH$_3$, —CH$_2$CH$_2$OH, —C(CH$_3$)$_2$OH, —CH(OH)CH(CH$_3$)$_2$, —C(CH$_3$)$_2$CH$_2$OH, —CH$_2$CH$_2$CH$_2$OH, —CH$_2$CH$_2$C(CH$_3$)$_2$OH, —CH$_2$CH$_2$OCH$_3$, —CH$_2$CH(CH$_3$)OCH$_3$, —CH$_2$CH$_2$CH$_2$OCH$_3$, —CH$_2$CH$_2$C(CH$_3$)$_2$OCH$_3$, —CH$_2$CH$_2$SO$_2$CH$_3$, —CH$_2$OP(O)(OH)$_2$, —CH$_2$F, —CHF$_2$, —CH$_2$NH$_2$, —CH$_2$NHSO$_2$CH$_3$, —CH$_2$NHCH$_3$, —CH$_2$N(CH$_3$)$_2$, —CF$_3$, —CH$_2$CF$_3$, —CH$_2$CHF$_2$, —CH$_2$CH$_2$CHF$_2$, —CH$_2$CH$_2$CF$_3$, —CH(CH$_3$)CN, —C(CH$_3$)$_2$CN, —CH$_2$CN, —CO$_2$H, —COCH$_3$, —CO$_2$CH$_3$, —CO$_2$C(CH$_3$)$_3$, —COCH(OH)CH$_3$, —CONH$_2$, —CONHCH$_3$, —CONHCH$_2$CH$_3$, —CONHCH(CH$_3$)$_2$, —CON(CH$_3$)$_2$, —C(CH$_3$)$_2$CONH$_2$, —NH$_2$, —NHCH$_3$, —N(CH$_3$)$_2$, —N(CH$_3$)CH$_2$CH$_3$, —NHCOCH$_3$, —N(CH$_3$)COCH$_3$, —NHS(O)$_2$CH$_3$, —N(CH$_3$)C(CH$_3$)$_2$CONH$_2$, —N(CH$_3$)CH$_2$CH$_2$S(O)$_2$CH$_3$, —NO$_2$, =O, —OH, —OCH$_3$, —OCH$_2$CH$_3$, —OCH$_2$CH$_2$OCH$_3$, —OCH$_2$CH$_2$OH, —OCH$_2$CH$_2$N(CH$_3$)$_2$, —OP(O)(OH)$_2$, —S(O)$_2$N(CH$_3$)$_2$, —SCH$_3$, —S(O)$_2$CH$_3$, —S(O)$_3$H, cyclopropyl, cyclopropylamide, cyclobutyl, oxetanyl, azetidinyl, 1-methylazetidin-3-yl)oxy, N-methyl-N-oxetan-3-ylamino, azetidin-1-ylmethyl, benzyloxyphenyl, pyrrolidin-1-yl, pyrrolidin-1-yl-methanone, phenyl, piperazin-1-yl, piperidin-1-yl, morpholinomethyl, morpholino-methanone, and morpholino.

In some embodiments of the compound of Formula I', or stereoisomers, tautomers, or pharmaceutically acceptable salts thereof, wherein $R^1$ is optionally substituted $C_3$-$C_{12}$ cycloalkyl or optionally substituted $C_3$-$C_{12}$ heterocyclyl. In some embodiments, $R^1$ is cyclohexyl or piperidinyl, optionally substituted with one or more (e.g., 1 to 2, 1 to 3, 1 to 4, or 1 to 5) substituents selected from the group consisting of F, —CH$_3$, and —NH$_2$. In some embodiments, $R^1$ is piperidinyl (e,g, 3-piperidinyl) optionally substituted with one or more substituents selected from the group consisting of F, —CH$_3$ and —OCH$_3$. In some embodiments, $R^1$ is piperidinyl (e,g, 3-piperidinyl) optionally substituted with one to four substituents selected from the group consisting of F, —CH$_3$ and —OCH$_3$. In some embodiments, $R^1$ is selected from the group consisting of piperidin-3-yl, 5-fluoropiperidin-3-yl, 5-methylpiperidin-3-yl and 5-fluoro-5-methylpiperidin-3-yl. In some embodiments, $R^2$ is H, F, Cl or $C_1$-$C_6$ alkyl. In some embodiments, $R^2$ is $C_1$-$C_6$ alkyl (e.g., methyl). In some embodiments, $R^3$ is H, $C_3$-$C_{12}$ heterocyclyl, —N($R^8$)($C_1$-$C_6$ alkyl), —NR$^8$C(O)R$^9$, —NR$^8$SO$_2$—($C_1$-$C_6$ alkyl), —NR$^8$SO$_2$—($C_1$-$C_6$ alkenyl), —NR$^8$SO$_2$—($C_3$-$C_{12}$ cycloalkyl), —NR$^8$SO$_2$—($C_1$-$C_{12}$ heteroaryl), —NR$^8$SO$_2$—($C_1$-$C_6$ alkyldiyl)-($C_3$-$C_{12}$ cycloalkyl), —NR$^8$SO$_2$—($C_1$-$C_6$ alkyldiyl)-($C_3$-$C_{12}$ heterocyclyl), —NR$^8$SO$_2$—($C_1$-$C_6$ alkyldiyl)-($C_1$-$C_{12}$ heteroaryl), —NR$^8$SO$_2$—($C_1$-$C_6$ alkyldiyl)-($C_6$-$C_{20}$ aryl), —NR$^8$SO$_2$NR$^8$R$^9$, or —SO$_2$NR$^8$R$^9$. In some embodiments, $R^3$ is H, and $R^4$ is $C_3$-$C_{12}$ cycloalkyl, $C_3$-$C_{12}$ heterocyclyl, $C_1$-$C_{12}$ heteroaryl, $C_6$-$C_{20}$ aryl, —O—($C_1$-$C_{12}$ heteroaryl), —O—($C_1$-$C_6$ alkyldiyl)-($C_6$-$C_{20}$ aryl), —NR$^8$R$^9$, —NR$^8$C(O)R$^9$, —NR$^8$C(O)OR$^9$, —NR$^8$C(O)NHR$^9$, —NR$^8$SO$_2$—($C_1$-$C_6$ alkyl), —NR$^8$SO$_2$—($C_1$-$C_6$ alkenyl), —NR$^8$SO$_2$—($C_1$-$C_{12}$ heteroaryl), —NR$^8$SO$_2$—($C_3$-$C_{12}$ cycloalkyl), —NR$^8$SO$_2$—($C_3$-$C_{12}$ heterocyclyl), —NR$^8$SO$_2$—($C_1$-$C_6$ alkyldiyl)-($C_3$-$C_{12}$ cycloalkyl), —NR$^8$SO$_2$—($C_1$-$C_6$ alkyldiyl)-($C_3$-$C_{12}$ heterocyclyl), —NR$^8$SO$_2$—($C_1$-$C_6$ alkyldiyl)-($C_1$-$C_{12}$ heteroaryl), —NR$^8$SO$_2$—($C_1$-$C_6$ alkyldiyl)-($C_6$-$C_{20}$ aryl), —NR$^8$SO$_2$NR$^8$R$^9$, or —SO$_2$NR$^8$R$^9$. In some embodiments, $R^5$ is H, F, Cl or CH$_3$. In some embodiments, $R^5$ is H. In some embodiments, $R^7$ is hydrogen or fluoro. In some embodiments, $R^5$ and $R^7$ are hydrogen. In any of these embodiments, cycloalkyl, heterocyclyl, heteroaryl, aryl, alkyl, alkyldiyl, and alkenyl are optionally and independently substituted as defined for Formula I'.

Exemplary embodiments of Formula I or I' compounds include Formula Ia:

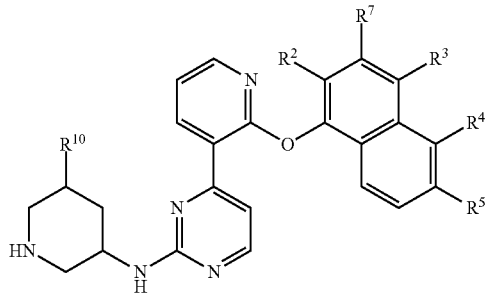

wherein $R^{10}$ is selected from H, F, —CH$_3$, and —NH$_2$.

Exemplary embodiments of Formula Ia compounds include Formula Ib:

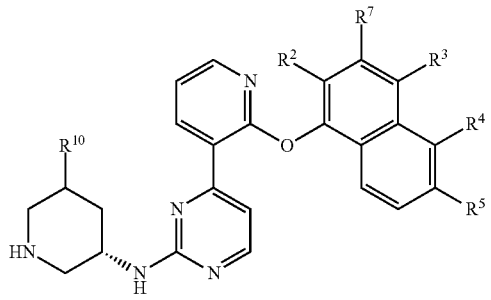

Exemplary embodiments of Formula I or I' compounds include Formula Ic:

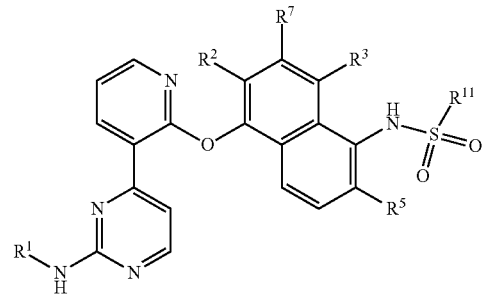

wherein $R^{11}$ is selected from C$_1$-C$_6$ alkyl, C$_1$-C$_6$ alkenyl, C$_1$-C$_{12}$ heteroaryl, (C$_1$-C$_6$ alkyldiyl)-(C$_3$-C$_{12}$ heterocyclyl), (C$_1$-C$_6$ alkyldiyl)-(C$_1$-C$_{12}$ heteroaryl), (C$_1$-C$_6$ alkyldiyl)-(C$_6$-C$_{20}$ aryl), (C$_1$-C$_6$ alkyldiyl)-(C$_6$-C$_{20}$ aryl), NR$^7$—(C$_1$-C$_{12}$ heteroaryl), NR$^7$—(C$_1$-C$_6$ alkyl), and NR$^7$—(C$_1$-C$_6$ alkyldiyl)-(C$_6$-C$_{20}$ aryl).

Formula Ic compounds include wherein $R^{11}$ is selected from benzyl, cyclopropyl, cyclopropylmethyl, cyclobutyl, cyclobutylmethyl, cyclopentanyl, cyclopentanylmethyl, cyclohexyl, cyclohexylmethyl, pyrrolidin-1-yl, piperidin-1-yl, pyridyl, pyridylmethyl, tetrahydrofuranyl, tetrahydrofuranylmethyl, and tetrahydropyranyl, tetrahydropyranylmethyl, thiazolyl, and thiazolylmethyl, optionally and independently substituted with one groups selected from fluoro, chloro, bromo, —CH$_3$, —CH$_2$CH$_3$, —CH$_2$OH, and —CN.

Formula Ic compounds include wherein $R^{11}$ is selected from —CH$_3$, —CH$_2$CH$_3$, —CH═CH$_2$, —CH$_2$CH$_2$CH$_3$, —CH(CH$_3$)$_2$, —CH$_2$CH(CH$_3$)$_2$, —CH(CH$_3$)CH$_2$CH$_3$, —CH$_2$C(CH$_3$)$_3$, —CH$_2$CHF$_2$, —CH$_2$CH$_2$CHF$_2$, —CH$_2$CF$_3$, —CH$_2$CH$_2$CF$_3$, —CH$_2$CH$_2$OCH$_3$, —CH$_2$CH$_2$CH$_2$OCH$_3$, —CH$_2$CH(CH$_3$)OCH$_3$, —CH$_2$F, —CH$_2$Cl, —CH$_2$Br, —CH$_2$CN, —NH$_2$, —NHCH$_3$, —N(CH$_3$)$_2$, and —N(CH$_3$)CH$_2$CH$_3$.

Exemplary embodiments of Formula Ic compounds have Formula Id:

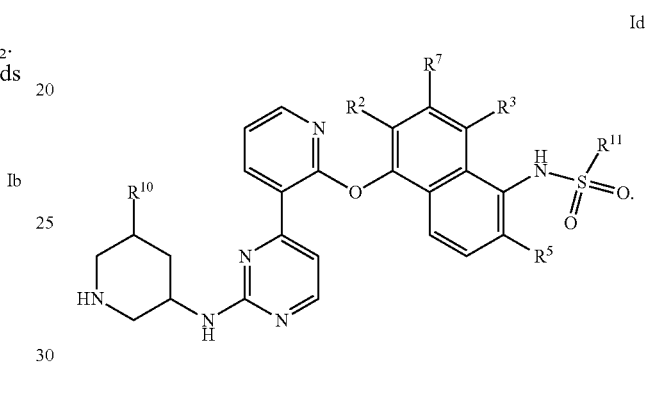

Exemplary embodiments of Formula Id compounds have Formula Ie:

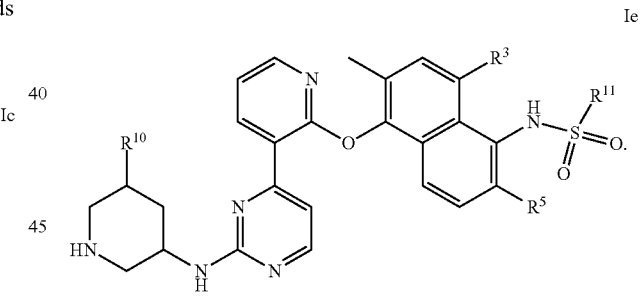

Exemplary embodiments of Formula Ie compounds have Formula If:

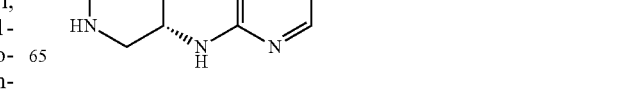

Formula If compounds include wherein $R^5$ is F, having Formula Ig:

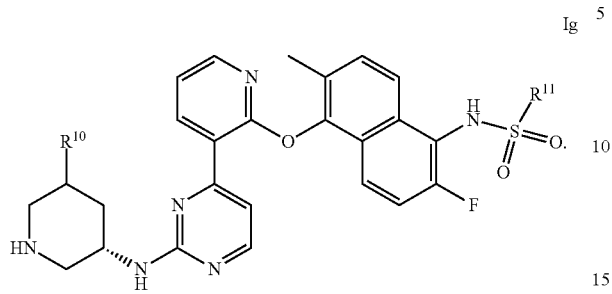

In some embodiments of the compound of Formula I or I', or stereoisomers, tautomers, or pharmaceutically acceptable salts thereof, wherein $R^1$ is optionally substituted piperidin-3-yl. In some embodiments, the compound is of Formula Ih:

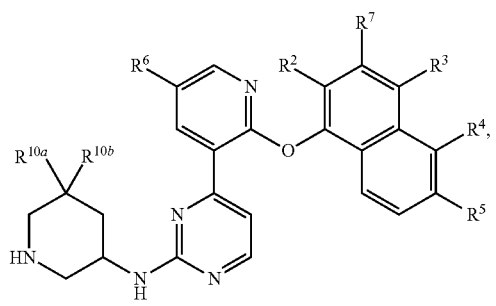

wherein $R^{10a}$ and $R^{10b}$ are independently H, F, —CH$_3$ or —NH$_2$; and $R^2$, $R^3$, $R^4$, $R^5$, $R^6$ and $R^7$ are as described for Formula I or I'. In some embodiments, $R^2$ is H, F, Cl or $C_1$-$C_6$ alkyl. In some embodiments, $R^2$ is $C_1$-$C_6$ alkyl (e.g., methyl). In some embodiments, $R^5$ is H, F, Cl or CH$_3$. In some embodiments, $R^7$ is hydrogen or fluoro. In some embodiments, $R^5$ and $R^7$ are hydrogen. In some embodiments, $R^6$ is H, F, Cl, Br, —OCH$_3$, or $C_1$-$C_6$ alkyl (e.g., methyl and ethyl). In some embodiments, $R^6$ is H. In some embodiments, $R^{10a}$ and $R^{10b}$ are independently H, F or —CH$_3$.

In some embodiments of the compound of Formula Ih, or a variation thereof, the compound is of the Formula Ii:

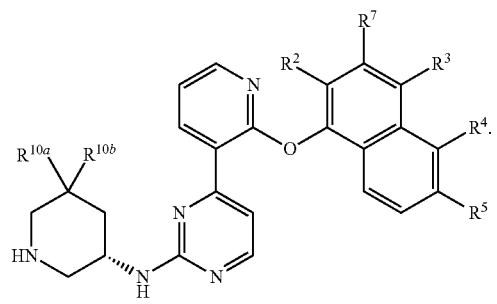

In some embodiments of the compound of Formula I', or stereoisomers, tautomers, or pharmaceutically acceptable salts thereof, n is 0 and the compound is of Formula Ij:

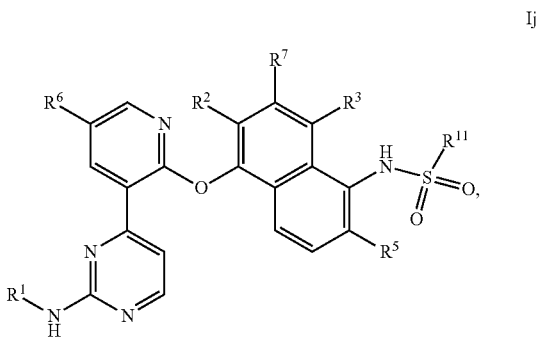

wherein $R^{11}$ is $C_1$-$C_6$ alkyl, $C_1$-$C_6$ alkenyl, $C_1$-$C_{12}$ heteroaryl, $C_3$-$C_{12}$ cycloalkyl, $C_3$-$C_{12}$ heterocyclyl, —($C_1$-$C_6$ alkyldiyl)-($C_3$-$C_{12}$ cycloalkyl), —($C_1$-$C_6$ alkyldiyl)-($C_3$-$C_{12}$ heterocyclyl), —($C_1$-$C_6$ alkyldiyl)-($C_1$-$C_{12}$ heteroaryl), —($C_1$-$C_6$ alkyldiyl)-($C_6$-$C_{20}$ aryl), —NR$^8$—($C_1$-$C_{12}$ heteroaryl), —NR$^8$—($C_1$-$C_6$ alkyl), or —NR$^8$—($C_1$-$C_6$ alkyldiyl)-($C_6$-$C_{20}$ aryl); and $R^1$, $R^2$, $R^3$, $R^4$, $R^5$, $R^6$, $R^7$ and $R^8$ are as described for Formula I'. In some embodiments, $R^{11}$ is $C_1$-$C_6$ alkyl, $C_1$-$C_6$ alkenyl, $C_1$-$C_{12}$ heteroaryl, $C_3$-$C_{12}$ cycloalkyl, $C_3$-$C_{12}$ heterocyclyl, —($C_1$-$C_6$ alkyldiyl)-($C_3$-$C_{12}$ cycloalkyl), —($C_1$-$C_6$ alkyldiyl)-($C_3$-$C_{12}$ heterocyclyl), —($C_1$-$C_6$ alkyldiyl)-($C_1$-$C_{12}$ heteroaryl), or —($C_1$-$C_6$ alkyldiyl)-($C_6$-$C_{20}$ aryl). In some embodiments, $R^{11}$ is —NR$^8$—($C_1$-$C_{12}$ heteroaryl), —NR$^8$—($C_1$-$C_6$ alkyl), or —NR$^8$—($C_1$-$C_6$ alkyldiyl)-($C_6$-$C_{20}$ aryl); and $R^8$ is H or —CH$_3$. In some embodiments, $R^{11}$ is selected from the group consisting of benzyl, cyclopropyl, cyclopropylmethyl, cyclobutyl, cyclobutylmethyl, cyclopentanyl, cyclopentanylmethyl, cyclohexyl, cyclohexylmethyl, pyrrolidin-1-yl, piperidin-1-yl, pyridyl, pyridylmethyl, tetrahydrofuranyl, tetrahydrofuranylmethyl, and tetrahydropyranyl, tetrahydropyranylmethyl, thiazolyl, and thiazolylmethyl; each of which is optionally and independently substituted with one or more (e.g., 1 to 2, 1 to 3, 1 to 4, or 1 to 5) substituents selected from fluoro, chloro, bromo, —CH$_3$, —CH$_2$CH$_3$, —CH$_2$OH, and —CN. In some embodiments, $R^{11}$ is selected from the group consisting of —CH$_3$, —CH$_2$CH$_3$, —CH═CH$_2$, —CH$_2$CH$_2$CH$_3$, —CH(CH$_3$)$_2$, —CH$_2$CH(CH$_3$)$_2$, —CH(CH$_3$)CH$_2$CH$_3$, —CH$_2$C(CH$_3$)$_3$, —CH$_2$CHF$_2$, —CH$_2$CH$_2$CHF$_2$, —CH$_2$CF$_3$, —CH$_2$CH$_2$CF$_3$, —CH$_2$CH$_2$OCH$_3$, —CH$_2$CH$_2$CH$_2$OCH$_3$, —CH$_2$CH(CH$_3$)OCH$_3$, —CH$_2$F, —CH$_2$Cl, —CH$_2$Br, —CH$_2$CN, —NH$_2$, —NHCH$_3$, —N(CH$_3$)$_2$, and —N(CH$_3$)CH$_2$CH$_3$. In some embodiments, $R^2$ is H, F, Cl or $C_1$-$C_6$ alkyl. In some embodiments, $R^2$ is $C_1$-$C_6$ alkyl (e.g., methyl). In some embodiments, $R^3$ is H. In some embodiments, $R^5$ is H, F, Cl or CH$_3$. In some embodiments, $R^7$ is hydrogen or fluoro. In some embodiments, $R^5$ and $R^7$ are hydrogen. In some embodiments, $R^6$ is H, F, Cl, Br, —OCH$_3$, or $C_1$-$C_6$ alkyl (e.g., methyl and ethyl). In some embodiments, $R^6$ is H.

In some embodiments of the compound of Formula Ij, or a variation thereof, the compound is of the Formula Ik:

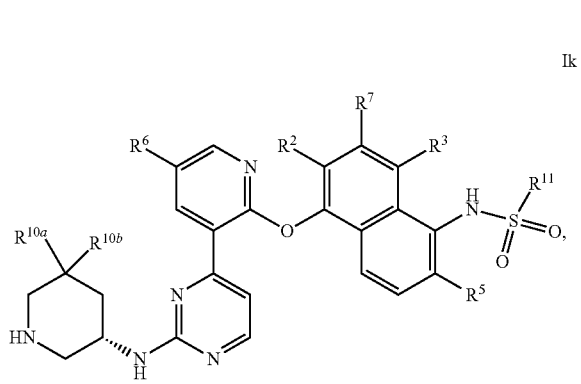

Ik wherein $R^{10a}$ and $R^{10b}$ are independently H, F or —CH$_3$. In some embodiments, $R^{10a}$ and $R^{10b}$ are H. In some embodiments, one of $R^{10a}$ and $R^{10b}$ is F and the other one of $R^{10a}$ and $R^{10b}$ is H. In some embodiments, one of $R^{10a}$ and $R^{10b}$ is H and the other one of $R^{10a}$ and $R^{10b}$ is —CH$_3$. In some embodiments, one of $R^{10a}$ and $R^{10b}$ is F and the other one of $R^{10a}$ and $R^{10b}$ is —CH$_3$.

In some embodiments of the compound of Formula Ik, or a variation thereof, $R^2$ is —CH$_3$, $R^3$, $R^6$ and $R^7$ are H, $R^5$ is F; and the compound is of the Formula Il:

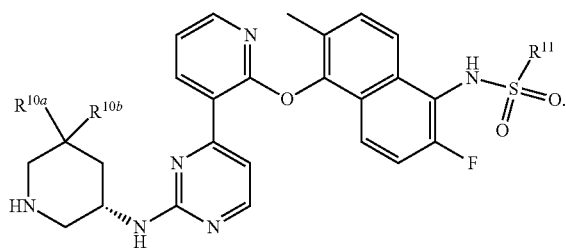

Il

In some embodiments of the compound of Formula Il, or a variation thereof, $R^{10a}$ and $R^{10b}$ are H; and the compound is of the Formula Im:

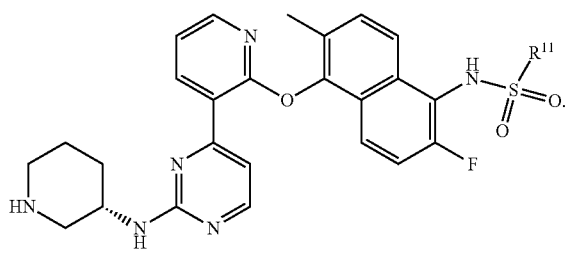

Im

In some embodiments of the compound of Formula Il, or a variation thereof, $R^{10a}$ is F and $R^{10b}$ is H; and the compound is of the Formula In:

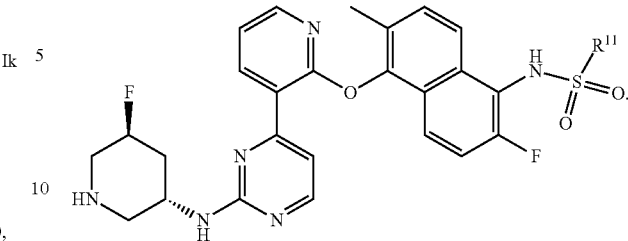

In

In some embodiments of the compound of Formula Il, or a variation thereof, $R^{10a}$ is H and $R^{10b}$ is —CH$_3$; and the compound is of the Formula Io:

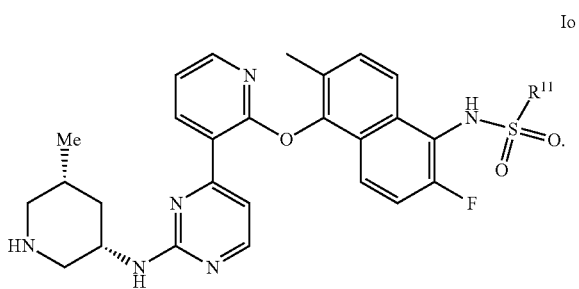

Io

In some embodiments of the compound of Formula Il, or a variation thereof, $R^{10a}$ is F and $R^{10b}$ is —CH$_3$; and the compound is of the Formula Ip:

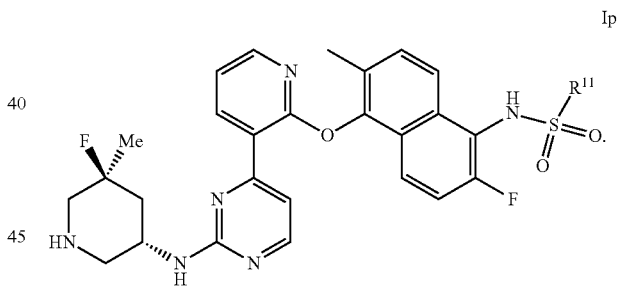

Ip

In some embodiments of the compound of Formula I or I', or stereoisomers, tautomers, or pharmaceutically acceptable salts thereof, wherein n is 0, $R^2$ is —CH$_3$, $R^3$ and $R^7$ are H, $R^1$ is optionally substituted piperidin-3-yl, and the compound is of Formula Iq:

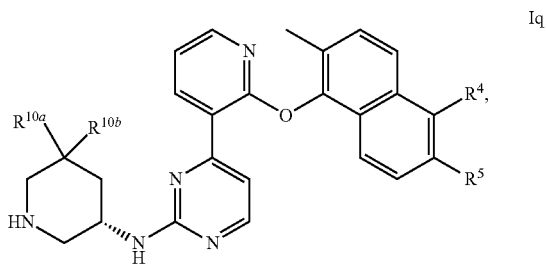

Iq wherein $R^{10a}$ and $R^{10b}$ are independently H, F or $CH_3$; and $R^4$ and $R^5$ are as described for Formula I or I'. In some embodiments, $R^4$ is —CN, $C_3$-$C_{12}$ cycloalkyl, $C_3$-$C_{12}$ heterocyclyl, $C_1$-$C_{12}$ heteroaryl, $C_6$-$C_{20}$ aryl, —O—($C_1$-$C_{12}$ heteroaryl), —O—($C_1$-$C_6$ alkyldiyl)-($C_6$-$C_{20}$ aryl), —$NR^8R^9$, —$NR^8C(O)R^9$, —$NR^8C(O)OR^9$, —$NR^8C(O)NHR^9$, or —$SO_2NR^8R^9$. In some embodiments, $R^4$ is $C_3$-$C_{12}$ heterocyclyl, $C_1$-$C_{12}$ heteroaryl, —$NR^8R^9$, —$NR^8C(O)R^9$, —$NR^8C(O)OR^9$, —$NR^8C(O)NHR^9$ or —$SO_2NR^8R^9$. In some embodiments, $R^4$ is $C_3$-$C_{12}$ heterocyclyl, $C_1$-$C_{12}$ heteroaryl, —$NR^8R^9$ or —$NR^8C(O)R^9$. In some embodiments, $R^5$ is H, F, Cl or $CH_3$. In some embodiments, $R^5$ is H or F. In one variation, $R^5$ is H. In another variation, $R^5$ is F. In some of these embodiments, $R^{10a}$ and $R^{10b}$ are H. In some of these embodiments, one of $R^{10a}$ and $R^{10b}$ is F and the other one of $R^{10a}$ and $R^{10b}$ are H. In some of these embodiments, one of $R^{10a}$ and $R^{10b}$ is H and the other one of $R^{10a}$ and $R^{10b}$ is —$CH_3$. In some of these embodiments, one of $R^{10a}$ and $R^{10b}$ is F and the other one of $R^{10a}$ and $R^{10b}$ is —$CH_3$.

In some embodiments of the compound of Formula Iq, or a variation thereof, the compound is of the Formula Ir:

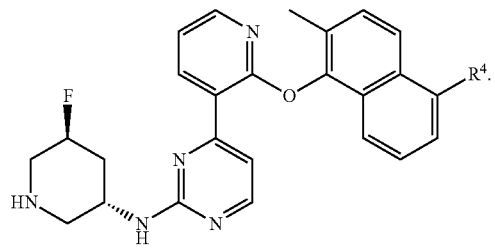

Ir

In some embodiments of the compound of Formula Iq, or a variation thereof, the compound is of the Formula Is:

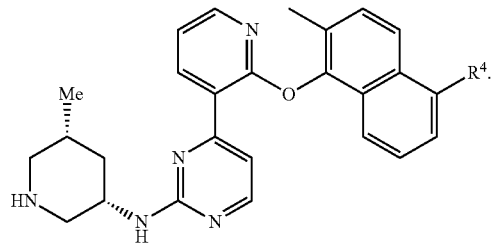

Is

In some embodiments of the compound of Formula Iq, or a variation thereof, the compound is of the Formula It:

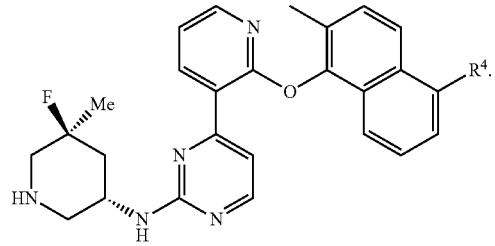

It

In some embodiments of the compound of Formula Iq, or a variation thereof, the compound is of the Formula Iu:

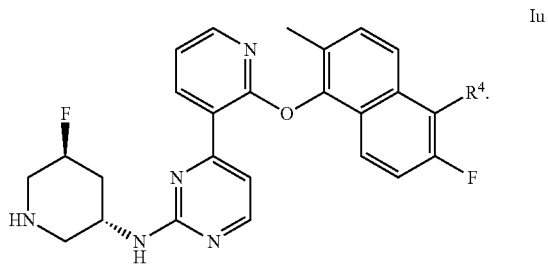

Iu

In some embodiments of the compound of Formula Iq, or a variation thereof, the compound is of the Formula Iv:

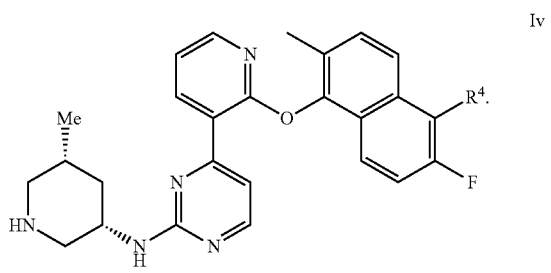

Iv

In some embodiments of the compound of Formula Iq, or a variation thereof, the compound is of the Formula Iw:

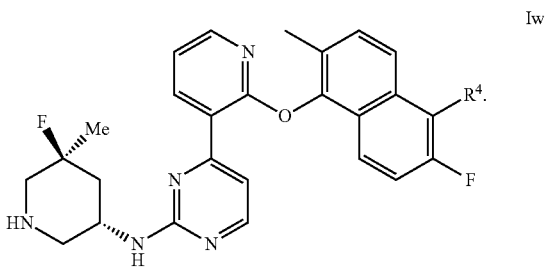

Iw

In some embodiments of the compound of Formula I or I', or stereoisomers, tautomers, or pharmaceutically acceptable salts thereof, wherein $R^4$ and $R^5$ are H, $R^1$ is optionally substituted piperidin-3-yl, and the compound is of Formula Ix:

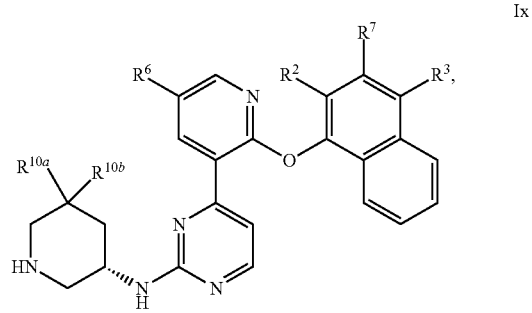

Ix wherein $R^{10a}$ and $R^{10b}$ are independently H, F or $CH_3$; and $R^2$, $R^3$, $R^6$ and $R^7$ are as described for Formula I or I'. In some embodiments, $R^2$ is H, F, Cl or $C_1$-$C_6$ alkyl. In some embodiments, $R^2$ is $C_1$-$C_6$ alkyl (e.g., methyl). In some embodiments, $R^6$ is H, F, Cl, Br, —$OCH_3$, or $C_1$-$C_6$ alkyl (e.g., methyl and ethyl). In some embodiments, $R^6$ is H. In some embodiments, $R^7$ is hydrogen or fluoro. In some embodiments, $R^7$ is hydrogen. In some embodiments, $R^3$ is —CN, $C_3$-$C_{12}$ cycloalkyl, $C_3$-$C_{12}$ heterocyclyl, $C_1$-$C_{12}$ heteroaryl, $C_6$-$C_{20}$ aryl, —O—($C_1$-$C_{12}$ heteroaryl), —O—($C_1$-$C_6$ alkyldiyl)-($C_6$-$C_{20}$ aryl), —N($R^8$)($C_1$-$C_6$ alkyl), —$NR^8$C(O)$R^9$, —$NR^8$C(O)O$R^9$, —$NR^8$C(O)NH$R^9$, —$NR^8SO_2$—($C_1$-$C_6$ alkyl), —$NR^8SO_2$—($C_1$-$C_6$ alkenyl), —$NR^8SO_2$—($C_3$-$C_{12}$ cycloalkyl), —$NR^8SO_2$—($C_1$-$C_{12}$ heteroaryl), —$NR^8SO_2$—($C_1$-$C_6$ alkyldiyl)-($C_3$-$C_{12}$ cycloalkyl), —$NR^8SO_2$—($C_1$-$C_6$ alkyldiyl)-($C_3$-$C_{12}$ heterocyclyl), —$NR^8SO_2$—($C_1$-$C_6$ alkyldiyl)-($C_1$-$C_{12}$ heteroaryl), —$NR^8SO_2$—($C_1$-$C_6$ alkyldiyl)-($C_6$-$C_{20}$ aryl), —$NR^8SO_2NR^8R^9$, or —$SO_2NR^8R^9$. In some embodiments, $R^3$ is $C_3$-$C_{12}$ heterocyclyl, —N($R^8$)($C_1$-$C_6$ alkyl) or —$NR^8$C(O)$R^9$. In some embodiments, $R^3$ is —$NR^8SO_2$—($C_1$-$C_6$ alkyl), —$NR^8SO_2$—($C_1$-$C_6$ alkenyl), —$NR^8SO_2$—($C_3$-$C_{12}$ cycloalkyl), —$NR^8SO_2$—($C_1$-$C_{12}$ heteroaryl), —$NR^8SO_2$—($C_1$-$C_6$ alkyldiyl)-($C_3$-$C_{12}$ cycloalkyl), —$NR^8SO_2$—($C_1$-$C_6$ alkyldiyl)-($C_3$-$C_{12}$ heterocyclyl), —$NR^8SO_2$—($C_1$-$C_6$ alkyldiyl)-($C_1$-$C_{12}$ heteroaryl), —$NR^8SO_2$—($C_1$-$C_6$ alkyldiyl)-($C_6$-$C_{20}$ aryl) or —$NR^8SO_2NR^8R^9$. In some embodiments, $R^3$ is —$NR^8SO_2$—($C_1$-$C_6$ alkyl). In some of these embodiments, $R^{10a}$ and $R^{10b}$ are H. In some of these embodiments, one of $R^{10a}$ and $R^{10b}$ is F and the other one of $R^{10a}$ and $R^{10b}$ are H. In some of these embodiments, one of $R^{10a}$ and $R^{10b}$ is H and the other one of $R^{10a}$ and $R^{10b}$ is —$CH_3$. In some of these embodiments, one of $R^{10a}$ and $R^{10b}$ is F and the other one of $R^{10a}$ and $R^{10b}$ is —$CH_3$.

In some embodiments of the compound of Formula Ix, $R^2$ is $C_1$-$C_6$ alkyl (e.g., methyl), $R^3$ is $C_3$-$C_{12}$ heterocyclyl, —N($R^8$)($C_1$-$C_6$ alkyl) or —$NR^8$C(O)$R^9$ and $R^7$ is hydrogen. In some embodiments of the compound of Formula Ix, $R^2$ is $C_1$-$C_6$ alkyl (e.g., methyl), $R^3$ is —$NR^8SO_2$—($C_1$-$C_6$ alkyl) and $R^7$ is fluoro.

In some embodiments of the compound of Formula Ix, or a variation thereof, where $R^2$ and $R^6$ are hydrogen, and the compound is of the Formula Iy:

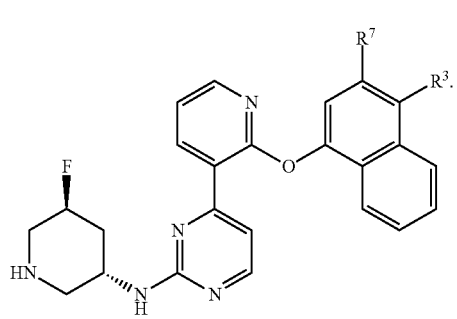

Iy

In some embodiments, $R^7$ is hydrogen or fluoro. In some embodiments, $R^7$ is hydrogen. In some embodiments, $R^7$ is fluoro.

In some embodiments of the compound of Formula Ix, or a variation thereof, where $R^2$ and $R^6$ are hydrogen, and the compound is of the Formula Iz:

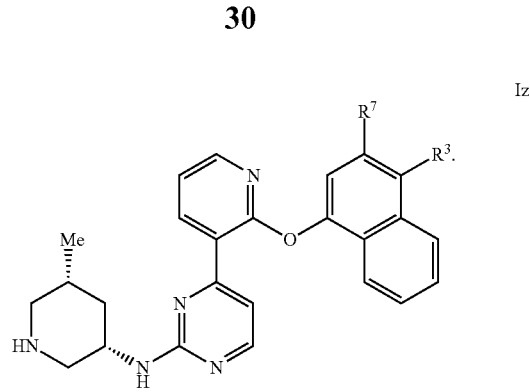

Iz

In some embodiments, $R^7$ is hydrogen or fluoro. In some embodiments, $R^7$ is hydrogen. In some embodiments, $R^7$ is fluoro.

In some embodiments of the compound of Formula Ix, or a variation thereof, where $R^2$ and $R^6$ are hydrogen, and the compound is of the Formula Iaa:

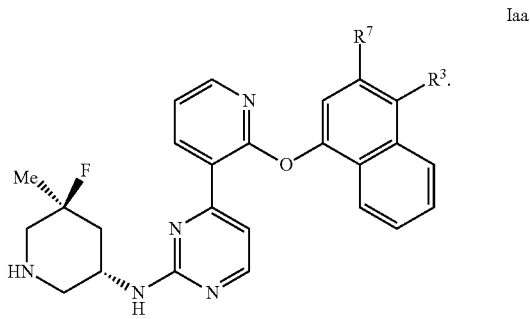

Iaa

In some embodiments, $R^7$ is hydrogen or fluoro. In some embodiments, $R^7$ is hydrogen. In some embodiments, $R^7$ is fluoro.

In some embodiments of the compound of Formula Ix, or a variation thereof, where $R^2$ is hydrogen and $R^7$ is fluoro, and the compound is of the Formula Iab:

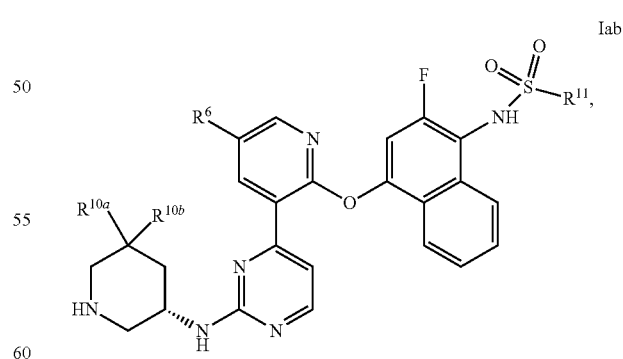

Iab wherein $R^{11}$ is as described for the Formula Ij or a variation thereof.

In some embodiments of the compound of Formula Iab, or a variation thereof, wherein $R^6$ is hydrogen, and the compound is of the Formula Iac:

Iac

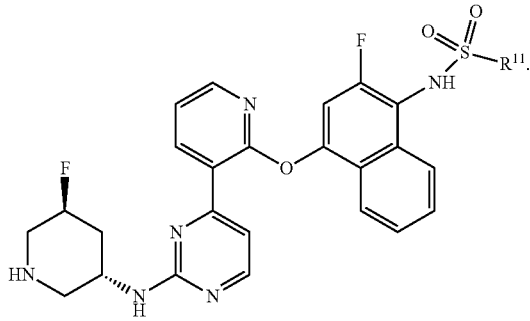

In some embodiments of the compound of Formula Iab, or a variation thereof, wherein $R^6$ is hydrogen, and the compound is of the Formula Iad:

Iad

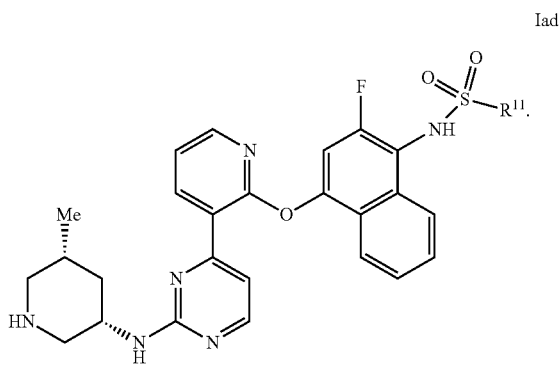

In some embodiments of the compound of Formula Iab, or a variation thereof, wherein $R^6$ is hydrogen, and the compound is of the Formula Iae:

Iae

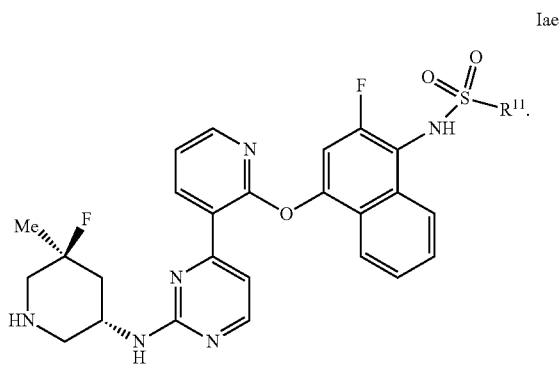

Formula I or I' compounds include wherein $R^1$ is $C_3$-$C_{12}$ cycloalkyl or $C_3$-$C_{12}$ heterocyclyl.

Formula I or I' compounds include wherein $R^1$ is cyclohexyl or piperidinyl, optionally substituted with one or more groups selected from F, —$CH_3$, and —$NH_2$.

Formula I or I' compounds include wherein $R^2$ is —$CH_3$.

Formula I compounds include wherein $R^3$ is selected from —$NR^6R^7$, —$NR^6C(O)R^7$, —$NR^6C(O)R^7$, —$NR^6C(O)OR^7$, —$NR^6C(O)NR^6$, —$NR^6SO_2$—($C_1$-$C_6$ alkyl), —$NR^6SO_2$—($C_1$-$C_6$ alkenyl), —$NR^6SO_2$—($C_1$-$C_{12}$ heteroaryl), —$NR^6SO_2$—($C_1$-$C_6$ alkyldiyl)-($C_3$-$C_{12}$ heterocyclyl), —$NR^6SO_2$—($C_1$-$C_6$ alkyldiyl)-($C_1$-$C_{12}$ heteroaryl), —$NR^6SO_2$—($C_1$-$C_6$ alkyldiyl)-($C_6$-$C_{20}$ aryl), —$NR^6SO_2NR^6$—($C_1$-$C_{12}$ heteroaryl), —$NR^6SO_2NR^6$—($C_1$-$C_6$ alkyl), and —$NR^6SO_2NR^6$—($C_1$-$C_6$ alkyldiyl)-($C_6$-$C_{20}$ aryl).

Formula I compounds include wherein each of the three $R^6$ is H.

Formula I compounds include wherein $R^4$ is selected from —$NR^6R^7$, —$NR^6C(O)R^7$, —$NR^6C(O)R^7$, —$NR^6C(O)OR^7$, —$NR^6C(O)NR^6$, —$NR^6SO_2$—($C_1$-$C_6$ alkyl), —$NR^6SO_2$—($C_1$-$C_6$ alkenyl), —$NR^6SO_2$—($C_1$-$C_{12}$ heteroaryl), —$NR^6SO_2$—($C_1$-$C_6$ alkyldiyl)-($C_3$-$C_{12}$ heterocyclyl), —$NR^6SO_2$—($C_1$-$C_6$ alkyldiyl)-($C_1$-$C_{12}$ heteroaryl), —$NR^6SO_2$—($C_1$-$C_6$ alkyldiyl)-($C_6$-$C_{20}$ aryl), —$NR^6SO_2NR^6$—($C_1$-$C_{12}$ heteroaryl), —$NR^6SO_2NR^6$—($C_1$-$C_6$ alkyl), and —$NR^6SO_2NR^6$—($C_1$-$C_6$ alkyldiyl)-($C_6$-$C_{20}$ aryl).

In any of the embodiments described for the Formulae Ia-Iad, or variations thereof, where applicable, cycloalkyl, heterocyclyl, heteroaryl, aryl, alkyl, alkyldiyl, and alkenyl are optionally and independently substituted as defined for Formula I or I'.

Exemplary embodiments of Formula I or I' compounds include the compounds of Tables 1, 2 and 3.

In some embodiments, provided is a compound of Formula I or I', or pharmaceutically acceptable salt thereof, wherein the compound is selected from the group consisting of one or more of Compound Nos. 101-392 of Table 1, Compound Nos. 393-500 of Table 2, and Compound Nos. 501-545 of Table 3. In some embodiments, the compound is selected from the group consisting of Compound Nos. 101-392 in Table 1. In some embodiments, the compound is selected from the group consisting of Compound Nos. 393-500 of Table 2. In some embodiments, the compound is selected from the group consisting of Compound Nos. 501-545 of Table 3.

Biological Evaluation

The relative efficacies of Formula I or I' compounds as inhibitors of an enzyme activity (or other biological activity) can be established by determining the concentrations at which each compound inhibits the activity to a predefined extent and then comparing the results. Typically, the preferred determination is the concentration that inhibits 50% of the activity in a biochemical assay, i.e., the 50% inhibitory concentration or "$IC_{50}$". Determination of $IC_{50}$ values can be accomplished using conventional techniques known in the art. In general, an $IC_{50}$ can be determined by measuring the activity of a given enzyme in the presence of a range of concentrations of the inhibitor under study. The experimentally obtained values of enzyme activity then are plotted against the inhibitor concentrations used. The concentration of the inhibitor that shows 50% enzyme activity (as compared to the activity in the absence of any inhibitor) is taken as the $IC_{50}$ value. Analogously, other inhibitory concentrations can be defined through appropriate determinations of activity. For example, in some settings it can be desirable to establish a 90% inhibitory concentration, i.e., $IC_{90}$, etc.

Cell proliferation, cytotoxicity, and cell viability of the Formula I or I' compounds can be measured by the CellTiter-Glo® Luminescent Cell Viability Assay (Promega Corp.). The CellTiter-Glo® Luminescent Cell Viability Assay is a homogeneous method of determining the number of viable cells in culture based on quantitation of the ATP present, an indicator of metabolically active cells. The CellTiter-Glo® Assay is designed for use with multiwell formats, making it ideal for automated high-throughput screening (HTS), cell proliferation and cytotoxicity assays. The homogeneous assay procedure involves adding the single reagent (CellTiter-Glo® Reagent) directly to cells cultured in serum-supplemented medium. Cell washing, removal of medium and multiple pipetting steps are not required. The system detects as few as 15 cells/well in a 384-well format in 10 minutes after adding reagent and mixing.

Biological activity of Formula I or I' compounds was measured by an IRE1 biochemical binding assay (Example 901), a biochemical RNase assay (Example 902), a cellular PD assay, XBP1s-LUC reporter (Example 903), and an IRE1α-based inhibition of multiple myeloma (MM) cell proliferation assay.

All of the exemplary Formula I or I' compounds in Tables 1 and 2 were made and characterized by LCMS [M+H]+ (liquid chromatography mass spectroscopy) with detection of parent ion. All of the exemplary Formula I compounds in Tables 1 and 2 were prepared according to the procedures of the Schemes, General Procedures, and Examples. All of the exemplary Formula I or I' compounds in Tables 1 and 2 were tested for binding to IRE1 (inositol requiring enzyme 1 alpha) and biological activity according to the assays and protocols of Example 901-903. Exemplary Formula I or I' compounds in Tables 1 and 2 have the following structures, corresponding IUPAC names (ChemBioDraw, Version 12.0.2, CambridgeSoft Corp., Cambridge Mass.), and biological activity. Where more than one name is associated with a Formula I or I' compound or intermediate in Tables 1 and 2 and the Experimental Procedures, the chemical structure shall define the compound. Assignment of configuration at chiral centers in separated stereoisomers may be tentative, and depicted in Tables 1 and 2 structures for illustrative purposes, before stereochemistry is definitively established, such as from x-ray crystallographic data. In some cases, stereoisomers are separated and tested for biological activity before the stereochemistry of the separated stereoisomers is determined; and stereochemistry in some instances was inferred based on structure-activity relationship (SAR) knowledge from previous compounds. In some cases, the compounds are tested as racemic or diastereomeric mixtures. Where more than one potency value is entered on a row, separated stereoisomers represented by the structure and name on that row were tested. Exemplary compounds of Formula I or I' in Table 3 can be prepared using methods known in the art or according to procedures similar to those described in the Schemes, General Procedures, and Examples 101-500. Biological activities of compounds in Table 3 can be tested in biological assays, for example, those in Examples 901, 902 and 903 described herein.

TABLE 1

| No. | Structure | Name | XBP1s-luc 293 LUC (IC$_{50}$) (μmol) |
|---|---|---|---|
| 101 | 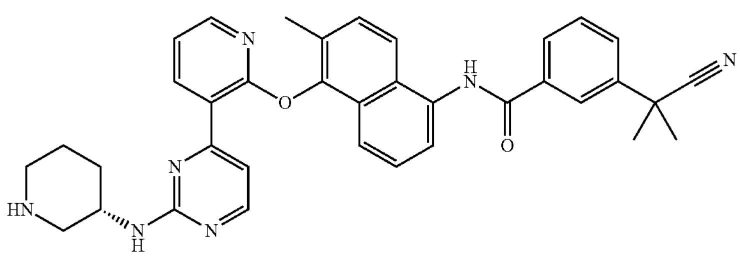 [SMILES: Cc1ccc2c(NC(=O)c3cccc(C(C)(C)C#N)c3)cccc2c1Oc1ncccc1-c1ccnc(N[C@H]2CCCNC2)n1] | (S)-3-(2-Cyanopropan-2-yl)-N-(6-methyl-5-((3-(2-(piperidin-3-ylamino)pyrimidin-4-yl)pyridin-2-yl)oxy)naphthalen-1-yl)benzamide | 0.102 |
| 102 | 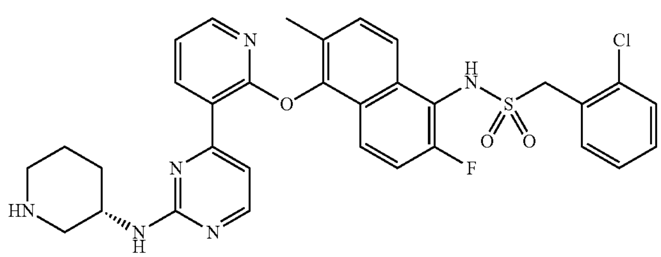 | (S)-1-(2-Chlorophenyl)-N-(2-fluoro-6-methyl-5-((3-(2-(piperidin-3-ylamino)pyrimidin-4-yl)pyridin-2-yl)oxy)naphthalen-1-yl)methanesulfonamide | 0.0046 |
| 103 | 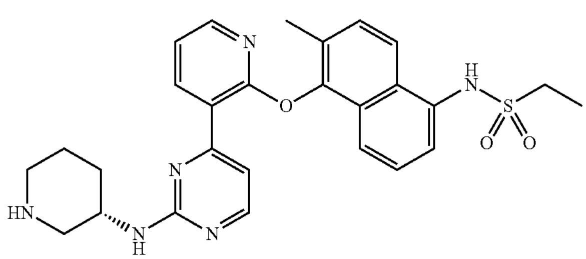 [SMILES: CCS(=O)(=O)Nc1cccc2c(Oc3ncccc3-c3ccnc(N[C@H]4CCCNC4)n3)c(C)ccc12] | (S)-N-(6-Methyl-5-(3-(2-(piperidin-3-ylamino)pyrimidin-4-yl)pyridin-2-yloxy)naphthalen-1-yl)ethanesulfonamide | 0.255 |

TABLE 1-continued

| No. | Structure | Name | XBP1s-luc 293 LUC (IC$_{50}$) (μmol) |
|---|---|---|---|
| 104 | 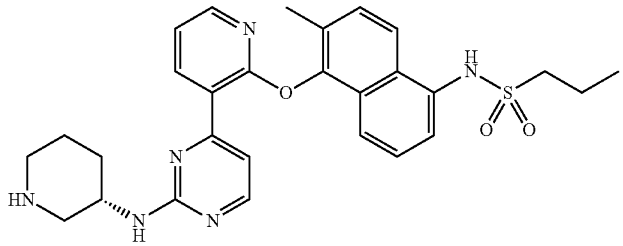 [SMILES: CCCS(=O)(=O)Nc1cccc2c(Oc3ncccc3-c3ccnc(N[C@H]4CCCNC4)n3)c(C)ccc12] | (S)-N-(6-Methyl-5-(3-(2-(piperidin-3-ylamino)pyrimidin-4-yl)pyridin-2-yloxy)naphthalen-1-yl)propane-1-sulfonamide | 0.131 |
| 105 | 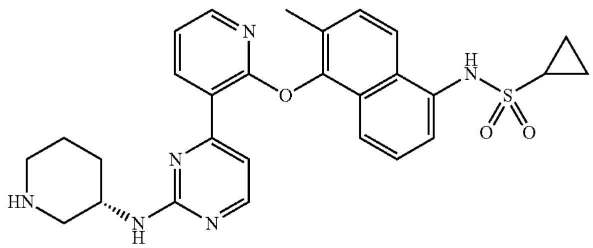 [SMILES: Cc1ccc2c(NS(=O)(=O)C3CC3)cccc2c1Oc1ncccc1-c1ccnc(N[C@H]2CCCNC2)n1] | (S)-N-(6-Methyl-5-((3-(2-(piperidin-3-ylamino)pyrimidin-4-yl)pyridin-2-yl)oxy)naphthalen-1-yl)cyclopropane-sulfonamide | 0.493 |
| 106 | 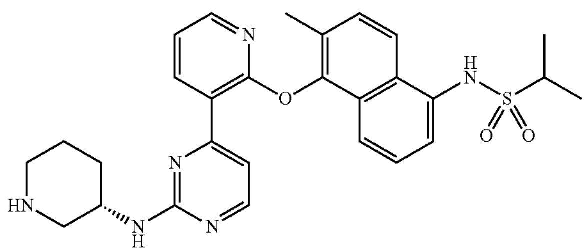 | (S)-N-(6-Methyl-5-((3-(2-(piperidin-3-ylamino)pyrimidin-4-yl)pyridin-2-yl)oxy)naphthalen-1-yl)methylethyl-sulfonamide | 0.349 |
| 107 | 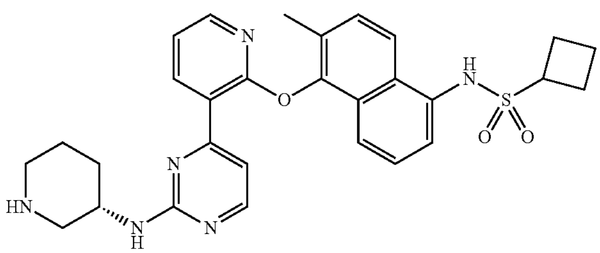 [SMILES: Cc1ccc2c(NS(=O)(=O)C3CCC3)cccc2c1Oc1ncccc1-c1ccnc(N[C@H]2CCCNC2)n1] | (S)-N-(6-Methyl-5-((3-(2-(piperidin-3-ylamino)pyrimidin-4-yl)pyridin-2-yl)oxy)naphthalen-1-yl)cyclobutane-sulfonamide | 0.252 |
| 108 | 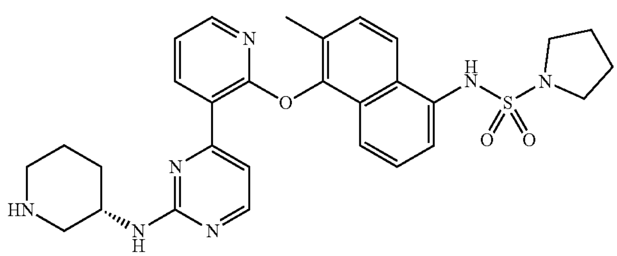 [SMILES: Cc1ccc2c(NS(=O)(=O)N3CCCC3)cccc2c1Oc1ncccc1-c1ccnc(N[C@H]2CCCNC2)n1] | (S)-N-(6-Methyl-5-((3-(2-(piperidin-3-ylamino)pyrimidin-4-yl)pyridin-2-yl)oxy)naphthalen-1-yl)pyrrolidine-1-sulfonamide | 0.298 |
| 109 | 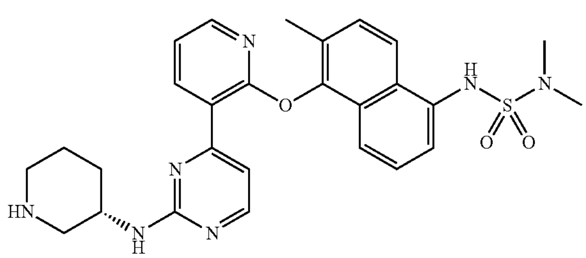 [SMILES: Cc1ccc2c(NS(=O)(=O)N(C)C)cccc2c1Oc1ncccc1-c1ccnc(N[C@H]2CCCNC2)n1] | 4-[2-[[5-(Dimethyl-sulfamoylamino)-2-methyl-1-naphthyl]oxy]-3-pyridyl]-2-[[(3S)-3-piperidyl]amino]pyrimidine | 0.222 |

TABLE 1-continued

| No. | Structure | Name | XBP1s-luc 293 LUC (IC$_{50}$) (μmol) |
|---|---|---|---|
| 110 | 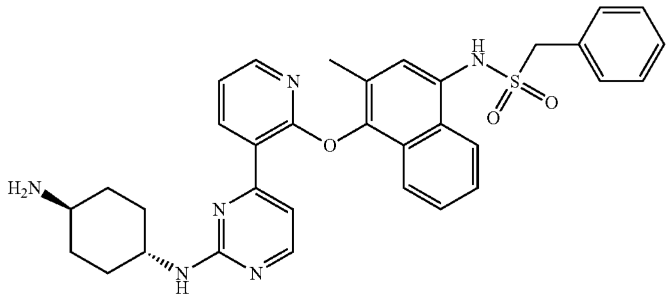 [SMILES: Cc1cc(NS(=O)(=O)Cc2ccccc2)c2ccccc2c1Oc1ncccc1-c1ccnc(N[C@H]2CC[C@H](N)CC2)n1] | N-(4-((3-(2-((((1R,4R)-4-Aminocyclohex-yl)amino)py-rimidin-4-yl)pyridin-2-yl)oxy)-3-methylnaphthalen-1-yl)-1-phenyl-methanesulfon-amide | 0.119 |
| 111 | 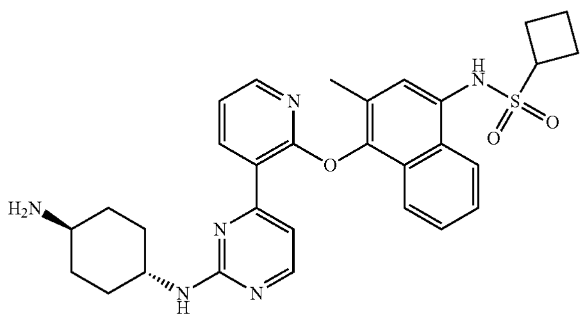 [SMILES: Cc1cc(NS(=O)(=O)C2CCC2)c2ccccc2c1Oc1ncccc1-c1ccnc(N[C@H]2CC[C@H](N)CC2)n1] | N-(4-((3-(2-((((1R,4R)-4-Aminocyclohex-yl)amino)pyrimi-din-4-yl)pyridin-2-yl)oxy)-3-methylnaphthalen-1-yl)-1-yl)cyclo-butanesulfonamide | 0.447 |
| 112 | 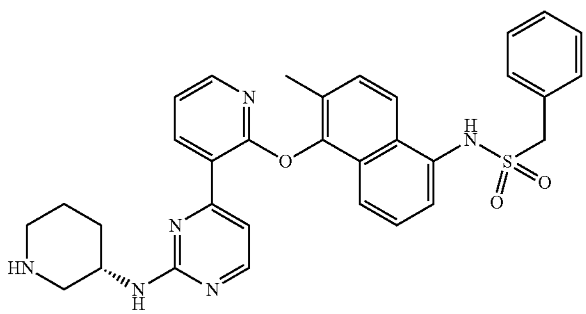 [SMILES: Cc1ccc2c(NS(=O)(=O)Cc3ccccc3)cccc2c1Oc1ncccc1-c1ccnc(N[C@H]2CCCNC2)n1] | N-[6-methyl-5-[[3-[2-[[(3S)-3-Piperidyl]a-mino]pyrimidin-4-yl]-2-pyridyl]oxy]-1-naphthyl]-1-phenyl-methane-sulfonamide | 0.021 |
| 113 | 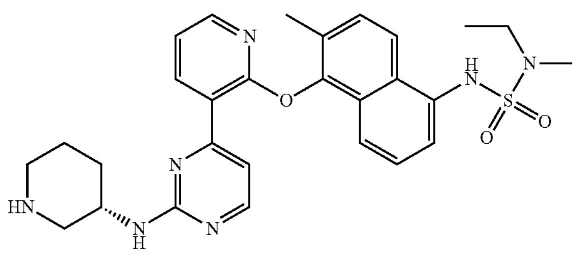 [SMILES: CCN(C)S(=O)(=O)Nc1cccc2c(Oc3ncccc3-c3ccnc(N[C@H]4CCCNC4)n3)c(C)ccc12] | 4-[2-[[5-[[Ethyl(methyl)sul-famoyl]amino]-2-methyl-1-naphthyl]oxy]-3-pyridyl]-2-[[(3S)-3-piperidyl]ami-no]pyrimidine | 0.343 |
| 114 | 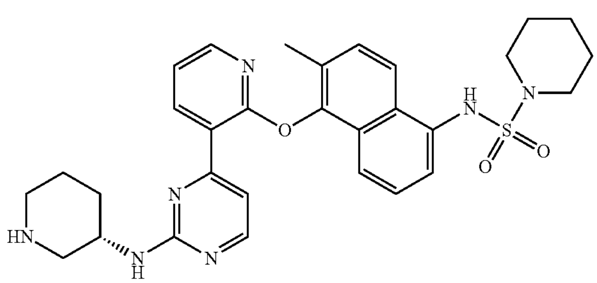 [SMILES: Cc1ccc2c(NS(=O)(=O)N3CCCCC3)cccc2c1Oc1ncccc1-c1ccnc(N[C@H]2CCCNC2)n1] | (S)-N-(6-methyl-5-((3-(2-(Piperidin-3-ylamino)pyrimidin-4-yl)pyridin-2-yl)oxy)naphthalen-1-yl)piperidine-1-sulfonamide | 0.382 |

TABLE 1-continued

| No. | Structure | Name | XBP1s-luc 293 LUC (IC$_{50}$) (μmol) |
|---|---|---|---|
| 115 | 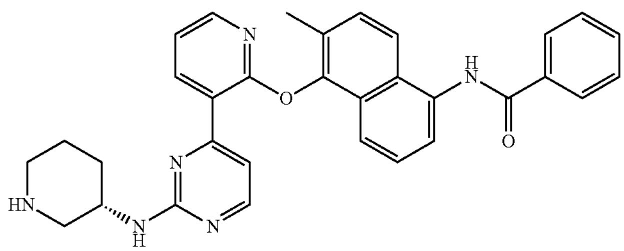 [SMILES: Cc1ccc2c(NC(=O)c3ccccc3)cccc2c1Oc1ncccc1-c1ccnc(N[C@H]2CCCNC2)n1] | N-[6-methyl-5-[[3-[2-[[(3S)-3-Piperidyl]amino]pyrimidin-4-yl]-2-pyridyl]oxy]-1-naphthyl]benzamide | 0.262 |
| 116 | 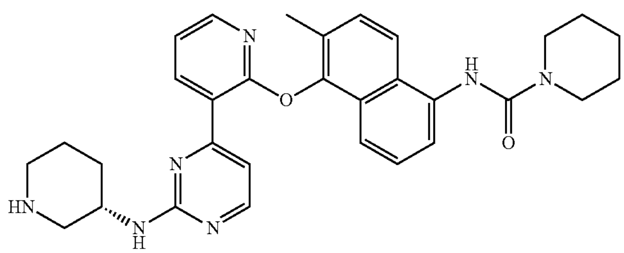 [SMILES: Cc1ccc2c(NC(=O)N3CCCCC3)cccc2c1Oc1ncccc1-c1ccnc(N[C@H]2CCCNC2)n1] | N-[6-methyl-5-[[3-[2-[[(3S)-3-Piperidyl]amino]pyrimidin-4-yl]-2-pyridyl]oxy]-1-naphthyl]piperidine-1-carboxamide | 0.43 |
| 117 | 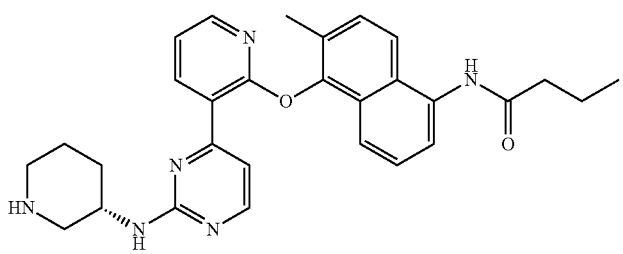 [SMILES: CCCC(=O)Nc1cccc2c(Oc3ncccc3-c3ccnc(N[C@H]4CCCNC4)n3)c(C)ccc12] | N-[6-methyl-5-[[3-[2-[[(3S)-3-Piperidyl]amino]pyrimidin-4-yl]-2-pyridyl]oxy]-1-naphthyl]butanamide | 0.145 |
| 118 | 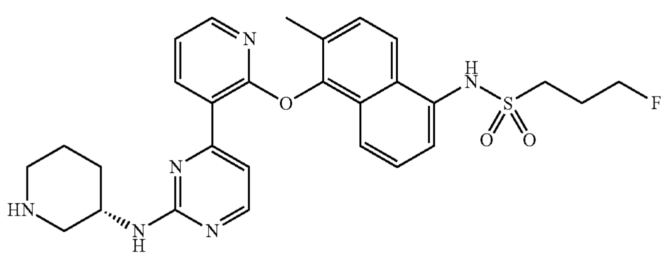 [SMILES: Cc1ccc2c(NS(=O)(=O)CCCF)cccc2c1Oc1ncccc1-c1ccnc(N[C@H]2CCCNC2)n1] | 3-Fluoro-N-[6-methyl-5-[[3-[2-[[(3S)-3-piperidyl]amino]pyrimidin-4-yl]-2-pyridyl]oxy]-1-naphthyl]propane-1-sulfonamide | 0.323 |
| 119 | 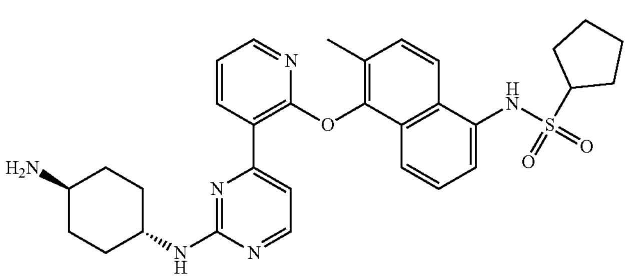 [SMILES: Cc1ccc2c(NS(=O)(=O)C3CCCC3)cccc2c1Oc1ncccc1-c1ccnc(N[C@H]2CC[C@H](N)CC2)n1] | N-(4-((3-(2-(((trans)-4-Aminocyclohexyl)amino)pyrimidin-4-yl)pyridin-2-yl)oxy)-3-methylnaphthalen-1-yl)cyclopentanesulfonamide | 0.312 |
| 120 | 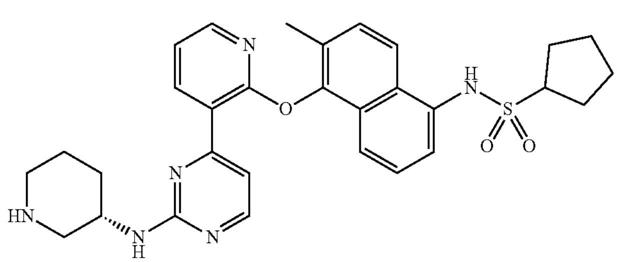 [SMILES: Cc1ccc2c(NS(=O)(=O)C3CCCC3)cccc2c1Oc1ncccc1-c1ccnc(N[C@H]2CCCNC2)n1] | (S)-N-(6-Methyl-5-((3-(2-(piperidin-3-ylamino)pyrimidin-4-yl)pyridin-2-yl)oxy)naphthalen-1-yl)cyclopentanesulfonamide | 0.18 |

TABLE 1-continued

| No. | Structure | Name | XBP1s-luc 293 LUC (IC$_{50}$) (μmol) |
|---|---|---|---|
| 121 | 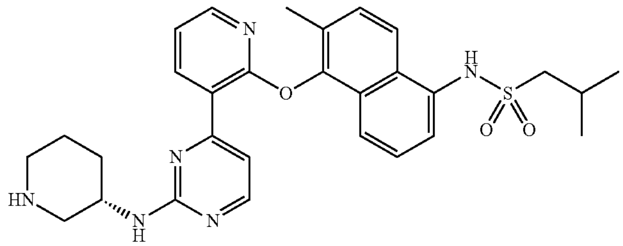 [SMILES: Cc1ccc2c(NS(=O)(=O)CC(C)C)cccc2c1Oc1ncccc1-c1ccnc(N[C@H]2CCCNC2)n1] | (S)-2-Methyl-N-(6-methyl-5-((3-(2-(piperidin-3-ylamino)pyrimidin-4-yl)pyridin-2-yl)oxy)naphthalen-1-yl)propane-1-sulfonamide | 0.103 |
| 122 | 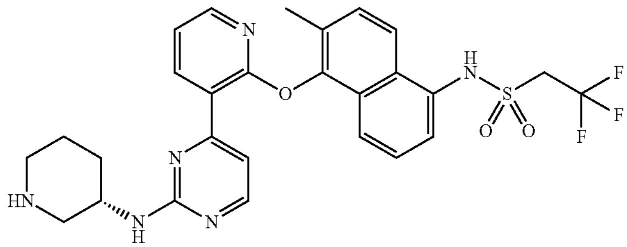 [SMILES: Cc1ccc2c(NS(=O)(=O)CC(F)(F)F)cccc2c1Oc1ncccc1-c1ccnc(N[C@H]2CCCNC2)n1] | (S)-2,2,2-Trifluoro-N-(6-methyl-5-((3-(2-(piperidin-3-ylamino)pyrimidin-4-yl)pyridin-2-yl)oxy)naphthalen-1-yl)ethane-1-sulfonamide | 0.105 |
| 123 | 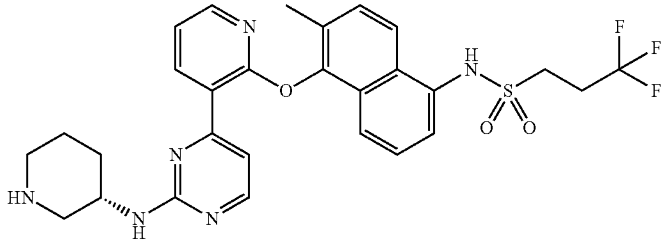 [SMILES: Cc1ccc2c(NS(=O)(=O)CCC(F)(F)F)cccc2c1Oc1ncccc1-c1ccnc(N[C@H]2CCCNC2)n1] | (S)-3,3,3-Trifluoro-N-(6-methyl-5-((3-(2-(piperidin-3-ylamino)pyrimidin-4-yl)pyridin-2-yl)oxy)naphthalen-1-yl)propane-1-sulfonamide | 0.084 |
| 124 | 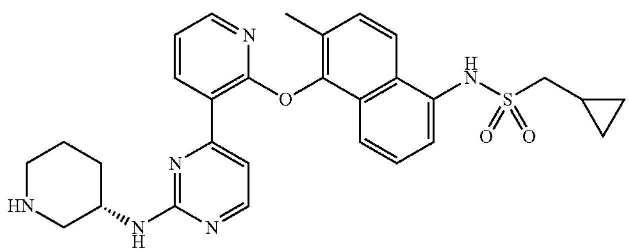 [SMILES: Cc1ccc2c(NS(=O)(=O)CC3CC3)cccc2c1Oc1ncccc1-c1ccnc(N[C@H]2CCCNC2)n1] | (S)-1-Cyclopropyl-N-(6-methyl-5-((3-(2-(piperidin-3-ylamino)pyrimidin-4-yl)pyridin-2-yl)oxy)naphthalen-1-yl)methanesulfonamide | 0.105 |
| 125 | 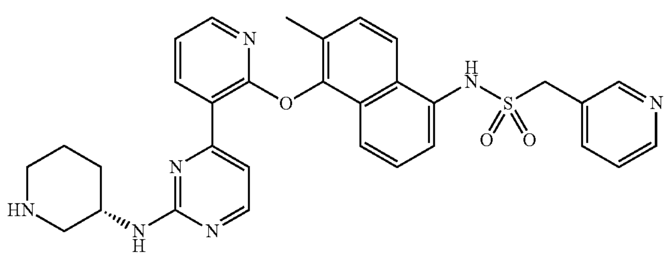 [SMILES: Cc1ccc2c(NS(=O)(=O)Cc3cccnc3)cccc2c1Oc1ncccc1-c1ccnc(N[C@H]2CCCNC2)n1] | (S)-N-(6-Methyl-5-((3-(2-(piperidin-3-ylamino)pyrimidin-4-yl)pyridin-2-yl)oxy)naphthalen-1-yl)-1-(pyridin-3-yl)methanesulfonamide | 0.318 |
| 126 | 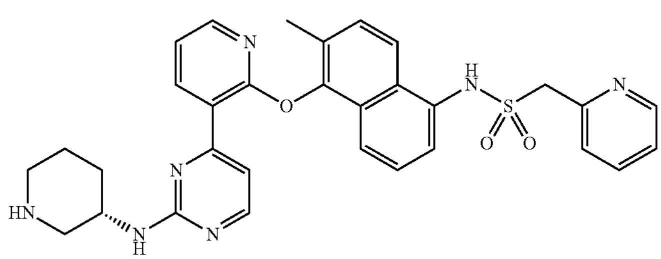 [SMILES: Cc1ccc2c(NS(=O)(=O)Cc3ccccn3)cccc2c1Oc1ncccc1-c1ccnc(N[C@H]2CCCNC2)n1] | (S)-N-(6-Methyl-5-((3-(2-(piperidin-3-ylamino)pyrimidin-4-yl)pyridin-2-yl)oxy)naphthalen-1-yl)-1-(pyridin-2-yl)methanesulfonamide | 0.054 |

TABLE 1-continued

| No. | Structure | Name | XBP1s-luc 293 LUC (IC$_{50}$) (μmol) |
|---|---|---|---|
| 127 | 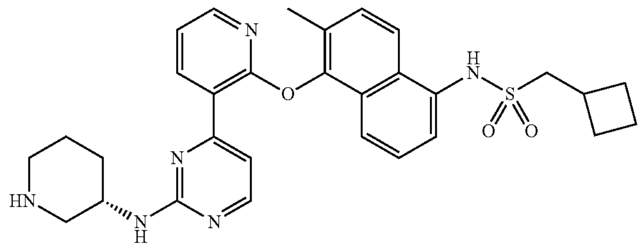 [SMILES: Cc1ccc2c(NS(=O)(=O)CC3CCC3)cccc2c1Oc1ncccc1-c1ccnc(N[C@H]2CCCNC2)n1] | 1-Cyclobutyl-N-[6-methyl-5-[[3-[2-[[(3S)-3-piperidyl]amino]pyrimidin-4-yl]-2-pyridyl]oxy]-1-naphthyl]methanesulfonamide | 0.233 |
| 128 | 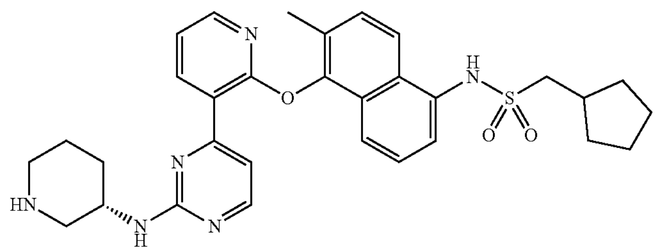 [SMILES: Cc1ccc2c(NS(=O)(=O)CC3CCCC3)cccc2c1Oc1ncccc1-c1ccnc(N[C@H]2CCCNC2)n1] | 1-Cyclopentyl-N-[6-methyl-5-[[3-[2-[[(3S)-3-piperidyl]amino]pyrimidin-4-yl]-2-pyridyl]oxy]-1-naphthyl]methanesulfonamide | 0.317 |
| 129 | 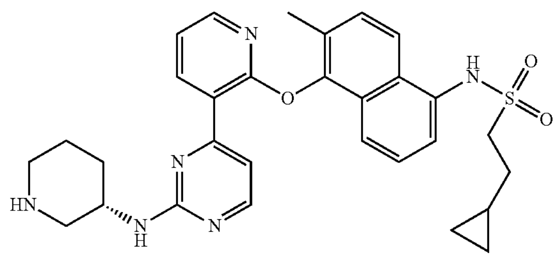 [SMILES: Cc1ccc2c(NS(=O)(=O)CCC3CC3)cccc2c1Oc1ncccc1-c1ccnc(N[C@H]2CCCNC2)n1] | 2-Cyclopropyl-N-[6-methyl-5-[[3-[2-[[(3S)-3-piperidyl]amino]pyrimidin-4-yl]-2-pyridyl]oxy]-1-naphthyl]ethanesulfonamide | 0.301 |
| 130 | 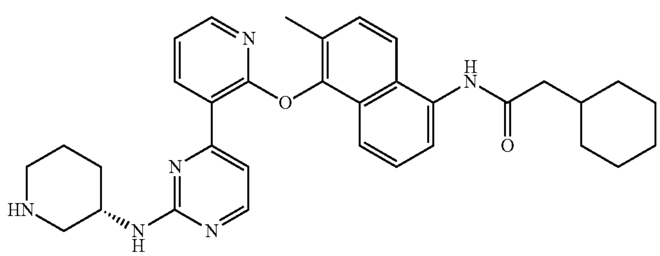 [SMILES: Cc1ccc2c(NC(=O)CC3CCCCC3)cccc2c1Oc1ncccc1-c1ccnc(N[C@H]2CCCNC2)n1] | 2-Cyclohexyl-N-[6-methyl-5-[[3-[2-[[(3S)-3-piperidyl]amino]pyrimidin-4-yl]-2-pyridyl]oxy]-1-naphthyl]acetamide | 0.228 |
| 131 | 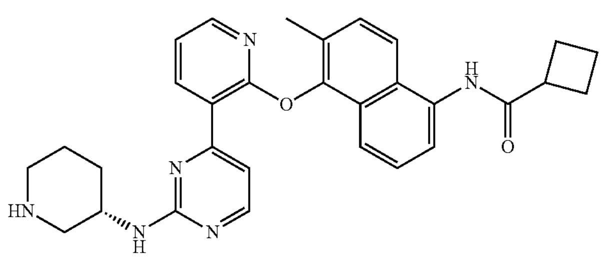 [SMILES: Cc1ccc2c(NC(=O)C3CCC3)cccc2c1Oc1ncccc1-c1ccnc(N[C@H]2CCCNC2)n1] | (S)-N-(6-Methyl-5-((3-(2-(piperidin-3-ylamino)pyrimidin-4-yl)pyridin-2-yl)oxy)naphthalen-1-yl)cyclobutanecarboxamide | 0.153 |
| 132 | 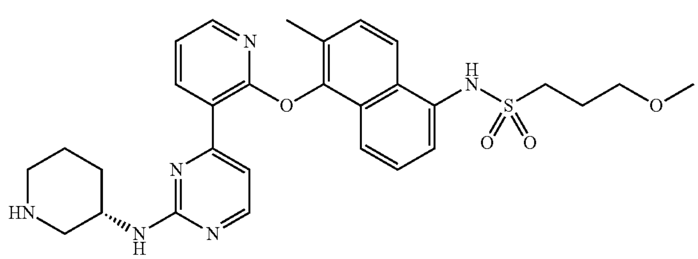 [SMILES: COCCCS(=O)(=O)Nc1cccc2c(Oc3ncccc3-c3ccnc(N[C@H]4CCCNC4)n3)c(C)ccc12] | (S)-3-Methoxy-N-(6-methyl-5-((3-(2-(piperidin-3-ylamino)pyrimidin-4-yl)pyridin-2-yl)oxy)naphthalen-1-yl)propane-1-sulfonamide | 0.365 |

TABLE 1-continued

| No. | Structure | Name | XBP1s-luc 293 LUC (IC$_{50}$) (μmol) |
|---|---|---|---|
| 133 | 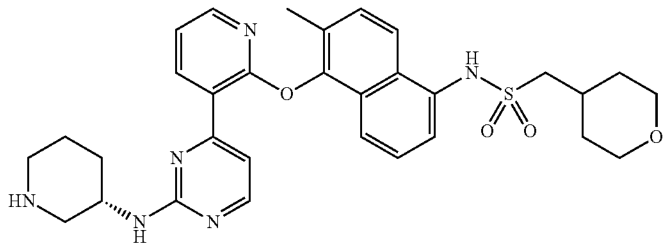 [SMILES: Cc1ccc2c(NS(=O)(=O)CC3CCOCC3)cccc2c1Oc1ncccc1-c1ccnc(N[C@H]2CCCNC2)n1] | (S)-N-(6-Methyl-5-((3-(2-(piperidin-3-ylamino)pyrimidin-4-yl)pyridin-2-yl)oxy)naphthalen-1-yl)-1-(tetrahydro-2H-pyran-4-yl)methanesulfonamide | 0.158 |
| 134 | 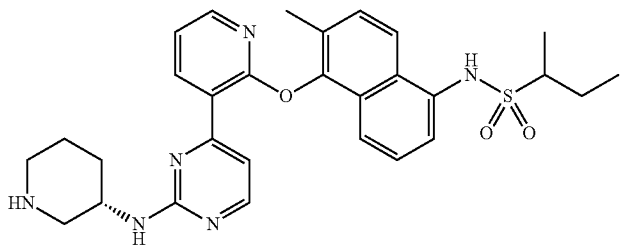 [SMILES: CCC(C)S(=O)(=O)Nc1cccc2c(Oc3ncccc3-c3ccnc(N[C@H]4CCCNC4)n3)c(C)ccc12] | N-(6-Methyl-5-((3-(2-((S)-piperidin-3-ylamino)pyrimidin-4-yl)pyridin-2-yl)oxy)naphthalen-1-yl)butane-2-sulfonamide | 0.26 |
| 135 | 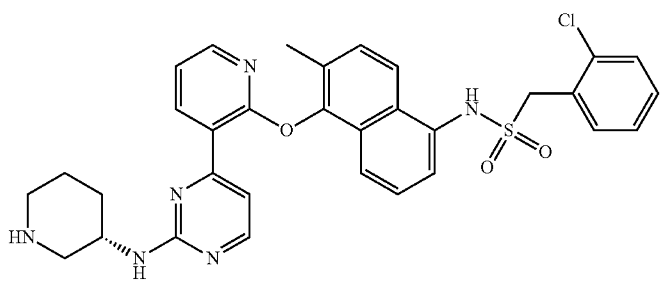 [SMILES: Cc1ccc2c(NS(=O)(=O)Cc3ccccc3Cl)cccc2c1Oc1ncccc1-c1ccnc(N[C@H]2CCCNC2)n1] | (S)-1-(2-Chlorophenyl)-N-(6-methyl-5-((3-(2-(piperidin-3-ylamino)pyrimidin-4-yl)pyridin-2-yl)oxy)naphthalen-1-yl)methanesulfonamide | 0.01 |
| 136 | 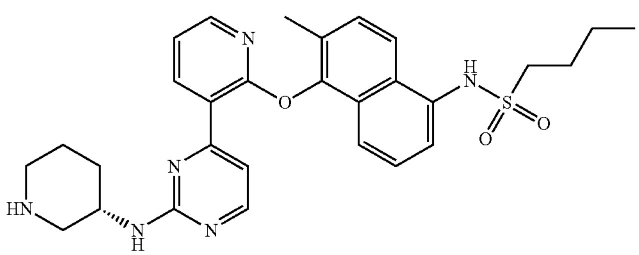 [SMILES: CCCCS(=O)(=O)Nc1cccc2c(Oc3ncccc3-c3ccnc(N[C@H]4CCCNC4)n3)c(C)ccc12] | (S)-N-(6-Methyl-5-((3-(2-(piperidin-3-ylamino)pyrimidin-4-yl)pyridin-2-yl)oxy)naphthalene-1-yl)butane-1-sulfonamide | 0.297 |
| 137 | 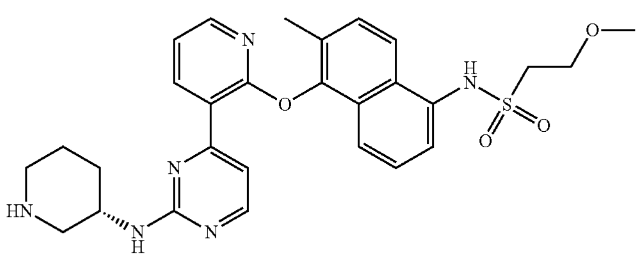 | (S)-2-Methoxy-N-(6-methyl-5-((3-(2-(piperidin-3-ylamino)pyrimidin-4-yl)pyridin-2-yl)oxy)naphthalen-1-yl)ethanesulfonamide | 0.477 |
| 138 | 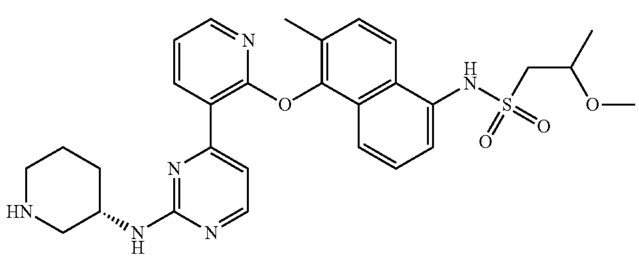 [SMILES: COC(C)CS(=O)(=O)Nc1cccc2c(Oc3ncccc3-c3ccnc(N[C@H]4CCCNC4)n3)c(C)ccc12] | 2-Methoxy-N-(6-methyl-5-((3-(2-((S)-piperidin-3-ylamino)pyrimidin-4-yl)pyridin-2-yl)oxy)naphthalen-1-yl)propane-1-sulfonamide | 0.388 |

TABLE 1-continued

| No. | Structure | Name | XBP1s-luc 293 LUC (IC$_{50}$) (μmol) |
|---|---|---|---|
| 139 | 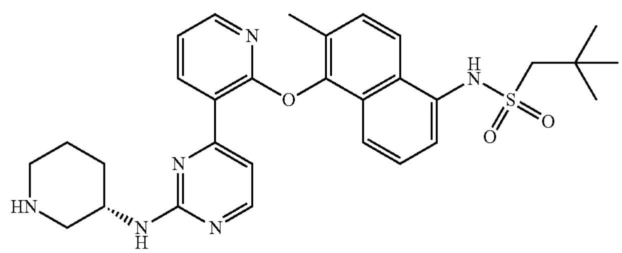 [SMILES: Cc1ccc2c(NS(=O)(=O)CC(C)(C)C)cccc2c1Oc1ncccc1-c1ccnc(N[C@H]2CCCNC2)n1] | ((S)-2,2-Dimethyl-N-(6-methyl-5-((3-(2-(piperidin-3-ylamino)pyrimidin-4-yl)pyridin-2-yl)oxy)naphthalen-1-yl)propane-1-sulfonamide | 0.241 |
| 140 | 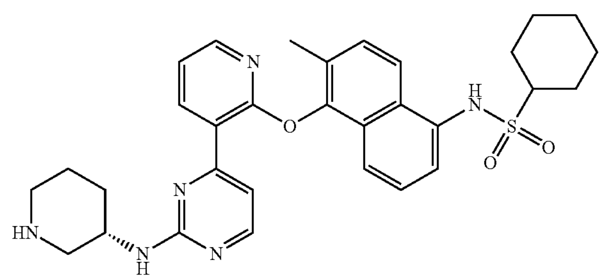 [SMILES: Cc1ccc2c(NS(=O)(=O)C3CCCCC3)cccc2c1Oc1ncccc1-c1ccnc(N[C@H]2CCCNC2)n1] | (S)-N-(6-Methyl-5-((3-(2-(piperidin-3-ylamino)pyrimidin-4-yl)pyridin-2-yl)oxy)naphthalen-1-yl)cyclohexane-sulfonamide | 0.177 |
| 141 | 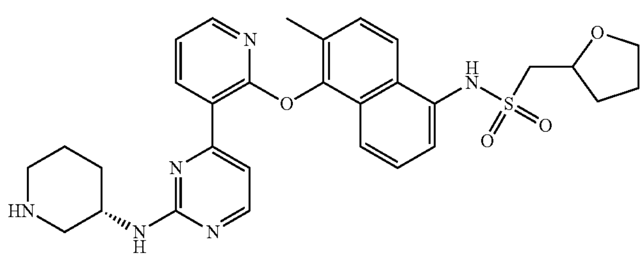 [SMILES: Cc1ccc2c(NS(=O)(=O)CC3CCCO3)cccc2c1Oc1ncccc1-c1ccnc(N[C@H]2CCCNC2)n1] | N-(6-Methyl-5-((3-(2-((S)-piperidin-3-ylamino)pyrimidin-4-yl)pyridin-2-yl)oxy)naphthalen-1-yl)-1-(tetrahydrofuran-2-yl)methanesulfon-amide | 0.457 |
| 142 | 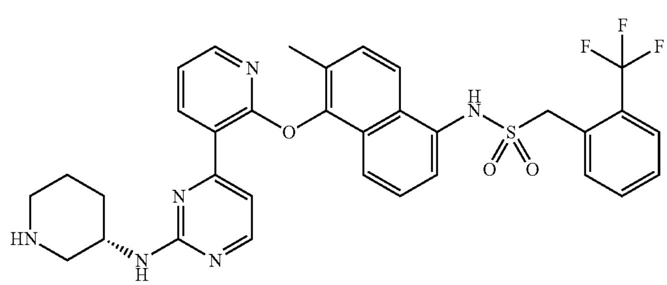 [SMILES: Cc1ccc2c(NS(=O)(=O)Cc3ccccc3C(F)(F)F)cccc2c1Oc1ncccc1-c1ccnc(N[C@H]2CCCNC2)n1] | (S)-N-(6-Methyl-5-((3-(2-(piperidin-3-ylamino)pyrimidin-4-yl)pyridin-2-yl)oxy)naphthalen-1-yl)-1-(2-(trifluoromethyl)phenyl)methanesulfon-amide | 0.008 |
| 143 | 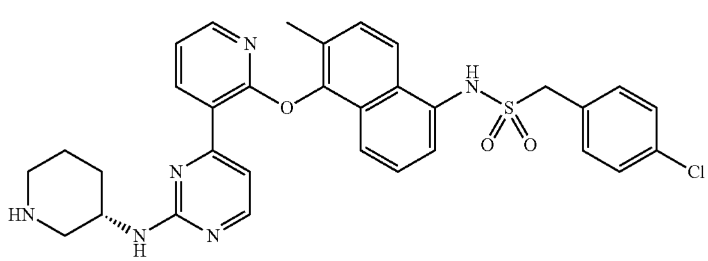 [SMILES: Cc1ccc2c(NS(=O)(=O)Cc3ccc(Cl)cc3)cccc2c1Oc1ncccc1-c1ccnc(N[C@H]2CCCNC2)n1] | (S)-1-(4-Chlorophenyl)-N-(6-methyl-5-((3-(2-(piperidin-3-ylamino)pyrimidin-4-yl)pyridin-2-yl)oxy)naphthalen-1-yl)methanesul-fonamide | 0.017 |

TABLE 1-continued

| No. | Structure | Name | XBP1s-luc 293 LUC (IC₅₀) (μmol) |
|---|---|---|---|
| 144 | 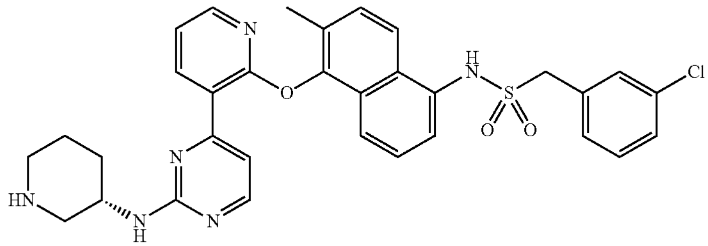 [SMILES: Cc1ccc2c(NS(=O)(=O)Cc3cccc(Cl)c3)cccc2c1Oc1ncccc1-c1ccnc(N[C@H]2CCCNC2)n1] | (S)-1-(3-Chlorophenyl)-N-(6-methyl-5-((3-(2-(piperidin-3-ylamino)pyrimidin-4-yl)pyridin-2-yl)oxy)naphthalen-1-yl)methanesulfonamide | 0.025 |
| 145 | 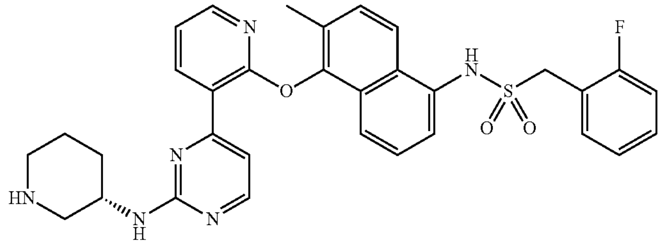 [SMILES: Cc1ccc2c(NS(=O)(=O)Cc3ccccc3F)cccc2c1Oc1ncccc1-c1ccnc(N[C@H]2CCCNC2)n1] | (S)-1-(2-Fluorophenyl)-N-(6-methyl-5-((3-(2-(piperidin-3-ylamino)pyrimidin-4-yl)pyridin-2-yl)oxy)naphthalen-1-yl)methanesulfonamide | 0.015 |
| 146 | 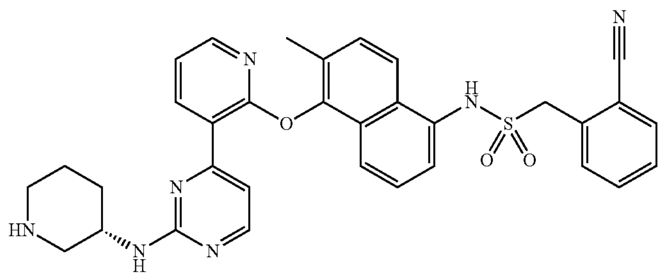 [SMILES: Cc1ccc2c(NS(=O)(=O)Cc3ccccc3C#N)cccc2c1Oc1ncccc1-c1ccnc(N[C@H]2CCCNC2)n1] | (S)-1-(2-Cyanophenyl)-N-(6-methyl-5-((3-(2-(piperidin-3-ylamino)pyrimidin-4-yl)pyridin-2-yl)oxy)naphthalen-1-yl)methanesulfonamide | 0.018 |
| 147 | 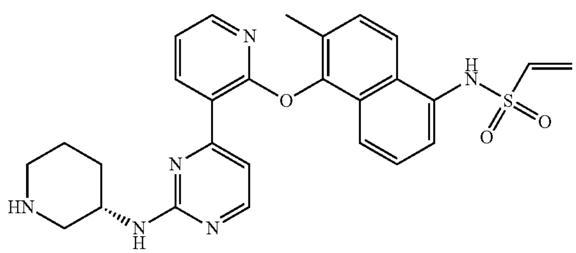 [SMILES: C=CS(=O)(=O)Nc1cccc2c(Oc3ncccc3-c3ccnc(N[C@H]4CCCNC4)n3)c(C)ccc12] | (S)-N-(6-Methyl-5-((3-(2-(piperidin-3-ylamino)pyrimidin-4-yl)pyridin-2-yl)oxy)naphthalen-1-yl)ethenesulfonamide | 0.139 |
| 148 | 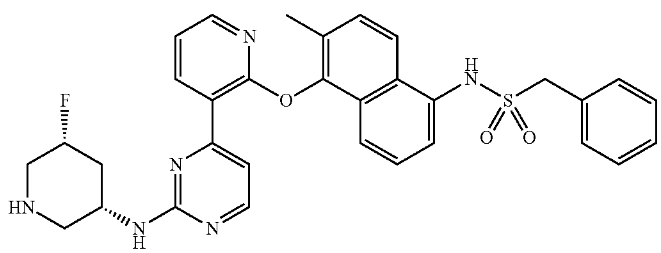 | N-(5-((3-(2-(((3S,5R)-5-Fluoropiperidin-3-yl)amino)pyrimidin-4-yl)pyridin-2-yl)oxy)-6-methylnaphthalen-1-yl)-1-phenylmethanesulfonamide | 0.211 |
| 149 | 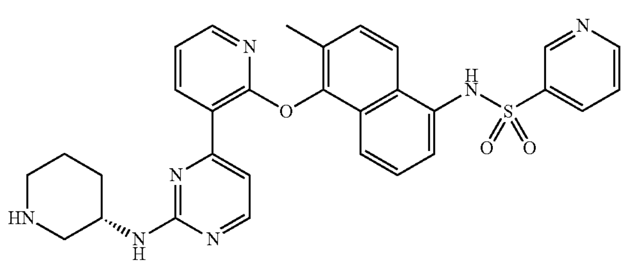 [SMILES: Cc1ccc2c(NS(=O)(=O)c3cccnc3)cccc2c1Oc1ncccc1-c1ccnc(N[C@H]2CCCNC2)n1] | (S)-N-(6-Methyl-5-((3-(2-(piperidin-3-ylamino)pyrimidin-4-yl)pyridin-2-yl)oxy)naphthalen-1-yl)pyridine-3-sulfonamide | 0.494 |

TABLE 1-continued

| No. | Structure | Name | XBP1s-luc 293 LUC (IC$_{50}$) (μmol) |
|---|---|---|---|
| 150 | 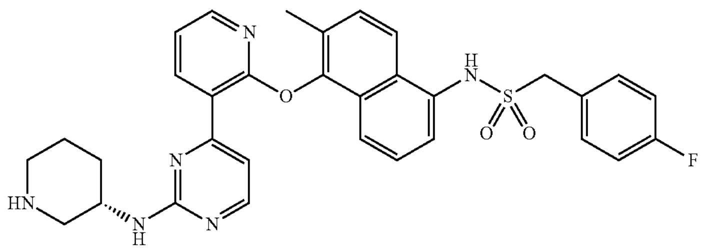 [SMILES: Cc1ccc2c(NS(=O)(=O)Cc3ccc(F)cc3)cccc2c1Oc1ncccc1-c1ccnc(N[C@H]2CCCNC2)n1] | (S)-1-(4-Fluorophenyl)-N-(6-methyl-5-((3-(2-(piperidin-3-ylamino)pyrimidin-4-yl)pyridin-2-yl)oxy)naphthalen-1-yl)methanesulfonamide | 0.025 |
| 151 | 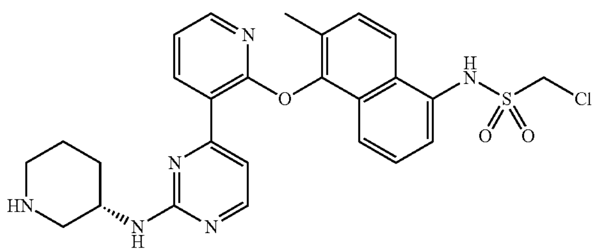 | (S)-1-Chloro-N-(6-methyl-5-((3-(2-(piperidin-3-ylamino)pyrimidin-4-yl)pyridin-2-yl)oxy)naphthalen-1-yl)methanesulfonamid | 0.14 |
| 152 | 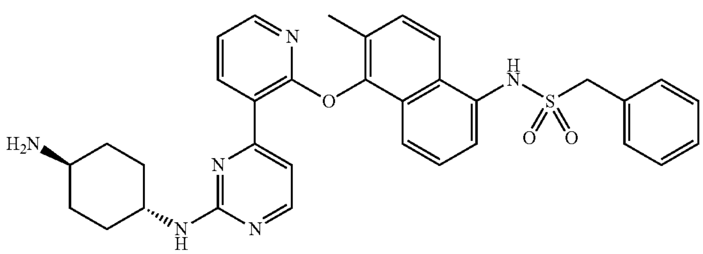 [SMILES: Cc1ccc2c(NS(=O)(=O)Cc3ccccc3)cccc2c1Oc1ncccc1-c1ccnc(N[C@H]2CC[C@H](N)CC2)n1] | N-(5-((3-(2-(((trans)-4-Aminocyclohex-yl)amino)pyrimidin-4-yl)pyridin-2-yl)oxy)-6-methylnaphthalen-1-yl)-1-phenylmethanesulfonamide | 0.241 |
| 153 | 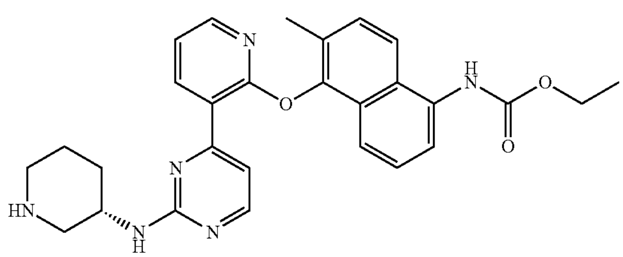 [SMILES: CCOC(=O)Nc1cccc2c(Oc3ncccc3-c3ccnc(N[C@H]4CCCNC4)n3)c(C)ccc12] | Ethyl N-[6-methyl-5-[[3-[2-[[(3S)-3-piperidyl]amino]pyrimidin-4-yl]-2-pyridyl]oxy]-1-naphthyl]carbamate | 0.143 |
| 154 | 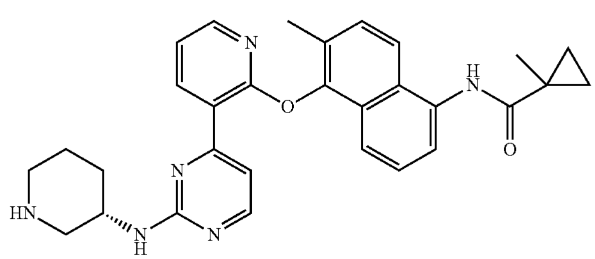 [SMILES: Cc1ccc2c(NC(=O)C3(C)CC3)cccc2c1Oc1ncccc1-c1ccnc(N[C@H]2CCCNC2)n1] | 1-Methyl-N-[6-methyl-5-[[3-[2-[[(3S)-3-piperidyl]amino]pyrimidin-4-yl]-2-pyridyl]oxy]-1-naphthyl]cyclopropanecarboxamide | 0.239 |
| 155 | 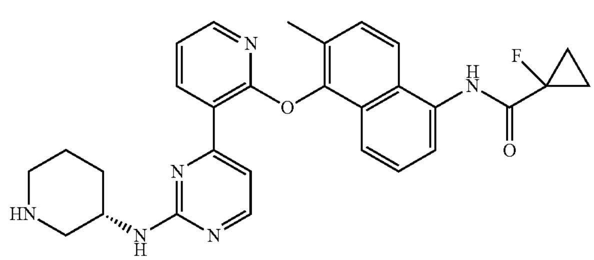 [SMILES: Cc1ccc2c(NC(=O)C3(F)CC3)cccc2c1Oc1ncccc1-c1ccnc(N[C@H]2CCCNC2)n1] | 1-Fluoro-N-[6-methyl-5-[[3-[2-[[(3S)-3-piperidyl]amino]pyrimidin-4-yl]-2-pyridyl]oxy]-1-naphthyl]cyclopropanecarboxamide | 0.38 |

TABLE 1-continued

| No. | Structure | Name | XBP1s-luc 293 LUC (IC$_{50}$) (μmol) |
|---|---|---|---|
| 156 | 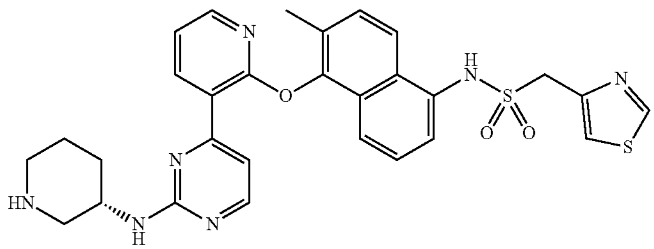 [SMILES: Cc1ccc2c(NS(=O)(=O)Cc3cscn3)cccc2c1Oc1ncccc1-c1ccnc(N[C@H]2CCCNC2)n1] | (S)-N-(6-Methyl-5-((3-(2-(piperidin-3-ylamino)pyrimidin-4-yl)pyridin-2-yl)oxy)naphthalen-1-yl)-1-(thiazol-4-yl)methanesulfonamide | 0.157 |
| 157 | 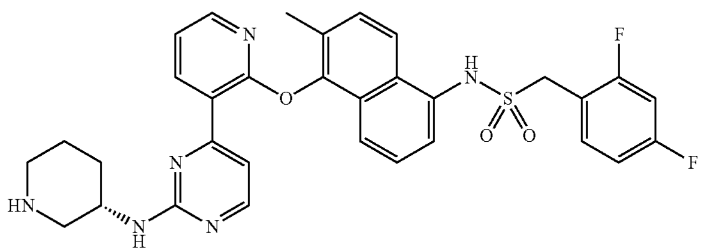 [SMILES: Cc1ccc2c(NS(=O)(=O)Cc3ccc(F)cc3F)cccc2c1Oc1ncccc1-c1ccnc(N[C@H]2CCCNC2)n1] | 1-(2,4-Difluorophenyl)-N-[6-methyl-5-[[3-[2-[[(3S)-3-piperidyl]amino]pyrimidin-4-yl]-2-pyridyl]oxy]-1-naphthyl]methanesulfonamide | 0.008 |
| 158 | 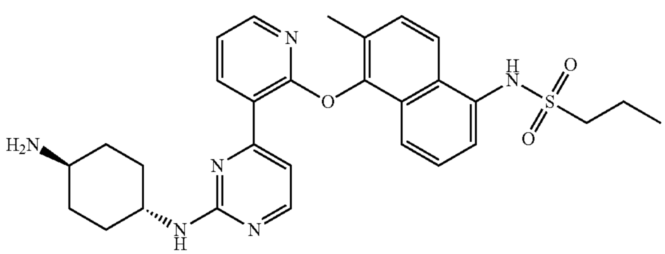 [SMILES: CCCS(=O)(=O)Nc1cccc2c(Oc3ncccc3-c3ccnc(N[C@H]4CC[C@H](N)CC4)n3)c(C)ccc12] | N-(5-((3-(2-(((trans)-4-Aminocyclohexyl)amino)pyrimidin-4-yl)pyridin-2-yl)oxy)-6-methylnaphthalen-1-yl)propane-1-sulfonamide | 0.471 |
| 159 | 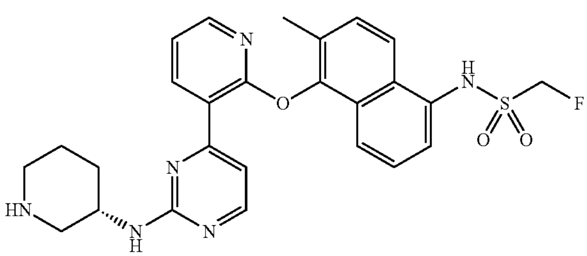 [SMILES: Cc1ccc2c(NS(=O)(=O)CF)cccc2c1Oc1ncccc1-c1ccnc(N[C@H]2CCCNC2)n1] | (S)-1-Fluoro-N-(6-methyl-5-(3-(2-(piperidin-3-ylamino)pyrimidin-4-yl)pyridin-2-yloxy)naphthalen-1-yl)methanesulfonamide | 0.174 |
| 160 | 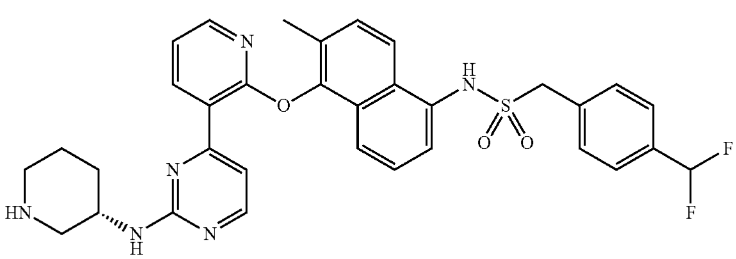 [SMILES: Cc1ccc2c(NS(=O)(=O)Cc3ccc(C(F)F)cc3)cccc2c1Oc1ncccc1-c1ccnc(N[C@H]2CCCNC2)n1] | 1-[4-(Difluoromethyl)phenyl]-N-[6-methyl-5-[[3-[2-[[(3S)-3-piperidyl]amino]pyrimidin-4-yl]-2-pyridyl]oxy]-1-naphthyl]methanesulfonamide | 0.013 |
| 161 | 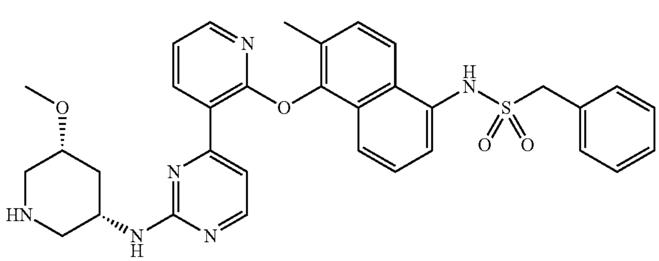 [SMILES: CO[C@H]1CNC[C@@H](Nc2nccc(-c3cccnc3Oc3c(C)ccc4c(NS(=O)(=O)Cc5ccccc5)cccc34)n2)C1] | N-(5-((3-(2-(((3S,5R)-5-Methoxypiperidin-3-yl)amino)pyrimidin-4-yl)pyridin-2-yl)oxy)-6-methylnaphthalen-1-yl)-1-phenylmethanesulfonamide | 0.046 |

TABLE 1-continued

| No. | Structure | Name | XBP1s-luc 293 LUC (IC$_{50}$) (μmol) |
|---|---|---|---|
| 162 | 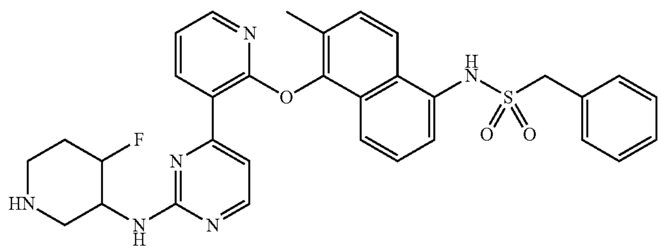 [SMILES: Cc1ccc2c(NS(=O)(=O)Cc3ccccc3)cccc2c1Oc1ncccc1-c1ccnc(NC2CNCCC2F)n1] | N-[5-[[3-[2-[(4-Fluoro-3-piperidyl)amino]pyrimidin-4-yl]-2-pyridyl]oxy]-6-methyl-1-naphthyl]-1-phenyl-methane-sulfonamide | 0.067 |
| 163 | 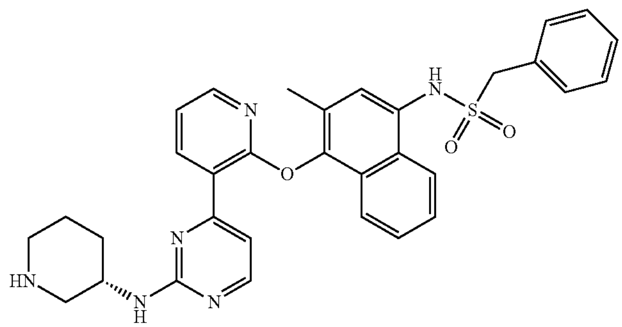 [SMILES: Cc1cc(NS(=O)(=O)Cc2ccccc2)c2ccccc2c1Oc1ncccc1-c1ccnc(N[C@H]2CCCNC2)n1] | N-[3-Methyl-4-[[3-[2-[[(3S)-3-piperidyl]amino]pyrimidin-4-yl]-2-pyridyl]oxy]-1-naphthyl]-1-phenyl-methane-sulfonamide | 0.047 |
| 164 | 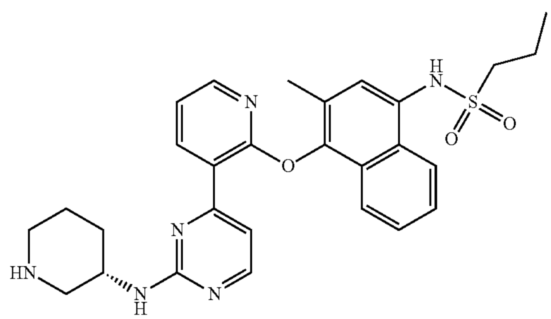 [SMILES: CCCS(=O)(=O)Nc1cc(C)c(Oc2ncccc2-c2ccnc(N[C@H]3CCCNC3)n2)c2ccccc12] | N-[3-Methyl-4-[[3-[2-[[(3S)-3-piperidyl]amino]pyrimidin-4-yl]-2-pyridyl]oxy]-1-naphthyl]propane-1-sulfonamide | 0.147 |
| 165 | 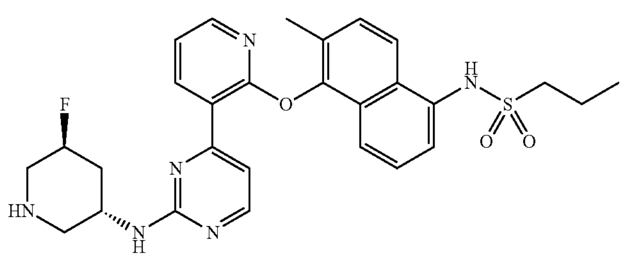 [SMILES: CCCS(=O)(=O)Nc1cccc2c(Oc3ncccc3-c3ccnc(N[C@@H]4CNC[C@@H](F)C4)n3)c(C)ccc12] | N-[5-[[3-[2-[[(3S,5S)-5-Fluoro-3-piperidyl]amino]py-rimidin-4-yl]-2-pyridyl]oxy]-6-methyl-1-naphthyl]propane-1-sulfonamide | 0.164 |
| 166 | 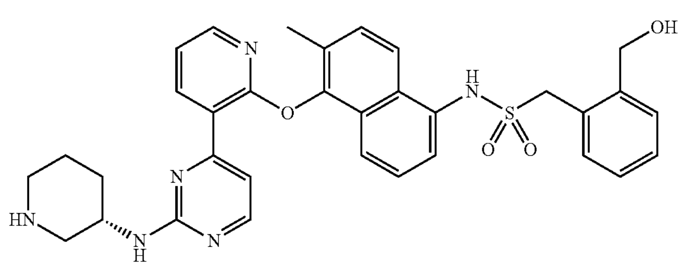 [SMILES: Cc1ccc2c(NS(=O)(=O)Cc3ccccc3CO)cccc2c1Oc1ncccc1-c1ccnc(N[C@H]2CCCNC2)n1] | 1-[2-(Hydroxymethyl)phenyl]-N-[6-methyl-5-[[3-[2-[[(3S)-3-piperidyl]amino]py-rimidin-4-yl]-2-pyridyl]oxy]-1-naphthyl]methane-sulfonamide | 0.118 |

TABLE 1-continued

| No. | Structure | Name | XBP1s-luc 293 LUC (IC$_{50}$) (μmol) |
|---|---|---|---|
| 167 | 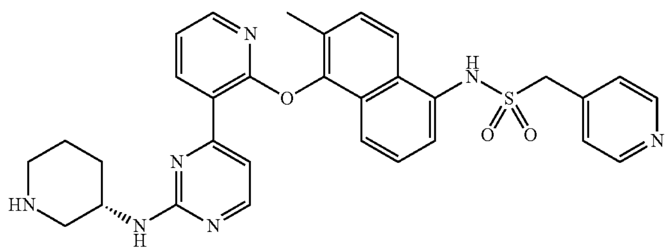 [SMILES: Cc1ccc2c(NS(=O)(=O)Cc3ccncc3)cccc2c1Oc1ncccc1-c1ccnc(N[C@H]2CCCNC2)n1] | N-[6-Methyl-5-[[3-[2-[[(3S)-3-piperidyl]amino]pyrimidin-4-yl]-2-pyridyl]oxy]-1-naphthyl]-1-(4-pyridyl)methanesulfonamide | 0.019 |
| 168 | 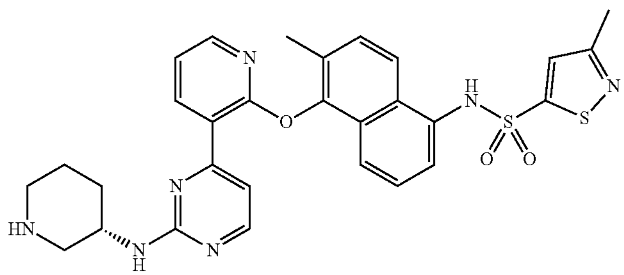 [SMILES: Cc1cc(S(=O)(=O)Nc2cccc3c(Oc4ncccc4-c4ccnc(N[C@H]5CCCNC5)n4)c(C)ccc23)sn1] | 3-Methyl-N-[6-methyl-5-[[3-[2-[[(3S)-3-piperidyl]amino]pyrimidin-4-yl]-2-pyridyl]oxy]-1-naphthyl]isothiazole-5-sulfonamide | 0.172 |
| 169 | 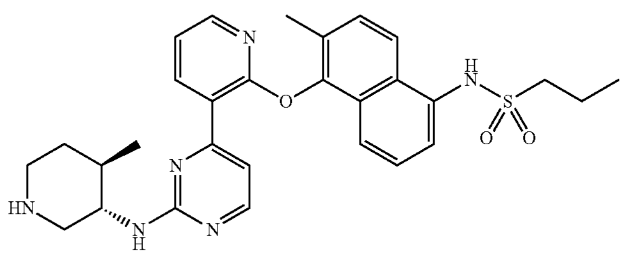 [SMILES: CCCS(=O)(=O)Nc1cccc2c(Oc3ncccc3-c3ccnc(N[C@@H]4CNCC[C@H]4C)n3)c(C)ccc12] | N-(6-Methyl-5-((3-(2-(((3S,4R)-4-methylpiperidin-3-yl)amino)pyrimidin-4-yl)pyridin-2-yl)oxy)naphthalen-1-yl)propane-1-sulfonamide | 0.121 |
| 170 | 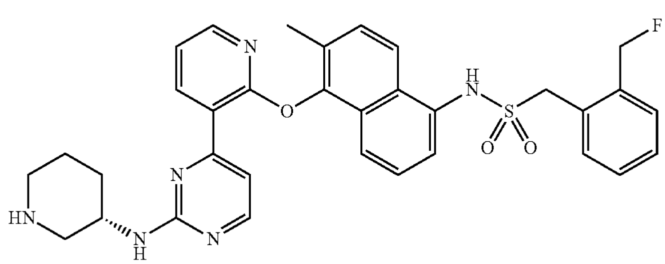 [SMILES: Cc1ccc2c(NS(=O)(=O)Cc3ccccc3CF)cccc2c1Oc1ncccc1-c1ccnc(N[C@H]2CCCNC2)n1] | 1-[2-(Fluoromethyl)phenyl]-N-[6-methyl-5-[[3-[2-[[(3S)-3-piperidyl]amino]pyrimidin-4-yl]-2-pyridyl]oxy]-1-naphthyl]methanesulfonamide | 0.015 |
| 171 | 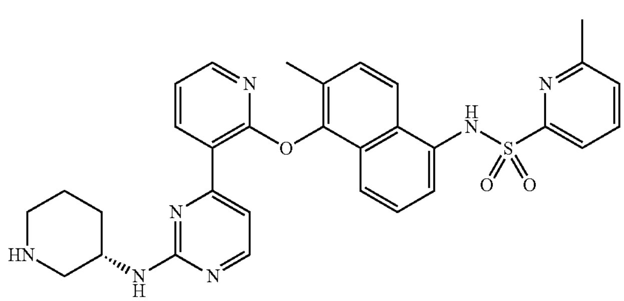 [SMILES: Cc1cccc(S(=O)(=O)Nc2cccc3c(Oc4ncccc4-c4ccnc(N[C@H]5CCCNC5)n4)c(C)ccc23)n1] | 6-Methyl-N-[6-methyl-5-[[3-[2-[[(3S)-3-piperidyl]amino]pyrimidin-4-yl]-2-pyridyl]oxy]-1-naphthyl]pyridine-2-sulfonamide | 0.309 |

TABLE 1-continued

| No. | Structure | Name | XBP1s-luc 293 LUC (IC$_{50}$) (μmol) |
|---|---|---|---|
| 172 | 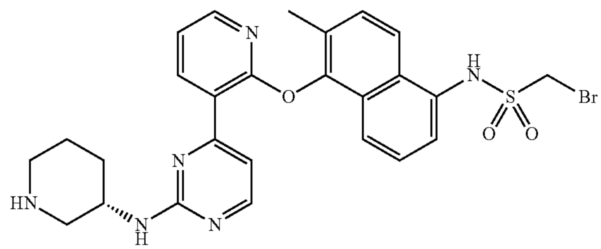 [SMILES: Cc1ccc2c(NS(=O)(=O)CBr)cccc2c1Oc1ncccc1-c1ccnc(N[C@H]2CCCNC2)n1] | (S)-1-Bromo-N-(6-methyl-5-(3-(2-(piperidin-3-ylamino)pyrimidin-4-yl)pyridin-2-yloxy)naphthalen-1-yl)methanesulfonamide | 0.393 |
| 173 | 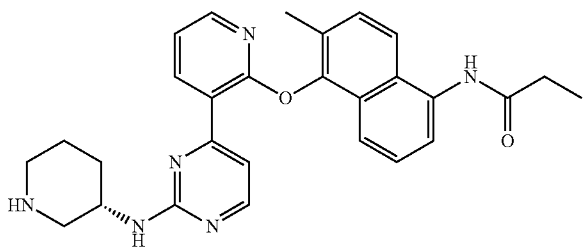 [SMILES: CCC(=O)Nc1cccc2c(Oc3ncccc3-c3ccnc(N[C@H]4CCCNC4)n3)c(C)ccc12] | N-[6-Methyl-5-[[3-[2-[[(3S)-3-piperidyl]amino]pyrimidin-4-yl]-2-pyridyl]oxy]-1-naphthyl]propanamide | 0.226 |
| 174 | 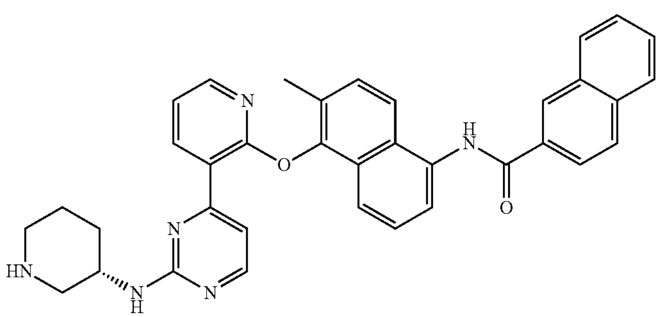 [SMILES: Cc1ccc2c(NC(=O)c3ccc4ccccc4c3)cccc2c1Oc1ncccc1-c1ccnc(N[C@H]2CCCNC2)n1] | N-[6-Methyl-5-[[3-[2-[[(3S)-3-piperidyl]amino]pyrimidin-4-yl]-2-pyridyl]oxy]-1-naphthyl]naphthalene-2-carboxamide | 0.278 |
| 175 | 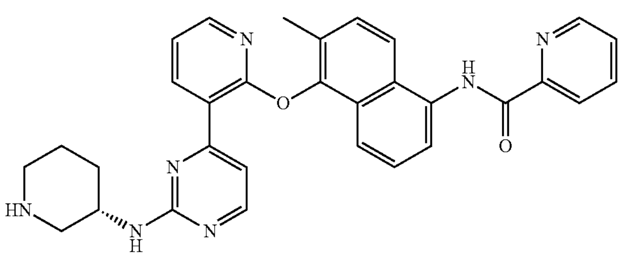 [SMILES: Cc1ccc2c(NC(=O)c3ccccn3)cccc2c1Oc1ncccc1-c1ccnc(N[C@H]2CCCNC2)n1] | N-[6-Methyl-5-[[3-[2-[[(3S)-3-piperidyl]amino]pyrimidin-4-yl]-2-pyridyl]oxy]-1-naphthyl]pyridine-2-carboxamide | 0.333 |
| 176 | 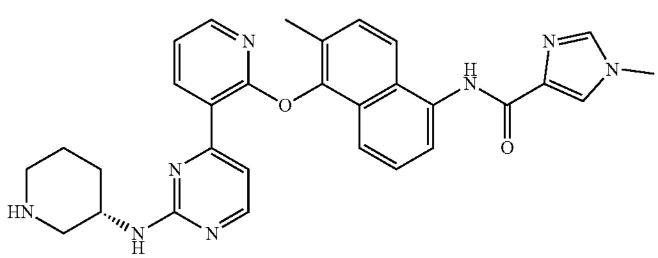 [SMILES: Cc1ccc2c(NC(=O)c3cn(C)cn3)cccc2c1Oc1ncccc1-c1ccnc(N[C@H]2CCCNC2)n1] | (S)-1-Methyl-N-(6-methyl-5-((3-(2-(piperidin-3-ylamino)pyrimidin-4-yl)pyridin-2-yl)oxy)naphthalen-1-yl)-1H-imidazole-4-carboxamide | 0.368 |

TABLE 1-continued

| No. | Structure | Name | XBP1s-luc 293 LUC (IC$_{50}$) (μmol) |
|---|---|---|---|
| 177 | 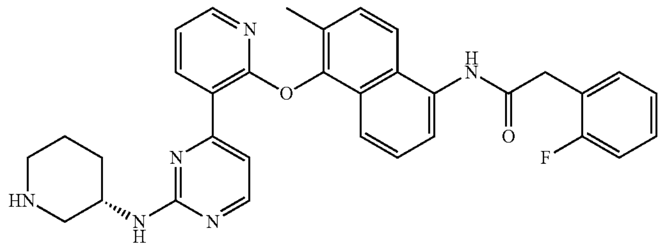 [SMILES: Cc1ccc2c(NC(=O)Cc3ccccc3F)cccc2c1Oc1ncccc1-c1ccnc(N[C@H]2CCCNC2)n1] | 2-(2-Fluorophenyl)-N-[6-methyl-5-[[3-[2-[[(3S)-3-piperidyl]amino]pyrimidin-4-yl]-2-pyridyl]oxy]-1-naphthyl]acetamide | 0.108 |
| 178 | 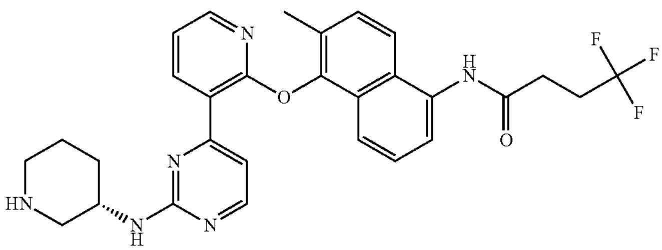 [SMILES: Cc1ccc2c(NC(=O)CCC(F)(F)F)cccc2c1Oc1ncccc1-c1ccnc(N[C@H]2CCCNC2)n1] | 4,4,4-Trifluoro-N-[6-methyl-5-[[3-[2-[[(3S)-3-piperidyl]amino]pyrimidin-4-yl]-2-pyridyl]oxy]-1-naphthyl]butanamide | 0.125 |
| 179 | 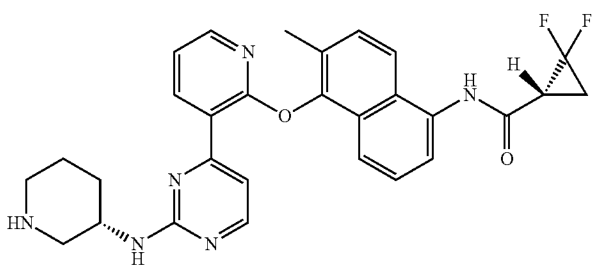 [SMILES: Cc1ccc2c(NC(=O)[C@H]3CC3(F)F)cccc2c1Oc1ncccc1-c1ccnc(N[C@H]2CCCNC2)n1] | (R)-2,2-Difluoro-N-(6-methyl-5-((3-(2-(((S)-piperidin-3-yl)amino)pyrimidin-4-yl)pyridin-2-yl)oxy)naphthalen-1-yl)cyclopropane-1-carboxamide | 0.076 |
| 180 | 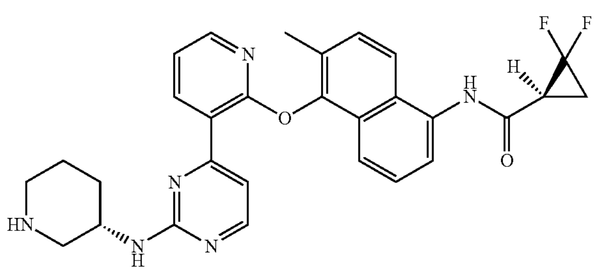 [SMILES: Cc1ccc2c(NC(=O)[C@@H]3CC3(F)F)cccc2c1Oc1ncccc1-c1ccnc(N[C@H]2CCCNC2)n1] | (S)-2,2-Difluoro-N-(6-methyl-5-((3-(2-(((S)-piperidin-3-yl)amino)pyrimidin-4-yl)pyridin-2-yl)oxy)naphthalen-1-yl)cyclopropane-1-carboxamide | 0.213 |
| 181 | 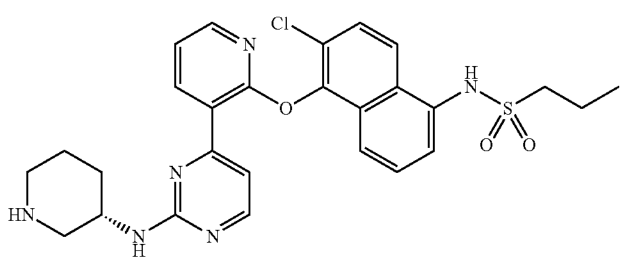 [SMILES: CCCS(=O)(=O)Nc1cccc2c(Oc3ncccc3-c3ccnc(N[C@H]4CCCNC4)n3)c(Cl)ccc12] | N-[6-Chloro-5-[[3-[2-[[(3S)-3-piperidyl]amino]pyrimidin-4-yl]-2-pyridyl]oxy]-1-naphthyl]propane-1-sulfonamide | 0.185 |
| 182 | 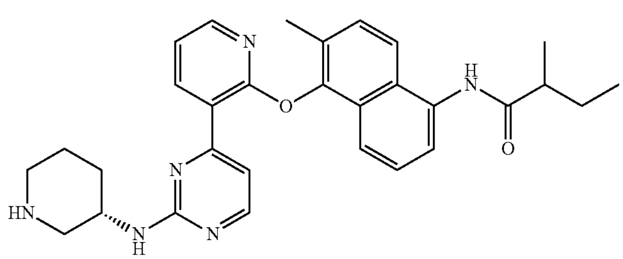 [SMILES: CCC(C)C(=O)Nc1cccc2c(Oc3ncccc3-c3ccnc(N[C@H]4CCCNC4)n3)c(C)ccc12] | 2-Methyl-N-(6-methyl-5-((3-(2-(((S)-piperidin-3-yl)amino)pyrimidin-4-yl)pyridin-2-yl)oxy)naphthalen-1-yl)butanamide | 0.154 |

TABLE 1-continued

| No. | Structure | Name | XBP1s-luc 293 LUC (IC$_{50}$) (μmol) |
|---|---|---|---|
| 183 | 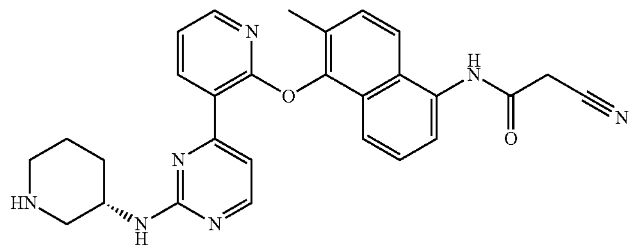 [SMILES: Cc1ccc2c(NC(=O)CC#N)cccc2c1Oc1ncccc1-c1ccnc(N[C@H]2CCCNC2)n1] | 2-Cyano-N-[6-methyl-5-[[3-[2-[[(3S)-3-piperidyl]amino]pyrimidin-4-yl]-2-pyridyl]oxy]-1-naphthyl]acetamide | 0.26 |
| 184 | 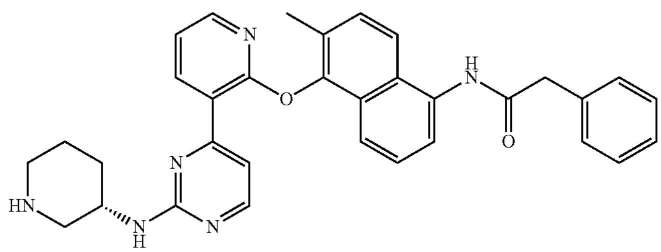 [SMILES: Cc1ccc2c(NC(=O)Cc3ccccc3)cccc2c1Oc1ncccc1-c1ccnc(N[C@H]2CCCNC2)n1] | N-[6-Methyl-5-[[3-[2-[[(3S)-3-piperidyl]amino]pyrimidin-4-yl]-2-pyridyl]oxy]-1-naphthyl]-2-phenyl-acetamide | 0.1 |
| 185 | 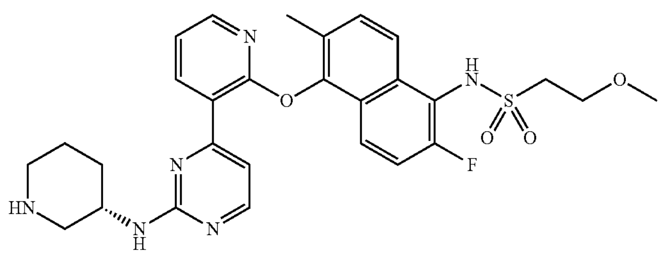 [SMILES: COCCS(=O)(=O)Nc1c(F)ccc2c(Oc3ncccc3-c3ccnc(N[C@H]4CCCNC4)n3)c(C)ccc12] | (S)-N-(2-Fluoro-6-methyl-5-((3-(2-(piperidin-3-ylamino)pyrimidin-4-yl)pyridin-2-yl)oxy)naphthalen-1-yl)-2-methoxyethanesulfonamid | 0.0735 |
| 186 | 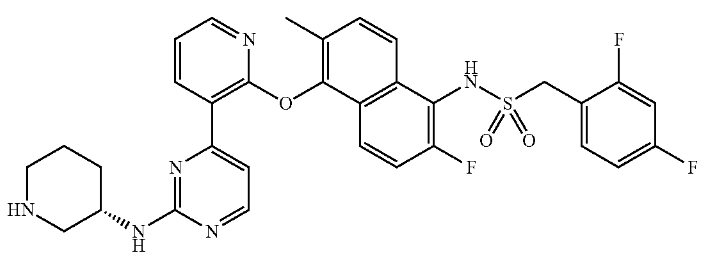 [SMILES: Cc1ccc2c(NS(=O)(=O)Cc3ccc(F)cc3F)c(F)ccc2c1Oc1ncccc1-c1ccnc(N[C@H]2CCCNC2)n1] | (S)-1-(2,4-Difluorophenyl)-N-(2-fluoro-6-methyl-5-((3-(2-(piperidin-3-ylamino)pyrimidin-4-yl)pyridin-2-yl)oxy)naphthalen-1-yl)methanesulfonamide | 0.00489 |
| 187 | 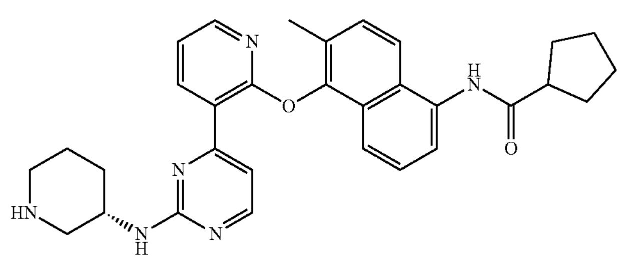 [SMILES: Cc1ccc2c(NC(=O)C3CCCC3)cccc2c1Oc1ncccc1-c1ccnc(N[C@H]2CCCNC2)n1] | N-[6-Methyl-5-[[3-[2-[[(3S)-3-piperidyl]amino]pyrimidin-4-yl]-2-pyridyl]oxy]-1-naphthyl]cyclopentanecarboxamide | 0.157 |
| 188 | 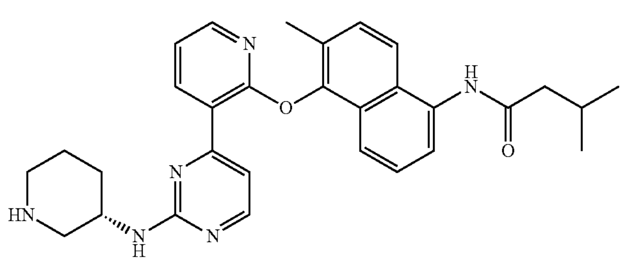 [SMILES: Cc1ccc2c(NC(=O)CC(C)C)cccc2c1Oc1ncccc1-c1ccnc(N[C@H]2CCCNC2)n1] | 3-Methyl-N-[6-methyl-5-[[3-[2-[[(3S)-3-piperidyl]amino]pyrimidin-4-yl]-2-pyridyl]oxy]-1-naphthyl]butanamide | 0.141 |

TABLE 1-continued

| No. | Structure | Name | XBP1s-luc 293 LUC (IC$_{50}$) (μmol) |
|---|---|---|---|
| 189 | 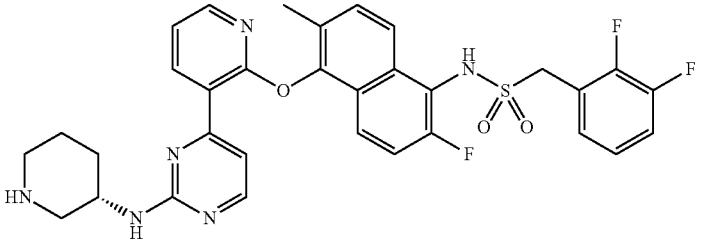 [SMILES: Cc1ccc2c(NS(=O)(=O)Cc3cccc(F)c3F)c(F)ccc2c1Oc1ncccc1-c1ccnc(N[C@H]2CCCNC2)n1] | (S)-1-(2,3-Difluorophenyl)-N-(2-fluoro-6-methyl-5-((3-(2-(piperidin-3-ylamino)pyrimidin-4-yl)pyridin-2-yl)oxy)naphthalen-1-yl)methanesulfonamide | 0.00507 |
| 190 | 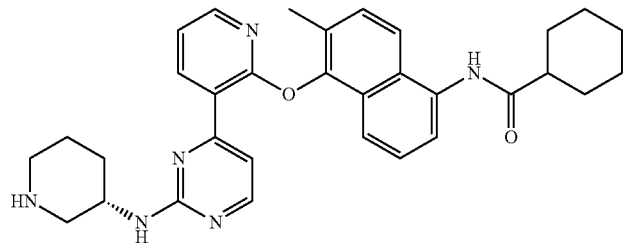 [SMILES: Cc1ccc2c(NC(=O)C3CCCCC3)cccc2c1Oc1ncccc1-c1ccnc(N[C@H]2CCCNC2)n1] | N-Methyl-5-[[3-[2-[[(3S)-3-piperidyl]amino]pyrimidin-4-yl]-2-pyridyl]oxy]-1-naphthyl]cyclohexanecarboxamide | 0.273 |
| 191 | 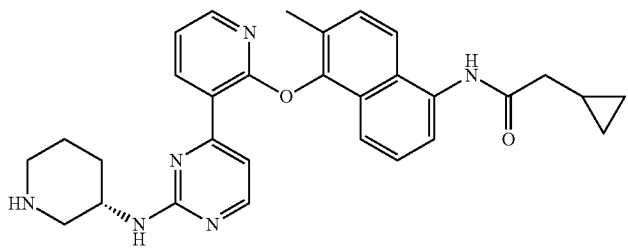 [SMILES: Cc1ccc2c(NC(=O)CC3CC3)cccc2c1Oc1ncccc1-c1ccnc(N[C@H]2CCCNC2)n1] | 2-Cyclopropyl-N-[6-methyl-5-[[3-[2-[[(3S)-3-piperidyl]amino]pyrimidin-4-yl]-2-pyridyl]oxy]-1-naphthyl]acetamide | 0.234 |
| 192 | 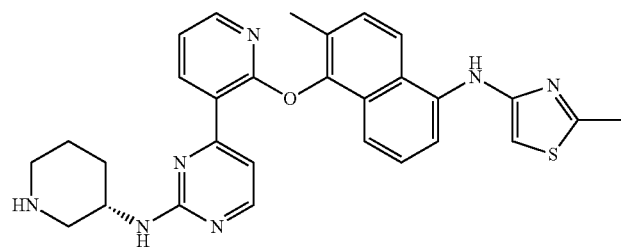 [SMILES: Cc1nc(Nc2cccc3c(Oc4ncccc4-c4ccnc(N[C@H]5CCCNC5)n4)c(C)ccc23)cs1] | 2-Methyl-N-[6-methyl-5-[[3-[2-[[(3S)-3-piperidyl]amino]pyrimidin-4-yl]-2-pyridyl]oxy]-1-naphthyl]thiazol-4-amine | 0.444 |
| 193 | 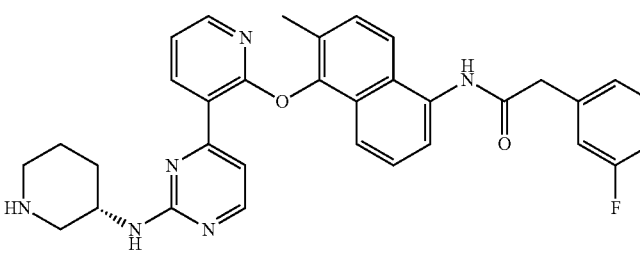 | 2-(3-Fluorophenyl)-N-[6-methyl-5-[[3-[2-[[(3S)-3-piperidyl]amino]pyrimidin-4-yl]-2-pyridyl]oxy]-1-naphthyl]acetamide | 0.086 |
| 194 | 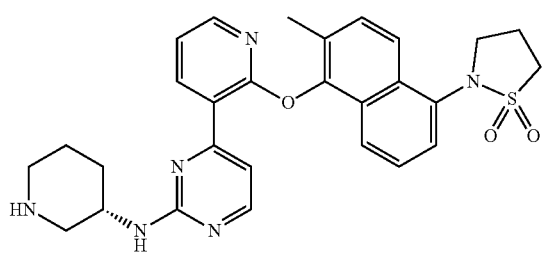 [SMILES: Cc1ccc2c(N3CCCS3(=O)=O)cccc2c1Oc1ncccc1-c1ccnc(N[C@H]2CCCNC2)n1] | 4-[2-[[5-(1,1-Dioxo-1,2-thiazolidin-2-yl)-2-methyl-1-naphthyl]oxy]-3-pyridyl]-N-[(3S)-3-piperidyl]pyrimidin-2-amine | 0.313 |

TABLE 1-continued

| No. | Structure | Name | XBP1s-luc 293 LUC (IC$_{50}$) (μmol) |
|---|---|---|---|
| 195 | 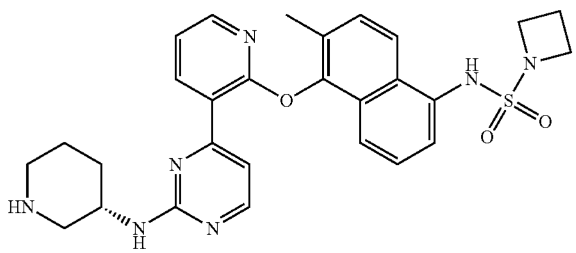 [SMILES: Cc1ccc2c(NS(=O)(=O)N3CCC3)cccc2c1Oc1ncccc1-c1ccnc(N[C@H]2CCCNC2)n1] | N-[6-Methyl-5-[[3-[2-[[(3S)-3-piperidyl]amino]py-rimidin-4-yl]-2-pyridyl]oxy]-1-naphthyl]azetidine-1-sulfonamide | 0.202 |
| 196 | 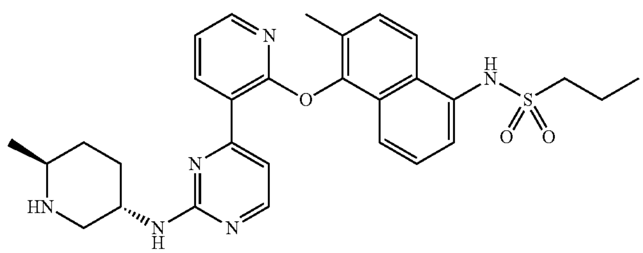 [SMILES: CCCS(=O)(=O)Nc1cccc2c(Oc3ncccc3-c3ccnc(N[C@H]4CC[C@H](C)NC4)n3)c(C)ccc12] | N-(6-Methyl-5-((3-(2-(((3S,6S)-6-methylpiperidin-3-yl)amino)pyrimidin-4-yl)pyridin-2-yl)oxy)naphthalen-1-yl)propane-1-sulfonamide | 0.162 |
| 197 | 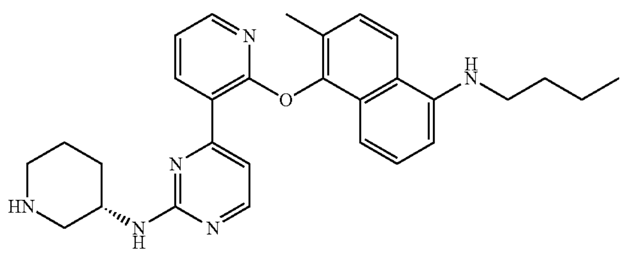 [SMILES: CCCCNc1cccc2c(Oc3ncccc3-c3ccnc(N[C@H]4CCCNC4)n3)c(C)ccc12] | 4-[2-[[5-(Butylamino)-2-methyl-1-naphthyl]oxy]-3-pyridyl]-N-[(3S)-3-piperidyl]pyrimidin-2-amine | 0.228 |
| 198 | 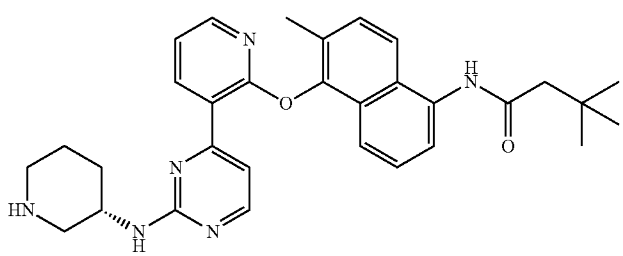 [SMILES: Cc1ccc2c(NC(=O)CC(C)(C)C)cccc2c1Oc1ncccc1-c1ccnc(N[C@H]2CCCNC2)n1] | 3,3-Dimethyl-N-[6-methyl-5-[[3-[2-[[(3S)-3-piperidyl]amino]pyrimidin-4-yl]-2-pyridyl]oxy]-1-naphthyl]butanamide | 0.161 |
| 199 | 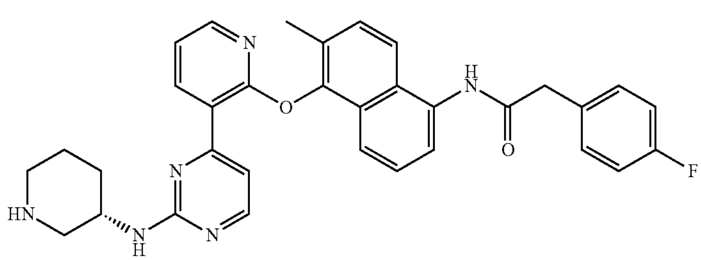 [SMILES: Cc1ccc2c(NC(=O)Cc3ccc(F)cc3)cccc2c1Oc1ncccc1-c1ccnc(N[C@H]2CCCNC2)n1] | 2-(4-Fluorophenyl)-N-[6-methyl-5-[[3-[2-[[(3S)-3-piperidyl]amino]pyrimidin-4-yl]-2-pyridyl]oxy]-1-naphthyl]acetamide | 0.155 |
| 200 | 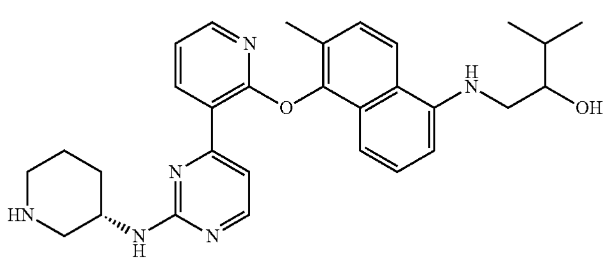 [SMILES: Cc1ccc2c(NCC(O)C(C)C)cccc2c1Oc1ncccc1-c1ccnc(N[C@H]2CCCNC2)n1] | 3-Methyl-1-((6-methyl-5-((3-(2-((S)-piperidin-3-ylamino)pyrimidin-4-yl)pyridin-2-yl)oxy)naphthalen-1-yl)amino)butan-2-ol | 0.077 |

TABLE 1-continued

| No. | Structure | Name | XBP1s-luc 293 LUC (IC$_{50}$) (μmol) |
|---|---|---|---|
| 201 | 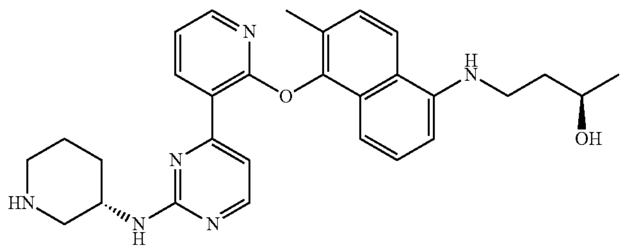 [SMILES: Cc1ccc2c(NCC[C@@H](C)O)cccc2c1Oc1ncccc1-c1ccnc(N[C@H]2CCCNC2)n1] | (R)-4-((6-Methyl-5-((3-(2-(((S)-piperidin-3-yl)amino)pyrimidin-4-yl)pyridin-2-yl)oxy)naphthalen-1-yl)amino)butan-2-ol | 0.133 |
| 202 | 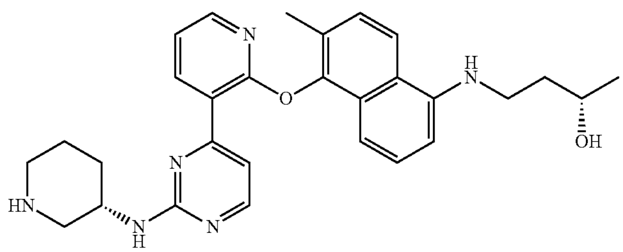 | (S)-4-((6-Methyl-5-((3-(2-(((S)-piperidin-3-yl)amino)pyrimidin-4-yl)pyridin-2-yl)oxy)naphthalen-1-yl)amino)butan-2-ol | 0.123 |
| 203 | 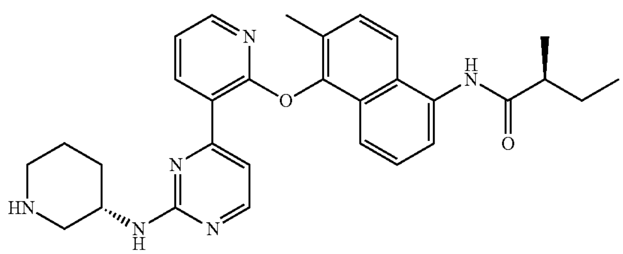 [SMILES: CC[C@H](C)C(=O)Nc1cccc2c(Oc3ncccc3-c3ccnc(N[C@H]4CCCNC4)n3)c(C)ccc12] | (S)-2-Methyl-N-(6-methyl-5-((3-(2-(((S)-piperidin-3-yl)amino)pyrimidin-4-yl)pyridin-2-yl)oxy)naphthalen-1-yl)butanamide | 0.161 |
| 204 | 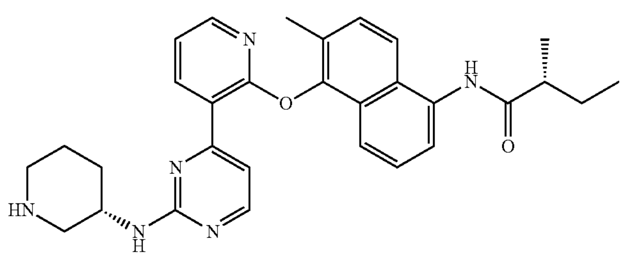 [SMILES: CC[C@@H](C)C(=O)Nc1cccc2c(Oc3ncccc3-c3ccnc(N[C@H]4CCCNC4)n3)c(C)ccc12] | (R)-2-methyl-N-(6-methyl-5-((3-(2-(((S)-piperidin-3-yl)amino)pyrimidin-4-yl)pyridin-2-yl)oxy)naphthalen-1-yl)butanamide | 0.449 |
| 205 | 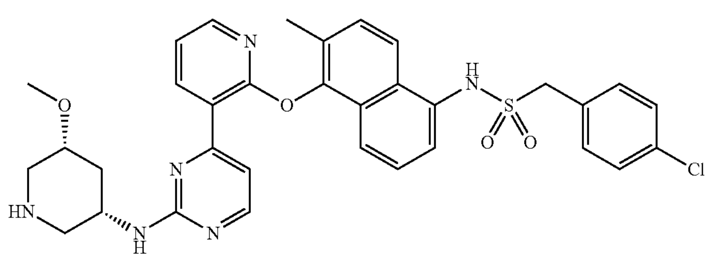 [SMILES: CO[C@H]1CNC[C@@H](Nc2nccc(-c3cccnc3Oc3c(C)ccc4c(NS(=O)(=O)Cc5ccc(Cl)cc5)cccc34)n2)C1] | 1-(4-Chlorophenyl)-N-(5-((3-(2-(((3S,5R)-5-methoxypiperidin-3-yl)amino)pyrimidin-4-yl)pyridin-2-yl)oxy)-6-methylnaphthalen-1-yl)methanesulfonamide | 0.13 |
| 206 | 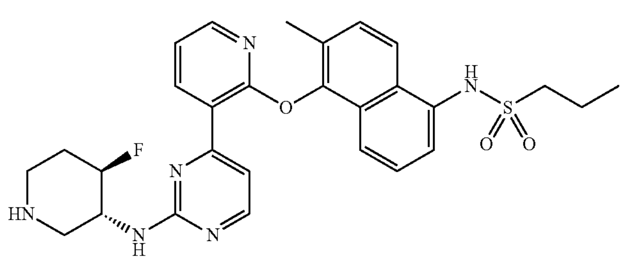 [SMILES: CCCS(=O)(=O)Nc1cccc2c(Oc3ncccc3-c3ccnc(N[C@@H]4CNCC[C@H]4F)n3)c(C)ccc12] | N-(5-((3-(2-(((3R,4R)-4-Fluoropiperidin-3-yl)amino)pyrimidin-4-yl)pyridin-2-yl)oxy)-6-methylnaphthalen-1-yl)propane-1-sulfonamide | 0.487 |

TABLE 1-continued

| No. | Structure | Name | XBP1s-luc 293 LUC (IC$_{50}$) (μmol) |
|---|---|---|---|
| 207 | 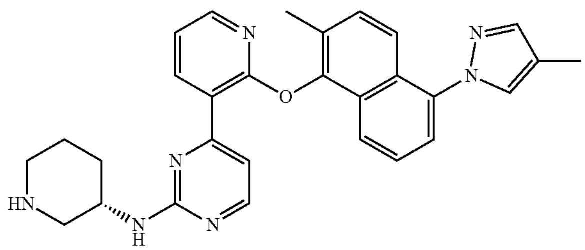 [SMILES: Cc1cnn(-c2cccc3c(Oc4ncccc4-c4ccnc(N[C@H]5CCCNC5)n4)c(C)ccc23)c1] | 4-[2-[[2-Methyl-5-(4-methylpyrazol-1-yl)-1-naphthyl]oxy]-3-pyridyl]-N-[(3S)-3-piperidyl]pyrimidin-2-amine | 0.251 |
| 208 | 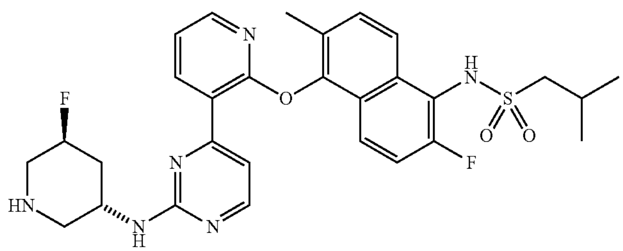 [SMILES: Cc1ccc2c(NS(=O)(=O)CC(C)C)c(F)ccc2c1Oc1ncccc1-c1ccnc(N[C@@H]2CNC[C@@H](F)C2)n1] | N-(2-Fluoro-5-((3-(2-(((3S,5S)-5-fluoropiperidin-3-yl)amino)pyrimidin-4-yl)pyridin-2-yl)oxy)-6-methylnaphthalen-1-yl)-2-methylpropane-1-sulfonamide | 0.0182 |
| 209 | 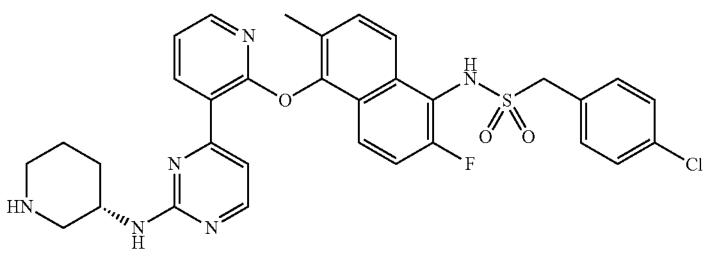 [SMILES: Cc1ccc2c(NS(=O)(=O)Cc3ccc(Cl)cc3)c(F)ccc2c1Oc1ncccc1-c1ccnc(N[C@H]2CCCNC2)n1] | (S)-1-(4-Chlorophenyl)-N-(2-fluoro-6-methyl-5-((3-(2-(piperidin-3-ylamino)pyrimidin-4-yl)pyridin-2-yl)oxy)naphthalen-1-yl)methanesulfonamide | 0.00804 |
| 210 | 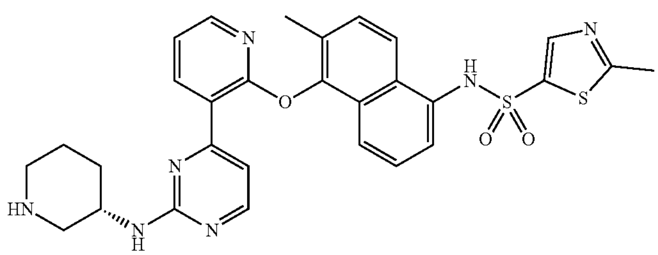 [SMILES: Cc1ncc(S(=O)(=O)Nc2cccc3c(Oc4ncccc4-c4ccnc(N[C@H]5CCCNC5)n4)c(C)ccc23)s1] | 2-Methyl-N-[6-methyl-5-[[3-[2-[[(3S)-3-piperidyl]amino]pyrimidin-4-yl]-2-pyridyl]oxy]-1-naphthyl]thiazole-5-sulfonamide | 0.459 |
| 211 | 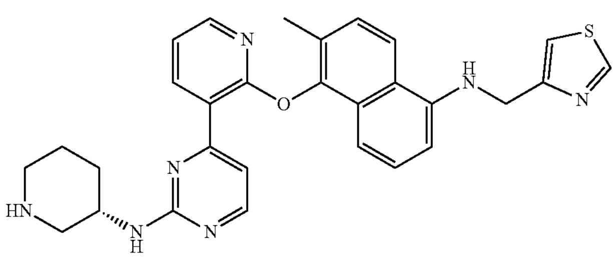 [SMILES: Cc1ccc2c(NCc3cscn3)cccc2c1Oc1ncccc1-c1ccnc(N[C@H]2CCCNC2)n1] | 4-[2-[[2-Methyl-5-(thiazol-4-ylmethylamino)-1-naphthyl]oxy]-3-pyridyl]-N-[(3S)-3-piperidyl]pyrimidin-2-amine | 0.07 |

US 10,968,203 B2

73 74

TABLE 1-continued

| No. | Structure | Name | XBP1s-luc 293 LUC (IC$_{50}$) (μmol) |
|---|---|---|---|
| 212 | 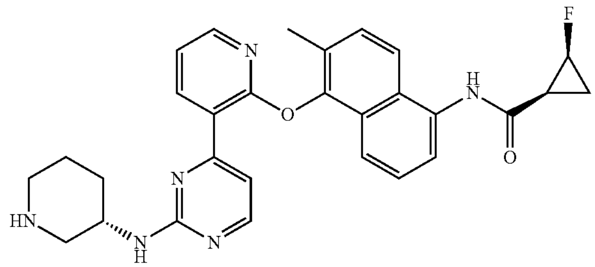 [SMILES: Cc1ccc2c(NC(=O)[C@@H]3C[C@@H]3F)cccc2c1Oc1ncccc1-c1ccnc(N[C@H]2CCCNC2)n1] | (1S,2S)-2-Fluoro-N-[6-methyl-5-[[3-[2-[[(3S)-3-piperidyl]amino]pyrimidin-4-yl]-2-pyridyl]oxy]-1-naphthyl]cyclopropanecarboxamide | 0.122 |
| 213 | 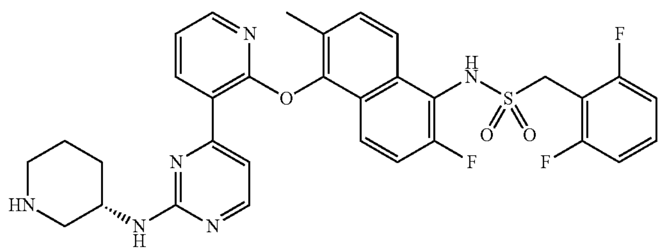 [SMILES: Cc1ccc2c(NS(=O)(=O)Cc3c(F)cccc3F)c(F)ccc2c1Oc1ncccc1-c1ccnc(N[C@H]2CCCNC2)n1] | (S)-1-(2,6-Difluorophenyl)-N-(2-fluoro-6-methyl-5-((3-(2-(piperidin-3-ylamino)pyrimidin-4-yl)pyridin-2-yl)oxy)naphthalen-1-yl)methanesulfonamide | 0.00457 |
| 214 | 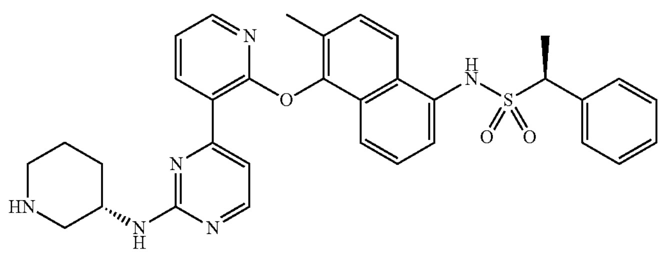 [SMILES: Cc1ccc2c(NS(=O)(=O)[C@@H](C)c3ccccc3)cccc2c1Oc1ncccc1-c1ccnc(N[C@H]2CCCNC2)n1] | (S)-N-(6-Methyl-5-((3-(2-((S)-piperidin-3-ylamino)pyrimidin-4-yl)pyridin-2-yl)oxy)naphthalen-1-yl)-1-phenylethanesulfonamide | 0.076 |
| 215 | 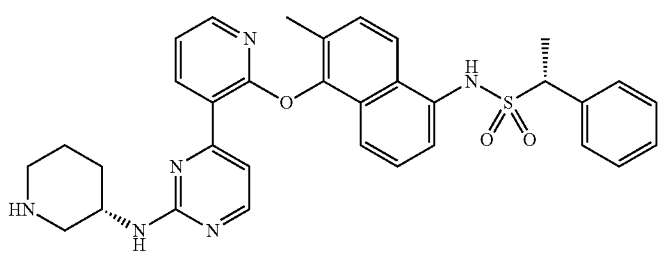 [SMILES: Cc1ccc2c(NS(=O)(=O)[C@H](C)c3ccccc3)cccc2c1Oc1ncccc1-c1ccnc(N[C@H]2CCCNC2)n1] | (R)-N-(6-Methyl-5-((3-(2-((S)-piperidin-3-ylamino)pyrimidin-4-yl)pyridin-2-yl)oxy)naphthalen-1-yl)-1-phenylethanesulfonamide | 0.211 |
| 216 | 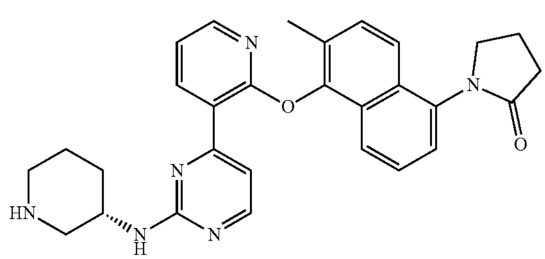 [SMILES: Cc1ccc2c(N3CCCC3=O)cccc2c1Oc1ncccc1-c1ccnc(N[C@H]2CCCNC2)n1] | 1-[6-Methyl-5-[[3-[2-[[(3S)-3-piperidyl]amino]pyrimidin-4-yl]-2-pyridyl]oxy]-1-naphthyl]pyrrolidin-2-one | 0.26 |
| 217 | 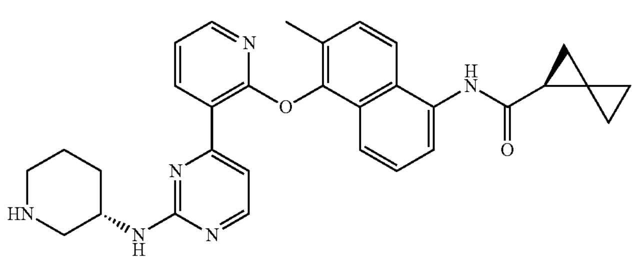 [SMILES: Cc1ccc2c(NC(=O)[C@H]3CC34CC4)cccc2c1Oc1ncccc1-c1ccnc(N[C@H]2CCCNC2)n1] | (S)-N-(6-Methyl-5-((3-(2-(((S)-piperidin-3-yl)amino)pyrimidin-4-yl)pyridin-2-yl)oxy)naphthalen-1-yl)spiro[2.2]pentane-1-carboxamide | 0.055 |

US 10,968,203 B2

75 76

TABLE 1-continued

| No. | Structure | Name | XBP1s-luc 293 LUC (IC$_{50}$) (μmol) |
|---|---|---|---|
| 218 | 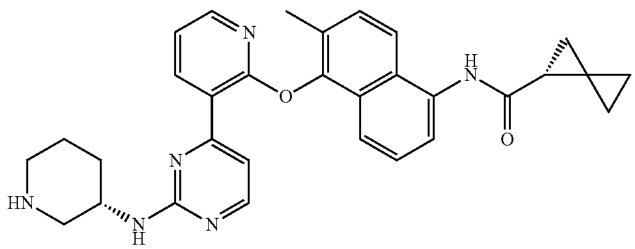 [SMILES: Cc1ccc2c(NC(=O)[C@@H]3CC34CC4)cccc2c1Oc1ncccc1-c1ccnc(N[C@H]2CCCNC2)n1] | (R)-N-(6-Methyl-5-((3-(2-(((S)-piperidin-3-yl)amino)pyrimidin-4-yl)pyridin-2-yl)oxy)naphthalen-1-yl)spiro[2.2]pentane-1-carboxamide | 0.174 |
| 219 | 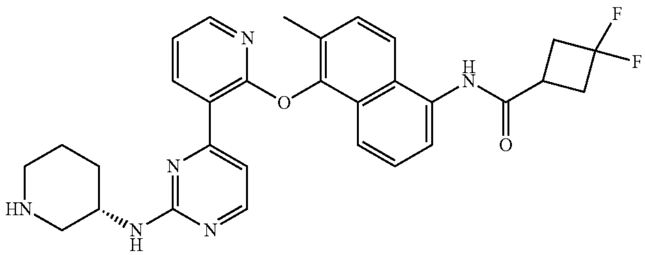 [SMILES: Cc1ccc2c(NC(=O)C3CC(F)(F)C3)cccc2c1Oc1ncccc1-c1ccnc(N[C@H]2CCCNC2)n1] | (S)-3,3-Difluoro-N-(6-methyl-5-(3-(2-(piperidin-3-ylamino)pyrimidin-4-yl)pyridin-2-yloxy)naphthalen-1-yl)cyclobutane-carboxamide | 0.119 |
| 220 | 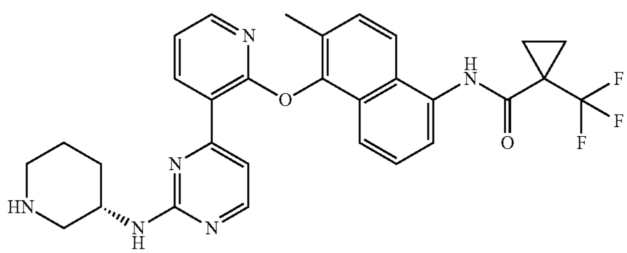 [SMILES: Cc1ccc2c(NC(=O)C3(C(F)(F)F)CC3)cccc2c1Oc1ncccc1-c1ccnc(N[C@H]2CCCNC2)n1] | (S)-N-(6-Methyl-5-(3-(2-(piperidin-3-ylamino)pyrimidin-4-yl)pyridin-2-yloxy)naphthalen-1-yl)-1-(trifluoromethyl)cyclopropanecarboxamide | 0.309 |
| 221 | 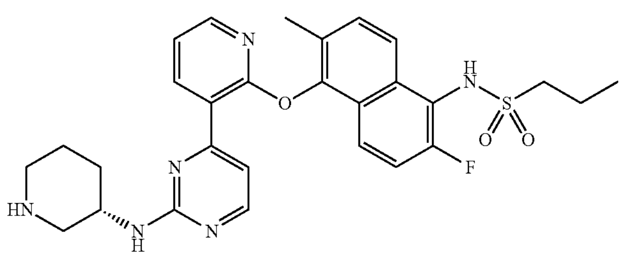 [SMILES: CCCS(=O)(=O)Nc1c(F)ccc2c(Oc3ncccc3-c3ccnc(N[C@H]4CCCNC4)n3)c(C)ccc12] | N-[2-Fluoro-6-methyl-5-[[3-[2-[[(3S)-3-piperidyl]amino]pyrimidin-4-yl]-2-pyridyl]oxy]-1-naphthyl]propane-1-sulfonamide | 0.037 |
| 222 | 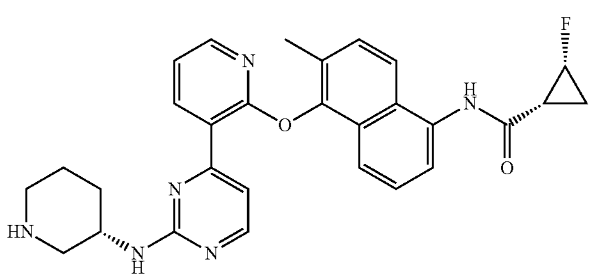 [SMILES: Cc1ccc2c(NC(=O)[C@H]3C[C@H]3F)cccc2c1Oc1ncccc1-c1ccnc(N[C@H]2CCCNC2)n1] | (1R,2R)-2-Fluoro-N-[6-methyl-5-[[3-[2-[[(3S)-3-piperidyl]amino]pyrimidin-4-yl]-2-pyridyl]oxy]-1-naphthyl]cyclopropanecarboxamide | 0.093 |

TABLE 1-continued

| No. | Structure | Name | XBP1s-luc 293 LUC (IC$_{50}$) (μmol) |
|---|---|---|---|
| 223 | 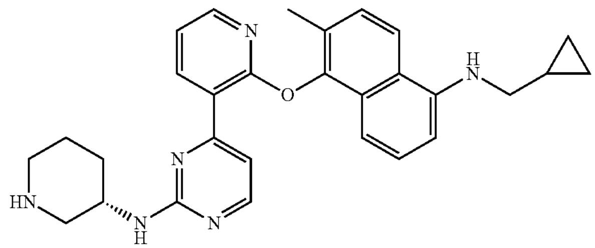 [SMILES: Cc1ccc2c(NCC3CC3)cccc2c1Oc1ncccc1-c1ccnc(N[C@H]2CCCNC2)n1] | 4-[2-[[5-(Cyclopropylmethylamino)-2-methyl-1-naphthyl]oxy]-3-pyridyl]-N-[(3S)-3-piperidyl]pyrimidin-2-amine | 0.212 |
| 224 | 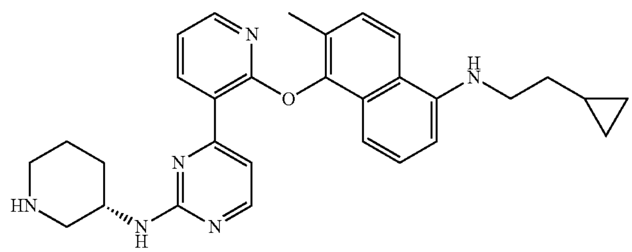 [SMILES: Cc1ccc2c(NCCC3CC3)cccc2c1Oc1ncccc1-c1ccnc(N[C@H]2CCCNC2)n1] | 4-[2-[[5-(2-Cyclopropylethylamino)-2-methyl-1-naphthyl]oxy]-3-pyridyl]-N-[(3S)-3-piperidyl]pyrimidin-2-amine | 0.177 |
| 225 | 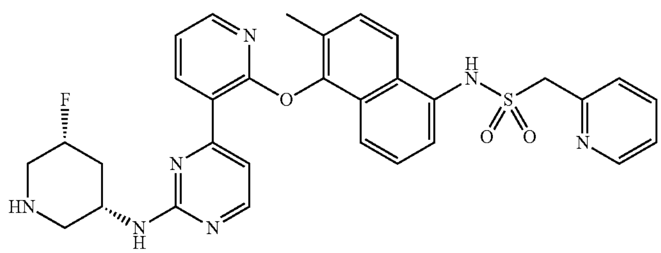 | N-[5-[[3-[2-[[(3S,5R)-5-Fluoro-3-piperidyl]amino]pyrimidin-4-yl]-2-pyridyl]oxy]-6-methyl-1-naphthyl]-1-(2-pyridyl)methanesulfonamide | 0.467 |
| 226 | 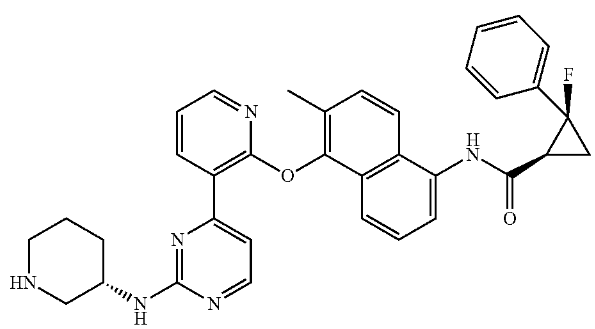 [SMILES: Cc1ccc2c(NC(=O)[C@@H]3C[C@@]3(F)c3ccccc3)cccc2c1Oc1ncccc1-c1ccnc(N[C@H]2CCCNC2)n1] | 2-Fluoro-N-(6-methyl-5-((3-(2-(((S)-piperidin-3-yl)amino)pyrimidin-4-yl)pyridin-2-yl)oxy)naphthalen-1-yl)-2-phenylcyclopropane-1-carboxamide | 0.223 |
| 227 | 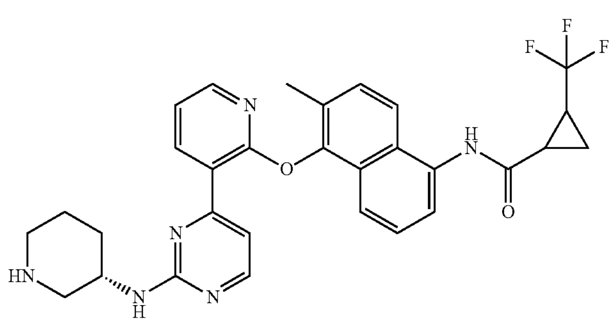 [SMILES: Cc1ccc2c(NC(=O)C3CC3C(F)(F)F)cccc2c1Oc1ncccc1-c1ccnc(N[C@H]2CCCNC2)n1] | N-(6-Methyl-5-((3-(2-(((S)-piperidin-3-yl)amino)pyrimidin-4-yl)pyridin-2-yl)oxy)naphthalen-1-yl)-2-(trifluoromethyl)cyclopropane-1-carboxamide | 0.493 |

TABLE 1-continued

| No. | Structure | Name | XBP1s-luc 293 LUC (IC$_{50}$) (μmol) |
|---|---|---|---|
| 228 | 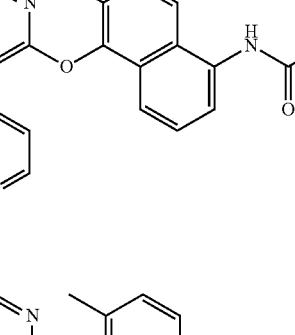 | N-(6-Methyl-5-((3-(2-(((S)-piperidin-3-yl)amino)pyrimidin-4-yl)pyridin-2-yl)oxy)naphthalen-1-yl)-2-(trifluoromethyl)cyclopropane-1-carboxamide | 0.088 |
| 229 | 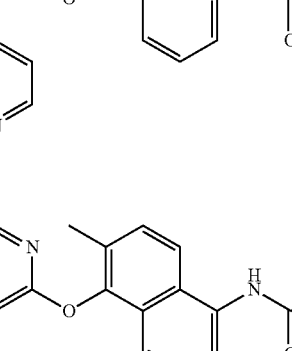 | 2-Isopropyl-N-(6-methyl-5-((3-(2-(((S)-piperidin-3-yl)amino)pyrimidin-4-yl)pyridin-2-yl)oxy)naphthalen-1-yl)cyclopropane-1-carboxamide | 0.454 |
| 230 | 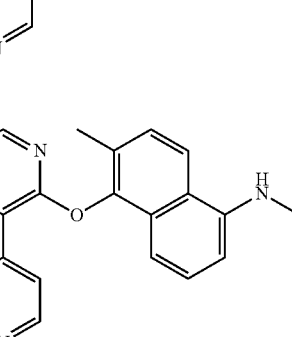 | 2-Isopropyl-N-(6-methyl-5-((3-(2-(((S)-piperidin-3-yl)amino)pyrimidin-4-yl)pyridin-2-yl)oxy)naphthalen-1-yl)cyclopropane-1-carboxamide | 0.08 |
| 231 | 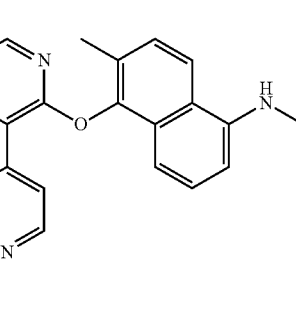 | (1R,2S)-2-Methyl-N-(6-methyl-5-((3-(2-(((S)-piperidin-3-yl)amino)pyrimidin-4-yl)pyridin-2-yl)oxy)naphthalen-1-yl)cyclopropane-1-carboxamide | 0.053<br>0.0333 |
| 232 | 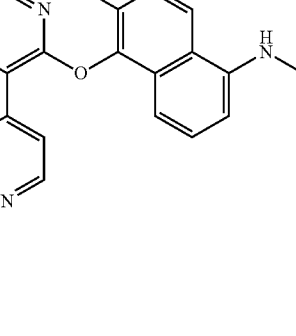 | (1R,2R)-2-Methyl-N-(6-methyl-5-((3-(2-(((S)-piperidin-3-yl)amino)pyrimidin-4-yl)pyridin-2-yl)oxy)naphthalen-1-yl)cyclopropane-1-carboxamide | 0.136 |

TABLE 1-continued

| No. | Structure | Name | XBP1s-luc 293 LUC (IC$_{50}$) (μmol) |
|---|---|---|---|
| 233 | 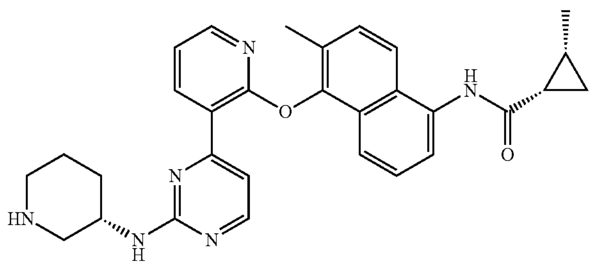 [SMILES: Cc1ccc2c(NC(=O)[C@H]3C[C@H]3C)cccc2c1Oc1ncccc1-c1ccnc(N[C@H]2CCCNC2)n1] | (1S,2R)-2-Methyl-N-(6-methyl-5-((3-(2-(((S)-piperidin-3-yl)amino)pyrimidin-4-yl)pyridin-2-yl)oxy)naphthalen-1-yl)cyclopropane-1-carboxamide | 0.332 0.11 |
| 234 | 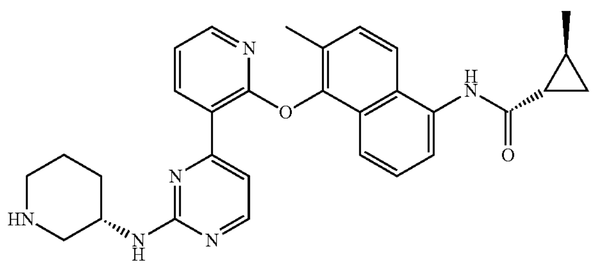 | (1S,2S)-2-Methyl-N-(6-methyl-5-((3-(2-(((S)-piperidin-3-yl)amino)pyrimidin-4-yl)pyridin-2-yl)oxy)naphthalen-1-yl)cyclopropane-1-carboxamide | 0.111 |
| 235 | 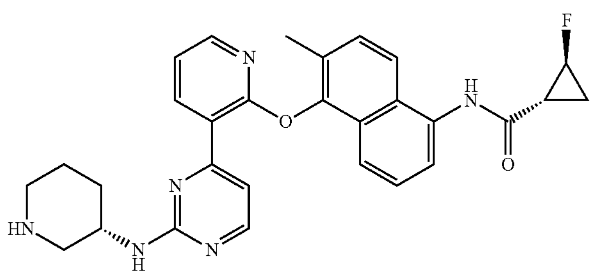 | (1R,2S)-2-Fluoro-N-(6-methyl-5-((3-(2-(((S)-piperidin-3-yl)amino)pyrimidin-4-yl)pyridin-2-yl)oxy)naphthalen-1-yl)cyclopropane-1-carboxamide | 0.145 |
| 236 | 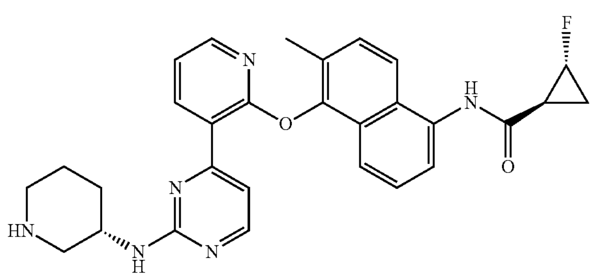 [SMILES: Cc1ccc2c(NC(=O)[C@@H]3C[C@H]3F)cccc2c1Oc1ncccc1-c1ccnc(N[C@H]2CCCNC2)n1] | (1S,2S)-2-Fluoro-N-(6-methyl-5-((3-(2-(((S)-piperidin-3-yl)amino)pyrimidin-4-yl)pyridin-2-yl)oxy)naphthalen-1-yl)cyclopropane-1-carboxamide | 0.174 |
| 237 | 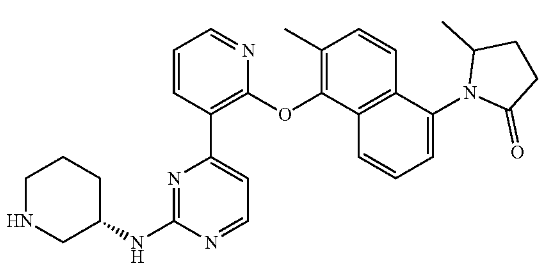 [SMILES: Cc1ccc2c(N3C(=O)CCC3C)cccc2c1Oc1ncccc1-c1ccnc(N[C@H]2CCCNC2)n1] | 5-Methyl-1-(6-methyl-5-((3-(2-(((S)-piperidin-3-yl)amino)pyrimidin-4-yl)pyridin-2-yl)oxy)naphthalen-1-yl)pyrrolidin-2-one | 0.472 |

TABLE 1-continued

| No. | Structure | Name | XBP1s-luc 293 LUC (IC$_{50}$) (μmol) |
|---|---|---|---|
| 238 | 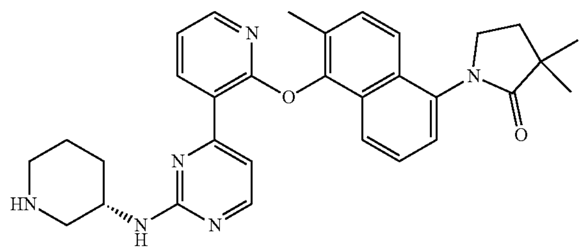 [SMILES: Cc1ccc2c(N3CCC(C)(C)C3=O)cccc2c1Oc1ncccc1-c1ccnc(N[C@H]2CCCNC2)n1] | 3,3-Dimethyl-1-[6-methyl-5-[[3-[2-[[(3S)-3-piperidyl]amino]pyrimidin-4-yl]-2-pyridyl]oxy]-1-naphthyl]pyrrolidin-2-one | 0.275 |
| 239 | 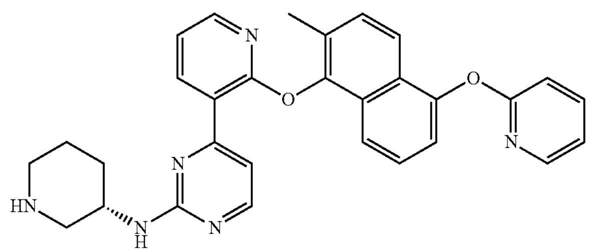 [SMILES: Cc1ccc2c(Oc3ccccn3)cccc2c1Oc1ncccc1-c1ccnc(N[C@H]2CCCNC2)n1] | 4-[2-[[2-Methyl-5-(2-pyridyloxy)-1-naphthyl]oxy]-3-pyridyl]-N-[(3S)-3-piperidyl]pyrimidin-2-amine | 0.245 |
| 240 | 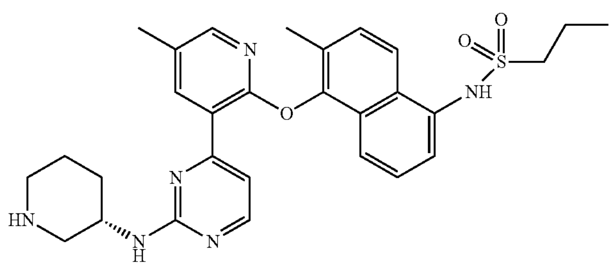 [SMILES: CCCS(=O)(=O)Nc1cccc2c(Oc3ncc(C)cc3-c3ccnc(N[C@H]4CCCNC4)n3)c(C)ccc12] | N-[6-Methyl-5-[[5-methyl-3-[2-[[(3S)-3-piperidyl]amino]pyrimidin-4-yl]-2-pyridyl]oxy]-1-naphthyl]propane-1-sulfonamide | 0.167 |
| 241 | 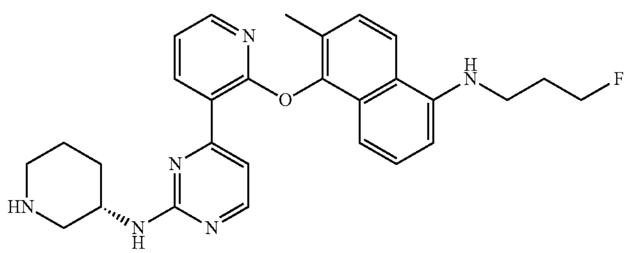 [SMILES: Cc1ccc2c(NCCCF)cccc2c1Oc1ncccc1-c1ccnc(N[C@H]2CCCNC2)n1] | 4-[2-[[5-(3-Fluoropropylamino)-2-methyl-1-naphthyl]oxy]-3-pyridyl]-N-[(3S)-3-piperidyl]pyrimidin-2-amine | 0.141 |
| 242 | 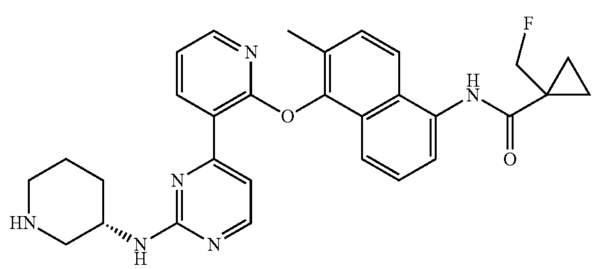 [SMILES: Cc1ccc2c(NC(=O)C3(CF)CC3)cccc2c1Oc1ncccc1-c1ccnc(N[C@H]2CCCNC2)n1] | 1-(Fluoromethyl)-N-[6-methyl-5-[[3-[2-[[(3S)-3-piperidyl]amino]pyrimidin-4-yl]-2-pyridyl]oxy]-1-naphthyl]cyclopropanecarboxamide | 0.361 |
| 243 | 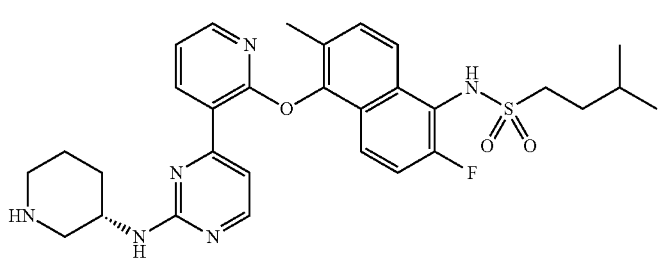 [SMILES: Cc1ccc2c(NS(=O)(=O)CCC(C)C)c(F)ccc2c1Oc1ncccc1-c1ccnc(N[C@H]2CCCNC2)n1] | (S)-N-(2-Fluoro-6-methyl-5-((3-(2-(piperidin-3-ylamino)pyrimidin-4-yl)pyridin-2-yl)oxy)naphthalen-1-yl)-3-methylbutane-1-sulfonamide | 0.068 |

… TABLE 1-continued

| No. | Structure | Name | XBP1s-luc 293 LUC (IC$_{50}$) (μmol) |
|---|---|---|---|
| 244 | 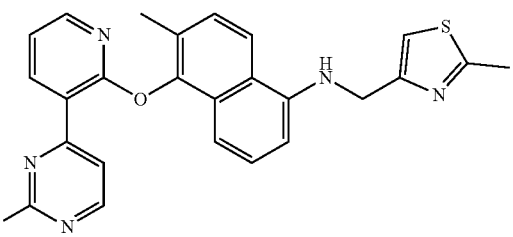 | 4-[2-[[2-Methyl-5-[(2-methylthiazol-4-yl)methylamino]-1-naphthyl]oxy]-3-pyridyl]-N-[(3S)-3-piperidyl]pyrimidin-2-amine | 0.012 |
| 245 | 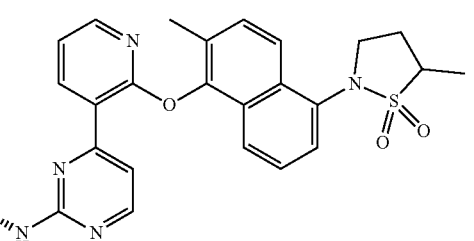 | 5-Methyl-2-(6-methyl-5-((3-(2-(((S)-piperidin-3-yl)amino)pyrimidin-4-yl)pyridin-2-yl)oxy)naphthalen-1-yl)isothiazolidine 1,1-dioxide | 0.294 |
| 246 | 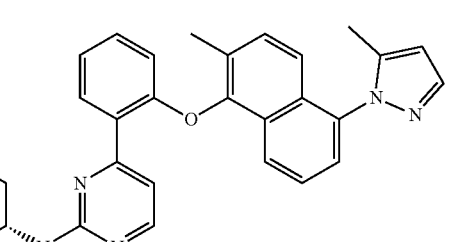 | 4-[2-[[2-Methyl-5-(5-methylpyrazol-1-yl)-1-naphthyl]oxy]-3-pyridyl]-N-[(3S)-3-piperidyl]pyrimidin-2-amine | 0.235 |
| 247 | 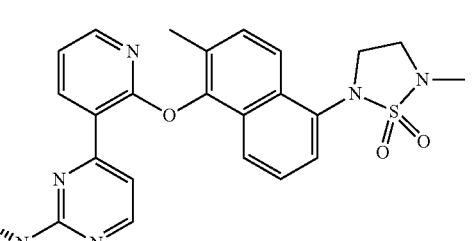 | 4-[2-[[2-Methyl-5-(5-methyl-1,1-dioxo-1,2,5-thiadiazolidin-2-yl)-1-naphthyl]oxy]-3-pyridyl]-N-[(3S)-3-piperidyl]pyrimidin-2-amine | 0.36 |
| 248 | 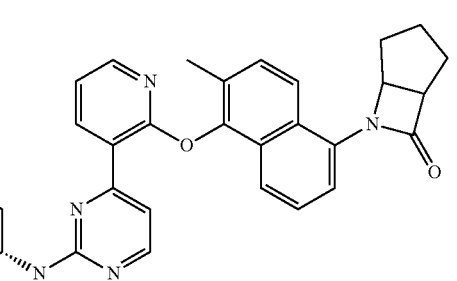 | 6-(6-Methyl-5-((3-(2-(((S)-piperidin-3-yl)amino)pyrimidin-4-yl)pyridin-2-yl)oxy)naphthalen-1-yl)-6-azabicyclo[3.2.0]heptan-7-one | 0.457 |

TABLE 1-continued

| No. | Structure | Name | XBP1s-luc 293 LUC (IC$_{50}$) (μmol) |
|---|---|---|---|
| 249 | 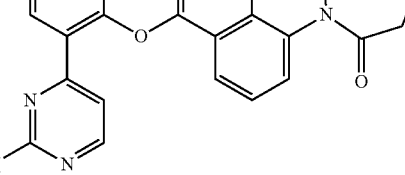 | 1-[6-Methyl-5-[[3-[2-[[(3S)-3-piperidyl]amino]pyrimidin-4-yl]-2-pyridyl]oxy]-1-naphthyl]azepan-2-one | 0.309 |
| 250 | 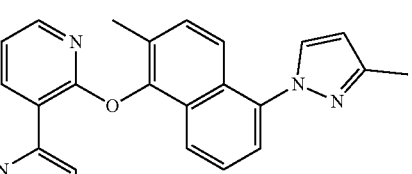 | 4-[2-[[2-Methyl-5-(3-methylpyrazol-1-yl)-1-naphthyl]oxy]-3-pyridyl]-N-[(3S)-3-piperidyl]pyrimidin-2-amine | 0.258 |
| 251 | 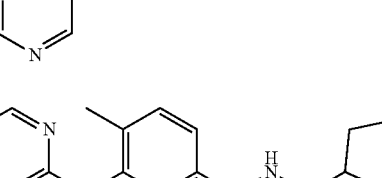 | 2,2-Difluoro-N-(6-methyl-5-((3-(2-(((S)-piperidin-3-yl)amino)pyrimidin-4-yl)pyridin-2-yl)oxy)naphthalen-1-yl)cyclopentane-1-carboxamide | 0.145 |
| 252 | 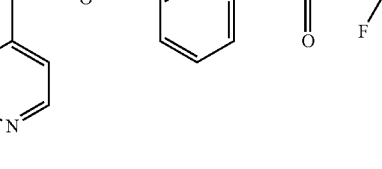 | 3,3,3-Trifluoro-N-[6-methyl-5-[[3-[2-[[(3S)-3-piperidyl]amino]pyrimidin-4-yl]-2-pyridyl]oxy]-1-naphthyl]propanamide | 0.134 |
| 253 | 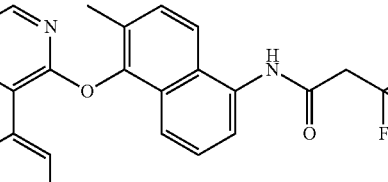 | (S)-N-(6-Methyl-5-((3-(2-(((S)-piperidin-3-yl)amino)pyrimidin-4-yl)pyridin-2-yl)oxy)naphthalen-1-yl)spiro[2.4]heptane-1-carboxamide | 0.352 |
| 254 | 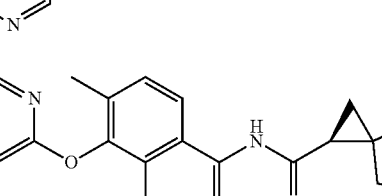 | (R)-N-(6-Methyl-5-((3-(2-(((S)-piperidin-3-yl)amino)pyrimidin-4-yl)pyridin-2-yl)oxy)naphthalen-1-yl)spiro[2.4]heptane-1-carboxamide | 0.069 |

TABLE 1-continued

| No. | Structure | Name | XBP1s-luc 293 LUC (IC$_{50}$) (μmol) |
|---|---|---|---|
| 255 | 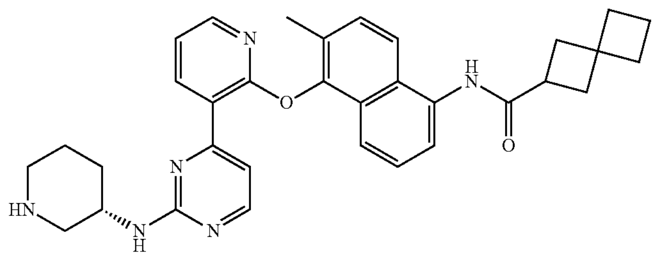 [SMILES: Cc1ccc2c(NC(=O)C3CC4(CCC4)C3)cccc2c1Oc1ncccc1-c1ccnc(N[C@H]2CCCNC2)n1] | N-[6-Methyl-5-[[3-[2-[[(3S)-3-piperidyl]amino]pyrimidin-4-yl]-2-pyridyl]oxy]-1-naphthyl]spiro[3.3]heptane-2-carboxamide | 0.182 |
| 256 | 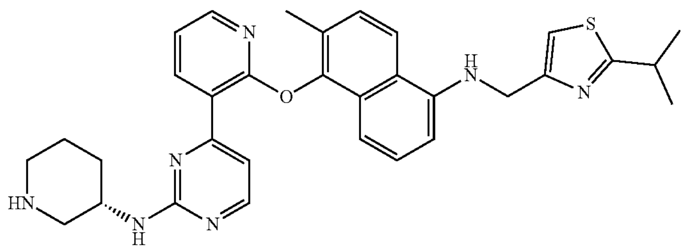 [SMILES: Cc1ccc2c(NCc3csc(C(C)C)n3)cccc2c1Oc1ncccc1-c1ccnc(N[C@H]2CCCNC2)n1] | 4-[2-[[5-[(2-Isopropylthiazol-4-yl)methylamino]-2-methyl-1-naphthyl]oxy]-3-pyridyl]-N-[(3S)-3-piperidyl]pyrimidin-2-amine | 0.21 |
| 257 | 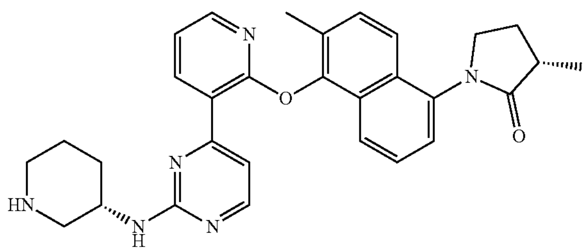 [SMILES: Cc1ccc2c(N3CC[C@H](C)C3=O)cccc2c1Oc1ncccc1-c1ccnc(N[C@H]2CCCNC2)n1] | (S)-3-Methyl-1-(6-methyl-5-((3-(2-((S)-piperidin-3-ylamino)pyrimidin-4-yl)pyridin-2-yl)oxy)naphthalen-1-yl)pyrrolidin-2-one | 0.264 |
| 258 | 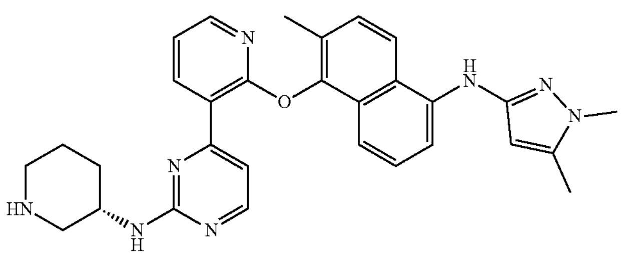 [SMILES: Cc1ccc2c(Nc3cc(C)n(C)n3)cccc2c1Oc1ncccc1-c1ccnc(N[C@H]2CCCNC2)n1] | 4-[2-[[5-[(1,5-Dimethylpyrazol-3-yl)amino]-2-methyl-1-naphthyl]oxy]-3-pyridyl]-N-[(3S)-3-piperidyl]pyrimidin-2-amine | 0.419 |
| 259 | 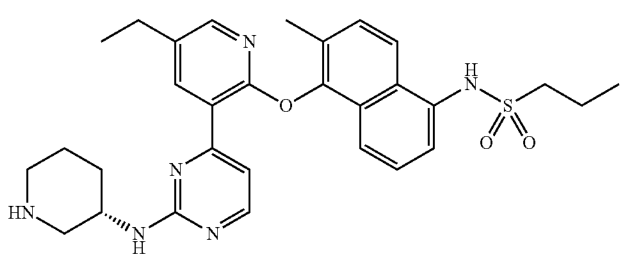 [SMILES: CCCS(=O)(=O)Nc1cccc2c(Oc3ncc(CC)cc3-c3ccnc(N[C@H]4CCCNC4)n3)c(C)ccc12] | (S)-N-(5-((5-Ethyl-3-(2-(piperidin-3-ylamino)pyrimidin-4-yl)pyridin-2-yl)oxy)-6-methylnaphthalen-1-yl)propane-1-sulfonamide | 0.361 |
| 260 | 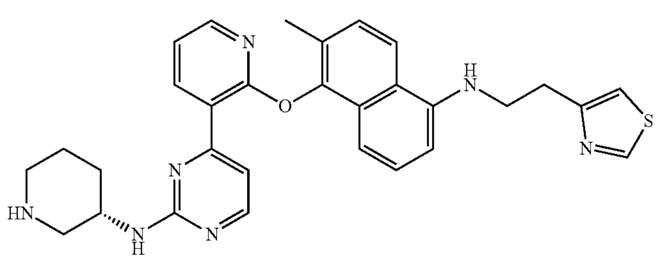 [SMILES: Cc1ccc2c(NCCc3cscn3)cccc2c1Oc1ncccc1-c1ccnc(N[C@H]2CCCNC2)n1] | 4-[2-[[2-Methyl-5-(2-thiazol-4-ylethylamino)-1-naphthyl]oxy]-3-pyridyl]-N-[(3S)-3-piperidyl]pyrimidin-2-amine | 0.103 |

TABLE 1-continued

| No. | Structure | Name | XBP1s-luc 293 LUC (IC$_{50}$) (μmol) |
|---|---|---|---|
| 261 | 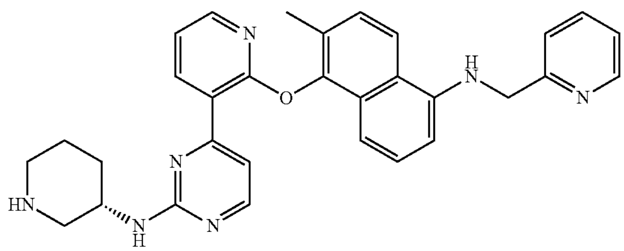 [SMILES: Cc1ccc2c(NCc3ccccn3)cccc2c1Oc1ncccc1-c1ccnc(N[C@H]2CCCNC2)n1] | 4-[2-[[2-Methyl-5-(2-pyridylmethylamino)-1-naphthyl]oxy]-3-pyridyl]-N-[(3S)-3-piperidyl]pyrimidin-2-amine | 0.22 |
| 262 | 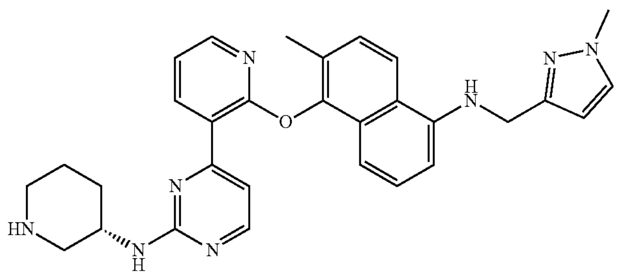 [SMILES: Cc1ccc2c(NCc3ccn(C)n3)cccc2c1Oc1ncccc1-c1ccnc(N[C@H]2CCCNC2)n1] | 4-[2-[[2-Methyl-5-[(1-methylpyrazol-3-yl)methylamino]-1-naphthyl]oxy]-3-pyridyl]-N-[(3S)-3-piperidyl]pyrimidin-2-amine | 0.171 |
| 263 | 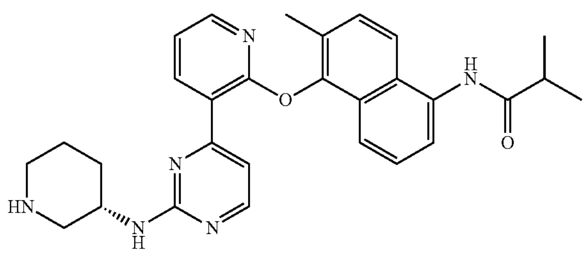 [SMILES: Cc1ccc2c(NC(=O)C(C)C)cccc2c1Oc1ncccc1-c1ccnc(N[C@H]2CCCNC2)n1] | (S)-N-(6-Methyl-5-((3-(2-(piperidin-3-ylamino)pyrimidin-4-yl)pyridin-2-yl)oxy)naphthalen-1-yl)isobutyramide | 0.362 |
| 264 | 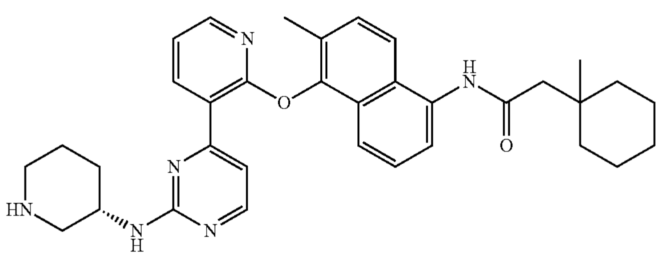 [SMILES: Cc1ccc2c(NC(=O)CC3(C)CCCCC3)cccc2c1Oc1ncccc1-c1ccnc(N[C@H]2CCCNC2)n1] | (S)-N-(6-Methyl-5-((3-(2-(piperidin-3-ylamino)pyrimidin-4-yl)pyridin-2-yl)oxy)naphthalen-1-yl)-2-(1-methylcyclohexyl)acetamide | 0.350 |
| 265 | 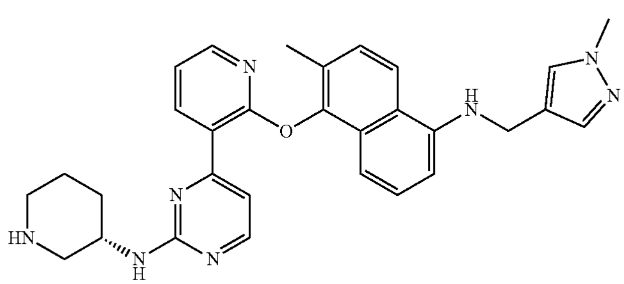 [SMILES: Cc1ccc2c(NCc3cnn(C)c3)cccc2c1Oc1ncccc1-c1ccnc(N[C@H]2CCCNC2)n1] | 4-[2-[[2-Methyl-5-[(1-methylpyrazol-4-yl)methylamino]-1-naphthyl]oxy]-3-pyridyl]-N-[(3S)-3-piperidyl]pyrimidin-2-amine | 0.393 |

TABLE 1-continued

| No. | Structure | Name | XBP1s-luc 293 LUC (IC$_{50}$) (μmol) |
|---|---|---|---|
| 266 | 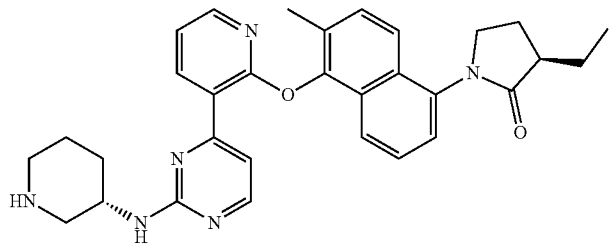 [SMILES: CC[C@@H]1CCN(c2cccc3c(Oc4ncccc4-c4ccnc(N[C@H]5CCCNC5)n4)c(C)ccc23)C1=O] | (R)-3-Ethyl-1-(6-methyl-5-((3-(2-(((S)-piperidin-3-yl)amino)pyrimidin-4-yl)pyridin-2-yl)oxy)naphthalen-1-yl)pyrrolidin-2-one | 0.121 |
| 267 | 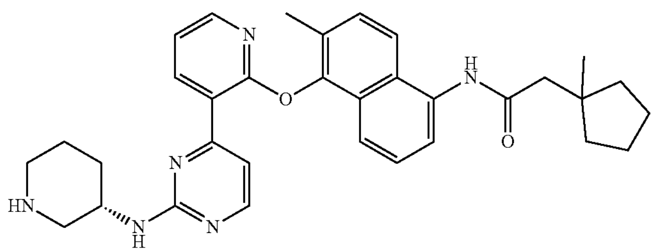 [SMILES: Cc1ccc2c(NC(=O)CC3(C)CCCC3)cccc2c1Oc1ncccc1-c1ccnc(N[C@H]2CCCNC2)n1] | 2-(1-Methylcyclopentyl)-N-[6-methyl-5-[[3-[2-[[(3S)-3-piperidyl]amino]pyrimidin-4-yl]-2-pyridyl]oxy]-1-naphthyl]acetamide | 0.162 |
| 268 | 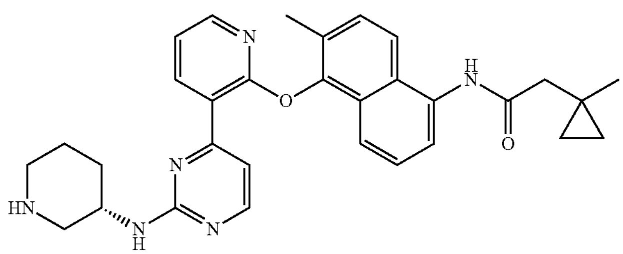 [SMILES: Cc1ccc2c(NC(=O)CC3(C)CC3)cccc2c1Oc1ncccc1-c1ccnc(N[C@H]2CCCNC2)n1] | 2-(1-Methylcyclopropyl)-N-[6-methyl-5-[[3-[2-[[(3S)-3-piperidyl]amino]pyrimidin-4-yl]-2-pyridyl]oxy]-1-naphthyl]acetamide | 0.257 |
| 269 | 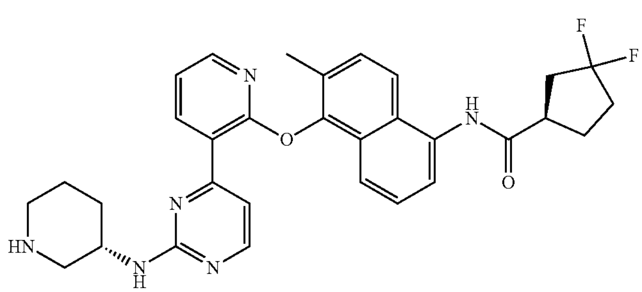 [SMILES: Cc1ccc2c(NC(=O)[C@@H]3CCC(F)(F)C3)cccc2c1Oc1ncccc1-c1ccnc(N[C@H]2CCCNC2)n1] | (R)-3,3-Difluoro-N-(6-methyl-5-((3-(2-(((S)-piperidin-3-yl)amino)pyrimidin-4-yl)pyridin-2-yl)oxy)naphthalen-1-yl)cyclopentane-1-carboxamide | 0.336 |
| 270 | 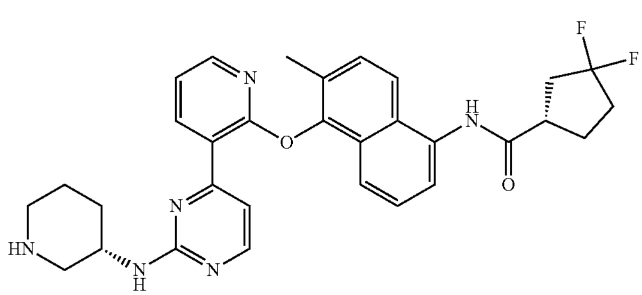 [SMILES: Cc1ccc2c(NC(=O)[C@H]3CCC(F)(F)C3)cccc2c1Oc1ncccc1-c1ccnc(N[C@H]2CCCNC2)n1] | (S)-3,3-Difluoro-N-(6-methyl-5-((3-(2-(((S)-piperidin-3-yl)amino)pyrimidin-4-yl)pyridin-2-yl)oxy)naphthalen-1-yl)cyclopentane-1-carboxamide | 0.189 |

TABLE 1-continued

| No. | Structure | Name | XBP1s-luc 293 LUC (IC$_{50}$) (μmol) |
|---|---|---|---|
| 271 | 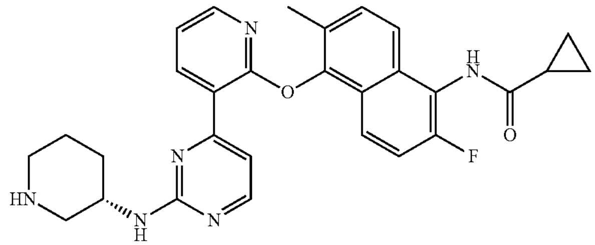 [SMILES: Cc1ccc2c(NC(=O)C3CC3)c(F)ccc2c1Oc1ncccc1-c1ccnc(N[C@H]2CCCNC2)n1] | N-[2-Fluoro-6-methyl-5-[[3-[2-[[(3S)-3-piperidyl]amino]pyrimidin-4-yl]-2-pyridyl]oxy]-1-naphthyl]cyclopropanecarboxamide | 0.271 |
| 272 | 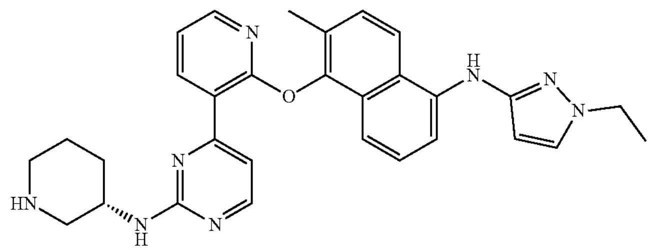 [SMILES: CCn1ccc(Nc2cccc3c(Oc4ncccc4-c4ccnc(N[C@H]5CCCNC5)n4)c(C)ccc23)n1] | 4-[2-[[5-[(1-Ethylpyrazol-3-yl)amino]-2-methyl-1-naphthyl]oxy]-3-pyridyl]-N-[(3S)-3-piperidyl]pyrimidin-2-amine | 0.463 |
| 273 | 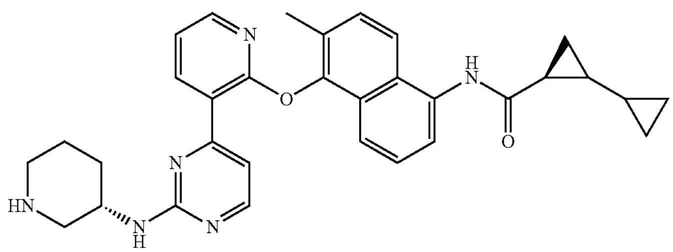 | (2S)-N-(6-Methyl-5-((3-(2-(((S)-piperidin-3-yl)amino)pyrimidin-4-yl)pyridin-2-yl)oxy)naphthalen-1-yl)-[1,1'-bi(cyclopropane)]-2-carboxamide | 0.305 |
| 274 | 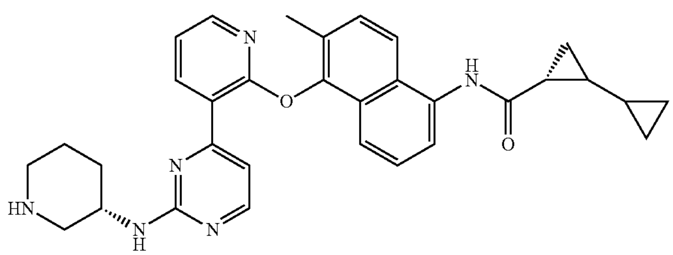 | (2R)-N-(6-Methyl-5-((3-(2-(((S)-piperidin-3-yl)amino)pyrimidin-4-yl)pyridin-2-yl)oxy)naphthalen-1-yl)-[1,1'-bi(cyclopropane)]-2-carboxamide | 0.10 |
| 275 | 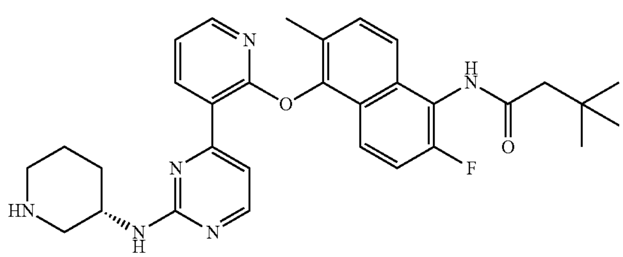 [SMILES: Cc1ccc2c(NC(=O)CC(C)(C)C)c(F)ccc2c1Oc1ncccc1-c1ccnc(N[C@H]2CCCNC2)n1] | N-[2-Fluoro-6-methyl-5-[[3-[2-[[(3S)-3-piperidyl]amino]pyrimidin-4-yl]-2-pyridyl]oxy]-1-naphthyl]-3,3-dimethylbutanamide | 0.075 |
| 276 | 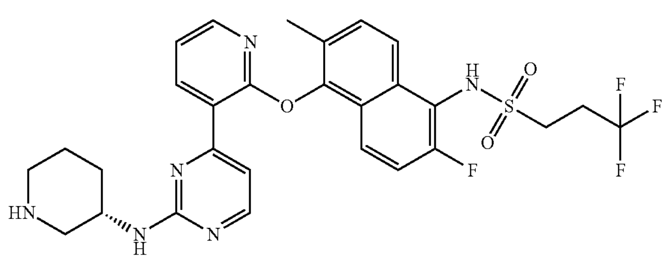 [SMILES: Cc1ccc2c(NS(=O)(=O)CCC(F)(F)F)c(F)ccc2c1Oc1ncccc1-c1ccnc(N[C@H]2CCCNC2)n1] | 3,3,3-Trifluoro-N-[2-fluoro-6-methyl-5-[[3-[2-[[(3S)-3-piperidyl]amino]pyrimidin-4-yl]-2-pyridyl]oxy]-1-naphthyl]propane-1-sulfonamide | 0.0441 |

TABLE 1-continued

| No. | Structure | Name | XBP1s-luc 293 LUC (IC$_{50}$) (μmol) |
|---|---|---|---|
| 277 | 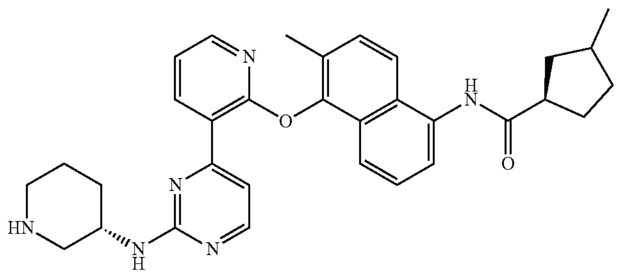 | (1R)-3-Methyl-N-(6-methyl-5-((3-(2-(((S)-piperidin-3-yl)amino)pyrimidin-4-yl)pyridin-2-yl)oxy)naphthalen-1-yl)cyclopentane-1-carboxamide | 0.171 |
| 278 | 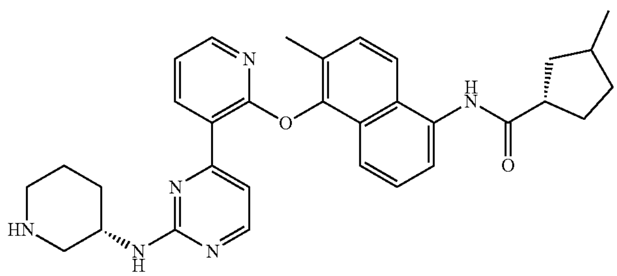 | (1S)-3-Methyl-N-(6-methyl-5-((3-(2-(((S)-piperidin-3-yl)amino)pyrimidin-4-yl)pyridin-2-yl)oxy)naphthalen-1-yl)cyclopentane-1-carboxamide | 0.313 |
| 279 | 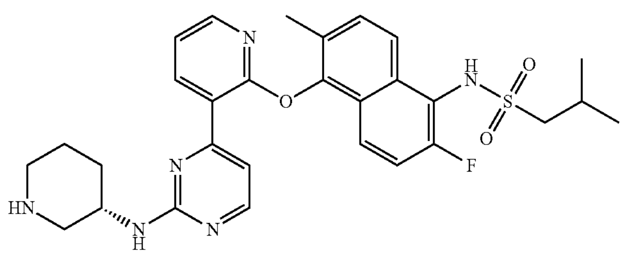 [SMILES: Cc1ccc2c(NS(=O)(=O)CC(C)C)c(F)ccc2c1Oc1ncccc1-c1ccnc(N[C@H]2CCCNC2)n1] | N-[2-Fluoro-6-methyl-5-[[3-[2-[[(3S)-3-piperidyl]amino]pyrimidin-4-yl]-2-pyridyl]oxy]-1-naphthyl]-2-methyl-propane-1-sulfonamide | 0.0247 |
| 280 | 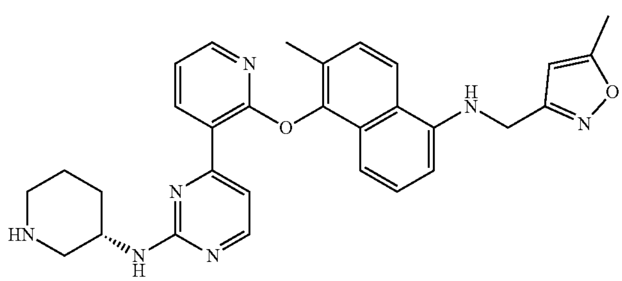 [SMILES: Cc1cc(CNc2cccc3c(Oc4ncccc4-c4ccnc(N[C@H]5CCCNC5)n4)c(C)ccc23)no1] | 4-[2-[[2-Methyl-5-[(5-methylisoxazol-3-yl)methylamino]-1-naphthyl]oxy]-3-pyridyl]-N-[(3S)-3-piperidyl]pyrimidin-2-amine | 0.134 |
| 281 | 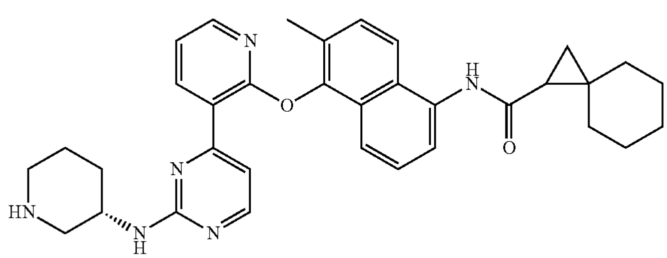 [SMILES: Cc1ccc2c(NC(=O)C3CC34CCCCC4)cccc2c1Oc1ncccc1-c1ccnc(N[C@H]2CCCNC2)n1] | N-(6-Methyl-5-((3-(2-(((S)-piperidin-3-yl)amino)pyrimidin-4-yl)pyridin-2-yl)oxy)naphthalen-1-yl)spiro[2.5]octane-1-carboxamide | 0.089 |

TABLE 1-continued

| No. | Structure | Name | XBP1s-luc 293 LUC (IC$_{50}$) (μmol) |
|---|---|---|---|
| 282 | 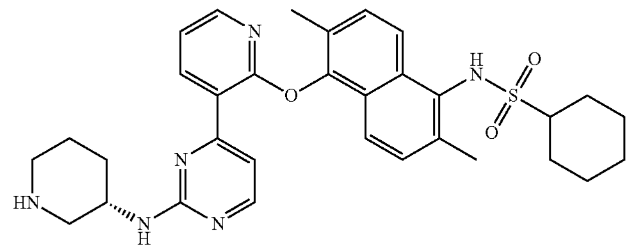 [SMILES: Cc1ccc2c(Oc3ncccc3-c3ccnc(N[C@H]4CCCNC4)n3)c(C)ccc2c1NS(=O)(=O)C1CCCCC1] | N-[2-Fluoro-6-methyl-5-[[3-[2-[[(3S)-3-piperidyl]amino]pyrimidin-4-yl]-2-pyridyl]oxy]-1-naphthyl]cyclohexanesulfonamide | 0.0248 |
| 283 | 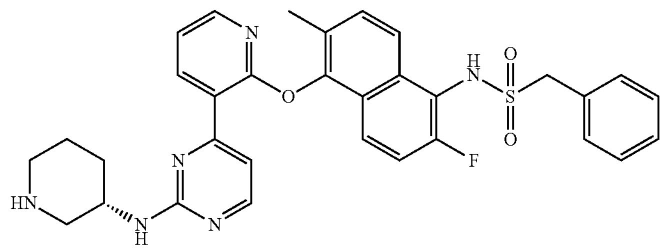 [SMILES: Cc1ccc2c(NS(=O)(=O)Cc3ccccc3)c(F)ccc2c1Oc1ncccc1-c1ccnc(N[C@H]2CCCNC2)n1] | N-[2-Fluoro-6-methyl-5-[[3-[2-[[(3S)-3-piperidyl]amino]pyrimidin-4-yl]-2-pyridyl]oxy]-1-naphthyl]-1-phenyl-methanesulfonamide | 0.00296 |
| 284 | 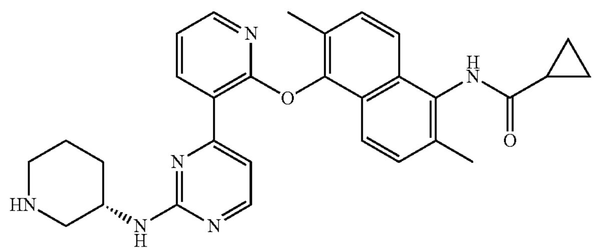 [SMILES: Cc1ccc2c(Oc3ncccc3-c3ccnc(N[C@H]4CCCNC4)n3)c(C)ccc2c1NC(=O)C1CC1] | N-[2,6-Dimethyl-5-[[3-[2-[[(3S)-3-piperidyl]amino]pyrimidin-4-yl]-2-pyridyl]oxy]-1-naphthyl]cyclopropanecarboxamide | 0.0982 |
| 285 | 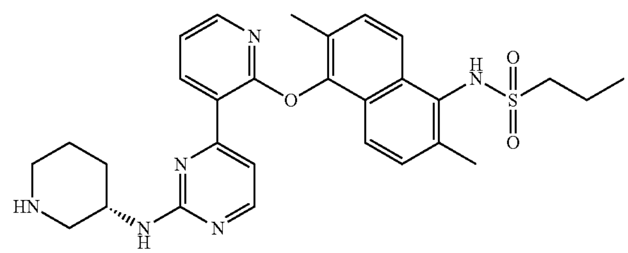 [SMILES: CCCS(=O)(=O)Nc1c(C)ccc2c(Oc3ncccc3-c3ccnc(N[C@H]4CCCNC4)n3)c(C)ccc12] | N-[2,6-Dimethyl-5-[[3-[2-[[(3S)-3-piperidyl]amino]pyrimidin-4-yl]-2-pyridyl]oxy]-1-naphthyl]propane-1-sulfonamide | 0.071 |
| 286 | 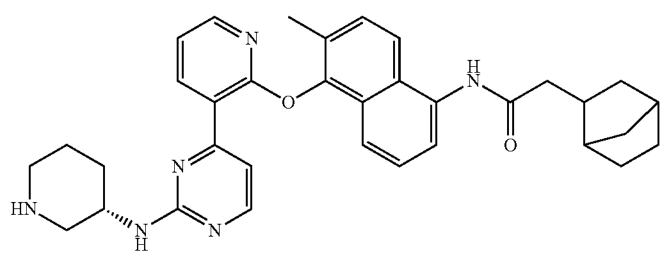 [SMILES: Cc1ccc2c(NC(=O)CC3CC4CCC3C4)cccc2c1Oc1ncccc1-c1ccnc(N[C@H]2CCCNC2)n1] | 2-(Bicyclo[2.2.1]heptan-2-yl)-N-(6-methyl-5-((3-(2-(((S)-piperidin-3-yl)amino)pyrimidin-4-yl)pyridin-2-yl)oxy)naphthalen-1-yl)acetamide | 0.174 |
| 287 | 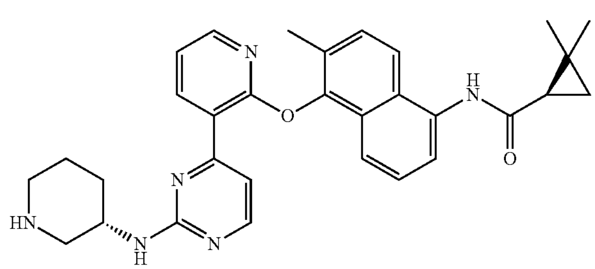 [SMILES: Cc1ccc2c(NC(=O)[C@@H]3CC3(C)C)cccc2c1Oc1ncccc1-c1ccnc(N[C@H]2CCCNC2)n1] | (R)-2,2-Dimethyl-N-(6-methyl-5-((3-(2-(((S)-piperidin-3-yl)amino)pyrimidin-4-yl)pyridin-2-yl)oxy)naphthalen-1-yl)cyclopropane-1-carboxamide | 0.0394 |

TABLE 1-continued

| No. | Structure | Name | XBP1s-luc 293 LUC (IC$_{50}$) (μmol) |
|---|---|---|---|
| 288 | 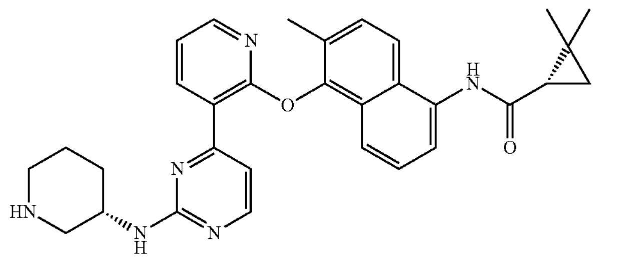 [SMILES: Cc1ccc2c(NC(=O)[C@H]3CC3(C)C)cccc2c1Oc1ncccc1-c1ccnc(N[C@H]2CCCNC2)n1] | (S)-2,2-Dimethyl-N-(6-methyl-5-((3-(2-(((S)-piperidin-3-yl)amino)pyrimidin-4-yl)pyridin-2-yl)oxy)naphthalen-1-yl)cyclopropane-1-carboxamide | 0.185 |
| 289 | 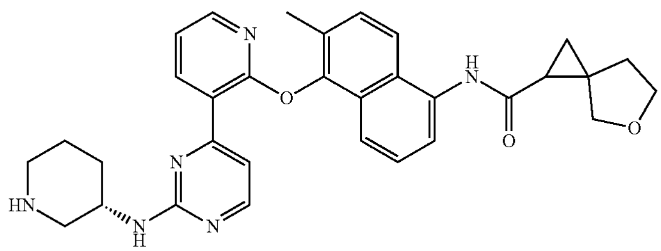 [SMILES: Cc1ccc2c(NC(=O)C3CC34CCOC4)cccc2c1Oc1ncccc1-c1ccnc(N[C@H]2CCCNC2)n1] | N-(6-Methyl-5-((3-(2-(((S)-piperidin-3-yl)amino)pyrimidin-4-yl)pyridin-2-yl)oxy)naphthalen-1-yl)-5-oxaspiro[2.4]heptane-1-carboxamide | 0.431 |
| 290 | 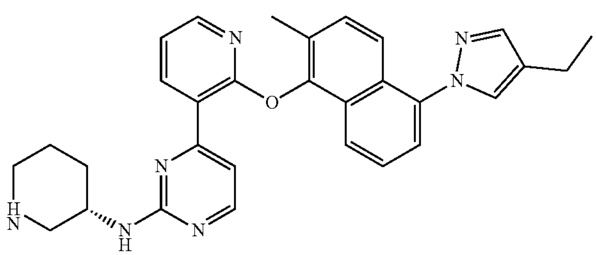 [SMILES: CCc1cnn(-c2cccc3c(Oc4ncccc4-c4ccnc(N[C@H]5CCCNC5)n4)c(C)ccc23)c1] | 4-[2-[[5-(4-Ethylpyrazol-1-yl)-2-methyl-1-naphthyl]oxy]-3-pyridyl]-N-[(3S)-3-piperidyl]pyrimidin-2-amine | 0.409 |
| 291 | 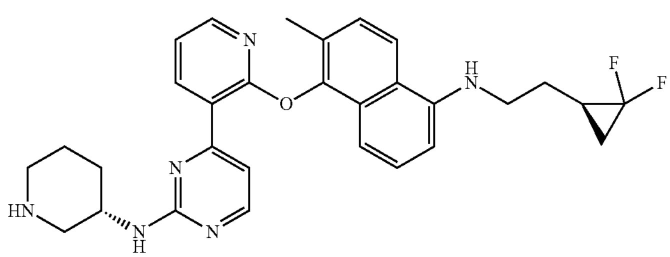 [SMILES: Cc1ccc2c(NCC[C@@H]3CC3(F)F)cccc2c1Oc1ncccc1-c1ccnc(N[C@H]2CCCNC2)n1] | 4-(2-((5-((2-((R)-2,2-difluorocyclopropyl)ethyl)amino)-2-methylnaphthalen-1-yl)oxy)pyridin-3-yl)-N-((S)-piperidin-3-yl)pyrimidin-2-amine | 0.361 |
| 292 | 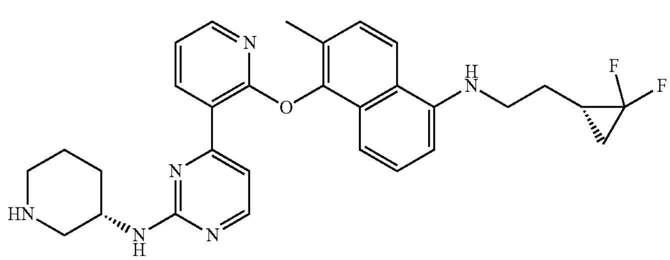 [SMILES: Cc1ccc2c(NCC[C@H]3CC3(F)F)cccc2c1Oc1ncccc1-c1ccnc(N[C@H]2CCCNC2)n1] | 4-(2-((5-((2-((S)-2,2-Difluorocyclopropyl)ethyl)amino)-2-methylnaphthalen-1-yl)oxy)pyridin-3-yl)-N-((S)-piperidin-3-yl)pyrimidin-2-amine | 0.294 |

TABLE 1-continued

| No. | Structure | Name | XBP1s-luc 293 LUC (IC$_{50}$) (μmol) |
|---|---|---|---|
| 293 | 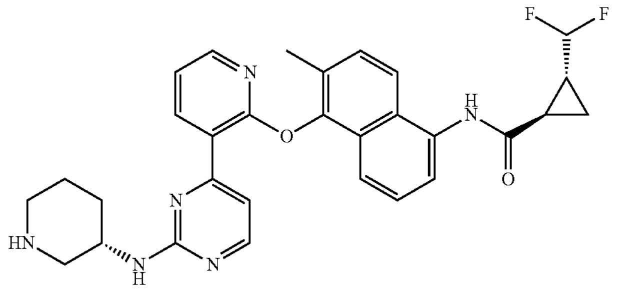 [SMILES: Cc1ccc2c(NC(=O)[C@@H]3C[C@H]3C(F)F)cccc2c1Oc1ncccc1-c1ccnc(N[C@H]2CCCNC2)n1] | (1R,2R)-2-(Difluoromethyl)-N-(6-methyl-5-((3-(2-(((S)-piperidin-3-yl)amino)pyrimidin-4-yl)pyridin-2-yl)oxy)naphthalen-1-yl)cyclopropane-1-carboxamide | 0.0905 |
| 294 | 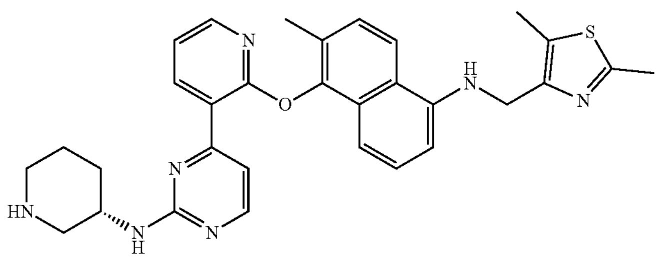 [SMILES: Cc1nc(CNc2cccc3c(Oc4ncccc4-c4ccnc(N[C@H]5CCCNC5)n4)c(C)ccc23)c(C)s1] | 4-[2-[[5-[(2,5-Dimethylthiazol-4-yl)methylamino]-2-methyl-1-naphthyl]oxy]-3-pyridyl]-N-[(3S)-3-piperidyl]pyrimidin-2-amine | 0.241 |
| 295 | 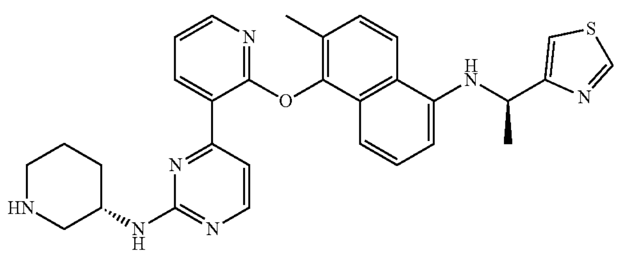 [SMILES: Cc1ccc2c(N[C@H](C)c3cscn3)cccc2c1Oc1ncccc1-c1ccnc(N[C@H]2CCCNC2)n1] | 4-(2-((2-Methyl-5-((1-(thiazol-4-yl)ethyl)amino)naphthalen-1-yl)oxy)pyridin-3-yl)-N-((S)-piperidin-3-yl)pyrimidin-2-amine | 0.209 |
| 296 | 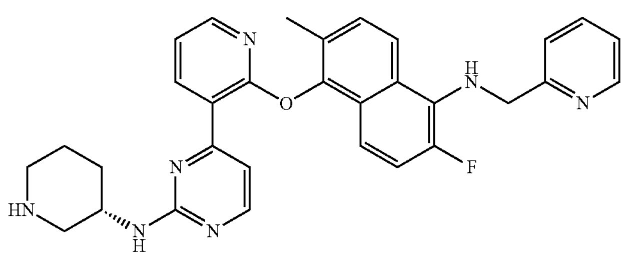 [SMILES: Cc1ccc2c(NCc3ccccn3)c(F)ccc2c1Oc1ncccc1-c1ccnc(N[C@H]2CCCNC2)n1] | 4-[2-[[6-Fluoro-2-methyl-5-(2-pyridylmethylamino)-1-naphthyl]oxy]-3-pyridyl]-N-[(3S)-3-piperidyl]pyrimidin-2-amine | 0.22 |
| 297 | 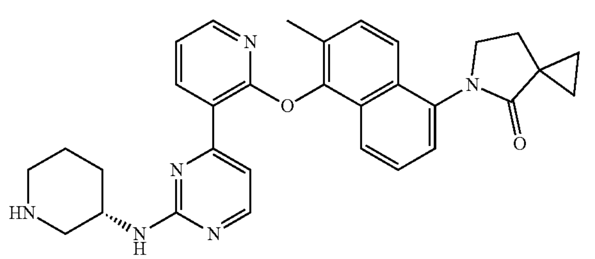 [SMILES: Cc1ccc2c(N3CCC4(CC4)C3=O)cccc2c1Oc1ncccc1-c1ccnc(N[C@H]2CCCNC2)n1] | 5-[6-Methyl-5-[[3-[2-[[(3S)-3-piperidyl]amino]pyrimidin-4-yl]-2-pyridyl]oxy]-1-naphthyl]-5-azaspiro[2.4]heptan-4-one | 0.173 |

TABLE 1-continued

| No. | Structure | Name | XBP1s-luc 293 LUC (IC$_{50}$) (μmol) |
|---|---|---|---|
| 298 | 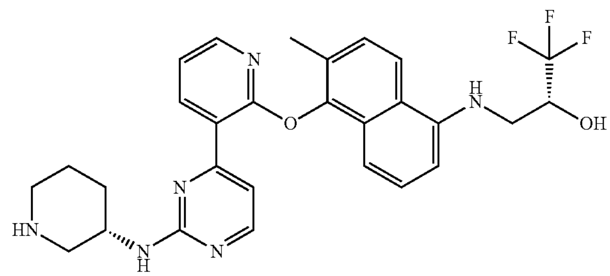 [SMILES: Cc1ccc2c(NC[C@@H](O)C(F)(F)F)cccc2c1Oc1ncccc1-c1ccnc(N[C@H]2CCCNC2)n1] | (2R)-1,1,1-Trifluoro-3-[[6-methyl-5-[[3-[2-[[(3S)-3-piperidyl]amino]pyrimidin-4-yl]-2-pyridyl]oxy]-1-naphthyl]amino]propan-2-ol | 0.0672 |
| 299 | 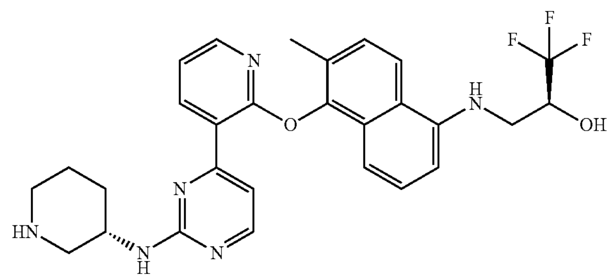 [SMILES: Cc1ccc2c(NC[C@H](O)C(F)(F)F)cccc2c1Oc1ncccc1-c1ccnc(N[C@H]2CCCNC2)n1] | (2S)-1,1,1-Trifluoro-3-[[6-methyl-5-[[3-[2-[[(3S)-3-piperidyl]amino]pyrimidin-4-yl]-2-pyridyl]oxy]-1-naphthyl]amino]propan-2-ol | 0.00858 |
| 300 | 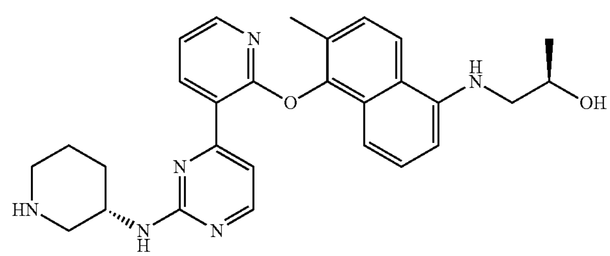 [SMILES: Cc1ccc2c(NC[C@@H](C)O)cccc2c1Oc1ncccc1-c1ccnc(N[C@H]2CCCNC2)n1] | (2R)-1-[[6-Methyl-5-[[3-[2-[[(3S)-3-piperidyl]amino]pyrimidin-4-yl]-2-pyridyl]oxy]-1-naphthyl]amino]propan-2-ol | 0.0554 |
| 301 | 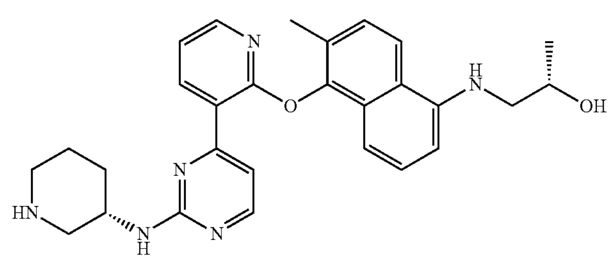 [SMILES: Cc1ccc2c(NC[C@H](C)O)cccc2c1Oc1ncccc1-c1ccnc(N[C@H]2CCCNC2)n1] | (2S)-1-[[6-Methyl-5-[[3-[2-[[(3S)-3-piperidyl]amino]pyrimidin-4-yl]-2-pyridyl]oxy]-1-naphthyl]amino]propan-2-ol | 0.424 |
| 302 | 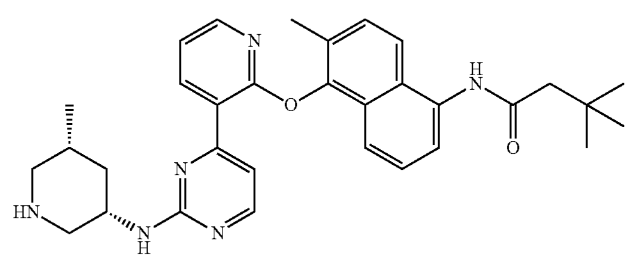 [SMILES: Cc1ccc2c(NC(=O)CC(C)(C)C)cccc2c1Oc1ncccc1-c1ccnc(N[C@@H]2CNC[C@H](C)C2)n1] | 3,3-Dimethyl-N-[6-methyl-5-[[3-[2-[[(3S,5R)-5-methyl-3-piperidyl]amino]pyrimidin-4-yl]-2-pyridyl]oxy]-1-naphthyl]butanamide | 0.0935 |

TABLE 1-continued

| No. | Structure | Name | XBP1s-luc 293 LUC (IC$_{50}$) (μmol) |
|---|---|---|---|
| 303 | 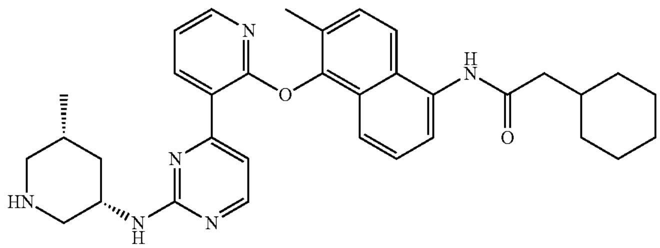 [SMILES: Cc1ccc2c(NC(=O)CC3CCCCC3)cccc2c1Oc1ncccc1-c1ccnc(N[C@@H]2CNC[C@H](C)C2)n1] | 2-Cyclohexyl-N-[6-methyl-5-[[3-[2-[[(3S,5R)-5-methyl-3-piperidyl]amino]pyrimidin-4-yl]-2-pyridyl]oxy]-1-naphthyl]acetamide | 0.126 |
| 304 | 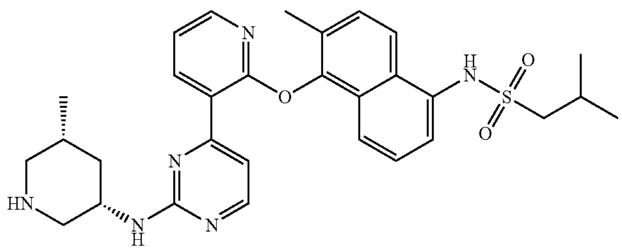 [SMILES: Cc1ccc2c(NS(=O)(=O)CC(C)C)cccc2c1Oc1ncccc1-c1ccnc(N[C@@H]2CNC[C@H](C)C2)n1] | 2-Methyl-N-[6-methyl-5-[[3-[2-[[(3S,5R)-5-methyl-3-piperidyl]amino]pyrimidin-4-yl]-2-pyridyl]oxy]-1-naphthyl]propane-1-sulfonamide | 0.105 |
| 305 | 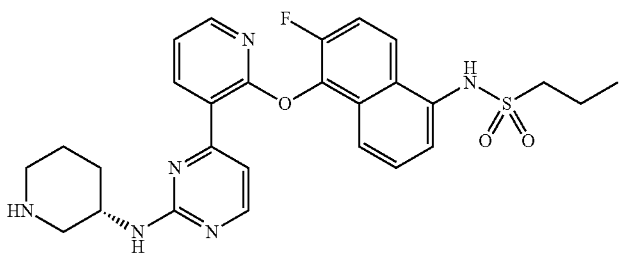 [SMILES: CCCS(=O)(=O)Nc1cccc2c(Oc3ncccc3-c3ccnc(N[C@H]4CCCNC4)n3)c(F)ccc12] | N-[6-Fluoro-5-[[3-[2-[[(3S)-3-piperidyl]amino]pyrimidin-4-yl]-2-pyridyl]oxy]-1-naphthyl]propane-1-sulfonamide | 0.481 |
| 306 | 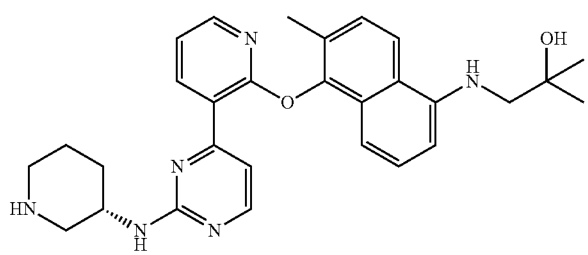 [SMILES: Cc1ccc2c(NCC(C)(C)O)cccc2c1Oc1ncccc1-c1ccnc(N[C@H]2CCCNC2)n1] | 2-Methyl-1-[[6-methyl-5-[[3-[2-[[(3S)-3-piperidyl]amino]pyrimidin-4-yl]-2-pyridyl]oxy]-1-naphthyl]amino]propan-2-ol | 0.24 |
| 307 | 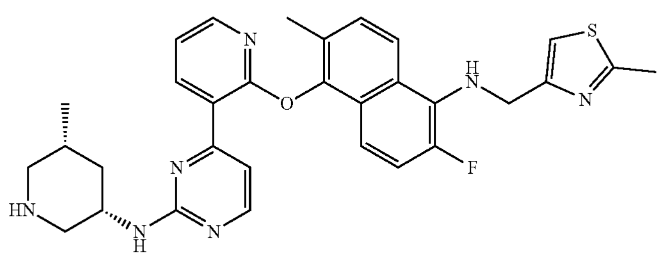 [SMILES: Cc1nc(CNc2c(F)ccc3c(Oc4ncccc4-c4ccnc(N[C@@H]5CNC[C@H](C)C5)n4)c(C)ccc23)cs1] | 4-[2-[[6-Fluoro-2-methyl-5-[(2-methylthiazol-4-yl)methylamino]-1-naphthyl]oxy]-3-pyridyl]-N-[(3S,5R)-5-methyl-3-piperidyl]pyrimidin-2-amine | 0.36 |
| 308 | 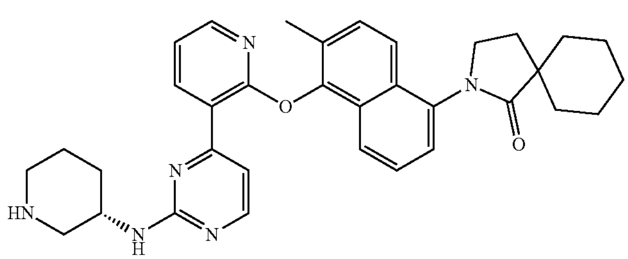 [SMILES: Cc1ccc2c(N3CCC4(CCCCC4)C3=O)cccc2c1Oc1ncccc1-c1ccnc(N[C@H]2CCCNC2)n1] | 2-[6-Methyl-5-[[3-[2-[[(3S)-3-piperidyl]amino]pyrimidin-4-yl]-2-pyridyl]oxy]-1-naphthyl]-2-azaspiro[4.5]decan-1-one | 0.211 |

TABLE 1-continued

| No. | Structure | Name | XBP1s-luc 293 LUC (IC$_{50}$) (μmol) |
|---|---|---|---|
| 309 | 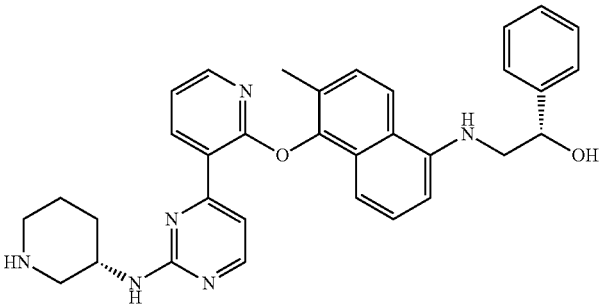 [SMILES: Cc1ccc2c(NC[C@@H](O)c3ccccc3)cccc2c1Oc1ncccc1-c1ccnc(N[C@H]2CCCNC2)n1] | (1S)-2-[[6-Methyl-5-[[3-[2-[[(3S)-3-piperidyl]amino]pyrimidin-4-yl]-2-pyridyl]oxy]-1-naphthyl]amino]-1-phenyl-ethanol | 0.433 |
| 310 | 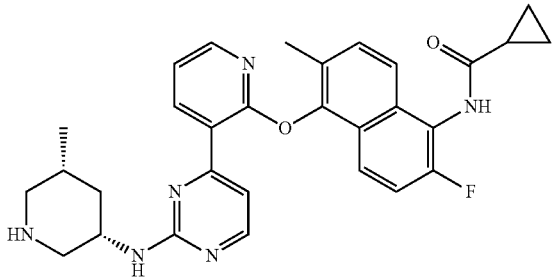 [SMILES: Cc1ccc2c(NC(=O)C3CC3)c(F)ccc2c1Oc1ncccc1-c1ccnc(N[C@@H]2CNC[C@H](C)C2)n1] | N-[2-Fluoro-6-methyl-5-[[3-[2-[[(3S,5R)-5-methyl-3-piperidyl]amino]pyrimidin-4-yl]-2-pyridyl]oxy]-1-naphthyl]cyclopropanecarboxamide | 0.135 |
| 311 | 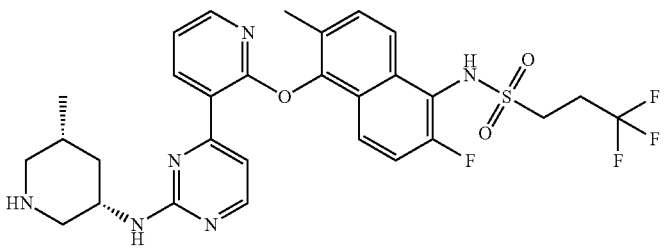 [SMILES: Cc1ccc2c(NS(=O)(=O)CCC(F)(F)F)c(F)ccc2c1Oc1ncccc1-c1ccnc(N[C@@H]2CNC[C@H](C)C2)n1] | 3,3,3-Trifluoro-N-[2-fluoro-6-methyl-5-[[3-[2-[[(3S,5R)-5-methyl-3-piperidyl]amino]pyrimidin-4-yl]-2-pyridyl]oxy]-1-naphthyl]propane-1-sulfonamide | 0.00616 |
| 312 | 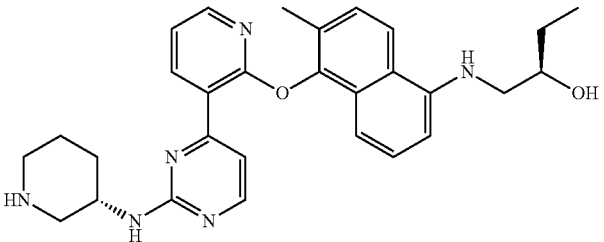 [SMILES: CC[C@@H](O)CNc1cccc2c(Oc3ncccc3-c3ccnc(N[C@H]4CCCNC4)n3)c(C)ccc12] | (2R)-1-[[6-Methyl-5-[[3-[2-[[(3S)-3-piperidyl]amino]pyrimidin-4-yl]-2-pyridyl]oxy]-1-naphthyl]amino]butan-2-ol | 0.0274 |
| 313 | 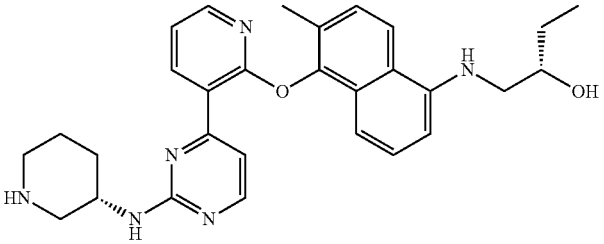 [SMILES: CC[C@H](O)CNc1cccc2c(Oc3ncccc3-c3ccnc(N[C@H]4CCCNC4)n3)c(C)ccc12] | (2S)-1-[[6-Methyl-5-[[3-[2-[[(3S)-3-piperidyl]amino]pyrimidin-4-yl]-2-pyridyl]oxy]-1-naphthyl]amino]butan-2-ol | 0.148 |

TABLE 1-continued

| No. | Structure | Name | XBP1s-luc 293 LUC (IC$_{50}$) (μmol) |
|---|---|---|---|
| 314 | 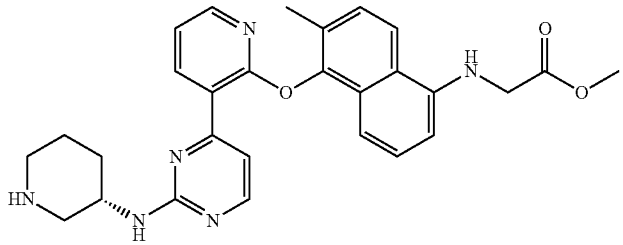 [SMILES: COC(=O)CNc1cccc2c(Oc3ncccc3-c3ccnc(N[C@H]4CCCNC4)n3)c(C)ccc12] | Methyl 2-[[6-methyl-5-[[3-[2-[[(3S)-3-piperidyl]amino]pyrimidin-4-yl]-2-pyridyl]oxy]-1-naphthyl]amino]acetate | 0.208 |
| 315 | 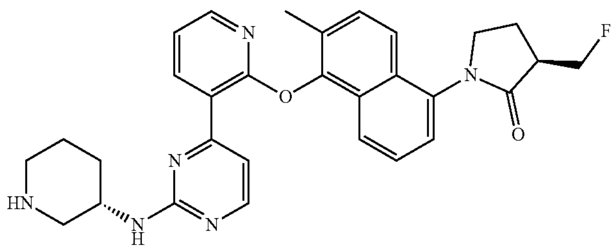 [SMILES: Cc1ccc2c(N3CC[C@@H](CF)C3=O)cccc2c1Oc1ncccc1-c1ccnc(N[C@H]2CCCNC2)n1] | (R)-3-(Fluoromethyl)-1-(6-methyl-5-((3-(2-(((S)-piperidin-3-yl)amino)pyrimidin-4-yl)pyridin-2-yl)oxy)naphthalen-1-yl)pyrrolidin-2-one | 0.471 |
| 316 | 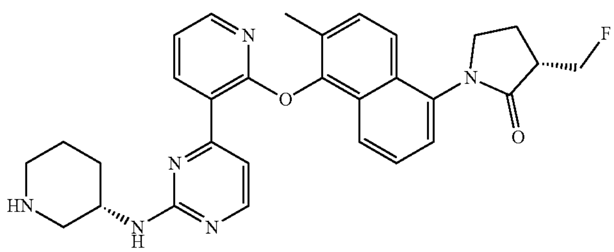 [SMILES: Cc1ccc2c(N3CC[C@H](CF)C3=O)cccc2c1Oc1ncccc1-c1ccnc(N[C@H]2CCCNC2)n1] | (S)-3-(Fluoromethyl)-1-(6-methyl-5-((3-(2-(((S)-piperidin-3-yl)amino)pyrimidin-4-yl)pyridin-2-yl)oxy)naphthalen-1-yl)pyrrolidin-2-one | 0.213 |
| 317 | 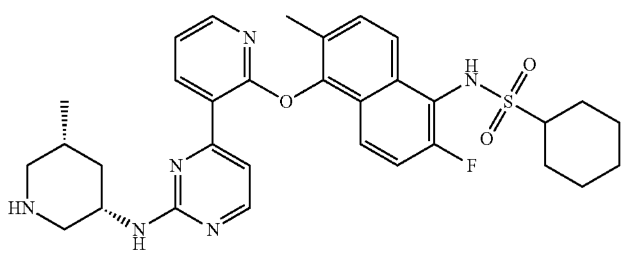 [SMILES: Cc1ccc2c(NS(=O)(=O)C3CCCCC3)c(F)ccc2c1Oc1ncccc1-c1ccnc(N[C@@H]2CNC[C@H](C)C2)n1] | N-[2-Fluoro-6-methyl-5-[[3-[2-[[(3S,5R)-5-methyl-3-piperidyl]amino]pyrimidin-4-yl]-2-pyridyl]oxy]-1-naphthyl]cyclohexanesulfonamide | 0.0176 |
| 318 | 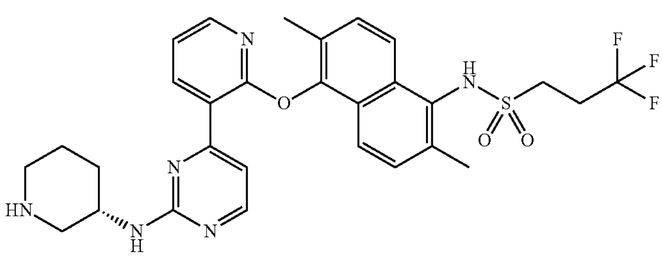 [SMILES: Cc1ccc2c(Oc3ncccc3-c3ccnc(N[C@H]4CCCNC4)n3)c(C)ccc2c1NS(=O)(=O)CCC(F)(F)F] | N-[2,6-Dimethyl-5-[[3-[2-[[(3S)-3-piperidyl]amino]pyrimidin-4-yl]-2-pyridyl]oxy]-1-naphthyl]-3,3,3-trifluoro-propane-1-sulfonamide | 0.0417 |
| 319 | 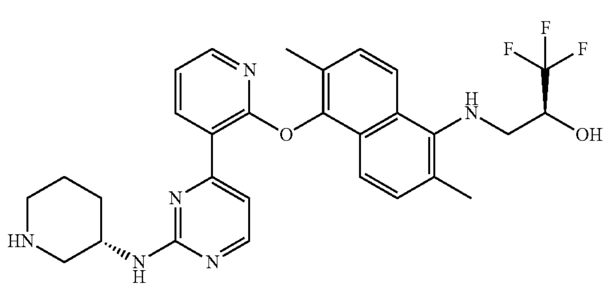 [SMILES: Cc1ccc2c(Oc3ncccc3-c3ccnc(N[C@H]4CCCNC4)n3)c(C)ccc2c1NC[C@H](O)C(F)(F)F] | (2S)-3-[[2,6-Dimethyl-5-[[3-[2-[[(3S)-3-piperidyl]amino]pyrimidin-4-yl]-2-pyridyl]oxy]-1-naphthyl]amino]-1,1,1-trifluoro-propan-2-ol | 0.0482 |

TABLE 1-continued

| No. | Structure | Name | XBP1s-luc 293 LUC (IC$_{50}$) (μmol) |
|---|---|---|---|
| 320 | 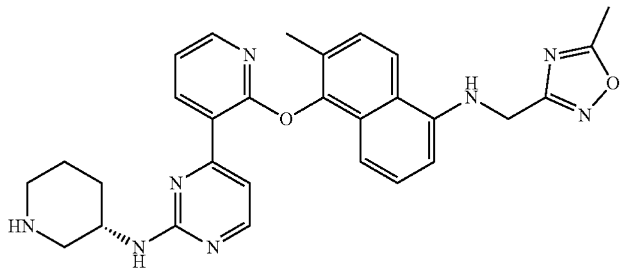 [SMILES: Cc1nc(CNc2cccc3c(Oc4ncccc4-c4ccnc(N[C@H]5CCCNC5)n4)c(C)ccc23)no1] | 4-[2-[[2-Methyl-5-[(5-methyl-1,2,4-oxadiazol-3-yl)methylamino]-1-naphthyl]oxy]-3-pyridyl]-N-[(3S)-3-piperidyl]pyrimidin-2-amine | 0.74 |
| 321 | 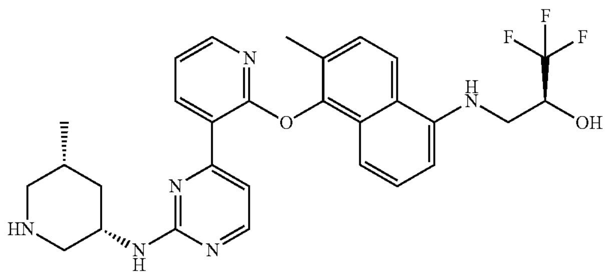 [SMILES: Cc1ccc2c(NC[C@H](O)C(F)(F)F)cccc2c1Oc1ncccc1-c1ccnc(N[C@@H]2CNC[C@H](C)C2)n1] | (2S)-1,1,1-Trifluoro-3-[[6-methyl-5-[[3-[2-[[(3S,5R)-5-methyl-3-piperidyl]amino]pyrimidin-4-yl]-2-pyridyl]oxy]-1-naphthyl]amino]propan-2-ol | 0.00736 |
| 322 | 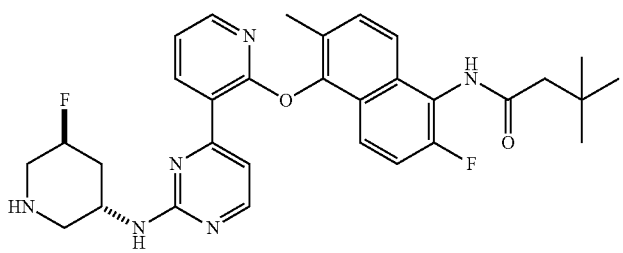 [SMILES: Cc1ccc2c(NC(=O)CC(C)(C)C)c(F)ccc2c1Oc1ncccc1-c1ccnc(N[C@@H]2CNC[C@@H](F)C2)n1] | N-(2-Fluoro-5-((3-(2-(((3S,5S)-5-fluoropiperidin-3-yl)amino)pyrimidin-4-yl)pyridin-2-yl)oxy)-6-methylnaphthalen-1-yl)-3,3-dimethylbutanamide | 0.0407 |
| 323 | 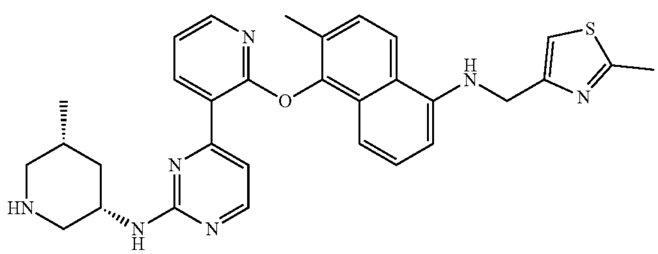 [SMILES: Cc1nc(CNc2cccc3c(Oc4ncccc4-c4ccnc(N[C@@H]5CNC[C@H](C)C5)n4)c(C)ccc23)cs1] | 4-(2-((2-Methyl-5-(((2-methylthiazol-4-yl)methyl)amino)naphthalen-1-yl)oxy)pyridin-3-yl)-N-((3S,5R)-5-methylpiperidin-3-yl)pyrimidin-2-amine | 0.0889 |
| 324 | 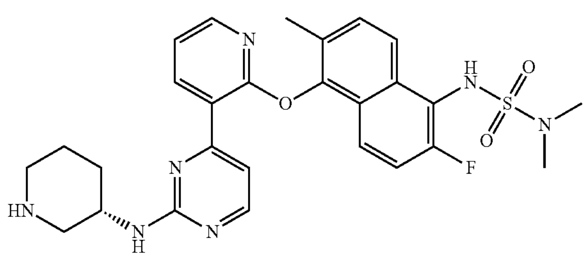 [SMILES: Cc1ccc2c(NS(=O)(=O)N(C)C)c(F)ccc2c1Oc1ncccc1-c1ccnc(N[C@H]2CCCNC2)n1] | 4-[2-[[5-(Dimethylsulfamoylamino)-6-fluoro-2-methyl-1-naphthyl]oxy]-3-pyridyl]-2-[[(3S)-3-piperidyl]amino]pyrimidine | 0.0455 |

TABLE 1-continued

| No. | Structure | Name | XBP1s-luc 293 LUC (IC$_{50}$) (μmol) |
|---|---|---|---|
| 325 | 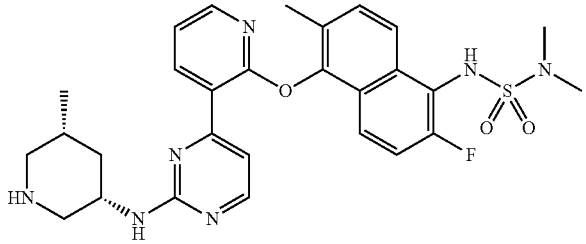 [SMILES: Cc1ccc2c(NS(=O)(=O)N(C)C)c(F)ccc2c1Oc1ncccc1-c1ccnc(N[C@@H]2CNC[C@H](C)C2)n1] | 4-[2-[[5-(Dimethylsulfamoylamino)-6-fluoro-2-methyl-1-naphthyl]oxy]-3-pyridyl]-2-[[(3S,5R)-5-methyl-3-piperidyl]amino]pyrimidine | 0.035 |
| 326 | 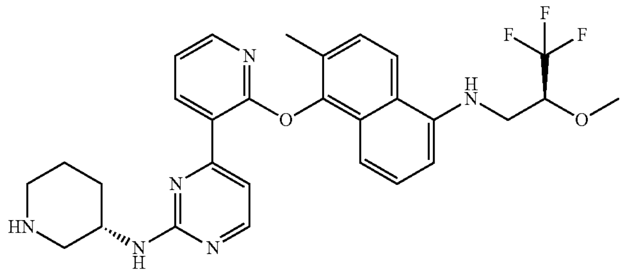 [SMILES: CO[C@@H](CNc1cccc2c(Oc3ncccc3-c3ccnc(N[C@H]4CCCNC4)n3)c(C)ccc12)C(F)(F)F] | 4-[2-[[2-Methyl-5-[[(2S)-3,3,3-trifluoro-2-methoxy-propyl]amino]-1-naphthyl]oxy]-3-pyridyl]-N-[(3S)-3-piperidyl]pyrimidin-2-amine | 0.0284 |
| 327 | 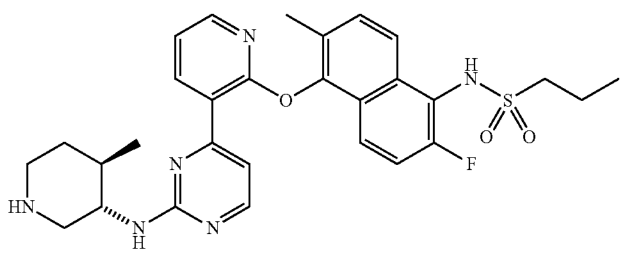 [SMILES: CCCS(=O)(=O)Nc1c(F)ccc2c(Oc3ncccc3-c3ccnc(N[C@@H]4CNCC[C@H]4C)n3)c(C)ccc12] | N-(2-Fluoro-6-methyl-5-((3-(2-(((3S,4R)-4-methylpiperidin-3-yl)amino)pyrimidin-4-yl)pyridin-2-yl)oxy)naphthalen-1-yl)propane-1-sulfonamide | 0.254 |
| 328 | 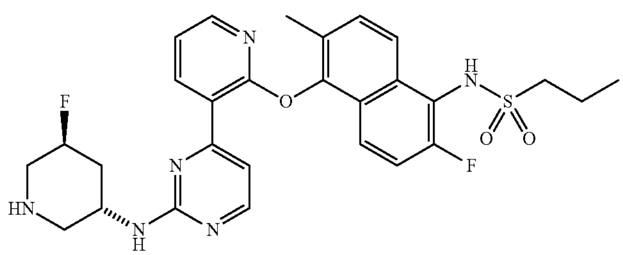 [SMILES: CCCS(=O)(=O)Nc1c(F)ccc2c(Oc3ncccc3-c3ccnc(N[C@@H]4CNC[C@@H](F)C4)n3)c(C)ccc12] | N-(2-Fluoro-5-((3-(2-(((3S,5S)-5-fluoropiperidin-3-yl)amino)pyrimidin-4-yl)pyridin-2-yl)oxy)-6-methylnaphthalen-1-yl)propane-1-sulfonamide | 0.0152 |
| 329 | 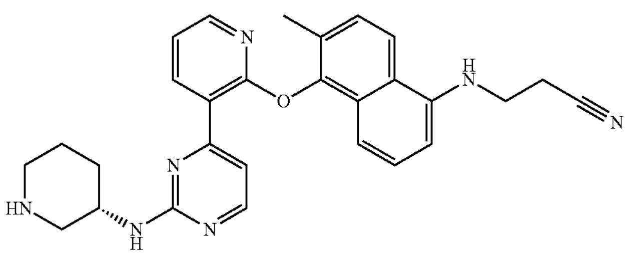 [SMILES: Cc1ccc2c(NCCC#N)cccc2c1Oc1ncccc1-c1ccnc(N[C@H]2CCCNC2)n1] | (S)-3-((6-Methyl-5-((3-(2-(piperidin-3-ylamino)pyrimidin-4-yl)pyridin-2-yl)oxy)naphthalen-1-yl)amino)propanenitrile | 0.123 |
| 330 | 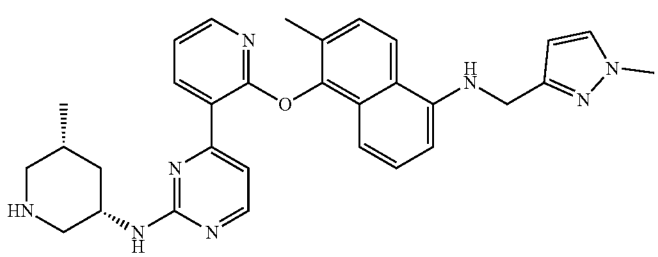 [SMILES: Cc1ccc2c(NCc3ccn(C)n3)cccc2c1Oc1ncccc1-c1ccnc(N[C@@H]2CNC[C@H](C)C2)n1] | 4-[2-[[2-Methyl-5-[(1-methylpyrazol-3-yl)methylamino]-1-naphthyl]oxy]-3-pyridyl]-N-[(3S,5R)-5-methyl-3-piperidyl]pyrimidin-2-amine | 0.197 |

TABLE 1-continued

| No. | Structure | Name | XBP1s-luc 293 LUC (IC$_{50}$) (μmol) |
|---|---|---|---|
| 331 | 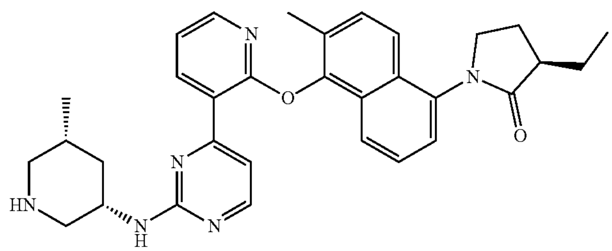 [SMILES: CC[C@@H]1CCN(c2cccc3c(Oc4ncccc4-c4ccnc(N[C@@H]5CNC[C@H](C)C5)n4)c(C)ccc23)C1=O] | (R)-3-Ethyl-1-(6-methyl-5-((3-(2-(((3S,5R)-5-methylpiperidin-3-yl)amino)pyrimidin-4-yl)pyridin-2-yl)oxy)naphthalen-1-yl)pyrrolidin-2-one | 0.0579 |
| 332 | 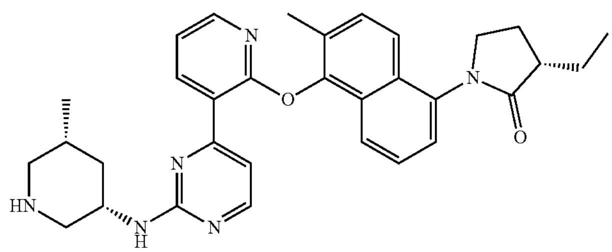 [SMILES: CC[C@H]1CCN(c2cccc3c(Oc4ncccc4-c4ccnc(N[C@@H]5CNC[C@H](C)C5)n4)c(C)ccc23)C1=O] | (S)-3-Ethyl-1-(6-methyl-5-((3-(2-(((3S,5R)-5-methylpiperidin-3-yl)amino)pyrimidin-4-yl)pyridin-2-yl)oxy)naphthalen-1-yl)pyrrolidin-2-one | 0.194 |
| 333 | 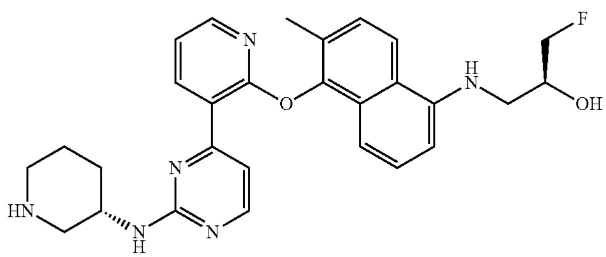 [SMILES: Cc1ccc2c(NC[C@H](O)CF)cccc2c1Oc1ncccc1-c1ccnc(N[C@H]2CCCNC2)n1] | (S)-1-Fluoro-3-((6-methyl-5-((3-(2-(((S)-piperidin-3-yl)amino)pyrimidin-4-yl)pyridin-2-yl)oxy)naphthalen-1-yl)amino)propan-2-ol | 0.0446 |
| 334 | 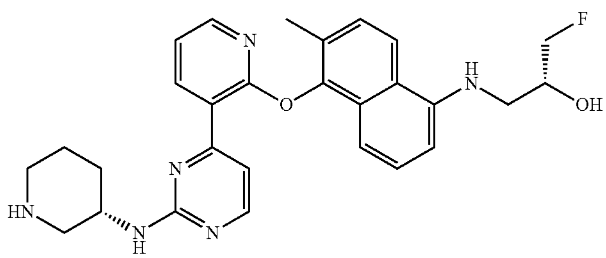 [SMILES: Cc1ccc2c(NC[C@@H](O)CF)cccc2c1Oc1ncccc1-c1ccnc(N[C@H]2CCCNC2)n1] | (R)-1-Fluoro-3-((6-methyl-5-((3-(2-(((S)-piperidin-3-yl)amino)pyrimidin-4-yl)pyridin-2-yl)oxy)naphthalen-1-yl)amino)propan-2-ol | 0.0897 |
| 335 | 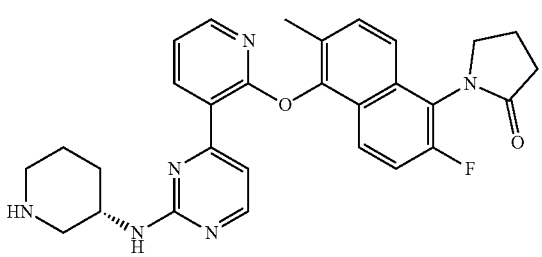 [SMILES: Cc1ccc2c(N3CCCC3=O)c(F)ccc2c1Oc1ncccc1-c1ccnc(N[C@H]2CCCNC2)n1] | (S)-1-(2-Fluoro-6-methyl-5-((3-(2-(piperidin-3-ylamino)pyrimidin-4-yl)pyridin-2-yl)oxy)naphthalen-1-yl)pyrrolidin-2-one | 0.384 |
| 336 | 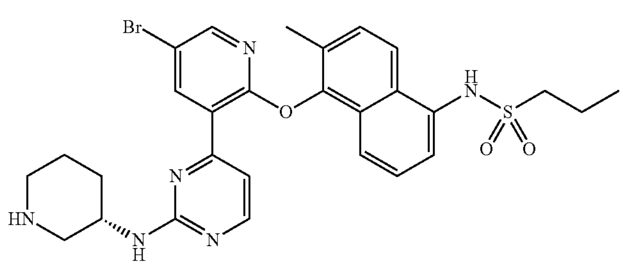 [SMILES: CCCS(=O)(=O)Nc1cccc2c(Oc3ncc(Br)cc3-c3ccnc(N[C@H]4CCCNC4)n3)c(C)ccc12] | (S)-N-(5-((5-Bromo-3-(2-(piperidin-3-ylamino)pyrimidin-4-yl)pyridin-2-yl)oxy)-6-methylnaphthalen-1-yl)propane-1-sulfonamide | 0.54 |

TABLE 1-continued

| No. | Structure | Name | XBP1s-luc 293 LUC (IC$_{50}$) (μmol) |
|---|---|---|---|
| 337 | 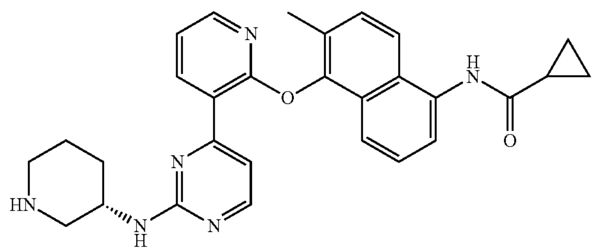 [SMILES: Cc1ccc2c(NC(=O)C3CC3)cccc2c1Oc1ncccc1-c1ccnc(N[C@H]2CCCNC2)n1] | (S)-N-(6-Methyl-5-((3-(2-(piperidin-3-ylamino)pyrimidin-4-yl)pyridin-2-yl)oxy)naphthalen-1-yl)cyclopropane-carboxamide | 0.0842 |
| 338 | 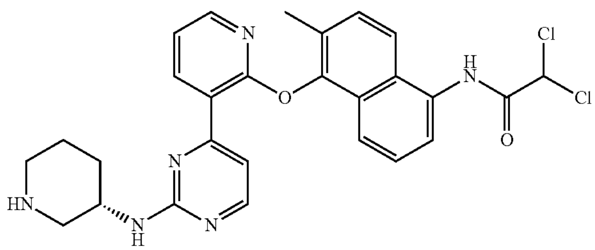 [SMILES: Cc1ccc2c(NC(=O)C(Cl)Cl)cccc2c1Oc1ncccc1-c1ccnc(N[C@H]2CCCNC2)n1] | (S)-2,2-Dichloro-N-(6-methyl-5-(3-(2-(piperidin-3-ylamino)pyrimidin-4-yl)pyridin-2-yloxy)naphthalen-1-yl)acetamide | 0.161 |
| 339 | 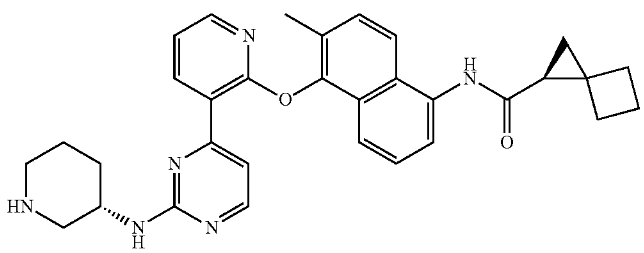 [SMILES: Cc1ccc2c(NC(=O)[C@H]3CC34CCC4)cccc2c1Oc1ncccc1-c1ccnc(N[C@H]2CCCNC2)n1] | (S)-N-(6-methyl-5-((3-(2-(((S)-piperidin-3-yl)amino)pyrimidin-4-yl)pyridin-2-yl)oxy)naphthalen-1-yl)spiro[2.3]hexane-1-carboxamide | 0.137 |
| 340 | 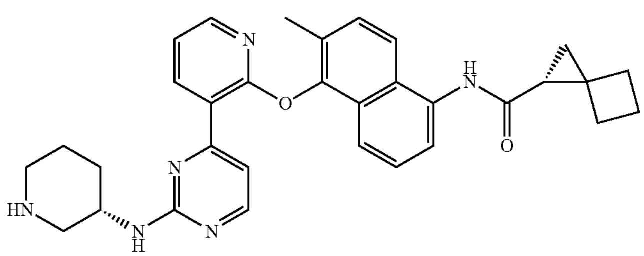 [SMILES: Cc1ccc2c(NC(=O)[C@@H]3CC34CCC4)cccc2c1Oc1ncccc1-c1ccnc(N[C@H]2CCCNC2)n1] | (R)-N-(6-Methyl-5-((3-(2-(((S)-piperidin-3-yl)amino)pyrimidin-4-yl)pyridin-2-yl)oxy)naphthalen-1-yl)spiro[2.3]hexane-1-carboxamide | 0.0177 |
| 341 | 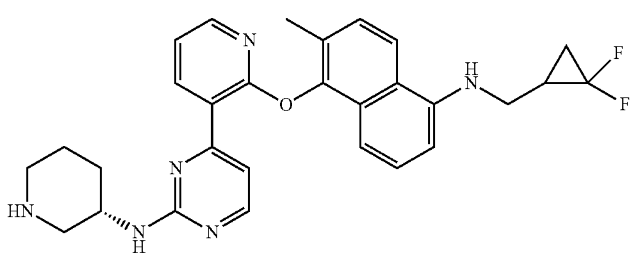 [SMILES: Cc1ccc2c(NCC3CC3(F)F)cccc2c1Oc1ncccc1-c1ccnc(N[C@H]2CCCNC2)n1] | 4-(2-((5-(((2,2-Difluorocyclopro-pyl)methyl)amino)-2-methylnaphthalen-1-yl)oxy)pyridin-3-yl)-N-((S)-piperidin-3-yl)pyrimidin-2-amine | 0.118 |
| 342 | 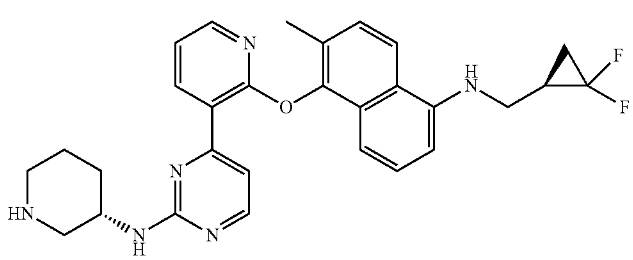 [SMILES: Cc1ccc2c(NC[C@H]3CC3(F)F)cccc2c1Oc1ncccc1-c1ccnc(N[C@H]2CCCNC2)n1] | 4-(2-((5-((((R)-2,2-Difluorocyclopro-pyl)methyl)amino)-2-methylnaphthalen-1-yl)oxy)pyridin-3-yl)-N-((S)-piperidin-3-yl)pyrimidin-2-amine | 0.121 |

TABLE 1-continued

| No. | Structure | Name | XBP1s-luc 293 LUC (IC$_{50}$) (μmol) |
|---|---|---|---|
| 343 | 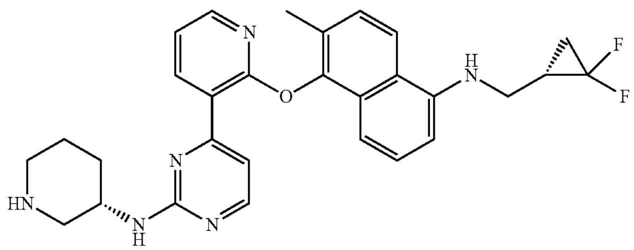 | 4-(2-((5-(((((S)-2,2-Difluorocyclopropyl)methyl)amino)-2-methylnaphthalen-1-yl)oxy)pyridin-3-yl)-N-((S)-piperidin-3-yl)pyrimidin-2-amine | 0.181 |
| 344 | 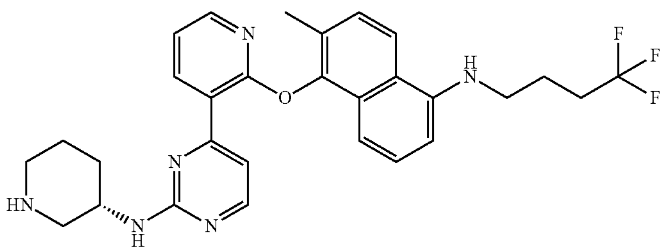 [SMILES: Cc1ccc2c(NCCCC(F)(F)F)cccc2c1Oc1ncccc1-c1ccnc(N[C@H]2CCCNC2)n1] | (S)-4-(2-((2-Methyl-5-((4,4,4-trifluorobutyl)amino)naphthalen-1-yl)oxy)pyridin-3-yl)-N-(piperidin-3-yl)pyrimidin-2-amine | 0.35 |
| 345 | 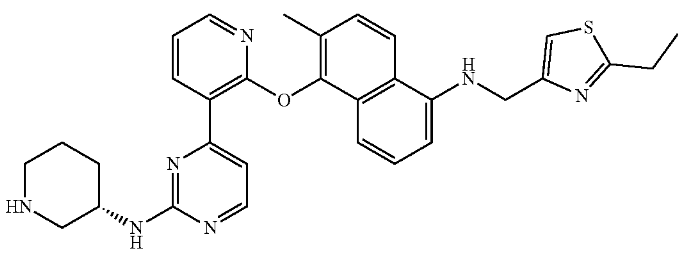 [SMILES: CCc1nc(CNc2cccc3c(Oc4ncccc4-c4ccnc(N[C@H]5CCCNC5)n4)c(C)ccc23)cs1] | (S)-4-(2-((5-(((2-Ethylthiazol-4-yl)methyl)amino)-2-methylnaphthalen-1-yl)oxy)pyridin-3-yl)-N-(piperidin-3-yl)pyrimidin-2-amine | 0.171 |
| 346 | 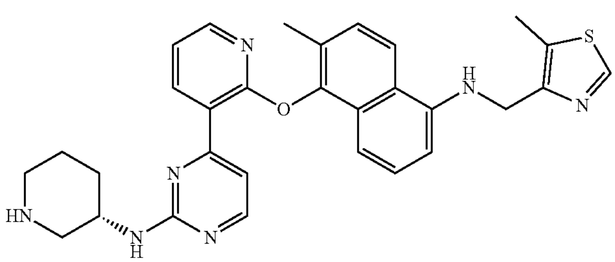 [SMILES: Cc1ccc2c(NCc3ncsc3C)cccc2c1Oc1ncccc1-c1ccnc(N[C@H]2CCCNC2)n1] | (S)-4-(2-((2-Methyl-5-(((5-methylthiazol-4-yl)methyl)amino)naphthalen-1-yl)oxy)pyridin-3-yl)-N-(piperidin-3-yl)pyrimidin-2-amine | 0.136 |
| 347 | 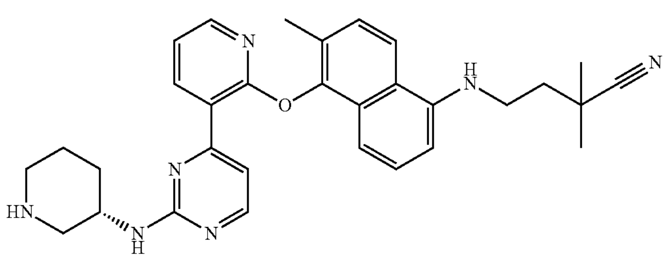 [SMILES: Cc1ccc2c(NCCC(C)(C)C#N)cccc2c1Oc1ncccc1-c1ccnc(N[C@H]2CCCNC2)n1] | (S)-2,2-Dimethyl-4-((6-methyl-5-((3-(2-(piperidin-3-ylamino)pyrimidin-4-yl)pyridin-2-yl)oxy)naphthalen-1-yl)amino)butanenitrile | 0.048 |
| 348 | 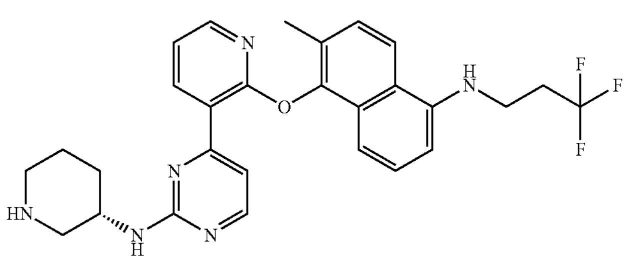 [SMILES: Cc1ccc2c(NCCC(F)(F)F)cccc2c1Oc1ncccc1-c1ccnc(N[C@H]2CCCNC2)n1] | (S)-4-(2-((2-Methyl-5-((3,3,3-trifluoropropyl)amino)naphthalen-1-yl)oxy)pyridin-3-yl)-N-(piperidin-3-yl)pyrimidin-2-amine | 0.079 |

TABLE 1-continued

| No. | Structure | Name | XBP1s-luc 293 LUC (IC$_{50}$) (μmol) |
|---|---|---|---|
| 349 | 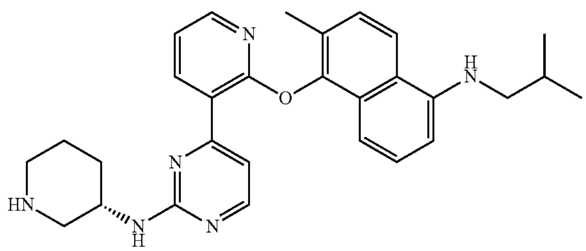 [SMILES: Cc1ccc2c(NCC(C)C)cccc2c1Oc1ncccc1-c1ccnc(N[C@H]2CCCNC2)n1] | (S)-4-(2-((5-(Isobutylamino)-2-methylnaphthalen-1-yl)oxy)pyridin-3-yl)-N-(piperidin-3-yl)pyrimidin-2-amine | 0.432 |
| 350 | 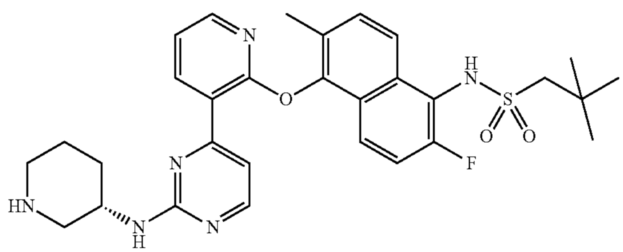 [SMILES: Cc1ccc2c(NS(=O)(=O)CC(C)(C)C)c(F)ccc2c1Oc1ncccc1-c1ccnc(N[C@H]2CCCNC2)n1] | (S)-N-(2-Fluoro-6-methyl-5-((3-(2-(piperidin-3-ylamino)pyrimidin-4-yl)pyridin-2-yl)oxy)naphthalen-1-yl)-2,2-dimethylpropane-1-sulfonamide | 0.0374 |
| 351 | 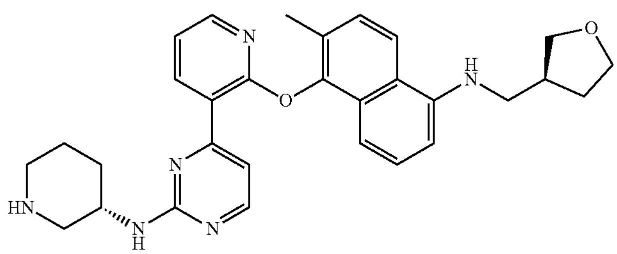 | 4-(2-((2-Methyl-5-((((S)-tetrahydrofuran-3-yl)methyl)amino)naphthalen-1-yl)oxy)pyridin-3-yl)-N-((S)-piperidin-3-yl)pyrimidin-2-amine | 0.50 |
| 352 | 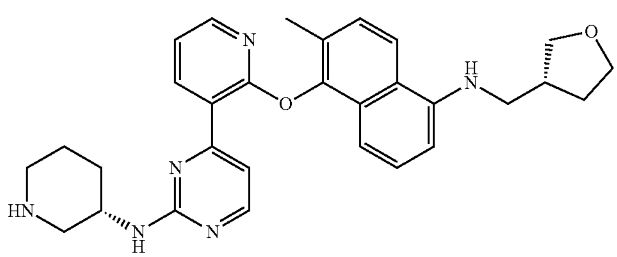 [SMILES: Cc1ccc2c(NC[C@H]3CCOC3)cccc2c1Oc1ncccc1-c1ccnc(N[C@H]2CCCNC2)n1] | 4-(2-((2-Methyl-5-((((R)-tetrahydrofuran-3-yl)methyl)amino)naphthalen-1-yl)oxy)pyridin-3-yl)-N-((S)-piperidin-3-yl)pyrimidin-2-amine | 0.499 |
| 353 | 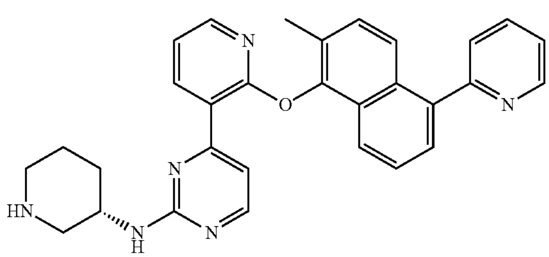 [SMILES: Cc1ccc2c(-c3ccccn3)cccc2c1Oc1ncccc1-c1ccnc(N[C@H]2CCCNC2)n1] | (S)-4-(2-((2-Methyl-5-(pyridin-2-yl)naphthalen-1-yl)oxy)pyridin-3-yl)-N-(piperidin-3-yl)pyrimidin-2-amine | 0.133 |
| 354 | 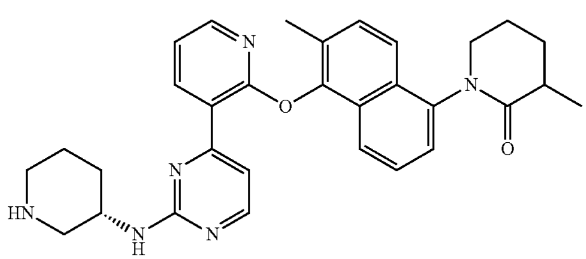 [SMILES: Cc1ccc2c(N3CCCC(C)C3=O)cccc2c1Oc1ncccc1-c1ccnc(N[C@H]2CCCNC2)n1] | 3-Methyl-1-(6-methyl-5-((3-(2-((S)-piperidin-3-ylamino)pyrimidin-4-yl)pyridin-2-yl)oxy)naphthalen-1-yl)piperidin-2-one | 0.318 |

TABLE 1-continued

| No. | Structure | Name | XBP1s-luc 293 LUC (IC$_{50}$) (μmol) |
|---|---|---|---|
| 355 | 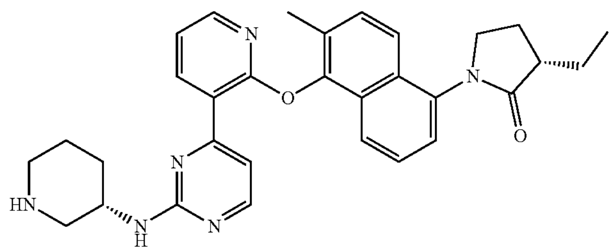 [SMILES: CC[C@H]1CCN(c2cccc3c(Oc4ncccc4-c4ccnc(N[C@H]5CCCNC5)n4)c(C)ccc23)C1=O] | (S)-3-Ethyl-1-(6-methyl-5-((3-(2-(((S)-piperidin-3-yl)amino)pyrimidin-4-yl)pyridin-2-yl)oxy)naphthalen-1-yl)pyrrolidin-2-one | 0.365 |
| 356 | 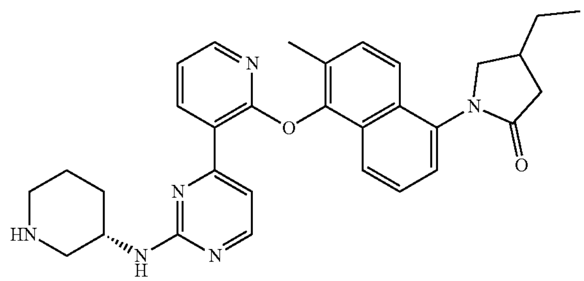 [SMILES: CCC1CC(=O)N(c2cccc3c(Oc4ncccc4-c4ccnc(N[C@H]5CCCNC5)n4)c(C)ccc23)C1] | 4-Ethyl-1-(6-methyl-5-((3-(2-((S)-piperidin-3-ylamino)pyrimidin-4-yl)pyridin-2-yl)oxy)naphthalen-1-yl)pyrrolidin-2-one | 0.279 |
| 357 | 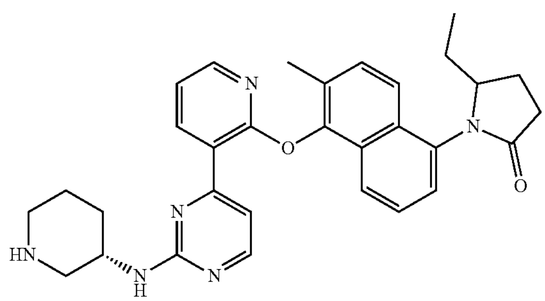 [SMILES: CCC1CCC(=O)N1c1cccc2c(Oc3ncccc3-c3ccnc(N[C@H]4CCCNC4)n3)c(C)ccc12] | 5-Ethyl-1-(6-methyl-5-((3-(2-((S)-piperidin-3-ylamino)pyrimidin-4-yl)pyridin-2-yl)oxy)naphthalen-1-yl)pyrrolidin-2-one | 0.26 |
| 358 | 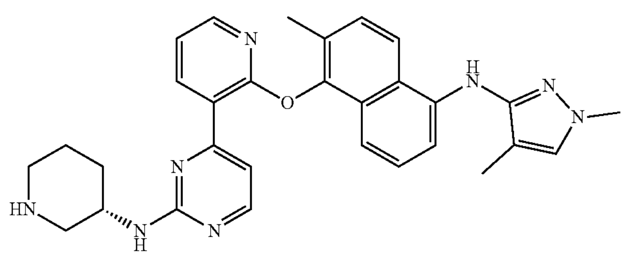 | (S)-4-(2-((5-((1,4-Dimethyl-1H-pyrazol-3-yl)amino)-2-methylnaphthalen-1-yl)oxy)pyridin-3-yl)-N-(piperidin-3-yl)pyrimidin-2-amine | 0.266 |
| 359 | 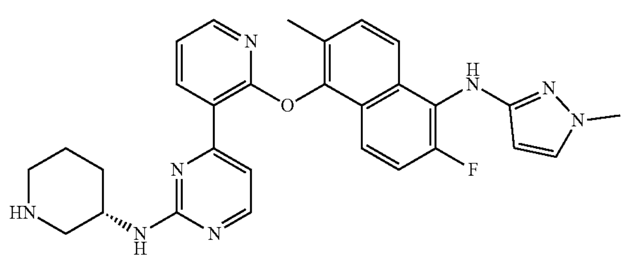 | (S)-4-(2-((6-Fluoro-2-methyl-5-((1-methyl-1H-pyrazol-3-yl)amino)naphthalen-1-yl)oxy)pyridin-3-yl)-N-(piperidin-3-yl)pyrimidin-2-amine | 0.438 |

TABLE 1-continued

| No. | Structure | Name | XBP1s-luc 293 LUC (IC$_{50}$) (μmol) |
|---|---|---|---|
| 360 | 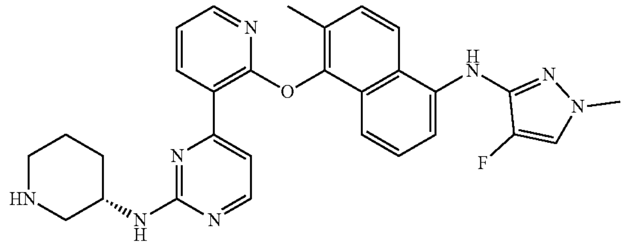 [SMILES: Cc1cn(C)nc1Nc1cccc2c(Oc3ncccc3-c3ccnc(N[C@H]4CCCNC4)n3)c(C)ccc12] | (S)-4-(2-((5-((4-Fluoro-1-methyl-1H-pyrazol-3-yl)amino)-2-methylnaphthalen-1-yl)oxy)pyridin-3-yl)-N-(piperidin-3-yl)pyrimidin-2-amine | 0.455 |
| 361 | 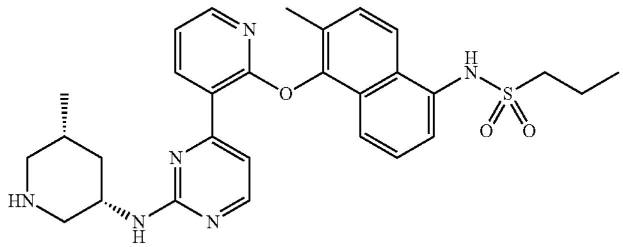 [SMILES: CCCS(=O)(=O)Nc1cccc2c(Oc3ncccc3-c3ccnc(N[C@@H]4CNC[C@H](C)C4)n3)c(C)ccc12] | N-(6-Methyl-5-((3-(2-(((3S,5R)-5-methylpiperidin-3-yl)amino)pyrimidin-4-yl)pyridin-2-yl)oxy)naphthalen-1-yl)propane-1-sulfonamide | 0.0851 |
| 362 | 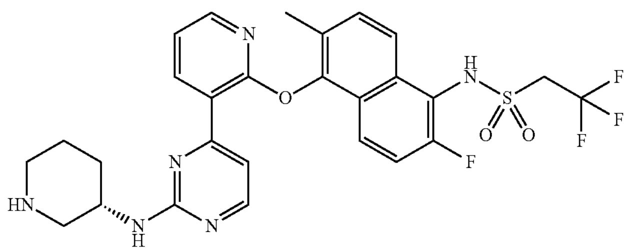 [SMILES: Cc1ccc2c(NS(=O)(=O)CC(F)(F)F)c(F)ccc2c1Oc1ncccc1-c1ccnc(N[C@H]2CCCNC2)n1] | (S)-2,2,2-Trifluoro-N-(2-fluoro-6-methyl-5-((3-(2-(piperidin-3-ylamino)pyrimidin-4-yl)pyridin-2-yl)oxy)naphthalen-1-yl)ethanesulfonamide | 0.0234 |
| 363 | 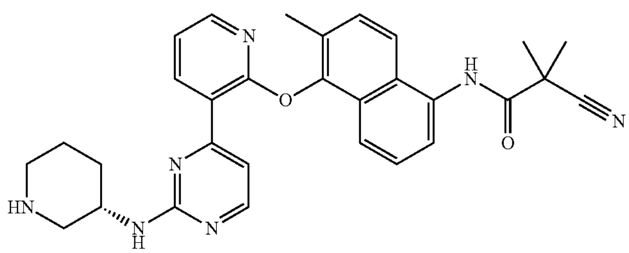 [SMILES: Cc1ccc2c(NC(=O)C(C)(C)C#N)cccc2c1Oc1ncccc1-c1ccnc(N[C@H]2CCCNC2)n1] | (S)-2-Cyano-2-methyl-N-(6-methyl-5-((3-(2-(piperidin-3-ylamino)pyrimidin-4-yl)pyridin-2-yl)oxy)naphthalene-1-yl)propanamide | 0.408 |
| 364 | 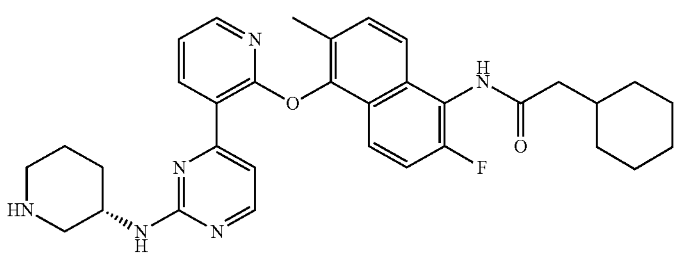 [SMILES: Cc1ccc2c(NC(=O)CC3CCCCC3)c(F)ccc2c1Oc1ncccc1-c1ccnc(N[C@H]2CCCNC2)n1] | (S)-2-Cyclohexyl-N-(2-fluoro-6-methyl-5-((3-(2-(piperidin-3-ylamino)pyrimidin-4-yl)pyridin-2-yl)oxy)naphthalen-1-yl)acetamide | 0.216 |
| 365 | 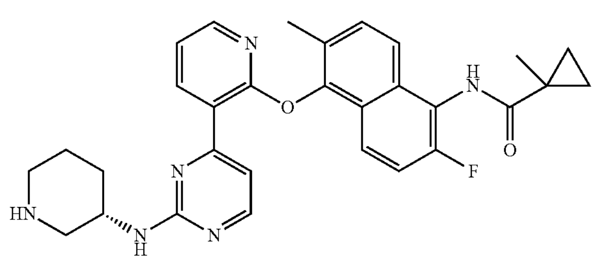 [SMILES: Cc1ccc2c(NC(=O)C3(C)CC3)c(F)ccc2c1Oc1ncccc1-c1ccnc(N[C@H]2CCCNC2)n1] | (S)-N-(2-Fluoro-6-methyl-5-((3-(2-(piperidin-3-ylamino)pyrimidin-4-yl)pyridin-2-yl)oxy)naphthalen-1-yl)-1-methylcyclopropanecarboxamide | 0.438 |

TABLE 1-continued

| No. | Structure | Name | XBP1s-luc 293 LUC (IC$_{50}$) (μmol) |
|---|---|---|---|
| 366 | 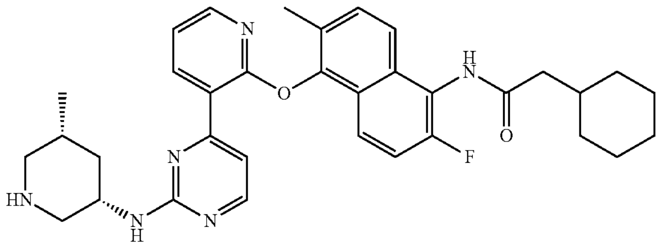 [SMILES: Cc1ccc2c(NC(=O)CC3CCCCC3)c(F)ccc2c1Oc1ncccc1-c1ccnc(N[C@@H]2CNC[C@H](C)C2)n1] | 2-Cyclohexyl-N-(2-fluoro-6-methyl-5-((3-(2-(((3S,5R)-5-methylpiperidin-3-yl)amino)pyrimidin-4-yl)pyridin-2-yl)oxy)naphthalen-1-yl)acetamide | 0.101 |
| 367 | 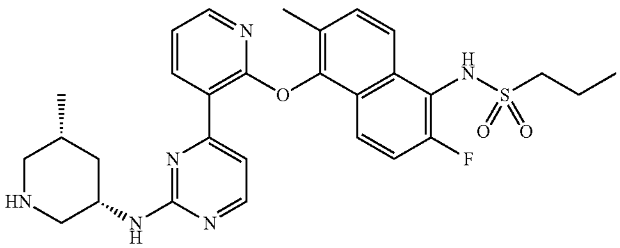 [SMILES: CCCS(=O)(=O)Nc1c(F)ccc2c(Oc3ncccc3-c3ccnc(N[C@@H]4CNC[C@H](C)C4)n3)c(C)ccc12] | N-(2-Fluoro-6-methyl-5-((3-(2-(((3S,5R)-5-methylpiperidin-3-yl)amino)pyrimidin-4-yl)pyridin-2-yl)oxy)naphthalen-1-yl)propane-1-sulfonamide | 0.0145 |
| 368 | 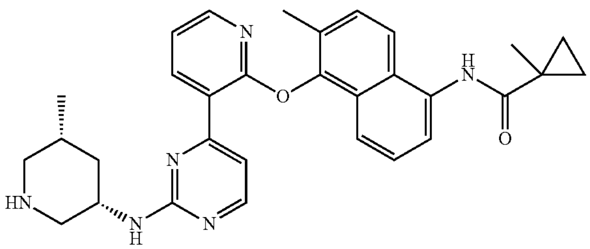 [SMILES: Cc1ccc2c(NC(=O)C3(C)CC3)cccc2c1Oc1ncccc1-c1ccnc(N[C@@H]2CNC[C@H](C)C2)n1] | 1-Methyl-N-(6-methyl-5-((3-(2-(((3S,5R)-5-methylpiperidin-3-yl)amino)pyrimidin-4-yl)pyridin-2-yl)oxy)naphthalen-1-yl)cyclopropanecarboxamide | 0.214 |
| 369 | 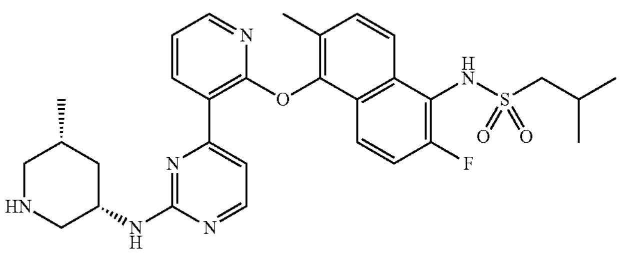 [SMILES: Cc1ccc2c(NS(=O)(=O)CC(C)C)c(F)ccc2c1Oc1ncccc1-c1ccnc(N[C@@H]2CNC[C@H](C)C2)n1] | N-(2-Fluoro-6-methyl-5-((3-(2-(((3S,5R)-5-methylpiperidin-3-yl)amino)pyrimidin-4-yl)pyridin-2-yl)oxy)naphthalen-1-yl)-2-methylpropane-1-sulfonamide | 0.0194 |
| 370 | 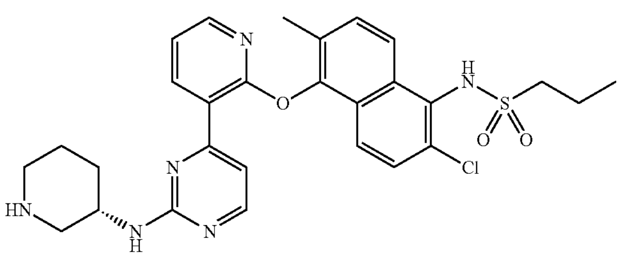 | (S)-N-(2-Chloro-6-methyl-5-((3-(2-(piperidin-3-ylamino)pyrimidin-4-yl)pyridin-2-yl)oxy)naphthalen-1-yl)propane-1-sulfonamide | 0.0276 |
| 371 | 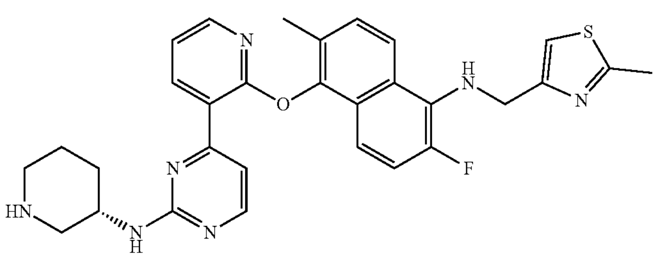 [SMILES: Cc1nc(CNc2c(F)ccc3c(Oc4ncccc4-c4ccnc(N[C@H]5CCCNC5)n4)c(C)ccc23)cs1] | (S)-4-(2-((6-Fluoro-2-methyl-5-(((2-methylthiazol-4-yl)methyl)amino)naphthalen-1-yl)oxy)pyridin-3-yl)-N-(piperidin-3-yl)pyrimidin-2-amine | 0.381 |

TABLE 1-continued

| No. | Structure | Name | XBP1s-luc 293 LUC (IC$_{50}$) (μmol) |
|---|---|---|---|
| 372 | 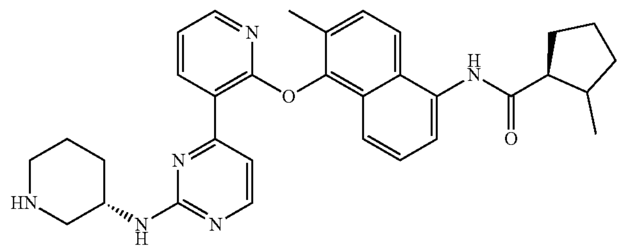 | (1S)-2-Methyl-N-(6-methyl-5-((3-(2-(((S)-piperidin-3-yl)amino)pyrimidin-4-yl)pyridin-2-yl)oxy)naphthalen-1-yl)cyclopentane-1-carboxamide | 0.47 |
| 373 | 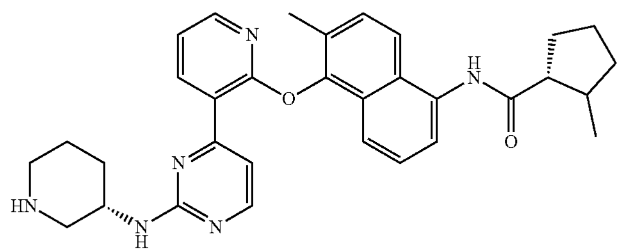 | (1R)-2-Methyl-N-(6-methyl-5-((3-(2-(((S)-piperidin-3-yl)amino)pyrimidin-4-yl)pyridin-2-yl)oxy)naphthalen-1-yl)cyclopentane-1-carboxamide | 0.193 |
| 374 | 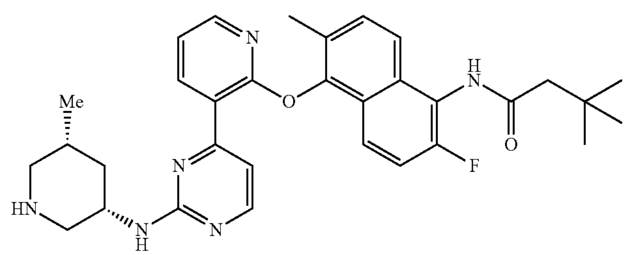 [SMILES: Cc1ccc2c(NC(=O)CC(C)(C)C)c(F)ccc2c1Oc1ncccc1-c1ccnc(N[C@@H]2CNC[C@H](C)C2)n1] | N-(2-Fluoro-6-methyl-5-((3-(2-(((3S,5R)-5-methylpiperidin-3-yl)amino)pyrimidin-4-yl)pyridin-2-yl)oxy)naphthalen-1-yl)-3,3-dimethylbutanamide | 0.0394 |
| 375 | 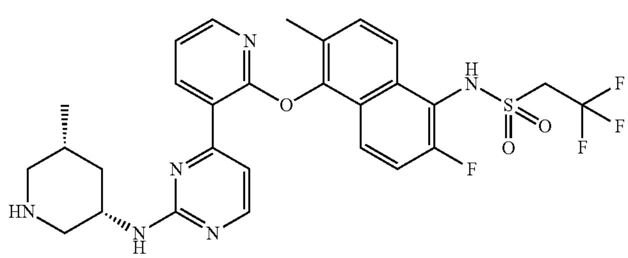 [SMILES: Cc1ccc2c(NS(=O)(=O)CC(F)(F)F)c(F)ccc2c1Oc1ncccc1-c1ccnc(N[C@@H]2CNC[C@H](C)C2)n1] | 2,2,2-Trifluoro-N-(2-fluoro-6-methyl-5-((3-(2-(((3R,5R)-5-methylpiperidin-3-yl)amino)pyrimidin-4-yl)pyridin-2-yl)oxy)naphthalen-1-yl)ethanesulfonamide | 0.0132 |
| 376 | 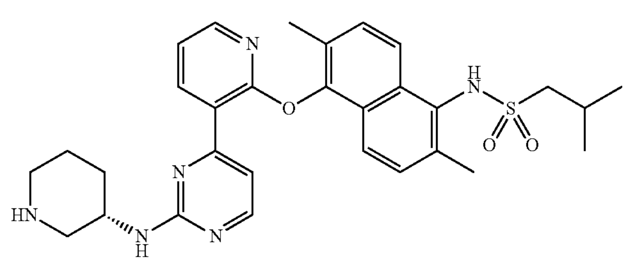 [SMILES: Cc1ccc2c(Oc3ncccc3-c3ccnc(N[C@H]4CCCNC4)n3)c(C)ccc2c1NS(=O)(=O)CC(C)C] | (S)-N-(2,6-Dimethyl-5-((3-(2-(piperidin-3-ylamino)pyrimidin-4-yl)pyridin-2-yl)oxy)naphthalen-1-yl)-2-methylpropane-1-sulfonamide | 0.0735 |
| 377 | 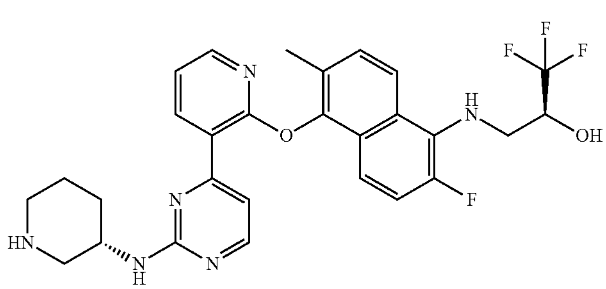 | (S)-1,1,1-Trifluoro-3-((2-fluoro-6-methyl-5-((3-(2-((S)-piperidin-3-ylamino)pyrimidin-4-yl)pyridin-2-yl)oxy)naphthalen-1-yl)amino)propan-2-ol | 0.0102 |

TABLE 1-continued

| No. | Structure | Name | XBP1s-luc 293 LUC (IC$_{50}$) (μmol) |
|---|---|---|---|
| 378 | 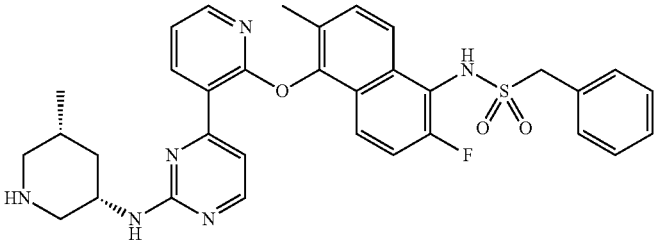 [SMILES: Cc1ccc2c(NS(=O)(=O)Cc3ccccc3)c(F)ccc2c1Oc1ncccc1-c1ccnc(N[C@@H]2CNC[C@H](C)C2)n1] | N-(2-Fluoro-6-methyl-5-((3-(2-(((3S,5R)-5-methylpiperidin-3-yl)amino)pyrimidin-4-yl)pyridin-2-yl)oxy)naphthalen-1-yl)-1-phenylmethanesulfonamide | 0.00141 |
| 379 | 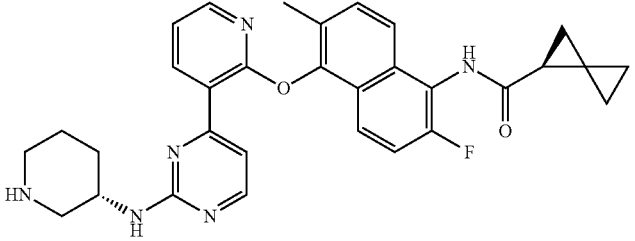 [SMILES: Cc1ccc2c(NC(=O)[C@H]3CC34CC4)c(F)ccc2c1Oc1ncccc1-c1ccnc(N[C@H]2CCCNC2)n1] | (S)-N-(2-Fluoro-6-methyl-5-((3-(2-(((S)-piperidin-3-yl)amino)pyrimidin-4-yl)pyridin-2-yl)oxy)naphthalen-1-yl)spiro[2.2]pentane-1-carboxamide | 0.279 |
| 380 | 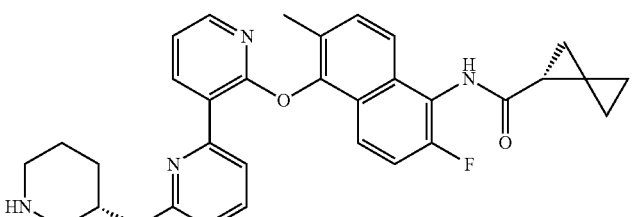 | (R)-N-(2-Fluoro-6-methyl-5-((3-(2-(((S)-piperidin-3-yl)amino)pyrimidin-4-yl)pyridin-2-yl)oxy)naphthalen-1-yl)spiro[2.2]pentane-1-carboxamide | 0.0566 |
| 381 | 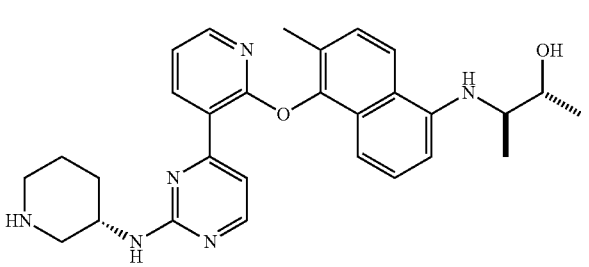 [SMILES: Cc1ccc2c(N[C@H](C)[C@@H](C)O)cccc2c1Oc1ncccc1-c1ccnc(N[C@H]2CCCNC2)n1] | anti-3-((6-Methyl-5-((3-(2-(((S)-piperidin-3-yl)amino)pyrimidin-4-yl)pyridin-2-yl)oxy)naphthalen-1-yl)amino)butan-2-ol | 0.403 |
| 382 | 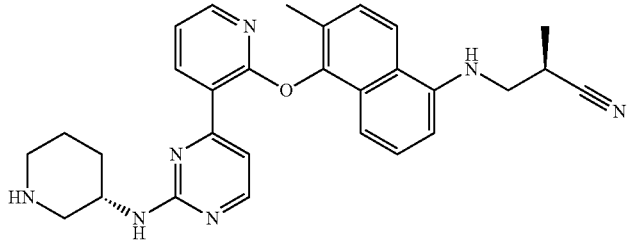 [SMILES: Cc1ccc2c(NC[C@@H](C)C#N)cccc2c1Oc1ncccc1-c1ccnc(N[C@H]2CCCNC2)n1] | (R)-2-Methyl-3-((6-methyl-5-((3-(2-((S)-piperidin-3-ylamino)pyrimidin-4-yl)pyridin-2-yl)oxy)naphthalen-1-yl)amino)propanenitrile | 0.0623 |
| 383 | 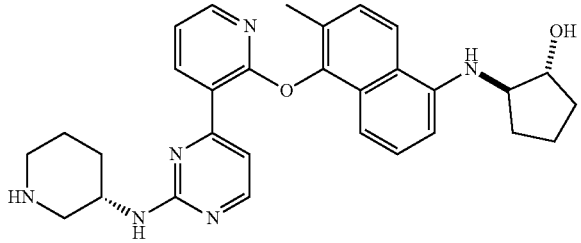 | anti-2-((6-Methyl-5-((3-(2-((S)-piperidin-3-ylamino)pyrimidin-4-yl)pyridin-2-yl)oxy)naphthalen-1-yl)amino)cyclopentanol | 0.231 |

TABLE 1-continued

| No. | Structure | Name | XBP1s-luc 293 LUC (IC$_{50}$) (μmol) |
|---|---|---|---|
| 384 | 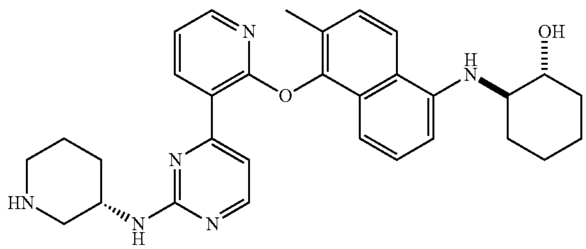 | trans-2-((6-Methyl-5-((3-(2-((S)-piperidin-3-ylamino)pyrimidin-4-yl)pyridin-2-yl)oxy)naphthalen-1-yl)amino)cyclohexanol | 0.146 |
| 385 | 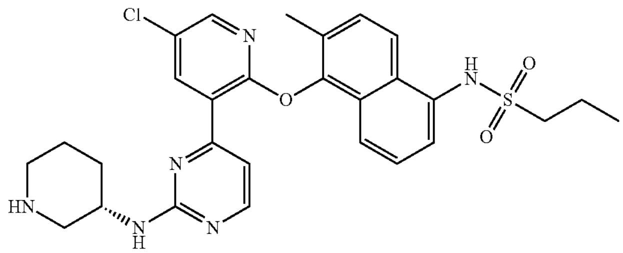 [SMILES: CCCS(=O)(=O)Nc1cccc2c(Oc3ncc(Cl)cc3-c3ccnc(N[C@H]4CCCNC4)n3)c(C)ccc12] | (S)-N-(5-((5-Chloro-3-(2-(piperidin-3-ylamino)pyrimidin-4-yl)pyridin-2-yl)oxy)-6-methylnaphthalen-1-yl)propane-1-sulfonamide | 0.366 |
| 386 | 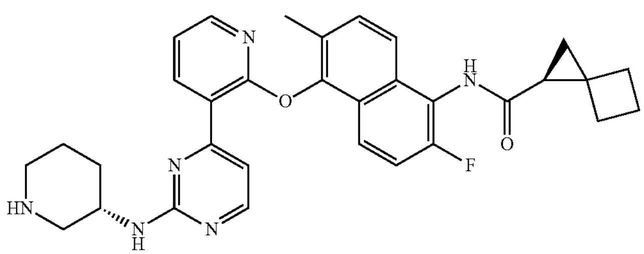 [SMILES: Cc1ccc2c(NC(=O)[C@H]3CC34CCC4)c(F)ccc2c1Oc1ncccc1-c1ccnc(N[C@H]2CCCNC2)n1] | (S)-N-(2-Fluoro-6-methyl-5-((3-(2-(((S)-piperidin-3-yl)amino)pyrimidin-4-yl)pyridin-2-yl)oxy)naphthalen-1-yl)spiro[2.3]hexane-1-carboxamide | 0.28 |
| 387 | 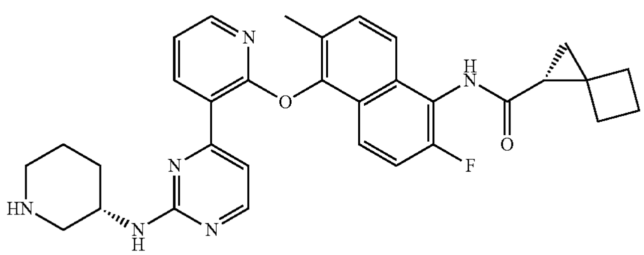 [SMILES: Cc1ccc2c(NC(=O)[C@@H]3CC34CCC4)c(F)ccc2c1Oc1ncccc1-c1ccnc(N[C@H]2CCCNC2)n1] | (R)-N-(2-Fluoro-6-methyl-5-((3-(2-(((S)-piperidin-3-yl)amino)pyrimidin-4-yl)pyridin-2-yl)oxy)naphthalen-1-yl)spiro[2.3]hexane-1-carboxamide | 0.0283 |
| 388 | 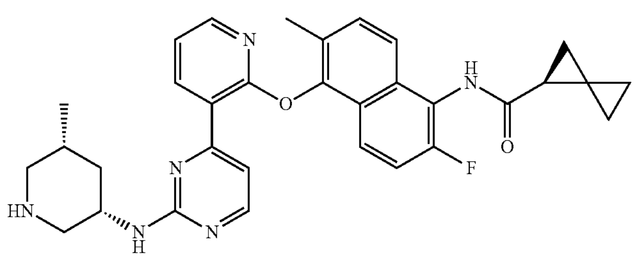 [SMILES: Cc1ccc2c(NC(=O)[C@H]3CC34CC4)c(F)ccc2c1Oc1ncccc1-c1ccnc(N[C@@H]2CNC[C@H](C)C2)n1] | (S)-N-(2-Fluoro-6-methyl-5-((3-(2-(((3S,5R)-5-methylpiperidin-3-yl)amino)pyrimidin-4-yl)pyridin-2-yl)oxy)naphthalen-1-yl)spiro[2.2]pentane-1-carboxamide | 0.136 |
| 389 | 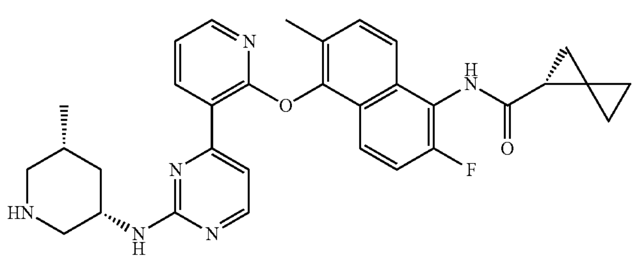 [SMILES: Cc1ccc2c(NC(=O)[C@@H]3CC34CC4)c(F)ccc2c1Oc1ncccc1-c1ccnc(N[C@@H]2CNC[C@H](C)C2)n1] | (R)-N-(2-Fluoro-6-methyl-5-((3-(2-(((3S,5R)-5-methylpiperidin-3-yl)amino)pyrimidin-4-yl)pyridin-2-yl)oxy)naphthalen-1-yl)spiro[2.2]pentane-1-carboxamide | 0.0417 |

TABLE 1-continued

| No. | Structure | Name | XBP1s-luc 293 LUC (IC$_{50}$) (µmol) |
|---|---|---|---|
| 390 | 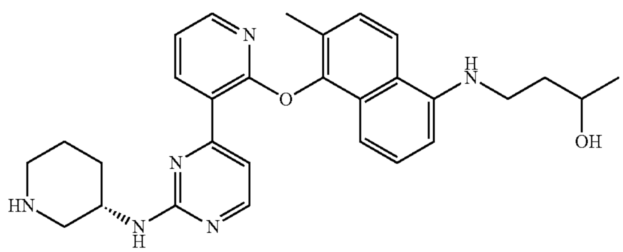 [SMILES: Cc1ccc2c(NCCC(C)O)cccc2c1Oc1ncccc1-c1ccnc(N[C@H]2CCCNC2)n1] | 4-((6-Methyl-5-((3-(2-((S)-piperidin-3-ylamino)pyrimidin-4-yl)pyridin-2-yl)oxy)naphthalen-1-yl)amino)butan-2-ol | 0.143 |
| 391 | 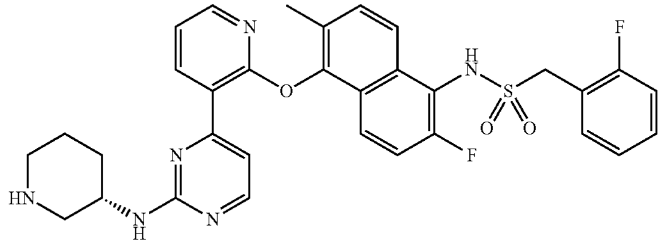 [SMILES: Cc1ccc2c(NS(=O)(=O)Cc3ccccc3F)c(F)ccc2c1Oc1ncccc1-c1ccnc(N[C@H]2CCCNC2)n1] | (S)-N-(2-Fluoro-6-methyl-5-((3-(2-(piperidin-3-ylamino)pyrimidin-4-yl)pyridin-2-yl)oxy)naphthalen-1-yl)-1-(2-fluorophenyl)methanesulfonamide | 0.00277 |
| 392 | 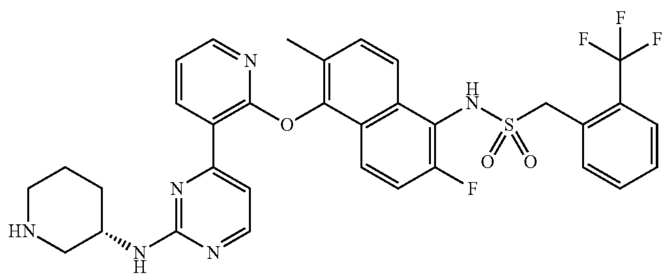 [SMILES: Cc1ccc2c(NS(=O)(=O)Cc3ccccc3C(F)(F)F)c(F)ccc2c1Oc1ncccc1-c1ccnc(N[C@H]2CCCNC2)n1] | (S)-N-(2-Fluoro-6-methyl-5-((3-(2-(piperidin-3-ylamino)pyrimidin-4-yl)pyridin-2-yl)oxy)naphthalen-1-yl)-1-(2-(trifluoromethyl)phenyl)methanesulfonamide | 0.00632 |

TABLE 2

| No. | Structure | Name | XBP1s-luc 293 LUC (IC$_{50}$) (µmol) |
|---|---|---|---|
| 393 | 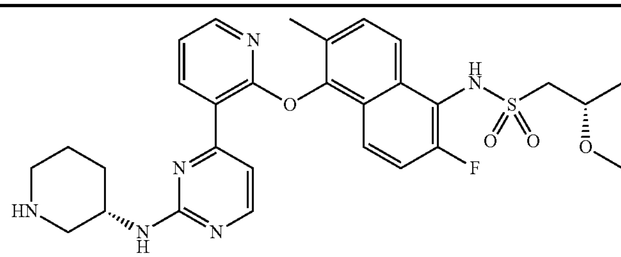 | (S)-N-(2-Fluoro-6-methyl-5-((3-(2-(((S)-piperidin-3-yl)amino)pyrimidin-4-yl)pyridin-2-yl)oxy)naphthalen-1-yl)-2-methoxypropane-1-sulfonamide | 0.076 |
| 394 | 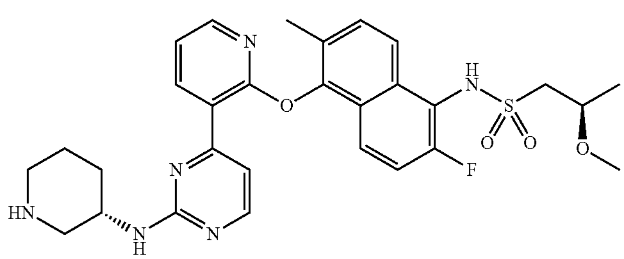 [SMILES: CO[C@H](C)CS(=O)(=O)Nc1c(F)ccc2c(Oc3ncccc3-c3ccnc(N[C@H]4CCCNC4)n3)c(C)ccc12] | (R)-N-(2-Fluoro-6-methyl-5-((3-(2-(((S)-piperidin-3-yl)amino)pyrimidin-4-yl)pyridin-2-yl)oxy)naphthalen-1-yl)-2-methoxypropane-1-sulfonamide | 0.028 |

TABLE 2-continued

| No. | Structure | Name | XBP1s-luc 293 LUC (IC$_{50}$) (μmol) |
|---|---|---|---|
| 395 | 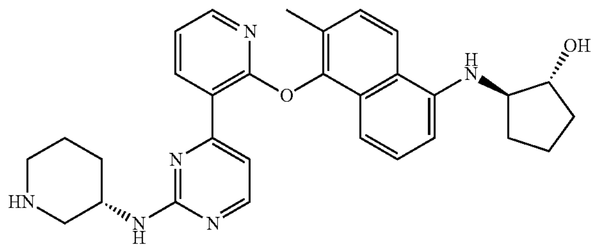 [SMILES: Cc1ccc2c(N[C@@H]3CCC[C@H]3O)cccc2c1Oc1ncccc1-c1ccnc(N[C@H]2CCCNC2)n1] | (1R,2R)-2-((6-Methyl-5-((3-(2-((S)-piperidin-3-ylamino)pyrimidin-4-yl)pyridin-2-yl)oxy)naphthalen-1-yl)amino)cyclopentanol | 0.109 |
| 396 | 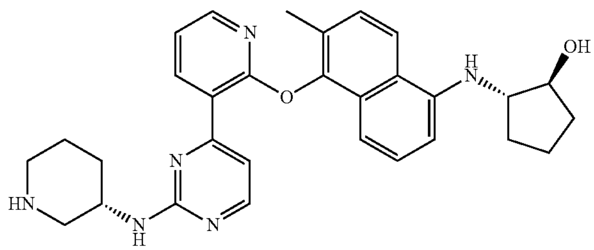 [SMILES: Cc1ccc2c(N[C@H]3CCC[C@@H]3O)cccc2c1Oc1ncccc1-c1ccnc(N[C@H]2CCCNC2)n1] | (1S,2S)-2-((6-Methyl-5-((3-(2-((S)-piperidin-3-ylamino)pyrimidin-4-yl)pyridin-2-yl)oxy)naphthalen-1-yl)amino)cyclopentanol | 0.27 |
| 397 | 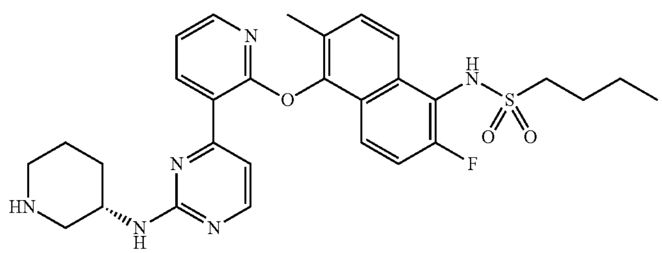 [SMILES: CCCCS(=O)(=O)Nc1c(F)ccc2c(Oc3ncccc3-c3ccnc(N[C@H]4CCCNC4)n3)c(C)ccc12] | N-[2-Fluoro-6-methyl-5-[[3-[2-[[(3S)-3-piperidyl]amino]pyrimidin-4-yl]-2-pyridyl]oxy]-1-naphthyl]butane-1-sulfonamide | 0.034 |
| 398 | 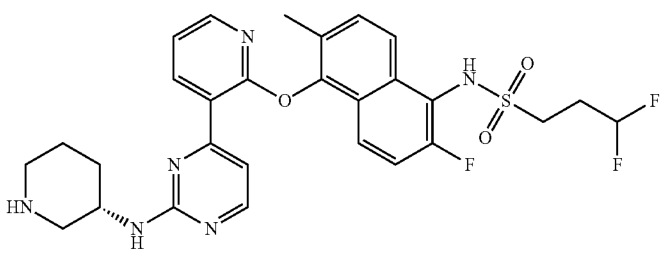 [SMILES: Cc1ccc2c(NS(=O)(=O)CCC(F)F)c(F)ccc2c1Oc1ncccc1-c1ccnc(N[C@H]2CCCNC2)n1] | 3,3-Difluoro-N-[2-fluoro-6-methyl-5-[[3-[2-[[(3S)-3-piperidyl]amino]pyrimidin-4-yl]-2-pyridyl]oxy]-1-naphthyl]propane-1-sulfonamide | 0.022 |
| 399 | 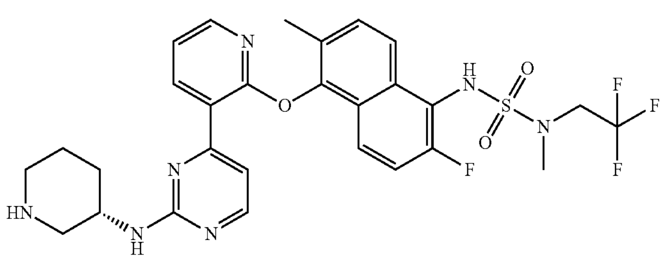 [SMILES: Cc1ccc2c(NS(=O)(=O)N(C)CC(F)(F)F)c(F)ccc2c1Oc1ncccc1-c1ccnc(N[C@H]2CCCNC2)n1] | 2-Cyclopropyl-N-[2-fluoro-6-methyl-5-[[3-[2-[[(3S)-3-piperidyl]amino]pyrimidin-4-yl]-2-pyridyl]oxy]-1-naphthyl]ethanesulfonamide | 0.072 |
| 400 | 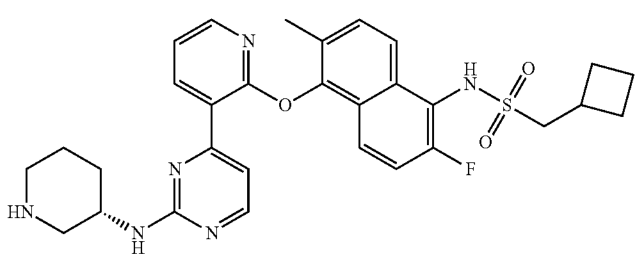 [SMILES: Cc1ccc2c(NS(=O)(=O)CC3CCC3)c(F)ccc2c1Oc1ncccc1-c1ccnc(N[C@H]2CCCNC2)n1] | 1-Cyclobutyl-N-[2-fluoro-6-methyl-5-[[3-[2-[[(3S)-3-piperidyl]amino]pyrimidin-4-yl]-2-pyridyl]oxy]-1-naphthyl]methanesulfonamide | 0.026 |

TABLE 2-continued

| No. | Structure | Name | XBP1s-luc 293 LUC (IC$_{50}$) (μmol) |
|---|---|---|---|
| 401 | 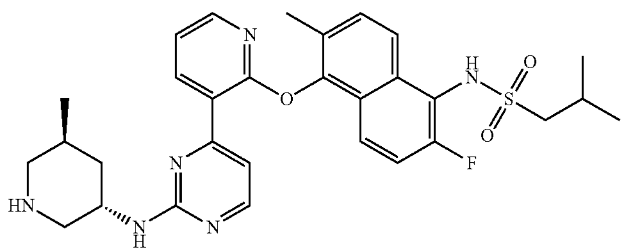 [SMILES: Cc1ccc2c(NS(=O)(=O)CC(C)C)c(F)ccc2c1Oc1ncccc1-c1ccnc(N[C@@H]2CNC[C@@H](C)C2)n1] | N-[2-Fluoro-6-methyl-5-[[3-[2-[[(3S,5S)-5-methyl-3-piperidyl]amino]pyrimidin-4-yl]-2-pyridyl]oxy]-1-naphthyl]-2-methyl-propane-1-sulfonamide | 0.067 |
| 402 | 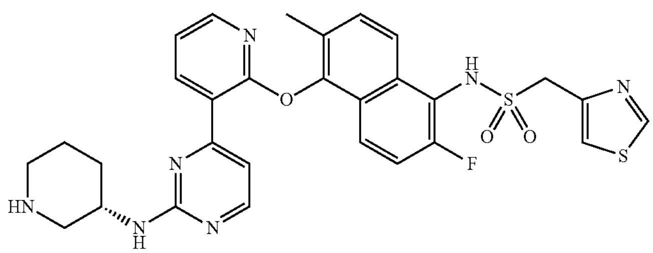 [SMILES: Cc1ccc2c(NS(=O)(=O)Cc3cscn3)c(F)ccc2c1Oc1ncccc1-c1ccnc(N[C@H]2CCCNC2)n1] | N-[2-Fluoro-6-methyl-5-[[3-[2-[[(3S)-3-piperidyl]amino]pyrimidin-4-yl]-2-pyridyl]oxy]-1-naphthyl]-1-thiazol-4-yl-methanesulfonamide | 0.051 |
| 403 | 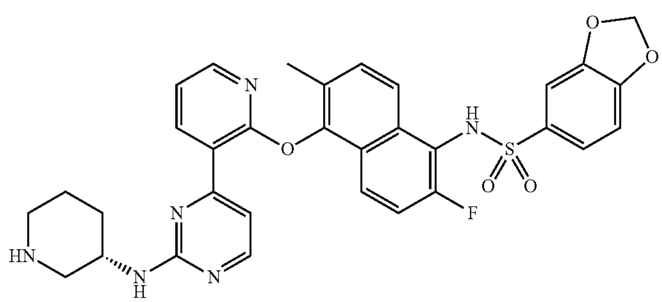 [SMILES: Cc1ccc2c(NS(=O)(=O)c3ccc4c(c3)OCO4)c(F)ccc2c1Oc1ncccc1-c1ccnc(N[C@H]2CCCNC2)n1] | N-[2-Fluoro-6-methyl-5-[[3-[2-[[(3S)-3-piperidyl]amino]pyrimidin-4-yl]-2-pyridyl]oxy]-1-naphthyl]-1,3-benzodioxole-5-sulfonamide | 0.044 |
| 404 | 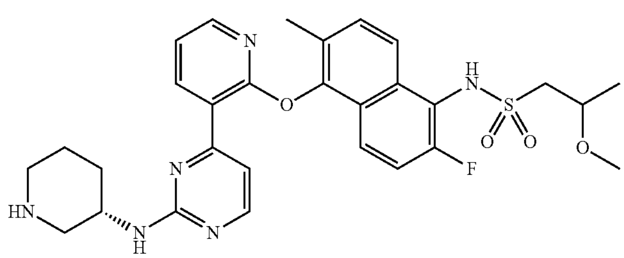 [SMILES: COC(C)CS(=O)(=O)Nc1c(F)ccc2c(Oc3ncccc3-c3ccnc(N[C@H]4CCCNC4)n3)c(C)ccc12] | N-(2-Fluoro-6-methyl-5-((3-(2-(((S)-piperidin-3-yl)amino)pyrimidin-4-yl)pyridin-2-yl)oxy)naphthalen-1-yl)-2-methoxypropane-1-sulfonamide | 0.034 |
| 405 | 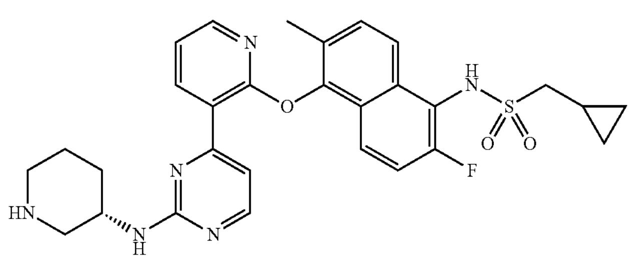 [SMILES: Cc1ccc2c(NS(=O)(=O)CC3CC3)c(F)ccc2c1Oc1ncccc1-c1ccnc(N[C@H]2CCCNC2)n1] | 1-Cyclopropyl-N-[2-fluoro-6-methyl-5-[[3-[2-[[(3S)-3-piperidyl]amino]pyrimidin-4-yl]-2-pyridyl]oxy]-1-naphthyl]methanesulfonamide | 0.025 |

TABLE 2-continued

| No. | Structure | Name | XBP1s-luc 293 LUC (IC$_{50}$) (μmol) |
|---|---|---|---|
| 406 | 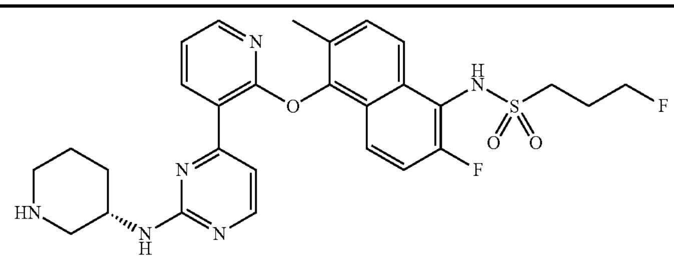 | 3-Fluoro-N-[2-fluoro-6-methyl-5-[[3-[2-[[(3S)-3-piperidyl]amino]pyrimidin-4-yl]-2-pyridyl]oxy]-1-naphthyl]propane-1-sulfonamide | 0.031 |
| 407 | 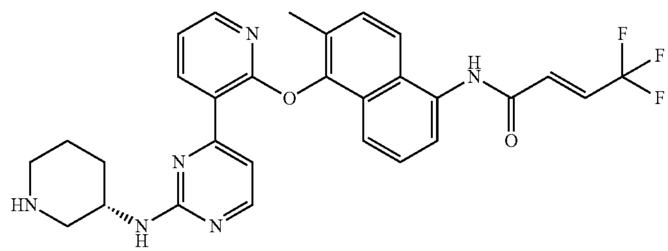 [SMILES: Cc1ccc2c(NC(=O)/C=C/C(F)(F)F)cccc2c1Oc1ncccc1-c1ccnc(N[C@H]2CCCNC2)n1] | (E)-4,4,4-Trifluoro-N-[6-methyl-5-[[3-[2-[[(3S)-3-piperidyl]amino]pyrimidin-4-yl]-2-pyridyl]oxy]-1-naphthyl]but-2-enamide | 0.221 |
| 408 | | 1-(6-Methyl-5-((3-(2-(((S)-piperidin-3-yl)amino)pyrimidin-4-yl)pyridin-2-yl)oxy)naphthalen-1-yl)pyrrolidin-3-ol | 0.47 (Isomer 1) |
| 409 | 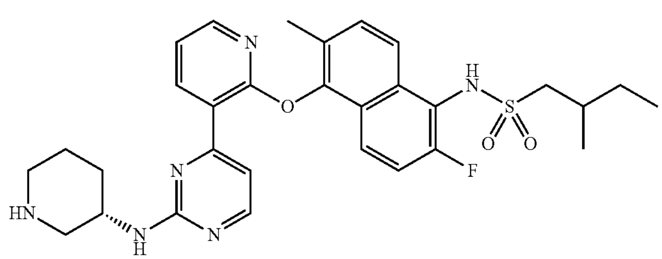 [SMILES: CCC(C)CS(=O)(=O)Nc1c(F)ccc2c(Oc3ncccc3-c3ccnc(N[C@H]4CCCNC4)n3)c(C)ccc12] | N-(2-Fluoro-6-methyl-5-((3-(2-(((S)-piperidin-3-yl)amino)pyrimidin-4-yl)pyridin-2-yl)oxy)naphthalen-1-yl)-2-methylbutane-1-sulfonamide | 0.025 |

TABLE 2-continued

| No. | Structure | Name | XBP1s-luc 293 LUC (IC$_{50}$) (μmol) |
|---|---|---|---|
| 410 | 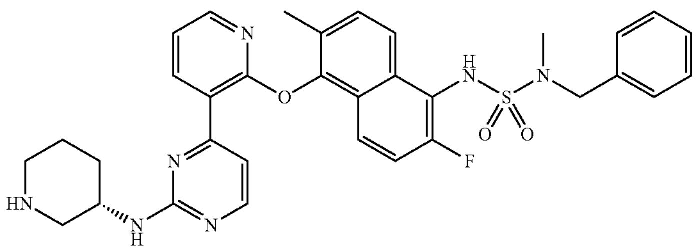 [SMILES: Cc1ccc2c(NS(=O)(=O)N(C)Cc3ccccc3)c(F)ccc2c1Oc1ncccc1-c1ccnc(N[C@H]2CCCNC2)n1] | 4-[2-[[5-[[Benzyl(methyl)sulfamoyl]amino]-6-fluoro-2-methyl-1-naphthyl]oxy]-3-pyridyl]-2-[[(3S)-3-piperidyl]amino]pyrimidine | 0.087 |
| 411 | 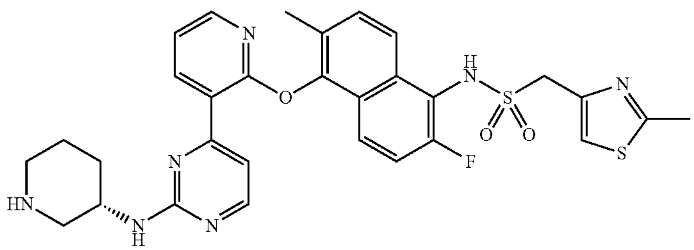 | N-[2-Fluoro-6-methyl-5-[[3-[2-[[(3S)-3-piperidyl]amino]pyrimidin-4-yl]-2-pyridyl]oxy]-1-naphthyl]-1-(2-methylthiazol-4-yl)methanesulfonamide | 0.012 |
| 412 | 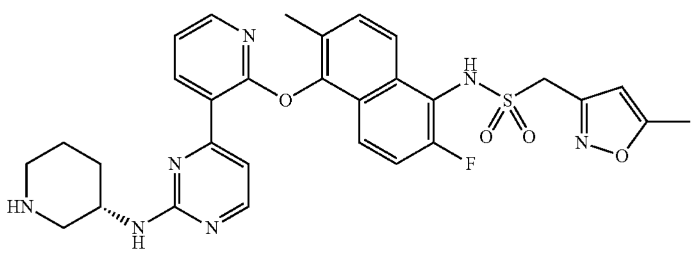 [SMILES: Cc1cc(CS(=O)(=O)Nc2c(F)ccc3c(Oc4ncccc4-c4ccnc(N[C@H]5CCCNC5)n4)c(C)ccc23)no1] | N-[2-Fluoro-6-methyl-5-[[3-[2-[[(3S)-3-piperidyl]amino]pyrimidin-4-yl]-2-pyridyl]oxy]-1-naphthyl]-1-(5-methylisoxazol-3-yl)methanesulfonamide | 0.007 |
| 413 | 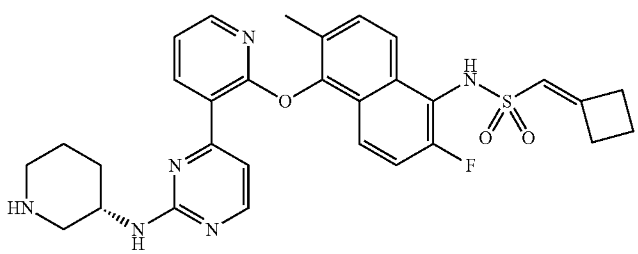 [SMILES: Cc1ccc2c(NS(=O)(=O)C=C3CCC3)c(F)ccc2c1Oc1ncccc1-c1ccnc(N[C@H]2CCCNC2)n1] | 1-Cyclobutylidene-N-[2-fluoro-6-methyl-5-[[3-[2-[[(3S)-3-piperidyl]amino]pyrimidin-4-yl]-2-pyridyl]oxy]-1-naphthyl]methanesulfonamide | 0.05 |
| 414 | 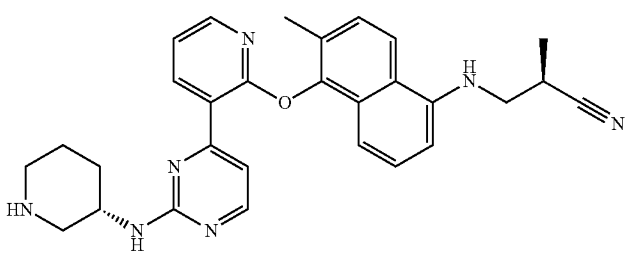 [SMILES: Cc1ccc2c(NC[C@@H](C)C#N)cccc2c1Oc1ncccc1-c1ccnc(N[C@H]2CCCNC2)n1] | (R)-2-Methyl-3-((6-methyl-5-((3-(2-(((S)-piperidin-3-yl)amino)pyrimidin-4-yl)pyridin-2-yl)oxy)naphthalen-1-yl)amino)propanenitrile | 0.059 |

TABLE 2-continued

| No. | Structure | Name | XBP1s-luc 293 LUC (IC$_{50}$) (μmol) |
|---|---|---|---|
| 415 | 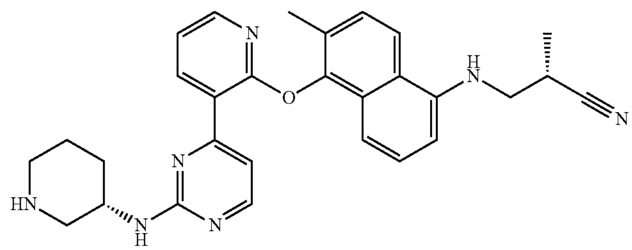 [SMILES: Cc1ccc2c(NC[C@H](C)C#N)cccc2c1Oc1ncccc1-c1ccnc(N[C@H]2CCCNC2)n1] | (S)-2-Methyl-3-((6-methyl-5-((3-(2-(((S)-piperidin-3-yl)amino)pyrimidin-4-yl)pyridin-2-yl)oxy)naphthalen-1-yl)amino)propanenitrile | 0.269 |
| 416 | 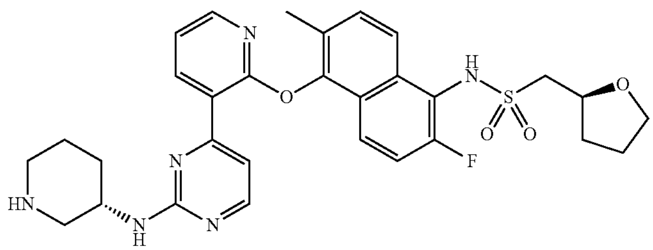 [SMILES: Cc1ccc2c(NS(=O)(=O)C[C@@H]3CCCO3)c(F)ccc2c1Oc1ncccc1-c1ccnc(N[C@H]2CCCNC2)n1] | N-(2-Fluoro-6-methyl-5-((3-(2-(((S)-piperidin-3-yl)amino)pyrimidin-4-yl)pyridin-2-yl)oxy)naphthalen-1-yl)-1-((S)-tetrahydrofuran-2-yl)methanesulfonamide | 0.105 |
| 417 | 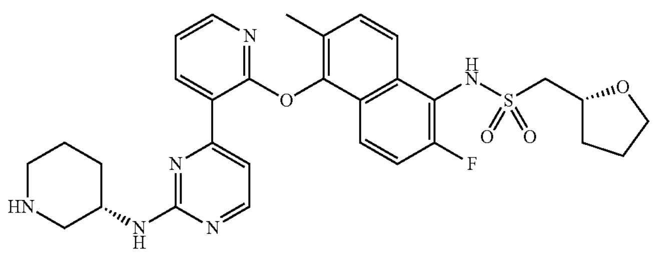 [SMILES: Cc1ccc2c(NS(=O)(=O)C[C@H]3CCCO3)c(F)ccc2c1Oc1ncccc1-c1ccnc(N[C@H]2CCCNC2)n1] | N-(2-Fluoro-6-methyl-5-((3-(2-(((S)-piperidin-3-yl)amino)pyrimidin-4-yl)pyridin-2-yl)oxy)naphthalen-1-yl)-1-((R)-tetrahydrofuran-2-yl)methanesulfonamide | 0.074 |
| 418 | 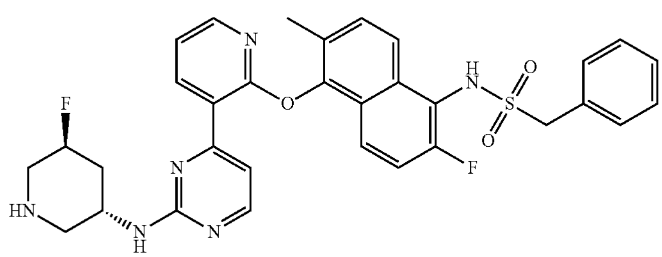 [SMILES: Cc1ccc2c(NS(=O)(=O)Cc3ccccc3)c(F)ccc2c1Oc1ncccc1-c1ccnc(N[C@@H]2CNC[C@@H](F)C2)n1] | N-[2-Fluoro-5-[[3-[2-[[(3S,5S)-5-fluoro-3-piperidyl]amino]pyrimidin-4-yl]-2-pyridyl]oxy]-6-methyl-1-naphthyl]-1-phenyl-methanesulfonamide | 0.002 |
| 419 | 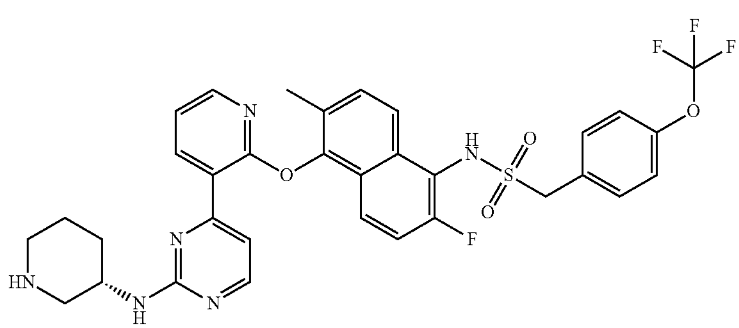 [SMILES: Cc1ccc2c(NS(=O)(=O)Cc3ccc(OC(F)(F)F)cc3)c(F)ccc2c1Oc1ncccc1-c1ccnc(N[C@H]2CCCNC2)n1] | N-[2-Fluoro-6-methyl-5-[[3-[2-[[(3S)-3-piperidyl]amino]pyrimidin-4-yl]-2-pyridyl]oxy]-1-naphthyl]-1-[4-(trifluoromethoxy)phenyl]methanesulfonamide | 0.129 |

TABLE 2-continued

| No. | Structure | Name | XBP1s-luc 293 LUC (IC$_{50}$) (μmol) |
|---|---|---|---|
| 420 | 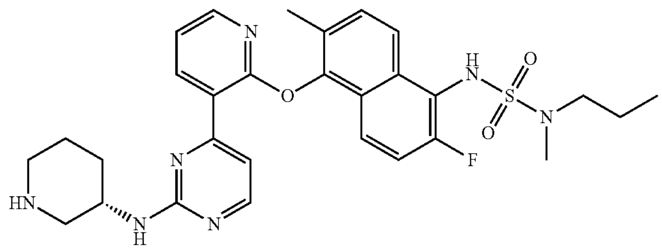 [SMILES: CCCN(C)S(=O)(=O)Nc1c(F)ccc2c(Oc3ncccc3-c3ccnc(N[C@H]4CCCNC4)n3)c(C)ccc12] | 4-[2-[[6-Fluoro-2-methyl-5-[[methyl(propyl)sulfamoyl]amino]-1-naphthyl]oxy]-3-pyridyl]-2-[[(3S)-3-piperidyl]amino]pyrimidine | 0.041 |
| 421 | 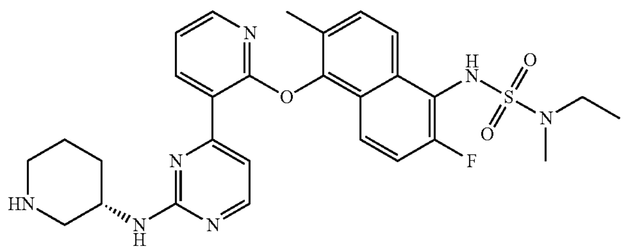 [SMILES: CCN(C)S(=O)(=O)Nc1c(F)ccc2c(Oc3ncccc3-c3ccnc(N[C@H]4CCCNC4)n3)c(C)ccc12] | 4-[2-[[5-[[Ethyl(methyl)sulfamoyl]amino]-6-fluoro-2-methyl-1-naphthyl]oxy]-3-pyridyl]-2-[[(3S)-3-piperidyl]amino]pyrimidine | 0.044 |
| 422 | 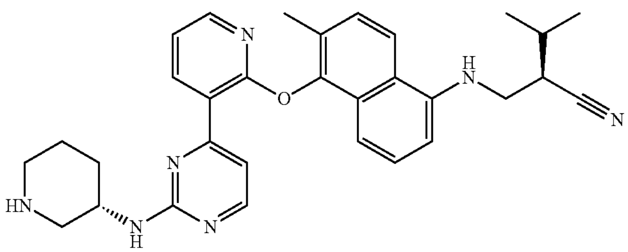 [SMILES: Cc1ccc2c(NC[C@H](C#N)C(C)C)cccc2c1Oc1ncccc1-c1ccnc(N[C@H]2CCCNC2)n1] | (R)-3-Methyl-2-(((6-methyl-5-((3-(2-(((S)-piperidin-3-yl)amino)pyrimidin-4-yl)pyridin-2-yl)oxy)naphthalen-1-yl)amino)methyl)butanenitrile | 0.083 |
| 423 | 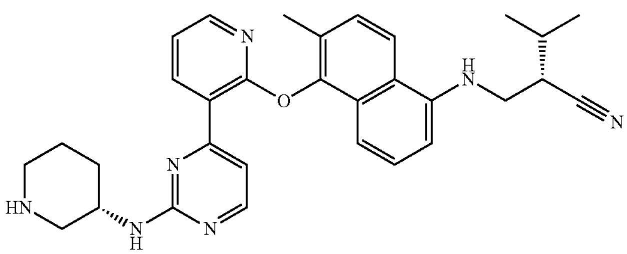 [SMILES: Cc1ccc2c(NC[C@@H](C#N)C(C)C)cccc2c1Oc1ncccc1-c1ccnc(N[C@H]2CCCNC2)n1] | (S)-3-Methyl-2-(((6-methyl-5-((3-(2-(((S)-piperidin-3-yl)amino)pyrimidin-4-yl)pyridin-2-yl)oxy)naphthalen-1-yl)amino)methyl)butanenitrile | 0.207 |
| 424 | 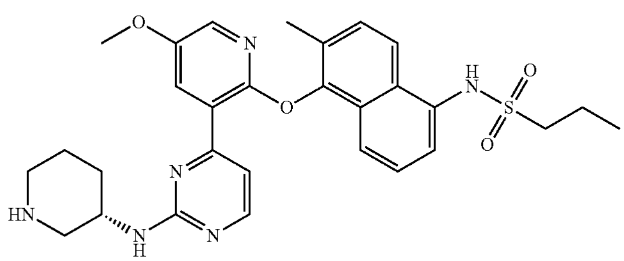 [SMILES: CCCS(=O)(=O)Nc1cccc2c(Oc3ncc(OC)cc3-c3ccnc(N[C@H]4CCCNC4)n3)c(C)ccc12] | N-[5-[[5-Methoxy-3-[2-[[(3S)-3-piperidyl]amino]pyrimidin-4-yl]-2-pyridyl]oxy]-6-methyl-1-naphthyl]propane-1-sulfonamide | 0.392 |
| 425 | 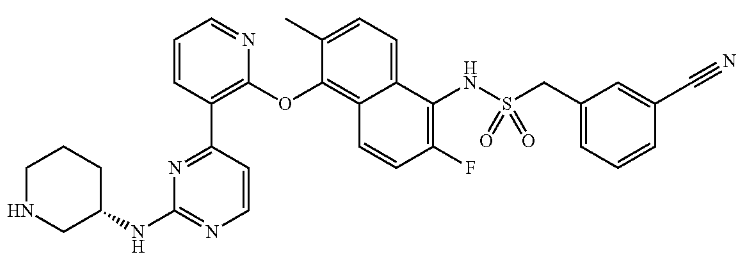 [SMILES: Cc1ccc2c(NS(=O)(=O)Cc3cccc(C#N)c3)c(F)ccc2c1Oc1ncccc1-c1ccnc(N[C@H]2CCCNC2)n1] | 1-(3-Cyanophenyl)-N-[2-fluoro-6-methyl-5-[[3-[2-[[(3S)-3-piperidyl]amino]pyrimidin-4-yl]-2-pyridyl]oxy]-1-naphthyl]methanesulfonamide | 0.016 |

TABLE 2-continued

| No. | Structure | Name | XBP1s-luc 293 LUC (IC$_{50}$) (μmol) |
|---|---|---|---|
| 426 | 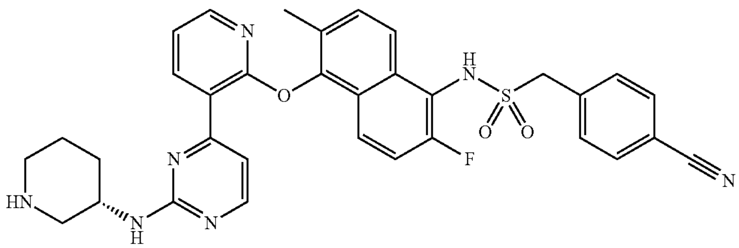 [SMILES: Cc1ccc2c(NS(=O)(=O)Cc3ccc(C#N)cc3)c(F)ccc2c1Oc1ncccc1-c1ccnc(N[C@H]2CCCNC2)n1] | 1-(4-Cyanophenyl)-N-[2-fluoro-6-methyl-5-[[3-[2-[[(3S)-3-piperidyl]amino]pyrimidin-4-yl]-2-pyridyl]oxy]-1-naphthyl]methanesulfonamide | 0.005 |
| 427 | 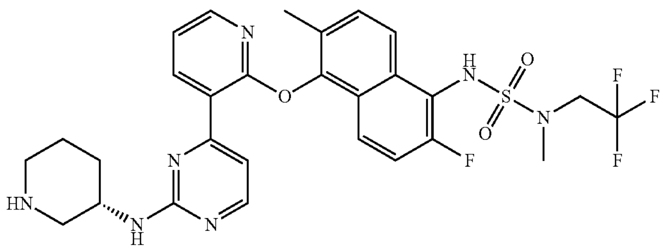 [SMILES: Cc1ccc2c(NS(=O)(=O)N(C)CC(F)(F)F)c(F)ccc2c1Oc1ncccc1-c1ccnc(N[C@H]2CCCNC2)n1] | 4-[2-[[6-Fluoro-2-methyl-5-[[methyl(2,2,2-trifluoroethyl)sulfamoyl]amino]-1-naphthyl]oxy]-3-pyridyl]-2-[[(3S)-3-piperidyl]amino]pyrimidine | 0.006 |
| 428 | 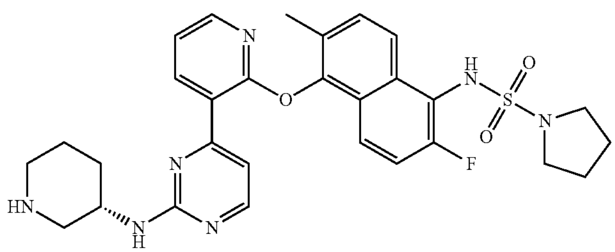 [SMILES: Cc1ccc2c(NS(=O)(=O)N3CCCC3)c(F)ccc2c1Oc1ncccc1-c1ccnc(N[C@H]2CCCNC2)n1] | N-[2-Fluoro-6-methyl-5-[[3-[2-[[(3S)-3-piperidyl]amino]pyrimidin-4-yl]-2-pyridyl]oxy]-1-naphthyl]pyrrolidine-1-sulfonamide | 0.028 |
| 429 | 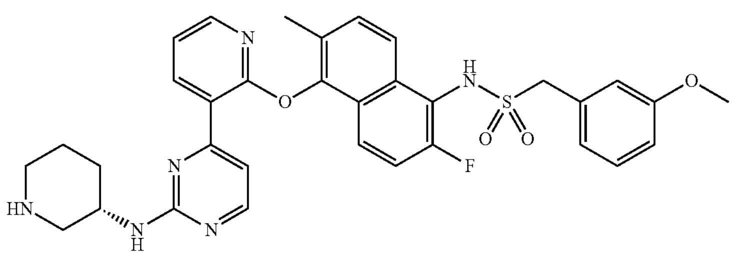 [SMILES: COc1cccc(CS(=O)(=O)Nc2c(F)ccc3c(Oc4ncccc4-c4ccnc(N[C@H]5CCCNC5)n4)c(C)ccc23)c1] | N-[2-Fluoro-6-methyl-5-[[3-[2-[[(3S)-3-piperidyl]amino]pyrimidin-4-yl]-2-pyridyl]oxy]-1-naphthyl]-1-(3-methoxyphenyl)methanesulfonamide | 0.005 |
| 430 | 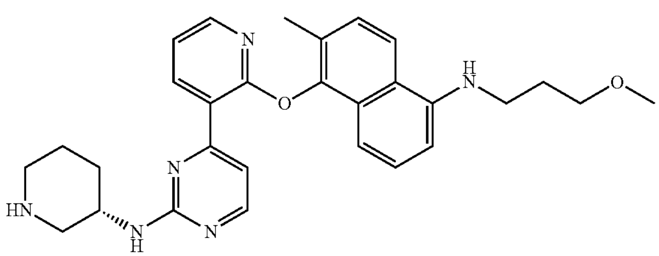 [SMILES: COCCCNc1cccc2c(Oc3ncccc3-c3ccnc(N[C@H]4CCCNC4)n3)c(C)ccc12] | 4-[2-[[5-(3-Methoxypropylamino)-2-methyl-1-naphthyl]oxy]-3-pyridyl]-N-[(3S)-3-piperidyl]pyrimidin-2-amine | 0.275 |

TABLE 2-continued

| No. | Structure | Name | XBP1s-luc 293 LUC (IC$_{50}$) (μmol) |
|---|---|---|---|
| 431 | 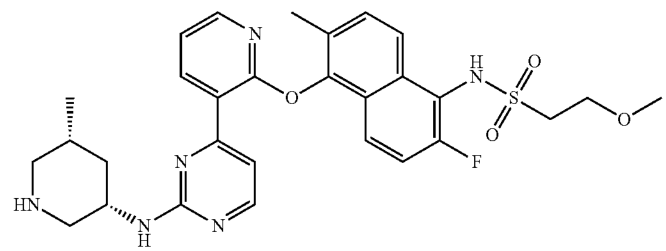 [SMILES: COCCS(=O)(=O)Nc1c(F)ccc2c(Oc3ncccc3-c3ccnc(N[C@@H]4CNC[C@H](C)C4)n3)c(C)ccc12] | N-[2-Fluoro-6-methyl-5-[[3-[2-[[(3S,5R)-5-methyl-3-piperidyl]amino]pyrimidin-4-yl]-2-pyridyl]oxy]-1-naphthyl]-2-methoxy-ethanesulfonamide | 0.034 |
| 432 | 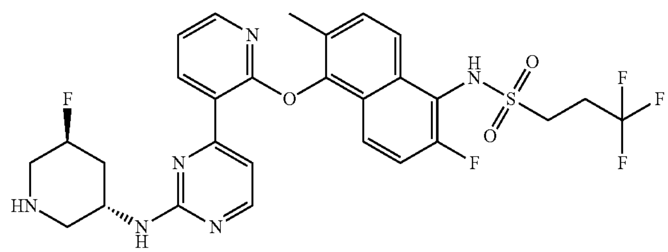 [SMILES: Cc1ccc2c(NS(=O)(=O)CCC(F)(F)F)c(F)ccc2c1Oc1ncccc1-c1ccnc(N[C@@H]2CNC[C@@H](F)C2)n1] | 3,3,3-Trifluoro-N-(2-fluoro-5-((3-(2-(((3S,5S)-5-fluoropiperidin-3-yl)amino)pyrimidin-4-yl)pyridin-2-yl)oxy)-6-methylnaphthalen-1-yl)propane-1-sulfonamide | 0.028 |
| 433 | 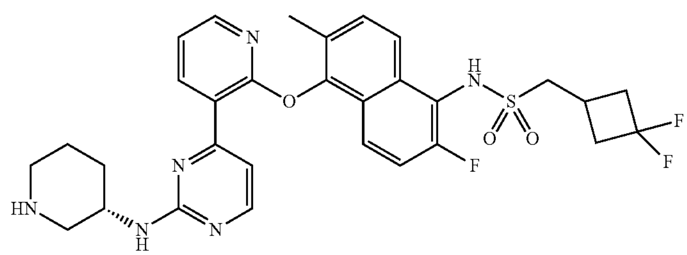 [SMILES: Cc1ccc2c(NS(=O)(=O)CC3CC(F)(F)C3)c(F)ccc2c1Oc1ncccc1-c1ccnc(N[C@H]2CCCNC2)n1] | 1-(3,3-Difluorocyclobutyl)-N-[2-fluoro-6-methyl-5-[[3-[2-[[(3S)-3-piperidyl]amino]pyrimidin-4-yl]-2-pyridyl]oxy]-1-naphthyl]methanesulfonamide | 0.076 |
| 434 | 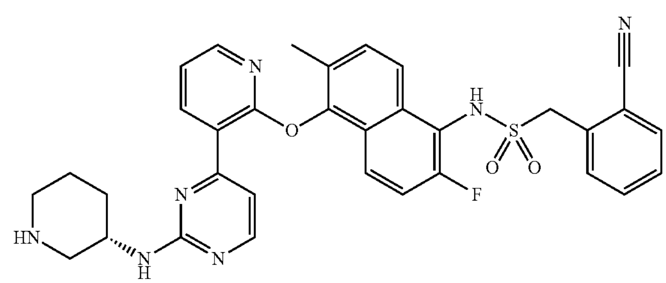 [SMILES: Cc1ccc2c(NS(=O)(=O)Cc3ccccc3C#N)c(F)ccc2c1Oc1ncccc1-c1ccnc(N[C@H]2CCCNC2)n1] | 1-(2-Cyanophenyl)-N-[2-fluoro-6-methyl-5-[[3-[2-[[(3S)-3-piperidyl]amino]pyrimidin-4-yl]-2-pyridyl]oxy]-1-naphthyl]methanesulfonamide | 0.006 |
| 435 | 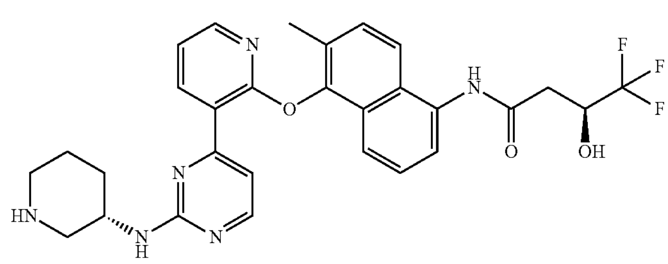 [SMILES: Cc1ccc2c(NC(=O)C[C@H](O)C(F)(F)F)cccc2c1Oc1ncccc1-c1ccnc(N[C@H]2CCCNC2)n1] | (S)-4,4,4-Trifluoro-3-hydroxy-N-(6-methyl-5-((3-(2-(((S)-piperidin-3-yl)amino)pyrimidin-4-yl)pyridin-2-yl)oxy)naphthalen-1-yl)butanamide | 0.338 |

TABLE 2-continued

| No. | Structure | Name | XBP1s-luc 293 LUC (IC$_{50}$) (μmol) |
|---|---|---|---|
| 436 | 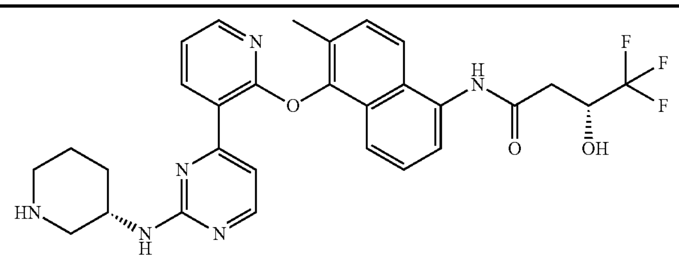 | (R)-4,4,4-Trifluoro-3-hydroxy-N-(6-methyl-5-((3-(2-(((S)-piperidin-3-yl)amino)pyrimidin-4-yl)pyridin-2-yl)oxy)naphthalen-1-yl)butanamide | 0.075 |
| 437 | 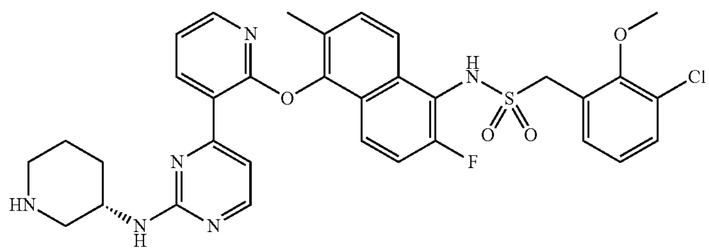 [SMILES: COc1c(Cl)cccc1CS(=O)(=O)Nc1c(F)ccc2c(Oc3ncccc3-c3ccnc(N[C@H]4CCCNC4)n3)c(C)ccc12] | 1-(3-Chloro-2-methoxy-phenyl)-N-[2-fluoro-6-methyl-5-[[3-[2-[[(3S)-3-piperidyl]amino]pyrimidin-4-yl]-2-pyridyl]oxy]-1-naphthyl]methanesulfonamide | 0.018 |
| 438 | 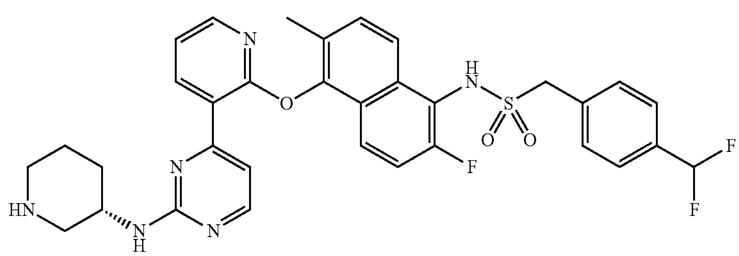 [SMILES: Cc1ccc2c(NS(=O)(=O)Cc3ccc(C(F)F)cc3)c(F)ccc2c1Oc1ncccc1-c1ccnc(N[C@H]2CCCNC2)n1] | 1-[4-(Difluoromethyl)phenyl]-N-[2-fluoro-6-methyl-5-[[3-[2-[[(3S)-3-piperidyl]amino]pyrimidin-4-yl]-2-pyridyl]oxy]-1-naphthyl]methanesulfonamide | 0.005 |
| 439 | 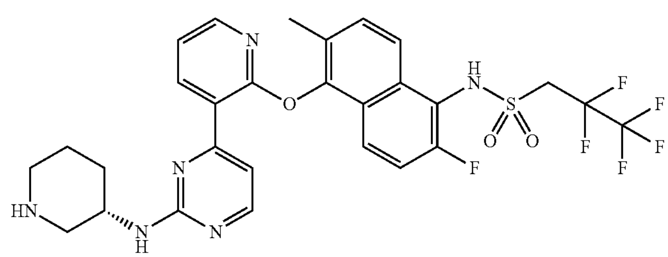 [SMILES: Cc1ccc2c(NS(=O)(=O)CC(F)(F)C(F)(F)F)c(F)ccc2c1Oc1ncccc1-c1ccnc(N[C@H]2CCCNC2)n1] | 2,2,3,3,3-Pentafluoro-N-[2-fluoro-6-methyl-5-[[3-[2-[[(3S)-3-piperidyl]amino]pyrimidin-4-yl]-2-pyridyl]oxy]-1-naphthyl]propane-1-sulfonamide | 0.155 |
| 440 | 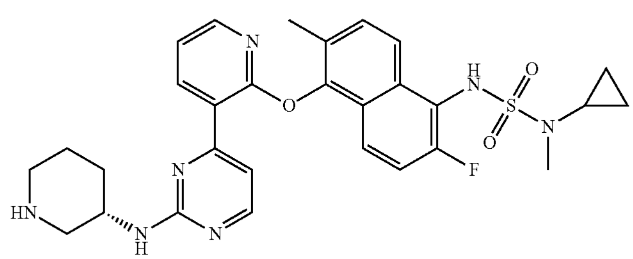 [SMILES: Cc1ccc2c(NS(=O)(=O)N(C)C3CC3)c(F)ccc2c1Oc1ncccc1-c1ccnc(N[C@H]2CCCNC2)n1] | 4-[2-[[5-[[Cyclopropyl(methyl)sulfamoyl]amino]-6-fluoro-2-methyl-1-naphthyl]oxy]-3-pyridyl]-2-[[(3S)-3-piperidyl]amino]pyrimidine | 0.026 |
| 441 | 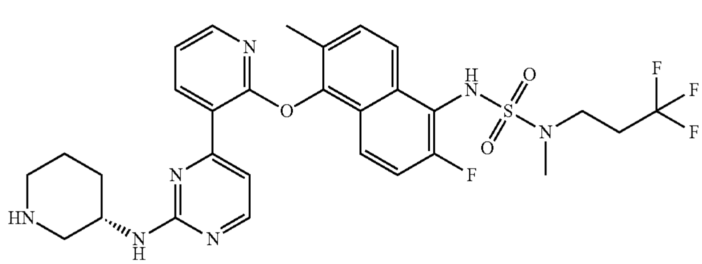 [SMILES: Cc1ccc2c(NS(=O)(=O)N(C)CCC(F)(F)F)c(F)ccc2c1Oc1ncccc1-c1ccnc(N[C@H]2CCCNC2)n1] | 4-[2-[[6-Fluoro-2-methyl-5-[[methyl(3,3,3-trifluoropropyl)sulfamoyl]amino]-1-naphthyl]oxy]-3-pyridyl]-2-[[(3S)-3-piperidyl]amino]pyrimidine | 0.048 |

TABLE 2-continued

| No. | Structure | Name | XBP1s-luc 293 LUC (IC$_{50}$) (μmol) |
|---|---|---|---|
| 442 | 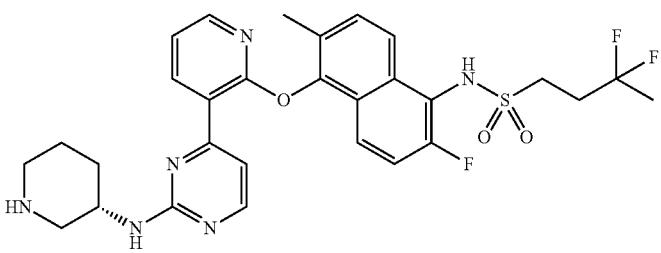 [SMILES: Cc1ccc2c(NS(=O)(=O)CCC(C)(F)F)c(F)ccc2c1Oc1ncccc1-c1ccnc(N[C@H]2CCCNC2)n1] | 3,3-Difluoro-N-[2-fluoro-6-methyl-5-[[3-[2-[[(3S)-3-piperidyl]amino]pyrimidin-4-yl]-2-pyridyl]oxy]-1-naphthyl]butane-1-sulfonamide | 0.04 |
| 443 | 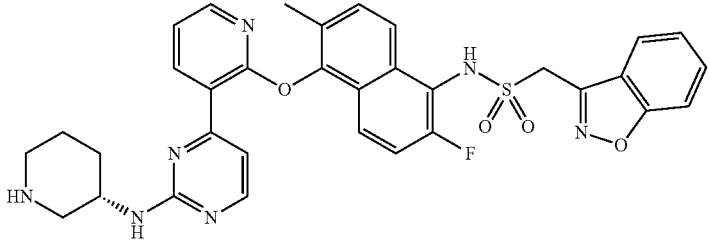 [SMILES: Cc1ccc2c(NS(=O)(=O)Cc3noc4ccccc34)c(F)ccc2c1Oc1ncccc1-c1ccnc(N[C@H]2CCCNC2)n1] | 1-(1,2-Benzoxazol-3-yl)-N-[2-fluoro-6-methyl-5-[[3-[2-[[(3S)-3-piperidyl]amino]pyrimidin-4-yl]-2-pyridyl]oxy]-1-naphthyl]methanesulfonamide | 0.008 |
| 444 | 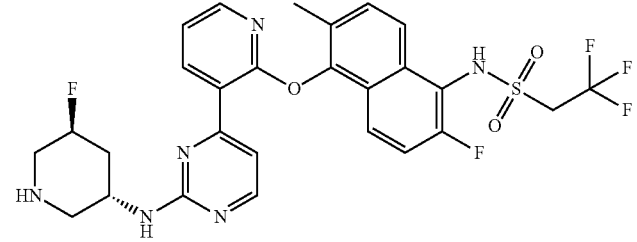 [SMILES: Cc1ccc2c(NS(=O)(=O)CC(F)(F)F)c(F)ccc2c1Oc1ncccc1-c1ccnc(N[C@@H]2CNC[C@@H](F)C2)n1] | 2,2,2-Trifluoro-N-(2-fluoro-5-((3-(2-(((3S,5S)-5-fluoropiperidin-3-yl)amino)pyrimidin-4-yl)pyridin-2-yl)oxy)-6-methylnaphthalen-1-yl)ethane-1-sulfonamide | 0.019 |
| 445 | 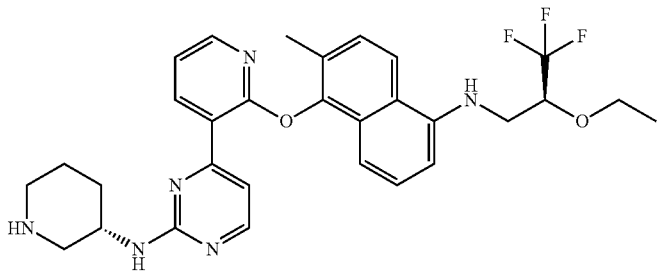 [SMILES: CCO[C@@H](CNc1cccc2c(Oc3ncccc3-c3ccnc(N[C@H]4CCCNC4)n3)c(C)ccc12)C(F)(F)F] | 4-[2-[[5-[[(2S)-2-Ethoxy-3,3,3-trifluoro-propyl]amino]-2-methyl-1-naphthyl]oxy]-3-pyridyl]-N-[(3S)-3-piperidyl]pyrimidin-2-amine | 0.078 |
| 446 | 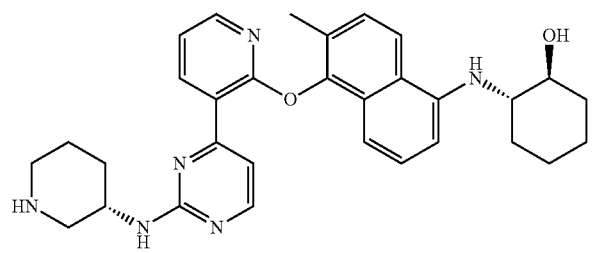 [SMILES: Cc1ccc2c(N[C@H]3CCCC[C@@H]3O)cccc2c1Oc1ncccc1-c1ccnc(N[C@H]2CCCNC2)n1] | (1S,2S)-2-((6-Methyl-5-((3-(2-((((S)-piperidin-3-yl)amino)pyrimidin-4-yl)pyridin-2-yl)oxy)naphthalen-1-yl)amino)cyclohexan-1-ol | 0.067 |

TABLE 2-continued

| No. | Structure | Name | XBP1s-luc 293 LUC (IC$_{50}$) (μmol) |
|---|---|---|---|
| 447 | 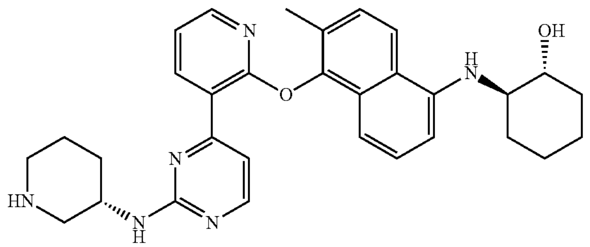 [SMILES: Cc1ccc2c(N[C@@H]3CCCC[C@H]3O)cccc2c1Oc1ncccc1-c1ccnc(N[C@H]2CCCNC2)n1] | (1R,2R)-2-((6-Methyl-5-((3-(2-(((S)-piperidin-3-yl)amino)pyrimidin-4-yl)pyridin-2-yl)oxy)naphthalen-1-yl)amino)cyclohexan-1-ol | 0.146 |
| 448 | 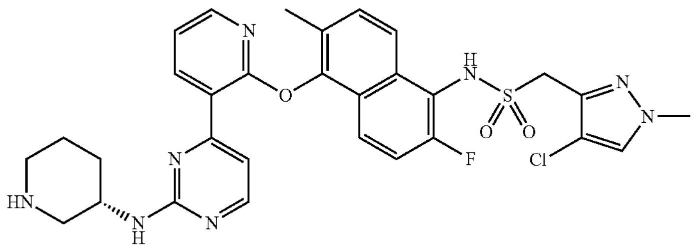 [SMILES: Cc1ccc2c(NS(=O)(=O)Cc3nn(C)cc3Cl)c(F)ccc2c1Oc1ncccc1-c1ccnc(N[C@H]2CCCNC2)n1] | 1-(4-Chloro-1-methyl-pyrazol-3-yl)-N-[2-fluoro-6-methyl-5-[[3-[2-[[(3S)-3-piperidyl]amino]pyrimidin-4-yl]-2-pyridyl]oxy]-1-naphthyl]methanesulfonamide | 0.019 |
| 449 | 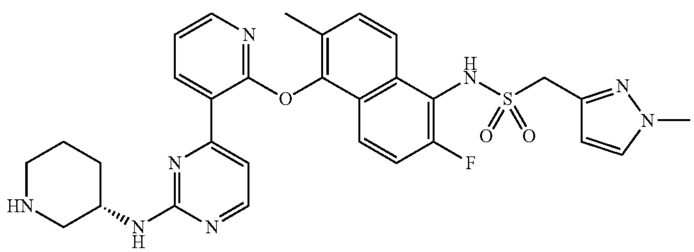 [SMILES: Cc1ccc2c(NS(=O)(=O)Cc3ccn(C)n3)c(F)ccc2c1Oc1ncccc1-c1ccnc(N[C@H]2CCCNC2)n1] | N-[2-Fluoro-6-methyl-5-[[3-[2-[[(3S)-3-piperidyl]amino]pyrimidin-4-yl]-2-pyridyl]oxy]-1-naphthyl]-1-(1-methylpyrazol-3-yl)methanesulfonamide | 0.025 |
| 450 | 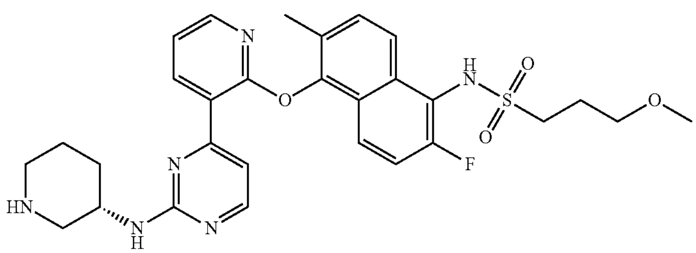 [SMILES: COCCCS(=O)(=O)Nc1c(F)ccc2c(Oc3ncccc3-c3ccnc(N[C@H]4CCCNC4)n3)c(C)ccc12] | N-[2-Fluoro-6-methyl-5-[[3-[2-[[(3S)-3-piperidyl]amino]pyrimidin-4-yl]-2-pyridyl]oxy]-1-naphthyl]-3-methoxy-propane-1-sulfonamide | 0.104 |
| 451 | 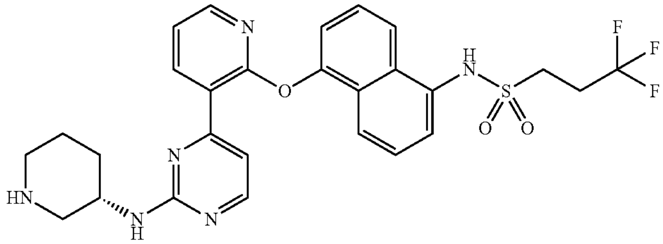 [SMILES: O=S(=O)(CCC(F)(F)F)Nc1cccc2c(Oc3ncccc3-c3ccnc(N[C@H]4CCCNC4)n3)cccc12] | 3,3,3-Trifluoro-N-[5-[[3-[2-[[(3S)-3-piperidyl]amino]pyrimidin-4-yl]-2-pyridyl]oxy]-1-naphthyl]propane-1-sulfonamide | 0.345 |
| 452 | 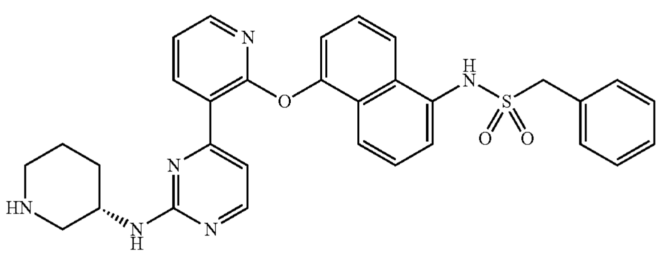 [SMILES: O=S(=O)(Cc1ccccc1)Nc1cccc2c(Oc3ncccc3-c3ccnc(N[C@H]4CCCNC4)n3)cccc12] | 1-Phenyl-N-[5-[[3-[2-[[(3S)-3-piperidyl]amino]pyrimidin-4-yl]-2-pyridyl]oxy]-1-naphthyl]methanesulfonamide | 0.019 |

TABLE 2-continued

| No. | Structure | Name | XBP1s-luc 293 LUC (IC$_{50}$) (μmol) |
|---|---|---|---|
| 453 | 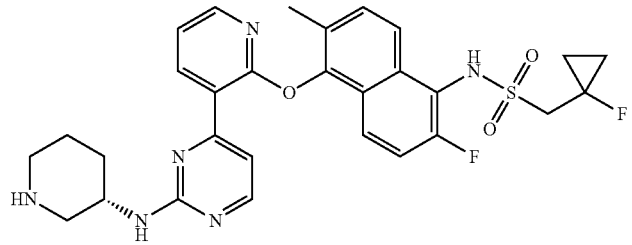 [SMILES: Cc1ccc2c(NS(=O)(=O)CC3(F)CC3)c(F)ccc2c1Oc1ncccc1-c1ccnc(N[C@H]2CCCNC2)n1] | 1-(1-Fluorocyclopropyl)-N-[2-fluoro-6-methyl-5-[[3-[2-[[(3S)-3-piperidyl]amino]pyrimidin-4-yl]-2-pyridyl]oxy]-1-naphthyl]methanesulfonamide | 0.018 |
| 454 | 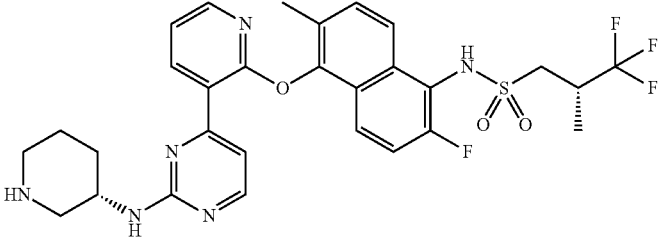 [SMILES: Cc1ccc2c(NS(=O)(=O)C[C@@H](C)C(F)(F)F)c(F)ccc2c1Oc1ncccc1-c1ccnc(N[C@H]2CCCNC2)n1] | (S)-3,3,3-Trifluoro-N-(2-fluoro-6-methyl-5-((3-(2-(((S)-piperidin-3-yl)amino)pyrimidin-4-yl)pyridin-2-yl)oxy)naphthalen-1-yl)-2-methylpropane-1-sulfonamide | 0.024 |
| 455 | 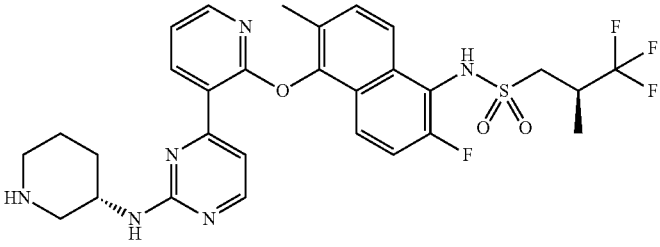 [SMILES: Cc1ccc2c(NS(=O)(=O)C[C@H](C)C(F)(F)F)c(F)ccc2c1Oc1ncccc1-c1ccnc(N[C@H]2CCCNC2)n1] | (R)-3,3,3-Trifluoro-N-(2-fluoro-6-methyl-5-((3-(2-(((S)-piperidin-3-yl)amino)pyrimidin-4-yl)pyridin-2-yl)oxy)naphthalen-1-yl)-2-methylpropane-1-sulfonamide | 0.018 |
| 456 | 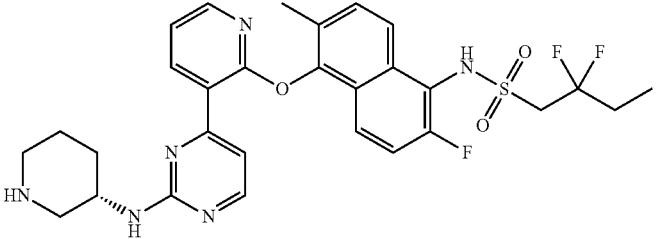 [SMILES: CCC(F)(F)CS(=O)(=O)Nc1c(F)ccc2c(Oc3ncccc3-c3ccnc(N[C@H]4CCCNC4)n3)c(C)ccc12] | 2,2-Difluoro-N-[2-fluoro-6-methyl-5-[[3-[2-[[(3S)-3-piperidyl]amino]pyrimidin-4-yl]-2-pyridyl]oxy]-1-naphthyl]butane-1-sulfonamide | 0.011 |
| 457 | 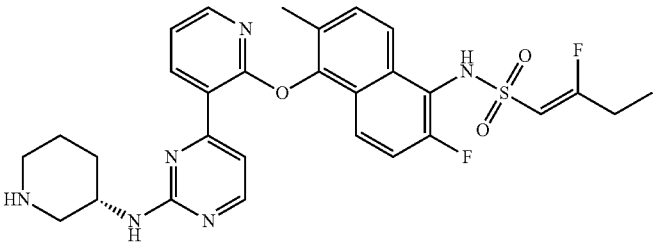 [SMILES: CC/C(F)=C/S(=O)(=O)Nc1c(F)ccc2c(Oc3ncccc3-c3ccnc(N[C@H]4CCCNC4)n3)c(C)ccc12] | (Z)-2-Fluoro-N-[2-fluoro-6-methyl-5-[[3-[2-[[(3S)-3-piperidyl]amino]pyrimidin-4-yl]-2-pyridyl]oxy]-1-naphthyl]but-1-ene-1-sulfonamide | 0.105 |

TABLE 2-continued

| No. | Structure | Name | XBP1s-luc 293 LUC (IC$_{50}$) (μmol) |
|---|---|---|---|
| 458 | 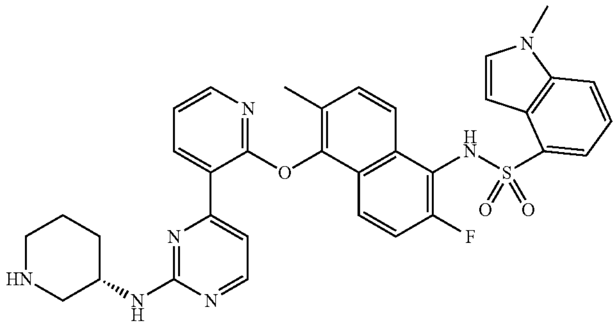 [SMILES: Cc1ccc2c(NS(=O)(=O)c3cccc4c3ccn4C)c(F)ccc2c1Oc1ncccc1-c1ccnc(N[C@H]2CCCNC2)n1] | N-[2-Fluoro-6-methyl-5-[[3-[2-[[(3S)-3-piperidyl]amino]pyrimidin-4-yl]-2-pyridyl]oxy]-1-naphthyl]-1-methyl-indole-4-sulfonamide | 0.019 |
| 459 | 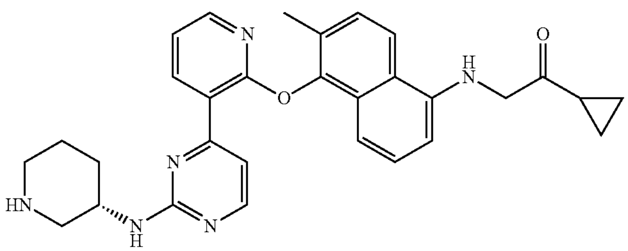 [SMILES: Cc1ccc2c(NCC(=O)C3CC3)cccc2c1Oc1ncccc1-c1ccnc(N[C@H]2CCCNC2)n1] | 1-Cyclopropyl-2-[[6-methyl-5-[[3-[2-[[(3S)-3-piperidyl]amino]pyrimidin-4-yl]-2-pyridyl]oxy]-1-naphthyl]amino]ethanone | 0.312 |
| 460 | 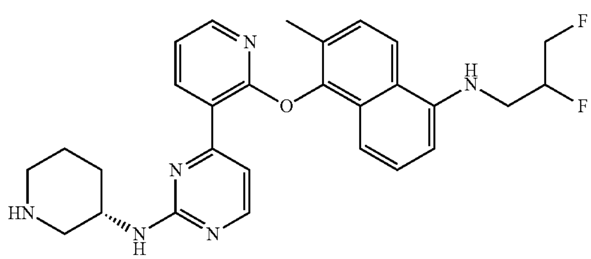 [SMILES: Cc1ccc2c(NCC(F)CF)cccc2c1Oc1ncccc1-c1ccnc(N[C@H]2CCCNC2)n1] | 4-(2-((5-((2,3-Difluoropropyl)amino)-2-methylnaphthalen-1-yl)oxy)pyridin-3-yl)-N-((S)-piperidin-3-yl)pyrimidin-2-amine | 0.092 |
| 461 | 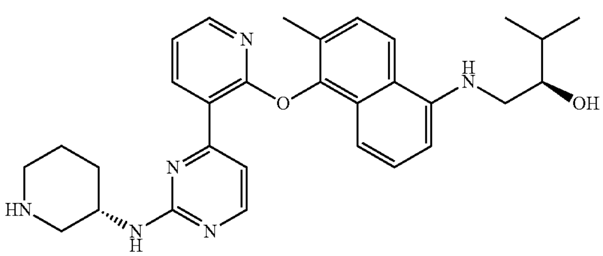 [SMILES: Cc1ccc2c(NC[C@H](O)C(C)C)cccc2c1Oc1ncccc1-c1ccnc(N[C@H]2CCCNC2)n1] | (R)-3-Methyl-1-((6-methyl-5-((3-(2-(((S)-piperidin-3-yl)amino)pyrimidin-4-yl)pyridin-2-yl)oxy)naphthalen-1-yl)amino)butan-2-ol | 0.042 |
| 462 | 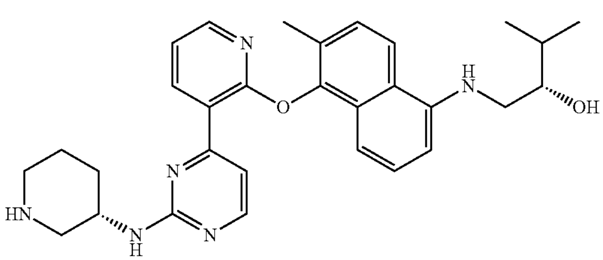 | (S)-3-Methyl-1-((6-methyl-5-((3-(2-(((S)-piperidin-3-yl)amino)pyrimidin-4-yl)pyridin-2-yl)oxy)naphthalen-1-yl)amino)butan-2-ol | 0.11 |

TABLE 2-continued

| No. | Structure | Name | XBP1s-luc 293 LUC (IC$_{50}$) (μmol) |
|---|---|---|---|
| 463 | 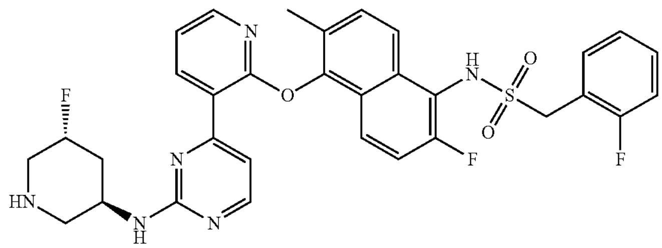 [SMILES: Cc1ccc2c(NS(=O)(=O)Cc3ccccc3F)c(F)ccc2c1Oc1ncccc1-c1ccnc(N[C@H]2CNC[C@H](F)C2)n1] | N-(2-Fluoro-5-((3-(2-(((3R,5R)-5-fluoropiperidin-3-yl)amino)pyrimidin-4-yl)pyridin-2-yl)oxy)-6-methylnaphthalen-1-yl)-1-(2-fluorophenyl)methanesulfonamide | 0.268 |
| 464 | 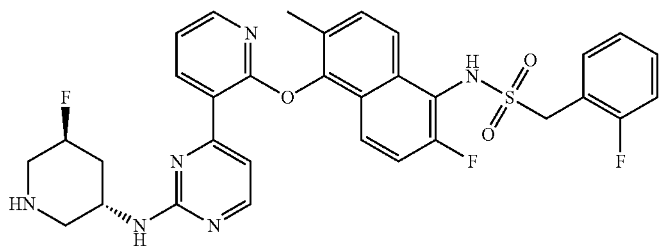 [SMILES: Cc1ccc2c(NS(=O)(=O)Cc3ccccc3F)c(F)ccc2c1Oc1ncccc1-c1ccnc(N[C@@H]2CNC[C@@H](F)C2)n1] | N-(2-Fluoro-5-((3-(2-(((3S,5S)-5-fluoropiperidin-3-yl)amino)pyrimidin-4-yl)pyridin-2-yl)oxy)-6-methylnaphthalen-1-yl)-1-(2-fluorophenyl)methanesulfonamide | 0.004 |
| 465 | 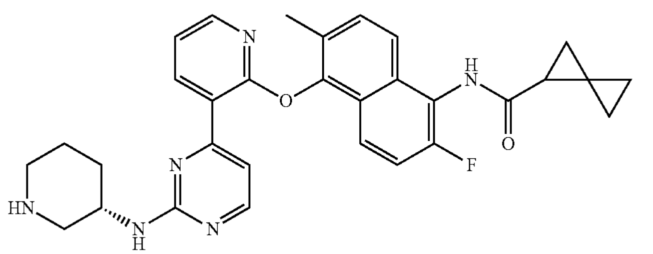 [SMILES: Cc1ccc2c(NC(=O)C3CC34CC4)c(F)ccc2c1Oc1ncccc1-c1ccnc(N[C@H]2CCCNC2)n1] | N-(2-Fluoro-6-methyl-5-((3-(2-(((S)-piperidin-3-yl)amino)pyrimidin-4-yl)pyridin-2-yl)oxy)naphthalen-1-yl)spiro[2.2]pentane-1-carboxamide | 0.057 |
| 466 | 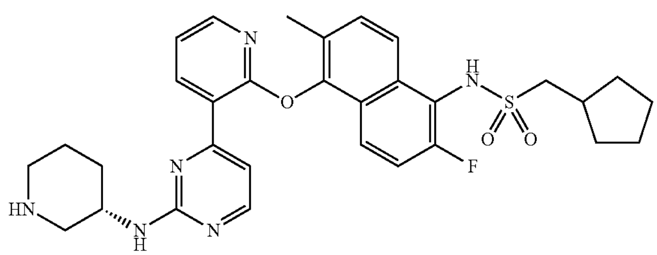 [SMILES: Cc1ccc2c(NS(=O)(=O)CC3CCCC3)c(F)ccc2c1Oc1ncccc1-c1ccnc(N[C@H]2CCCNC2)n1] | 1-Cyclopentyl-N-[2-fluoro-6-methyl-5-[[3-[2-[[(3S)-3-piperidyl]amino]pyrimidin-4-yl]-2-pyridyl]oxy]-1-naphthyl]methanesulfonamide | |
| 467 | 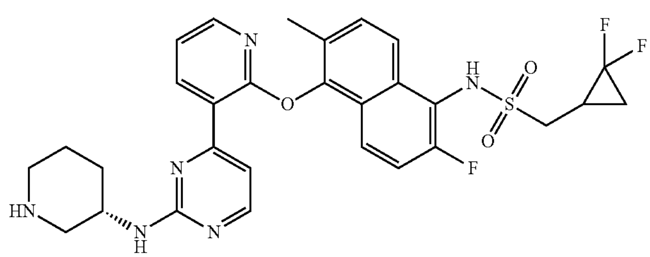 [SMILES: Cc1ccc2c(NS(=O)(=O)CC3CC3(F)F)c(F)ccc2c1Oc1ncccc1-c1ccnc(N[C@H]2CCCNC2)n1] | 1-(2,2-Difluorocyclopropyl)-N-(2-fluoro-6-methyl-5-((3-(2-(((S)-piperidin-3-yl)amino)pyrimidin-4-yl)pyridin-2-yl)oxy)naphthalen-1-yl)methanesulfonamide | 0.042 |
| 468 | 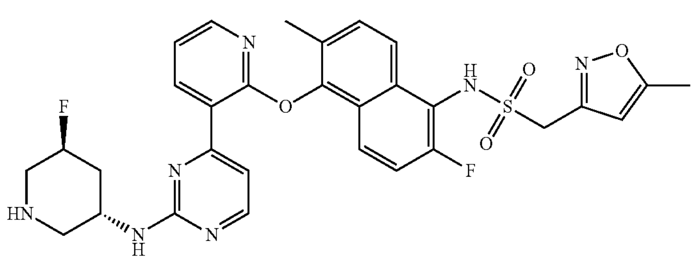 [SMILES: Cc1cc(CS(=O)(=O)Nc2c(F)ccc3c(Oc4ncccc4-c4ccnc(N[C@@H]5CNC[C@@H](F)C5)n4)c(C)ccc23)no1] | N-(2-Fluoro-5-((3-(2-(((3S,5S)-5-fluoropiperidin-3-yl)amino)pyrimidin-4-yl)pyridin-2-yl)oxy)-6-methylnaphthalen-1-yl)-1-(5-methylisoxazol-3-yl)methanesulfonamide | 0.01 |

TABLE 2-continued

| No. | Structure | Name | XBP1s-luc 293 LUC (IC$_{50}$) (μmol) |
|---|---|---|---|
| 469 | 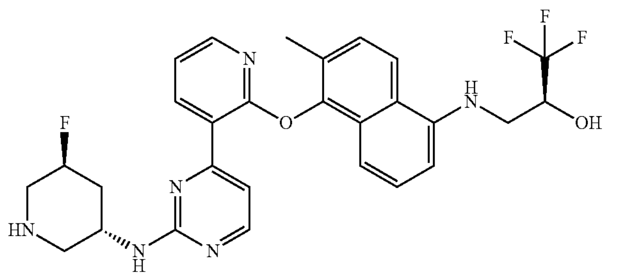 | (S)-1,1,1-Trifluoro-3-((5-(3-(2-(((3S,5S)-5-fluoropiperidin-3-yl)amino)pyrimidin-4-yl)pyridin-2-yl)oxy)-6-methylnaphthalen-1-yl)amino)propan-2-ol | 0.005 |
| 470 | 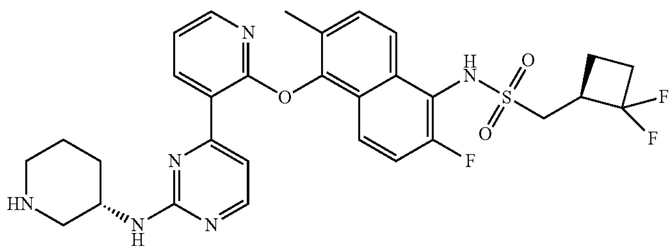 [SMILES: Cc1ccc2c(NS(=O)(=O)C[C@H]3CCC3(F)F)c(F)ccc2c1Oc1ncccc1-c1ccnc(N[C@H]2CCCNC2)n1] | 1-((S)-2,2-Difluorocyclobutyl)-N-(2-fluoro-6-methyl-5-((3-(2-(((S)-piperidin-3-yl)amino)pyrimidin-4-yl)pyridin-2-yl)oxy)naphthalen-1-yl)methanesulfonamide | 0.024 |
| 471 | 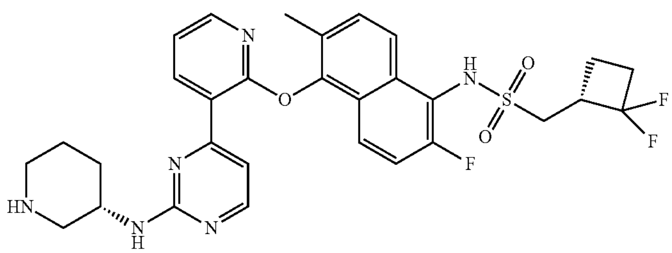 [SMILES: Cc1ccc2c(NS(=O)(=O)C[C@@H]3CCC3(F)F)c(F)ccc2c1Oc1ncccc1-c1ccnc(N[C@H]2CCCNC2)n1] | 1-((R)-2,2-Difluorocyclobutyl)-N-(2-fluoro-6-methyl-5-((3-(2-(((S)-piperidin-3-yl)amino)pyrimidin-4-yl)pyridin-2-yl)oxy)naphthalen-1-yl)methanesulfonamide | 0.017 |
| 472 | 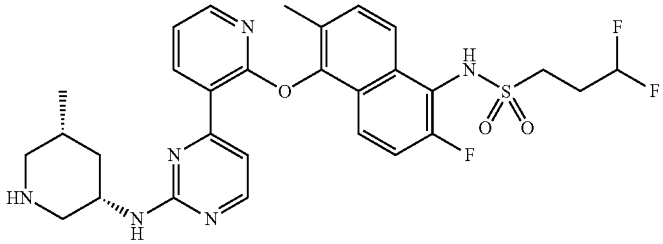 [SMILES: Cc1ccc2c(NS(=O)(=O)CCC(F)F)c(F)ccc2c1Oc1ncccc1-c1ccnc(N[C@@H]2CNC[C@H](C)C2)n1] | 3,3-Difluoro-N-[2-fluoro-6-methyl-5-[[3-[2-[[(3S,5R)-5-methyl-3-piperidyl]amino]pyrimidin-4-yl]-2-pyridyl]oxy]-1-naphthyl]propane-1-sulfonamide | 0.008 |
| 473 | 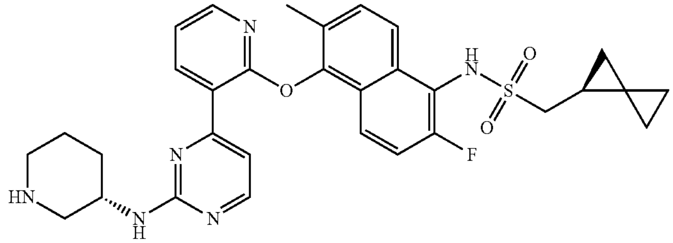 [SMILES: Cc1ccc2c(NS(=O)(=O)C[C@H]3CC34CC4)c(F)ccc2c1Oc1ncccc1-c1ccnc(N[C@H]2CCCNC2)n1] | N-(2-Fluoro-6-methyl-5-((3-(2-(((S)-piperidin-3-yl)amino)pyrimidin-4-yl)pyridin-2-yl)oxy)naphthalen-1-yl)-1-((S)-spiro[2.2]pentan-1-yl)methanesulfonamide | 0.076 |

TABLE 2-continued

| No. | Structure | Name | XBP1s-luc 293 LUC (IC$_{50}$) (μmol) |
|---|---|---|---|
| 474 | 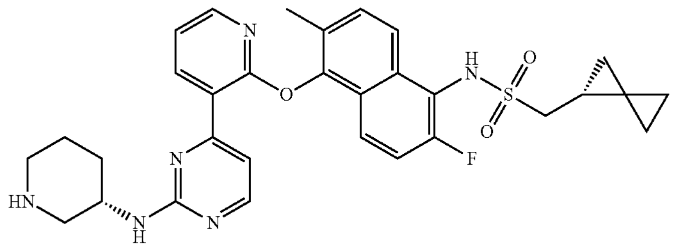 [SMILES: Cc1ccc2c(NS(=O)(=O)C[C@@H]3CC34CC4)c(F)ccc2c1Oc1ncccc1-c1ccnc(N[C@H]2CCCNC2)n1] | N-(2-Fluoro-6-methyl-5-((3-(2-(((S)-piperidin-3-yl)amino)pyrimidin-4-yl)pyridin-2-yl)oxy)naphthalen-1-yl)-1-((R)-spiro[2.2]pentan-1-yl)methanesulfonamide | 0.052 |
| 475 | 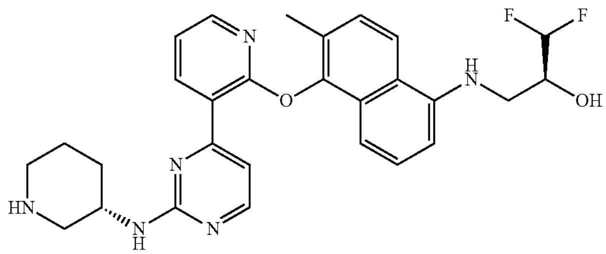 [SMILES: Cc1ccc2c(NC[C@H](O)C(F)F)cccc2c1Oc1ncccc1-c1ccnc(N[C@H]2CCCNC2)n1] | (S-1,1-Difluoro-3-((6-methyl-5-((3-(2-(((S)-piperidin-3-yl)amino)pyrimidin-4-yl)pyridin-2-yl)oxy)naphthalen-1-yl)amino)propan-2-ol | 0.019 |
| 476 | 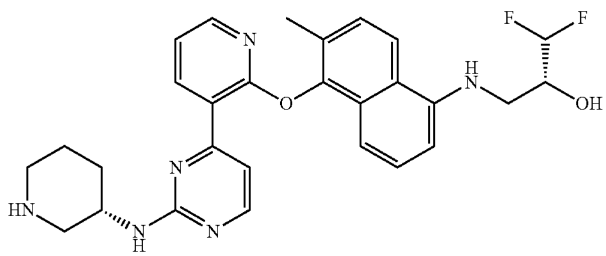 | (R)-1,1-Difluoro-3-((6-methyl-5-((3-(2-(((S)-piperidin-3-yl)amino)pyrimidin-4-yl)pyridin-2-yl)oxy)naphthalen-1-yl)amino)propan-2-ol | 0.129 |
| 477 | 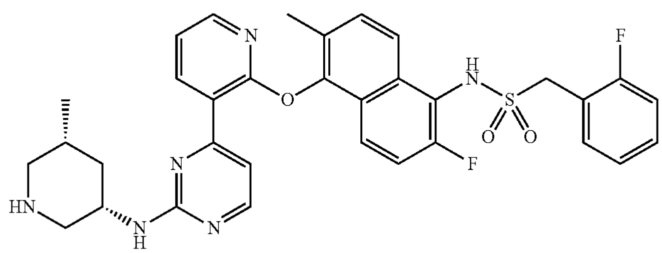 [SMILES: Cc1ccc2c(NS(=O)(=O)Cc3ccccc3F)c(F)ccc2c1Oc1ncccc1-c1ccnc(N[C@@H]2CNC[C@H](C)C2)n1] | N-[2-Fluoro-6-methyl-5-[[3-[2-[[(3S,5R)-5-methyl-3-piperidyl]amino]pyrimidin-4-yl]-2-pyridyl]oxy]-1-naphthyl]-1-(2-fluorophenyl)methanesulfonamide | 0.007 |
| 478 | 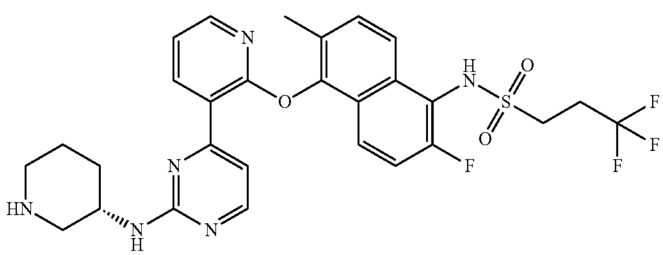 [SMILES: Cc1ccc2c(NS(=O)(=O)CCC(F)(F)F)c(F)ccc2c1Oc1ncccc1-c1ccnc(N[C@H]2CCCNC2)n1] | 3,3,3-Trifluoro-N-[3-methyl-4-[[3-[2-[[(3S)-3-piperidyl]amino]pyrimidin-4-yl]-2-pyridyl]oxy]-1-naphthyl]propane-1-sulfonamide | 0.118 |
| 479 | 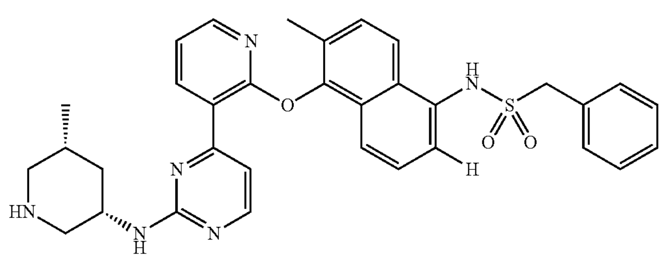 [SMILES: Cc1ccc2c(NS(=O)(=O)Cc3ccccc3)cccc2c1Oc1ncccc1-c1ccnc(N[C@@H]2CNC[C@H](C)C2)n1] | N-[6-Methyl-5-[[3-[2-[[(3S,5R)-5-methyl-3-piperidyl]amino]pyrimidin-4-yl]-2-pyridyl]oxy]-1-naphthyl]-1-phenyl-methanesulfonamide | 0.012 |

TABLE 2-continued

| No. | Structure | Name | XBP1s-luc 293 LUC (IC$_{50}$) (μmol) |
|---|---|---|---|
| 480 | 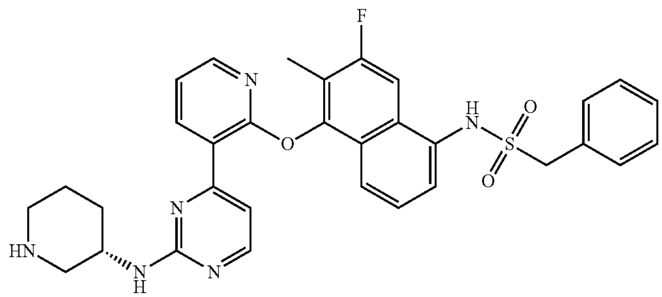 [SMILES: Cc1c(F)cc2c(NS(=O)(=O)Cc3ccccc3)cccc2c1Oc1ncccc1-c1ccnc(N[C@H]2CCCNC2)n1] | N-[2-Fluoro-3-methyl-4-[[3-[2-[[(3S)-3-piperidyl]amino]pyrimidin-4-yl]-2-pyridyl]oxy]-1-naphthyl]-1-phenyl-methanesulfonamide | 0.007 |
| 481 | 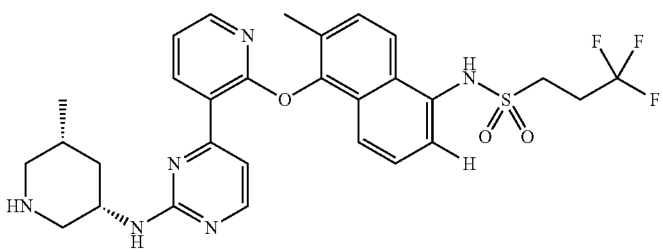 [SMILES: Cc1ccc2c(NS(=O)(=O)CCC(F)(F)F)cccc2c1Oc1ncccc1-c1ccnc(N[C@@H]2CNC[C@H](C)C2)n1] | 3,3,3-Trifluoro-N-[6-methyl-5-[[3-[2-[[(3S,5R)-5-methyl-3-pipendyl]amino]pyrimidin-4-yl]-2-pyridyl]oxy]-1-naphthyl]propane-1-sulfonamide | 0.07 |
| 482 | 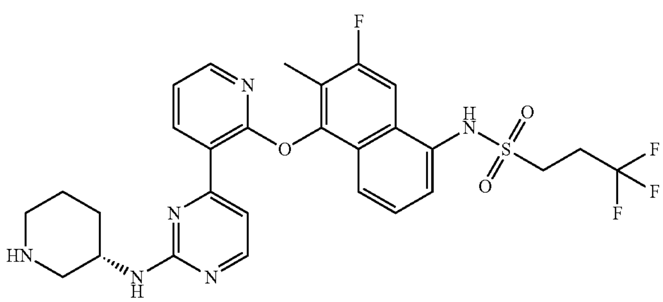 [SMILES: Cc1c(F)cc2c(NS(=O)(=O)CCC(F)(F)F)cccc2c1Oc1ncccc1-c1ccnc(N[C@H]2CCCNC2)n1] | 3,3,3-Trifluoro-N-[2-fluoro-3-methyl-4-[[3-[2-[[(3S)-3-piperidyl]amino]pyrimidin-4-yl]-2-pyridyl]oxy]-1-naphthyl]propane-1-sulfonamide | 0.065 |
| 483 | 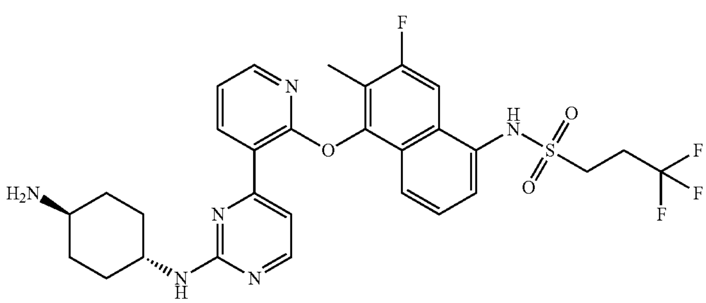 [SMILES: Cc1c(F)cc2c(NS(=O)(=O)CCC(F)(F)F)cccc2c1Oc1ncccc1-c1ccnc(N[C@H]2CC[C@H](N)CC2)n1] | N-(4-((3-(2-(((trans)-4-Aminocyclohexyl)amino)pyrimidin-4-yl)pyridin-2-yl)oxy)-2-fluoro-3-methylnaphthalen-1-yl)-3,3,3-trifluoropropane-1-sulfonamide | 0.146 |
| 484 | 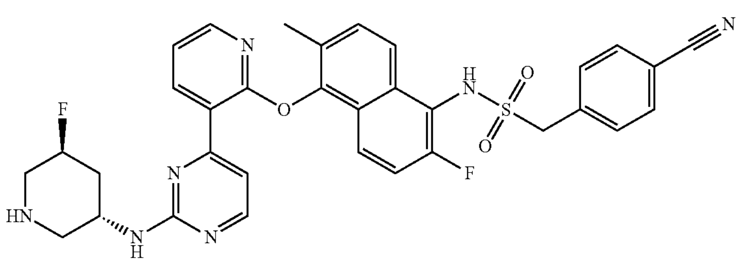 [SMILES: Cc1ccc2c(NS(=O)(=O)Cc3ccc(C#N)cc3)c(F)ccc2c1Oc1ncccc1-c1ccnc(N[C@@H]2CNC[C@@H](F)C2)n1] | 1-(4-Cyanophenyl)-N-(2-fluoro-5-((3-(2-(((3S,5S)-5-fluoropiperidin-3-yl)amino)pyrimidin-4-yl)pyridin-2-yl)oxy)-6-methylnaphthalen-1-yl)methanesulfonamide | 0.005 |

TABLE 2-continued

| No. | Structure | Name | XBP1s-luc 293 LUC (IC$_{50}$) (μmol) |
|---|---|---|---|
| 485 | 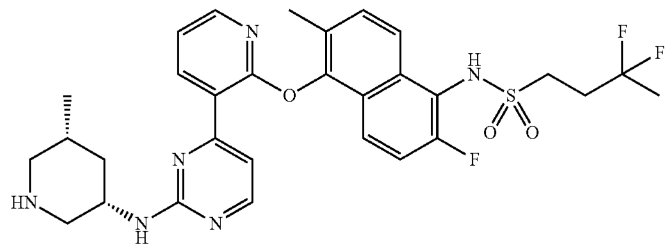 [SMILES: Cc1ccc2c(NS(=O)(=O)CCC(C)(F)F)c(F)ccc2c1Oc1ncccc1-c1ccnc(N[C@@H]2CNC[C@H](C)C2)n1] | 3,3-Difluoro-N-[2-fluoro-6-methyl-5-[[3-[2-[[(3S,5R)-5-methyl-3-piperidyl]amino]pyrimidin-4-yl]-2-pyridyl]oxy]-1-naphthyl]butane-1-sulfonamide | 0.006 |
| 486 | 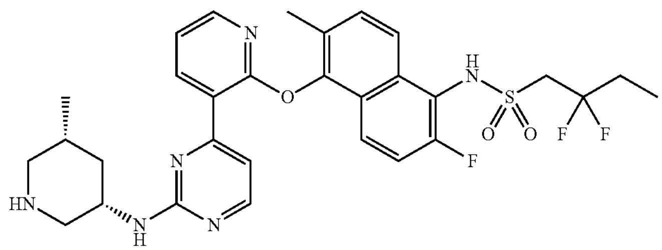 [SMILES: CCC(F)(F)CS(=O)(=O)Nc1c(F)ccc2c(Oc3ncccc3-c3ccnc(N[C@@H]4CNC[C@H](C)C4)n3)c(C)ccc12] | 2,2-Difluoro-N-[2-fluoro-6-methyl-5-[[3-[2-[[(3S,5R)-5-methyl-3-piperidyl]amino]pyrimidin-4-yl]-2-pyridyl]oxy]-1-naphthyl]butane-1-sulfonamide | 0.003 |
| 487 | 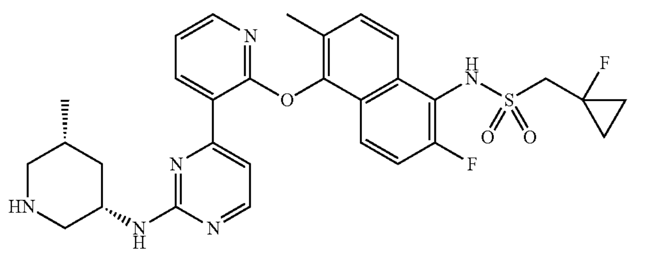 [SMILES: Cc1ccc2c(NS(=O)(=O)CC3(F)CC3)c(F)ccc2c1Oc1ncccc1-c1ccnc(N[C@@H]2CNC[C@H](C)C2)n1] | 1-(1-Fluorocyclopropyl)-N-[2-fluoro-6-methyl-5-[[3-[2-[[(3S,5R)-5-methyl-3-piperidyl]amino]pyrimidin-4-yl]-2-pyridyl]oxy]-1-naphthyl]methanesulfonamide | 0.009 |
| 488 | 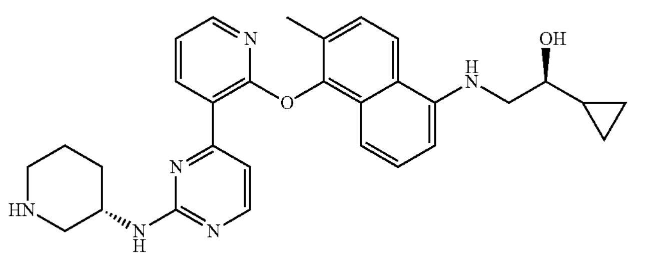 [SMILES: Cc1ccc2c(NC[C@@H](O)C3CC3)cccc2c1Oc1ncccc1-c1ccnc(N[C@H]2CCCNC2)n1] | (S)-1-Cyclopropyl-2-((6-methyl-5-((3-(2-(((S)-piperidin-3-yl)amino)pyrimidin-4-yl)pyridin-2-yl)oxy)naphthalen-1-yl)amino)ethan-1-ol | 0.03 |
| 489 | 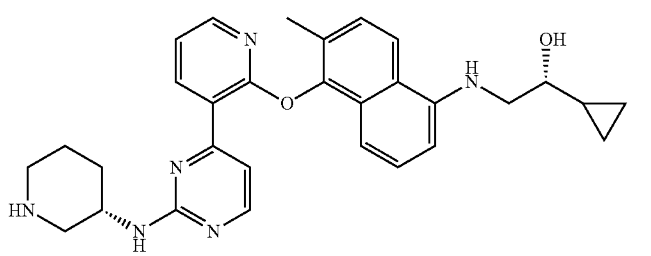 [SMILES: Cc1ccc2c(NC[C@H](O)C3CC3)cccc2c1Oc1ncccc1-c1ccnc(N[C@H]2CCCNC2)n1] | (R)-1-Cyclopropyl-2-((6-methyl-5-((3-(2-(((S)-piperidin-3-yl)amino)pyrimidin-4-yl)pyridin-2-yl)oxy)naphthalen-1-yl)amino)ethan-1-ol | 0.132 |
| 490 | 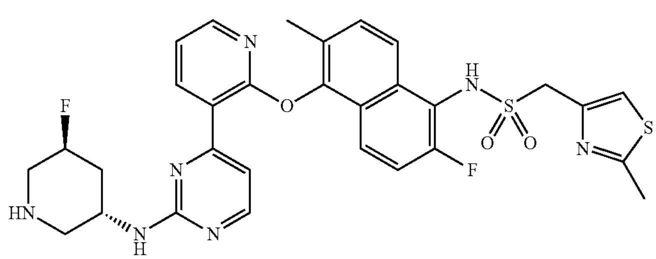 [SMILES: Cc1nc(CS(=O)(=O)Nc2c(F)ccc3c(Oc4ncccc4-c4ccnc(N[C@@H]5CNC[C@@H](F)C5)n4)c(C)ccc23)cs1] | N-(2-Fluoro-5-((3-(2-(((3S,5S)-5-fluoropiperidin-3-yl)amino)pyrimidin-4-yl)pyridin-2-yl)oxy)-6-methylnaphthalen-1-yl)-1-(2-methylthiazol-4-yl)methanesulfonamide | 0.004 |

TABLE 2-continued

| No. | Structure | Name | XBP1s-luc 293 LUC (IC$_{50}$) (μmol) |
|---|---|---|---|
| 491 | 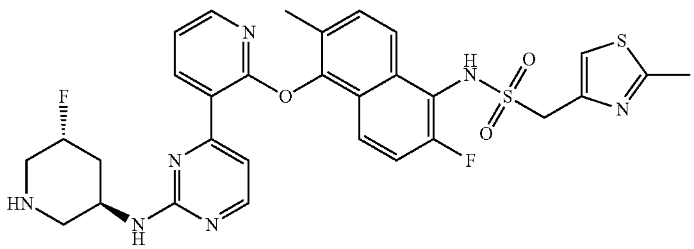 [SMILES: Cc1nc(CS(=O)(=O)Nc2c(F)ccc3c(Oc4ncccc4-c4ccnc(N[C@H]5CNC[C@H](F)C5)n4)c(C)ccc23)cs1] | N-(2-Fluoro-5-((3-(2-(((3R,5R)-5-fluoropiperidin-3-yl)amino)pyrimidin-4-yl)pyridin-2-yl)oxy)-6-methylnaphthalen-1-yl)-1-(2-methylthiazol-4-yl)methanesulfonamide | 0.117 |
| 492 | 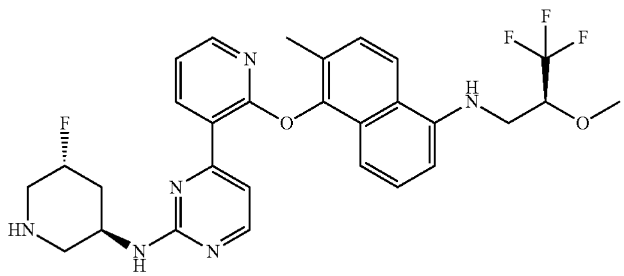 [SMILES: CO[C@@H](CNc1cccc2c(Oc3ncccc3-c3ccnc(N[C@H]4CNC[C@H](F)C4)n3)c(C)ccc12)C(F)(F)F] | N-((3R,5R)-5-Fluoropiperidin-3-yl)-4-(2-((2-methyl-5-(((S)-3,3,3-trifluoro-2-methoxypropyl)amino)naphthalen-1-yl)oxy)pyridin-3-yl)pyrimidin-2-amine | |
| 493 | 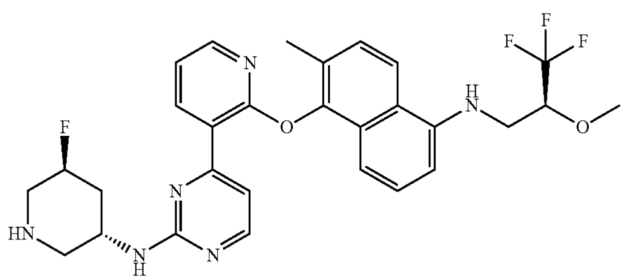 [SMILES: CO[C@@H](CNc1cccc2c(Oc3ncccc3-c3ccnc(N[C@@H]4CNC[C@@H](F)C4)n3)c(C)ccc12)C(F)(F)F] | N-((3S,5S)-5-Fluoropiperidin-3-yl)-4-(2-((2-methyl-5-(((S)-3,3,3-trifluoro-2-methoxypropyl)amino)naphthalen-1-yl)oxy)pyridin-3-yl)pyrimidin-2-amine | 0.021 |
| 494 | 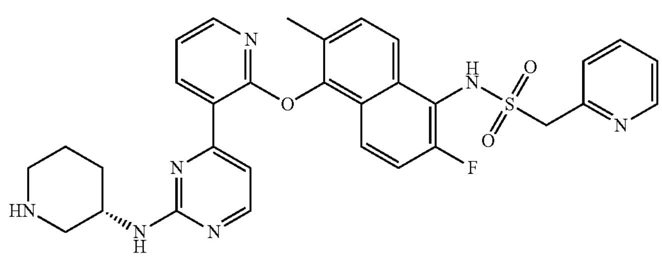 [SMILES: Cc1ccc2c(NS(=O)(=O)Cc3ccccn3)c(F)ccc2c1Oc1ncccc1-c1ccnc(N[C@H]2CCCNC2)n1] | N-[2-Fluoro-6-methyl-5-[[3-[2-[[(3S)-3-piperidyl]amino]pyrimidin-4-yl]-2-pyridyl]oxy]-1-naphthyl]-1-(2-pyridyl)methanesulfonamide | 0.0125 |
| 495 | 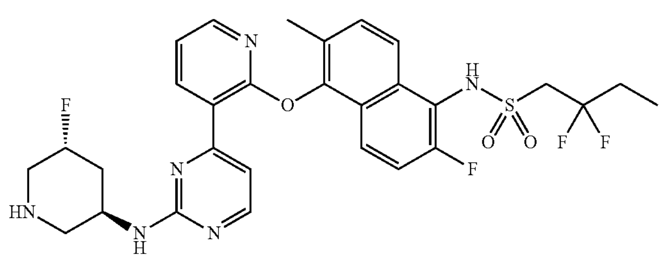 [SMILES: CCC(F)(F)CS(=O)(=O)Nc1c(F)ccc2c(Oc3ncccc3-c3ccnc(N[C@H]4CNC[C@H](F)C4)n3)c(C)ccc12] | 2,2-Difluoro-N-(2-fluoro-5-((3-(2-(((3R,5R)-5-fluoropiperidin-3-yl)amino)pyrimidin-4-yl)pyridin-2-yl)oxy)-6-methylnaphthalen-1-yl)butane-1-sulfonamide | 0.469 |

TABLE 2-continued

| No. | Structure | Name | XBP1s-luc 293 LUC (IC$_{50}$) (μmol) |
|---|---|---|---|
| 496 | 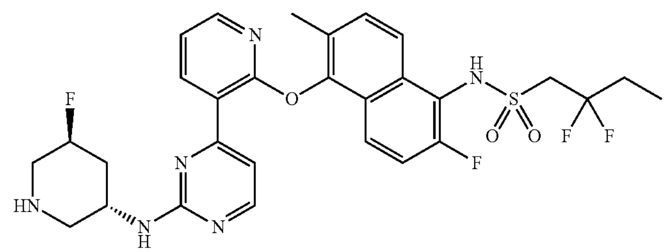 [SMILES: CCC(F)(F)CS(=O)(=O)Nc1c(F)ccc2c(Oc3ncccc3-c3ccnc(N[C@@H]4CNC[C@@H](F)C4)n3)c(C)ccc12] | 2,2-Difluoro-N-(2-fluoro-5-((3-(2-(((3S,5S)-5-fluoropiperidin-3-yl)amino)pyrimidin-4-yl)pyridin-2-yl)oxy)-6-methylnaphthalen-1-yl)butane-1-sulfonamide | 0.0179 |
| 497 | 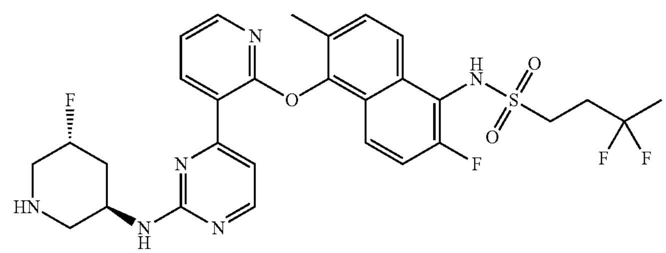 [SMILES: Cc1ccc2c(NS(=O)(=O)CCC(C)(F)F)c(F)ccc2c1Oc1ncccc1-c1ccnc(N[C@H]2CNC[C@H](F)C2)n1] | 3,3-Difluoro-N-(2-fluoro-5-((3-(2-(((3R,5R)-5-fluoropiperidin-3-yl)amino)pyrimidin-4-yl)pyridin-2-yl)oxy)-6-methylnaphthalen-1-yl)butane-1-sulfonamide | 5.1 |
| 498 | 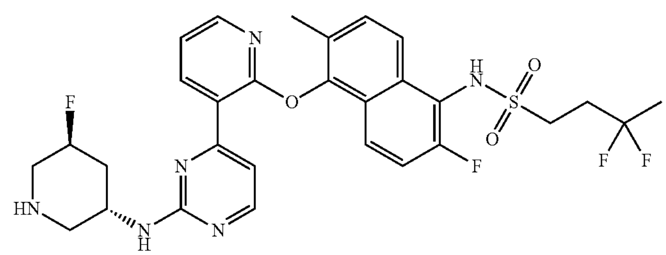 [SMILES: Cc1ccc2c(NS(=O)(=O)CCC(C)(F)F)c(F)ccc2c1Oc1ncccc1-c1ccnc(N[C@@H]2CNC[C@@H](F)C2)n1] | 3,3-Difluoro-N-(2-fluoro-5-((3-(2-(((3S,5S)-5-fluoropiperidin-3-yl)amino)pyrimidin-4-yl)pyridin-2-yl)oxy)-6-methylnaphthalen-1-yl)butane-1-sulfonamide | 0.033 |
| 499 | 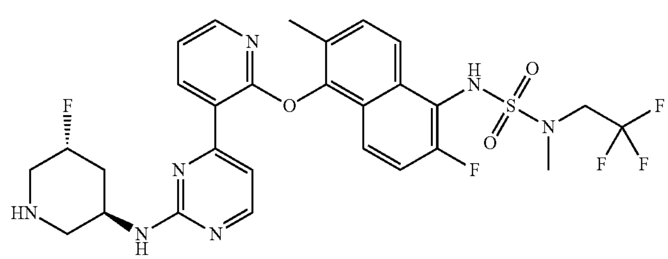 [SMILES: Cc1ccc2c(NS(=O)(=O)N(C)CC(F)(F)F)c(F)ccc2c1Oc1ncccc1-c1ccnc(N[C@H]2CNC[C@H](F)C2)n1] | 4-[2-[[6-Fluoro-2-methyl-5-[[methyl(2,2,2-trifluoroethyl)sulfamoyl]amino]-1-naphthyl]oxy]-3-pyridyl]-2-[[(3R,5R)-5-fluoro-3-piperidyl]amino]pyrimidine | 0.68 |
| 500 | 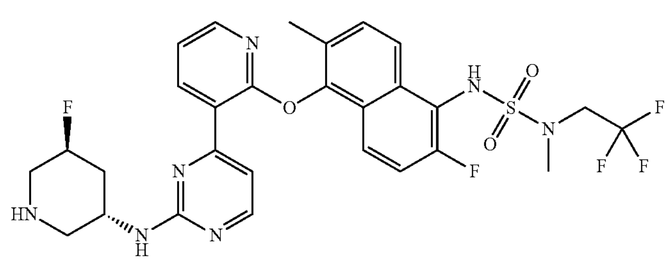 [SMILES: Cc1ccc2c(NS(=O)(=O)N(C)CC(F)(F)F)c(F)ccc2c1Oc1ncccc1-c1ccnc(N[C@@H]2CNC[C@@H](F)C2)n1] | 4-[2-[[6-Fluoro-2-methyl-5-[[methyl(2,2,2-trifluoroethyl)sulfamoyl]amino]-1-naphthyl]oxy]-3-pyridyl]-2-[[(3S,5S)-5-fluoro-3-piperidyl]amino]pyrimidine | 0.0087 |

TABLE 3

| No. | Structure | Name |
|---|---|---|
| 501 | 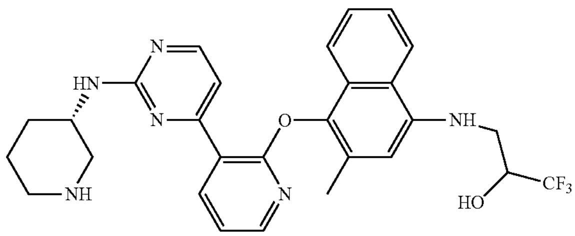 [SMILES: Cc1cc(NCC(O)C(F)(F)F)c2ccccc2c1Oc1ncccc1-c1ccnc(N[C@H]2CCCNC2)n1] | 1,1,1-Trifluoro-3-((3-methyl-4-((3-(2-(((S)-piperidin-3-yl)amino)pyrimidin-4-yl)pyridin-2-yl)oxy)naphthalen-1-yl)amino)propan-2-ol |
| 502 | 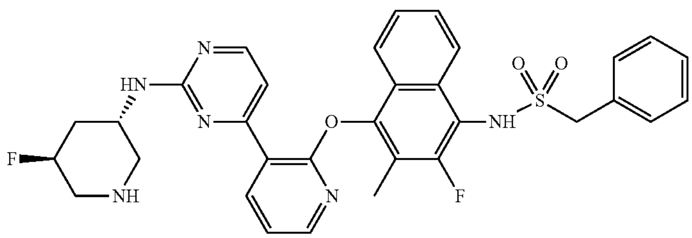 [SMILES: Cc1c(F)c(NS(=O)(=O)Cc2ccccc2)c2ccccc2c1Oc1ncccc1-c1ccnc(N[C@@H]2CNC[C@@H](F)C2)n1] | N-(2-Fluoro-4-((3-(2-(((3S,5S)-5-fluoropiperidin-3-yl)amino)pyrimidin-4-yl)pyridin-2-yl)oxy)-3-methylnaphthalen-1-yl)-1-phenylmethanesulfonamide |
| 503 | 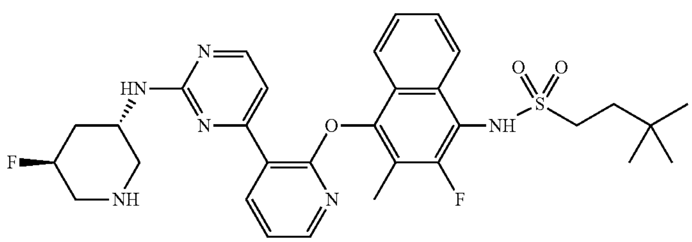 [SMILES: Cc1c(F)c(NS(=O)(=O)CCC(C)(C)C)c2ccccc2c1Oc1ncccc1-c1ccnc(N[C@@H]2CNC[C@@H](F)C2)n1] | N-(2-Fluoro-4-((3-(2-(((3S,5S)-5-fluoropiperidin-3-yl)amino)pyrimidin-4-yl)pyridin-2-yl)oxy)-3-methylnaphthalen-1-yl)-3,3-dimethylbutane-1-sulfonamide |
| 504 | 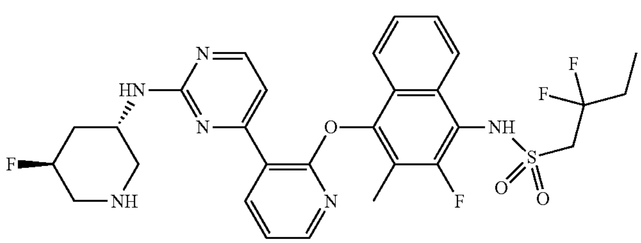 [SMILES: CCC(F)(F)CS(=O)(=O)Nc1c(F)c(C)c(Oc2ncccc2-c2ccnc(N[C@@H]3CNC[C@@H](F)C3)n2)c2ccccc12] | 2,2-D-N-(2-fluoro-4-((3-(2-(((3S,5S)-5-fluoropiperidin-3-yl)amino)pyrimidin-4-yl)pyridin-2-yl)oxy)-3-methylnaphthalen-1-yl)butane-1-sulfonamide |
| 505 | 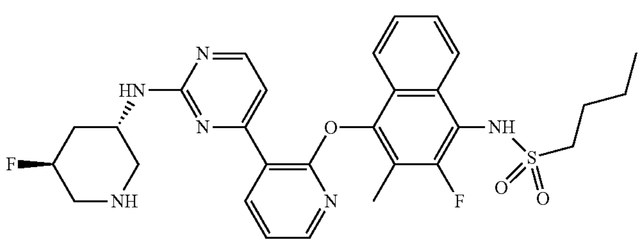 [SMILES: CCCCS(=O)(=O)Nc1c(F)c(C)c(Oc2ncccc2-c2ccnc(N[C@@H]3CNC[C@@H](F)C3)n2)c2ccccc12] | N-(2-Fluoro-4-((3-(2-(((3S,5S)-5-fluoropiperidin-3-yl)amino)pyrimidin-4-yl)pyridin-2-yl)oxy)-3-methylnaphthalen-1-yl)butane-1-sulfonamide |
| 506 | 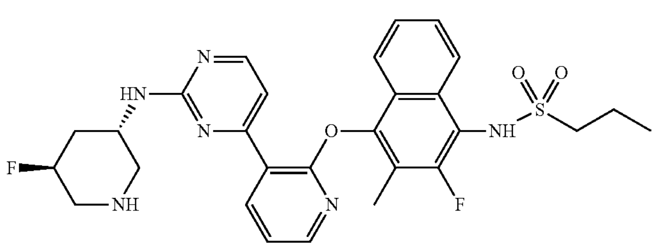 [SMILES: CCCS(=O)(=O)Nc1c(F)c(C)c(Oc2ncccc2-c2ccnc(N[C@@H]3CNC[C@@H](F)C3)n2)c2ccccc12] | N-(2-Fluoro-4-((3-(2-(((3S,5S)-5-fluoropiperidin-3-yl)amino)pyrimidin-4-yl)pyridin-2-yl)oxy)-3-methylnaphthalen-1-yl)propane-1-sulfonamide |

TABLE 3-continued

| No. | Structure | Name |
|---|---|---|
| 507 | 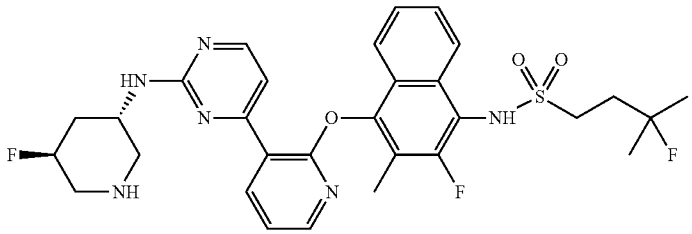 | 3-Fluoro-N-(2-fluoro-4-((3-(2-(((3S,5S)-5-fluoropiperidin-3-yl)amino)pyrimidin-4-yl)pyridin-2-yl)oxy)-3-methylnaphthalen-1-yl)-3-methylbutane-1-sulfonamide |
| 508 | 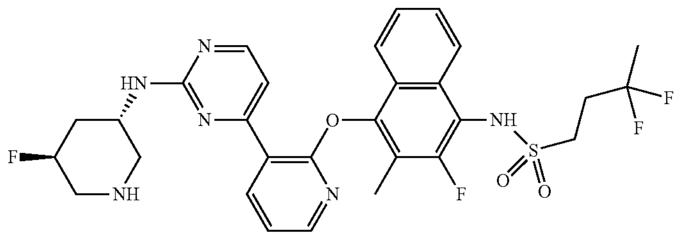 [SMILES: Cc1c(F)c(NS(=O)(=O)CCC(C)(F)F)c2ccccc2c1Oc1ncccc1-c1ccnc(N[C@@H]2CNC[C@@H](F)C2)n1] | 3,3-Difluoro-N-(2-fluoro-4-((3-(2-(((3S,5S)-5-fluoropiperidin-3-yl)amino)pyrimidin-4-yl)pyridin-2-yl)oxy)-3-methylnaphthalen-1-yl)butane-1-sulfonamide |
| 509 | 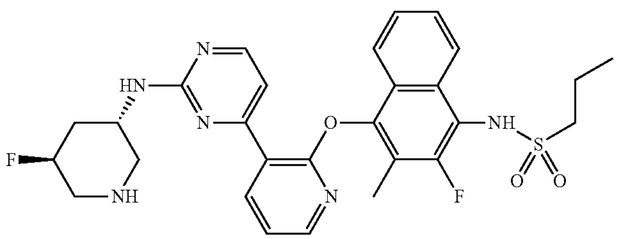 [SMILES: CCCS(=O)(=O)Nc1c(F)c(C)c(Oc2ncccc2-c2ccnc(N[C@@H]3CNC[C@@H](F)C3)n2)c2ccccc12] | N-(2-Fluoro-4-((3-(2-(((3S,5S)-5-fluoropiperidin-3-yl)amino)pyrimidin-4-yl)pyridin-2-yl)oxy)-3-methylnaphthalen-1-yl)propane-1-sulfonamide |
| 510 | 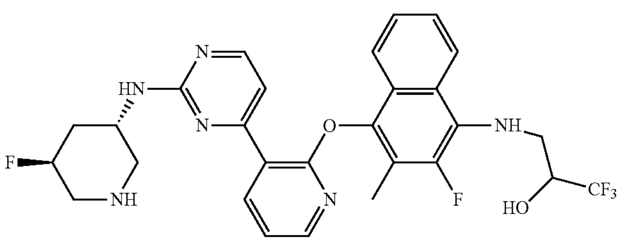 [SMILES: Cc1c(F)c(NCC(O)C(F)(F)F)c2ccccc2c1Oc1ncccc1-c1ccnc(N[C@@H]2CNC[C@@H](F)C2)n1] | 1,1,1-Trifluoro-3-((2-fluoro-4-((3-(2-(((3S,5S)-5-fluoropiperidin-3-yl)amino)pyrimidin-4-yl)pyridin-2-yl)oxy)-3-methylnaphthalen-1-yl)amino)propan-2-ol |
| 511 | 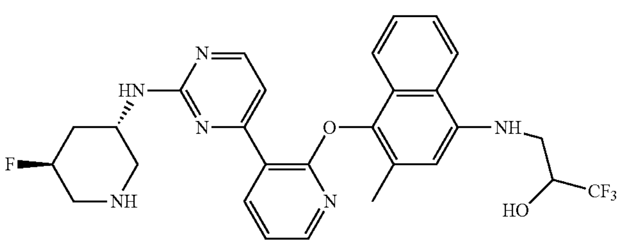 [SMILES: Cc1cc(NCC(O)C(F)(F)F)c2ccccc2c1Oc1ncccc1-c1ccnc(N[C@@H]2CNC[C@@H](F)C2)n1] | 1,1,1-Trifluoro-3-((4-((3-(2-(((3S,5S)-5-fluoropiperidin-3-yl)amino)pyrimidin-4-yl)pyridin-2-yl)oxy)-3-methylnaphthalen-1-yl)amino)propan-2-ol |
| 512 | 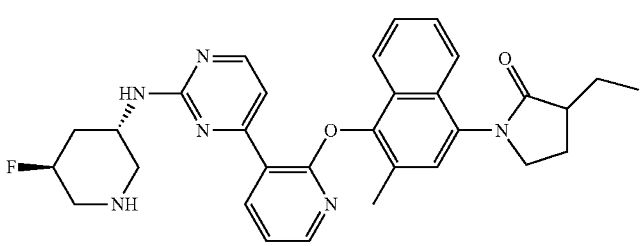 [SMILES: CCC1CCN(c2cc(C)c(Oc3ncccc3-c3ccnc(N[C@@H]4CNC[C@@H](F)C4)n3)c3ccccc23)C1=O] | 3-Ethyl-1-(4-((3-(2-(((3S,5S)-5-fluoropiperidin-3-yl)amino)pyrimidin-4-yl)pyridin-2-yl)oxy)-3-methylnaphthalen-1-yl)pyrrolidin-2-one |

TABLE 3-continued

| No. | Structure | Name |
|---|---|---|
| 513 | 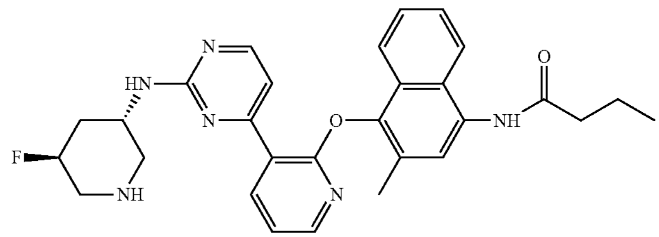 [SMILES: CCCC(=O)Nc1cc(C)c(Oc2ncccc2-c2ccnc(N[C@@H]3CNC[C@@H](F)C3)n2)c2ccccc12] | N-(4-((3-(2-(((3S,5S)-5-Fluoropiperidin-3-yl)amino)pyrimidin-4-yl)pyridin-2-yl)oxy)-3-methylnaphthalen-1-yl)butyramide |
| 514 | 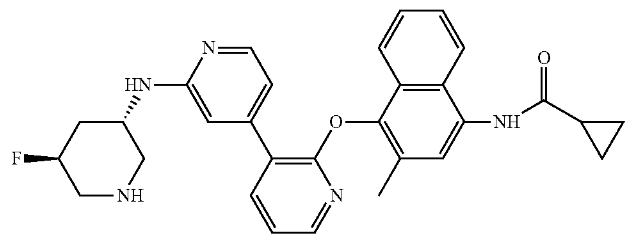 [SMILES: Cc1cc(NC(=O)C2CC2)c2ccccc2c1Oc1ncccc1-c1ccnc(N[C@@H]2CNC[C@@H](F)C2)c1] | N-(4-((2'-(((3S,5S)-5-fluoropiperidin-3-yl)amino)-[3,4'-bipyridin]-2-yl)oxy)-3-methylnaphthalen-1-yl)cyclopropanecarboxamide |
| 515 | 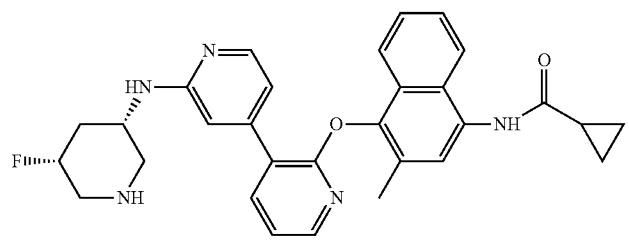 [SMILES: Cc1cc(NC(=O)C2CC2)c2ccccc2c1Oc1ncccc1-c1ccnc(N[C@@H]2CNC[C@H](F)C2)c1] | N-(4-((2'-(((3S,5R)-5-Fluoropiperidin-3-yl)amino)-[3,4'-bipyridin]-2-yl)oxy)-3-methylnaphthalen-1-yl)cyclopropanecarboxamide |
| 516 | 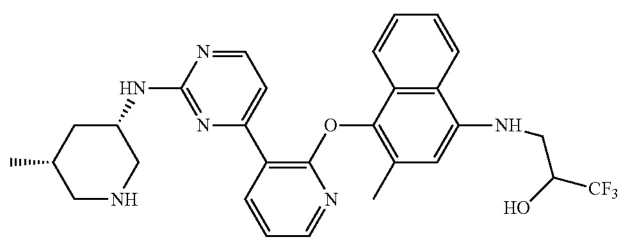 [SMILES: Cc1cc(NCC(O)C(F)(F)F)c2ccccc2c1Oc1ncccc1-c1ccnc(N[C@@H]2CNC[C@H](C)C2)n1] | 1,1,1-Trifluoro-3-((3-methyl-4-((3-(2-(((3S,5R)-5-methylpiperidin-3-yl)amino)pyrimidin-4-yl)pyridin-2-yl)oxy)naphthalen-1-yl)amino)propan-2-ol |
| 517 | 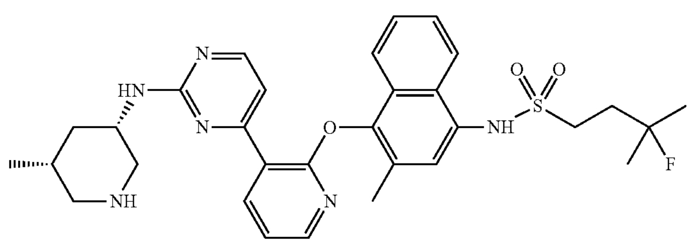 [SMILES: Cc1cc(NS(=O)(=O)CCC(C)(C)F)c2ccccc2c1Oc1ncccc1-c1ccnc(N[C@@H]2CNC[C@H](C)C2)n1] | 3-Fluoro-3-methyl-N-(3-methyl-4-((3-(2-(((3S,5R)-5-methylpiperidin-3-yl)amino)pyrimidin-4-yl)pyridin-2-yl)oxy)naphthalen-1-yl)butane-1-sulfonamide |
| 518 | 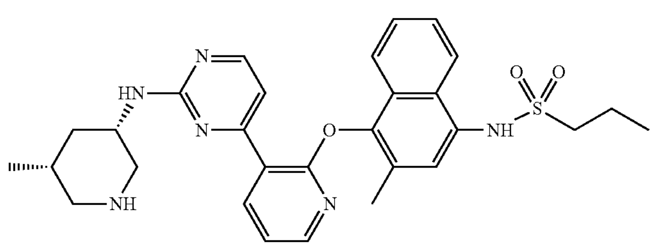 [SMILES: CCCS(=O)(=O)Nc1cc(C)c(Oc2ncccc2-c2ccnc(N[C@@H]3CNC[C@H](C)C3)n2)c2ccccc12] | N-(3-Methyl-4-((3-(2-(((3S,5R)-5-methylpiperidin-3-yl)amino)pyrimidin-4-yl)pyridin-2-yl)oxy)naphthalen-1-yl)propane-1-sulfonamide |

TABLE 3-continued

| No. | Structure | Name |
|---|---|---|
| 519 | 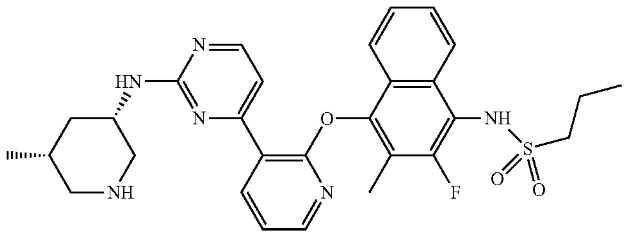 [SMILES: CCCS(=O)(=O)Nc1c(F)c(C)c(Oc2ncccc2-c2ccnc(N[C@@H]3CNC[C@H](C)C3)n2)c2ccccc12] | N-(2-Fuoro-3-methyl-4-((3-(2-(((3S,5R)-5-methylpiperidin-3-yl)amino)pyrimidin-4-yl)pyridin-2-yl)oxy)naphthalen-1-yl)propane-1-sulfonamide |
| 520 | 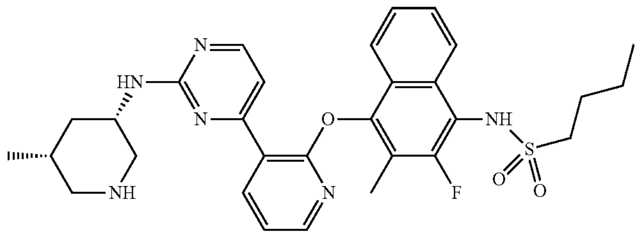 [SMILES: CCCCS(=O)(=O)Nc1c(F)c(C)c(Oc2ncccc2-c2ccnc(N[C@@H]3CNC[C@H](C)C3)n2)c2ccccc12] | N-(2-Fluoro-3-methyl-4-((3-(2-(((3S,5R)-5-methylpiperidin-3-yl)amino)pyrimidin-4-yl)pyridin-2-yl)oxy)naphthalen-1-yl)butane-1-sulfonamide |
| 521 | 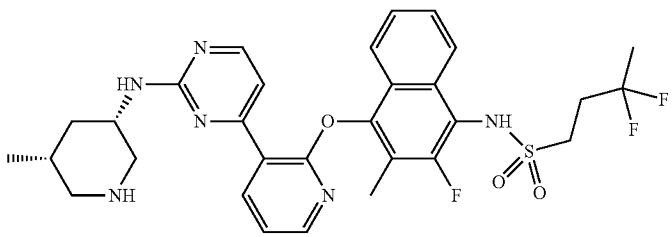 [SMILES: Cc1c(F)c(NS(=O)(=O)CCC(C)(F)F)c2ccccc2c1Oc1ncccc1-c1ccnc(N[C@@H]2CNC[C@H](C)C2)n1] | 3,3-Difluoro-N-(2-fluoro-3-methyl-4-((3-(2-(((3S,5R)-5-methylpiperidin-3-yl)amino)pyrimidin-4-yl)pyridin-2-yl)oxy)naphthalen-1-yl)butane-1-sulfonamide |
| 522 | 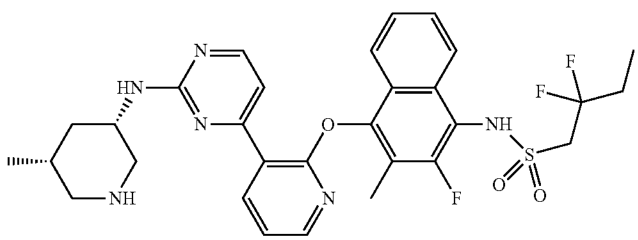 [SMILES: CCC(F)(F)CS(=O)(=O)Nc1c(F)c(C)c(Oc2ncccc2-c2ccnc(N[C@@H]3CNC[C@H](C)C3)n2)c2ccccc12] | N-2,2-Difluoro-N-(2-fluoro-3-methyl-4-((3-(2-(((3S,5R)-5-methylpiperidin-3-yl)amino)pyrimidin-4-yl)pyridin-2-yl)oxy)naphthalen-1-yl)butane-1-sulfonamide |
| 523 | 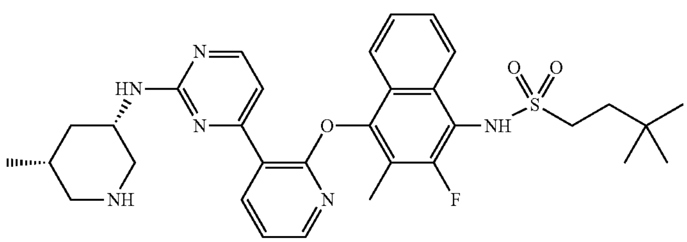 [SMILES: Cc1c(F)c(NS(=O)(=O)CCC(C)(C)C)c2ccccc2c1Oc1ncccc1-c1ccnc(N[C@@H]2CNC[C@H](C)C2)n1] | N-(2-Fluoro-3-methyl-4-((3-(2-(((3S,5R)-5-methylpiperidin-3-yl)amino)pyrimidin-4-yl)pyridin-2-yl)oxy)naphthalen-1-yl)-3,3-dimethylbutane-1-sulfonamide |
| 524 | 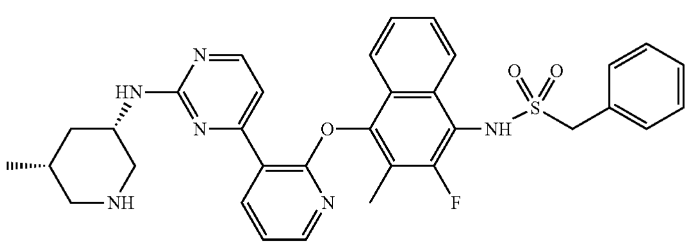 [SMILES: Cc1c(F)c(NS(=O)(=O)Cc2ccccc2)c2ccccc2c1Oc1ncccc1-c1ccnc(N[C@@H]2CNC[C@H](C)C2)n1] | N-(2-Fluoro-3-methyl-4-((3-(2-(((3S,5R)-5-methylpiperidin-3-yl)amino)pyrimidin-4-yl)pyridin-2-yl)oxy)naphthalen-1-yl)-1-phenylmethanesulfonamide |

TABLE 3-continued

| No. | Structure | Name |
|---|---|---|
| 525 | 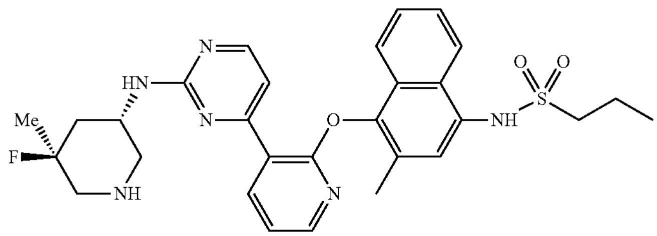 [SMILES: CCCS(=O)(=O)Nc1cc(C)c(Oc2ncccc2-c2ccnc(N[C@@H]3CNC[C@@](C)(F)C3)n2)c2ccccc12] | N-(4-((3-(2-(((3S,5S)-5-Fluoro-5-methylpiperidin-3-yl)amino)pyrimidin-4-yl)pyridin-2-yl)oxy)-3-methylnaphthalen-1-yl)propane-1-sulfonamide |
| 526 | 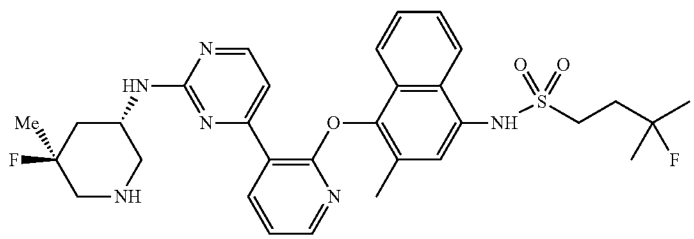 [SMILES: Cc1cc(NS(=O)(=O)CCC(C)(C)F)c2ccccc2c1Oc1ncccc1-c1ccnc(N[C@@H]2CNC[C@@](C)(F)C2)n1] | 3-fFuoro-N-(4-((3-(2-(((3S,5S)-5-fluoro-5-methylpiperidin-3-yl)amino)pyrimidin-4-yl)pyridin-2-yl)oxy)-3-methylnaphthalen-1-yl)-3-methylbutane-1-sulfonamide |
| 527 | 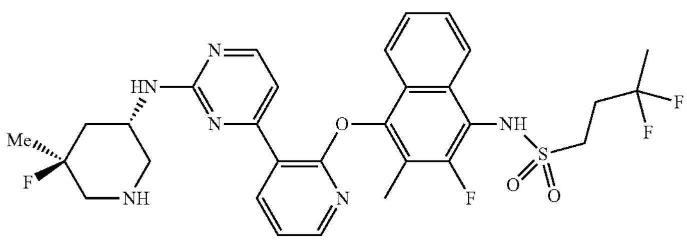 [SMILES: Cc1c(F)c(NS(=O)(=O)CCC(C)(F)F)c2ccccc2c1Oc1ncccc1-c1ccnc(N[C@@H]2CNC[C@@](C)(F)C2)n1] | 3,3-Difluoro-N-(2-fluoro-4-((3-(2-(((3S,5S)-5-fluoro-5-methylpiperidin-3-yl)amino)pyrimidin-4-yl)pyridin-2-yl)oxy)-3-methylnaphthalen-1-yl)butane-1-sulfonamide |
| 528 | 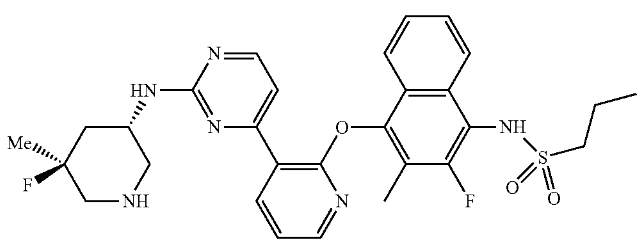 [SMILES: CCCS(=O)(=O)Nc1c(F)c(C)c(Oc2ncccc2-c2ccnc(N[C@@H]3CNC[C@@](C)(F)C3)n2)c2ccccc12] | N-(2-Fluoro-4-((3-(2-(((3S,5S)-5-fluoro-5-methylpiperidin-3-yl)amino)pyrimidin-4-yl)pyridin-2-yl)oxy)-3-methylnaphthalen-1-yl)propane-1-sulfonamide |
| 529 | 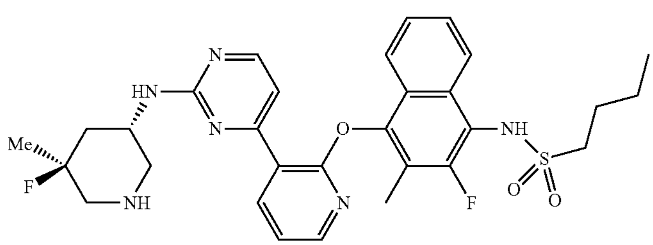 [SMILES: CCCCS(=O)(=O)Nc1c(F)c(C)c(Oc2ncccc2-c2ccnc(N[C@@H]3CNC[C@@](C)(F)C3)n2)c2ccccc12] | N-(2-Fluoro-4-((3-(2-(((3S,5S)-5-fluoro-5-methylpiperidin-3-yl)amino)pyrimidin-4-yl)pyridin-2-yl)oxy)-3-methylnaphthalen-1-yl)butane-1-sulfonamide |
| 530 | 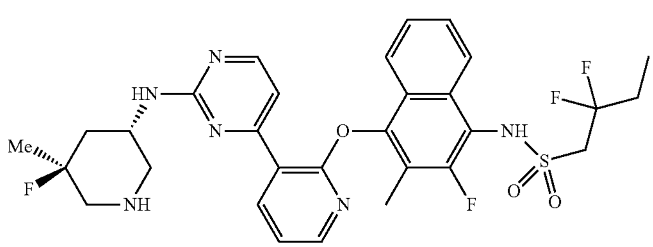 [SMILES: CCC(F)(F)CS(=O)(=O)Nc1c(F)c(C)c(Oc2ncccc2-c2ccnc(N[C@@H]3CNC[C@@](C)(F)C3)n2)c2ccccc12] | 2,2-Difluoro-N-(2-fluoro-4-((3-(2-(((3S,5S)-5-fluoro-5-methylpiperidin-3-yl)amino)pyrimidin-4-yl)pyridin-2-yl)oxy)-3-methylnaphthalen-1-yl)butane-1-sulfonamide |

TABLE 3-continued

| No. | Name |
|---|---|
| 531 | N-(2-Fluoro-4-((3-(2-(((3S,5S)-5-fluoro-5-methylpiperidin-3-yl)amino)pyrimidin-4-yl)pyridin-2-yl)oxy)-3-methylnaphthalen-1-yl)-3,3-dimethylbutane-1-sulfonamide |
| 532 | N-(2-fFuoro-4-((3-(2-(((3S,5S)-5-fluoro-5-methylpiperidin-3-yl)amino)pyrimidin-4-yl)pyridin-2-yl)oxy)-3-methylnaphthalen-1-yl)-1-phenylmethanesulfonamide |
| 533 | N-(5-((3-(2-(((3S,5S)-5-Fluoro-5-methylpiperidin-3-yl)amino)pyrimidin-4-yl)pyridin-2-yl)oxy)-6-methylnaphthalen-1-yl)butyramide |
| 534 | 3-Ethyl-1-(5-((3-(2-(((3S,5S)-5-fluoro-5-methylpiperidin-3-yl)amino)pyrimidin-4-yl)pyridin-2-yl)oxy)-6-methylnaphthalen-1-yl)pyrrolidin-2-one |
| 535 | 3-Ethyl-1-(2-fluoro-5-((3-(2-(((3S,5S)-5-fluoro-5-methylpiperidin-3-yl)amino)pyrimidin-4-yl)pyridin-2-yl)oxy)-6-methylnaphthalen-1-yl)pyrrolidin-2-one |
| 536 | (S)-1,1,1-Trifluoro-3-((2-fluoro-5-((3-(2-(((3S,5S)-5-fluoro-5-methylpiperidin-3-yl)amino)pyrimidin-4-yl)pyridin-2-yl)oxy)-6-methylnaphthalen-1-yl)amino)propan-2-ol |

TABLE 3-continued

| No. | Structure | Name |
|---|---|---|
| 537 | 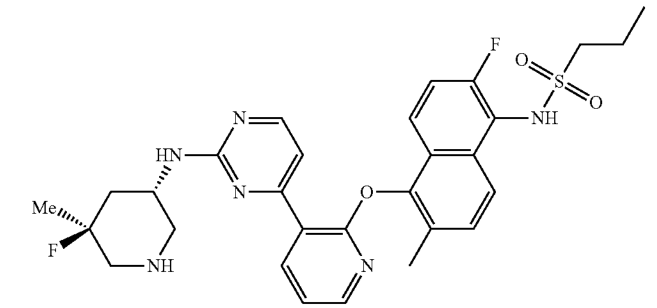 [SMILES: CCCS(=O)(=O)Nc1c(F)ccc2c(Oc3ncccc3-c3ccnc(N[C@@H]4CNC[C@@](C)(F)C4)n3)c(C)ccc12] | N-(2-Fluoro-5-((3-(2-(((3S,5S)-5-fluoro-5-methylpiperidin-3-yl)amino)pyrimidin-4-yl)pyridin-2-yl)oxy)-6-methylnaphthalen-1-yl)propane-1-sulfonamide |
| 538 | 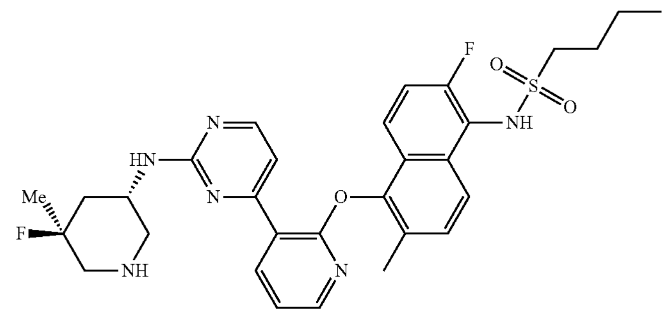 [SMILES: CCCCS(=O)(=O)Nc1c(F)ccc2c(Oc3ncccc3-c3ccnc(N[C@@H]4CNC[C@@](C)(F)C4)n3)c(C)ccc12] | N-(2-Fluoro-5-((3-(2-(((3S,5S)-5-fluoro-5-methylpiperidin-3-yl)amino)pyrimidin-4-yl)pyridin-2-yl)oxy)-6-methylnaphthalen-1-yl)butane-1-sulfonamide |
| 539 | 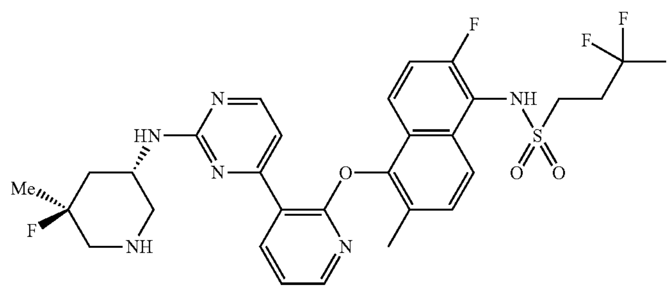 [SMILES: Cc1ccc2c(NS(=O)(=O)CCC(C)(F)F)c(F)ccc2c1Oc1ncccc1-c1ccnc(N[C@@H]2CNC[C@@](C)(F)C2)n1] | 3,3-Difluoro-N-(2-fluoro-5-((3-(2-(((3S,5S)-5-fluoro-5-methylpiperidin-3-yl)amino)pyrimidin-4-yl)pyridin-2-yl)oxy)-6-methylnaphthalen-1-yl)butane-1-sulfonamide |
| 540 | 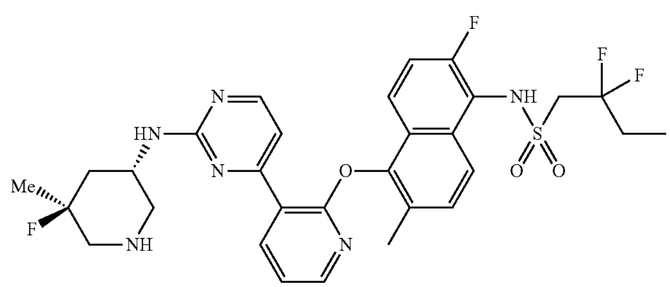 [SMILES: CCC(F)(F)CS(=O)(=O)Nc1c(F)ccc2c(Oc3ncccc3-c3ccnc(N[C@@H]4CNC[C@@](C)(F)C4)n3)c(C)ccc12] | 2,2-Difluoro-N-(2-fluoro-5-((3-(2-(((3S,5S)-5-fluoro-5-methylpiperidin-3-yl)amino)pyrimidin-4-yl)pyridin-2-yl)oxy)-6-methylnaphthalen-1-yl)butane-1-sulfonamide |
| 541 | 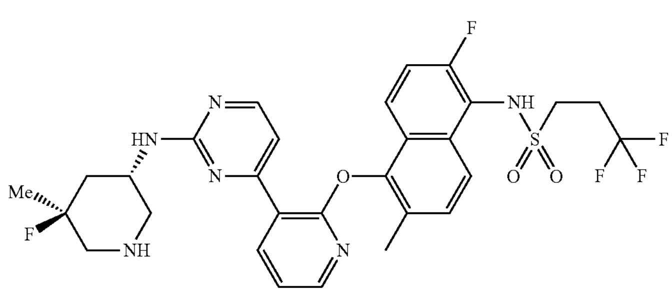 [SMILES: Cc1ccc2c(NS(=O)(=O)CCC(F)(F)F)c(F)ccc2c1Oc1ncccc1-c1ccnc(N[C@@H]2CNC[C@@](C)(F)C2)n1] | 3,3,3-Trifluoro-N-(2-fluoro-5-((3-(2-(((3S,5S)-5-fluoro-5-methylpiperidin-3-yl)amino)pyrimidin-4-yl)pyridin-2-yl)oxy)-6-methylnaphthalen-1-yl)propane-1-sulfonamide |

TABLE 3-continued

| No. | Structure | Name |
|---|---|---|
| 542 | 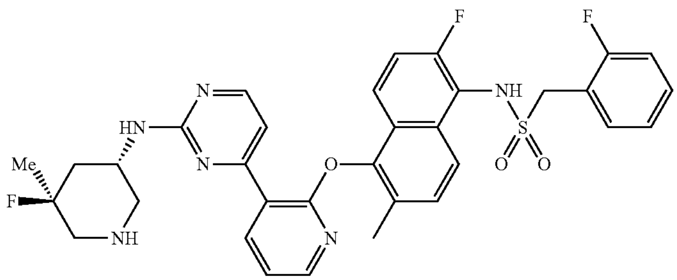 [SMILES: Cc1ccc2c(NS(=O)(=O)Cc3ccccc3F)c(F)ccc2c1Oc1ncccc1-c1ccnc(N[C@@H]2CNC[C@@](C)(F)C2)n1] | N-(2-Fluoro-5-((3-(2-(((3S,5S)-5-fluoro-5-methylpiperidin-3-yl)amino)pyrimidin-4-yl)pyridin-2-yl)oxy)-6-methylnaphthalen-1-yl)-1-(2-fluorophenyl)methanesulfonamide |
| 543 | 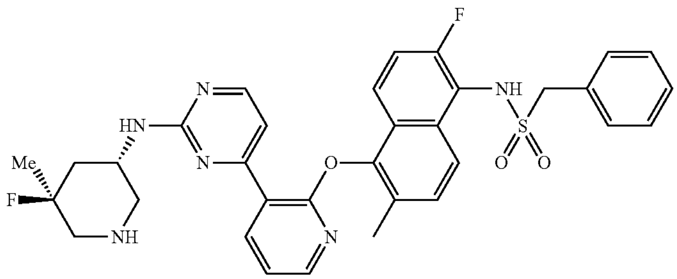 [SMILES: Cc1ccc2c(NS(=O)(=O)Cc3ccccc3)c(F)ccc2c1Oc1ncccc1-c1ccnc(N[C@@H]2CNC[C@@](C)(F)C2)n1] | N-(2-Fluoro-5-((3-(2-(((3S,5S)-5-fluoro-5-methylpiperidin-3-yl)amino)pyrimidin-4-yl)pyridin-2-yl)oxy)-6-methylnaphthalen-1-yl)-1-phenylmethanesulfonamide |
| 544 | 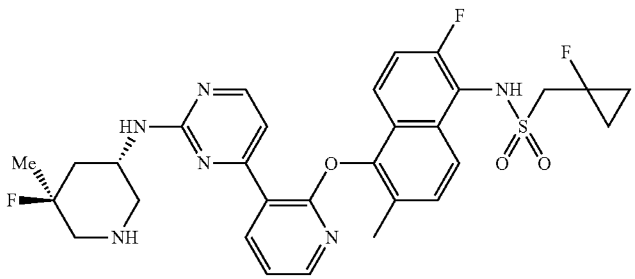 [SMILES: Cc1ccc2c(NS(=O)(=O)CC3(F)CC3)c(F)ccc2c1Oc1ncccc1-c1ccnc(N[C@@H]2CNC[C@@](C)(F)C2)n1] | N-(2-Fluoro-5-((3-(2-(((3S,5S)-5-fluoro-5-methylpiperidin-3-yl)amino)pyrimidin-4-yl)pyridin-2-yl)oxy)-6-methylnaphthalen-1-yl)-1-(1-fluorocyclopropyl)methanesulfonamide |
| 545 | 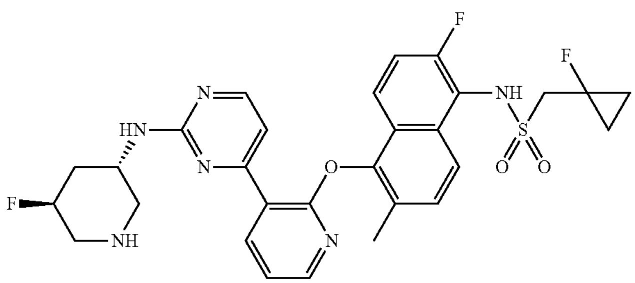 [SMILES: Cc1ccc2c(NS(=O)(=O)CC3(F)CC3)c(F)ccc2c1Oc1ncccc1-c1ccnc(N[C@@H]2CNC[C@@H](F)C2)n1] | N-(2-Fluoro-5-((3-(2-(((3S,5S)-5-fluoropiperidin-3-yl)amino)pyrimidin-4-yl)pyridin-2-yl)oxy)-6-methylnaphthalen-1-yl)-1-(1-fluorocyclopropyl)methanesulfonamide |

Administration of Compounds

The compounds of the invention may be administered by any route appropriate to the condition to be treated. Suitable routes include oral, parenteral (including subcutaneous, intramuscular, intravenous, intraarterial, intradermal, intrathecal and epidural), transdermal, rectal, nasal, topical (including buccal and sublingual), vaginal, intraperitoneal, intrapulmonary and intranasal. For local immunosuppressive treatment, the compounds may be administered by intralesional administration, including perfusing or otherwise contacting the graft with the inhibitor before transplantation. It will be appreciated that the preferred route may vary with for example the condition of the recipient. Where the compound is administered orally, it may be formulated as a pill, capsule, tablet, etc. with a pharmaceutically acceptable carrier or excipient. Where the compound is administered parenterally, it may be formulated with a pharmaceutically acceptable parenteral vehicle and in a unit dosage injectable form, as detailed below.

A dose to treat human patients may range from about 10 mg to about 1000 mg of Formula I or I' compound. A typical dose may be about 100 mg to about 300 mg of the compound. A dose may be administered once a day (QID), twice per day (BID), or more frequently, depending on the pharmacokinetic and pharmacodynamic properties, including absorption, distribution, metabolism, and excretion of the particular compound. In addition, toxicity factors may influence the dosage and administration regimen. When administered orally, the pill, capsule, or tablet may be ingested daily or less frequently for a specified period of time. The regimen may be repeated for a number of cycles of therapy.

Methods of Treatment

Formula I or I' compounds of the present invention are useful for treating a human or animal patient suffering from a disease or disorder arising from abnormal cell growth, function or behavior associated with the UPR pathway such as cancer, an immune disorder, cardiovascular disease, viral infection, inflammation, a metabolism/endocrine disorder or a neurological disorder, may thus be treated by a method comprising the administration thereto of a compound of the present invention as defined above. A human or animal patient suffering from cancer may also be treated by a method comprising the administration thereto of a compound of the present invention as defined above. The condition of the patient may thereby be improved or ameliorated.

Methods of the invention also include treating cancer selected from breast, ovary, cervix, prostate, testis, genitourinary tract, esophagus, larynx, glioblastoma, neuroblastoma, stomach, skin, keratoacanthoma, lung, epidermoid carcinoma, large cell carcinoma, non-small cell lung carcinoma (NSCLC), small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, pancreatic, myeloid disorders, lymphoma, hairy cells, buccal cavity, naso-pharyngeal, pharynx, lip, tongue, mouth, small intestine, colon-rectum, large intestine, rectum, brain and central nervous system, Hodgkin's, leukemia, bronchus, thyroid, liver and intrahepatic bile duct, hepatocellular, gastric, glioma/glioblastoma, endometrial, melanoma, kidney and renal pelvis, urinary bladder, uterine corpus, uterine cervix, multiple myeloma, acute myelogenous leukemia, chronic myelogenous leukemia, lymphocytic leukemia, chronic lymphoid leukemia (CLL), myeloid leukemia, oral cavity and pharynx, non-Hodgkin lymphoma, melanoma, and villous colon adenoma.

In one aspect, provided is a method of treating an IRE1-related disease or disorder in a patient comprising administering a therapeutically effective amount of a compound of Formula I or I', or any variations detailed herein, or a stereoisomer, tautomer, or pharmaceutically acceptable salt thereof, to a patient with an IRE1-related disease or condition. In another aspect, the method comprises administering to a patient with an IRE1-related disease or condition an effective amount of a pharmaceutical composition comprising a compound of Formula I or I', or any variations detailed herein, or a stereoisomer, tautomer, or pharmaceutically acceptable salt thereof, and a pharmaceutically acceptable carrier, glidant, diluent, or excipient. In some embodiments, the compound is of the Formula I excluding compounds of Table 1X. In other embodiments, the compound is of the Formula I including compounds of Table 1X. In some embodiments, the compound is of the Formula I' or variations thereof. In some embodiments, the compound is selected from Tables 1, 2 and 3, or a pharmaceutically acceptable salt thereof. In some embodiments, the patient is a human patient.

In one aspect, provided is a compound of Formula I or I', or any variations detailed herein, or a stereoisomer, tautomer, or pharmaceutically acceptable salt thereof, for use in a method for treating an IRE1-related disease or disorder. In one aspect, provided is a use of a compound of Formula I or I', or any variations detailed herein, or a stereoisomer, tautomer, or pharmaceutically acceptable salt thereof, in the manufacture of a medicament for the treatment of an IRE1-related disease or disorder.

In some embodiments, the IRE1-related disease or disorder is cancer selected from the group consisting of squamous cell cancer, small-cell lung cancer, non-small cell lung cancer ("NSCLC"), adenocarcinoma of the lung and squamous carcinoma of the lung, cancer of the peritoneum, hepatocellular cancer, stomach cancer, gastrointestinal cancer, esophageal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, and head and neck cancer.

In some embodiments, the IRE1-related disease or disorder is a hematological malignancy selected from the group consisting of lymphomas, lymphocytic leukemia, myeloma, acute and chronic myelogenous leukemia, myelodysplastic syndrome and myeloproliferative disease.

In some embodiments, the IRE1-related disease or disorder is multiple myeloma. In some embodiments, wherein the IRE1-related disease or disorder is a breast cancer (e.g., a triple-negative breast cancer ("TNBC")).

In some embodiments of the method of treating an IRE1-related disease or disorder in a patient comprising administering a therapeutically effective amount of a compound of Formula I or I', or any variations detailed herein, or a stereoisomer, tautomer, or pharmaceutically acceptable salt thereof, to a patient with an IRE1-related disease or condition, the method further comprising administering one or more additional therapeutic agent(s) selected from the group consisting of an anti-inflammatory agent, a corticosteroid, an immunomodulatory agent, chemotherapeutic agent, an apoptosis-enhancer, a neurotropic factor, an agent for treating cardiovascular disease, an agent for treating liver disease, an anti-viral agent, an agent for treating blood disorders, an agent for treating diabetes, an agent for treating metabolic disorders, an agent for treating autoimmune disorders, an agent for treating immunodeficiency disorders, and combinations thereof. In some embodiments, the additional therapeutic agent is a corticosteroid, a proteasome inhibitor, an IMiD, an antibody, or a combination thereof. In some embodiments, the additional therapeutic agent is a proteasome inhibitor (e.g. carfilzomib, bortezomib, or ixazomib). In some embodiments, the additional therapeutic agent is an IMiD (e.g. lenalidomide or pomalidomide). In some embodiments, the additional therapeutic agent is an antibody (e.g., an anti-CD38 antibody, an anti-VEGF-A antibody, an anti-PD-1 antibody, an anti-PD-L1 antibody or an anti-interleukin-6 antibody). In some embodiments, the additional therapeutic agent is a corticosteroid (e.g., dexamethasone). In some embodiments, the method further comprises radiotherapy.

Also provided herein is a method of treating a disease caused by abnormal levels of Ire1 activity in a human or animal patient in need of such treatment with a Formula I or I' compound. The disease may be caused by an amount of Ire1 activity that is too low or too high. For example, the disease may be caused by a deficiency in Ire1 activity or by abnormally high Ire1 activity (e.g., hyperactivity of Ire1). The method includes administering to the patient a therapeutically effective amount of an Ire1 modulator Formula I or I' compound.

Ire1 deficiency is a decreased amount of Ire1 activity compared to normal levels of Ire1 activity in a particular subject or a population of healthy subjects. The decreased amount of Ire1 activity results in excessive amounts of misfolded protein accumulation thereby causing the disease state.

Ire1 hyperactivity is an increased amount of Ire1 activity compared to normal levels of Ire1 activity in a particular subject or a population of healthy subjects. The increased amount of Ire1 activity may result in, for example, excessive amounts of cell proliferation thereby causing the disease state.

In some embodiments, the disease is associated with Ire1 deficiency. Such diseases include, but are not limited to, cystic fibrosis, retinitis pigmentosa, diabetes, or a neurodegenerative disease. The neurodegenerative disease may include Alexander's disease, Alper's disease, Alzheimer's disease, Amyotrophic lateral sclerosis, Ataxia telangiectasia, Batten disease (also known as Spielmeyer-Vogt-Sjogren-Batten disease). Bovine spongiform encephalopathy (BSF), Canavan disease, Cockayne syndrome, Corticobasal degeneration, Creutzfeldt-Jakob disease, Huntington's disease, HIV-associated dementia, Kennedy's disease, Krabbe's disease, Lewy body dementia, Machado-Joseph disease (Spinocerebellar ataxia type 3), Multiple sclerosis, Multiple System Atrophy, Narcolepsy, Neuroborreliosis, Parkinson's disease, Pelizaeus-Merzbacher Disease, Pick's disease, Primary lateral sclerosis, Prion diseases, Refsum's disease, Sandhoffs disease, Schilder's disease, Subacute combined degeneration of spinal cord secondary to Pernicious Anaemia, Schizophrenia, Spinocerebellar ataxia (multiple types with varying characteristics), Spinal muscular atrophy, Steele-Richardson-Olszewski disease, or *Tabes dorsalis*.

In other embodiments, the disease is associated with abnormally high Ire1. Such diseases include, but are not limited, to cancers, inflammatory diseases, and autoimmune diseases. Exemplary cancers include, but am not limited to, breast cancer and multiple myeloma. In one embodiment, the disease is multiple myeloma. In one embodiment, the disease is a triple-negative breast cancer. Exemplary inflammatory diseases include, but are not limited to, asthma, chronic inflammation, chronic prostatitis, glomerulonephritis, hypersensitivities, inflammatory bowel diseases, pelvic inflammatory disease; reperfusion injury, rheumatoid arthritis, transplant rejection, and vasculitis. Exemplary autoimmune diseases include, but are not limited to, XBP1-linked Crohn's disease, Coeliac disease, diabetes mellitus type 1 (IDDM), systemic lupus erythematosus (SLE), Sjogren's syndrome, Churg-Strauss Syndrome, Hashimoto's thyroiditis, Graves' disease, idiopathic thrombocytopenic purpura, and rheumatoid arthritis. In one embodiment, the disease is XBP1-linked. Crohn's disease.

Pharmaceutical Formulations

In order to use a Formula I or I' compound for the therapeutic treatment of mammals including humans, it is normally formulated in accordance with standard pharmaceutical practice as a pharmaceutical composition. According to this aspect of the invention there is provided a pharmaceutical composition comprising a compound of this invention in association with a pharmaceutically acceptable diluent or carrier.

A typical formulation is prepared by mixing a compound of the present invention and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water and the like. The particular carrier, diluent or excipient used will depend upon the means and purpose for which the compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

The formulations may be prepared using conventional dissolution and mixing procedures. For example, the bulk drug substance (i.e., compound of the present invention or stabilized form of the compound (e.g., complex with a cyclodextrin derivative or other known complexation agent) is dissolved in a suitable solvent in the presence of one or more of the excipients described above. The compound of the present invention is typically formulated into pharmaceutical dosage forms to provide an easily controllable dosage of the drug and to enable patient compliance with the prescribed regimen.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

Pharmaceutical formulations of the compounds of the present invention may be prepared for various routes and types of administration. For example, a compound of Formula I or I' having the desired degree of purity may optionally be mixed with pharmaceutically acceptable diluents, carriers, excipients or stabilizers (Remington's Pharmaceutical Sciences (1980) 16th edition, Osol, A. Ed.), in the form of a lyophilized formulation, milled powder, or an aqueous solution. Formulation may be conducted by mixing at ambient temperature at the appropriate pH, and at the desired degree of purity, with physiologically acceptable carriers, i.e., carriers that are non-toxic to recipients at the dosages and concentrations employed. The pH of the formulation depends mainly on the particular use and the concentration of compound, but may range from about 3 to about 8. Formulation in an acetate buffer at pH 5 is a suitable embodiment.

The compound ordinarily can be stored as a solid composition, a lyophilized formulation or as an aqueous solution.

The pharmaceutical compositions of the invention will be formulated, dosed and administered in a fashion, i.e., amounts, concentrations, schedules, course, vehicles and route of administration, consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the compound to be administered will be governed by such considerations, and is the minimum amount necessary to ameliorate, or treat the hyperproliferative disorder.

As a general proposition, the initial pharmaceutically effective amount of the inhibitor administered parenterally per dose will be in the range of about 0.01-100 mg/kg, namely about 0.1 to 20 mg/kg of patient body weight per day, with the typical initial range of compound used being 0.3 to 15 mg/kg/day.

Acceptable diluents, carriers, excipients and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). The active pharmaceutical ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations of compounds of Formula I or I' may be prepared. Suitable examples of sustained-release preparations include semipermeable matrices of solid hydrophobic polymers containing a compound of Formula I or I', which matrices are in the form of shaped articles, e.g., films, or microcapsules. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate) and poly-D-(-)-3-hydroxybutyric acid.

The formulations include those suitable for the administration routes detailed herein. The formulations may conveniently be presented in unit dosage form and may be prepared by any of the methods well known in the art of pharmacy. Techniques and formulations generally are found in *Remington's Pharmaceutical Sciences* (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of a compound of Formula I or I' suitable for oral administration may be prepared as discrete units such as pills, capsules, cachets or tablets each containing a predetermined amount of a compound of Formula I or I'. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom. Tablets, troches, lozenges, aqueous or oil suspensions, dispersible powders or granules, emulsions, hard or soft capsules, e.g., gelatin capsules, syrups or elixirs may be prepared for oral use. Formulations of compounds of Formula I or I' intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

For treatment of the eye or other external tissues, e.g., mouth and skin, the formulations are preferably applied as a topical ointment or cream containing the active ingredient(s) in an amount of, for example, 0.075 to 20% w/w. When formulated in an ointment, the active ingredients may be employed with either a paraffinic or a water-miscible ointment base. Alternatively, the active ingredients may be formulated in a cream with an oil-in-water cream base. If desired, the aqueous phase of the cream base may include a polyhydric alcohol, i.e., an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulfoxide and related analogs. The oily phase of the emulsions of this invention may be constituted from known ingredients in a known manner. While the phase may comprise merely an emulsifier, it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations. Emulsifiers and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

Aqueous suspensions of Formula I or I' compounds contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

The pharmaceutical compositions of compounds of Formula I or I' may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butanediol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 μg of the active ingredient per milliliter of solution in order that infusion of a suitable volume at a rate of about 30 mL/hr can occur.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of about 0.5 to 20% w/w, for example about 0.5 to 10% w/w, for example about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis disorders as described below.

Formulations suitable for vaginal administration may be presented as pessaries, tampons, creams, gels, pastes, foams or spray formulations containing in addition to the active ingredient such carriers as are known in the art to be appropriate.

The formulations may be packaged in unit-dose or multi-dose containers, for example sealed ampoules and vials, and may be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

The invention further provides veterinary compositions comprising at least one active ingredient as above defined together with a veterinary carrier therefore. Veterinary carriers are materials useful for the purpose of administering the composition and may be solid, liquid or gaseous materials which are otherwise inert or acceptable in the veterinary art and are compatible with the active ingredient. These veterinary compositions may be administered parenterally, orally or by any other desired route.

Combination Therapy

The compounds of Formula I or I' may be employed alone or in combination with additional therapeutic agents for the treatment of a disease or disorder described herein, such as inflammation or a hyperproliferative disorder (e.g., cancer). In certain embodiments, a compound of Formula I or I' is combined in a pharmaceutical combination formulation, or dosing regimen as combination therapy, with an additional, second therapeutic compound that has anti-inflammatory or anti-hyperproliferative properties or that is useful for treating an inflammation, immune-response disorder, or hyperproliferative disorder (e.g., cancer). The additional therapeutic may be a Bcl-2 inhibitor, a JAK inhibitor, a PI3K inhibitor, an mTOR inhibitor, an anti-inflammatory agent, an immunomodulatory agent, chemotherapeutic agent, an apoptosis-enhancer, a neurotropic factor, an agent for treating cardiovascular disease, an agent for treating liver disease, an anti-viral agent, an agent for treating blood disorders, an agent for treating diabetes, and an agent for treating immunodeficiency disorders. The second therapeutic agent may be an NSAID anti-inflammatory agent. The second therapeutic agent may be a chemotherapeutic agent. The second compound of the pharmaceutical combination formulation or dosing regimen preferably has complementary activities to the compound of Formula I or I' such that they do not adversely affect each other. Such compounds are suitably present in combination in amounts that are effective for the purpose intended. In one embodiment, a composition of this invention comprises a compound of Formula I or I', or a stereoisomer, tautomer, solvate, metabolite, or pharmaceutically acceptable salt or prodrug thereof, in combination with a therapeutic agent such as an NSAID.

The combination therapy may be administered as a simultaneous or sequential regimen. When administered sequentially, the combination may be administered in two or more administrations. The combined administration includes coadministration, using separate formulations or a single pharmaceutical formulation, and consecutive administration in either order, wherein preferably there is a time period while both (or all) active agents simultaneously exert their biological activities.

Suitable dosages for any of the above coadministered agents are those presently used and may be lowered due to the combined action (synergy) of the newly identified agent and other therapeutic agents or treatments.

The combination therapy may provide "synergy" and prove "synergistic", i.e., the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect may be attained when the compounds are administered or delivered sequentially, e.g., by different injections in separate syringes, separate pills or capsules, or separate infusions. In general, during alternation therapy, an effective dosage of each active ingredient is administered sequentially, i.e., serially, whereas in combination therapy, effective dosages of two or more active ingredients are administered together.

In a particular embodiment of therapy, a compound of Formula I or I', or a stereoisomer, tautomer, solvate, metabolite, or pharmaceutically acceptable salt or prodrug thereof, may be combined with other therapeutic, hormonal or antibody agents such as those described herein, as well as combined with surgical therapy and radiotherapy. Combination therapies according to the present invention thus comprise the administration of at least one compound of Formula I or I', or a stereoisomer, tautomer, solvate, metabolite, or pharmaceutically acceptable salt or prodrug thereof, and the use of at least one other cancer treatment method. The amounts of the compound(s) of Formula I or I', and the other pharmaceutically active therapeutic agent(s) and the relative timings of administration will be selected in order to achieve the desired combined therapeutic effect.

In some embodiments, a compound of Formula I or I', or a pharmaceutically acceptable salt thereof, is used in combination with an aromatase inhibitor, a phosphoinositide 3-kinase (PI3K)/mTOR pathway inhibitor, a CDK 4/6 inhibitor, a HER-2 inhibitor, an EGFR inhibitor, a PD-1 inhibitor, poly ADP-ribose polymerase (PARP) inhibitor, a histone deacetylase (HDAC) inhibitor, an HSP90 inhibitor, a VEGFR inhibitor, an AKT inhibitor, chemotherapy, or any combination thereof.

In some embodiments, a pharmaceutical composition comprising a compound of Formula I or I', or a pharmaceutically acceptable salt thereof, is administered in combination with a therapeutic agent selected from paclitaxel, anastrozole, exemestane, cyclophosphamide, epirubicin, fulvestrant, letrozole, palbociclib, gemcitabine, trastuzumab (HERCEPTIN®, Genentech), trastuzumab emtansine (KADCYLA®, Genentech), pegfilgrastim, filgrastim, tamoxifen, docetaxel, toremifene, vinorelbine, capecitabine, and ixabepilone.

In some embodiments, a compound of Formula I or I', or a pharmaceutically acceptable salt thereof, is used in combination with hormone blocking therapy, chemotherapy, radiation therapy, monoclonal antibodies, or combinations thereof.

Metabolites of Compounds of Formula I or I'

Also falling within the scope of this invention are the in vivo metabolic products of Formula I or I' described herein. Such products may result for example from the oxidation, reduction, hydrolysis, amidation, deamidation, esterification, deesterification, enzymatic cleavage, and the like, of the administered compound. Accordingly, the invention includes metabolites of compounds of Formula I or I', including compounds produced by a process comprising contacting a compound of this invention with a mammal for a period of time sufficient to yield a metabolic product thereof.

Metabolite products typically are identified by preparing a radiolabelled (e.g., $^{14}C$ or $^{3}H$) isotope of a compound of the invention, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies well known to those skilled in the art. The metabolite products, so long as they are not otherwise found in vivo, are useful in diagnostic assays for therapeutic dosing of the compounds of the invention.

Articles of Manufacture

In another embodiment of the invention, an article of manufacture, or "kit", containing materials useful for the treatment of the diseases and disorders described above is provided. In one embodiment, the kit comprises a container comprising a compound of Formula I or I', or a stereoisomer, tautomer, solvate, metabolite, or pharmaceutically acceptable salt or prodrug thereof. The kit may further comprise a label or package insert on or associated with the container. The term "package insert" is used to refer to instructions customarily included in commercial packages of therapeutic products, that contain information about the indications, usage, dosage, administration, contraindications and/or warnings concerning the use of such therapeutic products. Suitable containers include, for example, bottles, vials, syringes, blister pack, etc. The container may be formed from a variety of materials such as glass or plastic. The container may hold a compound of Formula I or I' or a formulation thereof which is effective for treating the condition and may have a sterile access port (for example, the container may be an intravenous solution bag or a vial having a stopper pierceable by a hypodermic injection needle). At least one active agent in the composition is a compound of Formula I or I'. The label or package insert indicates that the composition is used for treating the condition of choice, such as cancer. In addition, the label or package insert may indicate that the patient to be treated is one having a disorder such as a hyperproliferative disorder, neurodegeneration, cardiac hypertrophy, pain, migraine or a neurotraumatic disease or event. In one embodiment, the label or package inserts indicates that the composition comprising a compound of Formula I or I' can be used to treat a disorder resulting from abnormal cell growth. The label or package insert may also indicate that the composition can be used to treat other disorders. Alternatively, or additionally, the article of manufacture may further comprise a second container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The kit may further comprise directions for the administration of the compound of Formula I or I' and, if present, the second pharmaceutical formulation. For example, if the kit comprises a first composition comprising a compound of Formula I or I' and a second pharmaceutical formulation, the kit may further comprise directions for the simultaneous, sequential or separate administration of the first and second pharmaceutical compositions to a patient in need thereof.

In another embodiment, the kits are suitable for the delivery of solid oral forms of a compound of Formula I or I', such as tablets or capsules. Such a kit preferably includes a number of unit dosages. Such kits can include a card having the dosages oriented in the order of their intended use. An example of such a kit is a "blister pack". Blister packs are well known in the packaging industry and are widely used for packaging pharmaceutical unit dosage forms. If desired, a memory aid can be provided, for example in the form of numbers, letters, or other markings or with a calendar insert, designating the days in the treatment schedule in which the dosages can be administered.

According to one embodiment, a kit may comprise (a) a first container with a compound of Formula I or I' contained therein; and optionally (b) a second container with a second pharmaceutical formulation contained therein, wherein the second pharmaceutical formulation comprises a second compound with anti-hyperproliferative activity. Alternatively, or additionally, the kit may further comprise a third container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In certain other embodiments wherein the kit comprises a composition of Formula I or I' and a second therapeutic agent, the kit may comprise a container for containing the separate compositions such as a divided bottle or a divided foil packet, however, the separate compositions may also be contained within a single, undivided container. Typically, the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

Preparation of Formula I or I' Compounds

Formula I or I' compounds may be synthesized by synthetic routes that include processes analogous to those well-known in the chemical arts, particularly in light of the description contained herein, and those for other heterocycles described in: Comprehensive Heterocyclic Chemistry II, Editors Katritzky and Rees, Elsevier, 1997, e.g. Volume 3; Liebigs Annalen der Chemie, (9):1910-16, (1985); Helvetica Chimica Acta, 41:1052-60, (1958); Arzneimittel-Forschung, 40(12):1328-31, (1990), each of which are expressly incorporated by reference. Starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, *Reagents for Organic Synthesis*, v. 1-23, Wiley, N.Y. (1967-2006 ed.), or *Beilsteins Handbuch der organischen Chemie*, 4, Aufl. ed. Springer-Verlag, Berlin, including supplements (also available via the Beilstein online database). Formula I or I' compounds may also be made following the procedures found in U.S. Pat. Nos. 8,476,434, 7,880,000, WO 2005/113494, U.S. Pat. No. 7,868,177, and WO 2007/100646.

Synthetic chemistry transformations and protecting group methodologies (protection and deprotection) useful in synthesizing Formula I or I' compounds and necessary reagents and intermediates are known in the art and include, for example, those described in R. Larock, Comprehensive Organic Transformations, VCH Publishers (1989); T. W. Greene and P. G. M. Wuts, Protective Groups in Organic Synthesis, $3^{rd}$ Ed., John Wiley and Sons (1999); and L. Paquette, ed., Encyclopedia of Reagents for Organic Synthesis, John Wiley and Sons (1995) and subsequent editions thereof.

Compounds of Formula I or I' may be prepared singly or as compound libraries comprising at least 2, for example 5 to 1,000 compounds, or 10 to 100 compounds. Libraries of compounds of Formula I or I' may be prepared by a combinatorial 'split and mix' approach or by multiple parallel syntheses using either solution phase or solid phase chemistry, by procedures known to those skilled in the art. Thus according to a further aspect of the invention there is provided a compound library comprising at least 2 compounds, or pharmaceutically acceptable salts thereof.

The Examples provide exemplary methods for preparing Formula I or I' compounds. Those skilled in the art will appreciate that other synthetic routes may be used to synthesize the Formula I or I' compounds. Although specific starting materials and reagents are depicted and discussed in the Examples, other starting materials and reagents can be easily substituted to provide a variety of derivatives and/or reaction conditions. In addition, many of the exemplary compounds prepared by the described methods can be further modified in light of this disclosure using conventional chemistry well known to those skilled in the art.

In preparing compounds of Formula I or I', protection of remote functionality (e.g., primary or secondary amine) of intermediates may be necessary. The need for such protection will vary depending on the nature of the remote functionality and the conditions of the preparation methods. Suitable amino-protecting groups include acetyl, trifluoroacetyl, t-butoxycarbonyl (BOC), benzyloxycarbonyl (CBz) and 9-fluorenylmethyleneoxycarbonyl (Fmoc). The need for such protection is readily determined by one skilled in the art. For a general description of protecting groups and their use, see T. W. Greene, Protective Groups in Organic Synthesis, John Wiley & Sons, New York, 1991.

In the methods of preparing Formula I or I' compounds, it may be advantageous to separate reaction products from one another and/or from starting materials. The desired products of each step or series of steps is separated and/or purified to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed (SMB) and preparative thin or thick layer chromatography, as well as techniques of small scale thin layer and flash chromatography.

Another class of separation methods involves treatment of a mixture with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like. Selection of appropriate methods of separation depends on the nature of the materials involved, such as, boiling point and molecular weight in distillation and sublimation, presence or absence of polar functional groups in chromatography, stability of materials in acidic and basic media in multiphase extraction, and the like.

Diastereomeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers. Also, some of the compounds of the present invention may be atropisomers (e.g., substituted biaryls) and are considered as part of this invention. Enantiomers can also be separated by use of a chiral HPLC column.

A single stereoisomer, e.g., an enantiomer, substantially free of its stereoisomer may be obtained by resolution of the racemic mixture using a method such as formation of diastereomers using optically active resolving agents (Eliel, E. and Wilen, S. "Stereochemistry of Organic Compounds," John Wiley & Sons, Inc., New York, 1994; Lochmuller, C. H., (1975) J. Chromatogr., 113(3):283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: "Drug Stereochemistry, Analytical Methods and Pharmacology," Irving W. Wainer, Ed., Marcel Dekker, Inc., New York (1993).

Under method (1), diastereomeric salts can be formed by reaction of enantiomerically pure chiral bases such as brucine, quinine, ephedrine, strychnine, α-methyl-β-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, by method (2), the substrate to be resolved is reacted with one enantiomer of a chiral compound to form a diastereomeric pair (E. and Wilen, S. "Stereochemistry of Organic Compounds", John Wiley & Sons, Inc., 1994, p. 322). Diastereomeric compounds can be formed by reacting asymmetric compounds with enantiomerically pure chiral derivatizing reagents, such as menthyl derivatives, followed by separation of the diastereomers and hydrolysis to yield the pure or enriched enantiomer. A method of determining optical purity involves making chiral esters, such as a menthyl ester, e.g., (−) menthyl chloroformate in the presence of base, or Mosher ester, α-methoxy-α-(trifluoromethyl)phenyl acetate (Jacob III. J. Org. Chem. (1982) 47:4165), of the racemic mixture, and analyzing the $^1$H NMR spectrum for the presence of the two atropisomeric enantiomers or diastereomers. Stable diastereomers of atropisomeric compounds can be separated and isolated by normal- and reverse-phase chromatography following methods for separation of atropisomeric naphthyl-isoquinolines (WO 96/15111). By method (3), a racemic mixture of two enantiomers can be separated by chromatography using a chiral stationary phase ("Chiral Liquid Chromatography" (1989) W. J. Lough, Ed., Chapman and Hall, New York; Okamoto, J. Chromatogr., (1990) 513:375-378). Enriched or purified enantiomers can be distinguished by methods used to distinguish other chiral molecules with asymmetric carbon atoms, such as optical rotation and circular dichroism.

Formula I or I' compounds can be prepared by procedures in the Examples, the General Procedures, and generally by Schemes 1-4, where R groups are as described in Formula I or I' compounds, or precursors thereof.

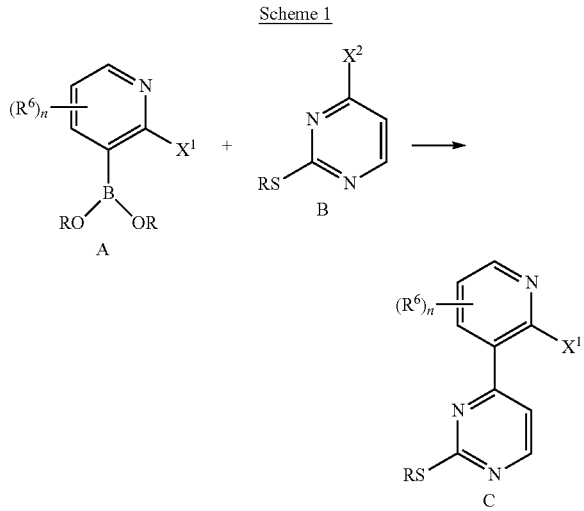

Scheme 1

Scheme 1 shows coupling of a (2-halopyridin-3-yl)boronic acid or ester compound A (R=H, $C_1$-$C_6$ alkyl, pinacol; $X^1$=halogen) with a 4-chloro-2-(methylthio)pyrimidine compound B (R=$C_1$-$C_6$ alkyl, $X^2$=halogen) under palladium catalysis to form 4-(2-halopyridin-3-yl)-2-(alkylthio)pyrimidine compound C.

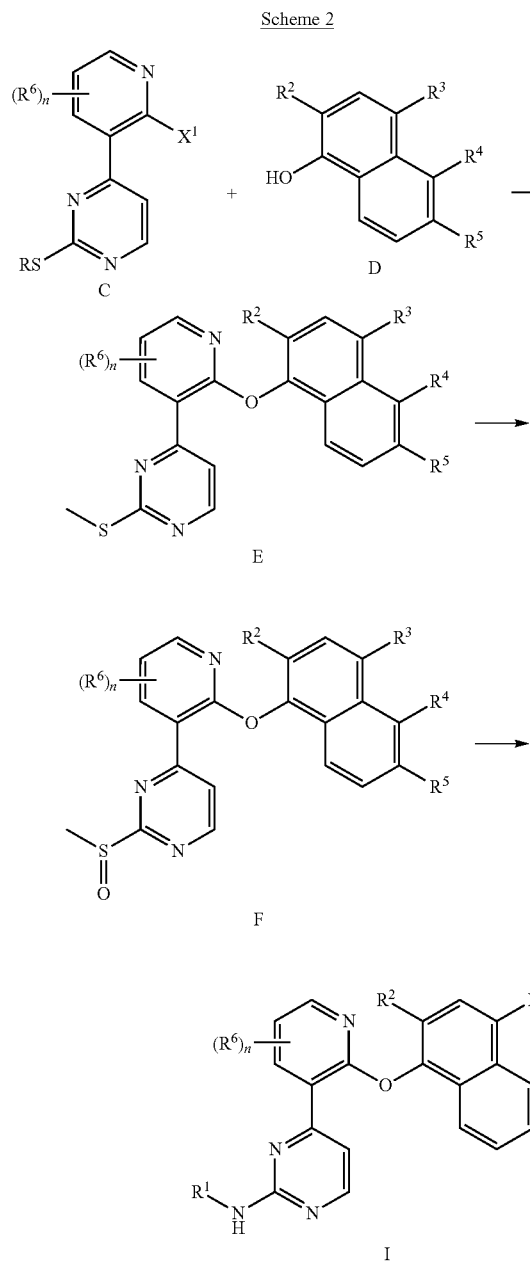

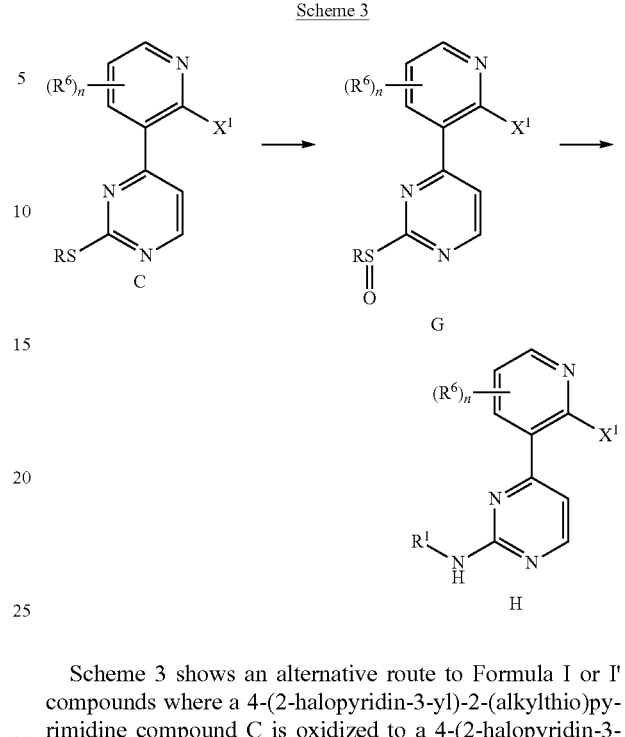

Scheme 3 shows an alternative route to Formula I or I' compounds where a 4-(2-halopyridin-3-yl)-2-(alkylthio)pyrimidine compound C is oxidized to a 4-(2-halopyridin-3-yl)-2-(alkylsulfinyl)pyrimidine compound G. The sulfoxide is displaced with a primary amine ($R^1$—$NH_2$) to form a 4-(2-halopyridin-3-yl)-N-alkylpyrimidin-2-amine compound H. Coupling of compound H with a naphthalen-1-ol compound D forms a Formula I or I' compound, or an intermediate to be converted to a Formula I or I' compound.

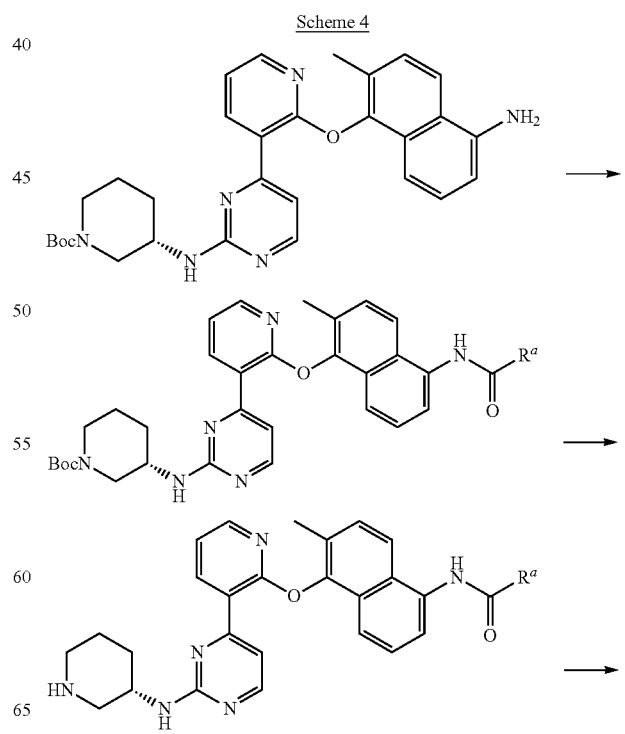

Scheme 2 shows coupling of a naphthalen-1-ol compound D with a 4-(2-halopyridin-3-yl)-2-(alkylthio)pyrimidine compound C to form a 4-(2-(naphthalen-1-yloxy)pyridin-3-yl)pyrimidine-2-alkylthiol E compound. Oxidation of the sulfur atom forms 2-(alkylsulfinyl)-4-(2-(naphthalen-1-yloxy)pyridin-3-yl)pyrimidine compound F. The sulfoxide is displaced with a primary amine ($R^1$—$NH_2$) to form a Formula I or I' compound, or an intermediate to be converted to a Formula I or I' compound.

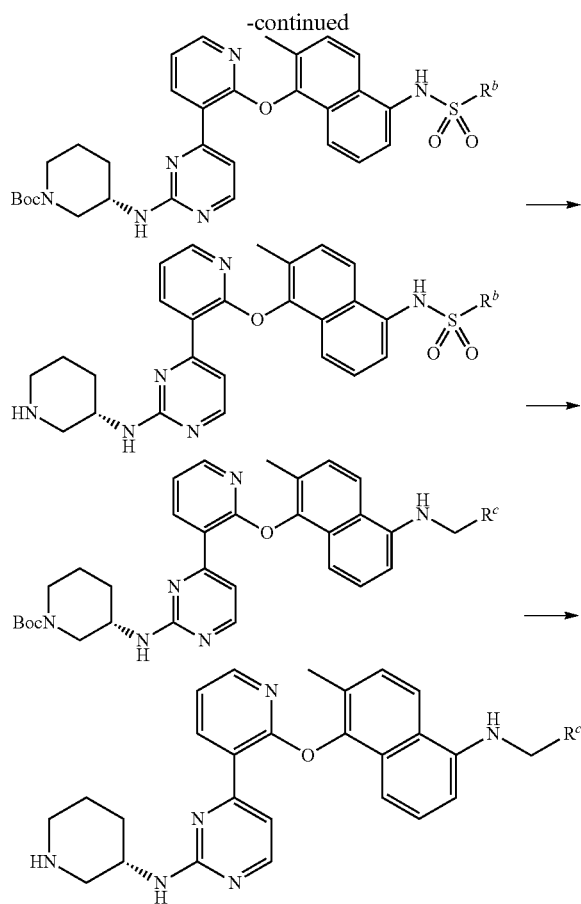

Scheme 4 shows the general preparation of exemplary compounds from aniline intermediate, tert-butyl (S)-3-((4-(2-((5-amino-2-methylnaphthalen-1-yl)oxy)pyridin-3-yl)pyrimidin-2-yl)amino)piperidine-1-carboxylate (see, Example 101). The aniline intermediate is treated with a carboxylic acid ($R^a$COOH) and a coupling reagent, such as 1-[Bis(dimethylamino)methylene]-1H-1,2,3-triazolo[4,5-b]pyridinium 3-oxide hexafluorophosphate (HATU) as in General Procedure C, or alternatively with an acid chloride ($R^a$COCl) and an amine base such as diisopropylethylamine (DIPEA) or pyridine, to form Boc-protected, amide intermediates (top). The aniline intermediate is treated with a sulfonyl chloride ($R^b$SO$_2$Cl) and an amine base to form Boc-protected, sulfonamide intermediates (middle) as in General Procedure A. The aniline intermediate is treated with an alkylating agent as in General Procedure G, or by reductive amination ($R^c$CHO) to form Boc-protected, amine intermediates (bottom) as in General Procedure E. The Boc-protected intermediates are deprotected with acid, such as hydrochloric acid as in General Procedure B, to form exemplary compounds, such as those in Tables 1 and 2 and the following Examples.

The following General Procedures illustrate synthetic reactions and operations useful to prepare certain Example compounds (Tables 1 and 2). The reagents, solvents, amounts, equivalents, and conditions are illustrative and exemplary, and not meant to be limiting.

General Procedure A—Sulfonamide Synthesis:

To a solution of the aniline (1.0 equiv) in pyridine (5 mL/mmol) and a solvent such as dichloromethane (DCM) at 0° C. or room temperature (rt) was added the corresponding sulfonyl chloride (1.2 equiv typically otherwise noted). After the addition was completed, the reaction solution was stirred at rt for about 16 h. Water (10 mL) was added. The mixture was extracted with DCM. The organic layer was dried over anhydrous sodium sulfate, filtered and concentrated in vacuo.

General Procedure B—Boc Deprotection

To a mixture of the t-butyl-carbamate (Boc) intermediate (100 mg, 0.16 mmol) in DCM (25 mL/mmol) or EtOAc was added hydrochloric acid (4 M in dioxane, 10 mL/mmol). The mixture was then stirred at rt for 1 h and concentrated in vacuo or the resulting HCl salt was isolated by filtration.

General Procedure C—Amide Coupling Using Carboxylic Acids:

To a solution of the aniline intermediate (1.05 equiv otherwise indicated) and DIPEA (3.0 equiv otherwise indicated) in DCM (16 mL/mmol otherwise indicated) was added HATU (2.0 equiv otherwise indicated). The mixture was stirred at rt for 0.5 h. The acid (1.0 equiv otherwise indicated) was added and the resulting mixture was refluxed overnight. The mixture was diluted in DCM, washed with water and brine, dried on anhydrous sodium sulfate, and concentrated in vacuo. Alternatively, to a solution of the aniline in CH$_2$Cl$_2$ was added the acid chloride followed by addition of (iPr)$_2$NEt or Et$_3$N or pyridine and stirring at rt. Alternatively, to a solution of the aniline in DMF was added the carboxylic acid and HATU followed by addition of (iPr)$_2$NEt or Et$_3$N and stirring at rt. Other coupling reagents may be used in General Procedure C. The crude product was isolated and purified using methods known in the art or as described in the Examples.

General Procedure E—Reductive Amination:

To a mixture of aniline and aldehyde in CH$_2$Cl$_2$ was added sodium triacetoxyborohydride and HOAc (caution bubbling—vent vessel) and the mixture stirred at rt. The crude product was isolated and purified using methods known in the art or as described in the Examples.

General Procedure F—Epoxide Ring Opening:

A mixture of aniline and epoxide in HOAc was stirred at rt unless otherwise noted. When complete, the mixture was concentrated in vacuo. The crude product was isolated and purified using methods known in the art or as described in the Examples.

General Procedure G—Aniline Alkylation with Alkyl Halides:

A mixture of aniline, alkyl-halide, cesium carbonate, Cs$_2$CO$_3$ and tetrabutylammonium iodide in DMF was heated at 50° C. The crude product was isolated and purified using methods known in the art or as described in the Examples.

General Procedure H—Cbz Deprotection:

A mixture of benzyl-carbamate, palladium on carbon (Pd/C) and ammonium formate in iPrOH was heated at 60° C. When complete, the mixture was filtered through celite using MeOH/CH$_2$Cl$_2$ and concentrated in vacuo.

Analytical Methods.

LCMS (Liquid Chromatography Mass Spectrometry) methods to separate and characterize the exemplary compounds were performed on the following:

SHIMADZU LC-MS 2010EV coupled with SHIMADZU LC20AB using ESI as ionization source. The LC separation was using Column: MERCK, RP-18e 25-2 mm; Detector: PDA, ELSD; Wavelength: UV 220 nm; Column temperature: 50° C.; mobile Phase: 1.5 mL/4 LTFA in water (solvent A) and 0.75 mL/4 L TFA in acetonitrile (solvent B), using the elution gradient 5%-95% (solvent B) over 0.7 minutes and holding at 95% for 0.4 minutes at a flow rate of 1.5 mL/min;

SHIMADZU LC-MS 2010EV coupled with SHIMADZU LC20AB using ESI as ionization source. The LC separation was using Column: MERCK, RP-18e 25-2 mm; Detector: PDA, ELSD; Wavelength: UV 220 nm; Column temperature: 50° C.; mobile Phase: 1.5 mL/4 L TFA in water (solvent A) and 0.75 mL/4 L TFA in acetonitrile (solvent B), using the elution gradient 5%-95% (solvent B) over 0.7 minutes and holding at 95% for 0.4 minutes at a flow rate of 1.5 mL/min;

Agilent 1200 Series coupled with 6110 Quadrupole mass spectrometer, using ESI as ionization source. The LC separation was using Column: Xtimate C18 2.1×30 mm, 3 µm; Wavelength: UV 220 nm; Column temperature: 50° C.; Detector: PDA&ELSD, mobile Phase: 1.5 mL/4 L TFA in water (solvent A) and 0.75 mL/4 LTFA in acetonitrile (solvent B), using the elution gradient 10%-80% (solvent B) over 0.9 minutes and holding at 80% for 0.6 minutes at a flow rate of 1.2 mL/min.

SHIMADZU 2020 HPLC coupled with SHIMADZU MSD mass spectrometer using ESI as ionization source. The LC separation was using an Shim-Pack XR-ODS-C18, 50×3.0 mm column with a 1 ml/minute flow rate. Solvent A is water with 0.05% TFA and solvent B is acetonitrile with 0.05% TFA. The gradient consisted with 5-100% solvent B over 2.2 minutes and hold 100% B for 1 minute. LC column temperature is 40° C. UV absorbance was collected from 190 nm to 400 nm and mass spec full scan was applied to all experiments.

SHIMADZU 2020 HPLC coupled with SHIMADZU MSD mass spectrometer using ESI as ionization source. The LC separation was using an Gemini-NX 3µ C18 110 A, 50×3.0 mm column with a 1.2 ml/minute flow rate. Solvent A is water with 0.4% NH4HCO3 and solvent B is acetonitrile. The gradient consisted with 10-50% solvent B over 4 minutes and hold 50% B for 1.2 minutes. LC column temperature is 40° C. UV absorbance was collected from 190 nm to 400 nm and mass spec full scan was applied to all experiments.

SHIMADZU UFLC-MS 2010EV coupled with SHIMADZU MSD mass spectrometer using ESI as ionization source. The LC separation was using a Shim-pack XR-ODS-C18, 50×3.0 mm column with a 1 ml/minute flow rate. Solvent A is water with 0.05% TFA and solvent B is acetonitrile with 0.05% TFA. The gradient consisted with 5-100% solvent B over 2.2 minutes and hold 100% B for 1 minute. LC column temperature is 40° C. UV absorbance was collected from 190 nm to 400 nm and mass spec full scan was applied to all experiments.

Waters Alliance 2695 HPLC with column heater coupled with Waters ZQ 2000 mass spectrometer using ESI as ionization source (ES+, 100-1200 amu). The LC separation was using an XBridge C18, 3.5 µm, 4.6×30 mm column at 25° C. with a 3.0 mL/minute flow rate. Solvent A is Milli-Q H2O+10 mM Ammonium Formate pH: 3.8, and solvent B is acetonitrile. The gradient consisted of isocratic 5% solvent B for 0.2 min, 5% to 100% B in 1.8 minutes; hold 100% B for 1 minute. LC column temperature is 25° C. UV absorbance was collected from 195-320 nm using a Waters PDA 996 UV detector and mass spec full scan was applied to all experiments.

Waters Alliance 2695 HPLC with column heater coupled with Waters ZQ 2000 mass spectrometer using ESI as ionization source (ES+, 100-1200 amu). The LC separation was using an XBridge C18, 3.5 µm, 4.6×30 mm column at 25° C. with a 3.0 mL/minute flow rate. Solvent A is Milli-Q H2O+10 mM Ammonium Bicarbonate pH: 10, and solvent B is acetonitrile. The gradient consisted of isocratic 5% solvent B for 0.2 min, 5% to 100% B in 1.8 minutes; hold 100% B for 1 minute. LC column temperature is 25° C. UV absorbance was collected from 195-320 nm using a Waters PDA 996 UV detector and mass spec full scan was applied to all experiments.

EXAMPLES

Synthetic Examples

Example 101 (S)-3-(2-Cyanopropan-2-yl)-N-(6-methyl-5-((3-(2-(piperidin-3-ylamino)pyrimidin-4-yl)pyridin-2-yl)oxy)naphthalen-1-yl)benzamide 101

Step 1: tert-Butyl 5-hydroxynaphthalen-1-ylcarbamate

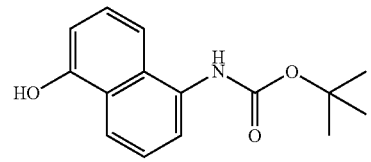 [SMILES: CC(C)(C)OC(=O)Nc1cccc2c(O)cccc12]

To a 5 L 4-necked round-bottom flask was placed 5-aminonaphthalen-1-ol (400 g, 2.51 mol, 1.00 equiv.), di-tert-butyl dicarbonate, Boc₂O (660 g, 3.01 mol, 1.20 equiv.) and 1,4-dioxane (2.5 L). The resulting solution was stirred at rt for 30 min and then heated under reflux for 3 h. The reaction mixture was then cooled to rt and concentrated in vacuo. The product was re-crystallized from ethyl acetate:petroleum ether (1:5) to yield 500 g (77%) of the title compound as a gray solid. LCMS (ESI) [M+H−56]⁺=204.

Step 2: tert-Butyl 6-((diethylamino)methyl)-5-hydroxynaphthalen-1-ylcarbamate

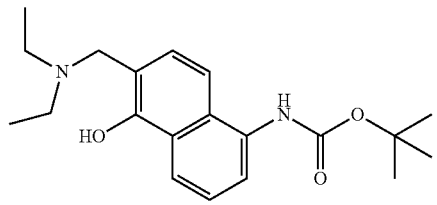 [SMILES: CCN(CC)Cc1ccc2c(NC(=O)OC(C)(C)C)cccc2c1O]

To a 2000-mL 4-necked round-bottom flask was placed tert-butyl N-(5-hydroxynaphthalen-1-yl)carbamate (100 g, 386 mmol), methanol (800 mL), diethylamine (31.4 g, 424 mmol, 1.10 equiv.) and formaldehyde (35 g, 424 mmol, 37% solution in water). The resulting solution was stirred at rt for 1 h and concentrated in vacuo. The residue was applied onto a silica gel column and eluted with ethyl acetate/petroleum ether (1:5-1:3) to yield 100 g (75%) of the title compound as a reddish oil. LCMS (ESI) [M+H]⁺=345.

Step 3; tert-Butyl 5-hydroxy-6-methylnaphthalen-1-ylcarbamate

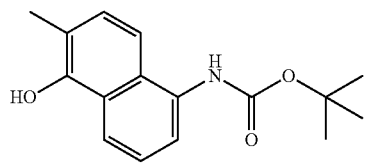 [SMILES: Cc1ccc2c(NC(=O)OC(C)(C)C)cccc2c1O]

To a 3 L 4-necked round-bottom flask was placed tert-butyl N-[6-[(diethylamino)methyl]-5-hydroxynaphthalen-1-yl]carbamate (200 g, 581 mmol), ethanol (1.5 L) and palladium on carbon (30 g). Hydrogen, H$_2$ (gas) was introduced via a hydrogen balloon) to the above system. The resulting suspension was stirred at rt (room temperature) overnight and filtered. The filtrate was concentrated in vacuo to yield 200 g of the crude title compound as a brown oil. LCMS (ESI) [M+H−56]$^+$=218.

Step 4: 5-Amino-2-methylnaphthalen-1-ol hydrochloride

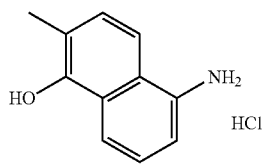

To a 5 L 4-necked round-bottom flask was placed a solution of tert-butyl N-(5-hydroxy-6-methylnaphthalen-1-yl)carbamate (100 g, 366 mmol) in dichloromethane, DCM (3 L) followed by bubbling hydrogen chloride, HCl (gas). The resulting solution was stirred at rt for 2 h and concentrated in vacuo. The crude product was purified by recrystallization from DCM. The solids were collected by filtration and dried in vacuo to yield 73 g (95%) of the title compound as a white solid. LCMS (ESI) [M+H]$^+$=174.

Step 5: 4-(2-Fluoropyridin-3-yl)-2-(methylthio)pyrimidine

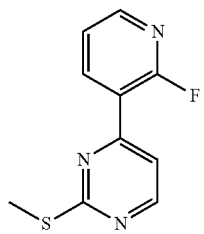

To a 3 L 4-necked round-bottom flask purged and maintained with an inert atmosphere of nitrogen was placed 4-chloro-2-(methylsulfanyl)pyrimidine (80 g, 498 mmol), (2-fluoropyridin-3-yl)boronic acid (98.7 g, 697 mmol), sodium carbonate (117 g, 1.10 mol), tetrakis(triphenylphosphine)palladium(0) (29 g, 24.9 mmol), water (160 mL) and 1,4-dioxane (1.6 L). The resulting solution was stirred at 100° C. in an oil bath overnight, cooled to rt, and filtered. The filtrate was diluted with brine and was then extracted with ethyl acetate. The combined organic layers were dried over anhydrous sodium sulfate, and concentrated in vacuo. The residue was purified via flash silica chromatography (solvent gradient: 10-50% ethyl acetate in petroleum ether) to yield 80 g (73%) of the title compound as a yellow solid. LCMS (ESI) [M+H]$^+$=222.

Step 6: 6-Methyl-5-(3-(2-(methylthio)pyrimidin-4-yl)pyridin-2-yloxy)naphthalen-1-amine

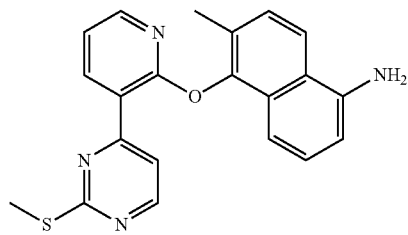 [SMILES: CSc1nccc(-c2cccnc2Oc2c(C)ccc3c(N)cccc23)n1]

To a 2 L 4-necked round-bottom flask purged and maintained with an inert atmosphere of nitrogen was placed 5-amino-2-methylnaphthalen-1-ol hydrochloride (100 g, 477 mmol), N-methyl-2-pyrrolidone, NMP (1 L), 4-(2-fluoropyridin-3-yl)-2-(methylsulfanyl)pyrimidine (105 g, 477 mmol), and caesium carbonate (328 g, 1.00 mol). The resulting solution was stirred at 120° C. in an oil bath overnight, cooled to room temperature, and diluted with 1 L of brine. The resulting solution was extracted with ethyl acetate. The combined organic layers were dried over anhydrous sodium sulfate, and concentrated in vacuo. The residue was purified via flash silica chromatography (solvent gradient: 20-50% ethyl acetate in petroleum ether) to yield 80 g (45%) of the title compound as a brown solid. LCMS (ESI) [M+H]$^+$=375.

Alternatively, the title compound can be prepared by the following scheme where 4-chloro-2-(methylthio)pyrimidine and (2-chloropyridin-3-yl)boronic acid are coupled as in Step 5 to form 4-(2-chloropyridin-3-yl)-2-(methylthio)pyrimidine which is reacted with 5-amino-2-methylnaphthalen-1-ol hydrochloride:

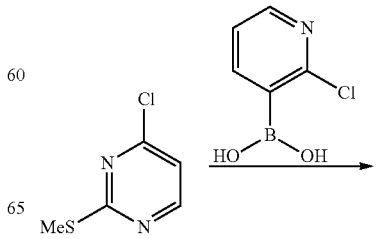

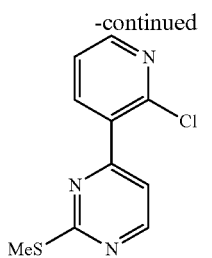

Step 7: 6-Methyl-5-((3-(2-(methylsulfinyl)pyrimidin-4-yl)pyridin-2-yl)oxy)naphthalen-1-amine

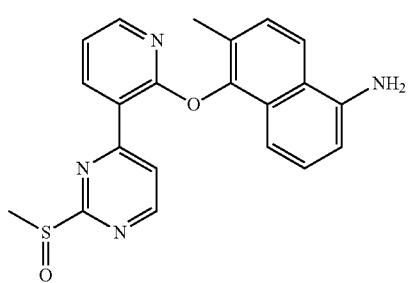 [SMILES: Cc1ccc2c(N)cccc2c1Oc1ncccc1-c1ccnc(S(C)=O)n1]

To a 3 L 4-necked round-bottom flask purged and maintained with an inert atmosphere of nitrogen was placed 6-methyl-5-([3-[2-(methylsulfanyl)pyrimidin-4-yl]pyridin-2-yl]oxy)naphthalen-1-amine (100 g, 267 mmol), DCM (2 L) and 3-chlorobenzene-1-carboperoxoic acid (56 g, 321 mmol). The resulting solution was stirred at rt for 4 h and quenched with the addition of 1 L of a saturated solution of sodium hydrogenocarbonate. The organic phase was separated, dried over anhydrous sodium sulfate, and concentrated in vacuo. The residue was purified via flash silica chromatography (solvent gradient: 20% ethyl acetate in petroleum ether and then 2% methanol in DCM) to yield 65 g (62%) of the title compound as a yellow solid.

Step 8: tert-Butyl (S)-3-((4-(2-((5-amino-2-methylnaphthalen-1-yl)oxy)pyridin-3-yl)pyrimidin-2-yl)amino)piperidine-1-carboxylate

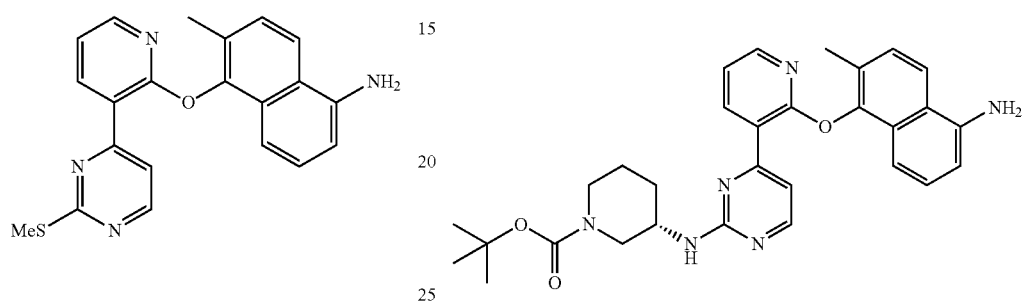

To a 2 L 3-necked round-bottom flask purged and maintained with an inert atmosphere of nitrogen was placed 5-[[3-(2-methanesulfinylpyrimidin-4-yl)pyridin-2-yl]oxy]-6-methylnaphthalen-1-amine (75 g, 192 mmol), tert-butyl (3S)-3-aminopiperidine-1-carboxylate (152 g, 768 mmol), 1,4-dioxane (1 L) and DIPEA (98 g, 768 mmol). The resulting solution was stirred at 110° C. in an oil bath overnight, cooled to rt and concentrated in vacuo. The residue was purified via flash silica chromatography (solvent gradient: 20% ethyl acetate in petroleum ether and then 2% methanol in DCM) to yield 50.5 g (50%) of the title compound as a yellow solid. LCMS: (ES, m/z): $[M+H]^+=527$.

Step 9: (S)-tert-Butyl 3-(4-(2-(4-(3-(2-cyanopropan-2-yl)benzamido)-2-methylnaphthalen-1-yloxy)pyridin-3-yl)pyrimidin-2-ylamino)piperidine-1-carboxylate

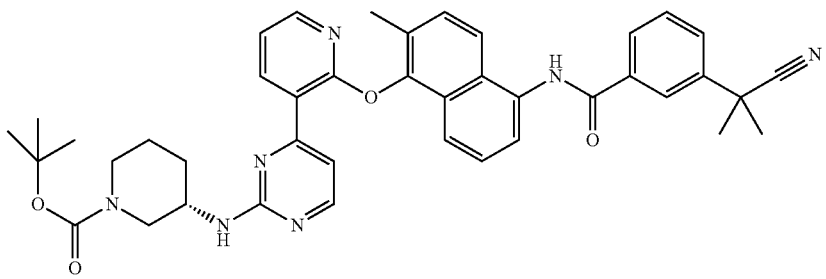 [SMILES: Cc1ccc2c(NC(=O)c3cccc(C(C)(C)C#N)c3)cccc2c1Oc1ncccc1-c1ccnc(N[C@H]2CCCN(C(=O)OC(C)(C)C)C2)n1]

A solution of tert-butyl (S)-3-((4-(2-((5-amino-2-methylnaphthalen-1-yl)oxy)pyridin-3-yl)pyrimidin-2-yl)amino)piperidine-1-carboxylate (275 mg, 0.52 mmol), 1-[Bis(dimethylamino)methylene]-1H-1,2,3-triazolo[4,5-b]pyridinium 3-oxide hexafluorophosphate, HATU, CAS Reg. No. 148893-10-1, (218 mg, 0.57 mmol), DIPEA (134 mg, 1.04 mmol), and 3-(2-cyanopropan-2-yl)benzoic acid (108 mg, 0.57 mmol) in dry N,N-dimethylformamide (10 mL) was stirred at room temperature for 12 h. The reaction mixture was poured into water and then extracted with ethyl acetate. The organic extracts were dried over magnesium sulfate, filtered, and concentrated under reduced pressure. The crude was purified by silica gel column chromatography (petroleum/EtOAc=2:1 to 1:1) to yield 200 mg (55% yield) of the title compound as a white solid. LCMS (ESI) $[M+H]^+=698.8$.

Step 10: (S)-3-(2-Cyanopropan-2-yl)-N-(6-methyl-5-((3-(2-(piperidin-3-ylamino)pyrimidin-4-yl)pyridin-2-yl)oxy)naphthalen-1-yl)benzamide

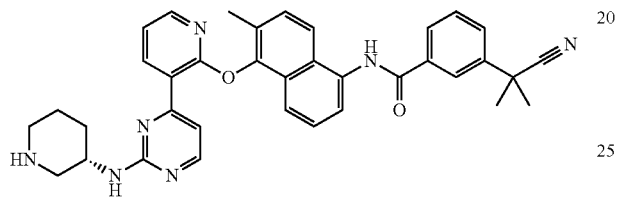

The General Procedure B was followed, using (S)-tert-butyl 3-(4-(2-(4-(3-(2-cyanopropan-2-yl)benzamido)-2-methylnaphthalen-1-yloxy)pyridin-3-yl)pyrimidin-2-ylamino)piperidine-1-carboxylate (200 mg, 0.31 mmol), ethylacetate (3 mL) and hydrochloric acid (4 M in dioxane, 3 mL, 12 mmol). The residue was purified by Prep-HPLC to yield 100 mg (65%) of 101 as a white solid. LCMS (ESI): $[M+H]^+=598.3$; NMR (400 MHz, DMSO-$d_6$) δ 10.57 (s, 1H), 8.51 (d, J=7.7 Hz, 1H), 8.42 (d, J=5.1 Hz, 1H), 8.20 (t, J=1.9 Hz, 1H), 8.13-8.08 (m, 1H), 8.06 (dd, J=5.0, 1.9 Hz, 1H), 7.85 (d, J=8.7 Hz, 1H), 7.83-7.78 (m, 1H), 7.65 (t, J=7.8 Hz, 2H), 7.55 (dd, J=7.4, 1.3 Hz, 1H), 7.50 (dd, J=8.4, 5.7 Hz, 2H), 7.46 (d, J=5.2 Hz, 1H), 7.27 (dd, J=7.6, 4.8 Hz, 1H), 7.11 (d, J=8.0 Hz, 1H), 4.09 (q, J=5.2 Hz, 1H), 3.89 (s, 1H), 3.10 (d, J=11.7 Hz, 1H), 2.78 (m, 1H), 2.47-2.37 (m, 2H), 2.23 (s, 3H), 1.93 (d, J=11.6 Hz, 1H), 1.78 (s, 6H), 1.64 (m, 1H), 1.56-1.36 (m, 2H).

Example 102 (S)-1-(2-Chlorophenyl)-N-(2-fluoro-6-methyl-5-((3-(2-(piperidin-3-ylamino)pyrimidin-4-yl)pyridin-2-yl)oxy)naphthalen-yl)oxy)naphthalen-1-yl)methanesulfonamide 102

Step 1: (S)-tert-Butyl 3-((4-(2-((5-((2-chlorophenyl)methylsulfonamido)-6-fluoro-2-methylnaphthalen-1-yl)oxy)pyridin-3-yl)pyrimidin-2-yl)amino)piperidine-1-carboxylate Prepared using (S)-tert-butyl 3-((4-(2-((5-amino-6-fluoro-2-methylnaphthalen-1-yl)oxy)pyridin-3-yl)pyrimidin-2-yl)amino)piperidine-1-carboxylate from Example 275 (65 mg, 0.12 mmol), pyridine (0.14 mL, 1.79 mmol), DMAP (1.5 mg, 0.01 mmol), DCM (0.9 mL), and (2-chlorophenyl)methanesulfonyl chloride (54 mg, 0.24 mmol). After stirring 1 h at rt, the reaction was diluted with DCM and washed with 1N KHSO$_4$(aq) (10 mL), dried (Na$_2$SO$_4$), filtered and evaporated. The crude product was purified by flash chromatography through silica gel (0-50% EtOAc/DCM) to provide 58 mg (88% yield) of the title compound as a solid. LCMS (ESI) [M+H]$^+$=733.5, rt=2.04 min.

Step 2: (S)-1-(2-Chlorophenyl)-N-(2-fluoro-6-methyl-5-((3-(2-(piperidin-3-ylamino)pyrimidin-4-yl)pyridin-2-yl)oxy)naphthalen-1-yl)methanesulfonamide

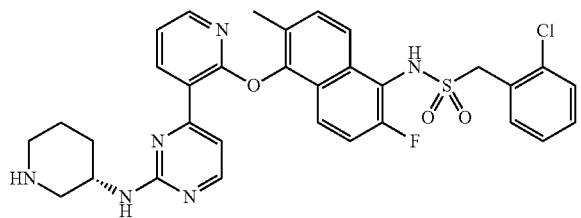 [SMILES: Cc1ccc2c(NS(=O)(=O)Cc3ccccc3Cl)c(F)ccc2c1Oc1ncccc1-c1ccnc(N[C@H]2CCCNC2)n1]

Prepared using (S)-tert-butyl 3-((4-(2-((5-((2-chlorophenyl)methylsulfonamido)-6-fluoro-2-methylnaphthalen-1-yl)oxy)pyridin-3-yl)pyrimidin-2-yl)amino)piperidine-1-carboxylate (58 mg, 0.08 mmol), 1,4-dioxane (0.5 mL) and hydrochloric acid (4 M in dioxane, 0.73 mL, 2.92 mmol). After 60 min, the suspension was diluted with Et$_2$O (15 mL) and the precipitate was filtered and washed with Et$_2$O. The precipitate was dissolved in MeCN and water and lyophilized to provide 46 mg (88% yield) of 102 as a fluffy light yellow solid. LCMS (ESI) [M+H]$^+$=633.5, rt=1.53 min; $^1$H NMR (400 MHz, d6-dmso) δ 10.04 (s, 1H), 8.84 (bs, 2H), 8.66 (s, 1H), 8.48 (d, J=5.2 Hz, 1H), 8.09 (dd, J=4.8, 2.0 Hz, 1H), 8.02 (d, J=8.8 Hz, 1H), 7.74 (dd, J=9.2, 5.1 Hz, 1H), 7.66-7.46 (m, 6H), 7.46-7.36 (m, 2H), 7.29 (dd, J=7.6, 4.8 Hz, 1H), 4.77 (s, 2H), 4.27 (s, 1H), 3.50-3.37 (m, 1H), 3.21 (d, J=12.0 Hz, 1H), 2.96-2.74 (m, 2H), 2.19 (s, 3H), 2.07-1.97 (m, 1H), 1.97-1.87 (m, 1H), 1.82-1.55 (m, 2H).

Example 103 (S)—N-(6-Methyl-5-((3-(2-(piperidin-3-ylamino)pyrimidin-4-yl)pyridin-2-yl)oxy)naphthalen-1-yl)ethanesulfonamide 103

Step 1: tert-Butyl (S)-3-(4-(2-(5-(ethylsulfonamido)-2-methylnaphthalen-1-yloxy)pyridin-3-yl)pyrimidin-2-ylamino)piperidine-1-carboxylate

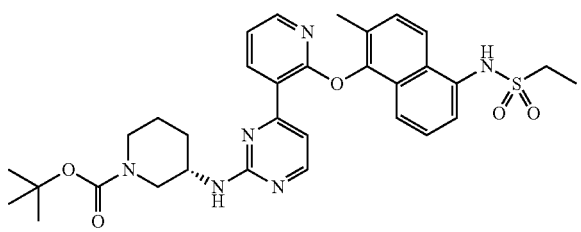 [SMILES: CCS(=O)(=O)Nc1cccc2c(Oc3ncccc3-c3ccnc(N[C@H]4CCCN(C(=O)OC(C)(C)C)C4)n3)c(C)ccc12]

The General Procedure A was followed, using tert-butyl (S)-3-((4-(2-((5-amino-2-methylnaphthalen-1-yl)oxy)pyridin-3-yl)pyrimidin-2-yl)amino)piperidine-1-carboxylate from Example 101 (100 mg, 0.19 mmol), pyridine (2 mL) and ethanesulfonyl chloride (29 mg, 0.23 mmol). The residue was purified by Prep-TLC (normal phase, petroleum ether/ethyl acetate=2/1) to yield 110 mg (93%) of the title compound as a white solid. LCMS (ESI) [M+H]$^+$=619.

Step 2: (S)—N-(6-Methyl-5-(3-(2-(piperidin-3-ylamino)pyrimidin-4-yl)pyridin-2-yloxy)naphthalen-1-yl)ethanesulfonamide hydrochloride

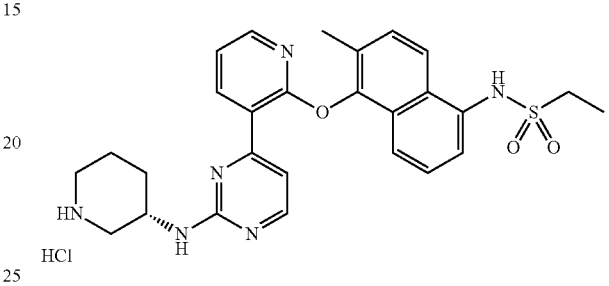

The General Procedure B was followed, using tert-butyl (S)-3-(4-(2-(5-(ethylsulfonamido)-2-methylnaphthalen-1-yloxy)pyridin-3-yl)pyrimidin-2-ylamino)piperidine-1-carboxylate (110 mg, 0.18 mmol), DCM (5 mL) and hydrochloric acid (4 M in dioxane, 2 mL, 8 mmol). The residue was purified by Prep-HPLC (mobile phase: A: water (0.05% TFA) B: ACN) to yield 40 mg (40%) of hydrochloride 103 as a white solid. LCMS (ESI): [M+H]$^+$=519.7; $^1$H NMR (400 MHz, CD$_3$OD) δ 8.67 (m, 1H), 8.46 (d, J=5.6 Hz, 1H), 8.16 (d, J=8.8 Hz, 1H), 8.01 (m, 1H), 7.71 (d, J=5.6 Hz, 1H), 7.64 (d, J=8.8 Hz, 1H), 7.57 (s, 1H), 7.54 (s, 1H), 7.39 (t, J=8 Hz, 15.6 Hz, 1H), 7.26-7.22 (m, 1H), 4.37-4.36 (m, 1H), 3.66-3.61 (m, 1H), 3.37-3.32 (m, 1H), 3.21-3.15 (m, 2H), 3.11-3.04 (m, 2H), 2.29 (s, 3H), 2.23-2.11 (m, 2H), 1.93-1.83 (m, 2H), 1.41-1.31 (m, 3H).

Example 104 (S)—N-(6-Methyl-5-(3-(2-(piperidin-3-ylamino)pyrimidin-4-yl)pyridin-2-yloxy)naphthalen-1-yl)propane-1-sulfonamide hydrochloride 104

Step 1: tert-Butyl (S)-3-(4-(2-(2-methyl-5-(propylsulfonamido)naphthalen-1-yloxy)pyridin-3-yl)pyrimidin-2-ylamino)piperidine-1-carboxylate

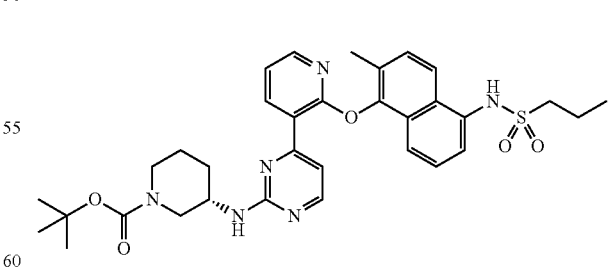

The General Procedure A was followed, using tert-butyl (3S)-3-[[4-[2-[(5-amino-2-methyl-1-naphthyl)oxy]-3-pyridyl]pyrimidin-2-yl]amino]piperidine-1-carboxylate (100 mg, 0.19 mmol), pyridine (2 mL) and 1-propanesulfonyl chloride (200 mg, 1.4 mmol). The crude was then purified by Prep-TLC (petroleum ether/ethyl acetate=1/1) to Step 2: (S)—N-(6-Methyl-5-(3-(2-(piperidin-3-ylamino)pyrimidin-4-yl)pyridin-2-yloxy)naphthalen-1-yl)propane-1-sulfonamide hydrochloride

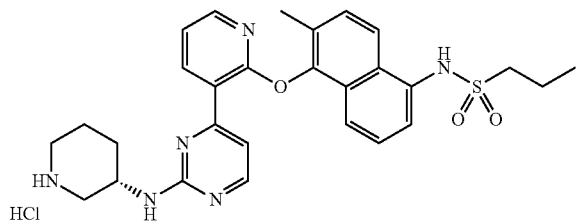 [SMILES: CCCS(=O)(=O)Nc1cccc2c(Oc3ncccc3-c3ccnc(N[C@H]4CCCNC4)n3)c(C)ccc12 ; Cl]

The General Procedure B was followed, using tert-butyl (3S)-3-[[4-[2-[[2-methyl-5-(propylsulfonylamino)-1-naphthyl]oxy]-3-pyridyl]pyrimidin-2-yl]amino]piperidine-1-carboxylate (100 mg, 0.16 mmol), DCM (5 mL) and hydrochloric acid (4 M in dioxane, 2 mL, 8 mmol). The residue was purified by Prep-HPLC to yield 52 mg (62%) of 104 as a white solid. LCMS (ESI): [M+H]⁺=533; ¹H NMR (400 MHz, DMSO-d₆) δ 8.54 (s, 1H), 8.43 (d, J=5.1 Hz, 1H), 8.33 (s, 1H), 8.13 (d, J=8.7 Hz, 1H), 8.04 (dd, J=4.8, 1.9 Hz, 1H), 7.56-7.51 (m, 2H), 7.49 (d, J=5.1 Hz, 1H), 7.46-7.37 (m, 2H), 7.32-7.24 (m, 2H), 4.06 (s, 1H), 3.24 (d, J=10.5 Hz, 1H), 3.16-3.08 (m, 2H), 2.97 (d, J=12.3 Hz, 1H), 2.71-2.54 (m, 2H), 2.21 (s, 3H), 1.96 (s, 1H), 1.83-1.69 (m, 3H), 1.56 (s, 2H), 0.96 (t, J=7.4 Hz).

Example 105 (S)—N-(6-Methyl-5-((3-(2-(piperidin-3-ylamino)pyrimidin-4-yl)pyridin-2-yl)oxy)naphthalen-1-yl)cyclopropanesulfonamide hydrochloride 105

Step 1: tert-Butyl (S)-3-(4-(2-(2-methyl-5-(cyclopropanesulfonamido)naphthalen-1-yloxy)pyridin-3-yl)pyrimidin-2-ylamino)piperidine-1-carboxylate

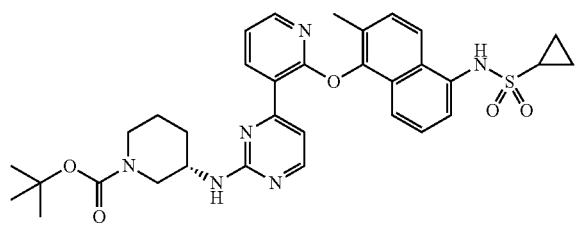 [SMILES: Cc1ccc2c(NS(=O)(=O)C3CC3)cccc2c1Oc1ncccc1-c1ccnc(N[C@H]2CCCN(C(=O)OC(C)(C)C)C2)n1]

The General Procedure A was followed, using tert-butyl (S)-3-((4-(2-((5-amino-2-methylnaphthalen-1-yl)oxy)pyridin-3-yl)pyrimidin-2-yl)amino)piperidine-1-carboxylate from Example 101 (100 mg, 0.19 mmol), pyridine (2 mL) and cyclopropanesulfonyl chloride (200 mg, 1.4 mmol). The crude was then purified by Prep-TLC (petroleum ether/ethyl acetate=1/1) to yield 37 mg (29% yield) of the title compound as a white solid. LCMS (ESI) [M+H]⁺=631.

Step 2: (S)—N-(6-Methyl-5-((3-(2-(piperidin-3-ylamino)pyrimidin-4-yl)pyridin-2-yl)oxy)naphthalen-1-yl)cyclopropanesulfonamide hydrochloride

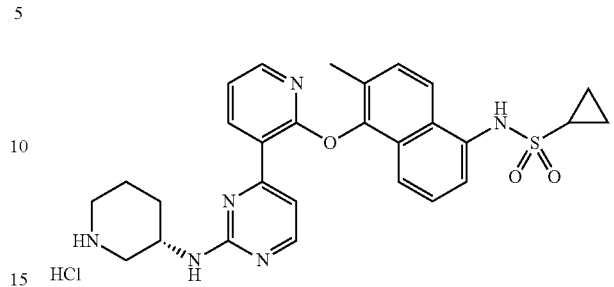

The General Procedure B was followed, using tert-butyl (S)-3-(4-(2-(2-methyl-5-(cyclopropanesulfonamido)naphthalen-1-yloxy)pyridin-3-yl)pyrimidin-2-ylamino)piperidine-1-carboxylate (37 mg, 0.16 mmol), DCM (5 mL) and hydrochloric acid (4 M in dioxane, 1 mL, 4 mmol). The residue was purified by Prep-HPLC to yield 16 mg (52%) of hydrochloride 105 as a white solid. LCMS (ESI): [M+H]⁺=531; 1H NMR (400 MHz, CD3OD) δ 8.67 (d, J=6.8 Hz, 1H), 8.58 (s, 1H), 8.44 (d, J=5.2 Hz, 1H), 8.21 (d, J=8.7 Hz, 1H), 8.07-7.95 (m, 1H), 7.76-7.65 (m, 2H), 7.56 (dd, J=12.2, 8.1 Hz, 2H), 7.39 (t, J=7.9 Hz, 15.8 Hz, 1H), 7.23 (dd, J=7.5, 4.9 Hz, 1H), 4.33 (s, 1H), 3.58 (d, J=9.8 Hz, 1H), 3.27 (s, 1H), 2.98 (t, J=10.8 Hz, 21.6 Hz, 2H), 2.73-2.56 (m, 1H), 2.28 (s, 3H), 2.19 (d, J=11.1 Hz, 1H), 2.07 (d, J=14.1 Hz, 1H), 1.96-1.68 (m, 2H), 1.03 (d, J=3.2 Hz, 2H), 0.95 (d, J=7.5 Hz, 2H).

Example 106 (S)—N-(6-Methyl-5-((3-(2-(piperidin-3-ylamino)pyrimidin-4-yl)pyridin-2-yl)oxy)naphthalen-1-yl) methylethylsulfonamide hydrochloride 106

Step 1: tert-Butyl (S)-3-(4-(2-(2-methyl-5-(methylethylpropanesulfonamido)naphthalen-1-yloxy)pyridin-3-yl)pyrimidin-2-ylamino)piperidine-1-carboxylate

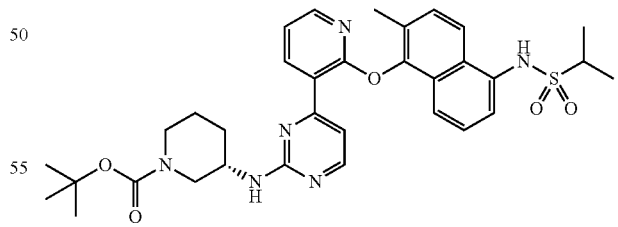

The General Procedure A was followed, using tert-butyl (S)-3-((4-(2-((5-amino-2-methylnaphthalen-1-yl)oxy)pyridin-3-yl)pyrimidin-2-yl)amino)piperidine-1-carboxylate from Example 101 (100 mg, 0.19 mmol), pyridine (2 mL) and isopropylsulfonyl chloride (32 mg, 0.23 mmol). The crude was then purified by Prep-TLC (petroleum ether/ethyl acetate=2/1) to yield (50 mg, 0.08 mmol, 40% yield) as a white solid.

Step 2: (S)—N-(6-Methyl-5-((3-(2-(piperidin-3-ylamino)pyrimidin-4-yl)pyridin-2-yl)oxy)naphthalen-1-yl) methylethylsulfonamide hydrochloride

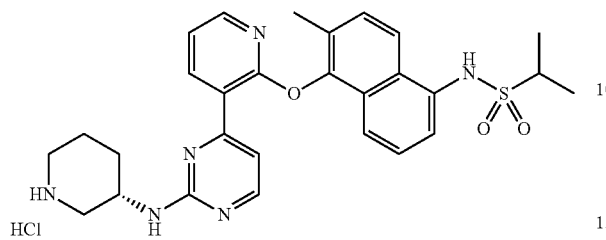

The General Procedure B was followed, using tert-butyl (3S)-3-[[4-[2-[[2-methyl-5-(propylsulfonylamino)-1-naphthyl]oxy]-3-pyridyl]pyrimidin-2-yl]amino]piperidine-1-carboxylate (50 mg, 0.08 mmol), DCM (5 mL) and hydrochloric acid (4 M in dioxane, 1 mL, 4 mmol). The residue was purified by Prep-HPLC (mobile phase: A: water (0.05% TFA) B: ACN) to yield 30 mg (60%) of hydrochloride 106 as a white solid. LCMS (ESI): [M+H]⁺=533.7; ¹H NMR (400 MHz, CD₃OD) δ 8.66 (d, J=6.8 Hz, 1H), 8.46 (d, J=5.2 Hz, 1H), 8.17 (d, J=8.8 Hz, 1H), 8.01 (m, 1H), 7.71 (d, J=5.2 Hz, 1H), 7.63-7.54 (m, 3H), 7.38 (t, J=8 Hz, 16.4 Hz, 1H), 7.26-7.22 (m, 1H), 4.37 (s, 1H), 3.66-3.62 (m, 1H), 3.41-3.28 (m, 2H), 3.11-3.04 (m, 2H), 2.28 (s, 3H), 2.23-2.11 (m, 2H), 1.92-1.80 (m, 2H), 1.42 (s, 3H), 1.40 (s, 3H).

Example 107 (S)—N-(6-Methyl-5-((3-(2-(piperidin-3-ylamino)pyrimidin-4-yl)pyridin-2-yl)oxy)naphthalen-1-yl)cyclobutanesulfonamide hydrochloride 107

Step 1: tert-Butyl (S)-3-((4-(2-((5-(Cyclobutanesulfonamido)-2-methylnaphthalen-1-yl)oxy)pyridin-3-yl)pyrimidin-2-yl)amino)piperidine-1-carboxylate

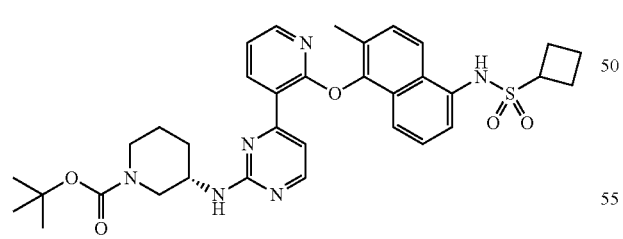

The General Procedure A was followed, using tert-butyl (S)-3-((4-(2-((5-amino-2-methylnaphthalen-1-yl)oxy)pyridin-3-yl)pyrimidin-2-yl)amino)piperidine-1-carboxylate from Example 101 (100 mg, 0.19 mmol), pyridine (2 mL) and cyclobutanesulfonyl chloride (35 mg, 0.23 mmol). The crude was then purified by Prep-TLC (petroleum ether/ethyl acetate=1/1) to yield 120 mg (95% yield) of the title compound as a brown solid. LCMS (ESI) [M+H]⁺=645.

Step 2: (S)—N-(6-Methyl-5-((3-(2-(piperidin-3-ylamino)pyrimidin-4-yl)pyridin-2-yl)oxy)naphthalen-1-yl)cyclobutanesulfonamide hydrochloride

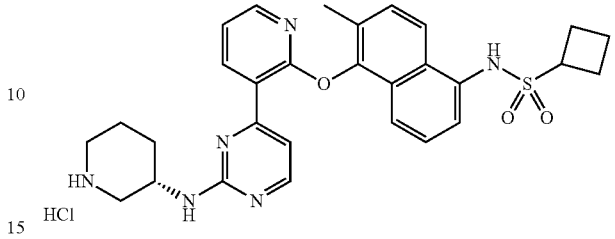

The General Procedure B was followed, using tert-butyl (3S)-3-[[4-[2-[[2-methyl-5-(propylsulfonylamino)-1-naphthyl]oxy]-3-pyridyl]pyrimidin-2-yl]amino]piperidine-1-carboxylate (120 mg, 0.19 mmol), DCM (5 mL) and hydrochloric acid (4 M in dioxane, 2 mL, 8 mmol). The residue was purified by Prep-HPLC to yield 90 mg (88% yield) of 107 as a white solid. LCMS (ESI): [M+H]⁺=560; ¹H NMR (400 MHz, CD₃OD) δ 8.68 (d, J=7.2 Hz, 1H), 8.45 (d, J=5.6 Hz, 1H), 8.10 (d, J=8.4 Hz, 1H), 8.01 (m, 1H), 7.74 (s, 1H), 7.64 (d, J=8.4 Hz, 1H), 7.53 (t, J=8.8 Hz, 16.4 Hz, 2H), 7.38 (t, J=8.4 Hz, 16.8 Hz, 1H), 7.26-7.23 (m, 1H), 4.39 (s, 1H), 3.97-3.88 (m, 1H), 3.66-3.62 (m, 1H), 3.37-3.32 (m, 1H), 3.11-3.03 (m, 2H), 2.56-2.46 (m, 2H), 2.28-2.21 (m, 7H), 2.12-1.88 (m, 4H).

Example 108 (S)—N-(6-Methyl-5-((3-(2-(piperidin-3-ylamino)pyrimidin-4-yl)pyridin-2-yl)oxy)naphthalen-1-yl)pyrrolidine-1-sulfonamide hydrochloride 108

Step 1: tert-Butyl (S)-3-((4-(2-((2-methyl-5-(pyrrolidine-1-sulfonamido)naphthalen-1-yl)oxy)pyridin-3-yl)pyrimidin-2-yl)amino)piperidine-1-carboxylate

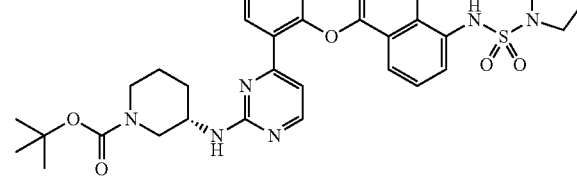

The General Procedure A was followed, using tert-butyl (S)-3-((4-(2-((5-amino-2-methylnaphthalen-1-yl)oxy)pyridin-3-yl)pyrimidin-2-yl)amino)piperidine-1-carboxylate from Example 101 (100 mg, 0.19 mmol), pyridine (2 mL) and pyrrolidine-1-sulfonyl chloride (200 mg, 1.18 mmol). The crude was then purified by Prep-TLC (petroleum ether/ethyl acetate=1/1) to yield 100 mg (73% yield) of the title compound as a white solid. LCMS (ESI) [M+H]⁺=660.

Step 2: (S)—N-(6-Methyl-5-((3-(2-(piperidin-3-ylamino)pyrimidin-4-yl)pyridin-2-yl)oxy)naphthalen-1-yl)pyrrolidine-1-sulfonamide hydrochloride

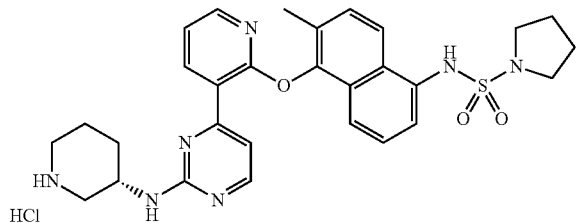 [SMILES: Cc1ccc2c(NS(=O)(=O)N3CCCC3)cccc2c1Oc1ncccc1-c1ccnc(N[C@H]2CCCNC2)n1 ; Cl]

The General Procedure B was followed, using tert-butyl (S)-3-((4-(2-((2-methyl-5-(pyrrolidine-1-sulfonamido)naphthalen-1-yl)oxy)pyridin-3-yl)pyrimidin-2-yl)amino)piperidine-1-carboxylate (100 mg, 0.15 mmol), DCM (5 mL) and hydrochloric acid (4 M in dioxane, 2 mL, 8 mmol). The residue was purified by Prep-HPLC to yield 36 mg (42% yield) of hydrochloride 108 as a white solid. LCMS (ESI): [M+H]$^+$=560; $^1$H NMR (400 MHz, DMSO-d$_6$) δ 8.54 (s, 1H), 8.43 (d, J=5.1 Hz, 1H), 8.35 (s, 1H), 8.15 (d, J=8.7 Hz, 1H), 8.04 (dd, J=4.7, 1.8 Hz, 1H), 7.51 (dd, J=13.4, 7.2 Hz, 4H), 7.39 (t, J=7.9 Hz, 15.8 Hz, 1H), 7.34-7.21 (m, 2H), 4.05 (s, 1H), 3.19 (s, 5H), 2.96 (d, J=11.2 Hz, 1H), 2.73-2.53 (m, 2H), 2.21 (s, 3H), 1.96 (s, 1H), 1.78-1.73 (m, 5H), 1.56 (d, J=8.6 Hz, 2H).

Example 109 4-[2-[[5-(Dimethylsulfamoylamino)-2-methyl-1-naphthyl]oxy]-3-pyridyl]-2-[[(3S)-3-piperidyl]amino]pyrimidine hydrochloride 109

Step 1: tert-Butyl 3-(4-(2-(5-(N,N-dimethylsulfamoylamino)-2-methylnaphthalen-1-yloxy)pyridin-3-yl)pyrimidin-2-ylamino)piperidine-1-carboxylate

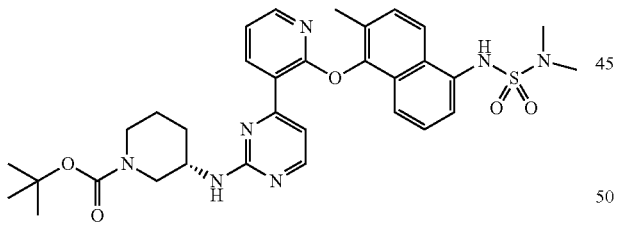

The General Procedure A was followed, using tert-butyl (S)-3-((4-(2-((5-amino-2-methylnaphthalen-1-yl)oxy)pyridin-3-yl)pyrimidin-2-yl)amino)piperidine-1-carboxylate from Example 101 (100 mg, 0.19 mmol), pyridine (2 mL) and dimethylsulfamoyl chloride (200 mg, 1.39 mmol). The crude was then purified by Prep-TLC (petroleum ether/ethyl acetate=1/1) to yield 90 mg (70% yield) of the title compound as a white solid. LCMS (ESI) [M+H]+=634.

Step 2: 4-[2-[[5-(Dimethylsulfamoylamino)-2-methyl-1-naphthyl]oxy]-3-pyridyl]-2-[[(3S)-3-piperidyl]amino]pyrimidine hydrochloride

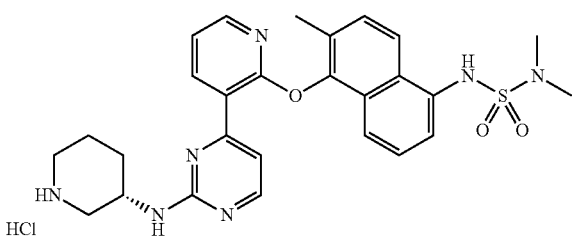 [SMILES: Cc1ccc2c(NS(=O)(=O)N(C)C)cccc2c1Oc1ncccc1-c1ccnc(N[C@H]2CCCNC2)n1 ; Cl]

The General Procedure B was followed, using tert-butyl (3S)-3-[[4-[2-[[5-(dimethylsulfamoylamino)-2-methyl-1-naphthyl]oxy]-3-pyridyl]pyrimidin-2-yl]amino]piperidine-1-carboxylate (90 mg, 0.14 mmol), DCM (5 mL) and hydrochloric acid (4 M in dioxane, 3 mL, 12 mmol). The residue was purified by Prep-HPLC to yield 42 mg (55% yield) of hydrochloride 109 as a white solid. LCMS (ESI): [M+H]$^+$=534; $^1$H NMR (400 MHz, DMSO-d$_6$) δ 8.55 (s, 1H), 8.43 (d, J=5.1 Hz, 1H), 8.34 (s, 1H), 8.17 (d, J=8.7 Hz, 1H), 8.04 (dd, J=4.8, 1.8 Hz, 1H), 7.49 (dd, J=16.7, 8.1 Hz, 4H), 7.40-7.33 (m, 1H), 7.33-7.22 (m, 2H), 4.06 (s, 1H), 3.23 (s, 1H), 2.95 (s, 1H), 2.72 (s, 6H), 2.62 (s, 2H), 2.21 (s, 3H), 1.97 (s, 1H), 1.76 (s, 1H), 1.56 (s, 2H).

Example 110 N-(4-((3-(2-(((1r,4r)-4-aminocyclohexyl)amino)pyrimidin-4-yl)pyridin-2-yl)oxy)-3-methylnaphthalen-1-yl)-1-phenylmethanesulfonamide hydrochloride 110

Step 1: tert-Butyl ((trans)-4-((4-(2-((2-methyl-4-((phenylmethyl)sulfonamido)naphthalen-1-yl)oxy)pyridin-3-yl)pyrimidin-2-yl)amino)cyclohexyl)carbamate

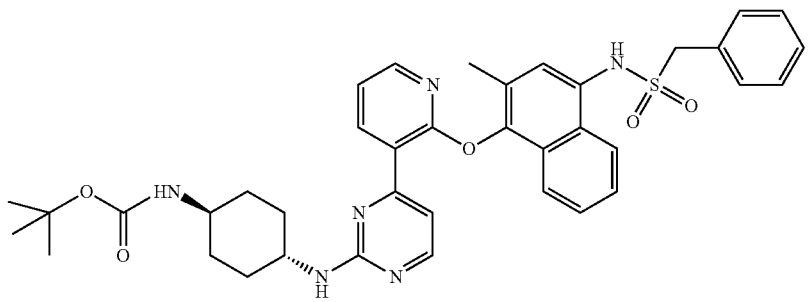 [SMILES: Cc1cc(NS(=O)(=O)Cc2ccccc2)c2ccccc2c1Oc1ncccc1-c1ccnc(N[C@H]2CC[C@H](NC(=O)OC(C)(C)C)CC2)n1]

The General Procedure A was followed, using tert-butyl N-[4-[[4-[2-[(4-amino-2-methyl-1-naphthyl)oxy]-3-pyridyl]pyrimidin-2-yl]amino]cyclohexyl]carbamate (90 mg, 0.17 mmol), pyridine (2 mL) and alpha-toluenesulfonylchloride (222 mg, 1.17 mmol). The crude was then purified by Prep-TLC (petroleum ether/ethyl acetate=1/1) to yield 100 mg (86% yield) of the title compound as a yellow solid. LCMS (ESI) [M+H]+=695.

Step 2: N-(4-((3-(2-(((trans)-4-aminocyclohexyl)amino)pyrimidin-4-yl)pyridin-2-yl)oxy)-3-methyl-naphthalen-1-yl)-1-phenylmethanesulfonamide

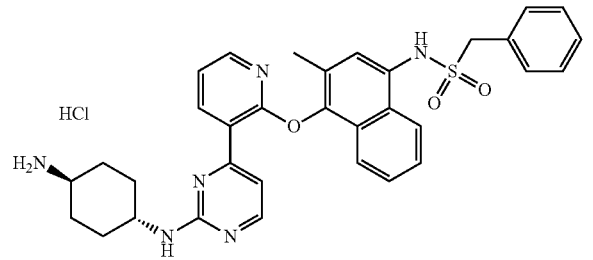 [SMILES: Cc1cc(NS(=O)(=O)Cc2ccccc2)c2ccccc2c1Oc1ncccc1-c1ccnc(N[C@H]2CC[C@H](N)CC2)n1 ; Cl]

The General Procedure B was followed, using tert-butyl ((1r,4r)-4-((4-(2-((2-methyl-4-((phenylmethyl)sulfonamido)naphthalen-1-yl)oxy)pyridin-3-yl)pyrimidin-2-yl)amino)cyclohexyl)carbamate (100 mg, 0.14 mmol), DCM (5 mL) and hydrochloric acid (4 M in dioxane, 3 mL, 12 mmol). The residue was purified by Prep-HPLC to yield 39 mg (42% yield) of the title compound as a yellow solid.

Example 111 N-(4-((3-(2-(((trans)-4-Aminocyclohexyl)amino)pyrimidin-4-yl)pyridin-2-yl)oxy)-3-methylnaphthalen-1-yl)cyclobutanesulfonamide hydrochloride 111

Step 1: tert-Butyl ((trans)-4-((4-(2-((4-(Cyclobutanesulfonamido)-2-methylnaphthalen-1-yl)oxy)pyridin-3-yl)pyrimidin-2-yl)amino)cyclohexyl)carbamate

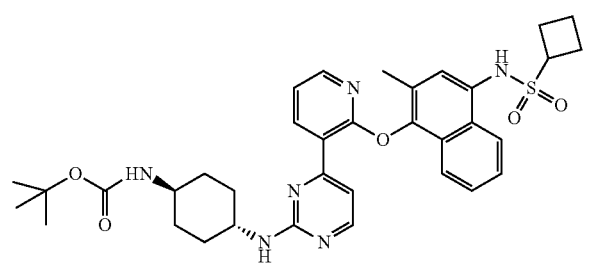 [SMILES: Cc1cc(NS(=O)(=O)C2CCC2)c2ccccc2c1Oc1ncccc1-c1ccnc(N[C@H]2CC[C@H](NC(=O)OC(C)(C)C)CC2)n1]

The General Procedure A was followed, using tert-butyl N-[4-[[4-[2-[(4-amino-2-methyl-1-naphthyl)oxy]-3-pyridyl]pyrimidin-2-yl]amino]cyclohexyl]carbamate (100 mg, 0.19 mmol), pyridine (2 mL) and cyclobutanesulfonyl chloride (43 mg, 0.28 mmol). The crude was then purified by Prep-TLC (petroleum ether/ethyl acetate=1/1) to yield 60 mg (50% yield) of the title compound as a white solid. LCMS (ESI) [M+H]+=660.

Step 2: N-(4-((3-(2-(((trans)-4-Aminocyclohexyl)amino)pyrimidin-4-yl)pyridin-2-yl)oxy)-3-methyl-naphthalen-1-yl)cyclobutanesulfonamide hydrochloride

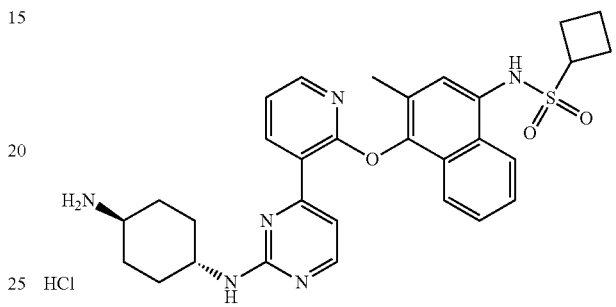

The General Procedure B was followed, using tert-butyl ((1r,4r)-4-((4-(2-((4-(cyclobutanesulfonamido)-2-methyl-naphthalen-1-yl)oxy)pyridin-3-yl)pyrimidin-2-yl)amino)cyclohexyl)carbamate (60 mg, 0.09 mmol), DCM (5 mL) and hydrochloric acid (4 M in dioxane, 1 mL, 4.1 mmol). The residue was purified by Prep-HPLC to yield 42 mg (55% yield) of 111 as a yellow solid. LCMS (ESI): [M+H]+=560; $^1$H NMR (400 MHz, CD$_3$OD) δ 8.61 (d, J=7.6 Hz, 1H), 8.40 (d, J=5.6 Hz, 1H), 8.23 (d, J=8.4 Hz, 1H), 8.04 (d, J=4.4 Hz, 1H), 7.75 (d, J=8.8 Hz, 1H), 7.76-7.68 (m, 1H), 7.56 (d, J=7.2 Hz, 1H), 7.53 (s, 1H), 7.46 (t, J=15.2, 8 Hz, Hz, 1H), 7.27-7.25 (m, 1H), 3.94-4.02 (m, 2H), 3.20-3.14 (m, 1H), 2.56-2.48 (m, 2H), 2.33-2.28 (m, 7H), 2.14-2.11 (m, 2H), 2.05-1.96 (m, 2H), 1.51-1.72 (m, 4H).

Example 112 (S)—N-(6-Methyl-5-((3-(2-(piperidin-3-ylamino)pyrimidin-4-yl)pyridin-2-yl)oxy)naphthalen-1-yl)-1-phenylmethanesulfonamide hydrochloride 112

Step 1: tert-Butyl (S)-3-((4-(2-((2-methyl-5-((phenylmethyl)sulfonamido)naphthalen-1-yl)oxy)pyridin-3-yl)pyrimidin-2-yl)amino)piperidine-1-carboxylate

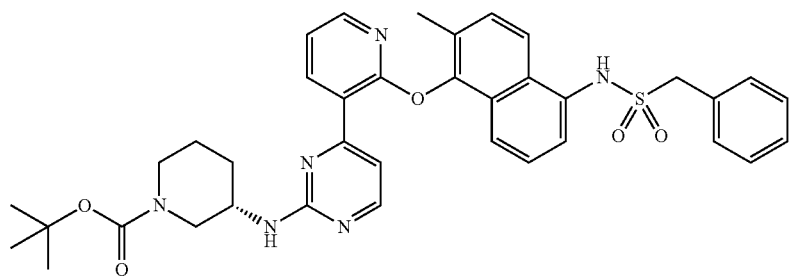 [SMILES: Cc1ccc2c(NS(=O)(=O)Cc3ccccc3)cccc2c1Oc1ncccc1-c1ccnc(N[C@H]2CCCN(C(=O)OC(C)(C)C)C2)n1]

The General Procedure A was followed, using tert-butyl (S)-3-((4-(2-((5-amino-2-methylnaphthalen-1-yl)oxy)pyridin-3-yl)pyrimidin-2-yl)amino)piperidine-1-carboxylate from Example 101 (90 mg, 0.17 mmol), pyridine (2 mL) and alpha-toluenesulfonylchloride (162 mg, 0.85 mmol). The crude was then purified by Prep-TLC (petroleum ether/ethyl acetate=1/1) to yield 130 mg (72% yield) of the title compound as a white solid. LCMS (ESI) [M+H]+=681.

Step 2: (S)—N-(6-Methyl-5-((3-(2-(piperidin-3-ylamino)pyrimidin-4-yl)pyridin-2-yl)oxy)naphthalen-1-yl)-1-phenylmethanesulfonamide hydrochloride

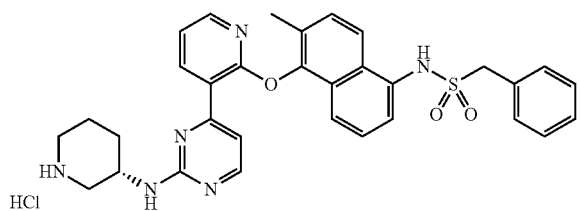 [SMILES: Cc1ccc2c(NS(=O)(=O)Cc3ccccc3)cccc2c1Oc1ncccc1-c1ccnc(N[C@H]2CCCNC2)n1 ; Cl]

The General Procedure B was followed, using tert-butyl (S)-3-((4-(2-((2-methyl-5-((phenylmethyl)sulfonamido)naphthalen-1-yl)oxy)pyridin-3-yl)pyrimidin-2-yl)amino)piperidine-1-carboxylate (130 mg, 0.19 mmol), DCM (5 mL) and hydrochloric acid (4 M in dioxane, 4 mL, 16 mmol). The residue was purified by Prep-HPLC to yield 60 mg (50% yield) of 112 as a white solid. LCMS (ESI): [M+H]+=581; 1H NMR (400 MHz, CD3OD) δ 8.68 (d, J=6.4 Hz, 1H), 8.46 (d, J=5.2 Hz, 1H), 8.02-8.00 (m, 2H), 7.74 (d, J=5.2 Hz, 1H), 7.62 (d, J=8.0 Hz, 1H), 7.51-7.48 (m, 2H), 7.38-7.33 (m, 6H), 7.26-7.23 (m, 1H), 4.48 (s, 2H), 4.41-4.36 (m, 1H), 3.64 (dd, J=12.4, 3.2 Hz, 1H), 3.32-3.42 (m, 1H), 3.11-3.03 (m, 2H), 2.33 (s, 3H), 2.28-2.11 (m, 2H), 1.93-1.80 (m, 2H).

Example 113 4-[2-[[5-[[Ethyl(methyl)sulfamoyl]amino]-2-methyl-1-naphthyl]oxy]-3-pyridyl]-2-[[(3S)-3-piperidyl]amino]pyrimidine hydrochloride 113

Step 1: tert-Butyl (S)-3-((4-(2-((5-((N-ethyl-N-methylsulfamoyl)amino)-2-methylnaphthalen-1-yl)oxy)pyridin-3-yl)pyrimidin-2-yl)amino)piperidine-1-carboxylate

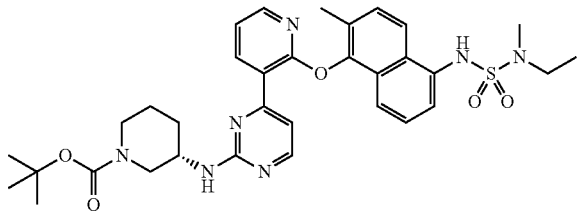 [SMILES: CCN(C)S(=O)(=O)Nc1cccc2c(Oc3ncccc3-c3ccnc(N[C@H]4CCCN(C(=O)OC(C)(C)C)C4)n3)c(C)ccc12]

The General Procedure A was followed, using tert-butyl (S)-3-((4-(2-((5-amino-2-methylnaphthalen-1-yl)oxy)pyridin-3-yl)pyrimidin-2-yl)amino)piperidine-1-carboxylate from Example 101 (90 mg, 0.17 mmol), pyridine (2 mL) and N-ethyl-N-methyl-sulfamoyl chloride (269 mg, 1.71 mmol). The crude was then purified by Prep-TLC (petroleum ether/ethyl acetate=1/1) to yield 80 mg (72% yield) of the title compound as a yellow solid. LCMS (ESI) [M+H]+=648.

Step 2: 4-[2-[[5-[[Ethyl(methyl)sulfamoyl]amino]-2-methyl-1-naphthyl]oxy]-3-pyridyl]-2-[[(3 S)-3-piperidyl]amino]pyrimidine hydrochloride

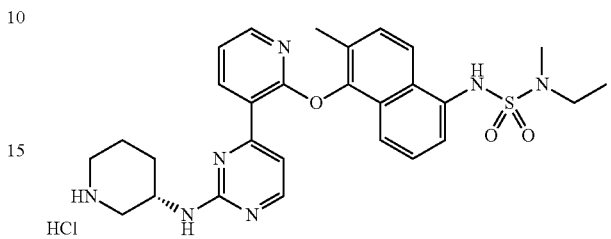

The General Procedure B was followed, using tert-butyl (S)-3-((4-(2-((5-((N-ethyl-N-methylsulfamoyl)amino)-2-methylnaphthalen-1-yl)oxy)pyridin-3-yl)pyrimidin-2-yl)amino)piperidine-1-carboxylate (80 mg, 0.12 mmol), DCM (8 mL) and hydrochloric acid (4 M in dioxane, 4 mL, 16 mmol). The residue was purified by Prep-HPLC to yield 18 mg (25% yield) of 113 as a white solid. LCMS (ESI): [M+H]+=548; 1H NMR (400 MHz, CD3OD) 8.66 (d, J=6.8 Hz, 1H), 8.46 (d, J=5.2 Hz, 1H), 8.16 (d, J=8.8 Hz, 1H), 8.01 (dd, J=1.6, 4.8 Hz, 1H), 7.71 (d, J=5.2 Hz, 1H), 7.60-7.52 (m, 3H), 7.39-7.35 (m, 1H), 7.25-7.22 (m, 1H), 4.40-4.33 (m, 1H), 3.63 (dd, J=3.2, 12.4 Hz, 1H), 3.38-3.32 (m, 1H), 3.25-3.18 (m, 2H), 3.08-3.02 (m, 2H), 2.83 (s, 3H), 2.28 (s, 3H), 2.24-2.09 (m, 2H), 1.95-1.77 (m, 2H), 1.09-1.05 (m, 3H).

Example 114 (S)—N-(6-Methyl-5-((3-(2-(piperidin-3-ylamino)pyrimidin-4-yl)pyridin-2-yl)oxy)naphthalen-1-yl)piperidine-1-sulfonamide hydrochloride 114

Step 1: tert-Butyl (S)-3-((4-(2-((2-methyl-5-(piperidine-1-sulfonamido)naphthalen-1-yl)oxy)pyridin-3-yl)pyrimidin-2-yl)amino)piperidine-1-carboxylate

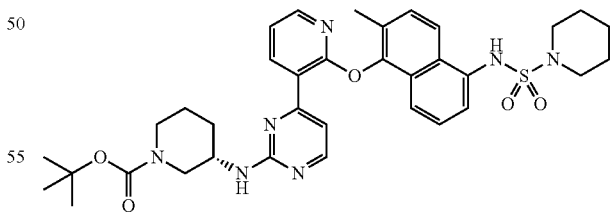

The General Procedure A was followed, using tert-butyl (S)-3-((4-(2-((5-amino-2-methylnaphthalen-1-yl)oxy)pyridin-3-yl)pyrimidin-2-yl)amino)piperidine-1-carboxylate from Example 101 (100 mg, 0.19 mmol), pyridine (2 mL) and piperidine-1-sulfonylchloride (200 mg, 1.09 mmol). The crude was then purified by Prep-TLC (petroleum ether/ethyl acetate=1/1) to yield 100 mg (78% yield) of the title compound as a white solid. LCMS (ESI) [M+H]+=674.

Step 2: (S)—N-(6-Methyl-5-((3-(2-(piperidin-3-ylamino)pyrimidin-4-yl)pyridin-2-yl)oxy)naphthalen-1-yl)piperidine-1-sulfonamide hydrochloride

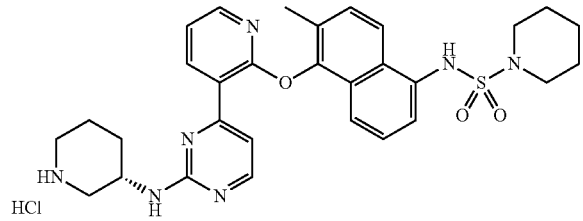 [SMILES: Cc1ccc2c(NS(=O)(=O)N3CCCCC3)cccc2c1Oc1ncccc1-c1ccnc(N[C@H]2CCCNC2)n1 ; Cl]

The General Procedure B was followed, using tert-butyl (S)-3-((4-(2-((2-methyl-5-(piperidine-1-sulfonamido)naphthalen-1-yl)oxy)pyridin-3-yl)pyrimidin-2-yl)amino)piperidine-1-carboxylate (100 mg, 0.15 mmol), DCM (5 mL) and hydrochloric acid (4 M in dioxane, 3 mL, 12 mmol). The residue was purified by Prep-HPLC to yield 42 mg (55% yield) of 114 as a white solid. LCMS (ESI): [M+H]$^+$=574; $^1$H NMR (400 MHz, DMSO-d$_6$) δ 9.77 (s, 1H), 8.71 (s, 2H), 8.58 (s, 1H), 8.48 (d, J=5.2 Hz, 1H), 8.15 (d, J=8.7 Hz, 1H), 8.06 (dd, J=4.7, 1.8 Hz, 1H), 7.65-7.48 (m, 5H), 7.41 (t, J=7.9 Hz, 15.8 Hz, 1H), 7.27 (dd, J=7.5, 4.9 Hz, 1H), 4.25 (s, 1H), 3.45 (s, 1H), 3.23 (d, J=12.8 Hz, 1H), 3.13 (s, 4H), 2.86 (s, 2H), 2.21 (s, 3H), 2.02 (d, J=10.0 Hz, 1H), 1.93 (d, J=13.9 Hz, 1H), 1.81-1.57 (m, 2H), 1.52-1.40 (m, 6H).

Example 115 (S)—N-(6-Methyl-5-((3-(2-(piperidin-3-ylamino)pyrimidin-4-yl)pyridin-2-yl)oxy)naphthalen-1-yl)benzamide hydrochloride 115

Step 1: tert-Butyl (S)-3-((4-(2-((5-benzamido-2-methylnaphthalen-1-yl)oxy)pyridin-3-yl)pyrimidin-2-yl)amino)piperidine-1-carboxylate

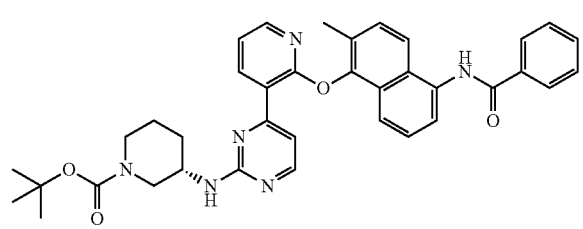 [SMILES: Cc1ccc2c(NC(=O)c3ccccc3)cccc2c1Oc1ncccc1-c1ccnc(N[C@H]2CCCN(C(=O)OC(C)(C)C)C2)n1]

To an ice-cooled solution of tert-butyl (3S)-3-[[4-[2-[(5-amino-2-methyl-1-naphthyl)oxy]-3-pyridyl]pyrimidin-2-yl]amino]piperidine-1-carboxylate (100 mg, 0.19 mmol) and pyridine (1 mL) in dichloromethane (5 mL) was added benzoyl chloride (29 mg, 0.21 mmol). After being stirred at room temperature for 1 h, the mixture was concentrated to give crude tert-butyl (3S)-3-[[4-[2-[(5-benzamido-2-methyl-1-naphthyl)oxy]-3-pyridyl]pyrimidin-2-yl]amino]piperidine-1-carboxylate (120 mg, 94% yield) as a yellow solid, which was used in the next step without further purification. LCMS (ESI) [M+H]+=631.3.

Step 2: (S)—N-(6-Methyl-5-((3-(2-(piperidin-3-ylamino)pyrimidin-4-yl)pyridin-2-yl)oxy)naphthalen-1-yl)benzamide hydrochloride

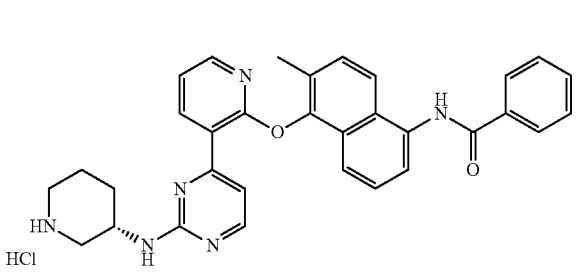 [SMILES: Cc1ccc2c(NC(=O)c3ccccc3)cccc2c1Oc1ncccc1-c1ccnc(N[C@H]2CCCNC2)n1 ; Cl]

The General Procedure B was followed, using tert-butyl (S)-3-((4-(2-((2-methyl-5-(piperidine-1-sulfonamido)naphthalen-1-yl)oxy)pyridin-3-yl)pyrimidin-2-yl)amino)piperidine-1-carboxylate (120 mg, 0.19 mmol), DCM (5 mL) and hydrochloric acid (4 M in dioxane, 2 mL, 8 mmol). The residue was purified by Prep-HPLC to yield 99 mg (91% yield) of 115 as a white solid. LCMS (ESI): RT (min)=1.562, [M+H]$^+$=531.3, method=A; $^1$H NMR (400 MHz, CD$_3$OD) δ 8.68 (d, J=6.8 Hz, 1H), 8.48 (d, J=5.2 Hz, 1H), 8.11-8.09 (m, 2H), 8.03-8.02 (m, 1H), 7.92-7.91 (m, 1H), 7.77-7.76 (m, 1H), 7.72-7.64 (m, 2H), 7.61-7.57 (m, 3H), 7.53-7.45 (m, 2H), 7.25 (dd, J=4.8, 7.6 Hz, 1H), 4.42-4.40 (m, 1H), 3.65-3.62 (m, 1H), 3.36-3.33 (m, 1H), 3.12-3.03 (m, 2H), 2.29 (s, 3H), 2.23-2.11 (m, 2H), 1.95-1.81 (m, 2H).

Example 116 (S)—N-(6-Methyl-5-((3-(2-(piperidin-3-ylamino)pyrimidin-4-yl)pyridin-2-yl)oxy)naphthalen-1-yl)piperidine-1-carboxamide hydrochloride 116

Step 1: tert-Butyl (S)-3-((4-(2-((2-methyl-5-(piperidine-1-carboxamido)naphthalen-1-yl)oxy)pyridin-3-yl)pyrimidin-2-yl)amino)piperidine-1-carboxylate

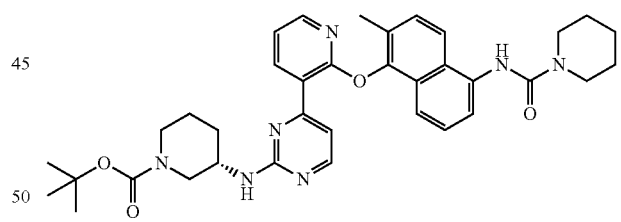

To a solution of tert-butyl (3S)-3-[[4-[2-[(5-amino-2-methyl-1-naphthyl)oxy]-3-pyridyl]pyrimidin-2-yl]amino]piperidine-1-carboxylate (100 mg, 0.19 mmol) and triethylamine (38 mg, 0.38 mmol) in dry tetrahydrofuran (5 mL) was added triphosgene (33 mg, 0.11 mmol) at 0° C. After addition, the reaction mixture was stirred at rt for 1 h. Then piperidine (16 mg, 0.19 mmol) was added to the reaction and continued to stir at rt for 2 h. The reaction was concentrated to dryness and the residue was taken up in ethyl acetate (20 mL). The organics were washed with water and brine. The organics were then separated and dried (magnesium sulphate) before concentration to dryness. The crude was then purified by Prep-TLC (petroleum ether/ethyl acetate=1/1) to yield 100 mg (56% yield) of the title compound as a white solid. LCMS (ESI) [M+H]+=638.

Step 2: (S)—N-(6-Methyl-5-((3-(2-(piperidin-3-ylamino)pyrimidin-4-yl)pyridin-2-yl)oxy)naphthalen-1-yl)piperidine-1-carboxamide hydrochloride

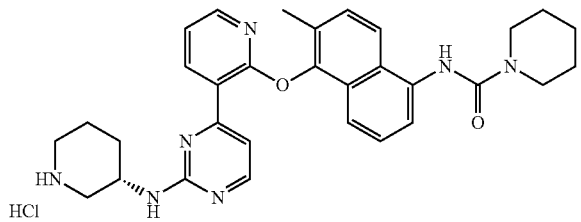 [SMILES: Cc1ccc2c(NC(=O)N3CCCCC3)cccc2c1Oc1ncccc1-c1ccnc(N[C@H]2CCCNC2)n1 ; Cl]

To a mixture of tert-butyl (S)-3-((4-(2-((2-methyl-5-(piperidine-1-carboxamido)naphthalen-1-yl)oxy)pyridin-3-yl)pyrimidin-2-yl)amino)piperidine-1-carboxylate (100 mg, 0.16 mmol) in DCM (5 mL) was added hydrochloric acid (4 M in dioxane, 3 mL, 12.48 mmol). Then the mixture was stirred at rt for 1 h. The mixture was concentrated to dryness. The residue was purified by Prep-HPLC to yield 34 mg (40% yield) of 116 as a white solid. LCMS (ESI): M+H]$^+$=538; $^1$H NMR (400 MHz, DMSO-d$_6$) δ 8.56 (s, 1H), 8.44 (d, J=5.2 Hz, 1H), 8.35 (s, 1H), 8.10-8.03 (m, 1H), 7.76 (d, J=8.7 Hz, 1H), 7.52 (d, J=5.1 Hz, 1H), 7.45 (d, J=8.7 Hz, 2H), 7.41-7.30 (m, 3H), 7.26 (dd, J=7.6, 4.7 Hz, 1H), 4.08 (s, 2H), 3.51 (d, J=5.6 Hz, 4H), 3.25 (s, 1H), 2.99 (d, J=11.0 Hz, 1H), 2.70-2.57 (m, 2H), 2.21 (s, 3H), 1.98 (s, 1H), 1.77 (s, 1H), 1.62 (s, 2H), 1.56 (s, 6H).

Example 117 (S)—N-(6-Methyl-5-((3-(2-(piperidin-3-ylamino)pyrimidin-4-yl)pyridin-2-yl)oxy)naphthalen-1-yl)butyramide hydrochloride 117

Step 1: tert-Butyl (S)-3-((4-(2-((5-butyramido-2-methylnaphthalen-1-yl)oxy)pyridin-3-yl)pyrimidin-2-yl)amino)piperidine-1-carboxylate

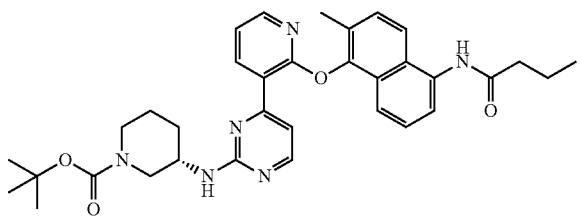 [SMILES: CCCC(=O)Nc1cccc2c(Oc3ncccc3-c3ccnc(N[C@H]4CCCN(C(=O)OC(C)(C)C)C4)n3)c(C)ccc12]

To a solution of tert-butyl (3S)-3-[[4-[2-[(5-amino-2-methyl-1-naphthyl)oxy]-3-pyridyl]pyrimidin-2-yl]amino]piperidine-1-carboxylate (100 mg, 0.19 mmol) and pyridine (0.05 mL, 0.57 mmol) in dry dichloromethane (10 mL) was added butyryl chloride (24 mg, 0.23 mmol) at 0° C. After addition completed, the mixture was stirred at 25° C. for 2 h. Methanol was added and the mixture was concentrated to yield 113 mg (99% yield) of the title compound as a yellow solid. LC-MS (ESI): [M+H]$^+$=597.4.

Step 2: (S)—N-(6-Methyl-5-((3-(2-(piperidin-3-ylamino)pyrimidin-4-yl)pyridin-2-yl)oxy)naphthalen-1-yl)butyramide hydrochloride

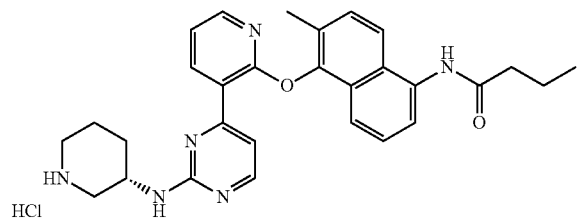 [SMILES: CCCC(=O)Nc1cccc2c(Oc3ncccc3-c3ccnc(N[C@H]4CCCNC4)n3)c(C)ccc12 ; Cl]

The General Procedure B was followed, using tert-butyl (S)-3-((4-(2-((2-methyl-5-(piperidine-1-sulfonamido)naphthalen-1-yl)oxy)pyridin-3-yl)pyrimidin-2-yl)amino)piperidine-1-carboxylate (113 mg, 0.19 mmol), DCM (3 mL) and hydrochloric acid (4 M in dioxane, 3 mL, 12 mmol). The residue was purified by Prep-HPLC to yield 50 mg (50% yield) of 117 as a white solid. LCMS (ESI): [M+H]$^+$=497.3; $^1$H NMR (400 MHz, CD$_3$OD) δ 8.69 (d, J=7.6 Hz, 1H), 8.47 (d, J=5.2 Hz, 1H), 8.02 (d, J=2.4 Hz, 1H), 7.90 (d, J=8.8 Hz, 1H), 7.77 (d, J=5.6 Hz, 1H), 7.63-7.51 (m, 3H), 7.40 (t, J=8.0 Hz, 1H), 7.27-7.23 (m, 1H), 4.41 (m, 1H), 3.63 (dd, J=12.4, 3.2 Hz, 1H), 3.12-3.03 (m, 2H), 2.56 (t, J=7.2 Hz, 2H), 2.29 (s, 3H), 2.16-2.11 (m, 2H), 1.93-1.81 (m, 4H), 1.12 (t, J=6.8 Hz, 3H).

Example 118 (S)-3-Fluoro-N-(6-methyl-5-((3-(2-(piperidin-3-ylamino)pyrimidin-4-yl)pyridin-2-yl)oxy)naphthalen-1-yl)propane-1-sulfonamide hydrochloride 118

Step 1: tert-Butyl (S)-3-((4-(2-((5-((3-fluoropropyl)sulfonamido)-2-methylnaphthalen-1-yl)oxy)pyridin-3-yl)pyrimidin-2-yl)amino)piperidine-1-carboxylate

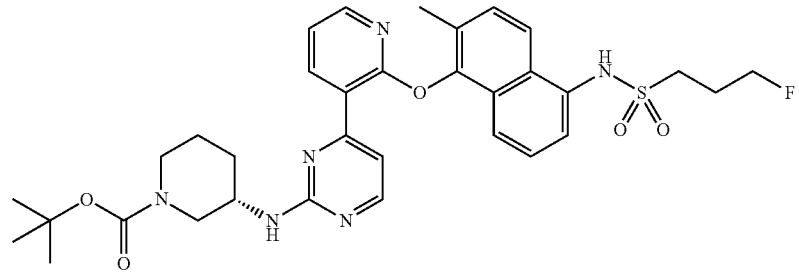 [SMILES: Cc1ccc2c(NS(=O)(=O)CCCF)cccc2c1Oc1ncccc1-c1ccnc(N[C@H]2CCCN(C(=O)OC(C)(C)C)C2)n1]

The General Procedure A was followed, using tert-butyl (S)-3-((4-(2-((5-amino-2-methylnaphthalen-1-yl)oxy)pyridin-3-yl)pyrimidin-2-yl)amino)piperidine-1-carboxylate from Example 101 (100 mg, 0.19 mmol), pyridine (2 mL) and 3-fluoropropane-1-sulfonyl chloride (30 mg, 0.19 mmol). The crude was then purified by Prep-TLC (petroleum ether/ethyl acetate=1/1) to yield 100 mg (81% yield) of the title compound as a white solid. LCMS (ESI) [M+H]+=651.

Step 2: (S)-3-Fluoro-N-(6-methyl-5-((3-(2-(piperidin-3-ylamino)pyrimidin-4-yl)pyridin-2-yl)oxy)naphthalen-1-yl)propane-1-sulfonamide hydrochloride

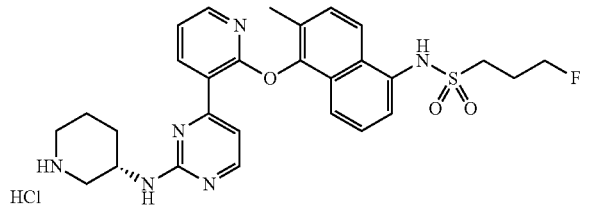 [SMILES: Cc1ccc2c(NS(=O)(=O)CCCF)cccc2c1Oc1ncccc1-c1ccnc(N[C@H]2CCCNC2)n1 ; Cl]

The General Procedure B was followed, using tert-butyl (S)-3-((4-(2-((5-((3-fluoropropyl)sulfonamido)-2-methylnaphthalen-1-yl)oxy)pyridin-3-yl)pyrimidin-2-yl)amino)piperidine-1-carboxylate (100 mg, 0.15 mmol), DCM (5 mL) and hydrochloric acid (4 M in dioxane, 2 mL, 8 mmol). The residue was purified by Prep-HPLC to yield 65 mg (75% yield) of 118 as a red solid. LCMS (ESI): [M+H]$^+$=551; $^1$H NMR (400 MHz, DMSO-d$_6$) δ 8.56 (s, 1H), 8.44 (d, J=5.1 Hz, 1H), 8.32 (s, 1H), 8.14 (d, J=8.6 Hz, 1H), 8.05 (d, J=4.6 Hz, 1H), 7.49 (t, J=10.1 Hz, 3H), 7.40 (t, J=8.5 Hz, 2H), 7.34 (d, J=7.3 Hz, 1H), 7.30-7.22 (m, 1H), 4.60 (t, J=5.9 Hz, 1H), 4.48 (t, J=5.8 Hz, 1H), 4.07 (s, 1H), 3.25 (s, 1H), 3.23-3.18 (m, 2H), 3.00 (d, J=12.0 Hz, 1H), 2.71-2.56 (m, 2H), 2.21 (s, 3H), 2.12 (d, J=24.7 Hz, 2H), 1.97 (s, 1H), 1.77 (s, 1H), 1.56 (s, 2H).

Example 119 N-(4-((3-(2-(((trans)-4-aminocyclohexyl)amino)pyrimidin-4-yl)pyridin-2-yl)oxy)-3-methylnaphthalen-1-yl)cyclopentanesulfonamide hydrochloride 119

Step 1: tert-Butyl ((trans)-4-((4-(2-((4-(cyclopentanesulfonamido)-2-methylnaphthalen-1-yl)oxy)pyridin-3-yl)pyrimidin-2-yl)amino)cyclohexyl)carbamate

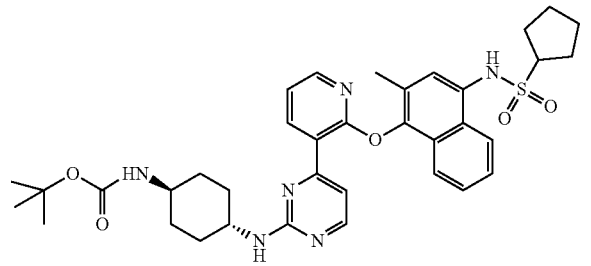 [SMILES: Cc1cc(NS(=O)(=O)C2CCCC2)c2ccccc2c1Oc1ncccc1-c1ccnc(N[C@H]2CC[C@H](NC(=O)OC(C)(C)C)CC2)n1]

The General Procedure A was followed, using tert-butyl N-[4-[[4-[2-[(4-amino-2-methyl-1-naphthyl)oxy]-3-pyridyl]pyrimidin-2-yl]amino]cyclohexyl]carbamate (100 mg, 0.18 mmol), pyridine (2 mL) and cyclopentanesulfonylchloride (31 mg, 0.18 mmol). The crude was then purified by Prep-TLC (petroleum ether/ethyl acetate=1/1) to yield 30 mg (24% yield) of the title compound as a yellow solid. LCMS (ESI) [M+H]+=573.

Step 2: N-(4-((3-(2-(((trans)-4-aminocyclohexyl)amino)pyrimidin-4-yl)pyridin-2-yl)oxy)-3-methylnaphthalen-1-yl)cyclopentanesulfonamide hydrochloride

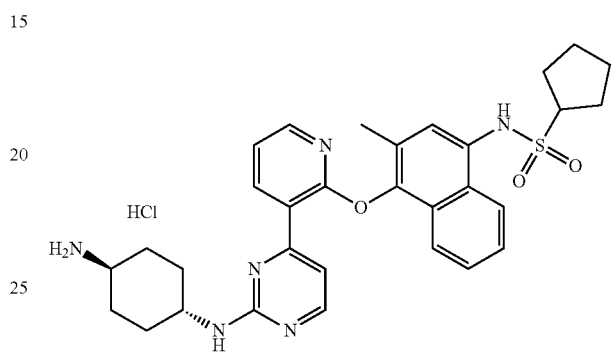

The General Procedure B was followed, using tert-Butyl ((trans)-4-((4-(2-((4-(cyclopentanesulfonamido)-2-methylnaphthalen-1-yl)oxy)pyridin-3-yl)pyrimidin-2-yl)amino)cyclohexyl)carbamate (30 mg, 0.04 mmol), DCM (2 mL) and hydrochloric acid (4 M in dioxane, 1 mL, 4 mmol). The residue was purified by Prep-HPLC to yield 17 mg (62% yield) of 119 as a white solid. LCMS (ESI): [M+H]$^+$=573; $^1$H NMR (400 MHz, CD3OD) δ 8.60 (d, J=6.4 Hz, 1H), 8.40 (d, J=5.6 Hz, 1H), 8.29 (d, J=8.4 Hz, 1H), 8.04-8.03 (m, 1H), 7.75 (d, J=8.4 Hz, 1H), 7.65 (d, J=6.4 Hz, 1H), 7.60-7.45 (m, 3H), 7.25 (dd, J=4.8, 7.6 Hz, 1H), 4.06-3.92 (m, 1H), 3.71-3.63 (m, 1H), 3.18-3.14 (m, 1H), 2.31-2.23 (m, 5H), 2.17-2.11 (m, 4H), 2.02-1.96 (m, 2H), 1.68-1.60 (m, 2H), 1.56-1.48 (m, 6H).

Example 120 (S)—N-(6-Methyl-5-((3-(2-(piperidin-3-ylamino)pyrimidin-4-yl)pyridin-2-yl)oxy)naphthalen-1-yl)cyclopentanesulfonamide hydrochloride 120

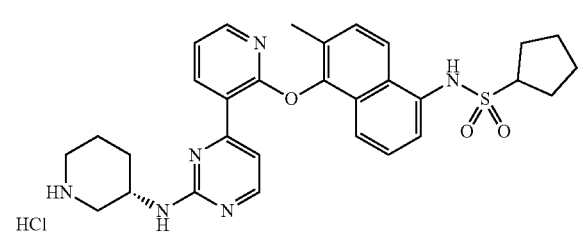 [SMILES: Cc1ccc2c(NS(=O)(=O)C3CCCC3)cccc2c1Oc1ncccc1-c1ccnc(N[C@H]2CCCNC2)n1 ; Cl]

Step 1: tert-Butyl (S)-3-((4-(2-((5-(cyclopentanesulfonamido)-2-methylnaphthalen-1-yl)oxy)pyridin-3-yl)pyrimidin-2-yl)amino)piperidine-1-carboxylate The General Procedure A was followed, using tert-butyl (S)-3-((4-(2-((5-amino-2-methylnaphthalen-1-yl)oxy)pyridin-3-yl)pyrimidin-2-yl)amino)piperidine-1-carboxylate from Example 101 (100 mg, 0.19 mmol), pyridine (2 mL) and cyclopentanesulfonylchloride (32 mg, 0.19 mmol). The crude was then purified by Prep-TLC (petroleum ether/ethyl acetate=1/1) to yield 90 mg (72% yield) of the title compound as a white solid. LCMS (ESI) [M+H]+=659.

Step 2: (S)—N-(6-Methyl-5-((3-(2-(piperidin-3-ylamino)pyrimidin-4-yl)pyridin-2-yl)oxy)naphthalen-1-yl)cyclopentanesulfonamide hydrochloride

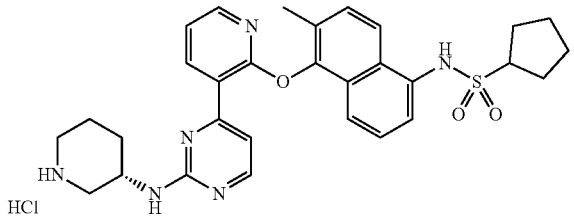 [SMILES: Cc1ccc2c(NS(=O)(=O)C3CCCC3)cccc2c1Oc1ncccc1-c1ccnc(N[C@H]2CCCNC2)n1 ; Cl]

The General Procedure B was followed, using tert-butyl (S)-3-((4-(2-((5-(cyclopentanesulfonamido)-2-methylnaphthalen-1-yl)oxy)pyridin-3-yl)pyrimidin-2-yl)amino)piperidine-1-carboxylate (140 mg, 0.22 mmol), DCM (4 mL) and hydrochloric acid (4 M in dioxane, 3 mL, 12 mmol). The residue was purified by Prep-HPLC to yield 15 mg (18% yield) of 120 as a yellow solid. LCMS (ESI): [M+H]+=559; $^1$H-NMR (400 MHz, CD$_3$OD) δ 8.68 (d, J=7.6 Hz, 1H), 8.46 (d, J=5.6 Hz, 1H), 8.16 (d, J=8.8 Hz, 1H), 8.01 (d, J=4.8 Hz, 1H), 7.73 (d, J=5.6 Hz, 1H), 7.64-7.54 (m, 3H), 7.40-7.36 (m, 1H), 7.26-7.23 (m, 1H), 4.43-4.34 (m, 1H), 3.65-3.60 (m, 2H), 3.39-3.32 (m, 1H), 3.10-3.03 (m, 2H), 2.28 (s, 3H), 2.22-1.76 (m, 10H), 1.67-1.57 (m, 2H).

Example 121 (S)-2-Methyl-N-(6-methyl-5-((3-(2-(piperidin-3-ylamino)pyrimidin-4-yl)pyridin-2-yl)oxy)naphthalen-1-yl)propane-1-sulfonamide hydrochloride 121

Step 1: tert-Butyl (S)-3-((4-(2-((2-methyl-5-((2-methylpropyl)sulfonamido)naphthalen-1-yl)oxy)pyridin-3-yl)pyrimidin-2-yl)amino)piperidine-1-carboxylate

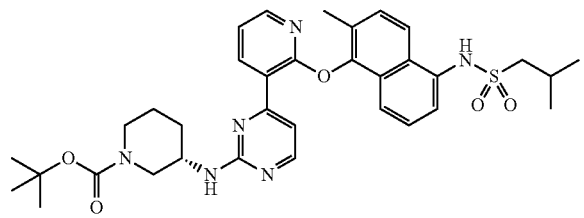 [SMILES: Cc1ccc2c(NS(=O)(=O)CC(C)C)cccc2c1Oc1ncccc1-c1ccnc(N[C@H]2CCCN(C(=O)OC(C)(C)C)C2)n1]

The General Procedure A was followed, using tert-butyl (S)-3-((4-(2-((5-amino-2-methylnaphthalen-1-yl)oxy)pyridin-3-yl)pyrimidin-2-yl)amino)piperidine-1-carboxylate from Example 101 (100 mg, 0.19 mmol), pyridine (3 mL) and isobutanesulfonylchloride (0.15 mL, 1.15 mmol). The crude was then purified by Prep-TLC (petroleum ether/ethyl acetate=1/1) to yield 120 mg (95% yield) of the title compound as a white solid. LCMS (ESI) [M+H]+=647.

Step 2: (S)-2-Methyl-N-(6-methyl-5-((3-(2-(piperidin-3-ylamino)pyrimidin-4-yl)pyridin-2-yl)oxy)naphthalen-1-yl)propane-1-sulfonamide hydrochloride

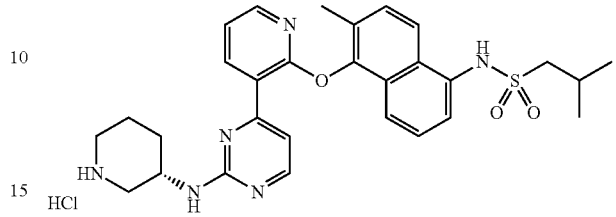

The General Procedure B was followed, using tert-butyl (S)-3-((4-(2-((2-methyl-5-((2-methylpropyl)sulfonamido)naphthalen-1-yl)oxy)pyridin-3-yl)pyrimidin-2-yl)amino)piperidine-1-carboxylate (140 mg, 0.22 mmol), DCM (3 mL) and hydrochloric acid (4 M in dioxane, 3 mL, 12 mmol). The residue was purified by Prep-HPLC to yield 37 mg (29% yield) of 121 as a white solid. LCMS (ESI): [M+H]+=547; $^1$H-NMR (400 MHz, CD$_3$OD) δ: 8.69 (d, J=7.3 Hz, 1H), 8.57-8.56 (m, 1H), 8.45-8.44 (m, 1H), 8.14 (d, J=4.6 Hz, 1H), 7.69-7.63 (m, 2H), 7.56 (s, 1H), 7.55 (s, 1H), 7.40 (t, J=8.1 Hz, 1H), 7.24 (q, J=5.0 Hz, 1H), 4.31-4.29 (m, 1H), 3.55 (d, J=7.2 Hz, 1H), 3.30-3.26 (m, 1H), 3.06 (s, 1H), 3.04 (s, 1H), 3.00-2.94 (m, 2H), 2.32-2.25 (m, 4H), 2.20-2.17 (m, 1H), 2.09-2.05 (m, 1H), 1.90-1.72 (m, 2H), 1.08 (d, J=7.8 Hz, 6H).

Example 122 (S)-2,2,2-Trifluoro-N-(6-methyl-5-((3-(2-(piperidin-3-ylamino)pyrimidin-4-yl)pyridin-2-yl)oxy)naphthalen-1-yl)ethane-1-sulfonamide hydrochloride 122

Step 1: tert-Butyl (S)-3-((4-(2-((2-methyl-5-((2,2,2-trifluoroethyl)sulfonamido)naphthalen-1-yl)oxy)pyridin-3-yl)pyrimidin-2-yl)amino)piperidine-1-carboxylate

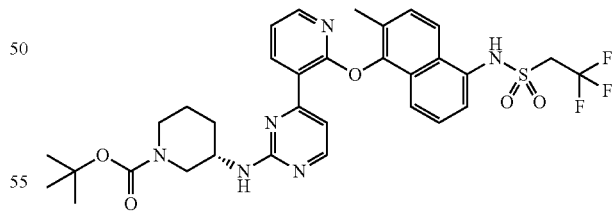

The General Procedure A was followed, using tert-butyl (S)-3-((4-(2-((5-amino-2-methylnaphthalen-1-yl)oxy)pyridin-3-yl)pyrimidin-2-yl)amino)piperidine-1-carboxylate from Example 101 (150 mg, 0.28 mmol), pyridine (2 mL) and 2,2,2-trifluoroethanesulfonyl chloride (52 mg, 0.28 mmol). The crude was then purified by Prep-TLC (petroleum ether/ethyl acetate=1/1) to yield 170 mg (89% yield) of the title compound as a colorless oil. LCMS (ESI) [M+H]+=673.

Step 2: (S)-2,2,2-Trifluoro-N-(6-methyl-5-((3-(2-(piperidin-3-ylamino)pyrimidin-4-yl)pyridin-2-yl)oxy)naphthalen-1-yl)ethane-1-sulfonamide hydrochloride

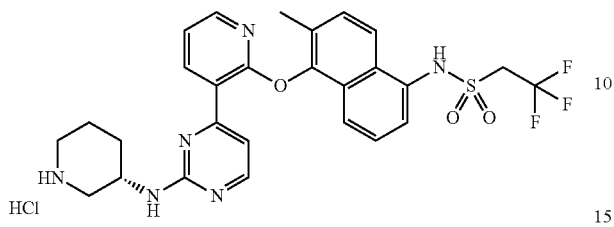

The General Procedure B was followed, using tert-butyl (S)-3-((4-(2-((2-methyl-5-((2,2,2-trifluoroethyl)sulfonamido)naphthalen-1-yl)oxy)pyridin-3-yl)pyrimidin-2-yl)amino)piperidine-1-carboxylate (170 mg, 0.25 mmol), DCM (4 mL) and hydrochloric acid (4 M in dioxane, 2 mL, 8 mmol). The residue was purified by Prep-HPLC to yield 100 mg (65% yield) of 122 as a white solid. LCMS (ESI): [M+H]$^+$=592; $^1$H-NMR (400 MHz, CD$_3$OD) δ 8.68 (d, J=6.8 Hz, 1H), 8.46 (d, J=5.2 Hz, 1H), 8.13 (d, J=8.8 Hz, 1H), 8.01 (d, J=2.8 Hz, 1H), 7.74-7.70 (m, 2H), 7.60-7.57 (m, 2H), 7.43 (t, J=8.0 Hz, 16 Hz, 1H), 7.25 (dd, J=4.8, 7.6 Hz, 1H), 4.40-4.38 (m, 1H), 4.24-4.18 (m, 2H), 3.65-3.62 (m, 1H), 3.10-3.03 (m, 2H), 2.29 (s, 3H), 2.23-2.11 (m, 2H), 1.92-1.81 (m, 2H).

Example 123 (S)-3,3,3-Trifluoro-N-(6-methyl-5-((3-(2-(piperidin-3-ylamino)pyrimidin-4-yl)pyridin-2-yl)oxy)naphthalen-1-yl)propane-1-sulfonamide hydrochloride 123

Step 1: tert-Butyl (S)-3-((4-(2-((2-methyl-5-((3,3,3-trifluoropropyl)sulfonamido)naphthalen-1-yl)oxy)pyridin-3-yl)pyrimidin-2-yl)amino)piperidine-1-carboxylate

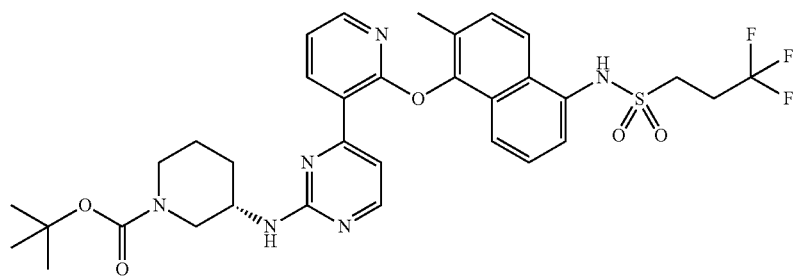 [SMILES: Cc1ccc2c(NS(=O)(=O)CCC(F)(F)F)cccc2c1Oc1ncccc1-c1ccnc(N[C@H]2CCCN(C(=O)OC(C)(C)C)C2)n1]

The General Procedure A was followed, using tert-butyl (S)-3-((4-(2-((5-amino-2-methylnaphthalen-1-yl)oxy)pyridin-3-yl)pyrimidin-2-yl)amino)piperidine-1-carboxylate from Example 101 (100 mg, 0.19 mmol), pyridine (3 mL) and 3,3,3-trifluoropropane-1-sulfonylchloride (300 mg, 1.53 mmol). The crude was then purified by Prep-TLC (petroleum ether/ethyl acetate=1/2) to yield 70 mg (54% yield) of the title compound as a white solid. LCMS (ESI) [M+H]+=587.

Step 2: (S)-3,3,3-Trifluoro-N-(6-methyl-5-((3-(2-(piperidin-3-ylamino)pyrimidin-4-yl)pyridin-2-yl)oxy)naphthalen-1-yl)propane-1-sulfonamide hydrochloride

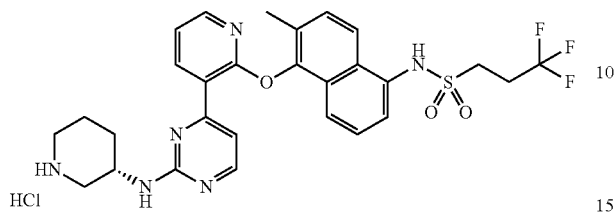

The General Procedure B was followed, using tert-butyl (S)-3-((4-(2-((2-methyl-5-((3,3,3-trifluoropropyl)sulfonamido)naphthalen-1-yl)oxy)pyridin-3-yl)pyrimidin-2-yl)amino)piperidine-1-carboxylate (70 mg, 0.10 mmol), DCM (3 mL) and hydrochloric acid (4 M in dioxane, 3 mL, 12 mmol). The residue was purified by Prep-HPLC to yield 51 mg (80% yield) of 123 as a yellow solid. LCMS (ESI): [M+H]$^+$=587.2; $^1$H-NMR (400 Hz, CD$_3$OD) δ 8.70 (d, J=7.2 Hz, 1H), 8.47 (d, J=5.5 Hz, 1H), 8.14 (d, J=8.7 Hz, 1H), 8.02 (dd, J=4.9, 1.6 Hz, 1H), 7.76 (d, J=4.9 Hz, 1H), 7.69 (d, J=8.5 Hz, 1H), 7.60-7.55 (m, 2H), 7.42 (t, J=2.0 Hz, 1H), 7.27-7.24 (m, 1H), 4.40 (s, 1H), 3.64 (dd, J=12.2, 8.6 Hz, 1H), 3.43-3.39 (m, 3H), 3.11-3.03 (m, 2H), 2.83-2.71 (m, 2H), 2.30 (s, 3H), 2.29-2.11 (m, 2H), 1.93-1.79 (m, 2H).

Example 124 (S)-1-Cyclopropyl-N-(6-methyl-5-((3-(2-(piperidin-3-ylamino)pyrimidin-4-yl)pyridin-2-yl)oxy)naphthalen-1-yl)methanesulfonamide hydrochloride 124

Step 1: tert-Butyl (S)-3-((4-(2-((5-((cyclopropylmethyl)sulfonamido)-2-methylnaphthalen-1-yl)oxy)pyridin-3-yl)pyrimidin-2-yl)amino)piperidine-1-carboxylate

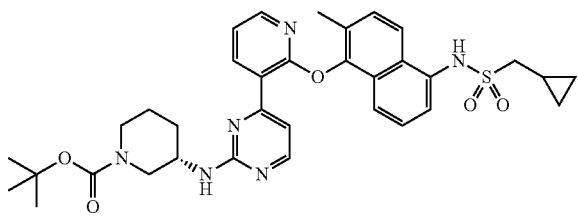 [SMILES: Cc1ccc2c(NS(=O)(=O)CC3CC3)cccc2c1Oc1ncccc1-c1ccnc(N[C@H]2CCCN(C(=O)OC(C)(C)C)C2)n1]

The General Procedure A was followed, using tert-butyl (S)-3-((4-(2-((5-amino-2-methylnaphthalen-1-yl)oxy)pyridin-3-yl)pyrimidin-2-yl)amino)piperidine-1-carboxylate from Example 101 (100 mg, 0.19 mmol), pyridine (2 mL) and cyclopropylmethanesulfonyl chloride (100 mg, 0.65 mmol). The crude was then purified by Prep-TLC (petroleum ether/ethyl acetate=1/1) to yield 120 mg (98% yield) of the title compound as a white solid. LCMS (ESI) [M+H]+=645.

Step 2: (S)-1-Cyclopropyl-N-(6-methyl-5-((3-(2-(piperidin-3-ylamino)pyrimidin-4-yl)pyridin-2-yl)oxy)naphthalen-1-yl)methanesulfonamide hydrochloride

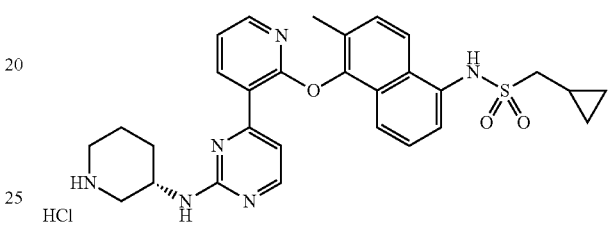

The General Procedure B was followed, using tert-butyl (S)-3-((4-(2-((5-((cyclopropylmethyl)sulfonamido)-2-methylnaphthalen-1-yl)oxy)pyridin-3-yl)pyrimidin-2-yl)amino)piperidine-1-carboxylate (120 mg, 0.19 mmol), DCM (4 mL) and hydrochloric acid (4 M in dioxane, 3 mL, 12 mmol). The residue was purified by Prep-HPLC to yield 97 mg (89% yield) of 124 as a yellow solid. LCMS (ESI): [M+H]$^+$=545; $^1$H-NMR: (400 MHz, CD$_3$OD) δ 8.68 (d, J=6.8 Hz, 1H), 8.46 (d, J=5.2 Hz, 1H), 8.16 (d, J=8.4 Hz, 1H), 8.01 (d, J=3.6 Hz, 1H), 7.74 (d, J=5.6 Hz, 1H), 7.63-7.54 (m, 3H), 7.41-7.37 (m, 1H), 7.24 (dd, J=4.8, 7.2 Hz, 1H), 4.43-4.32 (m, 1H), 3.66-3.62 (m, 1H), 3.39-3.36 (m, 1H), 3.13-3.03 (m, 4H), 2.29-2.11 (m, 5H), 1.92-1.80 (m, 2H), 1.21-1.12 (m, 1H), 0.66-0.61 (m, 2H), 0.37-0.33 (m, 2H).

Example 125 (S)—N-(6-Methyl-5-((3-(2-(piperidin-3-ylamino)pyrimidin-4-yl)pyridin-2-yl)oxy)naphthalen-1-yl)-1-(pyridin-3-yl)methanesulfonamide hydrochloride 125

Step 1: tert-Butyl (S)-3-((4-(2-((2-methyl-5-((pyridin-3-ylmethyl)sulfonamido)naphthalen-1-yl)oxy)pyridin-3-yl)pyrimidin-2-yl)amino)piperidine-1-carboxylate

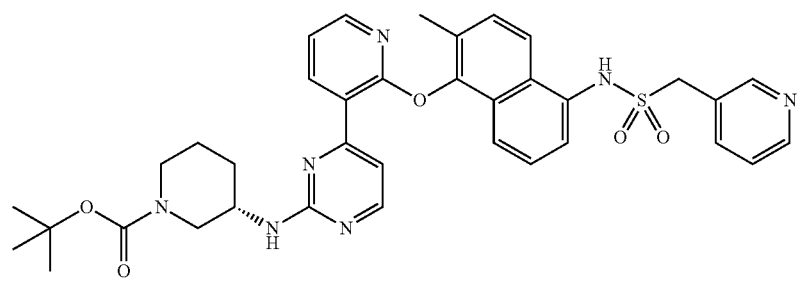 [SMILES: Cc1ccc2c(NS(=O)(=O)Cc3cccnc3)cccc2c1Oc1ncccc1-c1ccnc(N[C@H]2CCCN(C(=O)OC(C)(C)C)C2)n1]

The General Procedure A was followed, using tert-butyl (S)-3-((4-(2-((5-amino-2-methylnaphthalen-1-yl)oxy)pyridin-3-yl)pyrimidin-2-yl)amino)piperidine-1-carboxylate from Example 101 (100 mg, 0.19 mmol), pyridine (2 mL) and 3-pyridylmethanesulfonyl chloride (200 mg, 1.04 mmol). The crude was then purified by Prep-TLC (petroleum ether/ethyl acetate=1/1) to yield 25 mg (19% yield) of the title compound as a white solid. LCMS (ESI) [M+H]+=682.

Step 2: (S)—N-(6-Methyl-5-((3-(2-(piperidin-3-ylamino)pyrimidin-4-yl)pyridin-2-yl)oxy)naphthalen-1-yl)-1-(pyridin-3-yl)methanesulfonamide hydrochloride

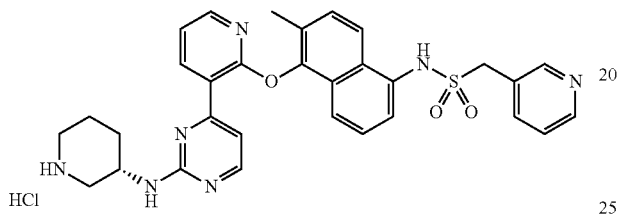

The General Procedure B was followed, using tert-butyl (S)-3-((4-(2-((2-methyl-5-((pyridin-3-ylmethyl)sulfonamido)naphthalen-1-yl)oxy)pyridin-3-yl)pyrimidin-2-yl)amino)piperidine-1-carboxylate (25 mg, 0.04 mmol), DCM (4 mL) and hydrochloric acid (4 M in dioxane, 1 mL, 4 mmol). The residue was purified by Prep-HPLC to yield 97 mg (89% yield) of 125 as a yellow solid. LCMS (ESI): [M+H]+=582; $^1$H-NMR: (400 MHz, CD$_3$OD) δ 8.86-8.79 (m, 3H), 8.59 (d, J=8.0 Hz, 1H), 8.49 (d, J=5.2 Hz, 1H), 8.11 (d, J=4.0 Hz, 1H), 8.04-7.98 (m, 2H), 7.91-7.87 (m, 1H), 7.69-7.58 (m, 3H), 7.45-7.41 (m, 1H), 7.34-7.31 (m, 1H), 4.92-4.83 (m, 2H), 4.62-4.47 (m, 1H), 3.69-3.62 (m, 1H), 3.43-3.36 (m, 1H), 3.13-3.09 (m, 2H), 2.31-2.13 (m, 5H), 1.98-1.81 (m, 2H).

Example 126 (S)—N-(6-Methyl-5-((3-(2-(piperidin-3-ylamino)pyrimidin-4-yl)pyridin-2-yl)oxy)naphthalen-1-yl)-1-(pyridin-2-yl)methanesulfonamide hydrochloride 126

Step 1: tert-Butyl (S)-3-((4-(2-((2-methyl-5-((pyridin-2-ylmethyl)sulfonamido)naphthalen-1-yl)oxy)pyridin-3-yl)pyrimidin-2-yl)amino)piperidine-1-carboxylate

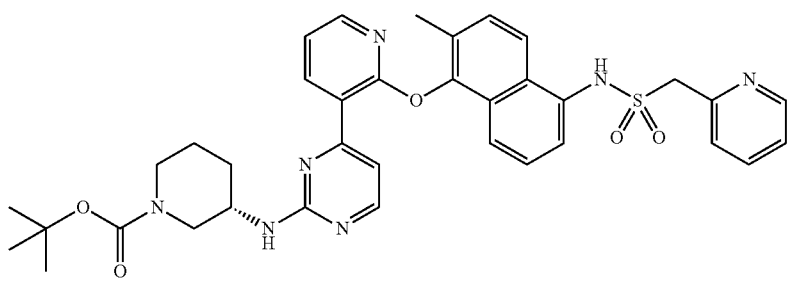 [SMILES: Cc1ccc2c(NS(=O)(=O)Cc3ccccn3)cccc2c1Oc1ncccc1-c1ccnc(N[C@H]2CCCN(C(=O)OC(C)(C)C)C2)n1]

The General Procedure A was followed, using tert-butyl (S)-3-((4-(2-((5-amino-2-methylnaphthalen-1-yl)oxy)pyridin-3-yl)pyrimidin-2-yl)amino)piperidine-1-carboxylate from Example 101 (100 mg, 0.19 mmol), pyridine (2 mL) and 2-pyridylmethanesulfonyl chloride (200 mg, 1.04 mmol). After addition completed, the reaction mixture was stirred at 40° C. overnight. The crude was then purified by Prep-TLC (petroleum ether/ethyl acetate=1/1) to yield 85 mg (65% yield) of the title compound as a white solid. LCMS (ESI) [M+H]+=682.

Step 2: (S)—N-(6-Methyl-5-((3-(2-(piperidin-3-ylamino)pyrimidin-4-yl)pyridin-2-yl)oxy)naphthalen-1-yl)-1-(pyridin-2-yl)methanesulfonamide hydrochloride

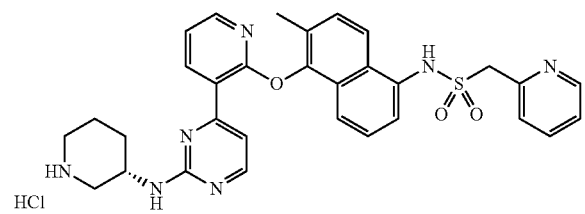

The General Procedure B was followed, using tert-butyl (S)-3-((4-(2-((2-methyl-5-((pyridin-2-ylmethyl)sulfonamido)naphthalen-1-yl)oxy)pyridin-3-yl)pyrimidin-2-yl)amino)piperidine-1-carboxylate (25 mg, 0.04 mmol), DCM (4 mL) and hydrochloric acid (4 M in dioxane, 1 mL, 4 mmol). The residue was purified by Prep-HPLC to yield 25 mg (32% yield) of 126 as a yellow solid. LCMS (ESI): [M+H]+=582; $^1$H-NMR: (400 MHz, CD$_3$OD) δ 8.86-8.79 (m, 3H), 8.59 (d, J=8.0 Hz, 1H), 8.49 (d, J=5.2 Hz, 1H), 8.11 (d, J=4.0 Hz, 1H), 8.04-7.98 (m, 2H), 7.91-7.87 (m, 1H), 7.69-7.58 (m, 3H), 7.45-7.41 (m, 1H), 7.34-7.31 (m, 1H), 4.92-4.83 (m, 2H), 4.62-4.47 (m, 1H), 3.69-3.62 (m, 1H), 3.43-3.36 (m, 1H), 3.13-3.09 (m, 2H), 2.31-2.13 (m, 5H), 1.98-1.81 (m, 2H).

Example 127 (S)-1-Cyclobutyl-N-(6-methyl-5-((3-(2-(piperidin-3-ylamino)pyrimidin-4-yl) pyridin-2-yl)oxy)naphthalen-1-yl)methanesulfonamide 127

Step 1: (S)-tert-Butyl 3-((4-(2-((5-(cyclobutylmethylsulfonamido)-2-methylnaphthalen-1-yl)oxy)pyridin-3-yl)pyrimidin-2-yl)amino)piperidine-1-carboxylate

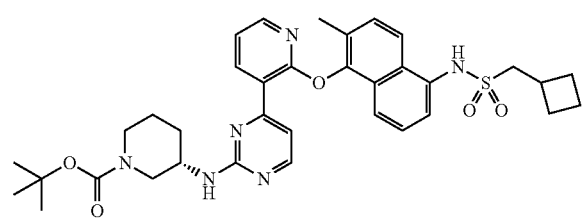 [SMILES: Cc1ccc2c(NS(=O)(=O)CC3CCC3)cccc2c1Oc1ncccc1-c1ccnc(N[C@H]2CCCN(C(=O)OC(C)(C)C)C2)n1]

The General Procedure A was followed, using (S)-tert-butyl 3-((4-(2-((5-amino-2-methylnaphthalen-1-yl)oxy)pyridin-3-yl)pyrimidin-2-yl)amino)piperidine-1-carboxylate (100 mg, 0.19 mmol), pyridine (2 mL) and cyclobutylmethanesulfonyl chloride (38 mg, 0.23 mmol). The mixture was concentrated, dissolved in dichloromethane (20 mL) and washed with H$_2$O (15 mL×2). The organic phase was dried over anhydrous sodium sulfate, concentrated to yield 100 mg (crude) of the title compound as a brown oil. LCMS (ESI) [M+H]+=659.2.

Step 2: (S)-1-Cyclobutyl-N-(6-methyl-5-((3-(2-(piperidin-3-ylamino)pyrimidin-4-yl)pyridin-2-yl)oxy)naphthalen-1-yl)methanesulfonamide The General Procedure B was followed, using (S)-tert-butyl 3-((4-(2-((5-(cyclobutylmethylsulfonamido)-2-methylnaphthalen-1-yl)oxy)pyridin-3-yl)pyrimidin-2-yl)amino)piperidine-1-carboxylate (100 mg, 0.15 mmol), dichloromethane (1 mL) and hydrochloric acid (4 M in ethyl acetate, 0.4 mL, 1.6 mmol). The residue was purified by Prep-HPLC (mobile phase: A: water (0.05% HCl); B: ACN) to yield 28 mg (30%, HCl salt) of 127 as a brown solid. LCMS (ESI) [M+H]+=559.1; $^1$H NMR (400 MHz, DMSO-d$_6$) δ 9.79 (s, 1H), 9.31-9.01 (m., 2H), 8.85-8.59 (m, 1H), 8.48 (d, J=5.2 Hz, 1H), 8.12 (d, J=8.4 Hz, 1H), 8.09-8.04 (m, 1H), 7.76-7.58 (m, 2H), 7.56-7.49 (m, 2H), 7.48-7.38 (m, 2H), 7.31-7.24 (m, 1H), 4.50-4.05 (m, 1H), 3.47-3.38 (m, 1H), 3.30-3.26 (m, 2H), 3.24-3.15 (m, 1H), 2.91-2.73 (m, 3H), 2.21 (s, 3H), 2.11-2.00 (m, 3H), 1.94-1.74 (m, 6H), 1.69-1.58 (m, 1H).

Example 128 (S)-1-Cyclopentyl-N-(6-methyl-5-((3-(2-(piperidin-3-ylamino)pyrimidin-4-yl)pyridin-2-yl)oxy)naphthalen-1-yl)methanesulfonamide 128

Step 1: (S)-tert-Butyl 3-((4-(2-((5-(cyclopentylmethylsulfonamido)-2-methylnaphthalen-1-yl)oxy)pyridin-3-yl)pyrimidin-2-yl)amino)piperidine-1-carboxylate

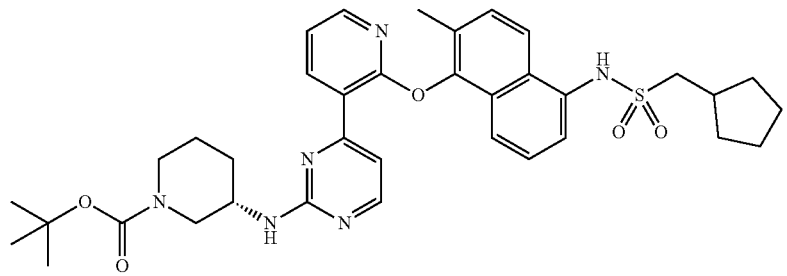 [SMILES: Cc1ccc2c(NS(=O)(=O)CC3CCCC3)cccc2c1Oc1ncccc1-c1ccnc(N[C@H]2CCCN(C(=O)OC(C)(C)C)C2)n1]

The General Procedure A was followed, using tert-butyl (3S)-3-[[4-[2-[(5-amino-2-methyl-1-naphthyl)oxy]-3-pyridyl]pyrimidin-2-yl]amino]piperidine-1-carboxylate (100 mg, 0.19 mmol), pyridine (2 mL) and cyclopentylmethanesulfonyl chloride (38 mg, 0.21 mmol). The resulting solution was extracted with ethyl acetate. The combined organic layers were dried over anhydrous sodium sulfate, and concentrated in vacuo to yield 110 mg of the crude title compound as a yellow solid. LCMS (ESI) [M+Na]$^+$=695.1.

Step 2: (S)-tert-Butyl 3-((4-(2-((5-(cyclopentylmethylsulfonamido)-2-methylnaphthalen-1-yl)oxy)pyridin-3-yl)pyrimidin-2-yl)amino)piperidine-1-carboxylate

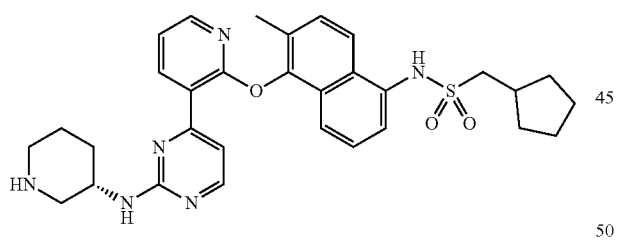

The General Procedure B was followed, using tert-butyl (3S)-3-[[4-[2-[[2-methyl-5-(sec-butylsulfonylamino)-1-naphthyl]oxy]-3-pyridyl]pyrimidin-2-yl]amino]piperidine-1-carboxylate (110 mg, 0.16 mmol), dichloromethane (2 mL) and hydrochloric acid (4 M in dioxane, 2 mL, 8 mmol). The residue was purified by Prep-HPLC (mobile phase: A: water (0.05% HCl); B: ACN) to yield 22.8 mg (22%, yield HCl salt) of 128 as a yellow solid. LCMS (ESI) [M+H]$^+$=573.1. $^1$H NMR (400 MHz, DMSO-d$_6$) δ 9.82 (s, 1H), 9.22 (s, 2H), 8.49 (d, J=4.8 Hz, 1H), 8.14 (d, J=8.8 Hz, 1H), 8.07 (s., 1H), 7.65 (s., 1H), 7.57-7.54 (m, 2H), 7.48-7.38 (m, 2H), 7.30-7.27 (m, 1H), 4.38 (s, 1H), 3.80 (s, 1H), 3.45-3.40 (m, 1H), 3.19 (d, J=6.4 Hz, 2H), 2.89-2.78 (m, 2H), 2.33-2.27 (m, 1H), 2.21 (s, 3H), 2.06-1.77 (m, 5H), 1.68-1.43 (m, 5H), 1.32-1.19 (m, 2H).

Example 129 (S)-2-Cyclopropyl-N-(6-methyl-5-((3-(2-(piperidin-3-ylamino)pyrimidin-4-yl)pyridin-2-yl)oxy)naphthalen-1-yl)ethanesulfonamide 129

Step 1: (S)-tert-Butyl 3-((4-(2-((5-(2-cyclopropyl-ethylsulfonamido)-2-methylnaphthalen-1-yl)oxy)pyridin-3-yl)pyrimidin-2-yl)amino)piperidine-1-carboxylate

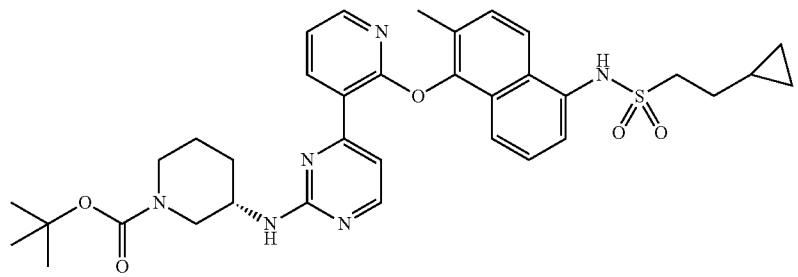 [SMILES: Cc1ccc2c(NS(=O)(=O)CCC3CC3)cccc2c1Oc1ncccc1-c1ccnc(N[C@H]2CCCN(C(=O)OC(C)(C)C)C2)n1]

The General Procedure A was followed, using (S)-tert-butyl 3-((4-(2-((5-amino-2-methylnaphthalen-1-yl)oxy)pyridin-3-yl)pyrimidin-2-yl)amino)piperidine-1-carboxylate (100 mg, 0.19 mmol), pyridine (2 mL) and 2-cyclopropylethanesulfonyl chloride (38 mg, 0.23 mmol). The mixture was concentrated, dissolved in dichloromethane (20 mL), and washed with $H_2O$ (15 mL×2). The organic phase was dried over anhydrous sodium sulfate, concentrated to give 100 mg (crude) of the title compound as a brown oil. LCMS (ESI) $[M+H]^+$=659.1.

Step 2: (S)-2-Cyclopropyl-N-(6-methyl-5-((3-(2-(piperidin-3-ylamino)pyrimidin-4-yl)pyridin-2-yl)oxy)naphthalen-1-yl)ethanesulfonamide

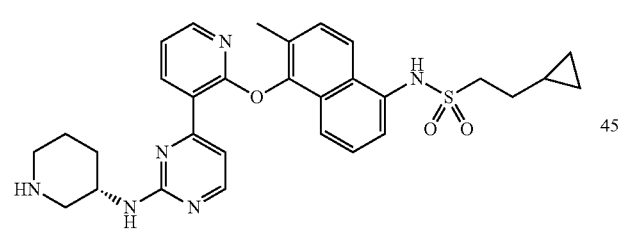

The General Procedure B was followed, using (S)-tert-butyl 3-((4-(2-((5-(2-cyclopropylethylsulfonamido)-2-methylnaphthalen-1-yl)oxy)pyridin-3-yl)pyrimidin-2-yl)amino) piperidine-1-carboxylate (100 mg, 0.15 mmol), dichloromethane (1 mL) and hydrochloric acid (4 M in ethyl acetate, 0.4 mL, 1.6 mmol). The residue was purified via Prep-HPLC (mobile phase: A: water (0.05% HCl); B: ACN) to yield 26 mg (28%, yield HCl salt) of 129 as a brown solid. LCMS (ESI) $[M+H]^+$=559.1; $^1$H NMR (400 MHz, DMSO-$d_6$) δ 9.85 (s, 1H), 9.51-9.14 (m, 2H), 8.90-8.67 (m, 1H), 8.50 (d, J=5.2 Hz, 1H), 8.13 (d, J=8.4 Hz, 1H), 8.09-8.06 (m, 1H), 7.94-7.62 (m, 2H), 7.59-7.53 (m, 2H), 7.48-7.40 (m, 2H), 7.31-7.25 (m, 1H), 4.51-4.27 (m, 1H), 3.47-3.37 (m, 1H), 3.26-3.15 (m, 3H), 2.89-2.79 (m, 2H), 2.22 (s, 3H), 2.07-1.98 (m, 1H), 1.96-1.87 (m, 1H), 1.85-1.72 (m, 1H), 1.70-1.60 (m, 3H), 0.86-0.72 (m, 1H), 0.42-0.35 (m, 2H), 0.09-0.01 (m, 2H).

Example 130 (S)-2-Cyclohexyl-N-(6-methyl-5-((3-(2-(piperidin-3-ylamino)pyrimidin-4-yl)pyridin-2-yl)oxy)naphthalen-1-yl)acetamide 130

Step 1: (S)-tert-Butyl 3-((4-(2-((5-(2-cyclohexylacetamido)-2-methylnaphthalen-1-yl)oxy)pyridin-3-yl)pyrimidin-2-yl)amino)piperidine-1-carboxylate

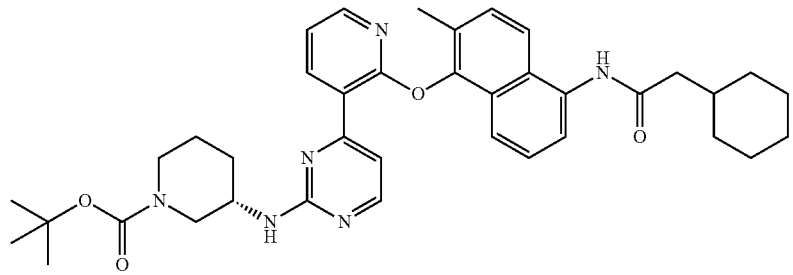 [SMILES: Cc1ccc2c(NC(=O)CC3CCCCC3)cccc2c1Oc1ncccc1-c1ccnc(N[C@H]2CCCN(C(=O)OC(C)(C)C)C2)n1]

The General Procedure A was followed, using (S)-tert-butyl 3-((4-(2-((5-amino-2-methylnaphthalen-1-yl)oxy)pyridin-3-yl)pyrimidin-2-yl)amino)piperidine-1-carboxylate (100 mg, 0.19 mmol), pyridine (2 mL) and 2-cyclohexylacetyl chloride (46 mg, 0.28 mmol). The mixture was concentrated, dissolved in dichloromethane (20 mL) and washed with $H_2O$ (15 mL×2). The organic phase was dried over anhydrous sodium sulfate and concentrated in vacuo to give 100 mg (crude) of the title compound as a brown oil. LCMS (ESI) $[M+H]^+$=651.3

Step 2: (S)-2-Cyclohexyl-N-(6-methyl-5-((3-(2-(piperidin-3-ylamino)pyrimidin-4-yl)pyridin-2-yl)oxy)naphthalen-1-yl)acetamide

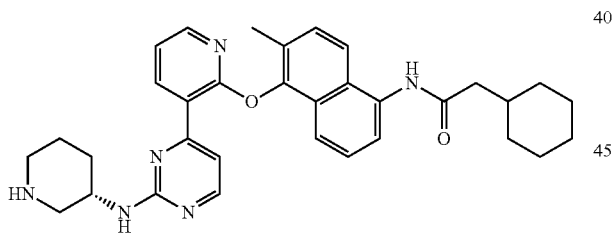

The General Procedure B was followed, using (S)-tert-butyl 3-((4-(2-((5-(2-cyclohexylacetamido)-2-methylnaphthalen-1-yl)oxy)pyridin-3-yl)pyrimidin-2-yl)amino)piperidine-1-carboxylate (100 mg, 0.15 mmol), dichloromethane (1 mL) and hydrochloric acid (4 M in ethyl acetate, 0.4 mL, 1.6 mmol). The residue was purified by Prep-HPLC (mobile phase: A: water (0.05% HCl); B: ACN) to yield 54 mg (59%, yield HCl salt) of 130 as a brown solid. LCMS (ESI) $[M+H]^+$=551.3; $^1$H NMR (400 MHz, DMSO-$d_6$) δ 9.95 (s, 1H), 9.45-9.11 (m, 2H), 8.90-8.67 (m, 1H), 8.50 (d, J=5.2 Hz, 1H), 8.07 (d, J=4.8 Hz, 1H), 7.95-7.89 (m, 1H), 7.87-7.73 (m, 1H), 7.67-7.57 (m, 2H), 7.54-7.45 (m, 2H), 7.42-7.37 (m, 1H), 7.30-7.25 (m, 1H), 4.46-4.33 (m, 1H), 3.49-3.36 (m, 1H), 3.25-3.14 (m, 1H), 2.91-2.76 (m, 2H), 2.40-2.36 (m, 2H), 2.22 (s, 3H), 2.07-1.98 (m, 1H), 1.96-1.88 (m, 1H), 1.83-1.61 (m, 8H), 1.32-1.15 (m, 3H), 1.12-1.00 (m, 2H).

Example 131 (S)—N-(6-Methyl-5-((3-(2-(piperidin-3-ylamino)pyrimidin-4-yl)pyridin-2-yl)oxy)naphthalen-1-yl)cyclobutanecarboxamide 131

Step 1: (S)-tert-Butyl 3-((4-(2-((5-(cyclobutanecarboxamido)-2-methylnaphthalen-1-yl)oxy)pyridin-3-yl)pyrimidin-2-yl)amino)piperidine-1-carboxylate

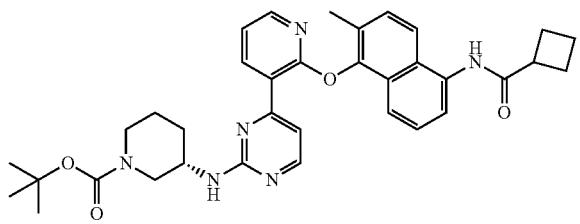 [SMILES: Cc1ccc2c(NC(=O)C3CCC3)cccc2c1Oc1ncccc1-c1ccnc(N[C@H]2CCCN(C(=O)OC(C)(C)C)C2)n1]

The General Procedure A was followed, using (S)-tert-butyl 3-((4-(2-((5-amino-2-methylnaphthalen-1-yl)oxy)pyridin-3-yl)pyrimidin-2-yl)amino)piperidine-1-carboxylate (100 mg, 0.19 mmol), pyridine (2 mL) and cyclobutanecarbonyl chloride (34 mg, 0.28 mmol). The mixture was concentrated, dissolved in dichloromethane (20 mL) and washed with H₂O (15 mL×2). The organic phase was dried over anhydrous sodium sulfate and concentrated in vacuo to yield 100 mg (crude) of the title compound as a yellow oil.

Step 2: (S)—N-(6-Methyl-5-((3-(2-(piperidin-3-ylamino)pyrimidin-4-yl)pyridin-2-yl)oxy)naphthalen-1-yl)cyclobutanecarboxamide

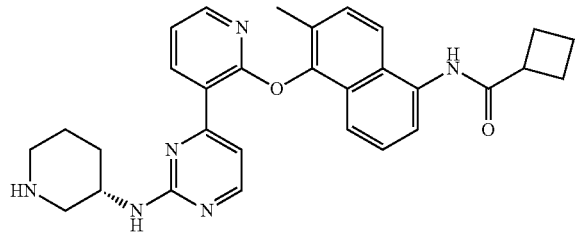 [SMILES: Cc1ccc2c(NC(=O)C3CCC3)cccc2c1Oc1ncccc1-c1ccnc(N[C@H]2CCCNC2)n1]

The General Procedure B was followed, using (S)-tert-butyl 3-((4-(2-((5-(cyclobutanecarboxamido)-2-methylnaphthalen-1-yl)oxy)pyridin-3-yl)pyrimidin-2-yl)amino)piperidine-1-carboxylate (100 mg, 0.16 mmol), dichloromethane (1 mL) and hydrochloric acid (4 M in ethyl acetate, 0.4 mL, 1.6 mmol). The residue was purified by Prep-HPLC (mobile phase: A: water (0.05% HCl); B: ACN) to yield 66 mg (72%, yield HCl salt) of 131 as a yellow solid. LCMS (ESI) [M+H]⁺=509.2; ¹H NMR (400 MHz, DMSO-d₆) δ 9.86 (s, 1H), 9.77-9.53 (m, 1H), 9.45-9.27 (m, 1H), 9.00-8.81 (m, 1H), 8.53 (d, J=4.8 Hz, 1H), 8.42-8.22 (m, 1H), 8.16-8.06 (m, 1H), 7.89 (d, J=8.4 Hz, 1H), 7.83-7.71 (m, 1H), 7.61 (d, J=6.8 Hz, 1H), 7.53-7.46 (m, 2H), 7.43-7.37 (m, 1H), 7.31-7.26 (m, 1H), 4.61-4.35 (m, 1H), 3.54-3.38 (m, 2H), 3.24-3.14 (m, 1H), 2.92-2.79 (m, 2H), 2.35-2.26 (m, 2H), 2.24-2.15 (m, 5H), 2.08-1.78 (m, 5H), 1.74-1.59 (m, 1H).

Example 132 (S)-3-Methoxy-N-(6-methyl-5-((3-(2-(piperidin-3-ylamino)pyrimidin-4-yl)pyridin-2-yl)oxy)naphthalen-1-yl)propane-1-sulfonamide hydrochloride 132

Step 1: tert-Butyl (S)-3-((4-(2-((5-((3-methoxypropyl)sulfonamido)-2-methylnaphthalen-1-yl)oxy)pyridin-3-yl)pyrimidin-2-yl)amino)piperidine-1-carboxylate

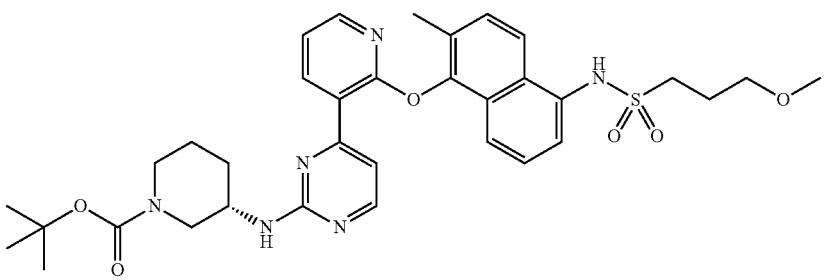 [SMILES: COCCCS(=O)(=O)Nc1cccc2c(Oc3ncccc3-c3ccnc(N[C@H]4CCCN(C(=O)OC(C)(C)C)C4)n3)c(C)ccc12]

The General Procedure A was followed, using tert-butyl (S)-3-((4-(2-((5-amino-2-methylnaphthalen-1-yl)oxy)pyridin-3-yl)pyrimidin-2-yl)amino)piperidine-1-carboxylate from Example 101 (100 mg, 0.19 mmol), pyridine (3 mL) and 3-methoxypropane-1-sulfonyl chloride (32 mg, 0.19 mmol). LCMS (ESI) [M+H]+=689.

Step 2: (S)-3-Methoxy-N-(6-methyl-5-((3-(2-(piperidin-3-ylamino)pyrimidin-4-yl)pyridin-2-yl)oxy)naphthalen-1-yl)propane-1-sulfonamide hydrochloride

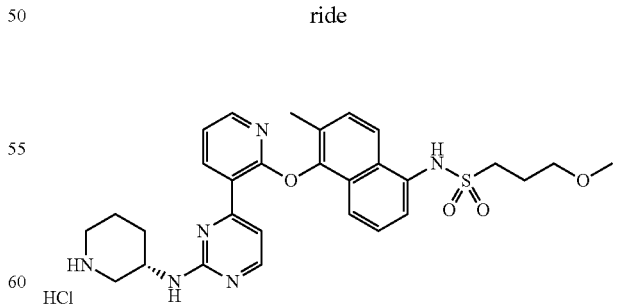

The General Procedure B was followed, using crude tert-butyl (S)-3-((4-(2-((5-((3-methoxypropyl)sulfonamido)-2-methylnaphthalen-1-yl)oxy)pyridin-3-yl)pyrimidin-2-yl)amino)piperidine-1-carboxylate, DCM (4 mL) and hydrochloric acid (4 M in dioxane, 3 mL, 12 mmol). The residue was purified by Prep-HPLC to yield 59 mg (52% yield over 2 steps) of 132 as a white solid. LCMS (ESI): [M+H]+=589; $^1$H-NMR: (400 MHz, CD$_3$OD) 1HNMR (400 MHz, CD3OD) δ 8.68 (d, J=6.9 Hz, 1H), 8.47 (d, J=5.5 Hz, 1H), 8.15 (d, J=9.7 Hz, 1H), 8.01 (d, J=4.7 Hz, 1H), 7.73 (s, 1H), 7.65 (d, J=8.5 Hz, 1H), 7.56 (d, J=8.1 Hz, 2H), 7.40 (t, J=7.9 Hz, 1H), 7.27-7.23 (m, 1H), 4.38 (s, 1H), 3.64 (dd, J=12.2, 2.8 Hz, 1H), 3.47 (t, J=6.0 Hz, 2H), 3.37 (s, 1H), 3.29 (s, 1H), 3.25-3.22 (m, 2H), 3.10-3.03 (m, 2H), 2.29 (s, 3H), 2.23-2.07 (m, 4H), 1.93-1.80 (m, 2H).

Example 133 (S)—N-(6-Methyl-5-((3-(2-(piperidin-3-ylamino)pyrimidin-4-yl)pyridin-2-yl)oxy)naphthalen-1-yl)-1-(tetrahydro-2H-pyran-4-yl)methanesulfonamide hydrochloride 133

Step 1: tert-Butyl (S)-3-((4-(2-((2-methyl-5-(((tetrahydro-2H-pyran-4-yl)methyl)sulfonamido)naphthalen-1-yl)oxy)pyridin-3-yl)pyrimidin-2-yl)amino)piperidine-1-carboxylate

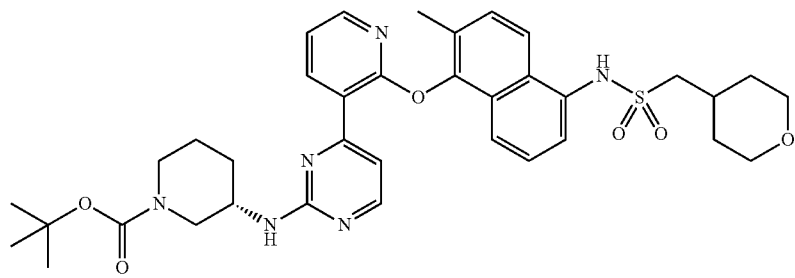 [SMILES: Cc1ccc2c(NS(=O)(=O)CC3CCOCC3)cccc2c1Oc1ncccc1-c1ccnc(N[C@H]2CCCN(C(=O)OC(C)(C)C)C2)n1]

The General Procedure A was followed, using tert-butyl (S)-3-((4-(2-((5-amino-2-methylnaphthalen-1-yl)oxy)pyridin-3-yl)pyrimidin-2-yl)amino)piperidine-1-carboxylate from Example 101 (100 mg, 0.19 mmol), pyridine (2 mL) and tetrahydropyran-4-ylmethanesulfonyl chloride (45 mg, 0.19 mmol). LCMS (ESI) [M+H]+=689.

Step 2: (S)—N-(6-Methyl-5-((3-(2-(piperidin-3-ylamino)pyrimidin-4-yl)pyridin-2-yl)oxy)naphthalen-1-yl)-1-(tetrahydro-2H-pyran-4-yl)methanesulfonamide hydrochloride

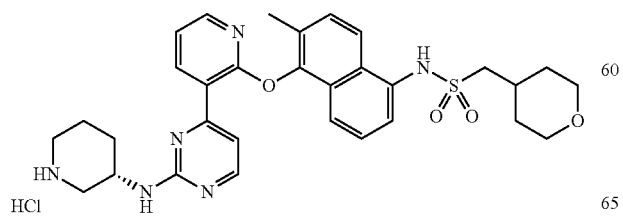

The General Procedure B was followed, using crude tert-butyl (S)-3-((4-(2-((2-methyl-5-(((tetrahydro-2H-pyran-4-yl)methyl)sulfonamido)naphthalen-1-yl)oxy)pyridin-3-yl)pyrimidin-2-yl)amino)piperidine-1-carboxylate, DCM (4 mL) and hydrochloric acid (4 M in dioxane, 3 mL, 12 mmol). The residue was purified by Prep-HPLC to yield 59 mg (52% yield over 2 steps) of 133 as a white solid. LCMS (ESI): [M+H]+=589; $^1$HNMR (400 MHz, CD$_3$OD) δ 8.70 (s, 1H), 8.46 (d, J=5.4 Hz, 1H), 8.14 (d, J=8.8 Hz, H), 8.02 (d, J=4.5 Hz, 1H), 7.77 (s, 1H), 7.65 (d, J=8.4 Hz, 1H), 7.56 (d, J=8.0 Hz, 2H), 740 (t, J=7.5 Hz, 1H), 7.25 (q, J=4.8 Hz, 1H), 4.41 (s, 1H), 3.91-3.88 (m, 2H), 3.65 (d, J=11.5 Hz, 1H), 3.40 (t, J=11.8 Hz, 3H), 3.12-3.04 (m, 4H), 2.29 (s, 3H), 2.26-2.11 (m, 3H), 1.96-1.80 (m, 4H), 1.45-1.35 (m, 2H).

Example 134 N-(6-Methyl-5-((3-(2-((S)-piperidin-3-ylamino)pyrimidin-4-yl)pyridin-2-yl)oxy)naphthalen-1-yl) butane-2-sulfonamide 134

Step 1: (3S)-tert-Butyl 3-((4-(2-((2-methyl-5-(1-methylpropylsulfonamido)naphthalen-1-yl)oxy)pyridin-3-yl)pyrimidin-2-yl)amino)piperidine-1-carboxylate

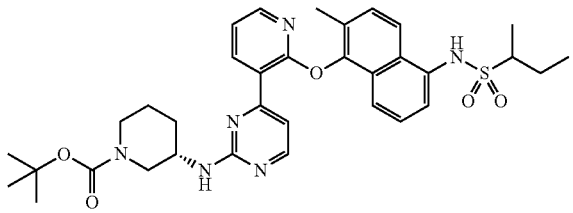

The General Procedure A was followed, using tert-butyl (3S)-3-[[4-[2-[(5-amino-2-methyl-1-naphthyl)oxy]-3-pyridyl]pyrimidin-2-yl]amino]piperidine-1-carboxylate (100 mg, 0.19 mmol), pyridine (2 mL) and butane-2-sulfonyl chloride (45 mg, 0.28 mmol). The resulting solution was extracted with ethyl acetate. The combined organic layers were dried over anhydrous sodium sulfate, and concentrated in vacuo to yield 110 mg of the crude title compound as a yellow solid. LCMS (ESI) [M+H]+=647.1.

Step 2: N-(6-Methyl-5-((3-(2-((S)-piperidin-3-ylamino)pyrimidin-4-yl)pyridin-2-yl)oxy)naphthalen-1-yl)butane-2-sulfonamide

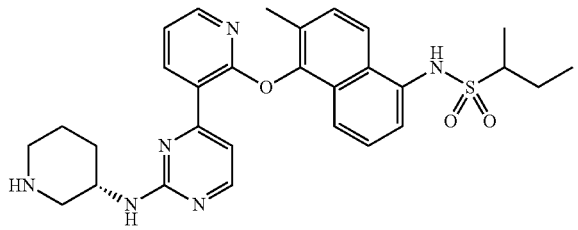 [SMILES: CCC(C)S(=O)(=O)Nc1cccc2c(Oc3ncccc3-c3ccnc(N[C@H]4CCCNC4)n3)c(C)ccc12]

The General Procedure B was followed, using tert-butyl (3S)-3-[[4-[2-[[2-methyl-5-(sec-butylsulfonylamino)-1-naphthyl]oxy]-3-pyridyl]pyrimidin-2-yl]amino]piperidine-1-carboxylate (100 mg, 0.15 mmol), dichloromethane (2 mL) and hydrochloric acid (4 M in dioxane, 2 mL, 8 mmol). The residue was purified by Prep-HPLC (mobile phase: A: water (0.05% HCl); B: ACN) to yield 38.4 mg (42%, yield HCl salt) of 134 as a yellow solid and as a racemic mixture of enantiomers. LCMS (ESI) [M+H]+=547.1. $^1$H NMR (400 MHz, DMSO-d$_6$) δ 9.81 (s, 1H), 9.49 (s, 1H), 9.22 (s, 1H), 8.84 (s, 1H), 8.50 (d, J=5.2 Hz, 1H), 8.15 (d, J=8.4 Hz, 1H), 8.08 (s, 1H), 7.70 (s, 1H), 7.58-7.52 (m, 2H), 7.50-7.45 (m, 1H), 7.44-7.37 (m, 1H), 7.32-7.26 (m, 1H), 4.50-4.30 (m, 1H), 3.45-3.40 (m, 1H), 3.25-3.16 (m, 1H), 3.15-3.05 (m, 1H), 2.95-2.80 (m, 2H), 2.23 (s, 3H), 2.02-1.82 (m, 3H), 1.81-1.70 (m, 1H), 1.69-1.55 (m, 1H), 1.51-1.47 (m, 1H), 1.31 (d, J=6.4 Hz, 3H), 0.94 (d, J=6.8 Hz, 3H).

Example 135 (S)-1-(2-Chlorophenyl)-N-(6-methyl-5-((3-(2-(piperidin-3-ylamino) pyrimidin-4-yl)pyridin-2-yl)oxy)naphthalen-1-yl)methanesulfonamide 135

Step 1: (S)-tert-Butyl 3-((4-(2-((5-((2-chlorophenyl)methylsulfonamido)-2-methylnaphthalen-1-yl)oxy)pyridin-3-yl)pyrimidin-2-yl)amino)piperidine-1-carboxylate

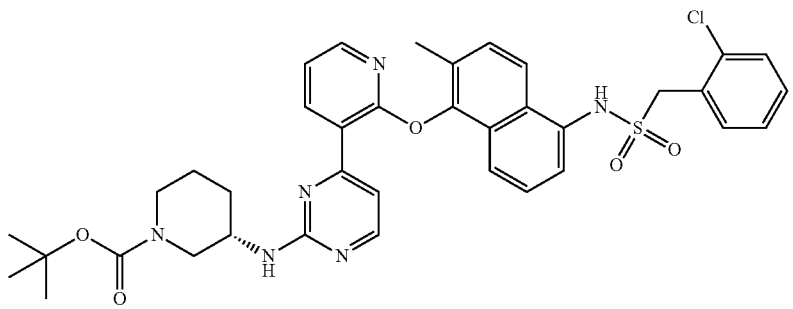 [SMILES: Cc1ccc2c(NS(=O)(=O)Cc3ccccc3Cl)cccc2c1Oc1ncccc1-c1ccnc(N[C@H]2CCCN(C(=O)OC(C)(C)C)C2)n1]

The General Procedure A was followed, using tert-butyl (3S)-3-[[4-[2-[(5-amino-2-methyl-1-naphthyl)oxy]-3-pyridyl]pyrimidin-2-yl]amino]piperidine-1-carboxylate (100 mg, 0.19 mmol), pyridine (2 mL) and (2-chlorophenyl)methanesulfonyl chloride (47 mg, 0.21 mmol). The reaction mixture was concentrated and the residue taken up in ethyl acetate (20 mL) and then washed with water (10 mL). The organic phase was dried over anhydrous sodium sulfate and concentrated in vacuo to yield (140 mg crude) of the title compound as a pale brown oil. LCMS (ESI) [M+H]$^+$=715.2.

Step 2: (S)-1-(2-Chlorophenyl)-N-(6-methyl-5-((3-(2-(piperidin-3-ylamino)pyrimidin-4-yl) pyridin-2-yl)oxy)naphthalen-1-yl)methanesulfonamide

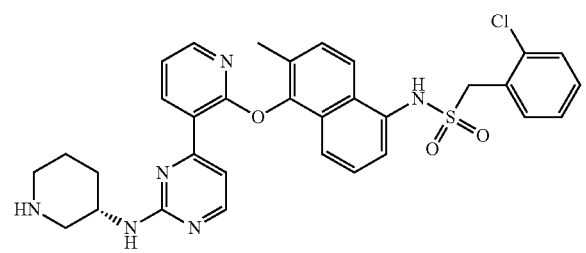 [SMILES: Cc1ccc2c(NS(=O)(=O)Cc3ccccc3Cl)cccc2c1Oc1ncccc1-c1ccnc(N[C@H]2CCCNC2)n1]

The General Procedure B was followed, using (S)-tert-butyl 3-((4-(2-((5-((2-chlorophenyl) methylsulfonamido)-2-methylnaphthalen-1-yl)oxy)pyridin-3-yl)pyrimidin-2-yl) amino) piperidine-1-carboxylate ((140 mg, 0.20 mmol)), ethyl acetate (2 mL) and hydrochloric acid (4 M in ethyl acetate, 2 mL, 8 mmol). The residue was purified by Prep-HPLC (mobile phase: A: water (0.05% HCl); B: ACN) to yield 59 mg (46%, yield HCl salt) of 135 as a white solid. LCMS (ESI): [M+H]$^+$=615.1; $^1$H NMR (400 MHz, DMSO-d$_6$) δ 10.12 (s, 1H), 9.35-8.78 (m, 2H), 8.49 (d, J=5.6 Hz, 1H), 8.10-8.06 (m, 2H), 7.80-7.60 (m, 1H), 7.58-7.32 (m, 8H), 7.30-7.25 (m, 1H), 4.72 (s, 2H), 4.40-4.35 (m, 1H), 3.45-3.40 (m, 1H), 3.22-3.17 (m, 1H), 2.80-2.70 (m, 2H), 2.22 (s, 3H), 2.05-1.90 (m, 2H), 1.88-1.63 (m, 2H).

Example 136 (S)—N-(6-Methyl-5-((3-(2-(piperidin-3-ylamino)pyrimidin-4-yl)pyridin-2-yl)oxy)naphthalen-1-yl) butane-1-sulfonamide 136

Step 1: (S)-tert-Butyl 3-((4-(2-((5-(butylsulfonamido)-2-methylnaphthalen-1-yl)oxy)pyridin-3-yl) pyrimidin-2-yl)amino)piperidine-1-carboxylate

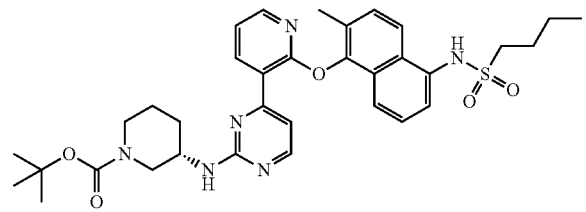 [SMILES: CCCCS(=O)(=O)Nc1cccc2c(Oc3ncccc3-c3ccnc(N[C@H]4CCCN(C(=O)OC(C)(C)C)C4)n3)c(C)ccc12]

The General Procedure A was followed, using tert-butyl (3S)-3-[[4-[2-[(5-amino-2-methyl-1-naphthyl)oxy]-3-pyridyl]pyrimidin-2-yl]amino]piperidine-1-carboxylate (100 mg, 0.19 mmol), pyridine (3 mL) and 1-butanesulfonyl chloride (36 mg, 0.23 mmol). The solution was concentrated to afford 120 mg of the crude title compound as a brown solid. LCMS (ESI) [M+H]$^+$=647.1.

Step 2: (S)—N-(6-Methyl-5-((3-(2-(piperidin-3-ylamino)pyrimidin-4-yl)pyridin-2-yl)oxy)naphthalen-1-yl)butane-1-sulfonamide

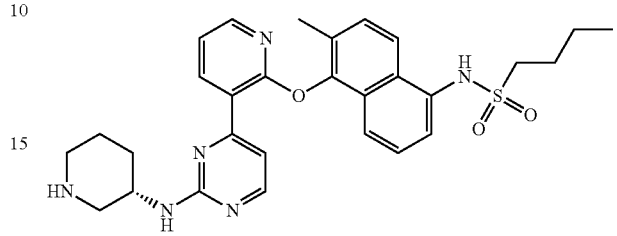

The General Procedure B was followed, using (S)-tert-butyl 3-((4-(2-((5-(butylsulfonamido)-2-methylnaphthalen-1-yl)oxy)pyridin-3-yl)pyrimidin-2-yl)amino)piperidine-1-carboxylate (100 mg, 0.15 mmol), dichloromethane (5 mL) and hydrochloric acid (4 M in ethyl acetate, 2 mL, 8 mmol). The residue was purified by Prep-HPLC (mobile phase: A: water (0.05% HCl); B: ACN) to yield 67 mg (80%, yield HCl salt) of 136 as a white solid. LCMS (ESI): [M+H]$^+$=547.1; $^1$H NMR (400 MHz, DMSO-d$_6$) δ 9.85 (s, 1H), 9.72 (s, 1H), 9.36 (s, 1H), 8.92 (s, 1H), 8.53 (d, J=5.2 Hz, 1H), 8.18-8.06 (m, 2H), 7.79 (s, 1H), 7.60-7.51 (m, 2H), 7.48-7.39 (m, 2H), 7.31-7.26 (m, 1H), 4.66-4.41 (m, 1H), 3.48-3.36 (m, 2H), 3.17-3.10 (m, 2H), 2.86 (d, J=10.0 Hz, 2H), 2.22 (s, 3H), 2.08-1.88 (m, 2H), 1.87-1.59 (m, 4H), 1.42-1.38 (m, 2H), 0.85 (t, J=7.2 Hz, 3H).

Example 137 (S)-2-Methoxy-N-(6-methyl-5-((3-(2-(piperidin-3-ylamino)pyrimidin-4-yl)pyridin-2-yl)oxy)naphthalen-1-yl)ethanesulfonamide 137

Step 1: (S)-tert-Butyl 3-((4-(2-((5-(2-methoxyethylsulfonamido)-2-methylnaphthalen-1-yl)oxy)pyridin-3-yl)pyrimidin-2-yl)amino)piperidine-1-carboxylate

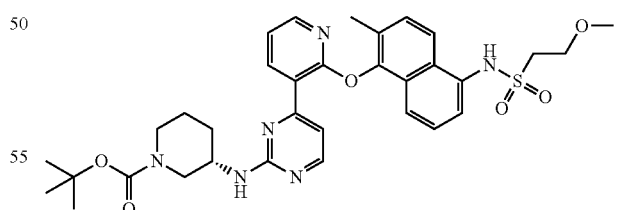

The General Procedure A was followed, using tert-butyl (3S)-3-[[4-[2-[(5-amino-2-methyl-1-naphthyl)oxy]-3-pyridyl]pyrimidin-2-yl]amino]piperidine-1-carboxylate (100 mg, 0.19 mmol), pyridine (3 mL) and 2-methoxy-1-ethanesulfonyl chloride (36 mg, 0.23 mmol). The solution was concentrated to yield 100 mg of the crude title compound as a yellow solid. LCMS (ESI) [M+H]$^+$=649.1.

263

Step 2: (S)-2-Methoxy-N-(6-methyl-5-((3-(2-(piperidin-3-ylamino)pyrimidin-4-yl)pyridin-2-yl)oxy)naphthalen-1-yl)ethanesulfonamide

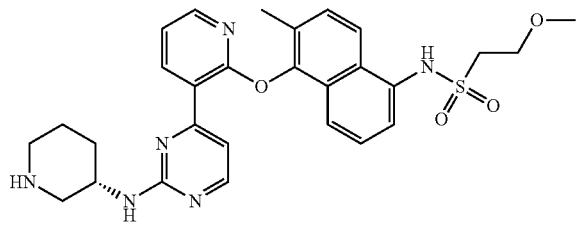 [SMILES: COCCS(=O)(=O)Nc1cccc2c(Oc3ncccc3-c3ccnc(N[C@H]4CCCNC4)n3)c(C)ccc12]

The General Procedure B was followed, using (S)-tert-butyl 3-((4-(2-((5-(2-methoxyethylsulfonamido)-2-methylnaphthalen-1-yl)oxy)pyridin-3-yl)pyrimidin-2-yl)amino)piperidine-1-carboxylate (100 mg, 0.15 mmol), dichloromethane (5 mL) and hydrochloric acid (4 M in ethyl acetate, 2 mL, 8 mmol). The residue was purified by Prep-HPLC (mobile phase: A: water (0.05% HCl); B: ACN) to yield 76 mg (84%, yield HCl salt) of 137 as a white solid. LCMS (ESI): [M+H]$^+$=549.1; $^1$H NMR (400 MHz, DMSO-d$_6$) δ 9.88 (s, 1H), 9.57 (s, 1H), 9.28 (s, 1H), 8.86 (s, 1H), 8.51 (d, J=5.4 Hz, 1H), 8.15 (d, J=8.5 Hz, 1H), 8.10 (d, J=3.5 Hz, 1H), 7.80-7.52 (m, 2H), 7.52-7.46 (m, 1H), 7.46-7.38 (m, 1H), 7.32-7.27 (m, 1H), 4.60-4.20 (m, 1H), 3.73 (t, J=6.0 Hz, 2H), 3.43 (t, J=6.4 Hz, 3H), 3.23 (s, 3H), 3.20-3.16 (m, 1H), 2.90-2.80 (m, 2H), 2.22 (s, 3H), 2.08-1.57 (m, 4H).

Example 138 2-Methoxy-N-(6-methyl-5-((3-(2-((S)-piperidin-3-ylamino)pyrimidin-4-yl)pyridin-2-yl)oxy)naphthalen-1-yl)propane-1-sulfonamide 138

Step 1: (3S)-tert-Butyl 3-((4-(2-((5-(2-methoxypropylsulfonamido)-2-methylnaphthalen-1-yl)oxy)pyridin-3-yl)pyrimidin-2-yl)amino)piperidine-1-carboxylate

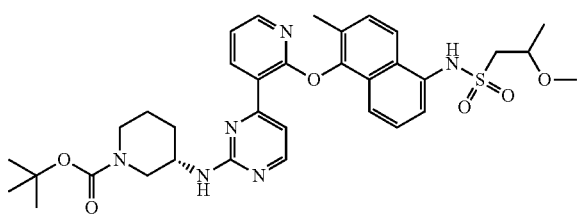 [SMILES: COC(C)CS(=O)(=O)Nc1cccc2c(Oc3ncccc3-c3ccnc(N[C@H]4CCCN(C(=O)OC(C)(C)C)C4)n3)c(C)ccc12]

The General Procedure A was followed, using tert-butyl (3S)-3-[[4-[2-[(5-amino-2-methyl-1-naphthyl)oxy]-3-pyridyl]pyrimidin-2-yl]amino]piperidine-1-carboxylate (100 mg, 0.19 mmol), pyridine (3 mL) and 2-methoxypropane-1-sulfonyl chloride (33 mg, 0.19 mmol). The solution was concentrated to afford 130 mg of the crude title compound as a yellow solid. LCMS (ESI) [M+H]$^+$=663.1.

264

Step 2: 2-Methoxy-N-(6-methyl-5-((3-(2-((S)-piperidin-3-ylamino)pyrimidin-4-yl)pyridin-2-yl)oxy)naphthalen-1-yl)propane-1-sulfonamide

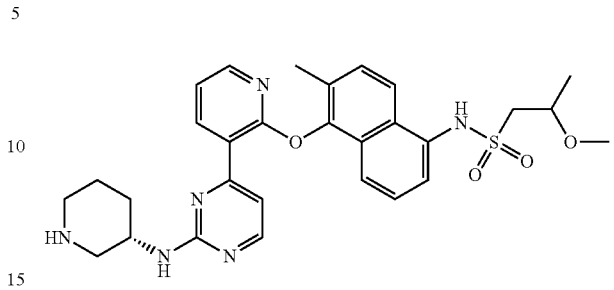

The General Procedure B was followed, using (3S)-tert-butyl 3-((4-(2-((5-(2-methoxypropylsulfonamido)-2-methylnaphthalen-1-yl)oxy)pyridin-3-yl)pyrimidin-2-yl)amino)piperidine-1-carboxylate (100 mg, 0.15 mmol), dichloromethane (5 mL) and hydrochloric acid (4 M in ethyl acetate, 2 mL, 8 mmol). The residue was purified by Prep-HPLC (mobile phase: A: water (0.05% HCl); B: ACN) to yield 73 mg (81%, yield HCl salt) of 138 as a yellow solid. LCMS (ESI): [M+H]$^+$=563.1; $^1$H NMR (400 MHz, DMSO-d$_6$) δ 9.91-9.80 (m, 1H), 9.68 (s, 1H), 9.34 (s, 1H), 8.89 (s, 1H), 8.52 (d, J=4.8 Hz, 1H), 8.16 (d, J=8.8 Hz, 1H), 8.10 (s, 1H), 7.76 (s, 1H), 7.56 (t, J=9.2 Hz, 2H), 7.52-7.47 (m, 1H), 7.47-7.36 (m, 1H), 7.33-7.26 (m, 1H), 4.47-4.53 (m, 1H), 3.85-3.76 (m, 1H), 3.46-3.35 (m, 2H), 3.27-3.20 (m, 2H), 3.19 (s, 3H), 2.85 (d, J=9.6 Hz, 2H), 2.22 (s, 3H), 2.07-1.61 (m, 4H), 1.20 (d, J=6.4 Hz, 3H).

Example 139 ((S)-2,2-Dimethyl-N-(6-methyl-5-((3-(2-(piperidin-3-ylamino)pyrimidin-4-yl)pyridin-2-yl)oxy)naphthalen-1-yl)propane-1-sulfonamide 139

Step 1: (S)-tert-Butyl 3-((4-(2-((5-(2,2-dimethylpropylsulfonamido)-2-methylnaphthalen-1-yl)oxy)pyridin-3-yl)pyrimidin-2-yl)amino)piperidine-1-carboxylate

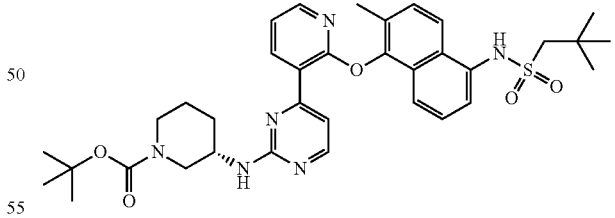

The General Procedure A was followed, using tert-butyl (3S)-3-[[4-[2-[(5-amino-2-methyl-1-naphthyl)oxy]-3-pyridyl]pyrimidin-2-yl]amino]piperidine-1-carboxylate (100 mg, 0.19 mmol), pyridine (2 mL) and 2,2-dimethyl-propane-1-sulfonyl chloride (39 mg, 0.230 mmol). The resulting solution was extracted with ethyl acetate. The combined organic layers were dried over anhydrous sodium sulfate, and concentrated in vacuo to yield 120 mg of the crude title compound as a yellow solid. LCMS (ESI) [M+H]$^+$=661.2.

Step 2: (S)-2,2-Dimethyl-N-(6-methyl-5-((3-(2-(piperidin-3-ylamino)pyrimidin-4-yl)pyridin-2-yl)oxy)naphthalen-1-yl)propane-1-sulfonamide

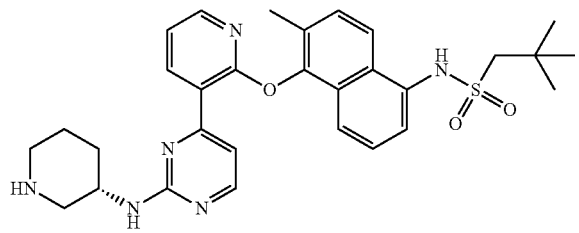 [SMILES: Cc1ccc2c(NS(=O)(=O)CC(C)(C)C)cccc2c1Oc1ncccc1-c1ccnc(N[C@H]2CCCNC2)n1]

The General Procedure B was followed, using (S)-tert-butyl-3-((4-(2-((5-(2,2-dimethylpropylsulfonamido)-2-methylnaphthalen-1-yl)oxy)pyridin-3-yl)pyrimidin-2-yl)amino)piperidine-1-carboxylate (110 mg, 0.16 mmol), dichloromethane (2 mL) and hydrochloric acid (4 M in dioxane, 2 mL, 8 mmol). The residue was purified by Prep-HPLC (mobile phase: A: water (0.05% HCl); B: ACN) to yield 31 mg (30%, yield HCl salt) of 139 as a yellow solid. LCMS (ESI) [M+H]$^+$=561.3. $^1$H NMR (400 MHz, DMSO-$d_6$) δ 9.82 (s, 1H), 9.05 (s, 1H), 8.48 (d, J=4.8 Hz, 1H), 8.13 (d, J=8.8 Hz, 1H), 8.07 (s, 1H), 7.70-7.61 (m, 2H), 7.54 (d, J=5.2 Hz, 2H), 7.50-7.40 (m, 2H), 7.31-7.25 (m, 1H), 3.45-3.40 (m, 1H), 3.22-3.18 (m, 1H), 3.13 (s, 2H), 2.90-2.80 (m, 3H), 2.21 (s, 3H), 2.04-1.97 (m, 1H), 1.95-1.85 (m, 1H), 1.83-1.76 (m, 1H), 1.72-1.65 (m, 1H), 1.09 (s, 9H).

Example 140 (S)—N-(6-Methyl-5-((3-(2-(piperidin-3-ylamino)pyrimidin-4-yl)pyridin-2-yl)oxy)naphthalen-1-yl)cyclohexanesulfonamide 140

Step 1: (S)-tert-Butyl 3-((4-(2-((5-(cyclohexanesulfonamido)-2-methylnaphthalen-1-yl)oxy)pyridin-3-yl)pyrimidin-2-yl)amino)piperidine-1-carboxylate

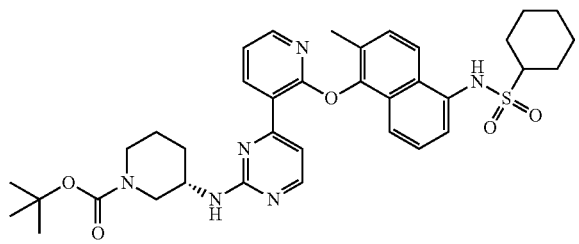 [SMILES: Cc1ccc2c(NS(=O)(=O)C3CCCCC3)cccc2c1Oc1ncccc1-c1ccnc(N[C@H]2CCCN(C(=O)OC(C)(C)C)C2)n1]

The General Procedure A was followed, using (S)-tert-butyl 3-((4-(2-((5-amino-2-methylnaphthalen-1-yl)oxy)pyridin-3-yl)pyrimidin-2-yl)amino)piperidine-1-carboxylate (100 mg, 0.19 mmol), pyridine (2 mL) and cyclohexanesulfonylchloride (42 mg, 0.23 mmol). The mixture was concentrated in vacuo and dissolved in dichloromethane (15 mL) and washed with H$_2$O (15 mL×2). The organic phase was dried over anhydrous sodium sulfate and concentrated in vacuo to yield 100 mg (crude) of the title compound as a yellow oil.

Step 2: (S)—N-(6-Methyl-5-((3-(2-(piperidin-3-ylamino)pyrimidin-4-yl)pyridin-2-yl)oxy)naphthalen-1-yl)cyclohexanesulfonamide

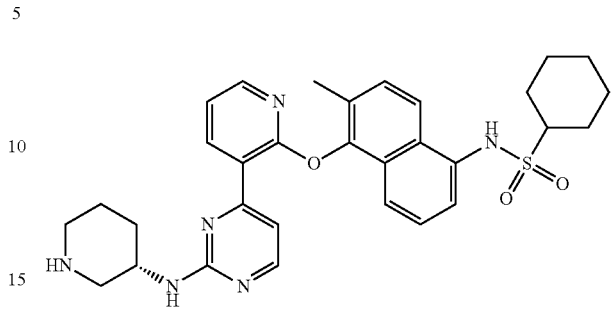

The General Procedure B was followed, using (S)-tert-butyl 3-((4-(2-((5-(cyclohexanesulfonamido)-2-methylnaphthalen-1-yl)oxy)pyridin-3-yl)pyrimidin-2-yl)amino)piperidine-1-carboxylate (100 mg, 0.15 mmol), dichloromethane (1 mL) and hydrochloric acid (4 M in ethyl acetate, 0.4 mL, 1.6 mmol). The residue was purified by Prep-HPLC (mobile phase: A: water (0.05% HCl); B: ACN) to yield 78 mg (85%, yield HCl salt) of 140 as a yellow solid. LCMS (ESI) [M+H]$^+$=573.1; $^1$H NMR (400 MHz, DMSO-$d_6$) δ 9.80 (s, 1H), 9.50-9.31 (m, 1H), 9.02-8.81 (m, 1H), 8.59-8.27 (m, 2H), 8.19-8.08 (m, 2H), 7.87-7.67 (m, 1H), 7.59-7.53 (m, 2H), 7.50-7.45 (m, 1H), 7.44-7.38 (m, 1H), 7.32-7.26 (m, 1H), 4.69-4.40 (m, 1H), 3.48-3.37 (m, 1H), 3.24-3.13 (m, 1H), 3.12-3.02 (m, 1H), 2.94-2.78 (m, 2H), 2.22 (s, 3H), 2.16-1.99 (m, 3H), 1.94-1.59 (m, 6H), 1.52-1.38 (m, 2H), 1.32-1.04 (m, 3H).

Example 141 N-(6-Methyl-5-((3-(2-((S)-piperidin-3-ylamino)pyrimidin-4-yl)pyridin-2-yl)oxy)naphthalen-1-yl)-1-(tetrahydrofuran-2-yl)methanesulfonamide 141

Step 1: (3S)-tert-Butyl 3-((4-(2-((2-methyl-5-((tetrahydrofuran-2-yl)methylsulfonamido)naphthalen-1-yl)oxy)pyridin-3-yl)pyrimidin-2-yl)amino)piperidine-1-carboxylate

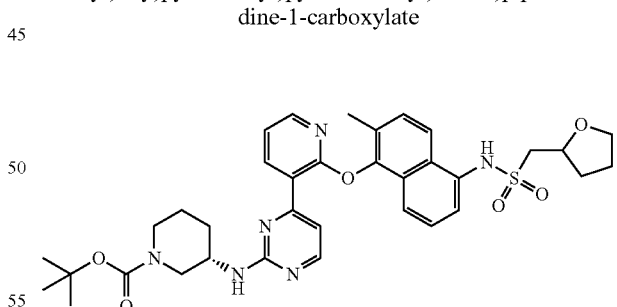

The General Procedure A was followed, using (S)-tert-butyl 3-((4-(2-((5-amino-2-methylnaphthalen-1-yl)oxy)pyridin-3-yl)pyrimidin-2-yl)amino)piperidine-1-carboxylate (100 mg, 0.19 mmol), pyridine (2 mL) and tetrahydrofuran-2-ylmethanesulfonyl chloride (70 mg, 0.38 mmol). The mixture was concentrated in vacuo and dissolved in dichloromethane (20 mL), washed with H$_2$O (15 mL×2). The organic phase was dried over anhydrous sodium sulfate and concentrated to yield 100 mg (crude) of the title compound as a brown oil.

Step 2: N-(6-Methyl-5-((3-(2-((S)-piperidin-3-ylamino)pyrimidin-4-yl)pyridin-2-yl)oxy)naphthalen-1-yl)-1-(tetrahydrofuran-2-yl)methanesulfonamide

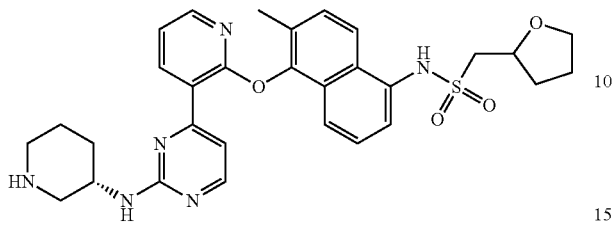

The General Procedure B was followed, using (S)-tert-butyl 3-((4-(2-((5-(cyclobutanecarboxamido)-2-methylnaphthalen-1-yl)oxy)pyridin-3-yl)pyrimidin-2-yl)amino)piperidine-1-carboxylate (100 mg, 0.15 mmol), dichloromethane (2 mL) and hydrochloric acid (4 M in ethyl acetate, 0.37 mL, 1.48 mmol). The residue was purified by Prep-HPLC (mobile phase: A: water (0.05% HCl); B: ACN) to yield 55 mg (65%, yield HCl salt) of 141 as a yellow solid. LCMS (ESI) [M+H]$^+$=575.1; $^1$H NMR (400 MHz, DMSO-d$_6$) δ 9.86 (s, 1H), 9.73-9.23 (m, 1H), 8.99-8.76 (m, 1H), 8.56-8.47 (m, 1H), 8.25-8.15 (m, 3H), 7.75-7.25 (m, 7H), 4.45-4.22 (m, 2H), 3.78-3.58 (m, 2H), 3.35-3.33 (m, 3H), 3.25-3.13 (m, 1H), 2.93-2.80 (m, 2H), 2.29-2.18 (m, 3H), 2.10-1.99 (m, 2H), 1.97-1.76 (m, 4H), 1.72-1.60 (m, 2H).

Example 142 (S)—N-(6-Methyl-5-((3-(2-(piperidin-3-ylamino)pyrimidin-4-yl)pyridin-2-yl)oxy)naphthalen-1-yl)-1-(2-(trifluoromethyl)phenyl)methanesulfonamide 142

Step 1: (S)-tert-Butyl 3-((4-(2-((2-methyl-5-((2-(trifluoromethyl)phenyl)methylsulfonamido)naphthalen-1-yl)oxy)pyridin-3-yl)pyrimidin-2-yl)amino)piperidine-1-carboxylate

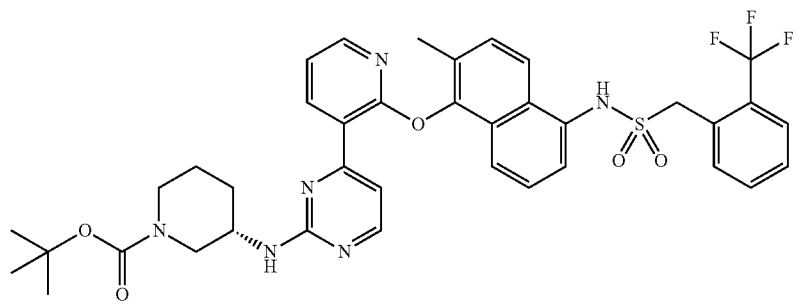 [SMILES: Cc1ccc2c(NS(=O)(=O)Cc3ccccc3C(F)(F)F)cccc2c1Oc1ncccc1-c1ccnc(N[C@H]2CCCN(C(=O)OC(C)(C)C)C2)n1]

Prepared using (S)-tert-butyl 3-((4-(2-((5-amino-2-methylnaphthalen-1-yl)oxy)pyridin-3-yl)pyrimidin-2-yl)amino)piperidine-1-carboxylate (400 mg, 0.760 mmol), pyridine (1 mL), DCM (3 mL), and (2-(trifluoromethyl)phenyl)methanesulfonyl chloride (295 mg, 1.14 mmol). After 20 h, the mixture was diluted with DCM (75 mL) and washed with saturated NaHCO$_3$(aq) (25 mL), dried (Na$_2$SO$_4$), filtered and concentrated in vacuo. The crude was purified by flash chromatography through silica gel (0-100% EtOAc/hexanes) to provide 392 mg (69% yield) of the title compound as a light yellow gum. LCMS (ESI) [M+H]+=749.1, rt=2.02 min.

Step 2: (S)—N-(6-Methyl-5-((3-(2-(piperidin-3-ylamino)pyrimidin-4-yl)pyridin-2-yl)oxy)naphthalen-1-yl)-1-(2-(trifluoromethyl)phenyl)methanesulfonamide

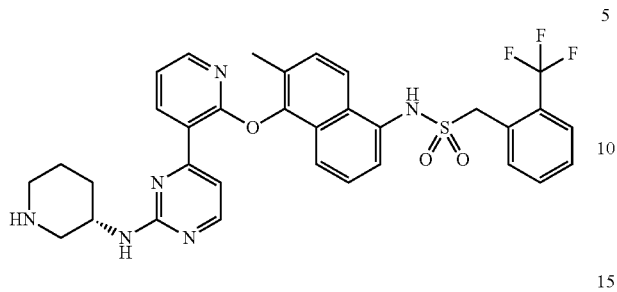

Prepared using (S)-tert-butyl 3-((4-(2-((2-methyl-5-((2-(trifluoromethyl)phenyl)methylsulfonamido)naphthalen-1-yl)oxy)pyridin-3-yl)pyrimidin-2-yl)amino)piperidine-1-carboxylate (392 mg, 0.524 mmol), EtOAc (3 mL), and hydrochloric acid (4 M in dioxane, 3 mL, 12 mmol). After 3 h, the mixture was concentrated in vacuo and the crude solid was washed with EtOAc (3×3 mL) and then MeCN (3×3 mL). The solid product was then sonicated, concentrated in vacuo with MeCN (3×3 mL) and then dissolved in H$_2$O and MeCN. Lyophilization provided 292 mg (81% yield) of 142 as a fluffy white solid. LCMS (ESI) [M+H]+=649.3, rt=1.48 min; $^1$H NMR (400 MHz, DMSO-d$_6$) δ 10.19 (s, 1H), 8.96-8.73 (m, 2H), 8.69-8.54 (m, 1H), 8.48 (d, J=5.2 Hz, 1H), 8.13-8.04 (m, 2H), 7.78 (d, J=7.9 Hz, 1H), 7.74-7.66 (m, 2H), 7.64-7.51 (m, 5H), 7.49-7.40 (m, 2H), 7.28 (dd, J=7.5, 4.8 Hz, 1H), 4.72 (s, 2H), 4.38-4.16 (m, 1H), 3.21 (d, J=11.3 Hz, 2H), 2.95-2.76 (m, 2H), 2.22 (s, 3H), 2.09-1.84 (m, 2H), 1.83-1.55 (m, 2H).

Example 143 (S)-1-(4-Chlorophenyl)-N-(6-methyl-5-((3-(2-(piperidin-3-ylamino)pyrimidin-4-yl)pyridin-2-yl)oxy)naphthalen-1-yl)methanesulfonamide 143

Step 1: (S)-tert-Butyl 3-((4-(2-((5-((4-chlorophenyl)methylsulfonamido)-2-methylnaphthalen-1-yl)oxy)pyridin-3-yl)pyrimidin-2-yl)amino)piperidine-1-carboxylate

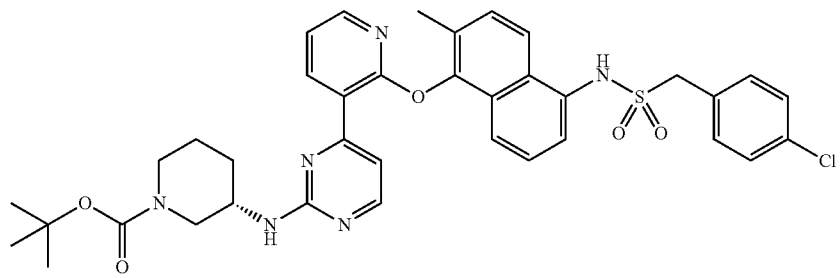 [SMILES: Cc1ccc2c(NS(=O)(=O)Cc3ccc(Cl)cc3)cccc2c1Oc1ncccc1-c1ccnc(N[C@H]2CCCN(C(=O)OC(C)(C)C)C2)n1]

The General Procedure A was followed, using (S)-tert-butyl 3-((4-(2-((5-amino-2-methylnaphthalen-1-yl)oxy)pyridin-3-yl)pyrimidin-2-yl)amino)piperidine-1-carboxylate (100 mg, 0.19 mmol), pyridine (2 mL) and (4-chlorophenyl)methanesulfonylchloride (64 mg, 0.28 mmol). The mixture was concentrated, dissolved in ethyl acetate (20 mL), and washed with H$_2$O (15 mL×2). The organic phase was dried over anhydrous sodium sulfate, concentrated to yield 100 mg (crude) of the title compound as a brown oil.

Step 2: (S)-1-(4-Chlorophenyl)-N-(6-methyl-5-((3-(2-(piperidin-3-ylamino)pyrimidin-4-yl)pyridin-2-yl)oxy)naphthalen-1-yl)methanesulfonamide

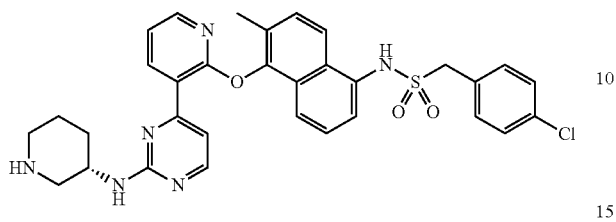

The General Procedure B was followed, using (S)-1-(4-chlorophenyl)-N-(6-methyl-5-((3-(2-(piperidin-3-ylamino)pyrimidin-4-yl)pyridin-2-yl)oxy)naphthalen-1-yl)methanesulfonamide (100 mg, 0.14 mmol), dichloromethane (1 mL) and hydrochloric acid (4 M in ethyl acetate, 0.4 mL, 1.6 mmol). The residue was purified by Prep-HPLC (mobile phase: A: water (0.05% HCl); B: ACN) to yield 42 mg (46%, yield HCl salt) of 143 as a brown solid. LCMS (ESI) [M+H]$^+$=615.1; $^1$H NMR (400 MHz, DMSO-d$_6$) δ 9.91 (s, 1H), 9.23-8.83 (m, 2H), 8.78-8.61 (m, 1H), 8.53-8.42 (m, 1H), 8.13-7.96 (m, 2H), 7.66-7.49 (m, 3H), 7.48-7.36 (m, 4H), 7.30-7.25 (m, 1H), 4.66-4.48 (m, 2H), 4.40-4.21 (m, 1H), 3.46-3.18 (m, 2H), 2.93-2.77 (m, 2H), 2.24-2.07 (m, 3H), 2.06-1.86 (m, 2H), 1.84-1.58 (m, 2H).

Example 144 (S)-1-(3-Chlorophenyl)-N-(6-methyl-5-((3-(2-(piperidin-3-ylamino)pyrimidin-4-yl)pyridin-2-yl)oxy)naphthalen-1-yl)methanesulfonamide 144

Step 1: (S)-tert-Butyl 3-((4-(2-((5-((3-Chlorophenyl)methylsulfonamido)-2-methylnaphthalen-1-yl)oxy)pyridin-3-yl)pyrimidin-2-yl)amino)piperidine-1-carboxylate

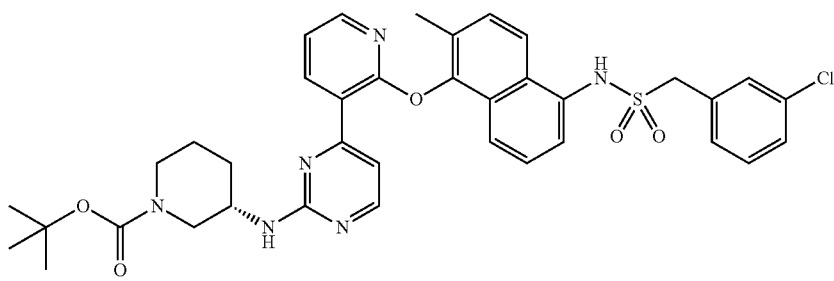 [SMILES: Cc1ccc2c(NS(=O)(=O)Cc3cccc(Cl)c3)cccc2c1Oc1ncccc1-c1ccnc(N[C@H]2CCCN(C(=O)OC(C)(C)C)C2)n1]

The General Procedure A was followed, using tert-butyl (3S)-3-[[4-[2-[(5-amino-2-methyl-1-naphthyl)oxy]-3-pyridyl]pyrimidin-2-yl]amino]piperidine-1-carboxylate (100 mg, 0.19 mmol), pyridine (2 mL) and (3-chlorophenyl)methanesulfonyl chloride (51 mg, 0.22 mmol). The resulting solution was extracted with ethyl acetate. The combined organic layers were dried over anhydrous sodium sulfate, and concentrated in vacuo to yield 115 mg of the crude title compound as a yellow solid. LCMS (ESI) [M+H]$^+$=715.0.

Step 2: (S)-1-(3-Chlorophenyl)-N-(6-methyl-5-((3-(2-(piperidin-3-ylamino)pyrimidin-4-yl)pyridin-2-yl)oxy)naphthalen-1-yl)methanesulfonamide

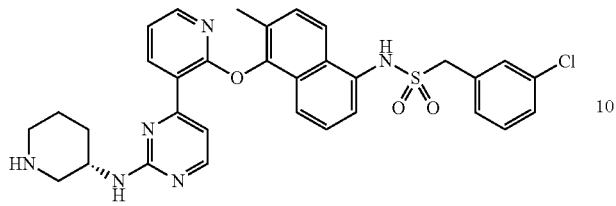

The General Procedure B was followed, using (S)-tert-butyl 3-((4-(2-((5-(((3-chlorophenyl)methylsulfonamido)-2-methylnaphthalen-1-yl)oxy)pyridin-3-yl)pyrimidin-2-yl)amino)piperidine-1-carboxylate (110 mg, 0.15 mmol), dichloromethane (2 mL) and hydrochloric acid (4 M in dioxane, 2 mL, 8 mmol). The residue was purified by Prep-HPLC (mobile phase: A: water (0.05% HCl); B: ACN) to yield 99 mg (95%, yield HCl salt) of 144 as a yellow solid. LCMS (ESI) $[M+H]^+=615.3$. $^1$H NMR (400 MHz, DMSO-$d_6$) δ 9.95 (s, 1H), 8.91 (s, 1H), 8.48 (d, J=5.2 Hz, 1H), 8.09-8.05 (m, 1H), 8.02 (d, J=8.8 Hz, 1H), 7.50-7.60 (m, 4H), 7.48-7.34 (m, 6H), 7.29-7.26 (m, 1H), 4.60 (s, 2H), 4.28 (s, 1H), 3.21 (d, J=12.0 Hz, 2H), 2.85-2.81 (m, 2H), 2.21 (s, 3H), 2.04-1.96 (m, 1H), 1.92-1.85 (m, 1H), 1.75-1.66 (m, 1H), 1.65-1.55 (m, 1H).

Example 145 (S)-1-(2-Fluorophenyl)-N-(6-methyl-5-((3-(2-(piperidin-3-ylamino)pyrimidin-4-yl)pyridin-2-yl)oxy)naphthalen-1-yl)methanesulfonamide 145

Step 1: (S)-tert-Butyl 3-((4-(2-((5-(((2-fluorophenyl)methylsulfonamido)-2-methylnaphthalen-1-yl)oxy)pyridin-3-yl)pyrimidin-2-yl)amino)piperidine-1-carboxylate

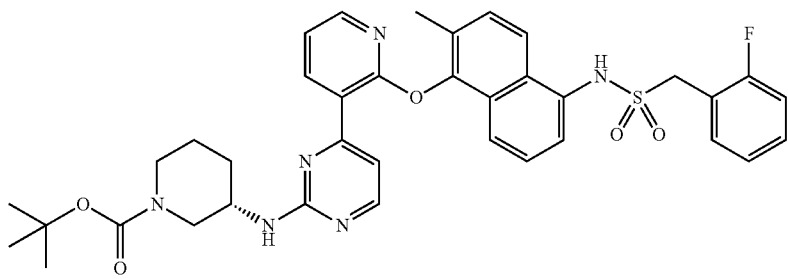 [SMILES: Cc1ccc2c(NS(=O)(=O)Cc3ccccc3F)cccc2c1Oc1ncccc1-c1ccnc(N[C@H]2CCCN(C(=O)OC(C)(C)C)C2)n1]

The General Procedure A was followed, using (S)-tert-butyl 3-((4-(2-((5-amino-2-methylnaphthalen-1-yl)oxy)pyridin-3-yl)pyrimidin-2-yl)amino)piperidine-1-carboxylate (100 mg, 0.19 mmol), pyridine (4 mL) and (2-fluorophenyl)methanesulfonyl chloride (47.5 mg, 0.23 mmol). The mixture was concentrated, dissolved in dichloromethane (30 mL) and washed with $H_2O$ (40 mL×2). The organic phase was dried over anhydrous sodium sulfate and concentrated to give 110 mg (83% yield) of the title compound as a brown oil.

Step 2: (S)-1-(2-Fluorophenyl)-N-(6-methyl-5-((3-(2-(piperidin-3-ylamino)pyrimidin-4-yl)pyridin-2-yl)oxy)naphthalen-1-yl)methanesulfonamide

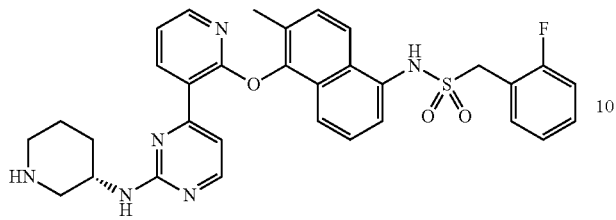

The General Procedure B was followed, using (S)-tert-butyl 3-((4-(2-((5-((2-fluorophenyl)methylsulfonamido)-2-methylnaphthalen-1-yl)oxy)pyridin-3-yl)pyrimidin-2-yl)amino)piperidine-1-carboxylate (110 mg, 0.16 mmol), ethyl acetate (1 mL) and hydrochloric acid (4 M in ethyl acetate, 3 mL, 12 mmol). The residue was purified by Prep-HPLC (mobile phase: A: water (0.05% HCl); B: ACN) to yield 45.7 mg (46%, yield HCl salt) of 145 as a white solid. LCMS (ESI) [M+H]$^+$=599.2.; $^1$H NMR (400 MHz, DMSO-d$_6$) δ 10.07 (s, 1H), 9.69-9.00 (m, 2H), 8.85 (s, 1H), 8.51 (d, J=5.2 Hz, 1H), 8.14-8.04 (m, 2H), 7.72 (m, 1H), 7.58 (d, J=8.4 Hz, 1H), 7.54 (d, J=8.8 Hz, 1H), 7.50-7.37 (m, 4H), 7.31-7.27 (m, 1H), 7.24-7.19 (m, 2H), 4.60 (s, 2H), 4.54-4.44 (m, 1H), 3.53-3.37 (m, 1H), 3.28-3.13 (m, 1H), 2.93-2.79 (m, 2H), 2.22 (s, 3H), 2.09-1.98 (m, 1H), 1.97-1.86 (m, 1H), 1.85-1.73 (m, 1H), 1.72-1.56 (m, 1H).

Example 146 (S)-1-(2-Cyanophenyl)-N-(6-methyl-5-((3-(2-(piperidin-3-ylamino)pyrimidin-4-yl)pyridin-2-yl)oxy)naphthalen-1-yl)methanesulfonamide 146

Step 1: (S)-tert-Butyl 3-((4-(2-((5-((2-chlorophenyl)methylsulfonamido)-2-methylnaphthalen-1-yl)oxy)pyridin-3-yl)pyrimidin-2-yl)amino)piperidine-1-carboxylate

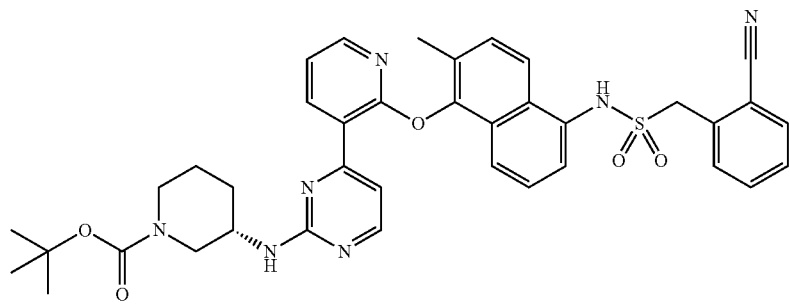 [SMILES: Cc1ccc2c(NS(=O)(=O)Cc3ccccc3C#N)cccc2c1Oc1ncccc1-c1ccnc(N[C@H]2CCCN(C(=O)OC(C)(C)C)C2)n1]

The General Procedure A was followed, using tert-butyl (3S)-3-[[4-[2-[(5-amino-2-methyl-1-naphthyl)oxy]-3-pyridyl]pyrimidin-2-yl]amino]piperidine-1-carboxylate (100 mg, 0.19 mmol), pyridine (2 mL) and (2-cyanophenyl)methanesulfonyl chloride (49 mg, 0.23 mmol) (47 mg, 0.21 mmol). The reaction mixture was concentrated and the residue was taken up in ethyl acetate (20 mL) and washed with water (10 mL). The organic phase was dried over anhydrous sodium sulfate and concentrated in vacuo to yield (130 mg crude) of the title compound as a pale brown oil. LCMS (ESI) [M+H]$^+$=705.1.

Step 2: (S)-1-(2-Cyanophenyl)-N-(6-methyl-5-((3-(2-(piperidin-3-ylamino)pyrimidin-4-yl)pyridin-2-yl)oxy)naphthalen-1-yl)methanesulfonamide

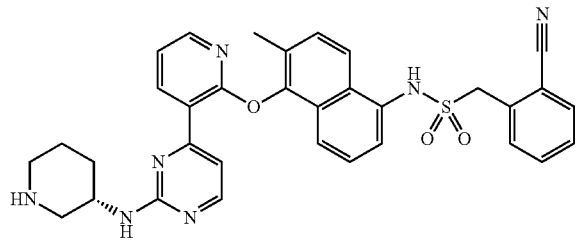

The General Procedure B was followed, using (S)-tert-butyl 3-((4-(2-((5-((2-chlorophenyl) methylsulfonamido)-2-methylnaphthalen-1-yl)oxy)pyridin-3-yl)pyrimidin-2-yl)amino)piperidine-1-carboxylate (130 mg, 0.18 mmol), ethyl acetate (2 mL) and hydrochloric acid (4 M in ethyl acetate, 2 mL, 8 mmol). The residue was purified by Prep-HPLC (mobile phase: A: water (0.05% NH$_4$OH); B: ACN) to yield 32 mg (30%, yield HCl salt) of 146 as a white solid. LCMS (ESI): [M+H]$^+$=606.1; $^1$H NMR (400 MHz, DMSO-d$_6$) δ 8.55 (s, 1H), 8.46 (d, J=5.2 Hz, 1H), 8.19 (d, J=8.8 Hz, 1H), 8.06-8.04 (m, 1H), 7.82 (d, J=7.6 Hz, 1H), 7.55 (t, J=4.8 Hz, 1H), 7.56-7.49 (m, 3H), 7.40-7.30 (m, 3H), 7.15-7.11 (m, 2H), 4.44 (s, 2H), 4.14-4.09 (m, 1H), 3.08-3.04 (m, 2H), 2.71-2.65 (m, 2H), 2.20 (s, 3H), 2.02-1.98 (m, 1H), 1.85-1.80 (m, 1H), 1.65-1.55 (m, 2H).

Example 147 (S)—N-(6-Methyl-5-((3-(2-(piperidin-3-ylamino)pyrimidin-4-yl)pyridin-2-yl)oxy)naphthalen-1-yl)ethenesulfonamide 147

Step 1: (S)-tert-Butyl 3-((4-(2-((2-methyl-5-(vinylsulfonamido)naphthalen-1-yl)oxy)pyridin-3-yl)pyrimidin-2-yl)amino)piperidine-1-carboxylate

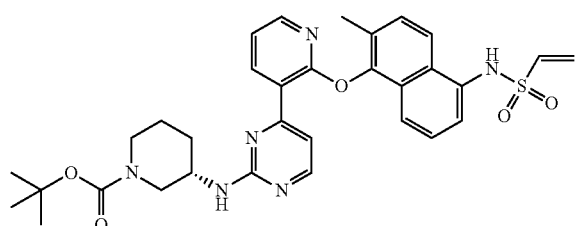

The General Procedure A was followed, using tert-butyl (3S)-3-[[4-[2-[(5-amino-2-methyl-1-naphthyl)oxy]-3-pyridyl]pyrimidin-2-yl]amino]piperidine-1-carboxylate (100 mg, 0.19 mmol), pyridine (3 mL) and 2-methoxypropane-1-sulfonyl chloride (33 mg, 0.19 mmol). The solution was concentrated to yield 140 mg of the crude title compound as a yellow solid. LCMS (ESI) [M+H]$^+$=617.1.

Step 2: (S)—N-(6-Methyl-5-((3-(2-(piperidin-3-ylamino)pyrimidin-4-yl)pyridin-2-yl)oxy)naphthalen-1-yl)ethenesulfonamide

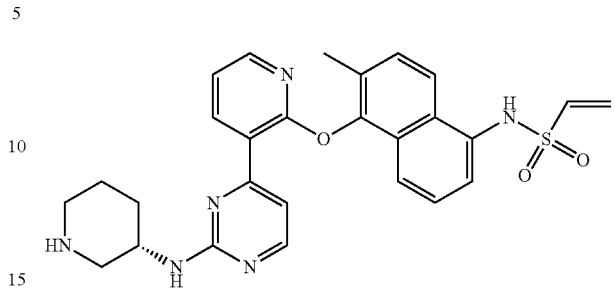

The General Procedure B was followed, using (S)-tert-butyl 3-((4-(2-((2-methyl-5-(vinylsulfonamido)naphthalen-1-yl)oxy)pyridin-3-yl)pyrimidin-2-yl)amino)piperidine-1-carboxylate (100 mg, 0.16 mmol), dichloromethane (5 mL) and hydrochloric acid (4 M in ethyl acetate, 2 mL, 8 mmol). The residue was purified by Prep-HPLC (mobile phase: A: water (0.05% HCl); B: ACN) to yield 3 mg (4%, yield HCl salt) of 147 as a yellow solid. LCMS (ESI): [M+H]$^+$=517.1; $^1$H NMR (400 MHz, DMSO-d$_6$) δ 8.87 (s, 1H), 8.49 (d, J=6.0 Hz, 1H), 8.12 (d, J=8.8 Hz, 3H), 7.62 (d, J=8.4 Hz, 1H), 7.54 (d, J=8.8 Hz, 1H), 7.47 (d, J=7.5 Hz, 1H), 7.41-7.29 (m, 2H), 6.79 (dd, J=16.4, 10.0, 1H), 6.08 (d, J=16.8 Hz, 1H), 5.91 (d, J=9.6 Hz, 1H), 4.63 (s, 1H), 3.68 (d, J=11.6 Hz, 1H), 3.40 (d, J=12.8 Hz, 1H), 3.18-3.03 (m, 2H), 2.34-2.09 (m, 5H), 2.05-1.81 (m, 2H).

Example 148 N-(5-((3-(2-(((3S,5R)-5-Fluoropiperidin-3-yl)amino)pyrimidin-4-yl)pyridin-2-yl)oxy)-6-methylnaphthalen-1-yl)-1-phenylmethanesulfonamide 148

Step 1: (3S,5R)-Benzyl 3-((tert-butoxycarbonyl)amino)-5-fluoropiperidine-1-carboxylate

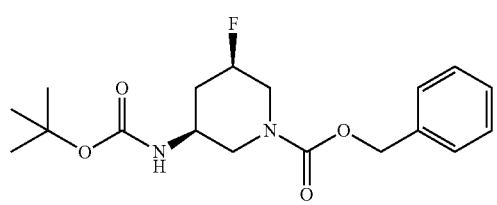 [SMILES: CC(C)(C)OC(=O)N[C@H]1C[C@@H](F)CN(C(=O)OCc2ccccc2)C1]

To a solution of tert-butyl ((3S,5R)-5-fluoropiperidin-3-yl) carbamate (500 mg, 0.23 mmol) in THF (2 mL) and H$_2$O (1 mL) was added sodium carbonate (48.6 mg, 0.46 mmol). Benzyl chloroformate (0.03 ml, 0.23 mmol) was added dropwise at 0° C. and stirred at 0° C. to rt for 1 h. The mixture was concentrated to dryness and the residue was dissolved in dichloromethane (20 mL) and washed with H$_2$O (10 mL×2). The organic phase was dried over anhydrous sodium sulfate, concentrated and purified by silica gel chromatography (eluting with 0-1% methanol in dichloromethane) to yield 200 mg (82% yield) of the title compound as a colorless oil; LCMS (ESI) [M+H]$^+$=398.1; $^1$H NMR (400 MHz, CDCl$_3$) δ 7.41-7.29 (m, 5H), 5.28-5.03 (m, 3H), 4.95-4.63 (m, 1H), 4.45-4.25 (m, 1H), 4.19-3.97 (m, 1H), 3.95-3.81 (m, 1H), 3.35-3.02 (m, 2H), 2.17-1.82 (m, 2H), 1.40 (s, 9H).

Step 2: (3S,5R)-Benzyl 3-amino-5-fluoropiperidine-1-carboxylate

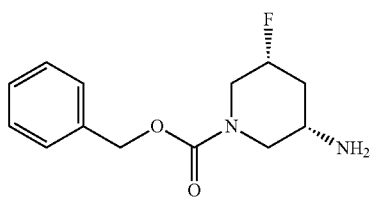 [SMILES: N[C@H]1C[C@@H](F)CN(C(=O)OCc2ccccc2)C1]

To a solution of benzyl (3S,5R)-3-(tert-butoxycarbonylamino)-5-fluoro-piperidine-1-carboxylate (200 mg, 0.57 mmol) in ethyl acetate (1 mL) was added (4 M in ethyl acetate, 3 mL, 12 mmol) and stirred at 25° C. for 1 h. The mixture was concentrated to yield 138 mg (84% yield) of the title compound as a white solid. $^1$H NMR (400 MHz, CD$_3$OD) δ 7.44-7.29 (m, 5H), 5.28-5.07 (m, 2H), 4.96 (s, 1H), 4.31-4.08 (m, 2H), 3.60-3.35 (m, 3H), 2.30-2.10 (m, 2H).

Step 3: (3R,5S)-Benzyl 3-fluoro-5-((4-(2-((2-methyl-5-(phenylmethylsulfonamido)naphthalen-1-yl)oxy)pyridin-3-yl)pyrimidin-2-yl)amino)piperidine-1-carboxylate

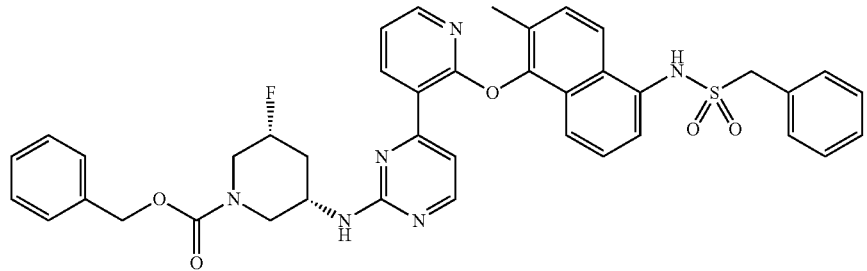 [SMILES: Cc1ccc2c(NS(=O)(=O)Cc3ccccc3)cccc2c1Oc1ncccc1-c1ccnc(N[C@H]2C[C@@H](F)CN(C(=O)OCc3ccccc3)C2)n1]

To a stirred solution of N-[6-methyl-5-[[3-(2-methylsulfinylpyrimidin-4-yl)-2-pyridyl]oxy]-1-naphthyl]-1-phenylmethanesulfonamide, made following the procedures of Example 101 (100 mg, 0.18 mmol):

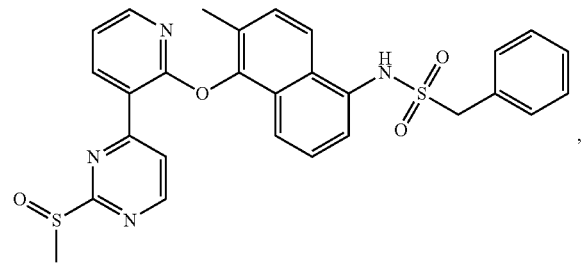 [SMILES: Cc1ccc2c(NS(=O)(=O)Cc3ccccc3)cccc2c1Oc1ncccc1-c1ccnc(S(C)=O)n1]

in 1,4-dioxane (3 mL) was added N,N-diethylpropan-2-amine (0.16 mL, 0.92 mmol) and (3S,5R)-benzyl 3-amino-5-fluoropiperidine-1-carboxylate (64 mg, 0.22 mmol), the mixture was stirred at 140° C. for 88 h. After cooling down, the mixture was concentrated and the residue was dissolved in ethyl acetate (20 mL) and washed with H$_2$O (20 mL). The organic phase was dried over anhydrous sodium sulfate, concentrated and purified by Prep-TLC (5% methanol in dichloromethane, R$_f$=0.5) to give 65 mg (48% yield) of the title compound as a white solid. LCMS (ESI) [M+H]$^+$=733.1.

Step 4: N-(5-((3-(2-(((3S,5R)-5-Fluoropiperidin-3-yl)amino)pyrimidin-4-yl)pyridin-2-yl)oxy)-6-methylnaphthalen-1-yl)-1-phenylmethanesulfonamide

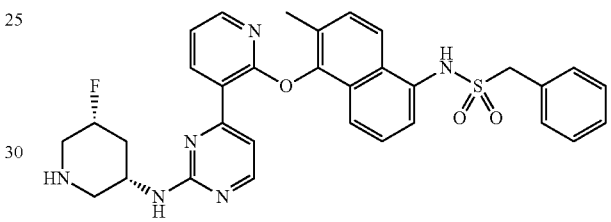

To a solution of (3R,5S)-benzyl 3-fluoro-5-((4-(2-((2-methyl-5-(phenylmethylsulfonamido)naphthalen-1-yl)oxy)pyridin-3-yl)pyrimidin-2-yl)amino)piperidine-1-carboxylate (80 mg, 0.11 mmol) in methanol (10 mL) was added 10% wet palladium (30 mg) on carbon followed by stirring at 40° C. under hydrogen gas (35 Psi) for 12 h. The mixture was filtered and purified by Prep-HPLC (mobile phase: A: water (0.05% HCl); B: ACN) to yield 2.6 mg (3.9% yield) of 148 as a white solid; LCMS (ESI) [M+H]$^+$=599.1; $^1$H NMR (400 MHz, DMSO-d$_6$) δ 9.87 (s, 1H), 9.37-9.19 (m, 1H), 8.51 (d, J=5.2 Hz, 1H), 8.12-8.02 (m, 2H), 7.65-7.55 (m, 2H), 7.52 (d, J=8.8 Hz, 1H), 7.45-7.40 (m, 2H), 7.38-7.33 (m, 5H), 7.29-7.26 (m, 1H), 5.16-4.98 (m, 1H), 4.54 (s, 2H), 4.50-4.41 (m, 1H), 3.53-3.42 (m, 2H), 3.26-3.18 (m, 1H), 3.08-3.02 (m, 1H), 2.21 (s, 3H), 2.13-2.00 (m, 2H).

Example 149 (S)—N-(6-Methyl-5-((3-(2-(piperidin-3-ylamino)pyrimidin-4-yl)pyridin-2-yl)oxy)naphthalen-1-yl)pyridine-3-sulfonamide 149

Step 1: (S)-tert-Butyl 3-((4-(2-((2-methyl-5-(pyridine-3-sulfonamido)naphthalen-1-yl)oxy)pyridin-3-yl)pyrimidin-2-yl)amino)piperidine-1-carboxylate

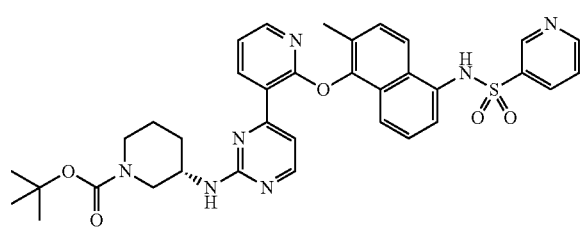 [SMILES: Cc1ccc2c(NS(=O)(=O)c3cccnc3)cccc2c1Oc1ncccc1-c1ccnc(N[C@H]2CCCN(C(=O)OC(C)(C)C)C2)n1]

The General Procedure A was followed, using (S)-tert-butyl 3-((4-(2-((5-amino-2-methylnaphthalen-1-yl)oxy)pyridin-3-yl)pyrimidin-2-yl)amino)piperidine-1-carboxylate (100 mg, 0.19 mmol), pyridine (3 mL) and pyridine-3-sulfonylchloride (37.1 mg, 0.21 mmol). The mixture was concentrated, dissolved in ethyl acetate (20 mL) and washed with H$_2$O (15 mL×2). The organic phase was dried over anhydrous sodium sulfate and concentrated to give 100 mg (crude) of the title compound as a brown solid.

Step 2: (S)—N-(6-Methyl-5-((3-(2-(piperidin-3-ylamino)pyrimidin-4-yl)pyridin-2-yl)oxy)naphthalen-1-yl)pyridine-3-sulfonamide

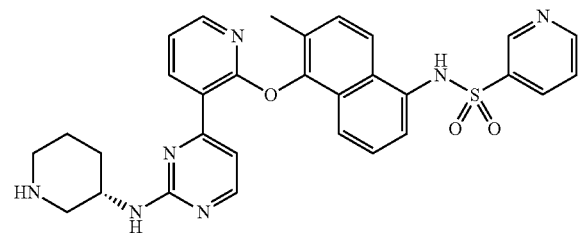 [SMILES: Cc1ccc2c(NS(=O)(=O)c3cccnc3)cccc2c1Oc1ncccc1-c1ccnc(N[C@H]2CCCNC2)n1]

The General Procedure B was followed, using (S)-tert-butyl 3-((4-(2-((5-(cyclobutanecarboxamido)-2-methylnaphthalen-1-yl)oxy)pyridin-3-yl)pyrimidin-2-yl)amino)piperidine-1-carboxylate (100 mg, 0.15 mmol), dichloromethane (2 mL) and hydrochloric acid (4 M in ethyl acetate, 0.4 mL, 1.6 mmol). The residue was purified by Prep-HPLC (mobile phase: A: water (0.05% HCl); B: ACN) to yield 29.4 mg (32%, yield as HCl salt) of 149 as a yellow solid. LCMS (ESI) [M+H]$^+$=568.1; $^1$H NMR (400 MHz, DMSO-d$_6$) δ 10.69-10.60 (m, 1H), 9.18-9.05 (m, 1H), 8.85-8.73 (m, 2H), 8.51-8.43 (m, 1H), 8.14-8.01 (m, 2H), 7.88-7.79 (m, 1H), 7.70-7.53 (m, 3H), 7.45-7.40 (m, 1H), 7.38-7.31 (m, 1H), 7.30-7.23 (m, 1H), 7.15-7.09 (m, 1H), 3.48-3.14 (m, 2H), 2.92-2.75 (m, 2H), 2.16 (s, 3H), 2.06-1.86 (m, 2H), 1.84-1.57 (m, 2H).

Example 150 (S)-1-(4-Fluorophenyl)-N-(6-methyl-5-((3-(2-(piperidin-3-ylamino)pyrimidin-4-yl)pyridin-2-yl)oxy)naphthalen-1-yl)methanesulfonamide 150

Step 1: (S)-tert-Butyl 3-((4-(2-((5-((4-fluorophenyl)methylsulfonamido)-2-methylnaphthalen-1-yl)oxy)pyridin-3-yl)pyrimidin-2-yl)amino)piperidine-1-carboxylate

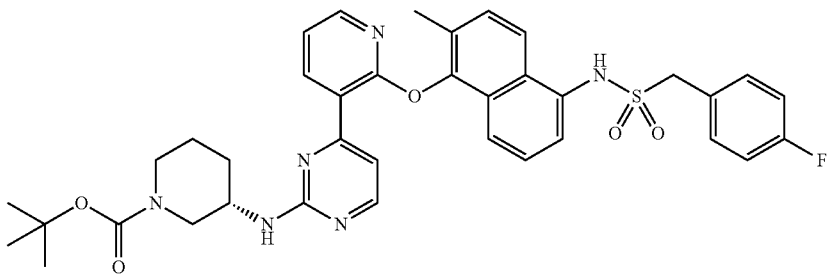 [SMILES: Cc1ccc2c(NS(=O)(=O)Cc3ccc(F)cc3)cccc2c1Oc1ncccc1-c1ccnc(N[C@H]2CCCN(C(=O)OC(C)(C)C)C2)n1]

The General Procedure A was followed, using tert-butyl (3S)-3-[[4-[2-[(5-amino-2-methyl-1-naphthyl)oxy]-3-pyridyl]pyrimidin-2-yl]amino]piperidine-1-carboxylate (100 mg, 0.19 mmol), pyridine (2 mL) and 4-fluorophenyl)methanesulfonylchloride (48 mg, 0.23 mmol). The reaction mixture was concentrated in vacuo and the residue taken up in ethyl acetate (20 mL) and washed with water (10 mL). The organic phase was dried over anhydrous sodium sulfate and concentrated in vacuo to yield (130 mg crude) of the title compound as a pale brown oil. LCMS (ESI) [M+H]$^+$=699.3.

Step 2: (S)-1-(4-Fluorophenyl)-N-(6-methyl-5-((3-(2-(piperidin-3-ylamino)pyrimidin-4-yl)pyridin-2-yl)oxy)naphthalen-1-yl)methanesulfonamide

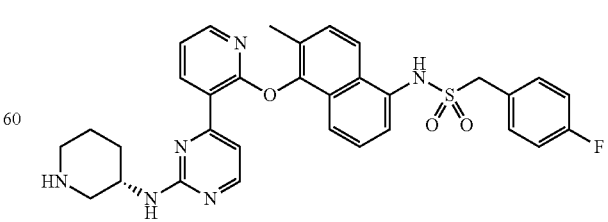

The General Procedure B was followed, using (S)-tert-butyl 3-((4-(2-((5-((4-fluorophenyl) methylsulfonamido)-2- methylnaphthalen-1-yl)oxy)pyridin-3-yl)pyrimidin-2-yl)amino)piperidine-1-carboxylate (130 mg, 0.19 mmol), ethyl acetate (2 mL) and hydrochloric acid (4 M in ethyl acetate, 2 mL, 8 mmol). The residue was purified by Prep-HPLC (mobile phase: A: water (0.05% HCl); B: ACN) to yield 47 mg (40% yield) of 150 as a white solid. LCMS (ESI): [M+H]$^+$=599.3; $^1$H NMR (400 MHz, DMSO-d$_6$) δ 9.90 (s, 1H), 9.17 (s, 1H), 8.50 (d, J=5.2 Hz, 1H), 8.13-8.00 (m, 2H), 7.65 (s, 1H), 7.58-7.50 (m, 2H), 7.47-7.34 (m, 3H), 7.30-7.27 (m, 1H), 7.20 (t, J=8.8 Hz, 2H), 4.56 (s, 2H), 4.40-4.35 (m, 1H), 3.45-3.38 (m, 1H), 3.22-3.15 (m, 1H), 2.90-2.80 (m, 2H), 2.22 (s, 3H), 2.07-2.00 (m, 1H), 1.96-1.88 (m, 1H), 1.85-1.71 (m, 1H), 1.69-1.62 (m, 1H).

Example 151 (S)-1-Chloro-N-(6-methyl-5-((3-(2-(piperidin-3-ylamino)pyrimidin-4-yl)pyridin-2-yl)oxy)naphthalen-1-yl)methanesulfonamide 151

Step 1: (S)-tert-Butyl 3-((4-(2-((5-(chloromethylsulfonamido)-2-methylnaphthalen-1-yl)oxy)pyridin-3-yl)pyrimidin-2-yl)amino)piperidine-1-carboxylate

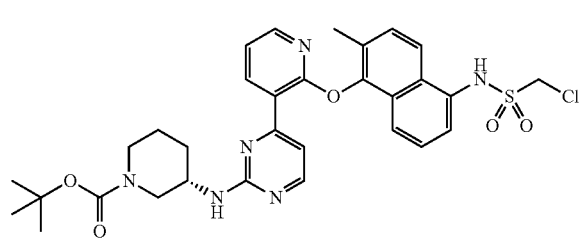 [SMILES: Cc1ccc2c(NS(=O)(=O)CCl)cccc2c1Oc1ncccc1-c1ccnc(N[C@H]2CCCN(C(=O)OC(C)(C)C)C2)n1]

The General Procedure A was followed, using (S)-tert-butyl 3-((4-(2-((5-amino-2-methylnaphthalen-1-yl)oxy)pyridin-3-yl)pyrimidin-2-yl)amino)piperidine-1-carboxylate (300 mg, 0.57 mmol), pyridine (2 mL) and chloromethanesulfonylchloride (0.06 mL, 0.68 mmol). The mixture was concentrated and dissolved in dichloromethane (100 mL) and washed with H$_2$O (80 mL×2). The organic phase was dried over anhydrous sodium sulfate and concentrated in vacuo to yield 110 mg (83% yield) of the title compound as a brown oil. LCMS (ESI) [M+H]$^+$=639.1.

Step 2: (S)-1-Chloro-N-(6-methyl-5-((3-(2-(piperidin-3-ylamino)pyrimidin-4-yl)pyridin-2-yl)oxy)naphthalen-1-yl)methanesulfonamide

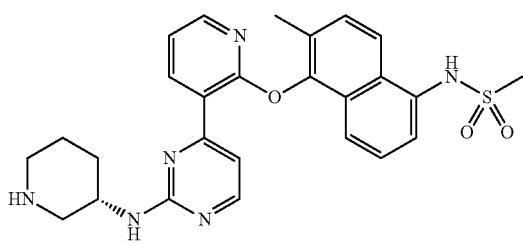

The General Procedure B was followed, using (S)-tert-butyl 3-((4-(2-((5-(chloromethylsulfonamido)-2-methylnaphthalen-1-yl)oxy)pyridin-3-yl)pyrimidin-2-yl)amino)piperidine-1-carboxylate (110 mg, 0.17 mmol), ethyl acetate (1 mL) and hydrochloric acid (4 M in ethyl acetate, 0.6 mL, 2.4 mmol). The residue was purified by Prep-HPLC (mobile phase: A: water (0.05% HCl); B: ACN) to yield 34 mg (34% yield) of 151 as a yellow solid. LCMS (ESI) [M+H]$^+$=539.1; $^1$H NMR (400 MHz, DMSO-d$_6$) δ 10.44 (s, 1H), 9.10-8.60 (m, 2H), 8.48 (d, J=5.6 Hz, 1H), 8.14 (d, J=8.8 Hz, 1H), 8.06 (d, J=3.2 Hz, 1H), 7.65-7.54 (m, 4H), 7.52-7.47 (m, 1H), 7.46-7.40 (m, 1H), 7.29-7.26 (m, 1H), 5.05 (s, 2H), 4.36-4.25 (m, 1H), 3.48-3.38 (m, 1H), 3.26-3.14 (m, 1H), 2.90-2.80 (m, 2H), 2.22 (s, 3H), 2.07-1.97 (m, 1H), 1.95-1.85 (m, 1H), 1.81-1.70 (m, 1H), 1.67-1.55 (m, 1H).

Example 152 N-(5-((3-(2-(((trans)-4-Aminocyclohexyl)amino)pyrimidin-4-yl)pyridin-2-yl)oxy)-6-methylnaphthalen-1-yl)-1-phenylmethanesulfonamide 152

Step 1: tert-Butyl ((trans)-4-((4-(2-((2-methyl-5-(phenylmethylsulfonamido)naphthalen-1-yl)oxy)pyridin-3-yl)pyrimidin-2-yl)amino)cyclohexyl)carbamate

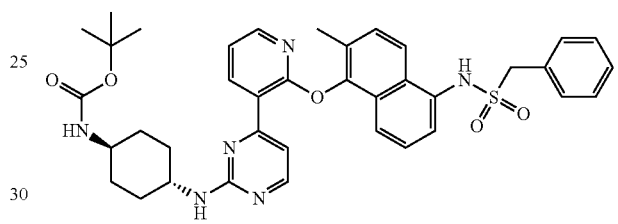

To a stirred solution of N-[6-methyl-5-[[3-(2-methylsulfinylpyrimidin-4-yl)-2-pyridyl]oxy]-1-naphthyl]-1-phenylmethanesulfonamide from Example 148 (100 mg, 0.18 mmol) in 1,4-dioxane (3 mL) was added N,N-diisopropylethylamine (0.1 mL, 0.55 mmol) and tert-butyl N-(4-aminocyclohexyl)carbamate (39 mg, 0.18 mmol). The mixture was stirred at 130° C. for 3 days and then concentrated in vacuo and purified by flash column chromatography eluting with 0-2% methanol in dichloromethane (Rf=0.5) to yield 100 mg (78% yield) of the title compound as a brown solid. LCMS (ESI) [M+H]$^+$=695.4.

Step 2: N-(5-((3-(2-(((trans)-4-Aminocyclohexyl)amino)pyrimidin-4-yl)pyridin-2-yl)oxy)-6-methylnaphthalen-1-yl)-1-phenylmethanesulfonamide

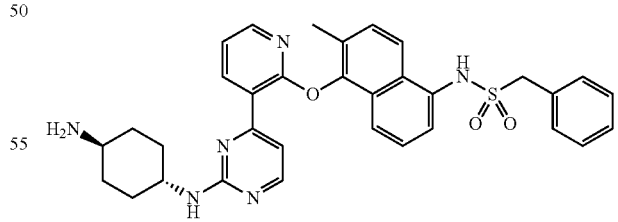

The General Procedure B was followed, using tert-butyl ((1r,4r)-4-((4-(2-((2-methyl-5-(phenylmethylsulfonamido)naphthalen-1-yl)oxy)pyridin-3-yl)pyrimidin-2-yl)amino)cyclohexyl) carbamate (100 mg, 0.14 mmol), dichloromethane (5 mL) and hydrochloric acid (4 M in ethyl acetate, 2 mL, 8 mmol). The residue was purified by Prep-HPLC (mobile phase: A: water (0.05% HCl); B: ACN) to yield 73 mg (80% yield) of 152 as a yellow solid. LCMS (ESI):

[M+H]⁺=595.4; ¹H NMR (400 MHz, DMSO-d₆) δ 9.92 (s, 1H), 8.59-8.43 (m, 2H), 8.25-8.04 (m, 5H), 7.74-7.27 (m, 12H), 4.58-4.51 (m, 2H), 3.99-3.84 (m, 1H), 3.09-2.97 (m, 1H), 2.22 (s, 3H), 2.15-1.98 (m, 4H), 1.60-1.39 (m, 4H).

Example 153 (S)-Ethyl (6-methyl-5-((3-(2-(piperidin-3-ylamino)pyrimidin-4-yl)pyridin-2-yl)oxy)naphthalen-1-yl)carbamate 153

Step 1: (S)-tert-Butyl 3-((4-(2-((5-((ethoxycarbonyl)amino)-2-methylnaphthalen-1-yl)oxy) pyridin-3-yl)pyrimidin-2-yl)amino)piperidine-1-carboxylate

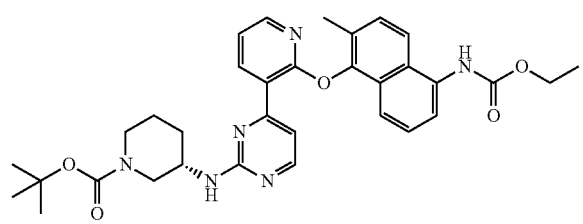 [SMILES: CCOC(=O)Nc1cccc2c(Oc3ncccc3-c3ccnc(N[C@H]4CCCN(C(=O)OC(C)(C)C)C4)n3)c(C)ccc12]

The General Procedure A was followed, using tert-butyl (3S)-3-[[4-[2-[(5-amino-2-methyl-1-naphthyl)oxy]-3-pyridyl]pyrimidin-2-yl]amino]piperidine-1-carboxylate (150 mg, 0.28 mmol), triethylamine (0.16 mL, 1.14 mmol) and ethyl chloroformate (0.26 mL, 2.76 mmol). The solution was concentrated to afford 200 mg of the crude title compound as a yellow solid. LCMS (ESI) [M+Na]⁺=621.1.

Step 2: (S)-Ethyl (6-methyl-5-((3-(2-(piperidin-3-ylamino)pyrimidin-4-yl)pyridin-2-yl)oxy)naphthalen-1-yl)carbamate

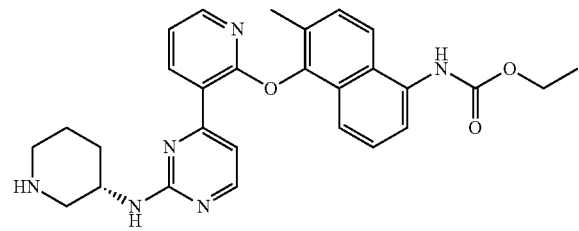 [SMILES: CCOC(=O)Nc1cccc2c(Oc3ncccc3-c3ccnc(N[C@H]4CCCNC4)n3)c(C)ccc12]

The General Procedure B was followed, using (S)-tert-butyl 3-((4-(2-((5-((ethoxycarbonyl)amino)-2-methylnaphthalen-1-yl)oxy)pyridin-3-yl)pyrimidin-2-yl)amino)piperidine-1-carboxylate (100 mg, 0.17 mmol), dichloromethane (5 mL) and hydrochloric acid (4 M in ethyl acetate, 2 mL, 8 mmol). The residue was purified by Prep-HPLC (mobile phase: A: water (0.05% HCl); B: ACN) to yield 29 mg (34% yield) of 153 as a yellow solid. LCMS (ESI): [M+H]⁺=517.2; ¹H NMR (400 MHz, DMSO-d₆) δ 9.59 (s, 1H), 9.22 (s, 1H), 8.50 (d, J=5.2 Hz, 1H), 8.07 (d, J=3.2 Hz, 1H), 7.94 (d, J=8.4 Hz, 1H), 7.67 (s, 1H), 7.56 (d, J=7.1 Hz, 1H), 7.48 (t, J=8.8 Hz, 2H), 7.43-7.36 (m, 1H), 7.27 (d, J=7.7 Hz, 1H), 4.42 (s, 1H), 4.14 (s, 2H), 3.43 (d, J=8.4 Hz, 1H), 3.19 (d, J=12.0 Hz, 1H), 2.85 (t, J=9.6 Hz, 2H), 2.27-2.13 (m, 3H), 2.03 (d, J=9.2 Hz, 1H), 1.96-1.87 (m, 1H), 1.86-1.72 (m, 1H), 1.65 (d, J=9.6 Hz, 1H), 1.28 (t, J=7.2 Hz, 3H).

Example 154 (S)-1-Methyl-N-(6-methyl-5-((3-(2-(piperidin-3-ylamino)pyrimidin-4-yl)pyridin-2-yl)oxy)naphthalen-1-yl)cyclopropane-1-carboxamide 154

Step 1: tert-Butyl (S)-3-((4-(2-((2-methyl-5-(1-methylcyclopropane-1-carboxamido)naphthalen-1-yl)oxy)pyridin-3-yl)pyrimidin-2-yl)amino)piperidine-1-carboxylate

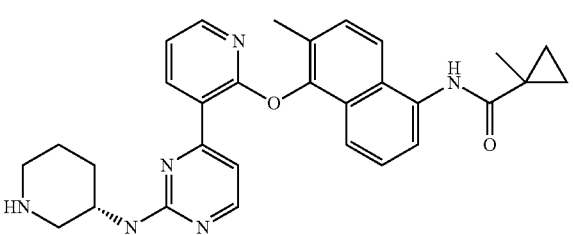

The General Procedure C was followed, using tert-butyl (S)-3-((4-(2-((5-amino-2-methylnaphthalen-1-yl)oxy)pyridin-3-yl)pyrimidin-2-yl)amino)piperidine-1-carboxylate from Example 101 (138 mg, 0.25 mmol), 1-methycyclopropane carboxylic acid (25 mg, 0.25 mmol), DIPEA (0.131 mL, 0.75 mmol), HATU (194 mg, 0.50 mmol) and DCM (4 mL). The crude was used in the next steps without further purification.

Step 2: (S)-1-Methyl-N-(6-methyl-5-((3-(2-(piperidin-3-ylamino)pyrimidin-4-yl)pyridin-2-yl)oxy)naphthalen-1-yl)cyclopropane-1-carboxamide The General Procedure B was followed, using crude tert-butyl (S)-3-((4-(2-((2-methyl-5-(1-methylcyclopropane-1-carboxamido)naphthalen-1-yl)oxy)pyridin-3-yl)pyrimidin-2-yl)amino)piperidine-1-carboxylate, DCM (4 mL) and hydrochloric acid (4 M in dioxane, 3 mL, 12 mmol). The residue was purified via reverse-phase HPLC and lyophilized to yield 50 mg (39% yield over 2 steps) of 154. LCMS (ESI): [M+H]⁺=509.2; ¹H NMR (400 MHz, DMSO-d₆) δ 9.47 (s, 1H), 8.54-8.47 (m, 1H), 8.42 (d, J=5.1 Hz, 1H), 8.03 (dd, J=4.8, 2.0 Hz, 1H), 7.71 (d, J=8.7 Hz, 1H), 7.56 (d, J=8.0 Hz, 1H), 7.51-7.45 (m, 2H), 7.42-7.34 (m, 2H), 7.25 (dd, J=7.6, 4.8 Hz, 1H), 7.19 (d, J=7.9 Hz, 1H), 3.96 (s, 1H), 3.20-3.12 (m, 1H), 2.87 (d, J=12.8 Hz, 1H), 2.22 (s, 3H), 1.99-1.90 (m, 1H), 1.73-1.65 (m, 1H), 1.52 (s, 3H), 1.54-1.46 (m, 1H), 1.18-1.13 (m, 2H), 0.72-0.68 (m, 2H).

Example 155 (S)-1-Fluoro-N-(6-methyl-5-((3-(2-(piperidin-3-ylamino)pyrimidin-4-yl)pyridin-2-yl)oxy)naphthalen-1-yl)cyclopropane-1-carboxamide 155

Step 1: tert-Butyl (S)-3-((4-(2-((5-(1-fluorocyclopropane-1-carboxamido)-2-methylnaphthalen-1-yl)oxy)pyridin-3-yl)pyrimidin-2-yl)amino)piperidine-1-carboxylate

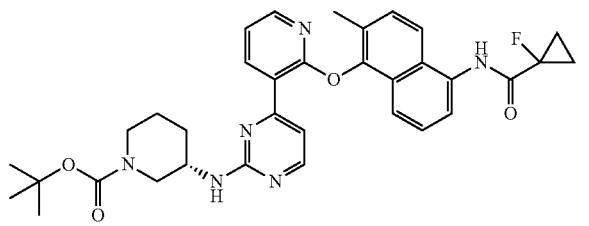 [SMILES: Cc1ccc2c(NC(=O)C3(F)CC3)cccc2c1Oc1ncccc1-c1ccnc(N[C@H]2CCCN(C(=O)OC(C)(C)C)C2)n1]

The General Procedure C was followed, using tert-butyl (S)-3-((4-(2-((5-amino-2-methylnaphthalen-1-yl)oxy)pyridin-3-yl)pyrimidin-2-yl)amino)piperidine-1-carboxylate from Example 101 (133 mg, 0.25 mmol), 1-fluorocyclopropanecarboxylic acid (25 mg, 0.24 mmol), DIPEA (0.126 mL, 0.72 mmol), HATU (186 mg, 0.48 mmol) and DCM (4 mL). The crude was directly used in the next step.

Step 2: (S)-1-Fluoro-N-(6-methyl-5-((3-(2-(piperidin-3-ylamino)pyrimidin-4-yl)pyridin-2-yl)oxy)naphthalen-1-yl)cyclopropane-1-carboxamide

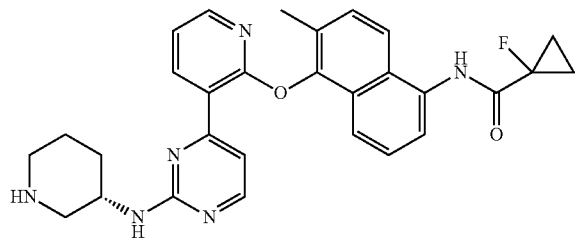

The General Procedure B was followed, using crude tert-butyl (S)-3-((4-(2-((5-(1-fluorocyclopropane-1-carboxamido)-2-methylnaphthalen-1-yl)oxy)pyridin-3-yl)pyrimidin-2-yl)amino)piperidine-1-carboxylate, DCM (4 mL) and hydrochloric acid (4 M in dioxane, 3 mL, 12 mmol). The residue was purified via reverse-phase HPLC and lyophilized to yield 68 mg (55% yield over 2 steps) of 155. LCMS (ESI): [M+H]$^+$=513.2; $^1$H NMR (400 MHz, DMSO-d$_6$) δ 10.45 (d, J=2.0 Hz, 1H), 8.50 (d, J=7.6 Hz, 1H), 8.41 (d, J=5.1 Hz, 1H), 8.04 (dd, J=4.8, 2.0 Hz, 1H), 7.75 (d, J=8.7 Hz, 1H), 7.65-7.58 (m, 1H), 7.52 (d, J=8.7 Hz, 1H), 7.48-7.40 (m, 3H), 7.26 (dd, J=7.5, 4.8 Hz, 1H), 7.13 (d, J=8.0 Hz, 1H), 3.90 (s, 1H), 3.14-3.05 (m, 1H), 2.85-2.75 (m, 1H), 2.48-2.41 (m, 2H), 2.22 (s, 3H), 1.97-1.88 (m, 1H), 1.68-1.59 (m, 1H), 1.58-1.27 (m, 6H).

Example 156 (S)—N-(6-Methyl-5-((3-(2-(piperidin-3-ylamino)pyrimidin-4-yl)pyridin-2-yl)oxy)naphthalen-1-yl)-1-(thiazol-4-yl)methanesulfonamide 156

Step 1: Thiazol-4-ylmethanesulfonyl chloride

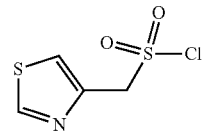

A mixture of 4-(chloromethyl)thiazole (1.0 g, 7.5 mmol), sodium sulfite (1.10 g, 9.0 mmol), and tetrabutylammonium bromide (120 mg, 0.37 mmol) in water (10 mL) was heated at 80° C. overnight, concentrated in vacuo, azeotroped with toluene (2×), and dried under high vacuum to afford thiazol-4-ylmethylsulfonyloxysodium. The crude product was used in the next step without further purification.

Thiazol-4-ylmethylsulfonyloxysodium (1.3 g, 6.5 mmol) was suspended in DMF (10 mL) cooled in ice bath. Thionyl chloride (0.71 mL, 9.7 mmol) was added dropwise. The resulting yellow mixture was allowed to warm to room temperature, stirred for 30 min. It was poured into crushed ice (~75 mL), extracted with iPrOAc (2×40 mL), washed with brine, dried over MgSO$_4$, filtered and concentrated in vacuo to afford 523 mg (41% yield) of the title compound as off-white solid. LCMS (ESI) [M+H]$^+$=198. The material obtained after workup was used immediately in the next step.

Step 2: tert-Butyl (S)-3-((4-(2-((2-methyl-5-((thiazol-4-ylmethyl)sulfonamido)naphthalen-1-yl)oxy)pyridin-3-yl)pyrimidin-2-yl)amino)piperidine-1-carboxylate

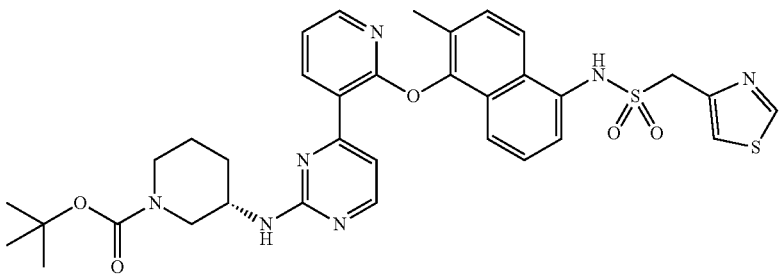 [SMILES: Cc1ccc2c(NS(=O)(=O)Cc3cscn3)cccc2c1Oc1ncccc1-c1ccnc(N[C@H]2CCCN(C(=O)OC(C)(C)C)C2)n1]

The General Procedure A was followed, using tert-butyl (3S)-3-[[4-[2-[(5-amino-2-methyl-1-naphthyl)oxy]-3-pyridyl]pyrimidin-2-yl]amino]piperidine-1-carboxylate (100 mg, 0.19 mmol), pyridine (2 mL), DCM (2 mL), and thiazol-4-ylmethanesulfonyl chloride (523 mg, 2.64 mmol). After work up, the title compound was obtained as a brown solid (145 mg, 100% yield). The product was used in the next step without further purification. LCMS (ESI) [M+H]+=688.

Step 4: (S)—N-(6-Methyl-5-((3-(2-(piperidin-3-ylamino)pyrimidin-4-yl)pyridin-2-yl)oxy)naphthalen-1-yl)-1-(thiazol-4-yl)methanesulfonamide

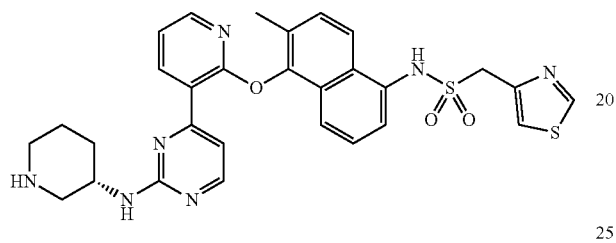

The General Procedure B was followed, using tert-butyl (S)-3-((4-(2-((2-methyl-5-(((thiazol-4-ylmethyl)sulfonamido)naphthalen-1-yl)oxy)pyridin-3-yl)pyrimidin-2-yl)amino)piperidine-1-carboxylate (145 mg, 211 mmol). The crude product was purified via reverse-phase HPLC and lyophilized to yield 20.3 mg (16.5% yield) of 156 as an off-white solid. LCMS (ESI) [M+H]+=588; $^1$H NMR (400 MHz, DMSO-d$_6$) δ 9.06 (d, J=2.0 Hz, 1H), 8.51 (d, J=7.7 Hz, 1H), 8.42 (d, J=5.1 Hz, 1H), 8.13 (d, J=8.7 Hz, 1H), 8.05 (dd, J=4.8, 2.0 Hz, 1H), 7.68 (d, J=2.0 Hz, 1H), 7.50-7.39 (m, 3H), 7.36-7.29 (m, 1H), 7.25 (dd, J=7.6, 4.8 Hz, 1H), 7.21 (d, J=7.9 Hz, 1H), 4.59 (s, 2H), 3.98 (s, 1H), 3.20 (d, J=16.6 Hz, 2H), 2.90 (d, J=12.2 Hz, 1H), 2.61-2.53 (m, 1H), 2.20 (s, 3H), 1.99-1.92 (m, 1H), 1.75-1.68 (m, 1H), 1.57-1.46 (m, 2H).

Example 157 (S)-1-(2,4-Difluorophenyl)-N-(6-methyl-5-((3-(2-(piperidin-3-ylamino)pyrimidin-4-yl)pyridin-2-yl)oxy)naphthalen-yl)oxy)naphthalen-1-yl)methanesulfonamide 157

Step 1: (S)-tert-Butyl 3-((4-(2-((5-((2,4-difluorophenyl)methylsulfonamido)-2-methylnaphthalen-1-yl)oxy)pyridin-3-yl)pyrimidin-2-yl)amino)piperidine-1-carboxylate

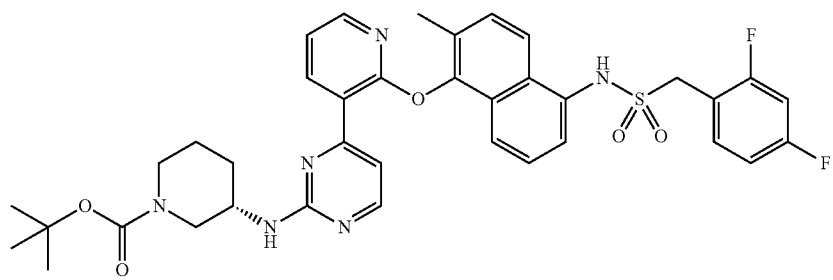 [SMILES: Cc1ccc2c(NS(=O)(=O)Cc3ccc(F)cc3F)cccc2c1Oc1ncccc1-c1ccnc(N[C@H]2CCCN(C(=O)OC(C)(C)C)C2)n1]

The General Procedure A was followed, using tert-butyl (3S)-3-[[4-[2-[(5-amino-2-methyl-1-naphthyl)oxy]-3-pyridyl]pyrimidin-2-yl]amino]piperidine-1-carboxylate (150 mg, 0.28 mmol), pyridine (3 mL) and 2,4-difluorophenyl)methanesulfonyl chloride (65 mg, 0.28 mmol). The solution was concentrated to afford 150 mg (74% yield) of the crude title compound as a yellow solid. LCMS (ESI) [M+H]⁺=717.1.

Step 2: (S)-1-(2,4-Difluorophenyl)-N-(6-methyl-5-((3-(2-(piperidin-3-ylamino)pyrimidin-4-yl)pyridin-2-yl)oxy)naphthalen-1-yl)methanesulfonamide

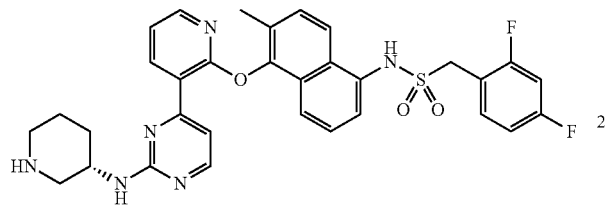

The General Procedure B was followed, using (S)-tert-butyl 3-((4-(2-((5-((2,4-difluorophenyl)methylsulfonamido)-2-methylnaphthalen-1-yl)oxy)pyridin-3-yl)pyrimidin-2-yl)amino) piperidine-1-carboxylate (150 mg, 0.21 mmol), dichloromethane (5 mL) and hydrochloric acid (4 M in ethyl acetate, 2 mL, 8 mmol). The residue was purified by Prep-HPLC (mobile phase: A: water (0.05% HCl); B: ACN) to yield 38 mg (29% yield) of 157 as a yellow solid. LCMS (ESI): [M+H]⁺=517.2; ¹H NMR (400 MHz, DMSO-d₆) δ 10.12-10.02 (m, 1H), 9.67 (s, 1H), 9.35 (s, 1H), 8.89 (s, 1H), 8.52 (d, J=5.6 Hz, 1H), 8.15-8.02 (m, 2H), 7.74 (s, 1H), 7.60-7.38 (m, 5H), 7.34-7.23 (m, 2H), 7.12 (t, J=8.4 Hz, 1H), 4.59 (s, 2H), 4.49 (s, 1H), 3.51-3.13 (m, 2H), 2.94-2.78 (m, 2H), 2.21 (s, 3H), 2.09-1.56 (m, 4H).

Example 158 N-(5-((3-(2-(((trans)-4-Aminocyclohexyl)amino)pyrimidin-4-yl)pyridin-2-yl)oxy)-6-methylnaphthalen-1-yl)propane-1-sulfonamide 158

Step 1: tert-Butyl ((trans)-4-((4-(2-((2-methyl-5-(propylsulfonamido)naphthalen-1-yl)oxy)pyridin-3-yl)pyrimidin-2-yl)amino)cyclohexyl)carbamate

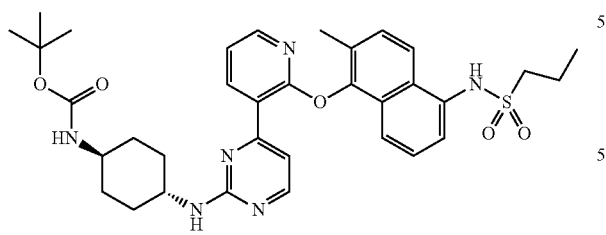

To a stirred solution of N-(6-methyl-5-((3-(2-(methylsulfinyl)pyrimidin-4-yl)pyridin-2-yl)oxy)naphthalen-1-yl)propane-1-sulfonamide (100 mg, 0.20 mmol) in 1,4-dioxane (3 mL) was added N,N-diisopropylethylamine (0.1 mL, 0.55 mmol) and tert-butyl N-(4-aminocyclohexyl)carbamate (65 mg, 0.30 mmol). The mixture was stirred at 130° C. for 16 h. The reaction was concentrated to dryness and purified by flash column chromatography eluting with 0-10% methanol in dichloromethane (Rf=0.5) to yield 100 mg (77% yield) of the title compound as a yellow solid. LCMS (ESI) [M+H]⁺=647.1.

Step 2: N-(5-((3-(2-(((trans)-4-Aminocyclohexyl)amino)pyrimidin-4-yl)pyridin-2-yl)oxy)-6-methyl-naphthalen-1-yl)propane-1-sulfonamide

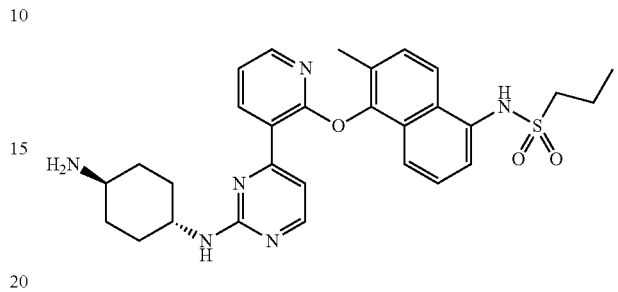

The General Procedure B was followed, using tert-butyl ((1r,4r)-4-((4-(2-((2-methyl-5-(propylsulfonamido)naphthalen-1-yl)oxy)pyridin-3-yl)pyrimidin-2-yl)amino)cyclohexyl)carbamate (100 mg, 0.15 mmol), dichloromethane (5 mL) and hydrochloric acid (4 M in ethyl acetate, 2 mL, 8 mmol). The residue was purified by Prep-HPLC (mobile phase: A: water (0.05% HCl); B: ACN) to yield 45 mg (49% yield) of 158 as a yellow solid. LCMS (ESI): [M+H]⁺=547.1; ¹H NMR (400 MHz, DMSO-d₆) δ 9.84 (s, 1H), 8.63-8.43 (m, 3H), 8.24-8.13 (m, 5H), 7.70-7.66 (m, 1H), 7.63-7.54 (m, 2H), 7.49-7.41 (m, 2H), 7.36-7.31 (m, 1H), 3.96-3.85 (m, 1H), 3.17-3.10 (m, 2H), 3.08-2.97 (m, 1H), 2.23 (s, 3H), 2.14-1.99 (m, 4H), 1.83-1.71 (m, 2H), 1.62-1.38 (m, 4H), 0.97 (t, J=7.2 Hz, 3H).

Example 159 (S)-1-Fluoro-N-(6-methyl-5-(3-(2-(piperidin-3-ylamino)pyrimidin-4-yl)pyridin-2-yloxy)naphthalen-1-yl)methanesulfonamide 159

Step 1: (S)-tert-Butyl 3-(4-(2-(5-(fluoromethylsulfonamido)-2-methylnaphthalen-1-yloxy)pyridin-3-yl) pyrimidin-2-ylamino)piperidine-1-carboxylate

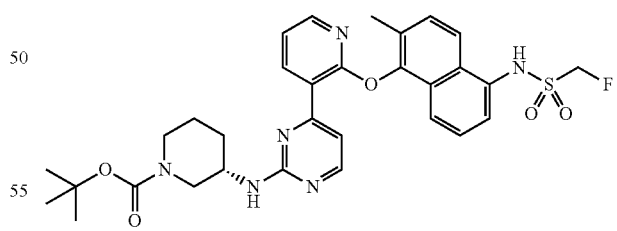

The General Procedure A was followed, using tert-butyl (3S)-3-[[4-[2-[(5-amino-2-methyl-1-naphthyl)oxy]-3-pyridyl]pyrimidin-2-yl]amino]piperidine-1-carboxylate (50 mg, 0.095 mmol), pyridine (1 mL) and fluoromethanesulfonyl chloride (81 mg, 0.61 mmol). The crude was then purified by flash chromatography (gradient 0 to 80% of 1:4 MeOH/DCM in DCM) to yield 38 mg (64% yield) of the title compound as a brown solid. LCMS (ESI) [M+H]⁺=623.3.

Step 2: (S)-1-Fluoro-N-(6-methyl-5-(3-(2-(piperidin-3-ylamino)pyrimidin-4-yl)pyridin-2-yloxy)naphthalen-1-yl)methanesulfonamide

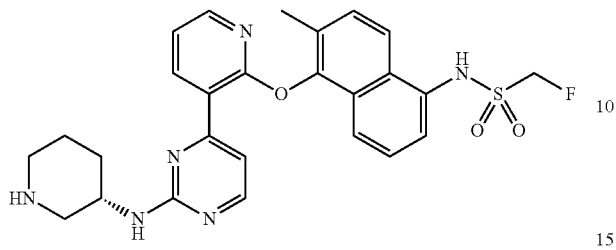

To (S)-tert-butyl 3-(4-(2-(5-(fluoromethylsulfonamido)-2-methylnaphthalen-1-yloxy)pyridin-3-yl)pyrimidin-2-ylamino)piperidine-1-carboxylate (38 mg, 0.061 mmol) in DCM (6 mL) was added trifluoroacetic acid (1 mL). The mixture was concentrated and the residue purified by Prep-HPLC to yield 19.8 mg (40% yield) of 159 as a white solid. LCMS (ESI): $[M+H]^+$=523.1; $^1$HNMR (400 MHz, DMSO-$d_6$) δ 8.45 (d, J=5.2 Hz, 2H), 8.23 (m, 1H), 8.04 (dd, J=4.8, 2.0 Hz, 1H), 7.54 (d, J=5.2 Hz, 1H), 7.37 (d, J=7.5 Hz, 1H), 7.29 (d, J=8.7 Hz, 1H), 7.23 (dd, J=7.6, 4.8 Hz, 1H), 7.21-7.10 (m, 2H), 7.01 (d, J=8.1 Hz, 1H), 5.03 (d, J=47.8 Hz, 2H), 4.14 (s, 1H), 3.09 (dd, J=10.4, 6.4 Hz, 1H), 2.82-2.68 (m, 2H), 2.18 (s, 3H), 2.00 (s, 1H), 1.84 (s, 1H), 1.62 (q, J=10.7 Hz, 2H).

Example 160 (S)-1-(4-(Difluoromethyl)phenyl)-N-(6-methyl-5-((3-(2-(piperidin-3-ylamino)pyrimidin-4-yl)pyridin-2-yl)oxy)naphthalen-1-yl)methanesulfonamide 160

Step 1: (S)-tert-Butyl 3-((4-(2-((5-((4-(difluoromethyl)phenyl)methylsulfonamido)-2-methylnaphthalen-1-yl)oxy)pyridin-3-yl)pyrimidin-2-yl)amino)piperidine-1-carboxylate

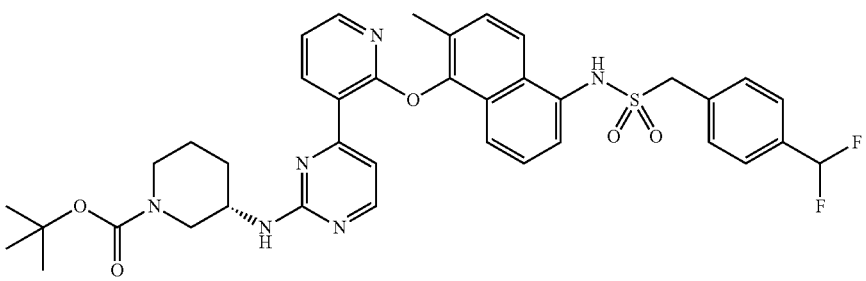 [SMILES: Cc1ccc2c(NS(=O)(=O)Cc3ccc(C(F)F)cc3)cccc2c1Oc1ncccc1-c1ccnc(N[C@H]2CCCN(C(=O)OC(C)(C)C)C2)n1]

The General Procedure A was followed, using tert-butyl (3S)-3-[[4-[2-[(5-amino-2-methyl-1-naphthyl)oxy]-3-pyridyl]pyrimidin-2-yl]amino]piperidine-1-carboxylate (100 mg, 0.19 mmol), pyridine (2 mL) and [4-(difluoromethyl)phenyl]methanesulfonyl chloride (91 mg, 0.38 mmol). The resulting solution was extracted with ethyl acetate. The combined organic layers were dried over anhydrous sodium sulfate, and concentrated in vacuo to yield 80 mg of the crude title compound as a yellow solid. LCMS (ESI) $[M+Na]^+$=753.1.

Step 2: (S)-1-(4-(Difluoromethyl)phenyl)-N-(6-methyl-5-((3-(2-(piperidin-3-ylamino)pyrimidin-4-yl)pyridin-2-yl)oxy)naphthalen-1-yl)methanesulfonamide

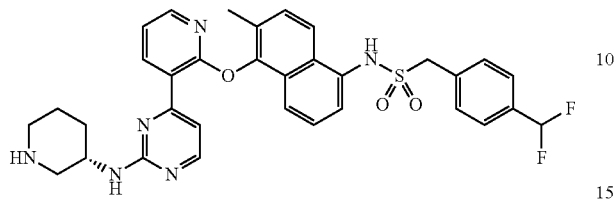

The General Procedure B was followed, using (S)-tert-butyl 3-((4-(2-((5-((4-(difluoromethyl)phenyl)methylsulfonamido)-2-methylnaphthalen-1-yl)oxy)pyridin-3-yl)pyrimidin-2-yl)amino)piperidine-1-carboxylate (80 mg, 0.11 mmol), dichloromethane (2 mL) and hydrochloric acid (4 M in dioxane, 2 mL, 8 mmol). The residue was purified by Prep-HPLC (mobile phase: A: water (0.05% HCl); B: ACN) to yield 33 mg (45% yield) of 160 as a yellow solid. LCMS (ESI) [M+H]$^+$=631.1. $^1$H NMR (400 MHz, DMSO-d$_6$) δ 9.96 (s, 1H), 9.44 (s, 1H), 9.22 (s, 1H), 8.82 (s, 1H), 8.50 (d, J=5.4 Hz, 1H), 8.09 (d, J=3.2 Hz, 1H), 8.04 (d, J=8.8 Hz, 1H), 7.90 (s, 1H), 7.68 (s, 1H), 7.60-7.50 (m, 5H), 7.49-7.38 (m, 2H), 7.31-7.26 (m, 1H), 7.05 (t, J=56.0 Hz 1H), 4.64 (s, 2H), 4.45-4.35 (m, 1H), 3.46-3.42 (m, 1H), 3.22-3.18 (m, 1H), 2.90-2.80 (m, 2H), 2.22 (s, 3H), 2.04-1.97 (m, 1H), 1.95-1.88 (m, 1H), 1.85-1.75 (m, 1H), 1.65 (m, 1H).

Example 161 N-(5-((3-(2-(((3S,5R)-5-Methoxypiperidin-3-yl)amino)pyrimidin-4-yl)pyridin-2-yl)oxy)-6-methylnaphthalen-1-yl)-1-phenylmethanesulfonamide 161

Step 1: Benzyl 3-((tert-butoxycarbonyl)amino)-5-hydroxypiperidine-1-carboxylate

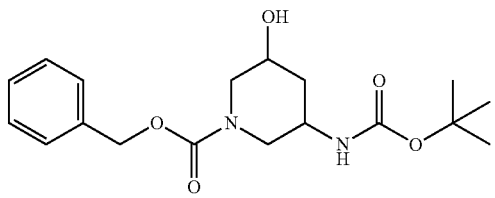 [SMILES: CC(C)(C)OC(=O)NC1CC(O)CN(C(=O)OCc2ccccc2)C1]

To a solution of benzyl chloroformate, Cbz-Cl (1.03 mL, 7.21 mmol), and sodium bicarbonate (505 mg, 6.01 mmol) in tetrahydrofuran (5 mL) was added tert-butyl-N-(5-hydroxy-3-piperidyl)carbamate (1.3 g, 6.01 mmol). The mixture was stirred at 21° C. for 4 h. The solution was concentrated and purified by chromatography on silica (solvent gradient: methanol in dichloromethane) to yield 2 g (95% yield) of the title compound as a white solid. LCMS (ESI) [M+Na]$^+$=372.9.

Step 2: Benzyl 3-((tert-butoxycarbonyl)amino)-5-methoxypiperidine-1-carboxylate

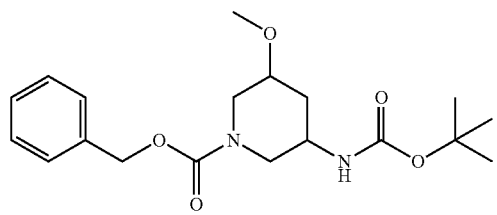 [SMILES: COC1CC(NC(=O)OC(C)(C)C)CN(C(=O)OCc2ccccc2)C1]

To a solution of benzyl 3-((tert-butoxycarbonyl)amino)-5-hydroxypiperidine-1-carboxylate (3.0 g, 8.6 mmol), silver oxide, Ag$_2$O (2 g, 8.6 mmol) in acetonitrile (60 mL) and N,N-dimethylformamide (15 mL) was added iodomethane, MeI (7.0 mL, 111.46 mmol). The mixture was stirred at 25° C. for 24 h. The solution was filtered and concentrated. The residue was purified by chromatography on silica (solvent gradient: 0-40% ethyl acetate in petroleum ether) to yield 2.3 g (74% yield) of the title compound as a colorless oil. LCMS (ESI) [M+Na]$^+$=387.1.

Step 3: Benzyl 3-amino-5-methoxypiperidine-1-carboxylate

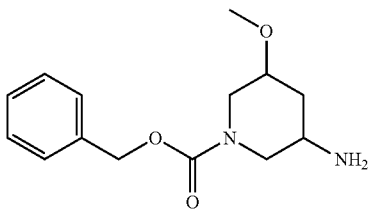 [SMILES: COC1CC(N)CN(C(=O)OCc2ccccc2)C1]

To a solution of benzyl 3-((tert-butoxycarbonyl)amino)-5-methoxypiperidine-1-carboxylate (2.2 g, 6.04 mmol) in dichloromethane (20 mL) was added 4M hydrochloric acid (10 mL, 44 mmol) in ethyl acetate and the mixture was stirred at 25° C. for 1 h. The reaction solution was concentrated in vacuo to yield 2 g of the crude title compound as a white solid. LCMS (ESI) [M+H]$^+$=264.9.

Step 4: Benzyl 3-methoxy-5-((4-(2-((2-methyl-5-(phenylmethylsulfonamido)naphthalen-1-yl)oxy)pyridin-3-yl)pyrimidin-2-yl)amino)piperidine-1-carboxylate

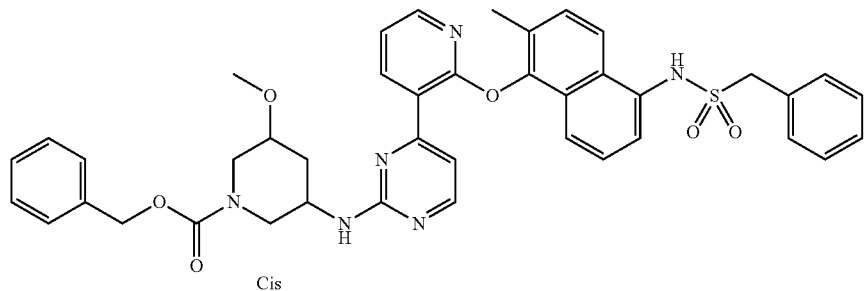 [SMILES: COC1CC(Nc2nccc(-c3cccnc3Oc3c(C)ccc4c(NS(=O)(=O)Cc5ccccc5)cccc34)n2)CN(C(=O)OCc2ccccc2)C1]

To a solution of N-[6-methyl-5-[[3-(2-methylsulfinylpyrimidin-4-yl)-2-pyridyl]oxy]-1-naphthyl]-1-phenyl-methanesulfonamide from Example 148 (600 mg, 1.1 mmol) in 1,4-dioxane (5 mL) was added N,N-diisopropylethylamine (0.59 mL, 3.3 mmol) and benzyl 3-amino-5-methoxypiperidine-1-carboxylate (420.0 mg, 1.59 mmol). The mixture was stirred at 130° C. for 16 h. The solution was concentrated and purified by prep-TLC (5% methanol in dichloromethane, Rf=0.5) and then purified by using chiral SFC (SFC80; Chiralpak AD 250×30 mm I.D., 10 μm; supercritical $CO_2$/MeOH+$NH_3$.$H_2O$=55/55; 80 mL/min) to afford (3S,5R)-benzyl 3-methoxy-5-((4-(2-((2-methyl-5-(phenylmethylsulfonamido) naphthalen-1-yl)oxy)pyridin-3-yl)pyrimidin-2-yl)amino)piperidine-1-carboxylate (300 mg, 40% yield, Rt=1.80 min) and (3R,5S)-benzyl-3-methoxy-5-((4-(2-((2-methyl-5-(phenylmethylsulfonamido)naphthalen-1-yl)oxy)pyridine-3-yl)pyrimidin-2-yl)amino)piperidine-1-carboxylate (250 mg, 33.3% yield, Rt=3.06 min) as a yellow solid. LCMS (ESI) $[M+H]^+$=745.2.

Step 5: N-(5-((3-(2-(((3S,5R)-5-Methoxypiperidin-3-yl)amino)pyrimidin-4-yl)pyridin-2-yl)oxy)-6-methylnaphthalen-1-yl)-1-phenylmethanesulfonamide

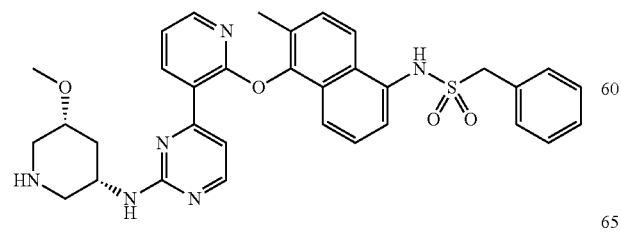

To a solution of thiourea (77 mg, 1.01 mmol), 1-methylimidazole (66 mg, 0.81 mmol) and (3R,5S)-benzyl3-methoxy-5-((4-(2-((2-methyl-5-(phenylmethylsulfonamido)naphthalen-1-yl)oxy)pyridin-3-yl)pyrimidin-2-yl)amino)piperidine-1-carboxylate (150 mg, 0.20 mmol, the second peak in step 2) in redistilled acetonitrile (2 mL) was added iodotrimethylsilane (0.23 mL, 1.65 mmol) dropwise. Then the mixture was stirred for 16 h. Then the mixture was quenched with water (15 mL) and extracted with ethyl acetate (20 mL×3). The combined organic extracts were concentrated in vacuo and the residue was purified by Prep-HPLC (mobile phase: A: water (0.05% NH$_4$OH); B: ACN) to afford 161 (37 mg, 29.5% yield) as a white solid (ee=95%). LCMS (ESI) [M+H]$^+$=611.1; $^1$H NMR (400 MHz, CDCl$_3$) δ 8.63-8.54 (m, 1H), 8.37 (d, J=5.4 Hz, 1H), 8.01 (d, J=4.8 Hz, 1H), 7.69 (d, J=8.4 Hz, 1H), 7.65-7.56 (m, 3H), 7.44-7.28 (m, 6H), 7.26 (d, J=2.0 Hz, 1H), 7.11 (d, J=7.6 Hz, 1H), 6.21 (s, 1H), 4.39 (s, 2H), 4.20-4.15 (m, 1H), 3.44 (s, 3H), 3.41-3.35 (m, 1H), 3.09-2.91 (m, 4H), 2.30 (s, 3H), 2.20-2.16 (m, 1H), 1.93-1.88 (m, 1H).

Example 162 N-(5-((3-(2-((4-Fluoropiperidin-3-yl)amino)pyrimidin-4-yl)pyridin-2-yl)oxy)-6-methyl-naphthalen-1-yl)-1-phenylmethanesulfonamide 162

Step 1: tert-Butyl 4-fluoro-3-((4-(2-((2-methyl-5-(phenylmethylsulfonamido)naphthalen-1-yl)oxy)pyridin-3-yl)pyrimidin-2-yl)amino)piperidine-1-carboxylate

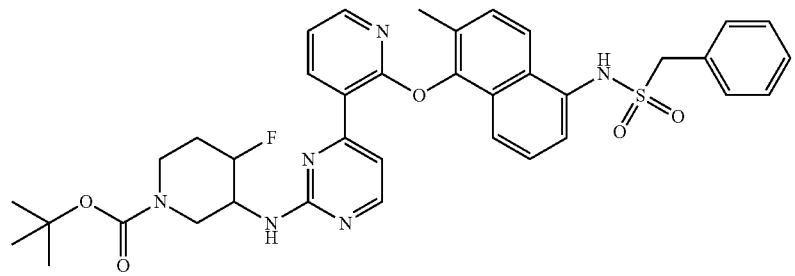 [SMILES: Cc1ccc2c(NS(=O)(=O)Cc3ccccc3)cccc2c1Oc1ncccc1-c1ccnc(NC2CN(C(=O)OC(C)(C)C)CCC2F)n1]

To a stirred solution of N-(6-methyl-5-((3-(2-(methylsulfinyl)pyrimidin-4-yl)pyridin-2-yl)oxy)naphthalen-1-yl)propane-1-sulfonamide (100 mg, 0.18 mmol) in 1,4-dioxane (3 mL) was added N,N-diisopropylethylamine (0.1 mL, 0.55 mmol) and trans-tert-butyl N-(4-aminocyclohexyl)carbamate (40 mg, 0.18 mmol), the mixture was stirred at 135° C. for 4 days. The reaction was concentrated in vacuo and purified by flash column chromatography eluting with 0-10% methanol in dichloromethane (Rf=0.5) to yield 100 mg (78% yield) of the title compound as a yellow solid. LCMS (ESI) [M+H]$^+$=699.1.

Step 2: N-(5-((3-(2-((4-Fluoropiperidin-3-yl)amino) pyrimidin-4-yl)pyridin-2-yl)oxy)-6-methylnaphthalen-1-yl)-1-phenylmethanesulfonamide

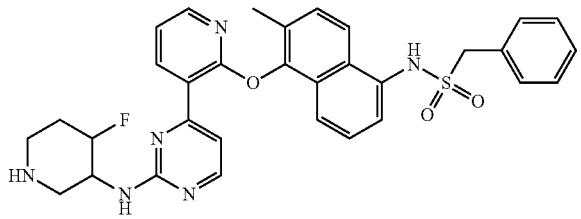 [SMILES: Cc1ccc2c(NS(=O)(=O)Cc3ccccc3)cccc2c1Oc1ncccc1-c1ccnc(NC2CNCCC2F)n1]

The General Procedure B was followed, using tert-butyl ((1r,4r)-4-((4-(2-((2-methyl-5-(propylsulfonamido)naphthalen-1-yl)oxy)pyridin-3-yl)pyrimidin-2-yl)amino)cyclohexyl)carbamate (100 mg, 0.14 mmol), dichloromethane (5 mL) and hydrochloric acid (4 M in ethyl acetate, 2 mL, 8 mmol). The residue was purified by Prep-HPLC (mobile phase: A: water (0.05% HCl); B: ACN) to yield 17 mg (18% yield) of 162 as a yellow solid (as mixture of enantiomers). LCMS (ESI): [M+H]$^+$=599.1; $^1$H NMR (400 MHz, DMSO-d$_6$) δ 9.90 (s, 1H), 9.44 (s, 1H), 8.98-8.42 (m, 2H), 8.13-7.92 (m, 3H), 7.80-7.62 (m, 1H), 7.59-7.49 (m, 2H), 7.44-7.33 (m, 7H), 7.31-7.25 (m, 1H), 5.03-4.74 (m, 2H), 4.59-4.48 (m, 2H), 3.53-3.26 (m, 2H), 3.11-2.89 (m, 2H), 2.39-2.29 (m, 1H), 2.21 (s, 3H), 2.13-1.98 (m, 1H).

Example 163 (S)—N-(3-Methyl-4-((3-(2-(piperidin-3-ylamino)pyrimidin-4-yl)pyridin-2-yl)oxy)naphthalen-1-yl)-1-phenylmethanesulfonamide 163

Step 1: (S)-tert-Butyl 3-((4-(2-((2-methyl-4-(phenylmethylsulfonamido)naphthalen-1-yl)oxy)pyridin-3-yl)pyrimidin-2-yl)amino)piperidine-1-carboxylate

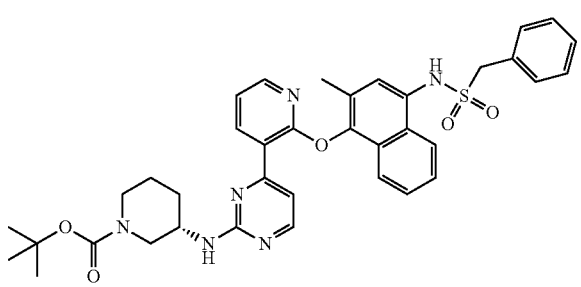 [SMILES: Cc1cc(NS(=O)(=O)Cc2ccccc2)c2ccccc2c1Oc1ncccc1-c1ccnc(N[C@H]2CCCN(C(=O)OC(C)(C)C)C2)n1]

The General Procedure A was followed, using tert-butyl (3S)-3-[[4-[2-[(4-amino-2-methyl-1-naphthyl)oxy]-3-pyridyl]pyrimidin-2-yl]amino]piperidine-1-carboxylate (200 mg, 0.38 mmol), pyridine (2 mL) and phenylmethanesulfonyl chloride (108 mg, 0.57 mmol). The reaction was then concentrated in vacuo to yield 200 mg of the crude title compound as a brown solid. LCMS (ESI) [M+Na]$^+$=703.1.

Step 2: (S)—N-(3-Methyl-4-((3-(2-(piperidin-3-ylamino)pyrimidin-4-yl)pyridin-2-yl)oxy)naphthalen-1-yl)-1-phenylmethanesulfonamide

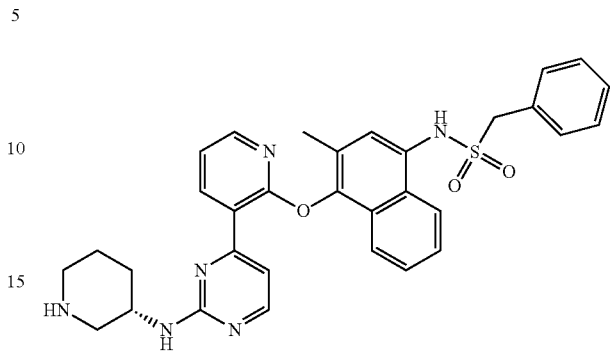

The General Procedure B was followed, using (S)-tert-butyl 3-((4-(2-((2-methyl-4-(phenylmethylsulfonamido) naphthalen-1-yl)oxy)pyridin-3-yl)pyrimidin-2-yl)amino)piperidine-1-carboxylate (200 mg, 0.29 mmol), dichloromethane (5 mL) and hydrochloric acid (4 M in dioxane, 2 mL, 8 mmol). The residue was purified by Prep-HPLC (mobile phase: A: water (0.05% HCl); B: ACN) to yield 56 mg (30% yield) of 163 as a yellow solid. LCMS (ESI): [M+H]$^+$=581.1; $^1$H NMR (400 MHz, DMSO-d$_6$) δ 9.89-9.78 (m, 1H), 9.60-9.18 (m, 2H), 8.94-8.70 (m, 1H), 8.55-8.46 (m, 1H), 8.40-8.07 (m, 2H), 8.05-7.62 (m, 3H), 7.54-7.37 (m, 6H), 7.33-7.26 (m, 2H), 4.58 (s, 2H), 4.46-4.38 (m, 1H), 3.49-3.38 (m, 1H), 3.26-3.14 (m, 1H), 2.93-2.77 (m, 2H), 2.18 (s, 3H), 2.07-1.87 (m, 2H), 1.86-1.59 (m, 2H).

Example 164 (S)—N-(3-Methyl-4-((3-(2-(piperidin-3-ylamino)pyrimidin-4-yl)pyridin-2-yl)oxy)naphthalen-1-yl)propane-1-sulfonamide 164

Step 1: (S)-tert-Butyl 3-((4-(2-((2-methyl-4-(propylsulfonamido)naphthalen-1-yl)oxy) pyridin-3-yl) pyrimidin-2-yl)amino)piperidine-1-carboxylate

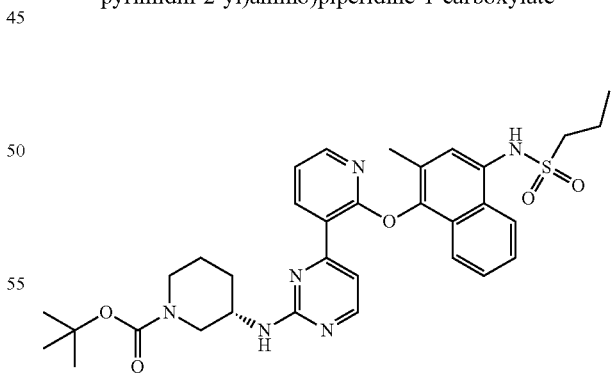

The General Procedure A was followed, using tert-butyl (3S)-3-[[4-[2-[(4-amino-2-methyl-1-naphthyl)oxy]-3-pyridyl]pyrimidin-2-yl]amino]piperidine-1-carboxylate (200 mg, 0.38 mmol), pyridine (2 mL) and 1-propanesulfonyl chloride (82 mg, 0.57 mmol). The reaction mixture was then concentrated to yield 200 mg of the crude title compound as a brown oil. LCMS (ESI) [M+Na]$^+$=655.1.

Step 2: (S)—N-(3-Methyl-4-((3-(2-(piperidin-3-ylamino)pyrimidin-4-yl)pyridin-2-yl)oxy)naphthalen-1-yl)propane-1-sulfonamide

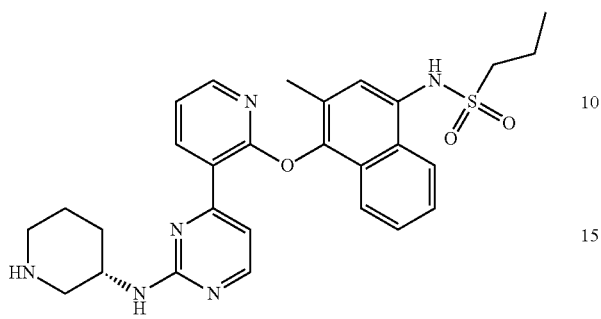

The General Procedure B was followed, using (S)-tert-butyl 3-((4-(2-((2-methyl-4-(propylsulfonamido)naphthalen-1-yl)oxy)pyridin-3-yl)pyrimidin-2-yl)amino)piperidine-1-carboxylate (200 mg, 0.31 mmol), dichloromethane (5 mL) and hydrochloric acid (4 M in dioxane, 2 mL, 8 mmol). The residue was purified by Prep-HPLC (mobile phase: A: water (0.05% HCl); B: ACN) to yield 56 mg (30% yield) of 164 as a yellow solid. LCMS (ESI): [M+H]$^+$=533.1; $^1$H NMR (400 MHz, DMSO-d$_6$) δ 9.83-9.47 (m, 2H), 9.41-9.19 (m, 1H), 9.02-8.74 (m, 1H), 8.56-8.46 (m, 1H), 8.30-8.05 (m, 3H), 7.83-7.62 (m, 2H), 7.59-7.52 (m, 1H), 7.48-7.42 (m, 2H), 7.32-7.27 (m, 1H), 4.67-4.33 (m, 1H), 3.48-3.38 (m, 1H), 3.24-3.11 (m, 3H), 2.92-2.79 (m, 2H), 2.22 (s, 3H), 2.09-1.99 (m, 1H), 1.96-1.87 (m, 1H), 1.86-1.74 (m, 3H), 1.73-1.60 (m, 1H), 0.99 (t, J=7.2 Hz, 3H).

Example 165 N-(5-((3-(2-(((3S,5S)-5-Fluoropiperidin-3-yl)amino) pyrimidin-4-yl)pyridin-2-yl)oxy)-6-methylnaphthalen-1-yl)propane-1-sulfonamide 165

Step 1: N-(5-((3-(2-(((3S,5S)-5-Fluoro-1-(4-methoxybenzyl)piperidin-3-yl)amino)pyrimidin-4-yl)pyridin-2-yl)oxy)-6-methylnaphthalen-1-yl)propane-1-sulfonamide

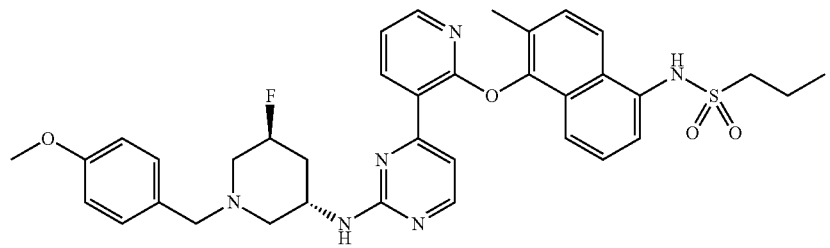 [SMILES: CCCS(=O)(=O)Nc1cccc2c(Oc3ncccc3-c3ccnc(N[C@H]4C[C@H](F)CN(Cc5ccc(OC)cc5)C4)n3)c(C)ccc12]

To a solution of N-[6-methyl-5-[[3-(2-methylsulfinylpyrimidin-4-yl)-2-pyridyl]oxy]-1-naphthyl]propane-1-sulfonamide (100 mg, 0.2 mmol) in 1,4-dioxane (3 mL) was added N,N-diisopropylethylamine (0.11 mL, 0.6 mmol) and (3S,5S)-5-fluoro-1-[(4-methoxyphenyl)methyl]piperidin-3-amine (52.8 mg, 0.22 mmol). The mixture was stirred at 120° C. for 64 h. After cooling down, the mixture was concentrated in vacuo, dissolved in dichloromethane (30 mL) and washed with H$_2$O (30 mL×2). The organic phase was dried over anhydrous sodium sulfate, concentrated in vacuo and the residue was purified by Prep-TLC (5% methanol in dichloromethane, Rf=0.6) to yield 34 mg (25% yield) of the title compound as a yellow solid; LCMS (ESI) [M+H]$^+$=671.0

Step 2: N-(5-((3-(2-(((3S,5S)-5-Fluoropiperidin-3-yl)amino)pyrimidin-4-yl)pyridin-2-yl)oxy)-6-methylnaphthalen-1-yl)propane-1-sulfonamide

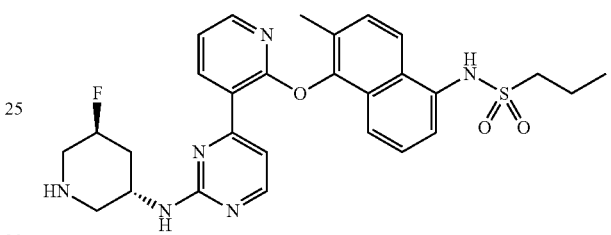

To a solution of N-[5-[[3-[2-[[(3S,5S)-5-fluoro-1-[(4-methoxyphenyl)methyl]-3-piperidyl]amino]pyrimidin-4-yl]-2-pyridyl]oxy]-6-methyl-1-naphthyl]propane-1-sulfonamide (24 mg, 0.04 mmol) in 1,2-dichloroethane (1 mL) was added triethylamine (6.8 mL, 0.36 mmol) and 1-chloroethyl chloroformate (51.2 mg, 0.36 mmol). The mixture was stirred at 20° C. for 4 h and then concentrated and dissolved in methanol (20 mL). Heating at 70° C. for 16 h, followed by concentration in vacuum and purification by Prep-HPLC (mobile phase: A: water (0.05% NH$_4$OH); B: ACN) yielded 5.1 mg (18% yield) of 165 as a white solid; LCMS (ESI) [M+H]$^+$=551.3; $^1$H NMR (400 MHz, DMSO-d$_6$) δ 8.58-8.47 (m, 1H), 8.42 (d, J=4.8 Hz, 1H), 8.12 (d, J=8.4 Hz, 1H), 8.04-8.03 (m, 1H), 7.60-7.51 (m, 2H), 7.49-7.38 (m, 3H), 7.30-7.19 (m, 2H), 4.92-4.71 (m, 1H), 4.28-4.09 (m, 1H), 3.15-3.00 (m, 3H), 2.95-2.82 (m, 1H), 2.77-2.70 (m, 1H), 2.42-2.39 (m, 1H), 2.26-2.08 (m, 4H), 1.95-1.67 (m, 3H), 0.96 (t, J=7.6 Hz, 3H).

Example 166 (S)-1-(2-(Hydroxymethyl)phenyl)-N-(6-methyl-5-((3-(2-(piperidin-3-ylamino)pyrimidin-4-yl)pyridin-2-yl)oxy)naphthalen-1-yl)methanesulfonamide 166

Step 1: (S)-tert-Butyl 3-((4-(2-((5-((2-(methoxycarbonyl)phenyl)methylsulfonamido)-2-methylnaphthalen-1-yl)oxy)pyridin-3-yl)pyrimidin-2-yl)amino)piperidine-1-carboxylate

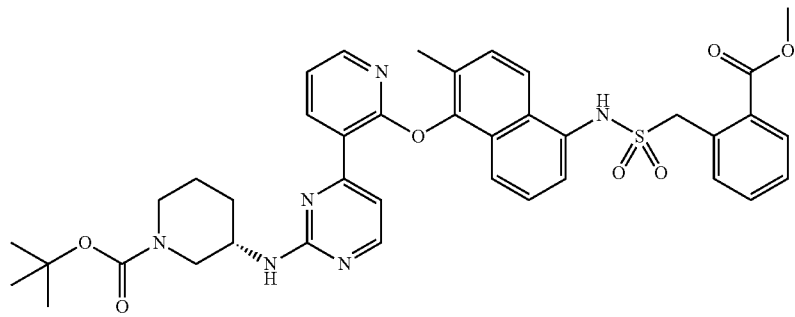 [SMILES: COC(=O)c1ccccc1CS(=O)(=O)Nc1cccc2c(Oc3ncccc3-c3ccnc(N[C@H]4CCCN(C(=O)OC(C)(C)C)C4)n3)c(C)ccc12]

The General Procedure A was followed, using tert-butyl (3S)-3-[[4-[2-[(5-amino-2-methyl-1-naphthyl)oxy]-3-pyridyl]pyrimidin-2-yl]amino]piperidine-1-carboxylate (400 mg, 0.76 mmol), pyridine (10 mL) and 2,4-difluorophenyl methanesulfonyl chloride (189 mg, 0.76 mmol). The organic layer was concentrated and purified by column chromatography on silica (solvent gradient: methanol in dichloromethane) to yield 500 mg (89% yield) of the title compound as a yellow solid. LCMS (ESI) $[M+H]^+=739.1$.

Step 2: (S)-tert-Butyl 3-((4-(2-((5-((2-(hydroxymethyl)phenyl)methylsulfonamido)-2-methylnaphthalen-1-yl)oxy)pyridin-3-yl)pyrimidin-2-yl)amino)piperidine-1-carboxylate

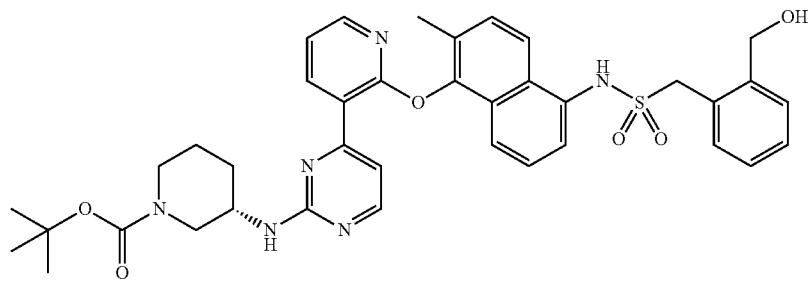 [SMILES: Cc1ccc2c(NS(=O)(=O)Cc3ccccc3CO)cccc2c1Oc1ncccc1-c1ccnc(N[C@H]2CCCN(C(=O)OC(C)(C)C)C2)n1]

To a solution of (S)-tert-butyl 3-((4-(2-((5-((2-(methoxycarbonyl)phenyl)methylsulfonamido)-2-methylnaphthalen-1-yl)oxy)pyridin-3-yl)pyrimidin-2-yl)amino)piperidine-1-carboxylate (400 mg, 0.54 mmol) in tetrahydrofuran (20 mL) was added lithium aluminum hydride (21 mg, 0.54 mmol) at −40° C. The mixture was stirred at −40° C. for 5 h. The solution was added water (10 mL) and anhydrous sodium sulfate (10 g). The solution was filtered and concentrated in vacuo to yield 300 mg (78% yield) as a yellow solid. LCMS (ESI) $[M+H]^+=711.3$.

Step 3: (S)-1-(2-(Hydroxymethyl)phenyl)-N-(6-methyl-5-((3-(2-(piperidin-3-ylamino)pyrimidin-4-yl)pyridin-2-yl)oxy)naphthalen-1-yl)methanesulfonamide

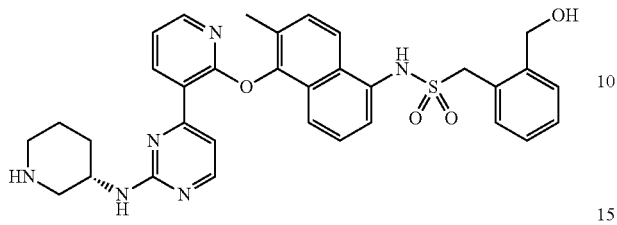

The General Procedure B was followed, using (S)-tert-butyl 3-((4-(2-((5-((2-(hydroxymethyl)phenyl)methylsulfonamido)-2-methylnaphthalen-1-yl)oxy)pyridin-3-yl)pyrimidin-2-yl)amino)piperidine-1-carboxylate (50 mg, 0.07 mmol), dichloromethane (5 mL) and hydrochloric acid (4 M in ethyl acetate, 2 mL, 8 mmol). The residue was purified by Prep-HPLC (mobile phase: A: water (0.05% NH$_4$OH); B: ACN) to yield 13 mg (28% yield) of 166 as a yellow solid. LCMS (ESI): [M+H]$^+$=611.1; $^1$H NMR (400 MHz, DMSO-d$_6$) δ 9.97 (s, 1H), 9.08 (s, 1H), 8.49 (d, J=5.6 Hz, 1H), 8.13-8.04 (m, 2H), 7.63 (s, 1H), 7.59-7.50 (m, 2H), 7.47-7.38 (m, 3H), 7.34 (t, J=7.2 Hz, 1H), 7.31-7.21 (m, 3H), 4.65 (s, 2H), 4.62 (s, 2H), 4.36-4.30 (m, 1H), 3.45-3.40 (m, 1H), 3.22-3.18 (m, 1H), 2.90-2.80 (m, 2H), 2.25 (s, 3H), 2.09-1.58 (m, 4H).

Example 167 (S)—N-(6-Methyl-5-((3-(2-(piperidin-3-ylamino)pyrimidin-4-yl)pyridin-2-yl)oxy)naphthalen-1-yl)-1-(pyridin-4-yl)methanesulfonamide 167

Step 1: tert-Butyl (S)-3-((4-(2-((2-methyl-5-((pyridin-4-ylmethyl)sulfonamido)naphthalen-1-yl)oxy)pyridin-3-yl)pyrimidin-2-yl)amino)piperidine-1-carboxylate

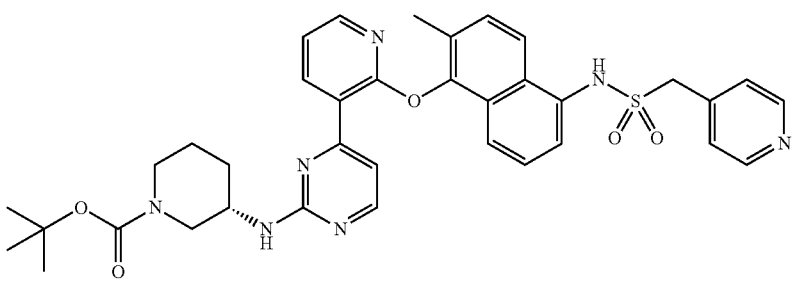 [SMILES: Cc1ccc2c(NS(=O)(=O)Cc3ccncc3)cccc2c1Oc1ncccc1-c1ccnc(N[C@H]2CCCN(C(=O)OC(C)(C)C)C2)n1]

The General Procedure A was followed. To a solution of tert-butyl (3S)-3-[[4-[2-[(5-amino-2-methyl-1-naphthyl)oxy]-3-pyridyl]pyrimidin-2-yl]amino]piperidine-1-carboxylate (100 mg, 0.19 mmol) in pyridine (1.25 mL) was added (4-pyridylmethyl)sulfonyl chloride triflate (97.3 mg, 0.29 mmol) followed by stirring at room temperature for 72 h with an extra (1.45 mmol) of (4-pyridylmethyl)sulfonyl chloride triflate added in between. The mixture was diluted with 10% citric acid, extracted with iPrOAc (2×10 mL), dried over MgSO$_4$ and concentrated. The residue was purified by silica gel chromatography (24 g column) eluting with 0-5% MeOH/DCM to give 32 mg (25% yield) of a brown solid. This product was used in the next step without further purification. LCMS (ESI) [M+H]$^+$=682.

Step 2: (S)—N-(6-Methyl-5-((3-(2-(piperidin-3-ylamino)pyrimidin-4-yl)pyridin-2-yl)oxy)naphthalen-1-yl)-1-(pyridin-4-yl)methanesulfonamide

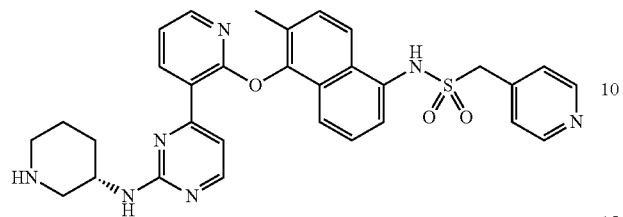

The General Procedure B was followed, using tert-butyl (S)-3-((4-(2-((2-methyl-5-((pyridin-4-ylmethyl)sulfonamido)naphthalen-1-yl)oxy)pyridin-3-yl)pyrimidin-2-yl)amino)piperidine-1-carboxylate (32 mg, 0.047 mmol). The crude product was purified via reverse-phase HPLC and lyophilized to yield 11.8 mg (43% yield) of 167 as an off-white solid. LCMS (ESI) [M+H]+=582; $^1$H NMR (400 MHz, DMSO-$d_6$) δ 8.53-8.50 (m, 2H), 8.45 (d, J=5.2 Hz, 1H), 8.09 (d, J=8.7 Hz, 1H), 8.05 (dd, J=4.8, 2.0 Hz, 1H), 7.53 (d, J=5.2 Hz, 1H), 7.43-7.39 (m, 1H), 7.39-7.30 (m, 5H), 7.26 (dd, J=7.6, 4.8 Hz, 1H), 4.44 (s, 2H), 4.12 (s, 1H), 3.06 (d, J=12.4 Hz, 1H), 2.77-2.65 (m, 2H), 2.20 (s, 3H), 2.02-1.94 (m, 1H), 1.86-1.78 (m, 1H), 1.69-1.54 (m, 2H).

Example 168 (S)-3-Methyl-N-(6-methyl-5-((3-(2-(piperidin-3-ylamino)pyrimidin-4-yl)pyridin-2-yl)oxy)naphthalen-1-yl)isothiazole-5-sulfonamide 168

Step 1: tert-Butyl (S)-3-((4-(2-((2-methyl-5-((3-methylisothiazole)-5-sulfonamido)naphthalen-1-yl)oxy)pyridin-3-yl)pyrimidin-2-yl)amino)piperidine-1-carboxylate

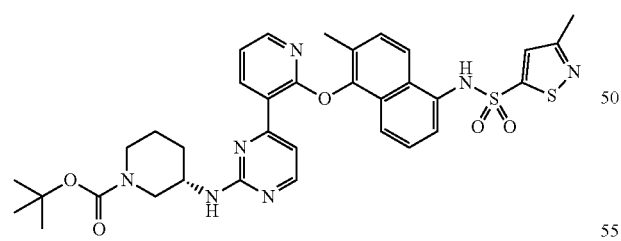

The General Procedure A was followed, using tert-butyl (3S)-3-[[4-[2-[(5-amino-2-methyl-1-naphthyl)oxy]-3-pyridyl]pyrimidin-2-yl]amino]piperidine-1-carboxylate (50 mg, 0.09 mmol) and 3-methylisothiazole-5-sulfonyl chloride (28.16 mg, 0.14 mmol) in pyridine (1 mL) to afford 55 mg (65.3% yield) of the title compound as a brown solid. It was carried on as is. LCMS (ESI) [M+H]+=688.

Step 2: (S)-3-Methyl-N-(6-methyl-5-((3-(2-(piperidin-3-ylamino)pyrimidin-4-yl)pyridin-2-yl)oxy)naphthalen-1-yl)isothiazole-5-sulfonamide

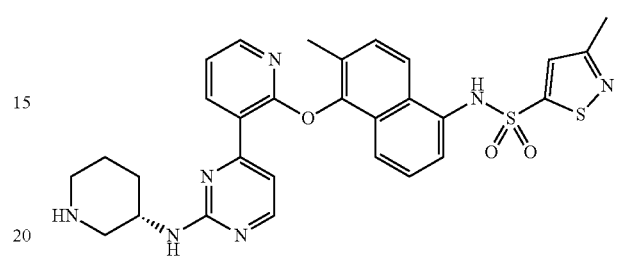

The General Procedure B was followed, using tert-butyl (S)-3-((4-(2-((2-methyl-5-((3-methylisothiazole)-5-sulfonamido)naphthalen-1-yl)oxy)pyridin-3-yl)pyrimidin-2-yl)amino)piperidine-1-carboxylate (55 mg, 0.08 mmol). The crude product was purified via reverse-phase HPLC and lyophilized to yield 11.5 mg (24.5% yield) of 168 as an off-white solid. LCMS (ESI) [M+H]+=588; $^1$H NMR (400 MHz, DMSO-$d_6$) δ 8.50 (s, 2H), 8.45 (d, J=5.2 Hz, 1H), 8.25 (d, J=8.6 Hz, 1H), 8.04 (dd, J=4.8, 2.0 Hz, 1H), 7.55 (d, J=5.2 Hz, 1H), 7.43 (d, J=7.4 Hz, 1H), 7.25-7.18 (m, 3H), 7.10 (dd, J=7.7, 1.2 Hz, 1H), 7.04 (t, J=7.9 Hz, 1H), 6.83 (d, J=8.2 Hz, 1H), 4.21 (s, 1H), 3.43 (d, J=12.6 Hz, 2H), 3.18 (d, J=12.8 Hz, 1H), 2.89-2.78 (m, 2H), 2.31 (s, 3H), 2.16 (s, 3H), 2.04-1.97 (m, 1H), 1.94-1.86 (m, 1H), 1.74-1.58 (m, 2H).

Example 169 N-(6-Methyl-5-((3-(2-((4-methylpiperidin-3-yl)amino)pyrimidin-4-yl)pyridin-2-yl)oxy)naphthalen-1-yl)propane-1-sulfonamide 169

Step 1: tert-Butyl 4-methyl-3-((4-(2-((2-methyl-5-(propylsulfonamido)naphthalen-1-yl)oxy)pyridin-3-yl)pyrimidin-2-yl)amino)piperidine-1-carboxylate

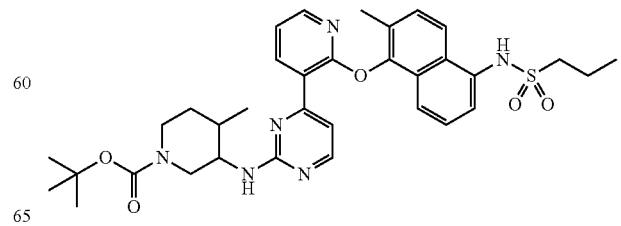

311

To a 100 mL 3-necked round-bottom flask purged and maintained with an inert atmosphere of nitrogen was placed N-[6-methyl-5-[[3-(2-methylsulfinylpyrimidin-4-yl)-2-pyridyl]oxy]-1-naphthyl]propane-1-sulfonamide (2.0 g, 4.03 mmol), tert-butyl 3-amino-4-methyl-piperidine-1-carboxylate (1.0 g, 4.83 mmol), 1,4-dioxane (20 mL) and N,N-diisopropylethylamine (2.11 mL, 12.08 mmol). The resulting solution was stirred at 130° C. in an oil bath for 36 h, cooled to room temperature and concentrated in vacuo. The residue was purified by Prep-HPLC (mobile phase: A: water (0.05% NH$_4$OH); B: ACN) to give two major products. First HPLC peak: 950 mg (16% yield); second HPLC peak: 170 mg (3% yield). The second peak corresponds to the title product which was obtained as a white solid. LCMS (ESI) [M+H]$^+$=647.1. The trans relative stereochemistry of the title compound was based on 2D-NMR analysis.

Step 2: tert-Butyl 4-methyl-3-((4-(2-((2-methyl-5-(propylsulfonamido)naphthalen-1-yl)oxy)pyridin-3-yl)pyrimidin-2-yl)amino)piperidine-1-carboxylate

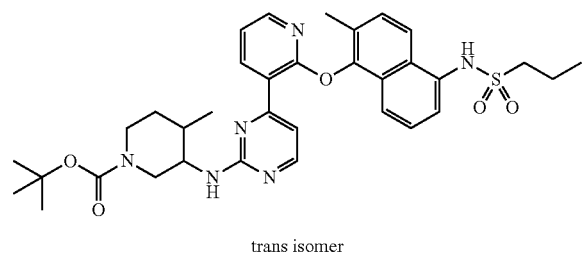 [SMILES: CCCS(=O)(=O)Nc1cccc2c(Oc3ncccc3-c3ccnc(NC4CN(C(=O)OC(C)(C)C)CCC4C)n3)c(C)ccc12]

trans isomer tert-Butyl4-methyl-3-[[4-[2-[[2-methyl-5-(propylsulfonylamino)-1-naphthyl]oxy]-3-pyridyl]pyrimidin-2-yl]amino]piperidine-1-carboxylate (170 mg, 0.26 mmol) (second peak on HPLC in step 1) was purified by SFC(AS (250 mm×30 mm, 10 μm); 0.1% NH$_3$H$_2$O EtOH: 40%; flow rate (80 mL/min) to give trans-tert-butyl 4-methyl-3-[[4-[2-[[2-methyl-5-(propylsulfonylamino)-1-naphthyl]oxy]-3-pyridyl]pyrimidin-2-yl]amino]piperidine-1-carboxylate (70 mg, 41% yield) (first peak on SFC, Rt=4.49 min) and trans-tert-butyl 4-methyl-3-[[4-[2-[[2-methyl-5-(propylsulfonylamino)-1-naphthyl]oxy]-3-pyridyl]pyrimidin-2-yl]amino]piperidine-1-carboxylate (70 mg, 41% yield) (second peak on SFC, Rt=4.82 min) as a white solid.

312

Step 3: N-(6-Methyl-5-((3-(2-(((3S,4R)-4-methylpiperidin-3-yl)amino)pyrimidin-4-yl)pyridin-2-yl)oxy)naphthalen-1-yl)propane-1-sulfonamide

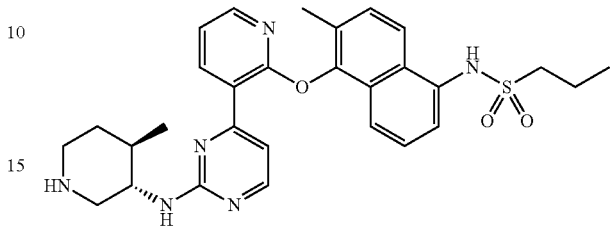

The General Procedure B was followed, using 4-methyl-3-[[4-[2-[[2-methyl-5-(propylsulfonylamino)-1-naphthyl]oxy]-3-pyridyl]pyrimidin-2-yl]amino]piperidine-1-carboxylate (70 mg, 0.11 mmol) (second peak on SFC in step 2), dichloromethane (2 mL) and hydrochloric acid (4 M in dioxane, 2 mL, 8 mmol). The residue was purified by Prep-HPLC (mobile phase: A: water (0.05% ammonia hydroxide) B: ACN) to yield 45 mg (74% yield) of 169 as a white solid. LCMS (ESI): [M+H]$^+$=547.1; $^1$H NMR (400 MHz, DMSO-d$_6$) δ 8.52 (s, 1H), 8.39 (d, J=5.2 Hz, 1H), 8.14 (d, J=8.8 Hz, 1H), 8.05-8.01 (m, 1H), 7.49 (d, J=8.8 Hz, 1H), 7.43 (d, J=5.2 Hz, 1H), 7.42-7.33 (m, 2H), 7.29-7.22 (m, 1H), 7.17 (d, J=8.8 Hz, 1H), 3.68 (s, 1H), 3.16 (s, 1H), 3.10-3.04 (m, 2H), 2.93-2.90 (m, 1H), 2.52-2.52 (m, 1H), 2.31 (d, J=10.4 Hz, 1H), 2.20 (s, 3H), 1.80-1.66 (m, 3H), 1.65-1.54 (m, 1H), 1.27-1.12 (m, 1H), 0.99-0.91 (m, 1H), 0.99-0.91 (m, 5H). The absolute stereochemistry was tentatively assigned based on the XBP1 reporter potency.

Example 170 (S)-1-(2-(Fluoromethyl)phenyl)-N-(6-methyl-5-((3-(2-(piperidin-3-ylamino)pyrimidin-4-yl)pyridin-2-yl)oxy)naphthalen-yl)oxy)naphthalen-1-yl)methanesulfonamide 170

Step 1: (S)-tert-Butyl 3-((4-(2-((5-((2-(fluoromethyl)phenyl)methylsulfonamido)-2-methylnaphthalen-1-yl)oxy)pyridin-3-yl)pyrimidin-2-yl)amino)piperidine-1-carboxylate

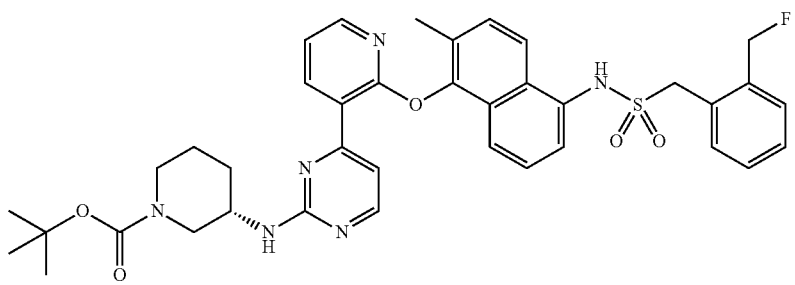 [SMILES: Cc1ccc2c(NS(=O)(=O)Cc3ccccc3CF)cccc2c1Oc1ncccc1-c1ccnc(N[C@H]2CCCN(C(=O)OC(C)(C)C)C2)n1]

To a solution of tert-butyl (3S)-3-[[4-[2-[[5-[[2-(hydroxymethyl)phenyl]methylsulfonylamino]-2-methyl-1-naphthyl]oxy]-3-pyridyl]pyrimidin-2-yl]amino]piperidine-1-carboxylate (200 mg, 0.28 mmol) in dichloromethane (2 mL) was added diethylaminosulfur trifluoride (59 mg, 0.37 mmol) in dichloromethane (2 mL) dropwised at −78° C. The mixture was stirred at −78° C. for 0.5 h. The solution was washed with water (10 mL) and extracted with dichloromethane (20 mL×3). The organic layer was concentrated to yield 200 mg (99% yield) of the title compound as a yellow solid. LCMS (ESI): [M+H]$^+$=713.0.

Step 2: (S)-1-(2-(Fluoromethyl)phenyl)-N-(6-methyl-5-((3-(2-(piperidin-3-ylamino)pyrimidin-4-yl)pyridin-2-yl)oxy)naphthalen-1-yl)methanesulfonamide

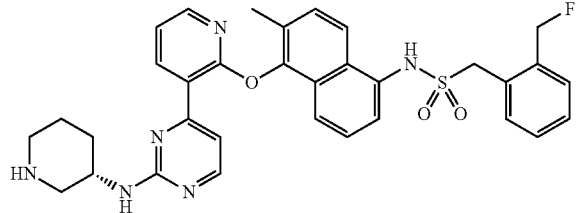 [SMILES: Cc1ccc2c(NS(=O)(=O)Cc3ccccc3CF)cccc2c1Oc1ncccc1-c1ccnc(N[C@H]2CCCNC2)n1]

The General Procedure B was followed, using (S)-tert-butyl 3-((4-(2-((5-((2-(fluoromethyl)phenyl)methylsulfonamido)-2-methylnaphthalen-1-yl)oxy)pyridin-3-yl)pyrimidin-2-yl)amino)piperidine-1-carboxylate (200 mg, 0.28 mmol), dichloromethane (5 mL) and hydrochloric acid (4 M in ethyl acetate, 2 mL, 8 mmol). The residue was purified by Prep-HPLC (mobile phase: A: water (0.05% HCl) B: ACN) to yield 13 mg (7%) yield of 170 as a yellow solid. LCMS (ESI): [M+H]$^+$=613.1; $^1$H NMR (400 MHz, DMSO-d$_6$) δ 10.08-10.01 (m, 1H), 9.11 (s, 1H), 8.50 (d, J=5.6 Hz, 1H), 8.08 (d, J=7.2 Hz, 2H), 7.70-7.51 (m, 3H), 7.51-7.36 (m, 6H), 7.29 (d, J=7.2 Hz, 1H), 5.67-5.48 (m, 2H), 4.73-4.62 (m, 2H), 4.41-4.34 (m, 1H), 3.49-3.13 (m, 2H), 2.93-2.76 (m, 2H), 2.22 (s, 3H), 2.09-1.58 (m, 4H).

Example 171 (S)-6-Methyl-N-(6-methyl-5-((3-(2-(piperidin-3-ylamino)pyrimidin-4-yl)pyridin-2-yl)oxy)naphthalen-1-yl)pyridine-2-sulfonamide 171

Step 1: (S)-tert-Butyl 3-((4-(2-((2-methyl-5-(6-methylpyridine-2-sulfonamido)naphthalen-1-yl)oxy)pyridin-3-yl)pyrimidin-2-yl)amino)piperidine-1-carboxylate

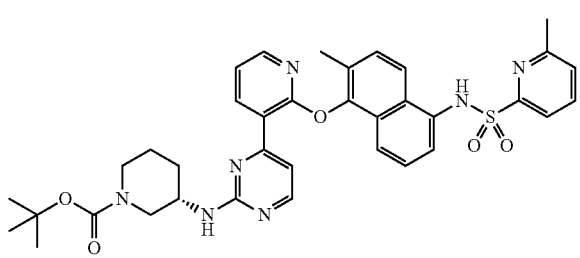 [SMILES: Cc1cccc(S(=O)(=O)Nc2cccc3c(Oc4ncccc4-c4ccnc(N[C@H]5CCCN(C(=O)OC(C)(C)C)C5)n4)c(C)ccc23)n1]

The General Procedure A was followed, using tert-butyl (3S)-3-[[4-[2-[(5-amino-2-methyl-1-naphthyl)oxy]-3-pyridyl]pyrimidin-2-yl]amino]piperidine-1-carboxylate (100 mg, 0.19 mmol), pyridine (2 mL) and 6-methylpyridine-2-sulfonyl chloride (44 mg, 0.23 mmol). The reaction mixture was concentrated in vacuo and the residue was taken up in ethyl acetate (20 mL), and washed with water (10 mL). The organic phase was dried over anhydrous sodium sulfate and concentrated in vacuo to yield (130 mg crude) of the title compound as a pale brown oil. LCMS (ESI) [M+H]$^+$=682.1.

Step 2: (S)-6-Methyl-N-(6-methyl-5-((3-(2-(piperidin-3-ylamino)pyrimidin-4-yl)pyridin-2-yl)oxy)naphthalen-1-yl)pyridine-2-sulfonamide The General Procedure B was followed, using (S)-tert-butyl 3-((4-(2-((2-methyl-5-(6-methylpyridine-2-sulfonamido)naphthalen-1-yl)oxy)pyridin-3-yl)pyrimidin-2-yl)amino)piperidine-1-carboxylate (130 mg, 0.19 mmol), ethyl acetate (2 mL) and hydrochloric acid (4 M in ethyl acetate, 2 mL, 8 mmol). The residue was purified by Prep-HPLC (mobile phase: A: water (0.05% HCl) B: ACN) to yield 73 mg (62% yield) of 171 as a white solid. LCMS (ESI): [M+H]$^+$=582.1; $^1$H NMR (400 MHz, DMSO-d$_6$) δ 10.58 (s, 1H), 9.37 (s, 1H), 8.51 (d, J=4.8 Hz, 1H), 8.12-7.99 (m, 2H), 7.91-7.81 (m, 1H), 7.61 (d, J=8.0 Hz, 1H), 7.55-7.39 (m, 3H), 7.36-7.24 (m, 2H), 7.21 (d, J=7.6 Hz, 1H), 4.40-4.35 (m, 1H), 3.45-3.40 (m, 1H), 3.20-3.15 (m, 1H), 2.90-2.80 (m, 2H), 2.57 (s, 3H), 2.17 (s, 3H), 2.04-1.99 (m, 1H), 1.97-1.58 (m, 3H).

Example 172 (S)-1-Bromo-N-(6-methyl-5-(3-(2-(piperidin-3-ylamino)pyrimidin-4-yl)pyridin-2-yloxy)naphthalen-1-yl)methanesulfonamide 172

Step 1: (S)-tert-Butyl 3-(4-(2-(5-(bromomethylsulfonamido)-2-methylnaphthalen-1-yloxy)pyridin-3-yl)pyrimidin-2-ylamino)piperidine-1-carboxylate The General Procedure A was followed, using tert-butyl (3S)-3-[[4-[2-[(5-amino-2-methyl-1-naphthyl)oxy]-3-pyridyl]pyrimidin-2-yl]amino]piperidine-1-carboxylate (50 mg, 0.095 mmol), pyridine (1 mL) and bromomethanesulfonyl chloride (250 mg, 1.3 mmol). The mixture was concentrated and the crude product was directly used in step 2. LCMS (ESI) [M+H]⁺=683.2.

Step 2: (S)-1-Bromo-N-(6-methyl-5-(3-(2-(piperidin-3-ylamino)pyrimidin-4-yl)pyridin-2-yloxy)naphthalen-1-yl)methanesulfonamide

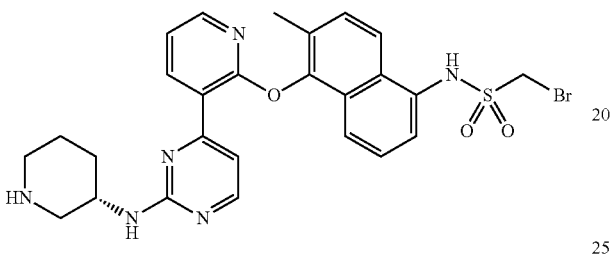

To the crude (S)-tert-butyl 3-(4-(2-(5-(bromomethylsulfonamido)-2-methylnaphthalen-1-yloxy)pyridin-3-yl)pyrimidin-2-ylamino)piperidine-1-carboxylate from step 1 in DCM (6 mL) was added trifluoroacetic acid (1 mL). The mixture was concentrated and the residue purified by Prep-HPLC to yield 4.7 mg (9% yield) of 172 as a white solid. LCMS (ESI): [M+H]⁺=583.1; ¹H NMR (400 MHz, DMSO-$d_6$) δ 8.55 (s, 1H), 8.47 (dd, J=5.2, 3.4 Hz, 1H), 8.21-8.10 (m, 1H), 8.07-8.00 (m, 1H), 7.63-7.27 (m, 6H), 7.11-6.97 (m, 1H), 4.87 (d, J=27.4 Hz, 2H), 4.23 (s, 1H), 3.21 (d, J=12.8 Hz, 1H), 2.85 (q, J=11.7 Hz, 2H), 2.21 (s, 3H), 2.01 (s, 1H), 1.90 (s, 1H), 1.75-1.62 (m, 2H).

Example 173 (S)—N-(6-Methyl-5-((3-(2-(piperidin-3-ylamino)pyrimidin-4-yl)pyridin-2-yl)oxy)naphthalen-1-yl)propionamide 173

Step 1: tert-Butyl (S)-3-((4-(2-((2-methyl-5-propionamidonaphthalen-1-yl)oxy)pyridin-3-yl)pyrimidin-2-yl)amino)piperidine-1-carboxylate

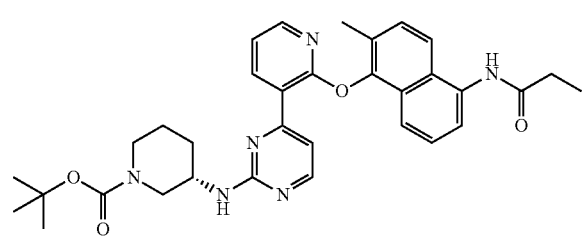 [SMILES: CCC(=O)Nc1cccc2c(Oc3ncccc3-c3ccnc(N[C@H]4CCCN(C(=O)OC(C)(C)C)C4)n3)c(C)ccc12]

The General Procedure C was followed, using tert-butyl (S)-3-((4-(2-((5-amino-2-methylnaphthalen-1-yl)oxy)pyridin-3-yl)pyrimidin-2-yl)amino)piperidine-1-carboxylate from Example 101 (90 mg, 0.17 mmol), propionic acid (19 mg, 0.26 mmol), DIPEA (0.089 mL, 0.51 mmol), HATU (97 mg, 0.26 mmol) and DCM (1.7 mL). The crude was directly used in the next step.

Step 2: (S)—N-(6-Methyl-5-((3-(2-(piperidin-3-ylamino)pyrimidin-4-yl)pyridin-2-yl)oxy)naphthalen-1-yl)propionamide

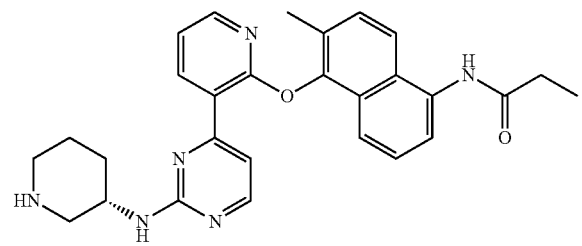 [SMILES: CCC(=O)Nc1cccc2c(Oc3ncccc3-c3ccnc(N[C@H]4CCCNC4)n3)c(C)ccc12]

The General Procedure B was followed, using crude tert-butyl (S)-3-((4-(2-((2-methyl-5-propionamidonaphthalen-1-yl)oxy)pyridin-3-yl)pyrimidin-2-yl)amino)piperidine-1-carboxylate, DCM (1.7 mL) and hydrochloric acid (4 M in dioxane, 0.430 mL, 1.71 mmol). The residue was purified via reverse-phase HPLC and lyophilized to yield 16.1 mg of 173. LCMS (ESI): [M+H]⁺=483.2; ¹H NMR (400 MHz, DMSO-$d_6$) δ 9.89 (s, 1H), 8.52-8.46 (m, 1H), 8.42-8.37 (m, 1H), 8.04-8.00 (m, 1H), 7.92 (d, J=8.7 Hz, 1H), 7.62 (d, J=7.4 Hz, 1H), 7.50 (d, J=8.7 Hz, 3H), 7.46-7.36 (m, 2H), 7.25 (dd, J=7.6, 4.8 Hz, 1H), 7.11 (d, J=7.7 Hz, 1H), 3.96-3.59 (m, 1H), 3.13-3.03 (m, 1H), 2.85-2.71 (m, 1H), 2.46-2.37 (m, 1H), 2.22 (s, 3H), 1.97-1.81 (m, 1H), 1.67-1.24 (m, 3H), 1.17 (t, J=7.6 Hz, 3H).

Example 174 (S)—N-(6-Methyl-5-((3-(2-(piperidin-3-ylamino)pyrimidin-4-yl)pyridin-2-yl)oxy)naphthalen-1-yl)-2-naphthamide 174

Step 1: tert-Butyl (S)-3-((4-(2-((5-(2-naphthamido)-2-methylnaphthalen-1-yl)oxy)pyridin-3-yl)pyrimidin-2-yl)amino)piperidine-1-carboxylate

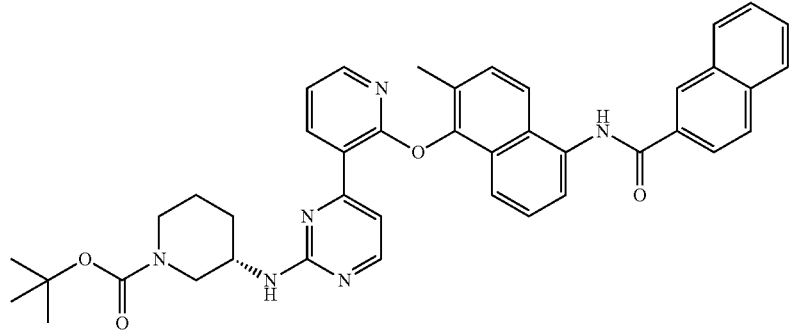 [SMILES: Cc1ccc2c(NC(=O)c3ccc4ccccc4c3)cccc2c1Oc1ncccc1-c1ccnc(N[C@H]2CCCN(C(=O)OC(C)(C)C)C2)n1]

The General Procedure C was followed, using tert-butyl (S)-3-((4-(2-((5-amino-2-methylnaphthalen-1-yl)oxy)pyridin-3-yl)pyrimidin-2-yl)amino)piperidine-1-carboxylate from Example 101 (90 mg, 0.17 mmol), naphthalene-2-carboxylic acid (44 mg, 0.26 mmol), DIPEA (0.089 mL, 0.51 mmol), HATU (97 mg, 0.26 mmol) and DCM (1.7 mL). The crude was directly used in the next step.

Step 2: (S)—N-(6-methyl-5-((3-(2-(piperidin-3-ylamino)pyrimidin-4-yl)pyridin-2-yl)oxy)naphthalen-1-yl)-2-naphthamide

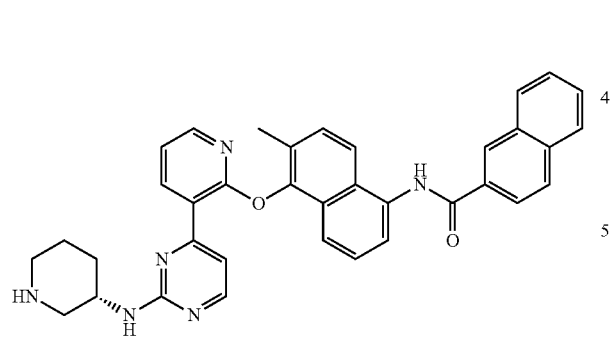

The General Procedure B was followed, using crude tert-butyl (S)-3-((4-(2-((5-(2-naphthamido)-2-methylnaphthalen-1-yl)oxy)pyridin-3-yl)pyrimidin-2-yl)amino)piperidine-1-carboxylate, DCM (1.7 mL) and hydrochloric acid (4 M in dioxane, 0.430 mL, 1.71 mmol). The residue was purified via reverse-phase HPLC and lyophilized to yield 31 mg of 174. LCMS (ESI): [M+H]$^+$=581.2; $^1$H NMR (400 MHz, DMSO-d6) δ 10.64 (s, 1H), 8.75 (d, J=1.6 Hz, 1H), 8.55-8.48 (m, 1H), 8.43 (d, J=5.1 Hz, 1H), 8.23-8.00 (m, 5H), 7.92 (d, J=8.7 Hz, 1H), 7.74-7.58 (m, 4H), 7.54-7.44 (m, 3H), 7.28 (dd, J=7.6, 4.8 Hz, 1H), 7.15 (d, J=8.0 Hz, 1H), 3.92 (s, 1H), 3.18-3.06 (m, 1H), 2.87-2.77 (m, 1H), 2.24 (s, 3H), 2.01-1.87 (m, 1H), 1.70-1.60 (m, 1H), 1.56-1.38 (m, 2H).

Example 175 (S)—N-(6-Methyl-5-((3-(2-(piperidin-3-ylamino)pyrimidin-4-yl)pyridin-2-yl)oxy)naphthalen-1-yl)picolinamide 175

Step 1: tert-Butyl (S)-3-((4-(2-((2-methyl-5-(picolinamido)naphthalen-1-yl)oxy)pyridin-3-yl)pyrimidin-2-yl)amino)piperidine-1-carboxylate The General Procedure C was followed, using tert-butyl (S)-3-((4-(2-((5-amino-2-methylnaphthalen-1-yl)oxy)pyridin-3-yl)pyrimidin-2-yl)amino)piperidine-1-carboxylate from Example 101 (90 mg, 0.17 mmol), pyridine-2-carboxylic acid (44 mg, 0.26 mmol), DIPEA (0.089 mL, 0.51 mmol), HATU (97 mg, 0.26 mmol) and DCM (1.7 mL). The crude was directly used in the next step.

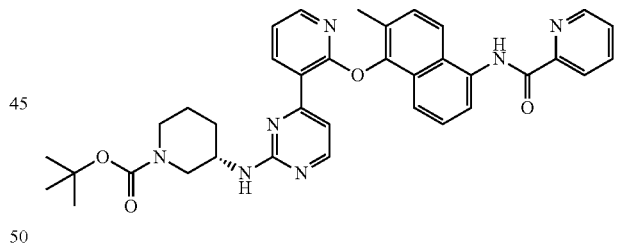

Step 2: (S)—N-(6-Methyl-5-((3-(2-(piperidin-3-ylamino)pyrimidin-4-yl)pyridin-2-yl)oxy)naphthalen-1-yl)picolinamide

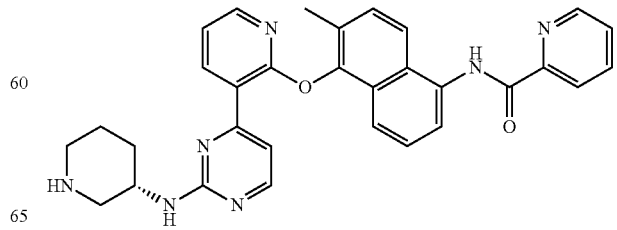

The General Procedure B was followed, using crude tert-butyl (S)-3-((4-(2-((2-methyl-5-(picolinamido)naphthalen-1-yl)oxy)pyridin-3-yl)pyrimidin-2-yl)amino)piperidine-1-carboxylate, DCM (1.7 mL) and hydrochloric acid (4 M in dioxane, 0.430 mL, 1.71 mmol). The residue was purified via reverse-phase HPLC and lyophilized to yield 40 mg of 175. LCMS (ESI): [M+H]$^+$=532.2; $^1$H NMR (400 MHz, DMSO-d$_6$) δ 10.94 (s, 1H), 8.85-8.82 (m, 1H), 8.54-8.47 (m, 1H), 8.42 (d, J=5.1 Hz, 1H), 8.23-8.19 (m, 1H), 8.12 (td, J=7.7, 1.7 Hz, 1H), 8.06 (dd, J=4.8, 1.9 Hz, 1H), 7.85 (t, J=7.7 Hz, 2H), 7.74 (ddd, J=7.5, 4.8, 1.3 Hz, 1H), 7.60 (d, J=8.5 Hz, 1H), 7.55 (d, J=8.8 Hz, 1H), 7.52-7.44 (m, 2H), 7.27 (dd, J=7.5, 4.8 Hz, 1H), 7.12 (d, J=8.0 Hz, 1H), 3.89 (s, 1H), 3.16-3.01 (m, 1H), 2.85-2.76 (m, 1H), 2.47-2.38 (m, 2H), 2.24 (s, 3H), 1.97-1.86 (m, 1H), 1.70-1.61 (m, 1H), 1.56-1.37 (m, 2H).

Example 176 (S)-1-Methyl-N-(6-methyl-5-((3-(2-(piperidin-3-ylamino)pyrimidin-4-yl)pyridin-2-yl)oxy)naphthalen-1-yl)-1H-imidazole-4-carboxamide 176

Step 1: tert-Butyl (S)-3-((4-(2-((2-methyl-5-(1-methyl-1H-imidazole-4-carboxamido)naphthalen-1-yl)oxy)pyridin-3-yl)pyrimidin-2-yl)amino)piperidine-1-carboxylate

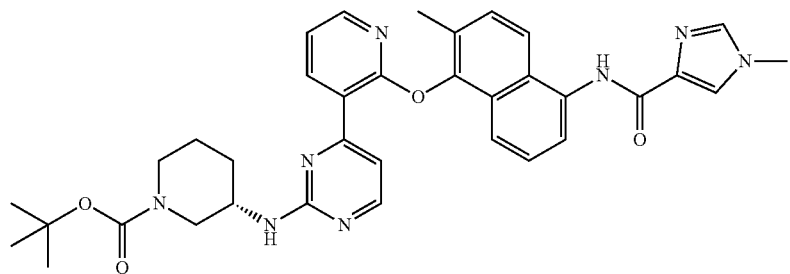 [SMILES: Cc1ccc2c(NC(=O)c3cn(C)cn3)cccc2c1Oc1ncccc1-c1ccnc(N[C@H]2CCCN(C(=O)OC(C)(C)C)C2)n1]

The General Procedure C was followed, using tert-butyl (S)-3-((4-(2-((5-amino-2-methylnaphthalen-1-yl)oxy)pyridin-3-yl)pyrimidin-2-yl)amino)piperidine-1-carboxylate from Example 101 (90 mg, 0.17 mmol), 1-methylimidazole-4-methyl carboxylic acid (32 mg, 0.26 mmol), DIPEA (0.089 mL, 0.51 mmol), HATU (97 mg, 0.26 mmol) and DCM (1.7 mL). The crude was directly used in the next step.

Step 2: (S)-1-Methyl-N-(6-methyl-5-((3-(2-(piperidin-3-ylamino)pyrimidin-4-yl)pyridin-2-yl)oxy)naphthalen-1-yl)-1H-imidazole-4-carboxamide

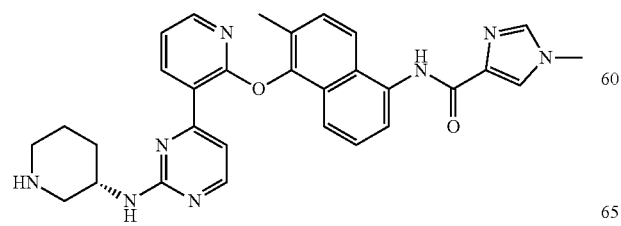

The General Procedure B was followed, using crude tert-butyl (S)-3-((4-(2-((2-methyl-5-(1-methyl-1H-imidazole-4-carboxamido)naphthalen-1-yl)oxy)pyridin-3-yl)pyrimidin-2-yl)amino)piperidine-1-carboxylate, (1.7 mL) and hydrochloric acid (4 M in dioxane, 0.430 mL, 1.71 mmol). The residue was purified via reverse-phase HPLC and lyophilized to yield 32 mg of 176 as a mixture of two rotamers (ratio=3:1). LCMS (ESI): [M+H]⁺=535.2; ¹H NMR (400 MHz, DMSO-d$_6$) δ 10.02, 9.99 (2s, 1H), 8.57-8.47 (m, 1H), 8.43 (d, J=5.1 Hz, 0.75H), 8.40 (d, J=5.1 Hz, 0.25H), 8.06 (dd, J=4.8, 2.0 Hz, 0.75H), 8.01-7.74 (m, 4.25H), 7.57-7.34 (m, 4H), 7.30-7.18 (m, 1.75H), 7.10-7.05 (m, 0.25H), 5.75 (s, 1H), 4.13-3.91 (m, 1H), 3.77 (s, 3H), 3.23-3.15 (m, 1H), 2.98-2.86 (m, 1H), 2.63-2.50 (m, 1H), 2.23 (s, 3H), 2.18 (s, 1H), 2.12-1.90 (m, 2H), 1.76-1.63 (m, 1H), 1.60-1.37 (m, 2H).

Example 177 (S)-2-(2-Fluorophenyl)-N-(6-methyl-5-((3-(2-(piperidin-3-ylamino)pyrimidin-4-yl)pyridin-2-yl)oxy)naphthalen-1-yl)acetamide 177

Step 1: tert-Butyl (S)-3-((4-(2-((5-(2-(2-fluorophenyl)acetamido)-2-methylnaphthalen-1-yl)oxy)pyridin-3-yl)pyrimidin-2-yl)amino)piperidine-1-carboxylate

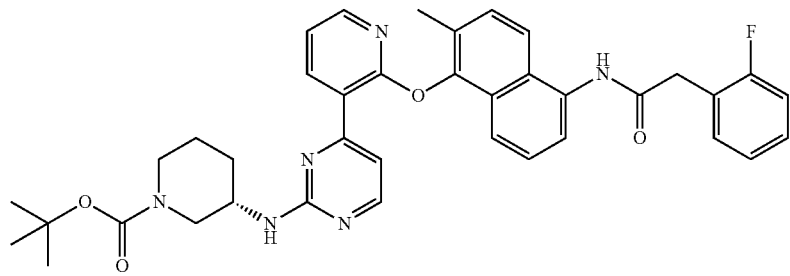 [SMILES: Cc1ccc2c(NC(=O)Cc3ccccc3F)cccc2c1Oc1ncccc1-c1ccnc(N[C@H]2CCCN(C(=O)OC(C)(C)C)C2)n1]

The General Procedure C was followed, using tert-butyl (S)-3-((4-(2-((5-amino-2-methylnaphthalen-1-yl)oxy)pyridin-3-yl)pyrimidin-2-yl)amino)piperidine-1-carboxylate from Example 101 (90 mg, 0.17 mmol), 2-(2-fluorophenyl)acetic acid (39.5 mg, 0.26 mmol), DIPEA (0.089 mL, 0.51 mmol), HATU (97 mg, 0.26 mmol) and DCM (1.7 mL). The crude was directly used in the next step.

Step 2: (S)-2-(2-Fluorophenyl)-N-(6-methyl-5-((3-(2-(piperidin-3-ylamino)pyrimidin-4-yl)pyridin-2-yl)oxy)naphthalen-1-yl)acetamide

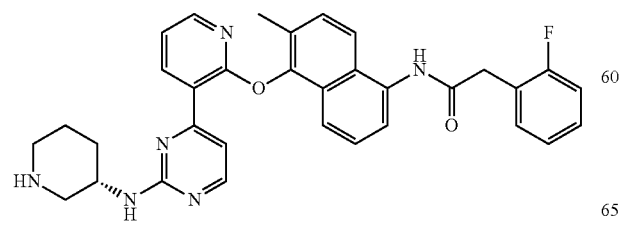

The General Procedure B was followed, using crude tert-butyl (S)-3-((4-(2-((5-(2-(2-fluorophenyl)acetamido)-2-methylnaphthalen-1-yl)oxy)pyridin-3-yl)pyrimidin-2-yl)amino)piperidine-1-carboxylate, DCM (1.7 mL) and hydrochloric acid (4 M in dioxane, 0.430 mL, 1.71 mmol). The residue was purified via reverse-phase HPLC and lyophilized to yield 33 mg of 177. LCMS (ESI): [M+H]$^+$=563.2; $^1$H NMR (400 MHz, DMSO-d$_6$) δ 10.22 (s, 1H), 8.69-8.52 (m, 2H), 8.48 (d, J=5.2 Hz, 1H), 8.05 (dd, J=4.8, 2.0 Hz, 1H), 7.97 (d, J=8.7 Hz, 1H), 7.65-7.18 (m, 11H), 4.30-4.17 (m, 1H), 3.93 (s, 2H), 3.52-3.42 (m, 1H), 3.27-3.19 (m, 1H), 2.96-2.83 (m, 1H), 2.22 (s, 3H), 2.07-1.90 (m, 2H), 1.78-1.57 (m, 2H).

Example 178 (S)-4,4,4-Trifluoro-N-(6-methyl-5-((3-(2-(piperidin-3-ylamino)pyrimidin-4-yl)pyridin-2-yl)oxy)naphthalen-1-yl) butanamide 178

Step 1: tert-Butyl (S)-3-((4-(2-((2-methyl-5-(4,4,4-trifluorobutanamido)naphthalen-1-yl)oxy)pyridin-3-yl)pyrimidin-2-yl)amino)piperidine-1-carboxylate

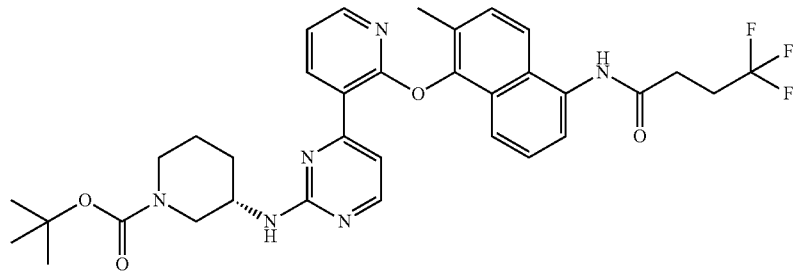 [SMILES: Cc1ccc2c(NC(=O)CCC(F)(F)F)cccc2c1Oc1ncccc1-c1ccnc(N[C@H]2CCCN(C(=O)OC(C)(C)C)C2)n1]

The General Procedure C was followed, using tert-butyl (S)-3-((4-(2-((5-amino-2-methylnaphthalen-1-yl)oxy)pyridin-3-yl)pyrimidin-2-yl)amino)piperidine-1-carboxylate from Example 101 (90 mg, 0.17 mmol), 4,4,4-trifluorobutanoic acid (36 mg, 0.26 mmol), DIPEA (0.089 mL, 0.51 mmol), HATU (97 mg, 0.26 mmol) and DCM (1.7 mL). The crude was directly used in the next step.

Step 2: (S)-4,4,4-Trifluoro-N-(6-methyl-5-((3-(2-(piperidin-3-ylamino)pyrimidin-4-yl)pyridin-2-yl)oxy)naphthalen-1-yl)butanamide

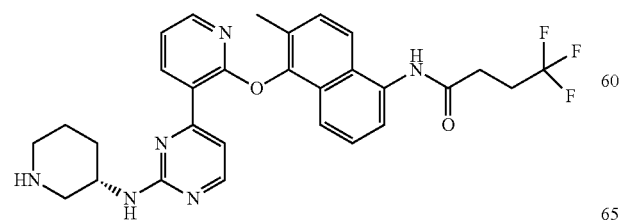

The General Procedure B was followed, using crude tert-butyl (S)-3-((4-(2-((2-methyl-5-(4,4,4-trifluorobutanamido)naphthalen-1-yl)oxy)pyridin-3-yl)pyrimidin-2-yl)amino)piperidine-1-carboxylate, DCM (1.7 mL) and hydrochloric acid (4 M in dioxane, 0.430 mL, 1.71 mmol). The residue was purified via reverse-phase HPLC and lyophilized to yield 25 mg of 178. LCMS (ESI): [M+H]$^+$=551.2; $^1$H NMR (400 MHz, DMSO-d$_6$) δ 10.10 (s, 1H), 8.69-8.51 (m, 2H), 8.48 (d, J=5.2 Hz, 1H), 8.06 (dd, J=4.8, 2.0 Hz, 1H), 7.95 (d, J=8.7 Hz, 1H), 7.66-7.46 (m, 4H), 7.41 (dd, J=8.4, 7.4 Hz, 1H), 7.27 (dd, J=7.5, 4.8 Hz, 1H), 4.25 (s, 1H), 3.27-3.18 (m, 1H), 2.94-2.77 (m, 3H), 2.75-2.57 (m, 2H), 2.22 (s, 3H), 2.06-1.98 (m, 1H), 1.98-1.89 (m, 1H), 1.77-1.57 (m, 1H), 1.28-1.23 (m, 1H).

Example 179 (R)-2,2-Difluoro-N-(6-methyl-5-((3-(2-(((S)-piperidin-3-yl)amino)pyrimidin-4-yl)pyridin-2-yl)oxy)naphthalen-1-yl)cyclopropane-1-carboxamide 179

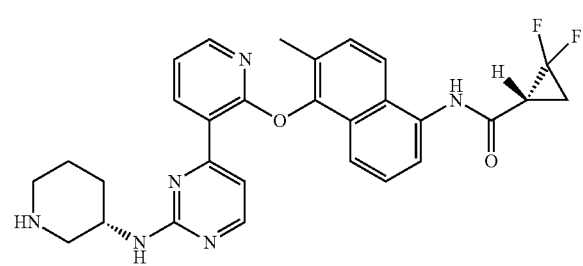 [SMILES: Cc1ccc2c(NC(=O)[C@H]3CC3(F)F)cccc2c1Oc1ncccc1-c1ccnc(N[C@H]2CCCNC2)n1]

Step 1: I-Butyl (S)-3-((4-(2-((5-((R)-2,2-difluorocyclopropane-1-carboxamido)-2-methylnaphthalen-1-yl)oxy)pyridin-3-yl)pyrimidin-2-yl)amino)piperidine-1-carboxylate

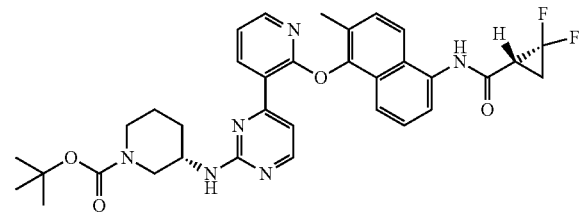

The General Procedure C was followed, using tert-butyl (S)-3-((4-(2-((5-amino-2-methylnaphthalen-1-yl)oxy)pyridin-3-yl)pyrimidin-2-yl)amino)piperidine-1-carboxylate from Example 101 (207 mg, 0.39 mmol), 2,2-difluorocyclopropanecarboxylic acid (40 mg, 0.33 mmol), DIPEA (0.171 mL, 0.98 mmol), HATU (381 mg, 0.98 mmol) and DCM (8 mL). The residue was purified via reverse-phase HPLC to provide a mixture of the two isomers. This mixture was then purified via chiral reverse-phase HPLC and lyophilized to yield 82 mg and 85 mg of the two single stereoisomers possessing a stereocenter at the 1 position of the cyclopropyl amide.

Step 2: (R)-2,2-difluoro-N-(6-methyl-5-((3-(2-(((S)-piperidin-3-yl)amino)pyrimidin-4-yl)pyridin-2-yl)oxy)naphthalen-1-yl)cyclopropane-1-carboxamide

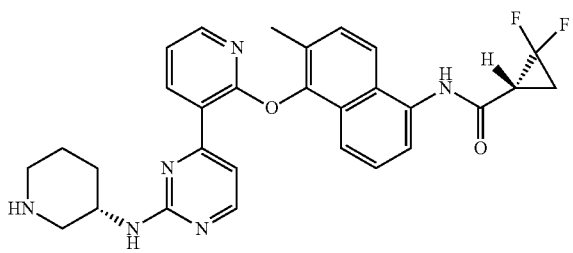 [SMILES: Cc1ccc2c(NC(=O)[C@H]3CC3(F)F)cccc2c1Oc1ncccc1-c1ccnc(N[C@H]2CCCNC2)n1]

The General Procedure B was followed, using tert-butyl (S)-3-((4-(2-((5-((R)-2,2-difluorocyclopropane-1-carboxamido)-2-methylnaphthalen-1-yl)oxy)pyridin-3-yl)pyrimidin-2-yl)amino)piperidine-1-carboxylate (85 mg, 0.132 mmol), DCM (4 mL) and hydrochloric acid (4 M in dioxane, 3 mL, 12 mmol). The residue was purified via reverse-phase HPLC and lyophilized to yield 39.8 mg (55% yield) of 179. The stereochemistry was tentatively and arbitrarily assigned. LCMS (ESI): [M+H]$^+$=531.2; $^1$H NMR (400 MHz, DMSO-d$_6$) δ 10.42 (s, 1H), 8.50 (d, J=7.5 Hz, 1H), 8.41 (d, J=5.1 Hz, 1H), 8.03 (dd, J=4.8, 2.0 Hz, 1H), 7.94 (d, J=8.7 Hz, 1H), 7.66 (d, J=7.3 Hz, 1H), 7.55 (d, J=8.7 Hz, 2H), 7.49-7.38 (m, 2H), 7.26 (dd, J=7.5, 4.8 Hz, 1H), 7.12 (d, J=8.0 Hz, 1H), 3.89 (s, 1H), 3.15-3.05 (m, 2H), 2.83-2.76 (m, 1H), 2.48-2.38 (m, 2H), 2.22 (s, 3H), 2.11-1.97 (m, 2H), 1.96-1.89 (m, 1H), 1.68-1.60 (m, 1H), 1.55-1.37 (m, 2H).

Example 180 (S)-2,2-Difluoro-N-(6-methyl-5-((3-(2-(((S)-piperidin-3-yl)amino)pyrimidin-4-yl)pyridin-2-yl)oxy)naphthalen-1-yl)cyclopropane-1-carboxamide 180

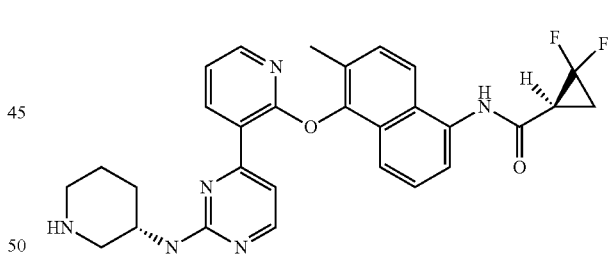

Following Example 179 and the General Procedure B, tert-butyl (S)-3-((4-(2-((5-((S)-2,2-difluorocyclopropane-1-carboxamido)-2-methylnaphthalen-1-yl)oxy)pyridin-3-yl)pyrimidin-2-yl)amino)piperidine-1-carboxylate (82 mg, 0.127 mmol), DCM (4 mL) and hydrochloric acid (4 M in dioxane, 3 mL, 12 mmol) were reacted. The residue was purified via reverse-phase HPLC and lyophilized to yield 23.8 mg (34% yield) of 180. The stereochemistry was tentatively and arbitrarily assigned. LCMS (ESI): [M+H]$^+$=531.2 $^1$H NMR (400 MHz, DMSO-d$_6$) δ 10.42 (s, 1H), 8.50 (d, J=7.5 Hz, 1H), 8.41 (d, J=5.1 Hz, 1H), 8.03 (dd, J=4.8, 2.0 Hz, 1H), 7.94 (d, J=8.7 Hz, 1H), 7.66 (d, J=7.3 Hz, 1H), 7.55 (d, J=8.7 Hz, 2H), 7.49-7.38 (m, 2H), 7.26 (dd, J=7.5, 4.8 Hz, 1H), 7.12 (d, J=8.0 Hz, 1H), 3.89 (s, 1H), 3.15-3.05 (m, 2H), 2.83-2.76 (m, 1H), 2.48-2.38 (m, 2H), 2.22 (s, 3H), 2.11-1.97 (m, 2H), 1.96-1.89 (m, 1H), 1.68-1.60 (m, 1H), 1.55-1.37 (m, 2H).

Example 181 N-(5-((3-(2-(((3S,5S)-5-Fluoropiperidin-3-yl)amino)pyrimidin-4-yl)pyridin-2-yl)oxy)-6-methylnaphthalen-1-yl)propane-1-sulfonamide 181

Step 1: tert-Butyl (5-hydroxynaphthalen-1-yl)carbamate

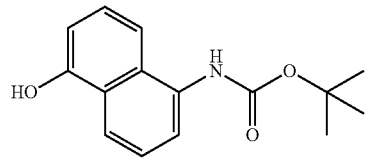 [SMILES: CC(C)(C)OC(=O)Nc1cccc2c(O)cccc12]

To a solution of 5-amino-1-naphthol (5 g, 31.4 mmol) in 1,4-dioxane (50 mL) was added di-tert-butyldicarbonate (8.43 g, 38.6 mmol), the mixture was stirred at 60° C. for 12 h. The reaction mixture was concentrated in vacuo and the residue purified by silica gel chromatography (solvent gradient: 0-50% ethyl acetate in petroleum ether, Rf=0.8) to yield 8 g (98% yield) of the title compound as red solid; $^1$H NMR (400 MHz, DMSO-$d_6$) δ 10.10 (s, 1H), 9.06 (s, 1H), 7.94 (d, J=7.6 Hz, 1H), 7.51 (d, J=7.2 Hz, 1H), 7.46 (d, J=8.8 Hz, 1H), 7.37 (t, J=7.6 Hz, 1H), 7.29 (t, J=8.2 Hz, 1H), 6.86 (d, J=7.6 Hz, 1H), 1.48 (s, 9H).

Step 2: tert-Butyl (6-chloro-5-hydroxynaphthalen-1-yl)carbamate

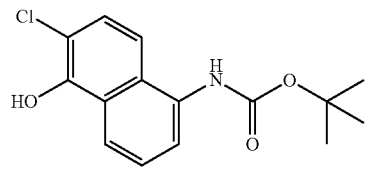 [SMILES: CC(C)(C)OC(=O)Nc1cccc2c(O)c(Cl)ccc12]

To a solution of tert-butyl N-(5-hydroxy-1-naphthyl)carbamate (600 mg, 2.3 mmol) in a solution of sodium hydroxide (1.4 mL, 2.8 mmol, 2N) in H$_2$O (6 mL) was added sodium hypochloride (1.9 mL, 2.3 mmol, 9%) and the mixture was stirred at 0° C. for 1 h. H$_2$O (50 mL) and ethyl acetate (60 mL) were added, the organic phase was dried over anhydrous sodium sulfate, concentrated and purified by silica gel chromatography (50% ethyl acetate in petroleum ether, Rf=0.8) to yield 300 mg (44% yield) of the title compound as a brown solid; $^1$H NMR (400 MHz, CD$_3$OD) δ 8.08 (d, J=8.4 Hz, 1H), 7.57 (d, J=7.6 Hz, 1H), 7.53-7.47 (m, 2H), 7.47-7.42 (m, 1H), 7.37 (d, J=9.2 Hz, 1H), 1.54 (s, 9H).

Step 3: 5-Amino-2-chloronaphthalen-1-ol

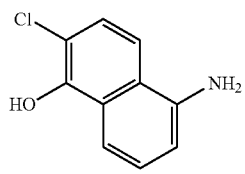 [SMILES: Nc1cccc2c(O)c(Cl)ccc12]

To a stirred solution of tert-butyl N-(6-chloro-5-hydroxy-1-naphthyl)carbamate (300 mg, 1.02 mmol) in ethyl acetate (1 mL) was added hydrochloric acid (4 M in ethyl acetate, 2.6 mL, 10.4 mmol) followed by stirring at 20° C. for 3 h. The mixture was concentrated and the residue was dissolved in ethyl acetate (50 mL) and washed with saturated sodium bicarbonate aqueous solution. The organic phase was dried over anhydrous sodium sulfate, concentrated and purified by Prep-TLC (9% ethyl acetate in petroleum ether, Rf=0.7) to yield 74 mg (37% yield) of the title compound as a tan solid. $^1$H NMR (400 MHz, DMSO-$d_6$) δ 9.59 (s, 1H), 7.56 (d, J=8.8 Hz, 1H), 7.38 (d, J=8.8 Hz, 1H), 7.25 (d, J=8.8 Hz, 1H), 7.20 (t, J=8.0 Hz, 1H), 6.67 (d, J=7.6 Hz, 1H), 5.71 (s, 2H).

Step 4: (S)-tert-Butyl 3-((4-(2-((5-amino-2-chloronaphthalen-1-yl)oxy)pyridin-3-yl)pyrimidin-2-yl)amino)piperidine-1-carboxylate

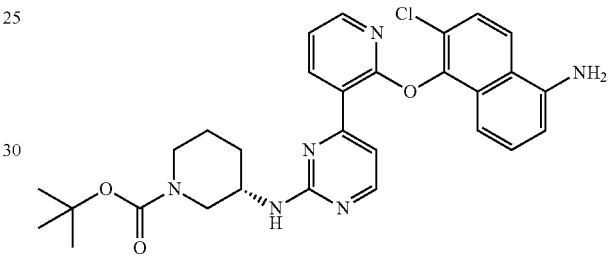

To a solution of tert-butyl (3S)-3-[[4-(2-fluoro-3-pyridyl)pyrimidin-2-yl]amino]piperidine-1-carboxylate (100 mg, 0.27 mmol) and 5-amino-2-chloro-naphthalen-1-ol hydrochloride (74 mg, 0.32 mmol):

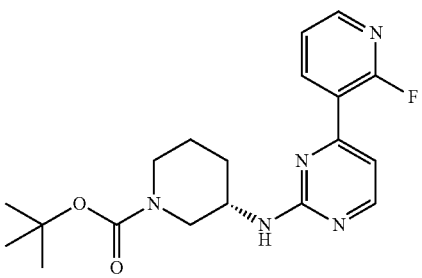 [SMILES: CC(C)(C)OC(=O)N1CCC[C@H](Nc2nccc(-c3cccnc3F)n2)C1]

in 1-methyl-2-pyrrolidinone (6 mL) was added caesium carbonate (262 mg, 0.8 mmol) followed by stirring at 120° C. for 12 h. After cooling down, the mixture was diluted in ethyl acetate (50 mL) and washed with H$_2$O (40 mL) and brine (40 mL). The organic phase was dried over anhydrous sodium sulfate, concentrated and purified by Prep-TLC (50% ethyl acetate in petroleum ether, Rf=0.8) to yield 90 mg (61% yield) of the title compound as a tan solid; LCMS (ESI) [M+H]$^+$=547.1.

Step 5: (S)-tert-Butyl 3-((4-(2-((2-chloro-5-(propylsulfonamido)naphthalen-1-yl)oxy)pyridin-3-yl)pyrimidin-2-yl)amino)piperidine-1-carboxylate

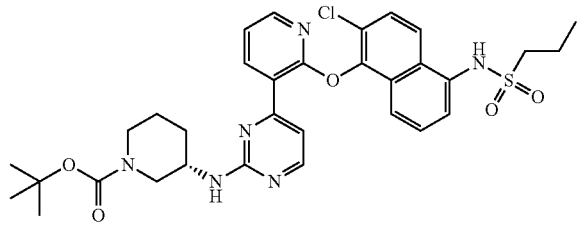 [SMILES: CCCS(=O)(=O)Nc1cccc2c(Oc3ncccc3-c3ccnc(N[C@H]4CCCN(C(=O)OC(C)(C)C)C4)n3)c(Cl)ccc12]

To a solution of tert-butyl (3S)-3-[[4-[2-[(5-amino-2-chloro-1-naphthyl)oxy]-3-pyridyl]pyrimidin-2-yl]amino]piperidine-1-carboxylate (90 mg, 0.16 mmol) in pyridine (3 mL) was added 1-propanesulfonyl chloride (0.02 mL, 0.2 mmol) and stirred at 26° C. for 12 h. The mixture was concentrated, dissolved in dichloromethane (50 mL) and washed with H$_2$O (40 mL). The organic phase was dried over anhydrous sodium sulfate, concentrated and purified by prep-TLC (50% ethyl acetate in petroleum ether, Rf=0.6) to yield 60 mg (42% yield) of the title compound as a white solid; LCMS (ESI) [M+H]$^+$=653.0.

Step 6: (S)—N-(6-Chloro-5-((3-(2-(piperidin-3-ylamino)pyrimidin-4-yl)pyridin-2-yl)oxy)naphthalen-1-yl)propane-1-sulfonamide

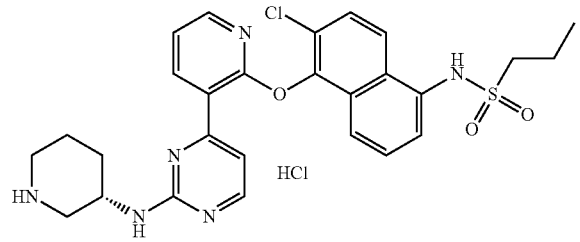 [SMILES: CCCS(=O)(=O)Nc1cccc2c(Oc3ncccc3-c3ccnc(N[C@H]4CCCNC4)n3)c(Cl)ccc12 ; Cl]

To a solution of tert-butyl (3S)-3-[[4-[2-[[2-chloro-5-(propylsulfonylamino)-1-naphthyl]oxy]-3-pyridyl]pyrimidin-2-yl]amino]piperidine-1-carboxylate (60 mg, 0.09 mmol) in ethyl acetate (0.5 mL) was added hydrochloric acid (4 M in ethyl acetate, 0.2 mL, 0.8 mmol) and stirred at 26° C. for 1 h. The residue was concentrated and purified by Prep-HPLC (mobile phase: A: water (0.05% HCl); B: ACN) to yield 22.7 mg (39% yield) of hydrochloride 181 as a white solid; LCMS (ESI) [M+H]$^+$=553.1; $^1$H NMR (400 MHz, DMSO-d$_6$) δ 9.95 (s, 1H), 9.20-9.00 (m, 2H), 8.82-8.63 (m, 1H), 8.49 (d, J=5.2 Hz, 1H), 8.24 (d, J=8.8 Hz, 1H), 8.09 (d, J=3.6 Hz, 1H), 7.76 (d, J=8.8 Hz, 1H), 7.69 (d, J=7.6 Hz, 1H), 7.66-7.51 (m, 4H), 7.34-7.31 (m, 1H), 4.43-4.19 (m, 1H), 3.49-3.37 (m, 1H), 3.26-3.11 (m, 3H), 2.94-2.75 (m, 2H), 2.06-1.98 (m, 1H), 1.96-1.87 (m, 1H), 1.83-1.69 (m, 3H), 1.68-1.58 (m, 1H), 0.98 (t, J=7.2 Hz, 3H).

Example 183 (S)-2-Cyano-N-(6-methyl-5-((3-(2-(piperidin-3-ylamino)pyrimidin-4-yl)pyridin-2-yl)oxy)naphthalen-1-yl)acetamide 183

Step 1: tert-Butyl (S)-3-((4-(2-((5-(2-cyanoacetamido)-2-methylnaphthalen-1-yl)oxy)pyridin-3-yl)pyrimidin-2-yl)amino)piperidine-1-carboxylate

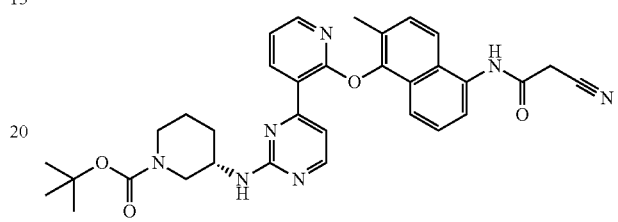

The General Procedure C was followed, using tert-butyl (S)-3-((4-(2-((5-amino-2-methylnaphthalen-1-yl)oxy)pyridin-3-yl)pyrimidin-2-yl)amino)piperidine-1-carboxylate from Example 101 (90 mg, 0.17 mmol), 2-cyanoacetic acid (22 mg, 0.26 mmol), DIPEA (0.089 mL, 0.51 mmol), HATU (97 mg, 0.26 mmol) and DCM (1.7 mL). The crude was directly used in the next step.

Step 2: (S)-2-Cyano-N-(6-methyl-5-((3-(2-(piperidin-3-ylamino)pyrimidin-4-yl)pyridin-2-yl)oxy)naphthalen-1-yl)acetamide

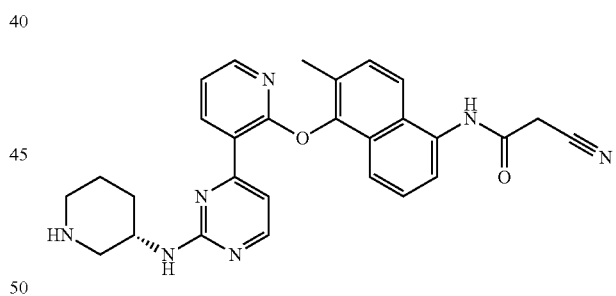

The General Procedure B was followed, using crude tert-butyl (S)-3-((4-(2-((5-(2-cyanoacetamido)-2-methylnaphthalen-1-yl)oxy)pyridin-3-yl)pyrimidin-2-yl)amino)piperidine-1-carboxylate, DCM (1.7 mL) and hydrochloric acid (4 M in dioxane, 0.430 mL, 1.71 mmol). The residue was purified via reverse-phase HPLC and lyophilized to yield 8 mg of 183. LCMS (ESI): [M+H]$^+$=494.2; $^1$H NMR (400 MHz, DMSO-d$_6$) δ 10.30 (s, 1H), 8.50 (d, J=7.5 Hz, 1H), 8.41 (d, J=5.1 Hz, 1H), 8.03 (dd, J=4.8, 2.0 Hz, 1H), 7.94 (d, J=8.7 Hz, 1H), 7.64-7.60 (m, 1H), 7.58-7.53 (m, 2H), 7.45-7.41 (m, 2H), 7.26 (dd, J=7.5, 4.8 Hz, 1H), 7.13 (d, J=8.0 Hz, 1H), 4.10 (s, 2H), 3.90 (s, 1H), 3.14-3.06 (m, 1H), 2.84-2.77 (m, 1H), 2.49-2.40 (m, 2H), 1.97-1.87 (m, 1H), 1.69-1.61 (m, 1H), 1.57-1.36 (m, 2H).

Example 184 N-[6-Methyl-5-[[3-[2-[[(3S)-3-piperidyl]amino]pyrimidin-4-yl]-2-pyridyl]oxy]-1-naphthyl]-2-phenyl-acetamide 184

Step 1: tert-Butyl (S)-3-((4-(2-((2-methyl-5-(2-phenylacetamido)naphthalen-1-yl)oxy)pyridin-3-yl)pyrimidin-2-yl)amino)piperidine-1-carboxylate

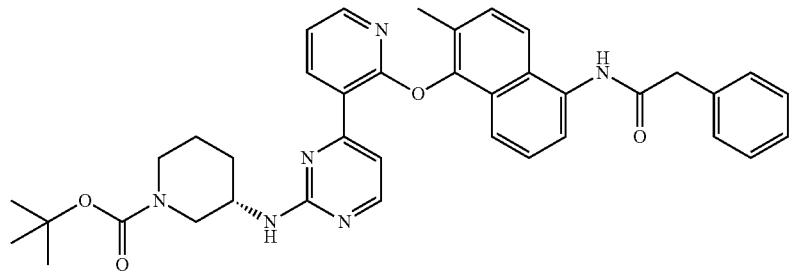 [SMILES: Cc1ccc2c(NC(=O)Cc3ccccc3)cccc2c1Oc1ncccc1-c1ccnc(N[C@H]2CCCN(C(=O)OC(C)(C)C)C2)n1]

The General Procedure C was followed, using tert-butyl (S)-3-((4-(2-((5-amino-2-methylnaphthalen-1-yl)oxy)pyridin-3-yl)pyrimidin-2-yl)amino)piperidine-1-carboxylate from Example 101 (90 mg, 0.17 mmol), 2-phenylacetic acid (35 mg, 0.26 mmol), DIPEA (0.089 mL, 0.51 mmol), HATU (97 mg, 0.26 mmol) and DCM (1.7 mL). The crude was directly used in the next step.

Step 2: N-[6-Methyl-5-[[3-[2-[[(3S)-3-piperidyl]amino]pyrimidin-4-yl]-2-pyridyl]oxy]-1-naphthyl]-2-phenyl-acetamide

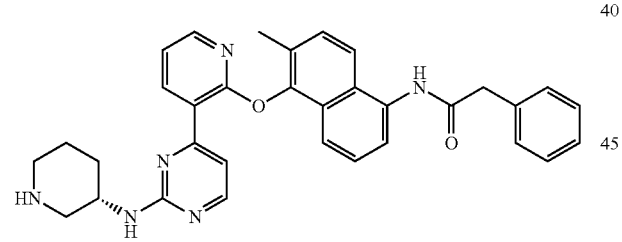

The General Procedure B was followed, using crude tert-butyl (S)-3-((4-(2-((2-methyl-5-(2-phenylacetamido)naphthalen-1-yl)oxy)pyridin-3-yl)pyrimidin-2-yl)amino)piperidine-1-carboxylate, DCM (1.7 mL) and hydrochloric acid (4 M in dioxane, 0.430 mL, 1.71 mmol). The residue was purified via reverse-phase HPLC and lyophilized to yield 13 mg of 184. LCMS (ESI): $[M+H]^+=$ $^1$H NMR (400 MHz, DMSO-$d_6$) δ 10.17 (s, 1H), 8.49 (d, J=7.2 Hz, 1H), 8.41 (d, J=5.2 Hz, 1H), 8.02 (dd, J=4.8, 2.0 Hz, 1H), 7.90 (d, J=8.8 Hz, 1H), 7.62 (d, J=7.4 Hz, 1H), 7.54-7.47 (m, 2H), 7.47-7.20 (m, 9H), 7.14 (d, J=7.9 Hz, 1H), 3.91 (s, 1H), 3.83 (s, 2H), 3.69-3.62 (m, 1H), 3.15-3.07 (d, J=11.6 Hz, 1H), 2.85-2.76 (m, 1H), 2.46-2.41 (m, 1H), 2.20 (s, 3H), 1.97-1.88 (m, 1H), 1.70-1.59 (m, 1H), 1.55-1.37 (m, 2H).

Example 185 (S)—N-(2-Fluoro-6-methyl-5-((3-(2-(piperidin-3-ylamino)pyrimidin-4-yl)pyridin-2-yl)oxy)naphthalen-1-yl)-2-methoxyethanesulfonamide 185

Step 1: (S)-tert-Butyl 3-((4-(2-((6-fluoro-5-(2-methoxyethylsulfonamido)-2-methylnaphthalen-1-yl)oxy)pyridin-3-yl)pyrimidin-2-yl)amino)piperidine-1-carboxylate

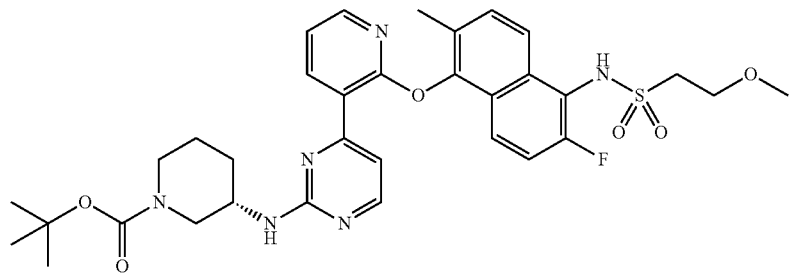 [SMILES: COCCS(=O)(=O)Nc1c(F)ccc2c(Oc3ncccc3-c3ccnc(N[C@H]4CCCN(C(=O)OC(C)(C)C)C4)n3)c(C)ccc12]

Prepared using (S)-tert-butyl 3-((4-(2-((5-amino-6-fluoro-2-methylnaphthalen-1-yl)oxy)pyridin-3-yl)pyrimidin-2-yl)amino)piperidine-1-carboxylate from Example 275 (75 mg, 0.138 mmol), pyridine (0.167 mL, 2.07 mmol), DCM (0.9 mL), 2-methoxyethanesulfonyl chloride (43.7 mg, 0.275 mmol) and DMAP (1.68 mg, 0.014 mmol). After 16 h, the mixture was diluted with 1M KHSO$_4$(aq), extracted twice with DCM, dried (Na$_2$SO$_4$), filtered and concentrated in vacuo. The crude was purified by flash chromatography through silica gel (0-55% EtOAc/DCM) to provide 42 mg (46% yield) of the title compound. LCMS (ESI) [M+H]$^+$=667.4, rt=1.82 min.

Step 2: (S)—N-(2-Fluoro-6-methyl-5-((3-(2-(piperidin-3-ylamino)pyrimidin-4-yl)pyridin-2-yl)oxy)naphthalen-1-yl)-2-methoxyethanesulfonamide

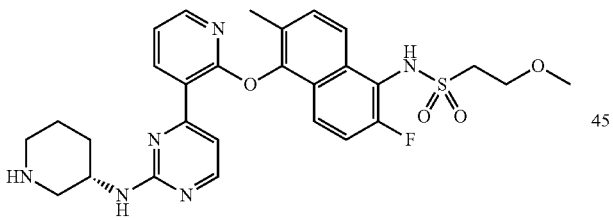

Prepared according to General Procedure B using (S)-tert-butyl 3-((4-(2-((6-fluoro-5-(2-methoxyethylsulfonamido)-2-methylnaphthalen-1-yl)oxy)pyridin-3-yl)pyrimidin-2-yl)amino)piperidine-1-carboxylate (42 mg, 0.063 mmol), 1,4-dioxane (0.5 mL) and hydrochloric acid (4 M in dioxane, 0.53 mL, 2.11 mmol). After 1 h, the reaction was diluted with Et$_2$O and sonicated for a few seconds. The solid was collected by filtration, washed with Et$_2$O, dissolved in H$_2$O and MeCN and lyophilized to provide 36 mg (95% yield) of 185. LCMS (ESI) [M+H]$^+$=567.4, rt=1.29 min; $^1$H NMR (400 MHz, DMSO-d$_6$) δ 9.80 (s, 1H), 8.92 (bs, 2H), 8.69 (s, 1H), 8.48 (d, J=5.2 Hz, 1H), 8.11-8.00 (m, 2H), 7.72 (dd, J=9.3, 5.2 Hz, 1H), 7.63 (d, J=8.8 Hz, 1H), 7.57 (d, J=5.5 Hz, 2H), 7.46 (t, J=9.5 Hz, 1H), 7.29 (dd, J=7.6, 4.8 Hz, 1H), 3.82 (t, J=6.5 Hz, 2H), 3.49 (t, J=6.5 Hz, 2H), 3.46-3.38 (m, 1H), 3.29 (s, 3H), 3.20 (d, J=12.2 Hz, 1H), 2.94-2.76 (m, 2H), 2.19 (s, 3H), 2.06-1.97 (m, 1H), 1.95-1.85 (m, 1H), 1.84-1.54 (m, 2H).

Example 186 (S)-1-(2,4-Difluorophenyl)-N-(2-fluoro-6-methyl-5-((3-(2-(piperidin-3-ylamino)pyrimidin-4-yl)pyridin-2-yl)oxy)naphthalen-yl)oxy)naphthalen-1-yl)methanesulfonamide 186

Step 1: (S)-tert-Butyl 3-((4-(2-((5-((2,4-difluorophenyl)methylsulfonamido)-6-fluoro-2-methylnaphthalen-1-yl)oxy)pyridin-3-yl)pyrimidin-2-yl)amino)piperidine-1-carboxylate

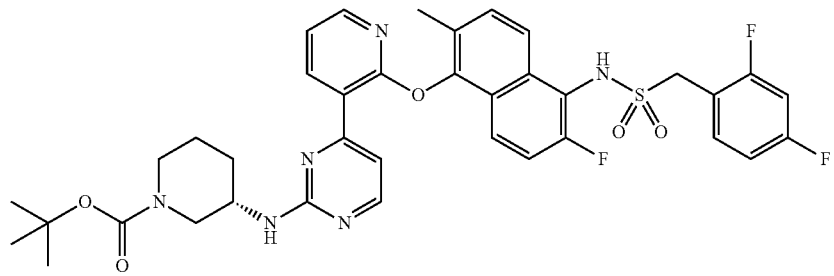 [SMILES: Cc1ccc2c(NS(=O)(=O)Cc3ccc(F)cc3F)c(F)ccc2c1Oc1ncccc1-c1ccnc(N[C@H]2CCCN(C(=O)OC(C)(C)C)C2)n1]

Prepared using (S)-tert-butyl 3-((4-(2-((5-amino-6-fluoro-2-methylnaphthalen-1-yl)oxy)pyridin-3-yl)pyrimidin-2-yl)amino)piperidine-1-carboxylate from Example 275 (50 mg, 0.092 mmol), pyridine (0.5 mL, 6.18 mmol), DCM (1 mL), and (2,4-difluorophenyl)methanesulfonyl chloride (52 mg, 0.23 mmol). After 16 h, the mixture was diluted with DCM (50 mL), washed with saturated NaHCO$_3$(aq) (10 mL), dried (Na$_2$SO$_4$), filtered and concentrated in vacuo. The crude was purified by flash chromatography through silica gel (0-75% EtOAc/Hexanes) to provide 45 mg (67% yield) of the title compound. LCMS (ESI) [M+H]$^+$=735.3, rt=2.00 min.

Step 2: (S)-1-(2,4-Difluorophenyl)-N-(2-fluoro-6-methyl-5-((3-(2-(piperidin-3-ylamino)pyrimidin-4-yl)pyridin-2-yl)oxy)naphthalen-1-yl)methanesulfonamide

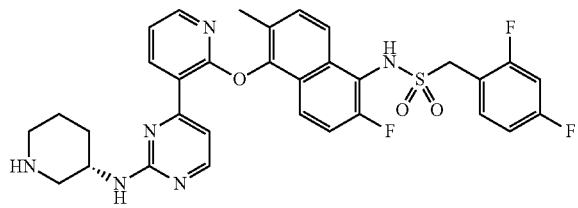 [SMILES: Cc1ccc2c(NS(=O)(=O)Cc3ccc(F)cc3F)c(F)ccc2c1Oc1ncccc1-c1ccnc(N[C@H]2CCCNC2)n1]

Prepared using (S)-tert-butyl 3-((4-(2-((5-((2,4-difluorophenyl)methylsulfonamido)-6-fluoro-2-methylnaphthalen-1-yl)oxy)pyridin-3-yl)pyrimidin-2-yl)amino)piperidine-1-carboxylate (45 mg, 0.061 mmol), EtOAc (2 mL), and hydrochloric acid (4 M in dioxane, 1 mL, 4 mmol). After 4 h, volatiles were removed in vacuo and the residue was washed with EtOAc (3×3 mL), then with MeCN (3×3 mL). The residue was then sonicated and concentrated in vacuo with MeCN (3×3 mL) and the resulting solid dissolved in water and MeCN and lyophilized to provide 28 mg (68% yield) of 186 as a white solid. LCMS (ESI) [M+H]$^+$=635.2, rt=1.50 min; $^1$H NMR (400 MHz, DMSO-d$_6$) δ 9.96 (s, 1H), 8.87-8.67 (m, 2H), 8.66-8.53 (m, 1H), 8.47 (d, J=7.0 Hz, 1H), 8.09 (dd, J=4.8, 1.9 Hz, 1H), 8.01 (d, J=8.7 Hz, 1H), 7.73 (dd, J=12.7, 6.5 Hz, 1H), 7.64-7.45 (m, 5H), 7.39-7.26 (m, 2H), 7.17 (td, J=8.5, 2.1 Hz, 1H), 4.62 (s, 2H), 4.16-4.33 (m, 1H), 3.47-3.42 (m, 1H), 3.21 (d, J=12.5 Hz, 1H), 2.96-2.76 (m, 2H), 2.19 (s, 3H), 2.08-1.97 (m, 1H), 1.97-1.85 (m, 1H), 1.81-1.56 (m, 2H).

Example 187 (S)—N-(6-Methyl-5-((3-(2-(piperidin-3-ylamino)pyrimidin-4-yl)pyridin-2-yl)oxy)naphthalen-1-yl)cyclopentanecarboxamide 187

Step 1: tert-Butyl (S)-3-((4-(2-((5-(cyclopentanecarboxamido)-2-methylnaphthalen-1-yl)oxy)pyridin-3-yl)pyrimidin-2-yl)amino)piperidine-1-carboxylate

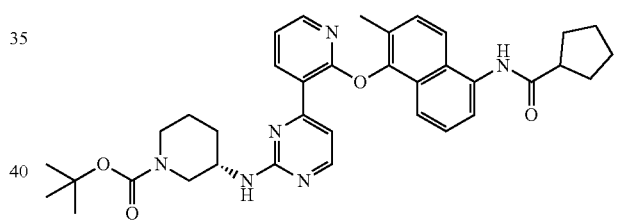

The General Procedure C was followed, using tert-butyl (S)-3-((4-(2-((5-amino-2-methylnaphthalen-1-yl)oxy)pyridin-3-yl)pyrimidin-2-yl)amino)piperidine-1-carboxylate from Example 101 (90 mg, 0.17 mmol), cyclopentanecarboxylic acid (29 mg, 0.26 mmol), DIPEA (0.089 mL, 0.51 mmol), HATU (97 mg, 0.26 mmol) and DCM (1.7 mL). The crude was directly used in the next step.

Step 2: (S)—N-(6-Methyl-5-((3-(2-(piperidin-3-ylamino)pyrimidin-4-yl)pyridin-2-yl)oxy)naphthalen-1-yl)cyclopentanecarboxamide

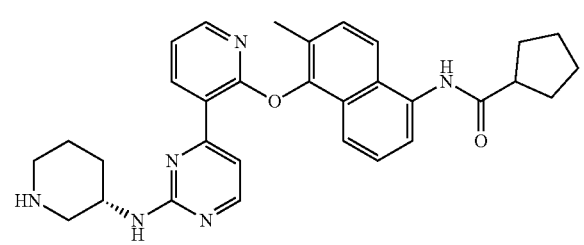 [SMILES: Cc1ccc2c(NC(=O)C3CCCC3)cccc2c1Oc1ncccc1-c1ccnc(N[C@H]2CCCNC2)n1]

The General Procedure B was followed, using crude tert-butyl (S)-3-((4-(2-((5-(cyclopentanecarboxamido)-2-methylnaphthalen-1-yl)oxy)pyridin-3-yl)pyrimidin-2-yl)amino)piperidine-1-carboxylate, DCM (1.7 mL) and hydrochloric acid (4 M in dioxane, 0.430 mL, 1.71 mmol). The residue was purified via reverse-phase HPLC and lyophilized to yield 16 mg of 187. LCMS (ESI): [M+H]⁺=523.3; ¹H NMR (400 MHz, DMSO-d₆) δ 9.87 (s, 1H), 8.49 (d, J=7.5 Hz, 1H), 8.41 (d, J=5.1 Hz, 1H), 8.02 (dd, J=4.8, 2.0 Hz, 1H), 7.89 (d, J=8.6 Hz, 1H), 7.59 (d, J=7.4 Hz, 1H), 7.50 (d, J=8.7 Hz, 3H), 7.35-7.46 (m, 2H), 7.25 (dd, J=7.5, 4.8 Hz, 1H), 7.10 (d, J=8.0 Hz, 1H), 3.88 (s, 1H), 2.97-3.11 (m, 2H), 2.82-2.74 (d, J=12.1 Hz, 1H), 2.35-2.46 (m, 2H), 2.22 (s, 3H), 1.88-2.02 (m, 3H), 1.36-1.87 (m, 9H).

Example 188 (S)-3-Methyl-N-(6-methyl-5-((3-(2-(piperidin-3-ylamino)pyrimidin-4-yl)pyridin-2-yl)oxy)naphthalen-1-yl)butanamide 188

Step 1: tert-Butyl (S)-3-((4-(2-((5-isobutyramido-2-methylnaphthalen-1-yl)oxy)pyridin-3-yl)pyrimidin-2-yl)amino)piperidine-1-carboxylate The General Procedure C was followed, using tert-butyl (S)-3-((4-(2-((5-amino-2-methylnaphthalen-1-yl)oxy)pyridin-3-yl)pyrimidin-2-yl)amino)piperidine-1-carboxylate from Example 101 (90 mg, 0.17 mmol), 3-methylbutanoic acid (26 mg, 0.26 mmol), DIPEA (0.089 mL, 0.51 mmol), HATU (97 mg, 0.26 mmol) and DCM (1.7 mL). The crude was directly used in the next step.

Step 2: (S)-3-Methyl-N-(6-methyl-5-((3-(2-(piperidin-3-ylamino)pyrimidin-4-yl)pyridin-2-yl)oxy)naphthalen-1-yl)butanamide

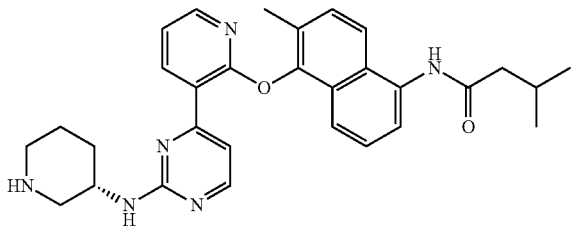

The General Procedure B was followed, using crude (S)-3-Methyl-N-(6-methyl-5-((3-(2-(piperidin-3-ylamino)pyrimidin-4-yl)pyridin-2-yl)oxy)naphthalen-1-yl)butanamide, DCM (1.7 mL) and hydrochloric acid (4 M in dioxane, 0.430 mL, 1.71 mmol). The residue was purified via reverse-phase HPLC and lyophilized to yield 11 mg of 188. LCMS (ESI): [M+H]⁺=511.2; ¹HNMR (400 MHz, DMSO-d₆) δ 9.88 (s, 1H), 8.49 (d, J=7.6 Hz, 1H), 8.41 (d, J=5.1 Hz, 1H), 8.02 (dd, J=4.8, 2.0 Hz, 1H), 7.91 (d, J=8.7 Hz, 1H), 7.60 (d, J=7.3 Hz, 1H), 7.51 (d, J=8.7 Hz, 2H), 7.46-7.39 (m, 2H), 7.25 (dd, J=7.6, 4.8 Hz, 1H), 7.10 (d, J=8.0 Hz, 1H), 3.88 (s, 1H), 3.13-3.05 (m, 1H), 2.82-2.74 (m, 1H), 2.47-2.30 (m, 4H), 2.22 (s, 3H), 2.19-2.10 (m, 1H), 1.96-1.88 (m, 1H), 1.68-1.60 (m, 1H), 1.54-1.37 (m, 2H), 1.02 (d, J=6.6 Hz, 6H).

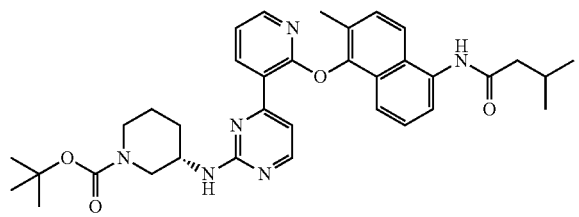 [SMILES: Cc1ccc2c(NC(=O)CC(C)C)cccc2c1Oc1ncccc1-c1ccnc(N[C@H]2CCCN(C(=O)OC(C)(C)C)C2)n1]

Example 189 (S)-1-(2,3-Difluorophenyl)-N-(2-fluoro-6-methyl-5-((3-(2-(piperidin-3-ylamino)pyrimidin-4-yl)pyridin-2-yl)oxy)naphthalen-yl)oxy)naphthalen-1-yl)methanesulfonamide 189

Step 1: (S)-tert-Butyl 3-((4-(2-((5-((2,3-difluorophenyl)methylsulfonamido)-6-fluoro-2-methylnaphthalen-1-yl)oxy)pyridin-3-yl)pyrimidin-2-yl)amino)piperidine-1-carboxylate

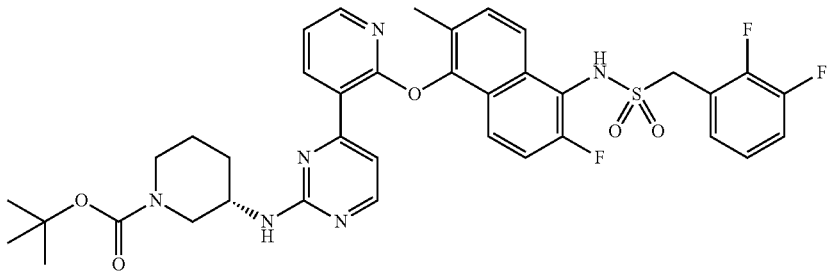 [SMILES: Cc1ccc2c(NS(=O)(=O)Cc3cccc(F)c3F)c(F)ccc2c1Oc1ncccc1-c1ccnc(N[C@H]2CCCN(C(=O)OC(C)(C)C)C2)n1]

Prepared using (S)-tert-butyl 3-((4-(2-((5-amino-6-fluoro-2-methylnaphthalen-1-yl)oxy)pyridin-3-yl)pyrimidin-2-yl)amino)piperidine-1-carboxylate from Example 275 (50 mg, 0.092 mmol), pyridine (0.5 mL, 6.18 mmol), DCM (1 mL), and (2,3-difluorophenyl)methanesulfonyl chloride (52 mg, 0.23 mmol). After 16 h, the mixture was diluted DCM (50 mL), washed with saturated NaHCO$_3$(aq) (10 mL), dried (Na$_2$SO$_4$), filtered and concentrated in vacuo. The crude was purified by flash chromatography through silica gel (0-70% EtOAc/Hexanes) to provide 45 mg (67% yield) of the title compound. LCMS (ESI) [M+H]$^+$=735.3, rt=1.99 min.

Step 2: (S)-1-(2,3-Difluorophenyl)-N-(2-fluoro-6-methyl-5-((3-(2-(piperidin-3-ylamino)pyrimidin-4-yl)pyridin-2-yl)oxy)naphthalen-1-yl)methanesulfonamide

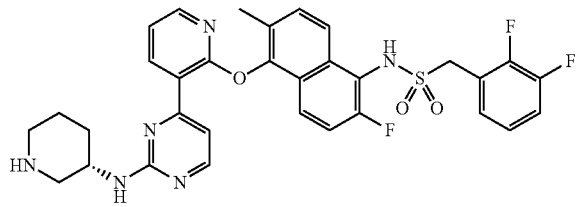 [SMILES: Cc1ccc2c(NS(=O)(=O)Cc3cccc(F)c3F)c(F)ccc2c1Oc1ncccc1-c1ccnc(N[C@H]2CCCNC2)n1]

Prepared using (S)-tert-butyl 3-((4-(2-((5-((2,3-difluorophenyl)methylsulfonamido)-6-fluoro-2-methylnaphthalen-1-yl)oxy)pyridin-3-yl)pyrimidin-2-yl)amino)piperidine-1-carboxylate (45 mg, 0.061 mmol), EtOAc (1 mL), and hydrochloric acid (4 M in dioxane, 1 mL, 4 mmol). After 90 min, volatiles were removed in vacuo and the residue was washed with EtOAc (3×3 mL), then with MeCN (3×3 mL). The residue was then sonicated and concentrated in vacuo with MeCN (3×3 mL) and the resulting solid dissolved in water and MeCN and lyophilized to provide 26 mg (63% yield) of 189 as a white solid. LCMS (ESI) [M+H]$^+$=635.2, rt=1.51 min; 1H NMR (400 MHz, d6-dmso) δ 10.04 (s, 1H), 8.95-8.72 (m, 2H), 8.69-8.53 (m, 1H), 8.47 (d, J=7.0 Hz, 1H), 8.09 (dd, J=4.8, 1.8 Hz, 1H), 8.01 (d, J=8.7 Hz, 1H), 7.74 (dd, J=9.3, 5.1 Hz, 1H), 7.62 (d, J=8.8 Hz, 1H), 7.59-7.43 (m, 4H), 7.40-7.20 (m, 3H), 4.70 (s, 2H), 4.34-4.18 (m, 1H), 3.44 (d, J=10.1 Hz, 1H), 3.21 (d, J=12.0 Hz, 1H), 2.96-2.78 (m, 2H), 2.19 (s, 3H), 2.07-1.87 (m, 2H), 1.81-1.54 (m, 2H).

Example 190 (S)—N-(6-Methyl-5-((3-(2-(piperidin-3-ylamino)pyrimidin-4-yl)pyridin-2-yl)oxy)naphthalen-1-yl)cyclohexanecarboxamide 190

Step 1: tert-Butyl (S)-3-((4-(2-((5-(cyclohexanecarboxamido)-2-methylnaphthalen-1-yl)oxy)pyridin-3-yl)pyrimidin-2-yl)amino)piperidine-1-carboxylate

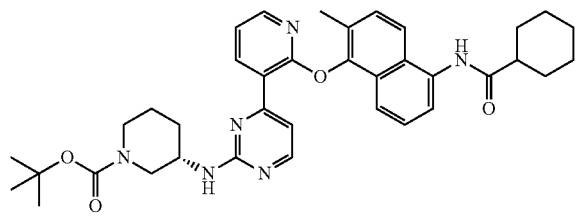 [SMILES: Cc1ccc2c(NC(=O)C3CCCCC3)cccc2c1Oc1ncccc1-c1ccnc(N[C@H]2CCCN(C(=O)OC(C)(C)C)C2)n1]

The General Procedure C was followed, using tert-butyl (S)-3-((4-(2-((5-amino-2-methylnaphthalen-1-yl)oxy)pyridin-3-yl)pyrimidin-2-yl)amino)piperidine-1-carboxylate from Example 101 (90 mg, 0.17 mmol), cyclopentanecarboxylic acid (mg, 0.26 mmol), DIPEA (0.089 mL, 0.51 mmol), HATU (97 mg, 0.26 mmol) and DCM (1.7 mL). The crude was directly used in the next step.

Step 2: (S)—N-(6-Methyl-5-((3-(2-(piperidin-3-ylamino)pyrimidin-4-yl)pyridin-2-yl)oxy)naphthalen-1-yl)cyclohexanecarboxamide

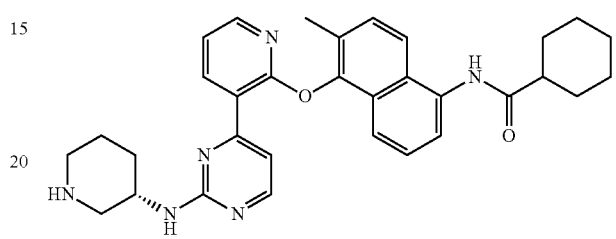

The General Procedure B was followed, using crude tert-butyl (S)-3-((4-(2-((5-(cyclohexanecarboxamido)-2-methylnaphthalen-1-yl)oxy)pyridin-3-yl)pyrimidin-2-yl)amino)piperidine-1-carboxylate, DCM (1.7 mL) and hydrochloric acid (4 M in dioxane, 0.430 mL, 1.71 mmol). The residue was purified via reverse-phase HPLC and lyophilized to yield 22 mg of 190. LCMS (ESI): [M+H]$^+$=537.3; $^1$H NMR (400 MHz, DMSO-d6) δ 9.80 (s, 1H), 8.49 (d, J=7.6 Hz, 1H), 8.41 (d, J=5.0 Hz, 1H), 8.02 (dd, J=4.8, 2.0 Hz, 1H), 7.88 (d, J=8.7 Hz, 1H), 7.58 (d, J=7.4 Hz, 1H), 7.50 (dd, J=8.7, 4.3 Hz, 2H), 7.43 (d, J=5.1 Hz, 1H), 7.39 (dd, J=8.5, 7.3 Hz, 1H), 7.25 (dd, J=7.5, 4.8 Hz, 1H), 7.10 (d, J=8.0 Hz, 1H), 3.88 (s, 1H), 3.08 (d, J=11.6 Hz, 1H), 2.82-2.75 (m, 1H), 2.47-2.38 (m, 2H), 2.21 (s, 3H), 1.99-1.89 (m, 3H), 1.84-1.76 (m, 1H), 1.73-1.60 (m, 2H), 1.54-1.18 (m, 7H).

Example 191 (S)-2-Cyclopropyl-N-(6-methyl-5-((3-(2-(piperidin-3-ylamino)pyrimidin-4-yl)pyridin-2-yl)oxy)naphthalen-1-yl)acetamide 191

Step 1: tert-Butyl (S)-3-((4-(2-((5-(2-cyclopropylacetamido)-2-methylnaphthalen-1-yl)oxy)pyridin-3-yl)pyrimidin-2-yl)amino)piperidine-1-carboxylate

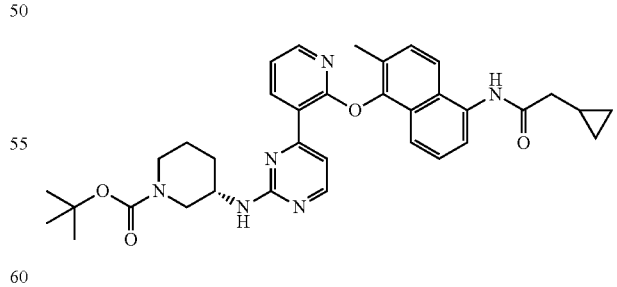

The General Procedure C was followed, using tert-butyl (S)-3-((4-(2-((5-amino-2-methylnaphthalen-1-yl)oxy)pyridin-3-yl)pyrimidin-2-yl)amino)piperidine-1-carboxylate from Example 101 (90 mg, 0.17 mmol), 2-cyclopropyl acetic acid (26 mg, 0.26 mmol), DIPEA (0.089 mL, 0.51 mmol), HATU (97 mg, 0.26 mmol) and DCM (1.7 mL). The crude was directly used in the next step.

Step 2: (S)-2-Cyclopropyl-N-(6-methyl-5-((3-(2-(piperidin-3-ylamino)pyrimidin-4-yl)pyridin-2-yl)oxy)naphthalen-1-yl)acetamide

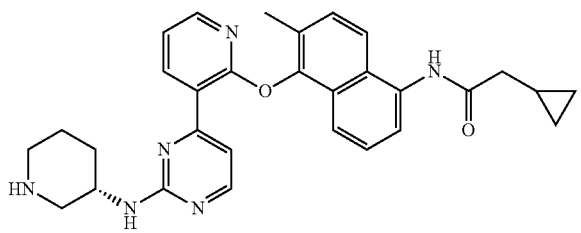 [SMILES: Cc1ccc2c(NC(=O)CC3CC3)cccc2c1Oc1ncccc1-c1ccnc(N[C@H]2CCCNC2)n1]

The General Procedure B was followed, using, DCM (1.7 mL) and hydrochloric acid (4 M in dioxane, 0.430 mL, 1.71 mmol). The residue was purified via reverse-phase HPLC and lyophilized to yield 15 mg of 191. LCMS (ESI): [M+H]+=509.2; 1H NMR (400 MHz, DMSO-d6) δ 9.82 (s, 1H), 8.49 (d, J=7.5 Hz, 1H), 8.41 (d, J=5.1 Hz, 1H), 8.03 (dd, J=4.8, 2.0 Hz, 1H), 7.92 (d, J=8.7 Hz, 1H), 7.63 (d, J=7.4 Hz, 1H), 7.51 (d, J=8.8 Hz, 2H), 7.48-7.36 (m, 2H), 7.25 (dd, J=7.6, 4.8 Hz, 1H), 7.11 (d, J=8.0 Hz, 1H), 3.89 (s, 1H), 3.13-3.06 (m, 1H), 2.82-2.76 (m, 1H), 2.45-2.32 (m, 3H), 2.22 (s, 3H), 1.96-1.89 (m, 1H), 1.67-1.60 (m 1H), 1.59-1.37 (m, 2H), 1.20-1.10 (m, 1H), 0.57-0.52 (m, 2H), 0.32-0.26 (m, 2H).

Example 192 (S)-2-Methyl-N-(6-methyl-5-((3-(2-(piperidin-3-ylamino)pyrimidin-4-yl)pyridin-2-yl)oxy)naphthalen-1-yl) thiazol-4-amine 192

Step 1: tert-Butyl (S)-3-((4-(2-((2-methyl-5-((2-methylthiazol-4-yl)amino)naphthalen-1-yl)oxy)pyridin-3-yl)pyrimidin-2-yl)amino)piperidine-1-carboxylate

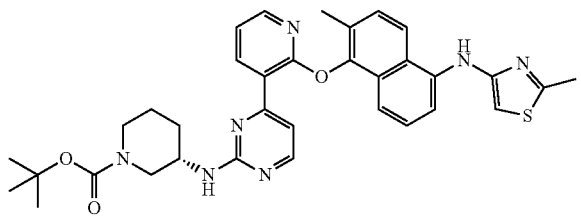 [SMILES: Cc1nc(Nc2cccc3c(Oc4ncccc4-c4ccnc(N[C@H]5CCCN(C(=O)OC(C)(C)C)C5)n4)c(C)ccc23)cs1]

A mixture of tert-butyl (3S)-3-[[4-[2-[(5-amino-2-methyl-1-naphthyl)oxy]-3-pyridyl]pyrimidin-2-yl]amino]piperidine-1-carboxylate (100 mg, 0.19 mmol), 4-bromo-2-methylthiazole (53.4 mg, 0.28 mmol), Brettphos Pd G3 (18.1 mg, 0.019 mmol), Brettphos (16.10 mg, 0.028 mmol), and sodium tert-butoxide (28.2 mg, 0.28 mmol) in 1,4-dioxane (1.5 mL) was capped in a microwave vial, degassed with N2, and heated in a microwave reactor at 120° C. for 45 min.

Additional 4-bromo-2-methylthiazole (53.4 mg), Brettphos Pd G3 (18 mg), Brettphos (16.0 mg), and sodium tert-butoxide (28.2 mg) were added followed by heating at 120° C. for 45 min. Additional Brettphos Pd G3 (18 mg) and Brettphos (16.0 mg) were added followed by additional heating at 120° C. for 45 min.

The mixture was diluted with iPrOAc (10 mL), filtered through Celite® (Johns Manville). The crude material was purified by chromatography (silica gel chromatography), 24 g column, eluting with 0-5% MeOH/DCM to afford 22 mg (18.6% yield) of the title compound as a brown solid. LCMS (ESI) [M+H]+=624.

Step 2: (S)-2-Methyl-N-(6-methyl-5-((3-(2-(piperidin-3-ylamino)pyrimidin-4-yl)pyridin-2-yl)oxy)naphthalen-1-yl)thiazol-4-amine

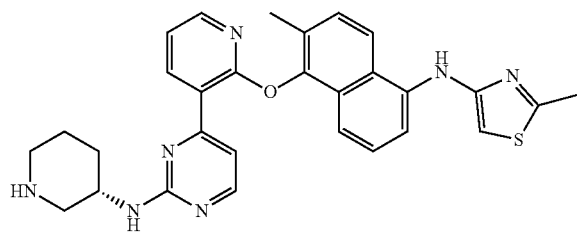 [SMILES: Cc1nc(Nc2cccc3c(Oc4ncccc4-c4ccnc(N[C@H]5CCCNC5)n4)c(C)ccc23)cs1]

The General Procedure B was followed, using tert-butyl (S)-3-((4-(2-((2-methyl-5-((2-methylthiazol-4-yl)amino)naphthalen-1-yl)oxy)pyridin-3-yl)pyrimidin-2-yl)amino)piperidine-1-carboxylate (22 mg, 0.03 mmol). The crude product was purified via reverse-phase HPLC and lyophilized to yield 6.7 mg (18.5% yield) of 192 as an off-white solid. LCMS (ESI) [M+H]+=524; 1H NMR (400 MHz, DMSO-d6) δ 8.78 (s, 1H), 8.49 (s, 1H), 8.41 (d, J=5.1 Hz, 1H), 8.13 (d, J=8.7 Hz, 1H), 8.03 (dd, J=4.8, 1.9 Hz, 1H), 7.48-7.40 (m, 2H), 7.37-7.32 (m, 1H), 7.31-7.22 (m, 2H), 7.18 (d, J=8.3 Hz, 1H), 7.15-7.08 (m, 1H), 3.90 (s, 1H), 3.10 (s, 1H), 2.81 (d, J=12.0 Hz, 1H), 2.64 (s, 3H), 2.45 (s, 1H), 2.21 (s, 3H), 1.97-1.90 (m, 1H), 1.69-1.63 (m, 1H), 1.55-1.40 (m, 2H).

Example 193 (S)-2-(3-Fluorophenyl)-N-(6-methyl-5-((3-(2-(piperidin-3-ylamino)pyrimidin-4-yl)pyridin-2-yl)oxy)naphthalen-1-yl)acetamide 193

Step 1: tert-Butyl (S)-3-((4-(2-((5-(2-(3-fluorophenyl)acetamido)-2-methylnaphthalen-1-yl)oxy)pyridin-3-yl)pyrimidin-2-yl)amino)piperidine-1-carboxylate

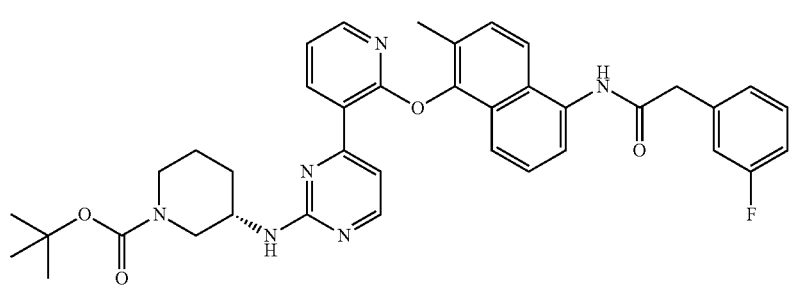 [SMILES: Cc1ccc2c(NC(=O)Cc3cccc(F)c3)cccc2c1Oc1ncccc1-c1ccnc(N[C@H]2CCCN(C(=O)OC(C)(C)C)C2)n1]

The General Procedure C was followed, using tert-butyl (S)-3-((4-(2-((5-amino-2-methylnaphthalen-1-yl)oxy)pyridin-3-yl)pyrimidin-2-yl)amino)piperidine-1-carboxylate from Example 101 (90 mg, 0.17 mmol), 2-(3-fluorophenyl)acetic acid (39.5 mg, 0.26 mmol), DIPEA (0.089 mL, 0.51 mmol), HATU (97 mg, 0.26 mmol) and DCM (1.7 mL). The crude was directly used in the next step.

Step 2: (S)-2-(3-Fluorophenyl)-N-(6-methyl-5-((3-(2-(piperidin-3-ylamino)pyrimidin-4-yl)pyridin-2-yl)oxy)naphthalen-1-yl)acetamide

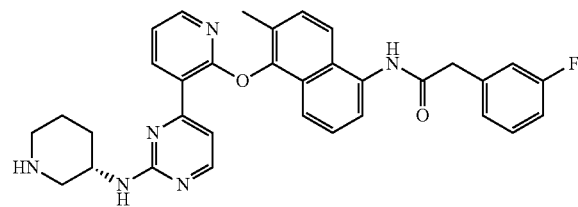 [SMILES: Cc1ccc2c(NC(=O)Cc3cccc(F)c3)cccc2c1Oc1ncccc1-c1ccnc(N[C@H]2CCCNC2)n1]

The General Procedure B was followed, using crude tert-butyl (S)-3-((4-(2-((5-(2-(3-fluorophenyl)acetamido)-2-methylnaphthalen-1-yl)oxy)pyridin-3-yl)pyrimidin-2-yl)amino)piperidine-1-carboxylate, DCM (1.7 mL) and hydrochloric acid (4 M in dioxane, 0.430 mL, 1.71 mmol). The residue was purified via reverse-phase HPLC and lyophilized to yield 6 mg of 193. LCMS (ESI): $[M+H]^+=563.2$; $^1$H NMR (400 MHz, DMSO-$d_6$) δ 10.20 (s, 1H), 8.49 (d, J=7.5 Hz, 1H), 8.40 (d, J=5.1 Hz, 1H), 8.02 (dd, J=4.8, 2.0 Hz, 1H), 7.91 (d, J=8.6 Hz, 0H), 7.62 (d, J=7.3 Hz, 1H), 7.55-7.50 (m, 2H), 7.46-7.35 (m, 3H), 7.30-7.21 (m, 3H), 7.14-7.08 (m, 2H), 3.87 (s, 3H), 3.12-3.05 (d, J=11.9 Hz, 1H), 2.81-2.74 (m, 1H), 2.46-2.37 (m, 1H), 2.22 (s, 3H), 1.96-1.88 (m, 1H), 1.67-1.58 (m, 1H), 1.55-1.35 (m, 2H).

Example 194 (S)-tert-Butyl 3-((4-(2-((5-(1,1-dioxidoisothiazolidin-2-yl)-2-methylnaphthalen-1-yl)oxy)pyridin-3-yl)pyrimidin-2-yl)pyrimidine-1-carboxylate 194

Step 1: (S)-tert-Butyl 3-((4-(2-((5-iodo-2-methylnaphthalen-1-yl)oxy)pyridin-3-yl)pyrimidin-2-yl)amino)piperidine-1-carboxylate

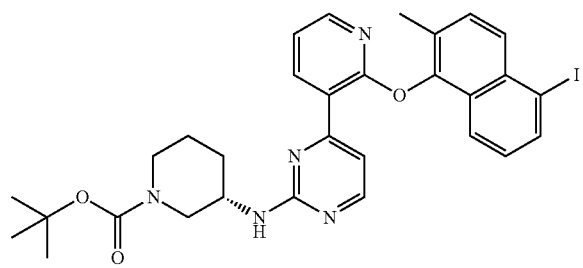 [SMILES: Cc1ccc2c(I)cccc2c1Oc1ncccc1-c1ccnc(N[C@H]2CCCN(C(=O)OC(C)(C)C)C2)n1]

To a solution of tert-butyl (3S)-3-[[4-[2-[(5-amino-2-methyl-1-naphthyl)oxy]-3-pyridyl]pyrimidin-2-yl]amino]piperidine-1-carboxylate (4 g, 7.6 mmol) in acetonitrile (200 mL) was added 4-methylbenzenesulfonic acid hydrate (4.3 g, 22.8 mmol) and the mixture was cooled to 0° C. Then a solution of potassium iodide (3.2 g, 19 mmol) and sodium nitrite (1.05 g, 15.2 mmol) in H$_2$O (60 mL) was added followed by stirring at 20° C. for 2 h. To the reaction mixture was then added H$_2$O (150 mL), sodium bicarbonate (1 M; until pH=9-10) and sodium thiosulfate (2 M, 120 mL). The precipitated was filtered off and the filtrate was extracted with ethyl acetate (30 mL). The organic extract was dried over anhydrous sodium sulfate and purified by silica gel chromatography (50% ethyl acetate in petroleum ether, Rf=0.6) to yield 1.5 g (31% yield) of the title compound as a white solid; LCMS (ESI) $[M+H]^+=638.0$.

Step 2: (S)-tert-Butyl 3-((4-(2-((5-(1,1-dioxidoisothiazolidin-2-yl)-2-methylnaphthalen-1-yl)oxy)pyridin-3-yl)pyrimidin-2-yl)amino)piperidine-1-carboxylate

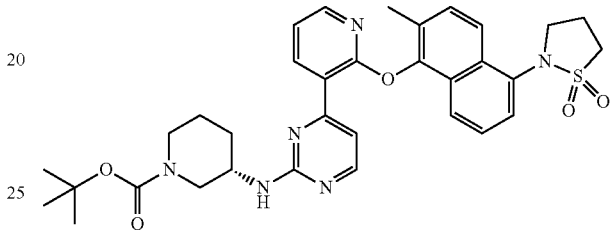

To a solution of tert-butyl (3S)-3-[[4-[2-[(5-iodo-2-methyl-1-naphthyl)oxy]-3-pyridyl]pyrimidin-2-yl]amino]piperidine-1-carboxylate (110 mg, 0.17 mmol) in CH$_3$CN (2 mL) was added 1,3-propanesultam (209.1 mg, 1.73 mmol), copper iodide (1.6 mg, 0.01 mmol), N,N'-dimethyl-1,2-ethanediamine (7.6 mg, 0.09 mmol) and potassium carbonate (47.8 mg, 0.34 mmol). The mixture was purged with N$_2$ and stirred at 80° C. for 88 h. After cooling down, the mixture was filtered, concentrated, dissolved in ethyl acetate (60 mL) and washed with H$_2$O (50 mL×2). The organic phase was dried over anhydrous sodium sulfate and concentrated and the residue was purified by Prep-TLC (50% ethyl acetate in petroleum ether, Rf=0.1) to yield 55 mg (51%) of the title compound as a brown oil. LCMS (ESI) $[M+H]^+=631.0$.

Step 3: (S)-2-(6-Methyl-5-((3-(2-(piperidin-3-ylamino)pyrimidin-4-yl)pyridin-2-yl)oxy)naphthalen-1-yl)isothiazolidine 1,1-dioxide

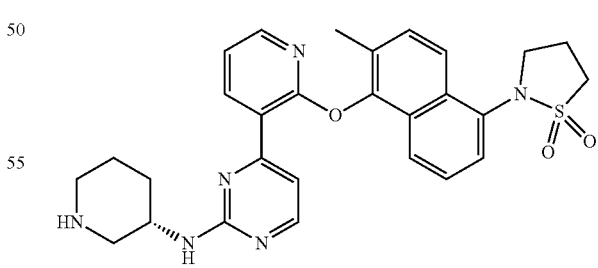

The General Procedure B was followed, using tert-butyl (3S)-3-[[4-[2-[[5-(1,1-dioxo-1,2-thiazolidin-2-yl)-2-methyl-1-naphthyl]oxy]-3-pyridyl]pyrimidin-2-yl]amino]piperidine-1-carboxylate (110 mg, 0.17 mmol), ethyl acetate (0.5 mL) and hydrochloric acid (4 M in ethyl acetate, 0.4 mL, 1.6 mmol). The residue was purified by Prep-HPLC (mobile phase: A: water (0.05% HCl); B: ACN) to yield 20 mg (21% yield) of 194 as a white solid. LCMS (ESI): [M+H]⁺=531.3; ¹H NMR (400 MHz, DMSO-d₆) δ 8.50 (s, 1H), 8.41 (d, J=5.2 Hz, 1H), 8.11 (d, J=8.4 Hz, 1H), 8.06-8.04 (m, 1H), 7.70 (d, J=8.4 Hz, 1H), 7.62-7.59 (m, 1H), 7.56 (d, J=8.8 Hz, 1H), 7.53-7.48 (m, 1H), 7.45 (d, J=5.6 Hz, 1H), 7.28-7.25 (m, 1H), 7.18 (d, J=8.0 Hz, 1H), 4.02-3.87 (m, 1H), 3.81 (t, J=6.4 Hz, 2H), 3.56 (t, J=7.2 Hz, 2H), 3.18-3.08 (m, 1H), 2.88-2.78 (m, 1H), 2.57-2.54 (m, 1H), 2.53-2.52 (m, 1H), 2.48-2.45 (m, 2H), 2.22 (s, 3H), 1.98-1.90 (m, 1H), 1.71-1.63 (m, 1H), 1.57-1.40 (m, 2H).

Example 195 (S)—N-(6-Methyl-5-((3-(2-(piperidin-3-ylamino)pyrimidin-4-yl)pyridin-2-yl)oxy)naphthalen-1-yl)azetidine-1-sulfonamide 195

Step 1: (S)-tert-Butyl 3-((4-(2-((5-(azetidine-1-sulfonamido)-2-methylnaphthalen-1-yl)oxy)pyridin-3-yl)pyrimidin-2-yl)amino)piperidine-1-carboxylate

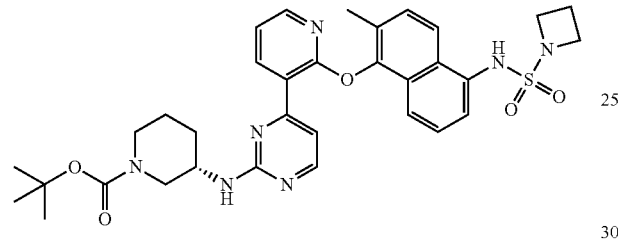

The General Procedure A was followed, using tert-butyl (3S)-3-[[4-[2-[(5-amino-2-methyl-1-naphthyl)oxy]-3-pyridyl]pyrimidin-2-yl]amino]piperidine-1-carboxylate (100 mg, 0.19 mmol), pyridine (2 mL) and azetidine-1-sulfonyl chloride (38 mg, 0.25 mmol). The residue was purified by Prep-TLC (normal phase, petroleum ether/ethyl acetate=2/1) to yield 60 mg (49% yield) of the title compound as a brown oil. LCMS (ESI) [M+H]⁺=646.1.

Step 2: (S)—N-(6-Methyl-5-((3-(2-(piperidin-3-ylamino)pyrimidin-4-yl)pyridin-2-yl)oxy)naphthalen-1-yl)azetidine-1-sulfonamide

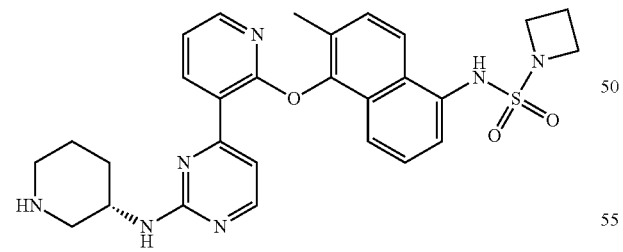

The General Procedure B was followed, using tert-butyl (3S)-3-[[4-[2-[[5-(azetidin-1-ylsulfonylamino)-2-methyl-1-naphthyl]oxy]-3-pyridyl]pyrimidin-2-yl]amino]piperidine-1-carboxylate (40 mg, 0.06 mmol), dichloromethane (1 mL) and 2,2,2-trifluoroacetic acid (0.1 mL, 1.34 mmol). The residue was purified by Prep-HPLC (mobile phase: A: water (0.05% NH₄OH) B: ACN) to yield 16 mg (46% yield) of 195 as a yellow solid. LCMS (ESI): [M+H]⁺=546.2; ¹H NMR (400 MHz, DMSO-d₆) δ 8.50 (s, 1H), 8.43-8.39 (m, 1H), 8.15 (m, 1H), 8.05-8.00 (m, 1H), 7.48-7.43 (m, 2H), 7.37-7.28 (m, 2H), 7.27-7.22 (m, 1H), 7.21-7.17 (m, 1H), 3.97-3.91 (m, 1H), 3.80-3.69 (m, 4H), 3.17 (s, 2H), 2.89-2.87 (m, 1H), 2.56-2.55 (m, 1H), 2.44-2.40 (m, 1H), 2.19 (s, 3H), 2.15-2.02 (m, 2H), 1.96-1.90 (m, 1H), 1.70-1.65 (m, 1H), 1.54-1.45 (m, 2H).

Example 196 N-(6-Methyl-5-((3-(2-(((3S,6S)-6-methylpiperidin-3-yl)amino)pyrimidin-4-yl)pyridin-2-yl)oxy)naphthalen-1-yl)propane-1-sulfonamide 196

Step 1: Benzyl 5-((tert-butoxycarbonyl)amino)-2-methylpiperidine-1-carboxylate

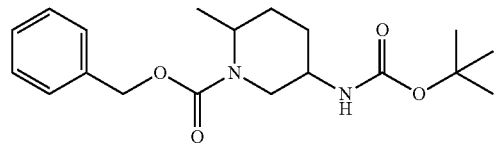 [SMILES: CC1CCC(NC(=O)OC(C)(C)C)CN1C(=O)OCc1ccccc1]

To a 100 mL 3-necked round-bottom flask was placed benzyl chloroformate (0.8 mL, 5.6 mmol), sodium bicarbonate (392 mg, 4.67 mmol), tert-butyl N-(6-methyl-3-piperidyl)carbamate (1.0 g, 4.67 mmol) and tetrahydrofuran (5 mL). The resulting solution was stirred at rt for 4 h. The reaction mixture was then cooled to room temperature and concentrated in vacuo. The residue was purified chromatography on silica (solvent gradient: 0-20% ethyl acetate in petroleum ether) to yield 1.1 g (68% yield) of the title compound as a colorless oil. ¹H-NMR: (400 MHz, DMSO-d₆) δ 7.36-7.33 (m, 4H), 6.86 (d, J=7.2 Hz, 1H), 5.07 (s, 2H), 4.29 (s, 1H), 3.93 (d, J=13.2 Hz, 1H), 3.20 (s, 1H), 2.57 (s, 1H), 1.63-1.49 (m, 4H), 1.38 (s, 9H), 1.07 (d, J=7.2 Hz, 3H)

Step 2: Benzyl 5-amino-2-methylpiperidine-1-carboxylate

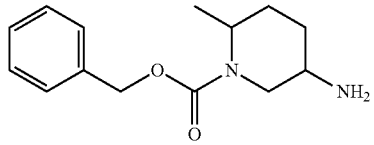 [SMILES: CC1CCC(N)CN1C(=O)OCc1ccccc1]

The General Procedure B was followed, using benzyl 5-((tert-butoxycarbonyl)amino)-2-methylpiperidine-1-carboxylate (1.0 g, 2.87 mmol), dichloromethane (5 mL) and hydrochloric acid (4 M in dioxane, 20 mL, 80 mmol). The organic phase was dried over anhydrous sodium sulfate, concentrated to yield 610 mg of the title crude product as a white solid.

Step 3: Benzyl 2-methyl-5-((4-(2-((2-methyl-5-(propylsulfonamido)naphthalen-1-yl)oxy)pyridin-3-yl)pyrimidin-2-yl)amino)piperidine-1-carboxylate

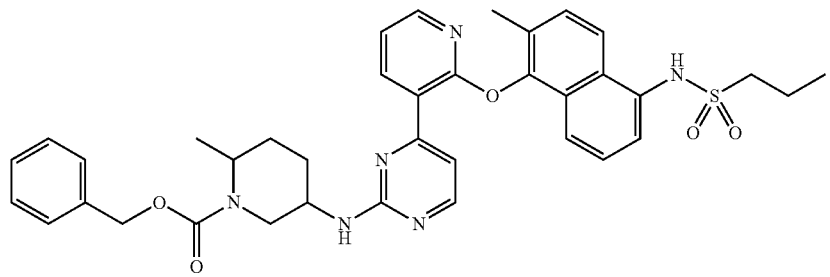 [SMILES: CCCS(=O)(=O)Nc1cccc2c(Oc3ncccc3-c3ccnc(NC4CCC(C)N(C(=O)OCc5ccccc5)C4)n3)c(C)ccc12]

To a 100 mL 3-necked round-bottom flask was placed N-[6-methyl-5-[[3-(2-methylsulfinylpyrimidin-4-yl)-2-pyridyl]oxy]-1-naphthyl]propane-1-sulfonamide (0.8 g, 1.61 mmol), N,N-diisopropylethylamine (0.84 mL, 4.83 mmol), benzyl 5-amino-2-methyl-piperidine-1-carboxylate (400.0 mg, 1.61 mmol) and 1,4-dioxane (10 mL). The resulting solution was stirred at 130° C. for 36 h. The solution was concentrated and purified by flash chromatography on silica gel eluting with 0-10% methanol/dichloromethane to yield 0.7 g (61% yield) of the title compound as a brown solid. LCMS (ESI) [M+H]$^+$=681.1.

Step 4: N-(6-Methyl-5-((3-(2-((6-methylpiperidin-3-yl)amino)pyrimidin-4-yl)pyridin-2-yl)oxy)naphthalen-1-yl)propane-1-sulfonamide

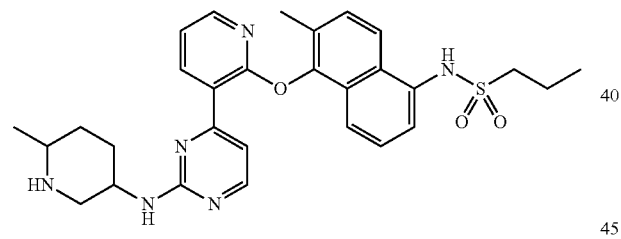

A solution of benzyl 2-methyl-5-[[4-[2-[[2-methyl-5-(propylsulfonylamino)-1-naphthyl]oxy]-3-pyridyl]pyrimidin-2-yl]amino]piperidine-1-carboxylate (600 mg, 0.88 mmol), 10% wet palladium (47 mg, 0.040 mmol) on carbon in methanol (20 mL) at 30° C. was exposed to a hydrogen atmosphere (15 Psi). The reaction was stirred at 30° C. for 14 h. Then the mixture was filtered and concentrated and the residue was purified by Prep-HPLC (mobile phase: A: water (0.05% NH$_4$OH) B: ACN) to give Peak 1: cis isomer mixture, N-[6-Methyl-5-[[3-[2-[(6-methyl-3-piperidyl)amino]pyrimidin-4-yl]-2-pyridyl]oxy]-1-naphthyl]propane-1-sulfonamide (80 mg, 17% yield) (peak 1 on HPLC). LCMS (ESI) [M+H]$^+$=547.1; $^1$H NMR (400 MHz, DMSO-d$_6$) δ 8.50 (s, 1H), 8.40 (d, J=4.8 Hz, 1H), 8.14 (d, J=8.8 Hz, 1H), 8.05-8.00 (m, 1H), 7.50 (d, J=8.8 Hz, 2H), 7.46-7.35 (m, 3H), 7.29-7.23 (m, 1H), 7.16 (d, J=7.2 Hz, 1H), 3.87 (s, 1H), 3.24 (s, 1H), 3.11-3.04 (m, 2H), 2.56-2.54 (m, 1H), 2.44 (s, 1H), 2.20 (s, 3H), 1.97 (d, J=10.8 Hz, 1H), 1.79-1.72 (m, 2H), 1.68 (d, J=12.4 Hz, 1H), 1.47-1.41 (m, 1H), 1.21-1.14 (m, 1H), 1.02 (d, J=6.4 Hz, 3H), 0.96 (t, J=7.6 Hz, 3H).

Peak 2: trans isomer mixture, N-[6-methyl-5-[[3-[2-[(6-methyl-3-piperidyl)amino]pyrimidin-4-yl]-2-pyridyl]oxy]-1-naphthyl]propane-1-sulfonamide (40 mg, 8% yield) (peak 2 on HPLC), obtained as a white solid. LCMS (ESI) [M+H]⁺=547.1; ¹H NMR (400 MHz, DMSO-d₆) δ 8.54-8.47 (m, 1H), 8.43 (d, J=5.2 Hz, 1H), 8.14 (d, J=8.8 Hz, 1H), 8.03 (d, J=3.2 Hz, 1H), 7.50 (d, J=8.6 Hz, 1H), 7.47 (d, J=5.0 Hz, 1H), 7.43-7.34 (m, 2H), 7.26-7.20 (m, 1H), 6.98 (d, J=7.6 Hz, 1H), 4.04 (s, 1H), 3.11-3.05 (m, 2H), 3.01 (d, J=12.4 Hz, 1H), 2.85 (d, J=10.8 Hz, 1H), 2.67 (s, 1H), 2.20 (s, 3H), 1.92 (s, 1H), 1.78-1.68 (m, 2H), 1.63 (t, J=12.4 Hz, 1H), 1.50-1.42 (m, 1H), 1.37 (d, J=12.8 Hz, 1H), 1.04 (d, J=6.4 Hz, 3H), 0.96 (t, J=7.2 Hz, 3H).

Step 5: N-(6-methyl-5-((3-(2-(((3S,6S)-6-methylpiperidin-3-yl)amino)pyrimidin-4-yl)pyridin-2-yl)oxy)naphthalen-1-yl)propane-1-sulfonamide

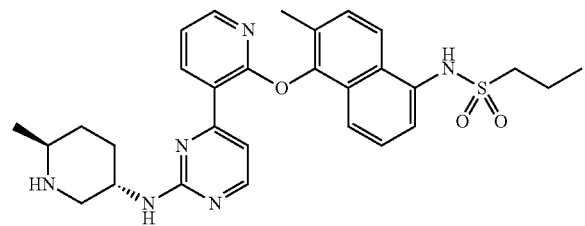 [SMILES: CCCS(=O)(=O)Nc1cccc2c(Oc3ncccc3-c3ccnc(N[C@H]4CC[C@H](C)NC4)n3)c(C)ccc12]

N-[6-methyl-5-[[3-[2-[(6-methyl-3-piperidyl)amino]pyrimidin-4-yl]-2-pyridyl]oxy]-1-naphthyl]propane-1-sulfonamide (40 mg, 0.070 mmol) was purified by SFC (AD (250 mm×30 mm, 5 μm); Base-EtOH: 40%; (flow rate 60 mL/min) to give 196 (10 mg, 24.5% yield) (second peak on SFC, Rt=6.64 min) as a white solid. The absolute stereochemistry inferred based on the activity in the XBP1 reporter potency. LCMS (ESI) [M+H]⁺=547.1; ¹H NMR (400 MHz, DMSO-d₆) δ 8.54-8.47 (m, 1H), 8.43 (d, J=5.2 Hz, 1H), 8.14 (d, J=8.8 Hz, 1H), 8.03 (d, J=3.2 Hz, 1H), 7.50 (d, J=8.6 Hz, 1H), 7.47 (d, J=5.0 Hz, 1H), 7.43-7.34 (m, 2H), 7.26-7.20 (m, 1H), 6.98 (d, J=7.6 Hz, 1H), 4.04 (s, 1H), 3.11-3.05 (m, 2H), 3.01 (d, J=12.4 Hz, 1H), 2.85 (d, J=10.8 Hz, 1H), 2.67 (s, 1H), 2.20 (s, 3H), 1.92 (s, 1H), 1.78-1.68 (m, 2H), 1.63 (t, J=12.4 Hz, 1H), 1.50-1.42 (m, 1H), 1.37 (d, J=12.8 Hz, 1H), 1.04 (d, J=6.4 Hz, 3H), 0.96 (t, J=7.2 Hz, 3H).

Example 197 (S)-4-(2-((5-(Butylamino)-2-methylnaphthalen-1-yl)oxy)pyridin-3-yl)-N-(piperidin-3-yl)pyrimidin-2-amine 197

Step 1: tert-Butyl (S)-3-((4-(2-((5-(butylamino)-2-methylnaphthalen-1-yl)oxy)pyridin-3-yl)pyrimidin-2-yl)amino)piperidine-1-carboxylate

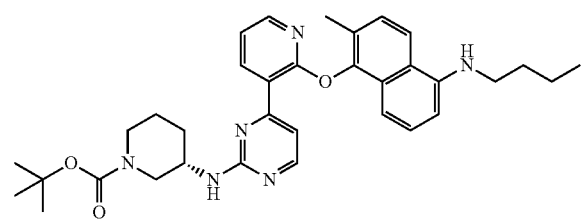 [SMILES: CCCCNc1cccc2c(Oc3ncccc3-c3ccnc(N[C@H]4CCCN(C(=O)OC(C)(C)C)C4)n3)c(C)ccc12]

The General Procedure E was followed, using tert-butyl (3S)-3-[[4-[2-[(5-amino-2-methyl-1-naphthyl)oxy]-3-pyridyl]pyrimidin-2-yl]amino]piperidine-1-carboxylate (100 mg, 0.19 mmol) and DIPEA (0.083 mL, 0.48 mmol) in DMF (1 mL), together with, 1-bromobutane (0.031 mL, 0.29 mmol). The reaction mixture was purified by silica gel chromatography (12 g column), eluting with 0-5% MeOH/DCM to afford 67 mg (60% yield) of the title compound as a brown solid. LCMS (ESI) [M+H]⁺=583.

Step 2: (S)-4-(2-((5-(Butylamino)-2-methylnaphthalen-1-yl)oxy)pyridin-3-yl)-N-(piperidin-3-yl)pyrimidin-2-amine

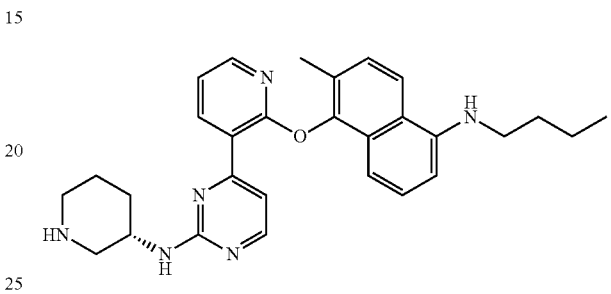

The General Procedure B was followed, using tert-butyl (S)-3-((4-(2-((5-(butylamino)-2-methylnaphthalen-1-yl)oxy)pyridin-3-yl)pyrimidin-2-yl)amino)piperidine-1-carboxylate (67 mg, 0.11 mmol). The crude product was purified via reverse-phase HPLC and lyophilized to yield 9.3 mg (17% yield) of 197 as a light brown solid. LCMS (ESI) [M+H]⁺=524; ¹H NMR (400 MHz, DMSO-d₆) δ 8.49 (s, 1H), 8.40 (d, J=5.1 Hz, 1H), 8.03-7.99 (m, 2H), 7.45 (d, J=5.2 Hz, 1H), 7.32 (d, J=8.7 Hz, 1H), 7.23 (dd, J=7.6, 4.8 Hz, 1H), 7.16 (t, J=8.2 Hz, 2H), 6.82 (d, J=8.3 Hz, 1H), 6.42 (dd, J=7.7, 0.9 Hz, 1H), 6.15 (t, J=5.3 Hz, 1H), 3.93 (s, 1H), 3.23-3.18 (m, 1H), 3.14 (d, J=13.8 Hz, 3H), 2.84 (d, J=12.3 Hz, 1H), 2.18 (s, 3H), 1.98-1.89 (m, 1H), 1.72-1.63 (m, 3H), 1.54-1.38 (m, 4H), 0.95 (t, J=7.4 Hz, 3H).

Example 198 (S)-3,3-Dimethyl-N-(6-methyl-5-((3-(2-(piperidin-3-ylamino)pyrimidin-4-yl)pyridin-2-yl)oxy)naphthalen-1-yl) butanamide 198

Step 1: tert-Butyl (S)-3-((4-(2-((5-(3,3-dimethylbutanamido)-2-methylnaphthalen-1-yl)oxy)pyridin-3-yl)pyrimidin-2-yl)amino)piperidine-1-carboxylate

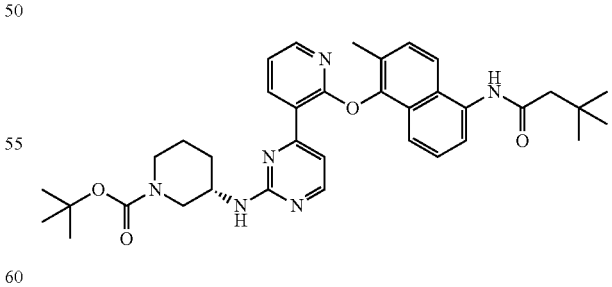

The General Procedure C was followed, using tert-butyl (S)-3-((4-(2-((5-amino-2-methylnaphthalen-1-yl)oxy)pyridin-3-yl)pyrimidin-2-yl)amino)piperidine-1-carboxylate from Example 101 (90 mg, 0.17 mmol), 3,3-dimethylbutanoic acid (30 mg, 0.26 mmol), DIPEA (0.089 mL, 0.51 mmol), HATU (97 mg, 0.26 mmol) and DCM (1.7 mL). The crude was directly used in the next step.

Step 2: (S)-3,3-Dimethyl-N-(6-methyl-5-((3-(2-(piperidin-3-ylamino)pyrimidin-4-yl)pyridin-2-yl)oxy)naphthalen-1-yl)butanamide

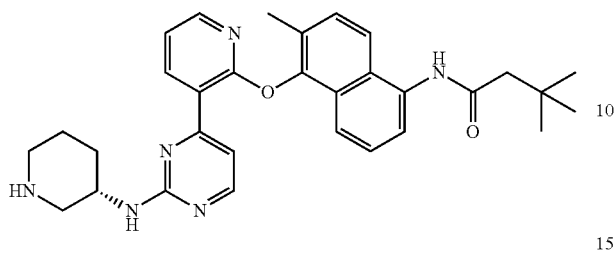

The General Procedure B was followed, using crude tert-butyl (S)-3-((4-(2-((5-(3,3-dimethylbutanamido)-2-methylnaphthalen-1-yl)oxy)pyridin-3-yl)pyrimidin-2-yl)amino)piperidine-1-carboxylate, DCM (1.7 mL) and hydrochloric acid (4 M in dioxane, 0.430 mL, 1.71 mmol). The residue was purified via reverse-phase HPLC and lyophilized to yield 27 mg of 198. LCMS (ESI): $[M+H]^+=525.2$; $^1$H NMR (400 MHz, DMSO-$d_6$) δ 9.83 (s, 1H), 8.54 (s, 1H), 8.47 (d, J=5.2 Hz, 1H), 8.04 (dd, J=4.8, 2.0 Hz, 1H), 7.95-7.91 (m, 1H), 7.62 (d, J=7.2 Hz, 1H), 7.58-7.36 (m, 5H), 7.27 (dd, J=7.6, 4.8 Hz, 1H), 4.18 (s, 1H), 3.44-3.36 (m, 2H), 3.20-3.12 (m, 1H), 2.86-2.74 (m, 2H), 2.38 (s, 2H), 2.22 (s, 3H), 2.03-1.97 (m, 1H), 1.93-1.84 (m, 1H), 1.73-1.56 (m, 2H), 1.10 (s, 9H).

Example 199 (S)-2-(4-Fluorophenyl)-N-(6-methyl-5-((3-(2-(piperidin-3-ylamino)pyrimidin-4-yl)pyridin-2-yl)oxy)naphthalen-1-yl)acetamide 199

Step 1: tert-Butyl (S)-3-((4-(2-((5-(2-(4-fluorophenyl)acetamido)-2-methylnaphthalen-1-yl)oxy)pyridin-3-yl)pyrimidin-2-yl)amino)piperidine-1-carboxylate

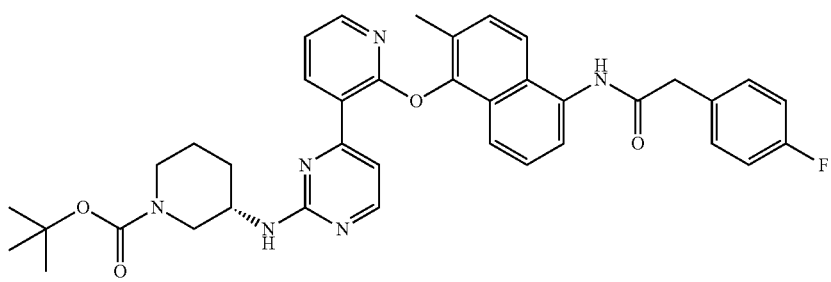 [SMILES: Cc1ccc2c(NC(=O)Cc3ccc(F)cc3)cccc2c1Oc1ncccc1-c1ccnc(N[C@H]2CCCN(C(=O)OC(C)(C)C)C2)n1]

The General Procedure C was followed, using tert-butyl (S)-3-((4-(2-((5-amino-2-methylnaphthalen-1-yl)oxy)pyridin-3-yl)pyrimidin-2-yl)amino)piperidine-1-carboxylate from Example 101 (90 mg, 0.17 mmol), 2-(4-fluorophenyl)acetic acid (39.5 mg), DIPEA (0.302 mL, 1.72 mmol), HATU (97 mg, 0.26 mmol) and DCM (1.7 mL). The crude was directly used in the next step.

Step 2: (S)-2-(4-Fluorophenyl)-N-(6-methyl-5-((3-(2-(piperidin-3-ylamino)pyrimidin-4-yl)pyridin-2-yl)oxy)naphthalen-1-yl)acetamide

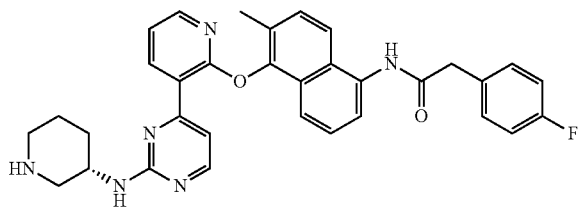 [SMILES: Cc1ccc2c(NC(=O)Cc3ccc(F)cc3)cccc2c1Oc1ncccc1-c1ccnc(N[C@H]2CCCNC2)n1]

The General Procedure B was followed, using crude (S)-2-(4-fluorophenyl)-N-(6-methyl-5-((3-(2-(piperidin-3-ylamino)pyrimidin-4-yl)pyridin-2-yl)oxy)naphthalen-1-yl)acetamide, DCM (1.7 mL) and hydrochloric acid (4 M in dioxane, 0.430 mL, 1.71 mmol). The residue was purified via reverse-phase HPLC and lyophilized to yield 7 mg of 199. LCMS (ESI): $[M+H]^+=563.2$; $^1$H NMR (400 MHz, DMSO-$d_6$) δ 10.20 (s, 1H), 8.49 (d, J=7.5 Hz, 1H), 8.40 (d, J=5.1 Hz, 1H), 8.02 (dd, J=4.8, 2.0 Hz, 1H), 7.91 (d, J=8.6 Hz, 1H), 7.62 (d, J=7.3 Hz, 1H), 7.57-7.43 (m, 2H), 7.48-7.37 (m, 3H), 7.31-7.21 (m, 3H), 7.14-7.07 (m, 2H), 3.87 (s, 3H), 3.13-3.05 (m, 1H), 2.82-2.74 (m, 1H), 2.46-2.38 (m, 3H), 2.22 (s, 3H), 1.96-1.88 (m, 1H), 1.67-1.60 (m, 1H), 1.52-1.36 (m, 2H).

Example 200 3-Methyl-1-((6-methyl-5-((3-(2-((S)-piperidin-3-ylamino)pyrimidin-4-yl)pyridin-2-yl)oxy)naphthalen-1-yl)amino) butan-2-ol 200

Step 1: (3S)-tert-Butyl 3-((4-(2-((5-((2-hydroxy-3-methylbutyl)amino)-2-methylnaphthalen-1-yl)oxy)pyridin-3-yl)pyrimidin-2-yl)amino)piperidine-1-carboxylate

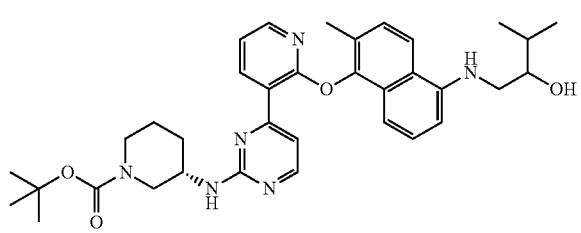 [SMILES: Cc1ccc2c(NCC(O)C(C)C)cccc2c1Oc1ncccc1-c1ccnc(N[C@H]2CCCN(C(=O)OC(C)(C)C)C2)n1]

Prepared using (S)-tert-butyl 3-((4-(2-((5-amino-2-methylnaphthalen-1-yl)oxy)pyridin-3-yl)pyrimidin-2-yl)amino)piperidine-1-carboxylate (200 mg, 0.380 mmol), 2-isopropyloxirane (0.052 mL, 0.492 mmol), in acetic acid (0.5 mL), at rt. After 16 h, the mixture was placed in a 75° C. bath overnight. After a further 16 h, acetic acid was evaporated in vacuo and the residue purified directly by C18 reverse phase flash chromatography (0-65% MeCN/10 mM aqueous ammonium formate, pH=3.8). The product fractions were combined and lyophilized to provide 84 mg (36% yield) of the title compound. LCMS (ESI) $[M+H]^+=613.4$, rt=2.02 min.

Step 2: 3-Methyl-1-((6-methyl-5-((3-(2-((S)-piperidin-3-ylamino)pyrimidin-4-yl)pyridin-2-yl)oxy)naphthalen-1-yl)amino)butan-2-ol

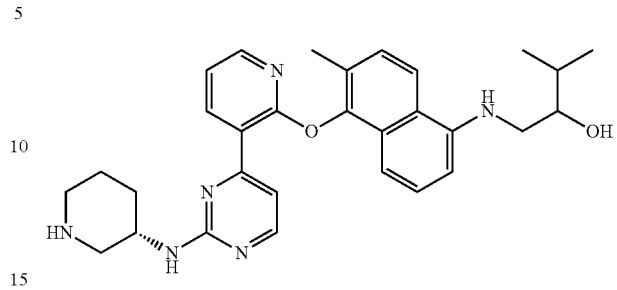

Prepared using (3S)-tert-butyl 3-((4-(2-((5-((2-hydroxy-3-methylbutyl)amino)-2-methylnaphthalen-1-yl)oxy)pyridin-3-yl)pyrimidin-2-yl)amino)piperidine-1-carboxylate (20 mg, 0.033 mmol), 1,4-dioxane (1 mL) and hydrochloric acid (4 M in dioxane, 0.5 mL, 2 mmol). After 4 h, the mixture was concentrated in vacuo. The residue was triturated in MeCN and the resulting solids collected by filtration, dissolved in MeCN and water and lyophilized to provide 17 mg (95% yield) of 200 as a mixture of the two isomers of the aminoalcohol. LCMS (ESI) $[M+H]^+=513.2$, r.t.=1.43 min; $^1$H NMR (400 MHz, d4-MeOH) δ 8.83-8.73 (m, 1H), 8.48 (d, J=5.6 Hz, 1H), 8.07-7.99 (m, 2H), 7.86 (s, 1H), 7.79 (d, J=8.0 Hz, 1H), 7.69 (d, J=8.8 Hz, 1H), 7.57-7.46 (m, 2H), 7.29 (dd, J=7.6, 4.9 Hz, 1H), 4.48 (s, 1H), 3.78-3.57 (m, 3H), 3.48-3.34 (m, 2H), 3.17-3.00 (m, 2H), 2.31 (s, 3H), 2.28-2.18 (m, 1H), 2.17-2.06 (m, 1H), 2.01-1.70 (m, 3H), 0.99 (dd, J=17.5, 6.8 Hz, 6H).

Example 201 (R)-4-((6-Methyl-5-((3-(2-(((S)-piperidin-3-yl)amino)pyrimidin-4-yl)pyridin-2-yl)oxy)naphthalen-1-yl)amino)butan-2-ol 201

Step 1: (S)-tert-Butyl 3-((4-(2-((2-methyl-5-((3-oxobutyl)amino)naphthalen-1-yl)oxy)pyridin-3-yl)pyrimidin-2-yl)amino)piperidine-1-carboxylate

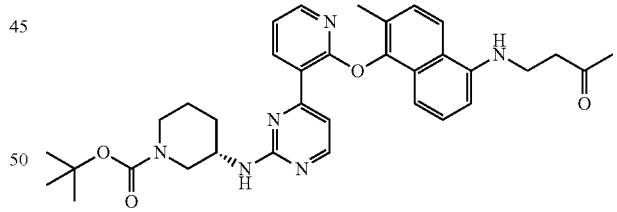

Following the procedures of Example 390, to a suspension of (S)-tert-butyl 3-((4-(2-((5-amino-2-methylnaphthalen-1-yl)oxy)pyridin-3-yl)pyrimidin-2-yl)amino)piperidine-1-carboxylate (140 mg, 0.266 mmol) in methanol (1.3 mL), was added but-3-en-2-one (65 µL, 0.80 mmol) followed by triethylamine (111 µL, 0.80 mmol) and the mixture stirred at rt. After 18 h, a further portion of but-3-en-2-one (32 µL, 0.40 mmol) was added and after a further 16 h at rt, the reaction mixture was diluted with $H_2O$ and extracted twice with DCM, dried ($Na_2SO_4$), filtered and concentrated in vacuo. The crude was purified by flash chromatography through Si (silica) gel (0-60% EtOAc/DCM) to provide 156 mg (98% yield) of the title compound. LCMS (ESI) $[M+H]^+=597.6$, rt=1.96 min.

Step 2: (3S)-tert-Butyl 3-((4-(2-((5-((3-hydroxybutyl)amino)-2-methylnaphthalen-1-yl)oxy)pyridin-3-yl)pyrimidin-2-yl)amino)piperidine-1-carboxylate

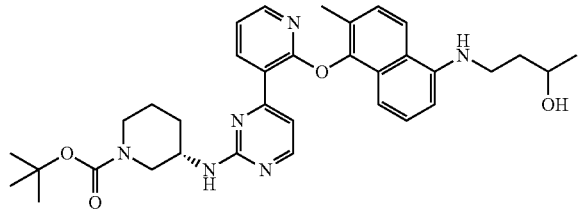 [SMILES: Cc1ccc2c(NCCC(C)O)cccc2c1Oc1ncccc1-c1ccnc(N[C@H]2CCCN(C(=O)OC(C)(C)C)C2)n1]

A solution of (S)-tert-butyl 3-((4-(2-((2-methyl-5-((3-oxobutyl)amino)naphthalen-1-yl)oxy)pyridin-3-yl)pyrimidin-2-yl)amino)piperidine-1-carboxylate (156 mg, 0.261 mmol) in THF (0.45 mL) and methanol (0.45 mL) was cooled 0° C. and to this was then added sodium borohydride (34 mg, 0.91 mmol). The mixture was stirred 30 min at 0° C., then diluted with H$_2$O and extracted three times with DCM, dried (Na$_2$SO$_4$), filtered and concentrated in vacuo. The crude was purified by C18 reverse phase flash chromatography (55-100% MeCN/10 mM aqueous ammonium formate, pH=3.8). The appropriate fractions were combined, concentrated to remove some MeCN, and lyophilized to provide 89 mg (57% yield) of the title compound. LCMS (ESI) [M+H]$^+$=599.7, rt=1.89 min.

Step 3: tert-Butyl (S)-3-((4-(2-((5-(((R)-3-hydroxybutyl)amino)-2-methylnaphthalen-1-yl)oxy)pyridin-3-yl)pyrimidin-2-yl)amino)piperidine-1-carboxylate (Isomer-1) and tert-butyl (S)-3-((4-(2-((5-(((S)-3-hydroxybutyl)amino)-2-methylnaphthalen-1-yl)oxy)pyridin-3-yl)pyrimidin-2-yl)amino)piperidine-1-carboxylate (Isomer-2)

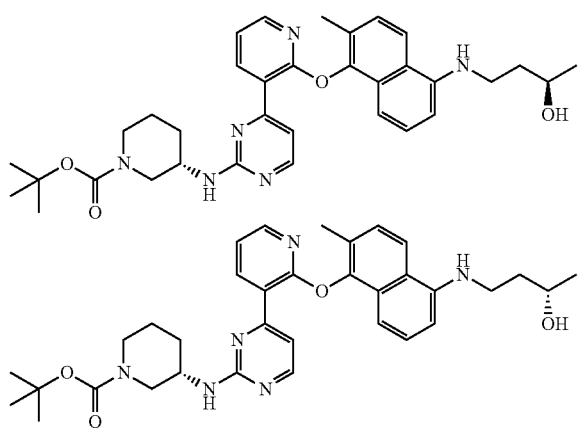

The stereoisomers from Step 2 (89 mg, 0.15 mmol), were subjected to chiral normal phase semi-prep purification (Conditions: Chiralpak IB, 5 uM, 20×250 mm, 6:6:88 MeOH:EtOH:Hexanes, 2-4 mg/inj.) to provide two stereoisomers possessing a stereocenter at the alcohol position: (isomer-1), 25 mg (16% yield), ee=98.4%, (ESI) [M+H]$^+$=599.7, rt=1.89 min; and (isomer-2), 27 mg (17% yield), ee=97.7%, (ESI) [M+H]$^+$=599.7, rt=1.89 min.

Step 4: (R)-4-((6-Methyl-5-((3-(2-(((S)-piperidin-3-yl)amino)pyrimidin-4-yl)pyridin-2-yl)oxy)naphthalen-1-yl)amino)butan-2-ol (Isomer-1)

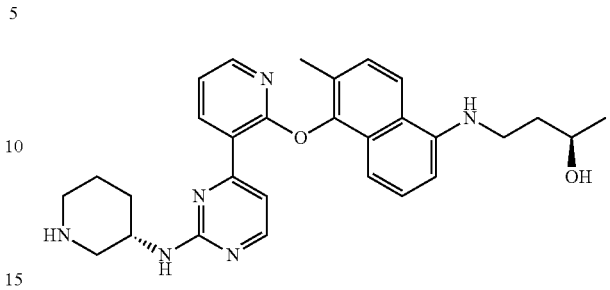

Prepared according to General Procedure B using tert-butyl (S)-3-((4-(2-((5-(((R)-3-hydroxybutyl)amino)-2-methylnaphthalen-1-yl)oxy)pyridin-3-yl)pyrimidin-2-yl)amino)piperidine-1-carboxylate (isomer-1) (25 mg, 0.042 mmol), 1,4-dioxane (0.5 mL) and hydrochloric acid (4 M in dioxane, 0.5 mL, 2 mmol). After 45 min, the reaction was diluted with Et$_2$O, and the resulting solids collected by filtration, dissolved in a mixture of MeCN and H$_2$O, and lyophilized to provide 15 mg (68% yield) of 201. The stereochemistry was tentatively and arbitrarily assigned. LCMS (ESI) [M+H]$^+$=499.2, rt=1.30 min; $^1$H NMR (400 MHz, d6-dmso) δ 9.02 (br.s, 2H), 8.69 (s, 1H), 8.48 (d, J=5.3 Hz, 1H), 8.19-7.95 (m, 2H), 7.61 (s, 2H), 7.41 (d, J=8.8 Hz, 1H), 7.36-7.16 (m, 2H), 7.00 (s, 1H), 6.70 (s, 1H), 3.87-3.69 (m, 1H), 3.51-3.35 (m, 1H), 3.35-3.25 (m, 2H), 3.20 (d, J=12.1 Hz, 1H), 2.96-2.75 (m, 2H), 2.19 (s, 3H), 2.10-1.97 (m, 1H), 1.97-1.86 (m, 1H), 1.86-1.50 (m, 4H), 1.13 (d, J=6.2 Hz, 3H).

Example 202 (S)-4-((6-Methyl-5-((3-(2-(((S)-piperidin-3-yl)amino)pyrimidin-4-yl)pyridin-2-yl)oxy)naphthalen-1-yl)amino)butan-2-ol 202

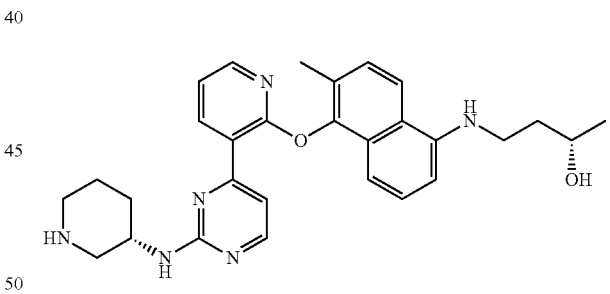

Prepared according to Example 201 and General Procedure B using tert-butyl (S)-3-((4-(2-((5-(((S)-3-hydroxybutyl)amino)-2-methylnaphthalen-1-yl)oxy)pyridin-3-yl)pyrimidin-2-yl)amino)piperidine-1-carboxylate (isomer-2) (27 mg, 0.045 mmol), 1,4-dioxane (0.5 mL) and hydrochloric acid (4 M in dioxane, 0.5 mL, 2 mmol). After 45 min, the reaction mixture was diluted with Et$_2$O, and the resulting solids collected by filtration, dissolved in a mixture of MeCN and H$_2$O, and lyophilized to provide 16 mg (64% yield) of 202. The stereochemistry was tentatively and arbitrarily assigned. LCMS (ESI) [M+H]$^+$=499.2, rt=1.30 min; $^1$H NMR (400 MHz, d6-dmso) δ 9.01 (br.s, 2H), 8.71 (s, 1H), 8.48 (d, J=5.3 Hz, 1H), 8.13-7.91 (m, 2H), 7.60 (s, 2H), 7.40 (d, J=8.6 Hz, 1H), 7.32-7.14 (m, 2H), 7.00 (s, 1H), 6.69 (s, 1H), 3.96-3.71 (m, 2H), 3.50-3.34 (m, 1H), 3.34-3.24 (m, 2H), 3.20 (d, J=12.3 Hz, 1H), 2.97-2.74 (m, 2H), 2.19 (s, 3H), 2.11-1.96 (m, 1H), 1.96-1.84 (m, 1H), 1.86-1.50 (m, 4H), 1.13 (d, J=6.2 Hz, 3H).

Example 203 (S)-2-methyl-N-(6-methyl-5-((3-(2-(((S)-piperidin-3-yl)amino)pyrimidin-4-yl)pyridin-2-yl)oxy)naphthalen-1-yl) butanamide 203

Step 1: tert-Butyl (3S)-3-((4-(2-((2-methyl-5-(2-methylbutanamido)naphthalen-1-yl)oxy)pyridin-3-yl)pyrimidin-2-yl)amino)piperidine-1-carboxylate

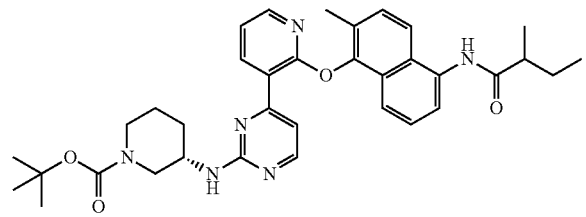 [SMILES: CCC(C)C(=O)Nc1cccc2c(Oc3ncccc3-c3ccnc(N[C@H]4CCCN(C(=O)OC(C)(C)C)C4)n3)c(C)ccc12]

The General Procedure C was followed, using tert-butyl (S)-3-((4-(2-((5-amino-2-methylnaphthalen-1-yl)oxy)pyridin-3-yl)pyrimidin-2-yl)amino)piperidine-1-carboxylate from Example 101 (90 mg, 0.17 mmol), 2-methylbutanoic acid (23 mg, 0.26 mmol), DIPEA (0.089 mL, 0.51 mmol), HATU (91 mg, 0.24 mmol) and DCM (1.7 mL). The crude mixture of diastereomers was directly used in the next step.

Step 2: (S)-2-methyl-N-(6-methyl-5-((3-(2-(((S)-piperidin-3-yl)amino)pyrimidin-4-yl)pyridin-2-yl)oxy)naphthalen-1-yl)butanamide

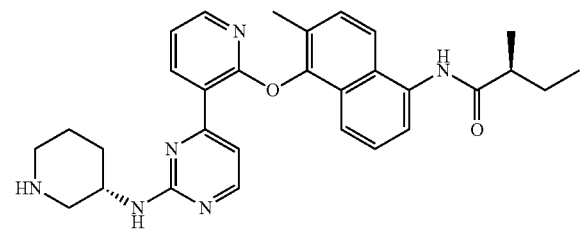 [SMILES: CC[C@H](C)C(=O)Nc1cccc2c(Oc3ncccc3-c3ccnc(N[C@H]4CCCNC4)n3)c(C)ccc12]

The General Procedure B was followed, using crude (S)-2-(4-fluorophenyl)-N-(6-methyl-5-((3-(2-(piperidin-3-ylamino)pyrimidin-4-yl)pyridin-2-yl)oxy)naphthalen-1-yl)acetamide, DCM (1.7 mL) and hydrochloric acid (4 M in dioxane, 0.430 mL, 1.71 mmol). The residue was purified via reverse-phase HPLC to provide a mixture of the two isomers, this mixture was then purified via chiral reverse-phase HPLC and lyophilized to yield 11.7 mg of 203 and 10.1 mg of 204, the two single stereoisomers enantiomeric at the 2 position of the butanamide. The stereochemical assignments of 203 and 204 were randomly assigned and may be determined later.

203: LCMS (ESI): [M+H]$^+$=511.2; $^1$H NMR (400 MHz, DMSO-d$_6$) δ 9.87 (s, 1H), 8.50 (d, J=7.6 Hz, 1H), 8.41 (d, J=5.1 Hz, 1H), 8.02 (dd, J=4.8, 2.0 Hz, 1H), 7.89 (d, J=8.6 Hz, 1H), 7.60-7.40 (m, 3H), 7.46-7.36 (m, 2H), 7.25 (dd, J=7.5, 4.8 Hz, 1H), 7.12 (d, J=8.0 Hz, 1H), 3.89 (s, 1H), 3.13-3.07 (m, 1H), 2.83-2.76 (m, 1H), 2.69-2.60 (m, 1H), 2.46-2.37 (m, 2H), 2.22 (s, 3H), 1.97-1.87 (m, 1H), 1.75-1.61 (m, 2H), 1.58-1.38 (m, 3H), 1.18 (d, J=6.8 Hz, 3H), 0.97 (t, J=7.4 Hz, 3H).

Example 204 (R)-2-methyl-N-(6-methyl-5-((3-(2-(((S)-piperidin-3-yl)amino)pyrimidin-4-yl)pyridin-2-yl)oxy)naphthalen-1-yl)butanamide 204

The procedures of Example 203 were followed to give 204: LCMS (ESI): [M+H]$^+$=511.2; $^1$H NMR (400 MHz, DMSO-d$_6$) δ 9.87 (s, 1H), 8.50 (d, J=7.6 Hz, 1H), 8.41 (d, J=5.1 Hz, 1H), 8.02 (dd, J=4.8, 2.0 Hz, 1H), 7.89 (d, J=8.6 Hz, 1H), 7.60-7.40 (m, 3H), 7.46-7.36 (m, 2H), 7.25 (dd, J=7.5, 4.8 Hz, 1H), 7.12 (d, J=8.0 Hz, 1H), 3.89 (s, 1H), 3.13-3.07 (m, 1H), 2.83-2.76 (m, 1H), 2.69-2.60 (m, 1H), 2.46-2.37 (m, 2H), 2.22 (s, 3H), 1.97-1.87 (m, 1H), 1.75-1.61 (m, 2H), 1.58-1.38 (m, 3H), 1.18 (d, J=6.8 Hz, 3H), 0.97 (t, J=7.4 Hz, 3H).

Example 205 1-(4-Chlorophenyl)-N-(5-((3-(2-(((3S,5R)-5-methoxypiperidin-3-yl)amino)pyrimidin-4-yl)pyridin-2-yl)oxy)-6-methylnaphthalen-1-yl)methanesulfonamide 205

Step 1: Benzyl 3-((4-(2-((5-(((4-chlorophenyl)methylsulfonamido)-2-methylnaphthalen-1-yl)oxy)pyridin-3-yl)pyrimidin-2-yl)amino)-5-methoxypiperidine-1-carboxylate

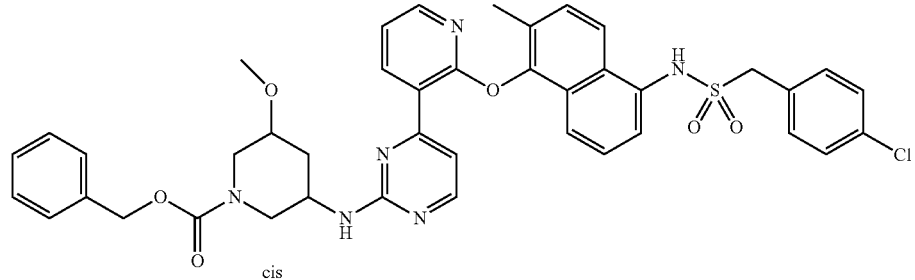 [SMILES: COC1CC(Nc2nccc(-c3cccnc3Oc3c(C)ccc4c(NS(=O)(=O)Cc5ccc(Cl)cc5)cccc34)n2)CN(C(=O)OCc2ccccc2)C1]

cis

To a 100 mL 3-necked round-bottom flask purged and maintained with an inert atmosphere of nitrogen was placed 1-(4-chlorophenyl)-N-[6-methyl-5-[[3-(2-methylsulfinylpyrimidin-4-yl)-2-pyridyl]oxy]-1-naphthyl]methanesulfonamide (500 mg, 0.86 mmol), benzyl 3-amino-5-methoxypiperidine-1-carboxylate (273 mg, 1.04 mmol), 1,4-dioxane (8 mL) and N,N-diisopropylethylamine (0.21 mL, 1.21 mmol). The resulting solution was stirred at 130° C. in an oil bath overnight, cooled to rt and concentrated in vacuo. The residue was purified via flash silica chromatography (solvent gradient: 2% methanol in dichloromethane) to yield 430 mg (64% yield) of the title compound as a yellow solid. LCMS: (ES, m/z): [M+H]⁺=779.1.

Step 2: Benzyl 3-((4-(2-((5-((4-chlorophenyl)methylsulfonamido)-2-methylnaphthalen-1-yl)oxy)pyridin-3-yl)pyrimidin-2-yl)amino)-5-methoxypiperidine-1-carboxylate

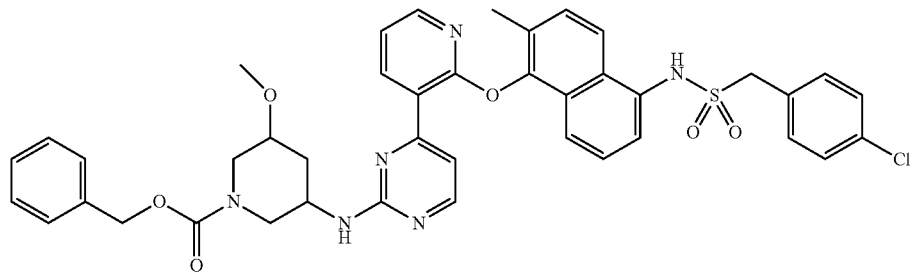 [SMILES: COC1CC(Nc2nccc(-c3cccnc3Oc3c(C)ccc4c(NS(=O)(=O)Cc5ccc(Cl)cc5)cccc34)n2)CN(C(=O)OCc2ccccc2)C1]

Benzyl 3-[[4-[2-[[5-[(4-chlorophenyl)methylsulfonylamino]-2-methyl-1-naphthyl]oxy]-3-pyridyl]pyrimidin-2-yl]amino]-5-methoxy-piperidine-1-carboxylate (360 mg, 0.46 mmol) was purified by SFC (AD (250 mm×30 mm, 10 μm); Base-EtOH: 40%; flow rate (80 ml/min) to give benzyl3-[[4-[2-[[5-[(4-chlorophenyl)methylsulfonylamino]-2-methyl-1-naphthyl]oxy]-3-pyridyl] pyrimidin-2-yl]amino]-5-methoxy-piperidine-1-carboxylate (120 mg, 33% yield) (first peak on SFC) and benzyl 3-[[4-[2-[[5-[(4-chlorophenyl)methylsulfonylamino]-2-methyl-1-naphthyl]oxy]-3-pyridyl]pyrimidin-2-yl]amino]-5-methoxy-piperidine-1-carboxylate (200 mg, 56% yield) (second peak on SFC) as a white solid.

Step 3: 1-(4-Chlorophenyl)-N-(5-((3-(2-(((3S,5R)-5-methoxypiperidin-3-yl)amino)pyrimidin-4-yl)pyridin-2-yl)oxy)-6-methylnaphthalen-1-yl)methanesulfonamide

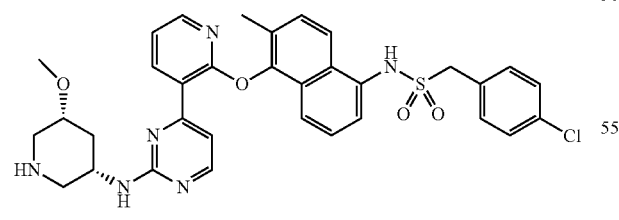

To a 100 mL 3-necked round-bottom flask was placed benzyl 3-[[4-[2-[[5-[(4-chlorophenyl)methylsulfonylamino]-2-methyl-1-naphthyl]oxy]-3-pyridyl]pyrimidin-2-yl]amino]-5-methoxy-piperidine-1-carboxylate (196 mg, 0.25 mmol) (second peak on SFC in step 2), 1-methylimidazole (33 mg, 0.42 mmol), thiourea (97 mg, 1.29 mmol), iodotrimethylane (0.30 mL, 2.1 mmol) and acetonitrile (2 mL). The mixture was stirred at room temperature for 12 h and concentrated in a vacuum. The residue was purified by Prep-HPLC (mobile phase: A: water (0.05% NH₄OH) B: ACN) to yield 42 mg (25% yield) of 205 as a white solid. LCMS (ESI): [M+H]⁺=645.2. ¹H NMR (400 MHz, DMSO-d₆) δ 8.49 (s, 1H), 8.42 (d, J=4.8 Hz, 1H), 8.06-8.01 (m, 2H), 7.51-7.48 (m, 1H), 7.46-7.43 (m, 2H), 7.41-7.38 (m, 4H), 7.37 (s, 1H), 7.28-7.19 (m, 2H), 4.53 (s, 2H), 4.10-3.90 (m, 1H), 3.25 (s, 3H), 3.15-3.10 (m, 2H), 2.56-2.53 (m, 2H), 2.45-2.40 (m, 1H), 2.27 (m, 1H), 2.21 (s, 3H), 1.40-1.29 (m, 1H). The absolute stereochemistry was tentatively assigned based on the potency in the XBP1 reporter assay.

Example 206 N-(5-((3-(2-(((3R,4R)-4-fluoropiperidin-3-yl)amino)pyrimidin-4-yl)pyridin-2-yl)oxy)-6-methylnaphthalen-1-yl)propane-1-sulfonamide 206

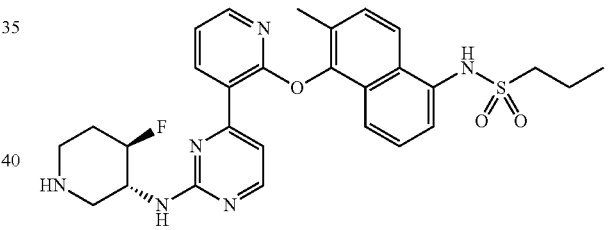

Step 1: tert-Butyl 4-fluoro-3-((4-(2-((2-methyl-5-(propylsulfonamido)naphthalen-1-yl)oxy)pyridin-3-yl)pyrimidin-2-yl)amino)piperidine-1-carboxylate

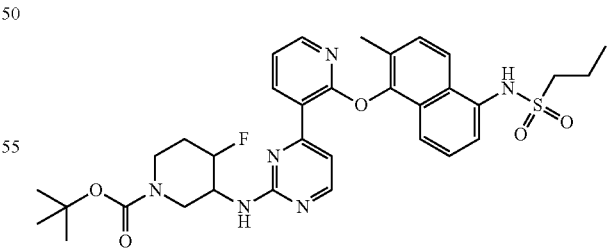

To a solution of N-[6-methyl-5-[[3-(2-methylsulfinylpyrimidin-4-yl)-2-pyridyl]oxy]-1-naphthyl]propane-1-sulfonamide (500 mg, 1.01 mmol) in 1,4-dioxane (5 mL) was added N,N-diisopropylethylamine (0.53 mL, 3.02 mmol) and tert-butyl 3-amino-4-fluoro-piperidine-1-carboxylate (263.7 mg, 1.21 mmol), the mixture was stirred at 120° C. for 80 h. After cooling, the mixture was concentrated to dryness and the residue was dissolved in DCM (50 mL) and washed with H₂O (40 mL×2). The organic phase was dried over anhydrous sodium sulfate, filtered and the filtrate was concentrated and purified by silica gel chromatography (solvent gradient: 0-50% ethyl acetate in petroleum ether, Rf=0.7) and prep-TLC (50% ethyl acetate in petroleum ether, Rf=0.7) to yield 100 mg (15% yield) of the title compound of the trans mixture product as a white solid. LCMS (ESI) [M+H]⁺=651.0.

Step 2: tert-Butyl 4-fluoro-3-((4-(2-((2-methyl-5-(propylsulfonamido)naphthalen-1-yl)oxy)pyridin-3-yl)pyrimidin-2-yl)amino)piperidine-1-carboxylate

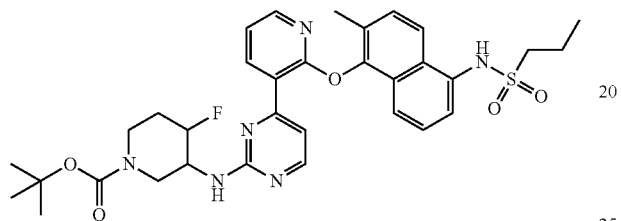

The trans mixture of tert-butyl 4-fluoro-3-((4-(2-((2-methyl-5-(propylsulfonamido)naphthalen-1-yl)oxy)pyridin-3-yl)pyrimidin-2-yl)amino)piperidine-1-carboxylate (300 mg, 0.46 mmol) was separated by chiral SFC (SFC 13, AS (250 mm×30 mm, 5 μm), 40% 40 mL/min, 0.1% NH₃H₂O in methanol) to yield tert-butyl 4-fluoro-3-[[4-[2-[[2-methyl-5-(propylsulfonylamino)-1-naphthyl]oxy]-3-pyridyl]pyrimidin-2-yl]amino]piperidine-1-carboxylate (90 mg, 14% yield) (first peak on SFC, Rt=4.95 min) as a white solid. LCMS (ESI) [M+H]⁺=651.1; and tert-butyl 4-fluoro-3-[[4-[2-[[2-methyl-5-(propylsulfonylamino)-1-naphthyl]oxy]-3-pyridyl]pyrimidin-2-yl]amino]piperidine-1-carboxylate (80 mg, 12% yield) (second peak on SFC, Rt=5.15 min) as a white solid. LCMS (ESI) [M+H]⁺=651.1.

Step 3: N-(5-((3-(2-(((3R,4R)-4-Fluoropiperidin-3-yl)amino)pyrimidin-4-yl)pyridin-2-yl)oxy)-6-methylnaphthalen-1-yl)propane-1-sulfonamide

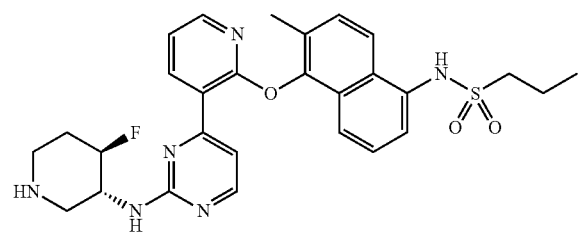 [SMILES: CCCS(=O)(=O)Nc1cccc2c(Oc3ncccc3-c3ccnc(N[C@@H]4CNCC[C@H]4F)n3)c(C)ccc12]

To a solution of tert-butyl 4-fluoro-3-[[4-[2-[[2-methyl-5-(propylsulfonylamino)-1-naphthyl]oxy]-3-pyridyl]pyrimidin-2-yl]amino]piperidine-1-carboxylate (80 mg, 0.12 mmol) (second peak on SFC in step 2) in ethyl acetate (1 mL) was added 4M of HCl (0.35 mL, 1.38 mmol) in ethyl acetate and the mixture was stirred at 20° C. for 2 h. The mixture was concentrated and the residue was purified by Prep-HPLC (mobile phase: A: water (0.05% NH₄OH) B: ACN) to yield 206 (38 mg, 56% yield) as a white solid; LCMS (ESI) [M+H]⁺=551.2; ¹H NMR (400 MHz, DMSO-d₆) δ 10.0-9.88 (m, 1H), 9.83 (s, 1H), 9.45 (s, 1H), 9.03-8.77 (m, 1H), 8.51 (d, J=5.6 Hz, 1H), 8.14 (d, J=8.8 Hz, 1H), 8.08 (d, J=3.2 Hz, 1H), 7.80-7.65 (m, 1H), 7.60-7.51 (m, 2H), 7.48-7.39 (m, 2H), 7.30-7.26 (m, 1H), 5.01-4.46 (m, 2H), 3.56-3.26 (m, 2H), 3.21-3.08 (m, 2H), 3.07-2.89 (m, 2H), 2.42-2.29 (m, 1H), 2.21 (s, 3H), 2.15-1.96 (m, 1H), 1.85-1.68 (m, 2H), 0.96 (t, J=7.2 Hz, 3H). The absolute stereochemistry was tentitiavely assigned based on potency in the XBP1 reporter assay.

Example 207 (S)-4-(2-((2-Methyl-5-(4-methyl-1H-pyrazol-1-yl)naphthalen-1-yl)oxy)pyridin-3-yl)-N-(piperidin-3-yl)pyrimidin-2-amine 207

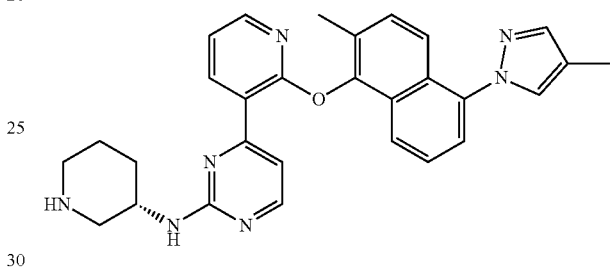

Step 1: tert-Butyl (S)-3-((4-(2-((2-methyl-5-(4-methyl-1H-pyrazol-1-yl)naphthalen-1-yl)oxy)pyridin-3-yl)pyrimidin-2-yl)amino)piperidine-1-carboxylate

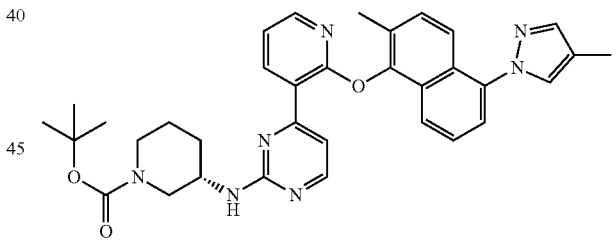

A mixture of 4-methyl-1H-pyrazole (23 mg, 0.28 mmol), tert-butyl (3S)-3-[[4-[2-[(5-iodo-2-methyl-1-naphthyl)oxy]-3-pyridyl]pyrimidin-2-yl]amino]piperidine-1-carboxylate (120 mg, 0.188 mmol), cuprous iodide 911 mg, 0.057 mmol), cesium carbonate (123 mg, 0.38 mmol) in DMF (1.5 mL) was evacuated and filled with nitrogen twice. The reaction mixture was stirred at rt for 30 min, and then at 120° C. overnight. After 16 hours, the mixture was cooled to room temperature and the mixture diluted with DCM and water, followed by separation of the layers. The organic phase was washed with saturated NaCl(aq), dried over sodium sulfate, filtered and concentrated in vacuo. The residue was purified on a silica column 5 to 80% (isopropylacetate/MeOH (3:1): heptanes) to provide 92 mg of the title compound (74% yield).

363

Step 2: (S)-4-(2-((2-Methyl-5-(4-methyl-1H-pyra-zol-1-yl)naphthalen-1-yl)oxy)pyridin-3-yl)-N-(piperidin-3-yl)pyrimidin-2-amine

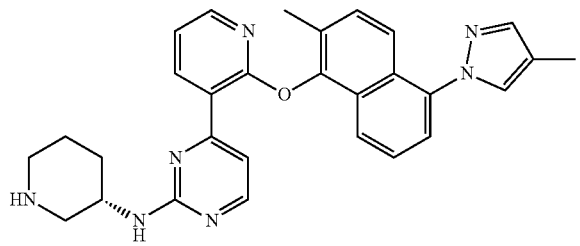 [SMILES: Cc1cnn(-c2cccc3c(Oc4ncccc4-c4ccnc(N[C@H]5CCCNC5)n4)c(C)ccc23)c1]

The General Procedure B was followed using tert-butyl (S)-3-((4-(2-((2-methyl-5-(4-methyl-1H-pyrazol-1-yl)naphthalen-1-yl)oxy)pyridin-3-yl)pyrimidin-2-yl)amino)piperidine-1-carboxylate (82 mg, 0.14 mmol), DCM (4 mL) and hydrochloric acid (4 M in dioxane, 3 mL, 12 mmol). The residue was purified via reverse-phase HPLC and lyophilized to yield 3.2 mg (5% yield) of 207. LCMS (ESI): [M+H]$^+$=492.2; $^1$H NMR (400 MHz, DMSO-d$_6$) δ 8.57-8.48 (m, 1H), 8.43 (d, J=5.1 Hz, 1H), 8.07-8.02 (m, 1H), 7.99-7.97 (m, 1H), 7.81-7.62 (m, 3H), 7.58-7.41 (m, 4H), 7.32-7.22 (m, 1H), 7.20 (d, J=7.8 Hz, 1H), 4.01-3.88 (m, 1H), 3.19-3.13 (m, 1H), 2.87 (d, J=12.3 Hz, 1H), 2.22 (s, 3H), 2.18 (s, 3H), 1.99-1.89 (m, 1H), 1.73-1.68 (m, 1H), 1.55-1.42 (m, 1H).

Example 208 N-(2-Fluoro-5-((3-(2-(((trans)-5-fluoropiperidin-3-yl)amino)pyrimidin-4-yl)pyridin-2-yl)oxy)-6-methylnaphthalen-1-yl)-2-methylpropane-1-sulfonamide 208

Step 1: trans-tert-Butyl 3-fluoro-5-((4-(2-((6-fluoro-2-methyl-5-(2-methylpropylsulfonamido)naphthalen-1-yl)oxy)pyridin-3-yl)pyrimidin-2-yl)amino)piperidine-1-carboxylate

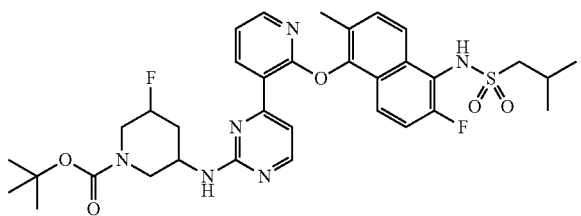 [SMILES: Cc1ccc2c(NS(=O)(=O)CC(C)C)c(F)ccc2c1Oc1ncccc1-c1ccnc(NC2CC(F)CN(C(=O)OC(C)(C)C)C2)n1]

Prepared using trans-tert-butyl 3-((4-(2-((5-amino-6-fluoro-2-methylnaphthalen-1-yl)oxy)pyridin-3-yl)pyrimidin-2-yl)amino)-5-fluoropiperidine-1-carboxylate (150 mg, 0.267 mmol), pyridine (0.323 mL, 4.00 mmol), DCM (0.89 mL), 2-methylpropane-1-sulfonyl chloride (0.070 mL, 0.533 mmol) and DMAP (1.63 mg, 0.013 mmol). After 16 h, a further portion of 2-methylpropane-1-sulfonyl chloride (0.070 mL, 0.533 mmol) was added and the reaction mixture stirred a further 6 h. The reaction mixture was diluted with 1M KHSO$_4$(aq), extracted twice with DCM, dried (Na$_2$SO$_4$), filtered and concentrated in vacuo. The crude was purified by flash chromatography through silica gel (0-50% EtOAc/DCM) to provide 92 mg (50% yield) of the title compound. LCMS (ESI) [M+H]$^+$=683.6, rt=1.93 min.

364

Step 2: tert-butyl (3S,5S)-3-fluoro-5-((4-(2-((6-fluoro-2-methyl-5-((2-methylpropyl)sulfonamido) naphthalen-1-yl)oxy)pyridin-3-yl)pyrimidin-2-yl) amino)piperidine-1-carboxylate (Isomer-1) and tert-butyl (3R,5R)-3-fluoro-5-((4-(2-((6-fluoro-2-methyl-5-((2-methylpropyl)sulfonamido)naphthalen-1-yl) oxy)pyridin-3-yl)pyrimidin-2-yl)amino)piperidine-1-carboxylate (Isomer-2)

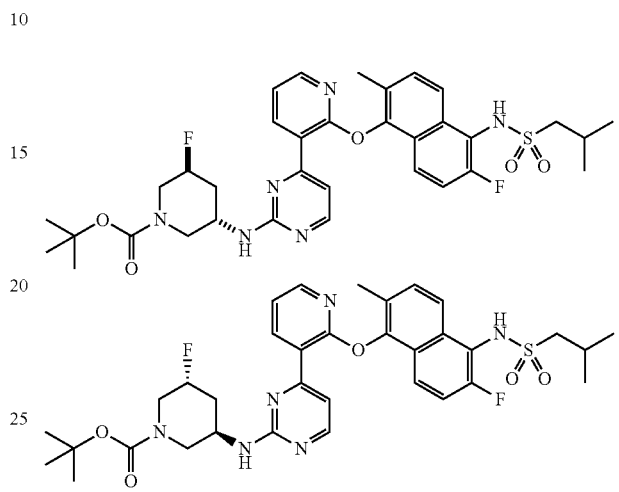

The trans enantiomers from Step 1 were subjected to chiral normal phase semi-prep purification (Conditions: Chiralpak IA, 5 uM, 20×250 mm, 10:5:85 MeOH:iPrOH: Hexanes, 7-10 mg/inj.) to provide two trans-piperidine enantiomers: (isomer-1), 65 mg (36% yield), ee=97.2%, (ESI) [M+H]$^+$=683.3, rt=1.91 min; and (isomer-2), 66 mg (37% yield), ee=97.7%, (ESI) [M+H]$^+$=683.3, rt=1.91 min.

Step 3: N-(2-Fluoro-5-((3-(2-(((3S,5S)-5-fluoropiperidin-3-yl)amino)pyrimidin-4-yl)pyridin-2-yl)oxy)-6-methylnaphthalen-1-yl)-2-methylpropane-1-sulfonamide (Isomer-1)

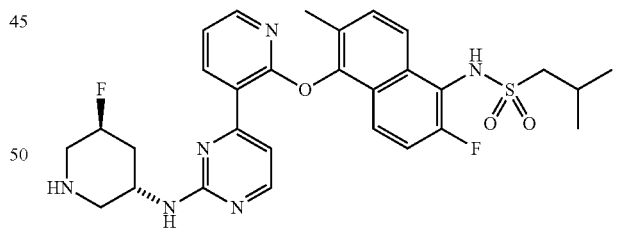

Prepared according to General Procedure B using tert-butyl (3S,5S)-3-fluoro-5-((4-(2-((6-fluoro-2-methyl-5-((2-methylpropyl)sulfonamido)naphthalen-1-yl)oxy)pyridin-3-yl)pyrimidin-2-yl)amino)piperidine-1-carboxylate (isomer-1) (66 mg, 0.097 mmol), 1,4-dioxane (0.5 mL) and hydrochloric acid (4 M in dioxane, 1 mL, 4 mmol). After 3 h, the reaction mixture was diluted with Et$_2$O and the resulting solids collected by filtration and washed with Et$_2$O. The collected solids were dissolved in a mixture of MeCN and H$_2$O and lyophilized to provide 54 mg (91% yield) of 208. LCMS (ESI) [M+H]$^+$=583.4, rt=1.44 min; $^1$H NMR (400 MHz, DMSO-d$_6$) δ 9.70 (s, 1H), 9.61 (d, J=11.4 Hz, 1H), 9.34-9.06 (m, 1H), 8.79-8.56 (m, 1H), 8.49 (d, J=5.2

Hz, 1H), 8.08 (dd, J=4.7, 1.9 Hz, 1H), 8.06 (d, J=9.0 Hz, 1H), 7.71 (dd, J=9.3, 5.1 Hz, 1H), 7.66-7.55 (m, 3H), 7.45 (t, J=9.5 Hz, 1H), 7.29 (dd, J=7.6, 4.8 Hz, 1H), 5.24 (d, J=45.4 Hz, 1H), 4.52 (s, 1H), 3.57-3.39 (m, 2H), 3.34-3.14 (m, 1H), 3.11 (d, J=6.4 Hz, 2H), 2.83 (q, J=10.9 Hz, 1H), 2.42-2.22 (m, 2H), 2.19 (s, 3H), 1.94 (dt, J=24.6, 12.8 Hz, 1H), 1.07 (d, J=6.7 Hz, 6H).

Example 209 (S)-1-(4-Chlorophenyl)-N-(2-fluoro-6-methyl-5-((3-(2-(piperidin-3-ylamino)pyrimidin-4-yl)pyridin-2-yl)oxy)naphthalen-yl)oxy)naphthalen-1-yl)methanesulfonamide 209

Step 1: (S)-tert-Butyl 3-((4-(2-((5-((4-chlorophenyl)methylsulfonamido)-6-fluoro-2-methylnaphthalen-1-yl)oxy)pyridin-3-yl)pyrimidin-2-yl)amino)piperidine-1-carboxylate

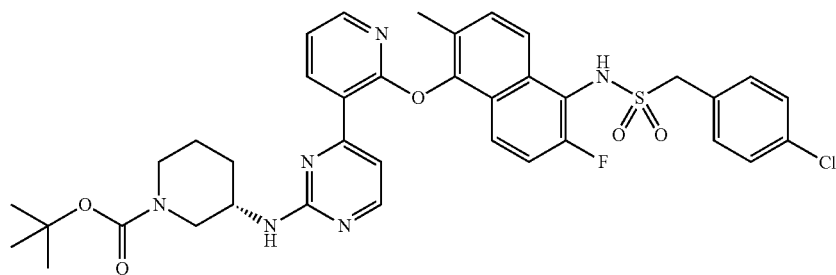 [SMILES: Cc1ccc2c(NS(=O)(=O)Cc3ccc(Cl)cc3)c(F)ccc2c1Oc1ncccc1-c1ccnc(N[C@H]2CCCN(C(=O)OC(C)(C)C)C2)n1]

Prepared using (S)-tert-butyl 3-((4-(2-((5-amino-6-fluoro-2-methylnaphthalen-1-yl)oxy)pyridin-3-yl)pyrimidin-2-yl)amino)piperidine-1-carboxylate from Example 275 (60 mg, 0.11 mmol), pyridine (0.090 mL, 1.11 mmol), DCM (1.5 mL), and (4-chlorophenyl)methanesulfonyl chloride (50 mg, 0.22 mmol). After 16 h, the reaction mixture was concentrated in vacuo and the residue diluted with EtOAc, then washed twice with 1M HCl(aq), followed by saturated NaHCO$_3$(aq) and brine. The solution was dried (MgSO$_4$), filtered and concentrated in vacuo, and the resulting crude product purified by C18 reverse phase flash chromatography (0-70% MeCN/10 mM aqueous ammonium formate, pH=3.8). The product fractions were combined, concentrated, and lyophilized to provide 54 mg (67% yield) of the title compound. LCMS (ESI) [M+H]$^+$=733.3, rt=2.06 min.

Step 2: (S)-1-(4-Chlorophenyl)-N-(2-fluoro-6-methyl-5-((3-(2-(piperidin-3-ylamino)pyrimidin-4-yl)pyridin-2-yl)oxy)naphthalen-1-yl)methanesulfonamide

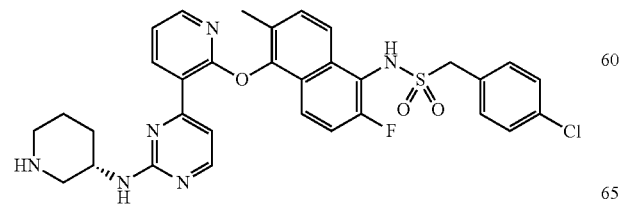

Prepared using (S)-tert-butyl 3-((4-(2-((5-((4-chlorophenyl)methylsulfonamido)-6-fluoro-2-methylnaphthalen-1-yl)oxy)pyridin-3-yl)pyrimidin-2-yl)amino)piperidine-1-carboxylate (54 mg, 0.074 mmol), 1,4-dioxane (1.5 mL), and hydrochloric acid (4 M in dioxane, 0.5 mL, 2 mmol). After 4 h, the reaction mixture was diluted with MTBE (5 mL), and the resulting solids collected by filtration and washed with MTBE. The solids were then dissolved in a mixture of MeCN and H$_2$O, and lyophilized to provide 42 mg (85% yield) of 209. LCMS (ESI) [M+H]$^+$=633.1, rt=1.56 min. $^1$H NMR (400 MHz, d4-MeOH) δ 8.69 (d, J=6.7 Hz, 1H), 8.46 (d, J=5.4 Hz, 1H), 8.09 (d, J=8.8 Hz, 1H), 8.02 (dd, J=4.8, 1.9 Hz, 1H), 7.78 (dd, J=9.3, 4.9 Hz, 1H), 7.73 (d, J=5.4 Hz, 1H), 7.56 (d, J=8.8 Hz, 1H), 7.50-7.45 (m, 2H), 7.43-7.32 (m, 3H), 7.25 (dd, J=7.6, 4.8 Hz, 1H), 4.56 (s, 2H), 4.47-4.32 (m, 1H), 3.63 (dd, J=12.2, 3.6 Hz, 1H), 3.39-3.33 (m, 1H), 3.11-2.99 (m, 2H), 2.24 (s, 3H), 2.23-2.06 (m, 2H), 1.98-1.74 (m, 2H).

Example 210 (S)-2-Methyl-N-(6-methyl-5-((3-(2-(piperidin-3-ylamino)pyrimidin-4-yl)pyridin-2-yl)oxy)naphthalen-1-yl) thiazole-5-sulfonamide 210

Step 1: tert-Butyl (S)-3-((4-(2-((2-methyl-5-((2-methylthiazole)-5-sulfonamido)naphthalen-1-yl)oxy)pyridin-3-yl)pyrimidin-2-yl)amino)piperidine-1-carboxylate

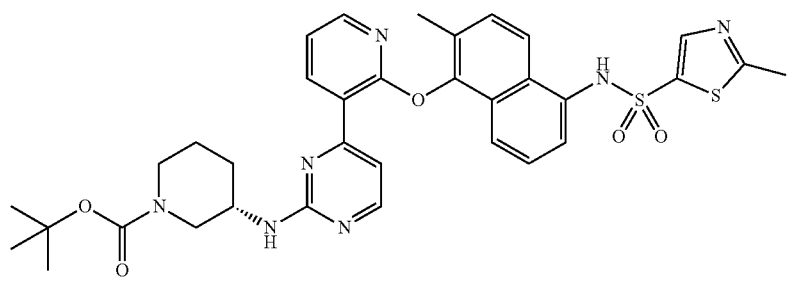 [SMILES: Cc1ncc(S(=O)(=O)Nc2cccc3c(Oc4ncccc4-c4ccnc(N[C@H]5CCCN(C(=O)OC(C)(C)C)C5)n4)c(C)ccc23)s1]

The General Procedure A was followed, using tert-butyl (3S)-3-[[4-[2-[(5-amino-2-methyl-1-naphthyl)oxy]-3-pyridyl]pyrimidin-2-yl]amino]piperidine-1-carboxylate (100 mg, 0.19 mmol) and 2-methylthiazole-5-sulfonyl chloride (56.31 mg, 0.56 mmol) in pyridine (1 mL), stirred at room temperature for 48 h. Purification was conducted by silica gel chromatography (12 g column) eluting with 0-5% MeOH/DCM to afford 50 mg (38% yield) of the title compound as a brown solid. LCMS (ESI) [M+H]$^+$=688.

Step 2: (S)-2-Methyl-N-(6-methyl-5-((3-(2-(piperidin-3-ylamino)pyrimidin-4-yl)pyridin-2-yl)oxy)naphthalen-1-yl)thiazole-5-sulfonamide

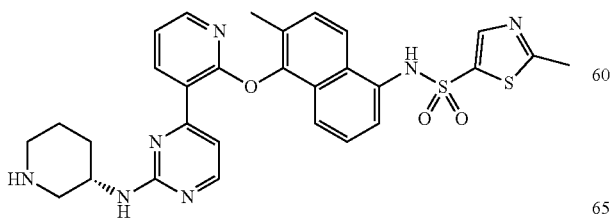

The General Procedure B was followed, using tert-butyl (S)-3-((4-(2-((2-methyl-5-((2-methylthiazole)-5-sulfonamido)naphthalen-1-yl)oxy)pyridin-3-yl)pyrimidin-2-yl)amino)piperidine-1-carboxylate (50 mg, 0.08 mmol). The crude product was purified via reverse-phase HPLC and lyophilized to yield 30.7 mg (72% yield) of 210 as a light gray solid: LCMS (ESI) [M+H]$^+$=588; $^1$H NMR (400 MHz, DMSO-d$_6$) δ 8.50 (s, 1H), 8.44 (d, J=5.2 Hz, 1H), 8.24 (d, J=8.7 Hz, 1H), 8.04 (dd, J=4.8, 2.0 Hz, 1H), 7.65 (s, 1H), 7.54 (d, J=5.2 Hz, 1H), 7.41 (d, J=7.5 Hz, 1H), 7.22 (dt, J=7.6, 4.8 Hz, 2H), 7.10-7.00 (m, 2H), 6.84 (s, 1H), 4.18 (s, 1H), 3.40 (d, J=11.0 Hz, 1H), 3.15 (d, J=12.9 Hz, 1H), 2.86-2.75 (m, 2H), 2.56-2.53 (m, 3H), 2.16 (s, 3H), 2.03-1.97 (m, 1H), 1.92-1.86 (m, 1H), 1.71-1.57 (m, 1H).

Example 211 (S)-4-(2-((2-Methyl-5-((thiazol-4-ylmethyl)amino)naphthalen-1-yl)oxy)pyridin-3-yl)-N-(piperidin-3-yl)pyrimidin-2-amine 211

Step 1: tert-Butyl (S)-3-((4-(2-((2-methyl-5-((thiazol-4-ylmethyl)amino)naphthalen-1-yl)oxy)pyridin-3-yl)pyrimidin-2-yl)amino)piperidine-1-carboxylate

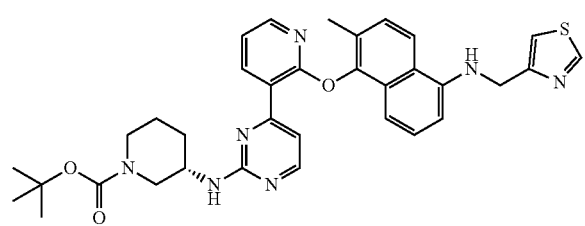 [SMILES: Cc1ccc2c(NCc3cscn3)cccc2c1Oc1ncccc1-c1ccnc(N[C@H]2CCCN(C(=O)OC(C)(C)C)C2)n1]

To a solution of tert-butyl (3S)-3-[[4-[2-[(5-amino-2-methyl-1-naphthyl)oxy]-3-pyridyl]pyrimidin-2-yl]amino]piperidine-1-carboxylate (100 mg, 0.19 mmol) and DIPEA (0.13 mL, 0.7596 mmol) in DMF (1 mL) was added 4-(chloromethyl)thiazole hydrochloride (64.59 mg, 0.38 mmol). The mixture was heated at 65° C. for 48 h. It was then diluted with 10% citric acid, extracted with iPrOAc (2×10 ml), dried over MgSO$_4$ and filtered. The crude material was purified by silica gel chromatography (12 g column) eluting with 0-5% MeOH/DCM to afford 51 mg (43% yield) of the title compound as a brown sticky gum. LCMS (ESI) [M+H]$^+$=624.

Step 2: (S)-4-(2-((2-Methyl-5-((thiazol-4-ylmethyl)amino)naphthalen-1-yl)oxy)pyridin-3-yl)-N-(piperidin-3-yl)pyrimidin-2-amine

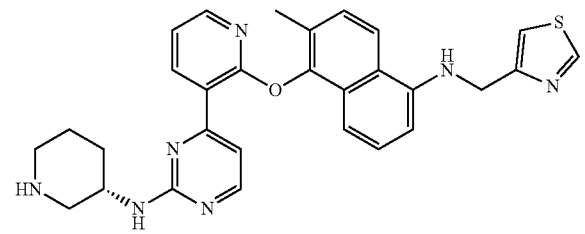

The General Procedure B was followed, using tert-butyl (S)-3-((4-(2-((2-methyl-5-((thiazol-4-ylmethyl)amino)naphthalen-1-yl)oxy)pyridin-3-yl)pyrimidin-2-yl)amino)piperidine-1-carboxylate (51 mg, 0.08 mmol). The crude product was purified via reverse-phase HPLC and lyophilized to yield 2.5 mg (6% yield) of 211 as a pale brown solid. LCMS (ESI) [M+H]$^+$=524; $^1$H NMR (400 MHz, DMSO-d$_6$) δ 8.48 (s, 1H), 8.39 (d, J=5.1 Hz, 1H), 8.08 (d, J=8.8 Hz, 1H), 8.01 (dd, J=4.8, 2.0 Hz, 1H), 7.48-7.41 (m, 2H), 7.37 (d, J=8.7 Hz, 1H), 7.22 (dd, J=7.6, 4.8 Hz, 1H), 7.14-7.07 (m, 2H), 6.95 (t, J=5.9 Hz, 1H), 6.85 (d, J=8.5 Hz, 1H), 6.42 (dd, J=7.6, 1.0 Hz, 1H), 4.62 (d, J=5.8 Hz, 2H), 3.89 (s, 1H), 3.14-3.07 (m, 1H), 2.80 (d, J=12.2 Hz, 1H), 2.19 (s, 3H), 1.96-1.87 (m, 1H), 1.68-1.62 (m, 1H), 1.52-1.40 (m, 2H).

Example 212 (1S,2S)-2-Fluoro-N-[6-methyl-5-[[3-[2-[[(3S)-3-piperidyl]amino]pyrimidin-4-yl]-2-pyridyl]oxy]-1-naphthyl]cyclopropanecarboxamide 212

Step 1: tert-Butyl (S)-3-((4-(2-((5-((1S,2S)-2-fluorocyclopropane-1-carboxamido)-2-methylnaphthalen-1-yl)oxy)pyridin-3-yl)pyrimidin-2-yl)amino)piperidine-1-carboxylate

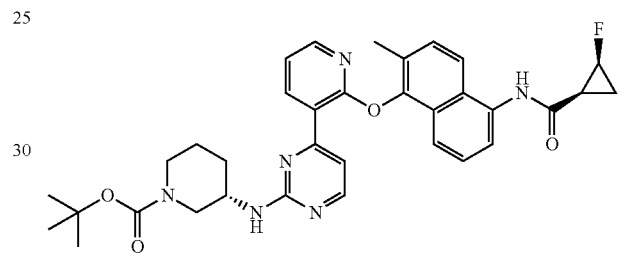

The General Procedure C was followed, using tert-butyl (S)-3-((4-(2-((5-amino-2-methylnaphthalen-1-yl)oxy)pyridin-3-yl)pyrimidin-2-yl)amino)piperidine-1-carboxylate from Example 101 (243 mg, 0.46 mmol), (cis)-2-fluorocyclopropanecarboxylic acid (40 mg, 0.38 mmol), DIPEA (0.201 mL, 1.15 mmol), HATU (671 mg, 1.73 mmol) and DCM (10 mL). The residue was purified via reverse-phase HPLC to provide a mixture of the two isomers. This mixture was then purified via chiral reverse-phase HPLC and lyophilized to yield 50 mg and 52 mg of the two single cis stereoisomers possessing a stereocenter at the 1 and 2 positions of the cyclopropyl amide moiety.

Step 2: (1S,2S)-2-Fluoro-N-[6-methyl-5-[[3-[2-[[(3S)-3-piperidyl]amino]pyrimidin-4-yl]-2-pyridyl]oxy]-1-naphthyl]cyclopropanecarboxamide

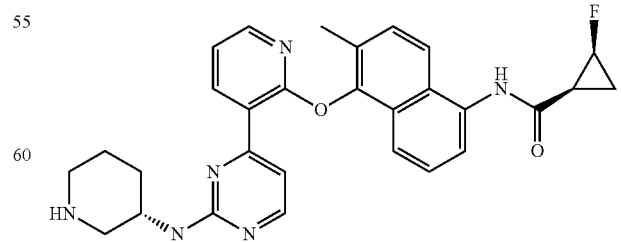

The General Procedure B was followed, using tert-butyl (3S)-3-((4-(2-((5-(2-fluorocyclopropane-1-carboxamido)-2- methylnaphthalen-1-yl)oxy)pyridin-3-yl)pyrimidin-2-yl)amino)piperidine-1-carboxylate (50 mg), DCM (4 mL) and hydrochloric acid (4 M in dioxane, 3 mL, 12 mmol). The residue was purified via reverse-phase HPLC and lyophilized to yield 17.8 mg of 212. The stereochemistry was tentatively and randomly assigned. LCMS (ESI): [M+H]$^+$=513.2; $^1$H NMR (400 MHz, DMSO-d$_6$) δ 10.24 (s, 1H), 8.55-8.50 (m, 1H), 8.42 (d, J=5.1 Hz, 1H), 8.03 (dd, J=4.8, 2.0 Hz, 1H), 7.94 (d, J=8.5 Hz, 1H), 7.64 (d, J=7.4 Hz, 1H), 7.52 (d, J=8.8 Hz, 2H), 7.46 (d, J=5.1 Hz, 1H), 7.44-7.37 (m, 1H), 7.26 (dd, J=7.6, 4.8 Hz, 1H), 7.18 (d, J=7.9 Hz, 1H), 5.12-4.89 (m, 1H), 3.95 (s, 1H), 3.19-3.10 (m, 1H), 2.88-2.82 (m, 1H), 2.31-2.25 (m, 1H), 2.22 (s, 3H), 2.01-1.88 (m, 1H), 1.73-1.62 (m, 2H), 1.56-1.42 (m, 2H), 1.23-1.14 (m, 1H).

Example 213 (S)-1-(2,6-Difluorophenyl)-N-(2-fluoro-6-methyl-5-((3-(2-(piperidin-3-ylamino)pyrimidin-4-yl)pyridin-2-yl)oxy)naphthalen-yl)oxy)naphthalen-1-yl)methanesulfonamide 213

Step 1: (S)-tert-butyl 3-((4-(2-((5-((2,6-difluorophenyl)methylsulfonamido)-6-fluoro-2-methylnaphthalen-1-yl)oxy)pyridin-3-yl)pyrimidin-2-yl)amino)piperidine-1-carboxylate

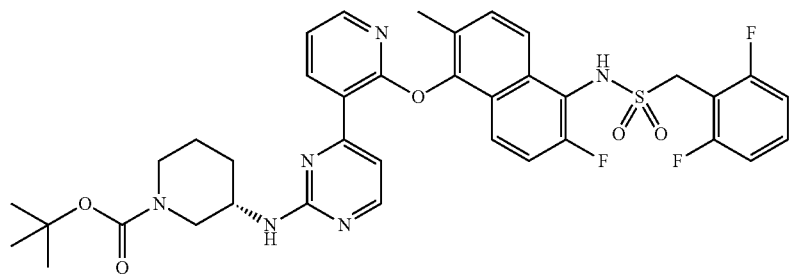 [SMILES: Cc1ccc2c(NS(=O)(=O)Cc3c(F)cccc3F)c(F)ccc2c1Oc1ncccc1-c1ccnc(N[C@H]2CCCN(C(=O)OC(C)(C)C)C2)n1]

Prepared using (S)-tert-butyl 3-((4-(2-((5-amino-6-fluoro-2-methylnaphthalen-1-yl)oxy)pyridin-3-yl)pyrimidin-2-yl)amino)piperidine-1-carboxylate from Example 275 (60 mg, 0.11 mmol), pyridine (0.090 mL, 1.11 mmol), DCM (1.5 mL), and (2,6-difluorophenyl)methanesulfonyl chloride (50 mg, 0.22 mmol). After 16 h, the reaction mixture was concentrated in vacuo and the residue was diluted with EtOAc, washed twice with 1M HCl(aq), then with saturated NaHCO$_3$(aq), then brine, dried (MgSO$_4$), filtered and concentrated in vacuo. The crude was purified by C18 reverse phase flash chromatography (0-70% MeCN/10 mM aqueous ammonium formate, pH=3.8). The product fractions were combined and concentrated to remove some MeCN, and lyophilized to provide 58 mg (72% yield) of the title compound. LCMS (ESI) [M+H]$^+$=735.3, rt=1.97 min.

Step 2: (S)-1-(2,6-Difluorophenyl)-N-(2-fluoro-6-methyl-5-((3-(2-(piperidin-3-ylamino)pyrimidin-4-yl)pyridin-2-yl)oxy)naphthalen-1-yl)methanesulfonamide

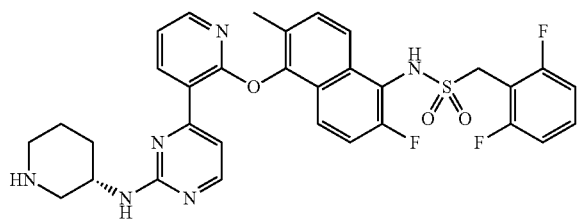 [SMILES: Cc1ccc2c(NS(=O)(=O)Cc3c(F)cccc3F)c(F)ccc2c1Oc1ncccc1-c1ccnc(N[C@H]2CCCNC2)n1]

Prepared using (S)-tert-butyl 3-((4-(2-((5-((2,6-difluorophenyl)methylsulfonamido)-6-fluoro-2-methylnaphthalen-1-yl)oxy)pyridin-3-yl)pyrimidin-2-yl)amino)piperidine-1-carboxylate (58 mg, 0.079 mmol), 1,4-dioxane (1.5 mL), and hydrochloric acid (4 M in dioxane, 0.5 mL, 2 mmol). After 4 h, the reaction mixture was diluted with MTBE (5 mL), and the resulting solids collected by filtration and washed with MTBE. The resulting solids were dissolved in a mixture of MeCN and H$_2$O, and lyophilized to provide 39 mg (74% yield) of 213. LCMS (ESI) [M+H]$^+$=635.2, rt=1.47 min. $^1$H NMR (400 MHz, CD$_3$OD) δ 8.72 (d, J=6.5 Hz, 1H), 8.47 (d, J=5.6 Hz, 1H), 8.12 (d, J=8.8 Hz, 1H), 8.05 (dd, J=4.8, 1.8 Hz, 1H), 7.84-7.75 (m, 2H), 7.57 (d, J=8.8 Hz, 1H), 7.51-7.40 (m, 1H), 7.36 (t, J=9.5 Hz, 1H), 7.27 (dd, J=7.6, 4.9 Hz, 1H), 7.10-6.99 (m, 2H), 4.74 (s, 2H), 4.50-4.34 (m, 1H), 3.66-3.60 (m, 1H), 3.41-3.34 (m, 1H), 3.12-2.99 (m, 2H), 2.25 (s, 3H), 2.23-2.07 (m, 2H), 1.98-1.74 (m, 2H).

Example 214 (S)—N-(6-Methyl-5-((3-(2-((S)-piperidin-3-ylamino)pyrimidin-4-yl)pyridin-2-yl)oxy)naphthalen-1-yl)-1-phenylethanesulfonamide 214

Step 1: N-(6-Methyl-5-((3-(2-(methylthio)pyrimidin-4-yl)pyridin-2-yl)oxy)naphthalen-1-yl)-1-phenylmethanesulfonamide

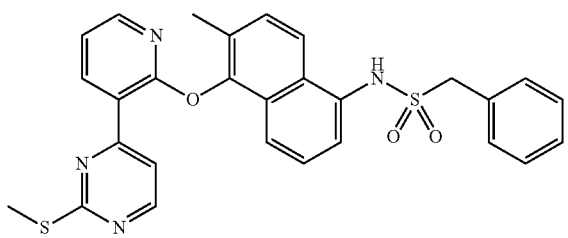 [SMILES: CSc1nccc(-c2cccnc2Oc2c(C)ccc3c(NS(=O)(=O)Cc4ccccc4)cccc23)n1]

The General Procedure A was followed, using 6-methyl-5-[[3-(2-methylsulfanylpyrimidin-4-yl)-2-pyridyl]oxy]naphthalen-1-amine (2.0 g, 5.34 mmol), pyridine (10 mL) and benzyl sulfonyl chloride (1.2 g, 6.41 mmol). The organic layer was concentrated and purified by chromatography on silica (solvent gradient: 0-30% ethyl acetate in petroleum ether) to yield 2.6 g (92% yield) of the title compound as a yellow solid.

Step 2: N-(methoxymethyl)-N-(6-methyl-5-((3-(2-(methylthio)pyrimidin-4-yl)pyridin-2-yl)oxy)naphthalen-1-yl)-1-phenylmethanesulfonamide

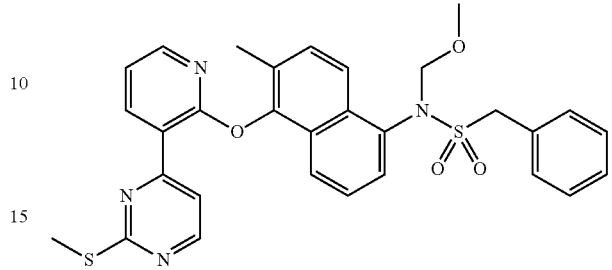

To a solution of N-[6-methyl-5-[[3-(2-methylsulfanylpyrimidin-4-yl)-2-pyridyl]oxy]-1-naphthyl]-1-phenyl-methanesulfonamide (2.4 g, 4.54 mmol), N,N-diisopropylethylamine (0.87 mL, 4.99 mmol) in dichloromethane (20 mL) was added chloromethyl methyl ether (0.85 mL, 11.18 mmol) at 25° C. The mixture was warmed to 25° C. for 1 h. The solution was concentrated and purified by chromatography on silica (solvent gradient: 0-50% ethyl acetate in petroleum ether) to yield 2.3 g (88% yield) of the title compound as a yellow solid.

Step 3: N-(Methoxymethyl)-N-(6-methyl-5-((3-(2-(methylthio)pyrimidin-4-yl)pyridin-2-yl)oxy)naphthalen-1-yl)-1-phenylethanesulfonamide

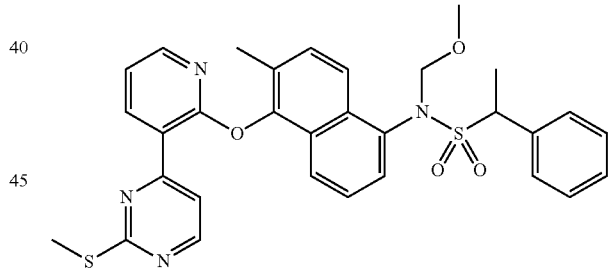

To a solution of N-(methoxymethyl)-N-[6-methyl-5-[[3-(2-methylsulfanylpyrimidin-4-yl)-2-pyridyl]oxy]-1-naphthyl]-1-phenyl-methanesulfonamide (1.2 g, 2.10 mmol) in tetrahydrofuran (5 mL) was added lithium bis(trimethylsilyl)azanide (4.19 mL, 4.19 mmol) at −78° C. and stirred for 30 min at −78° C. The solution was warmed to 18° C. and cooled to −78° C. Iodomethane (0.16 mL, 2.51 mmol) was added into the solution. The mixture was stirred at −78° C. for 2 h. Water (30 mL) was added and extracted by dichloromethane (50 mL×3). The organic layer was concentrated and purified by chromatography on silica (solvent gradient: 0-30% ethyl acetate in petroleum ether) to yield 2.0 g (95% yield) of the title compound as a white solid.

Step 4: N-(Methoxymethyl)-N-(6-methyl-5-((3-(2-(methylsulfinyl)pyrimidin-4-yl)pyridin-2-yl)oxy)naphthalen-1-yl)-1-phenylethanesulfonamide

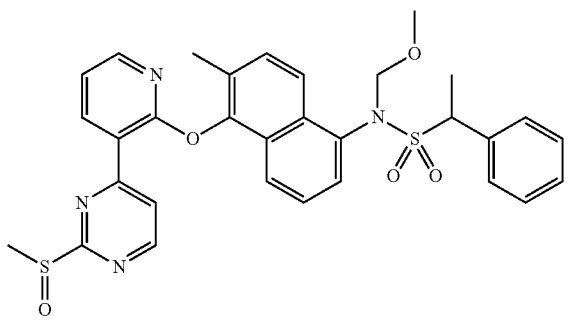 [SMILES: COCN(c1cccc2c(Oc3ncccc3-c3ccnc(S(C)=O)n3)c(C)ccc12)S(=O)(=O)C(C)c1ccccc1]

To a solution of N-(methoxymethyl)-N-[6-methyl-5-[[3-(2-methylsulfanylpyrimidin-4-yl)-2-pyridyl]oxy]-1-naphthyl]-1-phenyl-ethanesulfonamide (1.0 g, 1.70 mmol) in dichloromethane (3 mL) at 0° C. was added 80% 3-chloroperoxybenzoic acid (404 mg, 1.87 mmol). The resulting mixture was stirred at 0° C. for 0.5 h. To the solution was added saturated sodium bicarbonate to pH=9 and then sodium sulfite until the starch potassium iodide test does not change color. The solution was extracted by dichloromethane (30 mL×3) and water (30 mL×2) and the organic layer was concentrated to yield 1.0 g (97% yield) of the title compound as a yellow solid.

Step 5: (S)-tert-Butyl 3-((4-(2-((5-((S)—N-(methoxymethyl)-1-phenylethylsulfonamido)-2-methylnaphthalen-1-yl)oxy)pyridin-3-yl)pyrimidin-2-yl)amino)piperidine-1-carboxylate & (S)-tert-butyl 3-((4-(2-((5-((R)—N-(methoxymethyl)-1-phenylethylsulfonamido)-2-methylnaphthalen-1-yl)oxy)pyridin-3-yl)pyrimidin-2-yl)amino)piperidine-1-carboxylate

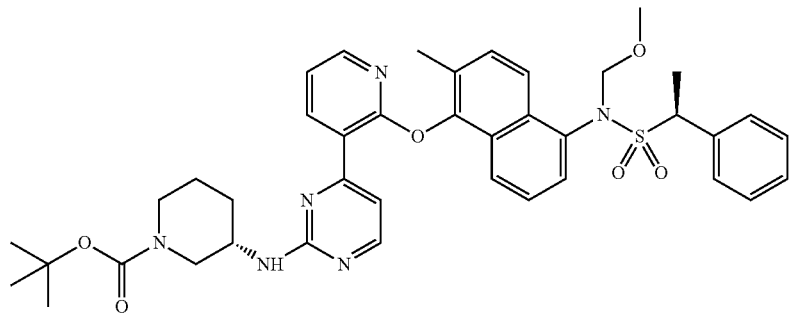

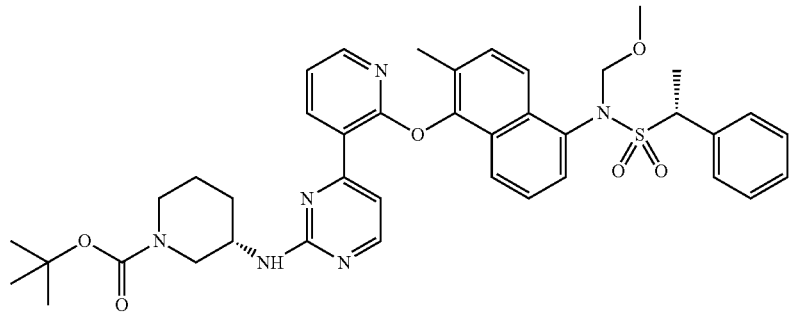

To a stirred solution of N,N-diisopropylethylamine (0.44 mL, 2.49 mmol) in 1,4-dioxane (5 mL) was added N-(methoxymethyl)-N-[6-methyl-5-[[3-(2-methylsulfinylpyrimidin-4-yl)-2-pyridyl]oxy]-1-naphthyl]-1-phenylethanesulfonamide (500 mg, 0.83 mmol) and tert-butyl (3S)-3-amino-1-piperidinecarboxylate (249 mg, 1.24 mmol), the mixture was stirred at 130° C. for 16 h. The solution was concentrated and purified by chromatography on silica (solvent gradient: 0-50% ethyl acetate in petroleum ether) and separated using chiral SFC (SFC80; Chiralpak AD 250×30 mm I.D., 10 μm; Supercritical $CO_2$/MEOH+ $NH_3.H_2O$=40/40; 80 mL/min) to yield tert-butyl (3S)-3-[[4-[2-[[2-methyl-5-(1-phenylethylsulfonylamino)-1-naphthyl]oxy]-3-pyridyl]pyrimidin-2-yl]amino]piperidine-1-carboxylate (210 mg, 48% yield) as a white solid and tert-butyl (3S)-3-[[4-[2-[[2-methyl-5-(1-phenylethylsulfonylamino)-1-naphthyl]oxy]-3-pyridyl]pyrimidin-2-yl]amino]piperidine-1-carboxylate (180 mg, 41% yield) as a white solid. LCMS (ESI): [M+Na]$^+$=761.0.

Step 6: (S)—N-(6-methyl-5-((3-(2-((S)-piperidin-3-ylamino)pyrimidin-4-yl)pyridin-2-yl)oxy)naphthalen-1-yl)-1-phenylethanesulfonamide The General Procedure B was followed, using (S)-tert-butyl 3-((4-(2-((5-((S)—N-(methoxymethyl)-1-phenylethylsulfonamido)-2-methylnaphthalen-1-yl)oxy)pyridin-3-yl)pyrimidin-2-yl)amino)piperidine-1-carboxylate (100 mg, 0.14 mmol) or (R)-tert-butyl 3-((4-(2-((5-((R)—N-(methoxymethyl)-1-phenylethylsulfonamido)-2-methylnaphthalen-1-yl)oxy)pyridin-3-yl)pyrimidin-2-yl)amino)piperidine-1-carboxylate (100 mg, 0.14 mmol), dichloromethane (5 mL) and trifluoroacetic acid (2 mL, 14 mmol). The residue was purified by Prep-HPLC (mobile phase: A: water (0.05% ammonia) B: ACN) to yield two separate isomers. The absolute stereochemistry of 214 and 215 was assigned arbitrarly.

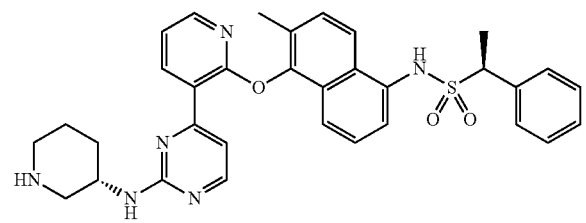 [SMILES: Cc1ccc2c(NS(=O)(=O)[C@@H](C)c3ccccc3)cccc2c1Oc1ncccc1-c1ccnc(N[C@H]2CCCNC2)n1]

214: (S)—N-(6-Methyl-5-((3-(2-((S)-piperidin-3-ylamino)pyrimidin-4-yl)pyridin-2-yl)oxy)naphthalen-1-yl)-1-phenylethanesulfonamide (3.2 mg 3.6% yield) as a yellow solid. LCMS (ESI): [M+H]$^+$=595.2. $^1$H NMR (400 MHz, CDCl$_3$) δ 8.67 (d, J=7.2 Hz, 1H), 8.35 (d, J=5.6 Hz, 1H), 8.01 (d, J=4.8 Hz, 1H), 7.67 (d, J=5.6 Hz, 1H), 7.61 (d, J=8.4 Hz, 1H), 7.54 (d, J=7.2 Hz, 1H), 7.40-7.27 (m, 8H), 7.11 (d, J=4.8 Hz, 1H), 5.69 (s, 1H), 4.45 (q, J=7.2 Hz, 1H), 4.30 (s, 1H), 3.44 (d, J=10.4 Hz, 1H), 3.05 (s, 1H), 2.93-2.86 (m, 2H), 2.27 (s, 3H), 2.08-1.94 (m, 2H), 1.84 (d, J=7.2 Hz, 3H), 1.79-1.68 (m, 2H).

Example 215 (R)—N-(6-methyl-5-((3-(2-((S)-piperidin-3-ylamino)pyrimidin-4-yl)pyridin-2-yl)oxy)naphthalen-1-yl)-1-phenylethanesulfonamide 215

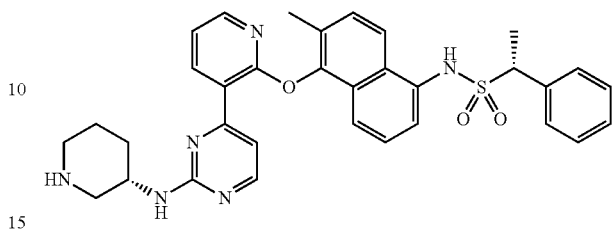

Following the procedures of Example 214, 215 was isolated (11.4 mg, 13% yield) as a white solid. LCMS (ESI): [M+H]$^+$=595.2. $^1$H NMR (400 MHz, CDCl$_3$) δ 8.63 (d, J=7.2 Hz, 1H), 8.38 (d, J=5.2 Hz, 1H), 8.04 (d, J=5.2 Hz, 1H), 7.67-7.54 (m, 3H), 7.43-7.28 (m, 8H), 7.12 (d, J=7.2 Hz, 1H), 5.43 (d, J=7.2 Hz, 1H), 4.45 (q, J=7.2 Hz, 1H), 4.11 (s, 1H), 3.32 (d, J=10.4 Hz, 1H), 3.00-2.89 (m, 1H), 2.80-2.67 (m, 2H), 2.29 (s, 3H), 2.05-1.94 (m, 2H), 1.85 (d, J=7.2 Hz, 3H), 1.74-1.72 (m, 2H).

Example 216 (S)-1-(6-Methyl-5-((3-(2-(piperidin-3-ylamino)pyrimidin-4-yl)pyridin-2-yl)oxy)naphthalen-1-yl)pyrrolidin-2-one 216

Step 1: (S)-tert-Butyl 3-((4-(2-((2-methyl-5-(2-oxopyrrolidin-1-yl)naphthalen-1-yl)oxy)pyridin-3-yl)pyrimidin-2-yl)amino)piperidine-1-carboxylate

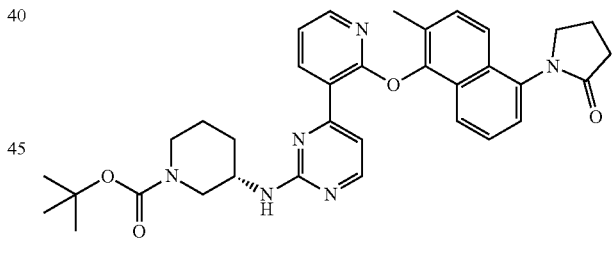

To a solution of tert-butyl (3S)-3-[[4-[2-[(5-iodo-2-methyl-1-naphthyl)oxy]-3-pyridyl]pyrimidin-2-yl]amino]piperidine-1-carboxylate (100 mg, 0.16 mmol) in 1,4-dioxane (2 mL) was added 2-pyrrolidone (100 mg, 1.18 mmol), copper (I) iodide (1.5 mg, 0.01 mmol), N, N'-dimethyl-1,2-ethanediamine (1.38 mg, 0.02 mmol) and potassium carbonate (65 mg, 0.47 mmol). The mixture was stirred at 110° C. for 12 h and then concentrated, dissolved in ethyl acetate (50 mL), and washed with H$_2$O (30 mL) and brine (30 mL). The organic phase was dried over anhydrous sodium sulfate and filtered, and the filtrate was concentrated and purified by Prep-TLC (50% ethyl acetate in petroleum ether, Rf=0.2) to yield 60 mg (64% yield) of the title compound as a white solid. LCMS (ESI) [M+H]$^+$=595.2.

Step 2: (S)-1-(6-Methyl-5-((3-(2-(piperidin-3-ylamino)pyrimidin-4-yl)pyridin-2-yl)oxy)naphthalen-1-yl)pyrrolidin-2-one

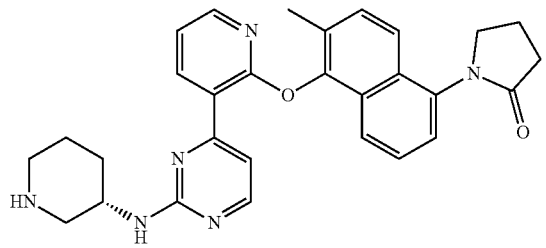 [SMILES: Cc1ccc2c(N3CCCC3=O)cccc2c1Oc1ncccc1-c1ccnc(N[C@H]2CCCNC2)n1]

To a solution of tert-butyl (3S)-3-[[4-[2-[[2-methyl-5-(2-oxopyrrolidin-1-yl)-1-naphthyl]oxy]-3-pyridyl]pyrimidin-2-yl]amino]piperidine-1-carboxylate (90 mg, 0.15 mmol) in ethyl acetate (1 mL) was added 4M hydrochloric acid (0.38 mL, 1.51 mmol) in ethyl acetate and the mixture was stirred at 20° C. for 1 h. The mixture was concentrated and ethyl acetate (50 mL) and was added followed by washing with saturated sodium bicarbonate aqueous solution (50 mL) and H$_2$O (40 mL×2). The organic phase was dried over anhydrous sodium sulfate, filtered and the filtrate was concentrated and purified by prep-TLC (50% ethyl acetate in petroleum ether, Rf=0.2) to yield 17.3 mg (22%) yield of 216 as a white solid. LCMS (ESI) [M+H]$^+$=495.2; $^1$H NMR (400 MHz, DMSO-d$_6$) δ 8.55-8.46 (m, 1H), 8.41 (d, J=5.2 Hz, 1H), 8.08-8.03 (m, 1H), 7.70-7.61 (m, 2H), 7.55-7.39 (m, 4H), 7.29-7.24 (m, 1H), 7.21-7.13 (m, 1H), 4.00-3.78 (m, 3H), 3.19-3.07 (m, 1H), 2.86-2.77 (m, 1H), 2.59-2.54 (m, 2H), 2.54-2.54 (m, 1H), 2.47-2.40 (m, 2H), 2.30-2.18 (m, 5H), 1.99-1.89 (m, 1H), 1.71-1.61 (m, 1H), 1.55-1.39 (m, 2H).

Example 217 (S)—N-(6-Methyl-5-((3-(2-(((S)-piperidin-3-yl)amino)pyrimidin-4-yl)pyridin-2-yl)oxy)naphthalen-1-yl)spiro[2.2]pentane-1-carboxamide 217

Step 1: tert-Butyl (S)-3-((4-(2-((2-methyl-5-((S)-spiro[2.2]pentane-1-carboxamido)naphthalen-1-yl)oxy)pyridin-3-yl)pyrimidin-2-yl)amino)piperidine-1-carboxylate

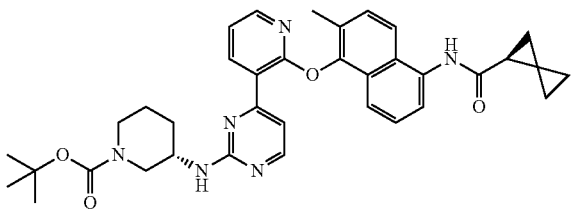 [SMILES: Cc1ccc2c(NC(=O)[C@H]3CC34CC4)cccc2c1Oc1ncccc1-c1ccnc(N[C@H]2CCCN(C(=O)OC(C)(C)C)C2)n1]

The General Procedure C was followed, using tert-butyl (3S)-3-[[4-[2-[(5-amino-2-methyl-1-naphthyl)oxy]-3-pyridyl]pyrimidin-2-yl]amino]piperidine-1-carboxylate (300 mg, 0.57 mmol), spiro[2.2]pentane-1-carboxylic acid (95.8 mg, 0.85 mmol), DIPEA (0.29 mL, 1.71 mmol), and HATU (442 mg, 1.14 mmol) in DMF (3 mL) was stirred at room temperature overnight to afford 325 mg (91.9% yield) of the title compound as a brown solid. The crude product was purified via reverse-phase HPLC and chiral SFC separation, isomer-1 (t$_R$=1.107 min) affording the desired product in a yield of 124 mg and isomer-2 (t$_R$=1.503 min) in a yield of 145 mg. LCMS (ESI) [M+H]$^+$=621.

Step 2: N-(6-Methyl-5-((3-(2-(((S)-piperidin-3-yl)amino)pyrimidin-4-yl)pyridin-2-yl)oxy)naphthalen-1-yl)spiro[2.2]pentane-1-carboxamide

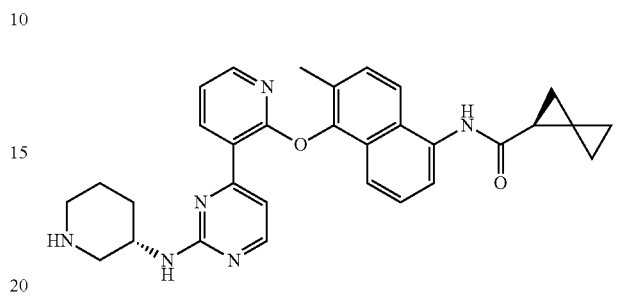

The General Procedure B was followed, using tert-butyl (S)-3-((4-(2-((2-methyl-5-((S)-spiro[2.2]pentane-1-carboxamido)naphthalen-1-yl)oxy)pyridin-3-yl)pyrimidin-2-yl)amino)piperidine-1-carboxylate (isomer-1, 124 mg, 0.20 mmol). The crude product was lyophilized to yield 111 mg (99.5% yield) of 217 (isomer-1) as an off-white solid. The absolute configuration of 217 and 218 was randomly assigned and may be later determined. LCMS (ESI) [M+H]$^+$=521; $^1$H NMR (400 MHz, DMSO-d$_6$) δ 10.00 (s, 1H), 8.82-8.53 (m, 4H), 8.48 (d, J=5.2 Hz, 1H), 8.05 (dd, J=4.8, 2.0 Hz, 1H), 7.94 (d, J=8.7 Hz, 1H), 7.67 (s, 1H), 7.58 (d, J=5.2 Hz, 1H), 7.54-7.44 (m, 3H), 7.38 (dd, J=8.5, 7.4 Hz, 1H), 7.27 (dd, J=7.6, 4.8 Hz, 1H), 4.26 (s, 1H), 3.23 (s, 1H), 2.86 (s, 2H), 2.46 (s, 1H), 2.22 (s, 3H), 2.07-1.89 (m, 2H), 1.81-1.59 (m, 2H), 1.44 (t, J=3.9 Hz, 1H), 1.36 (s, 1H), 1.00-0.76 (m, 4H).

Example 218 (R)—N-(6-Methyl-5-((3-(2-(((S)-piperidin-3-yl)amino)pyrimidin-4-yl)pyridin-2-yl)oxy)naphthalen-1-yl)spiro[2.2]pentane-1-carboxamide 218

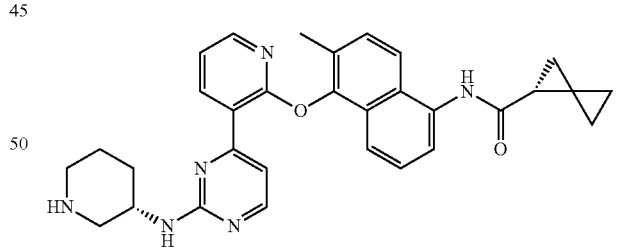

The General Procedure B was followed, using tert-butyl (S)-3-((4-(2-((2-methyl-5-((R)-spiro[2.2]pentane-1-carboxamido)naphthalen-1-yl)oxy)pyridin-3-yl)pyrimidin-2-yl)amino)piperidine-1-carboxylate (isomer-2, 145 mg, 0.26 mmol). The crude product was lyophilized to yield 109 mg (83.5% yield) of 218 (isomer-2) as an off-white solid. LCMS (ESI) [M+H]+=521; $^1$H NMR (400 MHz, DMSO-d$_6$) δ 10.01 (s, 1H), 8.83-8.53 (m, 4H), 8.48 (d, J=5.2 Hz, 1H), 8.05 (dd, J=4.8, 2.0 Hz, 1H), 7.94 (d, J=8.7 Hz, 1H), 7.66 (s, 1H), 7.58 (d, J=5.2 Hz, 1H), 7.55-7.43 (m, 3H), 7.38 (dd, J=8.5, 7.4 Hz, 1H), 7.27 (dd, J=7.6, 4.8 Hz, 1H), 4.26 (s, 1H), 3.21 (d, J=12.5 Hz, 1H), 2.85 (d, J=13.7 Hz, 2H), 2.48-2.40 (m, 1H), 2.22 (s, 3H), 2.07-1.98 (m, 1H), 1.97-1.88 (m, 1H), 1.79-1.57 (m, 2H), 1.44 (t, J=3.8 Hz, 1H), 1.41-1.32 (m, 1H), 1.01-0.78 (m, 4H).

Example 219 (S)-3,3-Difluoro-N-(6-methyl-5-(3-(2-(piperidin-3-ylamino)pyrimidin-4-yl)pyridin-2-yloxy)naphthalen-1-yl)cyclobutanecarboxamide 219

Step 1: (S)-tert-Butyl 3-(4-(2-(5-(3,3-difluorocyclobutanecarboxamido)-2-methylnaphthalen-1-yloxy)pyridin-3-yl)pyrimidin-2-ylamino)piperidine-1-carboxylate

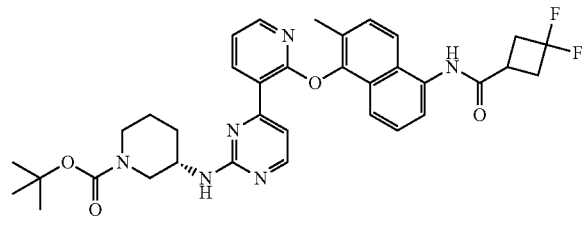 [SMILES: Cc1ccc2c(NC(=O)C3CC(F)(F)C3)cccc2c1Oc1ncccc1-c1ccnc(N[C@H]2CCCN(C(=O)OC(C)(C)C)C2)n1]

The General Procedure C was followed, using tert-butyl (3S)-3-[[4-[2-[(5-amino-2-methyl-1-naphthyl)oxy]-3-pyridyl]pyrimidin-2-yl]amino]piperidine-1-carboxylate (50 mg, 0.095 mmol), HATU (72 mg, 0.19 mmol), diisopropylethylamine (36 mg, 0.29 mmol), and 3,3-difluorocyclobutanecarboxylic acid (26 mg, 0.19 mmol). The product obtained after workup was used in step 2 without further purification. LCMS (ESI) [M+H]$^+$=645.4.

Step 2: (S)-3,3-Difluoro-N-(6-methyl-5-(3-(2-(piperidin-3-ylamino)pyrimidin-4-yl)pyridin-2-yloxy)naphthalen-1-yl)cyclobutanecarboxamide

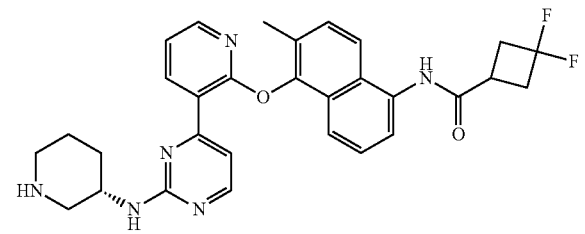 [SMILES: Cc1ccc2c(NC(=O)C3CC(F)(F)C3)cccc2c1Oc1ncccc1-c1ccnc(N[C@H]2CCCNC2)n1]

To the crude (S)-tert-butyl 3-(4-(2-(5-(3,3-difluorocyclobutanecarboxamido)-2-methylnaphthalen-1-yloxy)pyridin-3-yl)pyrimidin-2-ylamino)piperidine-1-carboxylate from step 1 in DCM (6 mL) was added trifluoroacetic acid (1 mL). The mixture was concentrated and the residue purified by Prep-HPLC to yield 24 mg (47% yield) of 219 as a white solid. LCMS (ESI): [M+H]$^+$=545.2; $^1$H NMR (400 MHz, DMSO-d$_6$) δ 10.11 (s, 1H), 8.56-8.43 (m, 1H), 8.41 (d, J=5.1 Hz, 1H), 8.03 (dd, J=4.8, 2.0 Hz, 1H), 7.90 (d, J=8.7 Hz, 1H), 7.71-7.60 (m, 1H), 7.55-7.51 (m, 2H), 7.42 (m, 2H), 7.26 (dd, J=7.6, 4.8 Hz, 1H), 7.12 (d, J=8.0 Hz, 1H), 1H), 3.89 (br s, 1H), 3.37 (m, 1H), 3.10 (d, J=11.8 Hz, 1H), 2.96-2.73 (m, 5H), 2.48-2.36 (m, 2H), 2.22 (s, 3H), 1.92-1.89 (m, 1H), 1.66-1.63 (m, 1H), 1.48-1.44 (m, 2H).

Example 220 (S)—N-(6-Methyl-5-(3-(2-(piperidin-3-ylamino)pyrimidin-4-yl)pyridin-2-yloxy)naphthalen-1-yl)-1-(trifluoromethyl)cyclopropanecarboxamide 220

Step 1: (S)-tert-Butyl 3-(4-(2-(2-methyl-5-(1-(trifluoromethyl)cyclopropanecarboxamido)naphthalen-1-yloxy)pyridin-3-yl)pyrimidin-2-ylamino)piperidine-1-carboxylate

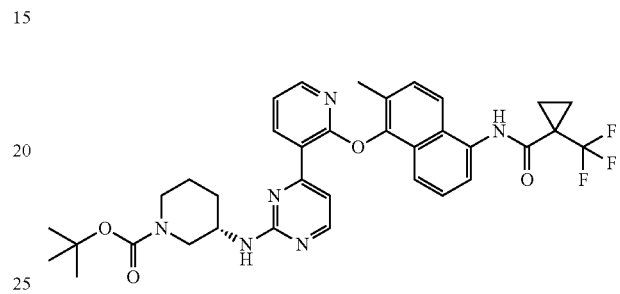

The General Procedure C was followed, using tert-butyl (3S)-3-[[4-[2-[(5-amino-2-methyl-1-naphthyl)oxy]-3-pyridyl]pyrimidin-2-yl]amino]piperidine-1-carboxylate (50 mg, 0.095 mmol), HATU (72 mg, 0.19 mmol), diisopropylethylamine (36 mg, 0.29 mmol), and 1-(trifluoromethyl)cyclopropane-1-carboxylic acid (22 mg, 0.14 mmol). The product obtained after workup was used in step 2 without further purification. LCMS (ESI) [M+H]$^+$=663.3.

Step 2: (S)—N-(6-Methyl-5-(3-(2-(piperidin-3-ylamino)pyrimidin-4-yl)pyridin-2-yloxy)naphthalen-1-yl)-1-(trifluoromethyl)cyclopropanecarboxamide

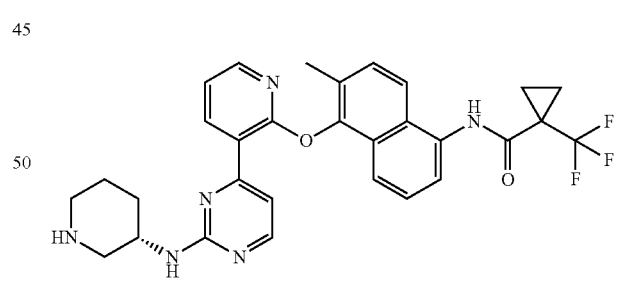

To the crude (S)-tert-butyl 3-(4-(2-(2-methyl-5-(1-(trifluoromethyl)cyclopropanecarboxamido)naphthalen-1-yloxy)pyridin-3-yl)pyrimidin-2-ylamino)piperidine-1-carboxylate from step 1 in DCM (6 mL) was added trifluoroacetic acid (1 mL). The mixture was concentrated and the residue purified by Prep-HPLC to yield 1.6 mg (3% yield) of 220 as a white solid. LCMS (ESI): [M+H]$^+$=563.2.

Example 221 (S)—N-(2-Fluoro-6-methyl-5-((3-(2-(piperidin-3-ylamino)pyrimidin-4-yl)pyridin-2-yl)oxy)naphthalen-1-yl)propane-1-sulfonamide 221

Step 1: ((5-Bromo-6-fluoro-3,4-dihydronaphthalen-1-yl)oxy)trimethylsilane

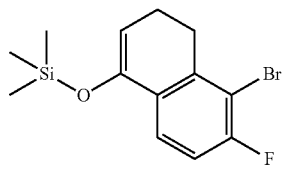 [SMILES: C[Si](C)(C)OC1=CCCc2c1ccc(F)c2Br]

To a solution of 5-bromo-6-fluoro-tetralin-1-one (5.0 g, 20.57 mmol) and triethylamine (11.56 mL, 82.28 mmol) in anhydrous dichloromethane (50 mL) was added trimethylsilyl trifluoromethanesulfonate (7.45 mL, 41.14 mmol) dropwise at 0° C. under nitrogen atmosphere. The reaction mixture was stirred at 25° C. for 2 h. The reaction was then quenched with ice water (50 mL) and extracted with methyl tert butyl ether (50 mL). The organic layer was separated, dried over anhydrous sodium sulfate, filtered and concentrated in vacuo to yield 6.4 g (crude) of the title compound as a yellow oil.

Step 2: 5-Bromo-6-fluoronaphthalen-1-ol

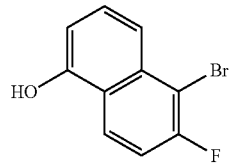 [SMILES: Oc1cccc2c(Br)c(F)ccc12]

To a solution of ((5-bromo-6-fluoro-3,4-dihydronaphthalen-1-yl)oxy)trimethylsilane (6.0 g, 19.03 mmol) in anhydrous dimethyl sulfoxide (180 mL) was added palladium (II)acetate (427 mg, 1.9 mmol). The reaction mixture was stirred at 35° C. for 16 h under an oxygen atmosphere (15 Psi). After the addition of water (200 mL) at 0° C., the reaction mixture was filtered and then extracted with ethyl acetate (100 mL×2). The combined organic layers were separated, dried over anhydrous sodium sulfate, filtered and concentrated in vacuo. The residue was purified via flash silica chromatography (solvent gradient: 0-2% ethyl acetate in petroleum ether) to yield 3.5 g (76% yield) of the title compound as a pale brown solid. $^1$H NMR (400 MHz, CDCl$_3$) δ 8.22-8.17 (m, 1H), 7.77 (d, J=8.4 Hz, 1H), 7.41 (t, J=8.4 Hz, 1H), 7.24 (d, J=7.6 Hz, 1H), 6.80 (d, J=7.6 Hz, 1H).

Step 3: 5-Bromo-2-((diethylamino)methyl)-6-fluoronaphthalen-1-ol

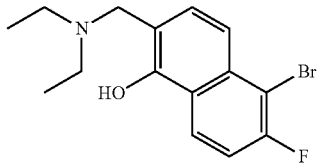 [SMILES: CCN(CC)Cc1ccc2c(Br)c(F)ccc2c1O]

To a solution of 5-bromo-6-fluoronaphthalen-1-ol (4.0 g, 16.59 mmol) and 38% aqueous formaldehyde (1.34 mL, 18.25 mmol) in methanol (30 mL) was added diethylamine (1.97 mL, 19.08 mmol). The mixture was stirred at 25° C. for 12 h. The mixture was concentrated in vacuo and the residue was taken up in ethyl acetate (50 mL), washed with H$_2$O (50 mL×2) and saturated brine solution (50 mL). The organic layer was dried over sodium sulfate, filtered and concentrated in vacuo. The residue was purified via flash silica chromatography (solvent gradient: 0-25% ethyl acetate in petroleum ether) to yield 3.5 g (65% yield) of the title compound as red brown oil. $^1$H NMR (400 MHz, CDCl$_3$) δ 8.26-8.21 (m, 1H), 7.60 (d, J=8.4 Hz, 2H), 7.25-7.19 (m, 2H), 3.93 (s, 2H), 2.69 (q, J=7.6 Hz, 4H), 1.16 (t, J=7.6 Hz, 6H).

Step 4: N-((1-(Benzyloxy)-5-bromo-6-fluoronaphthalen-2-yl)methyl)-N-ethylethanamine

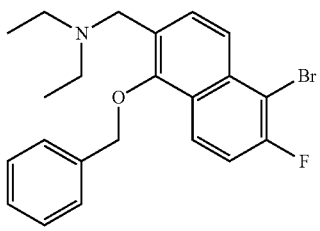 [SMILES: CCN(CC)Cc1ccc2c(Br)c(F)ccc2c1OCc1ccccc1]

To a solution of 5-bromo-2-((diethylamino)methyl)-6-fluoronaphthalen-1-ol (3.5 g, 10.73 mmol) and potassium carbonate (2.97 g, 21.46 mmol) in DMF (35 mL) was added benzyl bromide (1.84 g, 10.73 mmol) dropwise. The resulting mixture was stirred at 25° C. for 16 h. The mixture was filtered and concentrated in vacuo. The crude product was purified via flash silica chromatography (solvent gradient: 0-10% ethyl acetate in petroleum ether) to yield 3.5 g (78% yield) of the title compound as a red oil. $^1$H NMR (400 MHz, CDCl$_3$) δ 8.08-8.05 (m, 1H), 7.99 (d, J=8.4 Hz, 1H), 7.81 (d, J=8.4 Hz, 1H), 7.52-7.48 (m, 2H), 7.47-7.40 (m, 3H), 7.31-7.28 (m, 1H), 5.05 (s, 2H), 3.74 (s, 2H), 2.56 (q, J=7.6 Hz, 4H), 1.04 (t, J=7.6 Hz, 6H).

Step 5: N-(5-(Benzyloxy)-6-((diethylamino)methyl)-2-fluoronaphthalen-1-yl)propane-1-sulfonamide

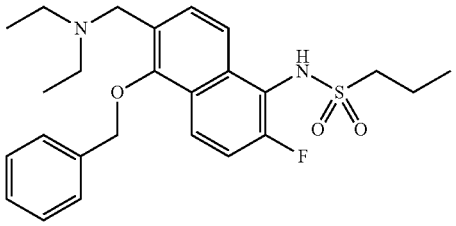 [SMILES: CCCS(=O)(=O)Nc1c(F)ccc2c(OCc3ccccc3)c(CN(CC)CC)ccc12]

To a solution of N-[(1-benzyloxy-5-bromo-6-fluoro-2-naphthyl)methyl]-N-ethyl-ethanamine (1.0 g, 2.4 mmol), propane-1-sulfonamide (355 mg, 2.88 mmol) and potassium carbonate (664 mg, 4.8 mmol) in 2-methyltetrahydrofuran (15 mL) were added 2-di-tert-butylphosphino-2',4',6'-triisopropylbiphenyl (102 mg, 0.24 mmol) and allyl palladium(II) chloride dimer (44 mg, 0.12 mmol). The mixture was heated to 80° C. for 12 h under an argon atmosphere. The mixture was filtered and concentrated in vacuo. The residue was purified via flash silica chromatography (solvent gradient: 0-1% methanol in dichloromethane) to yield 500 mg (45% yield) of the title compound as a white solid. $^1$H NMR (400 MHz, CDCl$_3$) δ 8.14-8.08 (m, 2H), 7.80 (d, J=8.8 Hz, 1H), 7.52 (d, J=8.8 Hz, 2H), 7.47-7.40 (m, 3H), 7.31-7.28 (m, 1H), 5.04 (s, 2H), 3.74 (s, 2H), 3.25-3.21 (m, 2H), 2.56 (q, J=7.6 Hz, 4H), 2.05-1.98 (m, 2H), 1.11 (t, J=7.6 Hz, 3H), 1.04 (t, J=7.2 Hz, 6H).

Step 6: N-(2-Fluoro-5-hydroxy-6-methylnaphthalen-1-yl)propane-1-sulfonamide

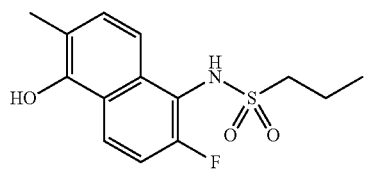 [SMILES: CCCS(=O)(=O)Nc1c(F)ccc2c(O)c(C)ccc12]

To a solution of N-[5-benzyloxy-6-(diethylaminomethyl)-2-fluoro-1-naphthyl]propane-1-sulfonamide (300 mg, 0.65 mmol) in ethanol (120 mL) was added 10% weight palladium (139 mg, 0.13 mmol) on carbon. The mixture was stirred at 25° C. under hydrogen gas (15 Psi) for 1 h. And acetic acid (0.12 mL, 1.96 mmol) was added and the mixture was stirred at 25° C. under hydrogen gas (15 Psi) for 16 h. The mixture was filtered and concentrated in vacuo. The residue was purified by Prep-TLC (50% ethyl acetate in petroleum ether) to 50 mg (26% yield) of the title compound as a yellow solid.

Step 7: (S)-tert-Butyl 3-((4-(2-((6-fluoro-2-methyl-5-(propylsulfonamido)naphthalen-1-yl)oxy) pyridine-3-yl)pyrimidin-2-yl)amino)piperidine-1-carboxylate

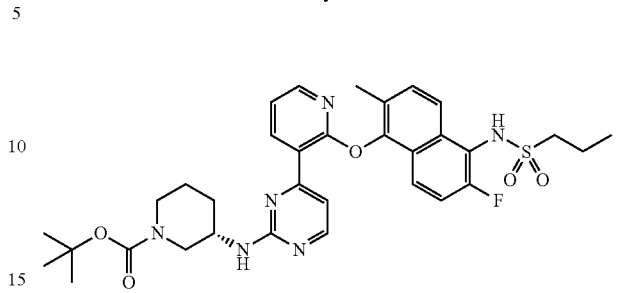

To a solution of (S)-tert-butyl 3-((4-(2-((6-fluoro-2-methyl-5-(propylsulfonamido)naphthalen-1-yl)oxy) pyridine-3-yl)pyrimidin-2-yl)amino)piperidine-1-carboxylate (38 mg, 0.10 mmol) and N-(2-fluoro-5-hydroxy-6-methyl-1-naphthyl)propane-1-sulfonamide (30 mg, 0.10 mmol) in anhydrous dimethyl sulfoxide (1.5 mL) was added cesium carbonate (66 mg, 0.20 mmol). The mixture was heated to 80° C. for 1 h. The mixture was filtered and water (5 mL) was added. The mixture was extracted with ethyl acetate (10 mL×2). The combined organic layers were dried over anhydrous sodium sulfate, filtered and concentrated in vacuo. The residue was purified by Prep-TLC (50% ethyl acetate in petroleum ether) to yield 30 mg (46% yield) of the title compound as a pale brown solid. LCMS (ESI) [M+Na]$^+$=673.1.

Step 8: (S)—N-(2-Fluoro-6-methyl-5-((3-(2-(piperidin-3-ylamino)pyrimidin-4-yl)pyridin-2-yl)oxy) naphthalen-1-yl)propane-1-sulfonamide

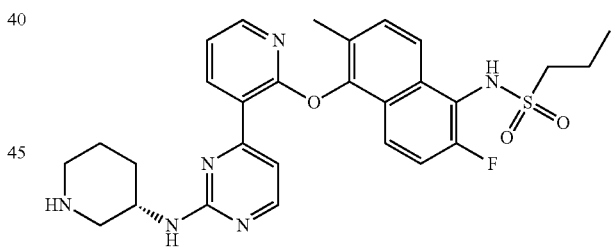

To a solution of (S)-tert-butyl 3-((4-(2-((6-fluoro-2-methyl-5-(propylsulfonamido)naphthalen-1-yl)oxy) pyridine-3-yl)pyrimidin-2-yl)amino)piperidine-1-carboxylate (30 mg, 0.05 mmol) in ethyl acetate (0.50 mL) was added hydrochloric acid (4 M in ethyl acetate, 0.35 mL, 1.38 mmol). The reaction mixture was stirred at 20° C. for 1 h. The mixture was concentrated in vacuo and the residue was taken up in ethyl acetate (10 mL) and saturated sodium bicarbonate (5 mL). The organic layer was separated, dried over anhydrous sodium sulfate, filtered and concentrated in vacuo. The residue was purified by prep-TLC (10% methanol in dichloromethane) to yield 15 mg (59% yield) of 221 as a pale yellow solid. LCMS (ESI): [M+H]$^+$=551. $^1$H NMR (400 MHz, DMSO-d$_6$) δ 8.54-8.50 (m, 1H), 8.42 (d, J=5.2 Hz, 1H), 8.08-8.04 (m, 2H), 7.71-7.68 (m, 1H), 7.61 (d, J=8.8 Hz, 1H), 7.50-7.44 (m, 2H), 7.29-7.21 (m, 2H), 3.99-3.95 (m, 1H), 3.18-3.13 (m, 3H), 2.90-2.86 (m, 1H), 2.54-2.51 (m, 2H), 2.19 (s, 3H), 1.98-1.92 (m, 1H), 1.88-1.82 (m, 2H), 1.73-1.69 (m, 1H), 1.54-1.46 (2H), 1.02 (t, J=7.6 Hz, 3H).

Example 222 (1R,2R)-2-Fluoro-N-[6-methyl-5-[[3-[2-[[(3S)-3-piperidyl]amino]pyrimidin-4-yl]-2-pyridyl]oxy]-1-naphthyl]cyclopropanecarboxamide 222

The General Procedure B was followed, using tert-butyl (S)-3-((4-(2-((5-(((1R,2R)-2-fluorocyclopropane-1-carboxamido)-2-methylnaphthalen-1-yl)oxy)pyridin-3-yl)pyrimidin-2-yl)amino)piperidine-1-carboxylate from Example 212 (52 mg), DCM (4 mL) and hydrochloric acid (4 M in dioxane, 3 mL, 12 mmol). The residue was purified via reverse-phase HPLC and lyophilized to yield 19.3 mg of 222. LCMS (ESI): [M+H]$^+$=513.2; $^1$H NMR (400 MHz, DMSO-d$_6$) δ 10.24 (s, 1H), 8.55-8.50 (m, 1H), 8.42 (d, J=5.1 Hz, 1H), 8.03 (dd, J=4.8, 2.0 Hz, 1H), 7.94 (d, J=8.5 Hz, 1H), 7.64 (d, J=7.4 Hz, 1H), 7.52 (d, J=8.8 Hz, 2H), 7.44 (d, J=5.1 Hz, 1H), 7.43-7.37 (m, 1H), 7.26 (dd, J=7.6, 4.8 Hz, 1H), 7.12 (d, J=7.9 Hz, 1H), 5.12-4.89 (m, 1H), 3.89 (s, 1H), 3.14-3.07 (m, 1H), 2.84-2.77 (m, 1H), 2.46-2.39 (m, 1H), 2.31-2.25 (m, 1H), 2.22 (s, 3H), 1.97-1.88 (m, 1H), 1.73-1.62 (m, 2H), 1.56-1.42 (m, 2H), 1.23-1.14 (m, 1H).

Example 223 (S)-4-(2-((5-((Cyclopropylmethyl)amino)-2-methylnaphthalen-1-yl)oxy)pyridin-3-yl)-N-(piperidin-3-yl)pyrimidin-2-amine 223

Step 1: tert-Butyl (S)-3-((4-(2-((5-(((cyclopropylmethyl)amino)-2-methylnaphthalen-1-yl)oxy)pyridin-3-yl)pyrimidin-2-yl)amino)piperidine-1-carboxylate

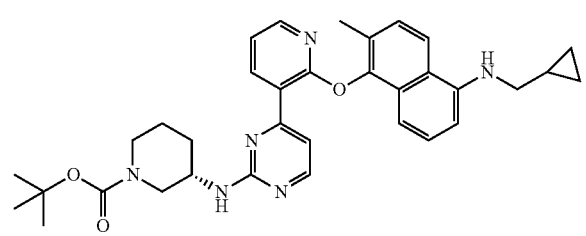 [SMILES: Cc1ccc2c(NCC3CC3)cccc2c1Oc1ncccc1-c1ccnc(N[C@H]2CCCN(C(=O)OC(C)(C)C)C2)n1]

The General Procedure E was followed, using tert-butyl (3S)-3-[[4-[2-[(5-amino-2-methyl-1-naphthyl)oxy]-3-pyridyl]pyrimidin-2-yl]amino]piperidine-1-carboxylate (100 mg, 0.19 mmol) and (bromomethyl)cyclopropane (77 mg, 0.57 mmol). The crude material was purified by silica gel chromatography (12 g column), eluting with 0-5% MeOH/DCM to afford 46 mg (42% yield) of the title compound as a brown solid. LCMS (ESI) [M+H]$^+$=581.

Step 2: (S)-4-(2-((5-((Cyclopropylmethyl)amino)-2-methylnaphthalen-1-yl)oxy)pyridin-3-yl)-N-(piperidin-3-yl)pyrimidin-2-amine

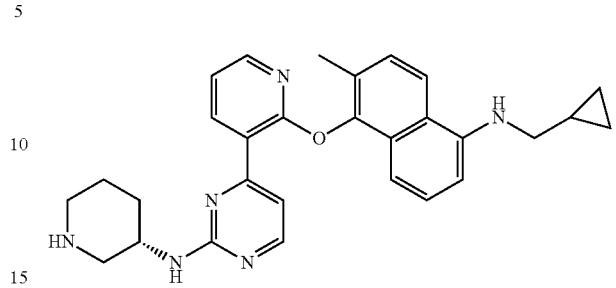

The General Procedure B was followed, using tert-butyl (S)-3-((4-(2-((5-((cyclopropylmethyl)amino)-2-methylnaphthalen-1-yl)oxy)pyridin-3-yl)pyrimidin-2-yl)amino)piperidine-1-carboxylate (46 mg, 0.08 mmol). The crude product was purified via reverse-phase HPLC and lyophilized to yield 21 mg (55.7% yield) of 223 as an off-white solid. LCMS (ESI) [M+H]$^+$=481; $^1$H NMR (400 MHz, DMSO-d$_6$) δ 8.48 (s, 1H), 8.39 (d, J=5.1 Hz, 1H), 8.04 (d, J=8.6 Hz, 1H), 8.00 (dd, J=4.8, 2.0 Hz, 1H), 7.43 (d, J=5.1 Hz, 1H), 7.34 (d, J=8.7 Hz, 1H), 7.22 (dd, J=7.6, 4.8 Hz, 1H), 7.16 (dd, J=8.3, 7.7 Hz, 1H), 7.09 (d, J=8.0 Hz, 1H), 6.83 (d, J=8.4 Hz, 1H), 6.49-6.45 (m, 1H), 6.28-6.21 (m, 1H), 3.87 (s, 1H), 3.09 (s, 3H), 2.78 (d, J=12.2 Hz, 1H), 2.43 (dd, J=12.8, 4.1 Hz, 3H), 2.18 (s, 3H), 1.92 (s, 1H), 1.64 (d, J=11.8 Hz, 1H), 1.54-1.38 (m, 1H), 1.26-1.16 (m, 1H), 0.54-0.46 (m, 2H), 0.29 (dd, J=4.8, 1.6 Hz, 2H).

Example 224 (S)-4-(2-((5-((2-Cyclopropylethyl)amino)-2-methylnaphthalen-1-yl)oxy)pyridin-3-yl)-N-(piperidin-3-yl)pyrimidin-2-amine 224

Step 1: tert-Butyl (S)-3-((4-(2-((5-((2-Cyclopropylethyl)amino)-2-methylnaphthalen-1-yl)oxy)pyridin-3-yl)pyrimidin-2-yl)amino)piperidine-1-carboxylate

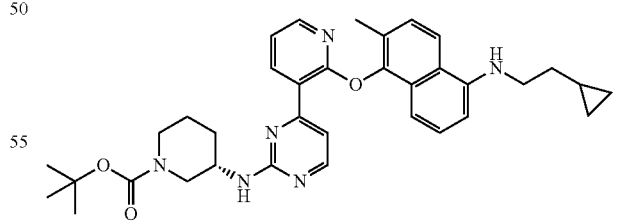

The General Procedure E was followed, using tert-butyl (3S)-3-[[4-[2-[(5-amino-2-methyl-1-naphthyl)oxy]-3-pyridyl]pyrimidin-2-yl]amino]piperidine-1-carboxylate (100 mg, 0.19 mmol) and (2-bromoethyl)cyclopropane (89 mg, 0.57 mmol) to afford 46 mg (47% yield) of the title compound as a brown solid. It was carried on as is. LCMS (ESI) [M+H]$^+$=595.

Step 2: (S)-4-(2-((5-((2-Cyclopropylethyl)amino)-2-methylnaphthalen-1-yl)oxy)pyridin-3-yl)-N-(piperidin-3-yl)pyrimidin-2-amine

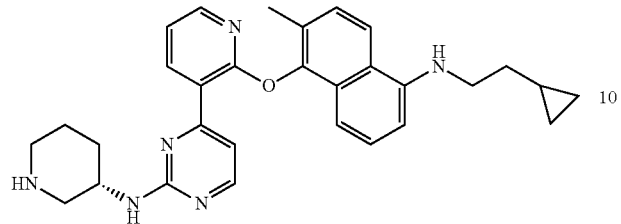

The General Procedure B was followed, using tert-butyl (S)-3-((4-(2-((5-((2-cyclopropylethyl)amino)-2-methylnaphthalen-1-yl)oxy)pyridin-3-yl)pyrimidin-2-yl)amino)piperidine-1-carboxylate (46 mg, 0.08 mmol). The crude product was purified via reverse-phase HPLC and lyophilized to yield 21 mg (55% yield) of 224 as an off-white solid. LCMS (ESI) [M+H]$^+$=495; $^1$H NMR (400 MHz, DMSO-d$_6$) δ 8.49 (d, J=11.6 Hz, 1H), 8.39 (d, J=5.1 Hz, 1H), 8.03-7.98 (m, 2H), 7.43 (d, J=5.1 Hz, 1H), 7.32 (d, J=8.7 Hz, 1H), 7.22 (dd, J=7.5, 4.8 Hz, 1H), 7.17 (t, J=8.0 Hz, 1H), 7.09 (d, J=8.0 Hz, 1H), 6.83 (d, J=8.3 Hz, 1H), 6.46-6.42 (m, 1H), 3.88 (s, 1H), 3.09 (d, J=10.9 Hz, 1H), 2.78 (d, J=12.2 Hz, 1H), 2.47-2.38 (m, 3H), 2.18 (s, 3H), 1.92 (s, 1H), 1.67-1.57 (m, 3H), 1.54-1.39 (m, 2H), 0.89-0.81 (m, 1H), 0.48-0.41 (m, 2H), 0.16-0.08 (m, 2H).

Example 225 N-(5-((3-(2-(((3S,5R)-5-Fluoropiperidin-3-yl)amino)pyrimidin-4-yl)pyridin-2-yl)oxy)-6-methylnaphthalen-1-yl)-1-(pyridin-2-yl) methanesulfonamide 225

Step 1: (3S,5R)-Benzyl 3-((tert-butoxycarbonyl)amino)-5-fluoropiperidine-1-carboxylate

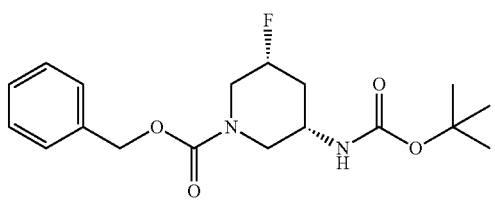 [SMILES: CC(C)(C)OC(=O)N[C@H]1C[C@@H](F)CN(C(=O)OCc2ccccc2)C1]

To a 100 mL 3-necked round-bottom flask was placed benzyl chloroformate (0.16 mL, 5.6 mmol), sodium bicarbonate (115 mg, 1.37 mmol), tert-butyl N-[(3S,5R)-5-fluoro-3-piperidyl]carbamate (300 mg, 1.37 mmol) and tetrahydrofuran (6 mL). The resulting solution was stirred at room temperature for 4 h. TLC (33% ethyl acetate in petroleum ether, Rf=0.4) showed that the reaction was complete. The residue was purified chromatography by silica gel chromatography (solvent gradient: 0-20% ethyl acetate in petroleum ether) to yield 0.35 g (72% yield) of the title compound as a white solid.

Step 2: (3S,5R)-Benzyl 3-amino-5-fluoropiperidine-1-carboxylate

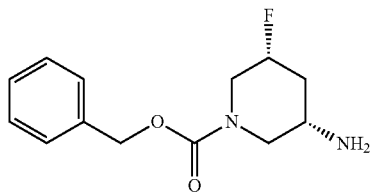 [SMILES: N[C@H]1C[C@@H](F)CN(C(=O)OCc2ccccc2)C1]

The General Procedure B was followed, using benzyl (3S,5R)-3-(tert-butoxycarbonylamino)-5-fluoro-piperidine-1-carboxylate (350 mg, 0.99 mmol), dichloromethane (5 mL) and hydrochloric acid (4 M in dioxane, 2 mL, 8 mmol). The resulting solution was stirred at room temperature for 2 h. The solution was concentrated to yield 330 mg (crude) of the title product as a white solid.

Step 3: (3S,5R)-Benzyl 3-((4-(2-((5-amino-2-methylnaphthalen-1-yl)oxy)pyridin-3-yl)pyrimidin-2-yl)amino)-5-fluoropiperidine-1-carboxylate To a 100 mL 3-necked round-bottom flask purged and maintained with an inert atmosphere of nitrogen was placed 6-methyl-5-[[3-(2-methylsulfinylpyrimidin-4-yl)-2-pyridyl]oxy]naphthalen-1-amine (300 mg, 0.77 mmol), benzyl (3S,5R)-3-amino-5-fluoro-piperidine-1-carboxylate (252 mg, 1 mmol), 1,4-dioxane (6 mL) and N,N-diisopropylethylamine (0.16 mL, 0.91 mmol). The resulting solution was stirred at 110° C. in an oil bath for 24 h, cooled to room temperature and concentrated in vacuo. The residue was purified via flash silica chromatography (solvent gradient: 5% methanol in dichloromethane) to yield 0.3 g (67% yield) of the title compound as a yellow solid. LCMS: (ES, m/z): [M+H]$^+$=579.2.

Step 4: (3R,5S)-Benzyl-3-fluoro-5-((4-(2-((2-methyl-5-(pyridin-2-ylmethylsulfonamido) naphthalen-1-yl)oxy)pyridin-3-yl)pyrimidin-2-yl)amino)piperidine-1-carboxylate

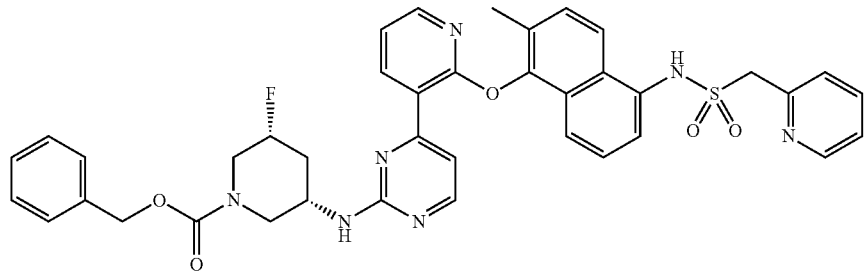

The General Procedure A was followed, using benzyl (3S,5R)-3-[[4-[2-[(5-amino-2-methyl-1-naphthyl)oxy]-3-pyridyl]pyrimidin-2-yl]amino]-5-fluoro-piperidine-1-carboxylate (300 mg, 0.52 mmol), pyridine (4 mL) and 2-pyridylmethanesulfonyl chloride (119 mg, 0.62 mmol). The residue was purified by Prep-TLC (normal phase, petroleum ether/ethyl acetate=2/1) to yield 60 mg (16% yield) of the title compound as a brown oil. LCMS (ESI) [M+H]$^+$=734.1.

Step 5: N-(5-((3-(2-(((3S,5R)-5-Fluoropiperidin-3-yl)amino)pyrimidin-4-yl)pyridin-2-yl)oxy)-6-methylnaphthalen-1-yl)-1-(pyridin-2-yl)methanesulfonamide

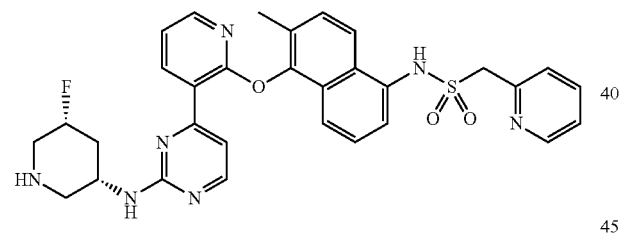

To a 100 mL 3-necked round-bottom flask was placed benzyl (3R,5S)-3-fluoro-5-[[4-[2-[[2-methyl-5-(2-pyridylmethylsulfonylamino)-1-naphthyl]oxy]-3-pyridyl]pyrimidin-2-yl]amino]piperidine-1-carboxylate (45 mg, 0.06 mmol), 1-methylimidazole (20 mg, 0.25 mmol), thiourea (23 mg, 0.31 mmol), iodotrimethylsilane (0.07 mL, 0.49 mmol) and acetonitrile (1 mL). The mixture was then stirred at room temperature for 1 h and concentrated in vacuo. The residue was purified by Prep-HPLC (mobile phase: A: water (0.05% NH$_4$OH) B: ACN) to yield 6.3 mg (17% yield) of 225 as a white solid. LCMS (ESI): [M+H]$^+$=600.2. $^1$H NMR (400 MHz, DMSO-d$_6$) δ 8.56 (d, J=4.6 Hz, 1H), 8.50 (s, 1H), 8.42 (d, J=5.2 Hz, 1H), 8.11-8.02 (m, 2H), 7.86-7.77 (m, 1H), 7.62-7.55 (m, 2H), 7.54-7.49 (m, 2H), 7.47 (d, J=5.2 Hz, 1H), 7.43 (d, J=8.0 Hz, 1H), 7.41-7.35 (m, 1H), 7.28-7.19 (m, 2H), 4.64 (s, 3H), 3.99 (s, 1H), 3.10 (m, 2H), 2.45 (m, 1H), 2.39-2.29 (m, 2H), 2.21 (s, 3H), 1.75-1.55 (m, 1H).

Example 226 2-Fluoro-N-(6-methyl-5-((3-(2-(((S)-piperidin-3-yl)amino)pyrimidin-4-yl)pyridin-2-yl)oxy)naphthalen-1-yl)-2-phenylcyclopropane-1-carboxamide 226

Step 1: tert-Butyl (3S)-3-((4-(2-((5-(2-fluoro-2-phenylcyclopropane-1-carboxamido)-2-methylnaphthalen-1-yl)oxy)pyridin-3-yl)pyrimidin-2-yl)amino)piperidine-1-carboxylate

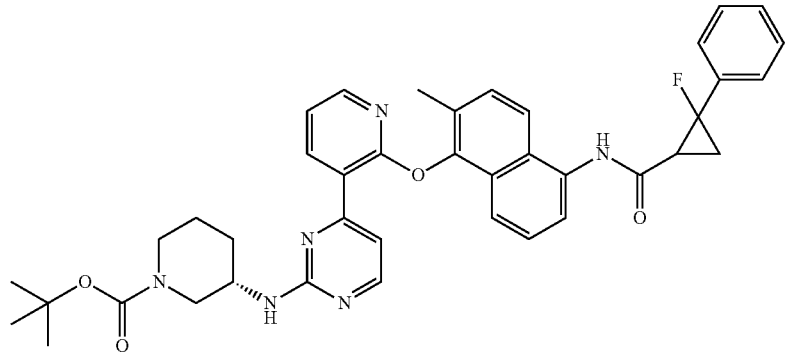 [SMILES: Cc1ccc2c(NC(=O)C3CC3(F)c3ccccc3)cccc2c1Oc1ncccc1-c1ccnc(N[C@H]2CCCN(C(=O)OC(C)(C)C)C2)n1]

The General Procedure C was followed, using tert-butyl (S)-3-((4-(2-((5-amino-2-methylnaphthalen-1-yl)oxy)pyridin-3-yl)pyrimidin-2-yl)amino)piperidine-1-carboxylate from Example 101 (210 mg, 0.40 mmol), 2-fluoro-2-phenylcyclopropanecarboxylic acid (60 mg, 0.33 mmol), DIPEA (0.174 mL, 1.0 mmol), HATU (388 mg, 1.73 mmol) and DCM (10 mL). The residue was purified via reverse-phase HPLC to provide a mixture of the two isomers. This mixture was purified via chiral reverse-phase HPLC and lyophilized to yield 31.6 mg and 34.4 mg of the two single stereoisomers enantiomeric at the 1 and 2 positions of the cyclopropyl amide.

Step 2: 2-Fluoro-N-(6-methyl-5-((3-(2-(((S)-piperidin-3-yl)amino)pyrimidin-4-yl)pyridin-2-yl)oxy)naphthalen-1-yl)-2-phenylcyclopropane-1-carboxamide

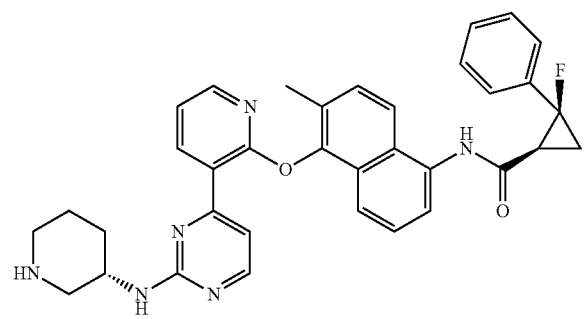 [SMILES: Cc1ccc2c(NC(=O)[C@@H]3C[C@@]3(F)c3ccccc3)cccc2c1Oc1ncccc1-c1ccnc(N[C@H]2CCCNC2)n1]

The General Procedure B was followed using tert-butyl (3S)-3-((4-(2-((5-(2-fluoro-2-phenylcyclopropane-1-carboxamido)-2-methylnaphthalen-1-yl)oxy)pyridin-3-yl)pyrimidin-2-yl)amino)piperidine-1-carboxylate (31.6 mg, 0.046 mmol), DCM (4 mL) and hydrochloric acid (4 M in dioxane, 3 mL, 12 mmol). The residue was purified via reverse-phase HPLC and lyophilized to yield 20.1 mg (74% yield) of 226. The stereochemistry was tentatively and randomly assigned. LCMS (ESI): [M+H]$^+$=589.2; $^1$H NMR (400 MHz, DMSO-d6) δ 10.35 (s, 1H), 8.50-8.45 (m, 1H), 8.43-8.39 (m, 1H), 8.00 (dd, J=4.9, 2.0 Hz, 1H), 7.61-7.53 (m, 3H), 7.47-7.36 (m, 7H), 7.31-7.27 (m, 1H), 7.25 (dd, J=7.5, 4.8 Hz, 1H), 7.12 (d, J=8.0 Hz, 1H), 3.90 (s, 1H), 2.84-2.78 (m, 1H), 2.81 (d, J=12.7 Hz, 1H), 2.50-2.40 (m, 1H), 2.19 (s, 3H), 2.07-1.99 (m, 12H), 1.95-1.83 (m, 2H), 1.68-1.61 (m, 1H), 1.53-1.39 (m, 2H).

Example 227 N-(6-Methyl-5-((3-(2-(((S)-piperidin-3-yl)amino)pyrimidin-4-yl)pyridin-2-yl)oxy)naphthalen-1-yl)-2-(trifluoromethyl)cyclopropane-1-carboxamide 227

Step 1: tert-Butyl (3S)-3-((4-(2-((2-methyl-5-(2-(trifluoromethyl)cyclopropane-1-carboxamido)naphthalen-1-yl)oxy)pyridin-3-yl)pyrimidin-2-yl)amino)piperidine-1-carboxylate

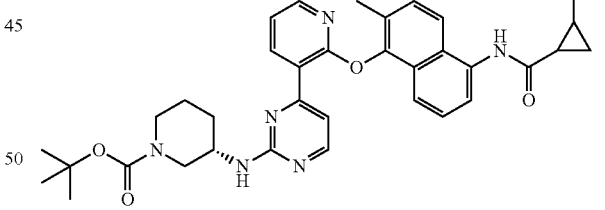

The General Procedure C was followed, using tert-butyl (S)-3-((4-(2-((5-amino-2-methylnaphthalen-1-yl)oxy)pyridin-3-yl)pyrimidin-2-yl)amino)piperidine-1-carboxylate from Example 101 (357 mg, 0.40 mmol), 2-(trifluoromethyl)cyclopropanecarboxylic acid (95 mg, 0.62 mmol), DIPEA (0.323 mL, 1.85 mmol), HATU (718 mg, 1.85 mmol) and DCM (10 mL). The residue was purified via reverse-phase HPLC to provide a mixture of the two isomers. This mixture was then purified via chiral reverse-phase HPLC and lyophilized to yield 71 mg and 61 mg of the two single stereoisomers possessing stereocenters at the 1 and 2 positions of the cyclopropyl amide.

Step 2: N-(6-Methyl-5-((3-(2-(((S)-piperidin-3-yl)amino)pyrimidin-4-yl)pyridin-2-yl)oxy)naphthalen-1-yl)-2-(trifluoromethyl)cyclopropane-1-carboxamide

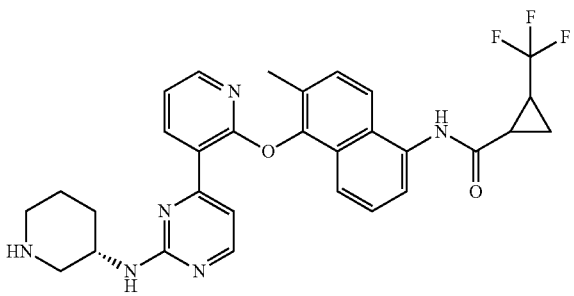 [SMILES: Cc1ccc2c(NC(=O)C3CC3C(F)(F)F)cccc2c1Oc1ncccc1-c1ccnc(N[C@H]2CCCNC2)n1]

The General Procedure B was followed, using tert-butyl (3S)-3-((4-(2-((2-methyl-5-(2-(trifluoromethyl)cyclopropane-1-carboxamido)naphthalen-1-yl)oxy)pyridin-3-yl)pyrimidin-2-yl)amino)piperidine-1-carboxylate (71 mg, 0.11 mmol), DCM (4 mL) and hydrochloric acid (4 M in dioxane, 3 mL, 12 mmol). The residue was purified via reverse-phase HPLC and lyophilized to yield 40.9 mg of 227. The stereochemistry was tentatively and randomly assigned. LCMS (ESI): [M+H]$^+$=563.2; $^1$H NMR (400 MHz, DMSO-d$_6$) δ 10.45 (s, 1H), 8.52-8.47 (m, 1H), 8.41 (d, J=5.1 Hz, 1H), 8.03 (dd, J=4.8, 2.0 Hz, 1H), 7.98 (d, J=8.7 Hz, 1H), 7.71 (d, J=7.5 Hz, 1H), 7.57-7.51 (m, 2H), 7.45-7.36 (m, 2H), 7.26 (dd, J=7.6, 4.8 Hz, 1H), 7.11 (d, J=8.1 Hz, 1H), 3.88 (s, 1H), 3.13-3.05 (m, 1H), 2.81-2.75 (m, 1H), 2.71-2.60 (m, 1H), 2.48-2.36 (m, 2H), 2.36-2.27 (m, 1H), 2.22 (s, 3H), 1.96-1.88 (m, 1H), 1.68-1.57 (m, 1H), 1.53-1.40 (m, 2H), 1.35 (t, J=7.4 Hz, 2H).

Example 228 N-(6-Methyl-5-((3-(2-(((S)-piperidin-3-yl)amino)pyrimidin-4-yl)pyridin-2-yl)oxy)naphthalen-1-yl)-2-(trifluoromethyl)cyclopropane-1-carboxamide 228

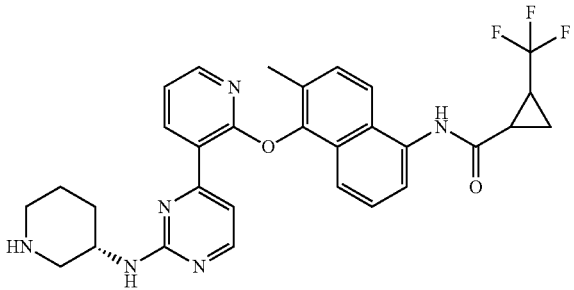 [SMILES: Cc1ccc2c(NC(=O)C3CC3C(F)(F)F)cccc2c1Oc1ncccc1-c1ccnc(N[C@H]2CCCNC2)n1]

The General Procedure B was followed, using tert-butyl (3S)-3-((4-(2-((2-methyl-5-(2-(trifluoromethyl)cyclopropane-1-carboxamido)naphthalen-1-yl)oxy)pyridin-3-yl)pyrimidin-2-yl)amino)piperidine-1-carboxylate from Example 227 (61 mg, 0.092 mmol), DCM (4 mL) and hydrochloric acid (4 M in dioxane, 3 mL, 12 mmol). The residue was purified via reverse-phase HPLC and lyophilized to yield 30.1 mg of 228. LCMS (ESI): [M+H]$^+$=563.3; $^1$H NMR (400 MHz, DMSO-d$_6$) δ 10.45 (s, 1H), 8.52-8.47 (m, 1H), 8.41 (d, J=5.1 Hz, 1H), 8.03 (dd, J=4.8, 2.0 Hz, 1H), 7.98 (d, J=8.7 Hz, 1H), 7.71 (d, J=7.5 Hz, 1H), 7.57-7.51 (m, 2H), 7.45-7.36 (m, 2H), 7.26 (dd, J=7.6, 4.8 Hz, 1H), 7.11 (d, J=8.1 Hz, 1H), 3.88 (s, 1H), 3.13-3.05 (m, 1H), 2.81-2.75 (m, 1H), 2.71-2.60 (m, 1H), 2.48-2.36 (m, 2H), 2.36-2.27 (m, 1H), 2.22 (s, 3H), 1.96-1.88 (m, 1H), 1.68-1.57 (m, 1H), 1.53-1.40 (m, 2H), 1.35 (t, J=7.4 Hz, 2H).

Example 229 2-Isopropyl-N-(6-methyl-5-((3-(2-(((S)-piperidin-3-yl)amino)pyrimidin-4-yl)pyridin-2-yl)oxy)naphthalen-1-yl)cyclopropane-1-carboxamide 229

Step 1: tert-Butyl (3S)-3-((4-(2-((5-(2-isopropylcyclopropane-1-carboxamido)-2-methylnaphthalen-1-yl)oxy)pyridin-3-yl)pyrimidin-2-yl)amino)piperidine-1-carboxylate

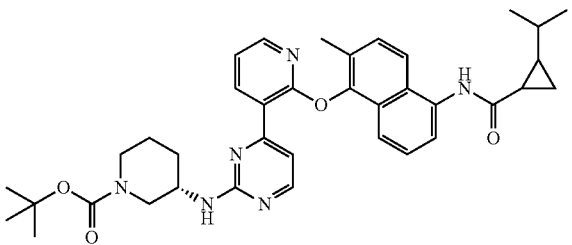 [SMILES: Cc1ccc2c(NC(=O)C3CC3C(C)C)cccc2c1Oc1ncccc1-c1ccnc(N[C@H]2CCCN(C(=O)OC(C)(C)C)C2)n1]

The General Procedure C was followed, using tert-butyl (S)-3-((4-(2-((5-amino-2-methylnaphthalen-1-yl)oxy)pyridin-3-yl)pyrimidin-2-yl)amino)piperidine-1-carboxylate from Example 101 (362 mg, 0.69 mmol), 2-isopropylcyclopropanecarboxylic acid (80 mg, 0.62 mmol), DIPEA (0.327 mL, 1.87 mmol), HATU (727 mg, 1.87 mmol) and DCM (10 mL). The residue was purified via reverse-phase HPLC to provide a mixture of the two isomers. This mixture purified via chiral reverse-phase HPLC and lyophilized to yield 98 mg and 78 mg of the two single stereoisomers enantiomeric at the 1 and 2 positions of the cyclopropyl amide.

Step 2: 2-Isopropyl-N-(6-methyl-5-((3-(2-(((S)-piperidin-3-yl)amino)pyrimidin-4-yl)pyridin-2-yl)oxy)naphthalen-1-yl)cyclopropane-1-carboxamide

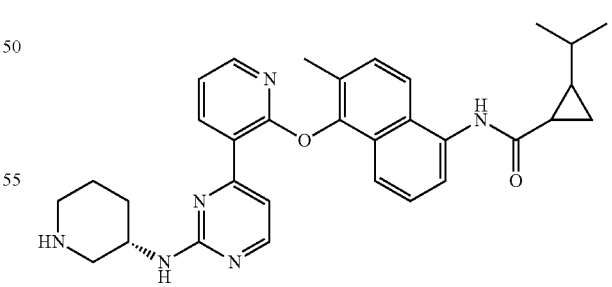

The General Procedure B was followed, using tert-butyl (3S)-3-((4-(2-((5-(2-isopropylcyclopropane-1-carboxamido)-2-methylnaphthalen-1-yl)oxy)pyridin-3-yl)pyrimidin-2-yl)amino)piperidine-1-carboxylate (98 mg, 0.153 mmol), DCM (4 mL) and hydrochloric acid (4 M in dioxane, 3 mL, 12 mmol). The residue was purified via reverse-phase HPLC and lyophilized to yield 45 mg of 229. LCMS (ESI):

[M+H]⁺=537.2; ¹H NMR (400 MHz, DMSO-d₆) δ 10.10 (s, 1H), 8.53-8.47 (m, 1H), 8.42 (d, J=5.1 Hz, 1H), 8.03 (dd, J=4.8, 2.0 Hz, 1H), 7.97 (d, J=8.6 Hz, 1H), 7.68 (d, J=7.5 Hz, 1H), 7.53 (d, J=8.8 Hz, 1H), 7.50-7.45 (m, 1H), 7.45 (d, J=5.1 Hz, 1H), 7.38 (dd, J=8.5, 7.5 Hz, 1H), 7.25 (dd, J=7.6, 4.8 Hz, 1H), 7.16 (d, J=7.9 Hz, 1H), 3.93 (s, 1H), 3.17-3.09 (m, 1H), 2.87-2.80 (m, 1H), 2.22 (s, 3H), 1.98-1.90 (m, 2H), 1.70-1.63 (m, 1H), 1.56-1.41 (m, 2H), 1.24-1.08 (m, 2H), 1.07-0.96 (m, 8H), 0.80-0.73 (m, 1H).

Example 230 2-Isopropyl-N-(6-methyl-5-((3-(2-(((S)-piperidin-3-yl)amino)pyrimidin-4-yl)pyridin-2-yl)oxy)naphthalen-1-yl)cyclopropane-1-carboxamide 230

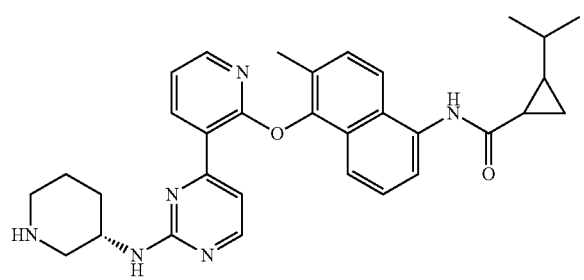 [SMILES: Cc1ccc2c(NC(=O)C3CC3C(C)C)cccc2c1Oc1ncccc1-c1ccnc(N[C@H]2CCCNC2)n1]

The General Procedure B was followed using tert-butyl (3S)-3-((4-(2-((5-(2-isopropylcyclopropane-1-carboxamido)-2-methylnaphthalen-1-yl)oxy)pyridin-3-yl)pyrimidin-2-yl)amino)piperidine-1-carboxylate (78 mg, 0.20 mmol), DCM (4 mL) and hydrochloric acid (4 M in dioxane, 3 mL, 12 mmol). The residue was purified via reverse-phase HPLC and lyophilized to yield 39.9 mg of 230. LCMS (ESI): [M+H]⁺=537.3; ¹H NMR (400 MHz, DMSO-d₆) δ 10.10 (s, 1H), 8.53-8.47 (m, 1H), 8.42 (d, J=5.1 Hz, 1H), 8.03 (dd, J=4.8, 2.0 Hz, 1H), 7.97 (d, J=8.6 Hz, 1H), 7.68 (d, J=7.5 Hz, 1H), 7.53 (d, J=8.8 Hz, 1H), 7.50-7.45 (m, 1H), 7.44 (d, J=5.1 Hz, 1H), 7.38 (dd, J=8.5, 7.5 Hz, 1H), 7.25 (dd, J=7.6, 4.8 Hz, 1H), 7.12 (d, J=7.9 Hz, 1H), 3.88 (s, 1H), 3.13-3.05 (m, 1H), 2.83-2.77 (m, 1H), 2.47-2.39 (m, 1H), 2.22 (s, 3H), 1.98-1.90 (m, 2H), 1.68-1.61 (m, 1H), 1.56-1.41 (m, 2H), 1.24-1.08 (m, 2H), 1.07-0.96 (m, 8H), 0.80-0.73 (m, 1H).

Example 231 (1R,2S)-2-Methyl-N-(6-methyl-5-((3-(2-(((S)-piperidin-3-yl)amino)pyrimidin-4-yl)pyridin-2-yl)oxy)naphthalen-1-yl)cyclopropane-1-carboxamide 231

Step 1: tert-Butyl (S)-3-((4-(2-((2-methyl-5-((1R,2S)-2-methylcyclopropane-1-carboxamido)naphthalen-1-yl)oxy)pyridin-3-yl)pyrimidin-2-yl)amino)piperidine-1-carboxylate

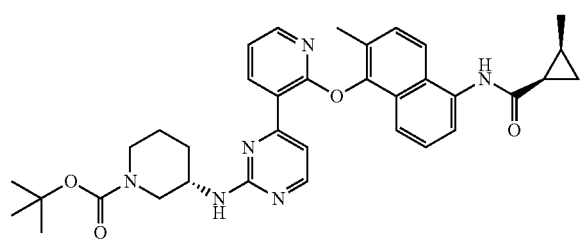 [SMILES: Cc1ccc2c(NC(=O)[C@@H]3C[C@@H]3C)cccc2c1Oc1ncccc1-c1ccnc(N[C@H]2CCCN(C(=O)OC(C)(C)C)C2)n1]

The General Procedure C was followed, using tert-butyl (S)-3-((4-(2-((5-amino-2-methylnaphthalen-1-yl)oxy)pyridin-3-yl)pyrimidin-2-yl)amino)piperidine-1-carboxylate from Example 101 (405 mg, 0.77 mmol), 2-methylcyclopropanecarboxylic acid (70 mg, 0.70 mmol), DIPEA (0.366 mL, 2.10 mmol), HATU (814 mg, 2.10 mmol) and DCM (10 mL). The residue was purified via reverse-phase HPLC to provide a mixture of the two isomers, this mixture was then purified via chiral reverse-phase HPLC and lyophilized to yield 8 mg, 57 mg, 32 mg and 13 mg of the four single stereoisomers at the 1 and 2 positions of the cyclopropyl amide.

Step 2: (1R,2S)-2-Methyl-N-(6-methyl-5-((3-(2-(((S)-piperidin-3-yl)amino)pyrimidin-4-yl)pyridin-2-yl)oxy)naphthalen-1-yl)cyclopropane-1-carboxamide

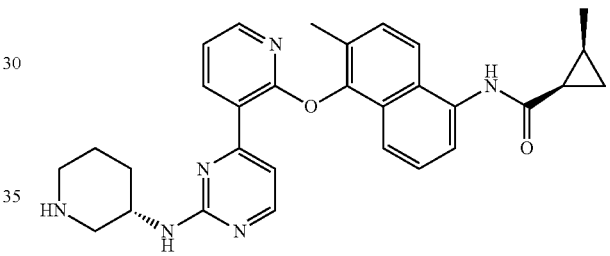

Prepared according to Example 233, following General Procedure B, and using tert-butyl (S)-3-((4-(2-((2-methyl-5-((1R,2S)-2-methylcyclopropane-1-carboxamido)naphthalen-1-yl)oxy)pyridin-3-yl)pyrimidin-2-yl)amino)piperidine-1-carboxylate (isomer-2) (43 mg, 0.071 mmol), 1,4-dioxane (1 mL) and hydrochloric acid (4 M in dioxane, 1 mL, 4 mmol). After 60 min reaction time, the resulting suspension was diluted with MTBE (15 mL) and the precipitate was filtered and washed with MTBE. The collected solids were dissolved in MeCN and water and lyophilized to provide 34 mg (88% yield) of 231 as a fluffy light yellow solid. LCMS (ESI) [M+H]⁺=509.5, rt=1.37 min; ¹H NMR (400 MHz, d6-dmso) δ 10.15 (s, 1H), 9.06-8.51 (m, 3H), 8.48 (d, J=5.2 Hz, 1H), 8.05 (dd, J=4.8, 2.0 Hz, 1H), 7.96 (d, J=8.7 Hz, 1H), 7.63 (d, J=7.1 Hz, 1H), 7.59 (d, J=4.9 Hz, 1H), 7.55 (d, J=7.7 Hz, 1H), 7.52 (d, J=8.9 Hz, 1H), 7.47 (d, J=8.3 Hz, 1H), 7.43-7.36 (m, 1H), 7.27 (dd, J=7.6, 4.8 Hz, 1H), 4.28 (s, 1H), 3.21 (d, J=12.1 Hz, 1H), 2.96-2.73 (m, 2H), 2.22 (s, 3H), 2.16-2.06 (m, 1H), 2.06-1.98 (m, 1H), 1.98-1.86 (m, 1H), 1.75 (q, J=12.5 Hz, 1H), 1.63 (d, J=10.7 Hz, 1H), 1.38-1.27 (m, 1H), 1.17 (d, J=6.1 Hz, 3H), 1.05-0.93 (m, 1H), 0.82 (dd, J=10.6, 5.4 Hz, 1H).

Example 232 (1R,2R)-2-Methyl-N-(6-methyl-5-((3-(2-(((S)-piperidin-3-yl)amino)pyrimidin-4-yl)pyridin-2-yl)oxy)naphthalen-1-yl)cyclopropane-1-carboxamide 232

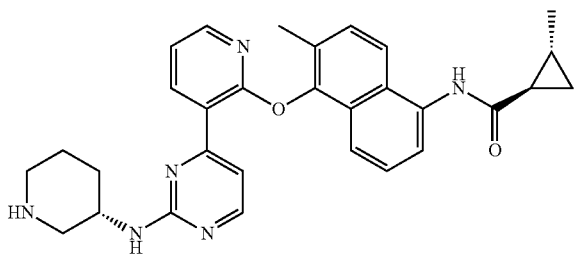 [SMILES: Cc1ccc2c(NC(=O)[C@@H]3C[C@H]3C)cccc2c1Oc1ncccc1-c1ccnc(N[C@H]2CCCNC2)n1]

The General Procedure B was followed using tert-butyl (S)-3-((4-(2-((2-methyl-5-(((1R,2R)-2-methylcyclopropane-1-carboxamido)naphthalen-1-yl)oxy)pyridin-3-yl)pyrimidin-2-yl)amino)piperidine-1-carboxylate (57 mg, 0.094 mmol), DCM (4 mL) and hydrochloric acid (4 M in dioxane, 3 mL, 12 mmol). The residue was purified via reverse-phase HPLC and lyophilized to yield 38.6 mg (81% yield) of 232. LCMS (ESI): [M+H]$^+$=509.2; $^1$H NMR (400 MHz, DMSO-d$_6$) δ 10.11 (s, 1H), 8.50 (d, J=7.7 Hz, 1H), 8.41 (d, J=5.1 Hz, 1H), 8.05-7.98 (m, 2H), 7.98-7.96 (m, 1H), 7.67 (d, J=7.5 Hz, 1H), 7.53-7.36 (m, 4H), 7.25 (dd, J=7.5, 4.9 Hz, 1H), 7.13 (d, J=7.9 Hz, 1H), 3.90 (s, 1H), 3.11 (d, J=12.0 Hz, 1H), 2.86-2.76 (m, 1H), 2.47-2.42 (m, 2H), 2.22 (s, 3H), 2.14-2.03 (m, 1H), 1.96-1.90 (m, 1H), 1.70-1.60 (m, 1H), 1.55-1.40 (m, 2H), 1.37-1.24 (m, 1H), 1.17 (d, J=6.1 Hz, 3H), 1.02-0.95 (m, 1H), 0.85-0.80 (m, 1H).

Example 233 (1S,2R)-2-Methyl-N-(6-methyl-5-((3-(2-(((S)-piperidin-3-yl)amino)pyrimidin-4-yl)pyridin-2-yl)oxy)naphthalen-1-yl)cyclopropane-1-carboxamide 233

Step 1: (3S)-tert-Butyl 3-((4-(2-((2-methyl-5-(2-methylcyclopropanecarboxamido)naphthalen-1-yl)oxy)pyridin-3-yl)pyrimidin-2-yl)amino)piperidine-1-carboxylate

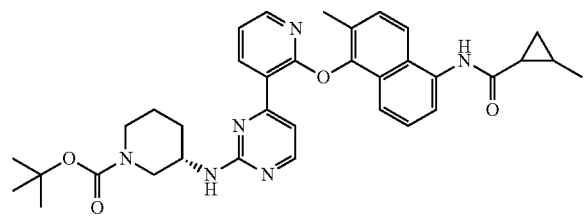 [SMILES: Cc1ccc2c(NC(=O)C3CC3C)cccc2c1Oc1ncccc1-c1ccnc(N[C@H]2CCCN(C(=O)OC(C)(C)C)C2)n1]

To a solution of cis-2-methylcyclopropanecarboxylic acid (0.07 mL, 0.67 mmol) in DCM (3 mL) cooled to 0° C. was added oxalyl chloride (86 μL, 1.0 mmol). The mixture was stirred for 30 min and then tert-butyl (3S)-3-[[4-[2-[(5-amino-2-methyl-1-naphthyl)oxy]-3-pyridyl]pyrimidin-2-yl]amino]piperidine-1-carboxylate (529 mg, 1.0 mmol) and pyridine (0.32 mL, 4.02 mmol) were added. The reaction mixture was stirred for 3 days and then diluted with water (10 mL) and EtOAc (30 mL), followed by separation of the layers. The organic phase was washed with saturated NaHCO$_3$(aq) (20 mL), then brine (20 mL), then saturated NH$_4$Cl(aq) (10 mL). The organic phase was then dried (MgSO$_4$), filtered and concentrated to dryness. The crude product was purified by flash chromatography through silica gel (0-100% EtOAc/DCM) followed by further purification by C18 reverse phase flash chromatography (40-70% MeCN/0.1% TFA in water). The product fractions were combined, 5 mL of ammonium hydroxide was added and most of the acetonitrile was removed on the rotavap. The product suspension in water was extracted with DCM (2×50 mL), dried (MgSO$_4$), filtered and concentrated to provide 103 mg (25% yield) of the title compound. LCMS (ESI) [M+H]$^+$=609.6, rt=1.93 min.

Step 2: tert-Butyl (S)-3-((4-(2-((2-methyl-5-(((1S,2R)-2-methylcyclopropane-1-carboxamido)naphthalen-1-yl)oxy)pyridin-3-yl)pyrimidin-2-yl)amino)piperidine-1-carboxylate (Isomer-1) and tert-butyl (S)-3-((4-(2-((2-methyl-5-(((1R,2S)-2-methylcyclopropane-1-carboxamido)naphthalen-1-yl)oxy)pyridin-3-yl)pyrimidin-2-yl)amino)piperidine-1-carboxylate (Isomer-2)

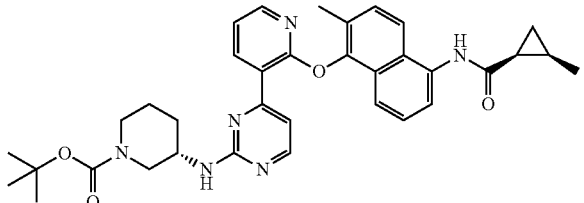

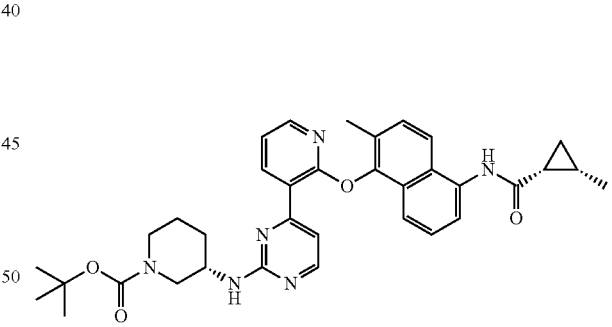

The mixture of stereoisomers from Step 1 were subjected to chiral normal phase semi-prep purification (conditions: Chiralpak IB, 5 uM, 20×250 mm, Isocratic 5% MeOH, 5% EtOH, 90% hexane, 15 mL/min, 5-10 mg/inj.) to provide two stereoisomers enantiomeric with respect to the cyclopropane: (isomer-1), 47 mg (46% yield), white solid, ee=99.4%, rt=15.2 min, LCMS (ESI) [M+H]$^+$=609.6, rt=1.90 min; and (isomer-2), 43 mg (42% yield), white solid, ee=98.9%, rt=17.8 min, LCMS (ESI) [M+H]$^+$=609.6, rt=1.91 min.

Step 3: (1S,2R)-2-Methyl-N-(6-methyl-5-((3-(2-(((S)-piperidin-3-yl)amino)pyrimidin-4-yl)pyridin-2-yl)oxy)naphthalen-1-yl)cyclopropane-1-carboxamide (Isomer-1)

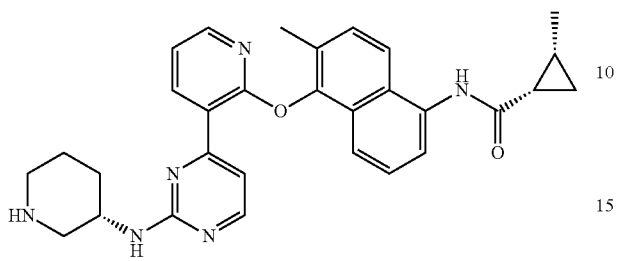

Prepared following General Procedure B and using tert-butyl (S)-3-((4-(2-((2-methyl-5-(((1S,2R)-2-methylcyclopropane-1-carboxamido)naphthalen-1-yl)oxy)pyridin-3-yl)pyrimidin-2-yl)amino)piperidine-1-carboxylate (isomer-1) (47 mg, 0.077 mmol), 1,4-dioxane (1 mL) and hydrochloric acid (4 M in dioxane, 1 mL, 4 mmol). After 60 min, the resulting suspension was diluted with MTBE (15 mL) and the precipitate was filtered and washed with MTBE. The collected solids were dissolved in MeCN and water and lyophilized to provide 36 mg (85% yield) of 233 as a fluffy light yellow solid. LCMS (ESI) [M+H]$^+$=509.5, rt=1.37 min; $^1$H NMR (400 MHz, d6-dmso) δ 10.15 (s, 1H), 9.11-8.51 (m, 3H), 8.48 (d, J=5.2 Hz, 1H), 8.05 (dd, J=4.8, 2.0 Hz, 1H), 7.96 (d, J=8.6 Hz, 1H), 7.63 (d, J=7.2 Hz, 1H), 7.59 (d, J=4.9 Hz, 1H), 7.53 (t, J=8.2 Hz, 2H), 7.47 (d, J=8.3 Hz, 1H), 7.43-7.34 (m, 1H), 7.27 (dd, J=7.6, 4.8 Hz, 1H), 4.28 (s, 1H), 3.21 (d, J=12.1 Hz, 1H), 2.89-2.79 (m, 2H), 2.22 (s, 3H), 2.16-2.07 (m, 1H), 2.07-1.97 (m, 1H), 1.97-1.85 (m, 1H), 1.74 (q, J=10.3 Hz, 1H), 1.63 (q, J=9.4 Hz, 1H), 1.37-1.26 (m, 1H), 1.17 (d, J=6.1 Hz, 3H), 1.06-0.94 (m, 1H), 0.82 (dd, J=10.7, 5.3 Hz, 1H).

Example 234 (1S,2S)-2-Methyl-N-(6-methyl-5-((3-(2-(((S)-piperidin-3-yl)amino)pyrimidin-4-yl)pyridin-2-yl)oxy)naphthalen-1-yl)cyclopropane-1-carboxamide 234

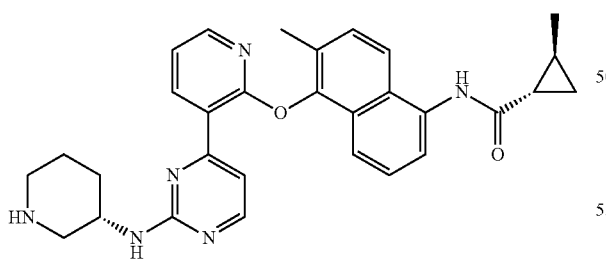

The General Procedure B was followed using tert-butyl (S)-3-((4-(2-((2-methyl-5-(((1S,2S)-2-methylcyclopropane-1-carboxamido)naphthalen-1-yl)oxy)pyridin-3-yl)pyrimidin-2-yl)amino)piperidine-1-carboxylate (13 mg, 0.021 mmol), DCM (4 mL) and hydrochloric acid (4 M in dioxane, 3 mL, 12 mmol). The residue was purified via reverse-phase HPLC and lyophilized to yield 5.2 mg (48% yield) of 234. LCMS (ESI): [M+H]$^+$=509.2; $^1$H NMR (400 MHz, DMSO-d$_6$) δ 10.11 (s, 1H), 8.50 (d, J=7.7 Hz, 1H), 8.41 (d, J=5.1 Hz, 1H), 8.05-7.98 (m, 2H), 7.98-7.96 (m, 1H), 7.67 (d, J=7.5 Hz, 1H), 7.53-7.36 (m, 4H), 7.25 (dd, J=7.5, 4.8 Hz, 1H), 7.12 (d, J=7.9 Hz, 1H), 3.90 (s, 1H), 3.18-3.09 (m, 1H), 2.87-2.79 (m, 1H), 2.48-2.40 (m, 2H), 2.22 (s, 3H), 2.14-2.03 (m, 1H), 1.96-1.90 (m, 1H), 1.70-1.60 (m, 1H), 1.57-1.38 (m, 2H), 1.36-1.24 (m, 1H), 1.17 (d, J=6.1 Hz, 3H), 1.02-0.95 (m, 1H), 0.85-0.80 (m, 1H).

Example 235 (1R, 2S)-2-Fluoro-N-(6-methyl-5-((3-(2-(((S)-piperidin-3-yl)amino)pyrimidin-4-yl)pyridin-2-yl)oxy)naphthalen-1-yl)cyclopropane-1-carboxamide 235

Step 1: tert-Butyl (S)-3-((4-(2-((5-(((1R,2S)-2-fluorocyclopropane-1-carboxamido)-2-methylnaphthalen-1-yl)oxy)pyridin-3-yl)pyrimidin-2-yl)amino)piperidine-1-carboxylate

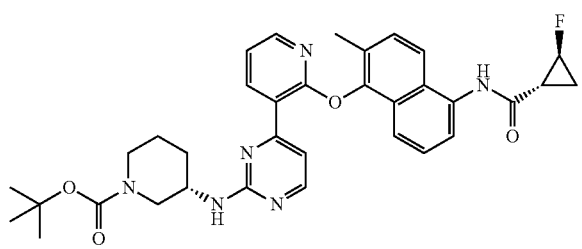 [SMILES: Cc1ccc2c(NC(=O)[C@H]3C[C@@H]3F)cccc2c1Oc1ncccc1-c1ccnc(N[C@H]2CCCN(C(=O)OC(C)(C)C)C2)n1]

The General Procedure C was followed, using tert-butyl (S)-3-((4-(2-((5-amino-2-methylnaphthalen-1-yl)oxy)pyridin-3-yl)pyrimidin-2-yl)amino)piperidine-1-carboxylate from Example 101 (364 mg, 0.69 mmol), (trans)-2-fluorocyclopropanecarboxylic acid (60 mg, 0.58 mmol), DIPEA (0.302 mL, 0.51 mmol), HATU (671 mg, 1.73 mmol) and DCM (10 mL). The residue was purified via reverse-phase HPLC to provide a mixture of the two isomers. This mixture was then purified via chiral reverse-phase HPLC and lyophilized to yield 62 mg and 56 mg of the two single trans stereoisomers enantiomeric at the 1 and 2 positions of the cyclopropyl amide.

Step 2: (1R,2S)-2-Fluoro-N-(6-methyl-5-((3-(2-(((S)-piperidin-3-yl)amino)pyrimidin-4-yl)pyridin-2-yl)oxy)naphthalen-1-yl)cyclopropane-1-carboxamide

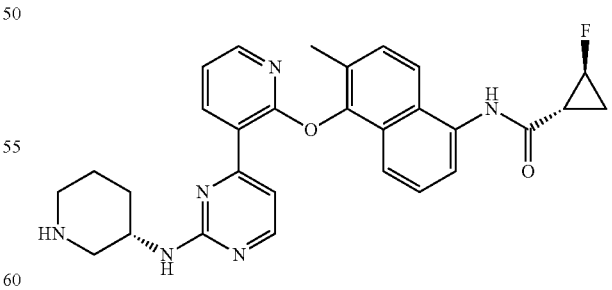

The General Procedure B was followed, using tert-butyl (3S)-3-((4-(2-((5-(2-fluorocyclopropane-1-carboxamido)-2-methylnaphthalen-1-yl)oxy)pyridin-3-yl)pyrimidin-2-yl)amino)piperidine-1-carboxylate (56 mg, 0.091 mmol), DCM (4 mL) and hydrochloric acid (4 M in dioxane, 3 mL, 12 mmol). The residue was purified via reverse-phase HPLC and lyophilized to yield 31.6 mg of 235. LCMS (ESI): [M+H]⁺=513.2; ¹H NMR (400 MHz, DMSO-d₆) δ 10.37 (s, 1H), 8.60-8.50 (m, 1H), 8.45 (d, J=5.1 Hz, 1H), 8.06-7.96 (m, 2H), 7.67 (d, J=7.5 Hz, 1H), 7.56-7.47 (m, 2H), 7.46-7.32 (m, 2H), 7.27 (dd, J=7.5, 4.8 Hz, 1H), 5.12-4.89 (m, 1H), 4.14 (s, 1H), 3.15-3.07 (m, 1H), 2.78-2.59 (m, 3H), 2.22 (s, 3H), 1.97-1.89 (m, 1H), 1.88-1.80 (m, 1H), 1.69-1.40 (m, 3H), 1.33-1.22 (m, 1H).

Example 236 (1S,2R)-2-Fluoro-N-(6-methyl-5-((3-(2-(((S)-piperidin-3-yl)amino)pyrimidin-4-yl)pyridin-2-yl)oxy)naphthalen-1-yl)cyclopropane-1-carboxamide 236

The General Procedure B was followed, using tert-butyl (S)-3-((4-(2-((5-((1S,2R)-2-fluorocyclopropane-1-carboxamido)-2-methylnaphthalen-1-yl)oxy)pyridin-3-yl)pyrimidin-2-yl)amino)piperidine-1-carboxylate (62 mg, 0.10 mmol), DCM (4 mL) and hydrochloric acid (4 M in dioxane, 3 mL, 12 mmol). The residue was purified via reverse-phase HPLC and lyophilized to yield 36.8 mg of 236. LCMS (ESI): [M+H]⁺=513.2; ¹H NMR (400 MHz, DMSO-d₆) δ 10.37 (s, 1H), 8.53-8.47 (m, 1H), 8.41 (d, J=5.1 Hz, 1H), 8.04-7.96 (m, 2H), 7.67 (d, J=7.5 Hz, 1H), 7.56-7.51 (m, 2H), 7.46-7.37 (m, 2H), 7.26 (dd, J=7.5, 4.8 Hz, 1H), 7.13 (d, J=8.0 Hz, 1H), 5.12-4.89 (m, 1H), 3.90 (s, 1H), 3.15-3.07 (m, 1H), 2.85-2.80 (m, 1H), 2.70-2.59 (m, 1H), 2.46-2.41 (m, 1H), 2.22 (s, 3H), 1.97-1.89 (m, 1H), 1.69-1.40 (m, 3H), 1.33-1.22 (m, 1H).

Example 237 5-Methyl-1-(6-methyl-5-((3-(2-((S)-piperidin-3-ylamino)pyrimidin-4-yl)pyridin-2-yl)oxy)naphthalen-1-yl)pyrrolidin-2-one 237

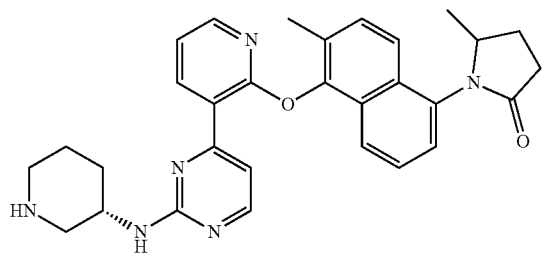 [SMILES: Cc1ccc2c(N3C(=O)CCC3C)cccc2c1Oc1ncccc1-c1ccnc(N[C@H]2CCCNC2)n1]

Step 1: (3S)-tert-Butyl 3-((4-(2-((2-methyl-5-(2-methyl-5-oxopyrrolidin-1-yl)naphthalen-1-yl)oxy)pyridin-3-yl)pyrimidin-2-yl)amino)piperidine-1-carboxylate To a solution of tert-butyl (3S)-3-[[4-[2-[(5-iodo-2-methyl-1-naphthyl)oxy]-3-pyridyl]pyrimidin-2-yl]amino] piperidine-1-carboxylate (110 mg, 0.17 mmol) in 1,4-dioxane (2 mL) was added copper (I) iodide (3 mg, 0.02 mmol), potassium carbonate (65 mg, 0.47 mmol), 5-methyl-2-pyrrolidinone (31 mg, 0.31 mmol) and N,N'-dimethyl-1,2-ethanediamine (2.77 mg, 0.03 mmol). The mixture was purged with N₂ and stirred at 110° C. for 12 h. After cooling, the mixture was filtered, concentrated and dissolved in ethyl acetate (60 mL), and subsequently washed with H₂O (50 mL×2). The organic phase was dried over anhydrous sodium sulfate and filtered and the filtrate was concentrated and purified by prep-TLC (50% ethyl acetate in petroleum ether, Rf=0.1) to yield 80 mg (83% yield) of the title compound as a white solid. LCMS (ESI) [M+H]⁺=609.1.

Step 2: 5-Methyl-1-(6-methyl-5-((3-(2-((S)-piperidin-3-ylamino)pyrimidin-4-yl)pyridin-2-yl)oxy)naphthalen-1-yl)pyrrolidin-2-one

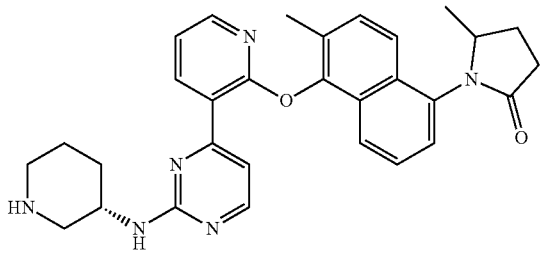 [SMILES: Cc1ccc2c(N3C(=O)CCC3C)cccc2c1Oc1ncccc1-c1ccnc(N[C@H]2CCCNC2)n1]

The General Procedure B was followed, using (3S)-tert-butyl 3-((4-(2-((2-methyl-5-(2-methyl-5-oxopyrrolidin-1-yl)naphthalen-1-yl)oxy)pyridin-3-yl)pyrimidin-2-yl)amino)piperidine-1-carboxylate (80 mg, 0.13 mmol), dichloromethane (2 mL) and hydrochloric acid (4 M in dioxane, 2 mL, 8 mmol). The residue was purified by Prep-HPLC (mobile phase: A: water (0.05% HCl); B: ACN) to yield 25.8 mg (36% yield) of 237 as a yellow solid and as mixture of diastereomers. LCMS (ESI) [M+H]⁺=509.2. ¹H NMR (400 MHz, DMSO-d₆) δ 9.99 (s, 1H), 9.51 (s, 1H), 9.15-8.75 (m, 1H), 8.57 (s, 1H), 8.18 (s, 1H), 7.93 (s, 1H), 7.67 (s, 2H), 7.53-7.43 (m, 2H), 7.33-7.30 (m, 1H), 4.65 (s, 1H), 4.28 (s, 1H), 3.43 (s, 1H), 3.19 (s, 1H), 2.89 (t, J=9.6 Hz, 2H), 2.56 (s, 2H), 2.48-2.36 (m, 1H), 2.22 (s, 3H), 2.09-2.00 (m, 1H), 1.97-1.64 (m, 4H), 1.03 (s, 3H).

Example 238 (S)-3,3-Dimethyl-1-(6-methyl-5-((3-(2-(piperidin-3-ylamino)pyrimidin-4-yl)pyridin-2-yl)oxy)naphthalen-1-yl)pyrrolidin-2-one 238

Step 1: (S)-tert-Butyl 3-((4-(2-((5-(3,3-dimethyl-2-oxopyrrolidin-1-yl)-2-methylnaphthalen-1-yl)oxy)pyridin-3-yl)pyrimidin-2-yl)amino)piperidine-1-carboxylate

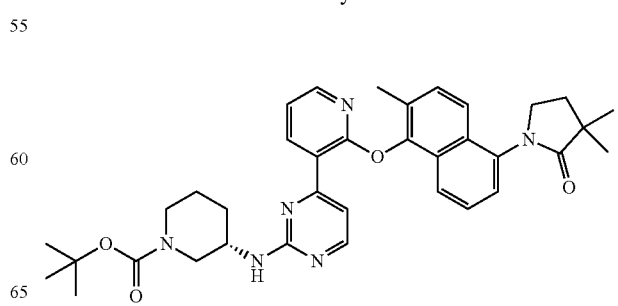

To a solution of tert-butyl (3S)-3-[[4-[2-[(5-iodo-2-methyl-1-naphthyl)oxy]-3-pyridyl]pyrimidin-2-yl]amino]piperidine-1-carboxylate (100 mg, 0.16 mmol) in 1,4-dioxane (2 mL) was added copper (I) iodide CuI (3 mg, 0.02 mmol), potassium carbonate (65 mg, 0.47 mmol), 3,3-dimethylpyrrolidin-2-one (35 mg, 0.31 mmol) and N,N'-dimethyl-1,2-ethanediamine (3 mg, 0.03 mmol), the mixture was subjected to a nitrogen atmosphere and stirred at 110° C. for 12 h. After cooling down, the mixture was filtered, concentrated and dissolved in ethyl acetate (60 mL), and then washed with H₂O (50 mL×2). The organic phase was dried over anhydrous sodium sulfate and filtered and the filtrate was concentrated and purified by prep-TLC (50% ethyl acetate in petroleum ether, Rf=0.1) to yield 80 mg (82% yield) of the title compound as a white solid. LCMS (ESI) [M+H]⁺=623.1.

Step 2: (S)-3,3-Dimethyl-1-(6-methyl-5-((3-(2-(piperidin-3-ylamino)pyrimidin-4-yl)pyridin-2-yl)oxy)naphthalen-1-yl)pyrrolidin-2-one

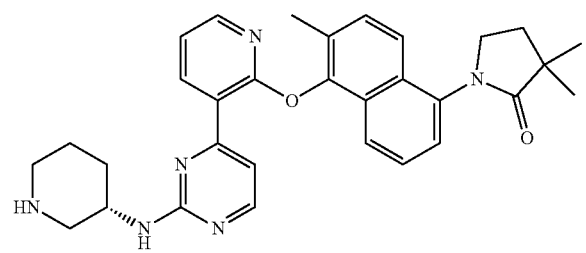 [SMILES: Cc1ccc2c(N3CCC(C)(C)C3=O)cccc2c1Oc1ncccc1-c1ccnc(N[C@H]2CCCNC2)n1]

The General Procedure B was followed, using (S)-tert-butyl 3-((4-(2-((5-(3,3-dimethyl-2-oxopyrrolidin-1-yl)-2-methylnaphthalen-1-yl)oxy)pyridin-3-yl)pyrimidin-2-yl)amino)piperidine-1-carboxylate (80 mg, 0.13 mmol), dichloromethane (2 mL) and hydrochloric acid (4 M in dioxane, 0.32 mL, 1.28 mmol). The residue was purified by Prep-HPLC (mobile phase: A: water (0.05% HCl); B: ACN) to yield 42.2 mg (58% yield) of 238 as a white solid. LCMS (ESI) [M+H]⁺=523.1. ¹H NMR (400 MHz, DMSO-d₆) δ 9.06 (s, 1H), 8.49 (d, J=5.2 Hz, 1H), 8.10-8.01 (m, 1H), 7.65 (d, J=8.4 Hz, 2H), 7.60-7.52 (m, 2H), 7.51-7.46 (m, 1H), 7.44-7.39 (m, 1H), 7.30-7.27 (m, 1H), 4.35 (s, 1H), 3.78 (s, 2H), 3.43 (d, J=9.2 Hz, 1H), 3.20 (d, J=11.2 Hz, 1H), 2.92-2.77 (m, 2H), 2.22 (s, 3H), 2.15 (t, J=6.8 Hz, 2H), 2.02 (d, J=8.8 Hz, 1H), 1.92 (m, 1H), 1.81-1.71 (m, 1H), 1.64 (m, 1H), 1.26 (s, 6H).

Example 239 (S)-4-(2-((2-Methyl-5-(pyridin-2-yloxy)naphthalen-1-yl)oxy)pyridin-3-yl)-N-(piperidin-3-yl)pyrimidin-2-amine 239

Step 1: (S)-tert-butyl 3-((4-(2-((2-methyl-5-(pyridin-2-yloxy)naphthalen-1-yl)oxy)pyridin-3-yl)pyrimidin-2-yl)amino)piperidine-1-carboxylate

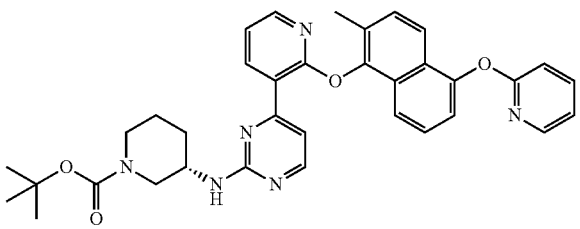 [SMILES: Cc1ccc2c(Oc3ccccn3)cccc2c1Oc1ncccc1-c1ccnc(N[C@H]2CCCN(C(=O)OC(C)(C)C)C2)n1]

To a solution of tert-butyl (3S)-3-[[4-[2-[(5-iodo-2-methyl-1-naphthyl)oxy]-3-pyridyl]pyrimidin-2-yl]amino]piperidine-1-carboxylate (100 mg, 0.16 mmol), 8-hydroxyquinoline (3 mg, 0.02 mmol), potassium carbonate (43 mg, 0.31 mmol), copper(I) iodide (3 mg, 0.02 mmol) in dimethyl sulfoxide (1 mL) was added 1H-pyridin-2-one (18 mg, 0.19 mmol). The mixture was stirred at 120° C. under nitrogen atmosphere for 24 h. The solution was concentrated and purified by prep-TLC (50% ethyl acetate in petroleum ether, Rf=0.5) to yield 50 mg (53% yield) of the title compound as a yellow solid. LCMS (ESI): [M+H]⁺=605.2.

Step 2: (S)-4-(2-((2-methyl-5-(pyridin-2-yloxy)naphthalen-1-yl)oxy)pyridin-3-yl)-N-(piperidin-3-yl)pyrimidin-2-amine

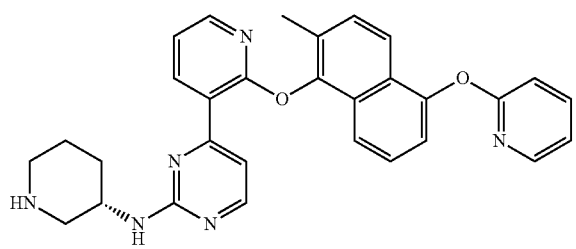 [SMILES: Cc1ccc2c(Oc3ccccn3)cccc2c1Oc1ncccc1-c1ccnc(N[C@H]2CCCNC2)n1]

The General Procedure B was followed, using (S)-tert-butyl 3-((4-(2-((2-methyl-5-(pyridin-2-yloxy)naphthalen-1-yl)oxy)pyridin-3-yl)pyrimidin-2-yl)amino)piperidine-1-carboxylate (50 mg, 0.08 mmol), dichloromethane (5 mL) and hydrochloric acid (4 M in ethyl acetate, 2 mL, 8 mmol). The residue was purified by Prep-HPLC (mobile phase: A: water (0.05% HCl); B: ACN) to yield 13 mg (29% yield) of 239 as a yellow solid. LCMS (ESI): [M+H]⁺=505.2. ¹H NMR (400 MHz, DMSO-d₆) δ 9.81 (s, 1H), 9.41 (s, 1H), 8.97 (s, 1H), 8.54 (s, 2H), 8.15 (s, 1H), 8.07 (d, J=3.6 Hz, 1H), 7.95-7.86 (m, 1H), 7.70 (d, J=8.4 Hz, 1H), 7.60-7.51 (m, 1H), 7.46 (dd, J=4.0, 8.0 Hz, 2H), 7.37-7.28 (m, 1H), 7.21 (d, J=8.0 Hz, 2H), 7.17-7.09 (m, 1H), 4.58 (s, 1H), 3.43 (s, 1H), 3.19 (s, 1H), 2.90-2.80 (m, 2H), 2.21 (s, 3H), 2.10-1.62 (m, 4H).

Example 240 (S)—N-(6-Methyl-5-((5-methyl-3-(2-(piperidin-3-ylamino)pyrimidin-4-yl)pyridin-2-yl)oxy)naphthalen-1-yl)propane-1-sulfonamide 240

Step 1: 2-Chloro-4-(2-fluoro-5-methylpyridin-3-yl)pyrimidine

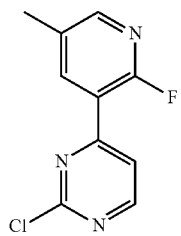

To the mixture of 2,4-dichloropyrimidine (149 mg, 1.0 mmol), 2-fluoro-5-methyl-3-(4,4,5,5-tetramethyl-1,3,2-dioxaborolan-2-yl)pyridine (237 mg, 1.0 mmol) and potassium carbonate (346 mg, 2.5 mmol) in 1,4-dioxane (3 mL) and water (1 mL) was added tetrakis(triphenylphosphine)palladium (0) (58 mg, 0.05 equiv). The reaction mixture was purged with nitrogen, heated to 90° C., stirred at the same temperature overnight, cooled to room temperature, filtered, and concentrated under vacuum. To the residue was added ethyl acetate and water. The organic layer was separated, washed with water and brine, dried over anhydrous sodium sulfate, and concentrated in vacuo. The residue was purified via silica gel column chromatography (isopropylacetate in heptanes, 0 to 80%) to yield 170 mg of the title compound (76% yield).

Step 2: tert-Butyl (S)-3-((4-(2-fluoro-5-methylpyridin-3-yl)pyrimidin-2-yl)amino)piperidine-1-carboxylate

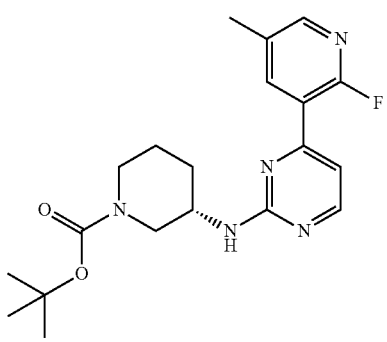 [SMILES: Cc1cnc(F)c(-c2ccnc(N[C@H]3CCCN(C(=O)OC(C)(C)C)C3)n2)c1]

The solution of 2-chloro-4-(2-fluoro-5-methyl-3-pyridyl)pyrimidine (170 mg, 0.76 mmol), tert-butyl (3S)-3-[[4-(2-fluoro-5-methyl-3-pyridyl)pyrimidin-2-yl]amino]piperidine-1-carboxylate (138 mg, 0.36 mmol) and triethylamine (0.212 mL, 1.52 mmol) in dimethylsulfoxide (1.5 mL) was stirred at 100° C. overnight. To the solution was added water and ethyl acetate. The organic layer was separated, washed with water and brine, dried over anhydrous sodium sulfate, and concentrated under vacuum to afford an oily residue. The residue was purified via silica gel column chromatography (isopropylacetate/methanol (3:1) in heptanes, 0 to 80%) to yield 138 mg of the title compound (47% yield).

Step 3: tert-Butyl (S)-3-((4-(2-((5-amino-2-methyl-naphthalen-1-yl)oxy)-5-methylpyridin-3-yl)pyrimidin-2-yl)amino)piperidine-1-carboxylate

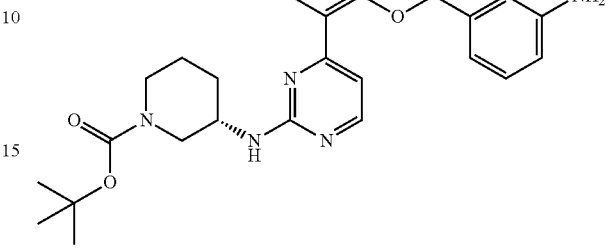

To a round-bottom flask purged and maintained with an inert atmosphere of nitrogen was placed tert-butyl (3S)-3-[[4-(2-fluoro-5-methyl-3-pyridyl)pyrimidin-2-yl]amino]piperidine-1-carboxylate (139 mg, 0.36 mmol), 5-amino-2-methylnaphathalene-1-ol HCl (72 mg, 0.33 mmol), cesium carbonate (0.98 mmol, 319 mg) and 1-methyl-2-pyrrolidinone (2 mL). The resulting mixture was stirred overnight at 125° C., cooled to room temperature, diluted with water, and extracted with ethyl acetate. The combined organic layers were dried over anhydrous sodium sulfate and concentrated under vacuum. The residue was purified via silica column chromatography (isopropylacetate/methanol (3:1) in heptanes, 0 to 80%) to yield 160 mg of the title compound (91% yield).

Step 4: tert-Butyl (S)-3-((4-(5-methyl-2-((2-methyl-5-(propylsulfonamido)naphthalen-1-yl)oxy)pyridin-3-yl)pyrimidin-2-yl)amino)piperidine-1-carboxylate

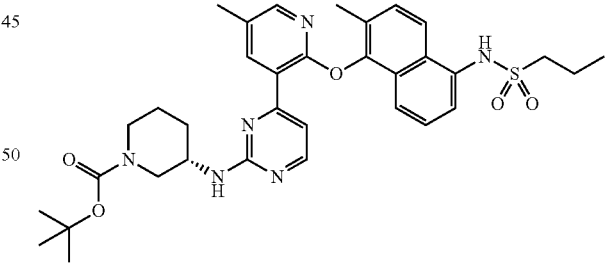

The General Procedure A was followed, using tert-butyl (S)-3-((4-(2-((5-amino-2-methylnaphthalen-1-yl)oxy)pyridin-3-yl)pyrimidin-2-yl)amino)piperidine-1-carboxylate from Example 101 (160 mg, 0.30 mmol), pyridine (3 mL) and 1-propanesulfonyl chloride (50 mg, 0.36 mmol). The crude was then purified by silica column chromatography (isopropylacetate/methanol (3:1) in heptanes, 0 to 80%) to yield 90 mg (47% yield) of the title compound as a white solid. LCMS (ESI) [M+H]$^+$=647.

Step 5: (S)—N-(6-Methyl-5-((5-methyl-3-(2-(piperidin-3-ylamino)pyrimidin-4-yl)pyridin-2-yl)oxy)naphthalen-1-yl)propane-1-sulfonamide

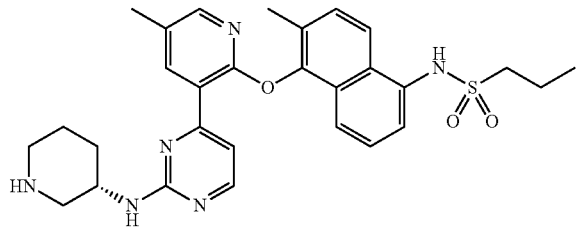 [SMILES: CCCS(=O)(=O)Nc1cccc2c(Oc3ncc(C)cc3-c3ccnc(N[C@H]4CCCNC4)n3)c(C)ccc12]

The General Procedure B was followed, using tert-butyl (S)-3-((4-(5-methyl-2-((2-methyl-5-(propylsulfonamido)naphthalen-1-yl)oxy)pyridin-3-yl)pyrimidin-2-yl)amino)piperidine-1-carboxylate (90 mg, 0.14 mmol), DCM (4 mL) and hydrochloric acid (4 M in dioxane, 3 mL, 12 mmol). The residue was purified via reverse-phase HPLC and lyophilized to yield 23.3 mg (14% yield) of 240; LCMS (ESI): [M+H]$^+$=547.2; $^1$H NMR (400 MHz, DMSO-$d_6$) δ 8.40 (d, J=5.1 Hz, 1H), 8.32 (d, J=3.5 Hz, 1H), 8.12 (d, J=8.8 Hz, 1H), 7.84 (d, J=2.4 Hz, 1H), 7.54-7.34 (m, 5H), 7.17 (d, J=7.9 Hz, 1H), 3.93 (s, 1H), 3.18-3.10 (m, 1H), 2.90-2.82 (m, 1H), 2.28 (s, 3H), 2.20 (s, 3H), 1.97-1.90 (m, 1H), 1.81-1.65 (m, 3H), 1.55-1.45 (m, 2H), 0.96 (t, J=7.4 Hz, 3H).

Example 241 (S)-4-(2-((5-((3-Fluoropropyl)amino)-2-methylnaphthalen-1-yl)oxy)pyridin-3-yl)-N-(piperidin-3-yl)pyrimidin-2-amine 241

Step 1: tert-Butyl (S)-3-((4-(2-((5-((3-fluoropropyl)amino)-2-methylnaphthalen-1-yl)oxy)pyridin-3-yl)pyrimidin-2-yl)amino)piperidine-1-carboxylate

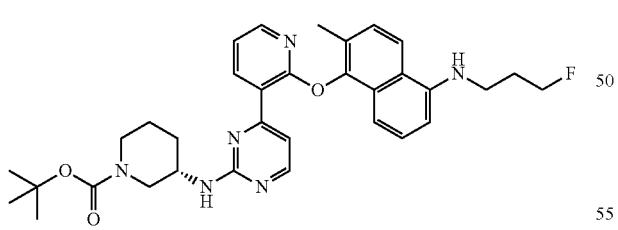

The General Procedure E was followed, using tert-butyl (3S)-3-[[4-[2-[(5-amino-2-methyl-1-naphthyl)oxy]-3-pyridyl]pyrimidin-2-yl]amino]piperidine-1-carboxylate (150 mg, 0.28 mmol) and 1-bromo-3-fluoro-propane (120.5 mg, 0.85 mmol) to afford 156 mg (93% yield) of the title compound as a brown gum. It was carried on as is. LCMS (ESI) [M+H]$^+$=587.

Step 2: (S)-4-(2-((5-((3-Fluoropropyl)amino)-2-methylnaphthalen-1-yl)oxy)pyridin-3-yl)-N-(piperidin-3-yl)pyrimidin-2-amine

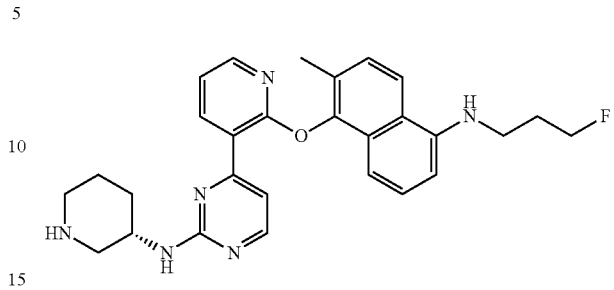

The General Procedure B was followed, using tert-butyl (S)-3-((4-(2-((5-((3-fluoropropyl)amino)-2-methylnaphthalen-1-yl)oxy)pyridin-3-yl)pyrimidin-2-yl)amino)piperidine-1-carboxylate (156 mg, 0.26 mmol). The crude product was purified via reverse-phase HPLC and lyophilized to yield 3.8 mg (3% yield) of 241 as an off-white solid. LCMS (ESI) [M+H]+=487; $^1$H NMR (400 MHz, DMSO-$d_6$) δ 8.48 (s, 1H), 8.40 (d, J=5.1 Hz, 1H), 8.03-7.99 (m, 2H), 7.43 (d, J=5.1 Hz, 1H), 7.34 (d, J=8.7 Hz, 1H), 7.23 (dd, J=7.6, 4.8 Hz, 1H), 7.18 (t, J=8.0 Hz, 1H), 7.11 (d, J=8.0 Hz, 1H), 6.86 (d, J=8.4 Hz, 1H), 6.48-6.43 (m, 1H), 6.28-6.22 (m, 1H), 4.68 (t, J=5.8 Hz, 1H), 4.56 (t, J=5.9 Hz, 1H), 3.89 (s, 1H), 3.15-3.06 (m, 1H), 2.84-2.76 (m, 2H), 2.45-2.42 (m, 2H), 2.18 (s, 3H), 2.11 (q, J=6.3 Hz, 1H), 2.04 (p, J=6.6 Hz, 1H), 1.96-1.89 (m, 2H), 1.69-1.60 (m, 1H), 1.52-1.41 (m, 2H).

Example 242 (S)-1-(Fluoromethyl)-N-(6-methyl-5-((3-(2-(piperidin-3-ylamino)pyrimidin-4-yl)pyridin-2-yl)oxy)naphthalen-1-yl)cyclopropane-1-carboxamide 242

Step 1: tert-Butyl (S)-3-((4-(2-((5-(1-(fluoromethyl)cyclopropane-1-carboxamido)-2-methylnaphthalen-1-yl)oxy)pyridin-3-yl)pyrimidin-2-yl)amino)piperidine-1-carboxylate

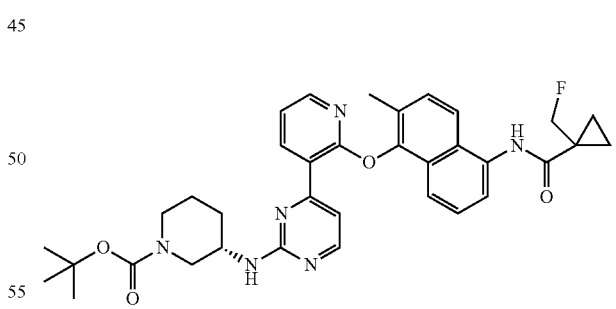

The General Procedure C was followed, using tert-butyl (3S)-3-[[4-[2-[(5-amino-2-methyl-1-naphthyl)oxy]-3-pyridyl]pyrimidin-2-yl]amino]piperidine-1-carboxylate (150 mg, 0.28 mmol) and 1-(fluoromethyl)cyclopropanecarboxylic acid (50.4 mg, 0.43 mmol), HATU (221.0 mg, 0.57 mmol), DIPEA (0.15 mL, 0.85 mmol), and DMF (1.5 mL). The crude material was purified by silica gel chromatography (12 g column), eluted with 0-5% MeOH/DCM to afford 123 mg (69% yield) of the title compound as a brown solid. LCMS (ESI) [M+H]$^+$=627.

Step 2: (S)-1-(Fluoromethyl)-N-(6-methyl-5-((3-(2-(piperidin-3-ylamino)pyrimidin-4-yl)pyridin-2-yl)oxy)naphthalen-1-yl)cyclopropane-1-carboxamide

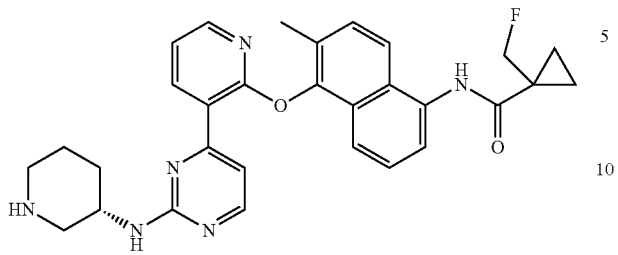

The General Procedure B was followed, using tert-butyl (S)-3-((4-(2-((5-(1-(fluoromethyl)cyclopropane-1-carboxamido)-2-methylnaphthalen-1-yl)oxy)pyridin-3-yl)pyrimidin-2-yl)amino)piperidine-1-carboxylate (123 mg, 0.19 mmol). The crude product was purified via reverse-phase HPLC and lyophilized to yield 90 mg (87% yield) of 242 as a brown solid. LCMS (ESI) [M+H]$^+$=487; $^1$H NMR (400 MHz, DMSO-d$_6$) δ 9.65 (s, 1H), 8.49 (d, J=7.4 Hz, 1H), 8.41 (d, J=5.1 Hz, 1H), 8.03 (dd, J=4.8, 2.0 Hz, 1H), 7.70 (dd, J=8.5, 0.8 Hz, 1H), 7.58 (d, J=7.9 Hz, 1H), 7.50 (d, J=8.7 Hz, 1H), 7.46-7.42 (m, 2H), 7.41-7.39 (m, 1H), 7.25 (dd, J=7.6, 4.8 Hz, 1H), 7.12 (d, J=8.0 Hz, 1H), 4.79 (d, J=48.5 Hz, 2H), 3.89 (s, 1H), 3.10 (d, J=11.9 Hz, 1H), 2.85-2.75 (m, 1H), 2.46-2.39 (m, 2H), 2.22 (s, 3H), 1.97-1.89 (m, 1H), 1.68-1.61 (m, 1H), 1.54-1.41 (m, 2H), 1.38-1.32 (m, 2H), 1.05-0.99 (m, 2H).

Example 243 (S)—N-(2-Fluoro-6-methyl-5-((3-(2-(piperidin-3-ylamino)pyrimidin-4-yl)pyridin-2-yl)oxy)naphthalen-1-yl)-3-methylbutane-1-sulfonamide 243

Step 1: (S)-tert-Butyl 3-((4-(2-((6-fluoro-2-methyl-5-(3-methylbutylsulfonamido)naphthalen-1-yl)oxy)pyridin-3-yl)pyrimidin-2-yl)amino)piperidine-1-carboxylate

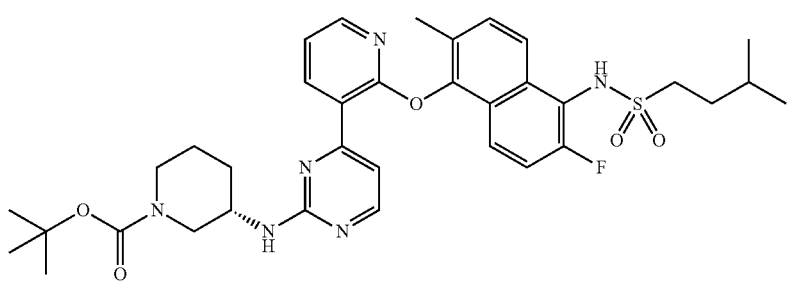 [SMILES: Cc1ccc2c(NS(=O)(=O)CCC(C)C)c(F)ccc2c1Oc1ncccc1-c1ccnc(N[C@H]2CCCN(C(=O)OC(C)(C)C)C2)n1]

Prepared using (S)-tert-butyl 3-((4-(2-((5-amino-6-fluoro-2-methylnaphthalen-1-yl)oxy)pyridin-3-yl)pyrimidin-2-yl)amino)piperidine-1-carboxylate from Example 275 (85 mg, 0.16 mmol), pyridine (0.19 mL, 2.3 mmol), DCM (0.78 mL), 3-methylbutane-1-sulfonyl chloride (53 mg, 0.31 mmol) and DMAP (1.9 mg, 0.016 mmol). After 18 h, a further portion of 3-methylbutane-1-sulfonyl chloride (53 mg, 0.31 mmol) was added and after a further 16 h, the mixture was diluted with 1M KHSO$_4$(aq), extracted twice with DCM, dried (Na$_2$SO$_4$), filtered and concentrated in vacuo. The crude was purified by flash chromatography through silica gel (0-50% EtOAc/DCM) to provide 53 mg (50% yield) of the title compound. LCMS (ESI) [M+H]$^+$=679.4, rt=2.03 min.

Step 2: (S)—N-(2-fluoro-6-methyl-5-((3-(2-(piperi-din-3-ylamino)pyrimidin-4-yl)pyridin-2-yl)oxy)naphthalen-1-yl)-3-methylbutane-1-sulfonamide

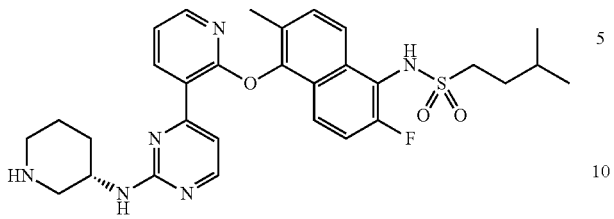

Prepared according to General Procedure B using (S)-tert-butyl 3-((4-(2-((6-fluoro-2-methyl-5-(3-methylbutylsulfonamido)naphthalen-1-yl)oxy)pyridin-3-yl)pyrimidin-2-yl)amino)piperidine-1-carboxylate (53 mg, 0.078 mmol), 1,4-dioxane (0.3 mL) and hydrochloric acid (4 M in dioxane, 0.4 mL, 1.60 mmol). After 45 min, the reaction was diluted with Et$_2$O and the resulting solids collected by filtration, washed with Et$_2$O, dissolved in a mixture of H$_2$O and MeCN and lyophilized to provide 42 mg (88% yield) of 243. LCMS (ESI) [M+H]$^+$=579.4, rt=1.52 min; $^1$H NMR (400 MHz, DMSO-d$_6$) δ 9.70 (s, 1H), 8.91 (bs, 2H), 8.69 (s, 1H), 8.48 (d, J=5.2 Hz, 1H), 8.11-8.01 (m, 2H), 7.71 (dd, J=9.2, 5.2 Hz, 1H), 7.63 (d, J=8.8 Hz, 1H), 7.57 (s, 2H), 7.46 (t, J=9.5 Hz, 1H), 7.29 (dd, J=7.6, 4.8 Hz, 1H), 4.29 (s, 1H), 3.50-3.36 (m, 1H), 3.28-3.10 (m, 3H), 3.01-2.73 (m, 2H), 2.19 (s, 3H), 2.06-1.85 (m, 2H), 1.83-1.52 (m, 5H), 0.92 (d, J=6.3 Hz, 6H).

Example 244 (S)-4-(2-((2-Methyl-5-(((2-methylthiazol-4-yl)methyl)amino)naphthalen-1-yl)oxy)pyridin-3-yl)-N-(piperidin-3-yl)pyrimidin-2-amine 244

Step 1: tert-Butyl (S)-3-((4-(2-((2-methyl-5-(((2-methylthiazol-4-yl)methyl)amino)naphthalen-1-yl)oxy)pyridin-3-yl)pyrimidin-2-yl)amino)piperidine-1-carboxylate

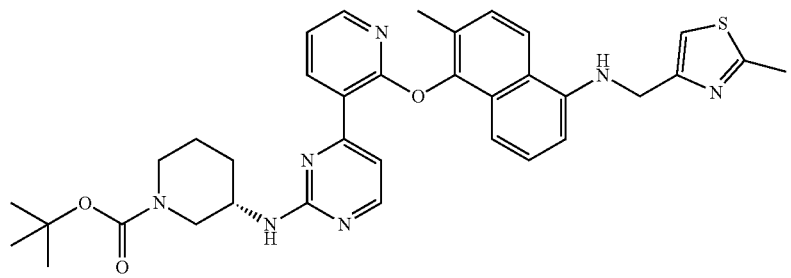 [SMILES: Cc1nc(CNc2cccc3c(Oc4ncccc4-c4ccnc(N[C@H]5CCCN(C(=O)OC(C)(C)C)C5)n4)c(C)ccc23)cs1]

A mixture of tert-butyl (3S)-3-[[4-[2-[(5-amino-2-methyl-1-naphthyl)oxy]-3-pyridyl]pyrimidin-2-yl]amino]piperidine-1-carboxylate (100 mg, 0.19 mmol) and 4-formyl-2-methylthiazole (33.05 mg, 0.25 mmol) in EtOH (2 mL) was added AcOH (3 drops). The resulting mixture was heated at 50° C. overnight.

After cooled, sodium borohydride (14.4 mg, 0.38 mmol) was added at once, followed by stirring at room temperature for 3 h. The reaction mixture was diluted with water, extracted with iPrOAc (2×10 mL), dried over MgSO$_4$, filtered, concentrated in vacuo. It was purified by silica gel chromatography (12 g column), eluting with 0-5% MeOH/DCM to afford 43 mg (35.5% yield) of the title compound as a brown solid. LCMS (ESI) [M+H]$^+$=638.

Step 2: (S)-4-(2-((2-Methyl-5-(((2-methylthiazol-4-yl)methyl)amino)naphthalen-1-yl)oxy)pyridin-3-yl)-N-(piperidin-3-yl)pyrimidin-2-amine

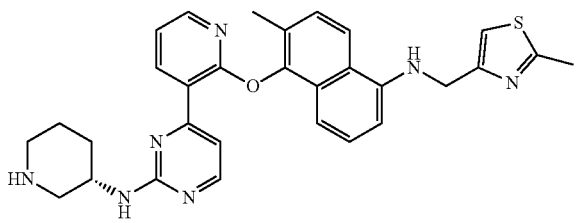

The General Procedure B was followed, using tert-butyl (S)-3-((4-(2-((2-methyl-5-(((2-methylthiazol-4-yl)methyl)amino)naphthalen-1-yl)oxy)pyridin-3-yl)pyrimidin-2-yl)amino)piperidine-1-carboxylate (43 mg, 0.07 mmol). The crude product was purified via reverse-phase HPLC and lyophilized to yield 37.2 mg (96% yield) of 244 as a yellow solid. LCMS (ESI) [M+H]$^+$=538. $^1$H NMR (400 MHz, DMSO-d$_6$) δ 8.76 (s, 2H), 8.46 (d, J=5.2 Hz, 1H), 8.08 (d, J=8.7 Hz, 1H), 8.03 (dd, J=4.8, 2.0 Hz, 1H), 7.56 (d, J=5.2 Hz, 1H), 7.50 (d, J=7.4 Hz, 1H), 7.38 (d, J=8.7 Hz, 1H), 7.27-7.20 (m, 2H), 7.15-7.07 (m, 1H), 6.82 (d, J=8.4 Hz, 1H), 6.46-6.39 (m, 1H), 4.52 (s, 2H), 4.26 (s, 1H), 3.21 (d, J=12.9 Hz, 2H), 2.84 (d, J=14.5 Hz, 2H), 2.64 (s, 3H), 2.19 (s, 3H), 2.06-1.97 (m, 1H), 1.96-1.88 (m, 1H), 1.79-1.56 (m, 2H).

Example 245 5-Methyl-2-(6-methyl-5-((3-(2-((S)-piperidin-3-ylamino)pyrimidin-4-yl)pyridin-2-yl)oxy)naphthalen-1-yl) isothiazolidine 1,1-dioxide 245

Step 1: 2-(4-Methoxybenzyl)isothiazolidine 1,1-dioxide

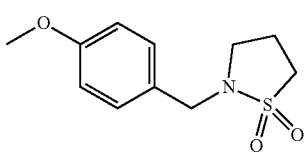 [SMILES: COc1ccc(CN2CCCS2(=O)=O)cc1]

To a solution of isothiazolidine 1,1-dioxide (500 mg, 4.13 mmol) in acetonitrile (10 mL) was added potassium carbonate (1.14 g, 8.25 mmol), 4-methoxybenzyl chloride (646 mg, 4.13 mmol). The mixture was heated to 80° C. for 12 h under nitrogen atmosphere. The mixture was poured into H$_2$O (50 mL) and extracted with ethyl acetate (50 mL). The organic layer was washed with H$_2$O (50 mL×2) and saturated brine solution (50 mL). The organic layers was dried over anhydrous sodium sulfate, filtered and concentrated in vacuo. The residue was purified via flash silica chromatography (solvent gradient: 0-40% ethyl acetate in petroleum ether) to yield 1.0 g (99% yield) of the title compound as a white solid. $^1$H NMR (400 MHz, CDCl$_3$) δ 7.28 (d, J=8.4 Hz, 2H), 9.89 (d, J=8.8 Hz, 2H), 4.13 (s, 2H), 3.82 (s, 3H), 3.23-3.18 (t, J=8.8 Hz, 2H), 3.12-3.07 (m, 2H), 2.34-2.25 (m, 2H).

Step 2: 2-(4-Methoxybenzyl)-5-methylisothiazolidine 1,1-dioxide

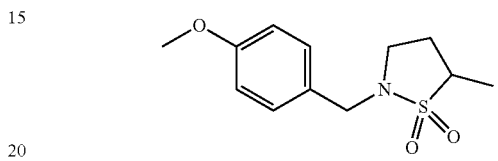

To a solution of 2-(4-methoxybenzyl)isothiazolidine 1,1-dioxide (800 mg, 3.32 mmol) in THF (10 mL) was added n-BuLi (2.5 M in hexanes, 1.99 mL, 4.97 mmol) dropwise at −78° C. under nitrogen atmosphere. After stirring at −78° C. for 1 h, iodomethane (600 mg, 4.23 mmol) was added at −78° C. After stirring at −78° C. for 1 h, the mixture was poured into saturated ammonium chloride solution (40 mL), extracted with ethyl acetate (2×30 mL) and the organic phase was washed with water (50 mL×2) and saturated brine solution (50 mL). The organic phase was dried over anhydrous sodium sulfate, filtered and concentrated in vacuo. The residue was purified by pre-TLC (50% ethyl acetate in petroleum ether) to yield 250 mg (30% yield) of the title compound as a yellow oil.

Step 3: 5-Methylisothiazolidine 1,1-dioxide

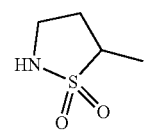

To a solution of 2-(4-methoxybenzyl)-5-methylisothiazolidine 1,1-dioxide (350 mg, 1.37 mmol) in anhydrous DCM (2 mL) was added trifluoroacetic acid (2.03 mL, 27.42 mmol). The mixture was stirred at for 1 h at room temperature. The mixture was concentrated in vacuo and the residue was dissolved in ethyl acetate (10 mL) and washed with saturated sodium bicarbonate (5 mL). The organic phase was separated, dried over anhydrous sodium sulfate, filtered and concentrated in vacuo. The residue was purified by prep-TLC (50% ethyl acetate in petroleum ether) to yield 120 mg (65% yield) of the title compound. as a pale yellow oil. $^1$H NMR (400 MHz, CDCl$_3$) δ 4.21 (s, 1H), 3.38-3.34 (m, 2H), 3.20-3.17 (m, 1H), 2.59-2.54 (m, 1H), 2.11-2.06 (m, 1H), 4.43 (d, J=7.2 Hz, 3H).

417

Step 4: (3S)-tert-Butyl 3-((4-(2-((2-methyl-5-(5-methyl-1,1-dioxidoisothiazolidin-2-yl)naphthalen-1-yl)oxy)pyridin-3-yl)pyrimidin-2-yl)amino)piperidine-1-carboxylate

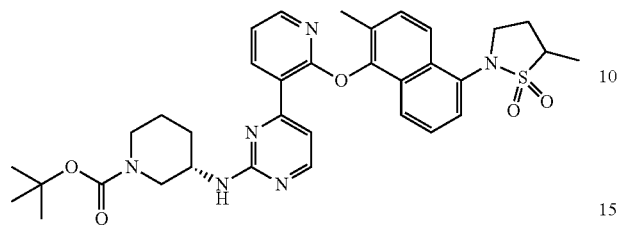

To a stirred solution of (S)-tert-butyl 3-((4-(2-((5-iodo-2-methylnaphthalen-1-yl)oxy)pyridin-3-yl)pyrimidin-2-yl)amino)piperidine-1-carboxylate (100 mg, 0.16 mmol) and 5-methyl-1,2-thiazolidine 1,1-dioxide (42 mg, 0.31 mmol) in N,N-dimethylacetamide (3 mL) was added tribasic potassium phosphate (100 mg, 0.47 mmol), CuI (12 mg, 0.06 mmol) and 2-(dimethylamino)acetic acid (6 mg, 0.06 mmol). The mixture was stirred at 130° C. for 40 h. After cooling to room temperature, the mixture was filtered and concentrated in vacuo. The residue was dissolved in ethyl acetate (50 mL) and washed with $H_2O$ (40 mL×2). The organic phase was dried over anhydrous sodium sulfate, filtered and concentrated in vacuo. The residue was purified by prep-TLC (50% ethyl acetate in petroleum ether) to yield 25 mg (25% yield) of the title compound as pale brown oil. LCMS (ESI): $[M+H]^+$=645.3.

Step 5: 5-Methyl-2-(6-methyl-5-((3-(2-((S)-piperidin-3-ylamino)pyrimidin-4-yl)pyridin-2-yl)oxy)naphthalen-1-yl)isothiazolidine 1,1-dioxide

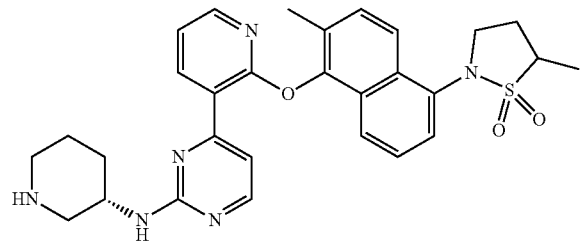 [SMILES: Cc1ccc2c(N3CCC(C)S3(=O)=O)cccc2c1Oc1ncccc1-c1ccnc(N[C@H]2CCCNC2)n1]

The General Procedure B was followed, using (3S)-tert-butyl 3-((4-(2-((2-methyl-5-(5-methyl-1,1-dioxidoisothiazolidin-2-yl)naphthalen-1-yl)oxy)pyridin-3-yl)pyrimidin-2-yl)amino)piperidine-1-carboxylate (25 mg, 0.04 mmol), dichloromethane (2 mL) and hydrochloric acid (4 M in dioxane, 2 mL, 8 mmol). The residue was purified by Prep-HPLC (mobile phase: A: water (0.05% $NH_4OH$); B: ACN) to yield 8 mg (38% yield) of the title compound as a white solid (mixture of diastereomers). LCMS (ESI): $[M+H]^+$=545.3; $^1H$ NMR (400 MHz, DMSO-$d_6$) δ 8.53-8.51 (m, 2H), 8.41 (d, J=5.2 Hz, 1H), 8.09 (d, J=8.8 Hz, 1H), 8.07-8.04 (m, 1H), 7.72 (d, J=7.6 Hz, 1H), 7.65-7.49 (m, 3H), 7.44 (d, J=5.2 Hz, 1H), 7.29-7.25 (m, 1H), 7.14 (d, J=8.0 Hz, 1H), 3.98-3.76 (m, 2H), 3.76-3.58 (m, 2H), 3.13-3.04 (m, 1H), 2.72-2.60 (m, 3H), 2.48-2.39 (m, 1H), 2.22-2.16 (m, 4H), 1.96-1.90 (m, 1H), 1.66-1.63 (m, 1H), 1.51-1.40 (m, 5H).

418

Example 246 (S)-4-(2-((2-Methyl-5-(5-methyl-1H-pyrazol-1-yl)naphthalen-1-yl)oxy)phenyl)-N-(piperidin-3-yl)pyrimidin-2-amine 246

Step 1: (S)-tert-Butyl 3-((4-(2-((2-methyl-5-(5-methyl-1H-pyrazol-1-yl)naphthalen-1-yl)oxy)pyridin-3-yl)pyrimidin-2-yl)amino)piperidine-1-carboxylate

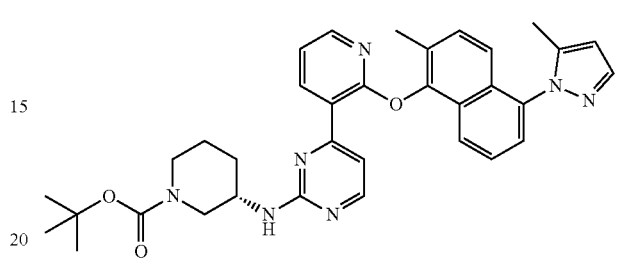

To a solution of tert-butyl (3S)-3-[[4-[2-[(5-iodo-2-methyl-1-naphthyl)oxy]-3-pyridyl]pyrimidin-2-yl]amino]piperidine-1-carboxylate (150 mg, 0.24 mmol) in DMSO (2 mL) was added 5-methyl-1H-pyrazole (23.2 mg, 0.28 mmol), copper (I) iodide (4.5 mg, 0.02 mmol), 8-hydroxyquinoline (6.8 mg, 0.05 mmol) and potassium carbonate (97.6 mg, 0.71 mmol) and stirred at 120° C. for 40 h. The mixture was concentrated and the residue was dissolved in ethyl acetate (50 mL), washed with $H_2O$ (50 mL) and brine (50 mL). The organic phase was dried over anhydrous sodium sulfate, concentrated and purified by prep-TLC (50% ethyl acetate in petroleum ether, Rf=0.5) to give a mixture of the title compound and its 5-methyl pyrazole isomer (10 mg, 7% yield) as a white solid. LCMS (ESI) $[M+H]^+$=592.3; $^1H$ NMR (400 MHz, $CDCl_3$) δ 8.89-8.57 (m, 1H), 8.42 (s, 1H), 8.10-8.02 (m, 1H), 7.89 (d, J=8.0 Hz, 1H), 7.70 (s, 2H), 7.50-7.35 (m, 3H), 7.18-7.10 (m, 2H), 6.29 (s, 1H), 5.27 (s, 1H), 4.20-4.08 (m, 1H), 4.03-3.76 (m, 1H), 3.69-3.52 (m, 1H), 3.47-3.10 (m, 1H), 2.30 (s, 3H), 2.15 (s, 3H), 2.10-2.00 (m, 1H), 1.89-1.77 (m, 2H), 1.75-1.67 (m, 3H), 1.42 (s, 9H);

and the 3-methyl pyrazole isomer: (S)-tert-Butyl 3-((4-(2-((2-methyl-5-(3-methyl-1H-pyrazol-1-yl)naphthalen-1-yl)oxy)pyridin-3-yl)pyrimidin-2-yl)amino)piperidine-1-carboxylate

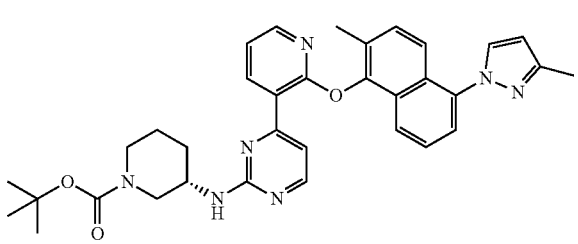 [SMILES: Cc1ccn(-c2cccc3c(Oc4ncccc4-c4ccnc(N[C@H]5CCCN(C(=O)OC(C)(C)C)C5)n4)c(C)ccc23)n1]

(an intermediate for Example 250) as a white solid (13 mg, 9% yield). LCMS (ESI) $[M+H]^+$=592.3; $^1H$ NMR (400 MHz, $CDCl_3$) δ 8.83-8.54 (m, 1H), 8.42 (s, 1H), 8.05 (d, J=4.8 Hz, 1H), 7.83 (d, J=8.4 Hz, 1H), 7.77-7.63 (m, 3H), 7.51-7.36 (m, 3H), 7.27-7.23 (m, 1H), 7.14-7.11 (m, 1H), 6.33 (s, 1H), 6.38-6.26 (m, 1H), 5.34-5.15 (m, 1H), 4.25-4.05 (m, 1H), 3.98-3.74 (m, 1H), 3.68-3.53 (m, 1H), 3.47-

3.20 (m, 1H), 2.45 (s, 3H), 2.30 (s, 3H), 2.14-1.97 (m, 1H), 1.86-1.77 (m, 1H), 1.75-1.64 (m, 3H), 1.42 (s, 9H).

Step 2: (S)-4-(2-((2-Methyl-5-(5-methyl-1H-pyrazol-1-yl)naphthalen-1-yl)oxy)phenyl)-N-(piperidin-3-yl)pyrimidin-2-amine

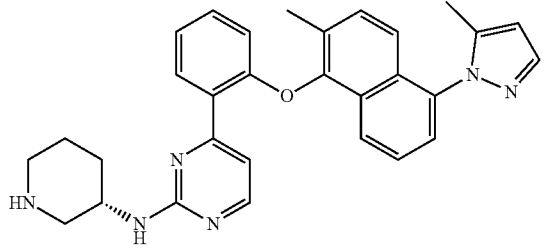 [SMILES: Cc1ccc2c(-n3nccc3C)cccc2c1Oc1ccccc1-c1ccnc(N[C@H]2CCCNC2)n1]

The General Procedure B was followed, using tert-butyl (3S)-3-[[4-[2-[[2-methyl-5-(5-methylpyrazol-1-yl)-1-naphthyl]oxy]-3-pyridyl]pyrimidin-2-yl]amino]piperidine-1-carboxylate (10 mg, 0.02 mmol) in ethyl acetate (0.5 mL). To this mixture was added hydrochloric acid (4 M in ethyl acetate, 0.04 mL, 0.16 mmol) followed by stirring at 25° C. for 1 h. The mixture was concentrated and dissolved in ethyl acetate (30 mL), washed with saturated sodium bicarbonate aqueous solution (30 mL). The organic phase was concentrated and purified by prep-TLC (10% methanol in dichloromethane, Rf=0.4) to yield 3 mg (31% yield) of 246 as a white solid. LCMS (ESI) [M+H]$^+$=492.2; $^1$H NMR (400 MHz, DMSO-d$_6$) δ 8.58-8.47 (m, 1H), 8.43 (d, J=5.2 Hz, 1H), 8.08-8.06 (m, 1H), 7.86 (d, J=8 Hz, 1H), 7.69 (d, J=1.6 Hz, 1H), 7.62-7.45 (m, 3H), 7.31-7.28 (m, 1H), 7.16 (d, J=8.0 Hz, 1H), 7.01 (d, J=8.8 Hz, 1H), 6.39 (s, 1H), 4.02-3.80 (m, 1H), 3.17-3.05 (m, 1H), 2.86-2.76 (m, 1H), 2.47-2.37 (m, 2H), 2.22 (s, 3H), 2.10 (s, 3H), 2.01-1.88 (m, 1H), 1.70-1.61 (m, 1H), 1.54-1.41 (m, 2H).

Example 247 (S)-2-Methyl-5-(6-methyl-5-((3-(2-(piperidin-3-ylamino)pyrimidin-4-yl)pyridin-2-yl)oxy)naphthalen-1-yl)-1,2,5-thiadiazolidine 1,1-dioxide 247

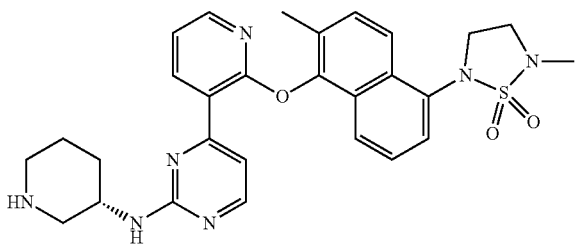 [SMILES: Cc1ccc2c(N3CCN(C)S3(=O)=O)cccc2c1Oc1ncccc1-c1ccnc(N[C@H]2CCCNC2)n1]

Step 1: (S)-tert-Butyl 3-((4-(2-((2-methyl-5-(5-methyl-1,1-dioxido-1,2,5-thiadiazolidin-2-yl)naphthalen-1-yl)oxy)pyridin-3-yl)pyrimidin-2-yl)amino)piperidine-1-carboxylate

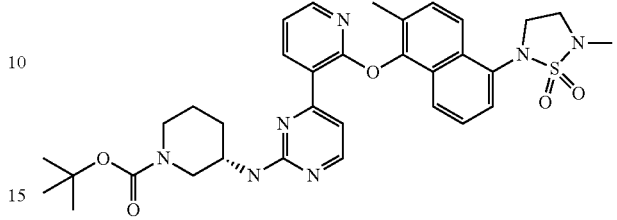

To a solution of tert-butyl (3S)-3-[[4-[2-[(5-iodo-2-methyl-1-naphthyl)oxy]-3-pyridyl]pyrimidin-2-yl]amino]piperidine-1-carboxylate (150 mg, 0.24 mmol) in acetonitrile (2 mL) was added 2-methyl-1,2,5-thiadiazolidine 1,1-dioxide (64.1 mg, 0.47 mmol), copper (I) iodide (22.4 mg, 0.12 mmol), N,N'-dimethyl-1,2-ethanediamine (20.7 mg, 0.24 mmol) and potassium carbonate (97.6 mg, 0.71 mmol) followed by stirring at 80° C. for 40 h. After cooling, the mixture was filtered, concentrated and dissolved in ethyl acetate (50 mL) and subsequently washed with H$_2$O (40 mL×2). The organic phase was dried over anhydrous sodium sulfate and filtered and the filtrate was concentrated in vacuo and purified by prep-TLC (50% ethyl acetate in petroleum ether, Rf=0.1) to yield 22 mg (15% yield) of the title compound as a white solid. LCMS (ESI) [M+Na]$^+$=646.1.

Step 2: (S)-2-Methyl-5-(6-methyl-5-((3-(2-(piperidin-3-ylamino)pyrimidin-4-yl)pyridin-2-yl)oxy)naphthalen-1-yl)-1,2,5-thiadiazolidine 1,1-dioxide

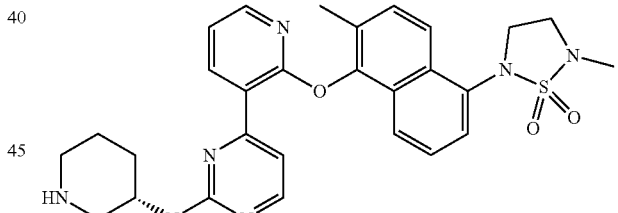

The General Procedure B was followed, using (S)-tert-butyl 3-((4-(2-((2-methyl-5-(5-methyl-1,1-dioxido-1,2,5-thiadiazolidin-2-yl)naphthalen-1-yl)oxy)pyridin-3-yl)pyrimidin-2-yl)amino)piperidine-1-carboxylate (22 mg, 0.03 mmol) in ethyl acetate (1 mL). To this mixture was added hydrochloric acid (4 M in ethyl acetate, 0.09 mL, 0.36 mmol) followed by stirring at 25° C. for 1 h. The mixture was diluted with ethyl acetate (30 mL) and washed with saturated sodium bicarbonate aqueous solution (30 mL) and the organic phase was dried over anhydrous sodium sulfate, concentrated, and purified by prep-TLC (50% ethyl acetate in petroleum ether, Rf=0.1) to yield 2.1 mg (11% yield) of 247 as a white solid. LCMS (ESI) [M+Na]$^+$=546.2; $^1$H NMR (400 MHz, DMSO-d$_6$) δ 8.56-8.48 (m, 1H), 8.42 (d, J=5.6 Hz, 1H), 8.13 (d, J=8.4 Hz, 1H), 8.06-8.04 (m, 1H), 7.73 (d, J=9.2 Hz, 1H), 7.66 (d, J=6.8 Hz, 1H), 7.58 (d, J=8.4 Hz, 1H), 7.56-7.50 (m, 1H), 7.46 (d, J=5.2 Hz, 1H), 7.29-7.25 (m, 1H), 7.22-7.17 (m, 1H), 4.00-3.91 (m, 3H), 3.62-

3.56 (m, 2H), 3.26-3.20 (m, 1H), 3.26-3.18 (m, 1H), 2.91-2.84 (m, 1H), 2.79 (s, 3H), 2.67 (t, J=2.0 Hz, 1H), 2.33 (t, J=2.0 Hz, 1H), 2.23 (s, 3H), 1.99-1.88 (m, 1H), 1.72-1.62 (m, 1H), 1.57-1.41 (m, 2H).

Example 248 6-(6-Methyl-5-((3-(2-((S)-piperidin-3-ylamino)pyrimidin-4-yl)pyridin-2-yl)oxy)naphthalen-1-yl)-6-azabicyclo[3.2.0]heptan-7-one 248

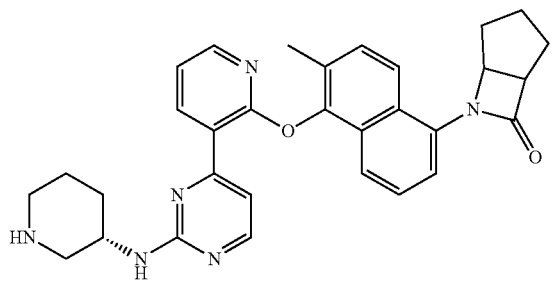 [SMILES: Cc1ccc2c(N3C(=O)C4CCCC43)cccc2c1Oc1ncccc1-c1ccnc(N[C@H]2CCCNC2)n1]

Step 1: (3S)-tert-Butyl 3-((4-(2-((2-methyl-5-(7-oxo-6-azabicyclo[3.2.0]heptan-6-yl)naphthalen-1-yl)oxy)pyridin-3-yl)pyrimidin-2-yl)amino)piperidine-1-carboxylate

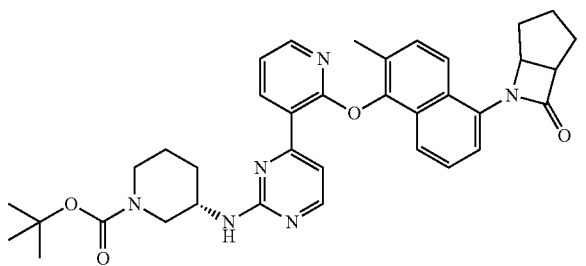 [SMILES: Cc1ccc2c(N3C(=O)C4CCCC43)cccc2c1Oc1ncccc1-c1ccnc(N[C@H]2CCCN(C(=O)OC(C)(C)C)C2)n1]

To a solution of (S)-tert-butyl 3-((4-(2-((5-iodo-2-methylnaphthalen-1-yl)oxy)pyridin-3-yl)pyrimidin-2-yl)amino)piperidine-1-carboxylate (50 mg, 0.08 mmol) in 1,4-dioxane (2 mL) was added 6-azabicyclo[3.2.0]heptan-7-one (17.4 mg, 0.16 mmol), copper (I) iodide (1.5 mg, 0.01 mmol), N,N'-dimethyl-1,2-ethanediamine (1.4 mg, 0.02 mmol), and potassium carbonate (32.5 mg, 0.24 mmol) and the mixture was stirred at 110° C. for 12 h. The mixture was concentrated and dissolved in ethyl acetate (50 mL) and subsequently washed with H$_2$O (30 mL) and brine (30 mL). The organic phase was dried over anhydrous sodium sulfate, concentrated and purified by prep-TLC (50% ethyl acetate in petroleum ether, Rf=0.2) to yield 35 mg (72% yield) of the title compound as a white solid. LCMS (ESI) [M+H]$^+$=621.1. The isomers were separated by chiral SFC (OD (250 mm×30 mm, 5 μm), 0.1% NH$_3$H$_2$O EtOH, 40% 60 mL/min) to give:

first peak on SFC: white solid; $^1$H-NMR (400 MHz, CDCl$_3$) δ 8.83-8.53 (m, 1H), 8.44-8.36 (m, 1H), 8.11-8.04 (m, 1H), 8.10-7.92 (m, 1H), 7.74-7.64 (m, 2H), 7.51-7.47 (m, 1H), 7.45-7.39 (m, 1H), 7.38-7.30 (m, 1H), 7.17-7.09 (m, 1H), 5.30-5.18 (m, 1H), 4.87-4.76 (m, 1H), 4.18-4.08 (m, 1H), 3.79-3.71 (m, 1H), 3.65-3.52 (m, 1H), 3.47-3.05 (m, 1H), 2.38-2.26 (m, 4H), 2.11-2.02 (m, 1H), 1.99-1.76 (m, 5H), 1.75-1.65 (m, 8H), 1.51-1.38 (m, 9H), second peak on SFC: 31 mg, 44% yield), white solid; $^1$H-NMR (400 MHz, CDCl$_3$) δ 8.80-8.54 (m, 1H), 8.39 (d, J=5.2 Hz, 1H), 8.10-8.02 (m, 1H), 7.99-7.91 (m, 1H), 7.74-7.64 (m, 2H), 7.53-7.46 (m, 1H), 7.45-7.38 (m, 1H), 7.45-7.38 (m, 1H), 7.38-7.31 (m, 1H), 7.30-7.24 (m, 2H), 7.17-7.07 (m, 1H), 5.31-5.24 (m, 1H), 4.81 (t, J=4.0 Hz, 1H), 4.20-4.05 (m, 1H), 3.79-3.70 (m, 1H), 3.67-3.49 (m, 1H), 3.47-3.16 (m, 1H), 2.35-2.26 (m, 4H), 2.11-2.00 (m, 1H), 1.98-1.79 (m, 5H), 1.75-1.63 (m, 8H), 1.51-1.35 (s, 9H).

Step 3: The first peak on SFC compound from Step 2 was deprotected by the General Procedure B (29 mg, 0.05 mmol) in dichloromethane (0.5 mL) and trifluoroacetic acid (0.5 mL, 6.53 mmol) and stirring at 25° C. for 1 h. The mixture was dissolved in dichloromethane (30 mL) and washed with saturated sodium bicarbonate aqueous solution (30 mL×2). The organic phase was dried over anhydrous sodium sulfate, and purified by prep-TLC (50% ethyl acetate in petroleum ether, Rf=0.2) to yield 10.3 mg (41% yield) as a white solid. LCMS (ESI) [M+H]$^+$=521.1; $^1$H-NMR (400 MHz, DMSO-d$_6$) δ 8.54-8.43 (m, 1H), 8.37 (d, J=4.8 Hz, 1H), 8.01-7.97 (m, 1H), 7.90 (d, J=8.8 Hz, 1H), 7.57 (d, J=7.2 Hz, 1H), 7.53-7.38 (m, 4H), 7.24-7.21 (m, 1H), 7.12-7.05 (m, 1H), 4.88 (t, J=4.0 Hz, 1H), 3.97-3.84 (m, 1H), 3.71-3.66 (m, 1H), 3.12-3.03 (m, 1H), 2.82-2.73 (m, 1H), 2.46-2.35 (m, 2H), 2.18 (s, 3H), 2.08-2.00 (m, 1H), 1.96-1.81 (m, 2H), 1.76-1.54 (m, 4H), 1.51-1.38 (m, 3H).

Step 4: 6-(6-Methyl-5-((3-(2-((S)-piperidin-3-ylamino)pyrimidin-4-yl)pyridin-2-yl)oxy)naphthalen-1-yl)-6-azabicyclo[3.2.0]heptan-7-one

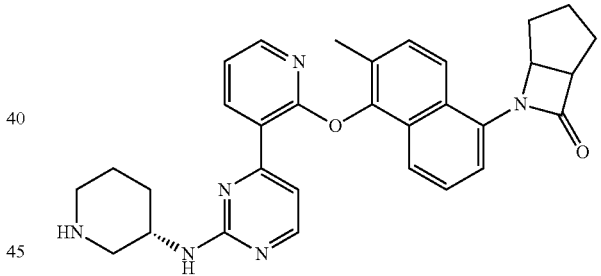

The second peak on SFC compound, (3S)-tert-butyl 3-((4-(2-((2-methyl-5-(7-oxo-6-azabicyclo[3.2.0]heptan-6-yl)naphthalen-1-yl)oxy)pyridin-3-yl)pyrimidin-2-yl)amino)piperidine-1-carboxylate (31 mg, 0.05 mmol) from Step 2 was deprotected using General Procedure B in dichloromethane (0.5 mL) and trifluoroacetic acid (0.5 mL, 6.53 mmol) and stirring at 25° C. for 1 h. The mixture was dissolved in dichloromethane (30 mL) and washed with saturated sodium bicarbonate aqueous solution (30 mL×2). The organic phase was dried over anhydrous sodium sulfate, and purified by prep-TLC (50% ethyl acetate in petroleum ether, Rf=0.2) to yield 15 mg (57% yield) of 248 as a white solid. LCMS (ESI) [M+H]$^+$=521.1. $^1$H NMR (400 MHz, DMSO-d$_6$) δ 8.55-8.48 (m, 1H), 8.42 (d, J=4.8 Hz, 1H), 8.05-8.03 (m, 1H), 7.95 (d, J=8.8 Hz, 1H), 7.61 (d, J=7.2 Hz, 1H), 7.55-7.43 (m, 3H), 7.26-7.26 (m, 1H), 7.14 (d, J=7.6 Hz, 1H), 4.93 (t, J=4.0 Hz, 1H), 3.97-3.84 (m, 1H), 3.73-3.70 (m, 1H), 3.15-3.07 (m, 1H), 2.87-2.78 (m, 1H), 2.48-2.40 (m, 2H), 2.22 (s, 3H), 2.12-2.04 (m, 1H), 1.98-1.85 (m, 2H), 1.79-1.61 (m, 4H), 1.56-1.37 (m, 3H).

Example 249 (S)-1-(6-Methyl-5-((3-(2-(piperidin-3-ylamino)pyrimidin-4-yl)pyridin-2-yl)oxy)naphthalen-1-yl)azepan-2-one 249

Step 1: (S)-tert-Butyl 3-((4-(2-((2-methyl-5-(2-oxoazepan-1-yl)naphthalen-1-yl)oxy)pyridin-3-yl)pyrimidin-2-yl)amino)piperidine-1-carboxylate

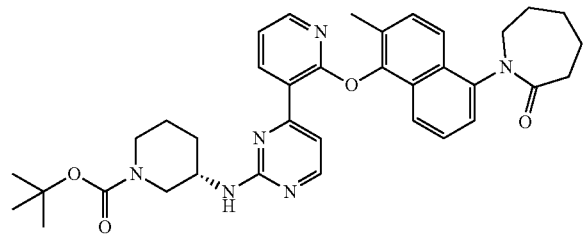 [SMILES: Cc1ccc2c(N3CCCCCC3=O)cccc2c1Oc1ncccc1-c1ccnc(N[C@H]2CCCN(C(=O)OC(C)(C)C)C2)n1]

To a solution of tert-butyl (3S)-3-[[4-[2-[(5-iodo-2-methyl-1-naphthyl)oxy]-3-pyridyl]pyrimidin-2-yl]amino]piperidine-1-carboxylate (100 mg, 0.16 mmol) in 1,4-dioxane (2 mL) was added copper (I) iodide (2 mg, 0.01 mmol), potassium carbonate (65 mg, 0.47 mmol), N,N'-dimethyl-1,2-ethanediamine (1 mg, 0.02 mmol) and 2-azepanone (36 mg, 0.31 mmol). The mixture was stirred at 110° C. for 36 h. The reaction was concentrated and purified by pre-TLC (50% ethyl acetate in petroleum ether, Rf=0.2) to yield 80 mg (82% yield) of the title compound as a yellow solid. LCMS (ESI): [M+H]$^+$=623.2.

Step 2: (S)-1-(6-Methyl-5-((3-(2-(piperidin-3-ylamino)pyrimidin-4-yl)pyridin-2-yl)oxy)naphthalen-1-yl)azepan-2-one

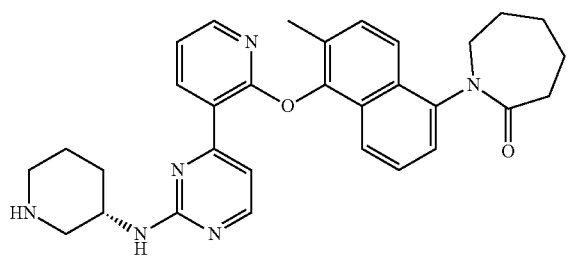 [SMILES: Cc1ccc2c(N3CCCCCC3=O)cccc2c1Oc1ncccc1-c1ccnc(N[C@H]2CCCNC2)n1]

The General Procedure B was followed, using (S)-tert-butyl 3-((4-(2-((2-methyl-5-(2-oxoazepan-1-yl)naphthalen-1-yl)oxy)pyridin-3-yl)pyrimidin-2-yl)amino)piperidine-1-carboxylate (80 mg, 0.13 mmol), dichloromethane (5 mL) and hydrochloric acid (4 M in dioxane, 2 mL, 8 mmol). The residue was purified by Prep-HPLC (mobile phase: A: water (0.05% HCl) B: ACN) to yield 14 mg (19% yield) of 249 as a yellow solid. LCMS (ESI): [M+H]$^+$=523.2; $^1$H NMR (400 MHz, DMSO-d$_6$) δ 9.77-9.43 (m, 1H), 9.42-9.24 (m, 1H), 8.98-8.75 (m, 1H), 8.52-8.50 (m, 1H), 8.32-8.06 (m, 2H), 7.82-7.71 (m, 1H), 7.67 (d, J=8.6 Hz, 1H), 7.62 (d, J=8.4 Hz, 1H), 7.51 (d, J=8.8 Hz, 1H), 7.44 (t, J=7.8 Hz, 1H), 7.34-7.27 (m, 2H), 4.61-4.19 (m, 1H), 4.01-3.90 (m, 1H), 3.59-3.37 (m, 2H), 3.25-3.13 (m, 1H), 2.94-2.80 (m, 3H), 2.61-2.53 (m, 1H), 2.21 (s, 3H), 2.08-1.99 (m, 1H), 1.95-1.64 (m, 9H).

Example 250 (S)-4-(2-((2-methyl-5-(3-methyl-1H-pyrazol-1-yl)naphthalen-1-yl)oxy)pyridin-3-yl)-N-(piperidin-3-yl)pyrimidin-2-amine 250

Step 1: (S)-tert-Butyl 3-((4-(2-((2-methyl-5-(3-methyl-1H-pyrazol-1-yl)naphthalen-1-yl)oxy)pyridin-3-yl)pyrimidin-2-yl)amino)piperidine-1-carboxylate

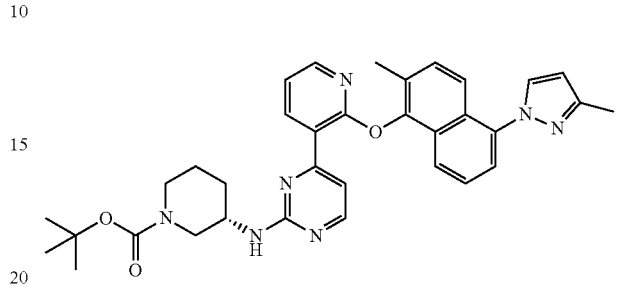

Following the procedures of Example 246, the 3-methyl pyrazole isomer was obtained as a white solid (13 mg, 9% yield). LCMS (ESI) [M+H]$^+$=592.3; $^1$H NMR (400 MHz, CDCl$_3$) δ 8.83-8.54 (m, 1H), 8.42 (s, 1H), 8.05 (d, J=4.8 Hz, 1H), 7.83 (d, J=8.4 Hz, 1H), 7.77-7.63 (m, 3H), 7.51-7.36 (m, 3H), 7.27-7.23 (m, 1H), 7.14-7.11 (m, 1H), 6.33 (s, 1H), 6.38-6.26 (m, 1H), 5.34-5.15 (m, 1H), 4.25-4.05 (m, 1H), 3.98-3.74 (m, 1H), 3.68-3.53 (m, 1H), 3.47-3.20 (m, 1H), 2.45 (s, 3H), 2.30 (s, 3H), 2.14-1.97 (m, 1H), 1.86-1.77 (m, 1H), 1.75-1.64 (m, 3H), 1.42 (s, 9H).

Step 2: (S)-4-(2-((2-Methyl-5-(3-methyl-1H-pyrazol-1-yl)naphthalen-1-yl)oxy)pyridin-3-yl)-N-(piperidin-3-yl)pyrimidin-2-amine

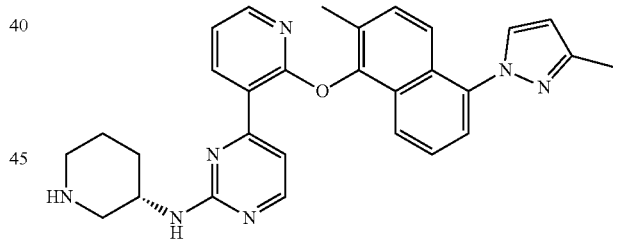

The General Procedure B was followed, using (S)-tert-Butyl 3-((4-(2-((2-methyl-5-(3-methyl-1H-pyrazol-1-yl)naphthalen-1-yl)oxy)pyridin-3-yl)pyrimidin-2-yl)amino)piperidine-1-carboxylate (13 mg, 0.02 mmol) in ethyl acetate (0.5 mL). To this mixture was added hydrochloric acid (4 M in ethyl acetate, 0.05 mL, 0.2 mmol) followed by stirring at 25° C. for 1 h. The mixture was concentrated in vacuo, dissolved in ethyl acetate (30 mL), and washed with saturated sodium bicarbonate aqueous solution (30 mL). The organic phase was concentrated and purified by prep-TLC (10% methanol in dichloromethane, Rf=0.4) to yield 2 mg (17% yield) of 250. LCMS (ESI) [M+H]$^+$=492.2; $^1$H-NMR (400 MHz, DMSO-d$_6$) δ 8.55-8.46 (m, 1H), 8.42 (d, J=5.2 Hz, 1H), 8.08 (d, J=2.0 Hz, 1H), 8.05-8.03 (m, 1H), 7.84-7.75 (m, 1H), 7.72 (d, J=8.8 Hz, 1H), 7.57-7.48 (m, 3H), 7.45 (d, J=5.2 Hz, 1H), 7.29-7.26 (m, 1H), 7.14 (d, J=8.0 Hz, 1H), 6.40 (d, J=2.4 Hz, 1H), 3.98-3.78 (m, 1H), 3.14-3.04

(m, 1H), 2.84-2.73 (m, 1H), 2.46-2.36 (m, 2H), 2.33 (s, 3H), 2.23 (s, 3H), 1.98-1.88 (m, 1H), 1.69-1.59 (m, 1H), 1.56-1.37 (m, 2H).

Example 251 2,2-Difluoro-N-(6-methyl-5-((3-(2-(((S)-piperidin-3-yl)amino)pyrimidin-4-yl)pyridin-2-yl)oxy)naphthalen-1-yl)cyclopentane-1-carboxamide 251

Step 1: (3S)-tert-Butyl 3-(4-(2-(5-(2,2-difluorocyclopentanecarboxamido)-2-methylnaphthalen-1-yloxy)pyridin-3-yl)pyrimidin-2-ylamino)piperidine-1-carboxylate

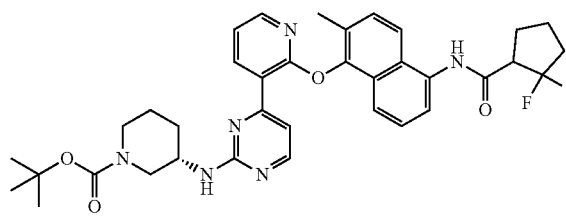

The General Procedure C was followed, using tert-butyl (3S)-3-[[4-[2-[(5-amino-2-methyl-1-naphthyl)oxy]-3-pyridyl]pyrimidin-2-yl]amino]piperidine-1-carboxylate (50 mg, 0.095 mmol), HATU (72 mg, 0.19 mmol), diisopropylethylamine (36 mg, 0.29 mmol), and 2,2-difluorocyclopentane-1-carboxylic acid (22 mg, 0.14 mmol). The product obtained after workup was used in step 2 without further purification. LCMS (ESI) [M+H]$^+$=659.3.

Step 2: 2,2-Difluoro-N-(6-methyl-5-((3-(2-(((S)-piperidin-3-yl)amino)pyrimidin-4-yl)pyridin-2-yl)oxy)naphthalen-1-yl)cyclopentane-1-carboxamide

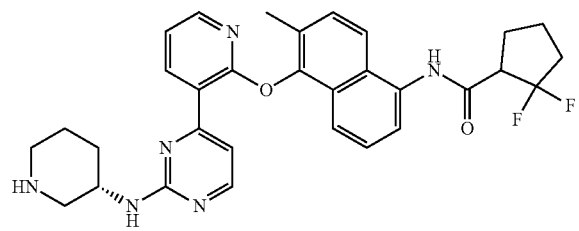 [SMILES: Cc1ccc2c(NC(=O)C3CCCC3(F)F)cccc2c1Oc1ncccc1-c1ccnc(N[C@H]2CCCNC2)n1]

To the crude (3S)-tert-Butyl 3-(4-(2-(5-(2,2-difluorocyclopentanecarboxamido)-2-methylnaphthalen-1-yloxy)pyridin-3-yl)pyrimidin-2-ylamino)piperidine-1-carboxylate from step 1 in DCM (6 mL) was added trifluoroacetic acid (1 mL). The mixture was concentrated and the residue purified by Prep-HPLC to yield 17.9 mg (34% yield) of 251 as a white solid. LCMS (ESI): [M+H]$^+$=559.2. $^1$H NMR (400 MHz, DMSO-d$_6$) δ 10.18 (s, 1H), 8.52 (s, 1H), 8.43 (d, J=5.1 Hz, 1H), 8.03 (dd, J=4.8, 2.0 Hz, 1H), 7.90 (m, 1H), 7.59-7.49 (m, 2H), 7.48 (d, J=5.1 Hz, 1H), 7.42 (dd, J=8.6, 7.3 Hz, 1H), 7.26 (dd, J=7.6, 4.8 Hz, 1H), 7.21 (d, J=7.9 Hz, 1H), 3.98 (s, 1H), 3.55 (m, 2H), 2.90 (d, J=12.3 Hz, 1H), 2.55 (d, J=6.1 Hz, 1H), 2.22 (s, 3H), 1.94 (m, 2H), 1.82-1.66 (m, 2H), 1.52 (d, J=8.6 Hz, 2H).

Example 252 (S)-3,3,3-Trifluoro-N-(6-methyl-5-(3-(2-(piperidin-3-ylamino)pyrimidin-4-yl)pyridin-2-yloxy)naphthalen-1-yl)propanamide 252

Step 1: (S)-tert-Butyl 3-(4-(2-(2-methyl-5-(3,3,3-trifluoropropanamido)naphthalen-1-yloxy)pyridin-3-yl)pyrimidin-2-ylamino)piperidine-1-carboxylate

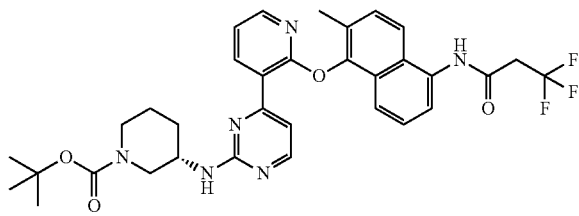 [SMILES: Cc1ccc2c(NC(=O)CC(F)(F)F)cccc2c1Oc1ncccc1-c1ccnc(N[C@H]2CCCN(C(=O)OC(C)(C)C)C2)n1]

The General Procedure C was followed, using tert-butyl (3S)-3-[[4-[2-[(5-amino-2-methyl-1-naphthyl)oxy]-3-pyridyl]pyrimidin-2-yl]amino]piperidine-1-carboxylate (50 mg, 0.095 mmol), HATU (72 mg, 0.19 mmol), diisopropylethylamine (36 mg, 0.29 mmol), and 3,3,3-trifluoropropionic acid (19 mg, 0.14 mmol). The product obtained after workup was used in step 2 without further purification. LCMS (ESI) [M+H]$^+$=637.3.

Step 2: (S)-3,3,3-Trifluoro-N-(6-methyl-5-(3-(2-(piperidin-3-ylamino)pyrimidin-4-yl)pyridin-2-yloxy)naphthalen-1-yl)propanamide

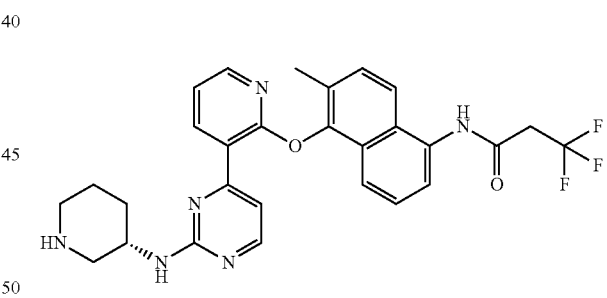

To the crude (S)-tert-butyl 3-(4-(2-(2-methyl-5-(3,3,3-trifluoropropanamido)naphthalen-1-yloxy)pyridin-3-yl)pyrimidin-2-ylamino)piperidine-1-carboxylate from step 1 in DCM (6 mL) was added trifluoroacetic acid (1 mL). The mixture was concentrated and the residue purified by Prep-HPLC to yield 23.6 mg (46% yield) of 252 as a white solid. LCMS (ESI): [M+H]$^+$=537.2. $^1$H NMR (400 MHz, DMSO-d$_6$) δ 10.32 (s, 1H), 8.50 (s, 1H), 8.42 (d, J=5.1 Hz, 1H), 8.03 (dd, J=4.8, 2.0 Hz, 1H), 7.91 (d, J=8.6 Hz, 1H), 7.63 (dd, J=7.4, 1.0 Hz, 1H), 7.56 (dd, J=8.6, 6.1 Hz, 2H), 7.44 (m, 2H), 7.26 (dd, J=7.6, 4.8 Hz, 1H), 7.16 (d, J=7.9 Hz, 1H), 3.93 (s, 1H), 3.71 (q, J=11.2 Hz, 2H), 3.14 (d, J=11.4 Hz, 1H), 2.84 (d, J=12.5 Hz, 1H), 2.22 (s, 3H), 1.97-1.91 (m, 1H), 1.69-1.66 (m, 1H), 1.53-1.47 (m, 2H).

Example 253 (S)—N-(6-Methyl-5-((3-(2-(((S)-piperidin-3-yl)amino)pyrimidin-4-yl)pyridin-2-yl)oxy)naphthalen-1-yl)spiro[2.4]heptane-1-carboxamide 253

Step 1: tert-Butyl (S)-3-((4-(2-((2-methyl-5-spiro[2.4]heptane-1-carboxamido)naphthalen-1-yl)oxy)pyridin-3-yl)pyrimidin-2-yl)amino)piperidine-1-carboxylate

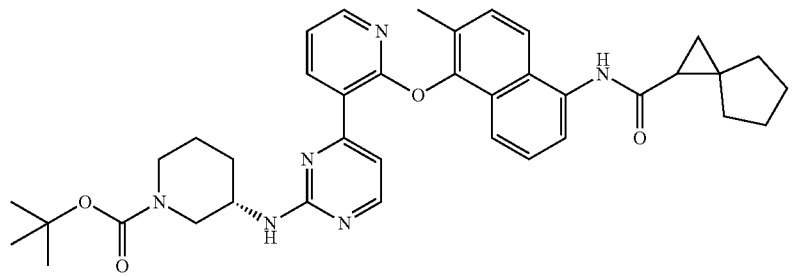

The General Procedure C was followed, using tert-butyl (3S)-3-[[4-[2-[(5-amino-2-methyl-1-naphthyl)oxy]-3-pyridyl]pyrimidin-2-yl]amino]piperidine-1-carboxylate (150 mg, 0.28 mmol) and spiro[2.4]heptane-1-carboxylic acid (63.05 mg, 0.43 mmol), HATU (221.0 mg, 0.57 mmol), DIPEA (0.15 mL, 0.85 mmol), and DMF (1.5 mL) to afford 142 mg (76.8% yield) of the title compound as a light brown solid. It was carried on as is. LCMS (ESI) [M+H]$^+$=649.

Step 2: (S)—N-(6-Methyl-5-((3-(2-(((S)-piperidin-3-yl)amino)pyrimidin-4-yl)pyridin-2-yl)oxy)naphthalen-1-yl)spiro[2.4]heptane-1-carboxamide

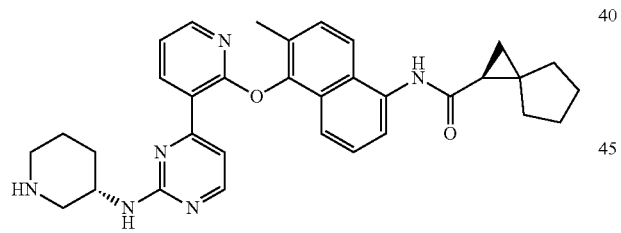

The General Procedure B was followed, using tert-butyl (S)-3-((4-(2-((2-methyl-5-((S)-spiro[2.4]heptane-1-carboxamido)naphthalen-1-yl)oxy)pyridin-3-yl)pyrimidin-2-yl)amino)piperidine-1-carboxylate (142 mg, 0.22 mmol). The crude product was purified via reverse-phase HPLC, chiral SFC, and lyophilized to yield 44.9 mg (37% yield) of 253 (isomer-1) as an off-white solid. LCMS (ESI) [M+H]$^+$=549. $t_R$: 1.191 min; $^1$H NMR (400 MHz, DMSO-$d_6$) δ 10.05 (s, 1H), 8.49 (s, 1H), 8.41 (d, J=5.1 Hz, 1H), 8.02 (dd, J=4.8, 1.9 Hz, 1H), 7.95 (d, J=8.7 Hz, 1H), 7.64 (s, 1H), 7.50 (t, J=9.0 Hz, 2H), 7.46-7.33 (m, 2H), 7.29-7.21 (m, 1H), 7.10 (d, J=8.0 Hz, 1H), 3.85 (s, 1H), 3.07 (d, 1H), 2.78 (d, J=12.4 Hz, 1H), 2.44-2.39 (m, 1H), 2.22 (s, 3H), 2.15-2.09 (m, 1H), 1.96 (s, 2H), 1.75-1.57 (m, 10H), 1.52-1.40 (m, 1H), 1.17 (dd, J=5.5, 3.8 Hz, 1H), 1.05-0.99 (m, 1H).

Example 254 (R)—N-(6-Methyl-5-((3-(2-(((S)-piperidin-3-yl)amino)pyrimidin-4-yl)pyridin-2-yl)oxy)naphthalen-1-yl)spiro[2.4]heptane-1-carboxamide 253

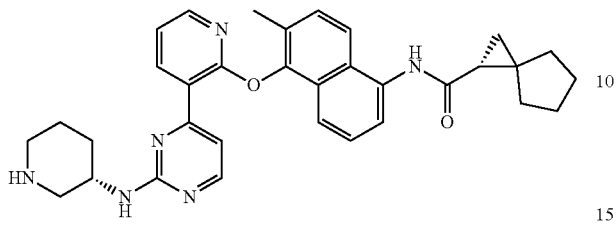

Following Example 253 and General Procedure B was followed, tert-butyl (S)-3-((4-(2-((2-methyl-5-((R)-spiro[2.4]heptane-1-carboxamido)naphthalen-1-yl)oxy)pyridin-3-yl)pyrimidin-2-yl)amino)piperidine-1-carboxylate was converted to 254 as isomer-2 was obtained 47 mg (39% yield) as an off-white solid. LCMS (ESI) [M+H]$^+$=549. $t_R$: 1.557 min. $^1$H NMR (400 MHz, DMSO-$d_6$) δ 10.05 (s, 1H), 8.49 (s, 1H), 8.41 (d, J=5.1 Hz, 1H), 8.02 (dd, J=4.8, 2.0 Hz, 1H), 7.95 (d, J=8.7 Hz, 1H), 7.64 (d, 1H), 7.54-7.47 (m, 2H), 7.44 (d, J=5.1 Hz, 1H), 7.39 (t, J=7.9 Hz, 1H), 7.25 (dd, J=7.6, 4.8 Hz, 1H), 7.12 (d, J=8.0 Hz, 1H), 3.89 (s, 1H), 3.09 (s, 1H), 2.80 (d, J=12.4 Hz, 1H), 2.46-2.40 (m, 1H), 2.22 (s, 3H), 2.14-2.07 (m, 5H), 1.96-1.89 (m, 1H), 1.76-1.59 (m, 7H), 1.53-1.39 (m, 1H), 1.17 (dd, J=5.4, 3.8 Hz, 1H), 1.02 (s, 1H).

Example 255 (S)—N-(6-Methyl-5-((3-(2-(piperidin-3-ylamino)pyrimidin-4-yl)pyridin-2-yl)oxy)naphthalen-1-yl)spiro[3.3]heptane-2-carboxamide 255

Step 1: tert-Butyl (S)-3-((4-(2-((2-methyl-5-(spiro[3.3]heptane-2-carboxamido)naphthalen-1-yl)oxy)pyridin-3-yl)pyrimidin-2-yl)amino)piperidine-1-carboxylate

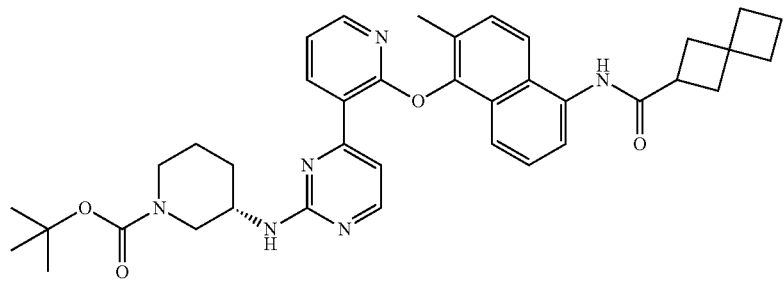 [SMILES: Cc1ccc2c(NC(=O)C3CC4(CCC4)C3)cccc2c1Oc1ncccc1-c1ccnc(N[C@H]2CCCN(C(=O)OC(C)(C)C)C2)n1]

The General Procedure of Example 217 was followed, using tert-butyl (3S)-3-[[4-[2-[(5-amino-2-methyl-1-naphthyl)oxy]-3-pyridyl]pyrimidin-2-yl]amino]piperidine-1-carboxylate (150 mg, 0.28 mmol) and spiro[3.3]heptane-2-carboxylic acid (61.7 mg, 0.43 mmol), HATU (221.0 mg, 0.57 mmol), DIPEA (0.15 mL, 0.85 mmol), and DMF (1.5 mL). The crude material was purified by silica gel chromatography (12 g column) eluting with 0-5% MeOH/DCM to afford 185 mg (100% yield) of the title compound as a brown solid. LCMS (ESI) [M+H]$^+$=649.

Step 2: (S)—N-(6-Methyl-5-((3-(2-(piperidin-3-ylamino)pyrimidin-4-yl)pyridin-2-yl)oxy)naphthalen-1-yl)spiro[3.3]heptane-2-carboxamide

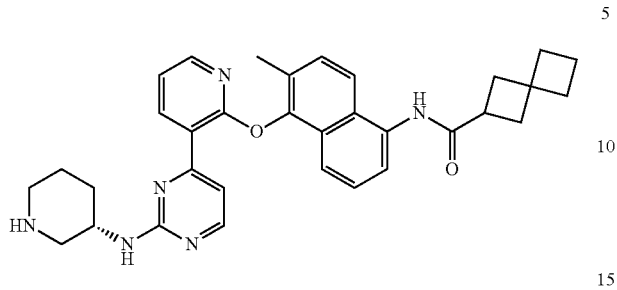

The General Procedure B was followed, using tert-butyl (S)-3-((4-(2-((2-methyl-5-(spiro[3.3]heptane-2-carboxamido)naphthalen-1-yl)oxy)pyridin-3-yl)pyrimidin-2-yl)amino)piperidine-1-carboxylate (185 mg, 0.28 mmol). The crude product was purified via reverse-phase HPLC and lyophilized to yield 79.1 mg (50.6% yield) of 255 as an off-white solid. LCMS (ESI) [M+H]$^+$=549. $^1$H NMR (400 MHz, DMSO-d$_6$) δ 9.74 (s, 1H), 8.49 (d, J=7.4 Hz, 1H), 8.40 (d, J=5.1 Hz, 1H), 8.02 (dd, J=4.8, 2.0 Hz, 1H), 7.86 (d, J=8.7 Hz, 1H), 7.61 (d, J=7.4 Hz, 1H), 7.49 (d, J=8.8 Hz, 2H), 7.45-7.32 (m, 2H), 7.25 (dd, J=7.6, 4.8 Hz, 1H), 7.10 (d, J=8.0 Hz, 1H), 3.87 (s, 1H), 3.08 (d, J=11.6 Hz, 1H), 2.78 (d, J=12.4 Hz, 1H), 2.42 (dd, J=12.4, 3.6 Hz, 3H), 2.24 (d, J=8.5 Hz, 4H), 2.21 (s, 3H), 2.08 (t, J=7.4 Hz, 2H), 1.91 (t, J=7.4 Hz, 3H), 1.81 (q, J=7.5 Hz, 2H), 1.67-1.59 (m, 1H), 1.54-1.37 (m, 2H).

Example 256 (S)-4-(2-((5-(((2-Isopropylthiazol-4-yl)methyl)amino)-2-methylnaphthalen-1-yl)oxy)pyridin-3-yl)-N-(piperidin-3-yl)pyrimidin-2-amine 256

Step 1: tert-Butyl (S)-3-((4-(2-((5-(((2-isopropylthiazol-4-yl)methyl)amino)-2-methylnaphthalen-1-yl)oxy)pyridin-3-yl)pyrimidin-2-yl)amino)piperidine-1-carboxylate

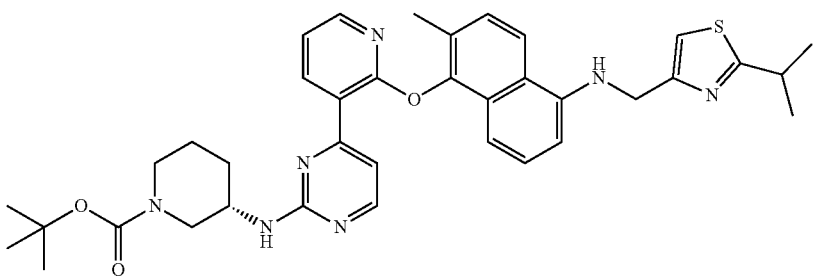

The General Procedure E was followed, using tert-butyl (3S)-3-[[4-[2-[(5-amino-2-methyl-1-naphthyl)oxy]-3-pyridyl]pyrimidin-2-yl]amino]piperidine-1-carboxylate (150 mg, 0.28 mmol) and 4-(chloromethyl)-2-isopropylthiazole (150 mg, 0.85 mmol). The crude material was purified by silica gel chromatography (12 g column) eluting with 0-5% MeOH/DCM to afford 69 mg (36.4% yield) of the title compound as a brown solid. LCMS (ESI) [M+H]$^+$=666.

Step 2: (S)-4-(2-((5-(((2-Isopropylthiazol-4-yl)methyl)amino)-2-methylnaphthalen-1-yl)oxy)pyridin-3-yl)-N-(piperidin-3-yl)pyrimidin-2-amine

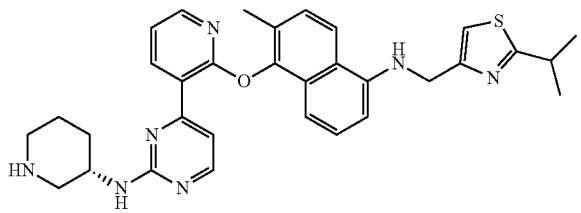 [SMILES: Cc1ccc2c(NCc3csc(C(C)C)n3)cccc2c1Oc1ncccc1-c1ccnc(N[C@H]2CCCNC2)n1]

The General Procedure B was followed, using tert-butyl (S)-3-((4-(2-((5-(((2-isopropylthiazol-4-yl)methyl)amino)-2-methylnaphthalen-1-yl)oxy)pyridin-3-yl)pyrimidin-2-yl)amino)piperidine-1-carboxylate (69 mg, 0.10 mmol). The crude product was purified via reverse-phase HPLC and lyophilized to yield 24.1 mg (41% yield) of 256 as an off-white solid. LCMS (ESI) [M+H]$^+$=566. $^1$H NMR (400 MHz, DMSO-d$_6$) δ 8.50-8.46 (m, 1H), 8.39 (d, J=5.1 Hz, 1H), 8.07 (d, J=8.7 Hz, 1H), 8.01 (dd, J=4.8, 2.0 Hz, 1H), 7.43 (d, J=5.2 Hz, 1H), 7.37 (d, J=8.7 Hz, 1H), 7.30 (s, 1H), 7.25-7.20 (m, 2H), 7.10 (dd, J=8.1, 2.2 Hz, 2H), 6.92-6.83 (m, 2H), 6.43 (dd, J=7.8, 1.0 Hz, 1H), 4.53 (d, J=5.5 Hz, 2H), 3.87 (s, 1H), 3.09 (d, J=11.7 Hz, 1H), 2.85-2.75 (m, 2H), 2.47-2.40 (m, 2H), 2.19 (s, 3H), 1.90 (d, J=7.2 Hz, 1H), 1.64 (d, J=12.2 Hz, 1H), 1.54-1.38 (m, 2H), 1.33 (d, J=6.9 Hz, 6H).

Example 257 (S)-3-Methyl-1-(6-methyl-5-((3-(2-((S)-piperidin-3-ylamino)pyrimidin-4-yl)pyridin-2-yl)oxy)naphthalen-1-yl)pyrrolidin-2-one 257

Step 1: (S)-tert-Butyl 3-((4-(2-((2-methyl-5-((S)-3-methyl-2-oxopyrrolidin-1-yl)naphthalen-1-yl)oxy)pyridin-3-yl)pyrimidin-2-yl)amino)piperidine-1-carboxylate & (S)-tert-butyl 3-((4-(2-((2-methyl-5-((R)-3-methyl-2-oxopyrrolidin-1-yl)naphthalen-1-yl)oxy)pyridin-3-yl)pyrimidin-2-yl)amino)piperidine-1-carboxylate

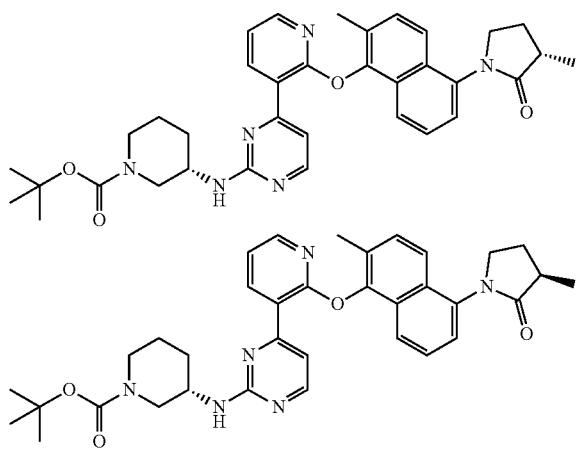

To a stirred solution of tert-butyl (3S)-3-[[4-[2-[(5-iodo-2-methyl-1-naphthyl)oxy]-3-pyridyl]pyrimidin-2-yl]amino]piperidine-1-carboxylate (150 mg, 0.24 mmol) in 1,4-dioxane (2 mL) was added copper(I) iodide (5 mg, 0.02 mmol), potassium carbonate (98 mg, 0.71 mmol), N,N'-dimethyl-1,2-ethanediamine (4 mg, 0.05 mmol) and 3-methyl-2-pyrrolidinone (23 mg, 0.24 mmol), the mixture was stirred at 110° C. for 12 h. The combined mixture was concentrated and dissolved in ethyl acetate (50 mL) and subsequently washed with H$_2$O (30 mL) and brine (30 mL). The organic phase was dried over anhydrous sodium sulfate and filtered and the filtrate was concentrated. The residue was purified by chromatography on silica (solvent gradient: 0-50% ethyl acetate in petroleum ether) and separated using chiral SFC (SFC80; Chiralpak AD 250×30 mm I.D., 10 μm; supercritical CO$_2$/MeOH+NH$_3$.H$_2$O=40/40; 60 mL/min) to afford Peak 1: tert-butyl (3S)-3-[[4-[2-[[2-methyl-5-[(3S)-3-methyl-2-oxo-pyrrolidin-1-yl]-1-naphthyl]oxy]-3-pyridyl]pyrimidin-2-yl]amino]piperidine-1-carboxylate (70 mg, 53.8% yield) as a white solid (first peak).

Peak 2: tert-butyl (3S)-3-[[4-[2-[[2-methyl-5-[(3R)-3-methyl-2-oxo-pyrrolidin-1-yl]-1-naphthyl]oxy]-3-pyridyl]pyrimidin-2-yl]amino]piperidine-1-carboxylate (60 mg, 46.2% yield) as a white solid (second peak). LCMS (ESI): [M+H]$^+$=609.3.

Step 2: (S)-3-Methyl-1-(6-methyl-5-((3-(2-((S)-piperidin-3-ylamino)pyrimidin-4-yl)pyridin-2-yl)oxy)naphthalen-1-yl)pyrrolidin-2-one & (R)-3-methyl-1-(6-methyl-5-((3-(2-((S)-piperidin-3-ylamino)pyrimidin-4-yl)pyridin-2-yl)oxy)naphthalen-1-yl)pyrrolidin-2-one

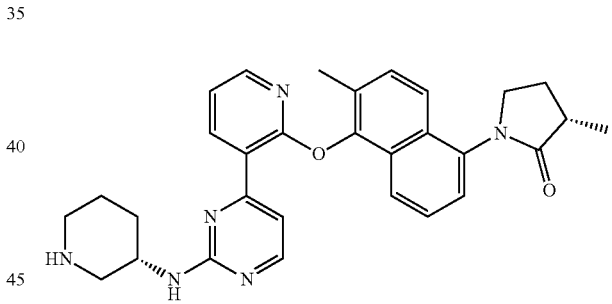

The General Procedure B was followed, using (S)-3-methyl-1-(6-methyl-5-((3-(2-((S)-piperidin-3-ylamino)pyrimidin-4-yl)pyridin-2-yl)oxy)naphthalen-1-yl)pyrrolidin-2-one (70 mg, 0.12 mmol) (first peak on SFC in step 1), dichloromethane (5 mL) and hydrochloric acid (4 M in ethyl acetate, 2 mL, 8 mmol). The residue was purified by Prep-HPLC (mobile phase: A: water (0.05% TFA) B: ACN) to yield 19 mg (31% yield) of 257 as a yellow solid. LCMS (ESI): [M+H]$^+$=509.3; $^1$H NMR (400 MHz, DMSO-d$_6$) δ 9.68 (s, 1H), 9.35 (s, 1H), 8.91 (s, 1H), 8.53 (s, 1H), 8.34 (s, 1H), 8.14 (s, 1H), 7.80 (s, 1H), 7.69-7.58 (m, 2H), 7.55-7.45 (m, 2H), 7.45-7.39 (m, 1H), 7.31 (dd, J=5.2, 7.6 Hz, 1H), 4.53 (s, 1H), 3.83 (s, 1H), 3.71 (s, 1H), 3.44 (d, J=6.4 Hz, 1H), 3.19 (s, 1H), 2.93-2.81 (m, 2H), 2.80-2.71 (m, 1H), 2.46 (s, 1H), 2.23 (s, 3H), 2.06-2.00 (m, 1H), 1.99-1.88 (m, 2H), 1.88-1.60 (m, 2H), 1.25 (d, J=7.2 Hz, 3H). The stereochemistry of the lactam was tentatively and randomly assigned.

435

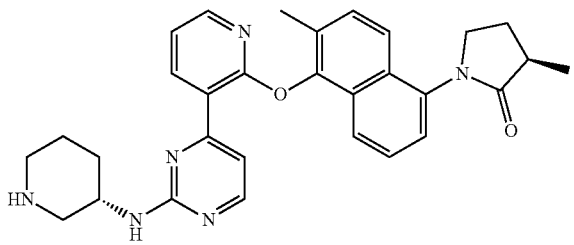 [SMILES: Cc1ccc2c(N3CC[C@@H](C)C3=O)cccc2c1Oc1ncccc1-c1ccnc(N[C@H]2CCCNC2)n1]

The R methyl isomer was also obtained using the General Procedure B, using (R)-3-methyl-1-(6-methyl-5-((3-(2-((S)-piperidin-3-ylamino)pyrimidin-4-yl)pyridin-2-yl)oxy)naphthalen-1-yl)pyrrolidin-2-one (60 mg, 0.10 mmol)) (second peak on SFC in step 1), dichloromethane (5 mL) and hydrochloric acid (4 M in ethyl acetate, 2 mL, 8 mmol). The residue was purified by Prep-HPLC (mobile phase: A: water (0.05% TFA) B: ACN) to yield 11 mg (22% yield) of (R)-3-methyl-1-(6-methyl-5-((3-(2-((S)-piperidin-3-ylamino)pyrimidin-4-yl)pyridin-2-yl)oxy)naphthalen-1-yl)pyrrolidin-2-one as a yellow solid. LCMS (ESI): $[M+H]^+$=509.2; $^1$H NMR (400 MHz, DMSO-d6) δ 9.78 (s, 1H), 9.41 (s, 1H), 8.94 (s, 1H), 8.53 (s, 1H), 8.40 (s, 1H), 8.13 (s, 1H), 7.82 (s, 1H), 7.66 (d, J=8.0 Hz, 1H), 7.63-7.57 (m, 1H), 7.54-7.44 (m, 2H), 7.44-7.37 (m, 1H), 7.30 (dd, J=5.2, 7.6 Hz, 1H), 4.74-4.45 (m, 1H), 3.90-3.63 (m, 2H), 3.50-3.35 (m, 1H), 3.18 (s, 1H), 2.93-2.80 (m, 2H), 2.79-2.69 (m, 1H), 2.48-2.40 (m, 1H), 2.22 (s, 3H), 2.06-2.00 (m, 1H), 1.99-1.88 (m, 2H), 1.87-1.59 (m, 2H), 1.24 (d, J=7.2 Hz, 3H). The stereochemistry of the lactam was tentatively and randomly assigned.

Example 258 (S)-4-(2-((5-((1,5-Dimethyl-1H-pyrazol-3-yl)amino)-2-methylnaphthalen-1-yl)oxy)pyridin-3-yl)-N-(piperidin-3-yl)pyrimidin-2-amine 258

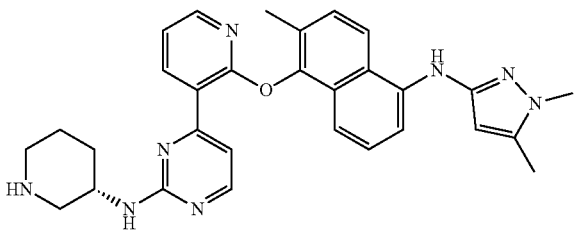 [SMILES: Cc1ccc2c(Nc3cc(C)n(C)n3)cccc2c1Oc1ncccc1-c1ccnc(N[C@H]2CCCNC2)n1]

Step 1: (S)-tert-Butyl 3-((4-(2-((5-((1,5-dimethyl-1H-pyrazol-3-yl)amino)-2-methylnaphthalen-1-yl)oxy)pyridin-3-yl)pyrimidin-2-yl)amino)piperidine-1-carboxylate

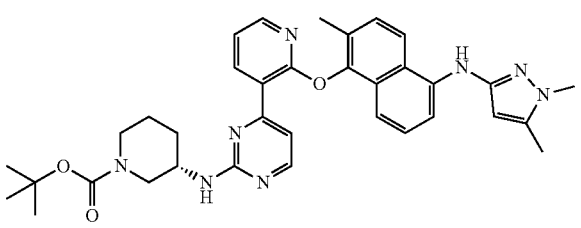 [SMILES: Cc1ccc2c(Nc3cc(C)n(C)n3)cccc2c1Oc1ncccc1-c1ccnc(N[C@H]2CCCN(C(=O)OC(C)(C)C)C2)n1]

To a solution of tert-butyl (3S)-3-[[4-[2-[(5-amino-2-methyl-1-naphthyl)oxy]-3-pyridyl]pyrimidin-2-yl]amino]piperidine-1-carboxylate (100 mg, 0.19 mmol), 3-bromo-1,5-dimethyl-pyrazole (50 mg, 0.28 mmol), 2-methylpropan-2-olate; sodium hydride (46 mg, 0.47 mmol) in 1,4-dioxane were added [2-(2-aminophenyl)phenyl]-methylsulfonyloxy-palladium; dicyclohexyl-[3,6-dimethoxy-2-(2,4,6-triisopropylphenyl)phenyl]phosphane (17 mg, 0.02 mmol), 2-(dicyclohexylphosphino)3,6-dimethoxy-2',4',6'-triisopropyl-1,1'-biphenyl (20 mg, 0.04 mmol) under nitrogen atmosphere. The mixture was stirred at 120° C. for 12 h. The solution was concentrated and purified by prep-TLC (50% ethyl acetate in petroleum ether, Rf=0.4) to yield 50 mg (42% yield) of the title compound as a white solid.

Step 2: (S)-4-(2-((5-((1,5-Dimethyl-1H-pyrazol-3-yl)amino)-2-methylnaphthalen-1-yl)oxy)pyridin-3-yl)-N-(piperidin-3-yl)pyrimidin-2-amine

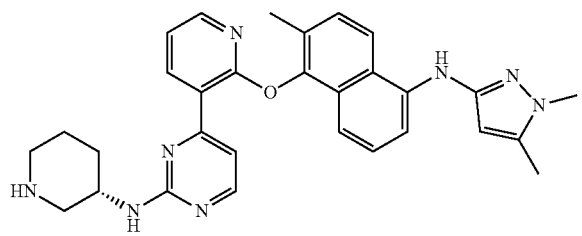 [SMILES: Cc1ccc2c(Nc3cc(C)n(C)n3)cccc2c1Oc1ncccc1-c1ccnc(N[C@H]2CCCNC2)n1]

The General Procedure B was followed, using (S)-tert-butyl 3-((4-(2-((5-((1,5-dimethyl-1H-pyrazol-3-yl)amino)-2-methylnaphthalen-1-yl)oxy)pyridin-3-yl)pyrimidin-2-yl)amino)piperidine-1-carboxylate (50 mg, 0.08 mmol), dichloromethane (5 mL) and hydrochloric acid (4 M in ethyl acetate, 2 mL, 8 mmol). The residue was purified by Prep-HPLC (mobile phase: A: water (0.05% HCl) B: ACN) to yield 14 mg (32% yield) of 258 as a yellow solid. LCMS (ESI): $[M+H]^+$=521.1; $^1$H NMR (400 MHz, DMSO-$d_6$) δ 9.74 (s, 1H), 9.38 (s, 1H), 8.91 (s, 1H), 8.53 (s, 1H), 8.18-8.02 (m, 2H), 7.80 (s, 1H), 7.64 (d, J=7.4 Hz, 1H), 7.46 (d, J=8.8 Hz, 1H), 7.34-7.25 (m, 2H), 7.21 (d, J=8.4 Hz, 1H), 5.90 (s, 1H), 4.64-4.47 (m, 1H), 3.69 (s, 3H), 3.42 (s, 1H), 3.18 (s, 1H), 2.93-2.79 (m, 2H), 2.26 (s, 3H), 2.21 (s, 3H), 2.09-1.60 (m, 4H).

Example 259 (S)—N-(5-((5-ethyl-3-(2-(piperidin-3-ylamino)pyrimidin-4-yl)pyridin-2-yl)oxy)-6-methyl-naphthalen-1-yl)propane-1-sulfonamide 259

Step 1: (S)-tert-Butyl 3-((4-(2-((5-amino-2-methyl-naphthalen-1-yl)oxy)-5-vinylpyridin-3-yl)pyrimidin-2-yl)amino)piperidine-1-carboxylate

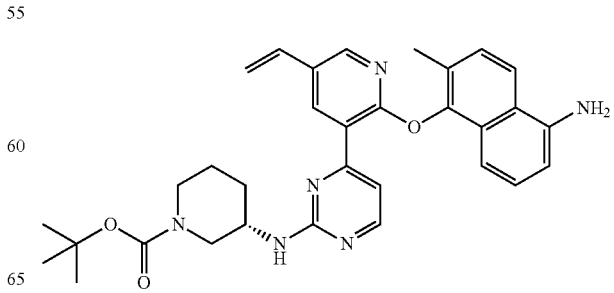

To a mixture of tert-butyl (3S)-3-[[4-[2-[(5-amino-2-methyl-1-naphthyl)oxy]-5-bromo-3-pyridyl]pyrimidin-2-yl]amino]piperidine-1-carboxylate (50 mg, 0.083 mmol), palladium(II) acetate (1.8 mg, 0.0083 mmol) and 2-dicyclohexylphosphino-2',6'-dimethoxybiphenyl (6.8 mg, 0.016 mmol)(S-Phos) was added degassed 1,4-dioxane (0.41 mL) followed by tributyl(vinyl)tin (34 µL, 0.12 mmol). The reaction mixture was heated in a microwave reactor for 35 min at 130° C. and then cooled to rt. The reaction mixture was used directly in the next step as is. LCMS (ESI) [M+H]⁺=553.3, rt=1.95 min.

Step 2: (S)-tert-Butyl 3-((4-(2-((6-fluoro-2-methyl-5-(propylsulfonamido)naphthalen-1-yl)oxy)-5-vinylpyridin-3-yl)pyrimidin-2-yl)amino)piperidine-1-carboxylate

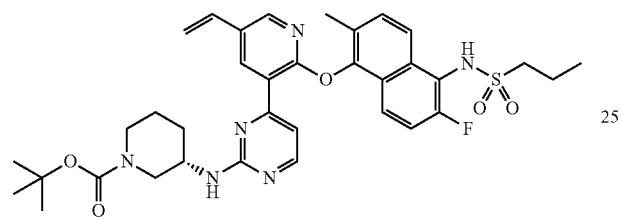

Prepared using the crude solution of (S)-tert-butyl 3-((4-(2-((5-amino-2-methylnaphthalen-1-yl)oxy)-5-vinylpyridin-3-yl)pyrimidin-2-yl)amino)piperidine-1-carboxylate (51 mg, 0.092 mmol) prepared in the previous step, pyridine (0.28 mL, 3.46 mmol), 1,4-dioxane (0.4 mL), and 1-propanesulfonyl chloride (71 mg, 0.50 mmol). After 4 h, the reaction mixture was diluted with EtOAc (50 mL) and H₂O (2 mL), washed with saturated NH₄Cl(aq), then saturated NaHCO₃(aq) and brine. The organic phase was dried (MgSO₄) filtered and concentrated in vacuo. The crude mixture was dissolved in MeCN, extracted with heptanes and concentrated in vacuo. The crude was purified by flash chromatography through silica gel (0-40% EtOAc/DCM) to provide 33 mg (54% yield) of the title compound. LCMS (ESI) [M+H]⁺=659.6, rt=2.05 min.

Step 3: (S)-tert-butyl 3-((4-(5-ethyl-2-((6-fluoro-2-methyl-5-(propylsulfonamido)naphthalen-1-yl)oxy)pyridin-3-yl)pyrimidin-2-yl)amino)piperidine-1-carboxylate

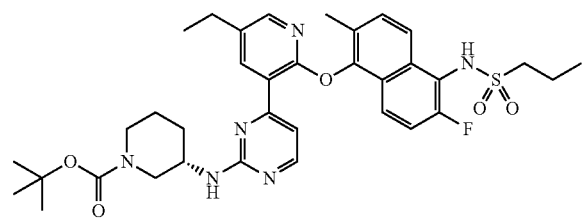 [SMILES: CCCS(=O)(=O)Nc1c(F)ccc2c(Oc3ncc(CC)cc3-c3ccnc(N[C@H]4CCCN(C(=O)OC(C)(C)C)C4)n3)c(C)ccc12]

A solution of (S)-tert-butyl 3-((4-(2-((6-fluoro-2-methyl-5-(propylsulfonamido)naphthalen-1-yl)oxy)-5-vinylpyridin-3-yl)pyrimidin-2-yl)amino)piperidine-1-carboxylate (50 mg, 0.076 mmol), in EtOAc (3 mL), was added to a flask containing 10% w/w Pd/C (26 mg, wet). The flask was purged for 5 min with N₂ and then purged for 10 min with H₂. Then a fresh H₂ balloon was attached followed by stirring at rt. After 18 h, the reaction mixture was filtered through celite eluting EtOAc (40 mL). The solution was concentrated in vacuo to provide 40 mg (80% yield) of the title compound as a clear wax which was used in the next step without further purification. LCMS (ESI) [M+H]⁺=661.4, rt=2.04 min.

Step 4: (S)—N-(5-((5-ethyl-3-(2-(piperidin-3-ylamino)pyrimidin-4-yl)pyridin-2-yl)oxy)-6-methyl-naphthalen-1-yl)propane-1-sulfonamide

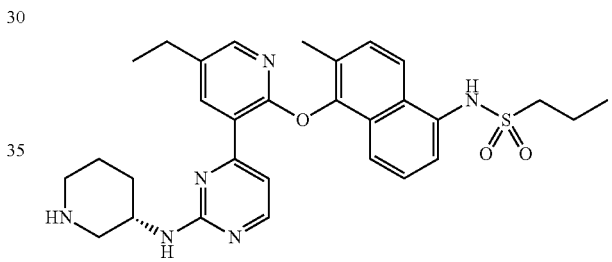

Prepared according to General Procedure B using (S)-tert-butyl 3-((4-(5-ethyl-2-((6-fluoro-2-methyl-5-(propylsulfonamido)naphthalen-1-yl)oxy)pyridin-3-yl)pyrimidin-2-yl)amino)piperidine-1-carboxylate (40 mg, 0.060 mmol), EtOAc (2 mL) and hydrochloric acid (4 M in dioxane, 1 mL, 4 mmol). After 16 h, the mixture was concentrated in vacuo and the residue was washed with EtOAc (3×3 mL) and then with MeCN (3×3 mL). The residue was then sonicated and concentrated in vacuo with MeCN (3×3 mL) and the resulting solid residue dissolved in water and MeCN followed by lyophilization to provide 30 mg (88% yield) of 259. LCMS (ESI) [M+H]⁺=561.2, rt=1.46 min. ¹H NMR (400 MHz, d6-dmso) δ 9.90-9.75 (m, 1H), 8.93-8.71 (m, 2H), 8.47 (d, J=5.2 Hz, 1H), 8.37 (s, 1H), 8.16-8.09 (m, 1H), 7.90 (d, J=2.3 Hz, 1H), 7.60-7.52 (m, 3H), 7.48-7.41 (m, 2H), 4.33-4.18 (m, 1H), 3.42-3.37 (m, 1H), 3.20 (d, J=12.2 Hz, 1H), 3.16-3.07 (m, 2H), 2.95-2.81 (m, 2H), 2.67-2.58 (m, 2H), 2.21 (s, 3H), 2.09-1.99 (m, 1H), 1.96-1.87 (m, 1H), 1.82-1.53 (m, 4H), 1.20 (t, J=7.5 Hz, 3H), 0.97 (t, J=7.4 Hz, 3H).

Example 260 (S)-4-(2-((2-Methyl-5-((2-(thiazol-4-yl)ethyl)amino)naphthalen-1-yl)oxy)pyridin-3-yl)-N-(piperidin-3-yl)pyrimidin-2-amine 260

Step 1: tert-Butyl (S)-3-((4-(2-((2-methyl-5-((2-(thiazol-4-yl)ethyl)amino)naphthalen-1-yl)oxy)pyridin-3-yl)pyrimidin-2-yl)amino)piperidine-1-carboxylate

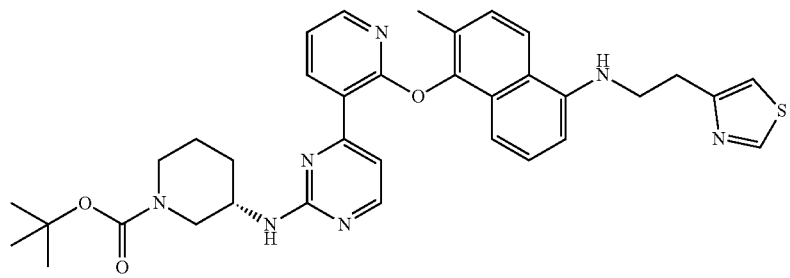 [SMILES: Cc1ccc2c(NCCc3cscn3)cccc2c1Oc1ncccc1-c1ccnc(N[C@H]2CCCN(C(=O)OC(C)(C)C)C2)n1]

The General Procedure E was followed, using tert-butyl (3S)-3-[[4-[2-[(5-amino-2-methyl-1-naphthyl)oxy]-3-pyridyl]pyrimidin-2-yl]amino]piperidine-1-carboxylate (150 mg, 0.28 mmol) and 4-(2-chloroethyl)thiazole (126.2 mg, 0.85 mmol). The crude material was purified by silica gel chromatography (12 g column) eluting with 0-5% MeOH/DCM to afford 34 mg (19% yield) of the title compound as a brown solid. LCMS (ESI) [M+H]$^+$=638.

Step 2: (S)-4-(2-((2-Methyl-5-((2-(thiazol-4-yl)ethyl)amino)naphthalen-1-yl)oxy)pyridin-3-yl)-N-(piperidin-3-yl)pyrimidin-2-amine

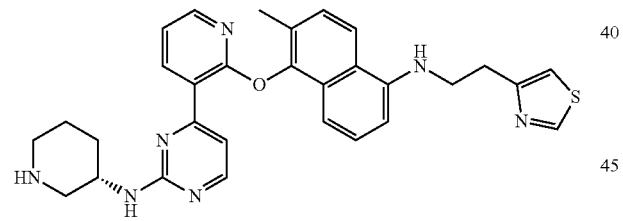

The General Procedure B was followed, using tert-butyl (S)-3-((4-(2-((2-methyl-5-((2-(thiazol-4-yl)ethyl)amino)naphthalen-1-yl)oxy)pyridin-3-yl)pyrimidin-2-yl)amino)piperidine-1-carboxylate (34 mg, 0.05 mmol). The crude product was purified via reverse-phase HPLC and lyophilized to yield 11 mg (39% yield) of 260 as a light brown solid. LCMS (ESI) [M+H]$^+$=538. $^1$H NMR (400 MHz, DMSO-$d_6$) δ 9.07 (d, J=2.0 Hz, 1H), 8.49 (s, 1H), 8.40 (d, J=5.1 Hz, 1H), 8.01 (dd, J=4.8, 2.0 Hz, 1H), 7.97 (d, J=8.8 Hz, 1H), 7.50 (d, J=2.0 Hz, 1H), 7.45 (d, J=5.2 Hz, 1H), 7.35 (d, J=8.7 Hz, 1H), 7.26-7.12 (m, 4H), 6.86 (d, J=8.3 Hz, 1H), 6.57-6.50 (m, 1H), 6.38 (t, J=5.5 Hz, 1H), 3.92 (s, 1H), 3.55 (q, J=6.8 Hz, 2H), 3.18 (t, J=7.3 Hz, 2H), 3.12 (d, 1H), 2.83 (d, J=12.4 Hz, 1H), 2.47-2.43 (m, 2H), 2.18 (s, 3H), 1.97-1.91 (m, 1H), 1.67 (d, J=11.7 Hz, 1H), 1.54-1.41 (m, 2H).

441

Example 261 (S)-4-(2-((2-Methyl-5-((pyridin-2-ylmethyl)amino)naphthalen-1-yl)oxy)pyridin-3-yl)-N-(piperidin-3-yl)pyrimidin-2-amine 261

Step 1: tert-Butyl (S)-3-((4-(2-((2-methyl-5-((pyridin-2-ylmethyl)amino)naphthalen-1-yl)oxy)pyridin-3-yl)pyrimidin-2-yl)amino)piperidine-1-carboxylate

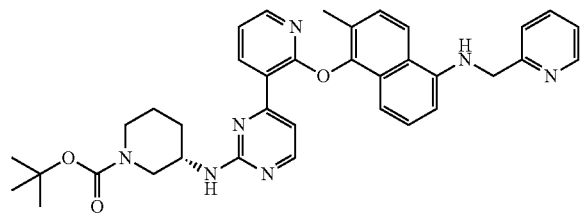 [SMILES: Cc1ccc2c(NCc3ccccn3)cccc2c1Oc1ncccc1-c1ccnc(N[C@H]2CCCN(C(=O)OC(C)(C)C)C2)n1]

The General Procedure E was followed, using tert-butyl (3S)-3-[[4-[2-[(5-amino-2-methyl-1-naphthyl)oxy]-3-pyridyl]pyrimidin-2-yl]amino]piperidine-1-carboxylate (150 mg, 0.28 mmol) and 2-(chloromethyl)pyridine hydrochloride (70.1 mg, 0.43 mmol). (Additional 2-(chloromethyl)pyridine hydrochloride, 35 mg, was added followed by heating for 48 h. The crude material was purified by silica gel chromatography (12 g column) eluting with 0-5% MeOH/DCM to afford 26 mg (15% yield) of the title compound as a brown solid. LCMS (ESI) [M+H]$^+$=618.

Step 2: (S)-4-(2-((2-Methyl-5-((pyridin-2-ylmethyl)amino)naphthalen-1-yl)oxy)pyridin-3-yl)-N-(piperidin-3-yl)pyrimidin-2-amine

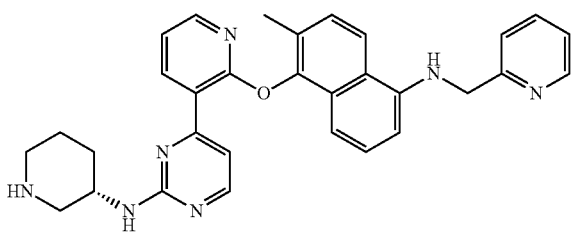 [SMILES: Cc1ccc2c(NCc3ccccn3)cccc2c1Oc1ncccc1-c1ccnc(N[C@H]2CCCNC2)n1]

The General Procedure B was followed, using tert-butyl (S)-3-((4-(2-((2-methyl-5-((pyridin-2-ylmethyl)amino)naphthalen-1-yl)oxy)pyridin-3-yl)pyrimidin-2-yl)amino)piperidine-1-carboxylate (26 mg, 0.04 mmol). The crude product was purified via reverse-phase HPLC and lyophilized to yield 3.2 mg (15% yield) of 261 as a yellow solid. LCMS (ESI) [M+H]$^+$=518. $^1$H NMR (400 MHz, DMSO-d$_6$) δ 8.54 (ddd, J=4.8, 1.8, 0.9 Hz, 1H), 8.51-8.44 (m, 1H), 8.42-8.36 (m, 1H), 8.10 (d, J=8.7 Hz, 1H), 8.01 (dd, J=4.8, 2.0 Hz, 1H), 7.70 (td, J=7.7, 1.9 Hz, 1H), 7.46-7.41 (m, 4H), 7.41-7.34 (m, 1H), 7.28-7.20 (m, 2H), 7.15-7.09 (m, 2H), 7.09-7.03 (m, 1H), 6.84 (d, J=8.5 Hz, 1H), 6.31-6.24 (m, 1H), 4.57 (d, J=5.8 Hz, 2H), 3.89 (s, 1H), 3.16-3.05 (m, 1H), 2.87-2.77 (m, 1H), 2.45-2.41 (m, 2H), 2.20 (s, 3H), 1.96-1.88 (m, 1H), 1.70-1.63 (m, 1H), 1.54-1.39 (m, 2H).

442

Example 262 (S)-4-(2-((2-Methyl-5-(((1-methyl-1H-pyrazol-3-yl)methyl)amino)naphthalen-1-yl)oxy)pyridin-3-yl)-N-(piperidin-3-yl)pyrimidin-2-amine 262

Step 1: tert-Butyl (S)-3-((4-(2-((2-methyl-5-(((1-methyl-1H-pyrazol-3-yl)methyl)amino)naphthalen-1-yl)oxy)pyridin-3-yl)pyrimidin-2-yl)amino)piperidine-1-carboxylate

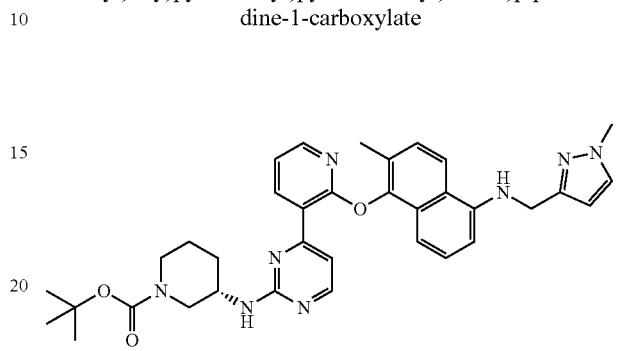

The General Procedure E was followed, using tert-butyl (3S)-3-[[4-[2-[(5-amino-2-methyl-1-naphthyl)oxy]-3-pyridyl]pyrimidin-2-yl]amino]piperidine-1-carboxylate (150 mg, 0.28 mmol) and 3-(chloromethyl)-1-methyl-pyrazole (74.4 mg, 0.57 mmol). The crude material was purified by silica gel chromatography (12 g column) eluting with 0-5% MeOH/DCM to afford 44 mg (25% yield) of the title compound as a brown solid. LCMS (ESI) [M+H]$^+$=621.

Step 2: (S)-4-(2-((2-Methyl-5-(((1-methyl-1H-pyrazol-3-yl)methyl)amino)naphthalen-1-yl)oxy)pyridin-3-yl)-N-(piperidin-3-yl)pyrimidin-2-amine

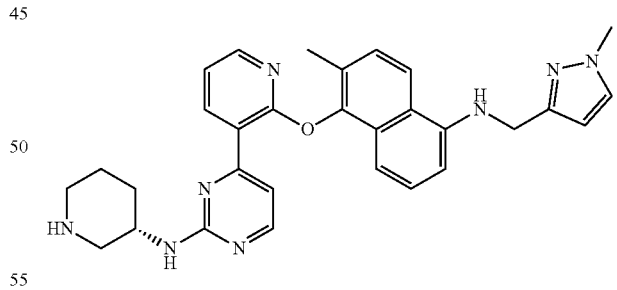

The General Procedure B was followed, using tert-butyl (S)-3-((4-(2-((2-methyl-5-(((1-methyl-1H-pyrazol-3-yl)methyl)amino)naphthalen-1-yl)oxy)pyridin-3-yl)pyrimidin-2-yl)amino)piperidine-1-carboxylate (44 mg, 0.07 mmol). The crude product was purified via reverse-phase HPLC and lyophilized to yield 19.3 mg (53% yield) of 262 as a light brown solid. LCMS (ESI) [M+H]$^+$=521. $^1$H NMR (400

MHz, DMSO-d₆) δ 8.48 (s, 1H), 8.39 (d, J=5.1 Hz, 1H), 8.00 (dd, J=4.8, 2.0 Hz, 1H), 7.55 (d, J=2.2 Hz, 1H), 7.43 (d, J=5.1 Hz, 1H), 7.34 (d, J=8.7 Hz, 1H), 7.22 (dd, J=7.6, 4.8 Hz, 1H), 7.15-7.08 (m, 2H), 6.82 (d, J=8.4 Hz, 1H), 6.72 (t, J=5.9 Hz, 1H), 6.48 (dd, J=7.9, 1.0 Hz, 1H), 6.14 (d, J=2.2 Hz, 1H), 4.38 (d, J=5.7 Hz, 2H), 3.91 (s, 1H), 3.79 (s, 3H), 3.12 (d, J=12.0 Hz, 1H), 2.83 (d, J=12.2 Hz, 1H), 2.47-2.42 (m, 2H), 2.18 (s, 3H), 1.96-1.89 (m, 1H), 1.71-1.63 (m, 1H), 1.55-1.42 (m, 2H).

Example 263 (S)—N-(6-M-5-((3-(2-(piperidin-3-ylamino)pyrimidin-4-yl)pyridin-2-yl)oxy)naphthalen-1-yl)isobutyramide hydrochloride 263

Step 1: (S)-tert-butyl 3-((4-(2-((5-Isobutyramido-2-methylnaphthalen-1-yl)oxy)pyridin-3-yl)pyrimidin-2-yl)amino)piperidine-1-carboxylate

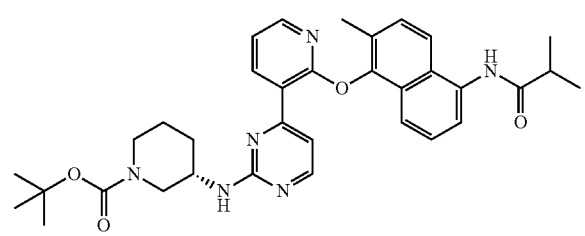 [SMILES: Cc1ccc2c(NC(=O)C(C)C)cccc2c1Oc1ncccc1-c1ccnc(N[C@H]2CCCN(C(=O)OC(C)(C)C)C2)n1]

Prepared using (S)-tert-butyl 3-((4-(2-((5-amino-2-methylnaphthalen-1-yl)oxy)pyridin-3-yl)pyrimidin-2-yl)amino)piperidine-1-carboxylate (70 mg, 0.133 mmol), pyridine (0.11 mL, 1.36 mmol), CH₂Cl₂ (1 mL), and isobutyryl chloride (28 mg, 0.26 mmol). After 16 h, the mixture was concentrated in vacuo and the crude was purified by C18 reverse phase flash chromatography (0-70% MeCN/10 mM pH=3.8 aqueous ammonium formate). The product fractions were collected and lyophilized to provide 68 mg (86% yield) of the title compound. LCMS (ESI) [M+H]⁺=597.2, rt=1.83 min.

Step 2: (S)—N-(6-Methyl-5-((3-(2-(piperidin-3-ylamino)pyrimidin-4-yl)pyridin-2-yl)oxy)naphthalen-1-yl)isobutyramide hydrochloride 263

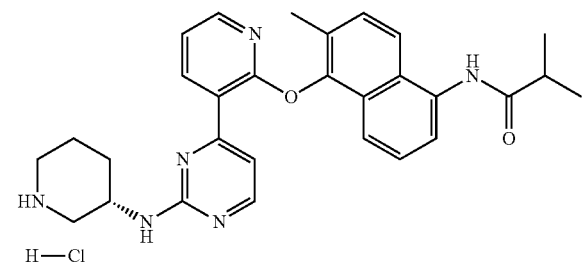

Prepared using (S)-tert-butyl 3-((4-(2-((5-isobutyramido-2-methylnaphthalen-1-yl)oxy)pyridin-3-yl)pyrimidin-2-yl)amino)piperidine-1-carboxylate (68 mg, 0.114 mmol), 1,4-dioxane (2 mL), and hydrochloric acid (4 M in dioxane, 2 mL, 8 mmol). After 5 h, the mixture was diluted with Et₂O and the solids were filtered off, washed with Et₂O then dissolved in H₂O and MeCN. Lyophilization provided 58 mg (95% yield) of 263 as a white solid. LCMS (ESI) [M+H]⁺=497.1, rt=1.29 min; ¹H NMR (400 MHz, d₆-DMSO) δ 9.90 (s, 1H), 9.13-8.60 (m, 2H), 8.48 (d, J=5.2 Hz, 1H), 8.06 (dd, J=4.8, 2.0 Hz, 1H), 7.89 (d, J=8.7 Hz, 1H), 7.63-7.57 (m, 3H), 7.51 (d, J=8.9 Hz, 1H), 7.49 (d, J=8.6 Hz, 1H), 7.43-7.36 (m, 1H), 7.27 (dd, J=7.6, 4.8 Hz, 1H), 4.29 (s, 1H), 3.51-3.39 (m, 1H), 3.25-3.14 (m, 1H), 2.95-2.77 (m, 3H), 2.22 (s, 3H), 2.07-1.87 (m, 2H), 1.83-1.55 (m, 2H), 1.20 (d, J=6.8 Hz, 6H).

Example 264 (S)—N-(6-Methyl-5-((3-(2-(piperidin-3-ylamino)pyrimidin-4-yl)pyridin-2-yl)oxy)naphthalen-1-yl)-2-(1-methylcyclohexyl)acetamide hydrochloride 264

Step 1: (S)-tert-Butyl 3-((4-(2-((2-methyl-5-(2-(1-methylcyclohexyl)acetamido)naphthalen-1-yl)oxy)pyridin-3-yl)pyrimidin-2-yl)amino)piperidine-1-carboxylate

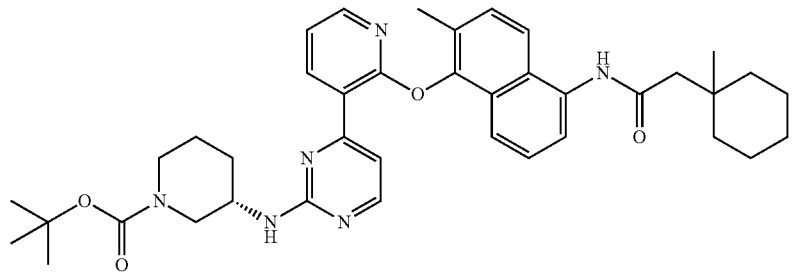 [SMILES: Cc1ccc2c(NC(=O)CC3(C)CCCCC3)cccc2c1Oc1ncccc1-c1ccnc(N[C@H]2CCCN(C(=O)OC(C)(C)C)C2)n1]

Prepared using (S)-tert-butyl 3-((4-(2-((5-amino-2-methylnaphthalen-1-yl)oxy)pyridin-3-yl)pyrimidin-2-yl)amino)piperidine-1-carboxylate (100 mg, 0.190 mmol), triethylamine (0.10 mL, 0.76 mmol), HATU (144 mg, 0.38 mmol), and 2-(1-methylcyclohexyl)acetic acid (74 mg, 0.47 mmol) in DMF (2 mL). After 16 h, a further portion of triethylamine (0.10 mL, 0.76 mmol), 2-(1-methylcyclohexyl)acetic acid (74 mg, 0.47 mmol), and HATU (144 mg, 0.38 mmol) were added and stirring at rt was continued. After 3 days, the mixture was diluted with EtOAc (50 mL) and washed with sat'd NaHCO$_3$(aq) (10 mL), 50% sat'd NaCl(aq) (4×10 mL), dried (Na$_2$SO$_4$), filtered and concentrated in vacuo. The crude residue was purified by flash chromatography through silica gel (0-100% EtOAc/hex) to provide 42 mg (33% yield) of the title compound as a tan powder. LCMS (ESI) [M+H]$^+$=665.4, rt=2.16 min.

Step 2: (S)—N-(6-Methyl-5-((3-(2-(piperidin-3-ylamino)pyrimidin-4-yl)pyridin-2-yl)oxy)naphthalen-1-yl)-2-(1-methylcyclohexyl)acetamide hydrochloride 264

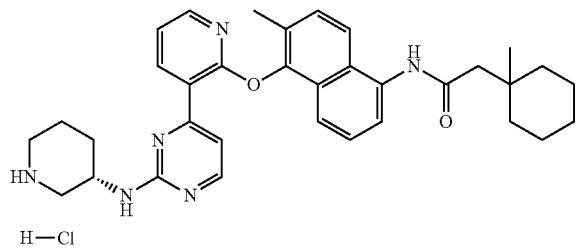

Prepared using (S)-tert-butyl 3-((4-(2-((2-methyl-5-(2-(1-methylcyclohexyl)acetamido)naphthalen-1-yl)oxy)pyridin-3-yl)pyrimidin-2-yl)amino)piperidine-1-carboxylate (42 mg, 0.063 mmol), EtOAc (4 mL), and hydrochloric acid (4 M in dioxane, 2 mL, 8 mmol). After 4 h, the mixture was concentrated in vacuo and the crude HCl salt solid was washed with EtOAc (3×3 mL) and then with MeCN (3×3 mL). The solid product was then sonicated and concentrated in vacuo with MeCN (3×3 mL) and then dissolved in H$_2$O and MeCN. Lyophilization provided 25 mg (68% yield) of 264 as a fluffy light yellow solid. LCMS (ESI) [M+H]$^+$=565.3, rt=1.58 min; $^1$H NMR (400 MHz, d$_6$-DMSO) δ 9.87 (s, 1H), 9.01-8.75 (m, 2H), 8.73-8.53 (m, 1H), 8.48 (d, J=5.2 Hz, 1H), 8.05 (dd, J=4.8, 2.0 Hz, 1H), 7.93 (d, J=8.7 Hz, 1H), 7.67-7.44 (m, 5H), 7.39 (dd, J=8.4, 7.4 Hz, 1H), 7.27 (dd, J=7.6, 4.8 Hz, 1H), 4.40-4.13 (m, 1H), 3.39-3.31 (m, 1H), 3.21 (d, J=13.5 Hz, 1H), 2.94-2.75 (m, 2H), 2.42 (s, 2H), 2.21 (s, 3H), 2.08-1.84 (m, 2H), 1.82-1.60 (m, 2H), 1.60-1.29 (m, 10H), 1.11 (s, 3H).

Example 265 (S)-4-(2-((2-Methyl-5-(((1-methyl-1H-pyrazol-4-yl)methyl)amino)naphthalen-1-yl)oxy)pyridin-3-yl)-N-(piperidin-3-yl)pyrimidin-2-amine 265

Step 1: tert-Butyl (S)-3-((4-(2-((2-methyl-5-(((1-methyl-1H-pyrazol-4-yl)methyl)amino)naphthalen-1-yl)oxy)pyridin-3-yl)pyrimidin-2-yl)amino)piperidine-1-carboxylate

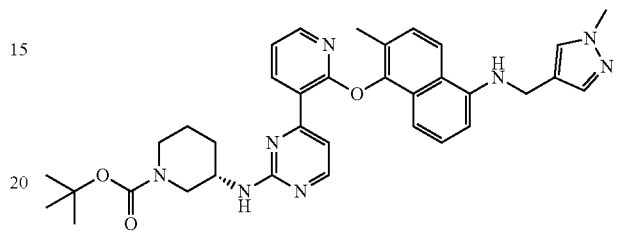

The General Procedure E was followed, using tert-butyl (3S)-3-[[4-[2-[(5-amino-2-methyl-1-naphthyl)oxy]-3-pyridyl]pyrimidin-2-yl]amino]piperidine-1-carboxylate (200 mg, 0.38 mmol) and 4-(chloromethyl)-1-methyl-1H-pyrazole hydrochloride (95.2 mg, 0.57 mmol). The crude material was purified by silica gel chromatography (12 g column), eluting with 0-5% MeOH/DCM to afford 50 mg (22% yield) of the title compound as a brown solid. LCMS (ESI) [M+H]$^+$=621.

Step 2: (S)-4-(2-((2-Methyl-5-(((1-methyl-1H-pyrazol-4-yl)methyl)amino)naphthalen-1-yl)oxy)pyridin-3-yl)-N-(piperidin-3-yl)pyrimidin-2-amine

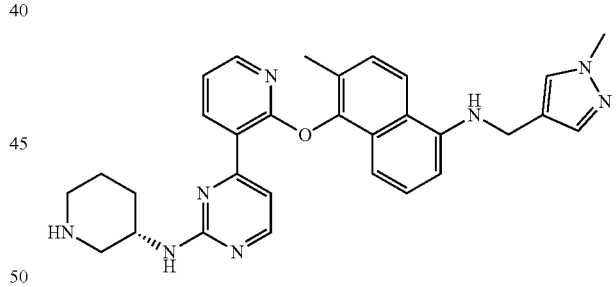

The General Procedure B was followed, using tert-butyl (S)-3-((4-(2-((2-methyl-5-(((1-methyl-1H-pyrazol-4-yl)methyl)amino)naphthalen-1-yl)oxy)pyridin-3-yl)pyrimidin-2-yl)amino)piperidine-1-carboxylate (50 mg, 0.08 mmol). The crude product was purified via reverse-phase HPLC and lyophilized to yield 24.2 mg (58% yield) of 265 as an off-white solid. LCMS (ESI) [M+H]$^+$=521. $^1$H NMR (400 MHz, DMSO-d$_6$) δ 8.48 (s, 1H), 8.40 (d, J=5.1 Hz, 1H), 8.04-7.98 (m, 2H), 7.62 (d, J=0.9 Hz, 1H), 7.44 (d, J=5.2 Hz, 1H), 7.40 (s, 1H), 7.33 (d, J=8.7 Hz, 1H), 7.22 (dd, J=7.5, 4.8 Hz, 1H), 7.13 (t, J=7.8 Hz, 2H), 6.83 (d, J=8.5 Hz, 1H), 6.58 (d, J=5.9 Hz, 1H), 6.48 (d, J=7.7 Hz, 1H), 4.29 (d, J=5.5 Hz, 2H), 3.93 (s, 1H), 3.77 (s, 3H), 3.13 (s, 1H), 2.84 (d, J=10.8 Hz, 1H), 2.43 (s, 2H), 2.18 (s, 3H), 1.97-1.89 (m, 1H), 1.70-1.65 (m, 1H), 1.54-1.43 (m, 2H).

Example 266 (R)-3-Ethyl-1-(6-methyl-5-((3-(2-(((S)-piperidin-3-yl)amino)pyrimidin-4-yl)pyridin-2-yl)oxy)naphthalen-1-yl)pyrrolidin-2-one 266

Step 1: tert-butyl (3S)-3-((4-(2-((5-(3-Ethyl-2-oxopyrrolidin-1-yl)-2-methylnaphthalen-1-yl)oxy)pyridin-3-yl)pyrimidin-2-yl)amino)piperidine-1-carboxylate

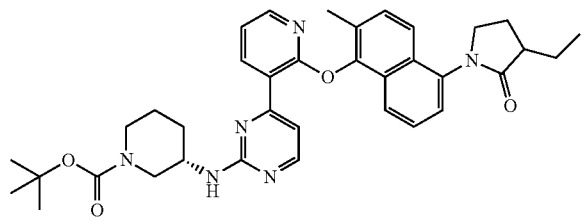 [SMILES: CCC1CCN(c2cccc3c(Oc4ncccc4-c4ccnc(N[C@H]5CCCN(C(=O)OC(C)(C)C)C5)n4)c(C)ccc23)C1=O]

To a 100 mL 3-necked round-bottom flask purged and maintained with an inert atmosphere of nitrogen was placed tert-butyl (3S)-3-[[4-[2-[(5-iodo-2-methyl-1-naphthyl)oxy]-3-pyridyl]pyrimidin-2-yl]amino]piperidine-1-carboxylate (120 mg, 0.19 mmol), 1,4-dioxane (2 mL), copper (I) iodide (4 mg, 0.02 mmol), potassium carbonate (78 mg, 0.56 mmol), 3-ethylpyrrolidin-2-one (21 mg, 0.19 mmol) and N,N'-dimethyl-1,2-ethanediamine (3.3 mg, 0.04 mmol), the mixture was purged with nitrogen atmosphere and stirred at 110° C. for 12 h. After cooling down, the mixture was filtered, concentrated and dissolved in ethyl acetate (60 mL), and subsequently washed with H$_2$O (50 mL×2). The organic phase was dried over anhydrous sodium sulfate and filtered, and the filtrate was concentrated and purified by prep-TLC (50% ethyl acetate in petroleum ether, Rf=0.3) to yield 110 mg (93% yield) of the title compound as a white solid. LCMS (ESI) [M+H]$^+$=623.3.

tert-Butyl (3S)-3-[[4-[2-[[5-(3-ethyl-2-oxo-pyrrolidin-1-yl)-2-methyl-1-naphthyl]oxy]-3-pyridyl]pyrimidin-2-yl]amino]piperidine-1-carboxylate (110.0 mg, 0.18 mmol) was purified by SFC (AD (250 mm×30 mm, 10 μm); 0.1% NH$_3$H$_2$O EtOH: 40%; flow rate (mL/min): 60) to give Peak 1: tert-Butyl (S)-3-((4-(2-((5-((R)-3-ethyl-2-oxopyrrolidin-1-yl)-2-methylnaphthalen-1-yl)oxy)pyridin-3-yl)pyrimidin-2-yl)amino)piperidine-1-carboxylate (35 mg, 32% yield) (first peak on SFC) as a white solid:

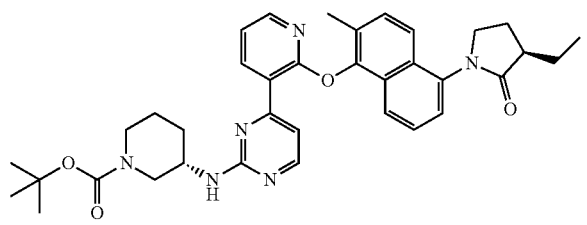 [SMILES: CC[C@@H]1CCN(c2cccc3c(Oc4ncccc4-c4ccnc(N[C@H]5CCCN(C(=O)OC(C)(C)C)C5)n4)c(C)ccc23)C1=O]

Peak 2: tert-Butyl (S)-3-((4-(2-((5-((S)-3-ethyl-2-oxopyrrolidin-1-yl)-2-methylnaphthalen-1-yl)oxy)pyridin-3-yl)pyrimidin-2-yl)amino)piperidine-1-carboxylate (35 mg, 32% yield) (second peak on SFC) as a white solid and used in Example 355:

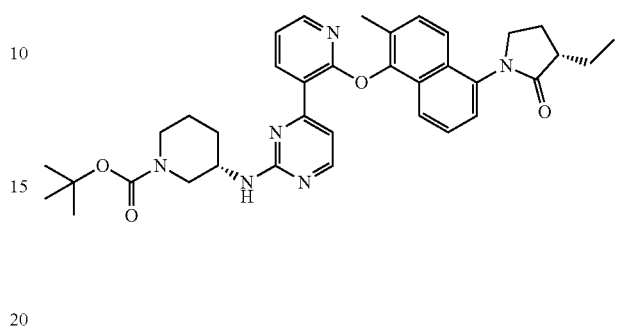

Step 2: (R)-3-Ethyl-1-(6-methyl-5-((3-(2-(((S)-piperidin-3-yl)amino)pyrimidin-4-yl)pyridin-2-yl)oxy)naphthalen-1-yl)pyrrolidin-2-one

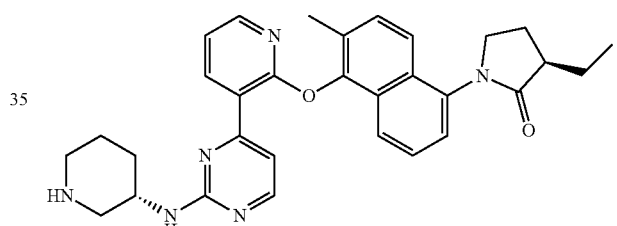

The General Procedure B was followed, using (3S)-tert-butyl 3-((4-(2-((5-(3-ethyl-2-oxopyrrolidin-1-yl)-2-methylnaphthalen-1-yl)oxy)pyridin-3-yl)pyrimidin-2-yl)amino)piperidine-1-carboxylate (30 mg, 0.05 mmol) (first peak on SFC in step 1), dichloromethane (2 mL) and hydrochloric acid (4 M in dioxane, 0.32 mL, 1.28 mmol). The residue was purified by Prep-HPLC (mobile phase: A: water (0.05% HCl); B: ACN) to yield 27 mg (99% yield) of 266 as a white solid. LCMS (ESI) [M+H]$^+$=523.3. $^1$H NMR (400 MHz, DMSO-d$_6$) δ 8.51 (s, 1H), 8.42 (d, J=5.2 Hz, 1H), 8.05-8.00 (m, 1H), 7.65 (d, J=7.2 Hz, 1H), 7.59-7.53 (m, 1H), 7.51-7.44 (m, 2H), 7.42 (d, J=5.2 Hz, 1H), 7.40-7.37 (m, 1H), 7.27-7.22 (m, 1H), 7.13 (d, J=7.6 Hz, 1H), 3.91-3.64 (m, 3H), 3.06 (m, 1H), 2.77 (m, 1H), 2.64-2.58 (m, 1H), 2.41 (d, J=14.8 Hz, 3H), 2.20 (s, 3H), 2.02-1.87 (m, 2H), 1.86-1.77 (m, 1H), 1.61 (m, 1H), 1.57-1.35 (m, 3H), 1.01 (t, J=7.2 Hz, 3H). The absolute stereochemistry of the lactam was assigned based on a crystal structure.

Example 267 (S)—N-(6-Methyl-5-((3-(2-(piperidin-3-ylamino)pyrimidin-4-yl)pyridin-2-yl)oxy)naphthalen-1-yl)-2-(1-methylcyclopentyl)acetamide 267

Step 1: (S)-tert-Butyl 3-((4-(2-((2-methyl-5-(2-(1-methylcyclopentyl)acetamido)naphthalen-1-yl)oxy)pyridin-3-yl)pyrimidin-2-yl)amino)piperidine-1-carboxylate

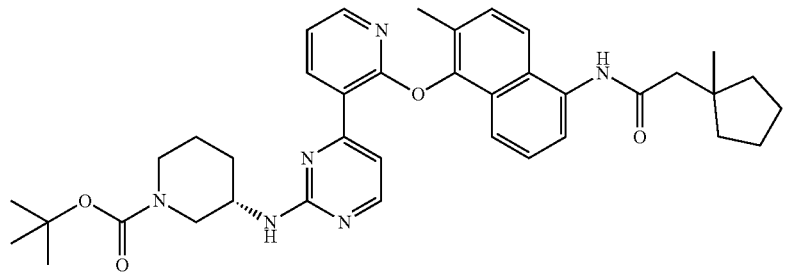 [SMILES: Cc1ccc2c(NC(=O)CC3(C)CCCC3)cccc2c1Oc1ncccc1-c1ccnc(N[C@H]2CCCN(C(=O)OC(C)(C)C)C2)n1]

Prepared using (S)-tert-butyl 3-((4-(2-((5-amino-2-methylnaphthalen-1-yl)oxy)pyridin-3-yl)pyrimidin-2-yl)amino)piperidine-1-carboxylate (100 mg, 0.190 mmol), triethylamine (58 mg, 0.08 mL, 0.57 mmol), HATU (108 mg, 0.285 mmol), and 2-(1-methylcyclopentyl)acetic acid (35 mg, 0.25 mmol) in DMF (0.63 mL). After 96 h, the mixture was diluted with EtOAc and washed with saturated NaCl(aq), then H$_2$O, then saturated NH$_4$Cl(aq). The organic extract was dried (MgSO$_4$), filtered and concentrated in vacuo. The crude residue was purified by flash chromatography through silica gel (0-100% EtOAc/DCM) to provide 90% pure material which was further purified by C18 reverse phase flash chromatography (40-90% MeCN/10 mM pH=3.8 aqueous ammonium formate). Appropriate fractions were combined and MeCN removed on a rotovap and the resulting aqueous solution was diluted with saturated NaCl(aq) and organics extracted with EtOAc, dried (MgSO$_4$), filtered and concentrated in vacuo to provide 104 mg (84% yield) of the title compound as a beige solid. LCMS (ESI) [M+H]$^+$ =651.3, rt=2.08 min.

Step 2: (S)—N-(6-Methyl-5-((3-(2-(piperidin-3-ylamino)pyrimidin-4-yl)pyridin-2-yl)oxy)naphthalen-1-yl)-2-(1-methylcyclopentyl)acetamide

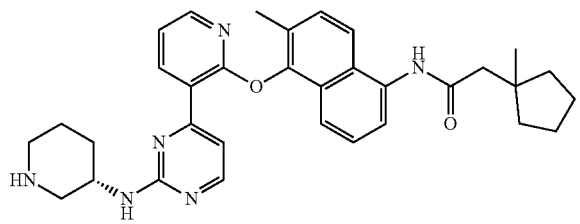 [SMILES: Cc1ccc2c(NC(=O)CC3(C)CCCC3)cccc2c1Oc1ncccc1-c1ccnc(N[C@H]2CCCNC2)n1]

Prepared using (S)-tert-butyl 3-((4-(2-((2-methyl-5-(2-(1-methylcyclopentyl)acetamido)naphthalen-1-yl)oxy)pyridin-3-yl)pyrimidin-2-yl)amino)piperidine-1-carboxylate (104 mg, 0.160 mmol), 1,4-dioxane (1 mL), and hydrochloric acid (4 M in dioxane, 2.5 mL, 9.9 mmol). After 4 h, the heterogeneous mixture was filtered and the collected solids were washed with 1,4-dioxane then Et$_2$O and dried. The solids were then dissolved in H$_2$O and MeCN and lyophilized to provide 92 mg (98% yield) of 267 as a pale yellow solid. LCMS (ESI) [M+H]$^+$=551.2, rt=1.53 min; $^1$H NMR (400 MHz, d6-dmso) δ 9.92 (s, 1H), 9.26 (br s, 1H), 9.12 (s, 1H), 8.74 (br s, 1H), 8.49 (d, J=5.3 Hz, 1H), 8.06 (dd, J=4.7, 1.8 Hz, 1H), 7.93 (d, J=8.7 Hz, 1H), 7.82-7.61 (m, 2H), 7.60 (d, J=7.3 Hz, 1H), 7.52 (d, J=8.8 Hz, 1H), 7.48 (d, J=8.4 Hz, 1H), 7.45-7.35 (m, 1H), 7.27 (dd, J=7.6, 4.8 Hz, 1H), 4.36 (s, 1H), 3.43 (d, J=9.1 Hz, 1H), 3.20 (d, J=11.5 Hz, 1H), 2.92-2.74 (m, 2H), 2.48 (s, 2H), 2.21 (s, 3H), 2.07-1.97 (m, J=8.9 Hz, 1H), 1.97-1.86 (m, J=14.2 Hz, 1H), 1.86-1.54 (m, 8H), 1.50-1.32 (m, 2H), 1.14 (s, 3H).

Example 268 (S)—N-(6-Methyl-5-((3-(2-(piperidin-3-ylamino)pyrimidin-4-yl)pyridin-2-yl)oxy)naphthalen-1-yl)-2-(1-methylcyclopropyl)acetamide 268

Step 1: (S)-tert-Butyl 3-((4-(2-((2-methyl-5-(2-(1-methylcyclopropyl)acetamido)naphthalen-1-yl)oxy)pyridin-3-yl)pyrimidin-2-yl)amino)piperidine-1-carboxylate

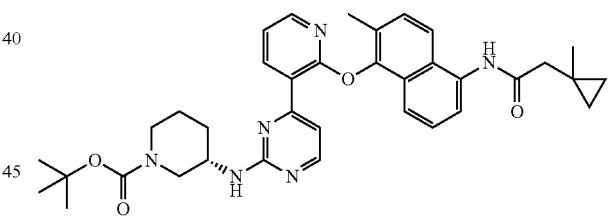

Prepared using (S)-tert-butyl 3-((4-(2-((5-amino-2-methylnaphthalen-1-yl)oxy)pyridin-3-yl)pyrimidin-2-yl)amino)piperidine-1-carboxylate (100 mg, 0.190 mmol), triethylamine (77 mg, 0.11 mL, 0.76 mmol), HATU (180 mg, 0.475 mmol), and 2-(1-methylcyclopropyl)acetic acid (54 mg, 0.47 mmol) in DMF (1 mL). After 64 h, the mixture was diluted with EtOAc (50 mL) and washed with saturated NaHCO$_3$(aq) (10 mL) and then 50% saturated NaCl(aq) (4×10 mL). The organic extract was dried (Na$_2$SO$_4$), filtered and concentrated in vacuo. The crude residue was purified by flash chromatography through silica gel (0-100% EtOAc/hexanes) to provide 111 mg (94% yield) of the title compound as tan solid. LCMS (ESI) [M+H]$^+$=623.3, rt=1.93 min.

Step 2: (S)—N-(6-Methyl-5-((3-(2-(piperidin-3-ylamino)pyrimidin-4-yl)pyridin-2-yl)oxy)naphthalen-1-yl)-2-(1-methylcyclopropyl)acetamide

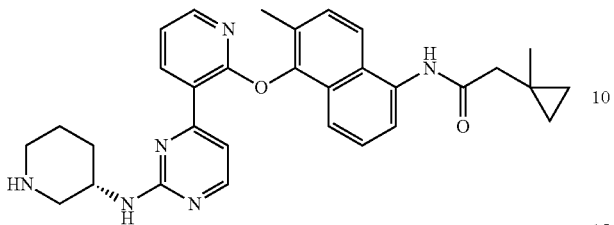

Prepared using (S)-tert-Butyl 3-((4-(2-((2-methyl-5-(2-(1-methylcyclopropyl)acetamido)naphthalen-1-yl)oxy)pyridin-3-yl)pyrimidin-2-yl)amino)piperidine-1-carboxylate (111 mg, 0.178 mmol), EtOAc (6 mL), and hydrochloric acid (4 M in dioxane, 2 mL, 8 mmol). After 4 h, the solution was concentrated in vacuo and the crude residue purified by C18 reverse phase flash chromatography (20-100% MeCN/10 mM pH=3.8 aqueous ammonium formate). The product fractions were combined and lyophilized to provide 6 mg (6% yield) of 268 as a tan powder. LCMS (ESI) [M+H]$^+$=523.3, rt=1.38 min; $^1$H NMR (400 MHz, d6-dmso) δ 9.82 (s, 1H), 8.55 (br.s, 1H), 8.44 (d, J=5.1 Hz, 1H), 8.35 (s, 1H), 8.03 (dd, J=4.8, 1.9 Hz, 1H), 7.92 (d, J=8.7 Hz, 1H), 7.62 (d, J=7.3 Hz, 1H), 7.56-7.46 (m, 3H), 7.41 (d, J=7.6 Hz, 1H), 7.31 (d, J=7.7 Hz, 1H), 7.26 (dd, J=7.5, 4.8 Hz, 1H), 4.18-3.94 (m, 1H), 3.24 (d, J=9.0 Hz, 1H), 2.97 (d, J=11.9 Hz, 1H), 2.60 (dd, J=22.3, 12.3 Hz, 2H), 2.40 (s, 2H), 2.22 (s, 3H), 2.04-1.91 (m, 1H), 1.81-1.71 (m, 1H), 1.64-1.50 (m, 2H), 1.19 (s, 3H), 0.59 (s, 2H), 0.36 (s, 2H).

Example 269 (R)-3,3-difluoro-N-(6-methyl-5-((3-(2-(((S)-piperidin-3-yl)amino)pyrimidin-4-yl)pyridin-2-yl)oxy)naphthalen-1-yl)cyclopentane-1-carboxamide 269

Step 1: 3,3-Difluoro-N-(6-methyl-5-((3-(2-(methylthio)pyrimidin-4-yl)pyridin-2-yl)oxy)naphthalen-1-yl)cyclopentanecarboxamide

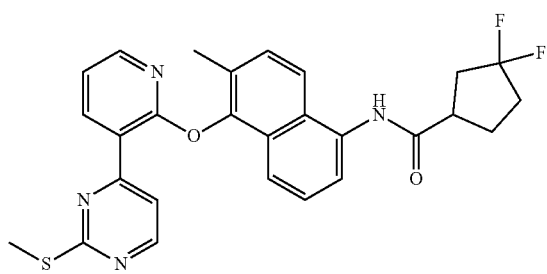 [SMILES: CSc1nccc(-c2cccnc2Oc2c(C)ccc3c(NC(=O)C4CCC(F)(F)C4)cccc23)n1]

Prepared using 6-methyl-5-((3-(2-(methylthio)pyrimidin-4-yl)pyridin-2-yl)oxy)naphthalen-1-amine (150 mg, 0.401 mmol), triethylamine (203 mg, 0.279 mL, 2.00 mmol), HATU (380 mg, 1.00 mmol), and 3,3-difluorocyclopentanecarboxylic acid (180 mg, 1.20 mmol) in DMF (2 mL). After 3 days, the mixture was diluted with EtOAc (75 mL) and washed with saturated NaHCO$_3$(aq) (10 mL), then 50% saturated NaCl(aq) (4×10 mL), dried (Na$_2$SO$_4$), filtered and concentrated in vacuo to provide 226 mg (111% yield) of the title compound as an orange solid which was used crude without further purification in the next step. LCMS (ESI) [M+H]$^+$=507.1, rt=1.88 min.

Step 2: 3,3-Difluoro-N-(6-methyl-5-((3-(2-(methylsulfinyl)pyrimidin-4-yl)pyridin-2-yl)oxy)naphthalen-1-yl)cyclopentanecarboxamide

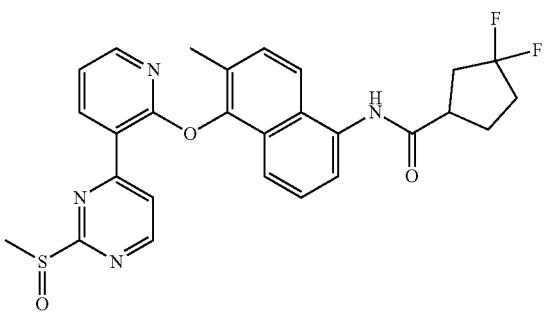 [SMILES: Cc1ccc2c(NC(=O)C3CCC(F)(F)C3)cccc2c1Oc1ncccc1-c1ccnc(S(C)=O)n1]

3,3-Difluoro-N-(6-methyl-5-((3-(2-(methylthio)pyrimidin-4-yl)pyridin-2-yl)oxy)naphthalen-1-yl)cyclopentanecarboxamide (226 mg, 0.446 mmol) was suspended in DCM (20 mL) and to this was then added 3-chloroperbenzoic acid (156 mg of 77% pure reagent, 0.710 mmol) and the mixture was stirred at rt. After 1 h, the mixture was diluted with DCM (75 mL) and washed with saturated NaHCO$_3$(aq) (2×25 mL), dried (Na$_2$SO$_4$), filtered and concentrated in vacuo to provide 245 mg (105% yield) of the title compound which was used crude without further purification in the next step. LCMS (ESI) [M+H]$^+$=523.1, rt=1.48 min.

Step 3: (3S)-tert-Butyl 3-((4-(2-((5-(3,3-difluorocyclopentanecarboxamido)-2-methylnaphthalen-1-yl)oxy)pyridin-3-yl)pyrimidin-2-yl)amino)piperidine-1-carboxylate

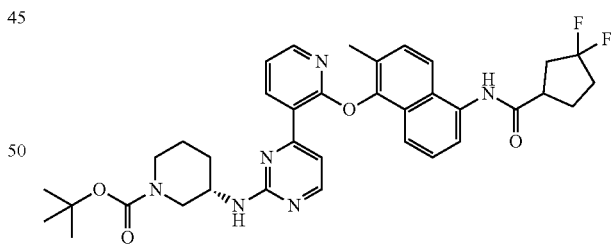

3,3-Difluoro-N-(6-methyl-5-((3-(2-(methylthio)pyrimidin-4-yl)pyridin-2-yl)oxy)naphthalen-1-yl)cyclopentanecarboxamide (245 mg, 0.469 mmol) and (S)-tert-butyl 3-aminopiperidine-1-carboxylate (141 mg, 0.703 mmol) were combined in 1,4-dioxane (3 mL). Triethylamine (142 mg, 0.196 mL, 1.41 mmol) was then added and the flask was sealed and placed in a 120° C. oil bath. After 20 h, the mixture was diluted with EtOAc (75 mL), and washed with saturated NaHCO$_3$(aq) (25 mL), H$_2$O (10 mL), and then saturated NaCl(aq) (10 mL). The solution was dried (MgSO$_4$), filtered and concentrated in vacuo. The crude was purified by flash chromatography through silica gel (0-100%

EtOAc/hexanes) to provide 130 mg (42% yield) of the title compound as an orange wax. LCMS (ESI) [M+H]⁺=659.2, rt=1.92 min.

Step 4: tert-Butyl (S)-3-((4-(2-((5-((R)-3,3-difluorocyclopentane-1-carboxamido)-2-methylnaphthalen-1-yl)oxy)pyridin-3-yl)pyrimidin-2-yl)amino)piperidine-1-carboxylate (Isomer-1) and tert-butyl (S)-3-((4-(2-((5-((S)-3,3-difluorocyclopentane-1-carboxamido)-2-methylnaphthalen-1-yl)oxy)pyridin-3-yl)pyrimidin-2-yl)amino)piperidine-1-carboxylate (Isomer-2)

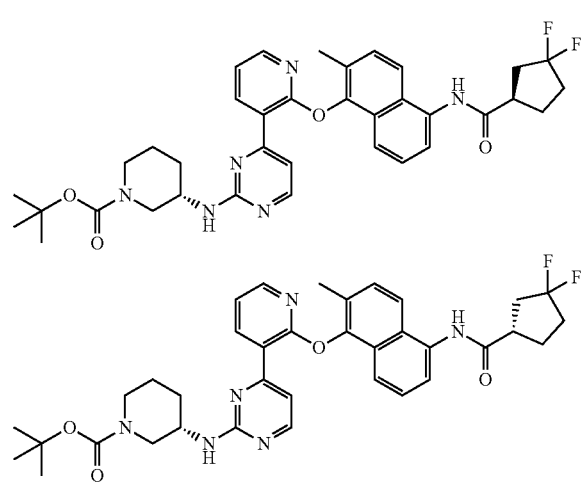

(3S)-tert-butyl 3-((4-(2-((5-(3,3-difluorocyclopentanecarboxamido)-2-methylnaphthalen-1-yl)oxy)pyridin-3-yl)pyrimidin-2-yl)amino)piperidine-1-carboxylate (128 mg, 0.194 mmol), was subjected to chiral normal phase semi-prep purification (Conditions: Chiralpak IB, 5 uM, 20×250 mm, 6:6:88 MeOH:DCM:Hexane+0.1% DIPEA, 400 uL (6 mg)/inj) to provide two single stereoisomers enantiomeric at the 4-cyclopentane position: (isomer-1), 43 mg (33% yield), white solid, ee≥99%, rt=14.01 min, LCMS (ESI) [M+H]⁺=659.5, rt=1.94 min; (isomer-2), 44 mg (34% yield), white solid, ee=98%, rt=15.9 min, LCMS (ESI) [M+H]⁺=659.5, rt=1.94 min. The absolute stereochemistry of the cyclopentane was randomly assigned.

Step 5: (R)-3,3-Difluoro-N-(6-methyl-5-((3-(2-(((S)-piperidin-3-yl)amino)pyrimidin-4-yl)pyridin-2-yl)oxy)naphthalen-1-yl)cyclopentane-1-carboxamide (Isomer-1)

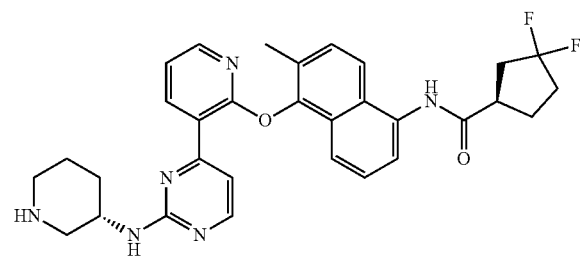 [SMILES: Cc1ccc2c(NC(=O)[C@@H]3CCC(F)(F)C3)cccc2c1Oc1ncccc1-c1ccnc(N[C@H]2CCCNC2)n1]

Prepared using tert-butyl (S)-3-((4-(2-((5-((R)-3,3-difluorocyclopentane-1-carboxamido)-2-methylnaphthalen-1-yl)oxy)pyridin-3-yl)pyrimidin-2-yl)amino)piperidine-1-carboxylate (isomer-1) (43 mg, 0.065 mmol), EtOAc (2 mL), and hydrochloric acid (4 M in dioxane, 1 mL, 4 mmol). After 16 h, the mixture was concentrated in vacuo and the crude HCl salt solid was washed with EtOAc (3×3 mL) then with MeCN (3×3 mL). The solid product was sonicated and concentrated in vacuo with MeCN (3×3 mL) and then dissolved in H₂O and MeCN and lyophilized to provide 29 mg (75% yield) of 269 as a fluffy light yellow solid. The absolute stereochemistries of 269 and 270 were randomly assigned and may be later determined. LCMS (ESI) [M+H]⁺=559.2, rt=1.38 min; ¹H NMR (400 MHz, DMSO-d₆) δ 10.07 (s, 1H), 8.93-8.53 (m, 3H), 8.48 (d, J=5.2 Hz, 1H), 8.05 (dd, J=4.8, 1.8 Hz, 1H), 7.91 (d, J=8.7 Hz, 1H), 7.62 (d, J=7.3 Hz, 1H), 7.58 (d, J=4.6 Hz, 1H), 7.56-7.47 (m, 3H), 7.42 (d, J=7.6 Hz, 1H), 7.27 (dd, J=7.5, 4.8 Hz, 1H), 4.38-4.15 (m, 1H), 3.34-3.29 (m, 1H), 3.21 (d, J=12.3 Hz, 1H), 2.97-2.75 (m, 2H), 2.48-2.35 (m, 2H), 2.36-2.09 (m, 7H), 2.09-1.98 (m, 2H), 1.98-1.86 (m, 1H), 1.80-1.54 (m, 2H).

Example 270 (S)-3,3-Difluoro-N-(6-methyl-5-((3-(2-(((S)-piperidin-3-yl)amino)pyrimidin-4-yl)pyridin-2-yl)oxy)naphthalen-1-yl)cyclopentane-1-carboxamide 270

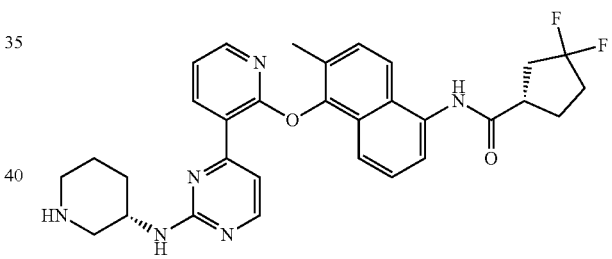

Prepared using tert-butyl (S)-3-((4-(2-((5-((S)-3,3-difluorocyclopentane-1-carboxamido)-2-methylnaphthalen-1-yl)oxy)pyridin-3-yl)pyrimidin-2-yl)amino)piperidine-1-carboxylate (isomer-2) (44 mg, 0.067 mmol), EtOAc (2 mL), and hydrochloric acid (4 M in dioxane, 1 mL, 4 mmol). After 16 h, the mixture was concentrated in vacuo and the crude solid was washed with EtOAc (3×3 mL) then with MeCN (3×3 mL). The solid product was then sonicated and concentrated in vacuo with MeCN (3×3 mL) then dissolved in H₂O and MeCN. Lyophilization provided 30 mg (75% yield) of 270 as a fluffy light yellow solid. LCMS (ESI) [M+H]⁺=559.2, rt=1.40 min; ¹H NMR (400 MHz, DMSO-d₆) δ 10.07 (s, 1H), 8.95-8.55 (m, 3H), 8.48 (d, J=5.2 Hz, 1H), 8.05 (dd, J=4.7, 1.8 Hz, 1H), 7.91 (d, J=8.7 Hz, 1H), 7.62 (d, J=7.3 Hz, 1H), 7.58 (d, J=4.7 Hz, 1H), 7.56-7.47 (m, 3H), 7.42 (d, J=7.7 Hz, 1H), 7.27 (dd, J=7.5, 4.8 Hz, 1H), 4.38-4.14 (m, 1H), 3.35-3.26 (m, 1H), 3.21 (d, J=12.0 Hz, 1H), 2.97-2.74 (m, 2H), 2.47-2.35 (m, 2H), 2.35-2.09 (m, 7H), 2.07-1.97 (m, 2H), 1.96-1.87 (m, 1H), 1.81-1.56 (m, 2H).

Example 271 (S)—N-(2-Fluoro-6-methyl-5-((3-(2-(piperidin-3-ylamino)pyrimidin-4-yl)pyridin-2-yl)oxy)naphthalen-1-yl)cyclopropanecarboxamide 271

Step 1: (S)-tert-Butyl 3-((4-(2-((5-(cyclopropanecarboxamido)-6-fluoro-2-methylnaphthalen-1-yl)oxy)pyridin-3-yl)pyrimidin-2-yl)amino)piperidine-1-carboxylate

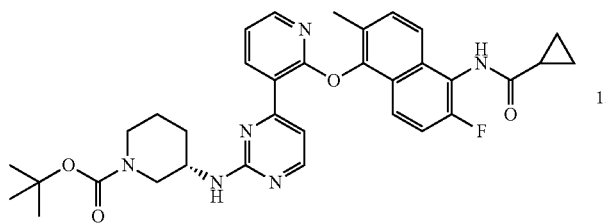

Prepared using (S)-tert-butyl 3-((4-(2-((5-amino-6-fluoro-2-methylnaphthalen-1-yl)oxy)pyridin-3-yl)pyrimidin-2-yl)amino)piperidine-1-carboxylate from Example 275 (40 mg, 0.073 mmol), pyridine (87 mg, 0.089 mL, 1.1 mmol), DCM (0.24 mL), and cyclopropanecarbonyl chloride (15 mg, 0.15 mmol). After 16 h, the mixture was concentrated in vacuo and the crude was purified by C18 reverse phase flash chromatography (45-70% MeCN/10 mM pH=3.8 aqueous ammonium formate). Appropriate fractions were collected and concentrated in vacuo and the resulting residue was diluted with EtOAc and washed with saturated NaHCO$_3$(aq), then saturated NaCl(aq). The solution was dried (Na$_2$SO$_4$), filtered and concentrated in vacuo to provide 18 mg (40% yield) of the title compound. LCMS (ESI) [M+H]$^+$=613.3, rt=1.81 min.

Step 2: (S)—N-(2-Fluoro-6-methyl-5-((3-(2-(piperidin-3-ylamino)pyrimidin-4-yl)pyridin-2-yl)oxy)naphthalen-1-yl)cyclopropanecarboxamide

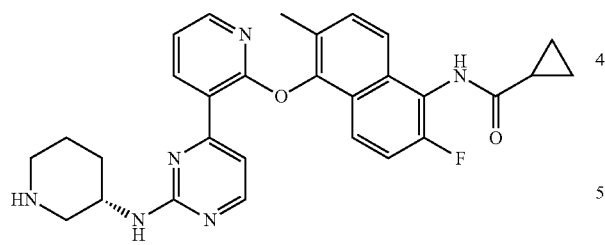

Prepared using (S)-tert-butyl 3-((4-(2-((5-(cyclopropanecarboxamido)-6-fluoro-2-methylnaphthalen-1-yl)oxy)pyridin-3-yl)pyrimidin-2-yl)amino)piperidine-1-carboxylate (18 mg, 0.114 mmol), 1,4-dioxane (0.3 mL), and hydrochloric acid (4 M in dioxane, 1 mL, 4 mmol). After 1.5 h, the mixture was diluted with Et$_2$O and the solids were filtered off, followed by washing with Et$_2$O and then dissolution in H$_2$O and MeCN. Lyophilization provided 16 mg (99% yield) of 271 as a white solid. LCMS (ESI) [M+H]$^+$=513.2, rt=1.27 min; $^1$H NMR (400 MHz, d6-dmso) δ 10.18 (s, 1H), 9.13-8.83 (m, 2H), 8.67 (s, 1H), 8.48 (d, J=5.2 Hz, 1H), 8.07 (dd, J=4.8, 2.0 Hz, 1H), 7.75 (d, J=8.7 Hz, 1H), 7.64 (dd, J=9.3, 5.1 Hz, 1H), 7.57 (dd, J=7.8, 5.0 Hz, 3H), 7.41 (t, J=9.4 Hz, 1H), 7.28 (dd, J=7.6, 4.8 Hz, 1H), 4.27 (s, 1H), 3.43 (d, J=9.6 Hz, 1H), 3.20 (d, J=12.2 Hz, 1H), 2.94-2.75 (m, 2H), 2.19 (s, 3H), 2.07-1.97 (m, 2H), 1.91 (dt, J=12.7, 4.1 Hz, 1H), 1.83-1.68 (m, 1H), 1.68-1.56 (m, 1H), 0.93-0.79 (m, 4H).

Example 272 (S)-4-(2-((5-(((1-Ethyl-1H-pyrazol-3-yl)amino)-2-methylnaphthalen-1-yl)oxy)pyridin-3-yl)-N-(piperidin-3-yl)pyrimidin-2-amine 272

Step 1: tert-Butyl (S)-3-((4-(2-((5-(((1-ethyl-1H-pyrazol-3-yl)amino)-2-methylnaphthalen-1-yl)oxy)pyridin-3-yl)pyrimidin-2-yl)amino)piperidine-1-carboxylate


The General Procedure F was followed, using tert-butyl (3S)-3-[[4-[2-[(5-amino-2-methyl-1-naphthyl)oxy]-3-pyridyl]pyrimidin-2-yl]amino]piperidine-1-carboxylate (200 mg, 0.38 mmol) and 3-bromo-1-ethyl-pyrazole (199.4 mg, 1.14 mmol). The crude material was purified by silica gel chromatography (12 g column), eluting with 0-5% MeOH/DCM to afford 162 mg (68.7% yield) of the title compound as a brown solid. LCMS (ESI) [M+H]$^+$=621.

Step 2: (S)-4-(2-((5-((1-Ethyl-1H-pyrazol-3-yl)amino)-2-methylnaphthalen-1-yl)oxy)pyridin-3-yl)-N-(piperidin-3-yl)pyrimidin-2-amine

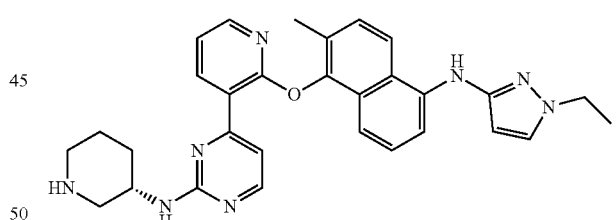

The General Procedure B was followed, using tert-butyl (S)-3-((4-(2-((5-(((1-ethyl-1H-pyrazol-3-yl)amino)-2-methylnaphthalen-1-yl)oxy)pyridin-3-yl)pyrimidin-2-yl)amino)piperidine-1-carboxylate (162 mg, 0.26 mmol). The crude product was purified via reverse-phase HPLC and lyophilized to yield 82.8 mg (60.9% yield) of 272 as an off-white solid. LCMS (ESI) [M+H]$^+$=521; $^1$H NMR (400 MHz, DMSO-d$_6$) δ 8.48 (s, 1H), 8.40 (d, J=5.1 Hz, 1H), 8.23 (d, J=8.9 Hz, 1H), 8.02 (dd, J=4.8, 2.0 Hz, 1H), 7.73 (dd, J=7.8, 1.0 Hz, 1H), 7.61 (d, J=2.3 Hz, 1H), 7.47-7.38 (m, 2H), 7.27-7.20 (m, 2H), 7.10 (d, J=8.0 Hz, 1H), 7.06 (d, J=8.4 Hz, 1H), 6.02 (d, J=2.3 Hz, 1H), 4.06 (q, J=7.2 Hz, 2H), 3.88 (s, 1H), 3.10 (d, J=11.1 Hz, 1H), 2.79 (d, J=12.4 Hz, 1H), 2.44 (d, J=9.0 Hz, 2H), 2.21 (s, 3H), 1.92 (s, 1H), 1.64 (s, 1H), 1.47 (d, J=9.3 Hz, 2H), 1.38 (t, J=7.2 Hz, 3H).

Example 273 (2S)—N-(6-Methyl-5-((3-(2-(((S)-piperidin-3-yl)amino)pyrimidin-4-yl)pyridin-2-yl)oxy)naphthalen-1-yl)-[1,1'-bi(cyclopropane)]-2-carboxamide 273

Step 1: tert-butyl (3S)-3-((4-(2-((5-((2S)-[1,1'-bi(cyclopropane)]-2-carboxamido)-2-methylnaphthalen-1-yl)oxy)pyridin-3-yl)pyrimidin-2-yl)amino)piperidine-1-carboxylate

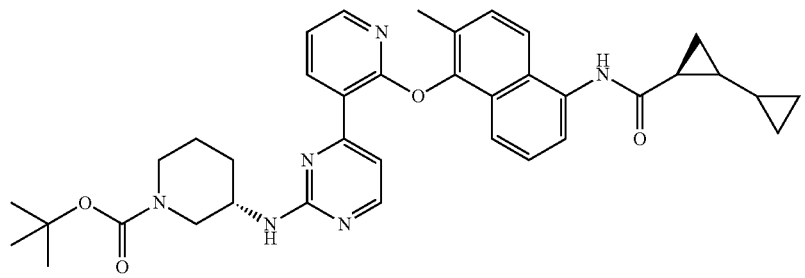

The General Procedure C was followed, using tert-butyl (3S)-3-[[4-[2-[(5-amino-2-methyl-1-naphthyl)oxy]-3-pyridyl]pyrimidin-2-yl]amino]piperidine-1-carboxylate (300 mg, 0.57 mmol), 2-cyclopropylcyclopropane-1-carboxylic acid (111 mg, 0.85 mmol), HATU (442.1 mg, 1.14 mmol), and DIPEA (0.30 mL, 1.71 mmol) in DMF (3 mL). The crude material was purified by silica gel chromatography (12 g column), eluting with 0-5% MeOH/DCM to afford 313 mg (86.5% yield) of the title compound as a brown solid. LCMS (ESI) [M+H]$^+$=635. The enantiomers were separated by chiral SFC to afford isomer-1 ($t_R$=1.213 min) 108.5 mg light yellow solid and isomer-2 ($t_R$=1.801 min) 110.6 mg light yellow solid. The absolute stereochemistry of the cyclopropyl was randomly assigned.

Step 2: (2S)—N-(6-Methyl-5-((3-(2-(((S)-piperidin-3-yl)amino)pyrimidin-4-yl)pyridin-2-yl)oxy)naphthalen-1-yl)-[1,1'-bi(cyclopropane)]-2-carboxamide

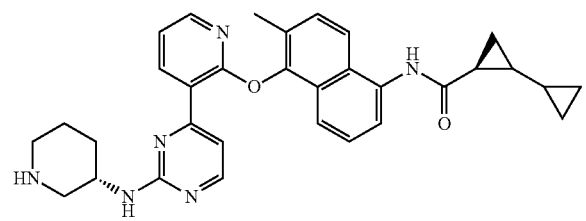

The General Procedure B was followed, using tert-butyl (3S)-3-((4-(2-((5-((2S)-[1,1'-bi(cyclopropane)]-2-carboxamido)-2-methylnaphthalen-1-yl)oxy)pyridin-3-yl)pyrimidin-2-yl)amino)piperidine-1-carboxylate (isomer-1, 108.5 mg, 0.17 mmol). The crude product was lyophilized to yield 95 mg (98% yield) of 273 as an off-white solid. The stereochemical assignments of 273 and 274 were randomly assigned and may be later determined. LCMS (ESI) [M+H]$^+$=535; $^1$H NMR (400 MHz, DMSO-d$_6$) δ 10.12 (s, 1H), 8.79-8.51 (m, 4H), 8.48 (d, J=5.2 Hz, 1H), 8.05 (dd, J=4.8, 2.0 Hz, 1H), 7.99 (d, J=8.7 Hz, 1H), 7.69 (d, J=7.4 Hz, 1H), 7.58 (d, J=5.1 Hz, 1H), 7.53 (d, J=8.8 Hz, 1H), 7.50 (d, J=7.4 Hz, 1H), 7.45 (d, J=8.5 Hz, 1H), 7.42-7.34 (m, 1H), 7.27 (dd, J=7.6, 4.8 Hz, 1H), 4.25 (s, 1H), 3.27-3.14 (m, 2H), 2.92-2.80 (m, 2H), 2.22 (s, 3H), 2.06-1.97 (m, 1H), 1.97-1.88 (m, 2H), 1.81-1.54 (m, 2H), 1.43-1.32 (m, 1H), 0.96 (dt, J=8.8, 4.4 Hz, 2H), 0.75-0.66 (m, 1H), 0.47-0.39 (m, 2H), 0.20-0.13 (m, 2H).

Example 274 (2R)—N-(6-Methyl-5-((3-(2-(((S)-piperidin-3-yl)amino)pyrimidin-4-yl)pyridin-2-yl)oxy)naphthalen-1-yl)-[1,1'-bi(cyclopropane)]-2-carboxamide 274

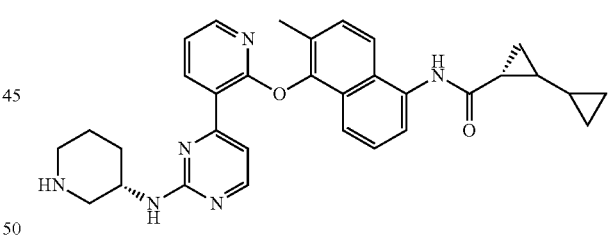

Following Example 273 and General Procedure B, tert-butyl (3S)-3-((4-(2-((5-((2R)-[1,1'-bi(cyclopropane)]-2-carboxamido)-2-methylnaphthalen-1-yl)oxy)pyridin-3-yl)pyrimidin-2-yl)amino)piperidine-1-carboxylate (isomer-2, 110.6 mg, 0.17 mmol) was deprotected. The crude product was lyophilized to yield 98 mg (100% yield) of 274 as an off-white solid. LCMS (ESI) [M+H]$^+$=535; $^1$H NMR (400 MHz, DMSO-d$_6$) δ 10.14 (s, 1H), 9.09-8.91 (m, 2H), 8.75-8.55 (m, 2H), 8.48 (d, J=5.2 Hz, 1H), 8.06 (dd, J=4.8, 2.0 Hz, 1H), 7.99 (d, J=8.7 Hz, 1H), 7.69 (d, J=7.3 Hz, 1H), 7.58 (dd, J=12.6, 6.4 Hz, 2H), 7.53 (d, J=8.8 Hz, 1H), 7.46 (d, J=8.4 Hz, 1H), 7.40-7.37 (m, 1H), 7.27 (dd, J=7.6, 4.8 Hz, 1H), 4.36-4.25 (m, 1H), 3.24-3.14 (m, 2H), 2.91-2.79 (m, 2H), 2.22 (s, 3H), 2.07-1.98 (m, 1H), 1.98-1.87 (m, 2H), 1.83-1.59 (m, 2H), 1.41-1.34 (m, 1H), 1.01-0.92 (m, 2H), 0.75-0.65 (m, 1H), 0.50-0.38 (m, 2H), 0.24-0.14 (m, 2H).

Example 275 (S)—N-(2-Fluoro-6-methyl-5-((3-(2-(piperidin-3-ylamino)pyrimidin-4-yl)pyridin-2-yl)oxy)naphthalen-1-yl)-3,3-dimethylbutanamide 275

Step 1: (S)-tert-Butyl 3-((4-(2-((5-amino-6-fluoro-2-methylnaphthalen-1-yl)oxy)pyridin-3-yl)pyrimidin-2-yl)amino)piperidine-1-carboxylate

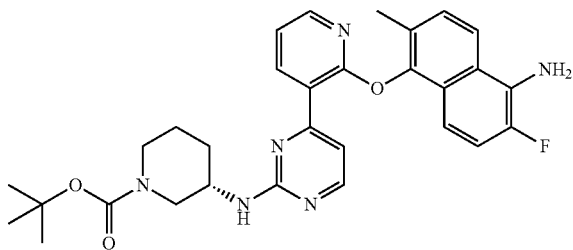

To a 100 mL 3-necked round-bottom flask purged and maintained with an inert atmosphere of nitrogen was placed tert-butyl (3S)-3-[[4-(2-fluoro-3-pyridyl)pyrimidin-2-yl]amino]piperidine-1-carboxylate (150 mg, 0.40 mmol), 5-amino-6-fluoro-2-methylnaphthalen-1-ol (150 mg, 0.52 mmol), cesium carbonate (392 mg, 1.21 mmol), dimethyl sulfoxide (2 mL). The resulting solution was stirred at 120° C. in an oil bath for 2 h, cooled to room temperature and concentrated in vacuo. The residue was purified prep-TLC (solvent gradient: 50% ethyl acetate in petroleum ether) to yield 160 mg (73% yield) of the title compound as a yellow solid. LCMS: (ES, m/z): [M+H]$^+$=545.1.

Step 2: (S)-tert-Butyl 3-((4-(2-((5-(3,3-dimethylbutanamido)-6-fluoro-2-methylnaphthalen-1-yl)oxy)pyridin-3-yl)pyrimidin-2-yl)amino)piperidine-1-carboxylate

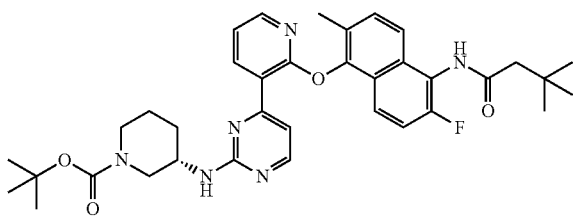 [SMILES: Cc1ccc2c(NC(=O)CC(C)(C)C)c(F)ccc2c1Oc1ncccc1-c1ccnc(N[C@H]2CCCN(C(=O)OC(C)(C)C)C2)n1]

The General Procedure A was followed, using tert-butyl (3S)-3-[[4-[2-[(5-amino-6-fluoro-2-methyl-1-naphthyl)oxy]-3-pyridyl]pyrimidin-2-yl]amino]piperidine-1-carboxylate (80 mg, 0.15 mmol), pyridine (2 mL), dichloromethane (1 mL) and 3,3-dimethylbutanoyl chloride (24 mg, 0.18 mmol). The residue was purified by Prep-TLC (normal phase, petroleum ether/ethyl acetate=2/1) to yield 90 mg (95% yield) of the title compound as a brown oil. LCMS (ESI) [M+H]$^+$=643.3

Step 3: (S)—N-(2-fluoro-6-methyl-5-((3-(2-(piperidin-3-ylamino)pyrimidin-4-yl)pyridin-2-yl)oxy)naphthalen-1-yl)-3,3-dimethylbutanamide

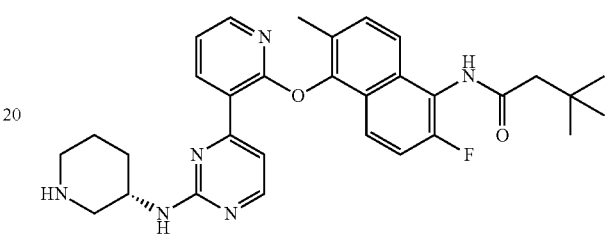

The General Procedure B was followed, using tert-butyl (3S)-3-[[4-[2-[[5-(3,3-dimethylbutanoylamino)-6-fluoro-2-methyl-1-naphthyl]oxy]-3-pyridyl]pyrimidin-2-yl]amino]piperidine-1-carboxylate (90 mg, 0.09 mmol), dichloromethane (2 mL) and hydrochloric acid (4 M in dioxane, 0.23 mL, 0.93 mmol). The residue was purified by Prep-HPLC (mobile phase: A: water (0.05% HCl) B: ACN) to yield 62 mg (83% yield) of 275 as a white solid. LCMS (ESI): [M+H]$^+$=543.1; $^1$H NMR (400 MHz, DMSO-d$_6$) δ 9.85 (s, 1H), 9.38 (s, 1H), 9.15 (s, 1H), 8.79 (s, 1H), 8.50 (d, J=5.4 Hz, 1H), 8.08 (d, J=3.2 Hz, 1H), 7.79 (d, J=8.6 Hz, 1H), 7.70-7.60 (m, 1H), 7.57 (d, J=8.6 Hz, 1H), 7.40 (t, J=9.6 Hz, 1H), 7.30-7.24 (m, 1H), 4.40 (s, 1H), 3.41 (m, 1H), 3.18 (m, 1H), 2.89-2.78 (m, 2H), 2.36 (s, 2H), 2.19 (s, 3H), 2.02 (m, 1H), 1.95-1.87 (m, 1H), 1.75-1.87 (m, 1H), 1.75-1.60 (m, 1H), 1.10 (s, 9H).

Example 276 (S)-3,3,3-Trifluoro-N-(2-fluoro-6-methyl-5-((3-(2-(piperidin-3-ylamino)pyrimidin-4-yl)pyridin-2-yl)oxy)naphthalen-1-yl)propane-1-sulfonamide hydrochloride 276

Step 1: (S)-tert-butyl 3-((4-(2-((6-fluoro-2-methyl-5-(3,3,3-trifluoropropylsulfonamido)naphthalen-1-yl)oxy)pyridin-3-yl)pyrimidin-2-yl)amino)piperidine-1-carboxylate

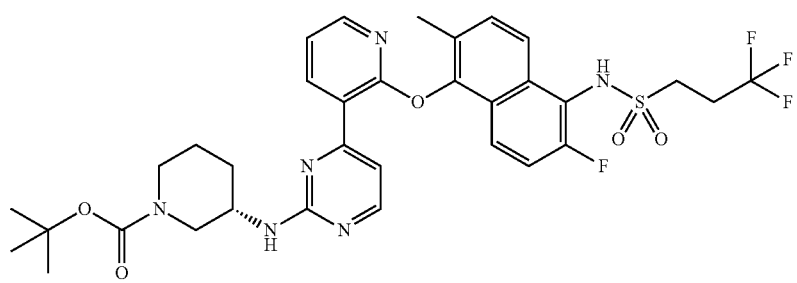

461

The General Procedure A was followed using (S)-tert-butyl 3-((4-(2-((5-amino-6-fluoro-2-methylnaphthalen-1-yl)oxy)pyridin-3-yl)pyrimidin-2-yl)amino)piperidine-1-carboxylate from Example 275 (500 mg, 0.918 mmol), pyridine (2 mL), CH₂Cl₂ (4 mL), and 3,3,3-trifluoropropane-1-sulfonyl chloride (452 mg, 2.30 mmol). After 16 h, the mixture was diluted with CH₂Cl₂ (50 mL) and washed with saturated NaHCO₃(aq) (10 mL), dried (Na₂SO₄), filtered and concentrated The crude was purified by flash chromatography through silica gel (0-50% EtOAc/CH₂Cl₂) to provide 355 mg (55% yield) of the title compound as a yellow wax. LCMS (ESI) [M+H]⁺=705.2, rt=1.97 min.

Step 2: (S)-3,3,3-Trifluoro-N-(2-fluoro-6-methyl-5-((3-(2-(piperidin-3-ylamino)pyrimidin-4-yl)pyridin-2-yl)oxy)naphthalen-1-yl)propane-1-sulfonamide hydrochloride 276

Prepared according to General Procedure B using (S)-tert-butyl 3-((4-(2-((6-fluoro-2-methyl-5-(3,3,3-trifluoropropylsulfonamido)naphthalen-1-yl)oxy)pyridin-3-yl)pyrimidin-2-yl)amino)piperidine-1-carboxylate (355 mg, 0.50 mmol), EtOAc (3 mL), and hydrochloric acid (4 M in dioxane, 2 mL, 8 mmol). After 16 h, the mixture was concentrated in vacuo and the crude HCl salt solid was washed with EtOAc (3×3 mL) then with MeCN (3×3 mL). The solid product was then sonicated and concentrated in vacuo with MeCN (3×3 mL) and the resulting solid was dissolved in H₂O and MeCN and lyophilized to provide 265 mg (82% yield) of 276 as a fluffy light yellow powder and as a HCl salt. LCMS (ESI) [M+H]⁺=705.2, rt=1.97 min; ¹H NMR (400 MHz, d₆-DMSO) δ 10.09 (s, 1H), 9.03-8.75 (m, 2H), 8.73-8.56 (m, 1H), 8.47 (d, J=5.2 Hz, 1H), 8.08 (dd, J=4.8, 1.9 Hz, 1H), 8.04 (d, J=8.7 Hz, 1H), 7.75 (dd, J=9.3, 5.1 Hz, 1H), 7.66 (d, J=8.8 Hz, 1H), 7.60-7.52 (m, 2H), 7.49 (t, J=9.5 Hz, 1H), 7.29 (dd, J=7.6, 4.8 Hz, 1H), 4.37-4.16 (m, 1H), 3.47-3.40 (m, 3H), 3.21 (d, J=11.9 Hz, 1H), 2.99-2.75 (m, 4H), 2.18 (s, 3H), 2.08-1.86 (m, 2H), 1.80-1.56 (m, 2H).

Example 277 (1R)-3-Methyl-N-(6-methyl-5-((3-(2-(((S)-piperidin-3-yl)amino)pyrimidin-4-yl)pyridin-2-yl)oxy)naphthalen-1-yl)cyclopentane-1-carboxamide 277

Step 1: 3-Methyl-N-(6-methyl-5-((3-(2-(methylthio)pyrimidin-4-yl)pyridin-2-yl)oxy)naphthalen-1-yl)cyclopentanecarboxamide

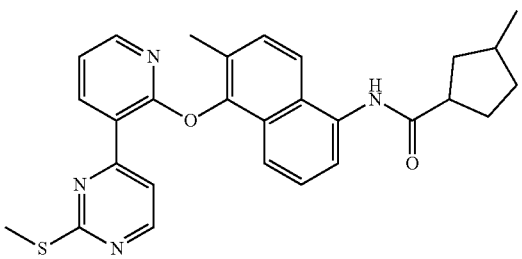

Prepared using 6-methyl-5-((3-(2-(methylthio)pyrimidin-4-yl)pyridin-2-yl)oxy)naphthalen-1-amine (260 mg, 0.694 mmol), triethylamine (211 mg, 0.290 mL, 2.08 mmol), HATU (343 mg, 0.903 mmol), and 3-methylcyclopentanecarboxylic acid (98 mg, 0.76 mmol) in DMF (2 mL). After 3 days, the mixture was diluted with EtOAc and H₂O and a precipitate formed which was filtered off, washed with EtOAc and H₂O and vacuum dried to provide 272 mg (80% yield) of the title compound as a white solid. LCMS (ESI) [M+H]⁺=485.3, rt=2.01 min.

Step 2: 3-Methyl-N-(6-methyl-5-((3-(2-(methylsulfinyl)pyrimidin-4-yl)pyridin-2-yl)oxy)naphthalen-1-yl)cyclopentanecarboxamide

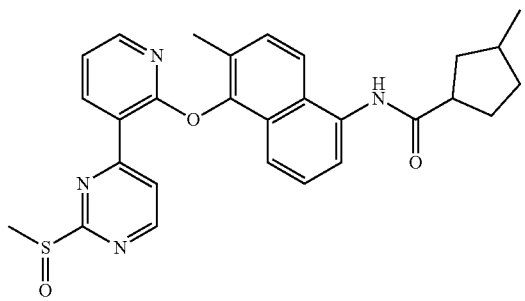

To 3-methyl-N-(6-methyl-5-((3-(2-(methylthio)pyrimidin-4-yl)pyridin-2-yl)oxy)naphthalen-1-yl)cyclopentanecarboxamide (268 mg, 0.553 mmol) in DCM (18 mL) was added 3-chloroperbenzoic acid (135 mg of 77% pure reagent, 0.610 mmol) and the mixture was stirred at rt. After 1 h, the mixture was diluted with DCM and washed with saturated NaHCO₃(aq), dried (Na₂SO₄), filtered and concentrated in vacuo to provide 276 mg (100% yield) of the title compound which was used without further purification in the next step. LCMS (ESI) [M+H]⁺=501.2, rt=1.59 min.

Step 3: (3S)-tert-Butyl 3-((4-(2-((2-methyl-5-(3-methylcyclopentanecarboxamido)naphthalen-1-yl)oxy)pyridin-3-yl)pyrimidin-2-yl)amino)piperidine-1-carboxylate

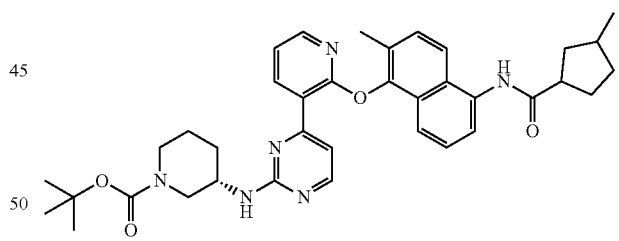

3-Methyl-N-(6-methyl-5-((3-(2-(methylsulfinyl)pyrimidin-4-yl)pyridin-2-yl)oxy)naphthalen-1-yl)cyclopentanecarboxamide (276 mg, 0.551 mmol) and (S)-tert-butyl 3-aminopiperidine-1-carboxylate (166 mg, 0.827 mmol) were combined in 1,4-dioxane (3 mL). Triethylamine (167 mg, 0.230 mL, 1.65 mmol) was then added and the flask was sealed and placed in a 120° C. oil bath. After 20 h, the mixture was diluted with EtOAc, and washed with saturated NaHCO₃(aq), then saturated NaCl(aq), dried (MgSO₄), filtered and concentrated in vacuo. The crude was purified by flash chromatography through silica gel (0-60% EtOAc/DCM) to provide 254 mg (72% yield) of the title compound as an off-white foam. LCMS (ESI) [M+H]⁺=637.4, rt=2.04 min.

Step 4: tert-Butyl (3S)-3-((4-(2-((2-methyl-5-((1R)-3-methylcyclopentane-1-carboxamido)naphthalen-1-yl)oxy)pyridin-3-yl)pyrimidin-2-yl)amino)piperidine-1-carboxylate (Isomer-1) and tert-butyl (3S)-3-((4-(2-((2-methyl-5-((1S)-3-methylcyclopentane-1-carboxamido)naphthalen-1-yl)oxy)pyridin-3-yl)pyrimidin-2-yl)amino)piperidine-1-carboxylate (Isomer-2)

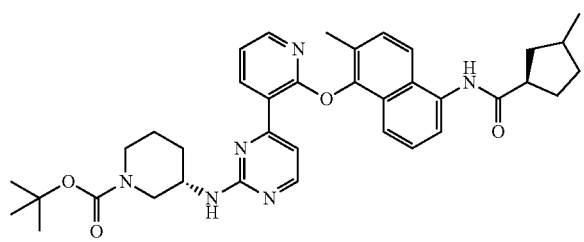

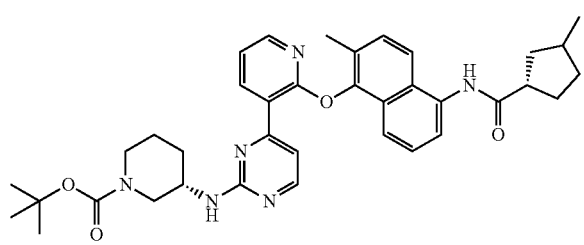

The mixture of stereoisomers from Step 3 (254 mg, 0.399 mmol) was subjected to chiral normal phase semi-prep purification (Conditions: Chiral pak IB, 5 um, 20×250 mm, 6:2:92 MeOH: IPA: hexanes, stached injection, 0.5-0.75 mg/injections) to provide stereoisomers with respect to the cyclopentane ring: (isomer-1), 101 mg (40% yield), ee≥99%, rt=16.21 min, LCMS (ESI) [M+H]⁺=637.7, rt=2.04 min; (isomer-2), 105 mg (41% yield), ee=95%, rt=16.75 min, LCMS (ESI) [M+H]⁺=637.7, rt=2.05 min.

Step 5: (1R)-3-Methyl-N-(6-methyl-5-((3-(2-(((S)-piperidin-3-yl)amino)pyrimidin-4-yl)pyridin-2-yl)oxy)naphthalen-1-yl)cyclopentane-1-carboxamide (Isomer-1)

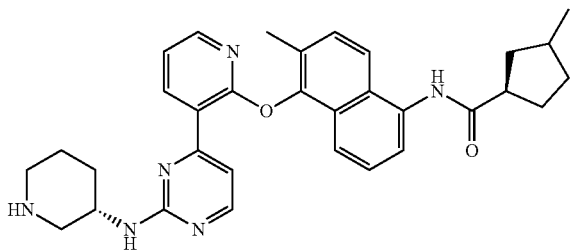

Prepared using (3S)-tert-butyl 3-((4-(2-((2-methyl-5-(3-methylcyclopentanecarboxamido)naphthalen-1-yl)oxy)pyridin-3-yl)pyrimidin-2-yl)amino)piperidine-1-carboxylate (isomer-1) (101 mg, 0.159 mmol), 1,4-dioxane (0.5 mL), and hydrochloric acid (4 M in dioxane, 2 mL, 8 mmol). After 30 min, the resulting solids were filtered off and washed with Et₂O, and dried. The collected solids were then dissolved in H₂O and MeCN and lyophilized to provide 75 mg (83% yield) of 277. The stereochemical assignments of 277 and 278 were randomly assigned and may be later determined. LCMS (ESI) [M+H]⁺=537.5, rt=1.49 min; ¹H NMR (400 MHz, d₆-DMSO) δ 9.90 (s, 1H), 9.44-8.96 (m, 2H), 8.71 (br.s, 1H), 8.49 (d, J=5.3 Hz, 1H), 8.06 (dd, J=4.8, 1.9 Hz, 1H), 7.89 (d, J=8.7 Hz, 1H), 7.74-7.55 (m, 3H), 7.49 (dd, J=12.5, 8.8 Hz, 2H), 7.44-7.34 (m, 1H), 7.27 (dd, J=7.6, 4.8 Hz, 1H), 3.43 (d, J=10.3 Hz, 1H), 3.28-3.03 (m, 2H), 2.95-2.74 (m, 2H), 2.21 (s, 3H), 2.18-2.07 (m, 1H), 2.08-1.96 (m, 2H), 1.98-1.87 (m, 3H), 1.87-1.68 (m, 2H), 1.70-1.55 (m, 1H), 1.39 (dd, J=21.9, 9.9 Hz, 1H), 1.33-1.14 (m, 1H), 1.10-0.96 (m, 3H).

Example 278 (1S)-3-Methyl-N-(6-methyl-5-((3-(2-(((S)-piperidin-3-yl)amino)pyrimidin-4-yl)pyridin-2-yl)oxy)naphthalen-1-yl)cyclopentane-1-carboxamide 278

Step 1: 3-Methyl-N-(6-methyl-5-((3-(2-((S)-piperidin-3-ylamino)pyrimidin-4-yl)pyridin-2-yl)oxy)naphthalen-1-yl)cyclopentanecarboxamide (Isomer-2)

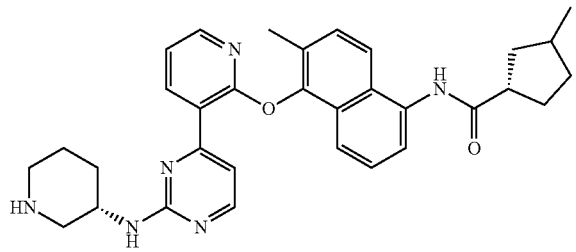

Prepared using tert-butyl (3S)-3-((4-(2-((2-methyl-5-((1S)-3-methylcyclopentane-1-carboxamido)naphthalen-1-yl)oxy)pyridin-3-yl)pyrimidin-2-yl)amino)piperidine-1-carboxylate (isomer-2) (105 mg, 0.165 mmol), 1,4-dioxane (0.5 mL), and hydrochloric acid (4 M in dioxane, 2 mL, 8 mmol). After 30 min, the resulting solids were filtered off and washed with Et₂O, and dried. The collected solids were then dissolved in H₂O and MeCN and lyophilized to provide 74 mg (78% yield) of 278. LCMS (ESI) [M+H]⁺=537.4, rt=1.49 min; ¹H NMR (400 MHz, d6-dmso) δ 9.93 (s, 1H), 9.49 (br.s, 1H), 9.27 (s, 1H), 8.81 (br.s, 1H), 8.50 (d, J=5.4 Hz, 1H), 8.44 (s, 1H), 8.07 (dd, J=4.7, 1.8 Hz, 1H), 7.90 (d, J=8.7 Hz, 1H), 7.67 (s, 1H), 7.59 (d, J=7.2 Hz, 1H), 7.54-7.45 (m, 2H), 7.44-7.33 (m, 1H), 7.27 (dd, J=7.6, 4.8 Hz, 1H), 4.41 (s, 1H), 3.49-3.34 (m, 1H), 3.28-3.02 (m, 2H), 2.96-2.73 (m, 2H), 2.21 (s, 3H), 2.19-2.08 (m, 1H), 2.08-1.96 (m, 2H), 1.97-1.87 (m, 3H), 1.87-1.72 (m, 2H), 1.72-1.56 (m, 1H), 1.39 (dd, J=21.9, 9.9 Hz, 1H), 1.32-1.15 (m, 1H), 1.10-0.98 (m, 3H).

Example 279 (S)—N-(2-Fluoro-6-methyl-5-((3-(2-(piperidin-3-ylamino)pyrimidin-4-yl)pyridin-2-yl)oxy)naphthalen-1-yl)-2-methylpropane-1-sulfonamide 279

Step 1: (S)-tert-Butyl 3-((4-(2-((6-fluoro-2-methyl-5-(2-methylpropylsulfonamido)naphthalen-1-yl)oxy)pyridin-3-yl)pyrimidin-2-yl)amino)piperidine-1-carboxylate

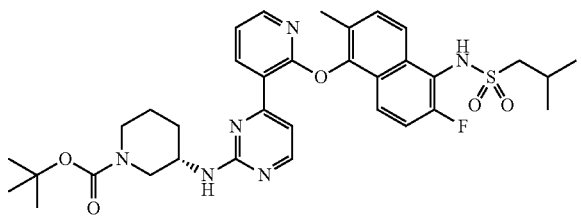 [SMILES: Cc1ccc2c(NS(=O)(=O)CC(C)C)c(F)ccc2c1Oc1ncccc1-c1ccnc(N[C@H]2CCCN(C(=O)OC(C)(C)C)C2)n1]

Prepared using (S)-tert-butyl 3-((4-(2-((5-amino-6-fluoro-2-methylnaphthalen-1-yl)oxy)pyridin-3-yl)pyrimidin-2-yl)amino)piperidine-1-carboxylate from Example 275 (45 mg, 0.083 mmol), pyridine (98 mg, 0.10 mL, 1.2 mmol), DCM (0.28 mL), DMAP (3 mg, 0.024 mmol), and 2-methylpropane-1-sulfonyl chloride (26 mg, 0.16 mmol). After 16 h, a further portion of 2-methylpropane-1-sulfonyl chloride (26 mg, 0.16 mmol) added and after stirring a further 20 h the mixture was concentrated in vacuo and the crude was purified by C18 reverse phase flash chromatography (25-75% MeCN/10 mM pH=10 aqueous ammonium bicarbonate). The product fractions were collected and concentrated in vacuo and the resulting residue was diluted with EtOAc and washed with saturated NaHCO$_3$(aq), then saturated NaCl(aq). The solution was dried (Na$_2$SO$_4$), filtered and concentrated in vacuo to provide 27 mg (49% yield) of the title compound. LCMS (ESI) [M+H]$^+$=665.3, rt=1.96 min.

Step 2: (S)—N-(2-Fluoro-6-methyl-5-((3-(2-(piperidin-3-ylamino)pyrimidin-4-yl)pyridin-2-yl)oxy)naphthalen-1-yl)-2-methylpropane-1-sulfonamide

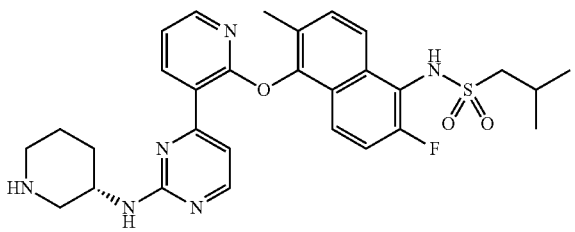 [SMILES: Cc1ccc2c(NS(=O)(=O)CC(C)C)c(F)ccc2c1Oc1ncccc1-c1ccnc(N[C@H]2CCCNC2)n1]

Prepared according to General Procedure B using (S)-tert-butyl 3-((4-(2-((6-fluoro-2-methyl-5-(2-methylpropylsulfonamido)naphthalen-1-yl)oxy)pyridin-3-yl)pyrimidin-2-yl)amino)piperidine-1-carboxylate (27 mg, 0.041 mmol), 1,4-dioxane (0.2 mL), and hydrochloric acid (4 M in dioxane, 1 mL, 4 mmol). After 1.5 h, the mixture was diluted with Et$_2$O and the solids were filtered off, washed with Et$_2$O and then dissolved in H$_2$O and purified by C18 reverse phase flash chromatography (25-45% MeCN/10 mM pH=10 aqueous ammonium bicarbonate). Appropriate fractions were collected and concentrated in vacuo and the resulting residue was diluted with EtOAc and washed with saturated NaHCO$_3$ (aq), dried (Na$_2$SO$_4$), filtered and concentrated in vacuo. The material thus obtained was dissolved in 1,4-dioxane (0.2 mL) and treated with hydrochloric acid (4 M in dioxane, 1 mL, 4 mmol) and stirred at rt. After 5 min, the mixture was diluted with Et$_2$O and the solids were filtered off, washed with Et$_2$O and then dissolved in H$_2$O and MeCN. Lyophilization provided 16 mg (64% yield) of the title compound as a white solid. LCMS (ESI) [M+H]$^+$=565.1, rt=1.43 min; $^1$H NMR (400 MHz, d$_6$-DMSO) δ 9.70 (s, 1H), 9.01-8.77 (m, 2H), 8.68 (s, 1H), 8.47 (d, J=5.2 Hz, 1H), 8.10-8.04 (m, 2H), 7.71 (dd, J=9.3, 5.1 Hz, 1H), 7.63 (d, J=8.8 Hz, 1H), 7.55 (dd, J=9.3, 6.4 Hz, 2H), 7.46 (t, J=9.5 Hz, 1H), 7.29 (dd, J=7.6, 4.8 Hz, 1H), 4.27 (s, 1H), 3.43 (d, J=8.7 Hz, 1H), 3.21 (d, J=12.2 Hz, 1H), 3.11 (d, J=6.4 Hz, 2H), 2.94-2.76 (m, 2H), 2.28 (dt, J=13.3, 6.6 Hz, 1H), 2.19 (s, 3H), 2.01 (d, J=12.2 Hz, 1H), 1.92 (dd, J=14.6, 3.5 Hz, 1H), 1.80-1.69 (m, 1H), 1.69-1.57 (m, 1H), 1.07 (d, J=6.7 Hz, 6H).

Example 280 (S)-4-(2-((2-Methyl-5-(((5-methylisoxazol-3-yl)methyl)amino)naphthalen-1-yl)oxy)pyridin-3-yl)-N-(piperidin-3-yl)pyrimidin-2-amine 280

Step 1: tert-Butyl (S)-3-((4-(2-((2-methyl-5-(((5-methylisoxazol-3-yl)methyl)amino)naphthalen-1-yl)oxy)pyridin-3-yl)pyrimidin-2-yl)amino)piperidine-1-carboxylate

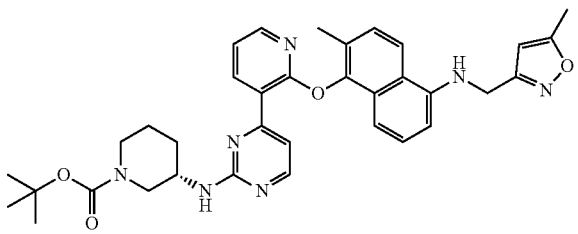 [SMILES: Cc1cc(CNc2cccc3c(Oc4ncccc4-c4ccnc(N[C@H]5CCCN(C(=O)OC(C)(C)C)C5)n4)c(C)ccc23)no1]

The General Procedure E was followed, using tert-butyl (3S)-3-[[4-[2-[(5-amino-2-methyl-1-naphthyl)oxy]-3-pyridyl]pyrimidin-2-yl]amino]piperidine-1-carboxylate (200 mg, 0.38 mmol) and 3-(bromomethyl)-5-methylisoxazole (137.8 mg, 0.76 mmol). The crude material was purified by silica gel chromatography (12 g column), eluting with 0-5% MeOH/DCM to afford 69 mg (29% yield) of the title compound as a brown solid. LCMS (ESI) [M+H]$^+$=622.

Step 2: (S)-4-(2-((2-Methyl-5-(((5-methylisoxazol-3-yl)methyl)amino)naphthalen-1-yl)oxy)pyridin-3-yl)-N-(piperidin-3-yl)pyrimidin-2-amine

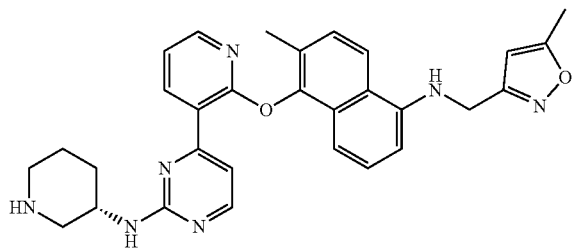 [SMILES: Cc1cc(CNc2cccc3c(Oc4ncccc4-c4ccnc(N[C@H]5CCCNC5)n4)c(C)ccc23)no1]

The General Procedure B was followed, using tert-butyl (S)-3-((4-(2-((2-methyl-5-(((5-methylisoxazol-3-yl)methyl)amino)naphthalen-1-yl)oxy)pyridin-3-yl)pyrimidin-2-yl)amino)piperidine-1-carboxylate (69 mg, 0.07 mmol). The crude product was purified via reverse-phase HPLC and lyophilized to yield 19.8 mg (52.6% yield) of 280 as an off-white solid. LCMS (ESI) [M+H]$^+$=522; $^1$H NMR (400 MHz, DMSO-d$_6$) δ 8.51-8.45 (m, 1H), 8.39 (d, J=5.2 Hz, 1H), 8.02-7.97 (m, 1H), 7.43 (d, J=5.1 Hz, 1H), 7.38 (d, J=8.7 Hz, 1H), 7.22 (dd, J=7.6, 4.8 Hz, 1H), 7.14-7.10 (m, 2H), 6.95-6.85 (m, 2H), 6.46 (dd, J=7.8, 1.0 Hz, 1H), 6.14 (s, 1H), 4.47 (d, J=6.0 Hz, 2H), 3.96-3.82 (m, 1H), 3.16-3.08 (m, 1H), 2.86-2.77 (m, 1H), 2.47-2.40 (m, 2H), 2.33 (d, J=0.9 Hz, 3H), 2.19 (s, 3H), 1.97-1.90 (m, 1H), 1.69-1.63 (m, 1H), 1.54-1.41 (m, 2H).

Example 281 N-(6-Methyl-5-((3-(2-(((S)-piperidin-3-yl)amino)pyrimidin-4-yl)pyridin-2-yl)oxy)naphthalen-1-yl)spiro[2.5]octane-1-carboxamide 281

Step 1: tert-Butyl (3S)-3-((4-(2-((2-methyl-5-(spiro[2.5]octane-1-carboxamido)naphthalen-1-yl)oxy)pyridin-3-yl)pyrimidin-2-yl)amino)piperidine-1-carboxylate

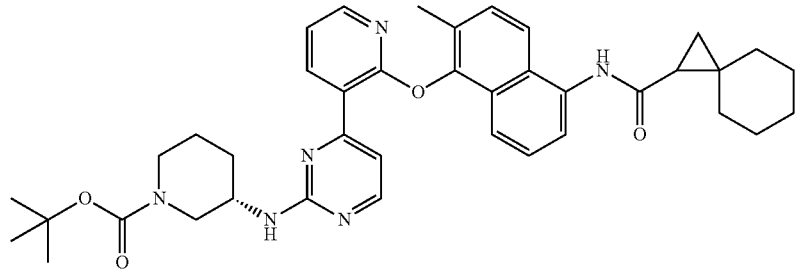 [SMILES: Cc1ccc2c(NC(=O)C3CC34CCCCC4)cccc2c1Oc1ncccc1-c1ccnc(N[C@H]2CCCN(C(=O)OC(C)(C)C)C2)n1]

The General Procedure C was followed, using tert-butyl (3S)-3-[[4-[2-[(5-amino-2-methyl-1-naphthyl)oxy]-3-pyridyl]pyrimidin-2-yl]amino]piperidine-1-carboxylate (200 mg, 0.38 mmol), spiro[2.5]octane-2-carboxylic acid (87.8 mg, 0.57 mmol), HATU (294.7 mg, 0.76 mmol), DMF (2 mL), and DIPEA (0.20 mL, 1.14 mmol). The crude material was purified by chromatography (silica gel chromatography) 12 g column, eluting with 0-5% MeOH/DCM to afford 239 mg (94.5 yield) of the title compound as a yellow solid. LCMS (ESI) [M+H]$^+$=663.

Step 2: N-(6-Methyl-5-((3-(2-(((S)-piperidin-3-yl)amino)pyrimidin-4-yl)pyridin-2-yl)oxy)naphthalen-1-yl)spiro[2.5]octane-1-carboxamide

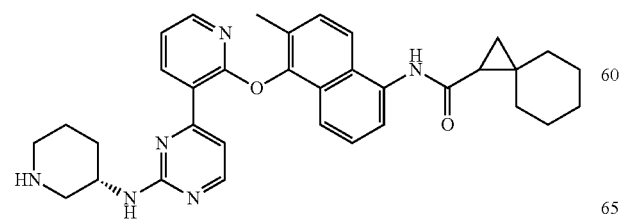

The General Procedure B was followed, using tert-butyl (3S)-3-((4-(2-((2-methyl-5-(spiro[2.5]octane-1-carboxamido)naphthalen-1-yl)oxy)pyridin-3-yl)pyrimidin-2-yl)amino)piperidine-1-carboxylate (239 mg, 0.36 mmol). The crude product was purified via reverse-phase HPLC and lyophilized to yield 18.8 mg (9.3% yield) of 281 as a white solid and as a mixture of two isomers enantiomeric at the 1-cyclopropane position. LCMS (ESI) [M+H]$^+$=563; $^1$H NMR (400 MHz, DMSO-d$_6$) δ 10.12 (s, 1H), 8.49 (d, J=7.5 Hz, 1H), 8.41 (d, J=5.1 Hz, 1H), 8.02 (dd, J=4.8, 2.0 Hz, 1H), 7.97 (d, J=8.7 Hz, 1H), 7.60 (d, J=7.3 Hz, 1H), 7.55-7.47 (m, 2H), 7.44 (d, J=5.1 Hz, 1H), 7.39 (t, J=7.9 Hz, 1H), 7.25 (dd, J=7.6, 4.8 Hz, 1H), 7.13-7.07 (m, 1H), 3.94-3.82 (m, 1H), 3.12-3.02 (m, 1H), 2.82-2.72 (m, 1H), 2.47-2.36 (m, 2H), 2.22 (s, 3H), 1.97-1.90 (m, 2H), 1.73-1.27 (m, 14H), 1.06-1.00 (m, 1H), 0.85-0.78 (m, 1H).

Example 282 (S)—N-(2-Fluoro-6-methyl-5-((3-(2-(piperidin-3-ylamino)pyrimidin-4-yl)pyridin-2-yl)oxy)naphthalen-1-yl)cyclohexanesulfonamide 282

Step 1: (S)-tert-Butyl 3-((4-(2-((5-(cyclohexanesulfonamido)-6-fluoro-2-methylnaphthalen-1-yl)oxy)pyridin-3-yl)pyrimidin-2-yl)amino)piperidine-1-carboxylate

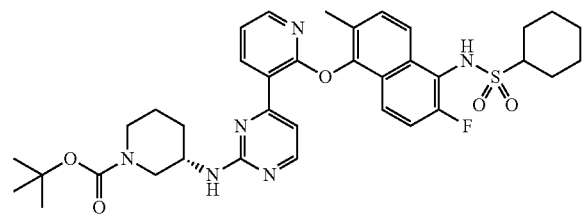 [SMILES: Cc1ccc2c(NS(=O)(=O)C3CCCCC3)c(F)ccc2c1Oc1ncccc1-c1ccnc(N[C@H]2CCCN(C(=O)OC(C)(C)C)C2)n1]

Prepared using (S)-tert-butyl 3-((4-(2-((5-amino-6-fluoro-2-methylnaphthalen-1-yl)oxy)pyridin-3-yl)pyrimidin-2-yl)amino)piperidine-1-carboxylate from Example 275 (50 mg, 0.092 mmol), pyridine (109 mg, 0.11 mL, 1.38 mmol), DCM (0.30 mL), DMAP (3 mg, 0.024 mmol), and cyclohexanesulfonyl chloride (117 mg, 0.643 mmol). After 16 h, a further portion of DMAP (3 mg, 0.024 mmol), and cyclohexanesulfonyl chloride (117 mg, 0.643 mmol) was added and after stirring a further 20 h the mixture was concentrated in vacuo and the crude was purified by C18 reverse phase flash chromatography (50-80% MeCN/10 mM pH=3.8 aqueous ammonium formate). Appropriate fractions were collected and concentrated in vacuo and the resulting residue was diluted with EtOAc and washed with saturated NaHCO$_3$(aq), then saturated NaCl(aq), dried (Na$_2$SO$_4$), filtered and concentrated in vacuo to provide 12 mg (19% yield) of the title compound. LCMS (ESI) [M+H]$^+$=691.3, rt=2.03 min.

Step 2: (S)—N-(2-Fluoro-6-methyl-5-((3-(2-(piperidin-3-ylamino)pyrimidin-4-yl)pyridin-2-yl)oxy)naphthalen-1-yl)cyclohexanesulfonamide

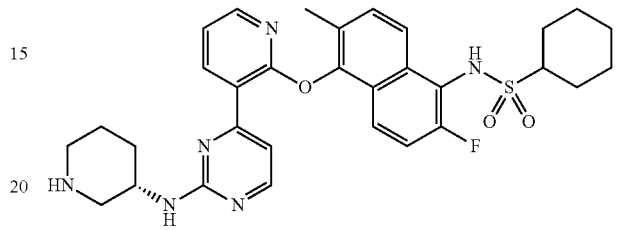

Prepared according to General Procedure B using (S)-tert-Butyl 3-((4-(2-((5-(cyclohexanesulfonamido)-6-fluoro-2-methylnaphthalen-1-yl)oxy)pyridin-3-yl)pyrimidin-2-yl)amino)piperidine-1-carboxylate (12 mg, 0.017 mmol), 1,4-dioxane (0.2 mL), and hydrochloric acid (4 M in dioxane, 1 mL, 4 mmol). After 1.5 h, the mixture was diluted with Et$_2$O and the solids were filtered off, washed with Et$_2$O and then dissolved in H$_2$O. Lyophilization provided 11 mg (103% yield) of 282 as a white solid. LCMS (ESI) [M+H]$^+$=591.2, rt=1.49 min; $^1$H NMR (400 MHz, d6-dmso) δ 9.58 (s, 1H), 8.95-8.72 (m, 2H), 8.70-8.57 (m, 1H), 8.47 (d, J=5.2 Hz, 1H), 8.10-8.04 (m, 2H), 7.70 (dd, J=9.3, 5.1 Hz, 1H), 7.63 (d, J=8.8 Hz, 1 Hz), 7.55 (dd, J=11.8, 6.2 Hz, 2H), 7.44 (t, J=9.5 Hz, 1H), 7.29 (dd, J=7.6, 4.8 Hz, 1H), 4.27 (s, 1H), 3.45-3.30 (m, 2H), 3.21 (d, J=12.6 Hz, 1H), 3.04 (tt, J=11.9, 3.0 Hz, 1H), 2.93-2.77 (m, 2H), 2.28-2.21 (m, 2H), 2.19 (s, 3H), 2.01 (d, J=9.4 Hz, 1H), 1.97-1.82 (m, 3H), 1.78-1.57 (m, 3H), 1.50 (qd, J=12.6, 3.2 Hz, 2H), 1.37-1.13 (m, 2H)

Example 283 (S)—N-(2-Fluoro-6-methyl-5-((3-(2-(piperidin-3-ylamino)pyrimidin-4-yl)pyridin-2-yl)oxy)naphthalen-1-yl)-1-phenylmethanesulfonamide 283

Step 1: (S)-tert-Butyl 3-((4-(2-((6-fluoro-2-methyl-5-(phenylmethylsulfonamido)naphthalen-1-yl)oxy)pyridin-3-yl)pyrimidin-2-yl)amino)piperidine-1-carboxylate

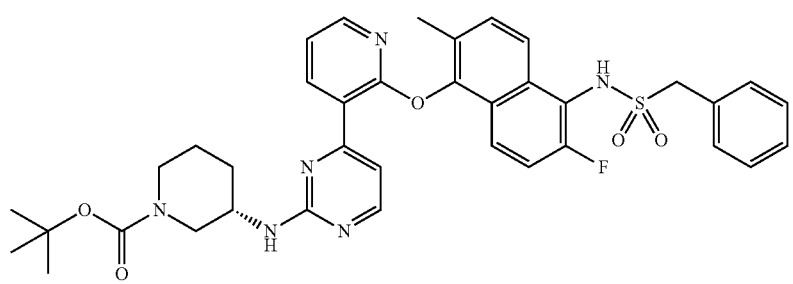 [SMILES: Cc1ccc2c(NS(=O)(=O)Cc3ccccc3)c(F)ccc2c1Oc1ncccc1-c1ccnc(N[C@H]2CCCN(C(=O)OC(C)(C)C)C2)n1]

Prepared using (S)-tert-Butyl 3-((4-(2-((5-amino-6-fluoro-2-methylnaphthalen-1-yl)oxy)pyridin-3-yl)pyrimidin-2-yl)amino)piperidine-1-carboxylate from Example 275 (700 mg, 1.28 mmol), pyridine (2 mL), DCM (7 mL), and phenylmethanesulfonyl chloride (367 mg, 1.93 mmol). After 64 h, a further portion of phenylmethanesulfonyl chloride (245 mg, 1.28 mmol) was added and stirring continued at rt. After a further 4 h, the mixture was diluted with DCM (50 mL) and washed with saturated NaHCO$_3$(aq) (25 mL), dried (Na$_2$SO$_4$), filtered and concentrated in vacuo. The crude was purified by flash chromatography through silica gel (0-50% EtOAc/DCM) to provide 340 mg (38% yield) of the title compound as a yellow foam. LCMS (ESI) [M+H]$^+$=699.3, rt=1.98 min.

Step 2: (S)—N-(2-Fluoro-6-methyl-5-((3-(2-(piperidin-3-ylamino)pyrimidin-4-yl)pyridin-2-yl)oxy)naphthalen-1-yl)-1-phenylmethanesulfonamide

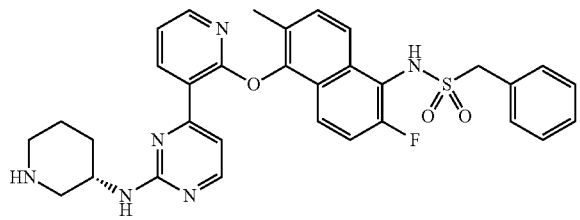 [SMILES: Cc1ccc2c(NS(=O)(=O)Cc3ccccc3)c(F)ccc2c1Oc1ncccc1-c1ccnc(N[C@H]2CCCNC2)n1]

Prepared according to General Procedure B using (S)-tert-butyl 3-((4-(2-((6-fluoro-2-methyl-5-(phenylmethylsulfonamido)naphthalen-1-yl)oxy)pyridin-3-yl)pyrimidin-2-yl)amino)piperidine-1-carboxylate (340 mg, 0.490 mmol), EtOAc (3 mL), and hydrochloric acid (4 M in dioxane, 2 mL, 8 mmol). After 3 h, the mixture was diluted with Et$_2$O (10 mL) and the resulting solids were filtered off, washed with Et$_2$O (2×5 mL), and dried. The collected solids were dissolved in H$_2$O and MeCN and lyophilized to provide 248 mg (80% yield) of 283 as a light yellow powder and as a HCl salt. LCMS (ESI) [M+H]$^+$=599.2, rt=1.45 min; $^1$H NMR (400 MHz, d$_6$-DMSO) δ 9.78 (s, 1H), 8.98-8.53 (m, 3H), 8.48 (d, J=5.2 Hz, 1H), 8.09 (dd, J=4.8, 1.8 Hz, 1H), 7.99 (d, J=8.7 Hz, 1H), 7.73 (dd, J=9.2, 5.1 Hz, 1H), 7.60 (d, J=8.8 Hz, 1H), 7.58-7.51 (m, 2H), 7.50-7.37 (m, 6H), 7.30 (dd, J=7.5, 4.8 Hz, 1H), 4.56 (s, 2H), 4.36-4.18 (m, 1H), 3.44 (d, J=9.5 Hz, 1H), 3.21 (d, J=11.6 Hz, 1H), 2.96-2.76 (m, 2H), 2.19 (s, 3H), 2.06-1.86 (m, 2H), 1.82-1.56 (m, 2H).

Example 284 (S)—N-(2,6-Dimethyl-5-((3-(2-(piperidin-3-ylamino)pyrimidin-4-yl)pyridin-2-yl)oxy)Naphthalen-1-yl)cyclopropanecarboxamide 284

Step 1: (S)-tert-Butyl 3-((4-(2-((5-(cyclopropanecarboxamido)-2,6-dimethylnaphthalen-1-yl)oxy)pyridin-3-yl)pyrimidin-2-yl)amino)piperidine-1-carboxylate

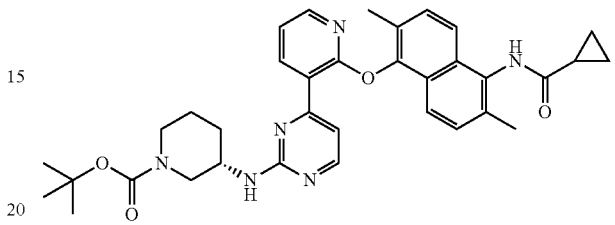

Prepared using (S)-tert-butyl 3-((4-(2-((5-amino-2,6-dimethylnaphthalen-1-yl)oxy)pyridin-3-yl)pyrimidin-2-yl)amino)piperidine-1-carboxylate (32 mg, 0.059 mmol), pyridine (0.072 mL), DCM (0.5 mL), and cyclopropanecarbonyl chloride (12 mg, 0.12 mmol). After 3 h, the mixture was diluted with DCM and washed with saturated NaHCO$_3$(aq), dried (Na$_2$SO$_4$), filtered and concentrated in vacuo. The crude was purified by flash chromatography through silica gel (20-100% EtOAc/hexanes) to provide 32 mg (89% yield) of the title compound. LCMS (ESI) [M+H]$^+$=609.6, rt=1.84 min.

Step 2: (S)—N-(2,6-Dimethyl-5-((3-(2-(piperidin-3-ylamino)pyrimidin-4-yl)pyridin-2-yl)oxy)Naphthalen-1-yl)cyclopropanecarboxamide

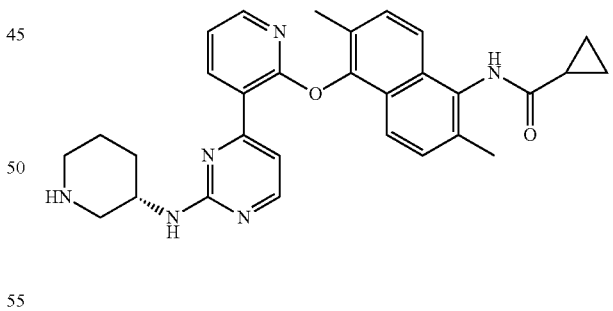

Prepared according to General Procedure B using (S)-tert-butyl 3-((4-(2-((5-(cyclopropanecarboxamido)-2,6-dimethylnaphthalen-1-yl)oxy)pyridin-3-yl)pyrimidin-2-yl)amino)piperidine-1-carboxylate (32 mg, 0.053 mmol), 1,4-dioxane (0.3 mL), and hydrochloric acid (4 M in dioxane, 0.4 mL, 1.6 mmol). After 3 h, the mixture was triturated with Et$_2$O, filtered and washed with Et$_2$O. The resulting solids were dissolved in H$_2$O and MeCN and lyophilized to provide 28 mg (97% yield) of 284. LCMS (ESI)

[M+H]⁺=509.4, rt=1.28 min; ¹H NMR (400 MHz, d₆-DMSO) δ 10.01 (s, 1H), 8.82 (s, 2H), 8.48 (d, J=5.2 Hz, 1H), 8.06 (dd, J=4.8, 2.0 Hz, 1H), 7.71 (d, J=8.7 Hz, 1H), 7.56 (dd, J=19.1, 6.1 Hz, 2H), 7.48 (d, J=8.9 Hz, 2H), 7.32 (d, J=8.8 Hz, 1H), 7.26 (dd, J=7.6, 4.8 Hz, 1H), 4.27 (s, 1H), 3.21 (d, J=12.5 Hz, 1H), 2.96-2.75 (m, 2H), 2.25 (s, 3H), 2.19 (s, 3H), 2.09-1.98 (m, 2H), 1.95-1.86 (m, 1H), 1.82-1.55 (m, 2H), 0.93-0.77 (m, 4H).

Example 285 (S)—N-(2,6-Dimethyl-5-((3-(2-(piperidin-3-ylamino)pyrimidin-4-yl)pyridin-2-yl)oxy)Naphthalen-1-yl)propane-1-sulfonamide 285

Step 1: (S)-tert-Butyl 3-((4-(2-((2,6-dimethyl-5-(propylsulfoNamido)Naphthalen-1-yl)oxy)pyridin-3-yl)pyrimidin-2-yl)amino)piperidine-1-carboxylate

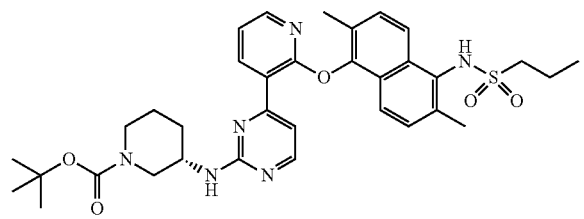 [SMILES: CCCS(=O)(=O)Nc1c(C)ccc2c(Oc3ncccc3-c3ccnc(N[C@H]4CCCN(C(=O)OC(C)(C)C)C4)n3)c(C)ccc12]

Prepared using (S)-tert-butyl 3-((4-(2-((5-amino-2,6-dimethylNaphthalen-1-yl)oxy)pyridin-3-yl)pyrimidin-2-yl)amino)piperidine-1-carboxylate (32 mg, 0.059 mmol), pyridine (0.072 mL), DCM (0.5 mL), and 1-propanesulfonyl chloride (17 mg, 0.12 mmol). After 4 h, a further portion of 1-propanesulfonyl chloride (84 mg, 0.59 mmol) was added. After 72 h, the mixture was diluted with DCM and washed with saturated NaHCO₃(aq), dried (Na₂SO₄), filtered and concentrated in vacuo. The crude was purified by flash chromatography through silica gel (15-80% EtOAc/hexanes) to provide 17 mg (44% yield) of the title compound. LCMS (ESI) [M+H]⁺=647.6, rt=1.94 min.

Step 2: (S)—N-(2,6-Dimethyl-5-((3-(2-(piperidin-1-ylamino)pyrimidin-4-yl)pyridin-2-yl)oxy)Naphthalen-1-yl)propane-1-sulfonamide

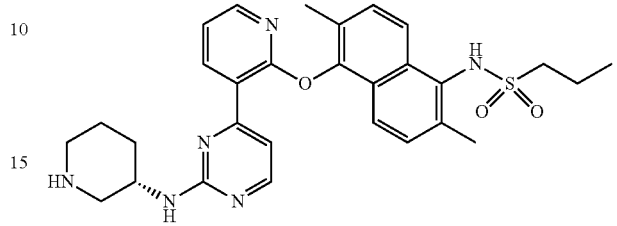

Prepared using (S)-tert-butyl 3-((4-(2-((2,6-dimethyl-5-(propylsulfoNamido)Naphthalen-1-yl)oxy)pyridin-3-yl)pyrimidin-2-yl)amino)piperidine-1-carboxylate (17 mg, 0.026 mmol), 1,4-dioxane (0.3 mL), and hydrochloric acid (4 M in dioxane, 0.2 mL, 8 mmol). After 3 h, the mixture was diluted with Et₂O and the resulting solids filtered and washed with Et₂O. The collected solids were dissolved in H₂O and MeCN and lyophilized to provide 13 mg (82% yield) of 285. LCMS (ESI) [M+H]⁺=547.4, rt=1.38 min; ¹H NMR (400 MHz, dmso) δ 9.38 (s, 1H), 8.75 (br.s, 3H), 8.47 (d, J=5.2 Hz, 1H), 8.10-7.99 (m, 2H), 7.57 (d, J=5.1 Hz, 2H), 7.53 (d, J=8.9 Hz, 3H), 7.35 (d, J=8.8 Hz, 1H), 7.27 (dd, J=7.6, 4.8 Hz, 1H), 4.25 (s, 1H), 3.26-3.09 (m, 3H), 3.00-2.74 (m, 2H), 2.48 (s, 4H), 2.19 (s, 3H), 2.01 (d, J=12.2 Hz, 1H), 1.97-1.78 (m, 3H), 1.78-1.56 (m, 2H), 1.03 (t, J=7.4 Hz, 3H).

Example 286 2-(Bicyclo[2.2.1]heptan-2-yl)-N-(6-methyl-5-((3-(2-((S)-piperidin-3-ylamino)pyrimidin-4-yl)pyridin-2-yl)oxy)naphthalen-1-yl)acetamide 286

Step 1: (3S)-tert-Butyl 3-((4-(2-((5-(2-(bicyclo[2.2.1]heptan-2-yl)acetamido)-2-methylnaphthalen-1-yl)oxy)pyridin-3-yl)pyrimidin-2-yl)amino)piperidine-1-carboxylate

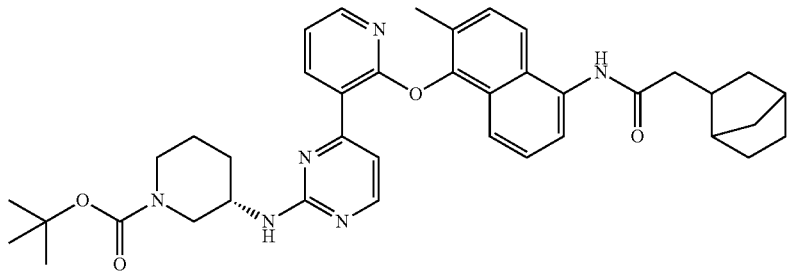 [SMILES: Cc1ccc2c(NC(=O)CC3CC4CCC3C4)cccc2c1Oc1ncccc1-c1ccnc(N[C@H]2CCCN(C(=O)OC(C)(C)C)C2)n1]

Prepared using (S)-tert-butyl 3-((4-(2-((5-amino-2-methylnaphthalen-1-yl)oxy)pyridin-3-yl)pyrimidin-2-yl)amino)piperidine-1-carboxylate (200 mg, 0.38 mmol), 2-norbornaneacetic acid (146 mg, 0.95 mmol), HATU (289 mg, 0.76 mmol), DMF (2 mL) in that order. Triethylamine (154 mg, 1.52 mmol) was then added and after 16 h, the mixture was diluted with ethyl acetate (50 mL) and washed with saturated sodium bicarbonate (10 mL) then 50% brine/water (4×10 mL), dried (Na$_2$SO$_4$), filtered and concentrated in vacuo. The crude residue was purified by flash chromatography through silica gel (0-100% EtOAc/hexanes) to provide 161 mg (64% yield) of the title compound. LCMS (ESI) [M+H]$^+$=663.3, rt=2.10 min.

Step 2: 2-(Bicyclo[2.2.1]heptan-2-yl)-N-(6-methyl-5-((3-(2-((S)-piperidin-3-ylamino)pyrimidin-4-yl)pyridin-2-yl)oxy)naphthalen-1-yl)acetamide

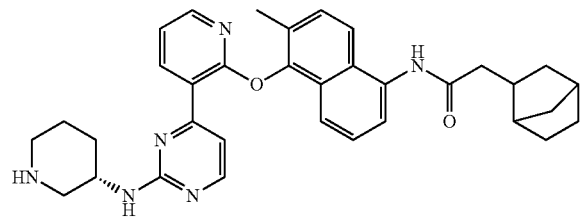 [SMILES: Cc1ccc2c(NC(=O)CC3CC4CCC3C4)cccc2c1Oc1ncccc1-c1ccnc(N[C@H]2CCCNC2)n1]

Prepared using (3S)-tert-butyl 3-((4-(2-((5-(2-(bicyclo[2.2.1]heptan-2-yl)acetamido)-2-methylnaphthalen-1-yl)oxy)pyridin-3-yl)pyrimidin-2-yl)amino)piperidine-1-carboxylate (150 mg, 0.226 mmol), EtOAc (6 mL), and hydrochloric acid (4 M in dioxane, 2 mL, 8 mmol). After 4 h, the mixture was concentrated in vacuo and the crude HCl salt solid was washed with EtOAc (3×3 mL) then with MeCN (3×3 mL). The solid product was then sonicated and concentrated in vacuo with MeCN (3×3 mL) and the resulting solid was dissolved in H$_2$O and MeCN and lyophilized to provide 132 mg (97% yield) of 286 of uncharacterized stereochemistry as a light yellow solid. LCMS (ESI) [M+H]$^+$=563.3, rt=1.52 min; $^1$H NMR (400 MHz, dmso) δ 9.92 (s, 1H), 9.11-8.83 (m, 2H), 8.80-8.53 (m, 1H), 8.48 (d, J=5.2 Hz, 1H), 8.05 (dd, J=4.8, 1.9 Hz, 1H), 7.91 (d, J=8.7 Hz, 1H), 7.56 (dt, J=13.7, 8.1 Hz, 4H), 7.44 (dd, J=29.8, 7.9 Hz, 2H), 7.27 (dd, J=7.6, 4.8 Hz, 1H), 4.40-4.17 (m, 1H), 4.07-3.86 (m, 1H), 3.20 (d, J=11.5 Hz, 2H), 2.95-2.77 (m, 2H), 2.47-2.29 (m, 2H), 2.24 (s, 1H), 2.21 (s, 3H), 2.11-1.86 (m, 4H), 1.82-1.59 (m, 2H), 1.56-1.40 (m, 4H), 1.27-1.11 (m, 4H).

Example 287 (R)-2,2-Dimethyl-N-(6-methyl-5-((3-(2-(((S)-piperidin-3-yl)amino)pyrimidin-4-yl)pyridin-2-yl)oxy)naphthalen-1-yl)cyclopropane-1-carboxamide Step 1: (3S)-tert-Butyl 3-((4-(2-((5-(2,2-dimethylcyclopropanecarboxamido)-2-methylNaphthalen-1-yl)oxy)pyridin-3-yl)pyrimidin-2-yl)amino)piperidine-1-carboxylate

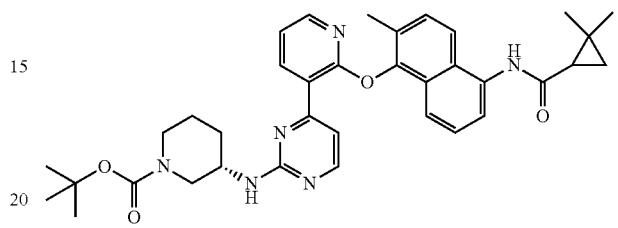

Prepared using (S)-tert-butyl 3-((4-(2-((5-amino-2-methylnaphthalen-1-yl)oxy)pyridin-3-yl)pyrimidin-2-yl)amino)piperidine-1-carboxylate (320 mg, 0.608 mmol), triethylamine (0.85 mL, 6.08 mmol), HATU (1155 mg, 3.04 mmol), and 2,2-dimethylcyclopropanecarboxylic acid (345 mg, 3.04 mmol) in DMF (5 mL). After 16 h, the mixture was diluted with EtOAc (75 mL) and washed with saturated NaHCO$_3$ (aq) (25 mL), then with water (10 mL) and 50% saturated NaCl(aq) (4×10 mL), dried (Na$_2$SO$_4$), filtered and concentrated in vacuo. The crude residue was purified by flash chromatography through silica gel (50 g, 0-100% EtOAc/hex) to provide 363 mg (96% yield) of the title compound as a tan solid. LCMS (ESI) [M+H]$^+$=623.3, rt=1.98 min.

Step 2: tert-butyl (S)-3-((4-(2-((5-((R)-2,2-dimethylcyclopropane-1-carboxamido)-2-methylnaphthalen-1-yl)oxy)pyridin-3-yl)pyrimidin-2-yl)amino)piperidine-1-carboxylate (Isomer-1) and tert-butyl (S)-3-((4-(2-((5-((S)-2,2-dimethylcyclopropane-1-carboxamido)-2-methylnaphthalen-1-yl)oxy)pyridin-3-yl)pyrimidin-2-yl)amino)piperidine-1-carboxylate (Isomer-2)

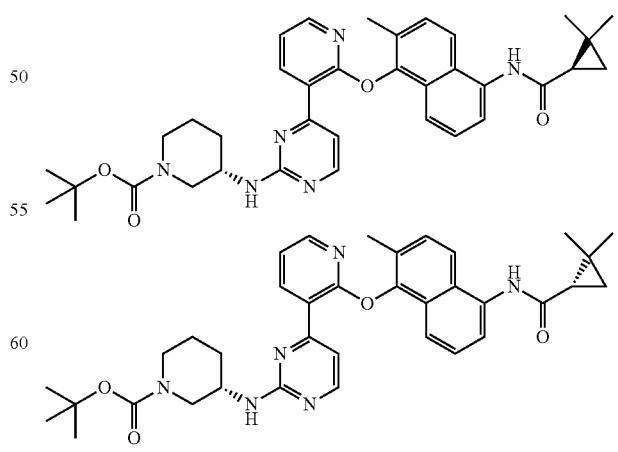

(3S)-tert-Butyl 3-((4-(2-((5-(2,2-dimethylcyclopropanecarboxamido)-2-methylnaphthalen-1-yl)oxy)pyridin-3-yl)

pyrimidin-2-yl)amino)piperidine-1-carboxylate (189 mg, 0.303 mmol), was subjected to chiral normal phase semi-prep purification (Conditions: Chiralpak IA, 5 uM, 20×250 mm, 1:10:89 MeOH:IPA:Hexane+0.1% DEA, 3.5 mg/inj.) to provide two stereoisomers possessing stereocenters at the 1-cyclopropane position. Isomer-1, 58 mg, 31% yield, white solid, ee=95%, rt=21.7 min, LCMS (ESI) [M+H]$^+$=623.4, rt=1.98 min. Isomer-2, 53 mg, 28% yield, white solid, ee=97%, rt=24.3 min, LCMS (ESI) [M+H]$^+$=623.4, rt=1.98 min.

Step 3: (R)-2,2-Dimethyl-N-(6-methyl-5-((3-(2-(((S)-piperidin-3-yl)amino)pyrimidin-4-yl)pyridin-2-yl)oxy)naphthalen-1-yl)cyclopropane-1-carboxamide (Isomer-1)

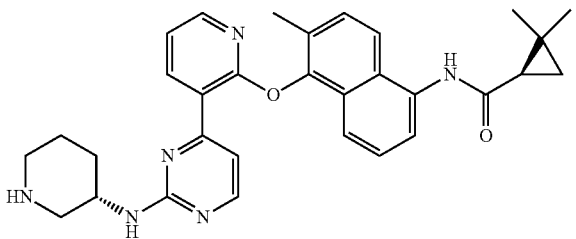

Prepared using tert-butyl (S)-3-((4-(2-((5-((R)-2,2-dimethylcyclopropane-1-carboxamido)-2-methylnaphthalen-1-yl)oxy)pyridin-3-yl)pyrimidin-2-yl)amino)piperidine-1-carboxylate (isomer-1) (58 mg, 0.093 mmol), EtOAc (5 mL), and hydrochloric acid (4 M in dioxane, 2 mL, 8 mmol). After 4 h, the mixture was concentrated in vacuo and the crude solid was washed with EtOAc (3×3 mL) then with MeCN (3×3 mL). The solid product was then sonicated and concentrated in vacuo with MeCN (3×3 mL) then dissolved in H$_2$O and MeCN and lyophilized to provide 39 mg (75% yield) of 287 as a fluffy light yellow solid. The stereochemical assignments of 287 and 288 were randomly assigned and may be later determined. LCMS (ESI) [M+H]+=523.5, rt=1.42 min; $^1$H NMR (400 MHz, DMSO-d$_6$) δ 10.11 (s, 1H), 9.08-8.78 (m, 2H), 8.75-8.54 (m, 1H), 8.48 (d, J=5.2 Hz, 1H), 8.05 (dd, J=4.7, 1.8 Hz, 1H), 7.96 (d, J=8.7 Hz, 1H), 7.68-7.49 (m, 4H), 7.43 (dd, J=26.2, 8.0 Hz, 2H), 7.27 (dd, J=7.5, 4.8 Hz, 1H), 4.40-4.12 (m, 1H), 3.21 (d, J=11.2 Hz, 2H), 2.95-2.76 (m, 2H), 2.22 (s, 3H), 2.10-1.86 (m, 3H), 1.83-1.54 (m, 2H), 1.23 (s, 3H), 1.21 (s, 3H), 1.04-0.99 (m, 1H), 0.88-0.79 (m, 1H).

Example 288 (S)-2,2-Dimethyl-N-(6-methyl-5-((3-(2-(((S)-piperidin-3-yl)amino)pyrimidin-4-yl)pyridin-2-yl)oxy)naphthalen-1-yl)cyclopropane-1-carboxamide 288

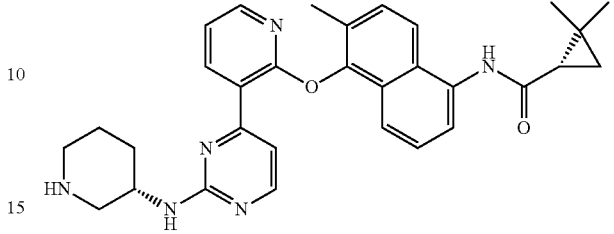

Prepared according to Example 287 using tert-butyl (S)-3-((4-(2-((5-((S)-2,2-dimethylcyclopropane-1-carboxamido)-2-methylnaphthalen-1-yl)oxy)pyridin-3-yl)pyrimidin-2-yl)amino)piperidine-1-carboxylate (isomer-2) (53 mg, 0.085 mmol), EtOAc (5 mL), and hydrochloric acid (4 M in dioxane, 2 mL, 8 mmol). After 4 h, the mixture was concentrated in vacuo and the crude solid was washed with EtOAc (3×3 mL) then with MeCN (3×3 mL). The solid product was sonicated and concentrated in vacuo with MeCN (3×3 mL) then dissolved in H$_2$O and MeCN and lyophilized to provide 35 mg (73% yield) of 288 as a fluffy light yellow solid. LCMS (ESI) [M+H]$^+$=523.5, rt=1.42 min; $^1$H NMR (400 MHz, DMSO-d$_6$) δ 10.11 (s, 1H), 9.05-8.78 (m, 2H), 8.76-8.52 (m, 1H), 8.48 (d, J=5.2 Hz, 1H), 8.05 (dd, J=4.7, 1.8 Hz, 1H), 7.96 (d, J=8.7 Hz, 1H), 7.68-7.49 (m, 4H), 7.43 (dd, J=26.1, 8.0 Hz, 2H), 7.27 (dd, J=7.5, 4.8 Hz, 1H), 4.38-4.15 (m, 1H), 3.21 (d, J=12.3 Hz, 2H), 2.96-2.76 (m, 2H), 2.22 (s, 3H), 2.08-1.86 (m, 3H), 1.82-1.56 (m, 2H), 1.23 (s, 3H), 1.21 (s, 3H), 1.04-0.99 (m, 1H), 0.90-0.78 (m, 1H).

Example 289 N-(6-Methyl-5-((3-(2-(((S)-piperidin-3-yl)amino)pyrimidin-4-yl)pyridin-2-yl)oxy)naphthalen-1-yl)-5-oxaspiro[2.4]heptane-1-carboxamide 289

Step 1: tert-Butyl (3S)-3-((4-(2-((2-methyl-5-(5-oxaspiro[2.4]heptane-1-carboxamido)naphthalen-1-yl)oxy)pyridin-3-yl)pyrimidin-2-yl)amino)piperidine-1-carboxylate

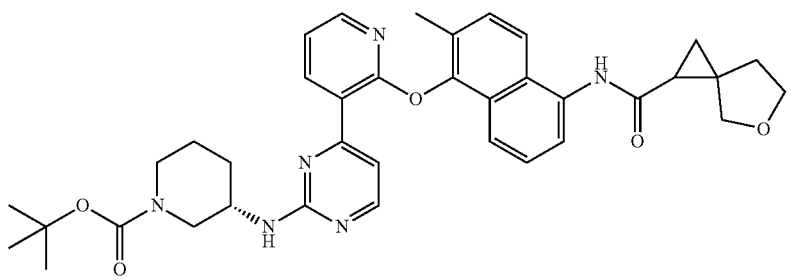 [SMILES: Cc1ccc2c(NC(=O)C3CC34CCOC4)cccc2c1Oc1ncccc1-c1ccnc(N[C@H]2CCCN(C(=O)OC(C)(C)C)C2)n1]

The General Procedure C was followed, using tert-butyl (3S)-3-[[4-[2-[(5-amino-2-methyl-1-naphthyl)oxy]-3-pyridyl]pyrimidin-2-yl]amino]piperidine-1-carboxylate (200 mg, 0.38 mmol), 5-oxaspiro[2.4]heptane-2-carboxylic acid (80.9 mg, 0.57 mmol), HATU (294.7 mg, 0.76 mmol), DMF (2 mL), and DIPEA (0.20 mL, 1.14 mmol). The crude material was purified by silica gel chromatography (12 g column), eluting with 0-5% MeOH/DCM to afford 250 mg (100% yield) of the title compound as a yellow solid and as a mixture of isomers. LCMS (ESI) [M+H]+=651.

Step 2: N-(6-Methyl-5-((3-(2-(((S)-piperidin-3-yl)amino)pyrimidin-4-yl)pyridin-2-yl)oxy)naphthalen-1-yl)-5-oxaspiro[2.4]heptane-1-carboxamide

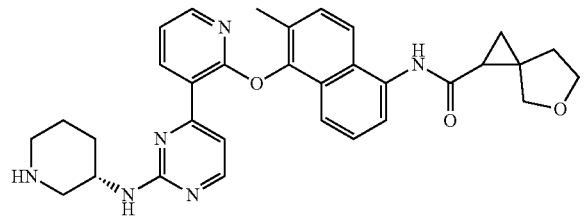 [SMILES: Cc1ccc2c(NC(=O)C3CC34CCOC4)cccc2c1Oc1ncccc1-c1ccnc(N[C@H]2CCCNC2)n1]

The General Procedure B was followed, using tert-butyl (3S)-3-((4-(2-((2-methyl-5-(5-oxaspiro[2.4]heptane-1-carboxamido)naphthalen-1-yl)oxy)pyridin-3-yl)pyrimidin-2-yl)amino)piperidine-1-carboxylate (250 mg, 0.38 mmol). The crude product was lyophilized to yield 108 mg (51% yield) of 289 as an off-white solid and as a mixture of isomers. LCMS (ESI) [M+H]+=551; $^1$H NMR (400 MHz, DMSO-$d_6$) δ 10.19 (d, J=9.8 Hz, 1H), 8.49 (d, J=7.5 Hz, 1H), 8.41 (d, J=5.1 Hz, 1H), 8.02 (dd, J=4.8, 2.0 Hz, 1H), 7.95 (d, J=8.7 Hz, 1H), 7.69-7.61 (m, 1H), 7.52 (t, J=8.2 Hz, 2H), 7.44 (d, J=5.1 Hz, 1H), 7.39 (t, J=8.0 Hz, 1H), 7.25 (dd, J=7.6, 4.8 Hz, 1H), 7.12 (d, J=8.0 Hz, 1H), 3.94-3.80 (m, 2H), 3.70 (q, J=9.2 Hz, 2H), 3.14-3.05 (m, 1H), 2.83-2.74 (m, 1H), 2.48-2.42 (m, 3H), 2.39-2.35 (m, 1H), 2.22 (s, 3H), 2.07-2.00 (m, 1H), 1.97-1.89 (m, 2H), 1.68-1.61 (m, 1H), 1.53-1.40 (m, 2H), 1.24 (d, J=6.4 Hz, 2H).

Example 290 (S)-4-(2-((5-(4-Ethyl-1H-pyrazol-1-yl)-2-methylnaphthalen-1-yl)oxy)pyridin-3-yl)-N-(piperidin-3-yl)pyrimidin-2-amine 290

Step 1: tert-Butyl (S)-3-((4-(2-((5-iodo-2-methylnaphthalen-1-yl)oxy)pyridin-3-yl)pyrimidin-2-yl)amino)piperidine-1-carboxylate

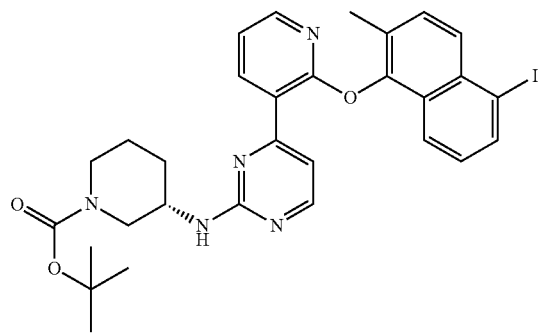 [SMILES: Cc1ccc2c(I)cccc2c1Oc1ncccc1-c1ccnc(N[C@H]2CCCN(C(=O)OC(C)(C)C)C2)n1]

To a solution of tert-butyl (3S)-3-[[4-[2-[(5-amino-2-methyl-1-naphthyl)oxy]-3-pyridyl]pyrimidin-2-yl]amino]piperidine-1-carboxylate (300 mg, 0.57 mmol) in acetonitrile (4 mL) was added 10% aq. p-toluenesulfonic acid (7 mL) in ice bath temperature followed by the addition of a solution of sodium nitrite (43.2 mg, 0.63 mmol) in water (0.5 mL), stirred for 30 min. Then a solution of sodium iodide (170.8 mg, 1.14 mmol) in water (1 mL) was added at once, followed by stirring for 3 h in ice-bath temperature. The mixture was diluted with water, extracted with iPrOAc (2×30 mL), dried over MgSO$_4$, filtered, concentrated in vacuo, and dried under high vacuum to afford 310 mg (85% yield) of the title compound as a brown solid. It was carried on without further purification. LCMS (ESI) [M+H]+=638.

Step 2: tert-Butyl (S)-3-((4-(2-((5-(4-ethyl-1H-pyrazol-1-yl)-2-methylnaphthalen-1-yl)oxy)pyridin-3-yl)pyrimidin-2-yl)amino)piperidine-1-carboxylate

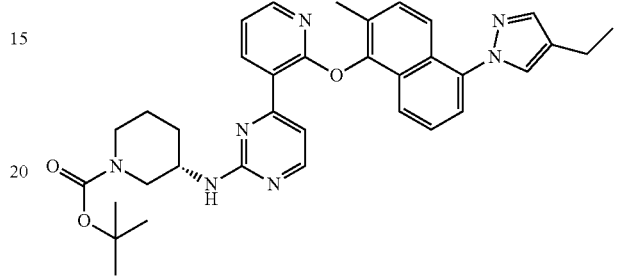

A mixture of tert-butyl (3S)-3-[[4-[2-[(5-iodo-2-methyl-1-naphthyl)oxy]-3-pyridyl]pyrimidin-2-yl]amino]piperidine-1-carboxylate (100 mg, 0.16 mmol, 100 mass %), 4-ethyl-1H-pyrazole (30.1 mg, 0.32 mmol), CuI (11.9 mg, 0.063 mmol), (1R,2R)—N,N-dimethyl-1,2-cyclohexanediamine (11.4 mg, 0.078 mmol), and K$_2$CO$_3$ (65.0 mg, 0.47 mmol) in 1,4-dioxane (2 mL) was capped in a microwave vial, degassed with N$_2$, heated in oil bath at 110° C. for 48 h.

More reagents were added and heated for another of 48 h. It was diluted with iPrOAc, filtered through Celite. The crude product was purified by silica gel chromatography (12 g column), eluting with 0-5% MeOH/DCM to afford 18 mg (18.9% yield) of the title compound as a brown solid. LCMS (ESI) [M+H]+=606.

Step 3: (S)-4-(2-((5-(4-Ethyl-1H-pyrazol-1-yl)-2-methylnaphthalen-1-yl)oxy)pyridin-3-yl)-N-(piperidin-3-yl)pyrimidin-2-amine

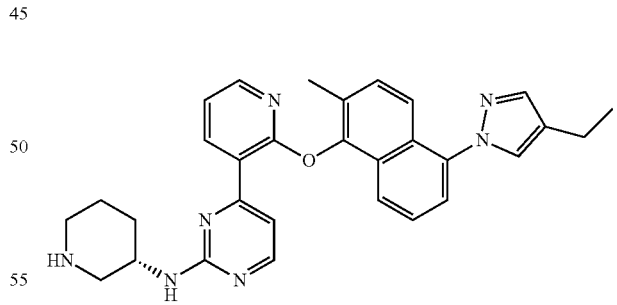

The General Procedure B was followed, using tert-Butyl (S)-3-((4-(2-((5-(4-ethyl-1H-pyrazol-1-yl)-2-methylnaphthalen-1-yl)oxy)pyridin-3-yl)pyrimidin-2-yl)amino)piperidine-1-carboxylate (18 mg, 0.03 mmol). The crude product was lyophilized to yield 14 mg (86.9% yield) of 290 as a brown solid. LCMS (ESI) [M+H]+=506; $^1$H NMR (400 MHz, DMSO-$d_6$) δ 8.82-8.58 (m, 4H), 8.50 (d, J=5.2 Hz, 1H), 8.08 (dd, J=4.8, 2.0 Hz, 1H), 8.01-7.99 (m, 1H), 7.77-7.70 (m, 3H), 7.60 (d, J=5.2 Hz, 1H), 7.56-7.49 (m, 4H), 7.29 (dd, J=7.6, 4.8 Hz, 1H), 4.33-4.21 (m, 1H), 3.26-3.19 (m, 1H), 2.93-2.81 (m, 3H), 2.59 (q, J=7.6 Hz, 2H), 2.23 (s, 3H), 2.06-1.99 (m, 1H), 1.97-1.89 (m, 1H), 1.80-1.59 (m, 2H), 1.26 (t, J=7.6 Hz, 3H).

Example 291 4-(2-((5-((2-((R)-2,2-Difluorocyclopropyl)ethyl)amino)-2-methylnaphthalen-1-yl)oxy) pyridin-3-yl)-N—((S)-piperidin-3-yl)pyrimidin-2-amine 291

Step 1: tert-butyl (S)-3-((4-(2-((5-((2-((R)-2,2-Difluorocyclopropyl)ethyl)amino)-2-methylnaphthalen-1-yl)oxy)pyridin-3-yl)pyrimidin-2-yl)amino)piperidine-1-carboxylate

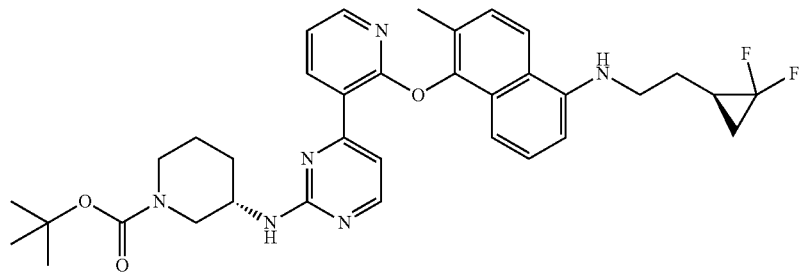 [SMILES: Cc1ccc2c(NCC[C@@H]3CC3(F)F)cccc2c1Oc1ncccc1-c1ccnc(N[C@H]2CCCN(C(=O)OC(C)(C)C)C2)n1]

The General Procedure E was followed, using tert-butyl (3S)-3-[[4-[2-[(5-amino-2-methyl-1-naphthyl)oxy]-3-pyridyl]pyrimidin-2-yl]amino]piperidine-1-carboxylate (200 mg, 0.38 mmol) and 2-(2-bromoethyl)-1,1-difluorocyclopropane (144.9 mg, 0.76 mmol). The crude material was purified by silica gel chromatography (12 g column), eluting with 0-5% MeOH/DCM to afford 79 mg (33% yield) of the title compound as a brown oil. LCMS (ESI) [M+H]⁺=631. The isomers were separated by chiral SFC to afford 17 mg isomer-1 (t$_R$=0.698 min) as an off-white solid and 17.5 mg isomer-2 (t$_R$=0.839 min) as an off-white solid.

Step 2: 4-(2-((5-((2-((R)-2,2-Difluorocyclopropyl) ethyl)amino)-2-methylnaphthalen-1-yl)oxy)pyridin-3-yl)-N—((S)-piperidin-3-yl)pyrimidin-2-amine

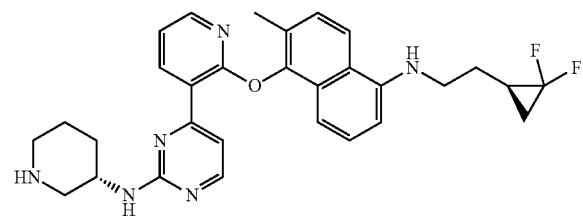 [SMILES: Cc1ccc2c(NCC[C@@H]3CC3(F)F)cccc2c1Oc1ncccc1-c1ccnc(N[C@H]2CCCNC2)n1]

The General Procedure B was followed, using tert-butyl (S)-3-((4-(2-((5-((2-((R)-2,2-difluorocyclopropyl)ethyl) amino)-2-methylnaphthalen-1-yl)oxy)pyridin-3-yl)pyrimidin-2-yl)amino)piperidine-1-carboxylate (isomer-1, 17 mg, 0.03 mmol). The crude product was lyophilized to yield 15 mg (95.5% yield) of 291 as a brown solid. The stereochemical assignments of 291 and 292 were randomly assigned and may be later determined. LCMS (ESI) [M+H]⁺=531; ¹H NMR (400 MHz, DMSO-d$_6$) δ 9.03-8.54 (m, 4H), 8.47 (d, J=5.2 Hz, 1H), 8.06-8.00 (m, 2H), 7.59 (d, J=5.1 Hz, 1H), 7.55 (d, J=7.7 Hz, 1H), 7.39-7.33 (m, 1H), 7.24 (dd, J=7.6, 4.8 Hz, 1H), 7.18 (dd, J=8.4, 7.7 Hz, 1H), 6.85 (d, J=8.4 Hz, 1H), 6.50 (d, J=7.7 Hz, 1H), 4.36-4.20 (m, 1H), 3.31 (dd, J=7.5, 5.8 Hz, 2H), 3.25-3.17 (m, 1H), 2.92-2.77 (m, 3H), 2.19 (s, 3H), 2.06-1.97 (m, 1H), 1.97-1.72 (m, 5H), 1.69-1.50 (m, 2H), 1.25-1.16 (m, 1H).

Example 292 4-(2-((5-((2-((S)-2,2-Difluorocyclopropyl)ethyl)amino)-2-methylnaphthalen-1-yl)oxy) pyridin-3-yl)-N—((S)-piperidin-3-yl)pyrimidin-2-amine 292

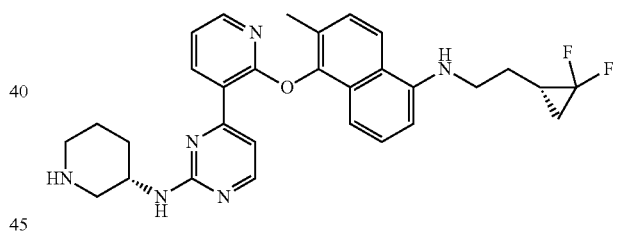

Following Example 291 and General Procedure B, tert-butyl (S)-3-((4-(2-((5-((2-((S)-2,2-difluorocyclopropyl) ethyl)amino)-2-methylnaphthalen-1-yl)oxy)pyridin-3-yl) pyrimidin-2-yl)amino)piperidine-1-carboxylate (isomer-2, 17.5 mg, 0.03 mmol) was deprotected. The crude product was lyophilized to yield 15 mg (95% yield) of 292 as a brown solid. LCMS (ESI) [M+H]⁺=531; ¹H NMR (400 MHz, DMSO-d$_6$) δ 8.97-8.51 (m, 4H), 8.47 (d, J=5.2 Hz, 1H), 8.06-8.00 (m, 2H), 7.58 (d, J=4.8 Hz, 1H), 7.53 (d, J=7.5 Hz, 1H), 7.35 (d, J=8.7 Hz, 1H), 7.24 (dd, J=7.6, 4.8 Hz, 1H), 7.18 (dd, J=8.4, 7.6 Hz, 1H), 6.84 (d, J=8.4 Hz, 1H), 6.49 (d, J=7.9 Hz, 1H), 4.34-4.21 (m, 1H), 3.34-3.27 (m, 2H), 3.21 (d, J=12.2 Hz, 1H), 2.93-2.79 (m, 3H), 2.19 (s, 3H), 2.06-1.99 (m, 1H), 1.96-1.71 (m, 6H), 1.69-1.49 (m, 1H), 1.25-1.15 (m, 1H).

Example 293 (1R,2R)-2-(Difluoromethyl)-N-(6-methyl-5-((3-(2-(((S)-piperidin-3-yl)amino)pyrimidin-4-yl)pyridin-2-yl)oxy)naphthalen-1-yl)cyclopropane-1-carboxamide 293

Step 1: tert-Butyl (S)-3-((4-(2-((5-((1R,2R)-2-(difluoromethyl)cyclopropane-1-carboxamido)-2-methylnaphthalen-1-yl)oxy)pyridin-3-yl)pyrimidin-2-yl)amino)piperidine-1-carboxylate

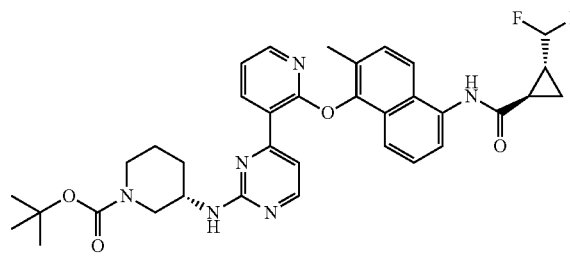

The General Procedure C was followed, using tert-butyl (S)-3-((4-(2-((5-amino-2-methylnaphthalen-1-yl)oxy)pyridin-3-yl)pyrimidin-2-yl)amino)piperidine-1-carboxylate from Example 101 (90 mg, 0.17 mmol), 2-(difluoromethyl)cyclopropane-1-carboxylic acid (35 mg, 0.26 mmol), DIPEA (0.089 mL, 0.51 mmol), HATU (97 mg, 0.26 mmol) and DCM (1.7 mL). The residue was purified via reverse-phase HPLC to provide a mixture of the two isomers. This mixture was then purified via chiral reverse-phase HPLC and lyophilized to yield 44 mg and 43 mg, of the two single stereoisomers at the 1 and 2 positions of the cyclopropyl amide.

Step 2: (1R,2R)-2-(Difluoromethyl)-N-(6-methyl-5-((3-(2-(((S)-piperidin-3-yl)amino)pyrimidin-4-yl)pyridin-2-yl)oxy)naphthalen-1-yl)cyclopropane-1-carboxamide

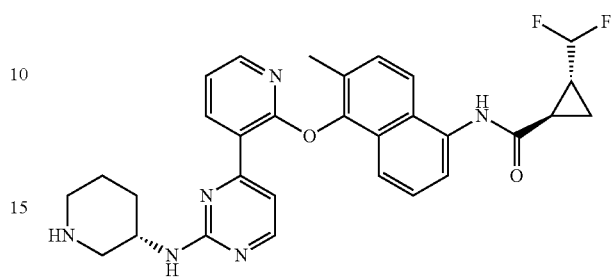

The General Procedure B was followed, using tert-butyl (S)-3-((4-(2-((5-((1R,2R)-2-(difluoromethyl)cyclopropane-1-carboxamido)-2-methylnaphthalen-1-yl)oxy)pyridin-3-yl)pyrimidin-2-yl)amino)piperidine-1-carboxylate (43 mg, 0.067 mmol), DCM (4 mL) and hydrochloric acid (4 M in dioxane, 3 mL, 12 mmol). The residue was purified via reverse-phase HPLC and lyophilized to yield 25 mg (70% yield) of 293. LCMS (ESI): [M+H]$^+$=545.2; $^1$H NMR (400 MHz, DMSO-d$_6$) δ 10.40 (s, 1H), 8.94-9.68 (m, 2H), 8.48 (d, J=5.2 Hz, 1H), 8.06 (dd, J=4.8, 2.0 Hz, 1H), 7.97 (d, J=8.7 Hz, 1H), 7.68 (d, J=7.4 Hz, 1H), 7.59-7.48 (m, 5H), 7.40 (dd, J=8.5, 7.4 Hz, 1H), 7.27 (dd, J=7.6, 4.8 Hz, 1H), 6.22-5.92 (m, 1H), 4.27 (s, 1H), 3.24-3.17 (m, 1H), 2.93-2.79 (m, 2H), 2.47-2.38 (m, 2H), 2.22 (s, 3H), 2.07-1.98 (m, 1H), 1.97-1.82 (m, 2H), 1.84-1.57 (m, 2H), 1.24-1.16 (m, 2H).

Example 294 (S)-4-(2-((5-(((2,5-Dimethylthiazol-4-yl)methyl)amino)-2-methylnaphthalen-1-yl)oxy)pyridin-3-yl)-N-(piperidin-3-yl)pyrimidin-2-amine 294

Step 1: (S)-tert-Butyl 3-((4-(2-((5-(((2,5-dimethylthiazol-4-yl)methyl)amino)-2-methylnaphthalen-1-yl)oxy)pyridin-3-yl)pyrimidin-2-yl)amino)piperidine-1-carboxylate

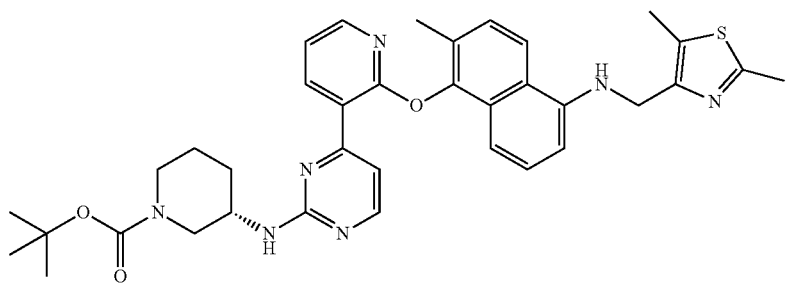 [SMILES: Cc1nc(CNc2cccc3c(Oc4ncccc4-c4ccnc(N[C@H]5CCCN(C(=O)OC(C)(C)C)C5)n4)c(C)ccc23)c(C)s1]

Prepared using (S)-tert-butyl 3-((4-(2-((5-amino-2-methylnaphthalen-1-yl)oxy)pyridin-3-yl)pyrimidin-2-yl)amino)piperidine-1-carboxylate (100 mg, 0.19 mmol), 1-thiazol-4-ylethanone (241 mg, 1.90 mmol), DCM (1 mL), acetic acid (0.016 mL, 0.28 mmol), and sodium triacetoxyborohydride (60 mg, 0.28 mmol). After 72 h, a further portion of sodium triacetoxyborohydride (60 mg, 0.28 mmol) was added. After 16 h, a further portion of sodium triacetoxyborohydride (60 mg, 0.28 mmol) and acetic acid (0.016 mL, 0.28 mmol) was added. After another 16 h, the mixture was diluted with water, followed by EtOAc. The phases were separated, and the organic phase was washed with saturated aqueous ammonium chloride solution, dried (MgSO$_4$), filtered, and concentrated in vacuo. The crude was purified by flash chromatography through silica gel (0-100% EtOAc/DCM) to provide 101 mg (83% yield) of the title compound as a pale brown oil. LCMS (ESI) [M+H]$^+$=638.3, rt=1.98 min.

Step 2: (S)-4-(2-((5-(((2,5-Dimethylthiazol-4-yl)methyl)amino)-2-methylnaphthalen-1-yl)oxy)pyridin-3-yl)-N-(piperidin-3-yl)pyrimidin-2-amine

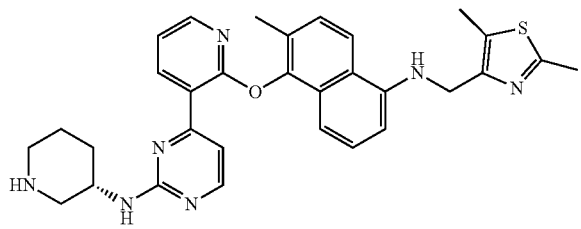 [SMILES: Cc1nc(CNc2cccc3c(Oc4ncccc4-c4ccnc(N[C@H]5CCCNC5)n4)c(C)ccc23)c(C)s1]

Prepared using (S)-tert-butyl 3-((4-(2-((5-(((2,5-dimethylthiazol-4-yl)methyl)amino)-2-methylnaphthalen-1-yl)oxy)pyridin-3-yl)pyrimidin-2-yl)amino)piperidine-1-carboxylate (92 mg, 0.14 mmol), EtOAc (1 mL), and hydrochloric acid (4 M in dioxane, 1 mL, 4 mmol). After 3 h, the resulting solids were collected by filtration, washed with DCM, then dissolved in H$_2$O and lyophilized to provide 81 mg (97% yield) of 294 as an orange solid. LCMS (ESI) [M+H]$^+$=552.3, rt=1.49 min; $^1$H NMR (400 MHz, DMSO-d$_6$) [NH signal hidden under HOD peak] δ 9.44 (s, 1H), 9.19 (s, 1H), 8.81 (s, 1H), 8.49 (d, J=5.5 Hz, 1H), 8.11-8.02 (m, 2H), 7.95 (br s, 1H), 7.68 (br s, 1H), 7.39 (d, J=8.8 Hz, 1H), 7.25 (dd, J=7.6, 4.8 Hz, 1H), 7.21-7.13 (m, 1H), 6.91 (d, J=8.4 Hz, 1H), 6.58 (d, J=7.6 Hz, 1H), 4.48 (s, 3H), 3.42 (d, J=8.5 Hz, 1H), 3.19 (d, J=12.0 Hz, 1H), 2.91-2.77 (m, 2H), 2.66 (s, 3H), 2.44 (s, 3H), 2.19 (s, 3H), 2.02 (d, J=8.9 Hz, 1H), 1.97-1.86 (m, 1H), 1.79 (q, J=10.4 Hz, 1H), 1.65 (q, J=9.0 Hz, 1H).

Example 295 4-(2-((2-Methyl-5-((1-(thiazol-4-yl)ethyl)amino)naphthalen-1-yl)oxy)pyridin-3-yl)-N-((S)-piperidin-3-yl)pyrimidin-2-amine 295

Step 1: (3S)-tert-Butyl 3-((4-(2-((2-methyl-5-((1-(thiazol-4-yl)ethyl)amino)naphthalen-1-yl)oxy)pyridin-3-yl)pyrimidin-2-yl)amino)piperidine-1-carboxylate

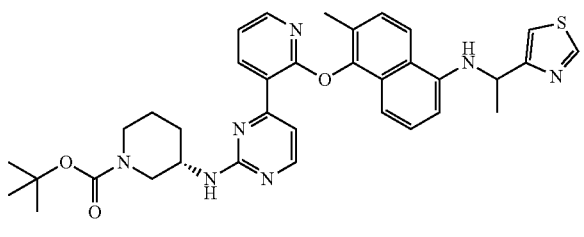 [SMILES: Cc1ccc2c(NC(C)c3cscn3)cccc2c1Oc1ncccc1-c1ccnc(N[C@H]2CCCN(C(=O)OC(C)(C)C)C2)n1]

Prepared using (S)-tert-butyl 3-((4-(2-((5-amino-2-methylnaphthalen-1-yl)oxy)pyridin-3-yl)pyrimidin-2-yl)amino)piperidine-1-carboxylate (150 mg, 0.280 mmol), cesium carbonate (310 mg, 0.95 mmol), tetrabutylammonium iodide (11 mg, 0.030 mmol), 4-(chloromethyl)-2,5-dimethyl-thiazole (113 mg, 0.57 mmol), and DMF (1.5 mL). The mixture was stirred at 50° C. for 16 h, cooled to room temperature and was dissolved in EtOAc and water. The phases were separated and the organic phase was washed with water, then brine, followed by a solution of aqueous saturated ammonium chloride. The organic phase was dried (MgSO$_4$), filtered and concentrated in vacuo. The crude product was purified by flash chromatography through silica gel (0-10% MeOH/DCM) followed by C18 reverse phase flash chromatography (40-90% % MeCN/10 mM aqueous ammonium formate, pH 3.8). The appropriate fractions were combined and concentrated in vacuo to provide 92 mg (50% yield) of the title compound as an off-white solid. LCMS (ESI) [M+H]$^+$=652.4, rt=2.08 min. (3S)-tert-Butyl 3-((4-(2-((2-methyl-5-((1-(thiazol-4-yl)ethyl)amino)naphthalen-1-yl)oxy)pyridin-3-yl)pyrimidin-2-yl)amino)piperidine-1-carboxylate (isomer-1) and (3S)-tert-butyl 3-((4-(2-((2-methyl-5-((1-(thiazol-4-yl)ethyl)amino)naphthalen-1-yl)oxy)pyridin-3-yl)pyrimidin-2-yl)amino)piperidine-1-carboxylate (isomer-2)

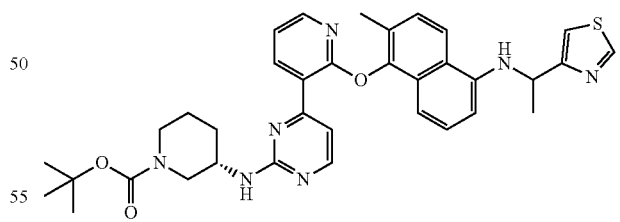

(3S)-tert-Butyl 3-((4-(2-((2-methyl-5-((1-(thiazol-4-yl)ethyl)amino)naphthalen-1-yl)oxy)pyridin-3-yl)pyrimidin-2-yl)amino)piperidine-1-carboxylate (87 mg, 0.14 mmol) was subjected to chiral SFC purification (Conditions: Column IB 10×250 mm, 5 um Isocratic 55% MeOH, 10 mL/min, 100 Bar, Column temp: 35° C., Run Time (min): 8.00, Injection Volume (uL): 30, Wavelength (nm): 240 nm) to provide two stereoisomers enantiomeric at the 1-(thiazol-4-yl)ethyl) amino position: (3S)-tert-butyl 3-((4-(2-((2-methyl-5-((1-(thiazol-4-yl)ethyl)amino)naphthalen-1-yl)oxy)pyridin-3- yl)pyrimidin-2-yl)amino)piperidine-1-carboxylate (isomer-1), 32 mg (37% yield), ee=98.9%, rt=4.2 min, (ESI) [M+H]+=638.4, rt=1.99 min. (3S)-tert-butyl 3-((4-(2-((2-methyl-5-((1-(thiazol-4-yl)ethyl)amino)naphthalen-1-yl)oxy)pyridin-3-yl)pyrimidin-2-yl)amino)piperidine-1-carboxylate (isomer-2), 28 mg (32% yield), ee=98.3%, rt=5.7 min, LCMS (ESI) [M+H]+=638.3, rt=1.98 min.

Step 2: 4-(2-((2-Methyl-5-((1-(thiazol-4-yl)ethyl)amino)naphthalen-1-yl)oxy)pyridin-3-yl)-N—((S)-piperidin-3-yl)pyrimidin-2-amine

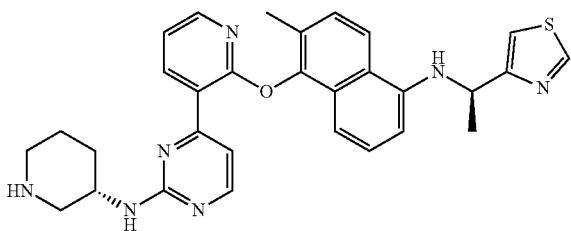 [SMILES: Cc1ccc2c(N[C@H](C)c3cscn3)cccc2c1Oc1ncccc1-c1ccnc(N[C@H]2CCCNC2)n1]

Prepared using (3S)-tert-butyl 3-((4-(2-((2-methyl-5-((1-(thiazol-4-yl)ethyl)amino)naphthalen-1-yl)oxy)pyridin-3-yl)pyrimidin-2-yl)amino)piperidine-1-carboxylate (isomer-2) (28 mg, 0.040 mmol), EtOAc (1 mL), and hydrochloric acid (4 M in dioxane, 0.44 mL, 1.75 mmol). After 3 h, the resulting solids were collected by filtration, washed using DCM, then dissolved in H2O and lyophilized to provide 22 mg (87% yield) of 295 as a brown solid. LCMS (ESI) [M+H]+=538.2, rt=1.41 min; 1H NMR (400 MHz, DMSO-d6) [NH signal hidden under HOD peak] δ 9.22 (br s, 1H), 9.07 (s, 1H), 9.05 (br m, 1H), 8.73 (br s, 1H), 8.47 (s, 1H), 8.22 (d, J=8.2 Hz, 1H), 8.04 (s, 1H), 7.78 (br s, 1H), 7.62 (br s, 1H), 7.45 (s, 1H), 7.40 (d, J=8.5 Hz, 1H), 7.24 (s, 1H), 7.08 (t, J=7.4 Hz, 1H), 6.86 (d, J=8.1 Hz, 1H), 6.42 (s, 1H), 4.96 (q, J=6.6 Hz, 1H), 4.35 (s, 1H), 3.43 (d, J=9.9 Hz, 1H), 3.19 (d, J=11.0 Hz, 1H), 2.89-2.77 (m, 2H), 2.19 (s, 3H), 2.01 (d, J=12.1 Hz, 1H), 1.91 (d, J=13.2 Hz, 1H), 1.76 (q, J=10.1 Hz, 1H), 1.67 (d, J=6.5 Hz, 4H). The absolute stereochemistry of the methyl was randomly assigned.

Example 296 (S)-4-(2-((6-Fluoro-2-methyl-5-((pyridin-2-ylmethyl)amino)naphthalen-1-yl)oxy)pyridin-3-yl)-N-(piperidin-3-yl)pyrimidin-2-amine 296

Step 1: (S)-tert-Butyl 3-((4-(2-((6-fluoro-2-methyl-5-((pyridin-2-ylmethyl)amino)naphthalen-1-yl)oxy)pyridin-3-yl)pyrimidin-2-yl)amino)piperidine-1-carboxylate

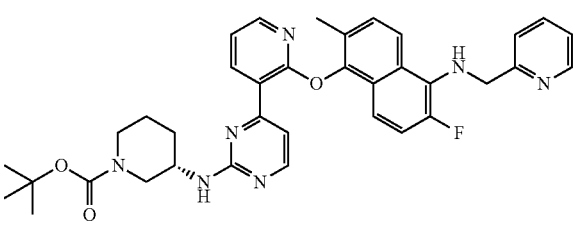 [SMILES: Cc1ccc2c(NCc3ccccn3)c(F)ccc2c1Oc1ncccc1-c1ccnc(N[C@H]2CCCN(C(=O)OC(C)(C)C)C2)n1]

Prepared using tert-butyl (3S)-3-[[4-[2-[(5-amino-2-methyl-1-naphthyl)oxy]-3-pyridyl]pyrimidin-2-yl]amino]piperidine-1-carboxylate (80 mg, 0.15 mmol), 2-pyridine carboxaldehyde (79 mg, 0.73 mmol), acetic acid (25 μL, 0.44 mmol), sodium triacetoxyborohydride (92 mg, 0.44 mmol) in DCM (1 mL). After 18 h at rt, the reaction was still not complete and more sodium triacetoxyborohydride (92 mg, 0.44 mmol) and acetic acid (25 μL, 0.44 mmol) were added and followed by continued stirring at rt. After 5 h, the reaction mixture was diluted with DCM (50 mL), washed with saturated NaHCO3 (aq) (2×25 mL), dried (Na2SO4), filtered and concentrated in vacuo. The residue was purified by flash chromatography through silica gel (0-100 EtOAc/Hexanes) to provide 15 mg (16% yield) of the title compound as a yellow wax. LCMS (ESI) [M+H]+=636.7, rt=1.99 min.

Step 2: (S)-4-(2-((6-Fluoro-2-methyl-5-((pyridin-2-ylmethyl)amino)naphthalen-1-yl)oxy)pyridin-3-yl)-N-(piperidin-3-yl)pyrimidin-2-amine

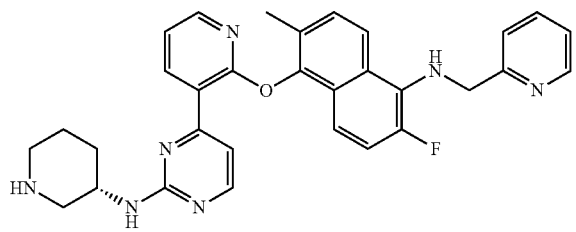 [SMILES: Cc1ccc2c(NCc3ccccn3)c(F)ccc2c1Oc1ncccc1-c1ccnc(N[C@H]2CCCNC2)n1]

Prepared according to General Procedure B using (S)-tert-butyl 3-((4-(2-((6-Fluoro-2-methyl-5-((pyridin-2-ylmethyl)amino)naphthalen-1-yl)oxy)pyridin-3-yl)pyrimidin-2-yl)amino)piperidine-1-carboxylate (15 mg, 0.02 mmol), EtOAc (1.0 mL), and hydrochloric acid (4 M in dioxane, 1.0 mL, 4.0 mmol). After 30 min, the volatiles were removed under vacuum. The residue was washed with EtOAc (3×3 mL) and MeCN (3×3 mL). The resulting solid was dissolved in water and MeCN and lyophilized to provide 13 mg (96% yield) of 296. LCMS (ESI) [M+H]+=536.2, rt=1.34 min; 1H NMR (400 MHz, d6-dmso) δ 9.06-8.77 (m, 3H), 8.69 (d, J=4.5 Hz, 1H), 8.66-8.51 (m, 1H), 8.46 (d, J=5.2 Hz, 1H), 8.17 (d, J=8.8 Hz, 2H), 8.05 (dd, J=4.8, 1.9 Hz, 1H), 7.83-7.58 (m, 2H), 7.57-7.46 (m, 3H), 7.26 (dd, J=7.6, 4.8 Hz, 1H), 7.15 (dd, J=12.9, 9.2 Hz, 1H), 7.03 (dd, J=9.1, 4.6 Hz, 1H), 4.85 (s, 2H), 4.38-4.14 (m, 1H), 3.20 (d, J=11.8 Hz, 2H), 2.96-2.75 (m, 2H), 2.18 (s, 3H), 2.06-1.83 (m, 2H), 1.82-1.51 (m, 2H).

Example 297 (S)-5-(6-Methyl-5-((3-(2-(piperidin-3-ylamino)pyrimidin-4-yl)pyridin-2-yl)oxy)naphthalen-1-yl)-5-azaspiro[2.4]heptan-4-one 297

Step 1: tert-Butyl (S)-3-((4-(2-((2-methyl-5-(4-oxo-5-azaspiro[2.4]heptan-5-yl)naphthalen-1-yl)oxy)pyridin-3-yl)pyrimidin-2-yl)amino)piperidine-1-carboxylate

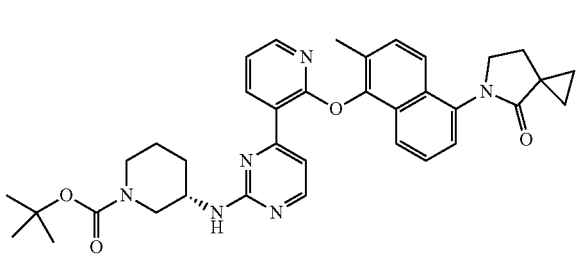 [SMILES: Cc1ccc2c(N3CCC4(CC4)C3=O)cccc2c1Oc1ncccc1-c1ccnc(N[C@H]2CCCN(C(=O)OC(C)(C)C)C2)n1]

489

A flask containing tert-butyl (3S)-3-[[4-[2-[(5-iodo-2-methyl-1-naphthyl)oxy]-3-pyridyl]pyrimidin-2-yl]amino]piperidine-1-carboxylate (100 mg, 0.157 mmol) was charged with 5-azaspiro[2.4]heptan-4-one (31 mg, 0.214 mmol), copper(I) iodide (6.0 mg, 0.0314 mmol), N,N'-dimethylethylenediamine (10 µL, 0.094 mmol), potassium carbonate (54 mg, 0.392 mmol) and 1,4 dioxane (3 mL). The mixture was sparged with nitrogen for 15 min and the flask was heated at reflux overnight. After 16 hours, the mixture was cooled to room temperature and the mixture was diluted with ethyl acetate and water and the phases were separated. The organic extract was washed with saturated NaCl(aq), dried over sodium sulfate, filtered and concentrated in vacuo. The crude product was purified via reverse-phase HPLC and lyophilized to yield to yield 80 mg (82% yield). LCMS (ESI): [M+H]$^+$=621.2.

Step 2: (S)-5-(6-Methyl-5-((3-(2-(piperidin-3-ylamino)pyrimidin-4-yl)pyridin-2-yl)oxy)naphthalen-1-yl)-5-azaspiro[2.4]heptan-4-one hydrochloride

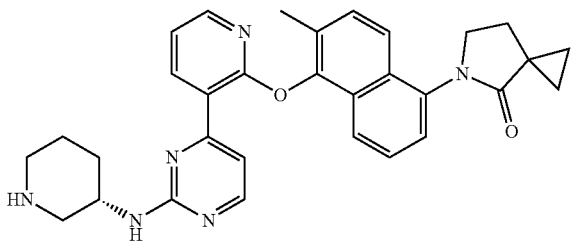 [SMILES: Cc1ccc2c(N3CCC4(CC4)C3=O)cccc2c1Oc1ncccc1-c1ccnc(N[C@H]2CCCNC2)n1]

The General Procedure B was followed, tert-butyl (S)-3-((4-(2-((2-methyl-5-(4-oxo-5-azaspiro[2.4]heptan-5-yl)naphthalen-1-yl)oxy)pyridin-3-yl)pyrimidin-2-yl)amino)piperidine-1-carboxylate (80 mg, 0.13 mmol), DCM (4 mL) and hydrochloric acid (4 M in dioxane, 3 mL, 12 mmol). After 3 h, the mixture was concentrated in vacuo and the crude solid was washed with ethyl acetate (3×3 mL) then with ACN (3×3 mL). The solid product was sonicated and concentrated in vacuo with ACN (3×3 mL) and then dissolved in water and acetonitrile. Lyophilization provided 58 mg (86% yield) of 297 as its hydrochloride salt. LCMS (ESI): [M+H]$^+$=521.2; $^1$H-NMR: (400 MHz, DMSO-d$_6$) δ 9.05-8.87 (m, 2H), 8.74-8.54 (m, 1H), 8.48 (d, J=5.2 Hz, 1H), 8.09 (dd, J=4.8, 2.0 Hz, 1H), 7.67-7.44 (m, 7H), 7.28 (dd, J=7.6, 4.8 Hz, 1H), 4.33-4.22 (m, 1H), 3.98-3.87 (m, 2H), 3.52-3.45 (m, 1H), 3.24-3.15 (m, 1H), 2.92-2.79 (m, 2H), 2.39 (t, J=7.1 Hz, 2H), 2.22 (s, 3H), 2.05-1.99 (m, 1H), 1.94-1.88 (m, 1H), 1.81-1.59 (m, 2H), 1.08-0.91 (m, 4H).

Example 298 (R)-1,1,1-Trifluoro-3-((6-methyl-5-((3-(2-((S)-piperidin-3-ylamino)pyrimidin-4-yl)pyridin-2-yl)oxy)naphthalen-1-yl)amino)propan-2-ol 298

Step 1: (S)-tert-Butyl 3-((4-(2-((2-methyl-5-(((R)-3,3,3-trifluoro-2-hydroxypropyl)amino)naphthalen-1-yl)oxy)pyridin-3-yl)pyrimidin-2-yl)amino)piperidine-1-carboxylate

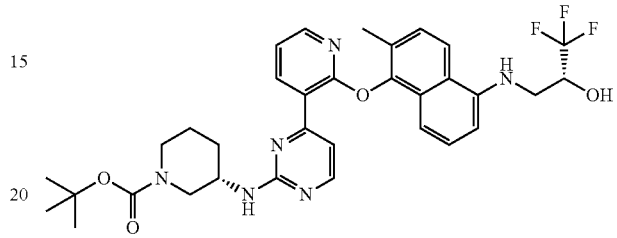

Prepared using tert-butyl (3S)-3-[[4-[2-[(5-amino-2-methyl-1-naphthyl)oxy]-3-pyridyl]pyrimidin-2-yl]amino]piperidine-1-carboxylate (30 mg, 0.06 mmol), (2R)-2-(trifluoromethyl)oxirane (13 mg, 0.11 mmol) and acetic acid (0.30 mL) and heating at 75° C. After 3 h, acetic acid was evaporated under vacuum. The residue was purified by prep TLC (MTBE (methyl t-butyl ether)/hexanes: 1/1). The product containing band was scratched off and stirred in EtOAc (20 mL) for 10 min. The mixture was filtered through celite and the solvent evaporated to provide 20 mg (55% yield) of the title compound. LCMS (ESI) [M+H]$^+$=639.7, rt=1.97 min.

Step 2: (R)-1,1,1-Trifluoro-3-((6-methyl-5-((3-(2-((S)-piperidin-3-ylamino)pyrimidin-4-yl)pyridin-2-yl)oxy)naphthalen-1-yl)amino)propan-2-ol

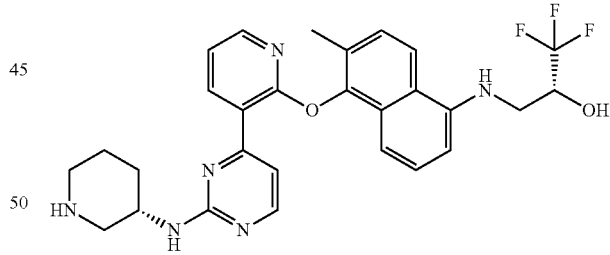

Prepared according to General Procedure B using (S)-tert-butyl 3-[[4-[2-[[2-methyl-5-[[(2R)-3,3,3-trifluoro-2-hydroxy-propyl]amino]-1-naphthyl]oxy]-3-pyridyl]pyrimidin-2-yl]amino]piperidine-1-carboxylate (20 mg, 0.03 mmol), 1,4-dioxane (1.0 mL), and hydrochloric acid (4 M in dioxane, 1.0 mL, 4.0 mmol). After 30 min, MTBE, methyl t-butyl ether (15 mL) was added to the suspension to further precipitate out the product. The suspension was stirred at rt overnight and the resulting solids collected by filtration and then dissolved in water and MeCN and lyophilized to provide 17 mg (94% yield) of 298. LCMS (ESI) [M+H]$^+$=539.5, rt=1.41 min; $^1$H NMR (400 MHz, d6-DMSO) δ 8.75 (s, 1H), 8.45 (d, J=5.2 Hz, 1H), 8.04-7.96 (m, 2H), 7.59-7.47 (m, 2H), 7.36 (d, J=9.0 Hz, 1H), 7.25-7.13 (m, 2H), 6.85 (d, J=8.3 Hz, 1H), 6.47 (d, J=7.5 Hz, 1H), 4.29 (s, 1H), 3.18 (s, 1H), 2.82 (s, 2H), 2.17 (s, 3H), 2.01 (m, 1H), 1.89 (s, 1H), 1.63 (s, 1H)

Example 299 ((S)-1,1,1-Trifluoro-3-((6-methyl-5-((3-(2-((S)-piperidin-3-ylamino)pyrimidin-4-yl)pyridin-2-yl)oxy)naphthalen-1-yl)amino)propan-2-ol 299

Step 1: (S)-tert-Butyl 3-((4-(2-((2-methyl-5-(((S)-3,3,3-trifluoro-2-hydroxypropyl)amino)naphthalen-1-yl)oxy)pyridin-3-yl)pyrimidin-2-yl)amino)piperidine-1-carboxylate

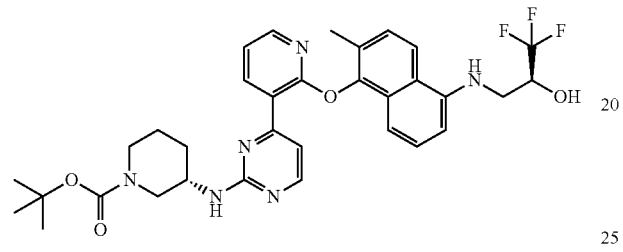

Prepared using tert-butyl (3S)-3-[[4-[2-[(5-amino-2-methyl-1-naphthyl)oxy]-3-pyridyl]pyrimidin-2-yl]amino]piperidine-1-carboxylate (50 mg, 0.09 mmol), (2S)-2-(trifluoromethyl)oxirane (21 mg, 0.19 mmol), acetic acid (0.30 mL) and heating at 75° C. After 3 h, acetic acid was evaporated under vacuum. The residue was purified by prep TLC (MTBE/Hexanes: 1/1). The product containing band was scratched off and stirred in EtOAc (20 mL) for 10 min. The mixture was filtered through celite and the solvent evaporated to provide 42 mg (69% yield) of the title compound. LCMS (ESI) [M+H]$^+$=639.7, rt=1.97 min.

Step 2: ((S)-1,1,1-Trifluoro-3-((6-methyl-5-((3-(2-((S)-piperidin-3-ylamino)pyrimidin-4-yl)pyridin-2-yl)oxy)naphthalen-1-yl)amino)propan-2-ol

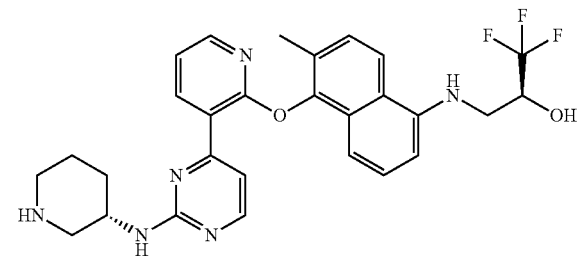 [SMILES: Cc1ccc2c(NC[C@H](O)C(F)(F)F)cccc2c1Oc1ncccc1-c1ccnc(N[C@H]2CCCNC2)n1]

Prepared according to General Procedure B using (S)-tert-butyl 3-((4-(2-((2-methyl-5-(((S)-3,3,3-trifluoro-2-hydroxypropyl)amino)naphthalen-1-yl)oxy)pyridin-3-yl)pyrimidin-2-yl)amino)piperidine-1-carboxylate (42 mg, 0.07 mmol), 1,4-dioxane (1.0 mL), and hydrochloric acid (4 M in dioxane, 1.0 mL, 4.0 mmol). After 30 min, MTBE (15 mL) was added to the suspension to further precipitate out the product and the suspension was stirred at rt overnight. The resulting solids were collected by filtration and dissolved in water and MeCN and lyophilized to provide 35 mg (93% yield) of 299. LCMS (ESI) [M+H]$^+$=539.5, rt=1.41 min; $^1$H NMR (400 MHz, d$_6$-DMSO) δ 9.06 (s, 2H), 8.46 (t, J=5.2 Hz, 1H), 8.16-7.95 (m, 2H), 7.62 (s, 2H), 7.36 (d, J=8.9 Hz, 1H), 7.27-7.15 (m, 2H), 6.86 (d, J=8.4 Hz, 1H), 6.47 (d, J=7.5 Hz, 1H), 3.55 (d, J=14.1 Hz, 1H), 3.45-3.30 (m, 2H), 3.17 (s, 1H), 2.94-2.76 (m, 2H), 2.17 (s, 3H), 2.01 (s, 1H), 1.88 (s, 1H), 1.70 (d, J=55.3 Hz, 2H).

Example 300 (R)-1-((6-Methyl-5-((3-(2-((S)-piperidin-3-ylamino)pyrimidin-4-yl)pyridin-2-yl)oxy)naphthalen-1-yl)amino)propan-2-ol 300

Step 1: (S)-tert-Butyl 3-((4-(2-((5-(((R)-2-hydroxypropyl)amino)-2-methylnaphthalen-1-yl)oxy)pyridin-3-yl)pyrimidin-2-yl)amino)piperidine-1-carboxylate Prepared using tert-butyl (3S)-3-[[4-[2-[(5-amino-2-methyl-1-naphthyl)oxy]-3-pyridyl]pyrimidin-2-yl]amino]piperidine-1-carboxylate (50 mg, 0.09 mmol), (R)-(+)-propylene oxide (0.01 mL, 0.09 mmol), acetic acid (0.30 mL) and stirring at rt. After 16 h, acetic acid was evaporated under vacuum. The residue was purified by flash chromatography through silica gel (EtOAc/Hexanes) to provide 25 mg (45% yield) of the title compound. LCMS (ESI) [M+H]$^+$=585.3, rt=1.83 min. $^1$H NMR (400 MHz, CDCl$_3$) δ 8.62 (s, 1H), 8.36 (d, J=5.2 Hz, 1H), 8.04 (dd, J=4.8, 2.0 Hz, 1H), 7.72 (d, J=8.3 Hz, 2H), 7.36 (d, J=8.7 Hz, 1H), 7.22 (d, J=7.6 Hz, 1H), 7.16 (d, J=8.3 Hz, 1H), 7.08 (dd, J=7.6, 4.8 Hz, 1H), 6.61 (dd, J=29.6, 7.1 Hz, 1H), 5.35 (s, 1H), 4.18 (s, 1H), 3.58 (s, 1H), 3.42-3.36 (m, 1H), 3.15 (dd, J=12.6, 8.6 Hz, 1H), 2.26 (s, 4H), 1.79 (s, 2H), 1.75-1.57 (m, 4H), 1.34 (d, J=6.3 Hz, 4H).

Step 2: (((R)-1-((6-Methyl-5-((3-(2-((S)-piperidin-3-ylamino)pyrimidin-4-yl)pyridin-2-yl)oxy)naphthalen-1-yl)amino)propan-2-ol Prepared according to General Procedure B using (S)-tert-butyl 3-((4-(2-((5-(((R)-2-hydroxypropyl)amino)-2-methylnaphthalen-1-yl)oxy)pyridin-3-yl)pyrimidin-2-yl)amino)piperidine-1-carboxylate (43 mg, 0.070 mmol), 1,4-dioxane (1.0 mL), and hydrochloric acid (4 M in dioxane, 1.0 mL, 4.0 mmol). After 30 min, MTBE (15 mL) was added to the suspension to further precipitate out the product and the suspension was stirred at rt overnight. The resulting solids were collected by filtration, dissolved in water and MeCN and lyophilized to provide 35 mg (91% yield) of 300. LCMS (ESI) [M+H]⁺=485.5, rt=1.25 min; ¹H NMR (400 MHz, d6-dmso) δ 9.04 (s, 2H), 8.46 (s, 1H), 8.02 (d, J=8.8 Hz, 2H), 7.62 (s, 2H), 7.39 (d, J=8.8 Hz, 1H), 7.23 (ddd, J=16.0, 12.2, 6.9 Hz, 2H), 6.95 (d, J=8.4 Hz, 1H), 6.67 (s, 1H), 3.99 (d, J=6.0 Hz, 2H), 3.40 (s, 1H), 3.17 (s, 3H), 2.81 (d, J=10.3 Hz, 1H), 2.18 (s, 3H), 2.01 (s, 1H), 1.88 (s, 1H), 1.70 (d, J=52.3 Hz, 2H), 1.15 (d, J=6.2 Hz, 3H).

Example 301 (S)-1-((6-Methyl-5-((3-(2-((S)-piperidin-3-ylamino)pyrimidin-4-yl)pyridin-2-yl)oxy)naphthalen-1-yl)amino)propan-2-ol 301

Step 1: (S)-tert-Butyl 3-((4-(2-((5-(((S)-2-hydroxypropyl)amino)-2-methylnaphthalen-1-yl)oxy)pyridin-3-yl)pyrimidin-2-yl)amino)piperidine-1-carboxylate

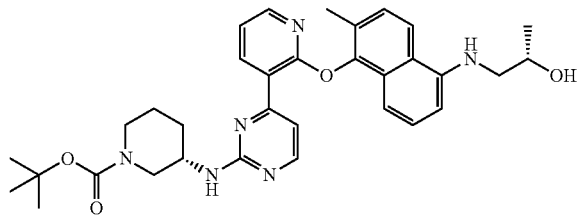 [SMILES: Cc1ccc2c(NC[C@H](C)O)cccc2c1Oc1ncccc1-c1ccnc(N[C@H]2CCCN(C(=O)OC(C)(C)C)C2)n1]

Prepared using tert-butyl (3S)-3-[[4-[2-[(5-amino-2-methyl-1-naphthyl)oxy]-3-pyridyl]pyrimidin-2-yl]amino]piperidine-1-carboxylate (50 mg, 0.09 mmol), (R)-(+)-propylene oxide (0.01 mL, 0.09 mmol), acetic acid (0.30 mL) and stirring at rt. After 16 h, acetic acid was evaporated under vacuum. The residue was purified by flash chromatography through silica gel (EtOAc/Hexanes) to provide 25 mg (45% yield) of the title compound. LCMS (ESI) [M+H]+=585.3, rt=1.83 min. ¹H NMR (400 MHz, CDCl₃) δ 8.62 (s, 1H), 8.36 (d, J=5.2 Hz, 1H), 8.04 (dd, J=4.8, 2.0 Hz, 1H), 7.72 (d, J=8.3 Hz, 2H), 7.36 (d, J=8.7 Hz, 1H), 7.22 (d, J=7.6 Hz, 1H), 7.16 (d, J=8.3 Hz, 1H), 7.08 (dd, J=7.6, 4.8 Hz, 1H), 6.61 (dd, J=29.6, 7.1 Hz, 1H), 5.35 (s, 1H), 4.18 (s, 1H), 3.58 (s, 1H), 3.42-3.36 (m, 1H), 3.15 (dd, J=12.6, 8.6 Hz, 1H), 2.26 (s, 4H), 1.79 (s, 2H), 1.75-1.57 (m, 4H), 1.34 (d, J=6.3 Hz, 4H).

Step 2: (S)-1-((6-Methyl-5-((3-(2-((S)-piperidin-3-ylamino)pyrimidin-4-yl)pyridin-2-yl)oxy)naphthalen-1-yl)amino)propan-2-ol

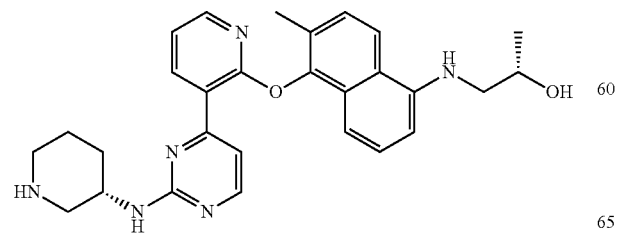

Prepared according to General Procedure B using (S)-tert-butyl 3-((4-(2-((5-(((S)-2-hydroxypropyl)amino)-2-methylnaphthalen-1-yl)oxy)pyridin-3-yl)pyrimidin-2-yl)amino)piperidine-1-carboxylate (23 mg, 0.04 mmol), 1,4-dioxane (1.0 mL), and hydrochloric acid (4 M in dioxane, 1.0 mL, 4.0 mmol). After 30 min, MTBE (15 mL) was added to the suspension to further precipitate out the product and the suspension was stirred at rt overnight. The resulting solids were collected by filtration, dissolved in water and MeCN and lyophilized to provide 17 mg (83% yield) of 301. LCMS (ESI) [M+H]⁺=485.5, rt=1.25 min; ¹H NMR (400 MHz, d6-dmso) δ 8.88 (s, 2H), 8.46 (d, J=5.3 Hz, 1H), 8.06-7.96 (m, 2H), 7.58 (s, 3H), 7.36 (d, J=8.8 Hz, 1H), 7.24-7.14 (m, 2H), 6.86 (d, J=8.5 Hz, 1H), 6.53 (d, J=7.8 Hz, 1H), 3.97 (d, J=6.1 Hz, 2H), 3.47-3.38 (m, 2H), 3.15 (d, J=17.8 Hz, 3H), 2.82 (s, 2H), 2.17 (s, 3H), 1.94 (d, J=51.6 Hz, 2H), 1.62 (s, 2H), 1.15 (d, J=6.2 Hz, 3H).

Example 302 3,3-Dimethyl-N-(6-methyl-5-((3-(2-(((3S,5R)-5-methylpiperidin-3-yl)amino)pyrimidin-4-yl)pyridin-2-yl)oxy)naphthalen-1-yl)butanamide 302

Step 1: tert-Butyl (6-methyl-5-((3-(2-(methylthio)pyrimidin-4-yl)pyridin-2-yl)oxy)naphthalen-1-yl)carbamate

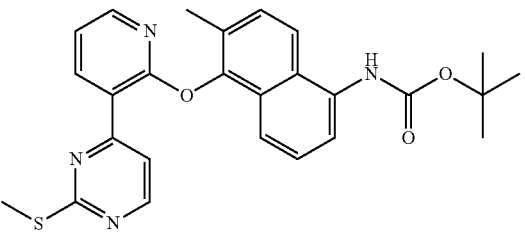 [SMILES: CSc1nccc(-c2cccnc2Oc2c(C)ccc3c(NC(=O)OC(C)(C)C)cccc23)n1]

To a suspension of 6-methyl-5-[[3-(2-methylsulfanylpyrimidin-4-yl)-2-pyridyl]oxy]naphthalen-1-amine (1.00 g, 2.67 mmol) in 1,4-dioxane (8 mL) was added di-tert-butyl dicarbonate (0.73 g, 3.34 mmol) followed by triethylamine (0.41 mL, 2.94 mmol) and the mixture was heated at 60° C. After 16 h, EtOAc (16 mL) and brine (32 mL) were added and the phases were separated. The organic extract was washed with saturated NH₄Cl(aq) (50 mL), dried (MgSO₄), filtered and concentrated under vacuum. The residue was purified by flash chromatography through silica gel (0-10% EtOAc/DCM) to provide 640 mg (50% yield) of the title compound. LCMS (ESI) [M+H]⁺=475.2, rt=2.06 min.

Step 2: tert-Butyl (6-methyl-5-((3-(2-(methylsulfinyl)pyrimidin-4-yl)pyridin-2-yl)oxy)naphthalen-1-yl)carbamate

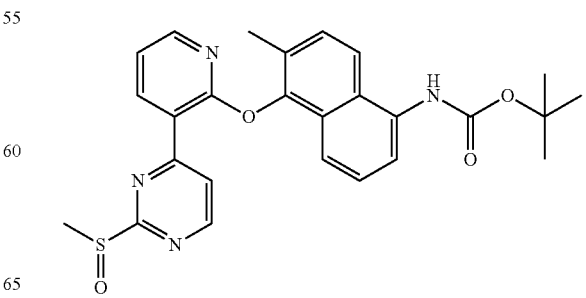

To tert-butyl N-[6-methyl-5-[[3-(2-methylsulfanylpyrimidin-4-yl)-2-pyridyl]oxy]-1-naphthyl]carbamate (200 mg, 0.420 mmol) in DCM (18 mL) was added 3-chloroperbenzoic acid (103 mg of ~78% pure reagent, 0.460 mmol). After 30 min at rt, the reaction was diluted with DCM (10 mL) and saturated NaHCO$_3$(aq) (60 mL). The phases were separated and the aqueous layer was extracted with DCM (2×20 mL), washed with saturated aq. NaHCO$_3$(aq) (50 mL), dried over Na$_2$SO$_4$ and evaporated under vacuum to provide 200 mg (100% yield) of the title compound which was used in the next step without further purification. LCMS (ESI) [M+H]$^+$=491.1, rt=1.61 min.

Step 3: (3S,5R)-Benzyl 3-((4-(2-((5-((tert-butoxycarbonyl)amino)-2-methylnaphthalen-1-yl)oxy)pyridin-3-yl)pyrimidin-2-yl)amino)-5-methylpiperidine-1-carboxylate

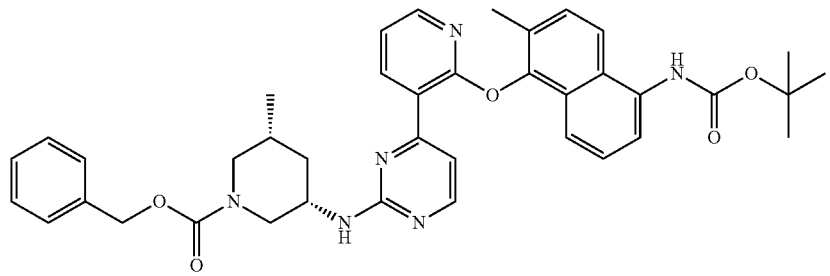 [SMILES: Cc1ccc2c(NC(=O)OC(C)(C)C)cccc2c1Oc1ncccc1-c1ccnc(N[C@H]2C[C@@H](C)CN(C(=O)OCc3ccccc3)C2)n1]

To a solution of tert-butyl N-[6-methyl-5-[[3-(2-methylsulfinylpyrimidin-4-yl)-2-pyridyl]oxy]-1-naphthyl]carbamate (200 mg, 0.410 mmol) and benzyl (3S,5R)-3-amino-5-methyl-piperidine-1-carboxylate hydrochloride (145 mg, 0.510 mmol) in 1,4-dioxane (4.6 mL) was added triethylamine (0.28 mL, 2.04 mmol). The reaction mixture was stirred at 120° C. After 16 h, the mixture was diluted with EtOAc (20 mL) and 1N KHSO$_4$(aq) (40 mL). The phases were separated and the aqueous layer was extracted with EtOAc (2×20 mL), washed with saturated NaHCO$_3$(aq) (50 mL), dried (Na$_2$SO$_4$) and evaporated under vacuum. The residue was purified by flash chromatography through silica gel (0-30% EtOAc/DCM) to provide 120 mg (44% yield) of the title compound. LCMS (ESI) [M+H]$^+$=675.4, rt=2.14 min.

Step 4: (3S,5R)-Benzyl 3-((4-(2-((5-amino-2-methylnaphthalen-1-yl)oxy)pyridin-3-yl)pyrimidin-2-yl)amino)-5-methylpiperidine-1-carboxylate hydrochloride

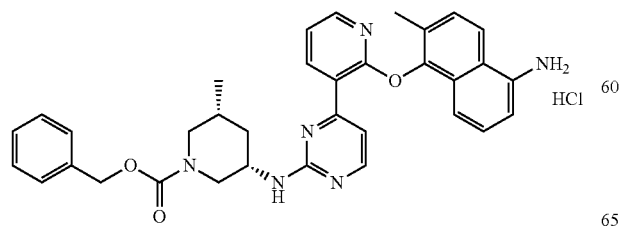

Prepared according to General Procedure B using (3S,5R)-3-[[4-[2-[[5-(tert-butoxycarbonylamino)-2-methyl-1-naphthyl]oxy]-3-pyridyl]pyrimidin-2-yl]amino]-5-methyl-piperidine-1-carboxylate (125 mg, 0.190 mmol), 1,4-dioxane (1.4 mL), and hydrochloric acid (4 M in dioxane, 1.0 mL, 4.0 mmol). After 2.5 h, Et$_2$O (15 mL) was added and the volatiles were evaporated under vacuum. The same process was repeated twice to provide 120 mg (106% yield) of the title compound as a solid. LCMS (ESI) [M+H]$^+$=575.0, rt=1.90 min Step 5: (3S,5R)-Benzyl 3-((4-(2-((5-(3,3-dimethylbutanamido)-2-methylnaphthalen-1-yl)oxy)pyridin-3-yl)pyrimidin-2-yl)amino)-5-methylpiperidine-1-carboxylate

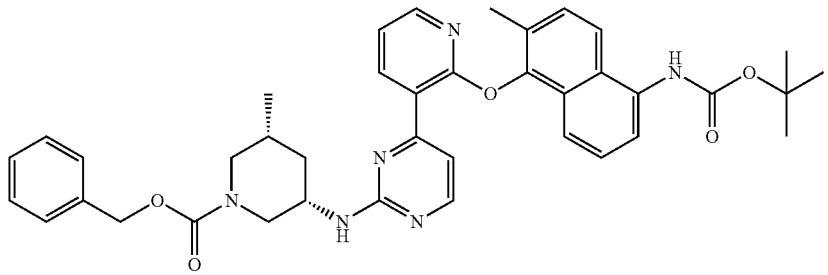 [SMILES: Cc1ccc2c(NC(=O)OC(C)(C)C)cccc2c1Oc1ncccc1-c1ccnc(N[C@H]2C[C@@H](C)CN(C(=O)OCc3ccccc3)C2)n1]

Prepared using (3S,5R)-3-[[4-[2-[(5-amino-2-methyl-1-naphthyl)oxy]-3-pyridyl]pyrimidin-2-yl]amino]-5-methyl-piperidine-1-carboxylate hydrochloride (40 mg, 0.07 mmol) in DCM (0.22 mL), tert-butyl acetylchloride (0.02 mL, 0.13 mmol), pyridine (0.08 mL, 0.98 mmol). After 16 h at rt, the reaction was diluted with DCM (15 mL) and saturated NaHCO$_3$(aq) (40 mL). The phases were separated and the aqueous layer was extracted with DCM (2×15 mL), washed with 1N KHSO$_4$(aq) (50 mL), dried (Na$_2$SO$_4$) and evaporated under vacuum to provide 38 mg (86% yield) of the title compound which was used in the next step without further purification. LCMS (ESI) [M+H]$^+$=673.2, rt=2.06 min.

Step 6: 3,3-Dimethyl-N-(6-methyl-5-((3-(2-(((3S,5R)-5-methylpiperidin-3-yl)amino)pyrimidin-4-yl)pyridin-2-yl)oxy)naphthalen-1-yl)butanamide

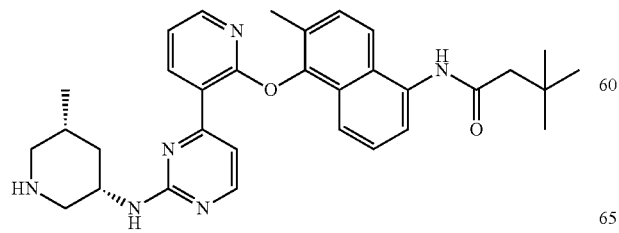

Prepared using (3S,5R)-benzyl 3-((4-(2-((5-(3,3-dimethylbutanamido)-2-methylnaphthalen-1-yl)oxy)pyridin-3-yl)pyrimidin-2-yl)amino)-5-methylpiperidine-1-carboxylate (38 mg, 0.06 mmol), iPrOH (1.1 mL), ammonium formate (36 mg, 0.56 mmol), palladium (10 mg of 10 wt % on carbon) and heating at 60° C. After 1 h, the reaction mixture was filtered through celite, washed with MeOH (75 mL), DCM (75 mL) and the filtrate evaporated under vacuum. The residue was diluted with saturated NaHCO$_3$(aq) (50 mL) and EtOAc (25 mL) and the phases were separated. The aqueous layer was extracted with EtOAc (2×25 mL), dried (Na$_2$SO$_4$) and the combined organic phases evaporated under vacuum. The residue was dissolved in dioxane (0.2 mL) and hydrochloric acid (4 M in dioxane, 1.0 mL, 4.0 mmol) was added. After 10 min at rt, the reaction mixture was diluted with Et$_2$O (15 mL). The precipitate was filtered, washed with Et$_2$O (10 mL), dissolved in water and lyophilized to provide 21 mg (65% yield) of 302. LCMS (ESI) [M+H]$^+$=539.2, rt=1.49 min; $^1$H NMR (400 MHz, d$_6$-DMSO) δ 9.88 (s, 1H), 9.23-8.83 (m, 2H), 8.73 (s, 1H), 8.48 (d, J=5.2 Hz, 1H), 8.05 (dd, J=4.8, 2.0 Hz, 1H), 7.94 (d, J=8.8 Hz, 1H), 7.65-7.45 (m, 5H), 7.40 (dd, J=8.4, 7.4 Hz, 1H), 7.27 (dd, J=7.6, 4.8 Hz, 1H), 4.32 (s, 1H), 3.20 (d, J=10.6 Hz, 1H), 2.69-2.55 (m, 2H), 2.38 (s, 2H), 2.21 (s, 3H), 2.07 (d, J=12.9 Hz, 1H), 1.95 (s, 1H), 1.34-1.23 (m, 1H), 1.10 (s, 10H), 0.93 (d, J=6.3 Hz, 3H).

Example 303 2-Cyclohexyl-N-(6-methyl-5-((3-(2-(((3S,5R)-5-methylpiperidin-3-yl)amino)pyrimidin-4-yl)pyridin-2-yl)oxy)naphthalen-1-yl)acetamide 303

Step 1: (3S,5R)-Benzyl 3-((4-(2-((5-(2-cyclohexylacetamido)-2-methylnaphthalen-1-yl)oxy)pyridin-3-yl)pyrimidin-2-yl)amino)-5-methylpiperidine-1-carboxylate

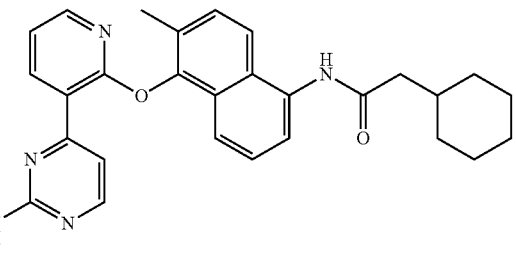

Prepared using benzyl (3S,5R)-3-[[4-[2-[(5-amino-2-methyl-1-naphthyl)oxy]-3-pyridyl]pyrimidin-2-yl]amino]-5-methyl-piperidine-1-carboxylate hydrochloride (40 mg, 0.07 mmol) in DCM (0.22 mL), 2-cyclohexylacetyl chloride (0.02 mL, 0.13 mmol), and pyridine (0.08 mL, 0.98 mmol). After 16 h at rt, the mixture was diluted with DCM (15 mL) and saturated NaHCO$_3$(aq) (40 mL). The phases were separated and the aqueous layer was extracted with DCM (2×15 mL), washed with 1N KHSO$_4$(aq) (50 mL), dried (Na$_2$SO$_4$) and evaporated under vacuum to provide 42 mg (86% yield) of the title compound which was used in the next step without further purification. LCMS (ESI) [M+H]$^+$=699.4, rt=2.13 min.

Step 2: 2-Cyclohexyl-N-(6-methyl-5-((3-(2-(((3S,5R)-5-methylpiperidin-3-yl)amino)pyrimidin-4-yl)pyridin-2-yl)oxy)naphthalen-1-yl)acetamide

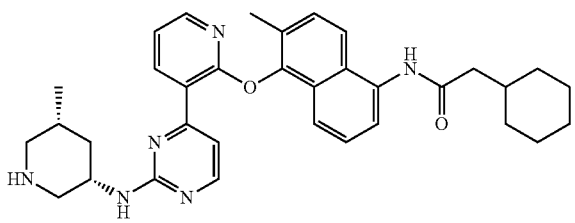 [SMILES: Cc1ccc2c(NC(=O)CC3CCCCC3)cccc2c1Oc1ncccc1-c1ccnc(N[C@@H]2CNC[C@H](C)C2)n1]

Prepared using (3S,5R)-benzyl 3-((4-(2-((5-(2-cyclohexylacetamido)-2-methylnaphthalen-1-yl)oxy)pyridin-3-yl)pyrimidin-2-yl)amino)-5-methylpiperidine-1-carboxylate (42 mg, 0.06 mmol), iPrOH (1.2 mL), ammonium formate (38 mg, 0.60 mmol), palladium (10 mg of 10 wt % on carbon) and heating at 60° C. After 2 h, the reaction mixture was filtered through celite, washed with MeOH (75 mL), DCM (75 mL) and the filtrate evaporated under vacuum. The residue was diluted with saturated NaHCO$_3$(aq) (50 mL) and EtOAc (25 mL) and the phases were separated. The aqueous layer was extracted with EtOAc (2×25 mL) and the combined organic phases dried (Na$_2$SO$_4$) and evaporated under vacuum. The residue was dissolved in dioxane (0.5 mL) and hydrochloric acid (4 M in dioxane, 1.0 mL, 4.0 mmol) was added. After 10 min at rt, the reaction was diluted with Et$_2$O (15 mL), the precipitate was filtered, washed with Et$_2$O (10 mL), dissolved in water (15 mL) and lyophilized to provide 19 mg (53% yield) of 303. LCMS (ESI) [M+H]$^+$=565.3, rt=1.57 min; $^1$H NMR (400 MHz, d6-dmso) δ 9.93 (s, 1H), 9.22-8.84 (m, 2H), 8.73 (s, 1H), 8.47 (d, J=5.2 Hz, 1H), 8.05 (dd, J=4.8, 2.0 Hz, 1H), 7.91 (d, J=8.7 Hz, 1H), 7.65-7.44 (m, 5H), 7.43-7.35 (m, 1H), 7.26 (dd, J=7.6, 4.8 Hz, 1H), 4.32 (s, 1H), 3.20 (d, J=12.4 Hz, 1H), 2.68-2.54 (m, 2H), 2.37 (d, J=7.0 Hz, 2H), 2.21 (s, 3H), 2.06 (d, J=9.9 Hz, 1H), 1.95 (s, 1H), 1.89-1.59 (m, 6H), 1.35-1.13 (m, 4H), 1.06 (q, J=11.0 Hz, 2H), 0.93 (d, J=6.2 Hz, 3H).

Example 304 2-Methyl-N-(6-methyl-5-((3-(2-(((3S,5R)-5-methylpiperidin-3-yl)amino)pyrimidin-4-yl)pyridin-2-yl)oxy)naphthalen-1-yl)propane-1-sulfonamide 304

Step 1: (3R,5S)-Benzyl 3-methyl-5-((4-(2-((2-methyl-5-(2-methylpropylsulfonamido)naphthalen-1-yl)oxy)pyridin-3-yl)pyrimidin-2-yl)amino)piperidine-1-carboxylate

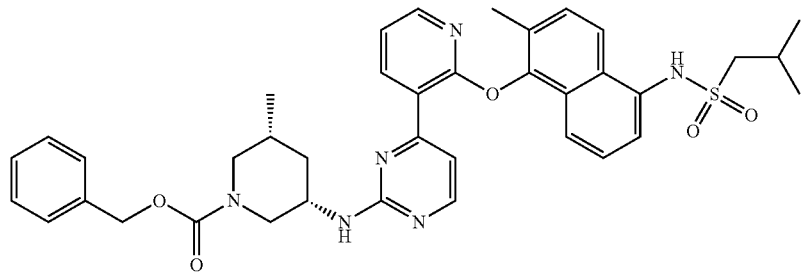 [SMILES: Cc1ccc2c(NS(=O)(=O)CC(C)C)cccc2c1Oc1ncccc1-c1ccnc(N[C@H]2C[C@@H](C)CN(C(=O)OCc3ccccc3)C2)n1]

Prepared using benzyl (3S,5R)-3-[[4-[2-[(5-amino-2-methyl-1-naphthyl)oxy]-3-pyridyl]pyrimidin-2-yl]amino]-5-methyl-piperidine-1-carboxylate hydrochloride (60 mg, 0.10 mmol), DCM (0.28 mL), 2-methylpropane-1-sulfonyl chloride (0.03 mL, 0.20 mmol), and pyridine (0.12 mL, 1.47 mmol). After 16 h at rt, the mixture was diluted with DCM (15 mL) and saturated NaHCO$_3$(aq) (40 mL) and the phases were separated and the aqueous layer was extracted with DCM (2×15 mL). The combined organic extracts were washed with 1 N KHSO$_4$(aq) (50 mL), dried (Na$_2$SO$_4$) and evaporated under vacuum. The residue was purified by flash chromatography through silica gel (0-35% EtOAc/DCM) to provide 57 mg (84% yield) of the title compound. LCMS (ESI) [M+H]$^+$=695.4, rt=2.02 min.

Step 2: 2-Methyl-N-(6-methyl-5-((3-(2-(((3S,5R)-5-methylpiperidin-3-yl)amino)pyrimidin-4-yl)pyridin-2-yl)oxy)naphthalen-1-yl)propane-1-sulfonamide

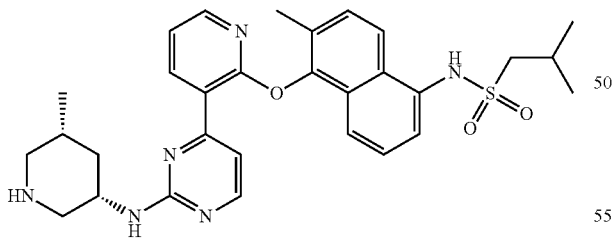

Prepared using (3R,5S)-benzyl 3-methyl-5-((4-(2-((2-methyl-5-(2-methylpropylsulfonamido)naphthalen-1-yl)oxy)pyridin-3-yl)pyrimidin-2-yl)amino)piperidine-1-carboxylate (33 mg, 0.05 mmol), iPrOH (0.95 mL), ammonium formate (30 mg, 0.47 mmol), palladium (10 mg of 10 wt % on carbon). After 1 h at 60° C., the reaction mixture was filtered through celite, washed with MeOH (75 mL), DCM (75 mL) and evaporated under vacuum. The residue was diluted with saturated NaHCO$_3$(aq) (50 mL) and EtOAc (25 mL) and the phases were separated. The aqueous layer was extracted with EtOAc (2×25 mL), and the combined organic extracts were dried (Na$_2$SO$_4$) and evaporated under vacuum. The residue was dissolved in 1,4-dioxane (0.5 mL) and hydrochloric acid (4 M in dioxane, 1.0 mL, 4.0 mmol) was added. After 10 min at rt, the reaction mixture was diluted with Et$_2$O (15 mL), the precipitate was filtered, washed with Et$_2$O (20 mL), dissolved in water and lyophilized to provide 24 mg (86% yield) of 304. LCMS (ESI) [M+H]$^+$=561.3, rt=1.44 min; $^1$H NMR (400 MHz, d$_6$-DMSO) δ 9.84 (s, 1H), 9.17-8.83 (m, 1H), 8.78-8.66 (m, 1H), 8.47 (d, J=5.2 Hz, 1H), 8.12 (d, J=8.7 Hz, 1H), 8.06 (dd, J=4.8, 1.9 Hz, 1H), 7.61-7.52 (m, 4H), 7.48-7.39 (m, 2H), 7.27 (dd, J=7.6, 4.8 Hz, 1H), 4.38-4.16 (m, 1H), 3.20 (d, J=10.2 Hz, 1H), 3.04 (d, J=6.4 Hz, 2H), 2.71-2.54 (m, 2H), 2.25-2.14 (m, 4H), 2.06 (d, J=10.8 Hz, 1H), 1.95 (s, 1H), 1.27 (q, J=12.0 Hz, 1H), 1.01 (d, J=6.7 Hz, 7H), 0.91 (d, J=18.3 Hz, 3H).

Example 305 (S)—N-(6-Fluoro-5-((3-(2-(piperidin-3-ylamino)pyrimidin-4-yl)pyridin-2-yl)oxy)naphthalen-1-yl)propane-1-sulfonamide 305

Step 1: tert-Butyl (5-hydroxynaphthalen-1-yl)carbamate

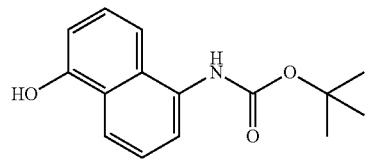 [SMILES: CC(C)(C)OC(=O)Nc1cccc2c(O)cccc12]

To a solution of 5-amino-1-naphthol (2000 mg, 12.56 mmol) in 1,4-dioxane (12.6 mL) was added di-tert-butyl dicarbonate (3428 mg, 15.71 mmol) and the reaction mixture was stirred at 60° C. After 3 h, the reaction mixture was adsorbed onto silica and purified by flash chromatography through silica gel (10-30% EtOAc/Hexanes) to provide 2538 mg (78% yield) of the title compound as a solid. LCMS (ESI) [M−t−Bu+H]$^+$=203.4, rt=1.58 min; $^1$H NMR (400 MHz, CDCl$_3$) δ 7.96 (d, J=8.4 Hz, 1H), 7.91 (d, J=6.7 Hz, 1H), 7.45 (dd, J=12.6, 4.7 Hz, 2H), 7.36-7.29 (m, 1H), 6.81 (d, J=7.4 Hz, 2H), 5.47-5.42 (m, 1H), 1.56 (s, 9H).

Step 2: tert-Butyl (5-hydroxynaphthalen-1-yl)carbamate

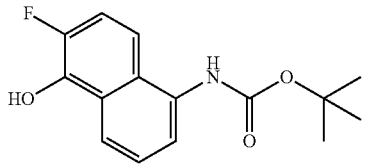 [SMILES: CC(C)(C)OC(=O)Nc1cccc2c(O)c(F)ccc12]

tert-Butyl N-(5-hydroxy-1-naphthyl)carbamate (600 mg, 2.31 mmol) was dissolved in EtOH (10 mL) and NMP (10 mL) to give a homogeneous purple solution. To this solution was then added Selectfluor (1393 mg, 3.930 mmol) and the mixture was stirred at rt. After 16 h, volatiles were removed under vacuum and the resulting solution was diluted with EtOAc (75 mL) and H$_2$O (25 mL). The phases were separated and the organic layer was washed with saturated NaHCO$_3$(aq) (10 mL), then with 50% saturated NaCl(aq) (4×15 mL), dried (Na$_2$SO$_4$), filtered and concentrated in vacuo. The residue was adsorbed on silica and purified by flash chromatography through silica gel (10-20% EtOAc/Hexanes) followed by further purification by C18 reverse phase flash chromatography (20-100% MeCN/10 mM ammonium formate aqueous solution, pH=3.8) to provide 75 mg (12% yield) of the title compound. LCMS (ESI) [M−H]$^+$=276.4, rt=1.59 min; $^1$H NMR (400 MHz, CDCl$_3$) δ 7.96 (d, J=8.5 Hz, 1H), 7.82-7.77 (m, 1H), 7.46 (dd, J=8.0 Hz, 1H), 7.39 (dd, J=9.3, 4.7 Hz, 1H), 7.26 (dd, J=9.5 Hz, 1H), 6.76 (s, 1H), 1.56 (s, 9H).

Step 3: 5-Amino-2-fluoronaphthalen-1-ol hydrochloride

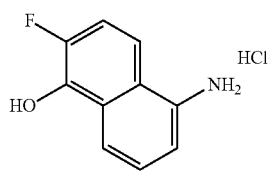 [SMILES: Nc1cccc2c(O)c(F)ccc12 ; Cl]

tert-Butyl N-(6-fluoro-5-hydroxy-1-naphthyl)carbamate (120 mg, 0.430 mmol) was dissolved in EtOAc (5 mL) and treated with hydrochloric acid (4 M in dioxane, 2 mL, 8 mmol) and the reaction mixture was stirred at rt. After 16 h, the reaction was concentrated under vacuum to provide 87 mg (94% yield) of the title compound which was used directly in the next step without further purification. LCMS (ESI) [M+H]$^+$=178.4, rt=1.09 min.

Step 4: (S)-tert-Butyl 3-((4-(2-((5-amino-2-fluoronaphthalen-1-yl)oxy)pyridin-3-yl)pyrimidin-2-yl)amino)piperidine-1-carboxylate

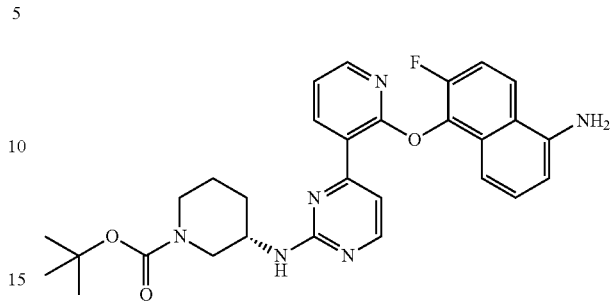

tert-Butyl (3S)-3-[[4-(2-fluoro-3-pyridyl)pyrimidin-2-yl]amino]piperidine-1-carboxylate (140 mg, 0.370 mmol) and 5-amino-2-fluoro-naphthalen-1-ol hydrochloride (88 mg, 0.41 mmol) were combined in DMSO (2 mL). Cesium carbonate (492 mg, 1.50 mmol) was added and the flask sealed and placed in a 120° C. oil bath. After 3 h, the reaction was diluted with EtOAc (75 mL) and washed with saturated NaHCO$_3$(aq) (25 mL), then H$_2$O (10 mL), then 50% sat'd NaCl(aq) (4×10 mL), dried (Na$_2$SO$_4$), filtered and concentrated under vacuum to provided 112 mg (56% yield) of the title compound as a purple waxy gum which was used directly in the next step without further purification. LCMS (ESI) [M+H]$^+$=631.2, rt=1.80 min.

Step 5: (S)-tert-Butyl 3-((4-(2-((2-fluoro-5-(propylsulfonamido)naphthalen-1-yl)oxy)pyridin-3-yl)pyrimidin-2-yl)amino)piperidine-1-carboxylate

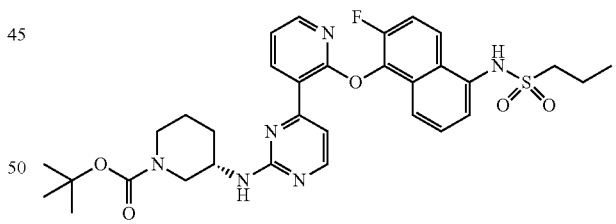

Prepared using tert-butyl (3S)-3-[[4-[2-[(5-amino-2-fluoro-1-naphthyl)oxy]-3-pyridyl]pyrimidin-2-yl]amino]piperidine-1-carboxylate (112 mg, 0.210 mmol), DCM (2 mL), 1-propanesulfonyl chloride (0.06 mL, 0.53 mmol) and pyridine (1 mL). After 16 h at rt, the reaction was diluted with DCM (50 mL) and washed with saturated NaHCO$_3$(aq) (15 mL), dried (Na$_2$SO$_4$) and evaporated under vacuum. The residue was purified by flash chromatography through silica gel (0-100% EtOAc/Hexanes) to provide 15 mg (11% yield) of the title compound as a yellow waxy gum. LCMS (ESI) [M+H]$^+$=637.3, rt=1.86 min.

Step 6: (S)—N-(6-Fluoro-5-((3-(2-(piperidin-3-ylamino)pyrimidin-4-yl)pyridin-2-yl)oxy)naphthalen-1-yl)propane-1-sulfonamide

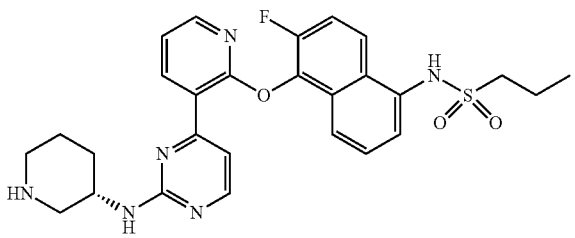 [SMILES: CCCS(=O)(=O)Nc1cccc2c(Oc3ncccc3-c3ccnc(N[C@H]4CCCNC4)n3)c(F)ccc12]

Prepared according to General Procedure B using (3S)-3-[[4-[2-[[2-fluoro-5-(propylsulfonylamino)-1-naphthyl]oxy]-3-pyridyl]pyrimidin-2-yl]amino]piperidine-1-carboxylate (15 mg, 0.02 mmol), EtOAc (2 mL), and hydrochloric acid (4 M in dioxane, 1 m, 4 mmol). After 3 h, the volatiles were evaporated. The residue was purified by C18 reverse phase flash chromatography (0-100% MeCN/10 mM ammonium formate aqueous solution, pH=3.8) and the appropriate fractions were lyophilized to provide 5 mg (40% yield) of 305. LCMS (ESI) [M+H]⁺=537.2, rt=1.34 min; ¹H NMR (400 MHz, d₆-DMSO) δ 8.59-8.45 (m, 1H), 8.43 (d, J=5.1 Hz, 1H), 8.32-8.22 (m, 2H), 8.10 (dd, J=4.8, 1.9 Hz, 1H), 7.65-7.51 (m, 2H), 7.50-7.39 (m, 3H), 7.38-7.26 (m, 2H), 4.12-3.93 (m, 2H), 3.10-3.04 (m, 2H), 2.97 (d, J=11.0 Hz, 2H), 2.69-2.55 (m, 2H), 2.02-1.91 (m, 1H), 1.81-1.68 (m, 3H), 1.61-1.46 (m, 2H), 0.96 (t, J=7.5 Hz, 3H).

Example 306 (S)-2-Methyl-1-((6-methyl-5-((3-(2-(piperidin-3-ylamino)pyrimidin-4-yl)pyridin-2-yl)oxy)naphthalen-1-yl)amino)propan-2-ol 306

Step 1: (S)-tert-Butyl 3-((4-(2-((5-((2-hydroxy-2-methylpropyl)amino)-2-methylnaphthalen-1-yl)oxy)pyridin-3-yl)pyrimidin-2-yl)amino)piperidine-1-carboxylate

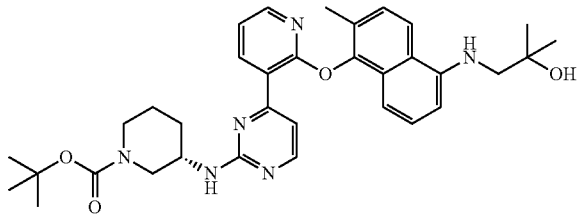 [SMILES: Cc1ccc2c(NCC(C)(C)O)cccc2c1Oc1ncccc1-c1ccnc(N[C@H]2CCCN(C(=O)OC(C)(C)C)C2)n1]

tert-Butyl (3S)-3-[[4-[2-[(5-amino-2-methyl-1-naphthyl)oxy]-3-pyridyl]pyrimidin-2-yl]amino]piperidine-1-carboxylate (120 mg, 0.230 mmol) and 1,2-epoxy-2-methylpropane (0.01 mL, 0.21 mmol) were combined in Et₂O (1 mL). To this was added lithium perchlorate (221 mg, 2.08 mmol) and the mixture stirred at rt. After 16 h, the reaction mixture was diluted with EtOAc (50 mL), washed with H₂O (20 mL), dried (Na₂SO₄), filtered and concentrated under vacuum. The residue was purified by flash chromatography through silica gel (0-100% EtOAc/Hexanes) to provide 31 mg (25% yield) of the title compound. LCMS (ESI) [M+H]⁺=599.2, rt=1.91 min.

Step 2: (S)-2-Methyl-1-((6-methyl-5-((3-(2-(piperidin-3-ylamino)pyrimidin-4-yl)pyridin-2-yl)oxy)naphthalen-1-yl)amino)propan-2-ol

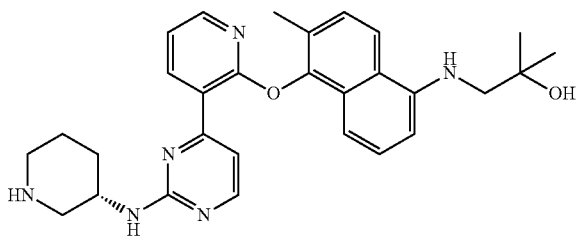 [SMILES: Cc1ccc2c(NCC(C)(C)O)cccc2c1Oc1ncccc1-c1ccnc(N[C@H]2CCCNC2)n1]

Prepared according to General Procedure B using (S)-tert-butyl 3-((4-(2-((5-((2-hydroxy-2-methylpropyl)amino)-2-methylnaphthalen-1-yl)oxy)pyridin-3-yl)pyrimidin-2-yl)amino)piperidine-1-carboxylate (31 mg, 0.05 mmol), EtOAc (2 mL), and hydrochloric acid (4 M in dioxane, 1 mL, 4 mmol). After 30 min, the volatiles were evaporated. The residue was purified by C18 reverse phase flash chromatography (0-100% MeCN/10 mM ammonium formate aqueous solution, pH=3.8) and the appropriate fractions were lyophilized to provide 5 mg (19% yield) of 306. LCMS (ESI) [M+H]⁺=499.3, rt=1.33 min; ¹H NMR (400 MHz, d₆-DMSO) δ 6 8.59-8.44 (m, 1H), 8.42 (d, J=5.1 Hz, 1H), 8.31 (s, 1H), 8.01 (dd, J=4.8, 1.9 Hz, 1H), 7.98 (d, J=8.7 Hz, 1H), 7.47 (d, J=5.1 Hz, 1H), 7.37 (d, J=8.7 Hz, 1H), 7.23 (dd, J=7.4, 4.7 Hz, 2H), 7.17 (t, J=8.0 Hz, 1H), 6.85 (d, J=8.2 Hz, 1H), 6.52 (d, J=7.7 Hz, 1H), 5.65 (t, J=5.3 Hz, 1H), 4.89-4.57 (m, 1H), 4.09-3.86 (m, J=18.9, 9.8 Hz, 1H), 3.15-3.10 (m, 4H), 2.89 (d, J=10.7 Hz, 2H), 2.19 (s, 3H), 2.01-1.89 (m, 1H), 1.78-1.66 (m, 1H), 1.60-1.46 (m, 2H), 1.25 (s, 6H).

Example 307 4-(2-((6-Fluoro-2-methyl-5-(((2-methylthiazol-4-yl)methyl)amino)naphthalen-1-yl)oxy)pyridin-3-yl)-N-((3S,5R)-5-methylpiperidin-3-yl)pyrimidin-2-amine 307

Step 1: (3S,5R)-Benzyl 3-((4-(2-((6-fluoro-2-methyl-5-(((2-methylthiazol-4-yl)methyl)amino)naphthalen-1-yl)oxy)pyridin-3-yl)pyrimidin-2-yl)amino)-5-methylpiperidine-1-carboxylate

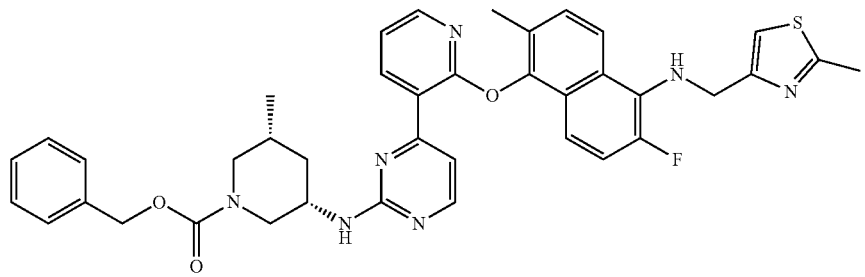 [SMILES: Cc1nc(CNc2c(F)ccc3c(Oc4ncccc4-c4ccnc(N[C@H]5C[C@@H](C)CN(C(=O)OCc6ccccc6)C5)n4)c(C)ccc23)cs1]

Prepared according to General Procedure G using benzyl (5R)-3-[[4-[2-[(5-amino-6-fluoro-2-methyl-1-naphthyl)oxy]-3-pyridyl]pyrimidin-2-yl]amino]-5-methyl-piperidine-1-carboxylate (75 mg, 0.13 mmol), DMF (1 mL), 4-(chloromethyl)-2-methyl-thiazole hydrochloride (0.01 mL, 0.19 mmol), cesium carbonate (166 mg, 0.51 mmol) and tetrabutylammonium iodide (4.7 mg, 0.01 mmol) and heating at 50° C. After 16 h, a further portion of 4-(chloromethyl)-2-methyl-thiazole hydrochloride (0.01 mL, 0.19 mmol) and cesium carbonate (166 mg, 0.510 mmol) were added and heating continued. After 24 h, the reaction was diluted with EtOAc (15 mL) and water (50 mL). The phases were separated, and the organic layer was washed with water (40 mL), brine (40 mL), saturated NH$_4$Cl(aq) (40 mL), dried (MgSO$_4$), filtered and concentrated under vacuum. The residue was purified by flash chromatography through silica gel (0-10% MeOH/DCM) to provide 24 mg (27% yield) of the title compound. LCMS (ESI) [M+H]$^+$=704.3, rt=2.08 min.

Step 2: 4-(2-((6-Fluoro-2-methyl-5-(((2-methylthiazol-4-yl)methyl)amino)naphthalen-1-yl)oxy)pyridin-3-yl)-N-((3S,5R)-5-methylpiperidin-3-yl)pyrimidin-2-amine

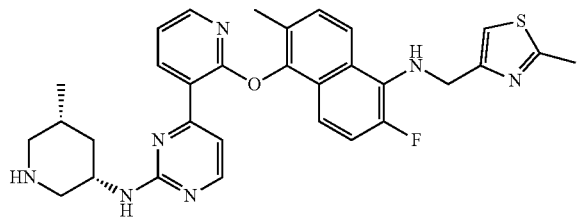 [SMILES: Cc1nc(CNc2c(F)ccc3c(Oc4ncccc4-c4ccnc(N[C@@H]5CNC[C@H](C)C5)n4)c(C)ccc23)cs1]

Prepared using (3S,5R)-benzyl 3-((4-(2-((6-fluoro-2-methyl-5-(((2-methylthiazol-4-yl)methyl)amino)naphthalen-1-yl)oxy)pyridin-3-yl)pyrimidin-2-yl)amino)-5-methylpiperidine-1-carboxylate (20 mg, 0.03 mmol), iPrOH (2 mL), ammonium formate (240 mg, 3.81 mmol), and palladium hydroxide on carbon (40 mg, 0.06 mmol) and heating at 75° C. After 4 h, the reaction mixture was filtered on celite, washed with MeOH (75 mL) and evaporated under vacuum. The residue was purified by C18 reverse phase flash chromatography (0-100% MeCN/10 mM ammonium formate aqueous solution, pH=3.8). The appropriate fractions were combined and lyophilized and the resulting residue dissolved in EtOAc (0.5 mL) and then hydrochloric acid (4 M in dioxane, 1.0 mL, 4 mmol) was added. After 10 min at rt, the resulting precipitate was collected by filtration, washed with DCM (20 mL), dissolved in water and lyophilized to provide 1.5 mg (9% yield) of 307 as an off-white solid. LCMS (ESI) [M+H]$^+$=570.2, rt=1.47 min; $^1$H NMR (400 MHz, CD$_3$OD) δ 8.80 (s, 1H), 8.46 (d, J=5.6 Hz, 1H), 8.13-7.99 (m, 2H), 7.91 (br s, 1H), 7.54 (d, J=8.4 Hz, 1H), 7.50 (d, J=7.6 Hz, 1H), 7.37 (s, 1H), 7.32-7.27 (m, 1H), 7.20 (t, J=9.5 Hz, 1H), 4.62-4.46 (m, 1H), 3.75 (d, J=11.5 Hz, 1H), 3.37 (d, J=14.4 Hz, 2H), 2.89-2.75 (m, 4H), 2.65 (t, J=12.4 Hz, 1H), 2.33-2.18 (m, 5H), 2.18-2.05 (m, 1H), 1.46 (q, J=12.2 Hz, 1H), 1.08 (d, J=6.6 Hz, 3H).

Example 308 (S)-2-(6-Methyl-5-((3-(2-(piperidin-3-ylamino)pyrimidin-4-yl)pyridin-2-yl)oxy)naphthalen-1-yl)-2-azaspiro[4.5]decan-1-one 308

Step 1: tert-Butyl (S)-3-((4-(2-((2-methyl-5-(1-oxo-2-azaspiro[4.5]decan-2-yl)naphthalen-1-yl)oxy)pyridin-3-yl)pyrimidin-2-yl)amino)piperidine-1-carboxylate

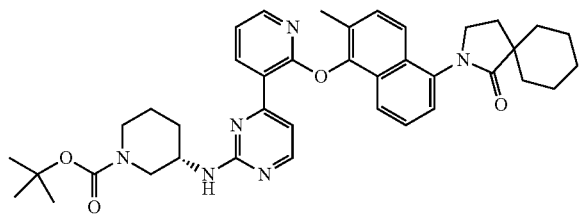 [SMILES: Cc1ccc2c(N3CCC4(CCCCC4)C3=O)cccc2c1Oc1ncccc1-c1ccnc(N[C@H]2CCCN(C(=O)OC(C)(C)C)C2)n1]

A flask containing tert-butyl (3S)-3-[[4-[2-[(5-iodo-2-methyl-1-naphthyl)oxy]-3-pyridyl]pyrimidin-2-yl]amino]piperidine-1-carboxylate (1.000 equiv, 0.2353 mmol, 150 mg) was charged with 2-azaspiro[4.5]decan-1-one (65 mg, 0.42 mmol), cuprous iodide (9.0 mg, 0.047 mmol), N,N'-dimethylethylenediamine (15.1 μL, 0.1412 mmol), potassium carbonate (0.59 mmol, 81 mg) and 1,4-dioxane (3 mL). The mixture was sparged with nitrogen for 15 min and the flask was heated at reflux overnight. After 16 hours, the mixture was cooled to room temperature and the mixture was diluted with ethyl acetate and water and the phases were separated. The organic extract was washed with saturated NaCl(aq), dried over sodium sulfate, filtered and concentrated in vacuo. The residue was purified on a silica column 10 to 80% (isopropylacetate/MeOH (3:1):heptanes) to provide 65 mg of the desired compound (42% yield).

Step 2: (S)-2-(6-Methyl-5-((3-(2-(piperidin-3-ylamino)pyrimidin-4-yl)pyridin-2-yl)oxy)naphthalen-1-yl)-2-azaspiro[4.5]decan-1-one

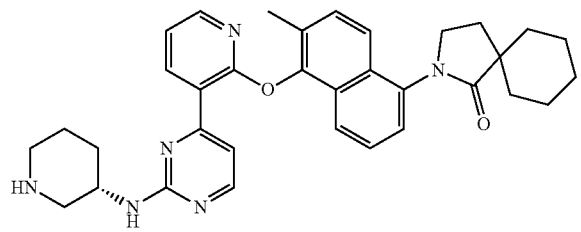 [SMILES: Cc1ccc2c(N3CCC4(CCCCC4)C3=O)cccc2c1Oc1ncccc1-c1ccnc(N[C@H]2CCCNC2)n1]

The General Procedure B was followed, using tert-Butyl (S)-3-((4-(2-((2-methyl-5-(1-oxo-2-azaspiro[4.5]decan-2-yl)naphthalen-1-yl)oxy)pyridin-3-yl)pyrimidin-2-yl)amino)piperidine-1-carboxylate (65 mg), DCM (4 mL) and hydrochloric acid (4 M in dioxane, 3 mL, 12 mmol). The residue was purified via reverse-phase HPLC and lyophilized to yield 19.9 mg (36% yield) of 308. LCMS (ESI): [M+H]$^+$=563.3; $^1$H NMR (400 MHz, DMSO-d$_6$) δ 8.55-8.45 (m, 1H), 8.43 (d, J=5.1 Hz, 1H), 8.06 (dd, J=4.8, 2.0 Hz, 1H), 7.67 (d, J=8.4 Hz, 1H), 7.58-7.36 (m, 4H), 7.31-7.19 (m, 2H), 3.99 (s, 1H), 3.79-3.75 (m, 2H), 3.21-3.18 (m, 1H), 7.41-7.39 (m, 1H), 4.04-3.93 (m, 1H), 3.78-3.75 (m, 2H), 3.22-3.17 (m, 1H), 2.95-2.86 (m, 1H), 2.63-2.51 (m, 1H), 2.21 (s, 3H), 1.99-1.88 (m, 1H), 1.78-1.22 (m, 14H).

Example 309 (R)-2-((6-Methyl-5-((3-(2-((S)-piperidin-3-ylamino)pyrimidin-4-yl)pyridin-2-yl)oxy)naphthalen-1-yl)amino)-1-phenylethanol 309

Step 1: (S)-tert-Butyl 3-((4-(2-((5-(((R)-2-hydroxy-2-phenylethyl)amino)-2-methylnaphthalen-1-yl)oxy)pyridin-3-yl)pyrimidin-2-yl)amino)piperidine-1-carboxylate

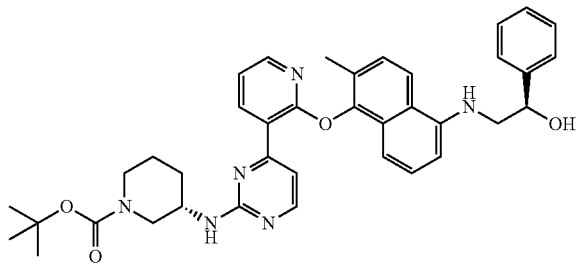 [SMILES: Cc1ccc2c(NC[C@H](O)c3ccccc3)cccc2c1Oc1ncccc1-c1ccnc(N[C@H]2CCCN(C(=O)OC(C)(C)C)C2)n1]

Prepared using tert-butyl (3S)-3-[[4-[2-[(5-amino-2-methyl-1-naphthyl)oxy]-3-pyridyl]pyrimidin-2-yl]amino]piperidine-1-carboxylate (100 mg, 0.19 mmol), (R)-styrene oxide (0.02 mL, 0.19 mmol) and acetic acid (0.30 mL). After 3 h at rt, a further portion of (R)-styrene oxide (0.02 mL, 0.19 mmol) was added. After 2 h at rt, acetic acid was evaporated under vacuum and the residue was purified by flash chromatography through silica gel (0-100% EtOAc/Hexanes) to provide 102 mg (83% yield) of the title compound. LCMS (ESI) [M+H]⁺=647.7, rt=1.99.

Step 2: (R)-2-((6-Methyl-5-((3-(2-((S)-piperidin-3-ylamino)pyrimidin-4-yl)pyridin-2-yl)oxy)naphthalen-1-yl)amino)-1-phenylethanol

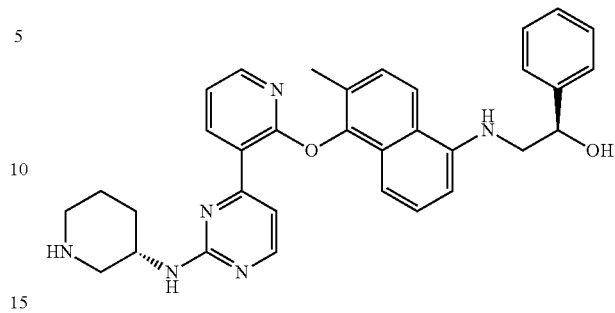

Prepared according to General Procedure B using tert-butyl 3-[[4-[2-[[5-[[(2R)-2-hydroxy-2-phenyl-ethyl]amino]-2-methyl-1-naphthyl]oxy]-3-pyridyl]pyrimidin-2-yl]amino]piperidine-1-carboxylate (20 mg, 0.02 mmol), 1,4-dioxane (1.0 mL), and hydrochloric acid (4 M in dioxane, 1.0 mL, 4.0 mmol). After 30 min, MTBE (15 mL) was added and the resulting solids were collected by filtration and purified by C18 reverse phase flash chromatography (MeCN/10 mM ammonium formate aqueous solution, pH=3.8). Appropriate fractions were combined and lyophilized and the residue thus obtained was dissolve in EtOAc (10 mL) and washed with 10% Na₂CO₃ (aq) (3 mL). The organic extract was dried (Na₂SO₄), and evaporated under vacuum. The residue obtained was dissolved in 1,4-dioxane (0.5 mL) and hydrochloric acid (4 M in dioxane, 0.1 mL, 0.4 mmol) was added and the resulting precipitate was collected by filtration, dissolved in MeCN and H₂O and lyophilized to provide 6 mg (44% yield) of 309. LCMS (ESI) [M+H]⁺=547.5, rt=1.21 min; ¹H NMR (400 MHz, d₆-DMSO) δ 9.01-8.92 (m, 1H), 8.46 (s, 1H), 8.25 (d, J=8.5 Hz, 1H), 8.04 (s, 1H), 7.59 (s, 2H), 7.47-7.41 (m, 3H), 7.29 (t, J=7.5 Hz, 2H), 7.21 (t, J=7.4 Hz, 2H), 7.00 (t, J=8.0 Hz, 1H), 6.79 (d, J=8.4 Hz, 1H), 6.20 (d, J=8.0 Hz, 1H), 4.56 (s, 1H), 3.45-3.41 (m, 1H), 3.22-3.16 (m, 1H), 2.84 (s, 2H), 2.21 (s, 3H), 2.02 (s, 1H), 1.90 (s, 1H), 1.80-1.71 (m, 1H), 1.64 (s, 1H).

Example 310 N-(2-Fluoro-6-methyl-5-((3-(2-(((3S,5R)-5-methylpiperidin-3-yl)amino)pyrimidin-4-yl)pyridin-2-yl)oxy)naphthalen-1-yl)cyclopropanecarboxamide 310

Step 1: (3S,5R)-Benzyl 3-((4-(2-((5-(cyclopropanecarboxamido)-6-fluoro-2-methylnaphthalen-1-yl)oxy)pyridin-3-yl)pyrimidin-2-yl)amino)-5-methylpiperidine-1-carboxylate

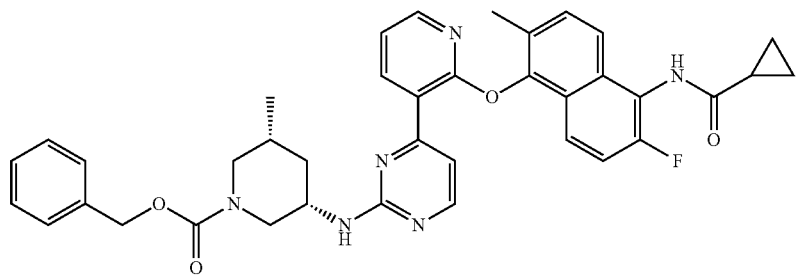 [SMILES: Cc1ccc2c(NC(=O)C3CC3)c(F)ccc2c1Oc1ncccc1-c1ccnc(N[C@H]2C[C@@H](C)CN(C(=O)OCc3ccccc3)C2)n1]

Prepared using (3S,5R)-benzyl 3-((4-(2-((5-amino-6-fluoro-2-methylnaphthalen-1-yl)oxy)pyridin-3-yl)pyrimidin-2-yl)amino)-5-methylpiperidine-1-carboxylate (100 mg, 0.17 mmol), in DCM (0.70 mL), pyridine (0.20 mL, 2.53 mmol) and cyclopropanecarbonyl chloride (36 μL, 0.34 mmol). After 3 h at rt, the reaction was diluted with DCM (15 mL), washed with saturated NH$_4$Cl(aq) (2×30 mL), brine (30 mL), dried (Na$_2$SO$_4$) and evaporated under vacuum. The residue was purified by flash chromatography through silica gel (0-50% EtOAc/DCM) to provide 68 mg (61% yield) of the title compound. LCMS (ESI) [M+H]$^+$=661.6, rt=1.92 min.

Step 2: N-(2-Fluoro-6-methyl-5-((3-(2-(((3S,5R)-5-methylpiperidin-3-yl)amino)pyrimidin-4-yl)pyridin-2-yl)oxy)naphthalen-1-yl)cyclopropanecarboxamide

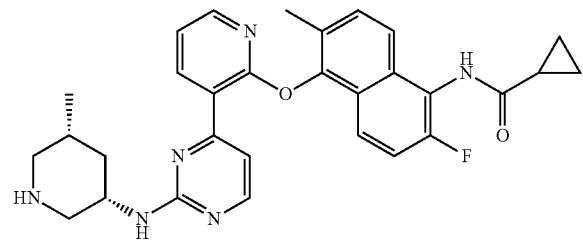 [SMILES: Cc1ccc2c(NC(=O)C3CC3)c(F)ccc2c1Oc1ncccc1-c1ccnc(N[C@@H]2CNC[C@H](C)C2)n1]

Prepared using (3S,5R)-benzyl 3-((4-(2-((5-(cyclopropanecarboxamido)-6-fluoro-2-methylnaphthalen-1-yl)oxy)pyridin-3-yl)pyrimidin-2-yl)amino)-5-methylpiperidine-1-carboxylate (70 mg, 0.11 mmol), iPrOH (2.1 mL), ammonium formate (67 mg, 1.1 mmol), palladium (23 mg of 10 wt % on carbon) and heating at 60° C. After 3 h, the reaction mixture was filtered on celite, washed with MeOH (75 mL), then DCM (75 mL) and the filtrate evaporated under vacuum. The residue was diluted with saturated NaHCO$_3$(aq) (50 mL) and DCM (25 mL) and the phases were separated and the aqueous layer was extracted with DCM (2×25 mL). The combined organic extracts were dried (Na$_2$SO$_4$), filtered, and evaporated under vacuum. The residue was dissolved in 1,4-dioxane (0.2 mL) and hydrochloric acid (4 M in dioxane, 0.13 mL, 0.53 mmol) was added. After 10 min at rt, the reaction was diluted with Et$_2$O (10 mL) and the resulting precipitate was filtered, washed with Et$_2$O (10 mL), dissolved in water and lyophilized to provide 44 mg (74% yield) of 310. LCMS (ESI) [M+H]$^+$=527.5, rt=1.32 min; $^1$H NMR (400 MHz, d$_6$-DMSO) δ 10.16 (s, 1H), 9.04 (bs, 2H), 8.72 (bs, 1H), 8.47 (d, J=5.2 Hz, 1H), 8.07 (dd, J=4.8, 2.0 Hz, 1H), 7.75 (d, J=8.6 Hz, 1H), 7.64 (dd, J=9.3, 5.0 Hz, 1H), 7.61-7.49 (m, 3H), 7.40 (t, J=9.4 Hz, 1H), 7.28 (dd, J=7.6, 4.8 Hz, 1H), 4.30 (bs, 1H), 3.20 (d, J=11.7 Hz, 1H), 2.66-2.55 (m, 1H), 2.19 (s, 3H), 2.14-1.85 (m, 3H), 1.27 (q, J=12.1 Hz, 1H), 0.93 (d, J=5.8 Hz, 3H), 0.90-0.76 (m, 4H).

Example 311 3,3,3-Trifluoro-N-(2-fluoro-6-methyl-5-((3-(2-(((3S,5R)-5-methylpiperidin-3-yl)amino)pyrimidin-4-yl)pyridin-2-yl)oxy)naphthalen-1-yl)propane-1-sulfonamide 311

Step 1: (3S,5R)-Benzyl 3-((4-(2-((6-fluoro-2-methyl-5-(3,3,3-trifluoropropylsulfonamido)naphthalen-1-yl)oxy)pyridin-3-yl)pyrimidin-2-yl)amino)-5-methylpiperidine-1-carboxylate

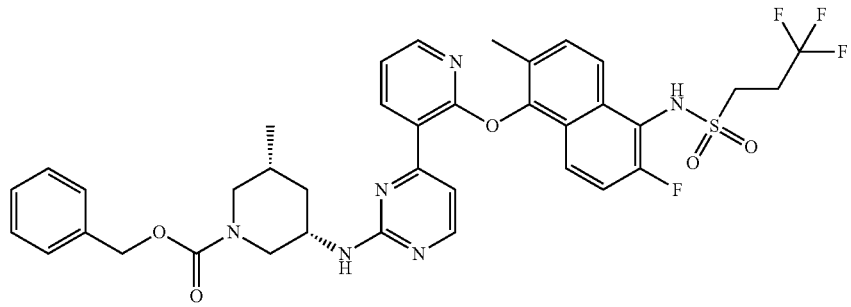 [SMILES: Cc1ccc2c(NS(=O)(=O)CCC(F)(F)F)c(F)ccc2c1Oc1ncccc1-c1ccnc(N[C@H]2C[C@@H](C)CN(C(=O)OCc3ccccc3)C2)n1]

Prepared using (3S,5R)-benzyl 3-((4-(2-((5-amino-6-fluoro-2-methylnaphthalen-1-yl)oxy)pyridin-3-yl)pyrimidin-2-yl)amino)-5-methylpiperidine-1-carboxylate (100 mg, 0.17 mmol), DCM (0.56 mL), 3,3,3-trifluoropropane-1-sulfonyl chloride (0.04 mL, 0.34 mmol), pyridine (0.2 mL, 2.5 mmol) and DMAP (3 mg, 0.02 mmol). After 16 h at rt, the reaction was diluted with DCM (15 mL) and 1N KHSO$_4$ (aq) (40 mL). The phases were separated and the aqueous layer was extracted with DCM (2×15 mL), and the combined organic extracts dried (Na$_2$SO$_4$) and evaporated under vacuum. The crude residue was purified by flash chromatography through silica gel (0-50% EtOAc/DCM) to provide 69 mg (54% yield) of the title compound. LCMS (ESI) [M+H]$^+$=753.3, rt=2.00 min.

Step 2: 3,3,3-Trifluoro-N-(2-fluoro-6-methyl-5-((3-(2-(((3S,5R)-5-methylpiperidin-3-yl)amino)pyrimidin-4-yl)pyridin-2-yl)oxy)naphthalen-1-yl)propane-1-sulfonamide

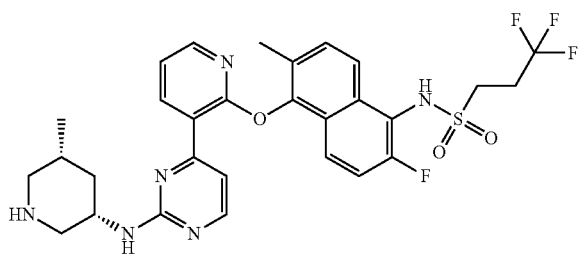 [SMILES: Cc1ccc2c(NS(=O)(=O)CCC(F)(F)F)c(F)ccc2c1Oc1ncccc1-c1ccnc(N[C@@H]2CNC[C@H](C)C2)n1]

Prepared using (3S,5R)-benzyl 3-((4-(2-((6-fluoro-2-methyl-5-(3,3,3-trifluoropropylsulfonamido)naphthalen-1-yl)oxy)pyridin-3-yl)pyrimidin-2-yl)amino)-5-methylpiperidine-1-carboxylate (69 mg, 0.09 mmol), iPrOH (0.95 mL), ammonium formate (58 mg, 0.92 mmol), palladium (20 mg of 10 wt % on carbon) and heating at 60° C. After 1.5 h, the reaction mixture was filtered on celite, washed with MeOH (75 mL), then DCM (75 mL) and the filtrate evaporated under vacuum. The residue was diluted with saturated NaHCO₃(aq) (50 mL) and EtOAc (25 mL) and the phases were separated and the aqueous layer was extracted with EtOAc (2×25 mL). The combined organic extracts were dried (Na₂SO₄), and evaporated under vacuum. The residue was dissolved in 1,4-dioxane (0.5 mL) and hydrochloric acid (4 M in dioxane, 1.0 mL, 4.0 mmol) was added. After 10 min at rt, the reaction was diluted with Et₂O (15 mL) and the resulting precipitate was filtered, washed with Et₂O (10 mL), dissolved in water and lyophilized to provide 41 mg (68% yield) of 311. LCMS (ESI) [M+H]⁺=619.3, rt=1.49 min; ¹H NMR (400 MHz, d6-dmso) δ 10.11 (s, 1H), 9.27-8.90 (m, 2H), 8.76 (s, 1H), 8.47 (d, J=5.2 Hz, 1H), 8.07 (dd, J=4.8, 1.9 Hz, 1H), 8.04 (d, J=8.7 Hz, 1H), 7.75 (dd, J=9.3, 5.2 Hz, 1H), 7.65 (d, J=8.8 Hz, 1H), 7.56 (d, J=6.8 Hz, 2H), 7.49 (t, J=9.5 Hz, 1H), 7.29 (dd, J=7.6, 4.8 Hz, 1H), 4.31 (s, 1H), 3.19 (d, J=10.5 Hz, 1H), 2.99-2.84 (m, 2H), 2.66-2.54 (m, 1H), 2.47-2.41 (m, 1H), 2.20 (s, 3H), 2.06 (d, J=12.1 Hz, 1H), 1.95 (s, 1H), 1.26 (q, J=12.2 Hz, 1H), 0.92 (s, 3H).

Example 312 (R)-1-((6-Methyl-5-((3-(2-((S)-piperidin-3-ylamino)pyrimidin-4-yl)pyridin-2-yl)oxy)naphthalen-1-yl)amino)butan-2-ol 312

Step 1: (S)-tert-Butyl 3-((4-(2-((5-(((R)-2-hydroxybutyl)amino)-2-methylnaphthalen-1-yl)oxy)pyridin-3-yl)pyrimidin-2-yl)amino)piperidine-1-carboxylate

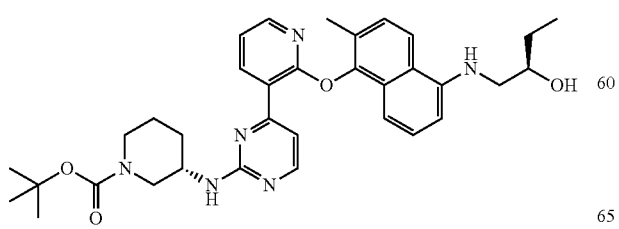

Prepared using tert-butyl (3S)-3-[[4-[2-[(5-amino-2-methyl-1-naphthyl)oxy]-3-pyridyl]pyrimidin-2-yl]amino]piperidine-1-carboxylate (75 mg, 0.14 mmol), (2R)-2-ethyloxirane (13 mg, 0.18 mmol), acetic acid (1 mL), and stirring at rt. After 16 h, the mixture was heated at 50° C. After 1 h, a further portion of (2R)-2-ethyloxirane (10.0 µL) was added and stirring continued at rt. After 72 h, acetic acid was evaporated under vacuum and the residue was purified by flash chromatography through silica gel (0-15% EtOAc/Hexanes) to provide 28 mg (33% yield) of the title compound. LCMS (ESI) [M+H]⁺=599.3, rt=1.91 min.

Step 2: (R)-1-((6-Methyl-5-((3-(2-((S)-piperidin-3-ylamino)pyrimidin-4-yl)pyridin-2-yl)oxy)naphthalen-1-yl)amino)butan-2-ol

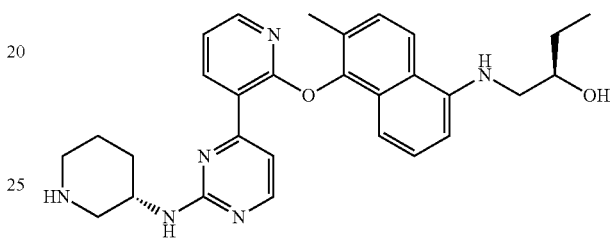

Prepared according to General Procedure B using ((S)-tert-butyl 3-((4-(2-((5-(((R)-2-hydroxybutyl)amino)-2-methylnaphthalen-1-yl)oxy)pyridin-3-yl)pyrimidin-2-yl)amino)piperidine-1-carboxylate (28 mg, 0.04 mmol), 1,4-dioxane (1.0 mL), and hydrochloric acid (4 M in dioxane, 0.5 mL, 2.0 mmol). After 3 h at rt, the volatiles were evaporated and the residue was triturated with MeCN (5 mL). The resulting precipitate was collected by filtration, dissolved in water and MeCN and lyophilized to provide 21 mg (84% yield) of 312. LCMS (ESI) [M+H]⁺=499.2, rt=1.33 min; ¹H NMR (400 MHz, CD₃OD) δ 8.83 (s, 1H), 8.49 (d, J=6.0 Hz, 1H), 8.11-8.00 (m, 2H), 7.94 (s, 1H), 7.84 (d, J=8.4 Hz, 1H), 7.71 (d, J=8.8 Hz, 1H), 7.59 (d, J=7.4 Hz, 1H), 7.55-7.48 (m, 1H), 7.32 (dd, J=7.6, 4.9 Hz, 1H), 4.55 (s, 1H), 3.95-3.83 (m, 1H), 3.71-3.57 (m, 2H), 3.46-3.35 (m, 2H), 3.17-3.01 (m, 2H), 2.32 (s, 3H), 2.24 (d, J=12.8 Hz, 1H), 2.19-2.07 (m, 1H), 2.04-1.78 (m, 2H), 1.66-1.52 (m, 2H), 1.01 (t, J=7.4 Hz, 3H).

Example 313 (S)-1-((6-Methyl-5-((3-(2-((S)-piperidin-3-ylamino)pyrimidin-4-yl)pyridin-2-yl)oxy)naphthalen-1-yl)amino)butan-2-ol 313

Step 1: (S)-tert-Butyl 3-((4-(2-((5-(((S)-2-hydroxybutyl)amino)-2-methylnaphthalen-1-yl)oxy)pyridin-3-yl)pyrimidin-2-yl)amino)piperidine-1-carboxylate

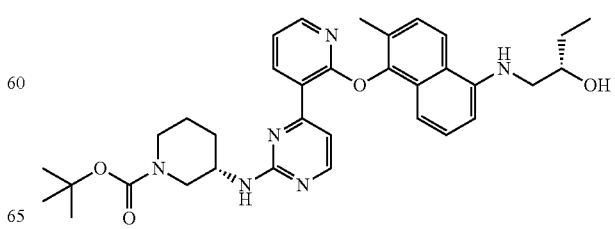

Prepared using tert-butyl (3S)-3-[[4-[2-[(5-amino-2-methyl-1-naphthyl)oxy]-3-pyridyl]pyrimidin-2-yl]amino]piperidine-1-carboxylate (75 mg, 0.14 mmol), (2S)-2-ethyloxirane (13 mg, 0.18 mmol), and acetic acid (1 mL). After 16 h at rt, the mixture was heated to 50° C. for 1 h. To the reaction mixture was then added (2S)-2-ethyloxirane (10 µL) and stirred at rt. After 72 h, acetic acid was evaporated under vacuum and the residue was purified by flash chromatography through silica gel (0-15% EtOAc/Hexanes) to provide 28 mg (33% yield) of the title compound. LCMS (ESI) [M+H]$^+$=599.4, rt=1.92 min.

Step 2: (S)-1-((6-Methyl-5-((3-(2-((S)-piperidin-3-ylamino)pyrimidin-4-yl)pyridin-2-yl)oxy)naphthalen-1-yl)amino)butan-2-ol

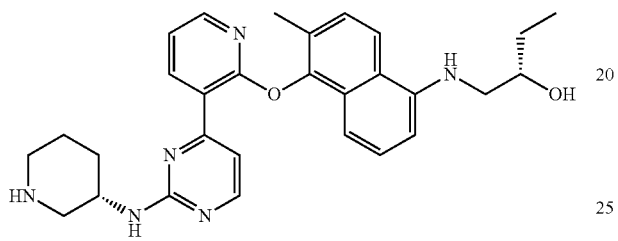

Prepared according to General Procedure B using ((S)-tert-butyl 3-((4-(2-((5-(((S)-2-hydroxybutyl)amino)-2-methylnaphthalen-1-yl)oxy)pyridin-3-yl)pyrimidin-2-yl)amino)piperidine-1-carboxylate (27 mg, 0.05 mmol), 1,4-dioxane (1.0 mL), and hydrochloric acid (4 M in dioxane, 0.5 mL, 2.0 mmol). After 3 h at rt, the volatiles were evaporated and the residue was triturated with MeCN (5 mL). The resulting precipitate was collected by filtration, dissolved in water and MeCN and lyophilized to provide 20 mg (83% yield) of 313. LCMS (ESI) [M+H]$^+$=499.2, rt=1.33 min; $^1$H NMR (400 MHz, CD$_3$OD) δ 8.86 (s, 1H), 8.49 (d, J=6.1 Hz, 1H), 8.11-8.02 (m, 2H), 7.98 (s, 1H), 7.84 (d, J=8.5 Hz, 1H), 7.72 (d, J=8.8 Hz, 1H), 7.61 (d, J=6.8 Hz, 1H), 7.57-7.49 (m, 1H), 7.33 (dd, J=7.6, 4.8 Hz, 1H), 4.58 (s, 1H), 3.93-3.84 (m, 1H), 3.71-3.57 (m, 2H), 3.46-3.35 (m, 2H), 3.16-3.02 (m, 2H), 2.32 (s, 3H), 2.29-2.20 (m, 1H), 2.19-2.08 (m, 1H), 2.05-1.79 (m, 2H), 1.66-1.51 (m, 2H), 1.01 (t, J=7.4 Hz, 3H).

Example 314 (S)-Methyl 2-((6-methyl-5-((3-(2-(piperidin-3-ylamino)pyrimidin-4-yl)pyridin-2-yl)oxy)naphthalen-1-yl)amino)acetate 314

Step 1: (S)-tert-Butyl 3-((4-(2-((5-((2-methoxy-2-oxoethyl)amino)-2-methylnaphthalen-1-yl)oxy)pyridin-3-yl)pyrimidin-2-yl)amino)piperidine-1-carboxylate

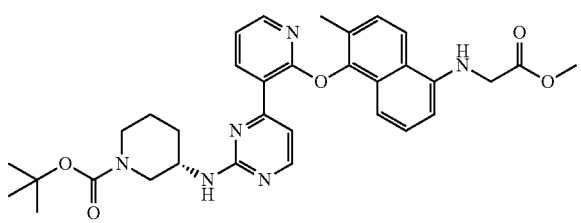 [SMILES: COC(=O)CNc1cccc2c(Oc3ncccc3-c3ccnc(N[C@H]4CCCN(C(=O)OC(C)(C)C)C4)n3)c(C)ccc12]

To a solution of tert-butyl (3S)-3-[[4-[2-[(5-amino-2-methyl-1-naphthyl)oxy]-3-pyridyl]pyrimidin-2-yl]amino]piperidine-1-carboxylate (250 mg, 0.470 mmol) and methyl bromoacetate (80 mg, 0.52 mmol) in DMF (2 mL) was added N,N-diisopropylethylamine (0.12 mL, 0.71 mmol) and the vial was sealed and placed in a 50° C. oil bath. After 16 h, the reaction mixture was diluted with EtOAc (75 mL), washed with H$_2$O (10 mL), saturated NaHCO$_3$(aq) (10 mL), 50% saturated NaCl(aq) (4×10 mL), dried (Na$_2$SO$_4$), filtered and concentrated under vacuum. The residue was purified by flash chromatography through silica gel (0-100% EtOAc/Hexanes) to provide 224 mg (79% yield) of the title compound as an orange powder. LCMS (ESI) [M+H]$^+$=599.3, rt=1.92 min.

Step 2: (S)-Methyl 2-((6-methyl-5-((3-(2-(piperidin-3-ylamino)pyrimidin-4-yl)pyridin-2-yl)oxy)naphthalen-1-yl)amino)acetate

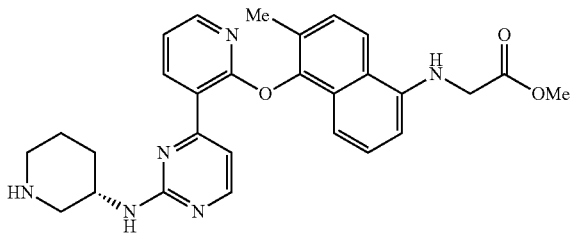 [SMILES: COC(=O)CNc1cccc2c(Oc3ncccc3-c3ccnc(N[C@H]4CCCNC4)n3)c(C)ccc12]

Prepared according to General Procedure B using ((S)-tert-butyl 3-((4-(2-((5-((2-methoxy-2-oxoethyl)amino)-2-methylnaphthalen-1-yl)oxy)pyridin-3-yl)pyrimidin-2-yl)amino)piperidine-1-carboxylate (40 mg, 0.07 mmol), EtOAc (2 mL), and hydrochloric acid (4 M in dioxane, 1 mL, 4 mmol). After 3 h, the volatiles were evaporated. The residue was purified directly by C18 reverse phase flash chromatography (20-100% MeCN/10 mM ammonium formate aqueous solution, pH=3.8). Appropriate fractions were combined and lyophilized to provide 7 mg (21% yield) of 314. LCMS (ESI) [M+H]$^+$=499.3, rt=1.05 min; $^1$H NMR (400 MHz, d6-dmso) δ 8.57-8.45 (m, 1H), 8.41 (d, J=5.1 Hz, 1H), 8.29 (s, 1H), 8.08-7.91 (m, 2H), 7.46 (d, J=5.1 Hz, 1H), 7.39 (d, J=8.7 Hz, 1H), 7.28-7.19 (m, 2H), 7.15 (t, J=8.0 Hz, 1H), 6.89 (d, J=8.2 Hz, 1H), 6.78 (t, J=6.3 Hz, 1H), 6.27 (d, J=7.6 Hz, 1H), 4.10 (d, J=6.1 Hz, 2H), 4.04-3.87 (m, 1H), 3.66 (s, 3H), 3.18 (d, J=10.2 Hz, 1H), 2.89 (d, J=11.8 Hz, 1H), 2.61-2.55 (m, 2H), 2.19 (s, 3H), 2.00-1.87 (m, 1H), 1.76-1.64 (m, 1H), 1.59-1.42 (m, 2H).

Example 315 (R)-3-(Fluoromethyl)-1-(6-methyl-5-((3-(2-(((S)-piperidin-3-yl)amino)pyrimidin-4-yl)pyridin-2-yl)oxy)naphthalen-1-yl)pyrrolidin-2-one

Step 1: tert-Butyl (S)-3-((4-(2-((5-(-3-(hydroxymethyl)-2-oxopyrrolidin-1-yl)-2-methylnaphthalen-1-yl)oxy)pyridin-3-yl)pyrimidin-2-yl)amino)piperidine-1-carboxylate

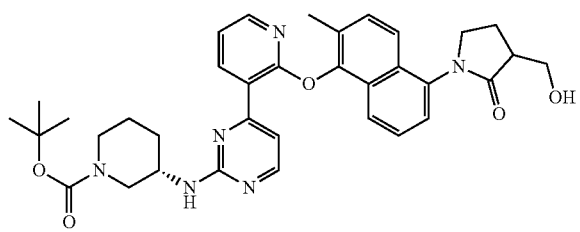 [SMILES: Cc1ccc2c(N3CCC(CO)C3=O)cccc2c1Oc1ncccc1-c1ccnc(N[C@H]2CCCN(C(=O)OC(C)(C)C)C2)n1]

A flask containing tert-butyl (3S)-3-[[4-[2-[(5-iodo-2-methyl-1-naphthyl)oxy]-3-pyridyl]pyrimidin-2-yl]amino]piperidine-1-carboxylate (200 mg, 0.31 mmol) was charged with 3-(hydroxymethyl)pyrrolidin-2-one (65 mg, 0.56 mmol), copper iodide (12 mg, 0.063 mmol), N,N'-dimethylethylenediamine (20 µL, 0.19 mmol), potassium carbonate (0.78 mmol, 108 mg) and 1,4-dioxane (3 mL). The mixture was sparged with nitrogen for 15 min and the flask was heated at reflux overnight. After 16 hours, the mixture was cooled to room temperature and the mixture was diluted with ethyl acetate and water and the phases were separated. The organic extract was washed with saturated NaCl(aq), dried over sodium sulfate, filtered and concentrated in vacuo. The residue was purified on a silica column 10 to 80% (isopropylacetate/MeOH (3:1):heptanes) to provide 150 mg of the desired compound (77% yield) as a mixture of two diastereomers.

Step 2: tert-Butyl (S)-3-((4-(2-((5-((R)-3-(fluoromethyl)-2-oxopyrrolidin-1-yl)-2-methylnaphthalen-1-yl)oxy)pyridin-3-yl)pyrimidin-2-yl)amino)piperidine-1-carboxylate

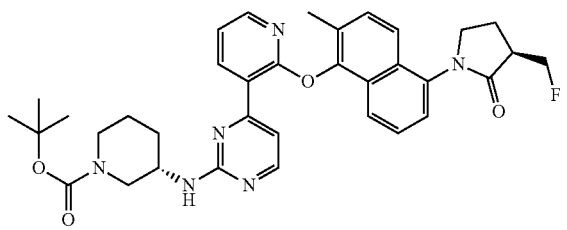 [SMILES: Cc1ccc2c(N3CC[C@@H](CF)C3=O)cccc2c1Oc1ncccc1-c1ccnc(N[C@H]2CCCN(C(=O)OC(C)(C)C)C2)n1]

To a solution of tert-butyl (S)-3-((4-(2-((5-(-3-(hydroxymethyl)-2-oxopyrrolidin-1-yl)-2-methylnaphthalen-1-yl)oxy)pyridin-3-yl)pyrimidin-2-yl)amino)piperidine-1-carboxylate (110 mg, 0.176 mmol) in DCM (10 mL), was added diethylaminosulfur trifluoride (83 µL, 0.63 mmol) dropwise at −78° C. The reaction mixture was slowly warmed until rt and stirred overnight. The residue was purified via reverse-phase HPLC to provide 51.3 mg of a mixture of the two isomers, this mixture was then purified via chiral reverse-phase HPLC and lyophilized to yield 16.2 mg and 16 mg, of the two single stereoisomers of the lactam.

Step 3: (R)-3-(Fluoromethyl)-1-(6-methyl-5-((3-(2-(((S)-piperidin-3-yl)amino)pyrimidin-4-yl)pyridin-2-yl)oxy)naphthalen-1-yl)pyrrolidin-2-one

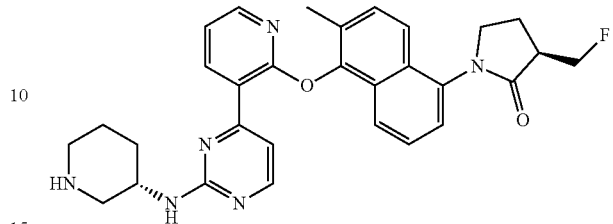

The General Procedure B was followed, using tert-butyl (S)-3-((4-(2-((5-((R)-3-(fluoromethyl)-2-oxopyrrolidin-1-yl)-2-methylnaphthalen-1-yl)oxy)pyridin-3-yl)pyrimidin-2-yl)amino)piperidine-1-carboxylate (16 mg, 0.0255 mmol), DCM (4 mL) and hydrochloric acid (4 M in dioxane, 3 mL, 12 mmol). The residue was purified via reverse-phase HPLC and lyophilized to yield 10.9 mg of 315. LCMS (ESI): [M+H]$^+$=527.2; $^1$H NMR (400 MHz, DMSO-d$_6$) δ 8.51 (d, J=7.6 Hz, 1H), 8.41 (d, J=5.1 Hz, 1H), 8.06 (dd, J=4.8, 2.0 Hz, 1H), 7.69 (d, J=8.3 Hz, 1H), 7.60 (d, J=8.5 Hz, 1H), 7.53-7.39 (m, 4H), 7.27 (dd, J=7.6, 4.8 Hz, 1H), 7.15 (d, J=8.0 Hz, 1H), 4.93-4.62 (m, 2H), 3.96-3.85 (m, 2H), 3.77-3.69 (m, 1H), 3.19-3.03 (m, 2H), 2.87-2.77 (m, 1H), 2.35-2.26 (m, 1H), 2.22 (s, 3H), 1.97-1.89 (m, 1H), 1.72-1.62 (m, 1H), 1.56-1.40 (m, 2H). The absolute stereochemistry of the lactam was assigned based on the cellular potency,

Example 316 (S)-3-(Fluoromethyl)-1-(6-methyl-5-((3-(2-(((S)-piperidin-3-yl)amino)pyrimidin-4-yl)pyridin-2-yl)oxy)naphthalen-1-yl)pyrrolidin-2-one


The General Procedure B was followed, using tert-butyl (S)-3-((4-(2-((5-((S)-3-(fluoromethyl)-2-oxopyrrolidin-1-yl)-2-methylnaphthalen-1-yl)oxy)pyridin-3-yl)pyrimidin-2-yl)amino)piperidine-1-carboxylate (16.2 mg, 0.0258 mmol), DCM (4 mL) and hydrochloric acid (4 M in dioxane, 3 mL, 12 mmol). The residue was purified via reverse-phase HPLC and lyophilized to yield 11.2 mg of 316. LCMS (ESI): [M+H]$^+$=527.2; $^1$H NMR (400 MHz, DMSO-d$_6$) δ 8.51 (d, J=7.5 Hz, 1H), 8.41 (d, J=5.1 Hz, 1H), 8.06 (dd, J=4.8, 2.0 Hz, 1H), 7.69 (d, J=8.4 Hz, 1H), 7.60 (d, J=8.6 Hz, 1H), 7.55-7.40 (m, 4H), 7.27 (dd, J=7.6, 4.8 Hz, 1H), 7.14 (d, J=8.0 Hz, 1H), 4.93-4.62 (m, 2H), 3.96-3.85 (m, 2H), 3.78-3.69 (m, 1H), 3.19-3.06 (m, 2H), 2.87-2.79 (m, 1H), 2.35-2.26 (m, 1H), 2.22 (s, 3H), 1.97-1.90 (m, 1H), 1.69-1.62 (m, 1H), 1.56-1.42 (m, 2H). The absolute stereochemistry of the lactam was assigned based on the cellular potency, Example 317 N-(2-Fluoro-6-methyl-5-((3-(2-(((3S,5R)-5-methylpiperidin-3-yl)amino)pyrimidin-4-yl)pyridin-2-yl)oxy)naphthalen-1-yl)cyclohexanesulfonamide 317

Step 1: (3S,5R)-Benzyl 3-((4-(2-((5-(cyclohexanesulfonamido)-6-fluoro-2-methylnaphthalen-1-yl)oxy)pyridin-3-yl)pyrimidin-2-yl)amino)-5-methylpiperidine-1-carboxylate

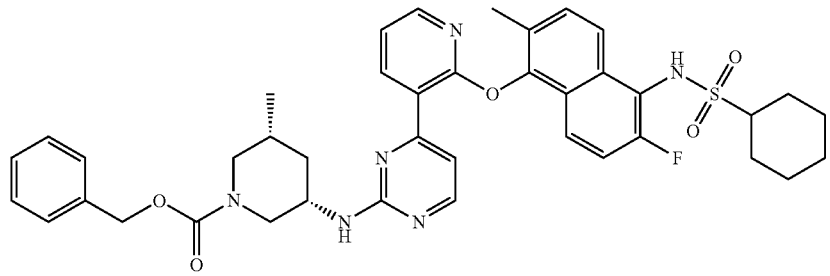 [SMILES: Cc1ccc2c(NS(=O)(=O)C3CCCCC3)c(F)ccc2c1Oc1ncccc1-c1ccnc(N[C@H]2C[C@@H](C)CN(C(=O)OCc3ccccc3)C2)n1]

Prepared using benzyl (3S,5R)-benzyl 3-((4-(2-((5-amino-6-fluoro-2-methylnaphthalen-1-yl)oxy)pyridin-3-yl)pyrimidin-2-yl)amino)-5-methylpiperidine-1-carboxylate (100 mg, 0.17 mmol), DCM (1 mL), cyclohexanesulfonyl chloride (0.17 mL, 1.18 mmol), pyridine (0.2 mL, 2.5 mmol) and DMAP (4 mg, 0.03 mmol). After 72 h at rt, the volatiles were evaporated and the residue was purified by prep TLC (EtOAc/Hexanes). The product containing band was scratched from the plate and EtOAc (20 mL) was added and the mixture stirred for 15 min, filtered and evaporated. The residue was further purified by C18 reverse phase flash chromatography (50-90% MeCN/10 mM ammonium formate aqueous solution, pH=3.8). Appropriate fractions were combined and lyophilized and the material was further purified by C18 reverse phase flash chromatography (50-90% MeCN/10 mM ammonium formate aqueous solution, pH=3.8). Appropriate fractions were combined and lyophilized to provide 12 mg (10% yield) of the title compound. LCMS (ESI) [M+H]$^+$=739.7, rt=2.10 min.

Step 2: N-(2-Fluoro-6-methyl-5-((3-(2-(((3S,5R)-5-methylpiperidin-3-yl)amino)pyrimidin-4-yl)pyridin-2-yl)oxy)naphthalen-1-yl)cyclohexanesulfonamide

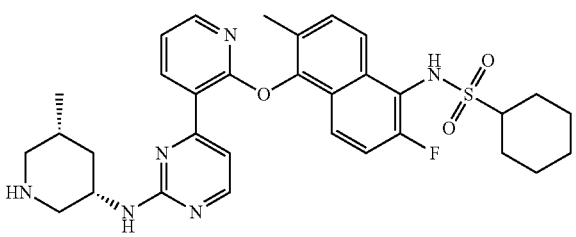 [SMILES: Cc1ccc2c(NS(=O)(=O)C3CCCCC3)c(F)ccc2c1Oc1ncccc1-c1ccnc(N[C@@H]2CNC[C@H](C)C2)n1]

Prepared using (3S,5R)-benzyl 3-((4-(2-((5-(cyclohexanesulfonamido)-6-fluoro-2-methylnaphthalen-1-yl)oxy)pyridin-3-yl)pyrimidin-2-yl)amino)-5-methylpiperidine-1-carboxylate (12 mg, 0.02 mmol), iPrOH (0.5 mL), ammonium formate (30 mg, 0.49 mmol), palladium (10 mg of 10 wt % on carbon) and heating at 70° C. After 1 h, the reaction mixture was filtered on celite, washed with MeOH (75 mL), EtOAc (75 mL) and evaporated under vacuum. The residue was diluted with saturated NaHCO$_3$(aq) (50 mL) and EtOAc (25 mL) and the phases were separated and the aqueous layer was extracted with EtOAc (2×25 mL), and the combined organic extracts were dried (MgSO$_4$), filtered, and evaporated under vacuum. The residue obtained was dissolved in 1,4-dioxane (1 mL) and hydrochloric acid (4 M in dioxane, 0.2 mL, 0.8 mmol) was added. After 10 min at rt, the reaction was diluted with MTBE (5 mL) and the resulting precipitate was filtered, dissolved with water and MeCN and lyophilized to provide 7 mg (67% yield) of 317. LCMS (ESI) [M+H]$^+$=605.6, rt=1.55 min; $^1$H NMR (400 MHz, d$_6$-DMSO) δ 9.55 (s, 1H), 8.80-8.70 (m, 2H), 8.45 (d, J=5.2 Hz, 1H), 8.05 (d, J=9.3 Hz, 2H), 7.73-7.66 (m, 1H), 7.62 (d, J=8.8 Hz, 1H), 7.58-7.47 (m, 2H), 7.42 (s, 1H), 7.27 (d, J=7.5 Hz, 1H), 3.06-2.98 (m, 1H), 2.44 (s, 2H), 2.18 (s, 3H), 2.07-2.00 (m, 1H), 1.87-1.80 (m, 2H), 1.69-1.62 (m, 1H), 1.55-1.40 (m, 2H), 1.27 (s, 4H), 0.92 (s, 2H).

Example 318 (S)—N-(2,6-Dimethyl-5-((3-(2-(piperidin-3-ylamino)pyrimidin-4-yl)pyridin-2-yl)oxy)naphthalen-1-yl)-3,3,3-trifluoropropane-1-sulfonamide 318

Step 1: (S)-tert-Butyl 3-((4-(2-((5-amino-6-bromo-2-methylnaphthalen-1-yl)oxy)pyridin-3-yl)pyrimidin-2-yl)amino)piperidine-1-carboxylate

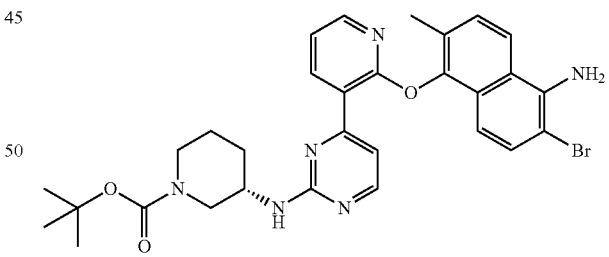

To a solution of tert-butyl (3S)-3-[[4-[2-[(5-amino-2-methyl-1-naphthyl)oxy]-3-pyridyl]pyrimidin-2-yl]amino]piperidine-1-carboxylate (1.0 g, 1.90 mmol) in MeCN (10 mL) and DCM (10 mL) at 0° C. was added a solution of N-bromosuccinimide (freshly recrystallized in water) (237 mg, 1.33 mmol) in MeCN (10 mL) dropwise. The reaction was stirred at 0° C. for 30 minutes then diluted with DCM and saturated NaHCO$_3$(aq), and the phases were separated. The aqueous phase was extracted twice more with DCM, and the combined organic phases were dried (Na$_2$SO$_4$), filtered and concentrated. The crude product was purified by flash chromatography through silica gel (15%-60% EtOAc/ hexanes) to provide 719 mg (62% yield) of the title compound. LCMS (ESI) [M+H]⁺=606.5, rt=2.03 min.

Step 2: (S)-tert-Butyl 3-((4-(2-((5-amino-2,6-dimethylnaphthalen-1-yl)oxy)pyridin-3-yl)pyrimidin-2-yl)amino)piperidine-1-carboxylate

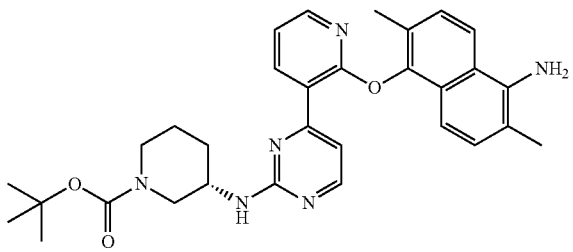 [SMILES: Cc1ccc2c(Oc3ncccc3-c3ccnc(N[C@H]4CCCN(C(=O)OC(C)(C)C)C4)n3)c(C)ccc2c1N]

In a disposable sealed tube under nitrogen were added tert-butyl (3S)-3-[[4-[2-[(5-amino-6-bromo-2-methyl-1-naphthyl)oxy]-3-pyridyl]pyrimidin-2-yl]amino]piperidine-1-carboxylate (630 mg, 1.04 mmol), cesium carbonate (1.02 g, 3.12 mmol), and methylboronic acid (934 mg, 15.6 mmol). Degassed 1,4-dioxane (8.7 mL) and degassed water (1.7 mL) were then added followed by 1,1-bis(diphenylphosphino)ferroce-palladium dichloride-CH₂Cl₂ adduct (170 mg, 0.21 mmol). The tube was sealed and the reaction mixture was stirred at 90° C. for 18 h. The mixture was then filtered through celite, washed with EtOAc and DCM and concentrated. The residue was partitioned between water and EtOAc and the phases were separated. The organic extract was washed twice with saturated NaCl(aq), dried (MgSO₄), filtered and concentrated. The crude was purified by C18 reverse phase flash chromatography (60%-100% MeCN/10 mM aqueous ammonium formate, pH=3.8). The appropriate fractions were combined and concentrated to remove most of the MeCN. The resulting aqueous solution was extracted three times with DCM, then dried by passing through a phase cartridge separator, and concentrated to provide 275 mg (49% yield) of the title compound. LCMS (ESI) [M+H]⁺=541.6, rt=1.90 min.

Step 3: (S)-tert-Butyl 3-((4-(2-((2,6-dimethyl-5-(3,3,3-trifluoropropylsulfonamido)naphthalen-1-yl)oxy)pyridin-3-yl)pyrimidin-2-yl)amino)piperidine-1-carboxylate

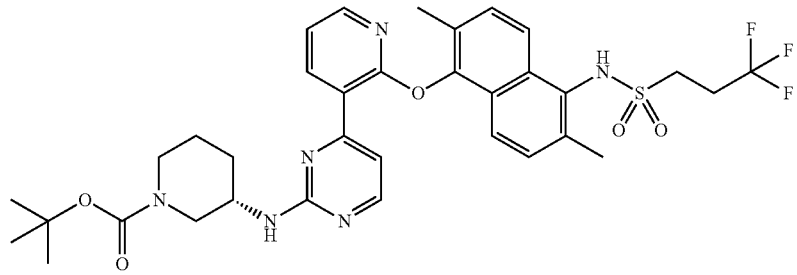 [SMILES: Cc1ccc2c(Oc3ncccc3-c3ccnc(N[C@H]4CCCN(C(=O)OC(C)(C)C)C4)n3)c(C)ccc2c1NS(=O)(=O)CCC(F)(F)F]

Prepared using tert-butyl (3S)-3-[[4-[2-[(5-amino-2,6-dimethyl-1-naphthyl)oxy]-3-pyridyl]pyrimidin-2-yl]amino]piperidine-1-carboxylate (90 mg, 0.17 mmol), 3,3,3-trifluoropropane-1-sulfonyl chloride (42.0 µL, 0.33 mmol), pyridine (202 µL, 2.5 mmol), 4-dimethylaminopyridine (2.0 mg, 0.02 mmol) and DCM (0.9 mL). The reaction mixture was stirred at rt for 18 h then diluted with DCM and 1M KHSO₄(aq). The phases were separated and the aqueous phase was extracted again with DCM. The combined organic phases were dried by passing through a phase cartridge separator and concentrated. The crude product was purified by flash chromatography through silica gel (0-60% EtOAc/DCM) to provide 107 mg (92% yield) of the title compound. LCMS (ESI) [M+H]⁺=701.4, rt=1.97 min.

Step 4: (S)—N-(2,6-Dimethyl-5-((3-(2-(piperidin-3-ylamino)pyrimidin-4-yl)pyridin-2-yl)oxy)naphthalen-1-yl)-3,3,3-trifluoropropane-1-sulfonamide

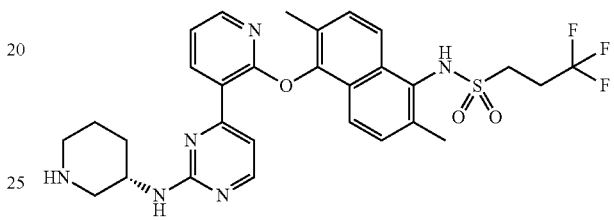

Prepared according to General Procedure B using tert-butyl (3S)-3-[[4-[2-[[2,6-dimethyl-5-(3,3,3-trifluoropropylsulfonylamino)-1-naphthyl]oxy]-3-pyridyl]pyrimidin-2-yl]amino]piperidine-1-carboxylate (107 mg, 0.15 mmol), 1,4-dioxane (0.5 mL) and hydrochloric acid (4N in dioxane, 1.2 mL, 4.84 mmol). The reaction mixture was stirred at rt for 40 min then diluted with Et₂O, and the resulting solids were collected by filtration and washed with Et₂O. The collected solids were dissolved in water and MeCN and lyophilized to provide 76 mg (78% yield) of 318. LCMS (ESI) [M+H]⁺=601.2, rt=1.46 min; ¹H NMR (400 MHz, d6-dmso) δ 9.75 (s, 1H), 8.89 (bs, 2H), 8.67 (s, 1H), 8.47 (dd, J=5.2, 0.6 Hz, 1H), 8.06 (dd, J=4.8, 1.9 Hz, 1H), 8.01 (d, J=8.7 Hz, 1H), 7.67-7.51 (m, 4H), 7.37 (d, J=8.8 Hz, 1H), 7.27 (dd, J=7.6, 4.8 Hz, 1H), 4.28 (s, 1H), 3.21 (d, J=12.5 Hz, 1H), 3.01-2.72 (m, 4H), 2.49 (s, 3H), 2.20 (s, 3H), 2.12-1.98 (m, 1H), 1.98-1.85 (m, 1H), 1.85-1.71 (m, 1H), 1.71-1.52 (m, 1H).

Example 319 (S)-3-((2,6-Dimethyl-5-((3-(2-((S)-piperidin-3-ylamino)pyrimidin-4-yl)pyridin-2-yl)oxy)naphthalen-1-yl)amino)-1,1,1-trifluoropropan-2-ol 319

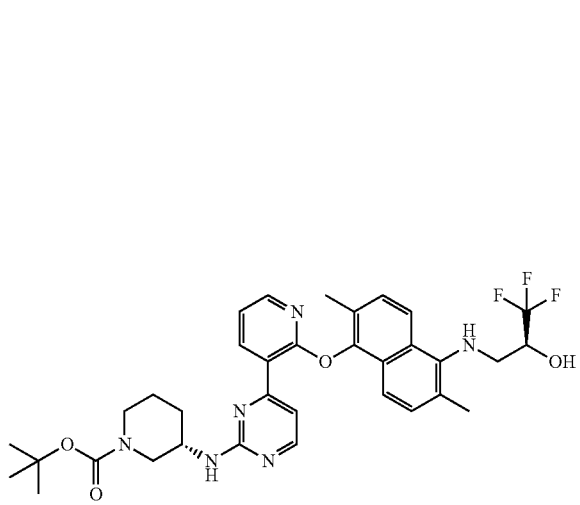

Step 1: (S)-tert-Butyl 3-((4-(2-((2,6-dimethyl-5-(((S)-3,3,3-trifluoro-2-hydroxypropyl)amino)naphthalen-1-yl)oxy)pyridin-3-yl)pyrimidin-2-yl)amino)piperidine-1-carboxylate Prepared using tert-butyl (3S)-3-[[4-[2-[(5-amino-2,6-dimethyl-1-naphthyl)oxy]-3-pyridyl]pyrimidin-2-yl]amino]piperidine-1-carboxylate (90 mg, 0.17 mmol), (2S)-2-(trifluoromethyl)oxirane (37 mg, 0.33 mmol) and acetic acid (0.9 mL). After 18 h at rt, the reaction mixture was stirred at 50° C. After 20 h, acetic acid was evaporated in vacuo then the residue was diluted with EtOAc, washed with saturated NaHCO₃(aq), dried (Na₂SO₄), filtered and concentrated. The crude product was purified by flash chromatography through silica gel (0-60% EtOAc/DCM) to provide 50 mg (46% yield) of the title compound. LCMS (ESI) [M+H]⁺=653.7, rt=2.03 min.

Step 2: (S)-3-((2,6-Dimethyl-5-((3-(2-((S)-piperidin-3-ylamino)pyrimidin-4-yl)pyridin-2-yl)oxy)naphthalen-1-yl)amino)-1,1,1-trifluoropropan-2-ol

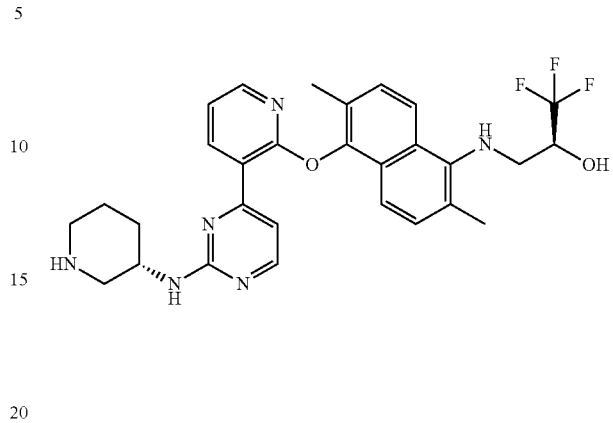

Prepared using tert-butyl (3S)-3-[[4-[2-[[2,6-dimethyl-5-[[(2S)-3,3,3-trifluoro-2-hydroxy-propyl]amino]-1-naphthyl]oxy]-3-pyridyl]pyrimidin-2-yl]amino]piperidine-1-carboxylate (50 mg, 0.08 mmol), 1,4-dioxane (0.5 mL) and hydrochloric acid (4N in dioxane, 0.6 mL, 2.4 mmol). The reaction mixture was stirred at rt for 40 min then diluted with Et₂O, and the resulting solids collected by filtration and washed with Et₂O. The solids were then dissolved in water and MeCN and lyophilized to provide 42 mg (93% yield) of 319. LCMS (ESI) [M+H]⁺=553.3, rt=1.44 min ¹H NMR (400 MHz, d6-dmso) δ 9.05 (bs, 2H), 8.74 (bs, 1H), 8.48 (d, J=5.3 Hz, 1H), 8.11-7.99 (m, 2H), 7.81-7.52 (m, 2H), 7.44 (d, J=8.8 Hz, 1H), 7.34-7.14 (m, 4H), 4.45-4.16 (m, 3H), 3.49-3.34 (m, 2H), 3.31-3.11 (m, 2H), 2.98-2.77 (m, 2H), 2.40 (s, 3H), 2.18 (s, 3H), 2.08-1.98 (m, 1H), 1.98-1.85 (m, 1H), 1.85-1.70 (m, 1H), 1.70-1.55 (m, 1H).

Example 321 (S)-1,1,1-Trifluoro-3-((6-methyl-5-((3-(2-(((3S,5R)-5-methylpiperidin-3-yl)amino)pyrimidin-4-yl)oxy)pyridin-2 naphthalen-1-yl)amino)propan-2-ol 321

Step 1: (3R,5S)-Benzyl 3-methyl-5-((4-(2-((2-methyl-5-(((S)-3,3,3-trifluoro-2-hydroxypropyl)amino)naphthalen-1-yl)oxy)pyridin-3-yl)pyrimidin-2-yl)amino)piperidine-1-carboxylate

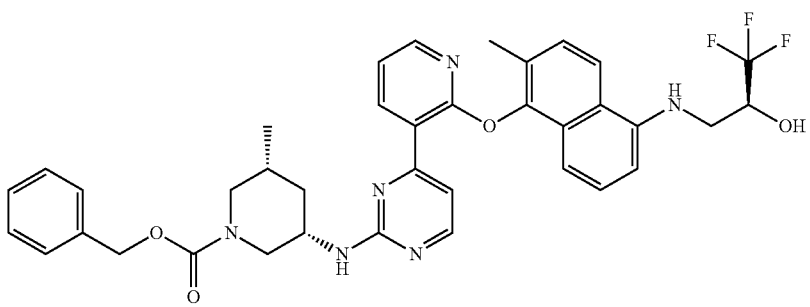 [SMILES: Cc1ccc2c(NC[C@H](O)C(F)(F)F)cccc2c1Oc1ncccc1-c1ccnc(N[C@H]2C[C@@H](C)CN(C(=O)OCc3ccccc3)C2)n1]

Prepared using benzyl (3S,5R)-3-[[4-[2-[(5-amino-2-methyl-1-naphthyl)oxy]-3-pyridyl]pyrimidin-2-yl]amino]-5-methyl-piperidine-1-carboxylate (100 mg, 0.17 mmol), (2S)-2-(trifluoromethyl)oxirane (0.03 mL, 0.35 mmol) and acetic acid (0.87 mL). After 16 h at rt, the mixture was then heated to 55° C. for 5.5 h. Acetic acid was then evaporated in vacuo and the residue was diluted with EtOAc and saturated NaHCO₃(aq), the phases were separated and the organic extract dried (Na₂SO₄), filtered and evaporated. The residue obtained was purified by flash chromatography through silica gel (0-25% EtOAc/DCM) to provide 55 mg (46% yield) of the title compound. LCMS (ESI) [M+H]⁺=687.4, rt=2.03 min.

Step 2: (S)-1,1,1-Trifluoro-3-((6-methyl-5-((3-(2-(((3S,5R)-5-methylpiperidin-3-yl)amino)pyrimidin-4-yl)pyridin-2-yl)oxy)naphthalen-1-yl)amino)propan-2-ol

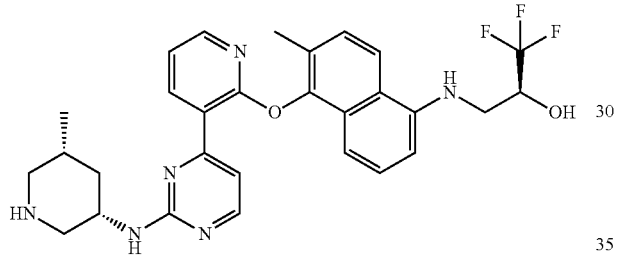

Prepared using benzyl (3R,5S)-3-methyl-5-[[4-[2-[[2-methyl-5-[[(2S)-3,3,3-trifluoro-2-hydroxy-propyl]amino]-1-naphthyl]oxy]-3-pyridyl]pyrimidin-2-yl]amino]piperidine-1-carboxylate (55 mg, 0.08 mmol), ammonium formate (50 mg, 0.8 mmol), palladium (17 mg of 10% w/w on activated carbon), and iPrOH (1.6 mL) and heating at 60° C. After 1 h, the reaction mixture was filtered through celite, washed with MeOH and DCM and the filtrate evaporated. The residue obtained was diluted with saturated NaHCO₃ (aq) and EtOAc and the phases were separated and the organic extract dried (Na₂SO₄), filtered and evaporated. The obtained residue was dissolved in 1,4-dioxane (0.5 mL) and hydrochloric acid (4N in dioxane, 1.0 mL, 4.0 mmol) was added. After 10 min at rt, the reaction mixture was diluted with Et₂O and the resulting solids collected by filtration and washed with Et₂O. The solids were then dissolved in water and lyophilized to provide 33 mg (70% yield) of 321. LCMS (ESI) [M+H]⁺=553.4, rt=1.47 min. ¹H NMR (400 MHz, d6-dmso) δ 9.04 (s, 2H), 8.71 (s, 1H), 8.46 (d, J=5.2 Hz, 1H), 8.06-7.99 (m, 2H), 7.62-7.51 (m, 2H), 7.38 (d, J=8.8 Hz, 1H), 7.27-7.17 (m, 2H), 6.87 (d, J=8.4 Hz, 1H), 6.49 (d, J=7.5 Hz, 1H), 6.69-6.20 (m, 1H), 4.39-4.27 (m, 2H), 3.57 (dd, J=13.6, 3.7 Hz, 1H), 3.53-3.43 (m, 1H), 3.36 (dd, J=13.9, 7.5 Hz, 1H), 3.20 (d, J=11.7 Hz, 1H), 2.62 (dd, J=23.7, 12.9 Hz, 1H), 2.47-2.42 (m, 1H), 2.19 (s, 3H), 2.11-2.02 (m, 1H), 1.96 (s, 1H), 1.28 (q, J=12.1 Hz, 1H), 0.94 (d, J=6.6 Hz, 3H).

Example 322 N-(2-Fluoro-5-((3-(2-(((3S,5S)-5-fluoropiperidin-3-yl)amino)pyrimidin-4-yl)pyridin-2-yl)oxy)-6-methylnaphthalen-1-yl)-3,3-dimethylbutanamide 322

Step 1: trans-tert-Butyl 3-((4-(2-((5-amino-6-fluoro-2-methylnaphthalen-1-yl)oxy)pyridin-3-yl)pyrimidin-2-yl)amino)-5-fluoropiperidine-1-carboxylate

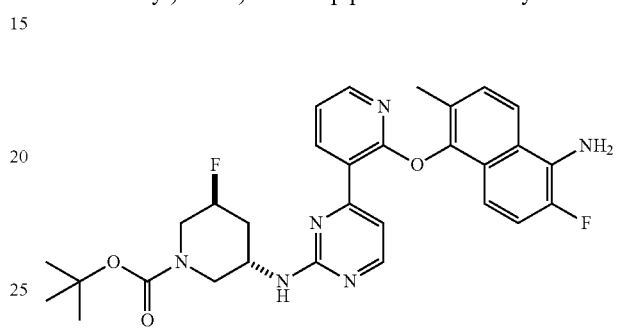

To a solution of 2-fluoro-6-methyl-5-[[3-(2-methylsulfanylpyrimidin-4-yl)-2-pyridyl]oxy]naphthalen-1-amine (275 mg, 0.70 mmol) in DCM (2.8 mL) under nitrogen was added 3-chloroperbenzoic acid (163 mg of ~78% pure reagent, 0.74 mmol). The reaction is stirred at rt for 45 min then diluted with DCM and saturated NaHCO₃(aq) and the phases were separated. The organic extract was washed again with saturated NaHCO₃(aq), dried (Na₂SO₄), filtered and evaporated to afford 286 mg (100% yield) of the sulfoxide 2-fluoro-6-methyl-5-((3-(2-(methylsulfinyl)pyrimidin-4-yl)pyridin-2-yl)oxy)naphthalen-1-amine which was used without further purification.

In a disposable sealed tube, 2-fluoro-6-methyl-5-[[3-(2-methylsulfinylpyrimidin-4-yl)-2-pyridyl]oxy]naphthalen-1-amine (285 mg, 0.70 mmol) and trans-tert-butyl 3-amino-5-fluoro-piperidine-1-carboxylate (198 mg, 0.91 mmol) were combined in 1,4-dioxane (2.3 mL). Triethylamine (0.49 mL, 3.49 mmol) was then added and the vial was sealed and the mixture placed in a 120° C. oil bath. After 3 days, a further portion of trans-tert-butyl 3-amino-5-fluoropiperidine-1-carboxylate (40 mg, 0.18 mmol) and continued heating at 120° C. After 16 h, a further portion of trans-tert-butyl 3-amino-5-fluoro-piperidine-1-carboxylate (40 mg, 0.18 mmol) was added and the reaction stirred for a further 16 h at 120° C. The reaction mixture was then diluted with EtOAc and 1M KHSO₄(aq), the phases were separated and the organic extract were dried (Na₂SO₄), filtered and evaporated. The residue obtained was purified by flash chromatography through silica gel (0-50% EtOAc/DCM) to provide 210 mg (54% yield) of the title compound. LCMS (ESI) [M+H]⁺=563.3, rt=1.82 min.

Step 2: trans-tert-Butyl 3-((4-(2-((5-(3,3-dimethylbutanamido)-6-fluoro-2-methylnaphthalen-1-yl)oxy)pyridin-3-yl)pyrimidin-2-yl)amino)-5-fluoropiperidine-1-carboxylate

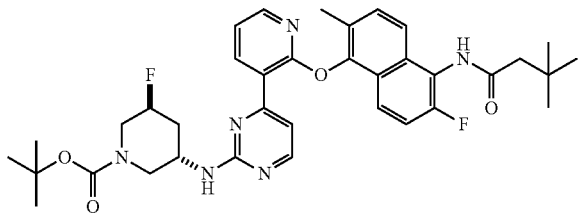 [SMILES: Cc1ccc2c(NC(=O)CC(C)(C)C)c(F)ccc2c1Oc1ncccc1-c1ccnc(N[C@H]2C[C@H](F)CN(C(=O)OC(C)(C)C)C2)n1]

Prepared according to General Procedure C using trans-tert-butyl 3-((4-(2-((5-amino-6-fluoro-2-methylnaphthalen-1-yl)oxy)pyridin-3-yl)pyrimidin-2-yl)amino)-5-fluoropiperidine-1-carboxylate (105 mg, 0.19 mmol), tert-butylacetyl chloride (0.05 mL, 0.37 mmol), pyridine (0.23 mL, 2.8 mmol) and DCM (0.62 mL). The reaction mixture was stirred at rt for 16 h then diluted with DCM and 1M KHSO$_4$(aq), the phases were separated and the organic extract dried (Na$_2$SO$_4$), filtered and evaporated. The obtained residue was purified by flash chromatography through silica gel (0-45% EtOAc/DCM) to provide 61 mg (50% yield) of the title compound. LCMS (ESI) [M+H]$^+$=661.4, rt=1.91 min.

Step 4: trans-tert-Butyl 3-((4-(2-((5-(3,3-dimethylbutanamido)-6-fluoro-2-methylnaphthalen-1-yl)oxy)pyridin-3-yl)pyrimidin-2-yl)amino)-5-fluoropiperidine-1-carboxylate (Isomer-1) and trans-tert-butyl 3-((4-(2-((5-(3,3-dimethylbutanamido)-6-fluoro-2-methylnaphthalen-1-yl)oxy)pyridin-3-yl)pyrimidin-2-yl)amino)-5-fluoropiperidine-1-carboxylate (Isomer-2)

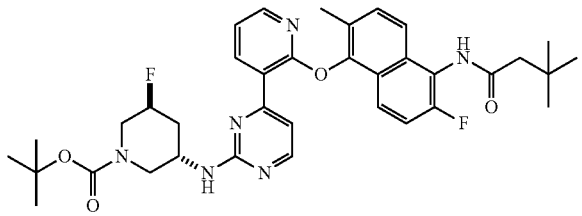 [SMILES: Cc1ccc2c(NC(=O)CC(C)(C)C)c(F)ccc2c1Oc1ncccc1-c1ccnc(N[C@H]2C[C@H](F)CN(C(=O)OC(C)(C)C)C2)n1]

trans-tert-Butyl 3-((4-(2-((5-(3,3-dimethylbutanamido)-6-fluoro-2-methylnaphthalen-1-yl)oxy)pyridin-3-yl)pyrimidin-2-yl)amino)-5-fluoropiperidine-1-carboxylate (61 mg, 0.09 mmol) was subjected to chiral normal phase semi-prep purification (conditions: Chiralpak IA, 5 uM, 20×250 mm, 15 mL/min 8:6:86 EtOH:DCM:Hexane) to provide two trans piperidine enantiomers: trans-tert-butyl 3-((4-(2-((5-(3,3-dimethylbutanamido)-6-fluoro-2-methylnaphthalen-1-yl)oxy)pyridin-3-yl)pyrimidin-2-yl)amino)-5-fluoropiperidine-1-carboxylate (isomer-1), 21 mg (17% yield), 92% ee, LCMS (ESI) [M+H]$^+$=661.4, rt=1.91 min; trans-tert-butyl 3-((4-(2-((5-(3,3-dimethylbutanamido)-6-fluoro-2-methylnaphthalen-1-yl)oxy)pyridin-3-yl)pyrimidin-2-yl)amino)-5-fluoropiperidine-1-carboxylate (isomer-2), 20 mg (16% yield), ee not determined, LCMS (ESI) [M+H]$^+$=661.4, rt=1.91 min.

Step 5: N-(2-Fluoro-5-((3-(2-(((3S,5S)-5-fluoropiperidin-3-yl)amino)pyrimidin-4-yl)pyridin-2-yl)oxy)-6-methylnaphthalen-1-yl)-3,3-dimethylbutanamide (Isomer-1)

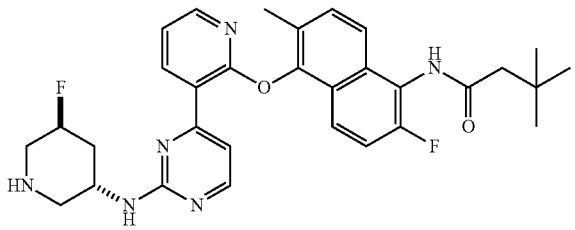 [SMILES: Cc1ccc2c(NC(=O)CC(C)(C)C)c(F)ccc2c1Oc1ncccc1-c1ccnc(N[C@@H]2CNC[C@@H](F)C2)n1]

Prepared according to General Procedure B using trans-tert-butyl 3-((4-(2-((5-(3,3-dimethylbutanamido)-6-fluoro-2-methylnaphthalen-1-yl)oxy)pyridin-3-yl)pyrimidin-2-yl)amino)-5-fluoropiperidine-1-carboxylate (isomer-1) (20 mg, 0.03 mmol), hydrochloric acid (4N in dioxane, 1 mL, 4 mmol) and 1,4-dioxane (0.5 mL). The reaction mixture was stirred at rt for 1 h then diluted with Et$_2$O and the resulting solids collected by filtration and washed with Et$_2$O. The solids were then dissolved in water and lyophilized to afford 17 mg (92% yield) of 322 as a white solid. LCMS (ESI) [M+H]$^+$=561.3, rt=1.45 min. $^1$H NMR (400 MHz, d$_6$-DMSO) δ 9.81 (s, 1H), 9.62 (d, J=9.7 Hz, 1H), 9.42-8.95 (m, 1H), 8.69 (s, 1H), 8.48 (d, J=5.2 Hz, 1H), 8.05 (dd, J=4.8, 1.9 Hz, 1H), 7.77 (d, J=8.7 Hz, 1H), 7.62 (dd, J=9.2, 4.7 Hz, 3H), 7.56 (d, J=8.8 Hz, 1H), 7.38 (t, J=9.4 Hz, 1H), 7.27 (dd, J=7.6, 4.8 Hz, 1H), 5.23 (d, J=45.1 Hz, 1H), 4.51 (s, 1H), 3.54-3.40 (m, 2H), 3.22 (dt, J=41.0, 12.1 Hz, 1H), 2.81 (q, J=10.5 Hz, 1H), 2.34 (s, 3H), 2.18 (s, 3H), 1.92 (dt, J=42.8, 12.4 Hz, 1H), 1.09 (s, 9H).

Example 323 4-(2-((2-Methyl-5-(((2-methylthiazol-4-yl)methyl)amino)naphthalen-1-yl)oxy)pyridin-3-yl)-N-((3S,5R)-5-methylpiperidin-3-yl)pyrimidin-2-amine 323

Step 1: (3R,5S)-Benzyl 3-methyl-5-((4-(2-((2-methyl-5-(((2-methylthiazol-4-yl)methyl)amino)naphthalen-1-yl)oxy)pyridin-3-yl)pyrimidin-2-yl)amino)piperidine-1-carboxylate

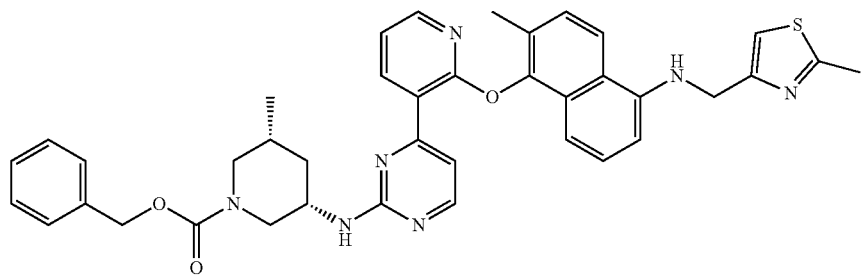 [SMILES: Cc1nc(CNc2cccc3c(Oc4ncccc4-c4ccnc(N[C@H]5C[C@@H](C)CN(C(=O)OCc6ccccc6)C5)n4)c(C)ccc23)cs1]

Prepared according to General Procedure G using benzyl (5R)-3-[[4-[2-[(5-amino-2-methyl-1-naphthyl)oxy]-3-pyridyl]pyrimidin-2-yl]amino]-5-methyl-piperidine-1-carboxylate (100 mg, 0.17 mmol), 4-(chloromethyl)-2-methyl-thiazole hydrochloride (0.01 mL, 0.30 mmol), cesium carbonate (228 mg, 0.70 mmol), tetrabutylammonium iodide (6 mg, 0.02 mmol) and DMF (1.2 mL) and heating at 50° C. After 3 days, the reaction was diluted with EtOAc and saturated NaHCO₃(aq), the phases were separated and the organic extract dried (Na₂SO₄), filtered and evaporated. The obtained residue was purified by flash chromatography through silica gel (0-5% MeOH/DCM) to provide 44 mg (37% yield) of the title compound. LCMS (ESI) [M+H]⁺=686.4; rt=2.04 min.

Step 2: 4-(2-((2-Methyl-5-(((2-methylthiazol-4-yl)methyl)amino)naphthalen-1-yl)oxy)pyridin-3-yl)-N-((3S,5R)-5-methylpiperidin-3-yl)pyrimidin-2-amine

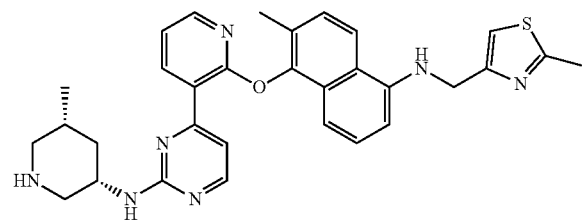 [SMILES: Cc1nc(CNc2cccc3c(Oc4ncccc4-c4ccnc(N[C@@H]5CNC[C@H](C)C5)n4)c(C)ccc23)cs1]

In a flask containing (3R,5S)-benzyl 3-methyl-5-((4-(2-((2-methyl-5-(((2-methylthiazol-4-yl)methyl)amino)naphthalen-1-yl)oxy)pyridin-3-yl)pyrimidin-2-yl)amino)piperidine-1-carboxylate (44 mg, 0.06 mmol) were added DCM (0.54 mL), MeCN (0.54 mL), dimethyl sulfide (0.3 mL, 4.1 mmol) and boron trifluoride diethyl etherate (0.1 mL, 0.8 mmol) in that order. After 3 h at rt, the mixture was diluted with EtOAc and saturated NaHCO₃(aq). The phases were separated and the organic phase was washed with saturated NaCl(aq), dried (MgSO₄), filtered and concentrated. The obtained residue was purified by C18 reverse phase flash chromatography (20-50% MeCN/10 mM aqueous ammonium formate, pH=3.8). Appropriate fractions were combined, concentrated to remove MeCN, and extracted with EtOAc, dried (Na₂SO₄), filtered and evaporated. The obtained residue was dissolved in 1,4-dioxane (0.2 mL) and hydrochlorid acid (4 N in dioxane, 0.6 mL, 2.4 mmol) was added. After 10 min at rt, the reaction was diluted with Et₂O and the resulting solids collected by filtration and washed with Et₂O. The solids were then dissolved in water and lyophilized to provide 26 mg (68% yield) of 323. LCMS (ESI) [M+H]⁺=552.6, rt=1.46 min. ¹H NMR (400 MHz, d₆-DMSO) δ 9.44-8.93 (m, 2H), 8.77 (s, 1H), 8.47 (d, J=5.3 Hz, 1H), 8.09 (d, J=8.7 Hz, 1H), 8.04 (dd, J=4.8, 1.9 Hz, 1H), 7.61 (s, 2H), 7.38 (d, J=8.8 Hz, 1H), 7.26 (s, 1H), 7.24 (dd, J=7.6, 4.8 Hz, 1H), 7.14-7.07 (m, 1H), 6.83 (d, J=8.4 Hz, 1H), 6.44 (d, J=7.7 Hz, 1H), 4.53 (s, 2H), 3.54-3.42 (m, 1H), 3.19 (d, J=11.5 Hz, 1H), 2.68-2.67 (m, 1H), 2.66 (s, 3H), 2.61 (d, J=11.5 Hz, 1H), 2.58-2.53 (m, 1H), 2.46-2.41 (m, 1H), 2.19 (s, 3H), 2.06 (d, J=12.2 Hz, 1H), 1.99 (s, 1H), 1.28 (q, J=12.1 Hz, 1H), 0.94 (d, J=6.5 Hz, 3H).

Example 324 4-[2-[[5-(Dimethylsulfamoylamino)-6-fluoro-2-methyl-1-naphthyl]oxy]-3-pyridyl]-2-[[(3S)-3-piperidyl]amino]pyrimidine 324

Step 1: (S)-tert-Butyl 3-((4-(2-((5-((N,N-dimethylsulfamoyl)amino)-6-fluoro-2-methylnaphthalen-1-yl)oxy)pyridin-3-yl)pyrimidin-2-yl)amino)piperidine-1-carboxylate

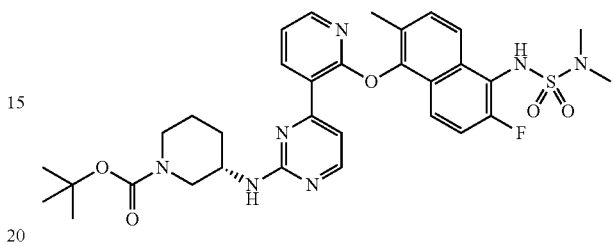

Prepared according to General Procedure A using tert-butyl (3S)-3-[[4-[2-[(5-amino-6-fluoro-2-methyl-1-naphthyl)oxy]-3-pyridyl]pyrimidin-2-yl]amino]piperidine-1-carboxylate (30 mg, 0.05 mmol) DCE (0.5 mL), pyridine (0.06 mL, 0.80 mmol), DMAP (6.5 mg, 0.05 mmol) and dimethylsulfamoyl chloride (0.06 mL, 0.53 mmol). The reaction mixture was stirred 16 h at rt then diluted with DCM (10 mL) and washed with 0.5 M HCl. The organic extract was dried (MgSO₄) filtered and concentrated. The crude material was purified by preparative TLC (2:1 EtOAc/Hexanes). The product containing band was scratched off and EtOAc was added and the suspension was stirred for 10 min and then filtered through celite and the solvent was removed to provide 17 mg (48% yield) of the title compound. LCMS (ESI) [M+H]⁺=652.6, rt=1.89 min.

Step 2: 4-[2-[[5-(Dimethylsulfamoylamino)-6-fluoro-2-methyl-1-naphthyl]oxy]-3-pyridyl]-2-[[(3S)-3-piperidyl]amino]pyrimidine


Prepared according to General Procedure B using (S)-tert-butyl 3-((4-(2-((5-((N,N-dimethylsulfamoyl)amino)-6-fluoro-2-methylnaphthalen-1-yl)oxy)pyridin-3-yl)pyrimidin-2-yl)amino)piperidine-1-carboxylate (17 mg, 0.03 mmol), 1,4-dioxane (0.5 mL) and hydrochloric acid (4 N in dioxane, 0.5 mL, 2 mmol). The reaction was stirred at rt for 2 h then MTBE (4 mL) was added and the precipitate was filtered, rinsed with MTBE and then dissolved in water and MeCN and lyophilized to provide 14 mg (91% yield) of 324. LCMS (ESI) [M+H]⁺=552.2, rt=1.34 min. ¹H NMR (400 MHz, D₂O) δ 8.33 (d, J=6.5 Hz, 1H), 8.20 (d, J=5.8 Hz, 1H), 8.00 (d, J=8.7 Hz, 1H), 7.83 (dd, J=5.0, 1.9 Hz, 1H), 7.65 (dd, J=9.3, 5.2 Hz, 1H), 7.50 (dd, J=12.7, 7.3 Hz, 2H), 7.14 (ddd, J=17.2, 10.7, 6.4 Hz, 2H), 4.22 (s, 1H), 3.43 (d, J=9.0

Hz, 1H), 3.20 (d, J=13.0 Hz, 1H), 3.04-2.88 (m, 4H), 2.74 (s, 6H), 2.07 (s, 3H), 2.06-2.00 (m, 1H), 1.91 (d, J=5.6 Hz, 1H), 1.65 (dd, J=24.4, 15.5 Hz, 2H).

Example 325 4-[2-[[5-(Dimethylsulfamoylamino)-6-fluoro-2-methyl-1-naphthyl]oxy]-3-pyridyl]-2-[[(3S,5R)-5-methyl-3-piperidyl]amino]pyrimidine 325

Step 1: Benzyl (3S,5R)-3-[[4-[2-[[5-(dimethylsulfamoylamino)-6-fluoro-2-methyl-1-naphthyl]oxy]-3-pyridyl]pyrimidin-2-yl]amino]-5-methyl-piperidine-1-carboxylate

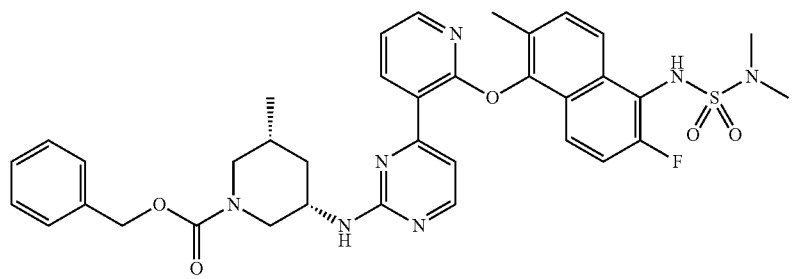 [SMILES: Cc1ccc2c(NS(=O)(=O)N(C)C)c(F)ccc2c1Oc1ncccc1-c1ccnc(N[C@H]2C[C@@H](C)CN(C(=O)OCc3ccccc3)C2)n1]

Prepared using benzyl (3S,5R)-3-[[4-[2-[(5-amino-6-fluoro-2-methyl-1-naphthyl)oxy]-3-pyridyl]pyrimidin-2-yl]amino]-5-methyl-piperidine-1-carboxylate (100 mg, 0.17 mmol), DCE (2 mL), pyridine (1 mL), dimethylsulfamoyl chloride (0.25 mL, 1.69 mmol) and DMAP (3 mg, 0.02 mmol) and heating at 50° C. After 22 h, the reaction mixture was diluted with DCM (75 mL), washed with saturated NaHCO₃(aq) (25 mL), then H₂O (10 mL), then saturated NaCl(aq) (10 mL), dried (Na₂SO₄), filtered and concentrated in vacuo. The crude product was purified by flash chromatography through silica gel (0-100% EtOAc/hexanes) to provide 43 mg (36% yield) of the title compound as an orange solid. LCMS (ESI) [M+H]⁺=700.4, rt=1.94 min.

Step 2: 4-[2-[[5-(Dimethylsulfamoylamino)-6-fluoro-2-methyl-1-naphthyl]oxy]-3-pyridyl]-2-[[(3S,5R)-5-methyl-3-piperidyl]amino]pyrimidine

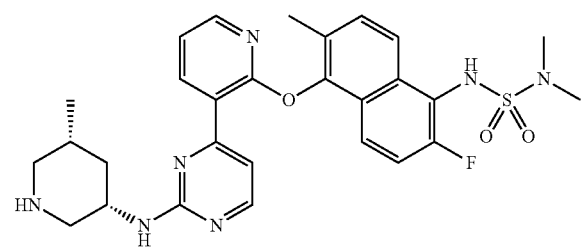 [SMILES: Cc1ccc2c(NS(=O)(=O)N(C)C)c(F)ccc2c1Oc1ncccc1-c1ccnc(N[C@@H]2CNC[C@H](C)C2)n1]

Benzyl (3S,5R)-3-[[4-[2-[[5-(dimethylsulfamoylamino)-6-fluoro-2-methyl-1-naphthyl]oxy]-3-pyridyl]pyrimidin-2-yl]amino]-5-methyl-piperidine-1-carboxylate (44 mg, 0.06 mmol) was dissolved in a mixture of DCM (0.5 mL) and MeCN (0.5 mL). To this solution was added dimethyl sulfide (0.28 mL, 3.8 mmol) followed by addition of boron trifluoride diethyl etherate (0.24 mL, 1.89 mmol) and the mixture was stirred at rt. After 1 h, a further portion of boron trifluoride diethyl etherate (0.11 mL, 0.87 mmol) was added and the reaction was stirred again for 1 h then diluted with EtOAc (50 mL) and washed with saturated NaHCO₃(aq) (2×10 mL), dried (Na₂SO₄), filtered and concentrated in vacuo. The obtained crude material was purified by C18 reverse phase flash chromatography (20-100% MeCN/10 mM aqueous ammonium formate, pH=3.8). Appropriate fractions were combined and lyophilized to provide 7 mg (19% yield) of 325 as a white solid. LCMS (ESI) [M+H]⁺=566.3, rt=1.38 min. ¹H NMR (400 MHz, d6-DMSO) δ 8.50 (br. s., 1H), 8.41 (d, J=5.2 Hz, 1H), 8.33 (s, 1H), 8.10 (d, J=8.7 Hz, 1H), 8.06 (dd, J=4.8, 2.0 Hz, 1H), 7.67 (s, 1H), 7.60 (d, J=8.8 Hz, 1H), 7.47-7.36 (m, 2H), 7.27 (dd, J=7.6, 4.8 Hz, 1H), 7.20 (d, J=8.1 Hz, 1H), 3.93 (br. s., 1H), 2.88 (d, J=10 Hz, 1H), 2.78 (s, 6H), 2.31-2.21 (m, 1H), 2.19 (s, 3H), 2.10-1.94 (m, 2H), 1.65-1.51 (m, 1H), 1.18-0.99 (m, 1H), 0.85-0.75 (m, 3H).

Example 326 4-(2-((2-Methyl-5-(((S)-3,3,3-trifluoro-2-methoxypropyl)amino)naphthalen-1-yl)oxy)pyridin-3-yl)-N—((S)-piperidin-3-yl)pyrimidin-2-amine 326

Step 1: (S)-tert-Butyl 3-((4-(2-((2-methyl-5-(((S)-3,3,3-trifluoro-2-hydroxypropyl)amino)naphthalen-1-yl)oxy)pyridin-3-yl)pyrimidin-2-yl)amino)piperidine-1-carboxylate

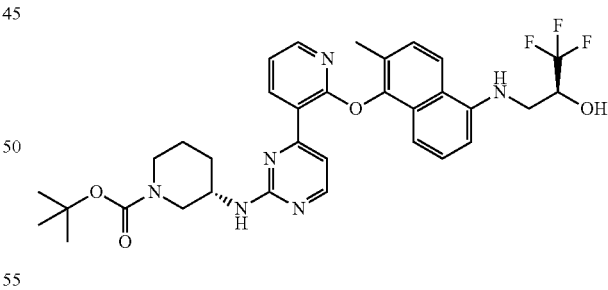

Prepared according to General Procedure F using tert-butyl (3S)-3-[[4-[2-[(5-amino-2-methyl-1-naphthyl)oxy]-3-pyridyl]pyrimidin-2-yl]amino]piperidine-1-carboxylate (100 mg, 0.19 mmol), (2S)-2-(trifluoromethyl)oxirane (64 mg, 0.57 mmol) and acetic acid (0.3 mL). The reaction was stirred at 75° C. for 2 h, then acetic acid was evaporated in vacuo. The residue was purified by flash chromatography through silica gel (0-100% EtOAc/DCM) to provide 86 mg (71% yield) of the title compound. LCMS (ESI) [M+H]⁺=639.6, rt=1.99 min.

Step 2: (S)-tert-Butyl 3-((4-(2-((2-methyl-5-(((S)-3,3,3-trifluoro-2-methoxypropyl)amino)naphthalen-1-yl)oxy)pyridin-3-yl)pyrimidin-2-yl)amino)piperidine-1-carboxylate

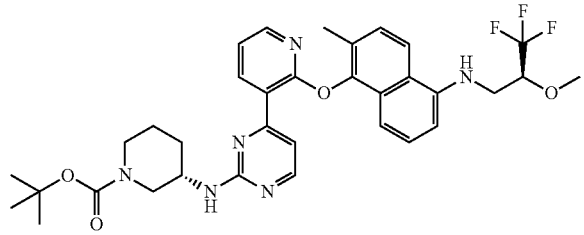 [SMILES: CO[C@@H](CNc1cccc2c(Oc3ncccc3-c3ccnc(N[C@H]4CCCN(C(=O)OC(C)(C)C)C4)n3)c(C)ccc12)C(F)(F)F]

To a solution of tert-butyl (3S)-3-[[4-[2-[[2-methyl-5-[[(2S)-3,3,3-trifluoro-2-hydroxy-propyl]amino]-1-naphthyl]oxy]-3-pyridyl]pyrimidin-2-yl]amino]piperidine-1-carboxylate (84 mg, 0.13 mmol) in DMF (0.5 mL) was added cesium carbonate (216 mg, 0.66 mmol) and methyl iodide (37 mg, 0.26 mmol). The reaction was stirred at 70° C. for 30 min then the reaction was quenched with water (10 mL) and EtOAc (30 mL) was added. The phases were separated and the organic extract was dried (MgSO$_4$), filtered and concentrated. The crude was purified by prep HPLC-MS (14 min 60-80% MeCN/10 mM pH: 3.8 NH$_4$CO$_2$H(aq), XBridge BEH C18 OBD Prep Column, 130 Å, 5 μm, 30 mm×50 mm). Appropriate fractions were combined, and lyophilized to provide 12 mg (10% yield) of the title compound. LCMS (ESI) [M+H]$^+$=653.7, rt=2.15 min. $^1$H NMR (400 MHz, CDCl$_3$) δ 8.64 (s, 1H), 8.37 (d, J=5.2 Hz, 2H), 8.05 (dd, J=4.8, 2.0 Hz, 1H), 7.70 (dd, J=15.6, 6.9 Hz, 2H), 7.30-7.19 (m, 2H), 7.09 (dd, J=7.6, 4.8 Hz, 1H), 6.58 (d, J=7.3 Hz, 1H), 4.78 (s, 1H), 4.17-4.05 (m, 2H), 3.95-3.84 (m, 1H), 3.71 (dd, J=13.6, 4.3 Hz, 2H), 3.60 (s, 3H), 3.49-3.39 (m, 2H), 2.28 (s, 3H), 1.78 (s, 3H), 1.71-1.59 (m, 2H).

Step 3: 4-(2-((2-Methyl-5-(((S)-3,3,3-trifluoro-2-methoxypropyl)amino)naphthalen-1-yl)oxy)pyridin-3-yl)-N—((S)-piperidin-3-yl)pyrimidin-2-amine

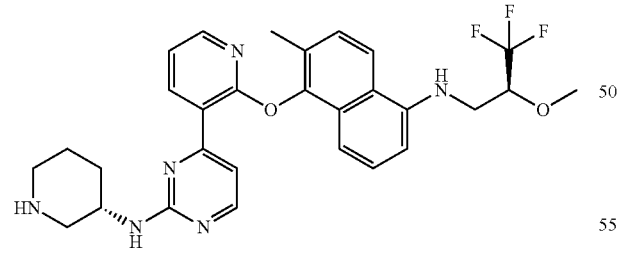

Prepared according to General Procedure B using tert-butyl (3S)-3-[[4-[2-[[2-methyl-5-[[(2S)-3,3,3-trifluoro-2-methoxy-propyl]amino]-1-naphthyl]oxy]-3-pyridyl]pyrimidin-2-yl]amino]piperidine-1-carboxylate (22 mg, 0.03 mmol), 1,4-dioxane (0.2 mL) and hydrochloric acid (4 M in dioxane, 0.2 mL, 0.8 mmol). The reaction stirred at rt for 1 h then MTBE (5 mL) was added and the resulting precipitate filtered, rinsed with MTBE and then dissolved in water and MeCN, and lyophilized to give 17 mg (85% yield) of 326. LCMS (ESI) [M+H]$^+$=553.5, rt=1.55 min. $^1$H NMR (400 MHz, D$_2$O) δ 8.44 (s, 1H), 8.14 (d, J=6.3 Hz, 1H), 7.85 (dd, J=5.0, 1.9 Hz, 1H), 7.78 (d, J=8.7 Hz, 1H), 7.69 (s, 1H), 7.36 (d, J=8.9 Hz, 1H), 7.14 (dd, J=7.7, 5.0 Hz, 2H), 7.09 (d, J=8.5 Hz, 1H), 6.70 (d, J=7.4 Hz, 1H), 4.30 (s, 1H), 4.06 (s, 1H), 3.62 (dd, J=14.3, 3.2 Hz, 1H), 3.43 (d, J=8.6 Hz, 1H), 3.40 (s, 3H), 3.20 (d, J=13.7 Hz, 1H), 2.95 (dd, J=25.3, 12.5 Hz, 2H), 2.08 (s, 3H), 1.89 (s, 1H), 1.66 (dd, J=21.6, 11.9 Hz, 2H).

Example 327 N-(2-F-6-methyl-5-((3-(2-(((3S,4R)-4-methylpiperidin-3-yl)amino)pyrimidin-4-yl)pyridin-2-yl)oxy)naphthalen-1-yl)propane-1-sulfonamide 327

Step 1: trans-tert-Butyl 3-amino-4-methylpiperidine-1-carboxylate

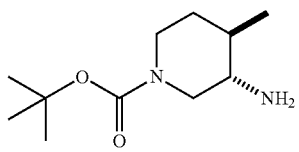

To a solution of trans-4-methylpiperidin-3-amine (200 mg, 1.75 mmol) in DCM (3.5 mL) was added triethylamine (0.29 mL, 2.1 mmol), followed by di-tert-butyl dicarbonate (382 mg, 1.75 mmol). The reaction mixture was stirred at rt for 4 h then the reaction was diluted with DCM and saturated NaHCO$_3$(aq), the phases were separated and the organic extract dried (Na$_2$SO$_4$), filtered and evaporated. The residue was purified by flash chromatography through silica gel (0-20% MeOH/DCM) to provide 140 mg (43% yield) of the title compound. LCMS (ESI) [M+H]$^+$=215.4, rt=1.00 min. $^1$H NMR (400 MHz, CDCl$_3$) δ 3.91 (s, 1H), 3.85 (dd, J=13.3, 2.5 Hz, 1H), 2.99 (dd, J=13.2, 2.4 Hz, 1H), 2.92-2.75 (m, 2H), 1.72 (dd, J=13.4, 6.6, 3.3 Hz, 1H), 1.47-1.44 (m, 10H), 1.43-1.36 (m, 1H), 0.96 (d, J=6.9 Hz, 3H).

Step 2: trans-tert-Butyl 3-((4-(2-((5-amino-6-fluoro-2-methylnaphthalen-1-yl)oxy)pyridin-3-yl)pyrimidin-2-yl)amino)-4-methylpiperidine-1-carboxylate

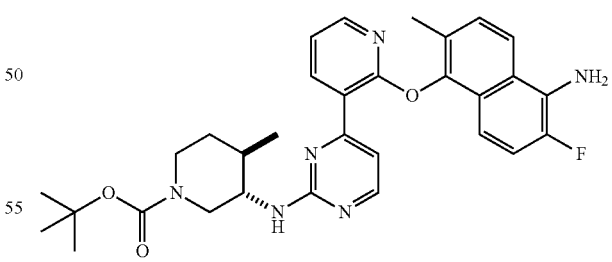

In a disposable sealed tube, 2-fluoro-6-methyl-5-[[3-(2-methylsulfinylpyrimidin-4-yl)-2-pyridyl]oxy]naphthalen-1-amine (225 mg, 0.55 mmol) and trans-tert-butyl 3-amino-4-methylpiperidine-1-carboxylate (154 mg, 0.72 mmol) were combined in 1,4-dioxane (2.8 mL). Triethylamine (0.38 mL, 2.75 mmol) was then added and the vial was sealed and the mixture placed in a 120° C. oil bath. After 3 days, the reaction was diluted with EtOAc and 1M KHSO$_4$ (aq) and the phases were separated. The organic extract was washed with 1M KHSO₄(aq), dried (Na₂SO₄), filtered and evaporated. The residue was purified by flash chromatography through silica gel (0-50% EtOAc/DCM) to provide 190 mg (62% yield) of the title compound. LCMS (ESI) [M+H]⁺=559.2, rt=1.93 min.

Step 3: trans-tert-Butyl 3-((4-(2-((6-fluoro-2-methyl-5-(propylsulfonamido)naphthalen-1-yl)oxy)pyridin-3-yl)pyrimidin-2-yl)amino)-4-methylpiperidine-1-carboxylate

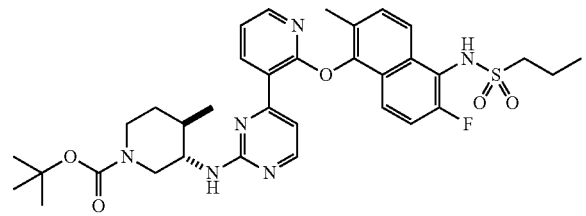 [SMILES: CCCS(=O)(=O)Nc1c(F)ccc2c(Oc3ncccc3-c3ccnc(N[C@@H]4CN(C(=O)OC(C)(C)C)CC[C@H]4C)n3)c(C)ccc12]

Prepared using trans-tert-butyl 3-((4-(2-((5-amino-6-fluoro-2-methylnaphthalen-1-yl)oxy)pyridin-3-yl)pyrimidin-2-yl)amino)-4-methylpiperidine-1-carboxylate (95 mg, 0.17 mmol), DCM (0.57 mL), 1-propanesulfonyl chloride (0.04 mL, 0.34 mmol), pyridine (0.21 mL, 2.55 mmol) and DMAP (1 crystal). The reaction mixture was stirred at rt for 16 h then diluted with DCM and washed with saturated NaHCO₃(aq), dried (Na₂SO₄) and evaporated. The residue was purified by flash chromatography through silica gel (0-50% EtOAc/DCM) to provide 75 mg (66% yield) of the title compound. LCMS (ESI) [M+H]⁺=665.3, rt=1.94.

Step 4: trans-tert-Butyl 3-((4-(2-((6-fluoro-2-methyl-5-(propylsulfonamido)naphthalen-1-yl)oxy)pyridin-3-yl)pyrimidin-2-yl)amino)-4-methylpiperidine-1-carboxylate (Isomer-1) and trans-tert-butyl 3-((4-(2-((6-fluoro-2-methyl-5-(propylsulfonamido)naphthalen-1-yl)oxy)pyridin-3-yl)pyrimidin-2-yl)amino)-4-methylpiperidine-1-carboxylate (Isomer-2)

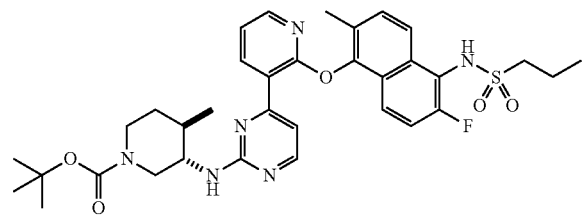 [SMILES: CCCS(=O)(=O)Nc1c(F)ccc2c(Oc3ncccc3-c3ccnc(N[C@@H]4CN(C(=O)OC(C)(C)C)CC[C@H]4C)n3)c(C)ccc12]

trans-tert-Butyl 3-((4-(2-((6-fluoro-2-methyl-5-(propylsulfonamido)naphthalen-1-yl)oxy)pyridin-3-yl)pyrimidin-2-yl)amino)-4-methylpiperidine-1-carboxylate (75 mg, 0.11 mmol) was subjected to chiral normal phase semi-prep purification (conditions: Chiralpak IA, 5 um, 20×250 mm, 15 mL/min, 12:88 EtOH:Hexanes, 7.5 mg/injections) to provide two trans piperidine enantiomers: trans-tert-Butyl 3-((4-(2-((6-fluoro-2-methyl-5-(propylsulfonamido)naphthalen-1-yl)oxy)pyridin-3-yl)pyrimidin-2-yl)amino)-4-methylpiperidine-1-carboxylate (isomer-1), 24 mg (21% yield), >97.7% ee, LCMS (ESI) [M+H]⁺=665.3, rt=1.94 min; trans-tert-Butyl 3-((4-(2-((6-fluoro-2-methyl-5-(propylsulfonamido)naphthalen-1-yl)oxy)pyridin-3-yl)pyrimidin-2-yl)amino)-4-methylpiperidine-1-carboxylate (isomer-2), 18 mg (16% yield), 94.8% ee, LCMS (ESI) [M+H]⁺=665.3, rt=1.94 min.

Step 5: N-(2-Fluoro-6-methyl-5-((3-(2-(((3S,4R)-4-methylpiperidin-3-yl)amino)pyrimidin-4-yl)pyridin-2-yl)oxy)naphthalen-1-yl)propane-1-sulfonamide

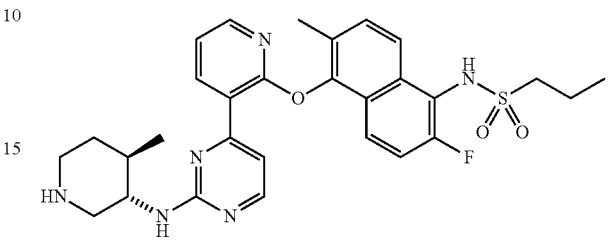

Prepared according to General Procedure B using trans-tert-Butyl 3-((4-(2-((6-fluoro-2-methyl-5-(propylsulfonamido)naphthalen-1-yl)oxy)pyridin-3-yl)pyrimidin-2-yl)amino)-4-methylpiperidine-1-carboxylate (isomer-1) (18 mg, 0.03 mmol), 1,4-dioxane (0.5 mL), hydrochloric acid (4N in dioxane, 1 mL, 4 mmol). The reaction mixture was stirred at rt for 1 h then diluted with Et₂O and the resulting solids collected by filtration and washed with Et₂O. The solids were then dissolved in water, and lyophilized to provide 15 mg, (93% yield) of 327. LCMS (ESI) [M+H]⁺=565.2, rt=1.43 min. ¹H NMR (400 MHz, d₆-DMSO) δ 9.70 (s, 1H), 8.98 (d, J=8.6 Hz, 1H), 8.63 (s, 1H), 8.56 (d, J=6.4 Hz, 1H), 8.49 (d, J=5.2 Hz, 1H), 8.10-8.04 (m, 2H), 7.78-7.69 (m, 1H), 7.63 (d, J=8.8 Hz, 1H), 7.56 (d, J=5.2 Hz, 1H), 7.46 (t, J=9.5 Hz, 1H), 7.39 (d, J=8.4 Hz, 1H), 7.30 (dd, J=7.6, 4.8 Hz, 1H), 4.53 (s, 1H), 3.33 (d, J=10.5 Hz, 1H), 3.22-3.10 (m, 4H), 3.03-2.88 (m, 1H), 2.19 (s, 3H), 2.17-2.08 (m, 1H), 1.91-1.81 (m, 2H), 1.81-1.65 (m, 2H), 1.02 (t, J=7.4 Hz, 3H), 0.97 (d, J=6.9 Hz, 3H).

Example 328 trans-N-(2-Fluoro-5-((3-(2-(((3S,5S)-5-fluoropiperidin-3-yl)amino)pyrimidin-4-yl)pyridin-2-yl)oxy)-6-methylnaphthalen-1-yl)propane-1-sulfonamide 328

Step 1: trans-tert-Butyl 3-fluoro-5-((4-(2-((6-fluoro-2-methyl-5-(propylsulfonamido)naphthalen-1-yl)oxy)pyridin-3-yl)pyrimidin-2-yl)amino)piperidine-1-carboxylate

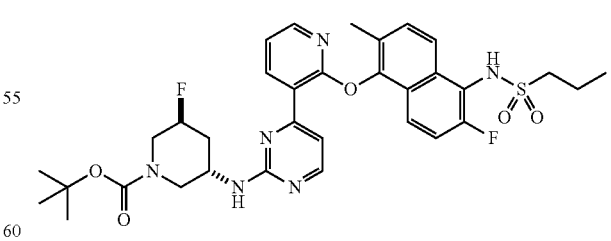

Prepared using trans-tert-butyl 3-((4-(2-((5-amino-6-fluoro-2-methylnaphthalen-1-yl)oxy)pyridin-3-yl)pyrimidin-2-yl)amino)-5-fluoropiperidine-1-carboxylate (105 mg, 0.19 mmol), DCM (0.62 mL), 1-propanesulfonyl chloride (0.04 mL, 0.37 mmol), pyridine (0.23 mL, 2.8 mmol) and DMAP (1 crystal). The reaction mixture was stirred at rt for 16 h then diluted with DCM and washed with 1N KHSO₄ (aq), dried (Na₂SO₄), filtered and concentrated. The residue was purified by flash chromatography through silica gel (0-50% EtOAc/DCM) to provide 81 mg (65% yield) of the title compound. LCMS (ESI) [M+H]⁺=669.2, rt=1.83 min.

Step 2: tert-butyl (3S,5S)-3-fluoro-5-((4-(2-((6-fluoro-2-methyl-5-(propylsulfonamido)naphthalen-1-yl)oxy)pyridin-3-yl)pyrimidin-2-yl)amino)piperidine-1-carboxylate (Isomer-1) and tert-butyl (3R,5S)-3-fluoro-5-((4-(2-((6-fluoro-2-methyl-5-(propylsulfonamido)naphthalen-1-yl)oxy)pyridin-3-yl)pyrimidin-2-yl)amino)piperidine-1-carboxylate (Isomer-2)

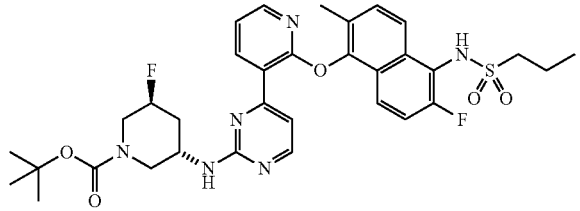 [SMILES: CCCS(=O)(=O)Nc1c(F)ccc2c(Oc3ncccc3-c3ccnc(N[C@H]4C[C@H](F)CN(C(=O)OC(C)(C)C)C4)n3)c(C)ccc12]

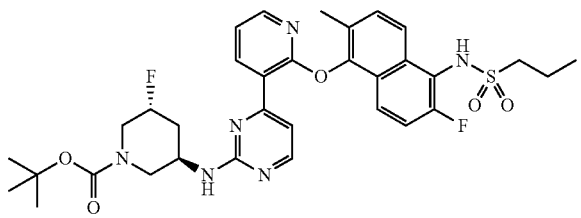

The mixture of enantiomers from Step 1 was subjected to chiral normal phase semi-prep purification (conditions: Chiralpak IA, 5 uM, 30×25 mm, 12 ML/min, 6:12:82 MeOH:EtOH:Hexanes, 4-12 mg/injection) to provide two trans piperidine enantiomers: (isomer-1), 23 mg (18% yield), 95.4% ee, LCMS (ESI) [M+H]⁺=669.2, rt=1.83 min; (isomer-2), 36 mg (29% yield), 96.9% ee, LCMS (ESI) [M+H]⁺=669.2, rt=1.83 min. The absolute stereochemistry assignments are tenuous and may be revised subject to additional characterization data.

Step 3: N-(2-Fluoro-5-((3-(2-(((3S,5S)-5-fluoropiperidin-3-yl)amino)pyrimidin-4-yl)pyridin-2-yl)oxy)-6-methylnaphthalen-1-yl)propane-1-sulfonamide (Isomer-1)

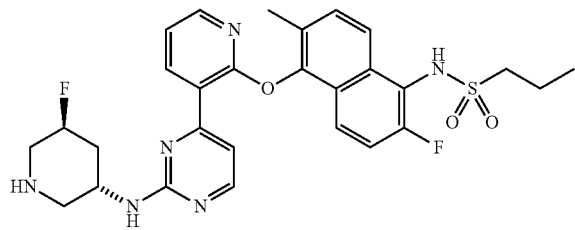 [SMILES: CCCS(=O)(=O)Nc1c(F)ccc2c(Oc3ncccc3-c3ccnc(N[C@@H]4CNC[C@@H](F)C4)n3)c(C)ccc12]

Prepared according to General Procedure B using tert-butyl (3S,5S)-3-fluoro-5-((4-(2-((6-fluoro-2-methyl-5-(propylsulfonamido)naphthalen-1-yl)oxy)pyridin-3-yl)pyrimidin-2-yl)amino)piperidine-1-carboxylate (isomer-1) (23 mg, 0.03 mmol), 1,4-dioxane (0.5 mL), hydrochloric acid (4 N in dioxane, 1 mL, 4 mmol). The reaction mixture was stirred at rt for 1.5 h, then diluted with Et₂O and the resulting solids collected by filtration and washed with Et₂O. The solids were then dissolved in water, and lyophilized to provide 20 mg (99% yield) of 328. LCMS (ESI) [M+H]⁺=569.2, rt=1.38 min. ¹H NMR (400 MHz, DMSO-d₆) δ 9.70 (s, 1H), 9.56 (d, J=10.8 Hz, 1H), 9.23 (s, 1H), 8.71 (s, 1H), 8.49 (d, J=5.2 Hz, 1H), 8.12-8.03 (m, 2H), 7.71 (dd, J=9.3, 5.1 Hz, 1H), 7.68-7.56 (m, 3H), 7.45 (t, J=9.5 Hz, 1H), 7.29 (dd, J=7.6, 4.8 Hz, 1H), 5.25 (d, J=44.3 Hz, 1H), 4.51 (s, 1H), 3.57-3.42 (m, 2H), 3.37-3.23 (m, 1H), 3.20-3.12 (m, 2H), 2.90-2.77 (m, 1H), 2.43-2.29 (m, 1H), 2.19 (s, 3H), 2.06-1.90 (m, 1H), 1.89-1.80 (m, 2H), 1.02 (t, J=7.4 Hz, 3H).

Example 329 (S)-3-((6-Methyl-5-((3-(2-(piperidin-3-ylamino)pyrimidin-4-yl)pyridin-2-yl)oxy)naphthalen-1-yl)amino)propanenitrile 329

Step 1: (S)-tert-Butyl 3-((4-(2-((5-((2-cyanoethyl)amino)-2-methylnaphthalen-1-yl)oxy)pyridin-3-yl)pyrimidin-2-yl)amino)piperidine-1-carboxylate

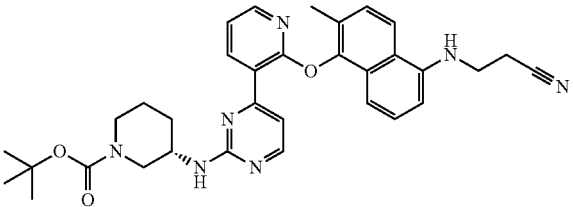

tert-Butyl (3S)-3-[[4-[2-[(5-amino-2-methyl-1-naphthyl)oxy]-3-pyridyl]pyrimidin-2-yl]amino]piperidine-1-carboxylate (100 mg, 0.19 mmol) was suspended in 1,4-dioxane (2 mL) and to the suspension was added acrylonitrile (0.06 mL, 0.95 mmol) followed by benzyltrimethylammonium hydroxide solution 40% in MeOH (96 mg, 0.57 mmol). The reaction was stirred at 80° C. for 20 min then a further portion of acrylonitrile (0.06 mL, 0.95 mmol) and benzyltrimethylammonium hydroxide solution 40% in MeOH (96 mg, 0.57 mmol) were added and the solution was stirred again at 80° C. for 20 min. A further portion of acrylonitrile (0.06 mL, 0.95 mmol) and benzyltrimethylammonium hydroxide solution 40% in MeOH (96 mg, 0.57 mmol) were added and the reaction was stirred at 80° C. for 30 min then the reaction was diluted with EtOAc and the clear solution was decanted. The crude was filtered through a short pad of silica gel and the pad was washed with EtOAc and the filtrate was concentrated. The crude was purified by prep HPLC-MS (14 min 50-70% MeCN/10 mM pH: 10 NH₄CO₃H(aq), XBridge BEH C18 OBD Prep Column, 130 Å, 5 μm, 30 mm×50 mm). Appropriate fractions were combined, most of the MeCN removed in vacuo, and lyophilized to provide 16 mg (14% yield) of the title compound. LCMS (ESI) [M+H]⁺=580.6, rt=1.91 min.

Step 2: (S)-3-((6-Methyl-5-((3-(2-(piperidin-3-ylamino)pyrimidin-4-yl)pyridin-2-yl)oxy)naphthalen-1-yl)amino)propanenitrile

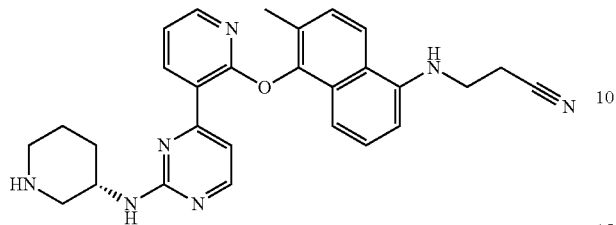

Prepared according to General Procedure B using tert-butyl (3S)-3-[[4-[2-[[5-(2-cyanoethylamino)-2-methyl-1-naphthyl]oxy]-3-pyridyl]pyrimidin-2-yl]amino]piperidine-1-carboxylate (27 mg, 0.05 mmol), 1,4-dioxane (1 mL) and hydrochloric acid (4 M in dioxane, 1 mL, 4 mmol). The reaction was stirred at rt for 15 min then diluted with MTBE (10 mL) and the suspension was filtered, and the solids washed with MTBE then dissolved in water and MeCN and lyophilized to provide 21 mg (87% yield) of 329. LCMS (ESI) [M+H]$^+$=480.2, rt=1.50 min. $^1$H NMR (400 MHz, D$_2$O) δ 8.38 (s, 1H), 8.18 (d, J=6.0 Hz, 1H), 7.84 (dd, J=5.0, 1.9 Hz, 1H), 7.78 (d, J=8.7 Hz, 1H), 7.61 (s, 1H), 7.35 (d, J=8.8 Hz, 1H), 7.19-7.11 (m, 2H), 7.06 (d, J=8.6 Hz, 1H), 6.64 (d, J=7.6 Hz, 1H), 4.26 (s, 1H), 3.55 (t, J=6.5 Hz, 2H), 3.42 (d, J=7.8 Hz, 1H), 3.17 (s, 1H), 2.95 (dd, J=25.1, 12.1 Hz, 2H), 2.76 (t, J=6.5 Hz, 2H), 2.12-2.00 (m, 4H), 1.90 (s, 1H), 1.63 (d, J=9.8 Hz, 2H).

Example 330 4-(2-((2-Methyl-5-(((1-methyl-1H-pyrazol-3-yl)methyl)amino)naphthalen-1-yl)oxy)pyridin-3-yl)-N-((3S,5R)-5-methylpiperidin-3-yl)pyrimidin-2-amine 330

Step 1: (3R,5S)-Benzyl 3-methyl-5-((4-(2-((2-methyl-5-(((1-methyl-1H-pyrazol-3-yl)methyl)amino)naphthalen-1-yl)oxy)pyridin-3-yl)pyrimidin-2-yl)amino)piperidine-1-carboxylate

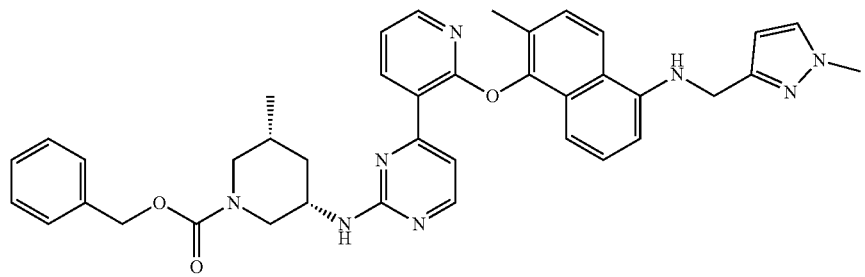 [SMILES: Cc1ccc2c(NCc3ccn(C)n3)cccc2c1Oc1ncccc1-c1ccnc(N[C@H]2C[C@@H](C)CN(C(=O)OCc3ccccc3)C2)n1]

In a vial were added benzyl (3S,5R)-3-[[4-[2-[(5-amino-2-methyl-1-naphthyl)oxy]-3-pyridyl]pyrimidin-2-yl]amino]-5-methyl-piperidine-1-carboxylate (100 mg, 0.19 mmol), DCE (1.9 mL), 1-methylpyrazole-3-carbaldehyde (0.04 mL, 0.38 mmol), acetic acid (0.05 mL, 0.95 mmol), then sodium cyanoborohydride (35.2 mg, 0.57 mmol). After 15 min at 55° C., the reaction was diluted with DCM, washed with saturated NaHCO$_3$(aq), dried (Na$_2$SO$_4$), filtered and evaporated. The residue was purified by flash chromatography through silica gel (0-3.5% MeOH/DCM) to provide 93 mg (73% yield) of the title compound. LCMS (ESI) [M+H]$^+$=669.4, rt=1.94 min.

Step 2: 4-(2-((2-Methyl-5-(((1-methyl-1H-pyrazol-3-yl)methyl)amino)naphthalen-1-yl)oxy)pyridin-3-yl)-N-((3S,5R)-5-methylpiperidin-3-yl)pyrimidin-2-amine

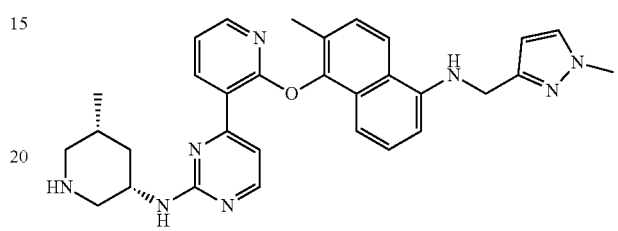

To a solution of (3R,5S)-benzyl 3-methyl-5-((4-(2-((2-methyl-5-(((1-methyl-1H-pyrazol-3-yl)methyl)amino)naphthalen-1-yl)oxy)pyridin-3-yl)pyrimidin-2-yl)amino)piperidine-1-carboxylate (93 mg, 0.14 mmol) in DCM (0.7 mL) and MeCN (0.7 mL), was added dimethyl sulfide (0.65 mL, 8.85 mmol) followed by boron trifluoride diethyl etherate (0.22 mL, 1.71 mmol) and the was mixture stirred at rt. After 5 h, the mixture was diluted with EtOAc and washed with saturated NaHCO$_3$(aq), then saturated NaCl(aq), dried (MgSO$_4$), filtered and concentrated in vacuo. The obtained residue was dissolved in dioxane (0.5 mL) and hydrochloric acid (4 N in dioxane, 1 mL, 4 mmol) was added. After 10 min at rt, the reaction mixture was diluted with Et$_2$O and the resulting solids collected by filtration and washed with Et$_2$O. The collected solids were then dissolved in water and lyophilized to provide 70 mg (88% yield) of 330. LCMS (ESI) [M+H]$^+$=535.2, rt=1.36 min. $^1$H NMR (400 MHz, d$_6$-DMSO) δ 9.50-8.95 (m, 2H), 8.78 (s, 1H), 8.47 (d, J=5.3 Hz, 1H), 8.04 (dd, J=5.4, 2.4 Hz, 2H), 7.82-7.59 (m, 2H), 7.57 (d, J=2.1 Hz, 1H), 7.37 (d, J=8.8 Hz, 1H), 7.24 (dd, J=7.6, 4.8 Hz, 1H), 7.17-7.09 (m, 1H), 6.85 (d, J=8.4 Hz, 1H), 6.55 (d, J=7.6 Hz, 1H), 6.16 (d, J=2.2 Hz, 1H), 4.39 (s, 2H), 3.79 (s, 3H), 3.57-3.42 (m, 1H), 3.19 (d, J=11.2 Hz, 1H), 2.62 (dd, J=22.6, 12.1 Hz, 1H), 2.45 (t, J=9.9 Hz, 1H), 2.19 (s, 3H), 2.07 (d, J=13.3 Hz, 1H), 1.99 (s, 1H), 1.34-1.21 (m, 1H), 0.94 (d, J=6.5 Hz, 3H).

Example 331 (R)-3-Ethyl-1-(6-methyl-5-((3-(2-(((3S,5R)-5-methylpiperidin-3-yl)amino)pyrimidin-4-yl)oxy)pyridin-2 naphthalen-1-yl)pyrrolidin-2-one 331

Step 1: 4-(2-((5-Bromo-2-methylnaphthalen-1-yl)oxy)pyridin-3-yl)-2-(methylthio)pyrimidine

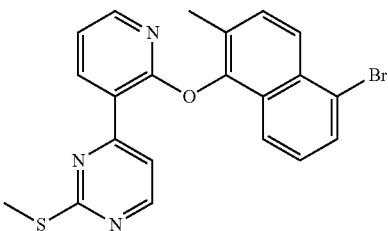 [SMILES: CSc1nccc(-c2cccnc2Oc2c(C)ccc3c(Br)cccc23)n1]

To a solution of 6-methyl-5-[[3-(2-methylsulfanylpyrimidin-4-yl)-2-pyridyl]oxy]naphthalen-1-amine (800 mg, 2.14 mmol) in MeCN (14.2 mL) was added copper (I) bromide (460 mg, 3.2 mmol), followed by tert-butyl nitrite (0.51 mL, 4.27 mmol). The reaction mixture was stirred at rt for 16 h and then diluted with water and concentrated NH$_4$OH(aq) followed by extraction with EtOAc. The organic extract was washed with a mixture of water and concentrated NH$_4$OH (aq), dried (Na$_2$SO$_4$), filtered and evaporated. The residue was purified by flash chromatography through silica gel (100% DCM) to provide 350 mg (37% yield) of the title compound. LCMS (ESI) [M+H]$^+$=438.0, 444.0, rt=2.22 min.

Step 2: 4-(2-((5-Bromo-2-methylnaphthalen-1-yl)oxy)pyridin-3-yl)-2-(methylsulfinyl)pyrimidine

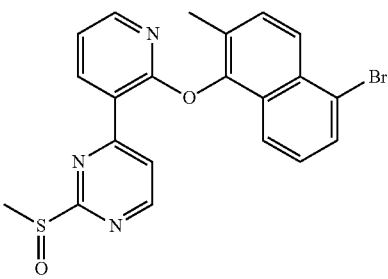 [SMILES: Cc1ccc2c(Br)cccc2c1Oc1ncccc1-c1ccnc(S(C)=O)n1]

To 4-[2-[(5-bromo-2-methyl-1-naphthyl)oxy]-3-pyridyl]-2-methylsulfanyl-pyrimidine (350 mg, 0.8 mmol) in DCM (2.7 mL) under nitrogen was added 3-chloroperbenzoic acid (186 mg of ~78% pure reagent, 0.84 mmol). The reaction was stirred at rt for 30 min then diluted with DCM and washed twice with saturated NaHCO$_3$(aq), dried (Na$_2$SO$_4$), filtered and evaporated to provide 362 mg (100% yield) of the title compound which was used in the next step without further purification. LCMS (ESI) [M+H]$^+$=454.0, 456.0, rt=1.72 min.

Step 3: (3S,5R)-Benzyl 3-((4-(2-((5-bromo-2-methylnaphthalen-1-yl)oxy)pyridin-3-yl)pyrimidin-2-yl)amino)-5-methylpiperidine-1-carboxylate

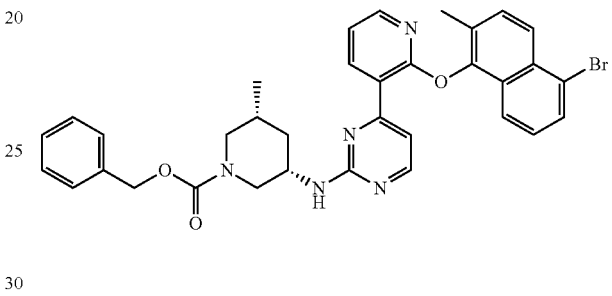

To a solution of 4-[2-[(5-bromo-2-methyl-1-naphthyl)oxy]-3-pyridyl]-2-methylsulfinyl-pyrimidine (360 mg, 0.79 mmol) in 1,4-dioxane (2.6 mL) was added benzyl (3S,5R)-3-amino-5-methyl-piperidine-1-carboxylate hydrochloride (293 mg, 1.03 mmol), followed by triethylamine (0.55 mL, 3.96 mmol). The reaction mixture was stirred at 120° C. for 16 h, diluted with EtOAc and then washed with saturated NaHCO$_3$(aq), dried (Na$_2$SO$_4$), filtered and evaporated. The residue was purified by flash chromatography through silica gel (0-40% EtOAc/DCM) to provide 359 mg (71% yield). LCMS (ESI) [M+H]$^+$=638.3, 640.2, rt=2.31 min.

Step 4: (3S,5R)-Benzyl 3-((4-(2-((5-(3-ethyl-2-oxopyrrolidin-1-yl)-2-methylnaphthalen-1-yl)oxy)pyridin-3-yl)pyrimidin-2-yl)amino)-5-methylpiperidine-1-carboxylate

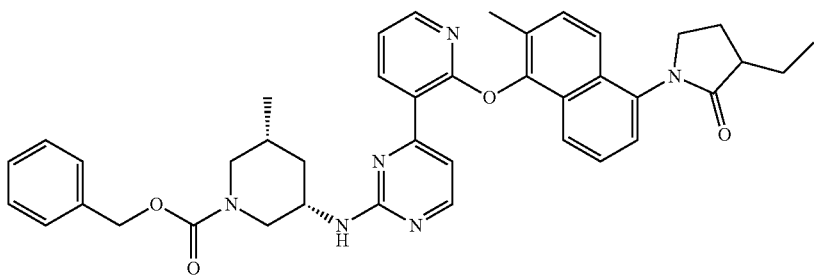

(3S,5R)-Benzyl 3-((4-(2-((5-bromo-2-methylnaphthalen-1-yl)oxy)pyridin-3-yl)pyrimidin-2-yl)amino)-5-methylpiperidine-1-carboxylate (150 mg, 0.23 mmol), 3-ethylpyrrolidin-2-one (0.10 mL, 0.94 mmol), CuI (42 mg, 0.23 mmol), trans-N,N'-dimethylcyclohexyldiamine (0.07 mL, 0.47 mmol) and cesium carbonate (228 mg, 0.70 mmol) were added to a reaction tube followed by addition of toluene (2.3 mL). The solution was degassed with nitrogen and heated at 110° C. for 16 h then diluted with EtOAc and washed with saturated NaHCO$_3$(aq), dried (Na$_2$SO$_4$), filtered and evaporated. The residue was purified by flash chromatography through silica gel (0-50% EtOAc/DCM) to provide 140 mg (88% yield) of the title compound as a mixture of two isomers. LCMS (ESI) [M+H]$^+$=671.4, rt=2.03 min.

Step 5: benzyl (3S,5R)-3-((4-(2-((5-((R)-3-ethyl-2-oxopyrrolidin-1-yl)-2-methylnaphthalen-1-yl)oxy)pyridin-3-yl)pyrimidin-2-yl)amino)-5-methylpiperidine-1-carboxylate (Isomer-1) and benzyl (3S,5R)-3-((4-(2-((5-((S)-3-ethyl-2-oxopyrrolidin-1-yl)-2-methylnaphthalen-1-yl)oxy)pyridin-3-yl)pyrimidin-2-yl)amino)-5-methylpiperidine-1-carboxylate (Isomer-2)

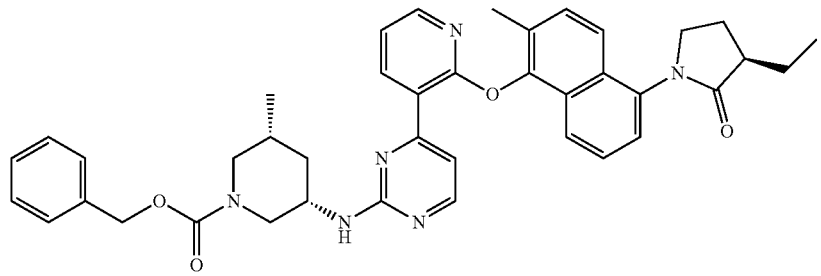

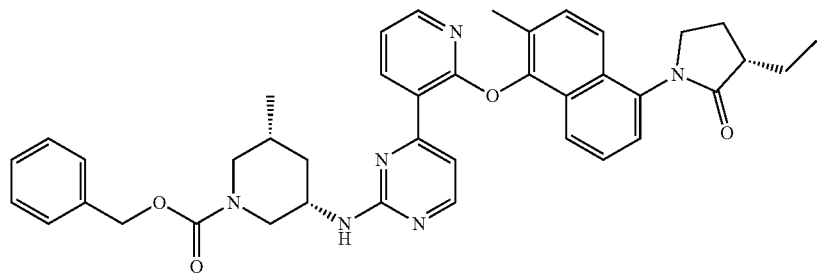 [SMILES: CCC1CCN(c2cccc3c(Oc4ncccc4-c4ccnc(N[C@H]5C[C@@H](C)CN(C(=O)OCc6ccccc6)C5)n4)c(C)ccc23)C1=O]

(3S,5R)-Benzyl 3-((4-(2-((5-(3-ethyl-2-oxopyrrolidin-1-yl)-2-methylnaphthalen-1-yl)oxy)pyridin-3-yl)pyrimidin-2-yl)amino)-5-methylpiperidine-1-carboxylate as a mixture of diastereomers (140 mg, 0.209 mmol) was subjected to chiral normal phase semi-prep purification (conditions: Chiralpak IA, 5 uM, 20×250 mm, 18:82 EtOH:Hexane, 12 et 15 mL/min, 5-10 mg/injection) to provide two stereoisomers enantiomeric at the pyrrolidinone 3-position: (isomer-1), 53 mg (39% yield), 98.6% ee, LCMS (ESI) [M+H]$^+$=671.4, rt=2.03 min; (isomer-2), 52 mg, (38% yield), 96% ee, LCMS (ESI) [M+H]$^+$=671.4, rt=2.03 min.

Step 6: (R)-3-Ethyl-1-(6-methyl-5-((3-(2-(((3S,5R)-5-methylpiperidin-3-yl)amino)pyrimidin-4-yl)pyridin-2-yl)oxy)naphthalen-1-yl)pyrrolidin-2-one

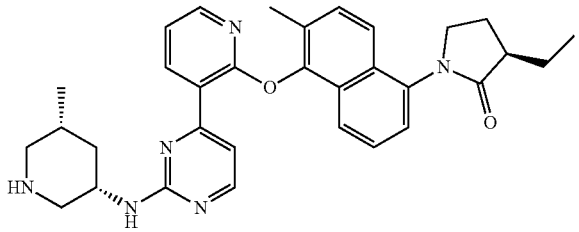 [SMILES: CC[C@@H]1CCN(c2cccc3c(Oc4ncccc4-c4ccnc(N[C@@H]5CNC[C@H](C)C5)n4)c(C)ccc23)C1=O]

Prepared according to General Procedure H using benzyl (3S,5R)-3-((4-(2-((5-((R)-3-ethyl-2-oxopyrrolidin-1-yl)-2-methylnaphthalen-1-yl)oxy)pyridin-3-yl)pyrimidin-2-yl)amino)-5-methylpiperidine-1-carboxylate (isomer-1) (52 mg, 0.08 mmol), iPrOH (1.55 mL), ammonium formate (49 mg, 0.78 mmol), palladium (16 mg of 10% wt on activated carbon) and heating at 55° C. After 1 h, the reaction was filtered on celite, washed with MeOH and DCM and the filtrate evaporated. The obtained residue was partitioned between saturated NaHCO$_3$(aq) and EtOAc, and the phases separated. The organic phase was dried (Na$_2$SO$_4$) and evaporated. The residue was dissolved in 1,4-dioxane (0.2 mL) and hydrochloric acid (4N in dioxane, 1 mL, 4 mmol) was added. After 10 min at rt, the reaction was diluted with Et$_2$O and the resulting solids collected by filtration and washed with Et$_2$O. The solids were then dissolved in water and lyophilized to provide 29 mg (65% yield) of 331. LCMS (ESI) [M+H]$^+$=537.2, rt=1.44 min. $^1$H NMR (400 MHz, d$_6$-DMSO) δ 9.24-8.84 (m, 2H), 8.82-8.64 (m, 1H), 8.47 (d, J=5.2 Hz, 1H), 8.08 (dd, J=4.8, 1.9 Hz, 1H), 7.64 (d, J=8.4 Hz, 1H), 7.62-7.44 (m, 5H), 7.41 (dd, J=7.3, 1.1 Hz, 1H), 7.28 (dd, J=7.6, 4.8 Hz, 1H), 4.30 (s, 1H), 3.77 (d, J=44.8 Hz, 1H), 3.20 (d, J=11.0 Hz, 1H), 2.73-2.55 (m, 2H), 2.49-2.36 (m, 2H), 2.22 (s, 3H), 2.11-1.78 (m, 4H), 1.63-1.46 (m, 1H), 1.27 (q, J=12.0 Hz, 1H), 1.03 (t, J=7.4 Hz, 3H), 0.93 (d, J=6.2 Hz, 3H). The absolute stereochemistry of the lactam was assigned based on the cellular potency.

Example 332 (S)-3-Ethyl-1-(6-methyl-5-((3-(2-(((3S,5R)-5-methylpiperidin-3-yl)amino)pyrimidin-4-yl)oxy)pyridin-2 naphthalen-1-yl)pyrrolidin-2-one 332

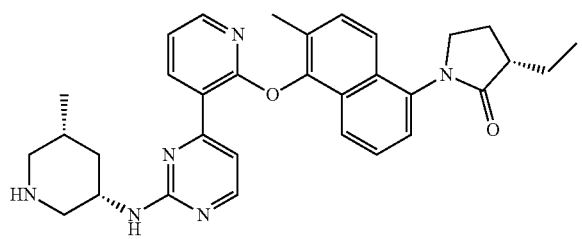 [SMILES: CC[C@H]1CCN(c2cccc3c(Oc4ncccc4-c4ccnc(N[C@@H]5CNC[C@H](C)C5)n4)c(C)ccc23)C1=O]

Prepared according to General Procedure H using benzyl (3S,5R)-3-((4-(2-((5-(((S)-3-ethyl-2-oxopyrrolidin-1-yl)-2-methylnaphthalen-1-yl)oxy)pyridin-3-yl)pyrimidin-2-yl)amino)-5-methylpiperidine-1-carboxylate (isomer-2) (53 mg, 0.08 mmol), iPrOH (1.55 mL), ammonium formate (49 mg, 0.78 mmol), palladium (16 mg of 10% wt on activated carbon) and heating at 55° C. After 1 h, the reaction was filtered on celite, washed with MeOH and DCM and the filtrate was evaporated. The obtained residue was partitioned between saturated NaHCO₃(aq) and EtOAc, and the phases separated and the organic phase dried (Na₂SO₄) and concentrated in vacuo. The residue was dissolved in 1,4-dioxane (0.2 mL) and hydrochloric acid (4N in dioxane, 1 mL, 4 mmol) was added. After 10 min at rt, the reaction mixture was diluted with Et₂O and the resulting solids collected by filtration and washed with Et₂O. The solids were then dissolved in water and lyophilized to provide 30 mg (67% yield) of 332. LCMS (ESI) [M+H]⁺=537.3, rt=1.44 min. ¹H NMR (400 MHz, d6-dmso) δ 9.33-8.89 (m, 2H), 8.76 (s, 1H), 8.47 (d, J=5.2 Hz, 1H), 8.08 (dd, J=4.8, 1.9 Hz, 1H), 7.68-7.44 (m, 6H), 7.41 (dd, J=7.3, 1.1 Hz, 1H), 7.28 (dd, J=7.6, 4.8 Hz, 1H), 4.32 (s, 1H), 3.77 (d, J=45.9 Hz, 1H), 3.20 (d, J=12.3 Hz, 1H), 2.72-2.55 (m, 2H), 2.46-2.35 (m, 2H), 2.22 (s, 3H), 2.11-1.78 (m, 4H), 1.62-1.47 (m, 1H), 1.28 (q, J=11.9 Hz, 1H), 1.03 (t, J=7.4 Hz, 3H), 0.93 (d, J=6.0 Hz, 3H). The absolute stereochemistry of the lactam was assigned based on the cellular potency.

Example 333 (S)-1-Fluoro-3-((6-methyl-5-((3-(2-(((S)-piperidin-3-yl)amino)pyrimidin-4-yl)pyridin-2-yl)oxy)naphthalen-1-yl)amino)propan-2-ol 333

Step 1: (3S)-tert-Butyl 3-((4-(2-((5-((3-fluoro-2-hydroxypropyl)amino)-2-methylnaphthalen-1-yl)oxy)pyridin-3-yl)pyrimidin-2-yl)amino)piperidine-1-carboxylate

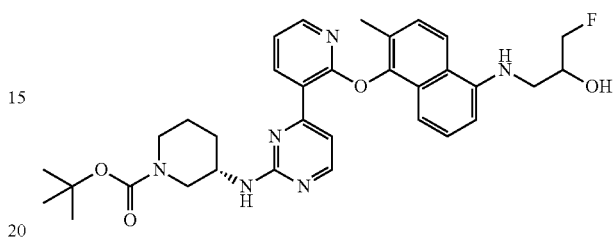

Prepared using (S)-tert-Butyl 3-((4-(2-((5-amino-2-methylnaphthalen-1-yl)oxy)pyridin-3-yl)pyrimidin-2-yl)amino)piperidine-1-carboxylate (150 mg, 0.280 mmol), epifluorohydrin (33 mg, 0.43 mmol), and acetic acid (1 mL). After 16 h, the mixture was concentrated in vacuo and the crude was diluted with H₂O and extracted with EtOAc. The organic extract was dried (MgSO₄), filtered and concentrated in vacuo. The material thus obtained was purified by flash chromatography through silica gel (0-85% EtOAc/DCM) to provide 93 mg (54% yield) of the title compound as a mixture of two isomers. LCMS (ESI) [M+H]⁺=603.2, rt=1.82 min.

Step 2: tert-Butyl (S)-3-((4-(2-((5-(((S)-3-fluoro-2-hydroxypropyl)amino)-2-methylnaphthalen-1-yl)oxy)pyridin-3-yl)pyrimidin-2-yl)amino)piperidine-1-carboxylate (Isomer-1) and tert-butyl (S)-3-((4-(2-((5-(((R)-3-fluoro-2-hydroxypropyl)amino)-2-methylnaphthalen-1-yl)oxy)pyridin-3-yl)pyrimidin-2-yl)amino)piperidine-1-carboxylate (Isomer-2)

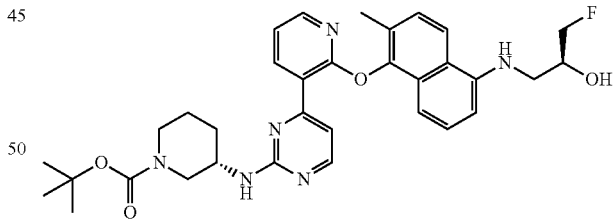

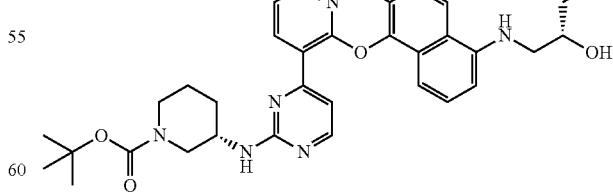

The diastereomers from Step 1 were subjected to chiral semi-prep SFC purification (conditions: IB 10×250 mm, 5 um Isocratic 40% MeOH, 10 mL/min 100 Bar, Column temp: 35° C., Run Time (min): 9.00) to provide two stereoisomers enantiomeric at the alcohol position: (isomer-1), 27 mg (25% yield), rt=5.34, LCMS (ESI) [M+H]⁺=603.3, rt=1.82 min; (isomer-2), 27 mg (25% yield), 97.7% ee, rt=6.76, LCMS (ESI) [M+H]⁺=603.4, rt=1.82 min.

Step 3: (S)-1-Fluoro-3-((6-methyl-5-((3-(2-(((S)-piperidin-3-yl)amino)pyrimidin-4-yl)pyridin-2-yl)oxy)naphthalen-1-yl)amino)propan-2-ol

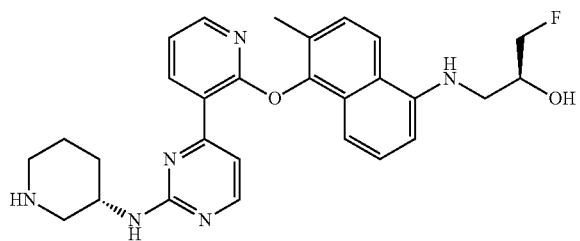 [SMILES: Cc1ccc2c(NC[C@H](O)CF)cccc2c1Oc1ncccc1-c1ccnc(N[C@H]2CCCNC2)n1]

Prepared using tert-butyl (S)-3-((4-(2-((5-(((S)-3-fluoro-2-hydroxypropyl)amino)-2-methylnaphthalen-1-yl)oxy)pyridin-3-yl)pyrimidin-2-yl)amino)piperidine-1-carboxylate (isomer-1) (19 mg, 0.032 mmol), 1,4-dioxane (1 mL), and hydrochloric acid (4 M in dioxane, 1 mL, 4 mmol). After 3 h, the mixture was concentrated in vacuo and the resulting residue was triturated in EtOAc and the solids were filtered off. The collected solids were dissolved in H₂O and MeCN and lyophilized to provide 16 mg (94% yield) of 333. The stereochemical assignments of 333 and 334 were randomly assigned and may be later determined. LCMS (ESI) [M+H]⁺=503.1, rt=1.22 min; ¹H NMR (400 MHz, d6-dmso) δ 9.23 (s, 1H), 9.07 (s, 1H), 8.75 (s, 1H), 8.49 (d, J=5.0 Hz, 1H), 8.12-7.98 (m, 2H), 7.73 (s, 1H), 7.63 (s, 1H), 7.38 (d, J=8.8 Hz, 1H), 7.25 (dd, J=7.5, 4.8 Hz, 1H), 7.19 (t, J=8.0 Hz, 1H), 6.88 (d, J=8.3 Hz, 1H), 6.56 (d, J=7.7 Hz, 1H), 4.60-4.48 (m, 1H), 4.46-4.33 (m, 1H), 4.14-4.00 (m, 2H), 3.50-3.39 (m, 1H), 3.33 (dd, J=13.0, 5.9 Hz, 1H), 3.26-3.13 (m, 2H), 2.95-2.75 (m, 2H), 2.19 (s, 3H), 2.09-1.86 (m, 2H), 1.87-1.55 (m, 2H).

Example 334 (R)-1-Fluoro-3-((6-methyl-5-((3-(2-(((S)-piperidin-3-yl)amino)pyrimidin-4-yl)pyridin-2-yl)oxy)naphthalen-1-yl)amino)propan-2-ol 334

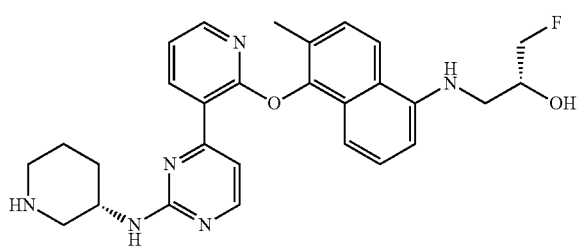 [SMILES: Cc1ccc2c(NC[C@@H](O)CF)cccc2c1Oc1ncccc1-c1ccnc(N[C@H]2CCCNC2)n1]

Following the procedures of Example 333, tert-butyl (S)-3-((4-(2-((5-(((R)-3-fluoro-2-hydroxypropyl)amino)-2-methylnaphthalen-1-yl)oxy)pyridin-3-yl)pyrimidin-2-yl)amino)piperidine-1-carboxylate (isomer-2) was deprotected with 1,4-dioxane and hydrochloric acid (4 M in dioxane) to give 334: LCMS (ESI) [M+H]⁺=503.1, rt=1.22 min; ¹H NMR (400 MHz, d₆-DMSO) δ 9.23 (s, 1H), 9.07 (s, 1H), 8.75 (s, 1H), 8.49 (d, J=5.0 Hz, 1H), 8.12-7.98 (m, 2H), 7.73 (s, 1H), 7.63 (s, 1H), 7.38 (d, J=8.8 Hz, 1H), 7.25 (dd, J=7.5, 4.8 Hz, 1H), 7.19 (t, J=8.0 Hz, 1H), 6.88 (d, J=8.3 Hz, 1H), 6.56 (d, J=7.7 Hz, 1H), 4.60-4.48 (m, 1H), 4.46-4.33 (m, 1H), 4.14-4.00 (m, 2H), 3.50-3.39 (m, 1H), 3.33 (dd, J=13.0, 5.9 Hz, 1H), 3.26-3.13 (m, 2H), 2.95-2.75 (m, 2H), 2.19 (s, 3H), 2.09-1.86 (m, 2H), 1.87-1.55 (m, 2H).

Example 335 (S)-1-(2-Fluoro-6-methyl-5-((3-(2-(piperidin-3-ylamino)pyrimidin-4-yl)pyridin-2-yl)oxy)naphthalen-1-yl)pyrrolidin-2-one 335

Step 1: (S)-tert-Butyl 3-((4-(2-((5-bromo-6-fluoro-2-methylnaphthalen-1-yl)oxy)pyridin-3-yl)pyrimidin-2-yl)amino)piperidine-1-carboxylate

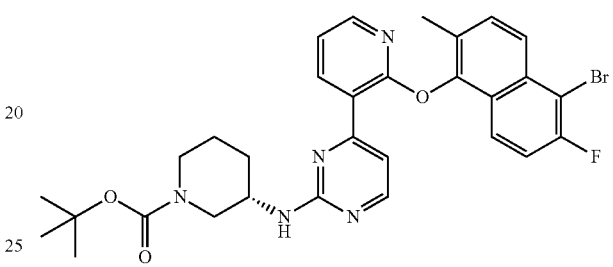

To a solution of tert-butyl (3S)-3-[[4-[2-[(5-amino-6-fluoro-2-methyl-1-naphthyl)oxy]-3-pyridyl]pyrimidin-2-yl]amino]piperidine-1-carboxylate (1000 mg, 1.84 mmol) in MeCN (7.3 mL) was added copper (I) bromide (922 mg, 6.43 mmol), followed by tert-butyl nitrite (0.33 mL, 2.75 mmol). The reaction mixture was stirred at rt for 16 h then diluted with water and concentrated NH₄OH(aq) and extracted with EtOAc. The organic extract was washed with a mixture of water and concentrated NH₄OH(aq), dried (Na₂SO₄), filtered and evaporated. The residue was purified by flash chromatography through silica gel (100% DCM then 0-20% EtOAc/DCM) to provide 265 mg (17% yield) of the title compound. LCMS (ESI) [M+H]⁺=608.2, 610.2, rt=2.28 min.

Step 2: (S)-tert-Butyl 3-((4-(2-((6-fluoro-2-methyl-5-(2-oxopyrrolidin-1-yl)naphthalen-1-yl)oxy)pyridin-3-yl)pyrimidin-2-yl)amino)piperidine-1-carboxylate

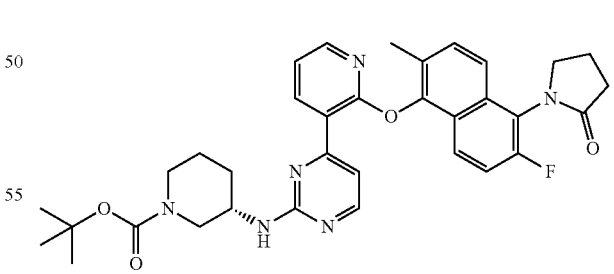

A reaction tube was charged with tert-butyl (3S)-3-[[4-[2-[(5-bromo-6-fluoro-2-methyl-1-naphthyl)oxy]-3-pyridyl]pyrimidin-2-yl]amino]piperidine-1-carboxylate (25 mg, 0.04 mmol), CuI (7.4 mg, 0.04 mmol), trans-N,N-dimethylcyclohexyldiamine (0.01 mL, 0.08 mmol), cesium carbonate (40 mg, 0.12 mmol) and 2-pyrrolidinone (0.01 mL, 0.16 mmol) in that order. Toluene (0.41 mL) was then added and the solution was degassed with nitrogen and heated at 110° C. for 16 h. The reaction was diluted with EtOAc and washed with saturated NaHCO₃(aq), dried (Na₂SO₄) filtered and evaporated. The residue was purified by flash chromatography through silica gel (0-100% EtOAc/DCM) to provide 23 mg (91% yield). LCMS (ESI) [M+H]⁺=613.3, rt=1.83 min.

Step 3: (S)-1-(2-Fluoro-6-methyl-5-((3-(2-(piperidin-3-ylamino)pyrimidin-4-yl)pyridin-2-yl)oxy)naphthalen-1-yl)pyrrolidin-2-one

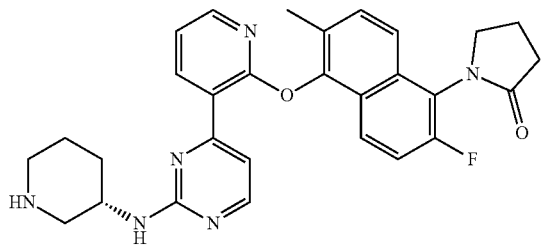 [SMILES: Cc1ccc2c(N3CCCC3=O)c(F)ccc2c1Oc1ncccc1-c1ccnc(N[C@H]2CCCNC2)n1]

Prepared according to General Procedure B using (S)-tert-butyl 3-((4-(2-((6-fluoro-2-methyl-5-(2-oxopyrrolidin-1-yl)naphthalen-1-yl)oxy)pyridin-3-yl)pyrimidin-2-yl)amino)piperidine-1-carboxylate (23 mg, 0.04 mmol), 1,4-dioxane (0.5 mL), hydrochloric acid (4N in dioxane, 1 mL, 4 mmol). The reaction mixture was stirred at rt for 1.5 h then diluted with Et₂O and the resulting solids collected by filtration and washed with Et₂O. The solids were then dissolved in water, and lyophilized to provide 18 mg (86% yield) of 335. LCMS (ESI) [M+H]⁺=513.3, rt=1.29 min. ¹H NMR (400 MHz, d₆-DMSO) δ 9.18-8.84 (m, 1H), 8.78-8.59 (m, 1H), 8.48 (d, J=5.2 Hz, 1H), 8.09 (dd, J=4.4, 1.5 Hz, 1H), 7.76 (dd, J=9.4, 5.2 Hz, 1H), 7.68 (d, J=8.7 Hz, 1H), 7.63-7.53 (m, 3H), 7.48 (t, J=9.5 Hz, 1H), 7.29 (dd, J=7.6, 4.8 Hz, 2H), 4.29 (s, 1H), 3.82-3.75 (m, 2H), 3.43 (d, J=8.9 Hz, 1H), 3.20 (d, J=11.8 Hz, 1H), 2.92-2.76 (m, 2H), 2.68-2.52 (m, 2H), 2.43-2.23 (m, 2H), 2.20 (s, 3H), 2.02 (dd, J=12.8, 4.2 Hz, 1H), 1.92 (dt, J=13.2, 3.9 Hz, 2H), 1.83-1.57 (m, 1H).

Example 337 (S)—N-(6-Methyl-5-((3-(2-(piperidin-3-ylamino)pyrimidin-4-yl)pyridin-2-yl)oxy)naphthalen-1-yl)cyclopropanecarboxamide hydrochloride 337

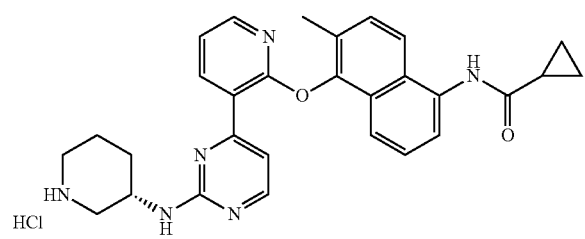 [SMILES: Cc1ccc2c(NC(=O)C3CC3)cccc2c1Oc1ncccc1-c1ccnc(N[C@H]2CCCNC2)n1 ; Cl]

Step 1: tert-Butyl (S)-3-((4-(2-((5-(Cyclopropanecarboxamido)-2-methylnaphthalen-1-yl)oxy)pyridin-3-yl)pyrimidin-2-yl)amino)piperidine-1-carboxylate

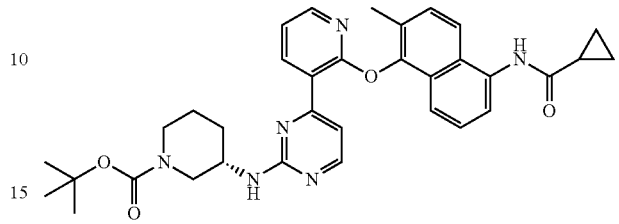

To a solution of tert-butyl (3S)-3-[[4-[2-[(5-amino-2-methyl-1-naphthyl)oxy]-3-pyridyl]pyrimidin-2-yl]amino]piperidine-1-carboxylate (100 mg, 0.19 mmol) and pyridine (0.20 mL, 0.57 mmol) in dry dichloromethane (5 mL) was added cyclopropanecarbonyl chloride (0.03 mL, 0.29 mmol) at 0° C. After addition completed, the mixture was stirred at 25° C. for 4 h. Methanol was added and the mixture was concentrated to yield 112 mg (99% yield) of the title compound as a yellow solid. LC-MS (ESI): [M+H]⁺=595.

Step 2: (S)—N-(6-Methyl-5-((3-(2-(piperidin-3-ylamino)pyrimidin-4-yl)pyridin-2-yl)oxy)naphthalen-1-yl)cyclopropanecarboxamide hydrochloride

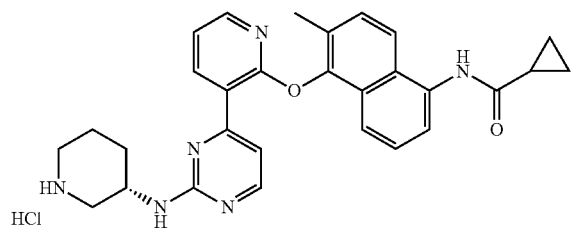 [SMILES: Cc1ccc2c(NC(=O)C3CC3)cccc2c1Oc1ncccc1-c1ccnc(N[C@H]2CCCNC2)n1 ; Cl]

The General Procedure B was followed, using tert-butyl (S)-3-((4-(2-((5-(cyclopropanecarboxamido)-2-methylnaphthalen-1-yl)oxy)pyridin-3-yl)pyrimidin-2-yl)amino)piperidine-1-carboxylate (112 mg, 0.19 mmol), DCM (3 mL) and hydrochloric acid (4 M in dioxane, 3 mL, 12 mmol). The residue was purified by Prep-HPLC to yield 62 mg (58% yield) of 337 as a red solid. LCMS (ESI): [M+H]⁺=495; ¹H-NMR (400 MHz, CD₃OD) δ 8.65 (d, J=6.9 Hz, 1H), 8.56 (s, 1H), 8.46 (d, J=5.2 Hz, 1H), 8.00-7.99 (m, 1H), 7.94 (d, J=4.3 Hz, 1H), 7.69 (d, J=5.3 Hz, 1H), 7.66 (t, J=7.7 Hz, 2H), 7.52 (d, J=8.7 Hz, 1H), 7.39 (t, J=8.0 Hz, 1H), 7.23 (q, J=4.9 Hz, 1H), 4.38-4.35 (m, 1H), 3.61 (dd, J=11.6, 2.5 Hz, 1H), 3.07-3.00 (m, 2H), 2.29 (s, 3H), 2.29 (s, 3H), 2.22-2.19 (m, 1H), 2.14-2.00 (m, 2H), 1.93-1.76 (m, 2H), 1.05-0.93 (m, 4H).

Example 338 (S)-2,2-Dichloro-N-(6-methyl-5-(3-(2-(piperidin-3-ylamino)pyrimidin-4-yl)pyridin-2-yloxy)naphthalen-1-yl)acetamide 338

Step 1: (S)-tert-Butyl 3-(4-(2-(5-(2,2-dichloroacetamido)-2-methylnaphthalen-1-yloxy)pyridin-3-yl)pyrimidin-2-ylamino)piperidine-1-carboxylate

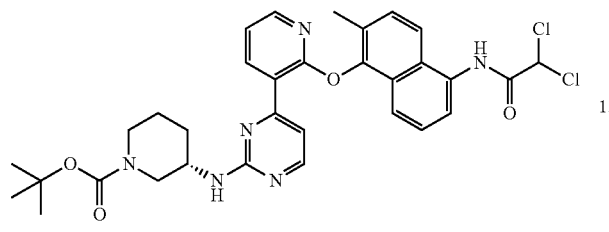

The General Procedure C was followed, using tert-butyl (3S)-3-[[4-[2-[(5-amino-2-methyl-1-naphthyl)oxy]-3-pyridyl]pyrimidin-2-yl]amino]piperidine-1-carboxylate (50 mg, 0.095 mmol), HATU (72 mg, 0.19 mmol), diisopropylethylamine (36 mg, 0.29 mmol), and dichloroacetic acid (50 mg, 0.38 mmol). The product obtained after workup was used in step 2 without further purification. LCMS (ESI) [M+H]$^+$=637.2.

Step 2: (S)-2,2-Dichloro-N-(6-methyl-5-(3-(2-(piperidin-3-ylamino)pyrimidin-4-yl)pyridin-2-yloxy)naphthalen-1-yl)acetamide

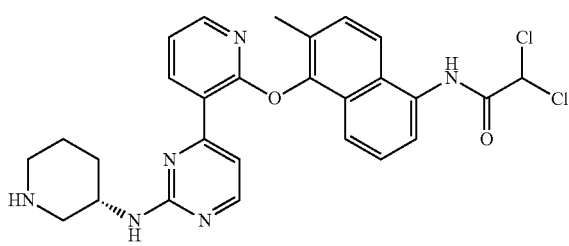 [SMILES: Cc1ccc2c(NC(=O)C(Cl)Cl)cccc2c1Oc1ncccc1-c1ccnc(N[C@H]2CCCNC2)n1]

To the crude (S)-tert-butyl 3-(4-(2-(5-(2,2-dichloroacetamido)-2-methylnaphthalen-1-yloxy)pyridin-3-yl)pyrimidin-2-ylamino)piperidine-1-carboxylate from step 1 in DCM (6 mL) was added trifluoroacetic acid (1 mL). The mixture was concentrated and the residue purified by Prep-HPLC to yield 23.6 mg (46% yield) of 338 as a white solid. LCMS (ESI): [M+H]$^+$=537.1. $^1$H NMR (400 MHz, DMSO-d$_6$) δ 10.67 (s, 1H), 8.49 (s, 1H), 8.41 (d, J=5.1 Hz, 1H), 8.03 (dd, J=4.8, 2.0 Hz, 1H), 7.85 (d, J=8.7 Hz, 1H), 7.64-7.56 (m, 3H), 7.49-7.43 (m, 2H), 7.27 (dd, J=7.6, 4.8 Hz, 1H), 7.12 (d, J=8.0 Hz, 1H), 6.87 (s, 1H), 3.89 (s, 1H), 3.13-3.08 (m, 1H), 2.80 (d, J=12.3 Hz, 1H), 2.23 (s, 3H), 1.92 (s, 1H), 1.67-1.61 (m, 1H), 1.51-1.42 (m, 2H).

Example 339 (S)—N-(6-Methyl-5-((3-(2-(((S)-piperidin-3-yl)amino)pyrimidin-4-yl)pyridin-2-yl)oxy)naphthalen-1-yl)spiro[2.3]hexane-1-carboxamide 339

Step 1: tert-Butyl (S)-3-((4-(2-((2-methyl-5-((S)-spiro[2.3]hexane-1-carboxamido)naphthalen-1-yl)oxy)pyridin-3-yl)pyrimidin-2-yl)amino)piperidine-1-carboxylate

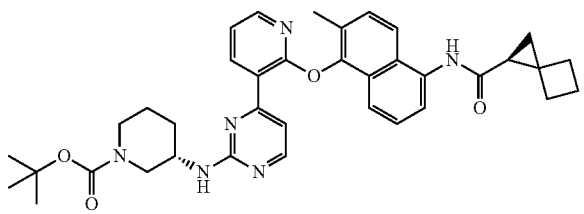 [SMILES: Cc1ccc2c(NC(=O)[C@H]3CC34CCC4)cccc2c1Oc1ncccc1-c1ccnc(N[C@H]2CCCN(C(=O)OC(C)(C)C)C2)n1]

The General Procedure C was followed, using tert-butyl (3S)-3-[[4-[2-[(5-amino-2-methyl-1-naphthyl)oxy]-3-pyridyl]pyrimidin-2-yl]amino]piperidine-1-carboxylate (100 mg, 0.19 mmol) and spiro[2.3]hexane-2-carboxylic acid (35.9 mg, 0.28 mmol), DIPEA (0.10 mL, 0.57 mmol), and HATU (147.4 mg, 0.38 mmol) in DMF (1 mL) was stirred at room temperature overnight. The crude material was purified by silica gel chromatography (12 g column), eluting with 0-5% MeOH/DCM to afford 73 mg (60.5% yield) of the title compound as a yellow solid. LCMS (ESI) [M+H]$^+$=635.

Step 2: (S)—N-(6-Methyl-5-((3-(2-(((S)-piperidin-3-yl)amino)pyrimidin-4-yl)pyridin-2-yl)oxy)naphthalen-1-yl)spiro[2.3]hexane-1-carboxamide

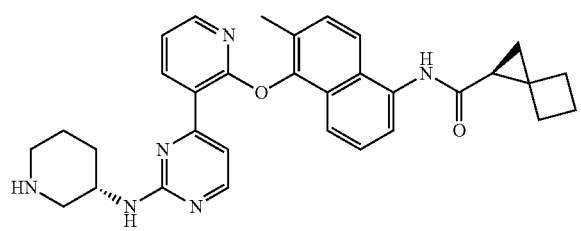 [SMILES: Cc1ccc2c(NC(=O)[C@H]3CC34CCC4)cccc2c1Oc1ncccc1-c1ccnc(N[C@H]2CCCNC2)n1]

The General Procedure B was followed, using tert-butyl (3S)-3-((4-(2-((2-methyl-5-(spiro[2.3]hexane-1-carboxamido)naphthalen-1-yl)oxy)pyridin-3-yl)pyrimidin-2-yl)amino)piperidine-1-carboxylate (73 mg, 0.12 mmol). The crude product was purified via reverse-phase HPLC, chiral SFC, and lyophilized to yield 22 mg (35.5% yield) of 339 (isomer-1) as an off-white solid. The stereochemical assignments of 339 and 340 were randomly assigned and may be later determined. LCMS (ESI) [M+H]$^+$=535; $t_R$=1.139 min; $^1$H NMR (400 MHz, DMSO-d$_6$) δ 10.07 (s, 1H), 8.52-8.47 (m, 1H), 8.41 (d, J=5.1 Hz, 1H), 8.02 (dd, J=4.8, 2.0 Hz, 1H), 7.99 (d, J=8.7 Hz, 1H), 7.67 (d, J=7.1 Hz, 1H), 7.53 (d, J=8.8 Hz, 1H), 7.49 (d, J=8.7 Hz, 2H), 7.44 (d, J=5.1 Hz, 1H), 7.39 (dd, J=8.4, 7.4 Hz, 1H), 7.25 (dd, J=7.6, 4.8 Hz, 1H), 7.11 (d, J=8.0 Hz, 1H), 3.88 (s, 1H), 3.09 (d, J=11.4 Hz, 1H), 2.78 (d, J=12.4 Hz, 1H), 2.47-2.37 (m, 3H), 2.30-1.98 (m, 6H), 1.96-1.89 (m, 1H), 1.69-1.61 (m, 1H), 1.55-1.38 (m, 2H), 1.12 (dd, J=5.4, 4.1 Hz, 1H), 1.04-0.95 (m, 1H).

Example 340 (R)—N-(6-Methyl-5-((3-(2-(((S)-piperidin-3-yl)amino)pyrimidin-4-yl)pyridin-2-yl)oxy)naphthalen-1-yl)spiro[2.3]hexane-1-carboxamide 340

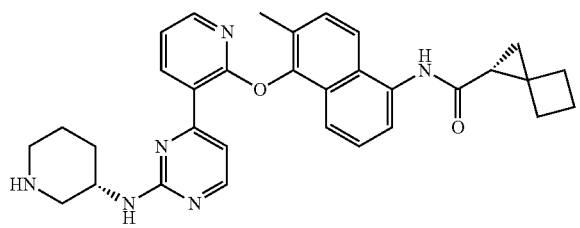 [SMILES: Cc1ccc2c(NC(=O)[C@@H]3CC34CCC4)cccc2c1Oc1ncccc1-c1ccnc(N[C@H]2CCCNC2)n1]

Following the procedures for Example 339, tert-butyl (3S)-3-((4-(2-((2-methyl-5-(spiro[2.3]hexane-1-carboxamido)naphthalen-1-yl)oxy)pyridin-3-yl)pyrimidin-2-yl)amino)piperidine-1-carboxylate was deprotected by General Procedure B to give 340 as isomer-2, 22 mg (35.7% yield) as an off-white solid. LCMS (ESI) [M+H]$^+$=535; $t_R$=1.491 min; $^1$H NMR (400 MHz, DMSO-d$_6$) δ 10.07 (s, 1H), 8.49 (d, J=7.5 Hz, 1H), 8.41 (d, J=5.1 Hz, 1H), 8.02 (dd, J=4.8, 2.0 Hz, 1H), 7.99 (d, J=8.7 Hz, 1H), 7.67 (d, J=7.3 Hz, 1H), 7.53 (d, J=8.7 Hz, 1H), 7.49 (d, J=8.2 Hz, 1H), 7.44 (d, J=5.1 Hz, 1H), 7.39 (dd, J=8.4, 7.5 Hz, 1H), 7.25 (dd, J=7.6, 4.8 Hz, 1H), 7.11 (d, J=8.0 Hz, 1H), 3.88 (s, 1H), 3.09 (d, J=11.5 Hz, 1H), 2.79 (d, J=12.3 Hz, 1H), 2.47-2.40 (m, 3H), 2.30-1.99 (m, 6H), 1.95-1.89 (m, 1H), 1.67-1.60 (m, 1H), 1.55-1.39 (m, 2H), 1.12 (dd, J=5.4, 4.1 Hz, 1H), 1.03-0.98 (m, 1H).

Example 341 4-(2-((5-(((2,2-Difluorocyclopropyl)methyl)amino)-2-methylnaphthalen-1-yl)oxy)pyridin-3-yl)-N—((S)-piperidin-3-yl)pyrimidin-2-amine 341

Step 1: tert-Butyl (3S)-3-((4-(2-((5-(((2,2-difluorocyclopropyl)methyl)amino)-2-methylnaphthalen-1-yl)oxy)pyridin-3-yl)pyrimidin-2-yl)amino)piperidine-1-carboxylate

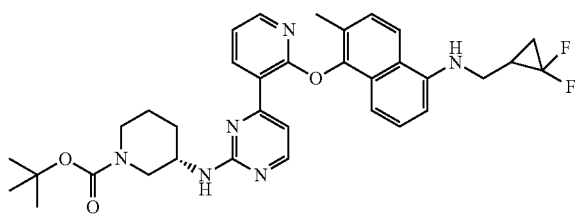 [SMILES: Cc1ccc2c(NCC3CC3(F)F)cccc2c1Oc1ncccc1-c1ccnc(N[C@H]2CCCN(C(=O)OC(C)(C)C)C2)n1]

The General Procedure E was followed, using tert-butyl (3S)-3-[[4-[2-[(5-amino-2-methyl-1-naphthyl)oxy]-3-pyridyl]pyrimidin-2-yl]amino]piperidine-1-carboxylate (150 mg, 0.28 mmol) and 1-bromomethyl-2,2-difluorocyclopropane (154 mg, 0.85 mmol). The crude material was purified by silica gel chromatography, 12 g column, eluting with 0-5% MeOH/DCM to afford 79 mg (45% yield) of the title compound as a brown oil. LCMS (ESI) [M+H]$^+$=617.

Step 2: 4-(2-((5-(((2,2-Difluorocyclopropyl)methyl)amino)-2-methylnaphthalen-1-yl)oxy)pyridin-3-yl)-N—((S)-piperidin-3-yl)pyrimidin-2-amine

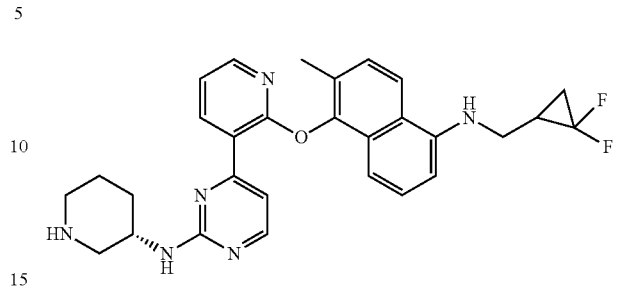

The General Procedure B was followed, using tert-butyl (3S)-3-((4-(2-((5-(((2,2-difluorocyclopropyl)methyl)amino)-2-methylnaphthalen-1-yl)oxy)pyridin-3-yl)pyrimidin-2-yl)amino)piperidine-1-carboxylate (79 mg, 0.13 mmol). The crude product was purified via reverse-phase HPLC and lyophilized to yield 36 mg (54% yield) to afford 36 mg (54% yield) of racemic 341 as an off-white solid. LCMS (ESI) [M+H]$^+$=517; $^1$H NMR (400 MHz, DMSO-d$_6$) δ 8.48 (s, 1H), 8.40 (d, J=5.1 Hz, 1H), 8.06-7.96 (m, 2H), 7.43 (d, J=5.1 Hz, 1H), 7.36 (d, J=8.7 Hz, 1H), 7.26-7.16 (m, 2H), 7.10 (d, J=8.0 Hz, 1H), 6.89 (d, J=8.4 Hz, 1H), 6.55-6.49 (m, 1H), 6.46 (t, J=5.7 Hz, 1H), 3.88 (s, 1H), 3.44-3.35 (m, 1H), 3.09 (d, J=11.8 Hz, 1H), 2.79 (d, J=12.3 Hz, 1H), 2.48-2.39 (m, 3H), 2.21-2.11 (m, 3H), 1.96-1.88 (m, 1H), 1.68-1.54 (m, 2H), 1.52-1.32 (m, 2H).

Example 342 4-(2-((5-((((R)-2,2-Difluorocyclopropyl)methyl)amino)-2-methylnaphthalen-1-yl)oxy)pyridin-3-yl)-N—((S)-piperidin-3-yl)pyrimidin-2-amine 342

Step 1: tert-butyl (S)-3-((4-(2-((5-((((S)-2,2-Difluorocyclopropyl)methyl)amino)-2-methylnaphthalen-1-yl)oxy)pyridin-3-yl)pyrimidin-2-yl)amino)piperidine-1-carboxylate

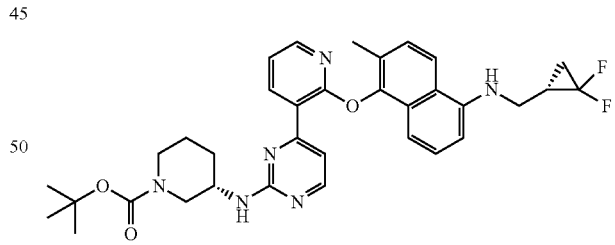

The Example 341 and General Procedure E were followed, using tert-butyl (3S)-3-[[4-[2-[(5-amino-2-methyl-1-naphthyl)oxy]-3-pyridyl]pyrimidin-2-yl]amino]piperidine-1-carboxylate (400 mg, 0.76 mmol), 2-(bromomethyl)-1,1-difluoro-cyclopropane (259.7 mg, 1.52 mmol). The crude material was purified by silica gel chromatography, 24 g column, eluting with 0-5% MeOH/DCM to afford 325 mg (69.4% yield) of the title compound as a brown gum. LCMS (ESI) [M+H]$^+$=617. The enantiomers were separated by chiral SFC to afford 87.3 mg isomer-1 ($t_R$=1.512 min) as an off-white solid and 98.3 mg isomer-2 ($t_R$=1.780 min) as an off-white solid.

Step 2: 4-(2-((5-((((R)-2,2-Difluorocyclopropyl)methyl)amino)-2-methylnaphthalen-1-yl)oxy)pyridin-3-yl)-N—((S)-piperidin-3-yl)pyrimidin-2-amine

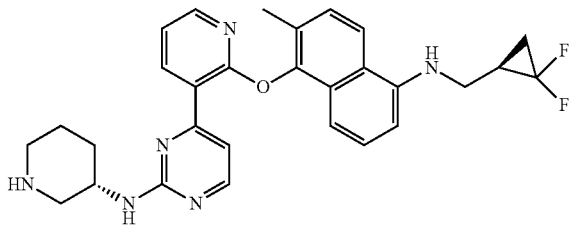 [SMILES: Cc1ccc2c(NC[C@H]3CC3(F)F)cccc2c1Oc1ncccc1-c1ccnc(N[C@H]2CCCNC2)n1]

The General Procedure B was followed, using tert-butyl (S)-3-((4-(2-((5-((((S)-2,2-difluorocyclopropyl)methyl)amino)-2-methylnaphthalen-1-yl)oxy)pyridin-3-yl)pyrimidin-2-yl)amino)piperidine-1-carboxylate (isomer-1, 87 mg, 0.14 mmol). The crude product was lyophilized to yield 78 mg (100% yield) of 342 as a light brown solid. The stereochemical assignments of 342 and 343 were randomly assigned and may be later determined. LCMS (ESI) [M+H]⁺=517; ¹H NMR (400 MHz, DMSO-d₆) δ 8.88-8.70 (m, 2H), 8.65-8.54 (m, 1H), 8.47 (d, J=5.2 Hz, 1H), 8.06-8.01 (m, 2H), 7.57 (d, J=5.2 Hz, 1H), 7.51 (d, J=7.4 Hz, 1H), 7.37 (d, J=8.7 Hz, 1H), 7.24 (dd, J=7.5, 4.8 Hz, 1H), 7.19 (dd, J=8.4, 7.7 Hz, 1H), 6.86 (d, J=8.3 Hz, 1H), 6.56-6.46 (m, 1H), 4.31-4.20 (m, 1H), 3.33-3.27 (m, 1H), 3.25-3.18 (m, 1H), 2.92-2.80 (m, 2H), 2.19 (s, 3H), 2.18-2.12 (m, 1H), 2.07-1.97 (m, 1H), 1.96-1.90 (m, 1H), 1.79-1.56 (m, 2H), 1.40-1.32 (m, 1H).

Example 343 4-(2-((5-((((S)-2,2-Difluorocyclopropyl)methyl)amino)-2-methylnaphthalen-1-yl)oxy)pyridin-3-yl)-N—((S)-piperidin-3-yl)pyrimidin-2-amine 343

Following Examples 342 and 343, and General Procedure B, tert-butyl (S)-3-((4-(2-((5-((((S)-2,2-difluorocyclopropyl)methyl)amino)-2-methylnaphthalen-1-yl)oxy)pyridin-3-yl)pyrimidin-2-yl)amino)piperidine-1-carboxylate (isomer-2, 98 mg, 0.16 mmol). The crude product was lyophilized to afford 88 mg (94% yield) of 343 as a light brown solid. LCMS (ESI) [M+H]⁺=517; ¹H NMR (400 MHz, DMSO-d₆) δ 8.81-8.66 (m, 3H), 8.47 (d, J=5.2 Hz, 1H), 8.06-8.02 (m, 2H), 7.57 (d, J=5.2 Hz, 1H), 7.49 (d, J=7.4 Hz, 1H), 7.37 (d, J=8.7 Hz, 1H), 7.24 (dd, J=7.6, 4.8 Hz, 1H), 7.19 (dd, J=8.4, 7.7 Hz, 1H), 6.86 (d, J=8.4 Hz, 1H), 6.55-6.48 (m, 1H), 4.30-4.20 (m, 1H), 3.25-3.18 (m, 2H), 2.93-2.79 (m, 2H), 2.19 (s, 3H), 2.18-2.12 (m, 1H), 2.05-1.98 (m, 1H), 1.96-1.90 (m, 1H), 1.79-1.54 (m, 2H), 1.41-1.31 (m, 1H).

Example 344 (S)-4-(2-((2-Methyl-5-((4,4,4-trifluorobutyl)amino)naphthalen-1-yl)oxy)pyridin-3-yl)-N-(piperidin-3-yl)pyrimidin-2-amine 344

Step 1: tert-Butyl (S)-3-((4-(2-((2-methyl-5-((4,4,4-trifluorobutyl)amino)naphthalen-1-yl)oxy)pyridin-3-yl)pyrimidin-2-yl)amino)piperidine-1-carboxylate

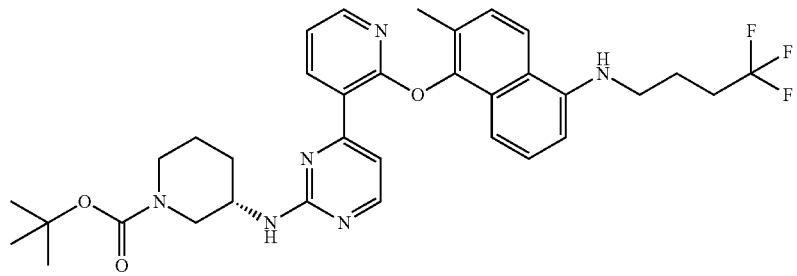 [SMILES: Cc1ccc2c(NCCCC(F)(F)F)cccc2c1Oc1ncccc1-c1ccnc(N[C@H]2CCCN(C(=O)OC(C)(C)C)C2)n1]

The General Procedure E was followed, using tert-butyl (3S)-3-[[4-[2-[(5-amino-2-methyl-1-naphthyl)oxy]-3-pyridyl]pyrimidin-2-yl]amino]piperidine-1-carboxylate (200 mg, 0.38 mmol) and 1-bromo-4,4,4-trifluorobutane (148 mg, 0.76 mmol). The crude material was purified by silica gel chromatography, 12 g column, eluting with 0-5% MeOH/DCM to afford 141 mg (58.3% yield) of the title compound as a brown solid. LCMS (ESI) [M+H]⁺=637.

Step 2: (S)-4-(2-((2-Methyl-5-((4,4,4-trifluorobutyl)amino)naphthalen-1-yl)oxy)pyridin-3-yl)-N-(piperidin-3-yl)pyrimidin-2-amine

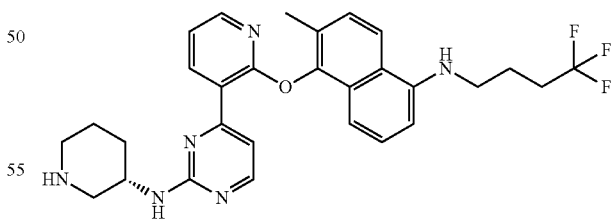

The General Procedure B was followed, using tert-butyl (S)-3-((4-(2-((2-methyl-5-((4,4,4-trifluorobutyl)amino)naphthalen-1-yl)oxy)pyridin-3-yl)pyrimidin-2-yl)amino)piperidine-1-carboxylate (141 mg, 0.22 mmol). The crude product was purified via reverse-phase HPLC and lyophilized to yield 68.7 mg (58% yield) of 344 as an off-white solid. LCMS (ESI) [M+H]⁺=537; ¹H NMR (400 MHz, DMSO-d₆) δ 8.48 (d, J=7.5 Hz, 1H), 8.39 (d, J=5.1 Hz, 1H), 8.01 (dd, J=4.8, 2.0 Hz, 2H), 7.43 (d, J=5.1 Hz, 1H), 7.35 (d, J=8.7 Hz, 1H), 7.23 (dd, J=7.5, 4.8 Hz, 1H), 7.21-7.14 (m, 1H), 7.09 (d, J=8.0 Hz, 1H), 6.86 (d, J=8.4 Hz, 1H), 6.47 (dd, J=7.8, 1.0 Hz, 1H), 6.28 (t, J=5.5 Hz, 1H), 3.87 (s, 1H), 3.29-3.24 (m, 2H), 3.09 (d, J=11.8 Hz, 1H), 2.82-2.74 (m, 1H), 2.46-2.37 (m, 4H), 2.18 (s, 3H), 1.95-1.86 (m, 3H), 1.67-1.60 (m, 1H), 1.54-1.38 (m, 2H).

Example 345 (S)-4-(2-((5-(((2-Ethylthiazol-4-yl)methyl)amino)-2-methylnaphthalen-1-yl)oxy)pyridin-3-yl)-N-(piperidin-3-yl)pyrimidin-2-amine 345

Step 1: tert-Butyl (S)-3-((4-(2-((5-(((2-ethylthiazol-4-yl)methyl)amino)-2-methylnaphthalen-1-yl)oxy)pyridin-3-yl)pyrimidin-2-yl)amino)piperidine-1-carboxylate

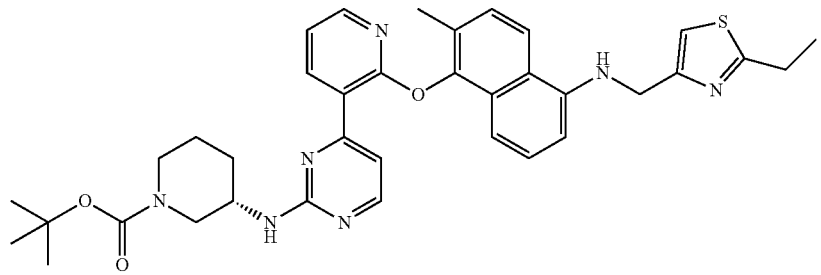 [SMILES: CCc1nc(CNc2cccc3c(Oc4ncccc4-c4ccnc(N[C@H]5CCCN(C(=O)OC(C)(C)C)C5)n4)c(C)ccc23)cs1]

The General Procedure E was followed, using tert-butyl (3S)-3-[[4-[2-[(5-amino-2-methyl-1-naphthyl)oxy]-3-pyridyl]pyrimidin-2-yl]amino]piperidine-1-carboxylate (200 mg, 0.38 mmol) and 4-(chloromethyl)-2-ethyl-1,3-thiazole hydrochloride (150.5 mg, 0.76 mmol). The crude product was purified via reverse-phase HPLC to afford 48.6 mg (19.7% yield) of the title compound as a brown solid. LCMS (ESI) [M+H]$^+$=652.

Step 2: (S)-4-(2-((5-(((2-Ethylthiazol-4-yl)methyl)amino)-2-methylnaphthalen-1-yl)oxy)pyridin-3-yl)-N-(piperidin-3-yl)pyrimidin-2-amine

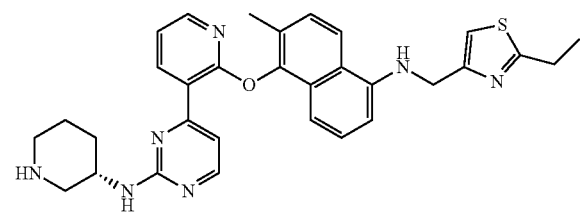

The General Procedure B was followed, using tert-butyl (S)-3-((4-(2-((5-(((2-ethylthiazol-4-yl)methyl)amino)-2-methylnaphthalen-1-yl)oxy)pyridin-3-yl)pyrimidin-2-yl)amino)piperidine-1-carboxylate (48.6 mg, 0.07 mmol). The crude product was lyophilized to yield 44 mg (100% yield) of 345 as a yellow solid. LCMS (ESI) [M+H]$^+$=552; $^1$H NMR (400 MHz, DMSO-d$_6$) 8.91-8.75 (m, 2H), 8.65-8.51 (m, 2H), 8.46 (d, J=5.2 Hz, 1H), 8.09 (d, J=8.7 Hz, 1H), 8.04 (dd, J=4.8, 2.0 Hz, 1H), 7.57 (d, J=5.2 Hz, 1H), 7.51 (d, J=7.4 Hz, 1H), 7.38 (d, J=8.7 Hz, 1H), 7.26-7.21 (m, 2H), 7.11 (dd, J=8.4, 7.7 Hz, 1H), 6.82 (d, J=8.3 Hz, 1H), 6.43 (dd, J=7.8, 1.0 Hz, 1H), 4.53 (s, 2H), 4.32-4.19 (m, 1H), 3.24-3.15 (m, 1H), 2.97 (q, J=7.5 Hz, 2H), 2.92-2.79 (m, 2H), 2.19 (s, 3H), 2.06-1.98 (m, 1H), 1.96-1.88 (m, 1H), 1.80-1.59 (m, 2H), 1.32-1.27 (m, 3H).

Example 346 (S)-4-(2-((2-Methyl-5-(((5-methylthiazol-4-yl)methyl)amino)naphthalen-1-yl)oxy)pyridin-3-yl)-N-(piperidin-3-yl)pyrimidin-2-amine 346

Step 1: tert-Butyl (S)-3-((4-(2-((2-methyl-5-(((5-methylthiazol-4-yl)methyl)amino)naphthalen-1-yl)oxy)pyridin-3-yl)pyrimidin-2-yl)amino)piperidine-1-carboxylate The General Procedure E was followed, using tert-butyl (3S)-3-[[4-[2-[(5-amino-2-methyl-1-naphthyl)oxy]-3-pyridyl]pyrimidin-2-yl]amino]piperidine-1-carboxylate (200 mg, 0.38 mmol) and 4-(chloromethyl)-5-methyl-1,3-thiazole hydrochloride (139.8 mg, 0.76 mmol). The crude material was purified by silica gel chromatography, 12 g column, eluting with 0-5% MeOH/DCM and reverse-phase HPLC to afford 57.4 mg (23.7% yield) of the title compound as a brown solid. LCMS (ESI) [M+H]$^+$=638.

Step 2: (S)-4-(2-((2-Methyl-5-(((5-methylthiazol-4-yl)methyl)amino)naphthalen-1-yl)oxy)pyridin-3-yl)-N-(piperidin-3-yl)pyrimidin-2-amine

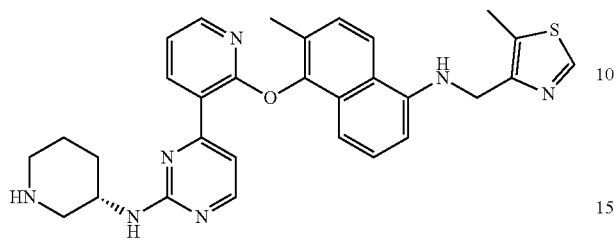

The General Procedure B was followed, using tert-butyl (S)-3-((4-(2-((2-methyl-5-(((5-methylthiazol-4-yl)methyl)amino)naphthalen-1-yl)oxy)pyridin-3-yl)pyrimidin-2-yl)amino)piperidine-1-carboxylate (57.4 mg, 0.09 mmol). The crude product was lyophilized to yield 50 mg (96.7% yield) of 346 as a brown solid. LCMS (ESI) [M+H]$^+$=538; $^1$H NMR (400 MHz, DMSO-$d_6$) δ 9.43-9.09 (m, 2H), 8.93 (d, J=3.2 Hz, 1H), 8.81-8.67 (m, 1H), 8.49 (d, J=5.4 Hz, 1H), 8.11-8.01 (m, 2H), 7.64 (s, 1H), 7.38 (d, J=8.7 Hz, 1H), 7.25 (dd, J=7.6, 4.8 Hz, 1H), 7.15 (t, J=8.0 Hz, 1H), 6.89 (d, J=8.4 Hz, 1H), 6.62 (d, J=7.9 Hz, 1H), 4.54 (s, 2H), 4.44-4.28 (m, 1H), 3.23-3.16 (m, 1H), 2.93-2.79 (m, 3H), 2.19 (s, 3H), 2.06-1.99 (m, 1H), 1.97-1.88 (m, 1H), 1.85-1.73 (m, 1H), 1.71-1.59 (m, 1H).

Example 347 (S)-2,2-Dimethyl-4-((6-methyl-5-((3-(2-(piperidin-3-ylamino)pyrimidin-4-yl)pyridin-2-yl)oxy)naphthalen-1-yl)amino)butanenitrile 347

Step 1: tert-Butyl (S)-3-((4-(2-((5-((3-cyano-3-methylbutyl)amino)-2-methylnaphthalen-1-yl)oxy)pyridin-3-yl)pyrimidin-2-yl)amino)piperidine-1-carboxylate

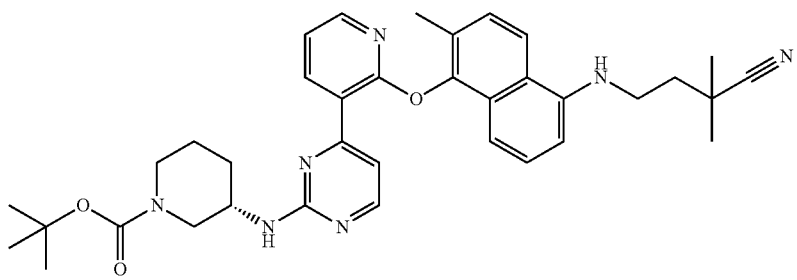 [SMILES: Cc1ccc2c(NCCC(C)(C)C#N)cccc2c1Oc1ncccc1-c1ccnc(N[C@H]2CCCN(C(=O)OC(C)(C)C)C2)n1]

The General Procedure E was followed, using tert-butyl (3S)-3-[[4-[2-[(5-amino-2-methyl-1-naphthyl)oxy]-3-pyridyl]pyrimidin-2-yl]amino]piperidine-1-carboxylate (200 mg, 0.38 mmol), 2,2-dimethyl-4-oxo-butanenitrile (84.4 mg, 0.76 mmol), sodium cyanoborohydride (47.7 mg, 0.76 mmol), EtOH (4 mL), and catalytic amount of AcOH. The crude product was purified via reverse-phase HPLC to afford 92.6 mg (39% yield) of the title compound as a brown solid. LCMS (ESI) [M+H]$^+$=622.

Step 2: (S)-2,2-Dimethyl-4-((6-methyl-5-((3-(2-(piperidin-3-ylamino)pyrimidin-4-yl)pyridin-2-yl)oxy)naphthalen-1-yl)amino)butanenitrile

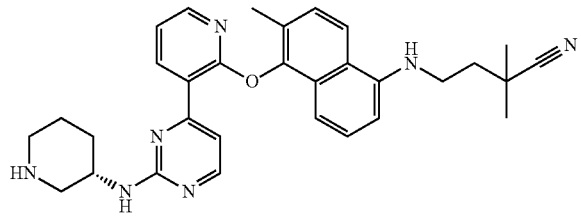 [SMILES: Cc1ccc2c(NCCC(C)(C)C#N)cccc2c1Oc1ncccc1-c1ccnc(N[C@H]2CCCNC2)n1]

The General Procedure B was followed, using tert-butyl (S)-3-((4-(2-((5-((3-cyano-3-methylbutyl)amino)-2-methylnaphthalen-1-yl)oxy)pyridin-3-yl)pyrimidin-2-yl)amino)piperidine-1-carboxylate (92.6 mg, 0.15 mmol). The crude product was lyophilized to yield 36.8 mg (47.4% yield) of 347 as an off-white solid. LCMS (ESI) [M+H]$^+$=522; $^1$H NMR (400 MHz, DMSO-$d_6$) δ 8.52-8.46 (m, 1H), 8.40 (d, J=5.1 Hz, 1H), 8.03-7.96 (m, 2H), 7.44 (d, J=5.1 Hz, 1H), 7.34 (d, J=8.7 Hz, 1H), 7.25-7.16 (m, 2H), 7.11 (d, J=8.0 Hz, 1H), 6.87 (d, J=8.4 Hz, 1H), 6.51-6.45 (m, 1H), 6.30 (t, J=5.5 Hz, 1H), 3.97-3.84 (m, 1H), 3.41-3.35 (m, 2H), 3.14-3.07 (m, 1H), 2.85-2.77 (m, 1H), 2.48-2.41 (m, 2H), 2.18 (s, 3H), 2.01-1.90 (m, 3H), 1.69-1.62 (m, 1H), 1.54-1.42 (m, 2H), 1.41 (s, 6H).

Example 348 (S)-4-(2-((2-Methyl-5-((3,3,3-trifluoropropyl)amino)naphthalen-1-yl)oxy)pyridin-3-yl)-N-(piperidin-3-yl)pyrimidin-2-amine 348

Step 1: tert-Butyl (S)-3-((4-(2-((2-methyl-5-((3,3,3-trifluoropropyl)amino)naphthalen-1-yl)oxy)pyridin-3-yl)pyrimidin-2-yl)amino)piperidine-1-carboxylate

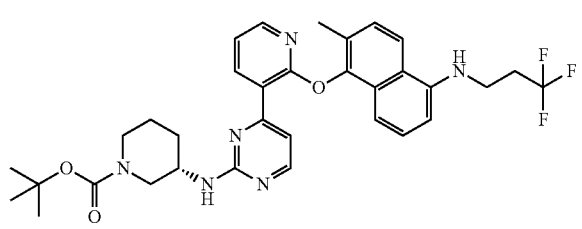

The General Procedure E was followed, using tert-butyl (3S)-3-[[4-[2-[(5-amino-2-methyl-1-naphthyl)oxy]-3-pyridyl]pyrimidin-2-yl]amino]piperidine-1-carboxylate (200 mg, 0.38 mmol) and 3-bromo-1,1,1-trifluoropropane (134.4 mg, 0.76 mmol). The crude product was purified via reverse-phase HPLC to afford 36 mg (15.2% yield) of the title compound as an off-white solid. LCMS (ESI) [M+H]$^+$=623.

Step 2: (S)-4-(2-((2-Methyl-5-((3,3,3-trifluoropropyl)amino)naphthalen-1-yl)oxy)pyridin-3-yl)-N-(piperidin-3-yl)pyrimidin-2-amine

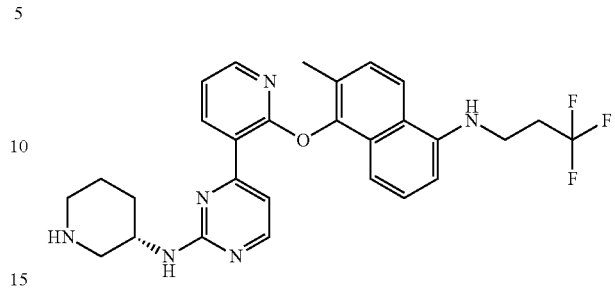

The General Procedure B was followed, using tert-butyl (S)-3-((4-(2-((2-methyl-5-((3,3,3-trifluoropropyl)amino)naphthalen-1-yl)oxy)pyridin-3-yl)pyrimidin-2-yl)amino)piperidine-1-carboxylate (36 mg, 0.06 mmol). The crude product was lyophilized to yield 34 mg (100% yield) of 348 as a brown solid. LCMS (ESI) [M+H]$^+$=523; $^1$H NMR (400 MHz, DMSO-$d_6$) δ 8.81 (d, J=27.1 Hz, 2H), 8.58 (s, 2H), 8.47 (d, J=5.2 Hz, 1H), 8.04 (dd, J=4.8, 2.0 Hz, 1H), 7.98 (d, J=8.7 Hz, 1H), 7.57 (d, J=5.2 Hz, 1H), 7.51 (d, J=7.4 Hz, 1H), 7.38 (d, J=8.7 Hz, 1H), 7.24 (dd, J=7.6, 4.8 Hz, 1H), 7.22-7.17 (m, 1H), 6.88 (d, J=8.4 Hz, 1H), 6.51-6.46 (m, 1H), 4.27 (s, 1H), 3.25-3.17 (m, 2H), 2.93-2.80 (m, 2H), 2.76-2.64 (m, 3H), 2.19 (s, 3H), 2.06-1.98 (m, 1H), 1.97-1.88 (m, 1H), 1.80-1.58 (m, 2H).

Example 349 (S)-4-(2-((5-(Isobutylamino)-2-methylnaphthalen-1-yl)oxy)pyridin-3-yl)-N-(piperidin-3-yl)pyrimidin-2-amine Step 1: tert-Butyl (S)-3-((4-(2-((5-(isobutylamino)-2-methylnaphthalen-1-yl)oxy)pyridin-3-yl)pyrimidin-2-yl)amino)piperidine-1-carboxylate

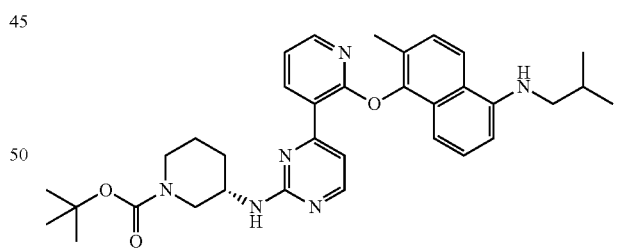

The General Procedure E was followed, using tert-butyl (3S)-3-[[4-[2-[(5-amino-2-methyl-1-naphthyl)oxy]-3-pyridyl]pyrimidin-2-yl]amino]piperidine-1-carboxylate (200 mg, 0.38 mmol), isobutyraldehyde (82.1 mg, 1.14 mmol), sodium borohydride (43.1 mg, 1.14 mmol), catalytic AcOH, and EtOH (4 ml). The crude product was purified via reverse-phase HPLC to afford 33.4 mg (15.1% yield) of the title compound as an off-white solid. LCMS (ESI) [M+H]$^+$=583.

Step 2: (S)-4-(2-((5-(Isobutylamino)-2-methylnaphthalen-1-yl)oxy)pyridin-3-yl)-N-(piperidin-3-yl)pyrimidin-2-amine

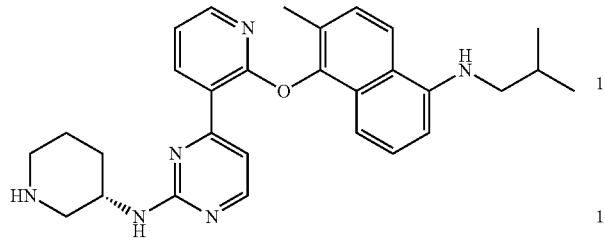

The General Procedure B was followed, using tert-butyl (S)-3-((4-(2-((5-(isobutylamino)-2-methylnaphthalen-1-yl)oxy)pyridin-3-yl)pyrimidin-2-yl)amino)piperidine-1-carboxylate (33.4 mg, 0.06 mmol). The crude product was lyophilized to yield 33 mg (100% yield) of 349 as a brown solid. LCMS (ESI) [M+H]$^+$=483; $^1$H NMR (400 MHz, DMSO-d$_6$) δ 8.72 (d, J=26.7 Hz, 4H), 8.47 (d, J=5.2 Hz, 1H), 8.07 (d, J=8.7 Hz, 1H), 8.03 (dd, J=4.8, 2.0 Hz, 1H), 7.57 (d, J=5.2 Hz, 1H), 7.49 (d, J=7.4 Hz, 1H), 7.34 (d, J=8.7 Hz, 1H), 7.24 (dd, J=7.6, 4.8 Hz, 1H), 7.15 (t, J=8.0 Hz, 1H), 6.79 (d, J=8.3 Hz, 1H), 6.42 (d, J=7.7 Hz, 1H), 4.25 (s, 1H), 3.25-3.18 (m, 1H), 3.02 (d, J=6.9 Hz, 2H), 2.92-2.78 (m, 3H), 2.18 (s, 3H), 2.07-1.99 (m, 2H), 1.96-1.89 (m, 1H), 1.80-1.59 (m, 2H), 0.98 (d, J=6.6 Hz, 6H).

Example 350 (S)—N-(2-Fluoro-6-methyl-5-((3-(2-(piperidin-3-ylamino)pyrimidin-4-yl)pyridin-2-yl)oxy)naphthalen-1-yl)-2,2-dimethylpropane-1-sulfonamide 350

Step 1: tert-Butyl (S)-3-((4-(2-((5-((2,2-dimethylpropyl)sulfonamido)-6-fluoro-2-methylnaphthalen-1-yl)oxy)pyridin-3-yl)pyrimidin-2-yl)amino)piperidine-1-carboxylate

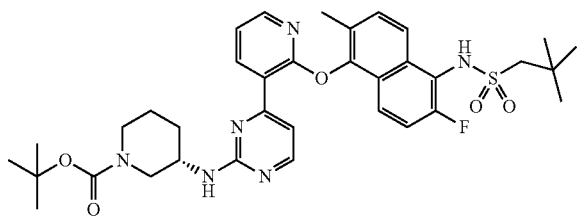 [SMILES: Cc1ccc2c(NS(=O)(=O)CC(C)(C)C)c(F)ccc2c1Oc1ncccc1-c1ccnc(N[C@H]2CCCN(C(=O)OC(C)(C)C)C2)n1]

The General Procedure A was followed, using tert-butyl (3S)-3-[[4-[2-[(5-amino-6-fluoro-2-methyl-1-naphthyl)oxy]-3-pyridyl]pyrimidin-2-yl]amino]piperidine-1-carboxylate (200 mg, 0.37 mmol) and 2,2-dimethylpropane-1-sulfonyl chloride (191.9 mg, 1.10 mmol). The crude product was purified via reverse-phase HPLC to afford 20.8 mg (8.3% yield) of the title compound as an off-white solid. LCMS (ESI) [M+H]$^+$=679.

Step 2: (S)—N-(2-Fluoro-6-methyl-5-((3-(2-(piperidin-3-ylamino)pyrimidin-4-yl)pyridin-2-yl)oxy)naphthalen-1-yl)-2,2-dimethylpropane-1-sulfonamide

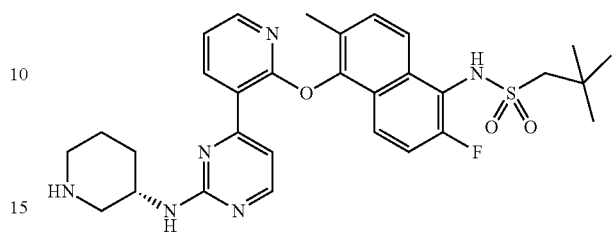

The General Procedure B was followed, using tert-butyl (S)-3-((4-(2-((5-((2,2-dimethylpropyl)sulfonamido)-6-fluoro-2-methylnaphthalen-1-yl)oxy)pyridin-3-yl)pyrimidin-2-yl)amino)piperidine-1-carboxylate (20.8 mg, 0.03 mmol). The crude product was lyophilized to yield 16.2 mg (86% yield) of 350 as an off-white solid. LCMS (ESI) [M+H]$^+$=579; $^1$H NMR (400 MHz, DMSO-d$_6$) δ 9.67 (s, 1H), 8.75-8.54 (m, 4H), 8.47 (d, J=5.2 Hz, 1H), 8.10-8.04 (m, 2H), 7.71 (dd, J=9.3, 5.1 Hz, 1H), 7.62 (d, J=8.8 Hz, 1H), 7.56 (d, J=5.2 Hz, 1H), 7.52-7.47 (m, 1H), 7.44 (d, J=9.4 Hz, 1H), 7.29 (dd, J=7.6, 4.8 Hz, 1H), 4.24 (s, 1H), 3.26-3.22 (m, 2H), 3.21 (s, 2H), 2.93-2.82 (m, 2H), 2.19 (s, 3H), 2.05-1.98 (m, 1H), 1.96-1.88 (m, 1H), 1.79-1.55 (m, 2H), 1.12 (s, 9H).

Example 351 4-(2-((2-Methyl-5-((((S)-tetrahydrofuran-3-yl)methyl)amino)naphthalen-1-yl)oxy)pyridin-3-yl)-N—((S)-piperidin-3-yl)pyrimidin-2-amine 351

Step 1: tert-Butyl (S)-3-((4-(2-((2-methyl-5-((((S)-tetrahydrofuran-3-yl)methyl)amino)naphthalen-1-yl)oxy)pyridin-3-yl)pyrimidin-2-yl)amino)piperidine-1-carboxylate

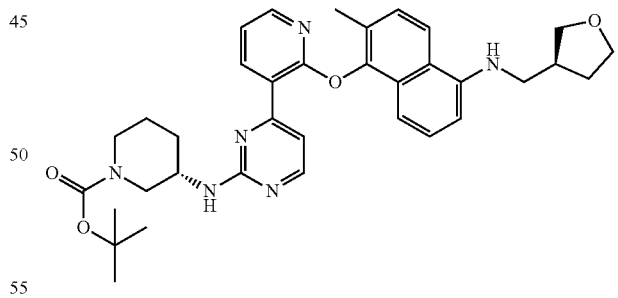

The General Procedure E was followed, using tert-butyl (3S)-3-[[4-[2-[(5-amino-2-methyl-1-naphthyl)oxy]-3-pyridyl]pyrimidin-2-yl]amino]piperidine-1-carboxylate (200 mg, 0.38 mmol) and 3-(bromomethyl)tetrahydrofuran (395 mg, 2.28 mmol). The crude material was purified by silica gel chromatography, 12 g column, eluting with 0-5% MeOH/DCM to afford 150 mg (64.6% yield) of the title compound as a brown solid. LCMS (ESI) [M+H]$^+$=610. The enantiomers were separated by chiral SFC to afford 39 mg isomer-1 (t$_R$=0.849 min) as an off-white solid and 39.7 mg isomer-2 (t$_R$=1.104 min) as an off-white solid.

Step 2: 4-(2-((2-Methyl-5-((((S)-tetrahydrofuran-3-yl)methyl)amino)naphthalen-1-yl)oxy)pyridin-3-yl)-N—((S)-piperidin-3-yl)pyrimidin-2-amine

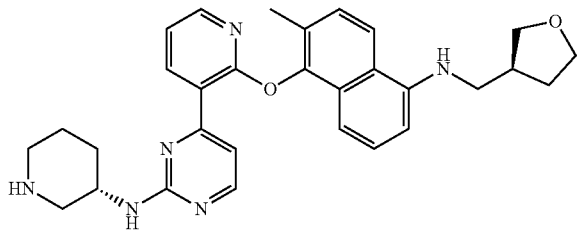

The General Procedure B was followed, using tert-butyl (S)-3-((4-(2-((2-methyl-5-((((S)-tetrahydrofuran-3-yl)methyl)amino)naphthalen-1-yl)oxy)pyridin-3-yl)pyrimidin-2-yl)amino)piperidine-1-carboxylate (isomer-1, 39 mg, 0.06 mmol). The crude product was lyophilized to yield 33 mg (94.3% yield) of 351 as an off-white solid. The stereochemical assignments of 351 and 352 were randomly assigned and may be later determined. LCMS (ESI) [M+H]$^+$=510; $^1$H NMR (400 MHz, DMSO-d$_6$) δ 8.99-8.80 (m, 2H), 8.60 (s, 2H), 8.47 (d, J=5.2 Hz, 1H), 8.07-8.01 (m, 2H), 7.58 (d, J=5.4 Hz, 1H), 7.54 (d, J=7.6 Hz, 1H), 7.35 (d, J=8.7 Hz, 1H), 7.24 (dd, J=7.6, 4.8 Hz, 1H), 7.17 (t, J=8.0 Hz, 1H), 6.83 (d, J=8.4 Hz, 1H), 6.50 (d, J=7.7 Hz, 1H), 4.30 (s, 1H), 3.57 (s, 2H), 3.46-3.41 (m, 1H), 3.24-3.16 (m, 3H), 2.92-2.80 (m, 2H), 2.74-2.64 (m, 1H), 2.19 (s, 3H), 2.10-1.99 (m, 2H), 1.97-1.88 (m, 1H), 1.81-1.59 (m, 3H).

Example 352 4-(2-((2-Methyl-5-((((R)-tetrahydrofuran-3-yl)methyl)amino)naphthalen-1-yl)oxy)pyridin-3-yl)-N—((S)-piperidin-3-yl)pyrimidin-2-amine 352

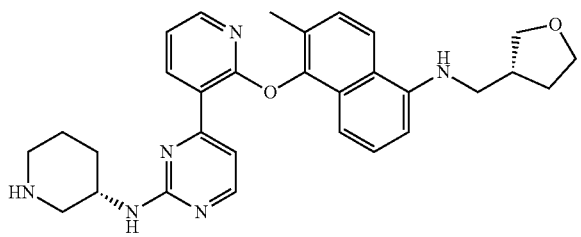

Following Example 351 and General Procedure B, tert-butyl (S)-3-((4-(2-((2-methyl-5-((((R)-tetrahydrofuran-3-yl)methyl)amino)naphthalen-1-yl)oxy)pyridin-3-yl)pyrimidin-2-yl)amino)piperidine-1-carboxylate (isomer-2, 39.7 mg, 0.06 mmol). The crude product was lyophilized to yield 33.1 mg (94.3% yield) of 352 as an off-white solid. LCMS (ESI) [M+H]$^+$=510; $^1$H NMR (400 MHz, DMSO-d$_6$) δ 9.04-8.55 (m, 4H), 8.47 (d, J=5.3 Hz, 1H), 8.07-8.02 (m, 2H), 7.62-7.53 (m, 2H), 7.36 (d, J=8.7 Hz, 1H), 7.24 (dd, J=7.6, 4.8 Hz, 1H), 7.17 (dd, J=8.4, 7.7 Hz, 1H), 6.84 (d, J=8.4 Hz, 1H), 6.50 (d, J=7.7 Hz, 1H), 4.31 (s, 1H), 3.57 (s, 2H), 3.46-3.42 (m, 1H), 3.19 (d, J=7.2 Hz, 3H), 2.92-2.79 (m, 2H), 2.74-2.65 (m, 1H), 2.19 (s, 3H), 2.07-1.99 (m, 2H), 1.95-1.88 (m, 1H), 1.82-1.57 (m, 3H).

Example 353 (S)-4-(2-((2-Methyl-5-(pyridin-2-yl)naphthalen-1-yl)oxy)pyridin-3-yl)-N-(piperidin-3-yl)pyrimidin-2-amine 353

Step 1: (S)-tert-Butyl 3-((4-(2-((2-methyl-5-(pyridin-2-yl)naphthalen-1-yl)oxy)pyridin-3-yl)pyrimidin-2-yl)amino)piperidine-1-carboxylate

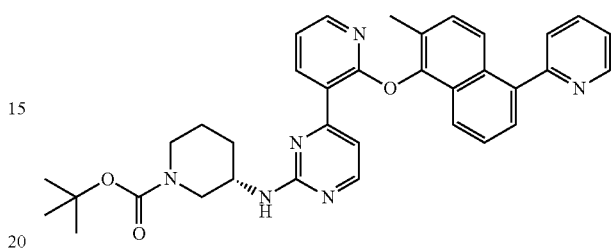

To a solution of tert-butyl (3S)-3-[[4-[2-[(5-iodo-2-methyl-1-naphthyl)oxy]-3-pyridyl]pyrimidin-2-yl]amino]piperidine-1-carboxylate (50 mg, 0.08 mmol) in toluene (5 mL) was added 2-(tributylstannyl)pyridine (35 mg, 0.09 mmol) and tetrakis[triphenylphosphine]palladium(0) (9 mg, 0.01 mmol) and the mixture was stirred at 120° C. for 12 h. The mixture was concentrated and the residue was dissolved in ethyl acetate (50 mL), washed with H$_2$O (50 mL), brined (50 mL). The organic phase was dried over anhydrous sodium sulfate, filtered and the filtrate was concentrated in vacuo. The residue was purified by Prep-HPLC (mobile phase: A: water (0.05% NH$_4$OH) B: ACN) to yield 35 mg (76% yield) of the title compound as a white solid. LCMS (ESI) [M+Na]$^+$=611.1.

Step 2: (S)-4-(2-((2-Methyl-5-(pyridin-2-yl)naphthalen-1-yl)oxy)pyridin-3-yl)-N-(piperidin-3-yl)pyrimidin-2-amine

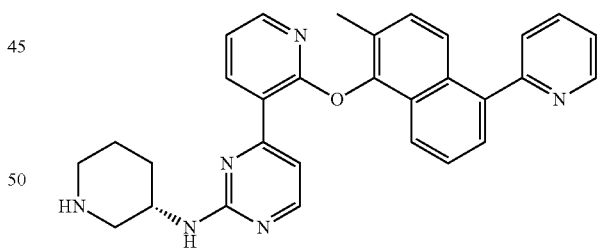

The General Procedure B was followed, using tert-butyl (3S)-3-[[4-[2-[[2-methyl-5-(2-pyridyl)-1-naphthyl]oxy]-3-pyridyl]pyrimidin-2-yl]amino]piperidine-1-carboxylate (35 mg, 0.06 mmol) in ethyl acetate (1 mL) was added hydrochloric acid (4 M in ethyl acetate, 0.15 mL, 0.59 mmol) and stirred at 20° C. for 1 h. The residue was purified by Prep-HPLC (mobile phase: A: water (0.05% NH$_4$OH) B: ACN) to yield 9 mg (39% yield) of 353 as a yellow solid. LCMS (ESI) [M+H]$^+$=489.2; $^1$H NMR (400 MHz, DMSO-d$_6$) δ 9.39-9.10 (m, 1H), 8.94 (d, J=4.8 Hz, 1H), 8.54-8.42 (m, 2H), 8.14-8.03 (m, 2H), 7.96-7.83 (m, 2H), 7.73-7.69 (m, 3H), 7.66-7.59 (m, 2H), 7.55 (d, J=8.8 Hz, 1H), 7.30-7.27 (m, 1H), 4.46-4.26 (m, 1H), 3.45-3.29 (m, 1H), 3.25-

3.10 (m, 1H), 2.90-2.76 (m, 2H), 2.22 (s, 3H), 2.09-1.97 (m, 1H), 1.96-1.85 (m, 1H), 1.84-1.70 (m, 1H), 1.69-1.55 (m, 1H).

Example 354 3-Methyl-1-(6-methyl-5-((3-(2-((S)-piperidin-3-ylamino)pyrimidin-4-yl)pyridin-2-yl)oxy)naphthalen-1-yl)piperidin-2-one 354

Step 1: (3S)-tert-Butyl 3-((4-(2-((2-methyl-5-(3-methyl-2-oxopiperidin-1-yl)naphthalen-1-yl)oxy)pyridin-3-yl)pyrimidin-2-yl)amino)piperidine-1-carboxylate

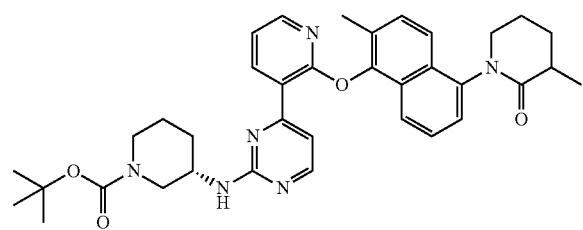 [SMILES: Cc1ccc2c(N3CCCC(C)C3=O)cccc2c1Oc1ncccc1-c1ccnc(N[C@H]2CCCN(C(=O)OC(C)(C)C)C2)n1]

To a 100 mL 3-necked round-bottom flask purged and maintained with an inert atmosphere of nitrogen was placed tert-butyl (3S)-3-[[4-[2-[(5-iodo-2-methyl-1-naphthyl)oxy]-3-pyridyl]pyrimidin-2-yl]amino]piperidine-1-carboxylate (120 mg, 0.19 mmol), 1,4-dioxane (2 mL), copper (I) iodide (4 mg, 0.02 mmol), potassium carbonate (78 mg, 0.56 mmol), 3-methylpiperidin-2-one (21 mg, 0.19 mmol) and N,N'-dimethyl-1,2-ethanediamine (3.3 mg, 0.04 mmol), the mixture was purged with nitrogen atmosphere and stirred at 110° C. for 12 h. After cooling down, the mixture was filtered, concentrated and dissolved in ethyl acetate (60 mL), washed with H$_2$O (50 mL×2). The organic phase was dried over anhydrous sodium sulfate, filtered and the filtrate was concentrated and purified by prep-TLC (50% ethyl acetate in petroleum ether, Rf=0.3) to yield 100 mg (85% yield) of the title compound as a white solid. LCMS (ESI) [M+H]$^+$=623.3.

Step 2: 3-Methyl-1-(6-methyl-5-((3-(2-((S)-piperidin-3-ylamino)pyrimidin-4-yl)pyridin-2-yl)oxy)naphthalen-1-yl)piperidin-2-one

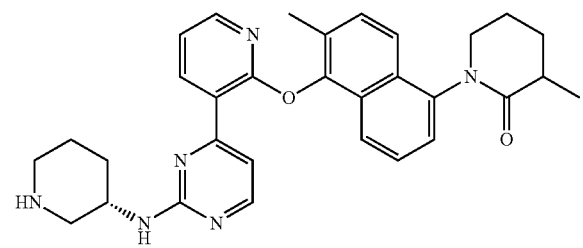 [SMILES: Cc1ccc2c(N3CCCC(C)C3=O)cccc2c1Oc1ncccc1-c1ccnc(N[C@H]2CCCNC2)n1]

The General Procedure B was followed, using (3S)-tert-butyl 3-((4-(2-((2-methyl-5-(3-methyl-2-oxopiperidin-1-yl)naphthalen-1-yl)oxy)pyridin-3-yl)pyrimidin-2-yl)amino)piperidine-1-carboxylate (60 mg, 0.098 mmol), dichloromethane (2 mL) and hydrochloric acid (4 M in dioxane, 0.32 mL, 1.28 mmol). The residue was purified by Prep-HPLC (mobile phase: A: water (0.05% HCl); B: ACN) to yield 27 mg (54% yield) of 354 as a white solid and as a mixture of two lactam isomers. LCMS (ESI) [M+H]$^+$=523.3. $^1$H NMR (400 MHz, DMSO-d$_6$) δ 8.50 (s, 1H), 8.40 (d, J=4.4 Hz, 1H), 8.07 (s, 1H), 7.61 (d, J=8.6 Hz, 1H), 7.54-7.49 (m, 1H), 7.48-7.42 (m, 1H), 7.48-7.42 (m, 1H), 7.36 (d, J=7.6 Hz, 1H), 7.29-7.24 (m, 1H), 7.14 (d, J=8.4 Hz, 1H), 3.88 (m, 1H), 3.75-3.64 (m, 1H), 3.60 (m, 1H), 3.07 (m, 2H), 2.78 (d, J=12.8 Hz, 1H), 2.38 (s, 2H), 2.21 (s, 3H), 2.08 (m, 2H), 1.91 (m, 1H), 1.82-1.68 (m, 2H), 1.64 (m, 1H), 1.50-1.38 (m, 2H), 1.30-1.19 (m, 3H).

Example 355 (S)-3-Ethyl-1-(6-methyl-5-((3-(2-(((S)-piperidin-3-yl)amino)pyrimidin-4-yl)pyridin-2-yl)oxy)naphthalen-1-yl)pyrrolidin-2-one 355

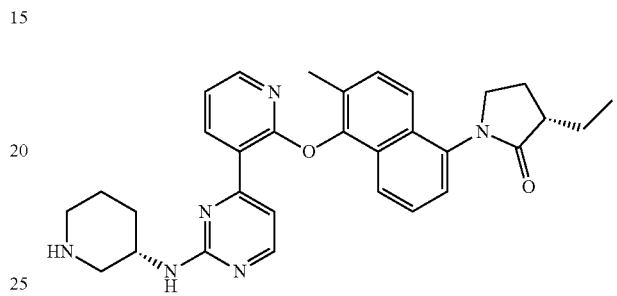

Following Example 266, General Procedure B was followed, using tert-butyl (S)-3-((4-(2-((5-((S)-3-ethyl-2-oxopyrrolidin-1-yl)-2-methylnaphthalen-1-yl)oxy)pyridin-3-yl)pyrimidin-2-yl)amino)piperidine-1-carboxylate (30 mg, 0.05 mmol) from the second peak on SFC in step 1 of Example 266, dichloromethane (2 mL) and hydrochloric acid (4 M in dioxane, 0.32 mL, 1.28 mmol). The residue was purified by Prep-HPLC (mobile phase: A: water (0.05% HCl); B: ACN) to yield 11 mg (40% yield) of 355 as a white solid. LCMS (ESI) [M+H]$^+$=523.3. $^1$H NMR (400 MHz, DMSO-d$_6$) δ 8.47 (s, 1H), 8.39 (d, J=5.2 Hz, 1H), 8.05-8.00 (m, 1H), 7.65 (d, J=7.2 Hz, 1H), 7.59-7.53 (m, 1H), 7.51-7.44 (m, 2H), 7.42 (d, J=5.2 Hz, 1H), 7.40-7.37 (m, 1H), 7.27-7.22 (m, 1H), 7.13 (d, J=7.6 Hz, 1H), 3.91-3.64 (m, 3H), 3.06 (s, 1H), 2.77 (m, 1H), 2.64-2.58 (m, 1H), 2.41 (m, 3H), 2.20 (s, 3H), 2.02-1.87 (m, 2H), 1.86-1.77 (m, 1H), 1.61 (m, 1H), 1.57-1.35 (m, 3H), 1.01 (t, J=7.2 Hz, 3H).

Example 356 4-Ethyl-1-(6-methyl-5-((3-(2-((S)-piperidin-3-ylamino)pyrimidin-4-yl)pyridin-2-yl)oxy)naphthalen-1-yl)pyrrolidin-2-one 356

Step 1: (3S)-tert-Butyl 3-((4-(2-((5-(4-ethyl-2-oxopyrrolidin-1-yl)-2-methylnaphthalen-1-yl)oxy)pyridin-3-yl)pyrimidin-2-yl)amino)piperidine-1-carboxylate

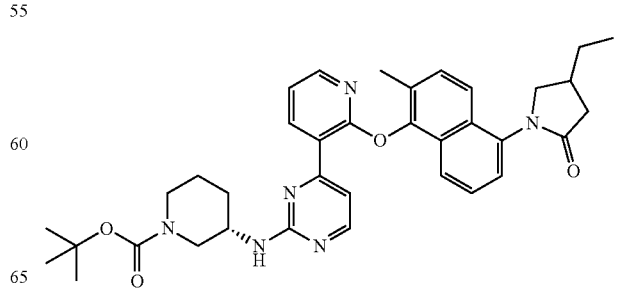

To a solution of (S)-tert-butyl 3-((4-(2-((5-iodo-2-methylnaphthalen-1-yl)oxy)pyridin-3-yl)pyrimidin-2-yl)amino)piperidine-1-carboxylate (100 mg, 0.16 mmol) in 1,4-dioxane (2 mL) was added 4-ethyl-2-pyrrolidinone (21 mg, 0.19 mmol), copper (I) iodide (3 mg, 0.02 mmol), N,N'-dimethyl-1,2-ethanediamine (2.8 mg, 0.03 mmol), and potassium carbonate (65 mg, 0.47 mmol). The mixture was stirred at 110° C. for 16 h, concentrated and dissolved in ethyl acetate (50 mL), washed with H$_2$O (30 mL), brine (30 mL). The organic phase was dried over anhydrous sodium sulfate, filtered and the filtrate was concentrated and purified by pre-TLC (50% ethyl acetate in petroleum ether, Rf=0.2) to yield 70 mg (72% yield) of the title compound as a white solid. LCMS (ESI) [M+H]$^+$=623.3.

Step 2: (3S)-tert-Butyl 3-((4-(2-((5-(4-ethyl-2-oxopyrrolidin-1-yl)-2-methylnaphthalen-1-yl)oxy)pyridin-3-yl)pyrimidin-2-yl)amino)piperidine-1-carboxylate

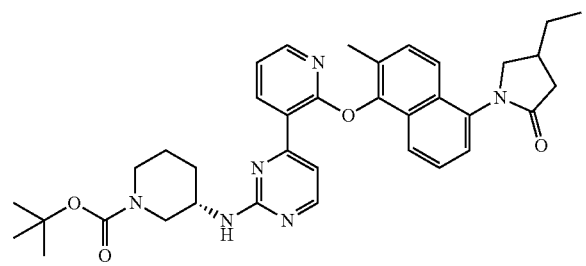 [SMILES: CCC1CC(=O)N(c2cccc3c(Oc4ncccc4-c4ccnc(N[C@H]5CCCN(C(=O)OC(C)(C)C)C5)n4)c(C)ccc23)C1]

(3S)-tert-Butyl 3-((4-(2-((5-(4-ethyl-2-oxopyrrolidin-1-yl)-2-methylnaphthalen-1-yl)oxy)pyridin-3-yl)pyrimidin-2-yl)amino)piperidine-1-carboxylate (70 mg, 0.11 mmol) was separated by chiral SFC (MG-II, C2 250 mm×30 mm, 10 μm, 0.1% NH$_3$H$_2$O, EtOH, 55% 80 mL/min) to give Peak 1: (3S)-tert-Butyl 3-((4-(2-((5-(4-ethyl-2-oxopyrrolidin-1-yl)-2-methylnaphthalen-1-yl)oxy)pyridin-3-yl)pyrimidin-2-yl)amino)piperidine-1-carboxylate (30 mg, 43% yield) as a white solid. LCMS (ESI) [M+H]$^+$=623.3;

Peak 2: (3S)-tert-Butyl 3-((4-(2-((5-(4-ethyl-2-oxopyrrolidin-1-yl)-2-methylnaphthalen-1-yl)oxy)pyridin-3-yl)pyrimidin-2-yl)amino)piperidine-1-carboxylate (30 mg, 43% yield) as a white solid. LCMS (ESI) [M+H]$^+$=623.3.

Step 3: 4-Ethyl-1-(6-methyl-5-((3-(2-((S)-piperidin-3-ylamino)pyrimidin-4-yl)pyridin-2-yl)oxy)naphthalen-1-yl)pyrrolidin-2-one

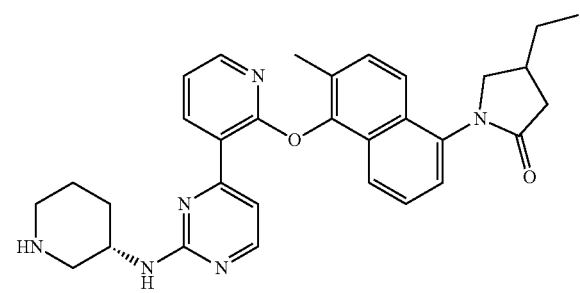 [SMILES: CCC1CC(=O)N(c2cccc3c(Oc4ncccc4-c4ccnc(N[C@H]5CCCNC5)n4)c(C)ccc23)C1]

The diastereomer eluting as the first peak on SFC in step 2, Peak 1 (30 mg, 0.05 mmol) was deprotected by General Procedure B in ethyl acetate (0.5 mL) and HCl (4 M in ethyl acetate, 0.5 mL, 2 mmol). The residue was purified by Prep-HPLC (mobile phase: A: water (0.05% NH$_4$OH) B: ACN) to give the purified diastereomer (4.3 mg, 27% yield) as a white solid. LCMS (ESI) [M+H]$^+$=523.1; $^1$H NMR (400 MHz, DMSO-d$_6$) δ 8.55-8.44 (m, 1H), 8.41 (d, J=4.8 Hz, 1H), 8.06 (d, J=4.8 Hz, 1H), 7.71-7.60 (m, 2H), 7.53-7.37 (m, 4H), 7.30-7.22 (m, 1H), 7.16 (d, J=8.0 Hz, 1H), 3.99-3.77 (m, 2H), 3.58-3.48 (m, 1H), 3.15-3.04 (m, 1H), 2.85-2.77 (m, 1H), 2.75-2.64 (m, 2H), 2.45-2.26 (m, 3H), 2.22 (s, 3H), 1.97-1.88 (m, 1H), 1.71-1.56 (m, 3H), 1.55-1.35 (m, 2H), 0.96 (t, J=7.2 Hz, 3H).

The General Procedure B was followed, using (3S)-tert-butyl 3-((4-(2-((5-(4-ethyl-2-oxopyrrolidin-1-yl)-2-methylnaphthalen-1-yl)oxy)pyridin-3-yl)pyrimidin-2-yl)amino)piperidine-1-carboxylate (30 mg, 0.05 mmol) (second peak on SFC in step 2) in ethyl acetate (0.5 mL) was added hydrochloric acid (4 M in ethyl acetate, 0.5 mL, 2 mmol). The residue was purified by Prep-HPLC (mobile phase: A: water (0.05% NH$_4$OH) B: ACN) to give 356 (3.4 mg, 13% yield) as a white solid. LCMS (ESI) [M+H]$^+$=523.1; $^1$H NMR (400 MHz, DMSO-d$_6$) δ 8.55-8.44 (m, 1H), 8.39 (d, J=4.8 Hz, 1H), 8.04 (d, J=3.2 Hz, 1H), 7.69-7.58 (m, 2H), 7.53-7.36 (m, 4H), 7.26-7.23 (m, 1H), 7.15 (d, J=8.0 Hz, 1H), 3.97-3.78 (m, 2H), 3.58-3.47 (m, 1H), 3.14-3.04 (m, 1H), 2.83-2.75 (m, 1H), 2.73-2.62 (m, 2H), 2.44-2.24 (m, 3H), 2.20 (s, 3H), 1.98-1.85 (m, 1H), 1.68-1.54 (m, 3H), 1.52-1.35 (m, 2H), 0.95 (t, J=7.2 Hz, 3H).

Example 357 5-Ethyl-1-(6-methyl-5-((3-(2-((S)-piperidin-3-ylamino)pyrimidin-4-yl)pyridin-2-yl)oxy)naphthalen-1-yl)pyrrolidin-2-one 357

Step 1: (3S)-tert-Butyl 3-((4-(2-((5-(2-ethyl-5-oxopyrrolidin-1-yl)-2-methylnaphthalen-1-yl)oxy)pyridin-3-yl)pyrimidin-2-yl)amino)piperidine-1-carboxylate

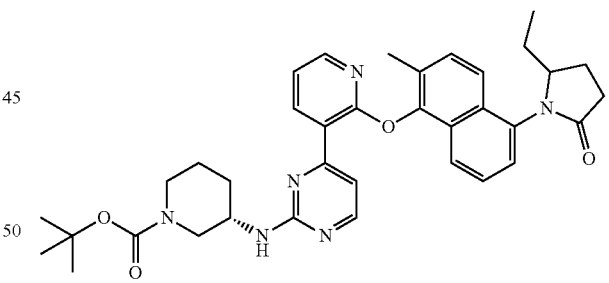

To a solution of (S)-tert-butyl 3-((4-(2-((5-iodo-2-methylnaphthalen-1-yl)oxy)pyridin-3-yl)pyrimidin-2-yl)amino)piperidine-1-carboxylate (100 mg, 0.16 mmol) in 1,4-dioxane (2 mL) was added 5-ethylpyrrolidin-2-one (35.5 mg, 0.31 mmol), copper (I) iodide (1.5 mg, 0.01 mmol), N$^1$,N$^1$,N$^2$,N$^2$-tetramethylethane-1,2-diamine (1.82 mg, 0.02 mmol) and potassium carbonate (65 mg, 0.47 mmol). The mixture was stirred at 110° C. for 3 d, concentrated and the residue was dissolved in ethyl acetate (30 mL) and washed with H$_2$O (25 mL×2), brine (25 mL). The organic phase was then separated and dried over anhydrous sodium sulfate, concentrated and purified by TLC (50% ethyl acetate in petroleum ether, Rf=0.1) to yield 35 mg (24% yield) of the title compound as a yellow solid. LCMS (ESI) [M+H]$^+$=623.3.

Step 2: (3S)-tert-Butyl 3-((4-(2-((5-(2-ethyl-5-oxopyrrolidin-1-yl)-2-methylnaphthalen-1-yl)oxy)pyridin-3-yl)pyrimidin-2-yl)amino)piperidine-1-carboxylate

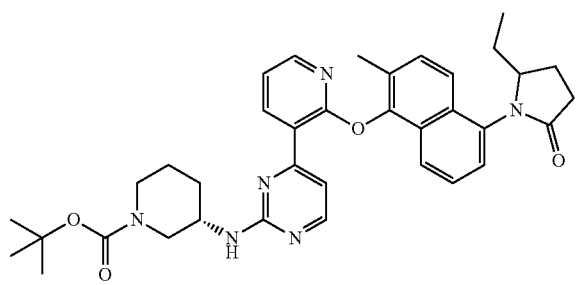 [SMILES: CCC1CCC(=O)N1c1cccc2c(Oc3ncccc3-c3ccnc(N[C@H]4CCCN(C(=O)OC(C)(C)C)C4)n3)c(C)ccc12]

(3S)-tert-Butyl 3-((4-(2-((5-(2-ethyl-5-oxopyrrolidin-1-yl)-2-methylnaphthalen-1-yl)oxy)pyridin-3-yl)pyrimidin-2-yl)amino)piperidine-1-carboxylate (35 mg, 0.06 mmol) was separated by chiral SFC (MG-II, C2 250 mm×30 mm, 10 μm, 0.1% NH₃H₂O, EtOH, 55% 80 mL/min) to give Peak 1: (3S)-tert-Butyl 3-((4-(2-((5-(2-ethyl-5-oxopyrrolidin-1-yl)-2-methylnaphthalen-1-yl)oxy)pyridin-3-yl)pyrimidin-2-yl)amino)piperidine-1-carboxylate (18 mg, 51% yield) as a white solid. LCMS (ESI) [M+H]⁺=623.3. and Peak 2: (3S)-tert-Butyl 3-((4-(2-((5-(2-ethyl-5-oxopyrrolidin-1-yl)-2-methylnaphthalen-1-yl)oxy)pyridin-3-yl)pyrimidin-2-yl)amino)piperidine-1-carboxylate (14 mg, 40% yield) as a white solid. LCMS (ESI) [M+H]⁺=623.3.

Step 3: 5-Ethyl-1-(6-methyl-5-((3-(2-((S)-piperidin-3-ylamino)pyrimidin-4-yl)pyridin-2-yl)oxy)naphthalen-1-yl)pyrrolidin-2-one

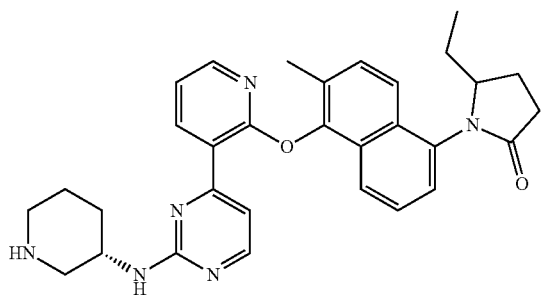 [SMILES: CCC1CCC(=O)N1c1cccc2c(Oc3ncccc3-c3ccnc(N[C@H]4CCCNC4)n3)c(C)ccc12]

The General Procedure B was followed, using (3S)-tert-butyl 3-((4-(2-((5-(2-ethyl-5-oxopyrrolidin-1-yl)-2-methylnaphthalen-1-yl)oxy)pyridin-3-yl)pyrimidin-2-yl)amino)piperidine-1-carboxylate (18 mg, 0.03 mmol) (first peak on SFC in step 2) in ethyl acetate (0.5 mL) was added hydrochloric acid (4 M in ethyl acetate, 0.5 mL, 2 mmol). The residue was purified by Prep-HPLC (mobile phase: A: water (0.05% HCl) B: ACN) to give 357 (9.7 mg, 59% yield) as a white solid. LCMS (ESI) [M+H]⁺=523.2. ¹H-NMR (400 MHz, DMSO-d₆) δ 9.09-8.02 (m, 2H), 8.47 (d, J=5.2 Hz, 1H), 8.15-8.05 (m, 1H), 7.74-7.39 (m, 6H), 7.30-7.27 (m, 1H), 4.47-3.83 (m, 2H), 3.24-3.12 (m, 1H), 2.90-2.77 (m, 2H), 2.64-2.54 (m, 3H), 2.21 (s, 3H), 2.08-1.56 (m, 6H), 1.46-1.28 (m, 2H), 0.84-0.65 (m, 3H).

The diastereomer eluting as the second peak on SFC in step 2, Peak 2 (14 mg, 0.02 mmol) was deprotected by General Procedure B in ethyl acetate (0.5 mL) and hydrochloric acid (4 M in ethyl acetate, 0.5 mL, 2 mmol) The residue was purified by Prep-HPLC (mobile phase: A: water (0.05% HCl) B: ACN) to give the purified diastereomer (5.6 mg, 44% yield) as a white solid. LCMS (ESI) [M+H]⁺=523.2. ¹H-NMR (400 MHz, DMSO-d₆) δ 8.97-8.72 (m, 2H), 8.46 (d, J=5.2 Hz, 1H), 8.14-8.05 (m, 1H), 7.72-7.41 (m, 6H), 7.34-7.24 (m, 1H), 4.41-4.10 (m, 1H), 4.05-3.80 (m, 1H), 3.26-3.14 (m, 1H), 2.93-2.80 (m, 2H), 2.64-2.55 (m, 3H), 2.21 (s, 3H), 2.07-1.56 (m, 6H), 1.45-1.28 (m, 2H), 0.87-0.63 (m, 3H).

Example 358. (S)-4-(2-((5-((1,4-Dimethyl-1H-pyrazol-3-yl)amino)-2-methylnaphthalen-1-yl)oxy)pyridin-3-yl)-N-(piperidin-3-yl)pyrimidin-2-amine 358

Step 1: (S)-tert-Butyl 3-((4-(2-((5-((1,4-dimethyl-1H-pyrazol-3-yl)amino)-2-methylnaphthalen-1-yl)oxy)pyridin-3-yl)pyrimidin-2-yl)amino)piperidine-1-carboxylate

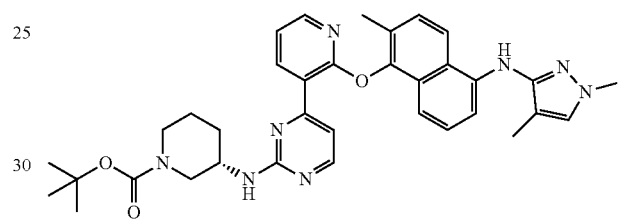

To a solution of tert-butyl (3S)-3-[[4-[2-[(5-amino-2-methyl-1-naphthyl)oxy]-3-pyridyl]pyrimidin-2-yl]amino]piperidine-1-carboxylate (150 mg, 0.28 mmol) in 1,4-dioxane (2 mL) were added 2-(dicyclohexylphosphino)3,6-dimethoxy-2',4',6'-triisopropyl-1,1'-biphenyl (31 mg, 0.06 mmol), [2-(2-aminophenyl)phenyl]-methylsulfonyloxy-palladium; dicyclohexyl-[3,6-dimethoxy-2-(2,4,6-triisopropylphenyl)phenyl]phosphane (26 mg, 0.03 mmol), 2-methylpropan-2-olate; sodium hydride (69 mg, 0.71 mmol) and 3-bromo-1,4-dimethyl-pyrazole (50 mg, 0.28 mmol). The mixture was stirred at 120° C. (MW) under nitrogen atmosphere for 1 h. The solution was concentrated and purified by prep-TLC (50% ethyl acetate in petroleum ether, Rf=0.4) to yield 100 mg (57% yield) of the title compound as a white solid. LCMS (ESI): [M+H]⁺=621.2.

Step 2: (S)-4-(2-((5-((1,4-Dimethyl-1H-pyrazol-3-yl)amino)-2-methylnaphthalen-1-yl)oxy)pyridin-3-yl)-N-(piperidin-3-yl)pyrimidin-2-amine

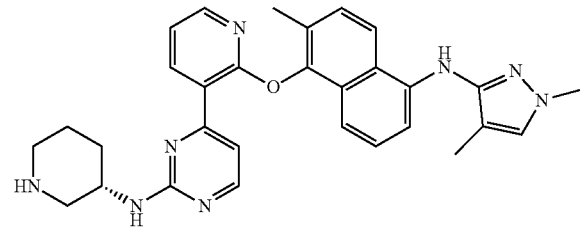

The General Procedure B was followed, using (S)-tert-butyl 3-((4-(2-((5-((1,5-dimethyl-1H-pyrazol-3-yl)amino)-

2-methylnaphthalen-1-yl)oxy)pyridin-3-yl)pyrimidin-2-yl) amino)piperidine-1-carboxylate (100 mg, 0.16 mmol), dichloromethane (5 mL) and hydrochloric acid (4 M in ethyl acetate, 2 mL, 8 mmol). The residue was purified by Prep-HPLC (mobile phase: A: water (0.05% HCl) B: ACN) to yield 30 mg (35% yield) of 358 as a yellow solid. LCMS (ESI): [M+H]$^+$=521.1; $^1$H NMR (400 MHz, DMSO-d$_6$) δ 9.90 (s, 1H), 9.44 (s, 1H), 8.98 (s, 1H), 8.74-8.43 (m, 2H), 8.23-8.05 (m, 2H), 7.97-7.79 (m, 1H), 7.60 (s, 1H), 7.44 (d, J=8.8 Hz, 1H), 7.29 (dd, J=4.8, 7.6 Hz, 1H), 7.25-7.17 (m, 1H), 7.09 (d, J=8.0 Hz, 1H), 6.80 (d, J=7.6 Hz, 1H), 4.61 (s, 1H), 3.75 (s, 3H), 3.42 (s, 1H), 3.18 (s, 1H), 2.87 (d, J=9.2 Hz, 2H), 2.21 (s, 3H), 2.10-2.00 (m, 1H), 1.98-1.82 (m, 5H), 1.70 (s, 1H).

Example 359 (S)-4-(2-((6-Fluoro-2-methyl-5-((1-methyl-1H-pyrazol-3-yl)amino)naphthalen-1-yl)oxy)pyridin-3-yl)-N-(piperidin-3-yl)pyrimidin-2-amine 359

Step 1: N-(5-(Benzyloxy)-6-chloro-2-fluoronaphthalen-1-yl)-1-methyl-1H-pyrazol-3-amine

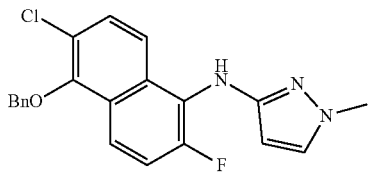 [SMILES: Cn1ccc(Nc2c(F)ccc3c(OCc4ccccc4)c(Cl)ccc23)n1]

To a solution of 1-benzyloxy-5-bromo-2-chloro-6-fluoronaphthalene (200 mg, 0.55 mmol) in 1,4-dioxane (4 mL) was added 1-methyl-1H-pyrazol-3-amine (58.4 mg, 0.6 mmol), tris(dibenzylideneacetone)dipalladium(0) (50.1 mg, 0.05 mmol), 4,5-bis(diphenylphosphino)-9,9-dimethylxanthene (63.3 mg, 0.11 mmol) and cesium carbonate (534.7 mg, 1.64 mmol). The mixture was stirred at 110° C. for 12 h under nitrogen atmosphere. The mixture was filtered and the filtrate was concentrated in vacuo, the residue was purified by pre-TLC (25% ethyl acetate in petroleum ether, Rf=0.6) to yield 120 mg (58% yield) of the title compound as a white solid. $^1$H NMR (400 MHz, CDCl$_3$) δ 7.92-7.89 (m, 1H), 7.77 (d, J=9.2 Hz, 1H), 7.59 (d, J=6.8 Hz, 2H), 7.48-7.36 (m, 4H), 7.32 (t, J=9.2 Hz, 1H), 7.11 (d, J=2.2 Hz, 1H), 6.00 (s, 1H), 5.36 (d, J=2.4 Hz, 1H), 5.16 (s, 2H), 3.78 (s, 3H).

Step 2: N-(5-(Benzyloxy)-2-fluoro-6-methylnaphthalen-1-yl)-1-methyl-1H-pyrazol-3-amine

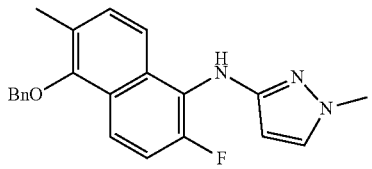 [SMILES: Cc1ccc2c(Nc3ccn(C)n3)c(F)ccc2c1OCc1ccccc1]

To a solution of N-(5-benzyloxy-6-chloro-2-fluoro-1-naphthyl)-1-methyl-pyrazol-3-amine (90 mg, 0.24 mmol) in 1,4-dioxane (2 mL), was added trimethylboroxine (118.4 mg, 0.94 mmol), dichloro[1,3-bis(2,6-di-3-pentylphenyl) imidazol-2-ylidene](3-chloropyridyl)palladium(ii) (16.1 mg, 0.020 mmol) and potassium carbonate (97.7 mg, 0.71 mmol). The mixture was purged with nitrogen atmosphere and heated to 100° C. for 12 h under nitrogen atmosphere. After cooling down, the mixture was filtered and the filtrate was diluted with ethyl acetate (40 mL), washed with H$_2$O (20 mL×2), The organic phase was dried over anhydrous sodium sulfate, filtered and the filtrate was purified by pre-TLC (15% ethyl acetate in petroleum ether, Rf=0.6) to yield 50 mg (59% yield) of the title compound as a white solid. LCMS (ESI) [M+H]$^+$=362.0; $^1$H NMR (400 MHz, CDCl$_3$) δ 7.93-7.90 (m, 1H), 7.75 (d, J=8.8 Hz, 1H), 7.56 (d, J=7.2 Hz, 2H), 7.47-7.38 (m, 3H), 7.34-7.29 (m, 2H), 7.10 (s, 1H), 6.01 (s, 1H), 5.36 (s, 1H), 5.01 (s, 2H), 3.79 (s, 3H), 2.45 (s, 3H).

Step 3: 6-Fluoro-2-methyl-5-((1-methyl-1H-pyrazol-3-yl)amino)naphthalen-1-ol

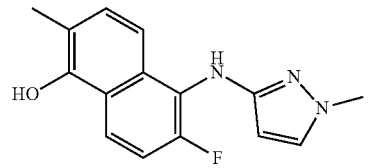 [SMILES: Cc1ccc2c(Nc3ccn(C)n3)c(F)ccc2c1O]

To a solution of N-(5-benzyloxy-2-fluoro-6-methyl-1-naphthyl)-1-methyl-pyrazol-3-amine (50 mg, 0.14 mmol) in ethyl acetate (2 mL) was added 10% wet Pd/C (14.7 mg) and stirred at 26° C. for 1 h under a hydrogen balloon (15 Psi). The mixture was filtered and the filtrate was concentrated to yield 30 mg (80% yield) of the title compound as a white solid. $^1$H NMR (400 MHz, CDCl$_3$) δ 7.98-7.94 (m, 1H), 7.54 (d, J=8.4 Hz, 1H), 7.22 (d, J=8.8 Hz, 1H), 7.08 (d, J=2.2 Hz, 1H), 6.00-5.91 (m, 1H), 5.39-5.32 (m, 1H), 3.78 (s, 3H), 2.39 (s, 3H).

Step 4: (S)-tert-Butyl 3-((4-(2-((6-fluoro-2-methyl-5-((1-methyl-1H-pyrazol-3-yl)amino)naphthalen-1-yl)oxy)pyridin-3-yl)pyrimidin-2-yl)amino)piperidine-1-carboxylate

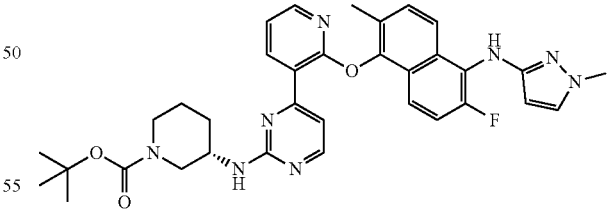

A solution of 6-fluoro-2-methyl-5-[(1-methylpyrazol-3-yl)amino]naphthalen-1-ol (30 mg, 0.11 mmol) and tert-butyl (3S)-3-[[4-(2-fluoro-3-pyridyl)pyrimidin-2-yl]amino]piperidine-1-carboxylate (49.6 mg, 0.13 mmol) in 1-methyl-2-pyrrolidinone (1 mL) was added cesium carbonate (90.1 mg, 0.28 mmol) and stirred at 120° C. for 1 h. The mixture was filtered and the filtrate was diluted with ethyl acetate (20 mL), washed with H$_2$O (20 mL×2). The organic phase was concentrated in vacuo and dried over anhydrous sodium sulfate, purified by prep-TLC (9% methanol in dichlo- Step 5: (S)-4-(2-((6-Fluoro-2-methyl-5-((1-methyl-1H-pyrazol-3-yl)amino)naphthalen-1-yl)oxy)pyridin-3-yl)-N-(piperidin-3-yl)pyrimidin-2-amine

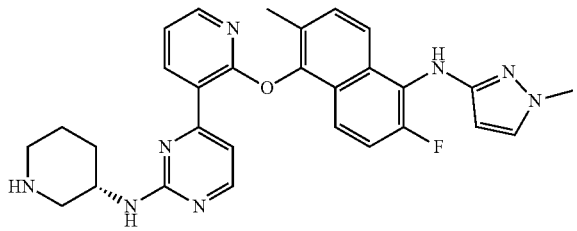 [SMILES: Cc1ccc2c(Nc3ccn(C)n3)c(F)ccc2c1Oc1ncccc1-c1ccnc(N[C@H]2CCCNC2)n1]

The General Procedure B was followed, using (S)-tert-butyl 3-((4-(2-((6-fluoro-2-methyl-5-((1-methyl-1H-pyrazol-3-yl)amino)naphthalen-1-yl)oxy)pyridin-3-yl)pyrimidin-2-yl)amino)piperidine-1-carboxylate (51 mg, 0.08 mmol) in ethyl acetate (1 mL) was added hydrochloric acid (4 M in ethyl acetate, 0.2 mL, 0.8 mmol) and stirred at 25° C. for 1 h. The residue was purified by Prep-HPLC (mobile phase: A: water (0.05% TFA) B: ACN) to yield 36.4 mg (79% yield) of 359 as a yellow solid; LCMS (ESI) [M+H]$^+$=525.2; $^1$H NMR (400 MHz, DMSO-d$_6$) δ 9.70-9.45 (m, 1H), 9.35-9.18 (m, 1H), 8.98-8.75 (m, 1H), 8.52 (d, J=5.2 Hz, 1H), 8.16-8.07 (m, 1H), 7.91 (d, J=8.8 Hz, 1H), 7.81-7.62 (m, 1H), 7.56 (d, J=2.4 Hz, 1H), 7.53-7.46 (m, 2H), 7.42-7.35 (m, 1H), 7.31-7.28 (m, 1H), 5.60 (d, J=2.4 Hz, 1H), 4.60-4.35 (m, 1H), 3.65 (s, 3H), 3.50-3.37 (m, 1H), 3.27-3.15 (m, 1H), 2.94-2.78 (m, 2H), 2.19 (s, 3H), 2.09-1.99 (m, 1H), 1.97-1.87 (m, 1H), 1.87-1.74 (m, 1H), 1.73-1.55 (m, 1H).

Example 360 (S)-4-(2-((5-((4-Fluoro-1-methyl-1H-pyrazol-3-yl)amino)-2-methylnaphthalen-1-yl)oxy)pyridin-3-yl)-N-(piperidin-3-yl)pyrimidin-2-amine 360

Step 1: 3-Bromo-4-fluoro-1-methyl-1H-pyrazole

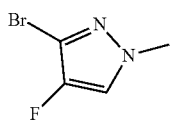

To a solution of 3-bromo-1-methyl-1H-pyrazole (650 mg, 4.04 mmol) in acetonitrile (10 mL) was added 1-chloromethyl-4-fluoro-1,4-diazoniabicyclo[2.2.2]octanebis(tetrafluoroborate) (2.15 g, 6.06 mmol). The mixture was stirred room temperature for 72 h. The reaction was concentrated in vacuo and the residue was dissolved in ethyl acetate (20 mL), washed with saturated sodium bicarbonate (20 mL). The organic layer was dried over anhydrous sodium sulfate, filtered and concentrated in vacuo. The residue was purified via flash silica chromatography (solvent gradient: 0-2% ethyl acetate in petroleum ether) to yield 150 mg crude of the title compound as a white solid.

Step 2: (S)-tert-Butyl 3-((4-(2-((5-((4-fluoro-1-methyl-1H-pyrazol-3-yl)amino)-2-methyl naphthalen-1-yl)oxy)pyridin-3-yl)pyrimidin-2-yl)amino) piperidine-1-carboxylate

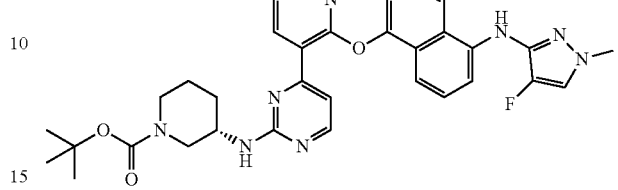

To a solution of 3-bromo-4-fluoro-1-methyl-1H-pyrazole (100 mg, 0.56 mmol) and (S)-tert-butyl 3-((4-(2-((5-amino-2-methylnaphthalen-1-yl)oxy)pyridin-3-yl)pyrimidin-2-yl)amino)piperidine-1-carboxylate in anhydrous 1,4-dioxane (3 mL) were added 2-(dicyclohexylphosphino)3,6-dimethoxy-2',4',6'-triisopropyl-1,1'-biphenyl (41 mg, 0.08 mmol), [2-(2-aminophenyl)phenyl]-methylsulfonyloxy-palladium; dicyclohexyl-[3,6-dimethoxy-2-(2,4,6-triisopropylphenyl)phenyl] phosphane (34 mg, 0.04 mmol) and sodium tert-butoxide (91 mg, 0.95 mmol). The mixture was purged with nitrogen atmosphere for 2 min and heated to 120° C. for 1 h under microwave condition. After cooling to room temperature, the mixture was filtered and concentrated in vacuo. The residue was purified via flash silica chromatography (solvent gradient: 0-50% ethyl acetate in petroleum ether) to yield 50 mg (21% yield) of 360 as a yellow oil. LCMS (ESI): [M+H]$^+$=625.4.

Step 3: (S)-4-(2-((5-((4-Fluoro-1-methyl-1H-pyrazol-3-yl)amino)-2-methylnaphthalen-1-yl)oxy)pyridin-3-yl)-N-(piperidin-3-yl)pyrimidin-2-amine

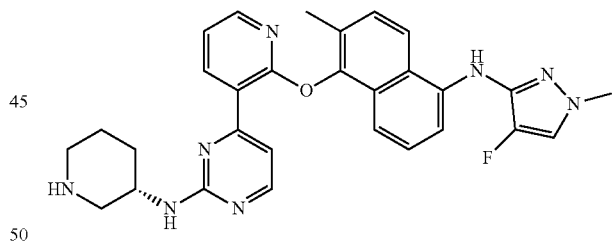

The General Procedure B was followed, using (S)-tert-butyl 3-((4-(2-((5-((4-fluoro-1-methyl-1H-pyrazol-3-yl)amino)-2-methylnaphthalen-1-yl)oxy)pyridin-3-yl)pyrimidin-2-yl)amino)piperidine-1-carboxylate (50 mg, 0.08 mmol), ethyl acetate (1 mL) and hydrochloric acid (4M in ethyl acetate, 0.5 mL, 2 mmol). The residue was purified by Prep-HPLC (mobile phase: A: water (0.05% HCl) B: ACN) to yield 28 mg (67% yield) of the title compound as orange solid. LCMS (ESI): [M+H]$^+$=525.1; $^1$H NMR (400 MHz, DMSO-d$_6$) δ 9.62 (s, 1H), 9.31 (s, 1H), 8.87 (s, 1H), 8.52 (d, J=5.6 Hz, 1H), 8.21 (d, J=8.4 Hz, 1H), 8.10-8.05 (m, 1H), 7.88 (d, J=4.4 Hz, 1H), 7.79-7.55 (m, 1H), 7.43 (d, J=8.4 Hz, 1H), 7.28-7.25 (m, 1H), 7.21-7.15 (m, 1H), 7.04 (d, J=8.4 Hz, 1H), 6.79 (d, J=7.6 Hz, 1H), 4.52-4.48 (m, 1H), 3.75 (s, 3H), 3.46-3.40 (m, 1H), 3.26-3.11 (m, 1H), 2.94-2.76 (m, 2H), 2.21 (s, 3H), 2.06-2.00 (m, 1H), 1.97-1.60 (m, 3H).

Example 361 N-(6-Methyl-5-((3-(2-(((3S,5R)-5-methylpiperidin-3-yl)amino)pyrimidin-4-yl)pyridin-2-yl)oxy)naphthalen-1-yl)propane-1-sulfonamide 361

Step 1: (3S,5R)-benzyl 3-amino-5-methylpiperidine-1-carboxylate hydrochloride

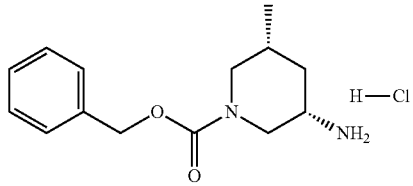

tert-Butyl ((3S,5R)-5-methylpiperidin-3-yl)carbamate (1000 mg, 4.67 mmol) dissolved in THF (10 mL) and H$_2$O (10 mL) and cooled to 0° C. Sodium bicarbonate (15.7 g, 18.7 mmol) was then added followed by dropwise addition of benzyl chloroformate (876 mg, 0.73 mL, 5.13 mmol). The mixture was then stirred overnight in the cooling bath allowing to slowly warm to rt. After 16 h, the mixture was diluted with EtOAc (75 mL) and H$_2$O (25 mL) and the phases were separated. The organic extract was washed with saturated NaHCO$_3$(aq) (10 mL), then with saturated NaCl (aq) (10 mL), dried (Na$_2$SO$_4$), and filtered through a 1"×1" Si plug topped with celite using 20% EtOAc/hexanes (100 mL) to wash/elute. The filtrate was concentrated in vacuo to provide (3S,5R)-benzyl 3-((tert-butoxycarbonyl)amino)-5-methylpiperidine-1-carboxylate (1560 mg, 95% yield) as a white solid in sufficient purity to use directly in the next step without further purification. LCMS (ESI) [M+H]$^+$=349.3, rt=1.80 min; $^1$H NMR (400 MHz, CDCl$_3$) δ 7.46-7.29 (m, 5H), 5.27-5.01 (m, 2H), 4.48-4.25 (m, 2H), 4.22-3.95 (m, 2H), 3.65-3.42 (m, 1H), 2.46-2.13 (m, 2H), 2.13-1.98 (m, 1H), 1.76-1.61 (m, 1H), 1.43 (s, 9H), 0.90 (d, J=6.6 Hz, 3H).

(3S,5R)-Benzyl 3-((tert-butoxycarbonyl)amino)-5-methylpiperidine-1-carboxylate prepared above (1560 mg, 4.48 mmol) was dissolved in EtOAc (15 mL) and to this was then added 4N HCl in dioxanes (5.0 mL, 20.0 mmol) and the mixture stirred at rt. After 2 h, LCMS shows ~50% conversion. A further portion of 4 N HCl in dioxanes was then added (5.0 mL, 20.0 mmol) and after stirring a further 4 h at rt LCMS shows complete deprotection. The mixture was concentrated in vacuo to provide a white solid which was suspended in EtOAc (10 mL) and the solids were filtered off and washed with EtOAc (5×5 mL) and dried to provide 1.36 g (106% yield) of the title compound as a white solid. LCMS (ESI) [M+H]$^+$=249.3, rt=1.16 min; $^1$H NMR (400 MHz, d6-DMSO) δ 8.36-8.10 (m, 3H), 7.49-7.20 (m, 5H), 5.08 (s, 2H), 4.30 (dd, J=12.7, 3.7 Hz, 1H), 3.95 (d, J=10.2 Hz, 1H), 3.18-2.94 (m, 1H), 2.81-2.55 (m, 1H), 2.47-2.16 (m, 1H), 2.02 (d, J=12.4 Hz, 1H), 1.70-1.45 (m, 1H), 1.12 (q, J=12.1 Hz, 1H), 0.88 (d, J=6.5 Hz, 3H).

Step 2: N-(6-Methyl-5-((3-(2-(methylthio)pyrimidin-4-yl)pyridin-2-yl)oxy)naphthalen-1-yl)propane-1-sulfonamide

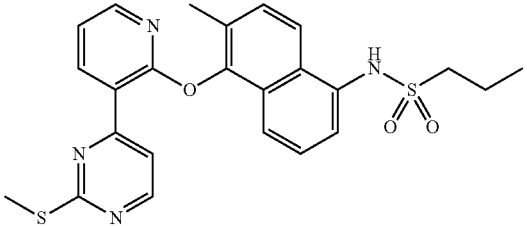 [SMILES: CCCS(=O)(=O)Nc1cccc2c(Oc3ncccc3-c3ccnc(SC)n3)c(C)ccc12]

Prepared using 6-methyl-5-((3-(2-(methylthio)pyrimidin-4-yl)pyridin-2-yl)oxy)naphthalen-1-amine (400 mg, 1.07 mmol), pyridine (1 mL), DCM (3 mL), and 1-propanesulfonyl chloride (381 mg, 2.67 mmol). After 3 days, the mixture was diluted with DCM (30 mL) and washed with 1M HCl (30 mL), dried (Na$_2$SO$_4$), filtered and concentrated in vacuo to provide 603 mg (117% yield) of the title compound as a brown solid which was used crude without further purification in the next step. LCMS (ESI) [M+H]$^+$=481.3, rt=1.89 min.

Step 3: N-(6-Methyl-5-((3-(2-(methylsulfinyl)pyrimidin-4-yl)pyridin-2-yl)oxy)naphthalen-1-yl)propane-1-sulfonamide

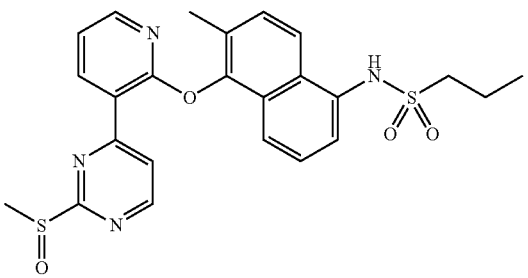 [SMILES: CCCS(=O)(=O)Nc1cccc2c(Oc3ncccc3-c3ccnc(S(C)=O)n3)c(C)ccc12]

N-(6-Methyl-5-((3-(2-(methylthio)pyrimidin-4-yl)pyridin-2-yl)oxy)naphthalen-1-yl)propane-1-sulfonamide (517 mg, 1.08 mmol) was dissolved in DCM (5 mL) and to this was then added 3-chloroperbenzoic acid (241 mg of 77% pure reagent, 1.08 mmol) and the mixture was stirred at rt. After 90 min, the mixture was diluted with DCM (75 mL) and washed with saturated NaHCO$_3$(aq) (2×25 mL), dried (Na$_2$SO$_4$), filtered and concentrated in vacuo to provide 534 mg (100% yield) of the title compound as a brown wax which was used crude without further purification in the next step. LCMS (ESI) [M+H]⁺=497.4, rt=1.44 min.

Step 4: (3R,5S)-Benzyl 3-methyl-5-((4-(2-((2-methyl-5-(propylsulfonamido)naphthalen-1-yl)oxy)pyridin-3-yl)pyrimidin-2-yl)amino)piperidine-1-carboxylate

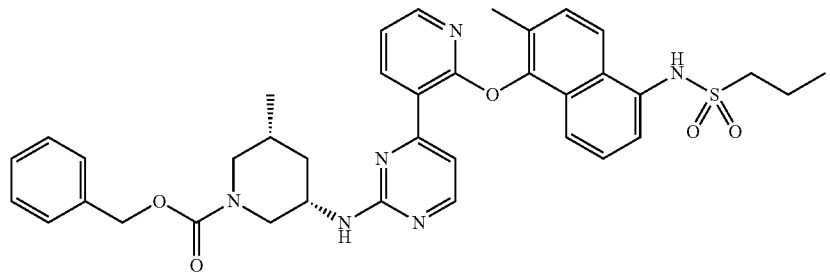 [SMILES: CCCS(=O)(=O)Nc1cccc2c(Oc3ncccc3-c3ccnc(N[C@H]4C[C@@H](C)CN(C(=O)OCc5ccccc5)C4)n3)c(C)ccc12]

N-(6-Methyl-5-((3-(2-(methylsulfinyl)pyrimidin-4-yl)pyridin-2-yl)oxy)naphthalen-1-yl)propane-1-sulfonamide (240 mg, 0.480 mmol) and (3S,5R)-benzyl 3-amino-5-methylpiperidine-1-carboxylate hydrochloride (151 mg, 0.530 mmol) were combined in 1,4-dioxane (2 mL). Triethylamine (244 mg, 0.34 mL, 2.42 mmol) was then added and the flask was sealed and placed in a 115° C. oil bath. After 16 h, the mixture was diluted with EtOAc (30 mL), and washed with H₂O (10 mL), dried (MgSO₄), filtered and concentrated in vacuo. The crude was purified by flash chromatography through silica gel (0-100% EtOAc/DCM) to provide 175 mg (53% yield) of the title compound. LCMS (ESI) [M+H]⁺=681.7, rt=1.98 min.

Step 5: N-(6-Methyl-5-((3-(2-(((3S,5R)-5-methylpiperidin-3-yl)amino)pyrimidin-4-yl)pyridin-2-yl)oxy)naphthalen-1-yl)propane-1-sulfonamide

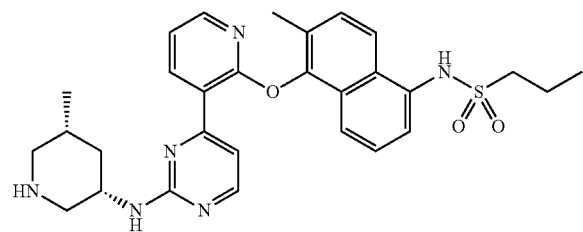 [SMILES: CCCS(=O)(=O)Nc1cccc2c(Oc3ncccc3-c3ccnc(N[C@@H]4CNC[C@H](C)C4)n3)c(C)ccc12]

(3R,5S)-Benzyl 3-methyl-5-((4-(2-((2-methyl-5-(propylsulfonamido)naphthalen-1-yl)oxy)pyridin-3-yl)pyrimidin-2-yl)amino)piperidine-1-carboxylate (175 mg, 0.240 mmol) dissolved in iPrOH (1 mL) and this solution was added to a mixture of 10% Pd/C (200 mg) and ammonium formate (452 mg, 7.17 mmol) in MeOH (6 mL). The resulting mixture was stirred at rt for 20 min at which time LCMS indicated complete deprotection. The mixture was filtered through celite using MeOH to wash/elute and the filtrate was concentrated in vacuo. The crude residue was dissolved in DMSO/H₂O and purified by reverse phase prep HPLC (14 min 20-40% MeCN/10 mM pH: 3.8 NH₄CO₂H(aq), XBridge BEH C18 OBD Prep Column, 130 Å, 5 μm, 30 mm×50 mm). Appropriate fractions were combined and MeCN removed on a rotovap and the resulting aqueous solution diluted with saturated NaHCO₃(aq) (10 mL) and extracted with EtOAc (2×100 mL). The organic extracts were combined, dried (MgSO₄), filtered and concentrated in vacuo. The residue thus obtained was dissolved in 1,4-dioxane (5 mL) and treated with 4N HCl in dioxanes (0.4 mL, 1.6 mmol) generating a precipitate. The mixture was diluted with MTBE (10 mL) and the solids filtered off, washed with MTBE and dried. The solids were then dissolved in MeCN/H₂O and lyophilized to provide 42 mg (30% yield) of 361. LCMS (ESI) [M+H]⁺=547.5, rt=1.39 min; ¹H NMR (400 MHz, D₂O) δ 8.35 (s, 1H), 8.06 (d, J=6.0 Hz, 1H), 7.93 (d, J=8.8 Hz, 1H), 7.80 (dd, J=5.0, 1.8 Hz, 1H), 7.50 (s, 2H), 7.40 (d, J=8.9 Hz, 1H), 7.29 (d, J=7.3 Hz, 1H), 7.18-7.09 (m, 2H), 4.24 (s, 1H), 3.51 (d, J=8.7 Hz, 1H), 3.17 (d, J=10.3 Hz, 1H), 3.11-3.05 (m, 2H), 2.68 (dd, J=16.4, 7.5 Hz, 1H), 2.42 (t, J=12.5 Hz, 1H), 2.03 (s, 3H), 1.66 (dq, J=15.0, 7.5 Hz, 2H), 1.16 (q, J=12.3 Hz, 1H), 0.79 (t, J=7.5 Hz, 3H), 0.71 (s, 3H).

Example 362 (S)-2,2,2-Trifluoro-N-(2-fluoro-6-methyl-5-((3-(2-(piperidin-3-ylamino)pyrimidin-4-yl)pyridin-2-yl)oxy)naphthalen-1-yl)ethanesulfonamide 362

Step 1: (S)-tert-Butyl 3-((4-(2-((6-fluoro-2-methyl-5-(2,2,2-trifluoroethylsulfonamido)naphthalen-1-yl)oxy)pyridin-3-yl)pyrimidin-2-yl)amino)piperidine-1-carboxylate

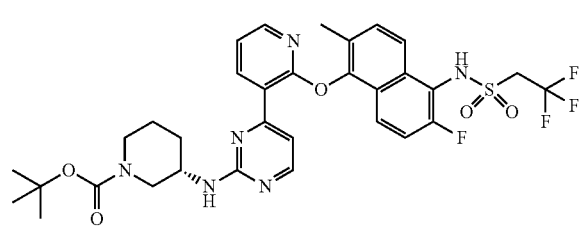 [SMILES: Cc1ccc2c(NS(=O)(=O)CC(F)(F)F)c(F)ccc2c1Oc1ncccc1-c1ccnc(N[C@H]2CCCN(C(=O)OC(C)(C)C)C2)n1]

Prepared using (S)-tert-butyl 3-((4-(2-((5-amino-6-fluoro-2-methylnaphthalen-1-yl)oxy)pyridin-3-yl)pyrimidin-2-yl)amino)piperidine-1-carboxylate from Example 275 (50 mg, 0.090 mmol), pyridine (109 mg, 1.38 mmol), DCM (0.3 mL), and 2,2,2-trifluoroethanesulfonyl chloride (34 mg, 0.18 mmol). After 16 h, the mixture was diluted with DCM and washed with saturated NaHCO₃(aq), dried (Na₂SO₄), filtered and concentrated in vacuo to provide a mixture of the title compound and bis-sulfonylated title compound. The crude residue was dissolved in THF (1 mL) and to this was then added tetrabutylammonium fluoride (0.5 mL of a 1 M solution in THF) and the mixture was stirred at rt. After 2.5 h, the mixture was diluted with EtOAc, washed with saturated NaHCO$_3$(aq), then with saturated NaCl(aq), dried (Na$_2$SO$_4$), filtered and concentrated in vacuo. The crude was purified by flash chromatography through silica gel (0-40% EtOAc/DCM) to provide 24 mg (38% yield) of the title compound. LCMS (ESI) [M+H]$^+$=691.6, rt=1.94 min.

Step 2: (S)-2,2,2-Trifluoro-N-(2-fluoro-6-methyl-5-((3-(2-(piperidin-3-ylamino)pyrimidin-4-yl)pyridin-2-yl)oxy)naphthalen-1-yl)ethanesulfonamide

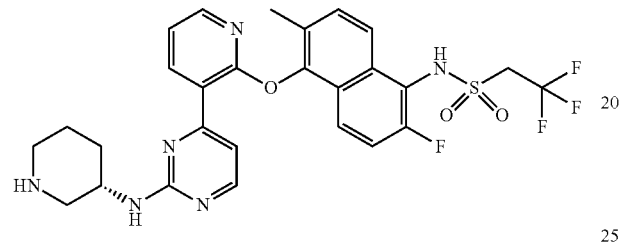

Prepared according to General Procedure B using (S)-tert-butyl 3-((4-(2-((6-fluoro-2-methyl-5-(2,2,2-trifluoroethylsulfonamido)naphthalen-1-yl)oxy)pyridin-3-yl)pyrimidin-2-yl)amino)piperidine-1-carboxylate (24 mg, 0.035 mmol), 1,4-dioxane (0.1 mL), and hydrochloric acid (4 M in dioxane, 0.7 mL, 2.8 mmol). After 15 min, the mixture was diluted with Et$_2$O and the solids were filtered off, washed with Et$_2$O then dissolved in H$_2$O and MeCN and lyophilized to provide 20 mg (94% yield) of 362. LCMS (ESI) [M+H]$^+$=591.4, rt=1.41 min; $^1$H NMR (400 MHz, d6-dmso) δ 10.45 (s, 1H), 9.22-8.87 (m, 2H), 8.71 (br.s, 1H), 8.48 (d, J=5.2 Hz, 1H), 8.08 (dd, J=4.8, 1.9 Hz, 1H), 8.02 (d, J=8.7 Hz, 1H), 7.76 (dd, J=9.3, 5.2 Hz, 1H), 7.65 (d, J=8.8 Hz, 1H), 7.59 (br.s, 2H), 7.48 (t, J=9.4 Hz, 1H), 7.29 (dd, J=7.6, 4.8 Hz, 1H), 4.58 (q, J=9.7 Hz, 2H), 4.30 (bs, 1H), 3.50-3.36 (m, 1H), 3.20 (d, J=12.5 Hz, 1H), 2.98-2.76 (m, 2H), 2.20 (s, 3H), 2.05-1.83 (m, 2H), 1.83-1.55 (m, 2H).

Example 363 (S)-2-Cyano-2-methyl-N-(6-methyl-5-((3-(2-(piperidin-3-ylamino)pyrimidin-4-yl)pyridin-2-yl)oxy)naphthalen-1-yl)propanamide 363

Step 1: (S)-tert-Butyl 3-((4-(2-((5-(2-cyano-2-methylpropanamido)-2-methylnaphthalen-1-yl)oxy)pyridin-3-yl)pyrimidin-2-yl)amino)piperidine-1-carboxylate

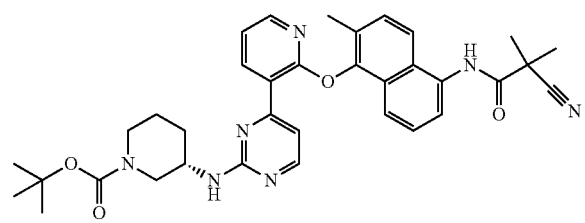 [SMILES: Cc1ccc2c(NC(=O)C(C)(C)C#N)cccc2c1Oc1ncccc1-c1ccnc(N[C@H]2CCCN(C(=O)OC(C)(C)C)C2)n1]

Prepared using (S)-tert-butyl 3-((4-(2-((5-amino-2-methylnaphthalen-1-yl)oxy)pyridin-3-yl)pyrimidin-2-yl)amino)piperidine-1-carboxylate (150 mg, 0.280 mmol), triethylamine (144 mg, 0.198 mL, 1.42 mmol), HATU (325 mg, 0.854 mmol), and 2-cyano-2-methylpropanoic acid (97 mg, 0.85 mmol) in DMF (2 mL). After 22 h, the mixture was diluted with EtOAc (50 mL) and washed with H$_2$O (10 mL), then saturated NaHCO$_3$(aq) (10 mL), followed by washing with 50% saturated NaCl(aq) (4×10 mL). The organic extract was dried (Na$_2$SO$_4$), filtered and concentrated in vacuo. The crude residue was purified by flash chromatography through silica gel (0-100% EtOAc/hexanes) to provide 111 mg (63% yield) of the title compound as a clear wax. LCMS (ESI) [M+H]$^+$=622.4, rt=1.85 min.

Step 2: (S)-2-Cyano-2-methyl-N-(6-methyl-5-((3-(2-(piperidin-3-ylamino)pyrimidin-4-yl)pyridin-2-yl)oxy)naphthalen-1-yl)propanamide

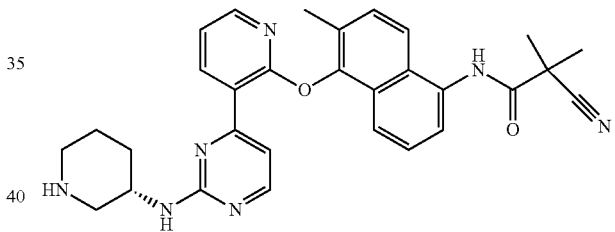

Prepared using (S)-tert-butyl 3-((4-(2-((5-(2-cyano-2-methylpropanamido)-2-methylnaphthalen-1-yl)oxy)pyridin-3-yl)pyrimidin-2-yl)amino)piperidine-1-carboxylate (111 mg, 0.180 mmol), 1,4-dioxane (1 mL), and hydrochloric acid (4 M in dioxane, 2.77 mL, 11.1 mmol). After 16 h, the resulting solids were filtered off and washed with 1,4-dioxane, then Et$_2$O, and dried. The collected solids were then dissolved in H$_2$O and lyophilized to provide 84 mg (84% yield) of 363 as a yellow/orange solid. LCMS (ESI) [M+H]$^+$=522.2, rt=1.30 min; $^1$H NMR (400 MHz, d$_6$-DMSO) [one CH signal hidden under the HOD signal] δ 10.35 (s, 1H), 9.54 (br s, 1H), 9.28 (s, 1H), 9.22-8.68 (m, 1H), 8.51 (d, J=5.5 Hz, 1H), 8.09 (d, J=3.2 Hz, 2H), 7.73 (d, J=8.6 Hz, 2H), 7.61 (d, J=8.3 Hz, 1H), 7.54 (d, J=8.8 Hz, 1H), 7.49-7.42 (m, 1H), 7.39 (d, J=7.0 Hz, 1H), 7.29 (dd, J=7.6, 4.8 Hz, 1H), 3.43 (d, J=7.9 Hz, 1H), 3.19 (d, J=11.2 Hz, 1H), 2.93-2.78 (m, 2H), 2.22 (s, 3H), 2.03 (d, J=9.5 Hz, 1H), 1.97-1.86 (m, 1H), 1.78 (s, 7H), 1.71-1.55 (m, 1H).

Example 364 (S)-2-Cyclohexyl-N-(2-fluoro-6-methyl-5-((3-(2-(piperidin-3-ylamino)pyrimidin-4-yl)oxy)pyridin-2-yl)oxy)naphthalen-1-yl)acetamide 364

Step 1: (S)-tert-Butyl 3-((4-(2-((5-(2-cyclohexylacetamido)-6-fluoro-2-methylnaphthalen-1-yl)oxy)pyridin-3-yl)pyrimidin-2-yl)amino)piperidine-1-carboxylate

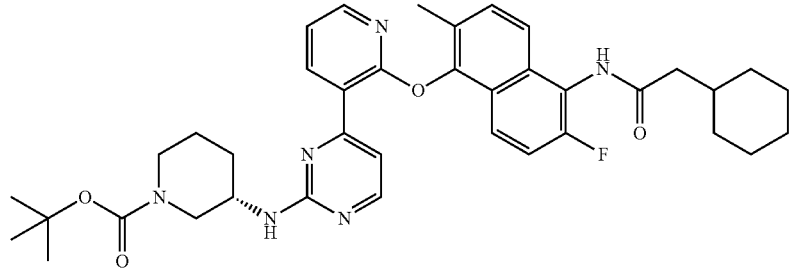 [SMILES: Cc1ccc2c(NC(=O)CC3CCCCC3)c(F)ccc2c1Oc1ncccc1-c1ccnc(N[C@H]2CCCN(C(=O)OC(C)(C)C)C2)n1]

2-cyclohexylacetic acid (33 mg, 0.23 mmol) dissolved in DCM (1 mL) and DMF (5 µL) and cooled to 0° C. Oxalyl chloride (26 mg, 0.017 mL, 0.20 mmol) was then added and the mixture stirred 30 min before addition of (S)-tert-butyl 3-((4-(2-((5-amino-6-fluoro-2-methylnaphthalen-1-yl)oxy)pyridin-3-yl)pyrimidin-2-yl)amino)piperidine-1-carboxylate from Example 275 (50 mg, 0.092 mmol) and pyridine (109 mg, 0.111 mL, 1.38 mmol). After stirring for 1 h, the mixture was diluted with EtOAc and H$_2$O and the phases were separated. The organic extract was washed with saturated NaHCO$_3$(aq), then saturated NaCl(aq), then saturated NH$_4$Cl(aq), dried (MgSO$_4$), filtered and concentrated in vacuo. The crude residue was purified by flash chromatography through silica gel (0-100% EtOAc/DCM) to provide 39 mg (64% yield) of the title compound as a yellow oil. LCMS (ESI) [M+H]$^+$=669.3, rt=2.06 min.

Step 2: (S)-2-Cyclohexyl-N-(2-fluoro-6-methyl-5-((3-(2-(piperidin-3-ylamino)pyrimidin-4-yl)pyridin-2-yl)oxy)naphthalen-1-yl)acetamide

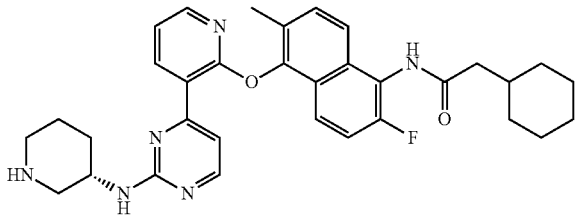 [SMILES: Cc1ccc2c(NC(=O)CC3CCCCC3)c(F)ccc2c1Oc1ncccc1-c1ccnc(N[C@H]2CCCNC2)n1]

Prepared using (S)-tert-butyl 3-((4-(2-((5-(2-cyclohexylacetamido)-6-fluoro-2-methylnaphthalen-1-yl)oxy)pyridin-3-yl)pyrimidin-2-yl)amino)piperidine-1-carboxylate (39 mg, 0.058 mmol), 1,4-dioxane (1 mL), and hydrochloric acid (4 M in dioxane, 0.9 mL, 3.6 mmol). After 4 h, the resulting solids were filtered off and washed with 1,4-dioxane, then Et$_2$O, and dried. The collected solids were dissolved in H$_2$O and MeCN and lyophilized to provide 33 mg (94% yield) of 364 as a pale yellow solid. LCMS (ESI) [M+H]$^+$=569.2, rt=1.54 min; $^1$H NMR (400 MHz, d6-dmso) δ 9.87 (s, 1H), 8.97 (s, 2H), 8.48 (d, J=5.1 Hz, 2H), 8.07 (d, J=4.5 Hz, 1H), 7.75 (d, J=8.6 Hz, 1H), 7.68-7.52 (m, 4H), 7.40 (t, J=9.3 Hz, 1H), 7.32-7.24 (m, 1H), 4.30 (s, 1H), 3.43 (d, J=8.8 Hz, 1H), 3.20 (d, J=11.6 Hz, 1H), 2.92-2.76 (m, 2H), 2.36 (d, J=6.7 Hz, 2H), 2.19 (s, 3H), 2.01 (d, J=10.4 Hz, 1H), 1.91 (d, J=14.2 Hz, 1H), 1.80 (d, J=12.3 Hz, 4H), 1.72 (d, J=12.7 Hz, 2H), 1.65 (d, J=9.4 Hz, 2H), 1.33-1.13 (m, 3H), 1.06 (q, J=11.3 Hz, 2H).

Example 365 (S)—N-(2-Fluoro-6-methyl-5-((3-(2-(piperidin-3-ylamino)pyrimidin-4-yl)pyridin-2-yl)oxy)naphthalen-1-yl)-1-methylcyclopropanecarboxamide 365

Step 1: (S)-tert-Butyl 3-((4-(2-((6-fluoro-2-methyl-5-(1-methylcyclopropanecarboxamido)naphthalen-1-yl)oxy)pyridin-3-yl)pyrimidin-2-yl)amino)piperidine-1-carboxylate

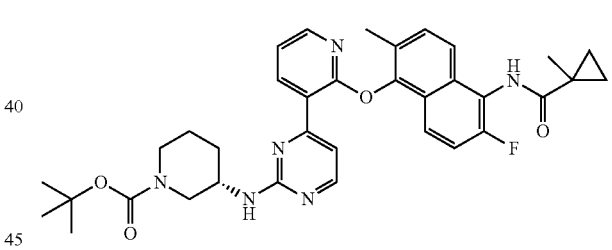

Prepared using (S)-tert-butyl 3-((4-(2-((5-amino-6-fluoro-2-methylnaphthalen-1-yl)oxy)pyridin-3-yl)pyrimidin-2-yl)amino)piperidine-1-carboxylate from Example 275 (50 mg, 0.090 mmol), DCM (1 mL), pyridine (0.11 mL, 1.4 mmol), and 1-methylcyclopropanecarbonyl chloride (prepared in situ from 1-methylcyclopropanecarboxylic acid (28 mg, 0.28 mmol) diluted in DCM (1 mL), cooled to 0° C. and oxalyl chloride (0.022 mL, 0.260 mmol) added followed by addition of 2 drops of DMF and stirring for 30 min). The mixture stirred at room temperature and after 2 h, the solvent was evaporated in vacuo. The residue was diluted with ethyl acetate, washed with 1M HCl, then with saturated aqueous sodium bicarbonate, and then with brine. The organic phase was dried (MgSO$_4$), filtered, and concentrated in vacuo. The crude product was purified by C18 reverse phase flash chromatography (0-70% MeCN/10 mM aqueous ammonium formate, pH 3.8). The appropriate fractions were combined and concentrated in vacuo to provide 28 mg (49% yield) of the title compound. LCMS (ESI) [M+H]$^+$=627.1, rt=1.88 min.

Step 2: (S)—N-(2-Fluoro-6-methyl-5-((3-(2-(piperi-din-3-ylamino)pyrimidin-4-yl)pyridin-2-yl)oxy)naphthalen-1-yl)-1-methylcyclopropanecarboxamide

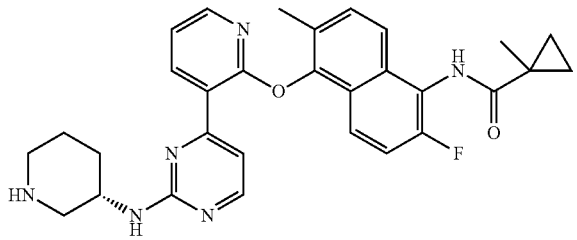 [SMILES: Cc1ccc2c(NC(=O)C3(C)CC3)c(F)ccc2c1Oc1ncccc1-c1ccnc(N[C@H]2CCCNC2)n1]

Prepared using (S)-tert-butyl 3-((4-(2-((6-fluoro-2-methyl-5-(1-methylcyclopropanecarboxamido)naphthalen-1-yl)oxy)pyridin-3-yl)pyrimidin-2-yl)amino)piperidine-1-carboxylate (28 mg, 0.040 mmol), 1,4-dioxane (1 mL), and hydrochloric acid (4 M in dioxane, 1 mL, 4 mmol). After 3 h, the mixture was concentrated in vacuo and the residue was diluted with EtOAc, washed twice with a solution of saturated aqueous sodium bicarbonate, then with brine. The organic phase was dried (MgSO$_4$), filtered, and concentrated in vacuo. The crude material thus obtained was purified by C18 reverse phase flash chromatography (40-90% % MeCN/10 mM aqueous ammonium formate, pH 3.8). The appropriate fractions were combined and lyophilized and the obtained solid was treated with hydrochloric acid (4 M in 1,4-dioxane). After 30 min, the mixture was concentrated in vacuo, dried on the vacuum pump, dissolved in a mixture of MeCN/water, and lyophilized to provide 8 mg (32% yield) of 365. LCMS (ESI) [M+H]$^+$=527.1, rt=1.35 min; $^1$H NMR (400 MHz, DMSO-d$_6$) δ 9.40 (s, 1H), 9.02 (s, 1H), 8.92 (s, 1H), 8.70 (s, 1H), 8.48 (d, J=5.2 Hz, 1H), 8.07 (dd, J=4.7, 1.7 Hz, 1H), 7.70 (d, J=8.7 Hz, 1H), 7.65 (dd, J=9.2, 5.1 Hz, 1H), 7.61-7.54 (m, J=8.6 Hz, 3H), 7.41 (t, J=9.3 Hz, 1H), 7.28 (dd, J=7.5, 4.8 Hz, 1H), 4.27 (s, 1H), 3.59-3.49 (m, 1H), 3.28-3.12 (m, 1H), 2.94-2.75 (m, 2H), 2.19 (s, 3H), 2.01 (d, J=9.7 Hz, 1H), 1.91 (d, J=14.3 Hz, 1H), 1.83-1.56 (m, 2H), 1.51 (s, 3H), 1.17-1.12 (m, 2H), 0.75-0.71 (m, 2H).

Example 366 2-Cyclohexyl-N-(2-fluoro-6-methyl-5-((3-(2-(((3S,5R)-5-methylpiperidin-3-yl)amino)pyrimidin-4-yl)pyridin-2-yl)oxy)naphthalen-1-yl)acetamide 266

Step 1: (3S,5R)-Benzyl 3-((4-(2-((5-(2-cyclohexylacetamido)-6-fluoro-2-methyl naphthalen-1-yl)oxy)pyridin-3-yl)pyrimidin-2-yl)amino)-5-methylpiperidine-1-carboxylate

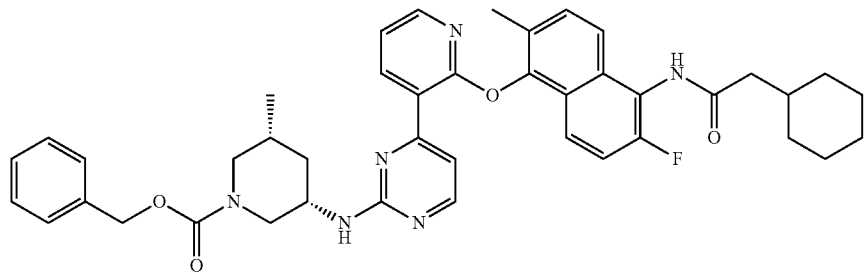 [SMILES: Cc1ccc2c(NC(=O)CC3CCCCC3)c(F)ccc2c1Oc1ncccc1-c1ccnc(N[C@H]2C[C@@H](C)CN(C(=O)OCc3ccccc3)C2)n1]

Prepared using (3S,5R)-benzyl 3-((4-(2-((5-amino-6-fluoro-2-methylnaphthalen-1-yl)oxy)pyridin-3-yl)pyrimidin-2-yl)amino)-5-methylpiperidine-1-carboxylate (50 mg, 0.080 mmol), 1,2-dichloroethane (0.5 mL), pyridine (0.070 mL, 0.84 mmol) and 2-cyclohexylacetyl chloride (20 mg, 0.13 mmol). After 30 minutes, the mixture was diluted with DCM, silica gel was added and the mixture was concentrated in vacuo. The crude product on silica gel was purified by flash chromatography through silica gel (0-100% EtOAc/hexanes) to provide 39 mg (64% yield) of the title compound. LCMS (ESI) [M+H]$^+$=717.7, rt=2.12 min.

Step 2: 2-Cyclohexyl-N-(2-fluoro-6-methyl-5-((3-(2-(((3S,5R)-5-methylpiperidin-3-yl)amino)pyrimidin-4-yl)pyridin-2-yl)oxy)naphthalen-1-yl)acetamide

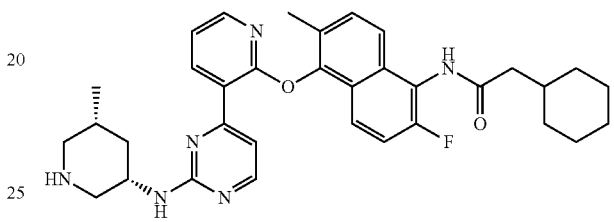

Prepared using (3S,5R)-benzyl 3-((4-(2-((5-(2-cyclohexylacetamido)-6-fluoro-2-methylnaphthalen-1-yl)oxy)pyridin-3-yl)pyrimidin-2-yl)amino)-5-methylpiperidine-1-carboxylate (39 mg, 0,054 mmol), Methanol (1 mL), ammonium formate (103 mg, 1.63 mmol) and palladium (10% on charcoal, 20 mg, 0,019 mmol). The reaction was stirred at rt for 30 min, filtered through Celite and the filter cake was washed with EtOAc and MeOH. The filtrate was concentrated in vacuo and diluted with water (10 mL), a solution of saturated aqueous sodium bicarbonate (2 mL) and EtOAc (20 mL) were added. The phases were separated and the aqueous phase was extracted with EtOAc (2×10 mL). The combined organic extracts were dried (MgSO$_4$), filtered and concentrated in vacuo. The residue thus obtained was dissolved in 1,4-dioxane (1 mL) and HCl (4 M in dioxane, 0.2 mL, 0.8 mmol) was added to precipitate the product. MTBE (10 mL) was added and the solids collected by filtration through a fritted funnel. The collected solids were dissolved in water and MeCN and lyophilized to provide 19 mg (60% yield) of 366. LCMS (ESI) [M+H]$^+$=583.6, rt=1.58 min; $^1$H NMR (400 MHz, DMSO-d$_6$) δ 9.84 (s, 1H), 8.99 (s, 2H), 8.46 (d, J=5.1 Hz, 1H), 8.05 (s, 1H), 7.73 (d, J=8.1 Hz, 1H), 7.65-7.49 (m, 4H), 7.39 (d, J=9.1 Hz, 1H), 7.26 (s, 1H), 3.22-3.15 (m, 1H), 2.34 (d, J=6.7 Hz, 2H), 2.17 (s, 3H), 1.84 (t, J=69.0 Hz, 9H), 1.19 (dd, J=47.9, 35.8 Hz, 7H), 0.92 (s, 3H).

Example 367 N-(2-Fluoro-6-methyl-5-((3-(2-(((3S, 5R)-5-methylpiperidin-3-yl)amino)pyrimidin-4-yl) pyridin-2-yl)oxy)naphthalen-1-yl)propane-1-sulfonamide 367

Step 1: (3S,5R)-Benzyl 3-((4-(2-((6-fluoro-2-methyl-5-(propylsulfoNamido)naphthalen-1-yl)oxy) pyridin-3-yl)pyrimidin-2-yl)amino)-5-methylpiperidine-1-carboxylate

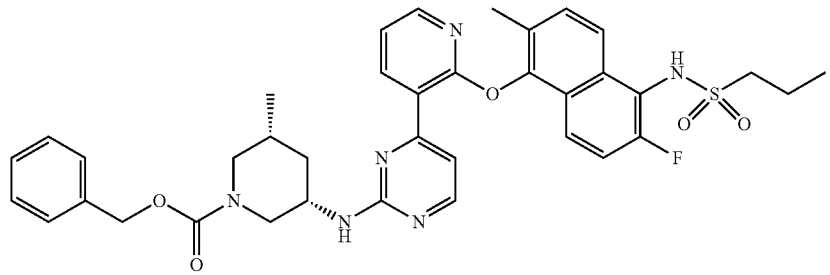 [SMILES: CCCS(=O)(=O)Nc1c(F)ccc2c(Oc3ncccc3-c3ccnc(N[C@H]4C[C@@H](C)CN(C(=O)OCc5ccccc5)C4)n3)c(C)ccc12]

Prepared using (3S,5R)-benzyl 3-((4-(2-((5-amino-6-fluoro-2-methylnaphthalen-1-yl)oxy)pyridin-3-yl)pyrimidin-2-yl)amino)-5-methylpiperidine-1-carboxylate (50 mg, 0.080 mmol), 1,2-dichloroethane (0.5 mL), pyridine (0.10 mL, 1.3 mmol), DMAP (1.0 mg, 0.010 mmol) and 1-propanesulfonyl chloride (24 mg, 0.17 mmol). After 16 hours, the mixture was diluted with DCM, silica gel was added and the mixture was concentrated in vacuo. The crude product on silica gel was purified by flash chromatography through silica gel (0-100% EtOAc/hexanes) to provide 35 mg (59% yield) of the title compound. LCMS (ESI) [M+H]+=699.6, rt=1.99 min.

Step 2: N-(2-Fluoro-6-methyl-5-((3-(2-(((3S,5R)-5-methylpiperidin-3-yl)amino)pyrimidin-4-yl)pyridin-2-yl)oxy)naphthalen-1-yl)propane-1-sulfonamide

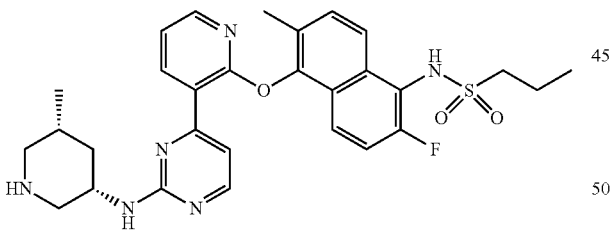

Prepared using (3S,5R)-benzyl 3-((4-(2-((6-fluoro-2-methyl-5-(propylsulfonamido)naphthalen-1-yl)oxy)pyridin-3-yl)pyrimidin-2-yl)amino)-5-methylpiperidine-1-carboxylate (35 mg, 0.050 mmol), isopropanol (0.5 mL), palladium (10% on charcoal, 20 mg, 0.019 mmol), and ammonium formate (95 mg, 1.5 mmol). The reaction was stirred at 60° C. for 30 min, filtered through Celite and the filter cake was washed with EtOAc and MeOH. The filtrate was concentrated in vacuo and diluted with water (10 mL), a solution of saturated aqueous sodium bicarbonate (2 mL) and EtOAc (20 mL) were added. The phases were separated and the aqueous phase was extracted with EtOAc (2×10 mL). The combined organic extracts were dried (MgSO$_4$), filtered, and concentrated in vacuo. The residue thus obtained was dissolved in 1,4-dioxane (1 mL) and HCl (4 M in dioxane, 0.2 mL, 0.8 mmol) was added to precipitate the product. MTBE (10 mL) was added and the solids were collected by filtration, dissolved in H₂O and MeCN and lyophilized to provide 12 mg (42% yield) of 367. LCMS (ESI) [M+H]⁺=565.5, rt=1.41 min; ¹H NMR (400 MHz, dmso) δ 9.67 (s, 1H), 8.82 (s, 2H), 8.45 (d, J=5.2 Hz, 1H), 8.07-8.02 (m, 2H), 7.69 (dd, J=9.2, 5.1 Hz, 1H), 7.61 (d, J=8.8 Hz, 1H), 7.51 (d, J=7.8 Hz, 2H), 7.43 (t, J=9.5 Hz, 1H), 7.27 (dd, J=7.6, 4.8 Hz, 1H), 3.19-3.11 (m, 3H), 2.17 (s, 3H), 2.04 (d, J=11.0 Hz, 1H), 1.96-1.78 (m, 3H), 1.25 (d, J=12.4 Hz, 1H), 1.01 (t, J=7.4 Hz, 3H), 0.92 (s, 3H).

Example 368 1-Methyl-N-(6-methyl-5-((3-(2-(((3S,5R)-5-methylpiperidin-3-yl)amino)pyrimidin-4-yl)pyridin-2-yl)oxy)naphthalen-1-yl)cyclopropanecarboxamide 368

Step 1: (3R,5S)-Benzyl 3-methyl-5-((4-(2-((2-methyl-5-(1-methylcyclopropanecarboxamido)naphthalen-1-yl)oxy)pyridin-3-yl)pyrimidin-2-yl)amino)piperidine-1-carboxylate

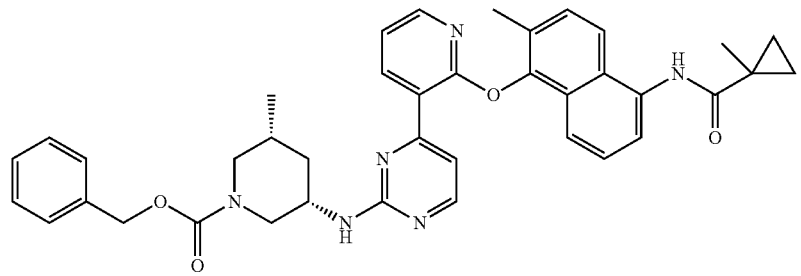 [SMILES: Cc1ccc2c(NC(=O)C3(C)CC3)cccc2c1Oc1ncccc1-c1ccnc(N[C@H]2C[C@@H](C)CN(C(=O)OCc3ccccc3)C2)n1]

Prepared using (3S,5R)-benzyl 3-((4-(2-((5-amino-2-methylnaphthalen-1-yl)oxy)pyridin-3-yl)pyrimidin-2-yl)amino)-5-methylpiperidine-1-carboxylate (60 mg, 0.10 mmol), DCM (0.5 mL), pyridine (0.12 mL, 1.5 mmol), and a solution of 1-methylcyclopropanecarbonyl chloride in DCM (prepared in situ from 1-methylcyclopropanecarboxylic acid (29 mg, 0.29 mmol) diluted in DCM (0.5 mL), cooled to 0° C. followed by addition of oxalyl chloride (0.024 mL, 0.270 mmol), and 2 drops of DMF and stirring for 30 min). After 16 hours, another portion of 1-methylcyclopropanecarbonyl chloride solution in DCM (prepared in situ from 1-methylcyclopropanecarboxylic acid (29 mg, 0.29 mmol) diluted in DCM (0.5 mL), cooled to 0° C. followed by addition of oxalyl chloride (0.024 mL, 0.270 mmol), and 2 drops of DMF and stirring for 30 min) was added and the mixture stirred for 24 h, then diluted with DCM, and a solution of saturated sodium bicarbonate was added and the phases were separated. The aqueous phase was extracted with ethyl acetate, and the combined organic extracts were dried (Na₂SO₄), filtered and was concentrated in vacuo. The crude product was purified by flash chromatography through silica gel (0-45% EtOAc/DCM) to provide 35 mg (54% yield) of the title compound. LCMS (ESI) [M+H]⁺=657.4, rt=1.96 min.

Step 2: 1-Methyl-N-(6-methyl-5-((3-(2-(((3S,5R)-5-methylpiperidin-3-yl)amino)pyrimidin-4-yl)pyridin-2-yl)oxy)naphthalen-1-yl)cyclopropanecarboxamide

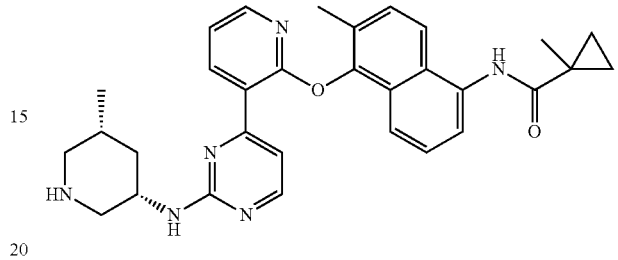

Prepared using (3R,5S)-benzyl 3-methyl-5-((4-(2-((2-methyl-5-(1-methylcyclopropanecarboxamido)naphthalen-1-yl)oxy)pyridin-3-yl)pyrimidin-2-yl)amino)piperidine-1-carboxylate (35 mg, 0.050 mmol), isopropanol (1 mL), palladium (10% on charcoal, 35 mg, 0.033 mmol), and ammonium formate (101 mg, 1.6 mmol). The reaction was stirred at 60° C. for 30 min, filtered through Celite and the filter cake was washed with EtOAc and MeOH. The filtrate was concentrated in vacuo and diluted with water (10 mL), a solution of saturated aqueous sodium bicarbonate (2 mL), and EtOAc (20 mL) were added. The phases were separated and the aqueous phase was extracted with EtOAc (2×10 mL). The combined organic extracts were dried (MgSO₄), filtered, and concentrated in vacuo. The residue was dissolved in 1,4-dioxane (1 mL) and HCl (4 M in dioxane, 0.2 mL, 0.8 mmol) was added to precipitate the product. MTBE (10 mL) was added and the solids collected by filtration and dissolved in H₂O and MeCN and lyophilized to provide 20 mg (72% yield) of 368. LCMS (ESI) [M+H]⁺=523.5, rt=1.38 min; ¹H NMR (400 MHz, dmso) δ 9.48 (s, 1H), 8.85 (s, 2H), 8.46 (d, J=5.2 Hz, 1H), 8.04 (dd, J=4.8, 2.0 Hz, 1H), 7.70 (d, J=8.8 Hz, 1H), 7.50 (dd, J=13.1, 8.2 Hz, 4H), 7.41-7.34 (m, 2H), 7.25 (dd, J=7.6, 4.8 Hz, 1H), 3.21 (s, 1H), 2.20 (s, 3H), 2.03 (s, 1H), 1.98-1.81 (m, 1H), 1.51 (s, 3H), 1.26 (d, J=12.3 Hz, 1H), 1.13 (d, J=2.7 Hz, 2H), 0.92 (d, J=6.5 Hz, 3H), 0.68 (d, J=2.8 Hz, 2H).

Example 369 N-(2-Fluoro-6-methyl-5-((3-(2-(((3S,5R)-5-methylpiperidin-3-yl)amino)pyrimidin-4-yl)pyridin-2-yl)oxy)naphthalen-1-yl)-2-methylpropane-1-sulfonamide 369

Step 1: (3S,5R)-Benzyl 3-((4-(2-((6-fluoro-2-methyl-5-(2-methylpropylsulfonamido)naphthalen-1-yl)oxy)pyridin-3-yl)pyrimidin-2-yl)amino)-5-methylpiperidine-1-carboxylate

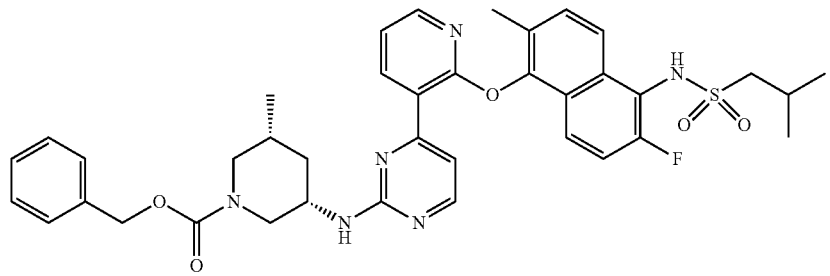 [SMILES: Cc1ccc2c(NS(=O)(=O)CC(C)C)c(F)ccc2c1Oc1ncccc1-c1ccnc(N[C@H]2C[C@@H](C)CN(C(=O)OCc3ccccc3)C2)n1]

Prepared using (3S,5R)-benzyl 3-((4-(2-((5-amino-6-fluoro-2-methylNaphthalen-1-yl)oxy)pyridin-3-yl)pyrimidin-2-yl)amino)-5-methylpiperidine-1-carboxylate (50 mg, 0.080 mmol), 1,2-dichloroethane (1 mL), pyridine (0.1 mL, 1.3 mmol), DMAP (1 mg, 0.01 mmol) and 2-methylpropane-1-sulfonyl chloride (66 mg, 0.42 mmol). After 5 days, the mixture was concentrated in vacuo and was purified directly by preparative thin layer chromatography on silica gel (66% MTBE/hexanes, MeOH used to remove the product from the silica) to provide 32 mg (53% yield) of the title compound. LCMS (ESI) [M+H]$^+$=713.7, rt=2.05 min.

Step 2: 1-N-(2-Fluoro-6-methyl-5-((3-(2-(((3S,5R)-5-methylpiperidin-3-yl)amino)pyrimidin-4-yl)pyridin-2-yl)oxy)naphthalen-1-yl)-2-methylpropane-1-sulfonamide

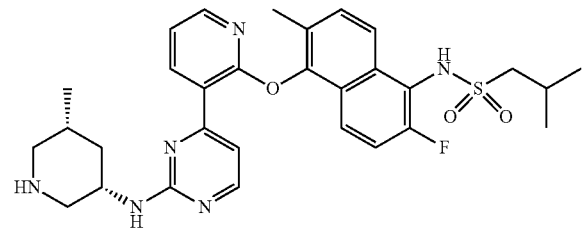 [SMILES: Cc1ccc2c(NS(=O)(=O)CC(C)C)c(F)ccc2c1Oc1ncccc1-c1ccnc(N[C@@H]2CNC[C@H](C)C2)n1]

Prepared using (3S,5R)-benzyl 3-((4-(2-((6-fluoro-2-methyl-5-(2-methylpropylsulfonamido)naphthalen-1-yl)oxy)pyridin-3-yl)pyrimidin-2-yl)amino)-5-methylpiperidine-1-carboxylate (32 mg, 0.040 mmol), isopropanol (0.5 mL), palladium (10% on charcoal, 30 mg, 0.028 mmol), and ammonium formate (85 mg, 1.3 mmol). The reaction was stirred at 60° C. for 60 min, filtered through Celite and the filter cake was washed with EtOAc and MeOH. The filtrate was concentrated in vacuo and diluted with water (10 mL), a solution of saturated aqueous sodium bicarbonate (2 mL) and EtOAc (20 mL) were added. The phases were separated and the aqueous phase was extracted with EtOAc (2×10 mL). The combined organic extracts were dried (MgSO$_4$), filtered and concentrated in vacuo. The residue thus obtained was dissolved in 1,4-dioxane (1 mL) and HCl (4 M in dioxane, 0.2 mL, 0.8 mmol) was added to precipitate the product. MTBE (10 mL) was added and the solids collected by filtration and dissolved in H$_2$O and MeCN and lyophilized to provide 20 mg (77% yield) of 369. LCMS (ESI) [M+H]$^+$=579.5, rt=1.46 min; $^1$H NMR (400 MHz, DMSO-d$_6$) δ 9.69 (s, 1H), 9.17-8.91 (m, 2H), 8.80-8.61 (m, 1H), 8.47 (d, J=5.2 Hz, 1H), 8.14-8.01 (m, 2H), 7.71 (dd, J=9.2, 5.1, 1H), 7.63 (d, J=8.8 Hz, 1H), 7.59-7.51 (m, 2H), 7.46 (t, J=9.4 Hz, 1H), 7.29 (dd, J=7.5, 4.8 Hz, 1H), 4.39-4.19 (m, 1H), 2.19 (s, 3H), 2.06 (d, J=12.6 Hz, 1H), 2.01-1.89 (m, 1H), 1.35-1.20 (m, 1H), 1.07 (d, J=6.7 Hz, 6H), 0.92 (d, J=5.2 Hz, 3H).

Example 370 (S)—N-(2-Chloro-6-methyl-5-((3-(2-(piperidin-3-ylamino)pyrimidin-4-yl)pyridin-2-yl)oxy)naphthalen-1-yl)propane-1-sulfonamide Step 1: (S)-tert-Butyl 3-((4-(2-((5-amino-6-chloro-2-methylnaphthalen-1-yl)oxy)pyridin-3-yl)pyrimidin-2-yl)amino)piperidine-1-carboxylate

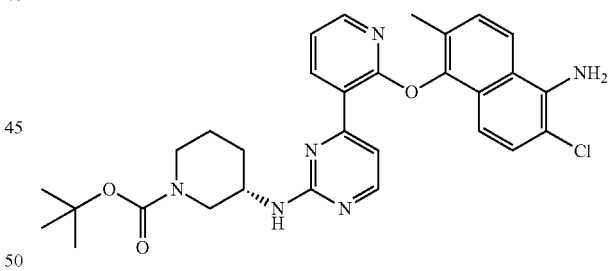

Copper (I) oxide (71 mg, 0.50 mmol) and L-proline (114 mg, 0.99 mmol) were suspended in ethanol (1 mL), whereto (S)-tert-butyl 3-((4-(2-((5-amino-6-bromo-2-methylnaphthalen-1-yl)oxy)pyridin-3-yl)pyrimidin-2-yl)amino)piperidine-1-carboxylate (100 mg, 0.170 mmol), and tetramethylammonium chloride (181 mg, 1.65 mmol) where added and the mixture placed in a 110° C. bath in a sealed tube. After 4 h, the reaction mixture was diluted with ethyl acetate (20 mL) and water (5 mL). The mixture was filtered through Celite and the phases were separated. silica gel was added to the organic extract and the solvent was removed in vacuo. The crude product on silica gel was purified by flash chromatography through silica gel (0-100% EtOAc/hexanes) to provide 43 mg (46% yield) of the title compound. LCMS (ESI) [M+H]$^+$=561.1, rt=1.98 min.

Step 2: (S)-tert-Butyl 3-((4-(2-((6-chloro-2-methyl-5-(propylsulfonamido)naphthalen-1-yl)oxy)pyridin-3-yl)pyrimidin-2-yl)amino)piperidine-1-carboxylate

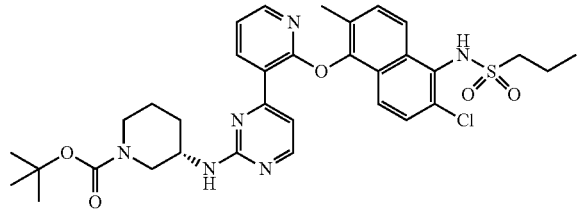

Prepared using (S)-tert-butyl 3-((4-(2-((5-amino-6-chloro-2-methylnaphthalen-1-yl)oxy)pyridin-3-yl)pyrimidin-2-yl)amino)piperidine-1-carboxylate (30 mg, 0.050 mmol), 1,2-dichloroethane (0.5 mL), pyridine (0.06 mL, 0.8 mmol), DMAP (0.7 mg, 0.01 mmol) and 1-propanesulfonyl chloride (30 mg, 0.21 mmol). After 5 days, the mixture was concentrated in vacuo and was purified directly by preparative thin layer chromatography on silica gel (66% MTBE/hexanes, MeOH used to remove the product from the silica) to provide 12 mg (34% yield) of the title compound. LCMS (ESI) [M+H]$^+$=667.6, rt=1.97 min.

Step 3: (S)—N-(2-Chloro-6-methyl-5-((3-(2-(piperidin-3-ylamino)pyrimidin-4-yl)pyridin-2-yl)oxy)naphthalen-1-yl)propane-1-sulfonamide

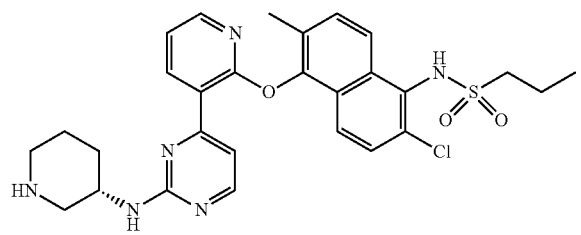 [SMILES: CCCS(=O)(=O)Nc1c(Cl)ccc2c(Oc3ncccc3-c3ccnc(N[C@H]4CCCNC4)n3)c(C)ccc12]

Prepared using (S)-tert-butyl 3-((4-(2-((6-chloro-2-methyl-5-(propylsulfonamido)naphthalen-1-yl)oxy)pyridin-3-yl)pyrimidin-2-yl)amino)piperidine-1-carboxylate (12 mg, 0.020 mmol), 1,4-dioxane (0.5 mL), and hydrochloric acid (4 M in dioxane, 1 mL, 4 mmol). After 16 h, the mixture was diluted with MTBE, the solids were collected by filtration then dissolved in H$_2$O and MeCN and lyophilized to provide 6.5 mg (60% yield) of 370. LCMS (ESI) [M+H]$^+$=567.5, rt=1.40 min; $^1$H NMR (400 MHz, DMSO-d$_6$) δ 9.76 (s, 1H), 8.82-8.58 (m, 3H), 8.46 (d, J=5.2 Hz, 1H), 8.14-8.04 (m, 2H), 7.63 (t, J=8.2 Hz, 2H), 7.52 (dd, J=18.0, 8.3 Hz, 2H), 7.28 (dd, J=7.6, 4.8 Hz, 1H), 3.28-3.23 (m, 3H), 2.90-2.80 (m, 1H), 2.18 (s, 3H), 1.88 (s, 4H), 1.75-1.58 (m, 2H), 1.02 (t, J=7.4 Hz, 3H).

Example 371 (S)-4-(2-((6-Fluoro-2-methyl-5-(((2-methylthiazol-4-yl)methyl)amino)naphthalen-1-yl)oxy)pyridin-3-yl)-N-(piperidin-3-yl)pyrimidin-2-amine 371

Step 1: (S)-tert-Butyl 3-((4-(2-((6-fluoro-2-methyl-5-(((2-methylthiazol-4-yl)methyl)amino)naphthalen-1-yl)oxy)pyridin-3-yl)pyrimidin-2-yl)amino)piperidine-1-carboxylate

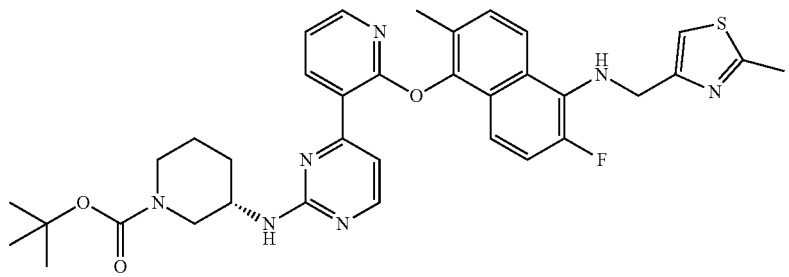 [SMILES: Cc1nc(CNc2c(F)ccc3c(Oc4ncccc4-c4ccnc(N[C@H]5CCCN(C(=O)OC(C)(C)C)C5)n4)c(C)ccc23)cs1]

Prepared using (S)-tert-butyl 3-((4-(2-((5-amino-6-fluoro-2-methylnaphthalen-1-yl)oxy)pyridin-3-yl)pyrimidin-2-yl)amino)piperidine-1-carboxylate from Example 275 (65 mg, 0.12 mmol), cesium carbonate (130 mg, 0.40 mmol), 4-(chloromethyl)-2-methyl-thiazole (26 mg, 0.14 mmol) and DMF (0.9 mL) and the mixture stirred at 50° C. After 16 h, tetrabutylammonium iodide (4.4 mg, 0.010 mmol) was then added and continued stirring at 50° C. After 24 h, further portions of 4-(chloromethyl)-2-methyl-thiazole (26 mg, 0.14 mmol) and cesium carbonate (130 mg, 0.400 mmol) were added and continued stirring at 50° C. After 72 h, the mixture was cooled to room temperature and was dissolved in EtOAc and water. The phases were separated and the organic phase was washed with water, then brine, and then a solution of aqueous saturated ammonium chloride. The organic phase was dried (MgSO$_4$), filtered and concentrated in vacuo. The crude product thus obtained was purified by flash chromatography through silica gel (0-100% EtOAc/DCM) to provide 19 mg (24% yield) of the title compound as a pale yellow oil. LCMS (ESI) [M+H]$^+$=656.3, rt=2.01 min.

Step 2: (S)-4-(2-((6-Fluoro-2-methyl-5-(((2-methyl-thiazol-4-yl)methyl)amino)naphthalen-1-yl)oxy)pyridin-3-yl)-N-(piperidin-3-yl)pyrimidin-2-amine

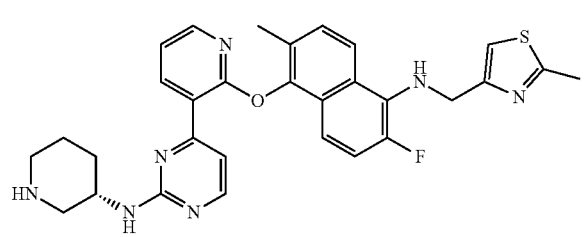 [SMILES: Cc1nc(CNc2c(F)ccc3c(Oc4ncccc4-c4ccnc(N[C@H]5CCCNC5)n4)c(C)ccc23)cs1]

Prepared using (S)-tert-butyl 3-((4-(2-((6-fluoro-2-methyl-5-(((2-methylthiazol-4-yl)methyl)amino)naphthalen-1-yl)oxy)pyridin-3-yl)pyrimidin-2-yl)amino)piperidine-1-carboxylate (18 mg, 0.030 mmol), EtOAc (1 mL), and hydrochloric acid (4 M in dioxane, 0.6 mL, 2.4 mmol). After 15 min, the resulting solids were collected by filtration, washed with DCM and then dissolved in H₂O and lyophilized to provide 15 mg (92% yield) of 371 as an orange solid. LCMS (ESI) [M+H]⁺=556.2, rt=1.42 min; ¹H NMR (400 MHz, dmso) [NH peak under the HOD signal] δ 9.27 (br s, 1H), 9.07 (s, 1H), 8.74 (br s, 1H), 8.46 (d, J=5.3 Hz, 1H), 8.13 (d, J=8.8 Hz, 1H), 8.05 (dd, J=4.6, 1.6 Hz, 1H), 7.74 (br s, 1H), 7.59 (s, 1H), 7.44 (d, J=8.8 Hz, 1H), 7.24 (dd, J=7.6, 4.8 Hz, 1H), 7.21-7.11 (m, 2H), 7.01 (dd, J=9.2, 4.5 Hz, 1H), 4.60 (s, 2H), 4.32 (s, 1H), 3.40 (d, J=9.7 Hz, 1H), 3.17 (d, J=12.3 Hz, 1H), 2.90-2.72 (m, 2H), 2.61 (s, 3H), 2.15 (s, 3H), 1.99 (d, J=9.0 Hz, 1H), 1.89 (d, J=14.2 Hz, 1H), 1.75 (q, J=11.7 Hz, 1H), 1.61 (q, J=10.8 Hz, 1H).

Example 372 (1S)-2-Methyl-N-(6-methyl-5-((3-(2-(((S)-piperidin-3-yl)amino)pyrimidin-4-yl)pyridin-2-yl)oxy)naphthalen-1-yl)cyclopentane-1-carboxamide 372

Step 1: 2-Methyl-N-(6-methyl-5-((3-(2-(methylthio)pyrimidin-4-yl)pyridin-2-yl)oxy)naphthalen-1-yl)cyclopentanecarboxamide

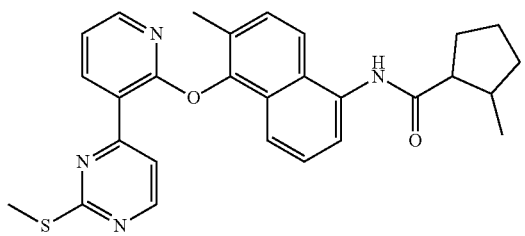 [SMILES: CSc1nccc(-c2cccnc2Oc2c(C)ccc3c(NC(=O)C4CCCC4C)cccc23)n1]

Prepared using 6-methyl-5-((3-(2-(methylthio)pyrimidin-4-yl)pyridin-2-yl)oxy)naphthalen-1-amine (260 mg, 0.690 mmol) and 2-methylcyclopentanecarboxylic acid (98 mg, 0.76 mmol), DMF (2 mL), HATU (317 mg, 0.830 mmol), and triethylamine (0.29 mL, 2.1 mmol) and the mixture was stirred at room temperature for 3 days. The mixture was diluted with EtOAc (75 mL) and washed with aqueous saturated sodium bicarbonate solution (10 mL) then with 50% brine (4×10 mL), and insoluble solids filtered off to provide 58 mg of the title compound as a white solid. The remaining organic extract was dried (Na₂SO₄), filtered and concentrated in vacuo. The crude was purified by flash chromatography through silica gel (0-100% EA/hexanes) to provide a further 90 mg of the title compound as a white solid. This material was combined with the solid previously obtained to provide 148 mg (44% yield) of the title compound as a white solid. LCMS (ESI) [M+H]⁺=485.1, rt=1.96 min.

Step 2: 2-Methyl-N-(6-methyl-5-((3-(2-(methylsulfinyl)pyrimidin-4-yl)pyridin-2-yl)oxy)naphthalen-1-yl)cyclopentanecarboxamide

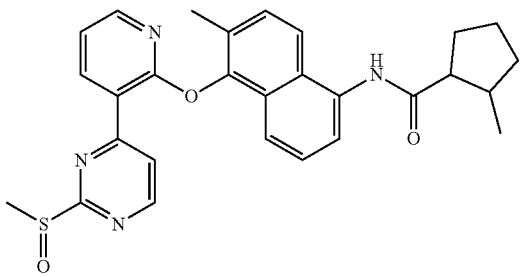 [SMILES: Cc1ccc2c(NC(=O)C3CCCC3C)cccc2c1Oc1ncccc1-c1ccnc(S(C)=O)n1]

To a solution of 2-methyl-N-(6-methyl-5-((3-(2-(methylthio)pyrimidin-4-yl)pyridin-2-yl)oxy)naphthalen-1-yl)cyclopentanecarboxamide (148 mg, 0.310 mmol) in DCM (15 mL) was added 3-chloroperbenzoic acid (68 mg of ~78% pure reagent, 0.31 mmol) and the mixture stirred at room temperature. After 1 h, the mixture was diluted with DCM (75 mL), washed with aqueous saturated sodium bicarbonate solution (25 mL), dried (Na₂SO₄), filtered, and concentrated in vacuo to provide 74 mg (48% yield) of the title compound as an orange wax. LCMS (ESI) [M+H]⁺=501.2, rt=1.56 min.

Step 3: (3S)-tert-Butyl 3-((4-(2-((2-methyl-5-(2-methylcyclopentanecarboxamido)naphthalen-1-yl)oxy)pyridin-3-yl)pyrimidin-2-yl)amino)piperidine-1-carboxylate

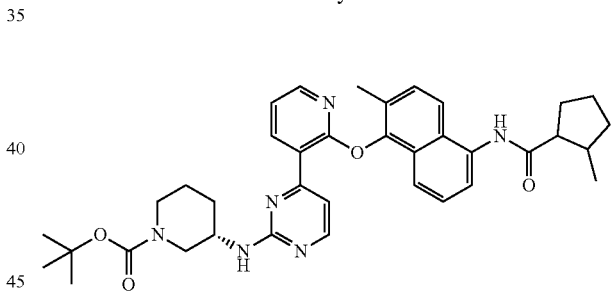

2-Methyl-N-(6-methyl-5-((3-(2-(methylsulfinyl)pyrimidin-4-yl)pyridin-2-yl)oxy)naphthalen-1-yl)cyclopentanecarboxamide (74 mg, 0.15 mmol) and (S)-(+)-3-amino-1-boc-piperidine (44 mg, 0.22 mmol) were combined in 1,4-dioxane (2 mL). Triethylamine (0.06 mL, 0.44 mmol) was then added and the mixture placed in a 120° C. oil bath sealed overnight. After 16 h, a further portion of (S)-(+)-3-amino-1-boc-piperidine (62 mg, 0.30 mmol) and triethylamine (0.1 mL, 0.75 mmol) were added in 1,4-dioxane (2 mL) and continued heating at 120° C. sealed. After 20 h, the mixture was cooled to room temperature, diluted with EtOAc (75 mL) and washed with aqueous saturated sodium bicarbonate solution (25 mL), H₂O (10 mL), brine (10 mL), dried (Na₂SO₄), filtered and concentrated in vacuo. The crude was purified by flash chromatography through silica gel (0-100% EtOAc/hexanes) to provide 80 mg (85% yield) of the title compound as a yellow solid. LCMS (ESI) [M+H]⁺=637.3, rt=2.01 min.

Step 4: tert-Butyl (3S)-3-((4-(2-((2-methyl-5-((1S)-2-methylcyclopentane-1-carboxamido)naphthalen-1-yl)oxy)pyridin-3-yl)pyrimidin-2-yl)amino)piperidine-1-carboxylate (Isomer-1) and tert-butyl (3S)-3-((4-(2-((2-methyl-5-((1R)-2-methylcyclopentane-1-carboxamido)naphthalen-1-yl)oxy)pyridin-3-yl)pyrimidin-2-yl)amino)piperidine-1-carboxylate (Isomer-2)

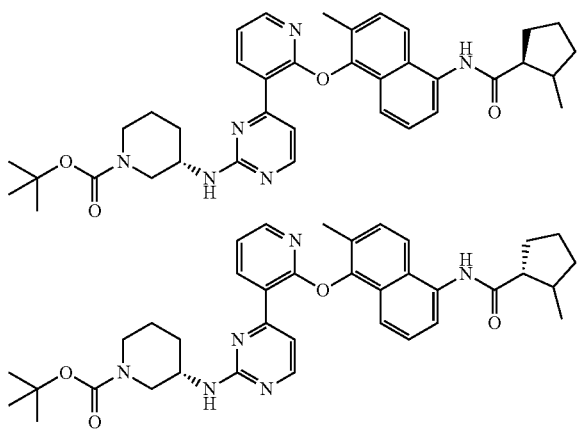

The mixture of stereoisomers from Step 3 (80 mg, 0.13 mmol) was subjected to chiral normal phase semi-prep purification (Conditions: Chiralpak IB, 5 uM, 20×250 mm, 2:12:86 EtOH:DCM:Hexane+0.1% ethylenediamine, 2 mg/inj.) to provide two stereoisomers enantiomeric with respect to the cyclopentane ring: (isomer-1), 74 mg (92% yield, contains residual ethylenediamine), ee=>99%, rt=11.4 min, (ESI) [M+H]$^+$=637.4, rt=2.01 min; (isomer-2), 57 mg (71% yield, contains residual ethylenediamine), ee=>95%, rt=12.5 min, MS (ESI) [M+H]$^+$=637.4, rt=2.01 min.

Step 5: (1S)-2-Methyl-N-(6-methyl-5-((3-(2-(((S)-piperidin-3-yl)amino)pyrimidin-4-yl)pyridin-2-yl)oxy)naphthalen-1-yl)cyclopentane-1-carboxamide (Isomer-1)

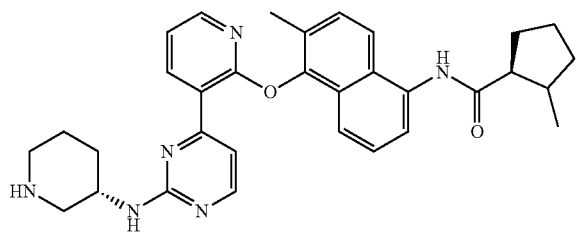

Prepared using (3S)-tert-butyl 3-((4-(2-((2-methyl-5-(2-methylcyclopentanecarboxamido)naphthalen-1-yl)oxy)pyridin-3-yl)pyrimidin-2-yl)amino)piperidine-1-carboxylate (isomer-1) (74 mg, 0.12 mmol), EtOAc (3 mL), and hydrochloric acid (4 M in dioxane, 1 mL, 4 mmol). After 18 h, the mixture was concentrated in vacuo and the crude solid was washed with EtOAc (3×3 mL) then with MeCN (3×3 mL). The solid product was then sonicated and concentrated in vacuo with MeCN (3×3 mL) then dissolved in H$_2$O and MeCN and lyophilized. The product obtained was purified by C18 reverse phase flash chromatography (20-100% MeCN/pH=3.8, 10 mM aqueous ammonium formate). The appropriate fractions were combined and lyophilized, then dissolved in ethyl acetate (2 mL) and hydrochloric acid (4 M in dioxane, 1 mL, 4 mmol) was added. After 20 min the volatiles were removed under an air stream and the residue was washed ethyl acetate (3×3 mL) then MeCN (3×3 mL). The residue was then sonicated and concentrated in vacuo with MeCN (3×3 mL) and the resulting solid dissolved in water and MeCN and lyophilized to provide 8 mg (12% yield) of 372 as a mix of diastereomers, and as a fluffy white solid. The stereochemical assignments of 372 and 373 were randomly assigned and may be later determined. LCMS (ESI) [M+H]$^+$=537.2, rt=1.45 min; $^1$H NMR (400 MHz, DMSO-d$_6$) δ 9.94 (s, 1H), 8.91-8.71 (m, 2H), 8.68-8.54 (m, 1H), 8.48 (d, J=5.2 Hz, 1H), 8.05 (d, J=4.6 Hz, 1H), 7.89 (d, J=8.7 Hz, 1H), 7.69-7.46 (m, 5H), 7.45-7.36 (m, 1H), 7.27 (dd, J=7.5, 4.8 Hz, 1H), 4.37-4.18 (m, 1H), 3.29-3.13 (m, 2H), 2.97-2.77 (m, 2H), 2.21 (s, 3H), 2.20-2.11 (m, 1H), 2.07-1.98 (m, 2H), 1.97-1.79 (m, 3H), 1.78-1.56 (m, 4H), 1.32-1.20 (m, 2H), 1.12 (d, J=6.5 Hz, 3H).

Example 373 (1R)-2-Methyl-N-(6-methyl-5-((3-(2-(((S)-piperidin-3-yl)amino)pyrimidin-4-yl)pyridin-2-yl)oxy)naphthalen-1-yl)cyclopentane-1-carboxamide 373

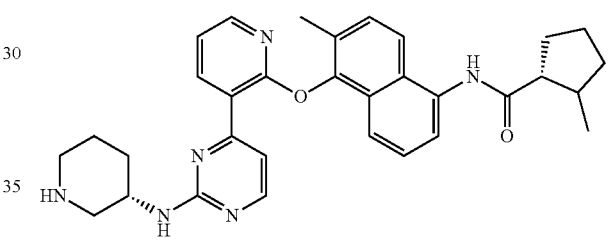

Prepared according to Example 372 using (3S)-tert-butyl 3-((4-(2-((2-methyl-5-(2-methylcyclopentanecarboxamido)naphthalen-1-yl)oxy)pyridin-3-yl)pyrimidin-2-yl)amino)piperidine-1-carboxylate (isomer-2) (57 mg, 0.090 mmol), EtOAc (3 mL), and hydrochloric acid (4 M in dioxane, 1 mL, 4 mmol). After 18 h, the mixture was concentrated in vacuo and the crude solid was washed with EtOAc (3×3 mL) then with MeCN (3×3 mL). The solid product was then sonicated and concentrated in vacuo with MeCN (3×3 mL) then dissolved in H$_2$O and MeCN and lyophilized. The product obtained was purified by C18 reverse phase flash chromatography (20-100% MeCN/pH=3.8, 10 mM aqueous ammonium formate). The appropriate fractions were combined and lyophilized, then dissolved in ethyl acetate (2 mL) and hydrochloric acid (4 M in dioxane, 1 mL, 4 mmol) was added. After 20 min the volatiles were removed under an air stream and the residue was washed ethyl acetate (3×3 mL) then MeCN (3×3 mL). The residue was then sonicated and concentrated in vacuo with MeCN (3×3 mL) and the resulting solid was dissolved in water and MeCN and lyophilized to provide 10 mg (19% yield) of the title compound as a fluffy white solid. LCMS (ESI) [M+H]$^+$=537.2, rt=1.47 min; $^1$H NMR (400 MHz, dmso) δ 9.93 (s, 1H), 8.87-8.52 (m, 3H), 8.48 (d, J=5.2 Hz, 1H), 8.06 (d, J=1.7 Hz, 1H), 7.88 (d, J=8.7 Hz, 1H), 7.67-7.44 (m, 5H), 7.44-7.34 (m, 1H), 7.27 (dd, J=7.5, 4.8 Hz, 1H), 4.38-4.12 (m, 1H), 3.30-3.11 (m, 2H), 2.99-2.79 (m, 2H), 2.21 (s, 3H), 2.19-2.10 (m, 1H), 2.08-1.97 (m, 2H), 1.97-1.79 (m, 3H), 1.78-1.59 (m, 4H), 1.32-1.19 (m, 2H), 1.12 (d, J=6.5 Hz, 3H).

Example 374 N-(2-Fluoro-6-methyl-5-((3-(2-(((3S,5R)-5-methylpiperidin-3-yl)amino)pyrimidin-4-yl)oxy)naphthalen-1-yl)-3,3-dimethylbutanamide 374

Step 1: (3S,5R)-Benzyl 3-((4-(2-((5-(3,3-dimethylbutanamido)-6-fluoro-2-methylnaphthalen-1-yl)oxy)pyridin-3-yl)pyrimidin-2-yl)amino)-5-methylpiperidine-1-carboxylate

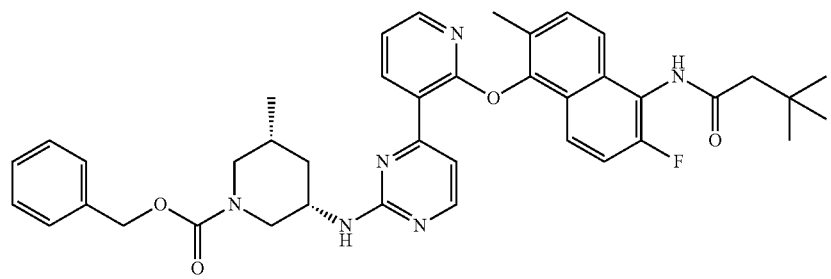 [SMILES: Cc1ccc2c(NC(=O)CC(C)(C)C)c(F)ccc2c1Oc1ncccc1-c1ccnc(N[C@H]2C[C@@H](C)CN(C(=O)OCc3ccccc3)C2)n1]

Prepared using (3S,5R)-benzyl 3-((4-(2-((5-amino-6-fluoro-2-methylNaphthalen-1-yl)oxy)pyridin-3-yl)pyrimidin-2-yl)amino)-5-methylpiperidine-1-carboxylate (50 mg, 0.080 mmol), DCM (2 mL), pyridine (1 mL) and tert-butylacetyl chloride (17 mg, 0.13 mmol). After 16 hours, a further portion of tert-butylacetyl chloride (34 mg, 0.26 mmol) was added. After a further 6 hours, a further portion of tert-butylacetyl chloride (34 mg, 0.26 mmol) was added. After 40 hours total the mixture was diluted with DCM (50 mL), washed with saturated NaHCO$_3$(aq) (10 mL), dried (Na$_2$SO$_4$), filtered and concentrated in vacuo to provide 60 mg (103% yield) of the title compound as an orange wax. LCMS (ESI) [M+H]$^+$=691.4, rt=2.04 min.

Step 2: N-(2-Fluoro-6-methyl-5-((3-(2-(((3S,5R)-5-methylpiperidin-3-yl)amino)pyrimidin-4-yl)pyridin-2-yl)oxy)naphthalen-1-yl)-3,3-dimethylbutanamide

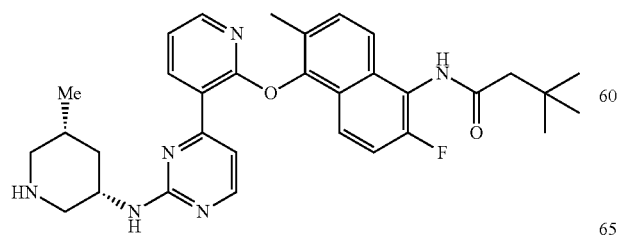

Prepared using (3S,5R)-benzyl 3-((4-(2-((5-(3,3-dimethylbutanamido)-6-fluoro-2-methylnaphthalen-1-yl)oxy)pyridin-3-yl)pyrimidin-2-yl)amino)-5-methylpiperidine-1-carboxylate (60 mg, 0.087 mmol), isopropanol (2 mL), palladium on charcoal (37 mg, 10% w/w wet, 0.035 mmol), and ammonium formate (329 mg, 5.21 mmol). The reaction vial was capped and placed in a 60° C. oil bath. After 2 h, the mixture was cooled to rt and purged with $N_2$ then filtered through celite using 40 mL MeOH to wash/elute and concentrated in vacuo. The residue obtained was re-subjected to the reaction conditions described above using 10% w/w Pd/C (60 mg, 0.057 mmol), isopropanol (1 mL), and ammonium formate (329 mg, 5.21 mmol). After 90 min, the mixture was cooled to room temperature and purged with nitrogen, then filtered through Celite using 40 mL MeOH to wash/elute and concentrated in vacuo. The crude material thus obtained was purified by C18 reverse phase flash column chromatography (20-100% MeCN/pH=3.8, 10 mM aqueous ammonium formate). Appropriate fractions were combined and treated with saturated $NaHCO_3$(aq) (50 mL) and the aqueous phase was extracted with EtOAc (2×50 mL). Organic extracts were combined, dried ($Na_2SO_4$), filtered, and concentrated in vacuo. The product thus obtained was dissolved in EtOAc (2 mL) and treated with hydrochloric acid (4M in 1,4-dioxanes, 1 mL, 4 mmol) and stirred 30 min at rt. Volatiles were then removed on a rotovap and the solid residue was washed with EtOAc (3×3 mL), then with MeCN (3×3 mL). The solids were then sonicated and concentrated in vacuo with MeCN (3×3 mL) and the resulting solid was dissolved in water and MeCN and lyophilized to provide 9 mg (17% yield) of 374 as a fluffy white solid. LCMS (ESI) $[M+H]^+$=557.3, rt=1.50 min; $^1$H NMR (400 MHz, DMSO-$d_6$) δ 9.79 (s, 1H), 8.88-8.56 (m, 3H), 8.47 (d, J=5.1 Hz, 1H), 8.07 (dd, J=4.7, 1.8 Hz, 1H), 7.78 (d, J=8.7 Hz, 1H), 7.64 (dd, J=9.2, 4.9 Hz, 1H), 7.61-7.49 (m, 3H), 7.40 (t, J=9.4 Hz, 1H), 7.28 (dd, J=7.5, 4.8 Hz, 1H), 4.38-4.12 (m, 1H), 3.23-3.12 (m, 2H), 2.62 (d, J=11.3 Hz, 1H), 2.36 (s, 2H), 2.19 (s, 3H), 2.07 (d, J=13.9 Hz, 1H), 2.01-1.83 (m, 1H), 1.28 (dd, J=23.6, 11.3 Hz, 2H), 1.11 (s, 9H), 0.94 (d, J=5.7 Hz, 3H).

Example 375 2,2,2-Trifluoro-N-(2-fluoro-6-methyl-5-((3-(2-(((3S,5R)-5-methylpiperidin-3-yl)amino)pyrimidin-4-yl)pyridin-2-yl)oxy)naphthalen-1-yl)ethanesulfonamide 375

Step 1: (3S,5R)-Benzyl 3-((4-(2-((6-fluoro-2-methyl-5-(2,2,2-trifluoroethylsulfonamido)naphthalen-1-yl)oxy)pyridin-3-yl)pyrimidin-2-yl)amino)-5-methylpiperidine-1-carboxylate

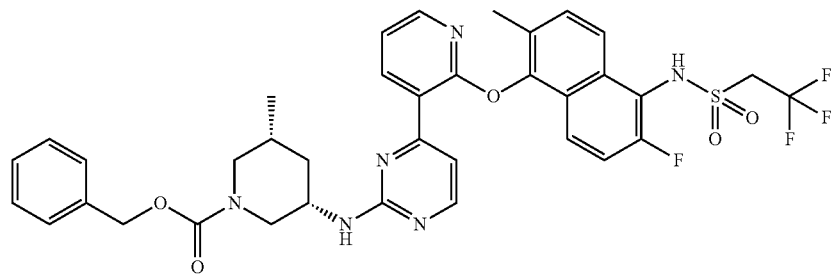 [SMILES: Cc1ccc2c(NS(=O)(=O)CC(F)(F)F)c(F)ccc2c1Oc1ncccc1-c1ccnc(N[C@H]2C[C@@H](C)CN(C(=O)OCc3ccccc3)C2)n1]

Prepared using (3S,5R)-benzyl 3-((4-(2-((5-amino-6-fluoro-2-methylnaphthalen-1-yl)oxy)pyridin-3-yl)pyrimidin-2-yl)amino)-5-methylpiperidine-1-carboxylate (59 mg, 0.10 mmol), DCM (1 mL), cooled to 0° C. and 2,2,2-trifluoroethylsulfonyl chloride (22 mg, 0.12 mmol) and pyridine (0.12 mL, 1.5 mmol) were added. After 60 minutes, the mixture was diluted with water and ethyl acetate and transferred to a separatory funnel. The phases were separated and the organic phase was washed with a solution of aqueous saturated sodium bicarbonate, then brine, then aqueous saturated ammonium chloride. The organic phase was dried ($MgSO_4$), filtered, and concentrated to dryness. The crude was purified by flash chromatography through silica gel (0-100% EtOAc/DCM) to provide 56 mg (76% yield) of the title compound as an off-white solid. LCMS (ESI) $[M+H]^+$=739.3, rt=1.98 min.

Step 2: 2,2,2-Trifluoro-N-(2-fluoro-6-methyl-5-((3-(2-(((3S,5R)-5-methylpiperidin-3-yl)amino)pyrimidin-4-yl)pyridin-2-yl)oxy)naphthalen-1-yl)ethanesulfonamide

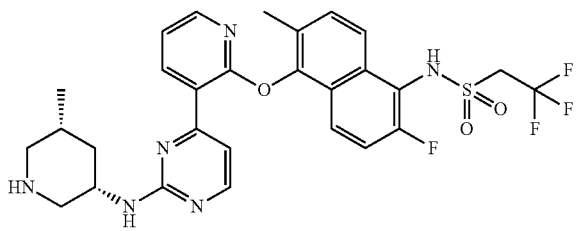

Prepared using (3S,5R)-benzyl 3-((4-(2-((6-fluoro-2-methyl-5-(2,2,2-trifluoroethylsulfonamido)naphthalen-1-yl)oxy)pyridin-3-yl)pyrimidin-2-yl)amino)-5-methylpiperidine-1-carboxylate (56 mg, 0.080 mmol), isopropanol (1 mL), ammonium formate (260 mg, 4.12 mmol), and palladium (10% on charcoal, 27 mg, 0.025 mmol). The reaction was stirred at 60° C. for 16 hours, filtered through Celite and the filter cake was washed with DCM and MeOH. The filtrate was concentrated in vacuo and the crude was purified by reverse phase prep HPLC-MS (14 min 40-60% MeCN/10 mM pH: 3.8 aqueous ammonium formate, XBridge BEH C18 OBD Prep Column, 130 Å, 5 μm, 30 mm×50 mm). Appropriate fractions were combined and MeCN was partially removed on the rotavap, the flask was frozen and lyophilized. The product obtained was dissolved in DCM and filtered, then treated with hydrochloric acid (4M in 1,4-dioxanes, 0.1 mL, 0.4 mmol) and the resulting solids collected by filtration, washed with DCM, dissolved in water and lyophilized to provide 18 mg (37% yield) of 375 as a white solid. LCMS (ESI) $[M+H]^+$=605.1, rt=1.46 min; $^1$H NMR (400 MHz, dmso) δ 10.43 (s, 1H), 8.97 (br s, 2H), 8.64

(br m, 1H), 8.47 (d, J=5.2 Hz, 1H), 8.07 (dd, J=4.8, 1.9 Hz, 1H), 8.02 (d, J=8.7 Hz, 1H), 7.76 (dd, J=9.3, 5.2 Hz, 1H), 7.65 (d, J=8.8 Hz, 1H), 7.55 (d, J=4.7 Hz, 1H), 7.52 (d, J=7.8 Hz, 1H), 7.48 (t, J=9.4 Hz, 1H), 7.29 (dd, J=7.6, 4.8 Hz, 1H), 4.57 (q, J=9.7 Hz, 2H), 4.27 (s, 1H), 3.53-3.47 (m, 1H), 3.20 (d, J=10.9 Hz, 1H), 2.61 (q, J=11.3 Hz, 1H), 2.45 (q, J=12.2 Hz, 1H), 2.20 (s, 3H), 2.06 (d, J=12.4 Hz, 1H), 1.95 (s, 1H), 1.27 (q, J=11.9 Hz, 1H), 0.93 (d, J=5.7 Hz, 3H).

Example 376 (S)—N-(2,6-Dimethyl-5-((3-(2-(piperidin-3-ylamino)pyrimidin-4-yl)pyridin-2-yl)oxy)naphthalen-1-yl)-2-methylpropane-1-sulfonamide 376

Step 1 (S)-tert-Butyl 3-((4-(2-((2,6-dimethyl-5-(2-methylpropylsulfonamido)naphthalen-1-yl)oxy)pyridin-3-yl)pyrimidin-2-yl)amino)piperidine-1-carboxylate

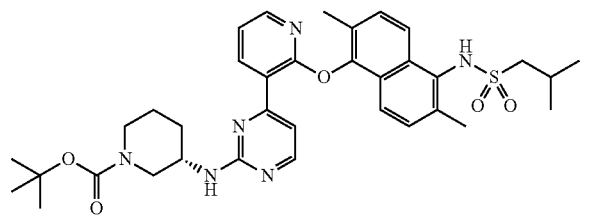 [SMILES: Cc1ccc2c(Oc3ncccc3-c3ccnc(N[C@H]4CCCN(C(=O)OC(C)(C)C)C4)n3)c(C)ccc2c1NS(=O)(=O)CC(C)C]

Prepared using tert-butyl (3S)-3-[[4-[2-[(5-amino-2,6-dimethyl-1-naphthyl)oxy]-3-pyridyl]pyrimidin-2-yl]amino]piperidine-1-carboxylate (90 mg, 0.17 mmol), 2-methylpropane-1-sulfonyl chloride (43 µL, 0.33 mmol), pyridine (202 µL, 2.5 mmol), 4-dimethylaminopyridine (2 mg, 0.02 mmol) and DCM (0.83 mL). After 16 h, a further portion of 2-methylpropane-1-sulfonyl chloride (22 µL, 0.16 mmol) was added. After 20 h at rt, the mixture was diluted with DCM, washed with saturated NaHCO₃(aq), then brine, dried (Na₂SO₄), filtered and concentrated. The crude product was purified by flash chromatography through silica gel (0-60% EtOAc/DCM) to provide 40 mg (36% yield) of the title compound. LCMS (ESI) [M+H]⁺=661.6, rt=2.00 min.

Step 2: (S)—N-(2,6-Dimethyl-5-((3-(2-(piperidin-3-ylamino)pyrimidin-4-yl)pyridin-2-yl)oxy)naphthalen-1-yl)-2-methylpropane-1-sulfonamide

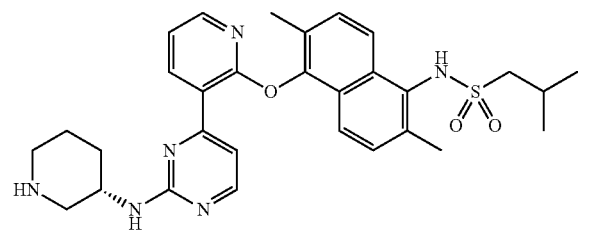

Prepared using tert-butyl (3S)-3-[[4-[2-[[5-(isobutylsulfonylamino)-2,6-dimethyl-1-naphthyl]oxy]-3-pyridyl]pyrimidin-2-yl]amino]piperidine-1-carboxylate (39 mg, 0.06 mmol), 1,4-dioxane (0.5 mL) and hydrochloric acid (4N in dioxane, 0.47 mL, 1.9 mmol). The reaction mixture is stirred at rt for 40 min then diluted with Et₂O and the resulting solids collected by filtration and washed with Et₂O. The solids were then dissolved in water and MeCN and lyophilized to provide 30 mg, (86% yield) of 376. LCMS (ESI) [M+H]⁺=561.8, rt=1.45 min; ¹H NMR (400 MHz, d6-dmso) δ 9.39 (s, 1H), 8.89 (bs, 2H), 8.64 (bs, 1H), 8.47 (d, J=5.2 Hz, 1H), 8.15-8.00 (m, 2H), 7.66-7.47 (m, 4H), 7.35 (d, J=8.8 Hz, 1H), 7.27 (dd, J=7.6, 4.8 Hz, 1H), 4.27 (s, 1H), 3.21 (d, J=12.0 Hz, 1H), 3.11 (d, J=6.4 Hz, 2H), 2.96-2.74 (m, 2H), 2.48 (s, 3H), 2.32-2.20 (m, 1H), 2.19 (s, 3H), 2.08-1.85 (m, 2H), 1.84-1.53 (m, 2H), 1.07 (d, J=6.7 Hz, 6H).

Example 377 (S)-1,1,1-Trifluoro-3-((2-fluoro-6-methyl-5-((3-(2-((S)-piperidin-3-ylamino)pyrimidin-4-yl)pyridin-2-yl)oxy)naphthalen-1-yl)amino)propan-2-ol 377

Step 1: (S)-tert-Butyl 3-((4-(2-((6-fluoro-2-methyl-5-(((S)-3,3,3-trifluoro-2-hydroxypropyl)amino)naphthalen-1-yl)oxy)pyridin-3-yl)pyrimidin-2-yl)amino)piperidine-1-carboxylate

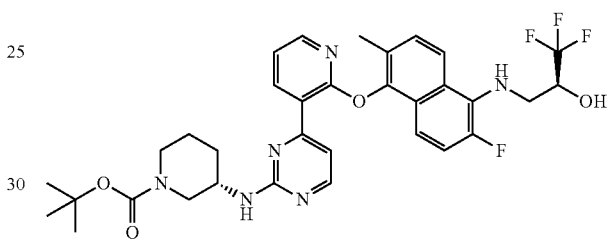

Prepared according to General Procedure F using tert-butyl (3S)-3-[[4-[2-[(5-amino-6-fluoro-2-methyl-1-naphthyl)oxy]-3-pyridyl]pyrimidin-2-yl]amino]piperidine-1-carboxylate (75 mg, 0.14 mmol), acetic acid (0.5 mL) and (2S)-2-(trifluoromethyl)oxirane (77 mg, 0.69 mmol). The reaction was capped in a microwave vial and heated at 70° C. for 3 h. The reaction was then diluted with MeOH and the volatiles were removed in vacuo. The obtained residue was purified by prep HPLC-MS (14 min 50-70% MeCN/10 mM pH: 3.8 NH₄CO₂H(aq), XBridge BEH C18 OBD Prep Column, 130 Å, 5 µm, 30 mm×50 mm). Appropriate fractions were combined and lyophilized to provide 37 mg (41% yield) of the title compound. LCMS (ESI) [M+H]⁺=657.4, rt=2.02 min.

Step 2: (S)-1,1,1-Trifluoro-3-((2-fluoro-6-methyl-5-((3-(2-((S)-piperidin-3-ylamino)pyrimidin-4-yl)pyridin-2-yl)oxy)naphthalen-1-yl)amino)propan-2-ol

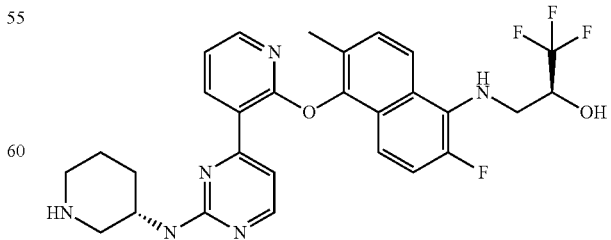

Prepared according to General Procedure B using (S)-tert-butyl 3-((4-(2-((6-fluoro-2-methyl-5-(((S)-3,3,3-trifluoro-2-hydroxypropyl)amino)naphthalen-1-yl)oxy)pyridin-3-yl)pyrimidin-2-yl)amino)piperidine-1-carboxylate (37 mg, 0.06 mmol), 1,4-dioxane (0.5 mL) and hydrochloric acid (4 N in dioxane, 0.5 mL, 2 mmol). The suspension was stirred at rt for 1 h then MTBE (5 mL) was added and the precipitate was filtered, rinsed with MTBE and then dissolved in water and MeCN and lyophilized to provide 29 mg (87% yield) of 377. LCMS (ESI) [M+H]⁺=557.5, rt=1.45 min. ¹H NMR (400 MHz, D₂O) δ 8.44 (s, 1H), 8.18 (d, J=5.8 Hz, 1H), 7.86 (d, J=8.0 Hz, 2H), 7.67 (s, 1H), 7.43 (d, J=8.8 Hz, 1H), 7.32 (dd, J=9.3, 4.9 Hz, 1H), 7.20-7.14 (m, 1H), 7.09 (t, J=10.1 Hz, 1H), 4.31 (s, 1H), 4.06 (s, 1H), 3.60 (d, J=14.1 Hz, 1H), 3.46 (d, J=11.4 Hz, 1H), 3.33 (dd, J=14.0, 9.8 Hz, 1H), 3.22 (d, J=12.2 Hz, 1H), 2.07 (s, 3H), 1.91 (s, 1H), 1.78-1.53 (m, 2H).

Example 378 N-(2-Fluoro-6-methyl-5-((3-(2-(((3S,5R)-5-methylpiperidin-3-yl)amino)pyrimidin-4-yl)pyridin-2-yl)oxy)naphthalen-1-yl)-1-phenylmethanesulfonamide 378

Step 1: (3S,5R)-Benzyl 3-((4-(2-((6-fluoro-2-methyl-5-(phenylmethylsulfonamido)naphthalen-1-yl)oxy)pyridin-3-yl)pyrimidin-2-yl)amino)-5-methylpiperidine-1-carboxylate

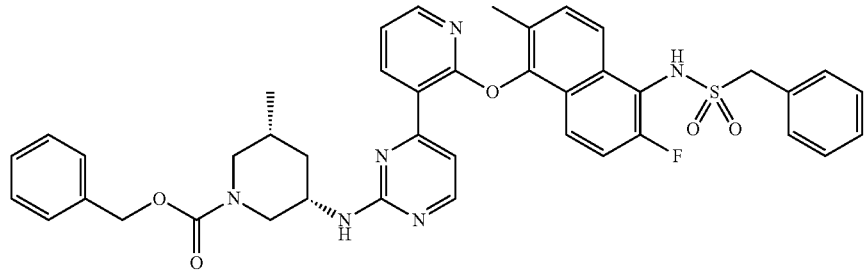 [SMILES: Cc1ccc2c(NS(=O)(=O)Cc3ccccc3)c(F)ccc2c1Oc1ncccc1-c1ccnc(N[C@H]2C[C@@H](C)CN(C(=O)OCc3ccccc3)C2)n1]

Prepared using (3S,5R)-benzyl 3-((4-(2-((5-amino-6-fluoro-2-methylnaphthalen-1-yl)oxy)pyridin-3-yl)pyrimidin-2-yl)amino)-5-methylpiperidine-1-carboxylate (520 mg, 0.877 mmol), pyridine (1 mL), DCM (5 mL), and phenylmethanesulfonyl chloride (251 mg, 1.31 mmol). After 5 h, the mixture was concentrated in vacuo. The crude reaction mixture was then purified by flash column chromatography through silica gel (0-40% MTBE/DCM) to provide 375 mg (57% yield) of the title compound as a yellow foam. LCMS (ESI) [M+H]⁺=747.5, rt=2.07 min.

Step 2: N-(2-Fluoro-6-methyl-5-((3-(2-(((3S,5R)-5-methylpiperidin-3-yl)amino)pyrimidin-4-yl)pyridin-2-yl)oxy)naphthalen-1-yl)-1-phenylmethanesulfonamide

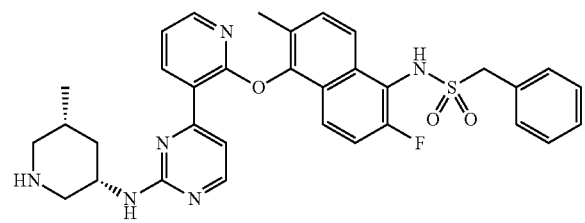 [SMILES: Cc1ccc2c(NS(=O)(=O)Cc3ccccc3)c(F)ccc2c1Oc1ncccc1-c1ccnc(N[C@@H]2CNC[C@H](C)C2)n1]

To a solution of (3S,5R)-benzyl 3-((4-(2-((6-fluoro-2-methyl-5-(phenylmethylsulfonamido)naphthalen-1-yl)oxy)pyridin-3-yl)pyrimidin-2-yl)amino)-5-methylpiperidine-1-carboxylate (51 mg, 0.07 mmol) in DCM (0.4 mL) and MeCN (0.4 mL), was added dimethyl sulfide (0.5 mL, 6.8 mmol) followed by boron trifluoride diethyl etherate (0.43 mL, 3.41 mmol). After 5 h at rt the mixture was diluted with EtOAc (30 mL) and washed with saturated NaHCO₃(aq) (20 mL), then saturated NaCl(aq), dried (MgSO₄), filtered, and concentrated in vacuo. The residue was dissolved in 1,4-dioxane (4 mL) and to the solution was added hydrochloric acid (4 M in dioxane, 1 mL, 4 mmol) with stirring. The suspension was stirred at rt for 10 min then the precipitate was filtered, washed with 1,4-dioxane and dissolved in H₂O and lyophilized to provide 29 mg (65% yield) of 378. LCMS (ESI) [M+H]⁺=613.5, rt=1.51 min; ¹H NMR (400 MHz, D₂O) δ 8.25 (s, 1H), 8.02 (s, 1H), 7.73 (d, J=7.6 Hz, 2H), 7.47 (s, 1H), 7.29 (s, 2H), 7.17 (s, 5H), 7.06 (s, 1H), 6.92 (s, 1H), 4.38 (s, 1H), 4.17-4.06 (m, 1H), 3.58 (s, 2H), 3.46 (d, J=20.8 Hz, 1H), 3.14 (s, 1H), 2.59 (s, 1H), 2.39 (t, J=12.7 Hz, 1H), 1.90 (s, 3H), 1.76-1.64 (m, 1H), 1.08 (d, J=12.5 Hz, 1H), 0.69 (s, 3H).

Example 379 (S)—N-(2-Fluoro-6-methyl-5-((3-(2-(((S)-piperidin-3-yl)amino)pyrimidin-4-yl)pyridin-2-yl)oxy)naphthalen-1-yl)spiro[2.2]pentane-1-carboxamide 379

Step 1: (3S)-tert-Butyl 3-((4-(2-((6-fluoro-2-methyl-5-(spiro[2.2]pentane-1-carboxamido)naphthalen-1-yl)oxy)pyridin-3-yl)pyrimidin-2-yl)amino)piperidine-1-carboxylate

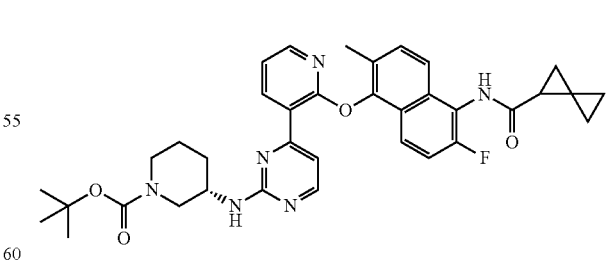

To a solution of spiro[2.2]pentane-2-carboxylic acid (93 mg, 0.83 mmol) in DCE (0.50 mL) was added DMF (1 µL, 0.01 mmol) followed by oxalyl chloride (0.07 mL, 0.83 mmol). The mixture was stirred at rt for 20 min and subsequently added to a pre-stirred solution of tert-butyl (3S)-3-[[4-[2-[(5-amino-6-fluoro-2-methyl-1-naphthyl)

oxy]-3-pyridyl]pyrimidin-2-yl]amino]piperidine-1-carboxylate (150 mg, 0.280 mmol) and triethylamine (139 mg, 1.38 mmol) in DCE (0.50 mL). After 30 min at rt, the reaction was diluted with DCM and concentrated in vacuo and the crude was purified by flash chromatography through silica gel (20-90% EtOAc/Hexanes) to provide 102 mg of the title compound as stereoisomers (58% yield). LCMS (ESI) [M+H]$^+$=639.7, rt=1.91 min.

Step 2: tert-Butyl (S)-3-((4-(2-((6-fluoro-2-methyl-5-((S)-spiro[2.2]pentane-1-carboxamido)naphthalen-1-yl)oxy)pyridin-3-yl)pyrimidin-2-yl)amino)piperidine-1-carboxylate (Isomer-1) and tert-Butyl (S)-3-((4-(2-((6-fluoro-2-methyl-5-((R)-spiro[2.2]pentane-1-carboxamido)naphthalen-1-yl)oxy)pyridin-3-yl)pyrimidin-2-yl)amino)piperidine-1-carboxylate (Isomer-2)

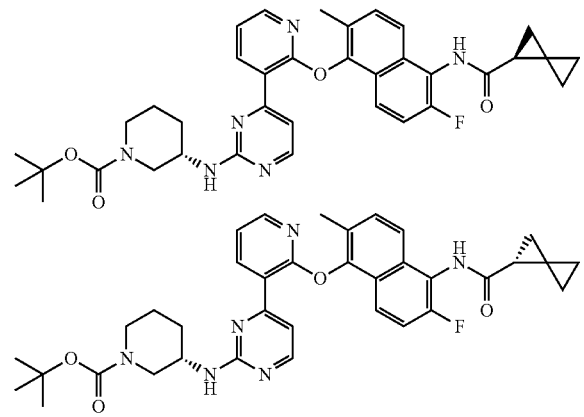

The stereoisomers from Step 1 were subjected to chiral normal phase semi-prep purification (conditions: Chiralpak IB, 5 uM, 20×250 mm, 5:5:90 MeOH:DCM:Hexane, 5.7 mg/inj.) to provide two stereoisomers enantiomeric at the spiro[2.2]pentane-1-carboxamido position: (isomer-1), 37 mg (36% yield), white solid, rt=31.5 min, LCMS (ESI) [M+H]$^+$=639.7, rt=1.91 min; (isomer-2), 35 mg (34% yield), white solid, rt=35.9 min, LCMS (ESI) [M+H]$^+$=639.7, rt=1.91 min.

Step 3: (S)—N-(2-Fluoro-6-methyl-5-((3-(2-(((S)-piperidin-3-yl)amino)pyrimidin-4-yl)pyridin-2-yl)oxy)naphthalen-1-yl)spiro[2.2]pentane-1-carboxamide (Isomer-1)

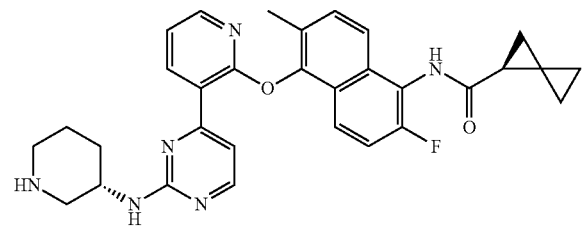 [SMILES: Cc1ccc2c(NC(=O)[C@H]3CC34CC4)c(F)ccc2c1Oc1ncccc1-c1ccnc(N[C@H]2CCCNC2)n1]

Prepared using (3S)-tert-butyl 3-((4-(2-((6-fluoro-2-methyl-5-(spiro[2.2]pentane-1-carboxamido)naphthalen-1-yl)oxy)pyridin-3-yl)pyrimidin-2-yl)amino)piperidine-1-carboxylate (isomer-1) (37 mg, 0.058 mmol), 1,4-dioxane (1 mL) and hydrochloric acid (4 M in dioxane, 1 mL, 4 mmol). After 30 min at rt, the suspension was diluted with MTBE (15 mL) and the precipitate was filtered and washed with MTBE. The precipitate was dissolved in MeCN and water and lyophilized to provide 28 mg (84% yield) of 379 as a fluffy light yellow solid. The stereochemical assignments of 379 and 380 were randomly assigned and may be later determined. LCMS (ESI) [M+H]$^+$=539.5, rt=1.38 min; $^1$H NMR (400 MHz, D$_2$O) δ 8.42 (s, 1H), 8.18 (d, J=6.2 Hz, 1H), 7.84 (d, J=4.9 Hz, 1H), 7.61 (d, J=8.4 Hz, 3H), 7.40 (d, J=8.7 Hz, 1H), 7.15 (dd, J=10.8, 8.2 Hz, 2H), 4.28 (s, 1H), 3.41 (s, 1H), 3.18 (s, 1H), 2.95 (dd, J=23.4, 11.4 Hz, 2H), 2.24 (s, 1H), 2.05 (s, 3H), 1.89 (s, 1H), 1.64 (s, 2H), 1.44 (s, 2H), 0.89 (d, J=28.2 Hz, 4H).

Example 380 (R)—N-(2-Fluoro-6-methyl-5-((3-(2-(((S)-piperidin-3-yl)amino)pyrimidin-4-yl)pyridin-2-yl)oxy)naphthalen-1-yl)spiro[2.2]pentane-1-carboxamide 380

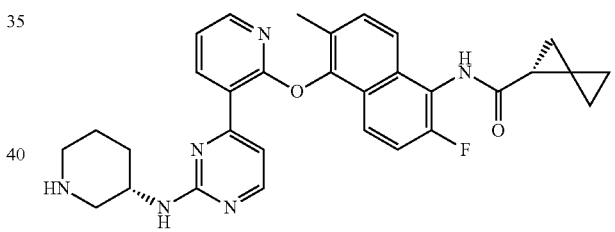

Prepared according to Example 279 using tert-butyl (S)-3-((4-(2-((6-fluoro-2-methyl-5-((R)-spiro[2.2]pentane-1-carboxamido)naphthalen-1-yl)oxy)pyridin-3-yl)pyrimidin-2-yl)amino)piperidine-1-carboxylate (isomer-2) (35 mg, 0.055 mmol), 1,4-dioxane (1 mL) and hydrochloric acid (4 M in dioxane, 1 mL, 4 mmol). After 30 min at rt, the suspension was diluted with MTBE (15 mL) and the precipitate was filtered and washed with MTBE. The precipitate was dissolved in MeCN and water and lyophilized to provide 26 mg (82% yield) of 380. LCMS (ESI) [M+H]$^+$=539.5, rt=1.37 min; $^1$H NMR (400 MHz, D$_2$O) δ 8.43 (s, 1H), 8.17 (d, J=6.2 Hz, 1H), 7.85 (d, J=3.5 Hz, 1H), 7.62 (d, J=8.3 Hz, 3H), 7.41 (d, J=8.8 Hz, 1H), 7.22-7.02 (m, 2H), 4.30 (s, 1H), 3.43 (d, J=10.4 Hz, 1H), 3.20 (d, J=13.0 Hz, 1H), 2.95 (dd, J=23.9, 11.7 Hz, 2H), 2.27-2.20 (m, 1H), 2.05 (s, 3H), 1.89 (s, 1H), 1.65 (t, J=10.2 Hz, 2H), 1.45 (d, J=4.6 Hz, 2H), 0.99-0.80 (m, 4H).

Example 381 anti-3-((6-Methyl-5-((3-(2-(((S)-piperidin-3-yl)amino)pyrimidin-4-yl)pyridin-2-yl)oxy) naphthalen-1-yl)amino) butan-2-ol

Step 1: tert-Butyl (S)-3-((4-(2-((5-(((2R,3R)-3-hydroxybutan-2-yl)amino)-2-methylnaphthalen-1-yl)oxy)pyridin-3-yl)pyrimidin-2-yl)amino)piperidine-1-carboxylate

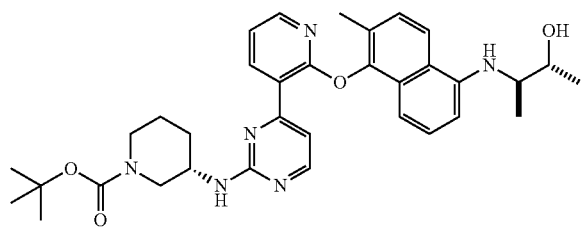 [SMILES: Cc1ccc2c(N[C@H](C)[C@@H](C)O)cccc2c1Oc1ncccc1-c1ccnc(N[C@H]2CCCN(C(=O)OC(C)(C)C)C2)n1]

In a capped microwave vial, a mixture of tert-butyl (3S)-3-[[4-[2-[(5-amino-2-methyl-1-naphthyl)oxy]-3-pyridyl]pyrimidin-2-yl]amino]piperidine-1-carboxylate (150 mg, 0.280 mmol) and trans-2,3-epoxybutane (0.03 mL, 0.340 mmol) in acetic acid (1 mL) was stirred at rt for 16 h, and then stirred at 60° C. for 3 days. Acetic acid was then removed under an air stream and the product was purified by flash chromatography through silica gel (40-100% EtOAc/hexanes) to provide 64 mg (37% yield) of the title compound. LCMS (ESI) [M+H]$^+$=599.6, rt=1.85 min.

Step 2: anti-3-((6-Methyl-5-((3-(2-(((S)-piperidin-3-yl)amino)pyrimidin-4-yl)pyridin-2-yl)oxy)naphthalen-1-yl)amino)butan-2-ol

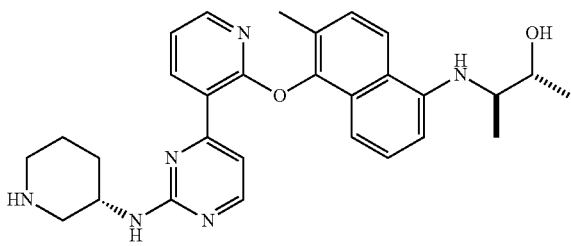 [SMILES: Cc1ccc2c(N[C@H](C)[C@@H](C)O)cccc2c1Oc1ncccc1-c1ccnc(N[C@H]2CCCNC2)n1]

(3S)-tert-Butyl 3-((4-(2-((5-anti-((3-hydroxybutan-2-yl)amino)-2-methylnaphthalen-1-yl)oxy)pyridin-3-yl)pyrimidin-2-yl)amino)piperidine-1-carboxylate (64 mg, 0.11 mmol) dissolved EtOAc (2 mL) and hydrochloric acid (4M in dioxanes, 1 mL, 4 mmol) was added and stirred at rt. After 16 h, the reaction was concentrated in vacuo and the product was purified by C18 reverse phase flash chromatography (0-100% MeCN/10 mM aqueous ammonium formate, pH=3.8). Appropriate fractions were combined and lyophilized to provide 5 mg (10% yield) of 381 as a tan solid. The stereochemical assignments of 381 were randomly assigned and may be later determined. LCMS (ESI) [M+H]$^+$=499.2, rt=1.33 min; $^1$H NMR (400 MHz, d6-dmso) δ 8.56-8.45 (m, 1H), 8.41 (d, J=5.1 Hz, 1H), 8.33 (s, 1H), 8.04-7.97 (m, 2H), 7.45 (d, J=5.1 Hz, 1H), 7.34 (d, J=8.7 Hz, 1H), 7.27-7.12 (m, 3H), 6.81 (d, J=8.1 Hz, 1H), 6.48 (d, J=7.8 Hz, 1H), 5.64 (d, J=8.5 Hz, 1H), 4.75 (s, 1H), 4.01-3.89 (m, 1H), 3.89-3.81 (m, 1H), 3.55-3.46 (m, 2H), 3.19-3.12 (m, 2H), 2.86 (d, J=12.5 Hz, 1H), 2.18 (s, 3H), 1.99-1.87 (m, 1H), 1.74-1.64 (m, 1H), 1.58-1.42 (m, 2H), 1.18 (d, J=6.3 Hz, 3H), 1.15 (d, J=6.3 Hz, 3H).

Example 382 2-Methyl-3-((6-methyl-5-((3-(2-((S)-piperidin-3-ylamino)pyrimidin-4-yl)pyridin-2-yl)oxy)naphthalen-1-yl)amino)propanenitrile 382

Step 1: (3S)-tert-Butyl 3-((4-(2-((5-((2-cyanopropyl)amino)-2-methylnaphthalen-1-yl)oxy)pyridin-3-yl)pyrimidin-2-yl)amino)piperidine-1-carboxylate

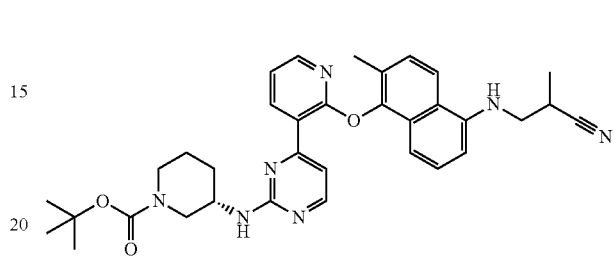

To a solution of tert-butyl (3S)-3-[[4-[2-[(5-amino-2-methyl-1-naphthyl)oxy]-3-pyridyl]pyrimidin-2-yl]amino]piperidine-1-carboxylate (500 mg, 0.950 mmol) in DMF (4 mL) was added methacrylonitrile (0.4 mL, 4.8 mmol) followed by addition of benzyltrimethylammonium hydroxide 40% in MeOH (480 mg, 2.85 mmol). The reaction was stirred at 80° C. for 20 min then diluted with EtOAc (100 mL) and washed with water (30 mL). The organic layer was separated and dried (MgSO$_4$), filtered and concentrated in vacuo. The crude material obtained was purified by C18 reverse phase flash chromatography (0-100% MeCN/10 mM aqueous ammonium formate, pH=3.8). Appropriate fractions were combined and concentrated to remove MeCN. To the aqueous mixture was then added saturated Na$_2$CO$_3$(aq) (2 mL) and the product was extracted with EtOAc (50 mL), dried (MgSO$_4$), filtered and concentrated in vacuo to provide 230 mg (41% yield) of the title compound. LCMS (ESI) [M+H]$^+$=594.4, rt=1.95 min.

Step 2: 2-Methyl-3-((6-methyl-5-((3-(2-((S)-piperidin-3-ylamino)pyrimidin-4-yl)pyridin-2-yl)oxy)naphthalen-1-yl)amino)propanenitrile

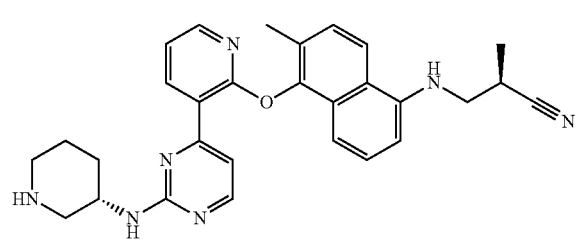

Prepared using (3S)-tert-butyl 3-((4-(2-((5-((2-cyanopropyl)amino)-2-methylnaphthalen-1-yl)oxy)pyridin-3-yl)pyrimidin-2-yl)amino)piperidine-1-carboxylate (21 mg, 0.035 mmol), 1,4-dioxane (0.5 mL), and hydrochloric acid (4 M in dioxane, 0.5 mL, 2 mmol). After 10 min, the mixture was quickly diluted with MTBE and the solids were filtered off, washed with MTBE then dissolved in H$_2$O and MeCN and lyophilized to provide 15 mg (80% yield) of 382 as a red solid. LCMS (ESI) [M+H]$^+$=494.4, rt=1.4 min; $^1$H NMR (400 MHz, D$_2$O) δ 8.45 (s, 1H), 8.13 (d, J=6.4 Hz, 1H), 7.86

(dd, J=5.0, 1.9 Hz, 1H), 7.80 (d, J=8.7 Hz, 1H), 7.71 (s, 1H), 7.35 (d, J=8.8 Hz, 1H), 7.15 (dd, J=7.7, 5.0 Hz, 2H), 7.03 (s, 1H), 6.62 (d, J=8.0 Hz, 1H), 4.31 (s, 1H), 3.47 (dd, J=24.4, 15.5 Hz, 3H), 3.16 (dd, J=16.4, 9.2 Hz, 2H), 2.95 (dd, J=25.2, 12.7 Hz, 2H), 2.08 (s, 3H), 1.91 (s, 1H), 1.67 (d, J=10.4 Hz, 2H), 1.24 (d, J=7.1 Hz, 3H). The stereochemistry of the aminonitrile has been randomly assigned.

Example 383 anti-2-((6-Methyl-5-((3-(2-((S)-piperidin-3-ylamino)pyrimidin-4-yl)pyridin-2-yl)oxy)naphthalen-1-yl)amino)cyclopentanol Step 1: (3S)-tert-Butyl 3-((4-(2-((5-trans-((2-hydroxycyclopentyl)amino)-2-methylnaphthalen-1-yl)oxy)pyridin-3-yl)pyrimidin-2-yl)amino)piperidine-1-carboxylate

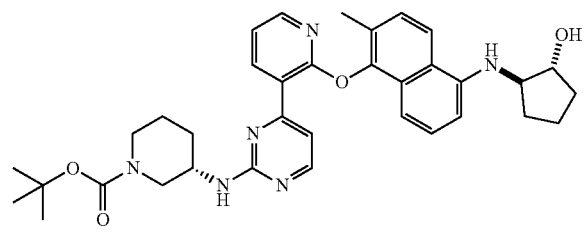

In a capped microwave vial, a mixture of tert-butyl (3S)-3-[[4-[2-[(5-amino-2-methyl-1-naphthyl)oxy]-3-pyridyl]pyrimidin-2-yl]amino]piperidine-1-carboxylate (200 mg, 0.380 mmol) and 1,2-epoxycyclopentane (40 mg, 0.48 mmol) in acetic acid (0.5 mL) was stirred at 70° C. overnight and then stirred at rt for 3 days. Acetic acid was then removed in vacuo and the product was purified by flash chromatography through silica gel (0-20% EtOAc/DCM) to provide 95 mg (41% yield) of the title compound. LCMS (ESI) [M+H]$^+$=611.3, rt=1.91 min.

Step 2: anti-2-((6-Methyl-5-((3-(2-((S)-piperidin-3-ylamino)pyrimidin-4-yl)pyridin-2-yl)oxy)naphthalen-1-yl)amino)cyclopentanol

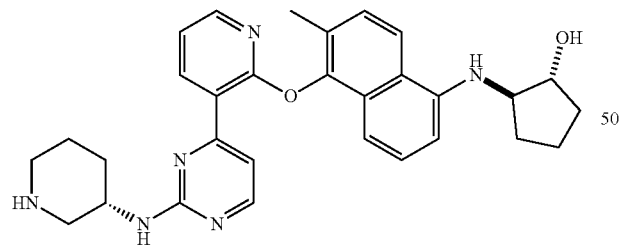

Prepared using (3S)-tert-butyl 3-((4-(2-((5-trans-((2-hydroxycyclopentyl)amino)-2-methylnaphthalen-1-yl)oxy)pyridin-3-yl)pyrimidin-2-yl)amino)piperidine-1-carboxylate (20 mg, 0.03 mmol), 1,4-dioxane (1 mL), and hydrochloric acid (4 M in dioxane, 0.5 mL, 2 mmol). After 3 h, the solvent was evaporated in vacuo and the residue was triturated in MeCN. The precipitate was filtered and dissolved in MeCN and H$_2$O and lyophilized to provide 18 mg (99% yield) of 383. The stereochemical assignments of 383 were randomly assigned and may be later determined. LCMS (ESI) [M+H]$^+$=511.2, rt=1.34 min; $^1$H NMR (400 MHz, CD$_3$OD) δ 8.72 (d, J=6.8 Hz, 1H), 8.46 (d, J=5.5 Hz, 1H), 8.01 (dd, J=4.9, 1.9 Hz, 1H), 7.99 (d, J=8.8 Hz, 1H), 7.79 (d, J=5.5 Hz, 1H), 7.58 (d, J=8.7 Hz, 1H), 7.54-7.47 (m, 1H), 7.39 (t, J=8.0 Hz, 1H), 7.26 (dd, J=7.6, 4.9 Hz, 1H), 7.24-7.18 (m, 1H), 4.42 (s, 1H), 4.31 (dd, J=11.8, 5.8 Hz, 1H), 3.84 (dd, J=12.7, 7.0 Hz, 1H), 3.64 (dd, J=12.2, 3.4 Hz, 1H), 3.42-3.32 (m, 1H), 3.12-2.99 (m, 2H), 2.28 (s, 3H), 2.25-2.04 (m, 4H), 2.00-1.75 (m, 5H), 1.75-1.62 (m, 1H).

Example 384 trans-2-((6-Methyl-5-((3-(2-((S)-piperidin-3-ylamino)pyrimidin-4-yl)pyridin-2-yl)oxy)naphthalen-1-yl)amino)cyclohexanol 384

Step 1: (3S)-tert-Butyl 3-((4-(2-((5-trans-((2-hydroxycyclohexyl)amino)-2-methylnaphthalen-1-yl)oxy)pyridin-3-yl)pyrimidin-2-yl)amino)piperidine-1-carboxylate

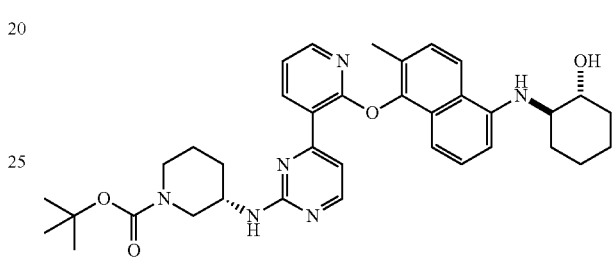

In a capped microwave vial, a mixture of tert-butyl (3S)-3-[[4-[2-[(5-amino-2-methyl-1-naphthyl)oxy]-3-pyridyl]pyrimidin-2-yl]amino]piperidine-1-carboxylate (200 mg, 0.380 mmol), and cyclohexene oxide (48 mg, 0.49 mmol) in acetic acid (0.5 mL) was stirred at 70° C. overnight and then stirred at rt for 3 days. Acetic acid was then removed in vacuo and the product was purified by C18 reverse phase flash chromatography (0-100% MeCN/10 mM aqueous ammonium formate, pH=3.8). Appropriate fractions were combined and the solvent was removed in vacuo to provide 115 mg (49% yield) of the title compound. LCMS (ESI) [M+H]$^+$=625.4, rt=2.00 min.

Step 2: trans-2-((6-Methyl-5-((3-(2-((S)-piperidin-3-ylamino)pyrimidin-4-yl)pyridin-2-yl)oxy)naphthalen-1-yl)amino)cyclohexanol

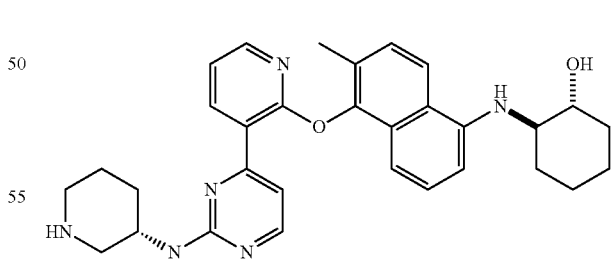

Prepared using (3S)-tert-butyl 3-((4-(2-((5-((2-hydroxycyclohexyl)amino)-2-methylnaphthalen-1-yl)oxy)pyridin-3-yl)pyrimidin-2-yl)amino)piperidine-1-carboxylate (21 mg, 0.03 mmol), 1,4-dioxane (1 mL), and hydrochloric acid (4 M in dioxane, 0.5 mL, 2 mmol). After 3 h, the solvent was evaporated in vacuo and the residue was triturated in MeCN. The precipitate was filtered and dissolved in MeCN and H$_2$O and lyophilized to provide 19 mg (99% yield) of 384. LCMS (ESI) [M+H]$^+$=525.3, rt=1.42 min; $^1$H NMR (400 MHz, CD$_3$OD) δ 8.69 (d, J=6.5 Hz, 1H), 8.45 (d, J=5.3 Hz, 1H), 8.07 (d, J=8.8 Hz, 1H), 7.98 (dd, J=4.9, 1.9 Hz, 1H), 7.70 (d, J=5.3 Hz, 1H), 7.68-7.55 (m, 2H), 7.42 (t, J=8.0 Hz, 1H), 7.33-7.27 (m, 1H), 7.24 (dd, J=7.6, 4.9 Hz, 1H), 4.43-4.31 (m, 1H), 3.76 (td, J=10.1, 4.5 Hz, 1H), 3.63 (dd, J=12.0, 3.7 Hz, 1H), 3.43-3.32 (m, 2H), 3.09-2.97 (m, 2H), 2.29 (s, 3H), 2.25-2.06 (m, 3H), 2.05-1.70 (m, 5H), 1.51-1.36 (m, 3H), 1.33-1.15 (m, 1H).

Example 385 (S)—N-(5-((5-Chloro-3-(2-(piperidin-3-ylamino)pyrimidin-4-yl)pyridin-2-yl)oxy)-6-methylnaphthalen-1-yl)propane-1-sulfonamide 385

Step 1: 4-(5-bromo-2-fluoropyridin-3-yl)-2-chloropyrimidine

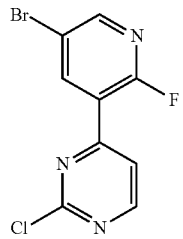

2,4-Dichloropyrimidine (13.6 g, 91.0 mmol), potassium carbonate (6.92 g, 50.0 mmol) and 1,1-bis(diphenylphosphino)ferrocene-palladium dichloride (0.84 g, 1.14 mmol) were suspended in a mixture of water (15 mL) and 1,4-dioxane (45 mL). To this was then added (5-bromo-2-fluoro-3-pyridyl)boronic acid (1.7 g, 7.5 mmol) and the mixture was degassed with nitrogen then stirred at 90° C. After 20 min, a further portion of (5-bromo-2-fluoro-3-pyridyl)boronic acid (1.7 g, 7.5 mmol) was added and after a further 20 min, another portion of (5-bromo-2-fluoro-3-pyridyl) boronic acid (1.7 g, 7.5 mmol) was added. After 20 min, the mixture was diluted with EtOAc (400 mL), water (300 mL), and brine (50 mL) and the suspension was filtered through celite and separated. The organic layer was dried (MgSO$_4$) and the solvent was removed in vacuo. The residue was dissolved in toluene and purified by flash chromatography through silica gel (0-5% EtOAc/DCM). Appropriate fractions combined and further purified by distillation under reduced pressure to provide 4.8 g (73% yield) of the title compound as a crystalline solid. LCMS (ESI) [M+H]$^+$=288.0, rt=1.68 min.

Step 2: (S)-tert-Butyl 3-((4-(2-((5-amino-2-methyl-naphthalen-1-yl)oxy)-5-bromopyridin-3-yl)pyrimidin-2-yl)amino)piperidine-1-carboxylate

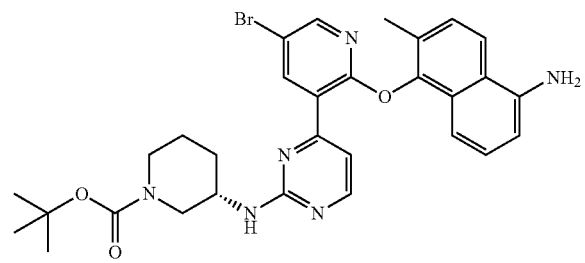 [SMILES: Cc1ccc2c(N)cccc2c1Oc1ncc(Br)cc1-c1ccnc(N[C@H]2CCCN(C(=O)OC(C)(C)C)C2)n1]

To a flask containing 4-(5-bromo-2-fluoro-3-pyridyl)-2-chloro-pyrimidine (500 mg, 1.73 mmol) was added (S)-(+)-3-amino-1-boc-piperidine (347 mg, 1.73 mmol), cesium carbonate (1000 mg, 3.05 mmol) and DMSO (7.5 mL). The mixture was heated to 120° C. and after 30 min the mixture was cooled to rt to provide a crude mixture of (S)-tert-butyl 3-((4-(5-bromo-2-fluoropyridin-3-yl)pyrimidin-2-yl)amino) piperidine-1-carboxylate which was used directly in the next step without further purification.

To a flask containing the crude solution of (S)-tert-butyl 3-((4-(5-bromo-2-fluoropyridin-3-yl)pyrimidin-2-yl)amino) piperidine-1-carboxylate obtained above was added 5-amino-2-methyl-naphthalen-1-ol hydrochloride (363 mg, 1.73 mmol) and cesium carbonate (1134 mg, 3.46 mmol). The mixture was heated to 120° C. for 1 h then cooled to rt and the mixture was purified directly by C18 reverse phase flash chromatography (50-90% MeCN/10 mM aqueous ammonium formate, pH=3.8). Appropriate fractions were combined and MeCN was removed in vacuo then lyophilized to provide 290 mg (28% yield) of the title compound as a brown solid. LCMS (ESI) [M+H]$^+$=605.4, 607.4, rt=2.06 min Step 4: (S)-tert-Butyl 3-((4-(5-bromo-2-((2-methyl-5-(propylsulfonamido)naphthalen-1-yl)oxy)pyridin-3-yl)pyrimidin-2-yl)amino)piperidine-1-carboxylate

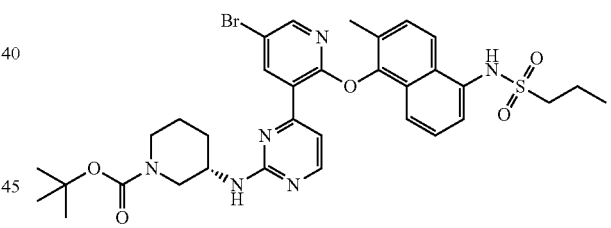

To a flask containing (S)-tert-Butyl 3-((4-(2-((5-amino-2-methylnaphthalen-1-yl)oxy)-5-bromopyridin-3-yl)pyrimidin-2-yl)amino)piperidine-1-carboxylate (26 mg, 0.040 mmol) was added DCM (0.50 mL), pyridine (0.05 mL, 0.64 mmol) and 1-propanesulfonyl chloride (0.01 mL, 0.090 mmol). The mixture was stirred at rt for 72 h then to the reaction was added water (2 mL) and EtOAc (50 mL) and the mixture was transferred to an extraction funnel containing saturated NH$_4$Cl(aq) (20 mL). The organic phase was separated and washed with brine, then saturated NaHCO$_3$ (aq) (20 mL), dried (MgSO$_4$), filtered and concentrated. The crude mixture was purified by flash chromatography through silica gel (0-80% EtOAc/DCM) to provide 20 mg (66% yield) of the title compound as a colorless oil. LCMS (ESI) [M+H]$^+$=711.3, 713.3, rt=2.06 min.

Step 5: (S)-tert-butyl 3-((4-(5-chloro-2-((2-methyl-5-(propylsulfonamido)naphthalen-1-yl)oxy)pyridin-3-yl)pyrimidin-2-yl)amino)piperidine-1-carboxylate

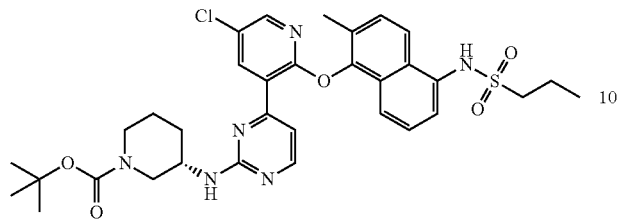

CuI (14.5 mg, 0.100 mmol) and L-proline (23 mg, 0.20 mmol) were suspended in ethanol (0.50 mL). To this solution was added (S)-tert-butyl 3-((4-(5-bromo-2-((2-methyl-5-(propylsulfonamido)naphthalen-1-yl)oxy)pyridin-3-yl)pyrimidin-2-yl)amino)piperidine-1-carboxylate (24 mg, 0.030 mmol) and tetrabutylammonium chloride hydrate (100 mg, 0.340 mmol) and the mixture was placed in a 110° C. oil bath sealed. After 16 h, the crude mixture was purified directly by C18 flash chromatography (0-100% MeCN/10 mM aqueous ammonium formate, pH=3.8). Appropriate fractions were combined and lyophilized to provide 10 mg (44% yield) of the title compound as a pale yellow solid. LCMS (ESI) [M+H]$^+$=667.6, rt=2.07 min.

Step 6: (S)—N-(5-((5-Chloro-3-(2-(piperidin-3-ylamino)pyrimidin-4-yl)pyridin-2-yl)oxy)-6-methyl-naphthalen-1-yl)propane-1-sulfonamide

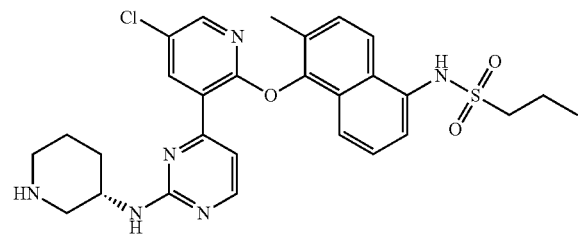

Prepared using (S)-tert-butyl 3-((4-(5-chloro-2-((2-methyl-5-(propylsulfonamido)naphthalen-1-yl)oxy)pyridin-3-yl)pyrimidin-2-yl)amino)piperidine-1-carboxylate (10 mg, 0.015 mmol), 1,4-dioxane (1 mL), and hydrochloric acid (4 M in dioxane, 0.5 mL, 2 mmol). After 4 h, the suspension was filtered and the precipitate was dissolved in MeCN and H$_2$O and lyophilized to provide 7 mg (78% yield) of 385. LCMS (ESI) [M+H]$^+$=567.5, rt=1.47 min; $^1$H NMR (400 MHz, CD$_3$OD) δ 8.78 (d, J=2.6 Hz, 1H), 8.54 (d, J=6.6 Hz, 1H), 8.15 (t, J=6.2 Hz, 2H), 8.12 (d, J=6.5 Hz, 1H), 7.63 (d, J=8.5 Hz, 1H), 7.55 (d, J=8.5 Hz, 2H), 7.41 (dd, J=8.4, 7.6 Hz, 1H), 4.68 (br s, 1H), 3.68 (dd, J=12.3, 3.7 Hz, 1H), 3.40 (dt, J=7.8, 3.3 Hz, 1H), 3.18 (d, J=10.4 Hz, 1H), 3.15-3.04 (m, 3H), 2.28 (s+m, 4H), 2.20-2.10 (m, 1H), 2.03-1.95 (m, 1H), 1.94-1.81 (m, 3H), 1.03 (t, J=7.5 Hz, 3H).

Example 386 (S)—N-(2-Fluoro-6-methyl-5-((3-(2-(((S)-piperidin-3-yl)amino)pyrimidin-4-yl)pyridin-2-yl)oxy)naphthalen-1-yl)spiro[2.3]hexane-1-carboxamide 386

Step 1: (3S)-tert-Butyl 3-((4-(2-((6-fluoro-2-methyl-5-(spiro[2.3]hexane-1-carboxamido)naphthalen-1-yl)oxy)pyridin-3-yl)pyrimidin-2-yl)amino)piperidine-1-carboxylate

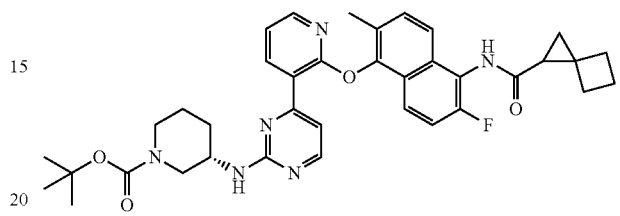

To a solution of spiro[2.3]hexane-2-carboxylic acid (104 mg, 0.830 mmol) in DCE (0.50 mL) was added DMF (2 µL, 0.02 mmol) followed by addition of oxalyl chloride (0.07 mL, 0.83 mmol). The reaction was stirred at rt for 20 min then added to a pre-stirred solution of tert-butyl (3S)-3-[[4-[2-[(5-amino-6-fluoro-2-methyl-1-naphthyl)oxy]-3-pyridyl]pyrimidin-2-yl]amino]piperidine-1-carboxylate (150 mg, 0.280 mmol) and triethylamine (139 mg, 1.38 mmol) in DCE (0.50 mL). The mixture was stirred for 1 h then purified directly by flash chromatography through silica gel (20-90% EtOAc/Hexanes) to provide 92 mg (51% yield) of the title compound. LCMS (ESI) [M+H]$^+$=653.7, rt=1.99 min.

Step 2: tert-Butyl (S)-3-((4-(2-((6-fluoro-2-methyl-5-((S)-spiro[2.3]hexane-1-carboxamido)naphthalen-1-yl)oxy)pyridin-3-yl)pyrimidin-2-yl)amino)piperidine-1-carboxylate (Isomer-1) and tert-butyl (S)-3-((4-(2-((6-fluoro-2-methyl-5-((R)-spiro[2.3]hexane-1-carboxamido)naphthalen-1-yl)oxy)pyridin-3-yl)pyrimidin-2-yl)amino)piperidine-1-carboxylate (Isomer-2)

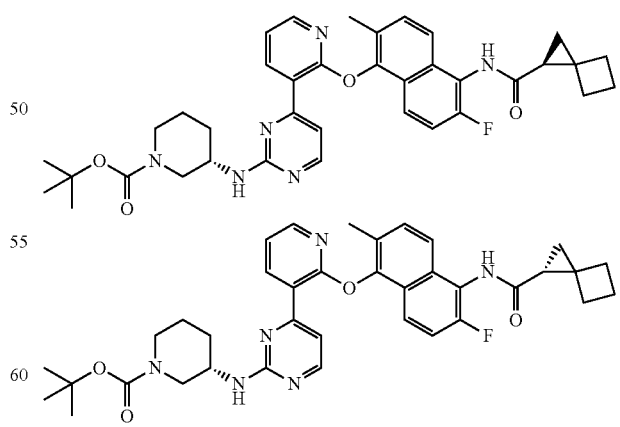

The stereoisomers from Step 1 were subjected to chiral normal phase semi-prep purification (conditions: Chiralpak IB, 5 uM, 20×250 mm, 5:5:90 MeOH:DCM:Hexane, 5-12 mg/inj.) to provide two stereoisomers enantiomeric at the spiro[2.3]hexane-1-position: (isomer-1), 30 mg (32% yield), white solid, ee=99.4%, rt=23.4 min, LCMS (ESI) [M+H]⁺=653.7, rt=1.99 min; and (isomer-2), 33 mg (36% yield), white solid, ee=98.0%, rt=27.9 min, LCMS (ESI) [M+H]⁺=653.7, rt=1.99 min.

Step 3: (S)—N-(2-Fluoro-6-methyl-5-((3-(2-(((S)-piperidin-3-yl)amino)pyrimidin-4-yl)pyridin-2-yl)oxy)naphthalen-1-yl)spiro[2.3]hexane-1-carboxamide (Isomer-1)

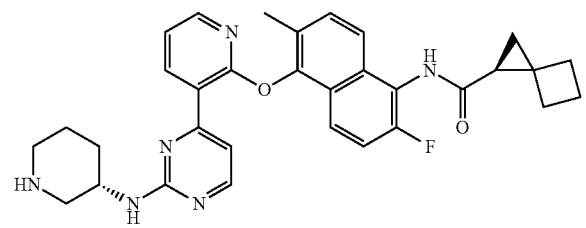 [SMILES: Cc1ccc2c(NC(=O)[C@H]3CC34CCC4)c(F)ccc2c1Oc1ncccc1-c1ccnc(N[C@H]2CCCNC2)n1]

Prepared using tert-butyl (S)-3-((4-(2-((6-fluoro-2-methyl-5-((S)-spiro[2.3]hexane-1-carboxamido)naphthalen-1-yl)oxy)pyridin-3-yl)pyrimidin-2-yl)amino)piperidine-1-carboxylate (isomer-1) (30 mg, 0.051 mmol), 1,4-dioxane (1 mL) and hydrochloric acid (4 M in dioxane, 1 mL, 4 mmol). After 30 min, the suspension was diluted with MTBE (15 mL) and the precipitate was filtered and washed with MTBE. The collected solids were then dissolved in MeCN and water and lyophilized to provide 26 mg (96% yield) of 386 as a fluffy light yellow solid. The stereochemical assignments of 386 and 387 were randomly assigned and may be later determined. LCMS (ESI) [M+H]⁺=553.5, rt=1.48 min; ¹H NMR (400 MHz, D₂O) δ 8.38 (s, 1H), 8.19 (d, J=6.1 Hz, 1H), 7.84 (s, 1H), 7.68 (d, J=8.5 Hz, 1H), 7.62 (s, 2H), 7.42 (d, J=8.8 Hz, 1H), 7.14 (dd, J=19.8, 8.8 Hz, 2H), 4.26 (s, 1H), 3.41 (s, 1H), 3.18 (s, 1H), 2.94 (dd, J=22.9, 11.5 Hz, 2H), 2.19 (s, 1H), 2.08-1.84 (m, 12H), 1.64 (s, 2H), 1.14-1.01 (m, 2H).

Example 387 (R)—N-(2-Fluoro-6-methyl-5-((3-(2-(((S)-piperidin-3-yl)amino)pyrimidin-4-yl)pyridin-2-yl)oxy)naphthalen-1-yl)spiro[2.3]hexane-1-carboxamide 387

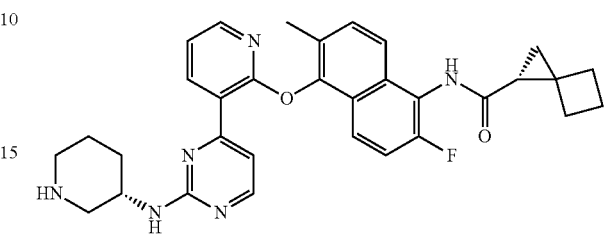

Prepared according to Example 386 using tert-butyl (S)-3-((4-(2-((6-fluoro-2-methyl-5-((R)-spiro[2.3]hexane-1-carboxamido)naphthalen-1-yl)oxy)pyridin-3-yl)pyrimidin-2-yl)amino)piperidine-1-carboxylate (isomer-2) (33 mg, 0.051 mmol), 1,4-dioxane (1 mL) and hydrochloric acid (4 M in dioxane, 1 mL, 4 mmol). After 30 min, the suspension was diluted with MTBE (15 mL) and the precipitate was filtered and washed with MTBE. The collected solids were then dissolved in MeCN and water and lyophilized to provide 22 mg (74% yield) of 387 as a fluffy light yellow solid. LCMS (ESI) [M+H]⁺=553.6, rt=1.48 min; ¹H NMR (400 MHz, D₂O) δ 8.37 (s, 1H), 8.20 (d, J=6.0 Hz, 1H), 7.84 (d, J=3.0 Hz, 1H), 7.69 (d, J=8.7 Hz, 1H), 7.61 (s, 2H), 7.42 (d, J=8.6 Hz, 1H), 7.16 (dd, J=7.7, 5.0 Hz, 2H), 4.26 (s, 1H), 3.40 (s, 1H), 3.17 (s, 1H), 2.94 (d, J=11.8 Hz, 2H), 2.19 (s, 1H), 2.08-1.85 (m, 11H), 1.64 (s, 2H), 1.08 (d, J=27.1 Hz, 2H).

Example 388 (S)—N-(2-Fluoro-6-methyl-5-((3-(2-(((3S,5R)-5-methylpiperidin-3-yl)amino)pyrimidin-4-yl)pyridin-2-yl)oxy)naphthalen-1-yl)spiro[2.2]pentane-1-carboxamide 388

Step 1: (3S,5R)-Benzyl 3-((4-(2-((6-fluoro-2-methyl-5-(spiro[2.2]pentane-1-carboxamido)naphthalen-1-yl)oxy)pyridin-3-yl)pyrimidin-2-yl)amino)-5-methylpiperidine-1-carboxylate

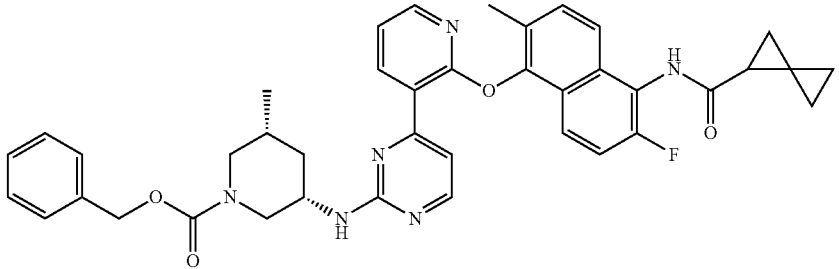 [SMILES: Cc1ccc2c(NC(=O)C3CC34CC4)c(F)ccc2c1Oc1ncccc1-c1ccnc(N[C@H]2C[C@@H](C)CN(C(=O)OCc3ccccc3)C2)n1]

619

To a solution of spiro[2.2]pentane-2-carboxylic acid (85 mg, 0.76 mmol) in DCE (0.50 mL) was added DMF (2 μL, 0.02 mmol) followed by addition of oxalyl chloride (0.07 mL, 0.83 mmol). The reaction was stirred at rt for 20 min then added to a pre-stirred solution of benzyl (3S,5R)-3-[[4-[2-[(5-amino-6-fluoro-2-methyl-1-naphthyl)oxy]-3-pyridyl]pyrimidin-2-yl]amino]-5-methyl-piperidine-1-carboxylate (150 mg, 0.250 mmol) and triethylamine (128 mg, 1.27 mmol) in DCE (0.50 mL). The mixture was stirred for 1 h at rt then purified directly by flash chromatography through silica gel (20-90% EtOAc/Hexanes) to provide 105 mg (61% yield) of the title compound. LCMS (ESI) [M+H]+=687.4, rt=1.96 min.

Step 2: Benzyl (3S,5R)-3-((4-(2-((6-fluoro-2-methyl-5-((S)-spiro[2.2]pentane-1-carboxamido)naphthalen-1-yl)oxy)pyridin-3-yl)pyrimidin-2-yl)amino)-5-methylpiperidine-1-carboxylate (Isomer-1) and benzyl (3S,5R)-3-((4-(2-((6-fluoro-2-methyl-5-((R)-spiro[2.2]pentane-1-carboxamido)naphthalen-1-yl)oxy)pyridin-3-yl)pyrimidin-2-yl)amino)-5-methylpiperidine-1-carboxylate (Isomer-2)

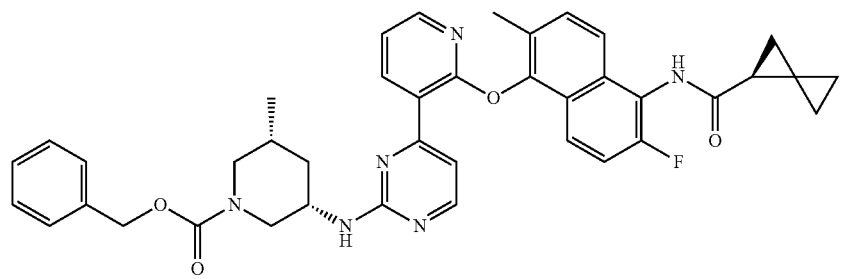

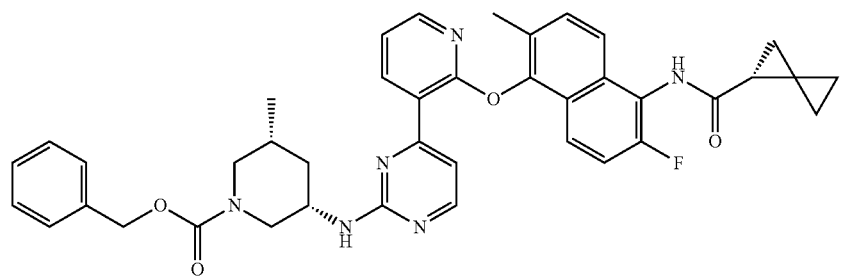

(3S,5R)-Benzyl 3-((4-(2-((6-fluoro-2-methyl-5-(spiro[2.2]pentane-1-carboxamido)naphthalen-1-yl)oxy)pyridin-3-yl)pyrimidin-2-yl)amino)-5-methylpiperidine-1-carboxylate (105 mg, 0.153 mmol) was subjected to chiral normal phase semi-prep purification (conditions: Chiralpak IB, 5 uM, 20×250 mm, 6:6:88 MeOH:DCM:Hexane, 10 mg/inj.) to provide two stereoisomers enantiomeric at the spiro[2.2]pentane-1-position: (isomer-1), 31 mg (29% yield), white solid, ee=97.8%, rt=2.3 min, LCMS (ESI) [M+H]+=653.7, rt=1.99 min; and (isomer-2), 33 mg (31% yield), white solid, ee=98.0%, rt=23.8 min. LCMS (ESI) [M+H]+=687.4, rt=1.96 min.

620

Step 3: (S)—N-(2-Fluoro-6-methyl-5-((3-(2-(((3S,5R)-5-methylpiperidin-3-yl)amino)pyrimidin-4-yl)pyridin-2-yl)oxy)naphthalen-1-yl)spiro[2.2]pentane-1-carboxamide (Isomer-1)

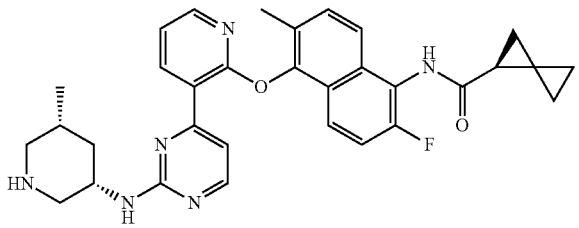 [SMILES: Cc1ccc2c(NC(=O)[C@H]3CC34CC4)c(F)ccc2c1Oc1ncccc1-c1ccnc(N[C@@H]2CNC[C@H](C)C2)n1]

Prepared using benzyl (3S,5R)-3-((4-(2-((6-fluoro-2-methyl-5-((S)-spiro[2.2]pentane-1-carboxamido)naphthalen-1-yl)oxy)pyridin-3-yl)pyrimidin-2-yl)amino)-5-methylpiperidine-1-carboxylate (isomer-1) (30 mg, 0.051 mmol), Pd/C (60 mg, 10% on charcoal), ammonium formate (300 mg, 4.8 mmol). The mixture was stirred at 60° C. for 1 h then filtered through a pad of celite, washed with EtOAc and MeOH, and the filtrate was concentrated in vacuo. The residue was dissolved in EtOAc (30 mL) and washed with 5% Na2CO3(aq), dried (MgSO4), filtered and concentrated in vacuo. The residue was dissolved in 1,4-dioxane (2 mL) and hydrochloric acid (4 M in dioxane, 0.1 mL, 0.4 mmol) was added. The suspension was stirred at rt for 10 min then diluted with MTBE (15 mL) and the precipitate was filtered and washed with MTBE. The collected solids were dissolved in MeCN and water and lyophilized to provide 25 mg (89% yield) of 388 as a fluffy light yellow solid. The stereochemical assignments of 388 and 389 were randomly assigned and may be later determined. LCMS (ESI)

[M+H]⁺=553.5, rt=1.42 min; ¹H NMR (400 MHz, D₂O) δ 8.39-8.28 (m, 1H), 8.20 (d, J=5.9 Hz, 1H), 7.83 (s, 1H), 7.62 (d, J=8.8 Hz, 2H), 7.55 (s, 1H), 7.41 (d, J=8.5 Hz, 1H), 7.15 (t, J=6.3 Hz, 2H), 4.28-4.15 (m, 1H), 3.56-3.47 (m, 1H), 3.22-3.13 (m, 1H), 2.67 (s, 1H), 2.45 (d, J=12.6 Hz, 1H), 2.23 (s, 1H), 2.05 (s, 4H), 1.90-1.62 (m, 1H), 1.44 (d, J=4.7 Hz, 2H), 1.16 (s, 1H), 0.89 (d, J=26.5 Hz, 4H), 0.74 (s, 3H).

Example 389 (R)—N-(2-Fluoro-6-methyl-5-((3-(2-(((3S,5R)-5-methylpiperidin-3-yl)amino)pyrimidin-4-yl)pyridin-2-yl)oxy)naphthalen-1-yl)spiro[2.2]pentane-1-carboxamide 389

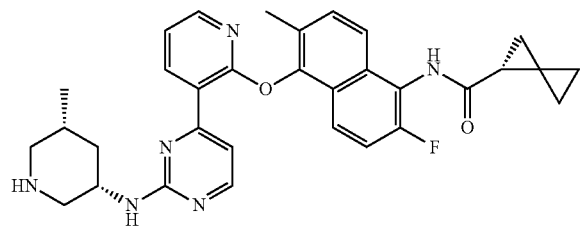 [SMILES: Cc1ccc2c(NC(=O)[C@@H]3CC34CC4)c(F)ccc2c1Oc1ncccc1-c1ccnc(N[C@@H]2CNC[C@H](C)C2)n1]

Prepared according to Example 388 using benzyl (3S, 5R)-3-((4-(2-((6-fluoro-2-methyl-5-((R)-spiro[2.2]pentane-1-carboxamido)naphthalen-1-yl)oxy)pyridin-3-yl)pyrimidin-2-yl)amino)-5-methylpiperidine-1-carboxylate (isomer-2) (33 mg, 0.051 mmol), Pd/C (60 mg, 10% on charcoal), and ammonium formate (300 mg, 4.8 mmol). The mixture was stirred at 60° C. for 1 h then filtered through a pad of celite, washed with EtOAc and MeOH, and the filtrate was concentrated in vacuo. The residue was dissolved in EtOAc (30 mL) and washed with 5% Na₂CO₃(aq), dried (MgSO₄), filtered and concentrated in vacuo. The residue was dissolved in 1,4-dioxane (2 mL) and hydrochloric acid (4 M in dioxane, 0.1 mL, 0.4 mmol) was added. The suspension was stirred at rt for 10 min then diluted with MTBE (15 mL) and the precipitate was filtered and washed with MTBE. The collected solids were dissolved in MeCN and water and lyophilized to provide 19 mg (64% yield) of 389 as a fluffy light yellow solid. LCMS (ESI) [M+H]⁺=553.5, rt=1.42 min; ¹H NMR (400 MHz, D₂O) δ 8.37 (s, 1H), 8.18 (d, J=6.1 Hz, 1H), 7.83 (s, 1H), 7.61 (d, J=8.2 Hz, 3H), 7.40 (d, J=8.5 Hz, 1H), 7.20-7.09 (m, 2H), 4.33-4.18 (m, 1H), 3.49 (s, 2H), 3.16 (s, 1H), 2.67 (s, 1H), 2.43 (s, 1H), 2.23 (s, 1H), 2.05 (s, 4H), 1.88-1.63 (m, 1H), 1.44 (d, J=4.7 Hz, 2H), 1.20 (s, 2H), 0.89 (d, J=26.4 Hz, 4H), 0.74 (s, 3H).

Example 390 4-((6-Methyl-5-((3-(2-((S)-piperidin-3-ylamino)pyrimidin-4-yl)pyridin-2-yl)oxy)naphthalen-1-yl)amino) butan-2-ol Step 1: (S)-tert-Butyl 3-((4-(2-((2-methyl-5-((3-oxobutyl)amino)naphthalen-1-yl)oxy)pyridin-3-yl)pyrimidin-2-yl)amino)piperidine-1-carboxylate

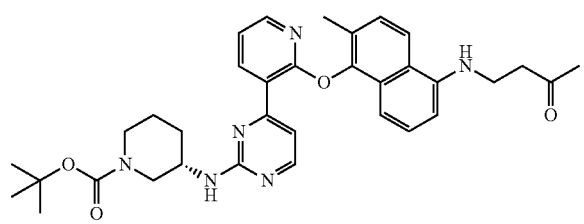 [SMILES: CC(=O)CCNc1cccc2c(Oc3ncccc3-c3ccnc(N[C@H]4CCCN(C(=O)OC(C)(C)C)C4)n3)c(C)ccc12]

To a suspension of tert-butyl (3S)-3-[[4-[2-[(5-amino-2-methyl-1-naphthyl)oxy]-3-pyridyl]pyrimidin-2-yl]amino]piperidine-1-carboxylate (140 mg, 0.270 mmol) in methanol (1.4 mL) was added but-3-en-2-one (65 μL, 0.80 mmol) followed by addition of triethylamine (111 μL, 0.800 mmol). The mixture was stirred at rt for 18 h, then a further portion of but-3-en-2-one (32 μL, 0.40 mmol) was added and continued stirring at rt. After 18 h, the mixture was diluted with water (20 mL) and DCM (30 mL). The phases were separated and the water phase was extracted with DCM (2×30 mL) and the organic phases were combined and dried (Na₂SO₄), filtered and concentrated in vacuo. The crude product was purified by flash chromatography through silica gel (0-60% EtOAc/DCM) to provide 102 mg (64% yield) of the title compound. LCMS (ESI) [M+H]⁺=597.6, rt=1.94 min.

Step 2: (3S)-tert-Butyl 3-((4-(2-((5-((3-hydroxybutyl)amino)-2-methylnaphthalen-1-yl)oxy)pyridin-3-yl)pyrimidin-2-yl)amino)piperidine-1-carboxylate

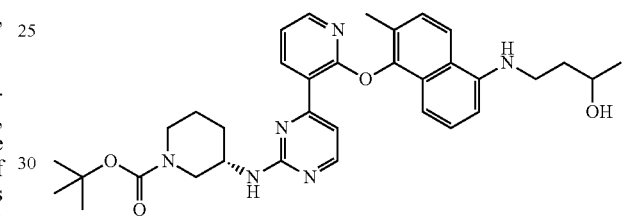

To a solution of tert-butyl (3S)-3-[[4-[2-[[2-methyl-5-(3-oxobutylamino)-1-naphthyl]oxy]-3-pyridyl]pyrimidin-2-yl]amino]piperidine-1-carboxylate (156 mg, 0.260 mmol) in THF (0.45 mL) and methanol (0.45 mL) at 0° C. was added sodium borohydride (34 mg, 0.91 mmol). The reaction was stirred at 0° C. for 30 min then diluted with DCM (20 mL) and water (20 mL) and the phases were separated. The aqueous phase was further extracted with DCM (3×20 mL), the organic extracts were combined, dried (Na₂SO₄), filtered and concentrated in vacuo. The crude product was purified by C18 reverse phase flash chromatography (0-100% MeCN/10 mM aqueous ammonium formate, pH=3.8) to provide 89 mg (57% yield) of the title compound. LCMS (ESI) [M+H]⁺=599.7, rt=1.89 min.

Step 3: 4-((6-Methyl-5-((3-(2-((S)-piperidin-3-ylamino)pyrimidin-4-yl)pyridin-2-yl)oxy)naphthalen-1-yl)amino)butan-2-ol

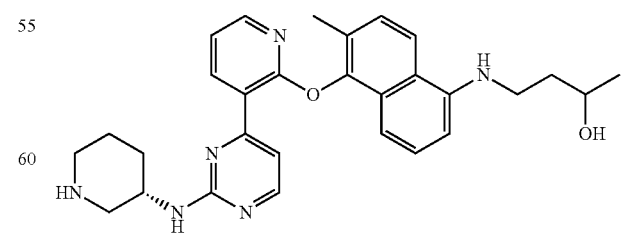

Prepared using (3S)-tert-butyl 3-((4-(2-((5-((3-hydroxybutyl)amino)-2-methylnaphthalen-1-yl)oxy)pyridin-3-yl)pyrimidin-2-yl)amino)piperidine-1-carboxylate (7 mg, 0.01 mmol), 1,4-dioxane (0.05 mL), and hydrochloric acid (4 M in dioxane, 0.1 mL, 0.4 mmol). After 40 min, the mixture was diluted with Et$_2$O and the solids were filtered off, washed with Et$_2$O then dissolved in H$_2$O and MeCN and lyophilized to provide 2.5 mg (40% yield) of diastereomeric mixture 390 as a red solid. LCMS (ESI) [M+H]$^+$=499.5, rt=1.29 min; $^1$H NMR (400 MHz, d$_6$-DMSO) δ 8.86 (bs, 2H), 8.52 (bs, 1H), 8.47 (d, J=5.2 Hz, 1H), 8.04 (dd, J=4.8, 2.0 Hz, 1H), 7.99 (d, J=8.7 Hz, 1H), 7.57 (dd, J=12.5, 5.3 Hz, 2H), 7.37 (d, J=8.7 Hz, 1H), 7.34-7.12 (m, 2H), 6.89 (d, J=6.9 Hz, 1H), 6.71-6.40 (m, 1H), 4.27 (s, 1H), 3.44 (d, J=10.1 Hz, 1H), 3.37-3.13 (m, 3H), 2.99-2.74 (m, 2H), 2.19 (s, 3H), 2.12-1.86 (m, 2H), 1.86-1.53 (m, 4H), 1.13 (d, J=6.2 Hz, 3H).

Example 391 (S)—N-(2-Fluoro-6-methyl-5-((3-(2-(piperidin-3-ylamino)pyrimidin-4-yl)pyridin-2-yl)oxy)naphthalen-1-yl)-1-(2-fluorophenyl)methanesulfonamide 391

Step 1: (S)-tert-Butyl 3-((4-(2-((6-fluoro-5-((2-fluorophenyl)methylsulfonamido)-2-methylnaphthalen-1-yl)oxy)pyridin-3-yl)pyrimidin-2-yl)amino)piperidine-1-carboxylate

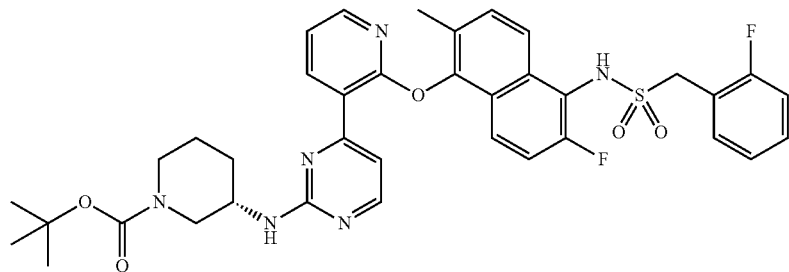

Prepared using (S)-tert-butyl 3-((4-(2-((5-amino-6-fluoro-2-methylnaphthalen-1-yl)oxy)pyridin-3-yl)pyrimidin-2-yl)amino)piperidine-1-carboxylate from Example 275 (60 mg, 0.11 mmol), pyridine (0.13 mL, 1.65 mmol), DCM (0.4 mL), and (2-fluorophenyl)methanesulfonyl chloride (0.03 mL, 0.220 mmol). After stirring overnight at rt, the reaction was diluted with DCM and washed with 1N KHSO$_4$ (aq) (10 mL), dried (Na$_2$SO$_4$), filtered and evaporated. The crude product was purified by flash chromatography through silica gel (0-50% EtOAc/DCM) to provide 57 mg (72% yield) of the title compound as a solid. LCMS (ESI) [M+H]$^+$=717.6, rt=2.00 min.

Step 2: (S)—N-(2-Fluoro-6-methyl-5-((3-(2-(piperidin-3-ylamino)pyrimidin-4-yl)pyridin-2-yl)oxy)naphthalen-1-yl)-1-(2-fluorophenyl)methanesulfonamide

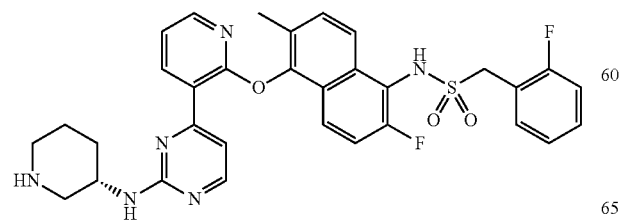

Prepared using (S)-tert-butyl 3-((4-(2-((6-fluoro-5-((2-fluorophenyl)methylsulfonamido)-2-methylnaphthalen-1-yl)oxy)pyridin-3-yl)pyrimidin-2-yl)amino)piperidine-1-carboxylate (55 mg, 0.08 mmol), 1,4-dioxane (0.5 mL) and hydrochloric acid (4 M in dioxane, 1 mL, 4 mmol). After 90 min, the suspension was diluted with Et$_2$O (15 mL) and the precipitate was filtered and washed with Et$_2$O. The precipitate was dissolved in MeCN and water and lyophilized to provide 49 mg (98% yield) of 391 as a fluffy light yellow solid. LCMS (ESI) [M+H]$^+$=617.3, rt=1.48 min; $^1$H NMR (400 MHz, d6-dmso) δ 9.99 (s, 1H), 9.20-8.91 (m, 2H), 8.71 (s, 1H), 8.48 (d, J=5.2 Hz, 1H), 8.09 (dd, J=4.8, 1.9 Hz, 1H), 8.02 (d, J=8.7 Hz, 1H), 7.74 (dd, J=9.3, 5.1 Hz, 1H), 7.64-7.41 (m, 6H), 7.27 (ddd, J=16.1, 8.1, 3.0 Hz, 3H), 4.63 (s, 2H), 4.29 (s, 1H), 3.43 (d, J=9.8 Hz, 1H), 3.20 (d, J=12.4 Hz, 1H), 2.94-2.75 (m, 2H), 2.19 (s, 3H), 2.02 (d, J=10.9 Hz, 1H), 1.96-1.87 (m, 1H), 1.82-1.70 (m, 1H), 1.68-1.57 (m, 1H).

Example 392 (S)—N-(2-Fluoro-6-methyl-5-((3-(2-(piperidin-3-ylamino)pyrimidin-4-yl)pyridin-2-yl)oxy)naphthalen-1-yl)-1-(2-(trifluoromethyl)phenyl)methanesulfonamide 392

Step 1: (S)-tert-Butyl 3-((4-(2-((6-fluoro-2-methyl-5-((2-(trifluoromethyl)phenyl)methylsulfonamido)naphthalen-1-yl)oxy)pyridin-3-yl)pyrimidin-2-yl)amino)piperidine-1-carboxylate

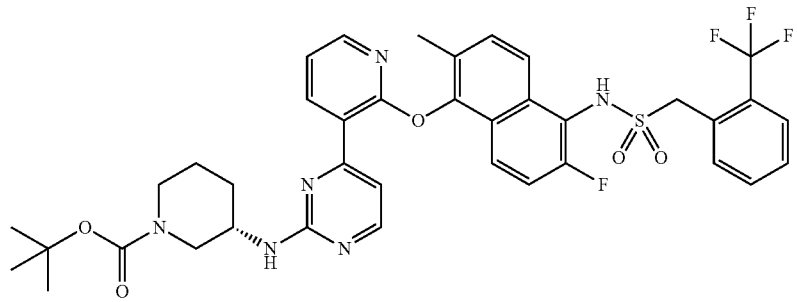 [SMILES: Cc1ccc2c(NS(=O)(=O)Cc3ccccc3C(F)(F)F)c(F)ccc2c1Oc1ncccc1-c1ccnc(N[C@H]2CCCN(C(=O)OC(C)(C)C)C2)n1]

Prepared using (S)-tert-butyl 3-((4-(2-((5-amino-6-fluoro-2-methylnaphthalen-1-yl)oxy)pyridin-3-yl)pyrimidin-2-yl)amino)piperidine-1-carboxylate from Example 275 (60 mg, 0.110 mmol), pyridine (0.13 mL, 1.65 mmol), DCM (0.4 mL), and (2-fluorophenyl)methanesulfonyl chloride (0.03 mL, 0.22 mmol). After stirring 2.5 h at rt, the reaction was diluted with DCM and washed with 1N KHSO$_4$(aq) (10 mL), dried (Na$_2$SO$_4$), filtered and evaporated. The crude product was purified by flash chromatography through silica gel (0-50% EtOAc/DCM) to provide 50 mg (84% yield) of the title compound as a solid. LCMS (ESI) [M+H]$^+$=767.6, rt=2.06 min.

Step 2: (S)—N-(2-Fluoro-6-methyl-5-((3-(2-(piperidin-3-ylamino)pyrimidin-4-yl)pyridin-2-yl)oxy)naphthalen-1-yl)-1-(2-fluorophenyl)methanesulfonamide

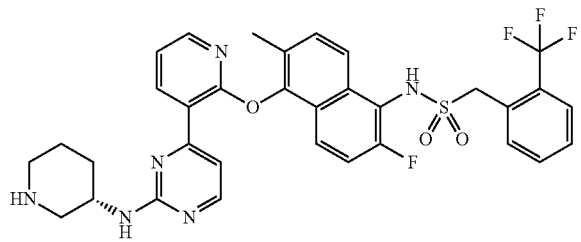 [SMILES: Cc1ccc2c(NS(=O)(=O)Cc3ccccc3C(F)(F)F)c(F)ccc2c1Oc1ncccc1-c1ccnc(N[C@H]2CCCNC2)n1]

Prepared using (S)-tert-butyl 3-((4-(2-((6-fluoro-2-methyl-5-((2-(trifluoromethyl)phenyl)methylsulfonamido)naphthalen-1-yl)oxy)pyridin-3-yl)pyrimidin-2-yl)amino)piperidine-1-carboxylate (58 mg, 0.08 mmol), 1,4-dioxane (0.5 mL) and hydrochloric acid (4 M in dioxane, 1 mL, 4 mmol). After 90 min, the suspension was diluted with Et$_2$O (15 mL) and the precipitate was filtered and washed with Et$_2$O. The precipitate was dissolved in MeCN and water and lyophilized to provide 40 mg (74% yield) of 392 as a fluffy light yellow solid. LCMS (ESI) [M+H]$^+$=667.4, rt=1.55 min; $^1$H NMR (400 MHz, d6-dmso) δ 10.13 (s, 1H), 8.97-8.73 (m, 2H), 8.72-8.52 (m, 1H), 8.48 (d, J=5.2 Hz, 1H), 8.09 (dd, J=4.8, 2.0 Hz, 1H), 8.03 (d, J=8.7 Hz, 1H), 7.80 (d, J=7.8 Hz, 1H), 7.78-7.70 (m, 3H), 7.66-7.47 (m, 5H), 7.30 (dd, J=7.6, 4.8 Hz, 1H), 4.81 (s, 2H), 4.26 (s, 1H), 3.38-3.29 (m, 1H), 3.21 (d, J=12.3 Hz, 1H), 2.96-2.77 (m, 2H), 2.19 (s, 3H), 2.01 (d, J=13.2 Hz, 1H), 1.97-1.86 (m, 1H), 1.81-1.56 (m, 2H).

Example 393 (S)—N-(2-Fluoro-6-methyl-5-((3-(2-((S)-piperidin-3-ylamino)pyrimidin-4-yl)pyridin-2-yl)oxy)naphthalen-1-yl)-2-methoxypropane-1-sulfonamide hydrochloride (Isomer-1)

Step 1: (3S)-tert-Butyl 3-((4-(2-((6-fluoro-5-(2-methoxypropylsulfonamido)-2-methylnaphthalen-1-yl)oxy)pyridin-3-yl)pyrimidin-2-yl)amino)piperidine-1-carboxylate

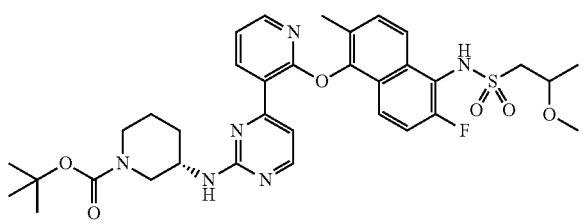 [SMILES: COC(C)CS(=O)(=O)Nc1c(F)ccc2c(Oc3ncccc3-c3ccnc(N[C@H]4CCCN(C(=O)OC(C)(C)C)C4)n3)c(C)ccc12]

The General Procedure A was followed using (S)-tert-butyl 3-((4-(2-((5-amino-6-fluoro-2-methylnaphthalen-1-yl)oxy)pyridin-3-yl)pyrimidin-2-yl)amino)piperidine-1-carboxylate from Example 275 (250 mg, 0.46 mmol), pyridine (0.38 mL), CH$_2$Cl$_2$ (2.5 mL), and 2-methoxypropane-1-sulfonyl chloride (158 mg, 0.92 mmol). After 18 h, a further portion of 2-methoxypropane-1-sulfonyl chloride (158 mg, 0.92 mmol) was added and stirred overnight. After a further 20 h, the mixture was diluted with EtOAc (50 mL), washed with 1M HCl (2×10 mL), then saturated aqueous NaHCO$_3$ (10 mL), then saturated aqueous NaCl (10 mL), dried (MgSO$_4$), filtered and concentrated in vacuo. The crude was purified by flash chromatography through silica gel (50% EtOAc/hexanes) to provide 182 mg (58% yield) of the title compound. LCMS (ESI) [M+H]$^+$=681.2.

Step 2: (S)-tert-Butyl 3-((4-(2-((6-fluoro-5-((S)-2-methoxypropylsulfonamido)-2-methylnaphthalen-1-yl)oxy)pyridin-3-yl)pyrimidin-2-yl)amino)piperidine-1-carboxylate (Isomer-1) and (S)-tert-butyl 3-((4-(2-((6-fluoro-5-((R)-2-methoxypropylsulfonamido)-2-methylnaphthalen-1-yl)oxy)pyridin-3-yl)pyrimidin-2-yl)amino)piperidine-1-carboxylate (Isomer-2)

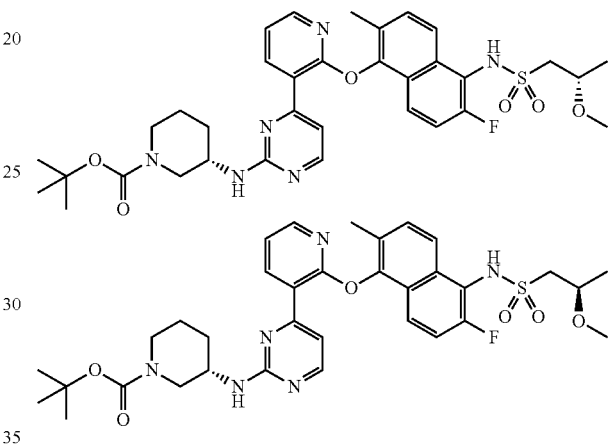

The stereoisomers from Step 1 were subjected to chiral SFC purification (conditions: Chiralpak IC at 40° C., 5 um, 10×250 mm, 10 mL/min, 40% MeOH, 150 bar, 20 min/inj.), to provide two stereoisomers enantiomeric at the 2-methoxypropane position. Isomer-1: (S)-tert-butyl 3-((4-(2-((6-fluoro-5-((S)-2-methoxypropylsulfonamido)-2-methylnaphthalen-1-yl)oxy)pyridin-3-yl)pyrimidin-2-yl)amino)piperidine-1-carboxylate, 50 mg (28% yield), LCMS (ESI) [M+H]$^+$=681.3; and Isomer-2: (S)-tert-butyl 3-((4-(2-((6-fluoro-5-((R)-2-methoxypropylsulfonamido)-2-methylnaphthalen-1-yl)oxy)pyridin-3-yl)pyrimidin-2-yl)amino)piperidine-1-carboxylate, 61 mg (34% yield), LCMS (ESI) [M+H]$^+$=681.3.

Step 2: (S)—N-(2-Fluoro-6-methyl-5-((3-(2-((S)-piperidin-3-ylamino)pyrimidin-4-yl)pyridin-2-yl)oxy)naphthalen-1-yl)-2-methoxypropane-1-sulfonamide hydrochloride 393

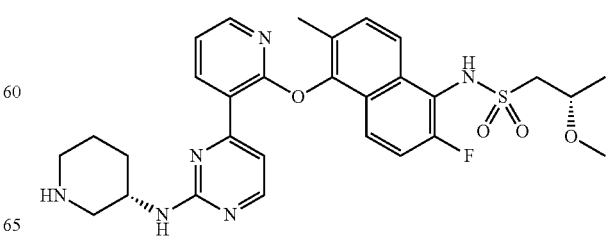

Prepared according to General Procedure B using (S)-tert-butyl 3-((4-(2-(((6-fluoro-5-((S)-2-methoxypropylsulfonamido)-2-methylnaphthalen-1-yl)oxy)pyridin-3-yl)pyrimidin-2-yl)amino)piperidine-1-carboxylate (isomer-1) (51 mg, 0.070 mmol), 1,4-dioxane (1.0 mL), and hydrochloric acid (4 M in dioxane, 0.5 mL, 2.0 mmol). After 4 h, the mixture was concentrated in vacuo, suspended in MeCN, the supernatant liquid was removed and the rinse was repeated twice. The residue was dissolved in H$_2$O and MeCN (acetonitrile) and lyophilized to provide 35 mg (76% yield) of 393. LCMS (ESI) [M+H]$^+$=581.1; $^1$H NMR (500 MHz, MeOD) δ 8.73 (s, 1H), 8.47 (d, J=5.0 Hz, 1H), 8.20 (d, J=8.7 Hz, 1H), 8.05 (d, J=4.0 Hz, 1H), 7.83 (s, 1H), 7.77 (dd, J=8.6, 5.1 Hz, 1H), 7.58 (d, J=8.7 Hz, 1H), 7.33 (t, J=9.1 Hz, 1H), 7.30-7.24 (m, 1H), 4.46 (s, 1H), 3.97 (h, J=6.2 Hz, 1H), 3.68-3.60 (m, 1H), 3.53 (dd, J=14.2, 6.3 Hz, 1H), 3.37 (s, 3H), 3.35-3.32 (m, 2H), 3.14-3.00 (m, 2H), 2.25 (s, 3H), 2.24-2.18 (m, 1H), 2.15-2.06 (m, 1H), 1.99-1.75 (m, 2H), 1.33 (d, J=6.2 Hz, 3H). The absolute stereochemistry of the methoxy group was randomly assigned.

Example 394 (R)—N-(2-Fluoro-6-methyl-5-((3-(2-((S)-piperidin-3-ylamino)pyrimidin-4-yl)pyridin-2-yl)oxy)naphthalen-1-yl)-2-methalen-yl)-2-methoxypropane-1-sulfonamide hydrochloride (Isomer-2)

Step 1: (R)—N-(2-Fluoro-6-methyl-5-((3-(2-((S)-piperidin-3-ylamino)pyrimidin-4-yl)pyridin-2-yl)oxy)naphthalen-1-yl)-2-methoxypropane-1-sulfonamide hydrochloride 394

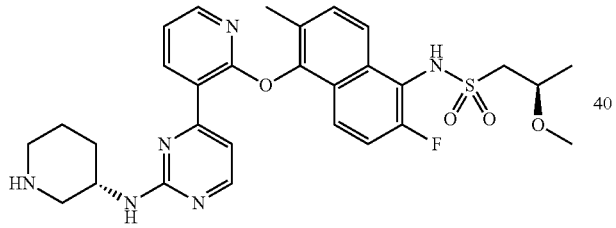

Prepared according to General Procedure B using (S)-tert-butyl 3-((4-(2-(((6-fluoro-5-((R)-2-methoxypropylsulfonamido)-2-methylnaphthalen-1-yl)oxy)pyridin-3-yl)pyrimidin-2-yl)amino)piperidine-1-carboxylate (isomer-2) (61 mg, 0.090 mmol), 1,4-dioxane (1.0 mL), and hydrochloric acid (4 M in dioxane, 0.5 mL, 2.0 mmol). After 4 h, the mixture was concentrated in vacuo, suspended in MeCN, the supernatant liquid was removed and the rinse was repeated twice. The residue was dissolved in H$_2$O and MeCN and lyophilized to provide 44 mg (80% yield) of 394. LCMS (ESI) [M+H]$^+$=581.1; $^1$H NMR (500 MHz, MeOD) δ 8.74 (s, 1H), 8.47 (d, J=5.8 Hz, 1H), 8.20 (d, J=8.8 Hz, 1H), 8.05 (dd, J=4.7, 1.8 Hz, 1H), 7.84 (s, 1H), 7.77 (dd, J=9.3, 5.0 Hz, 1H), 7.59 (d, J=8.8 Hz, 1H), 7.33 (t, J=9.5 Hz, 1H), 7.28 (dd, J=7.6, 4.8 Hz, 1H), 4.47 (s, 1H), 4.03-3.91 (m, 1H), 3.64 (dd, J=12.3, 3.4 Hz, 1H), 3.53 (dd, J=14.3, 6.3 Hz, 1H), 3.37 (s, 3H), 3.36-3.32 (m, 2H), 3.15-3.01 (m, 2H), 2.25 (s, 3H), 2.25-2.18 (m, 1H), 2.16-2.07 (m, 1H), 1.99-1.77 (m, 2H), 1.33 (d, J=6.3 Hz, 3H). The absolute stereochemistry of the methoxy group was randomly assigned.

Example 395 (1R,2R)-2-((6-Methyl-5-((3-(2-((S)-piperidin-3-ylamino)pyrimidin-4-yl)pyridin-2-yl)oxy)naphthalen-1-yl)amino)cyclopentanol hydrochloride (Isomer-1)

Step 1: tert-Butyl (3S)-3-[[4-[2-[[5-[(2-hydroxycyclopentyl)amino]-2-methyl-1-naphthyl]oxy]-3-pyridyl]pyrimidin-2-yl]amino]piperidine-1-carboxylate

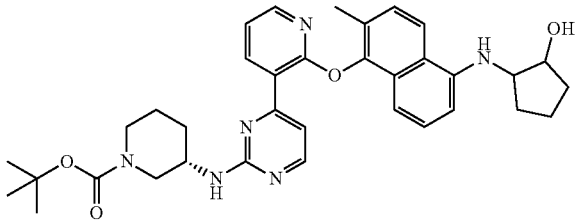 [SMILES: Cc1ccc2c(NC3CCCC3O)cccc2c1Oc1ncccc1-c1ccnc(N[C@H]2CCCN(C(=O)OC(C)(C)C)C2)n1]

Prepared according to General Procedure F using tert-butyl (3S)-3-[[4-[2-[(5-amino-2-methyl-1-naphthyl)oxy]-3-pyridyl]pyrimidin-2-yl]amino]piperidine-1-carboxylate (200 mg, 0.38 mmol), 1,2-epoxycyclopentane (40 mg, 0.48 mmol), AcOH (0.5 mL) and the reaction was stirred at 70° C. overnight. The crude reaction was concentrated in vacuo and purified by flash column chromatography through silica gel (0-100% EtOAc/CH$_2$Cl$_2$) to provide 95 mg (41% yield) of the title compound. LCMS (ESI) [M+H]$^+$=610.75.

Step 2: (S)-tert-Butyl 3-((4-(2-((5-(((1R,2R)-2-hydroxycyclopentyl)amino)-2-methylnaphthalen-1-yl)oxy)pyridin-3-yl)pyrimidin-2-yl)amino)piperidine-1-carboxylate (Isomer-1) and (S)-tert-butyl 3-((4-(2-((5-(((1S,2S)-2-hydroxycyclopentyl)amino)-2-methylnaphthalen-1-yl)oxy)pyridin-3-yl)pyrimidin-2-yl)amino)piperidine-1-carboxylate (Isomer-2)

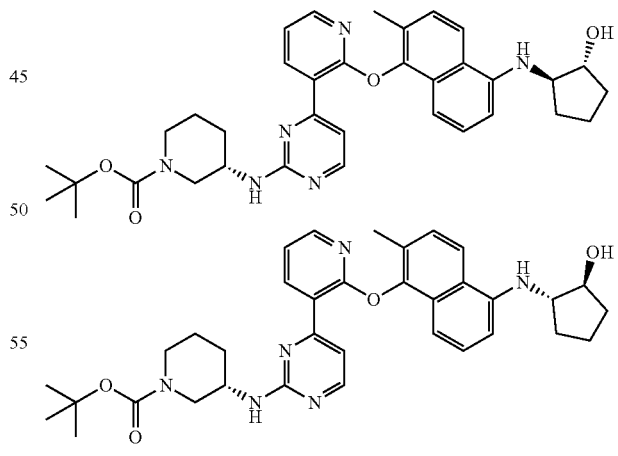

The stereoisomers from Step 1 were subjected to chiral normal phase semi-prep purification (conditions: Chiralpak IB, 5 uM, 20×250 mm, 5:5:90 MeOH:DCM:Hexane, 5 mg/inj.) to provide two stereoisomers enantiomeric at the trans-cyclopentyl position. Isomer-1: (S)-tert-butyl 3-((4-(2-((5-(((1R,2R)-2-hydroxycyclopentyl)amino)-2-methylnaphthalen-1-yl)oxy)pyridin-3-yl)pyrimidin-2-yl)amino)piperidine-1-carboxylate, 26 mg (40% yield), white solid, ee=99%; LCMS (ESI) [M+H]⁺=611.4; and Isomer-2: (S)-tert-butyl 3-((4-(2-((5-(((1S,2S)-2-hydroxycyclopentyl)amino)-2-methylnaphthalen-1-yl)oxy)pyridin-3-yl)pyrimidin-2-yl)amino)piperidine-1-carboxylate, 26 mg (40% yield), white solid, ee=99%, LCMS (ESI) [M+H]⁺=611.4.

Step 3: (1R,2R)-2-((6-Methyl-5-((3-(2-((S)-piperidin-3-ylamino)pyrimidin-4-yl)pyridin-2-yl)oxy)naphthalen-1-yl)amino)cyclopentanol hydrochloride (Isomer-1) 395

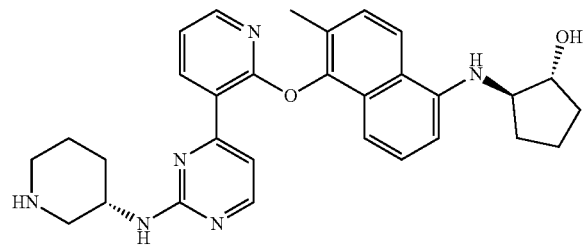 [SMILES: Cc1ccc2c(N[C@@H]3CCC[C@H]3O)cccc2c1Oc1ncccc1-c1ccnc(N[C@H]2CCCNC2)n1]

Prepared according to General Procedure B using (S)-tert-butyl 3-((4-(2-((5-(((1R,2R)-2-hydroxycyclopentyl)amino)-2-methylnaphthalen-1-yl)oxy)pyridin-3-yl)pyrimidin-2-yl)amino)piperidine-1-carboxylate (26 mg, 0.04 mmol), 1,4-dioxane (1 mL), and hydrochloric acid (4 M in dioxane, 0.5 mL, 2.0 mmol). After 3 hour, the mixture was diluted with Et₂O and the resulting solids collected by filtration then dissolved in H₂O and MeCN and lyophilized to provide 21 mg (90% yield) of 395. LCMS (ESI) [M+H]⁺=511.2; ¹H NMR (400 MHz, DMSO-d₆) 8.72 (d, J=7.0 Hz, 1H), 8.46 (d, J=5.6 Hz, 1H), 8.01 (dd, J=4.8, 1.9 Hz, 1H), 7.99 (d, J=8.8 Hz, 1H), 7.79 (d, J=5.3 Hz, 1H), 7.57 (d, J=8.7 Hz, 1H), 7.50 (d, J=8.0 Hz, 1H), 7.39 (t, J=8.0 Hz, 1H), 7.26 (dd, J=7.6, 4.9 Hz, 1H), 7.21 (d, J=7.0 Hz, 1H), 4.49-4.35 (m, 1H), 4.31 (dd, J=11.9, 5.8 Hz, 1H), 3.84 (dd, J=12.6, 6.7 Hz, 1H), 3.63 (dd, J=16.4, 7.7 Hz, 1H), 3.40-3.33 (m, 1H), 3.12-3.00 (m, 2H), 2.28 (s, 3H), 2.25-2.04 (m, 4H), 2.00-1.75 (m, 5H), 1.76-1.62 (m, 1H). The absolute stereochemistry of the alcohol was randomly assigned.

Example 396 (1S,2S)-2-((6-Methyl-5-((3-(2-((S)-piperidin-3-ylamino)pyrimidin-4-yl)pyridin-2-yl)oxy)naphthalen-1-yl)amino)cyclopentanol hydrochloride (Isomer-2)

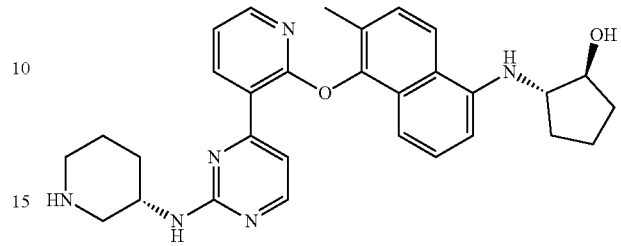

Prepared according to General Procedure B using (S)-tert-butyl 3-((4-(2-((5-(((1S,2S)-2-hydroxycyclopentyl)amino)-2-methylnaphthalen-1-yl)oxy)pyridin-3-yl)pyrimidin-2-yl)amino)piperidine-1-carboxylate (26 mg, 0.04 mmol), 1,4-dioxane (1 mL), and hydrochloric acid (4 M in dioxane, 0.5 mL, 2.0 mmol). After 3 hour, the mixture was diluted with Et₂O and the resulting solids collected by filtration then dissolved in H₂O and MeCN and lyophilized to provide 21 mg (90% yield) of 396. LCMS (ESI) [M+H]⁺=511.2; ¹H NMR (400 MHz, DMSO-d₆) 8.72 (d, J=7.0 Hz, 1H), 8.46 (d, J=5.6 Hz, 1H), 8.01 (dd, J=4.8, 1.9 Hz, 1H), 7.99 (d, J=8.8 Hz, 1H), 7.79 (d, J=5.3 Hz, 1H), 7.57 (d, J=8.7 Hz, 1H), 7.50 (d, J=8.0 Hz, 1H), 7.39 (t, J=8.0 Hz, 1H), 7.26 (dd, J=7.6, 4.9 Hz, 1H), 7.21 (d, J=7.0 Hz, 1H), 4.49-4.35 (m, 1H), 4.31 (dd, J=11.9, 5.8 Hz, 1H), 3.84 (dd, J=12.6, 6.7 Hz, 1H), 3.63 (dd, J=16.4, 7.7 Hz, 1H), 3.40-3.33 (m, 1H), 3.12-3.00 (m, 2H), 2.28 (s, 3H), 2.25-2.04 (m, 4H), 2.00-1.75 (m, 5H), 1.76-1.62 (m, 1H). The absolute stereochemistry of the alcohol was randomly assigned.

Example 397 (S)—N-(2-Fluoro-6-methyl-5-((3-(2-(piperidin-3-ylamino)pyrimidin-4-yl)pyridin-2-yl)oxy)naphthalen-1-yl)butane-1-sulfonamide hydrochloride Step 1: (S)-tert-Butyl 3-((4-(2-((5-(butylsulfonamido)-6-fluoro-2-methylnaphthalen-1-yl)oxy)pyridin-3-yl)pyrimidin-2-yl)amino)piperidine-1-carboxylate

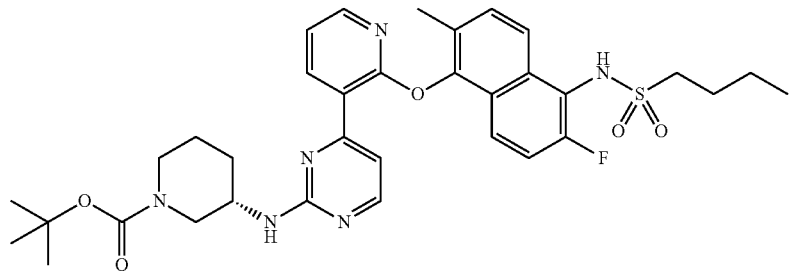 [SMILES: CCCCS(=O)(=O)Nc1c(F)ccc2c(Oc3ncccc3-c3ccnc(N[C@H]4CCCN(C(=O)OC(C)(C)C)C4)n3)c(C)ccc12]

The General Procedure A was followed using (S)-tert-butyl 3-((4-(2-((5-amino-6-fluoro-2-methylnaphthalen-1-yl)oxy)pyridin-3-yl)pyrimidin-2-yl)amino)piperidine-1-carboxylate from Example 275 (75 mg, 0.14 mmol), pyridine (0.17 mL), CH$_2$Cl$_2$ (0.8 mL), 4-dimethylaminopyridine (1.7 mg, 0.01 mmol) and butane-1-sulfonyl chloride (43 mg, 0.28 mmol). After 18 h, a further portion of butane-1-sulfonyl chloride (43 mg, 0.28 mmol) was added and after a further 18 h the mixture was diluted with CH$_2$Cl$_2$ (50 mL) and washed with 1M KHSO$_4$ (10 mL), dried by passing through a phase cartridge separator and concentrated in vacuo. The crude was purified by flash chromatography through silica gel (0-50% EtOAc/CH$_2$Cl$_2$) to provide 42 mg (46% yield) of the title compound. LCMS (ESI) [M+H]$^+$=665.5.

Step 2: (S)—N-(2-Fluoro-6-methyl-5-((3-(2-(piperidin-3-ylamino)pyrimidin-4-yl)pyridin-2-yl)oxy)naphthalen-1-yl)butane-1-sulfonamide hydrochloride 397

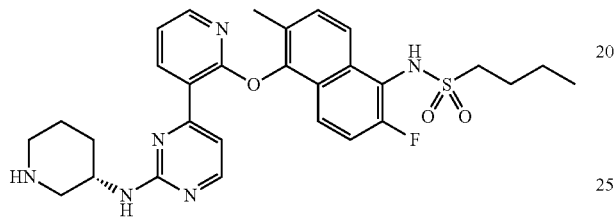

Prepared according to General Procedure B using (S)-tert-butyl 3-((4-(2-((5-(butylsulfonamido)-6-fluoro-2-methylnaphthalen-1-yl)oxy)pyridin-3-yl)pyrimidin-2-yl)amino)piperidine-1-carboxylate (42 mg, 0.06 mmol), 1,4-dioxane (0.2 mL), and hydrochloric acid (4 M in dioxane, 0.49 mL, 2.0 mmol). After 45 min, the mixture was diluted with Et$_2$O and the resulting solids collected by filtration then dissolved in H$_2$O and MeCN and lyophilized to provide 34 mg (90% yield) of 397. LCMS (ESI) [M+H]$^+$=565.5; $^1$H NMR (400 MHz, DMSO-d$_6$) δ 9.68 (s, 1H), 8.85 (bs, 2H), 8.63 (s, 1H), 8.47 (d, J=5.2 Hz, 1H), 8.12-8.03 (m, 2H), 7.71 (dd, J=9.3, 5.2 Hz, 1H), 7.62 (t, J=8.9 Hz, 1H), 7.60-7.50 (m, 2H), 7.45 (t, J=9.5 Hz, 1H), 7.29 (dd, J=7.6, 4.8 Hz, 1H), 4.28 (s, 1H), 3.47-3.36 (m, 1H), 3.27-3.11 (m, 3H), 2.94-2.76 (m, 2H), 2.19 (s, 3H), 2.07-1.96 (m, 1H), 1.97-1.87 (m, 1H), 1.87-1.55 (m, 4H), 1.51-1.38 (m, 2H), 0.92 (t, J=7.4 Hz, 3H).

Example 398 (S)-3,3-Difluoro-N-(2-fluoro-6-methyl-5-((3-(2-(piperidin-3-ylamino)pyrimidin-4-yl)pyridin-2-yl)oxy)naphthalen-1-yl)propane-1-sulfonamide hydrochloride Step 1: (S)-tert-Butyl 3-((4-(2-((5-(3,3-difluoropropylsulfonamido)-6-fluoro-2-methylnaphthalen-1-yl)oxy)pyridin-3-yl)pyrimidin-2-yl)amino)piperidine-1-carboxylate

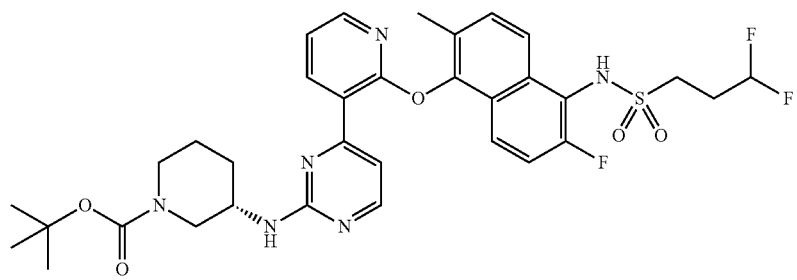 [SMILES: Cc1ccc2c(NS(=O)(=O)CCC(F)F)c(F)ccc2c1Oc1ncccc1-c1ccnc(N[C@H]2CCCN(C(=O)OC(C)(C)C)C2)n1]

The General Procedure A was followed using (S)-tert-butyl 3-((4-(2-((5-amino-6-fluoro-2-methylnaphthalen-1-yl)oxy)pyridin-3-yl)pyrimidin-2-yl)amino)piperidine-1-carboxylate from Example 275 (60 mg, 0.11 mmol), pyridine (0.13 mL), CH$_2$Cl$_2$ (0.37 mL), 4-dimethylaminopyridine (1.2 mg, 0.01 mmol) and 3,3-difluoropropane-1-sulfonyl chloride (39 mg, 0.22 mmol). After 18 h, the mixture was diluted with CH$_2$Cl$_2$ (50 mL) and washed with 1M KHSO$_4$ (10 mL), dried (Na$_2$SO$_4$), filtered and concentrated in vacuo. The crude was purified by flash chromatography through silica gel (0-50% EtOAc/CH$_2$Cl$_2$) to provide 30 mg (40% yield) of the title compound. LCMS (ESI) [M+H]$^+$=687.3.

Step 2: (S)-3,3-Difluoro-N-(2-fluoro-6-methyl-5-((3-(2-(piperidin-3-ylamino)pyrimidin-4-yl)pyridin-2-yl)oxy)naphthalen-1-yl)propane-1-sulfonamide hydrochloride 398

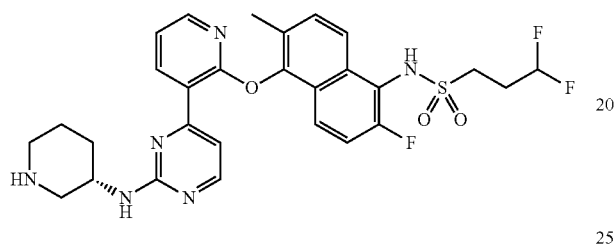

Prepared according to General Procedure B using (S)-tert-butyl 3-((4-(2-((5-(3,3-difluoropropylsulfonamido)-6-fluoro-2-methylnaphthalen-1-yl)oxy)pyridin-3-yl)pyrimidin-2-yl)amino)piperidine-1-carboxylate (30 mg, 0.04 mmol), 1,4-dioxane (0.5 mL), and hydrochloric acid (4 M in dioxane, 1.0 mL, 4.0 mmol). After 45 min, the mixture was diluted with Et$_2$O and the resulting solids collected by filtration then dissolved in H$_2$O and MeCN and lyophilized to provide 26 mg (94% yield) of 398. LCMS (ESI) [M+H]$^+$=587.3; $^1$H NMR (400 MHz, DMSO-d$_6$) δ 9.99 (d, J=2.4 Hz, 1H), 9.03-8.75 (m, 2H), 8.72-8.54 (m, 1H), 8.48 (d, J=5.2 Hz, 1H), 8.08 (dd, J=4.8, 2.0 Hz, 1H), 8.05 (d, J=8.7 Hz, 1H), 7.74 (dd, J=9.3, 5.2 Hz, 1H), 7.65 (d, J=8.8 Hz, 1H), 7.59-7.51 (m, 2H), 7.48 (t, J=9.5 Hz, 1H), 7.29 (dd, J=7.6, 4.8 Hz, 1H), 6.28 (tt, J=56.4, 4.1 Hz, 1H), 4.26 (s, 1H), 3.37-3.31 (m, 4H), 3.21 (d, J=11.5 Hz, 1H), 2.96-2.77 (m, 2H), 2.47-2.34 (m, 2H), 2.20 (s, 3H), 2.01 (d, J=9.2 Hz, 1H), 1.92 (d, J=15.0 Hz, 1H), 1.80-1.56 (m, 1H).

Example 399 (S)-2-Cyclopropyl-N-(2-fluoro-6-methyl-5-((3-(2-(piperidin-3-ylamino)pyrimidin-4-yl)pyridin-2-yl)oxy)naphthalen-1-yl)ethanesulfonamide hydrochloride Step 1: (S)-tert-Butyl 3-((4-(2-((5-(2-cyclopropylethylsulfonamido)-6-fluoro-2-methylnaphthalen-1-yl)oxy)pyridin-3-yl)pyrimidin-2-yl)amino)piperidine-1-carboxylate

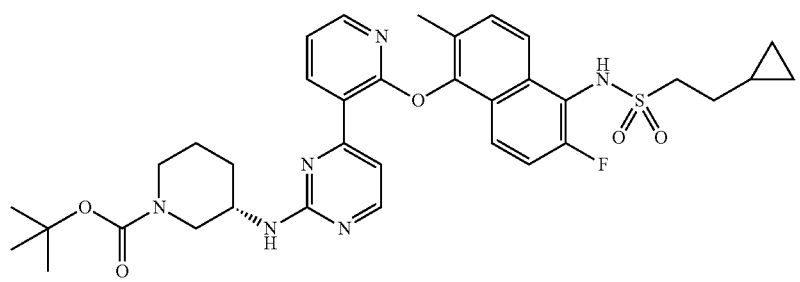 [SMILES: Cc1ccc2c(NS(=O)(=O)CCC3CC3)c(F)ccc2c1Oc1ncccc1-c1ccnc(N[C@H]2CCCN(C(=O)OC(C)(C)C)C2)n1]

The General Procedure A was followed using (S)-tert-butyl 3-((4-(2-((5-amino-6-fluoro-2-methylnaphthalen-1-yl)oxy)pyridin-3-yl)pyrimidin-2-yl)amino)piperidine-1-carboxylate from Example 275 (75 mg, 0.14 mmol), pyridine (0.17 mL), CH$_2$Cl$_2$ (0.8 mL), 4-dimethylaminopyridine (1.7 mg, 0.01 mmol) and 2-cyclopropylethanesulfonyl chloride (46 mg, 0.28 mmol). After 18 h, a further portion of 2-cyclopropylethanesulfonyl chloride (46 mg, 0.28 mmol) was added and after a further 18 h the mixture was diluted with CH$_2$Cl$_2$ (50 mL) and washed with 1M KHSO$_4$ (10 mL), dried by passing through a phase cartridge separator and concentrated in vacuo. The crude was purified by flash chromatography through silica gel (0-50% EtOAc/CH$_2$Cl$_2$) to provide 51 mg (55% yield) of the title compound. LCMS (ESI) [M+H]$^+$=677.3.

Example 400 (S)-1-Cyclobutyl-N-(2-fluoro-6-methyl-5-((3-(2-(piperidin-3-ylamino)pyrimidin-4-yl)pyridin-2-yl)oxy)naphthalen-1-yl)methanesulfonamide hydrochloride Step 1: (S)-tert-Butyl 3-((4-(2-((5-(cyclobutylmethylsulfonamido)-6-fluoro-2-methylnaphthalen-1-yl)oxy)pyridin-3-yl)pyrimidin-2-yl)amino)piperidine-1-carboxylate

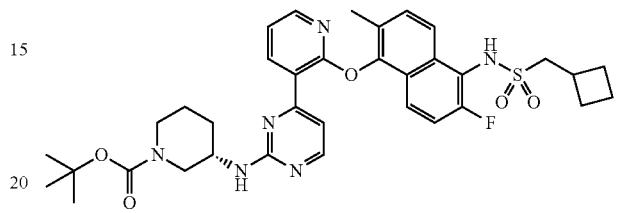

The General Procedure A was followed using (S)-tert-butyl 3-((4-(2-((5-amino-6-fluoro-2-methylnaphthalen-1-yl)oxy)pyridin-3-yl)pyrimidin-2-yl)amino)piperidine-1-carboxylate from Example 275 (150 mg, 0.28 mmol), pyridine (0.67 mL), CH$_2$Cl$_2$ (0.8 mL), and cyclobutylmethanesulfonyl chloride (139 mg, 0.83 mmol). After 18 h, the mixture was concentrated in vacuo and the crude was purified by flash chromatography through silica gel (0-50% EtOAc/CH$_2$Cl$_2$) to provide 110 mg (59% yield) of the title compound. LCMS (ESI) [M+H]$^+$=677.5.

Step 2: (S)-1-Cyclobutyl-N-(2-fluoro-6-methyl-5-((3-(2-(piperidin-3-ylamino)pyrimidin-4-yl)pyridin-2-yl)oxy)naphthalen-1-yl)methanesulfonamide hydrochloride 400

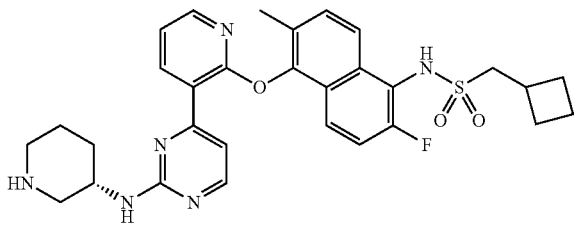

Prepared according to General Procedure B using (S)-tert-butyl 3-((4-(2-((5-(cyclobutylmethylsulfonamido)-6-fluoro-2-methylnaphthalen-1-yl)oxy)pyridin-3-yl)pyrimidin-2-yl)amino)piperidine-1-carboxylate (95 mg, 0.14 mmol), 1,4-dioxane (2.0 mL), and hydrochloric acid (4 M in dioxane, 2 mL, 8 mmol). After 1 h, the resulting solids were collected by filtration and washed with MTBE and 1,4-dioxane. The solids were then dissolved in H$_2$O and MeCN and lyophilized to provide 62 mg (72% yield) of 400. LCMS (ESI) [M+H]$^+$=577.1; $^1$HNMR (400 MHz, D$_2$O) δ 8.35 (s, 1H), 8.03 (d, J=6.0 Hz, 1H), 7.86 (d, J=8.7 Hz, 1H), 7.76 (d, J=3.2 Hz, 1H), 7.46 (s, 2H), 7.35 (d, J=8.7 Hz, 1H), 7.08 (dd, J=7.5, 5.0 Hz, 1H), 6.92 (s, 1H), 4.21 (s, 1H), 3.41 (d, J=9.2 Hz, 1H), 3.20 (t, J=10.1 Hz, 3H), 2.81-3.00 (m, 2H), 2.74-2.56 (m, 1H), 1.92 (d, J=14.8 Hz, 8H), 1.71-1.51 (m, 6H).

Step 2: (S)-2-Cyclopropyl-N-(2-fluoro-6-methyl-5-((3-(2-(piperidin-3-ylamino)pyrimidin-4-yl)pyridin-2-yl)oxy)naphthalen-1-yl)ethanesulfonamide hydrochloride 399

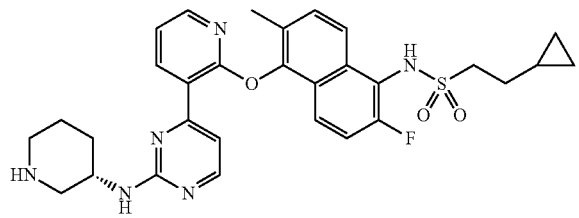 [SMILES: Cc1ccc2c(NS(=O)(=O)CCC3CC3)c(F)ccc2c1Oc1ncccc1-c1ccnc(N[C@H]2CCCNC2)n1]

Prepared according to General Procedure B using (S)-tert-butyl 3-((4-(2-((5-(2-cyclopropylethylsulfonamido)-6-fluoro-2-methylnaphthalen-1-yl)oxy)pyridin-3-yl)pyrimidin-2-yl)amino)piperidine-1-carboxylate (51 mg, 0.08 mmol), 1,4-dioxane (0.3 mL), and hydrochloric acid (4 M in dioxane, 0.6 mL, 2.4 mmol). After 1 h, the mixture was diluted with Et$_2$O and the resulting solids collected by filtration then dissolved in H$_2$O and MeCN and lyophilized to provide 40 mg (85% yield) of 399. LCMS (ESI) [M+H]$^+$=577.1; $^1$H NMR (400 MHz, DMSO-d$_6$) δ 9.72 (s, 1H), 8.93 (bs, 3H), 8.71 (s, 1H), 8.48 (d, J=5.2 Hz, 1H), 8.11-8.04 (m, 2H), 7.72 (dd, J=9.4, 5.2 Hz, 1H), 7.69-7.52 (m, 4H), 7.46 (t, J=9.5 Hz, 1H), 7.29 (dd, J=7.6, 4.8 Hz, 1H), 4.28 (s, 1H), 3.52-3.35 (m, 1H), 3.34-3.13 (m, 4H), 2.82 (d, J=9.8 Hz, 2H), 2.19 (s, 3H), 2.07-1.84 (m, 2H), 1.82-1.54 (m, 4H), 0.95-0.80 (m, 1H), 0.49-0.42 (m, 2H), 0.16-0.10 (m, 2H).

Example 401 N-[2-Fluoro-6-methyl-5-[[3-[2-[[(3S, 5S)-5-methyl-3-piperidyl]amino]pyrimidin-4-yl]-2-pyridyl]oxy]-1-naphthyl]-2-methyl-propane-1-sulfonamide hydrochloride Step 1: (3S,5S)-Benzyl 3-((4-(2-((5-amino-6-fluoro-2-methylnaphthalen-1-yl)oxy)pyridin-3-yl)pyrimidin-2-yl)amino)-5-methylpiperidine-1-carboxylate

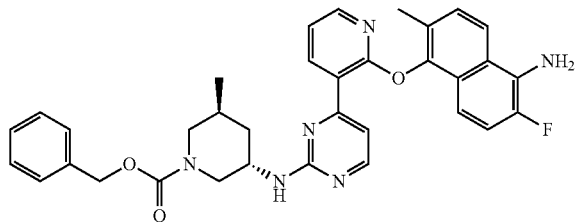 [SMILES: Cc1ccc2c(N)c(F)ccc2c1Oc1ncccc1-c1ccnc(N[C@H]2C[C@H](C)CN(C(=O)OCc3ccccc3)C2)n1]

To a solution of benzyl (3S,5S)-3-(tert-butoxycarbonylamino)-5-methyl-piperidine-1-carboxylate (812 mg, 2.33 mmol) in 1,4-dioxane (3 mL) was added 4 M HCl in dioxane (3 mL, 98 mmol). After 2 h, MTBE (15 mL) was added and the resulting solids were collected to provide (3S,5S)-benzyl 3-amino-5-methylpiperidine-1-carboxylate hydrochloride (490 mg, 74% yield).

To a solution of crude 2-fluoro-6-methyl-5-((3-(2-(methylsulfinyl)pyrimidin-4-yl)pyridin-2-yl)oxy)naphthalen-1-amine from Example 431 (272 mg, 0.95 mmol) in 1,4-dioxane (2 mL) was added triethylamine (0.26 mL, 193 mg, 1.91 mmol) and (3S,5S)-benzyl 3-amino-5-methylpiperidine-1-carboxylate hydrochloride (272 mg, 0.95 mmol). The mixture was stirred in a 115° C. oil bath overnight. After 18 h, the mixture was diluted with EtOAc (50 mL) and washed with H$_2$O (10 mL). The organic extract was adsorbed onto silica gel in vacuo and purified by flash chromatography through silica gel (0-100% EtOAc/hexanes) to provide 248 mg (66% yield) of the title compound. LCMS (ESI) [M+H]$^+$=593.5.

Step 2: Benzyl (3S,5S)-3-[[4-[2-[[6-fluoro-5-(isobutylsulfonylamino)-2-methyl-1-naphthyl]oxy]-3-pyridyl]pyrimidin-2-yl]amino]-5-methyl-piperidine-1-carboxylate

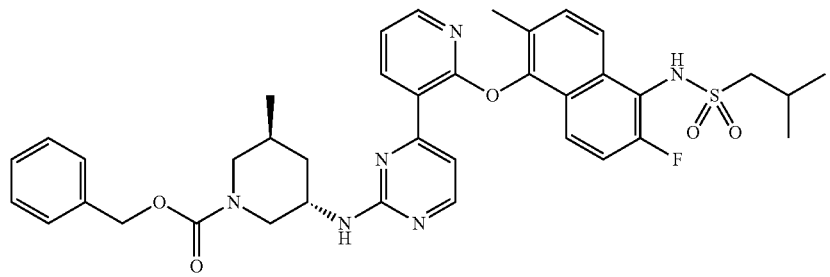 [SMILES: Cc1ccc2c(NS(=O)(=O)CC(C)C)c(F)ccc2c1Oc1ncccc1-c1ccnc(N[C@H]2C[C@H](C)CN(C(=O)OCc3ccccc3)C2)n1]

To a solution of benzyl (3S,5S)-3-[[4-[2-[(5-amino-6-fluoro-2-methyl-1-naphthyl)oxy]-3-pyridyl]pyrimidin-2-yl]amino]-5-methyl-piperidine-1-carboxylate (100 mg, 0.17 mmol) in DCM (0.8 mL) was added pyridine (409 uL, 5.06 mmol) and 2-methylpropane-1-sulfonyl chloride (79 mg, 0.51 mmol). The reaction mixture was stirred at rt for 2 days. The crude reaction was concentrated in vacuo and purified by flash column chromatography through silica gel (0-100% EtOAc/CH$_2$Cl$_2$) to provide 79 mg (66%) of the title compound. LCMS (ESI) [M+H]$^+$=712.83.

Step 3: N-[2-Fluoro-6-methyl-5-[[3-[2-[[(3S,5S)-5-methyl-3-piperidyl]amino]pyrimidin-4-yl]-2-pyridyl]oxy]-1-naphthyl]-2-methyl-propane-1-sulfonamide hydrochloride 401

Pd/C (10% in charcol) (150 mg) and ammonium formate (700 mg, 11 mmol) were suspended in methanol (5 mL). To the mixture was added benzyl (3S,5S)-3-[[4-[2-[[6-fluoro-5-(isobutylsulfonylamino)-2-methyl-1-naphthyl]oxy]-3-pyridyl]pyrimidin-2-yl]amino]-5-methyl-piperidine-1-carboxylate (79 mg, 0.11 mmol) in IPA/MeOH (2 mL/1 mL) solution. The reaction is stirred at RT for 20 min. The reaction mixture was filtered through a pad of Celite and was then washed with EtOAc and MeOH. The solvent was removed in vacuo and EtOAc/H$_2$O (30 mL/20 mL) was added to the residue. To the mixture was added Na$_2$CO$_3$ (saturated, 2 mL). The phases were separated and the organic extract was dried over MgSO$_4$, filtered and concentrated in vacuo. The resulting residue was dissolved in dioxane/MTBE (0.5 mL/5 mL). To the stirred solution was added HCl (100 μL, 4 M in dioxane). The precipitate was filtered and re-dissolved in MeCN/H$_2$O (2 mL/2 mL). Lyophilization provided 46 mg (67% yield) of 401. LCMS (ESI) [M+H]$^+$=579.4; $^1$H NMR (400 MHz, DMSO-d$_6$) 8.30 (d, J=7.5 Hz, 1H), 8.19 (d, J=5.9 Hz, 1H), 7.94 (d, J=8.7 Hz, 1H), 7.80 (dd, J=5.0, 1.8 Hz, 1H), 7.62 (s, 1H), 7.52 (d, J=5.8 Hz, 1H), 7.44 (d, J=8.7 Hz, 1H), 7.12 (dd, J=7.6, 5.1 Hz, 2H), 4.29 (s, 1H), 3.54 (d, J=12.2 Hz, 1H), 3.15 (t, J=12.5 Hz, 3H), 3.05 (s, 1H), 2.56 (s, 1H), 2.13 (dt, J=13.6, 6.6 Hz, 2H), 2.03 (s, 3H), 1.93 (d, J=14.7 Hz, 1H), 1.50 (s, 1H), 0.90 (d, J=6.7 Hz, 6H), 0.83 (d, J=6.7 Hz, 3H).

Example 402 (S)—N-(2-Fluoro-6-methyl-5-((3-(2-(piperidin-3-ylamino)pyrimidin-4-yl)pyridin-2-yl)oxy)naphthalen-1-yl)-1-(thiazol-4-yl)methanesulfonamide hydrochloride Step 1: (S)-tert-Butyl 3-((4-(2-((6-fluoro-2-methyl-5-(thiazol-4-ylmethylsulfonamido)naphthalen-1-yl)oxy)pyridin-3-yl)pyrimidin-2-yl)amino)piperidine-1-carboxylate

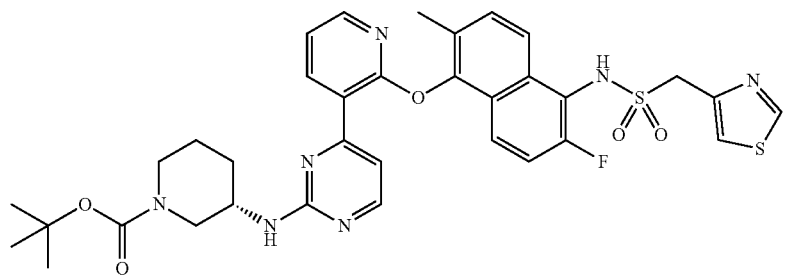 [SMILES: Cc1ccc2c(NS(=O)(=O)Cc3cscn3)c(F)ccc2c1Oc1ncccc1-c1ccnc(N[C@H]2CCCN(C(=O)OC(C)(C)C)C2)n1]

The General Procedure A was followed using (S)-tert-butyl 3-((4-(2-((5-amino-6-fluoro-2-methylnaphthalen-1-yl)oxy)pyridin-3-yl)pyrimidin-2-yl)amino)piperidine-1-carboxylate from Example 275 (80 mg, 0.15 mmol), pyridine (0.18 mL), $CH_2Cl_2$ (0.8 mL), and thiazol-4-ylmethanesulfonyl chloride (70 mg, 0.35 mmol). After 18 h, the mixture was diluted with $CH_2Cl_2$ (50 mL) and washed with 1M $KHSO_4$ (10 mL), dried over a phase cartridge separator and concentrated in vacuo. The crude was purified by flash chromatography through silica gel (0-50% EtOAc/$CH_2Cl_2$) to provide 62 mg (60% yield) of the title compound. LCMS (ESI) [M+H]$^+$=706.3.

Step 2: (S)—N-(2-Fluoro-6-methyl-5-((3-(2-(piperidin-3-ylamino)pyrimidin-4-yl)pyridin-2-yl)oxy)naphthalen-1-yl)-1-(thiazol-4-yl)methanesulfonamide hydrochloride 402

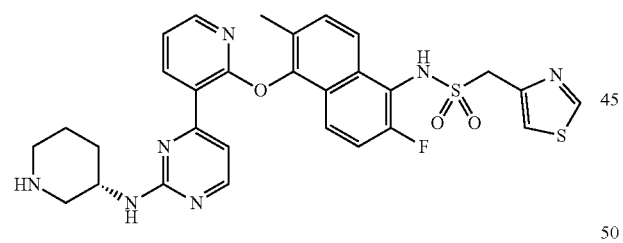

Prepared according to General Procedure B using (S)-tert-butyl 3-((4-(2-((6-fluoro-2-methyl-5-(thiazol-4-ylmethylsulfonamido)naphthalen-1-yl)oxy)pyridin-3-yl)pyrimidin-2-yl)amino)piperidine-1-carboxylate (62 mg, 0.09 mmol), 1,4-dioxane (0.3 mL), and hydrochloric acid (4 M in dioxane, 1 mL, 4 mmol). After 45 min, the mixture was diluted with $Et_2O$. The resulting solids were collected by filtration, dissolved in $H_2O$ and MeCN and lyophilized to provide 53 mg (93% yield) of 402. LCMS (ESI) [M+H]$^+$=606.2; $^1$H NMR (400 MHz, DMSO-$d_6$) δ 9.87 (s, 1H), 9.14 (d, J=2.0 Hz, 1H), 8.90 (bs, 2H), 8.77-8.55 (m, 1H), 8.48 (dd, J=5.2, 0.9 Hz, 1H), 8.08 (dd, J=5.7, 2.8 Hz, 2H), 7.81 (d, J=2.0 Hz, 1H), 7.73 (dd, J=9.2, 5.1 Hz, 1H), 7.66-7.53 (m, 3H), 7.48 (t, J=9.4 Hz, 1H), 7.29 (dd, J=7.6, 4.8 Hz, 1H), 4.77 (s, 2H), 4.43-4.15 (m, 1H), 3.21 (d, J=12.2 Hz, 2H), 2.95-2.76 (m, 2H), 2.19 (s, 3H), 2.06-1.72 (m, 2H), 1.71-1.55 (m, 2H).

Example 403 N-[2-Fluoro-6-methyl-5-[[3-[2-[[(3S)-3-piperidyl]amino]pyrimidin-4-yl]-2-pyridyl]oxy]-1-naphthyl]-1,3-benzodioxole-5-sulfonamide Step 1: tert-Butyl (3S)-3-[[4-[2-[[5-(1,3-benzodioxol-5-ylsulfonylamino)-6-fluoro-2-methyl-1-naphthyl]oxy]-3-pyridyl]pyrimidin-2-yl]amino]piperidine-1-carboxylate

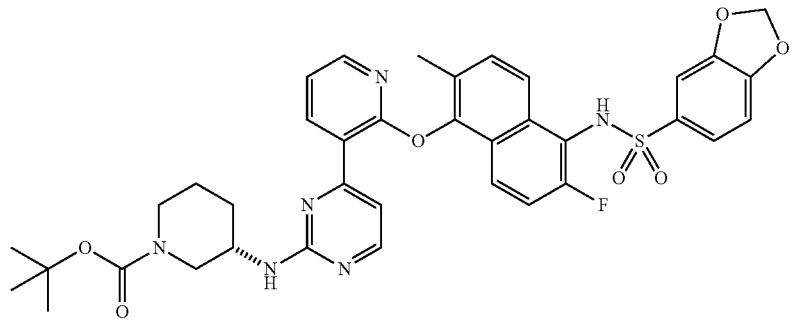 [SMILES: Cc1ccc2c(NS(=O)(=O)c3ccc4c(c3)OCO4)c(F)ccc2c1Oc1ncccc1-c1ccnc(N[C@H]2CCCN(C(=O)OC(C)(C)C)C2)n1]

Procedure A: To a two dram pressure-cap relief vial, tert-butyl (3S)-3-[[4-[2-[(5-amino-6-fluoro-2-methyl-1-naphthyl)oxy]-3-pyridyl]pyrimidin-2-yl]amino]piperidine-1-carboxylate (50 mg, 0.09 mmol), 1,2 dichloroethane (1.0 mL) was added, DMAP (1 mg), triethylamine (0.1 mL), and 1,3-benzodioxole-5-sulfonyl chloride (34 mg, 0.18 mmol). The reaction mixture was stirred at rt for 16 h and then concentrated to provide the title compound. LCMS [M+H]$^+$=728.8, rt=1.29 min.

Step 2: N-[2-Fluoro-6-methyl-5-[[3-[2-[[(3S)-3-piperidyl]amino]pyrimidin-4-yl]-2-pyridyl]oxy]-1-naphthyl]-1,3-benzodioxole-5-sulfonamide

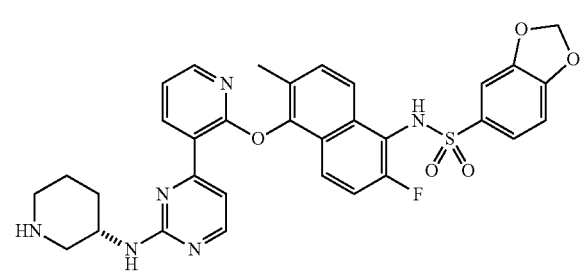 [SMILES: Cc1ccc2c(NS(=O)(=O)c3ccc4c(c3)OCO4)c(F)ccc2c1Oc1ncccc1-c1ccnc(N[C@H]2CCCNC2)n1]

Procedure B: tert-butyl (3S)-3-[[4-[2-[[5-(1,3-benzodioxol-5-ylsulfonylamino)-6-fluoro-2-methyl-1-naphthyl]oxy]-3-pyridyl]pyrimidin-2-yl]amino]piperidine-1-carboxylate (crude residue) was dissolved in methanol (1.4 mL). Hydrochloric acid (4 N in dioxane, 0.25 mL, 1.0 mmol) was subsequently added. The reaction was stirred at room temperature for 4 hours. The solution was concentrated, dissolved in DMF (1 mL) and purified by prep-HPLC (basic, 20-60% ACN) affording N-[2-fluoro-6-methyl-5-[[3-[2-[[(3S)-3-piperidyl]amino]pyrimidin-4-yl]-2-pyridyl]oxy]-1-naphthyl]-1,3-benzodioxole-5-sulfonamide (7.5 mg, 9.4%). LCMS [M+H]$^+$=628.7, rt=3.88 min. 1H NMR (400 MHz, DMSO-d$_6$) δ 8.51 (s, 1H), 8.42 (d, J=5.1 Hz, 1H), 8.30 (s, 1H), 8.05 (m, 1H), 7.92 (d, J=8.7 Hz, 1H), 7.56-7.40 (m, 3H), 7.36-7.09 (m, 6H), 6.97 (m, 1H), 6.62 (s, 1H), 6.14 (s, 2H), 3.99 (s, 2H), 2.92 (m, 1H), 2.64-2.52 (m, 1H), 2.16 (s, 3H), 1.94 (m, 1H), 1.72 (m, 1H), 1.57-1.43 (m, 2H).

Example 405 (S)-1-Cyclopropyl-N-(2-fluoro-6-methyl-5-((3-(2-(piperidin-3-ylamino)pyrimidin-4-yl)pyridin-2-yl)oxy)naphthalen-1-yl)methanesulfonamide hydrochloride Step 1: (S)-tert-Butyl 3-((4-(2-((5-(cyclopropylmethylsulfonamido)-6-fluoro-2-methylnaphthalen-1-yl)oxy)pyridin-3-yl)pyrimidin-2-yl)amino)piperidine-1-carboxylate

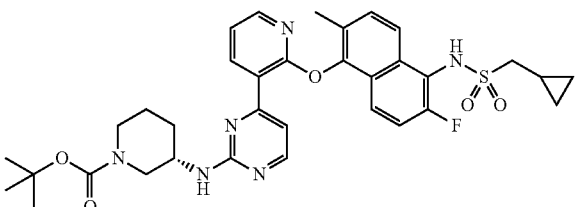

The General Procedure A was followed using (S)-tert-butyl 3-((4-(2-((5-amino-6-fluoro-2-methylnaphthalen-1-yl)oxy)pyridin-3-yl)pyrimidin-2-yl)amino)piperidine-1-carboxylate from Example 275 (400 mg, 0.68 mmol), pyridine (2.0 mL), CH$_2$Cl$_2$ (4.0 mL), and cyclopropylmethanesulfonyl chloride (260 mg, 1.68 mmol). After 16 h at room temperature, the mixture was placed in a 55° C. oil bath overnight. After 18 h, the mixture was diluted with CH$_2$Cl$_2$ (50 mL) and washed with saturated aqueous NaHCO$_3$ (10 mL), dried (Na$_2$SO$_4$), filtered and concentrated in vacuo to provide 400 mg (89% yield) of the title compound which was used directly in the next step. LCMS (ESI) [M+H]$^+$=663.3.

Step 2: (S)-1-Cyclopropyl-N-(2-fluoro-6-methyl-5-
((3-(2-(piperidin-3-ylamino)pyrimidin-4-yl)pyridin-
2-yl)oxy)naphthalen-1-yl)methanesulfonamide
hydrochloride 405

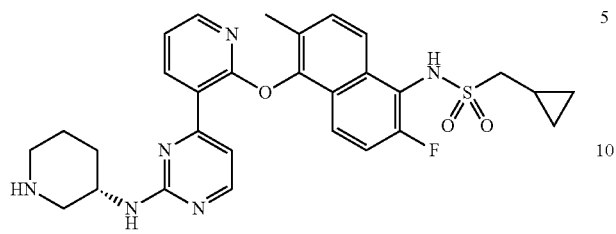

Prepared according to General Procedure B using crude (S)-tert-butyl 3-((4-(2-((5-(cyclopropylmethylsulfonamido)-6-fluoro-2-methylnaphthalen-1-yl)oxy)pyridin-3-yl)pyrimidin-2-yl)amino)piperidine-1-carboxylate (400 mg, 0.60 mmol), EtOAc (10 mL), and hydrochloric acid (4 M in dioxane, 4.0 mL, 16 mmol). After 16 h, the mixture was concentrated in vacuo and the crude residue was purified by reverse phase prep HPLC (14 min 30-50% MeCN/10 mM pH: 3.8 NH$_4$CO$_2$H(aq), XBridge BEH C18 OBD Prep Column, 130 Å, 5 µm, 30 mm×50 mm). Appropriate fractions were combined and concentrated in vacuo. The resulting residue was partitioned between EtOAc (50 mL) and saturated aqueous sodium bicarbonate (10 mL), The phases were theb separated. The organic extract was dried (Na$_2$SO$_4$), filtered and concentrated in vacuo. The material thus obtained was dissolved in EtOAc (2 mL) and treated with 4N HCl in dioxane (1 mL, 4 mmol) and stirred at rt. After 30 min the mixture was concentrated in vacuo and the resulting solids washed with EtOAc (3×3 mL) then with MeCN (3×3 mL), dissolved in H$_2$O and MeCN and lyophilized to provide 22 mg (5% yield) of 405. LCMS (ESI) [M+H]$^+$=563.2; $^1$H NMR (400 MHz, DMSO-d$_6$) δ 9.68 (s, 1H), 8.88-8.56 (m, 3H), 8.47 (d, J=5.2 Hz, 1H), 8.13-8.01 (m, 2H), 7.70 (dd, J=9.2, 5.1 Hz, 1H), 7.63 (d, J=8.8 Hz, 1H), 7.56 (d, J=5.1 Hz, 1H), 7.52 (d, J=7.4 Hz, 1H), 7.44 (t, J=9.5 Hz, 1H), 7.29 (dd, J=7.6, 4.8 Hz, 1H), 4.36-4.12 (m, 1H), 3.25-3.10 (m, 4H), 2.97-2.75 (m, 2H), 2.19 (s, 3H), 2.08-1.87 (m, 2H), 1.81-1.54 (m, 2H), 1.30-1.18 (m, 1H), 0.70-0.56 (m, 2H), 0.48-0.35 (m, 2H).

Example 406 (S)-3-Fluoro-N-(2-fluoro-6-methyl-5-
((3-(2-(piperidin-3-ylamino)pyrimidin-4-yl)pyridin-
2-yl)oxy)naphthalen-1-yl)propane-1-sulfonamide
hydrochloride Step 1: (S)-tert-Butyl 3-((4-(2-((6-fluoro-5-(3-fluoropropylsulfonamido)-2-methylnaphthalen-1-yl)oxy)pyridin-3-yl)pyrimidin-2-yl)amino)piperidine-1-carboxylate

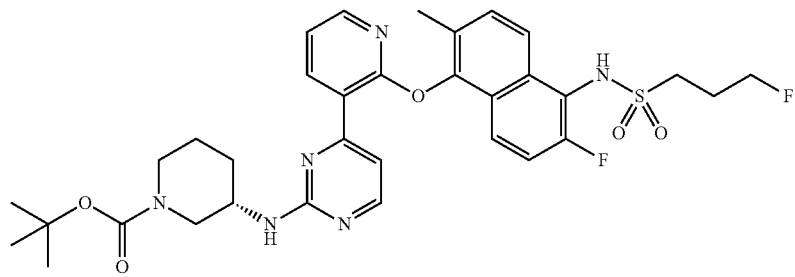 [SMILES: Cc1ccc2c(NS(=O)(=O)CCCF)c(F)ccc2c1Oc1ncccc1-c1ccnc(N[C@H]2CCCN(C(=O)OC(C)(C)C)C2)n1]

647

The General Procedure A was followed using (S)-tert-butyl 3-((4-(2-((5-amino-6-fluoro-2-methylnaphthalen-1-yl)oxy)pyridin-3-yl)pyrimidin-2-yl)amino)piperidine-1-carboxylate from Example 275 (75 mg, 0.14 mmol), pyridine (0.17 mL), CH₂Cl₂ (0.8 mL), and 3-fluoropropane-1-sulfonyl chloride (53 mg, 0.33 mmol). After 16 h, a further portion of 3-fluoropropane-1-sulfonyl chloride (53 mg, 0.33 mmol) was added and after a further 16 h at room temperature, the mixture was placed in a 50° C. oil bath. After 16 h, the mixture was directly purified by C18 reverse phase flash chromatography (40-80% MeCN/10 mM aqueous ammonium formate, pH=3.8). Appropriate fractions were combined and lyophilized to provide 22 mg of material which was further purified by flash chromatography through silica gel (0-100% EtOAc/CH₂Cl₂) to provide 15 mg (16% yield) of the title compound. LCMS (ESI) [M+H]⁺=669.2.

Step 2: (S)-3-Fluoro-N-(2-fluoro-6-methyl-5-((3-(2-(piperidin-3-ylamino)pyrimidin-4-yl)pyridin-2-yl)oxy)naphthalen-1-yl)propane-1-sulfonamide hydrochloride 406

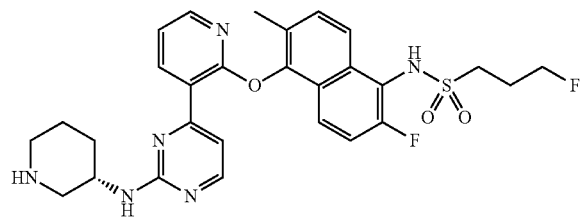 [SMILES: Cc1ccc2c(NS(=O)(=O)CCCF)c(F)ccc2c1Oc1ncccc1-c1ccnc(N[C@H]2CCCNC2)n1]

Prepared according to General Procedure B using (S)-tert-butyl 3-((4-(2-((6-fluoro-5-(3-fluoropropylsulfonamido)-2-methylnaphthalen-1-yl)oxy)pyridin-3-yl)pyrimidin-2-yl)amino)piperidine-1-carboxylate (15 mg, 0.02 mmol), EtOAc (1.0 mL), and hydrochloric acid (4 M in dioxane, 0.32 mL, 1.3 mmol). After 60 min, the resulting solids were collected by filtration, washed with CH₂Cl₂ then dissolved in H₂O and MeCN and lyophilized to provide 10 mg (74% yield) of 406. LCMS (ESI) [M+H]⁺=569.2; ¹H NMR (400 MHz, DMSO-d₆) [1 CH under the HOD signal] δ 9.85 (s, 1H), 9.06-8.50 (br m, 3H), 8.47 (d, J=5.2 Hz, 1H), 8.11-8.03 (m, 2H), 7.72 (dd, J=9.3, 5.1 Hz, 1H), 7.64 (d, J=8.8 Hz, 1H), 7.60-7.51 (m, J=7.0 Hz, 2H), 7.47 (t, J=9.5 Hz, 1H), 7.29 (dd, J=7.6, 4.8 Hz, 1H), 4.60 (dt, J=47.1, 5.9 Hz, 2H), 4.26 (s, 1H), 3.33-3.28 (m, 2H), 3.21 (d, J=12.2 Hz, 1H), 2.93-2.77 (m, 2H), 2.29-2.22 (m, 2H), 2.21-2.14 (m, 4H), 2.06-1.96 (m, J=8.8 Hz, 1H), 1.97-1.86 (m, 1H), 1.81-1.69 (m, 1H), 1.69-1.56 (m, 1H).

648

Example 407 (S)-4,4,4-Trifluoro-N-(6-methyl-5-((3-(2-(piperidin-3-ylamino)pyrimidin-4-yl)pyridin-2-yl)oxy)naphthalen-1-yl)but-2-enamide Step 1: tert-Butyl (S)-3-((4-(2-((2-methyl-5-(4,4,4-trifluorobut-2-enamido)naphthalen-1-yl)oxy)pyridin-3-yl)pyrimidin-2-yl)amino)piperidine-1-carboxylate

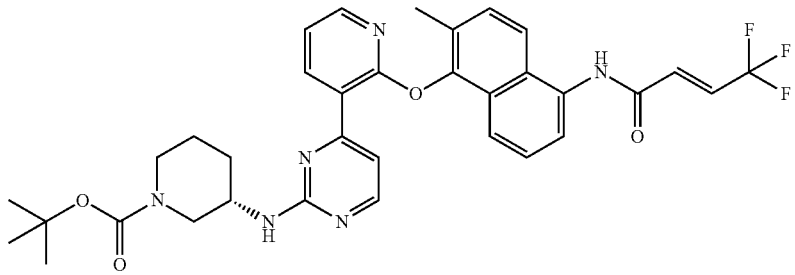 [SMILES: Cc1ccc2c(NC(=O)/C=C/C(F)(F)F)cccc2c1Oc1ncccc1-c1ccnc(N[C@H]2CCCN(C(=O)OC(C)(C)C)C2)n1]

The General Procedure C was followed, using tert-butyl (3S)-3-[[4-[2-[(5-amino-2-methyl-1-naphthyl)oxy]-3-pyridyl]pyrimidin-2-yl]amino]piperidine-1-carboxylate (200 mg, 0.38 mmol), 4,4,4-trifluoro-3-hydroxy-butanoic acid (90.1 mg, 0.57 mmol), HATU (294.7 mg, 0.76 mmol), DIPEA (0.20 mL, 1.14 mmol), and DMF (2 mL). The crude product was purified via reverse-phase HPLC to afford 75.6 mg (30.7% yield) of the title compound as an off-white solid. LCMS (ESI) [M+H]⁺=649.

Step 2: (S)-4,4,4-Trifluoro-N-(6-methyl-5-((3-(2-(piperidin-3-ylamino)pyrimidin-4-yl)pyridin-2-yl)oxy)naphthalen-1-yl)but-2-enamide

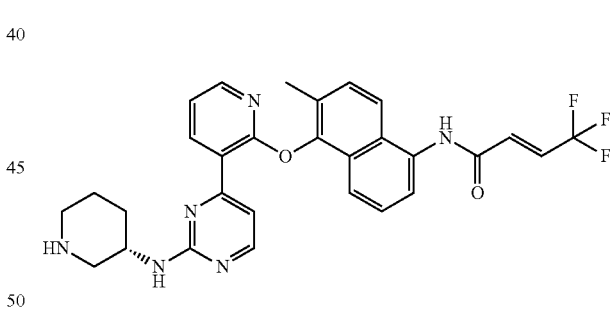

The General Procedure B was followed, using tert-butyl (S)-3-((4-(2-((2-methyl-5-(4,4,4-trifluorobut-2-enamido)naphthalen-1-yl)oxy)pyridin-3-yl)pyrimidin-2-yl)amino)piperidine-1-carboxylate (75.6 mg, 0.12 mmol) to afford 38 mg (63.9% yield) of the title compound as an off-white solid. LCMS (ESI) [M+H]⁺=549; ¹H NMR (400 MHz, DMSO-d₆) δ 10.55 (s, 1H), 8.50 (s, 1H), 8.42 (d, J=5.1 Hz, 1H), 8.04 (dd, J=4.8, 2.0 Hz, 1H), 7.99 (d, J=8.7 Hz, 1H), 7.85-7.76 (m, 1H), 7.56 (t, J=8.5 Hz, 2H), 7.51-7.41 (m, 2H), 7.34-7.22 (m, 2H), 7.17 (d, J=7.9 Hz, 1H), 7.07-6.94 (m, 1H), 3.93 (s, 1H), 3.14 (d, J=10.7 Hz, 1H), 2.85 (d, J=11.9 Hz, 1H), 2.23 (s, 3H), 1.97-1.90 (m, 1H), 1.72-1.64 (m, 1H), 1.56-1.42 (m, 2H).

Example 408 1-(6-Methyl-5-((3-(2-(((S)-piperidin-3-yl)amino)pyrimidin-4-yl)pyridin-2-yl)oxy)naphthalen-1-yl)pyrrolidin-3-ol (Isomer-1 and Isomer-2)

Step 1: tert-Butyl (3S)-3-((4-(2-((5-(3-hydroxypyrrolidin-1-yl)-2-methylnaphthalen-1-yl)oxy)pyridin-3-yl)pyrimidin-2-yl)amino)piperidine-1-carboxylate

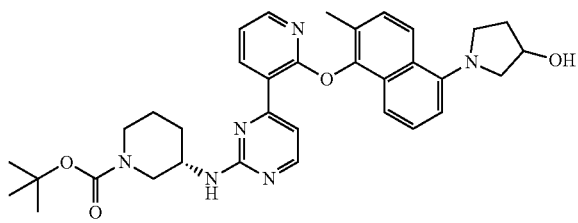 [SMILES: Cc1ccc2c(N3CCC(O)C3)cccc2c1Oc1ncccc1-c1ccnc(N[C@H]2CCCN(C(=O)OC(C)(C)C)C2)n1]

To a mixture of tert-butyl (3S)-3-[[4-[2-[(5-amino-2-methyl-1-naphthyl)oxy]-3-pyridyl]pyrimidin-2-yl]amino]piperidine-1-carboxylate (600 mg, 1.13 mmol), 1,4-dibromo-2-butanol (0.26 mL, 2.28 mmol), potassium iodide (398 mg, 2.28 mmol), and DIPEA (0.39 mL, 2.28 mmol) in toluene (6 mL) was heated at 90° C. overnight. It was diluted with water, extracted with iPrOAc (2×20 mL), dried over MgSO$_4$, filtered, and purified by silica flash chromatography, eluting with 0-5% MeOH/DCM to give 472 mg (69.6% yield) of the title compound as a brown solid. LCMS (ESI) [M+H]$^+$=597.170 mg of the racemic was subjected to chiral SFC to afford 69 mg of isomer-1 ($t_R$=0.965 min) and 70 mg of isomer-2 ($t_R$=1.536 min).

Step 2: 1-(6-Methyl-5-((3-(2-(((S)-piperidin-3-yl)amino)pyrimidin-4-yl)pyridin-2-yl)oxy)naphthalen-1-yl)pyrrolidin-3-ol

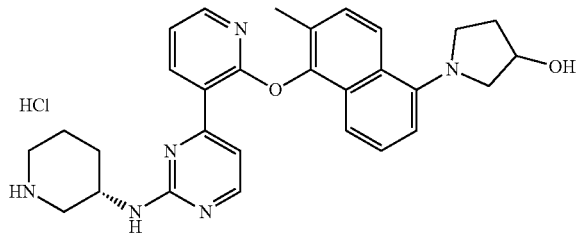 [SMILES: Cl ; Cc1ccc2c(N3CCC(O)C3)cccc2c1Oc1ncccc1-c1ccnc(N[C@H]2CCCNC2)n1]

Isomer-1

The General Procedure B was followed, using tert-butyl (3S)-3-((4-(2-((5-(3-hydroxypyrrolidin-1-yl)-2-methylnaphthalen-1-yl)oxy)pyridin-3-yl)pyrimidin-2-yl)amino)piperidine-1-carboxylate (isomer-1, 69 mg, 0.12 mmol). The product was lyophilized to yield 63 mg (100% yield) of the title compound as a yellow solid HCl salt. LCMS (ESI) [M+H]$^+$=497; $^1$H NMR (400 MHz, DMSO-d$_6$) δ 8.90-8.74 (m, 2H), 8.59 (s, 2H), 8.47 (d, J=5.2 Hz, 1H), 8.09-8.00 (m, 2H), 7.58 (d, J=5.2 Hz, 1H), 7.52 (d, J=7.5 Hz, 1H), 7.39 (d, J=8.8 Hz, 1H), 7.29-7.22 (m, 2H), 7.17 (d, J=8.3 Hz, 1H), 6.91 (d, J=7.6 Hz, 1H), 4.43 (dq, J=5.6, 2.9 Hz, 1H), 4.27 (s, 1H), 3.31 (s, 1H), 3.21 (d, J=11.6 Hz, 3H), 2.84 (d, J=12.8 Hz, 2H), 2.20 (s, 3H), 2.06-1.97 (m, 1H), 1.95-1.85 (m, 2H), 1.80-1.58 (m, 2H). Stereochemistry of the alcohol was randomly assigned.

Isomer-2

The General Procedure B was followed, using tert-butyl (3S)-3-((4-(2-((5-(3-hydroxypyrrolidin-1-yl)-2-methylnaphthalen-1-yl)oxy)pyridin-3-yl)pyrimidin-2-yl)amino)piperidine-1-carboxylate (isomer-2, 70 mg, 0.12 mmol). The product was lyophilized to yield 63 mg (100% yield) of the title compound as a yellow solid HCl salt. LCMS (ESI) [M+H]$^+$=497; $^1$H NMR (400 MHz, DMSO-d$_6$) δ 8.82 (s, 2H), 8.60 (s, 2H), 8.47 (d, J=5.2 Hz, 1H), 8.09-8.01 (m, 2H), 7.58 (d, J=5.2 Hz, 1H), 7.53 (d, J=7.5 Hz, 1H), 7.39 (d, J=8.8 Hz, 1H), 7.30-7.22 (m, 2H), 7.17 (d, J=8.4 Hz, 1H), 6.92 (d, J=7.4 Hz, 1H), 4.44 (dp, J=5.9, 3.0 Hz, 1H), 4.27 (s, 1H), 3.34 (d, J=17.3 Hz, 1H), 3.21 (d, J=11.7 Hz, 3H), 2.93-2.78 (m, 2H), 2.20 (s, 4H), 2.07-1.98 (m, 1H), 1.97-1.84 (m, 2H), 1.80-1.57 (m, 2H). Stereochemistry of the alcohol was randomly assigned.

Example 409 N-(2-Fluoro-6-methyl-5-((3-(2-(((S)-piperidin-3-yl)amino)pyrimidin-4-yl)pyridin-2-yl)oxy)naphthalen-1-yl)-2-methylbutane-1-sulfonamide Step 1: tert-Butyl (3S)-3-((4-(2-((6-fluoro-2-methyl-5-((2-methylbutyl)sulfonamido)naphthalen-1-yl)oxy)pyridin-3-yl)pyrimidin-2-yl)amino)piperidine-1-carboxylate

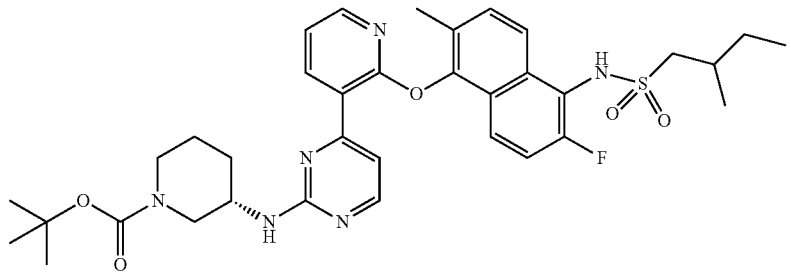 [SMILES: CCC(C)CS(=O)(=O)Nc1c(F)ccc2c(Oc3ncccc3-c3ccnc(N[C@H]4CCCN(C(=O)OC(C)(C)C)C4)n3)c(C)ccc12]

The general procedure A was followed, using tert-butyl (3S)-3-[[4-[2-[(5-amino-6-fluoro-2-methyl-1-naphthyl)oxy]-3-pyridyl]pyrimidin-2-yl]amino]piperidine-1-carboxylate (200 mg, 0.36 mmol) and 2-methylbutane-1-sulfonyl chloride (198 mg, 1.11 mmol) in pyridine (2 mL). The crude product was purified by silica gel chromatography to afford 67 mg (26.9% yield) of the title compound as an off-white solid and as a mixture of stereoisomers at 2 position of the sulfonamide. LCMS (ESI) [M+H]+=679.

Step 2: N-(2-Fluoro-6-methyl-5-((3-(2-(((S)-piperidin-3-yl)amino)pyrimidin-4-yl)pyridin-2-yl)oxy)naphthalen-1-yl)-2-methylbutane-1-sulfonamide

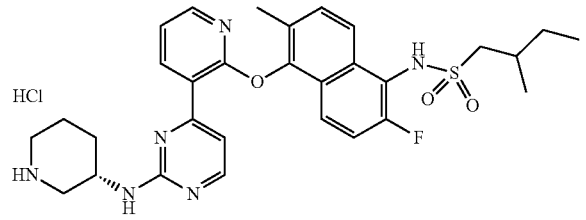 [SMILES: Cl ; CCC(C)CS(=O)(=O)Nc1c(F)ccc2c(Oc3ncccc3-c3ccnc(N[C@H]4CCCNC4)n3)c(C)ccc12]

The General Procedure B was followed, using tert-butyl (3S)-3-((4-(2-((6-fluoro-2-methyl-5-((2-methylbutyl)sulfonamido)naphthalen-1-yl)oxy)pyridin-3-yl)pyrimidin-2-yl)amino)piperidine-1-carboxylate (67 mg, 0.10 mmol). The product was lyophilized to yield 59 mg (97.2% yield) of the title compound as an off-white solid HCl salt and as a mixture of stereoisomers at 2 position of the sulfonamide. LCMS (ESI) [M+H]+=579; 1H NMR (400 MHz, DMSO-d6) δ 9.68 (s, 1H), 8.80 (s, 2H), 8.60 (s, 2H), 8.47 (d, J=5.2 Hz, 1H), 8.10-8.03 (m, 2H), 7.71 (dd, J=9.3, 5.1 Hz, 1H), 7.63 (d, J=8.8 Hz, 1H), 7.56 (d, J=5.2 Hz, 1H), 7.52 (d, J=7.5 Hz, 1H), 7.46 (t, J=9.5 Hz, 1H), 7.29 (dd, J=7.6, 4.8 Hz, 1H), 4.27 (s, 1H), 3.22 (dd, J=14.2, 5.0 Hz, 2H), 3.06 (dd, J=14.1, 7.6 Hz, 1H), 2.84 (d, J=12.4 Hz, 2H), 2.20 (s, 3H), 2.13-1.97 (m, 2H), 1.97-1.86 (m, 1H), 1.80-1.59 (m, 2H), 1.57-1.48 (m, 1H), 1.32 (dt, J=13.4, 7.4 Hz, 1H), 1.07 (d, J=6.7 Hz, 3H), 0.88 (t, J=7.4 Hz, 3H).

Example 410 4-[2-[[5-[[Benzyl(methyl)sulfamoyl]amino]-6-fluoro-2-methyl-1-naphthyl]oxy]-3-pyridyl]-2-[[(3S)-3-piperidyl]amino]pyrimidine hydrochloride Step 1: tert-Butyl (3S)-3-[[4-[2-[[5-[[benzyl(methyl)sulfamoyl]amino]-6-fluoro-2-methyl-1-naphthyl]oxy]-3-pyridyl]pyrimidin-2-yl]amino]piperidine-1-carboxylate

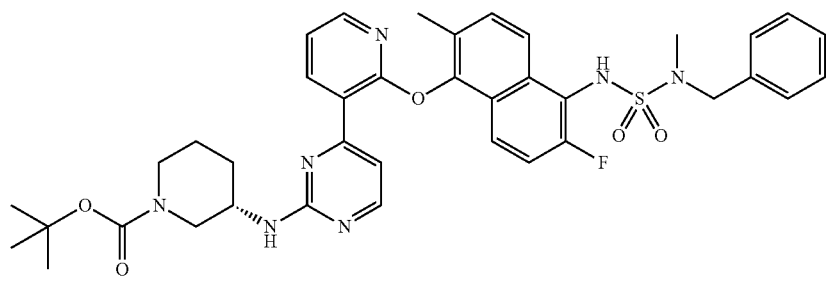 [SMILES: Cc1ccc2c(NS(=O)(=O)N(C)Cc3ccccc3)c(F)ccc2c1Oc1ncccc1-c1ccnc(N[C@H]2CCCN(C(=O)OC(C)(C)C)C2)n1]

A solution of sulfuryl chloride (2.04 mL, 25.2 mmol), in DCM (25 mL), was cooled to 0° C. To this solution was added a solution of N-methylbenzylamine (0.65 mL, 5.04 mmol) and triethylamine (1.05 mL, 7.56 mmol), in DCM (10 mL), over a period of 2 minutes. The reaction was stirred 15 minutes at 0° C. then quenched by the addition of water. The organic layer was separated and washed with 5 mL of 1 N hydrochloric acid, dried (MgSO4), filtered, and concentrated in vacuo to provide 1.1 g (99% yield) of N-benzyl-N-methyl-sulfamoyl chloride which was used as is without further purification. (S)-tert-butyl 3-((4-(2-((5-amino-6-fluoro-2-methylnaphthalen-1-yl)oxy)pyridin-3-yl)pyrimidin-2-yl)amino)piperidine-1-carboxylate from Example 275 (90 mg, 0.17 mmol), pyridine (1 mL) and N-benzyl-N-methyl-sulfamoyl chloride prepared above (100 mg, 0.46 mmol) were reacted according to general procedure A. After 16 h at rt, only trace of the desired compound was observed. 4-Dimethylaminopyridine (20 mg, 0.17 mmol) was added to the mixture and the reaction was stirred for 72 hours at 55° C. The mixture was directly purified by C18 reverse phase flash chromatography (40-80% MeCN/10 mM aqueous ammonium formate, pH=3.8). Appropriate fractions were combined and lyophilized to provide 40 mg (33% yield) of the title compound. LCMS (ESI) [M+H]+=728.4.

Step 3: 4-[2-[[5-[[Benzyl(methyl)sulfamoyl]amino]-6-fluoro-2-methyl-1-naphthyl]oxy]-3-pyridyl]-2-[[(3S)-3-piperidyl]amino]pyrimidine hydrochloride 410

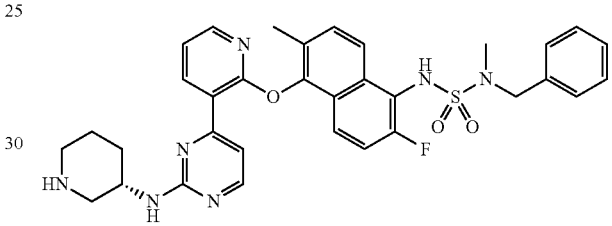

Prepared according to General Procedure B using tert-butyl (3S)-3-[[4-[2-[[5-[[benzyl(methyl)sulfamoyl]amino]-6-fluoro-2-methyl-1-naphthyl]oxy]-3-pyridyl]pyrimidin-2-yl]amino]piperidine-1-carboxylate (40 mg, 0.055 mmol), EtOAc (1 mL), and hydrochloric acid (4 M in dioxane, 0.71 mL, 2.85 mmol). After 60 min, the mixture was filtered. The collected solid was washed with DCM, then dissolved in H2O and lyophilized to provide 34 mg (93% yield) of 410. LCMS (ESI) [M+H]+=628.2; 1H NMR (400 MHz, DMSO-d6) δ 9.70 (s, 1H), 9.07 (br s, 1H), 8.98 (s, 1H), 8.70 (br s, 1H), 8.48 (d, J=5.2 Hz, 1H), 8.14 (d, J=8.8 Hz, 1H), 8.08 (dd, J=4.8, 1.9 Hz, 1H), 7.73 (dd, J=9.3, 5.1 Hz, 1H), 7.64 (d, J=8.8 Hz, 1H), 7.59 (d, J=4.3 Hz, 2H), 7.46 (t, J=9.4 Hz, 1H), 7.38-7.32 (m, 2H), 7.32-7.24 (m, 4H), 4.27 (s, 3H), 3.20 (d, J=12.7 Hz, 1H), 2.93-2.76 (m, 2H), 2.71 (s, 3H), 2.20 (s, 3H), 2.02 (d, J=9.4 Hz, 1H), 1.96-1.85 (m, 1H), 1.83-1.68 (m, 1H), 1.63 (q, J=10.4 Hz, 1H). 1 CH under the HOD signal.

Example 411 (S)—N-(2-Fluoro-6-methyl-5-((3-(2-(piperidin-3-ylamino)pyrimidin-4-yl)pyridin-2-yl)oxy)naphthalen-1-yl)-1-(2-methylthiazol-4-yl)methanesulfonamide hydrochloride Step 1: (S)-tert-Butyl 3-((4-(2-((6-fluoro-2-methyl-5-((2-methylthiazol-4-yl)methylsulfonamido)naphthalen-1-yl)oxy)pyridin-3-yl)pyrimidin-2-yl)amino)piperidine-1-carboxylate

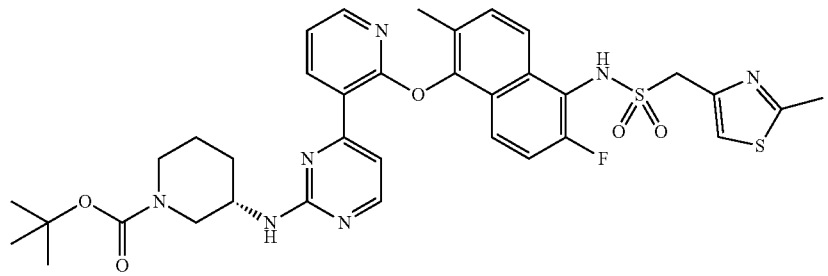 [SMILES: Cc1nc(CS(=O)(=O)Nc2c(F)ccc3c(Oc4ncccc4-c4ccnc(N[C@H]5CCCN(C(=O)OC(C)(C)C)C5)n4)c(C)ccc23)cs1]

The General Procedure A was followed using (S)-tert-butyl 3-((4-(2-((5-amino-6-fluoro-2-methylnaphthalen-1-yl)oxy)pyridin-3-yl)pyrimidin-2-yl)amino)piperidine-1-carboxylate from Example 275 (75 mg, 0.14 mmol), pyridine (0.17 mL), CH$_2$Cl$_2$ (0.8 mL), 4-dimethylaminopyridine (1.7 mg, 0.01 mmol) and (2-methylthiazol-4-yl)methanesulfonyl chloride (58 mg, 0.28 mmol). After 18 h, the mixture was diluted with CH$_2$Cl$_2$ (50 mL) and washed with 1M KHSO$_4$ (10 mL), dried by passing through a phase cartridge separator and concentrated in vacuo. The crude was purified by flash chromatography through silica gel (10-60% EtOAc/DCM) to provide 45 mg (45% yield) of the title compound. LCMS (ESI) [M+H]$^+$=720.4.

Step 2: (S)—N-(2-Fluoro-6-methyl-5-((3-(2-(piperidin-3-ylamino)pyrimidin-4-yl)pyridin-2-yl)oxy)naphthalen-1-yl)-1-(2-methylthiazol-4-yl)methanesulfonamide hydrochloride 411

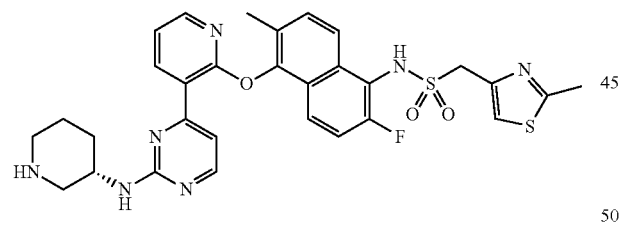

Prepared according to General Procedure B using (S)-tert-butyl 3-((4-(2-((6-fluoro-2-methyl-5-((2-methylthiazol-4-yl)methylsulfonamido)naphthalen-1-yl)oxy)pyridin-3-yl)pyrimidin-2-yl)amino)piperidine-1-carboxylate (51 mg, 0.07 mmol), 1,4-dioxane (0.3 mL), and hydrochloric acid (4 M in dioxane, 0.91 mL, 3.64 mmol). After 45 min, the mixture was diluted with Et$_2$O and the resulting solids collected by filtration then dissolved in H$_2$O and MeCN and lyophilized to provide 44 mg (95% yield) of 411. LCMS (ESI) [M+H]$^+$=620.1; $^1$H NMR (400 MHz, DMSO-d$_6$) δ 9.86 (s, 1H), 8.97 (bs, 2H), 8.72 (s, 1H), 8.49 (d, J=5.3 Hz, 1H), 8.14-8.05 (m, 2H), 7.73 (dd, J=9.3, 5.2 Hz, 1H), 7.69-7.54 (m, 4H), 7.48 (t, J=9.4 Hz, 1H), 7.29 (dd, J=7.6, 4.8 Hz, 1H), 4.66 (s, 2H), 4.31 (bs, 1H), 3.51-3.34 (m, 1H), 3.27-3.11 (m, 1H), 2.96-2.71 (m, 2H), 2.66 (s, 3H), 2.20 (s, J=14.9 Hz, 3H), 2.08-1.86 (m, 2H), 1.85-1.56 (m, 2H).

Example 412 (S)—N-(2-Fluoro-6-methyl-5-((3-(2-(piperidin-3-ylamino)pyrimidin-4-yl)pyridin-2-yl)oxy)naphthalen-1-yl)-1-(5-methylisoxazol-3-yl)methanesulfonamide hydrochloride Step 1: (S)-tert-Butyl 3-((4-(2-((6-fluoro-2-methyl-5-((5-methylisoxazol-3-yl)methylsulfonamido)naphthalen-1-yl)oxy)pyridin-3-yl)pyrimidin-2-yl)amino)piperidine-1-carboxylate lyophilized to provide 33 mg (87% yield) of 412. LCMS (ESI) [M+H]$^+$=604.1; $^1$H NMR (400 MHz, DMSO-d$_6$) δ 10.06 (s, 1H), 8.87 (bs, 2H), 8.68 (s, 1H), 8.48 (d, J=5.2 Hz, 1H), 8.12-7.99 (m, 2H), 7.74 (dd, J=9.3, 5.1 Hz, 1H), 7.63 (d, J=8.8 Hz, 1H), 7.57 (s, 2H), 7.48 (t, J=9.4 Hz, 1H), 7.29 (dd, J=7.6, 4.8 Hz, 1H), 6.36 (d, J=0.9 Hz, 1H), 4.65 (s, 2H), 3.52-3.35 (m, 1H), 3.21 (d, J=11.7 Hz, 1H), 2.96-2.74 (m, 2H), 2.43 (d, J=0.9 Hz, 3H), 2.20 (s, 3H), 2.09-1.84 (m, 2H), 1.85-1.52 (m, 2H).

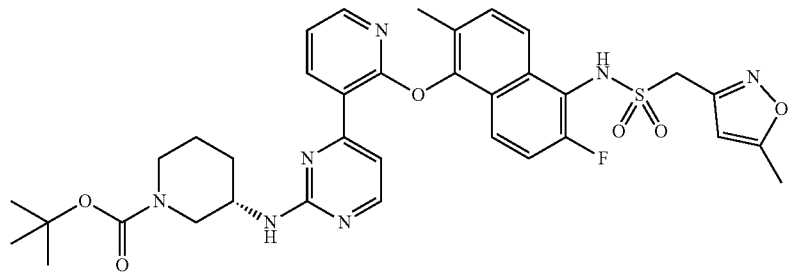 [SMILES: Cc1cc(CS(=O)(=O)Nc2c(F)ccc3c(Oc4ncccc4-c4ccnc(N[C@H]5CCCN(C(=O)OC(C)(C)C)C5)n4)c(C)ccc23)no1]

The General Procedure A was followed using (S)-tert-butyl 3-((4-(2-((5-amino-6-fluoro-2-methylnaphthalen-1-yl)oxy)pyridin-3-yl)pyrimidin-2-yl)amino)piperidine-1-carboxylate from Example 275 (75 mg, 0.14 mmol), pyridine (0.17 mL), CH$_2$Cl$_2$ (0.8 mL), 4-dimethylaminopyridine (1.7 mg, 0.01 mmol) and (5-methylisoxazol-3-yl)methanesulfonyl chloride (54 mg, 0.28 mmol). After 18 h, the mixture was diluted with CH$_2$Cl$_2$ (50 mL) and washed with 1M KHSO$_4$ (10 mL), dried by passing through a phase cartridge separator and concentrated in vacuo. The crude was purified by flash chromatography through silica gel (0-50% EtOAc/DCM) to provide 42 mg (43% yield) of the title compound. LCMS (ESI) [M+H]$^+$=704.3.

Step 2: (S)—N-(2-Fluoro-6-methyl-5-((3-(2-(piperidin-3-ylamino)pyrimidin-4-yl)pyridin-2-yl)oxy)naphthalen-1-yl)-1-(5-methylisoxazol-3-yl)methanesulfonamide hydrochloride 412

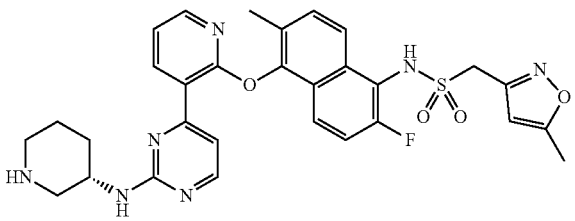 [SMILES: Cc1cc(CS(=O)(=O)Nc2c(F)ccc3c(Oc4ncccc4-c4ccnc(N[C@H]5CCCNC5)n4)c(C)ccc23)no1]

Prepared according to General Procedure B using (S)-tert-butyl 3-((4-(2-((6-fluoro-2-methyl-5-((5-methylisoxazol-3-yl)methylsulfonamido)naphthalen-1-yl)oxy)pyridin-3-yl)pyrimidin-2-yl)amino)piperidine-1-carboxylate (42 mg, 0.06 mmol), 1,4-dioxane (0.3 mL), and hydrochloric acid (4 M in dioxane, 0.8 mL, 3.2 mmol). After 90 min, the mixture was diluted with Et$_2$O. The resulting solids were collected by filtration then dissolved in H$_2$O and MeCN and Example 413 1-Cyclobutylidene-N-[2-fluoro-6-methyl-5-[[3-[2-[[(3S)-3-piperidyl]amino]pyrimidin-4-yl]-2-pyridyl]oxy]-1-naphthyl]methanesulfonamide hydrochloride Step 1: tert-Butyl (3S)-3-[[4-[2-[[5-(cyclobutylidenemethylsulfonylamino)-6-fluoro-2-methyl-1-naphthyl]oxy]-3-pyridyl]pyrimidin-2-yl]amino]piperidine-1-carboxylate

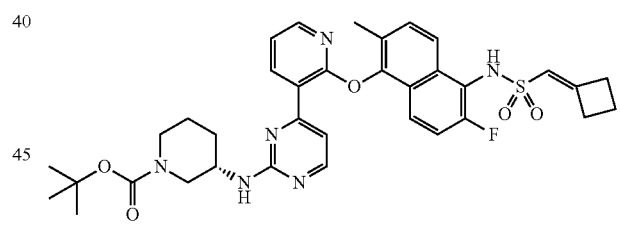

The General Procedure A was followed using (S)-tert-butyl 3-((4-(2-((5-amino-6-fluoro-2-methylnaphthalen-1-yl)oxy)pyridin-3-yl)pyrimidin-2-yl)amino)piperidine-1-carboxylate from Example 275 (120 mg, 0.22 mmol), pyridine (1.0 mL), 4-dimethylaminopyridine (27 mg, 0.22 mmol) and (1-fluorocyclobutyl)methanesulfonyl chloride (100 mg, 0.54 mmol). The mixture was stirred 30 minutes at 50° C. then 16 h at rt. 10 drops of a saturated aqueous solution of NaHCO$_3$ were added and the mixture was directly purified by C18 reverse phase flash chromatography (40-80% MeCN/10 mM aqueous ammonium formate, pH=3.8). Appropriate fractions were combined and lyophilized to provide 105 mg (70% yield) of the title compound. LCMS (ESI) [M+H]$^+$=675.3.

Step 2: 1-Cyclobutylidene-N-[2-fluoro-6-methyl-5-[[3-[2-[[(3S)-3-piperidyl]amino]pyrimidin-4-yl]-2-pyridyl]oxy]-1-naphthyl]methanesulfonamide hydrochloride 413

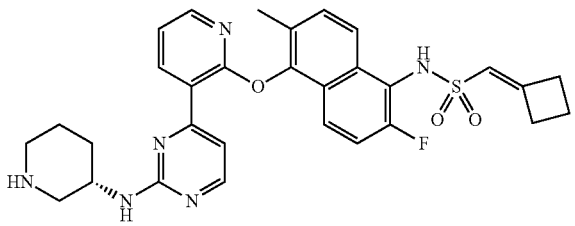 [SMILES: Cc1ccc2c(NS(=O)(=O)C=C3CCC3)c(F)ccc2c1Oc1ncccc1-c1ccnc(N[C@H]2CCCNC2)n1]

Prepared according to General Procedure B using tert-butyl (3S)-3-[[4-[2-[[5-(cyclobutylidenemethylsulfonylamino)-6-fluoro-2-methyl-1-naphthyl]oxy]-3-pyridyl]pyrimidin-2-yl]amino]piperidine-1-carboxylate (105 mg, 0.16 mmol), EtOAc (1 mL), and hydrochloric acid (4 M in dioxane, 1.03 mL, 4.12 mmol). After 60 min, the mixture was filtered. The collected solid was washed with DCM, then dissolved in H$_2$O and lyophilized to provide 88 mg (93% yield) of 413. LCMS (ESI) [M+H]$^+$=575.1; $^1$H NMR (400 MHz, DMSO-d$_6$) δ 9.72 (s, 1H), 9.38 (br s, 1H), 9.16 (s, 1H), 8.78 (br s, 1H), 8.49 (d, J=5.4 Hz, 1H), 8.10-8.02 (m, 2H), 7.70 (dd, J=9.3, 5.1 Hz, 2H), 7.61 (d, J=8.8 Hz, 2H), 7.45 (t, J=9.4 Hz, 1H), 7.28 (dd, J=7.6, 4.8 Hz, 1H), 6.30-6.12 (m, 1H), 4.34 (br s, 1H), 3.42 (d, J=9.9 Hz, 1H), 3.19 (d, J=12.4 Hz, 1H), 2.90-2.78 (m, 2H), 2.75 (t, J=7.8 Hz, 2H), 2.59 (t, J=6.9 Hz, 2H), 2.19 (s, 3H), 2.05-1.96 (m, 1H), 1.96-1.85 (m, 1H), 1.81 (qn, J=7.8 Hz, 3H), 1.63 (q, J=10.9 Hz, 1H).

Example 414 (R)-2-Methyl-3-((6-methyl-5-((3-(2-((S)-piperidin-3-ylamino)pyrimidin-4-yl)pyridin-2-yl)oxy)naphthalen-1-yl)amino)propanenitrile hydrochloride (Isomer-1)

Step 1: tert-Butyl (3S)-3-[[4-[2-[[5-(2-cyanopropylamino)-2-methyl-1-naphthyl]oxy]-3-pyridyl]pyrimidin-2-yl]amino]piperidine-1-carboxylate

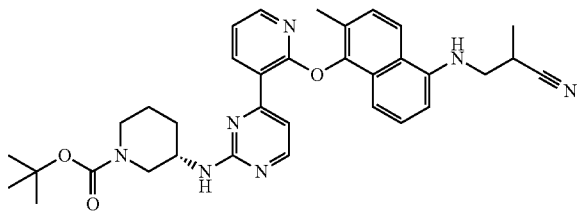 [SMILES: Cc1ccc2c(NCC(C)C#N)cccc2c1Oc1ncccc1-c1ccnc(N[C@H]2CCCN(C(=O)OC(C)(C)C)C2)n1]

tert-Butyl (3S)-3-[[4-[2-[(5-amino-2-methyl-1-naphthyl)oxy]-3-pyridyl]pyrimidin-2-yl]amino]piperidine-1-carboxylate (500 mg, 0.95 mmol) was dissolved in DMF (4 mL) and to the suspension was added methacrylonitrile (0.4 mL, 4.75 mmol) followed by benzyltrimethylammonium hydroxide solution 40% in MeOH (479 mg, 2.85 mmol). The reaction was stirred at 80° C. for 20 min, diluted the reaction with EtOAc (200 mL). The organic layer was washed with water (30 mL). The organic layer was separated and dried over MgSO$_4$. The crude was dissolved in DMSO and purified by C18 reverse phase flash chromatography (0-100% MeCN/H$_2$O). Appropriate fractions were combined and removed in vacuo. Saturated Na$_2$CO$_3$ (2 mL) was then added to the aqueous mixture and the product was extracted with EtOAc (50 mL), dried (MgSO$_4$), filtered, and concentrated in vacuo. The resulting residue was purified by flash column chromatography through C18 (0-100% MeCN/water) to provide 208 mg (36% yield) of the title compound. LCMS (ESI) [M+H]$^+$=594.4.

Step 2: (S)-tert-Butyl 3-((4-(2-((5-(((R)-2-cyanopropyl)amino)-2-methylnaphthalen-1-yl)oxy)pyridin-3-yl)pyrimidin-2-yl)amino)piperidine-1-carboxylate (Isomer-1) and (S)-tert-butyl 3-((4-(2-((5-(((S)-2-cyanopropyl)amino)-2-methylnaphthalen-1-yl)oxy)pyridin-3-yl)pyrimidin-2-yl)amino)piperidine-1-carboxylate (Isomer-2)

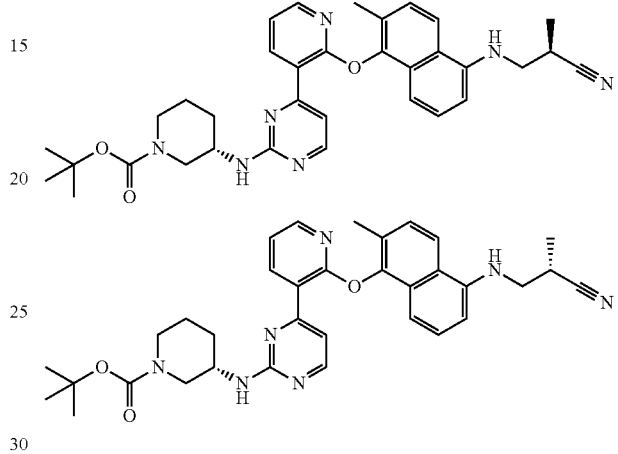

The mixture of stereoisomers from Step 1 were subjected to chiral normal phase semi-prep purification (conditions: Chiralpak IB, 5 uM, 20×250 mm, 5:5:90 MeOH:EtOH:Hexane, 5 mg/inj.) to provide two stereoisomers enantiomeric at the cyano position. Isomer-1: (S)-tert-Butyl 3-((4-(2-((5-(((R)-2-cyanopropyl)amino)-2-methylnaphthalen-1-yl)oxy)pyridin-3-yl)pyrimidin-2-yl)amino)piperidine-1-carboxylate, 68 mg (32% yield), white solid, ee=96.5%; LCMS (ESI) [M+H]$^+$=594.4; and isomer-2: (S)-tert-butyl 3-((4-(2-((5-(((S)-2-cyanopropyl)amino)-2-methylnaphthalen-1-yl)oxy)pyridin-3-yl)pyrimidin-2-yl)amino)piperidine-1-carboxylate, 71 mg (34% yield), white solid, ee=96.9%, LCMS (ESI) [M+H]$^+$=594.4.

Step 3: (R)-2-Methyl-3-((6-methyl-5-((3-(2-((S)-piperidin-3-ylamino)pyrimidin-4-yl)pyridin-2-yl)oxy)naphthalen-1-yl)amino)propanenitrile hydrochloride (Isomer-1) 414

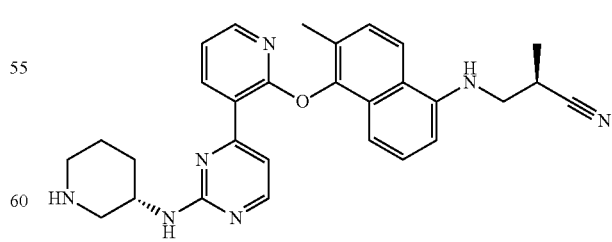

Prepared according to General Procedure B using (S)-tert-butyl 3-((4-(2-((5-(((R)-2-cyanopropyl)amino)-2-methylnaphthalen-1-yl)oxy)pyridin-3-yl)pyrimidin-2-yl)amino)piperidine-1-carboxylate (68 mg, 0.11 mmol), 1,4-dioxane (1 mL), and hydrochloric acid (4 M in dioxane, 1.0 mL, 4.0 mmol). After 10 min, the mixture was diluted with Et$_2$O and the resulting solids were collected by filtration then dissolved in H$_2$O and MeCN and lyophilized to provide 55 mg (90% yield) of 414. LCMS (ESI) [M+H]$^+$=494.1; $^1$H NMR (400 MHz, DMSO-d$_6$) 8.42 (s, 1H), 8.05 (s, 1H), 7.83 (dd, J=5.0, 1.9 Hz, 1H), 7.76 (d, J=8.8 Hz, 1H), 7.65 (s, 1H), 7.31 (d, J=8.9 Hz, 1H), 7.11 (dd, J=7.7, 5.0 Hz, 1H), 6.98 (s, 2H), 6.57 (s, 1H), 4.28 (s, 1H), 3.41 (qd, J=13.6, 7.2 Hz, 3H), 3.17 (s, 1H), 3.09 (dd, J=14.7, 7.1 Hz, 1H), 3.00-2.80 (m, 2H), 2.04 (s, 3H), 2.03-1.96 (m, 1H), 1.87 (s, 1H), 1.64 (dd, J=21.4, 11.9 Hz, 2H), 1.20 (d, J=7.1 Hz, 3H). The absolute stereochemistry of the propane nitrile was randomly assigned.

Example 415 (S)-2-Methyl-3-((6-methyl-5-((3-(2-((S)-piperidin-3-ylamino)pyrimidin-4-yl)pyridin-2-yl)oxy)naphthalen-1-yl)amino)propanenitrile hydrochloride (Isomer-2)

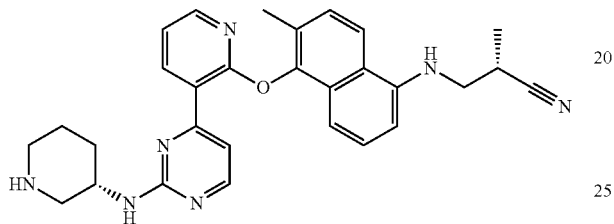

Prepared according to General Procedure B using (S)-tert-butyl 3-((4-(2-((5-(((S)-2-cyanopropyl)amino)-2-methylnaphthalen-1-yl)oxy)pyridin-3-yl)pyrimidin-2-yl)amino)piperidine-1-carboxylate (68 mg, 0.11 mmol), 1,4-dioxane (1 mL), and hydrochloric acid (4 M in dioxane, 1.0 mL, 4.0 mmol). After 10 min, the mixture was diluted with Et$_2$O and the resulting solids collected by filtration then dissolved in H$_2$O and MeCN and lyophilized to provide 57 mg (93% yield) of 415. LCMS (ESI) [M+H]$^+$=494.4; $^1$H NMR (400 MHz, DMSO-d$_6$) 8.42 (s, 1H), 8.05 (s, 1H), 7.83 (dd, J=5.0, 1.9 Hz, 1H), 7.76 (d, J=8.8 Hz, 1H), 7.65 (s, 1H), 7.31 (d, J=8.9 Hz, 1H), 7.11 (dd, J=7.7, 5.0 Hz, 1H), 6.98 (s, 2H), 6.57 (s, 1H), 4.28 (s, 1H), 3.41 (qd, J=13.6, 7.2 Hz, 3H), 3.17 (s, 1H), 3.09 (dd, J=14.7, 7.1 Hz, 1H), 3.00-2.80 (m, 2H), 2.04 (s, 3H), 2.03-1.96 (m, 1H), 1.87 (s, 1H), 1.64 (dd, J=21.4, 11.9 Hz, 2H), 1.20 (d, J=7.1 Hz, 3H). The absolute stereochemistry of the propane nitrile was randomly assigned.

Example 416 N-(2-Fluoro-6-methyl-5-((3-(2-((S)-piperidin-3-ylamino)pyrimidin-4-yl)pyridin-2-yl)oxy)naphthalen-1-yl)-1-((S)-tetrahydrofuran-2-yl)methanesulfonamide hydrochloride (Isomer-1)

Step 1: (3S)-tert-Butyl 3-((4-(2-((6-fluoro-2-methyl-5-((tetrahydrofuran-2-yl)methylsulfonamido)naphthalen-1-yl)oxy)pyridin-3-yl)pyrimidin-2-yl)amino)piperidine-1-carboxylate

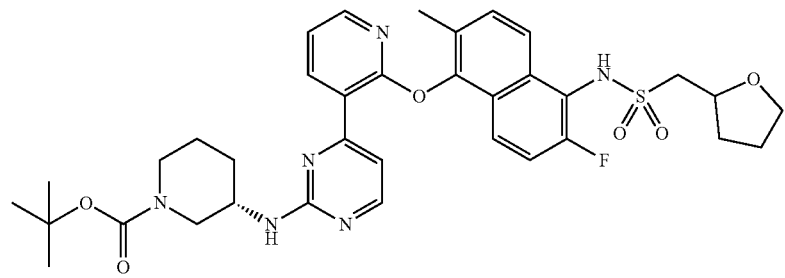

The General Procedure A was followed using (S)-tert-butyl 3-((4-(2-(((5-amino-6-fluoro-2-methylnaphthalen-1-yl)oxy)pyridin-3-yl)pyrimidin-2-yl)amino)piperidine-1-carboxylate from Example 275 (170 mg, 0.31 mmol), pyridine (378 μL, 4.68 mmol), DCM (1.6 mL), 4-Dimethylamino-pyridine (3.8 mg, 0.03 mmol) and tetrahydrofuran-2-ylmethanesulfonyl chloride (115 mg, 0.62 mmol). After 18 h, the mixture was diluted with CH$_2$Cl$_2$ and washed with 1M KHSO$_4$ dried by passing through a phase cartridge separator and concentrated in vacuo. The crude was purified by flash chromatography through silica gel (0-50% EtOAc/CH$_2$Cl$_2$) to provide 144 mg (67% yield) of the title compound. LCMS (ESI) [M+H]$^+$=693.6.

Step 2: (S)-tert-Butyl 3-((4-(2-((6-fluoro-2-methyl-5-(((S)-tetrahydrofuran-2-yl)methylsulfonamido)naphthalen-1-yl)oxy)pyridin-3-yl)pyrimidin-2-yl)amino)piperidine-1-carboxylate (Isomer-1) and (S)-tert-butyl 3-((4-(2-((6-fluoro-2-methyl-5-(((R)-tetrahydrofuran-2-yl)methylsulfonamido)naphthalen-1-yl)oxy)pyridin-3-yl)pyrimidin-2-yl)amino)piperidine-1-carboxylate (Isomer-2)

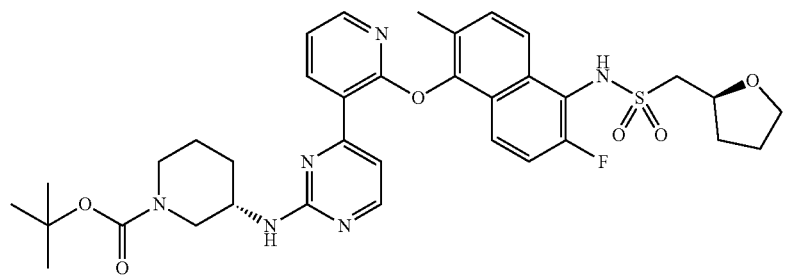

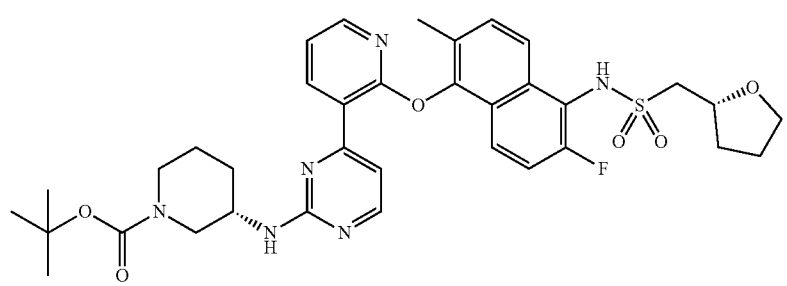 [SMILES: Cc1ccc2c(NS(=O)(=O)CC3CCCO3)c(F)ccc2c1Oc1ncccc1-c1ccnc(N[C@H]2CCCN(C(=O)OC(C)(C)C)C2)n1]

The stereoisomers from Step 1 were subjected to chiral SFC purification (ChiralPak IC (250 mm×10 mm, 5 μm); IPA 60%; flow rate (ml/min): 15, 150 bar, 40° C.) to provide two stereoisomers enantiomeric at the tetrahydrofuran position. Isomer-1: (S)-tert-butyl 3-((4-(2-((6-fluoro-2-methyl-5-(((S)-tetrahydrofuran-2-yl)methylsulfonamido)naphthalen-1-yl)oxy)pyridin-3-yl)pyrimidin-2-yl)amino)piperidine-1-carboxylate, 45 mg (21% yield), ee=98.0%; and isomer-2: (S)-tert-butyl 3-((4-(2-((6-fluoro-2-methyl-5-(((R)-tetrahydrofuran-2-yl)methylsulfonamido)naphthalen-1-yl)oxy)pyridin-3-yl)pyrimidin-2-yl)amino)piperidine-1-carboxylate, 45 mg (21% yield), ee=99.6%.

Step 3: N-(2-Fluoro-6-methyl-5-((3-(2-((S)-piperidin-3-ylamino)pyrimidin-4-yl)pyridin-2-yl)oxy)naphthalen-1-yl)-1-((S)-tetrahydrofuran-2-yl)methanesulfonamide hydrochloride (Isomer-1)

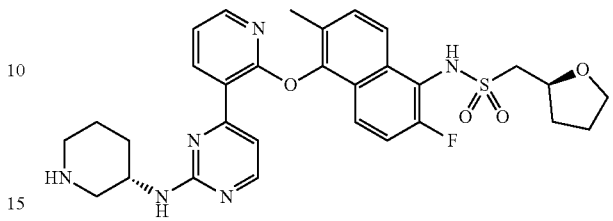

Prepared according to General Procedure B using (S)-tert-butyl 3-((4-(2-((6-fluoro-2-methyl-5-(((S)-tetrahydrofuran-2-yl)methylsulfonamido)naphthalen-1-yl)oxy)pyridin-3-yl)pyrimidin-2-yl)amino)piperidine-1-carboxylate (43 mg, 0.06 mmol) 1,4-dioxane (0.3 mL) and hydrochloric acid (4 M in dioxane, (0.8 mL, 3.2 mmol). After 90 min, the mixture was diluted with Et$_2$O and the resulting solids collected by filtration then dissolved in H$_2$O and MeCN and lyophilized to provide 34 mg (87% yield) of 416. LCMS (ESI) [M+H]$^+$=593.5, $^1$H NMR (400 MHz, DMSO-d$_6$) δ 9.77 (s, 1H), 8.91 (bs, 2H), 8.70 (s, 1H), 8.48 (d, J=5.2 Hz, 1H), 8.13-8.02 (m, 2H), 7.72 (dd, J=9.2, 5.1 Hz, 1H), 7.63 (d, J=8.8 Hz, 1H), 7.57 (bs, 2H), 7.46 (t, J=9.5 Hz, 1H), 7.29 (dd, J=7.6, 4.8 Hz, 1H), 4.39-4.22 (m, 2H), 3.84-3.73 (m, 1H), 3.66 (td, J=7.7, 6.2 Hz, 1H), 3.53-3.33 (m, 3H), 3.20 (d, J=11.5 Hz, 1H), 2.96-2.74 (m, 2H), 2.19 (s, 3H), 2.11 (ddd, J=14.9, 12.1, 7.2 Hz, 1H), 2.06-1.96 (m, 1H), 1.96-1.55 (m, 6H). The absolute stereochemistry of the tetrahydrofuran was randomly assigned.

Example 417 N-(2-Fluoro-6-methyl-5-((3-(2-((S)-piperidin-3-ylamino)pyrimidin-4-yl)pyridin-2-yl)oxy)naphthalen-1-yl)-1-((R)-tetrahydrofuran-2-yl)methanesulfonamide hydrochloride (Isomer-2)

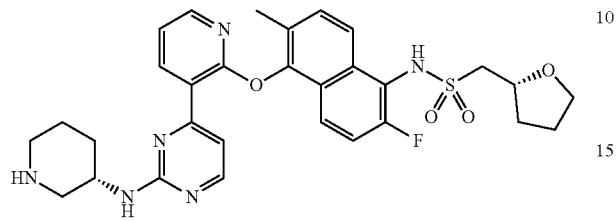

Prepared according to general procedure B using (S)-tert-butyl 3-((4-(2-((6-fluoro-2-methyl-5-(((R)-tetrahydrofuran-2-yl)methylsulfonamido)naphthalen-1-yl)oxy)pyridin-3-yl)pyrimidin-2-yl)amino)piperidine-1-carboxylat (41 mg, 0.06 mmol) 1,4-dioxane (0.3 mL) and hydrochloric acid (4 M in dioxane, (0.8 mL, 3.2 mmol). After 90 min, the mixture was diluted with Et$_2$O and the were resulting solids collected by filtration then dissolved in H$_2$O and MeCN and lyophilized to provide 31.6 mg (85% yield) of 417. LCMS (ESI) [M+H]$^+$=593.5, $^1$H NMR (400 MHz, DMSO-d$_6$) δ 9.77 (s, 1H), 8.83 (bs, 2H), 8.68 (s, 1H), 8.47 (d, J=5.2 Hz, 1H), 8.13-8.01 (m, 2H), 7.71 (dd, J=9.3, 5.2 Hz, 1H), 7.63 (d, J=8.8 Hz, 1H), 7.60-7.52 (m, 2H), 7.46 (t, J=9.5 Hz, 1H), 7.29 (dd, J=7.6, 4.8 Hz, 1H), 4.39-4.19 (m, 2H), 3.79 (dd, J=14.0, 7.6 Hz, 1H), 3.66 (td, J=7.7, 6.2 Hz, 1H), 3.50-3.32 (m, 3H), 3.20 (d, J=12.5 Hz, 1H), 2.97-2.75 (m, 2H), 2.19 (s, 3H), 2.17-2.05 (m, 1H), 2.05-1.97 (m, 1H), 1.97-1.51 (m, 6H). The absolute stereochemistry of the tetrahydrofuran was randomly assigned.

Example 418 N-(2-Fluoro-5-((3-(2-(((3S,5S)-5-fluoropiperidin-3-yl)amino)pyrimidin-4-yl)pyridin-2-yl)oxy)-6-methylnaphthalen-1-yl)-1-phenylmethanesulfonamide hydrochloride (Isomer-2)

Step 1: tert-Butyl 3-[[4-[2-[[5-(benzylsulfonylamino)-6-fluoro-2-methyl-1-naphthyl]oxy]-3-pyridyl]pyrimidin-2-yl]amino]-5-fluoro-piperidine-1-carboxylate

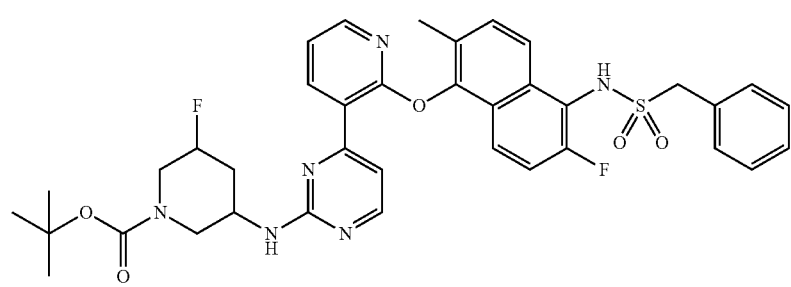 [SMILES: Cc1ccc2c(NS(=O)(=O)Cc3ccccc3)c(F)ccc2c1Oc1ncccc1-c1ccnc(NC2CC(F)CN(C(=O)OC(C)(C)C)C2)n1]

The General Procedure A was followed using tert-butyl 3-[[4-[2-[(5-amino-6-fluoro-2-methyl-1-naphthyl)oxy]-3-pyridyl]pyrimidin-2-yl]amino]-5-fluoro-piperidine-1-carboxylate from example 322 (175 mg, 0.31 mmol), pyridine (0.38 mL, 4.7 mmol), DCM (1 mL), 4-dimethylaminopyridine (3.8 mg, 0.03 mmol) and phenylmethanesulfonyl chloride (0.03 mL, 0.62 mmol). After 18 h, the mixture was diluted with CH$_2$Cl$_2$ and washed with 1M KHSO$_4$, dried over sodium sulfate, filtered and concentrated in vacuo. The crude was purified by flash chromatography through silica gel (0-50% EtOAc/CH$_2$Cl$_2$) to provide 85 mg (38% yield) of the title compound.

Step 2: (3R,5R)-tert-Butyl 3-fluoro-5-((4-(2-((6-fluoro-2-methyl-5-(phenylmethylsulfonamido)naphthalen-1-yl)oxy)pyridin-3-yl)pyrimidin-2-yl)amino)piperidine-1-carboxylate (Isomer 1) and (3S,5S)-tert-butyl 3-fluoro-5-((4-(2-((6-fluoro-2-methyl-5-(phenylmethylsulfonamido)naphthalen-1-yl)oxy)pyridin-3-yl)pyrimidin-2-yl)amino)piperidine-1-carboxylate (Isomer 2)

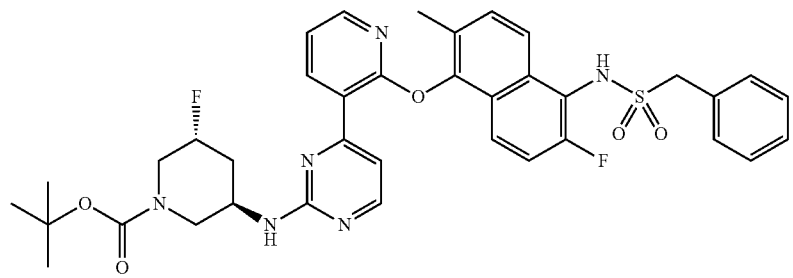

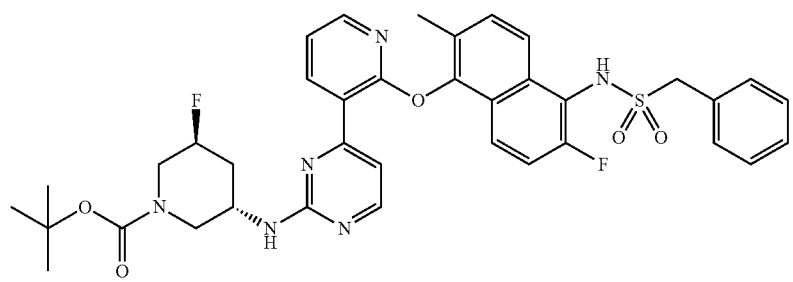

The stereoisomers from Step 1 were subjected to chiral SFC purification (Lux Cellulose-4 (250 mm×10 mm, 5 μm); MeOH 50%; flow rate 10 ml/min, 150 bar, 40° C.) to provide two trans piperidine enantiomers. Isomer-1: (3R,5R)-tert-butyl 3-fluoro-5-((4-(2-((6-fluoro-2-methyl-5 (phenylmethylsulfonamido)naphthalen-1-yl)oxy)pyridin-3-yl)pyrimidin-2-yl)amino)piperidine-1-carboxylate, 28 mg, ee=99.4%; Isomer-2: (3S,5S)-tert-butyl 3-fluoro-5-((4-(2-((6-fluoro-2-methyl-5-(phenylmethylsulfonamido)naphthalen-1-yl)oxy)pyridin-3-yl)pyrimidin-2-yl)amino)piperidine-1-carboxylate, 30 mg, ee=98.2%.

Step 3: N-(2-Fluoro-5-((3-(2-(((3S,5S)-5-fluoropiperidin-3-yl)amino)pyrimidin-4-yl)pyridin-2-yl)oxy)-6-methylnaphthalen-1-yl)-1-phenylmethanesulfonamide hydrochloride (Isomer-2)

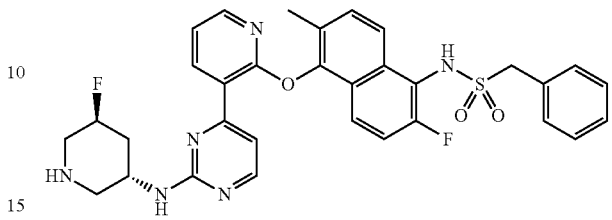

Prepared according to General Procedure B using (3S,5S)-tert-butyl 3-fluoro-5-((4-(2-((6-fluoro-2-methyl-5-(phenylmethylsulfonamido)naphthalen-1-yl)oxy)pyridin-3-yl)pyrimidin-2-yl)amino)piperidine-1-carboxylate (30 mg, 0.39 mmol), 1,4-dioxane (0.5 mL) and 4 M HCl in dioxane (1 mL). After 2 h, the mixture was diluted with Et$_2$O and the resulting solids were collected by filtration, dissolved in H$_2$O and MeCN and lyophilized to provide 22.5 mg (88% yield) of 418. LCMS (ESI) [M+H]$^+$=617.5, $^1$H NMR (400 MHz, DMSO-d$_6$) δ 9.80 (s, 1H), 9.60 (d, J=9.6 Hz, 1H), 9.24 (s, 1H), 8.73 (s, 1H), 8.50 (d, J=5.2 Hz, 1H), 8.09 (dd, J=4.8, 1.9 Hz, 1H), 7.99 (d, J=8.7 Hz, 1H), 7.73 (dd, J=9.3, 5.1 Hz, 1H), 7.65 (d, J=7.8 Hz, 1H), 7.60 (d, J=8.8 Hz, 2H), 7.50 (d, J=9.5 Hz, 1H), 7.48-7.44 (m, 2H), 7.44-7.37 (m, 3H), 7.30 (dd, J=7.6, 4.8 Hz, 1H), 5.25 (d, J=45.2 Hz, 1H), 4.56 (s, 2H), 4.51 (s, 1H), 3.58-3.40 (m, 2H), 3.37-3.13 (m, 1H), 2.83 (q, J=11.0 Hz, 1H), 2.43-2.30 (m, 1H), 2.19 (s, 3H), 1.93 (dt, J=44.3, 13.1 Hz, 1H). The absolute stereochemistry of the fluoropiperidine was assigned based on the cellular potency.

Example 419 (S)—N-(2-Fluoro-6-methyl-5-((3-(2-(piperidin-3-ylamino)pyrimidin-4 yl)pyridin-2-yl)oxy)naphthalen-1-yl)-1-(4-(trifluoromethoxy)phenyl)methanesulfonamide hydrochloride Step 1: (S)-tert-Butyl 3-((4-(2-((6-fluoro-2-methyl-5-((4-(trifluoromethoxy)phenyl)methylsulfonamido)naphthalen-1-yl)oxy)pyridin-3-yl)pyrimidin-2-yl)amino)piperidine-1-carboxylate

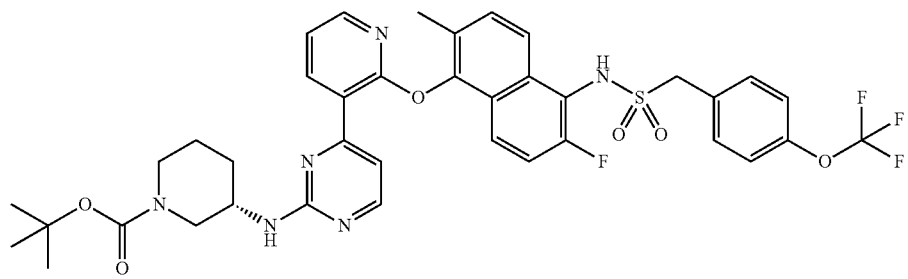 [SMILES: Cc1ccc2c(NS(=O)(=O)Cc3ccc(OC(F)(F)F)cc3)c(F)ccc2c1Oc1ncccc1-c1ccnc(N[C@H]2CCCN(C(=O)OC(C)(C)C)C2)n1]

The General Procedure A was followed using (S)-tert-butyl 3-((4-(2-((5-amino-6-fluoro-2-methylnaphthalen-1-yl)oxy)pyridin-3-yl)pyrimidin-2-yl)amino)piperidine-1-carboxylate from Example 275 (70 mg, 0.13 mmol), pyridine (0.16 mL), CH$_2$Cl$_2$ (0.43 mL), and (4-(trifluoromethoxy)phenyl)methanesulfonyl chloride (71 mg, 0.26 mmol). After 18 h, the mixture was diluted with CH$_2$Cl$_2$ (50 mL) and washed with 1M KHSO$_4$ (10 mL), dried (Na$_2$SO$_4$), filtered and concentrated in vacuo. The crude was purified by flash chromatography through silica gel (0-50% EtOAc/DCM) to provide 32 mg (31% yield) of the title compound. LCMS (ESI) [M+H]$^+$=783.6.

Step 2: (S)—N-(2-Fluoro-6-methyl-5-((3-(2-(piperidin-3-ylamino)pyrimidin-4-yl)pyridin-2-yl)oxy)naphthalen-1-yl)-1-(4-(trifluoromethoxy)phenyl)methanesulfonamide hydrochloride 419

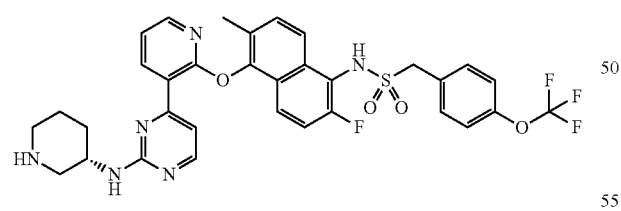

Prepared according to General Procedure B using (S)-tert-butyl 3-((4-(2-((6-fluoro-2-methyl-5-((4-(trifluoromethoxy)phenyl)methylsulfonamido)naphthalen-1-yl)oxy)pyridin-3-yl)pyrimidin-2-yl)amino)piperidine-1-carboxylate (32 mg, 0.04 mmol), 1,4-dioxane (0.5 mL), and hydrochloric acid (4 M in dioxane, 1.0 mL, 4.0 mmol). After 1 h, the mixture was diluted with Et$_2$O and the resulting solids collected by filtration then dissolved in H$_2$O and MeCN and lyophilized to provide 24 mg (82% yield) of 419. LCMS (ESI) [M+H]$^+$=683.5; $^1$H NMR (400 MHz, DMSO-d$_6$) δ 9.83 (s, 1H), 9.00-8.76 (m, 2H), 8.73-8.53 (m, 1H), 8.48 (d, J=5.2 Hz, 1H), 8.08 (dd, J=4.8, 2.0 Hz, 1H), 7.98 (d, J=8.8 Hz, 1H), 7.73 (dd, J=9.3, 5.1 Hz, 1H), 7.60 (d, J=8.7 Hz, 3H), 7.55 (dd, J=8.7, 6.7 Hz, 2H), 7.49 (t, J=9.5 Hz, 1H), 7.42 (d, J=7.9 Hz, 2H), 7.29 (dd, J=7.6, 4.8 Hz, 1H), 4.63 (s, 2H), 4.27 (s, 1H), 3.44 (d, J=12.3 Hz, 1H), 3.21 (d, J=12.4 Hz, 1H), 2.92-2.76 (m, 2H), 2.19 (s, 3H), 2.04-1.97 (m, 1H), 1.98-1.86 (m, 1H), 1.82-1.56 (m, 2H).

Example 420 4-[2-[[6-Fluoro-2-methyl-5-[[methyl(propyl)sulfamoyl]amino]-1-naphthyl]oxy]-3-pyridyl]-2-[[(3S)-3-piperidyl]amino]pyrimidine hydrochloride Step 1: tert-Butyl (3S)-3-[[4-[2-[[6-fluoro-2-methyl-5-[[methyl(propyl)sulfonylamino]-1-naphthyl]oxy]-3-pyridyl]pyrimidin-2-yl]amino]piperidine-1-carboxylate

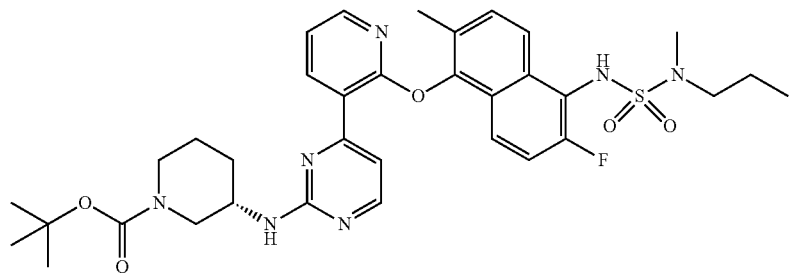 [SMILES: CCCN(C)S(=O)(=O)Nc1c(F)ccc2c(Oc3ncccc3-c3ccnc(N[C@H]4CCCN(C(=O)OC(C)(C)C)C4)n3)c(C)ccc12]

To a solution of tert-butyl (3S)-3-[[4-[2-[[6-fluoro-2-methyl-5-[(2-oxooxazolidin-3-yl)sulfonylamino]-1-naphthyl]oxy]-3-pyridyl]pyrimidin-2-yl]amino]piperidine-1-carboxylate (30 mg, 0.04 mmol) in MeCN (0.22 mL) was added triethylamine (0.02 mL, 0.13 mmol), followed by N-methyl-N-propylamine (0.005 mL, 0.05 mmol). The reaction mixture was stirred at 85° C. for 16 h at which time another portion of N-methyl-N-propylamine (0.005 mL, 0.05 mmol) was added and the reaction mixture was stirred at 85° C. for 72 h. The mixture was diluted with $CH_2Cl_2$ and washed with 1M $KHSO_4$, dried ($Na_2SO_4$), filtered and concentrated in vacuo. The crude was purified by flash chromatography through silica gel (0-50% EtOAc/$CH_2Cl_2$) to provide 12 mg (41% yield) of the title compound. LCMS (ESI) $[M+H]^+$=680.5.

Step 2: 4-[2-[[6-Fluoro-2-methyl-5-[[methyl(propyl)sulfamoyl]amino]-1-naphthyl]oxy]-3-pyridyl]-2-[[(3S)-3-piperidyl]amino]pyrimidine hydrochloride 420

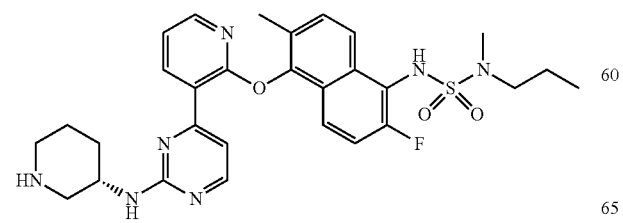

Prepared according to General Procedure B using tert-butyl (3S)-3-[[4-[2-[[6-fluoro-2-methyl-5-[[methyl(propyl)sulfamoyl]amino]-1-naphthyl]oxy]-3-pyridyl]pyrimidin-2-yl]amino]piperidine-1-carboxylate (12 mg, 0.02 mmol), 1,4-dioxane (0.5 mL), and hydrochloric acid (4 M in dioxane, 1.0 mL, 4.0 mmol). After 1 h, the mixture was diluted with Et₂O and the solids collected, washed with Et₂O, dissolved in H₂O and lyophilized to provide 9.4 mg (86% yield) of 420. LCMS (ESI) [M+H]⁺=580.5; ¹H NMR (400 MHz, DMSO-d₆) δ 9.46 (s, 1H), 9.04-8.75 (m, 2H), 8.65 (s, 1H), 8.47 (d, J=5.2 Hz, 1H), 8.14-8.05 (m, 2H), 7.69 (dd, J=9.3, 4.9 Hz, 1H), 7.62 (d, J=8.8 Hz, 1H), 7.55 (t, J=7.4 Hz, 2H), 7.43 (t, J=9.5 Hz, 1H), 7.29 (dd, J=7.6, 4.8 Hz, 1H), 4.25 (s, 1H), 3.44 (d, J=10.3 Hz, 1H), 3.21 (d, J=12.0 Hz, 1H), 3.09-2.98 (m, 2H), 2.96-2.82 (m, 2H), 2.80 (s, 3H), 2.19 (s, J=9.2 Hz, 3H), 2.01 (d, J=9.4 Hz, 1H), 1.91 (d, J=15.0 Hz, 1H), 1.81-1.54 (m, 2H), 1.55-1.43 (m, 2H), 0.80 (t, J=7.4 Hz, 3H).

Example 421 4-[2-[[5-[[Ethyl(methyl)sulfamoyl]amino]-6-fluoro-2-methyl-1-naphthyl]oxy]-3-pyridyl]-2-[[(3S)-3-piperidyl]amino]pyrimidine hydrochloride Step 1: N-Ethyl-N-methyl-sulfamoyl chloride

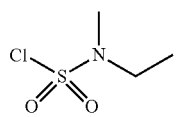

To a solution of sulfuryl chloride (0.35 mL, 4.3 mmol) in CH₂Cl₂ (3.6 mL) at 0° C. was added N-ethylmethylamine (0.092 ml, 1.1 mmol), followed by triethylamine (0.3 mL, 2.1 mmol). The reaction mixture was stirred at rt for 2 h. The reaction was diluted with CH₂Cl₂ and 1N HCl, extracted with CH₂Cl₂, dried (Na₂SO₄) and evaporated. The resulting residue was used directly in the next step.

Step 2: tert-Butyl (3S)-3-[[4-[2-[[5-[[ethyl(methyl)sulfamoyl]amino]-6-fluoro-2-methyl-1-naphthyl]oxy]-3-pyridyl]pyrimidin-2-yl]amino]piperidine-1-carboxylate

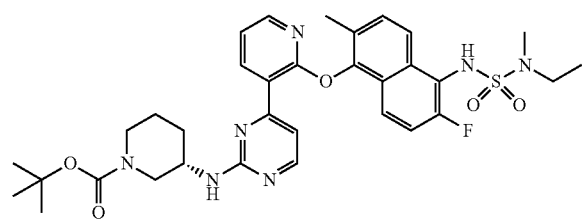 [SMILES: CCN(C)S(=O)(=O)Nc1c(F)ccc2c(Oc3ncccc3-c3ccnc(N[C@H]4CCCN(C(=O)OC(C)(C)C)C4)n3)c(C)ccc12]

To a solution of tert-butyl (3S)-3-[[4-[2-[(5-amino-6-fluoro-2-methyl-1-naphthyl)oxy]-3-pyridyl]pyrimidin-2-yl]amino]piperidine-1-carboxylate from Example 275 (75 mg, 0.14 mmol) in pyridine (1 mL, 12 mmol) was added N-ethyl-N-methyl-sulfamoyl chloride (163 mg, 1.03 mmol) and DMAP (5 mg, 0.01 mmol). The reaction mixture was stirred at 50° C. for 2 days and concentrated in vacuo. The crude was purified by C18 reverse phase flash chromatography (45-75% MeCN/10 mM aqueous ammonium formate, pH=3.8). Appropriate fractions were combined and lyophilized to provide 22 mg (24% yield) of the title compound. LCMS (ESI) [M+H]⁺=664.6.

Step 3: 4-[2-[[5-[[Ethyl(methyl)sulfamoyl]amino]-6-fluoro-2-methyl-1-naphthyl]oxy]-3-pyridyl]-2-[[(3S)-3-piperidyl]amino]pyrimidine hydrochloride 421

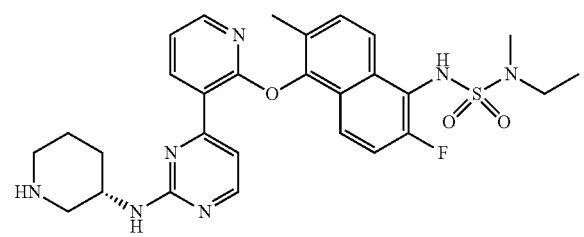 [SMILES: CCN(C)S(=O)(=O)Nc1c(F)ccc2c(Oc3ncccc3-c3ccnc(N[C@H]4CCCNC4)n3)c(C)ccc12]

Prepared according to General Procedure B using tert-butyl (3S)-3-[[4-[2-[[5-[[ethyl(methyl)sulfamoyl]amino]-6-fluoro-2-methyl-1-naphthyl]oxy]-3-pyridyl]pyrimidin-2-yl]amino]piperidine-1-carboxylate (22 mg, 0.03 mmol), 1,4-dioxane (0.5 mL), and hydrochloric acid (4 M in dioxane, 1.0 mL, 4.0 mmol). After 1 h, the mixture was diluted with Et₂O and the solids collected, washed with Et₂O, dissolved in H₂O and lyophilized to provide 17 mg (86% yield) of 421. LCMS (ESI) [M+H]⁺=566.5; ¹H NMR (400 MHz, DMSO-d₆) δ 9.47 (s, 1H), 9.18-8.80 (m, 2H), 8.67 (s, 1H), 8.47 (d, J=5.2 Hz, 1H), 8.11-8.06 (m, 2H), 7.69 (dd, J=9.4, 5.0 Hz, 1H), 7.62 (d, J=8.8 Hz, 1H), 7.57 (d, J=6.7 Hz, 2H), 7.43 (t, J=9.4 Hz, 1H), 7.29 (dd, J=7.6, 4.8 Hz, 1H), 4.27 (s, 1H), 3.43 (d, J=12.5 Hz, 1H), 3.20 (d, J=11.5 Hz, 1H), 3.14 (q, J=7.1 Hz, 2H), 2.94-2.82 (m, 2H), 2.80 (s, J=6.5 Hz, 3H), 2.19 (s, 3H), 2.01 (d, J=11.0 Hz, 1H), 1.96-1.84 (m, 1H), 1.74 (q, J=12.3 Hz, 1H), 1.62 (dd, J=21.8, 11.5 Hz, 1H), 1.06 (t, J=7.1 Hz, 3H).

Example 422 (R)-3-Methyl-2-(((6-methyl-5-((3-(2-(((S)-piperidin-3-yl)amino)pyrimidin-4-yl)pyridin-2-yl)oxy)naphthalen-1-yl)amino)methyl)butanenitrile Step 1: tert-Butyl (3S)-3-((4-(2-((5-((2-cyano-3-methylbutyl)amino)-2-methylnaphthalen-1-yl)oxy)pyridin-3-yl)pyrimidin-2-yl)amino)piperidine-1-carboxylate

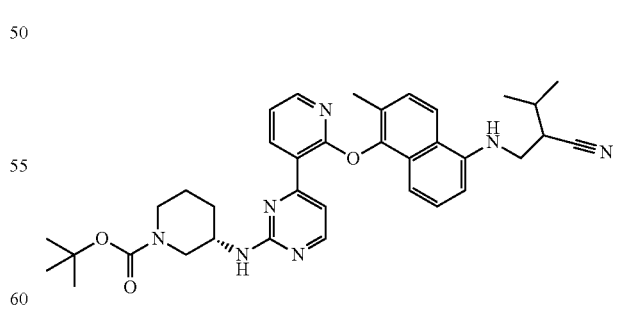

The general procedure E was followed, using tert-butyl (3S)-3-[[4-[2-[(5-amino-2-methyl-1-naphthyl)oxy]-3-pyridyl]pyrimidin-2-yl]amino]piperidine-1-carboxylate (200 mg, 0.38 mmol), 2-formyl-3-methyl-butanenitrile (126.6 mg, 1.14 mmol), sodium cyanoborohydride (71.60 mg, 1.14 mmol) catalytic AcOH in EtOH (4 mL). After aqueous workup, LCMS indicated the intermediate imine is the major product. The mixture was dissolved in EtOH (4 mL) treated with sodium borohydride (43.10 mg, 1.14 mmol) at room temperature for 3 hrs. It was diluted with water, extracted with iPrOAc (2×10 mL), dried over MgSO$_4$, concentrated in vacuo. The crude product was purified via reverse-phase HPLC, followed by chiral SFC to afford (isomer-1, $t_R$=1.447 min) 27.8 mg (11.8% yield) of the title compound as a brown solid, and (isomer-2, $t_R$=1.636 min) 27 mg (11.4% yield) as a brown solid. LCMS (ESI) [M+H]$^+$=622.

Step 2: 3-Methyl-2-((((6-methyl-5-((3-(2-(((S)-piperidin-3-yl)amino)pyrimidin-4-yl)pyridin-2-yl)oxy) naphthalen-1-yl)amino)methyl)butanenitrile 422

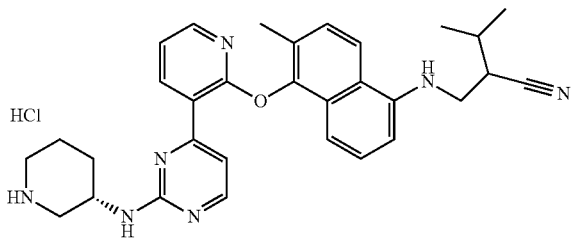 [SMILES: Cl ; Cc1ccc2c(NCC(C#N)C(C)C)cccc2c1Oc1ncccc1-c1ccnc(N[C@H]2CCCNC2)n1]

The General Procedure B was followed, using tert-butyl (3S)-3-((4-(2-((5-((2-cyano-3-methylbutyl)amino)-2-methylnaphthalen-1-yl)oxy)pyridin-3-yl)pyrimidin-2-yl)amino) piperidine-1-carboxylate (isomer-1, 27.8 mg, 0.04 mmol). The product was lyophilized to yield 22.9 mg (91.8% yield) of the title compound as a brown solid HCl salt. LCMS (ESI) [M+H]$^+$=522; $^1$H NMR (400 MHz, DMSO-d$_6$) δ 8.99-8.82 (m, 2H), 8.61 (s, 2H), 8.47 (d, J=5.3 Hz, 1H), 8.07-8.00 (m, 2H), 7.56 (dd, J=17.6, 6.3 Hz, 2H), 7.39 (d, J=8.7 Hz, 1H), 7.25 (dd, J=7.6, 4.8 Hz, 1H), 7.19 (t, J=8.0 Hz, 1H), 6.88 (d, J=8.4 Hz, 1H), 6.55 (d, J=7.7 Hz, 1H), 4.28 (s, 1H), 3.49-3.42 (m, 2H), 3.25-3.16 (m, 2H), 2.92-2.79 (m, 3H), 2.19 (s, 3H), 2.11-1.98 (m, 2H), 1.97-1.87 (m, 1H), 1.82-1.58 (m, 2H), 1.06 (dd, J=6.7, 3.1 Hz, 6H). The absolute stereochemistry of the nitrile was randomly assigned.

Example 423 (S)-3-Methyl-2-((((6-methyl-5-((3-(2-(((S)-piperidin-3-yl)amino)pyrimidin-4-yl)pyridin-2-yl)oxy)naphthalen-1-yl)amino)methyl) butanenitrile The General Procedure B was followed, using tert-butyl (3S)-3-((4-(2-((5-((2-cyano-3-methylbutyl)amino)-2-methylnaphthalen-1-yl)oxy)pyridin-3-yl)pyrimidin-2-yl)amino) piperidine-1-carboxylate (isomer-1, 27 mg, 0.04 mmol). The product was lyophilized to yield 22.9 mg (91.8% yield) of 423 as a brown solid HCl salt. LCMS (ESI) [M+H]$^+$=522; $^1$H NMR (400 MHz, DMSO-d$_6$) δ 8.98-8.81 (m, 2H), 8.60 (s, 2H), 8.47 (d, J=5.2 Hz, 1H), 8.07-8.00 (m, 2H), 7.61-7.52 (m, 2H), 7.39 (d, J=8.7 Hz, 1H), 7.25 (dd, J=7.6, 4.8 Hz, 1H), 7.19 (dd, J=8.4, 7.6 Hz, 1H), 6.88 (d, J=8.4 Hz, 1H), 6.54 (d, J=7.7 Hz, 1H), 4.30 (d, J=19.5 Hz, 1H), 3.55-3.51 (m, 1H), 3.50-3.40 (m, 2H), 3.25-3.16 (m, 2H), 2.91-2.78 (m, 2H), 2.19 (s, 3H), 2.11-1.99 (m, 2H), 1.96-1.88 (m, 1H), 1.80-1.58 (m, 2H), 1.06 (dd, J=6.7, 3.1 Hz, 6H). The absolute stereochemistry of the nitrile was randomly assigned.

Example 424 (S)—N-(5-((5-Methoxy-3-(2-(piperidin-3-ylamino)pyrimidin-4-yl)pyridin-2-yl)oxy)-6-methylnaphthalen-1-yl)propane-1-sulfonamide hydrochloride 424

Step 1: tert-Butyl (3S)-3-[[4-[2-[(5-amino-2-methyl-1-naphthyl)oxy]-5-(4,4,5,5-tetramethyl-1,3,2-dioxaborolan-2-yl)-3-pyridyl]pyrimidin-2-yl]amino]piperidine-1-carboxylate

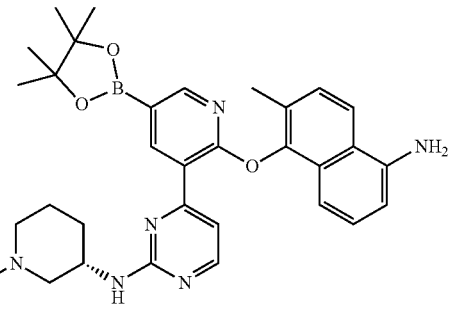

In a flask containing tert-butyl (3S)-3-[[4-[2-[(5-amino-2-methyl-1-naphthyl)oxy]-5-bromo-3-pyridyl]pyrimidin-2-yl]amino]piperidine-1-carboxylate from Example 385 (50 mg, 0.08 mmol) was added bis(pinacolato)diboron (25 mg, 0.10 mmol), potassium acetate (0.02 mL, 0.33 mmol), 1,1-bis(diphenylphosphino)ferrocene-palladium dichloride (6.13 mg, 0.01 mmol) and 1,4-dioxane (1 mL). Nitrogen was bubbled through the mixture then heated to 85° C. for 16 h. Additional bis(pinacolato)diboron (25 mg, 0.10 mmol) and potassium acetate (0.02 mL, 0.33 mmol) were then added and heating was continued for 5 h. After cooling to rt, the mixture was diluted with EtOAc (20 mL) and washed with brine. The phases were separated and the organic phase was dried over magnesium sulfate, filtered and concentrated. The crude was purified by flash chromatography through silica gel (0-100% EtOAc/CH$_2$Cl$_2$) to provide 40 mg (74% yield) of the title compound as an off-white solid. LCMS (ESI) [M+H]$^+$=653.3.

Step 2: tert-Butyl (3S)-3-[[4-[2-[(5-amino-2-methyl-1-naphthyl)oxy]-5-hydroxy-3-pyridyl]pyrimidin-2-yl]amino]piperidine-1-carboxylate

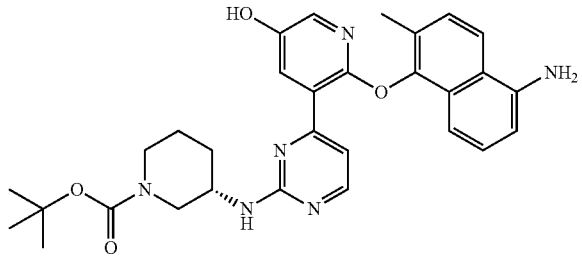 [SMILES: Cc1ccc2c(N)cccc2c1Oc1ncc(O)cc1-c1ccnc(N[C@H]2CCCN(C(=O)OC(C)(C)C)C2)n1]

In a flask containing tert-butyl (3S)-3-[[4-[2-[(5-amino-2-methyl-1-naphthyl)oxy]-5-(4,4,5,5-tetramethyl-1,3,2-dioxaborolan-2-yl)-3-pyridyl]pyrimidin-2-yl]amino]piperidine-1-carboxylate (40 mg, 0.06 mmol) was added hydrogen peroxide (0.06 mL, 0.61 mmol, 30% in water) and stirred for 1 h at 25° C. The crude was diluted with EtOAc (20 mL) and water (10 mL). The phases were separated and the organic phase was washed with sodium sulfite (10% solution in water), dried over magnesium sulfate, filtered and concentrated. The crude was purified by C18 reverse phase flash chromatography through (30-90% MeCN/10 mM aqueous ammonium formate, pH 3.8)) to provide 10 mg (31% yield) of the title compound as a pale yellow solid. LCMS (ESI) [M+H]$^+$=543.2.

Step 3: (S)-tert-Butyl 3-((4-(2-((5-amino-2-methyl-naphthalen-1-yl)oxy)-5-methoxypyridin-3-yl)pyrimidin-2-yl)amino)piperidine-1-carboxylate

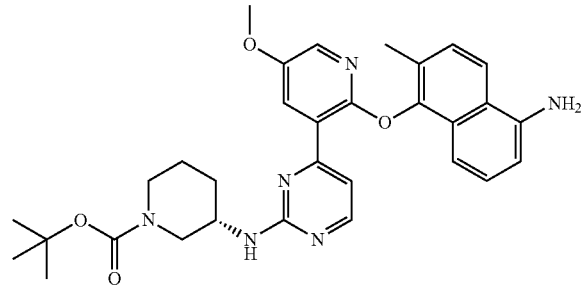 [SMILES: COc1cnc(Oc2c(C)ccc3c(N)cccc23)c(-c2ccnc(N[C@H]3CCCN(C(=O)OC(C)(C)C)C3)n2)c1]

In a flask containing iodomethane (3.9 mg, 0.028 mmol) was added Cs$_2$CO$_3$ (6.0 mg, 0.018 mmol), DMF (0.10 mL) and tert-butyl (3S)-3-[[4-[2-[(5-amino-2-methyl-1-naphthyl)oxy]-5-hydroxy-3-pyridyl]pyrimidin-2-yl]amino]piperidine-1-carboxylate (5 mg, 0.009 mmol) and the mixture was stirred at rt. After 1 h, the mixture was directly purified by C18 reverse phase flash chromatography (30-70% MeCN/10 mM aqueous ammonium formate, pH 3.8). Appropriate fractions were combined and lyophilized to provide 5 mg (97%) field of the title compound as an off-white solid. LCMS (ESI) [M+H]$^+$=557.2.

Step 4: (S)-tert-Butyl 3-((4-(5-methoxy-2-((2-methyl-5-(propylsulfonamido)naphthalen-1-yl)oxy)pyridin-3-yl)pyrimidin-2-yl)amino)piperidine-1-carboxylate

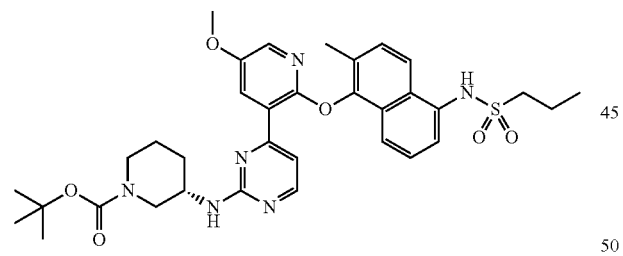

The General Procedure A was followed using (S)-tert-Butyl 3-((4-(2-((5-amino-2-methylnaphthalen-1-yl)oxy)-5-methoxypyridin-3-yl)pyrimidin-2-yl)amino)piperidine-1-carboxylate (5 mg, 0.009 mmol), pyridine (0.10 mL) and propane-1-sulfonyl chloride (6.4 mg, 0.044 mmol). After 2 h, the crude mixture was directly purified by C18 reverse phase flash chromatography (40-80% MeCN/10 mM aqueous ammonium formate, pH 3.8). Appropriate fractions combined and lyophilized to provide 5 mg (84% yield) of the title compound as an off-white solid. LCMS (ESI) [M+H]$^+$=663.2.

Step 5: (S)—N-(5-((5-Methoxy-3-(2-(piperidin-3-ylamino)pyrimidin-4-yl)pyridin-2-yl)oxy)-6-methyl-naphthalen-1-yl)propane-1-sulfonamide hydrochloride 424

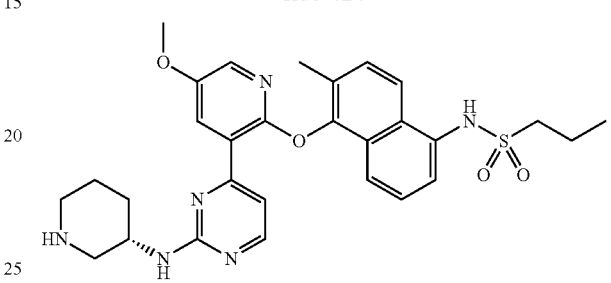

Prepared according to General Procedure B using (S)-tert-butyl 3-((4-(5-methoxy-2-((2-methyl-5-(propylsulfonamido)naphthalen-1-yl)oxy)pyridin-3-yl)pyrimidin-2-yl)amino)piperidine-1-carboxylate (5 mg, 0.008 mmol), EtOAc (1 mL), and hydrochloric acid (4 M in dioxane, 0.61 mL, 2.4 mmol). After 1 h, the resulting solids collected by filtration then dissolved in H$_2$O and MeCN and lyophilized to provide 3 mg (66% yield) of the 424. LCMS (ESI) [M+H]$^+$=563.1; $^1$H NMR (400 MHz, CD$_3$OD) δ 8.51 (d, J=6.5 Hz, 1H), 8.35 (d, J=3.1 Hz, 1H), 8.14 (d, J=8.7 Hz, 2H), 7.83 (d, J=3.0 Hz, 1H), 7.63 (d, J=8.5 Hz, 1H), 7.57-7.52 (m, 2H), 7.39 (dd, J=8.4, 7.6 Hz, 1H), 4.61 (br s, 1H), 3.91 (s, 3H), 3.68 (dd, J=12.5, 3.7 Hz, 1H), 3.38 (dt, J=12.6, 3.6 Hz, 1H), 3.18 (d, J=11.2 Hz, 1H), 3.15-3.04 (m, 3H), 2.28 (s, 4H), 2.20-2.08 (m, 1H), 2.01-1.79 (m, 4H), 1.03 (t, J=7.5 Hz, 3H). 4 NH are exchanged with CD$_3$OD.

Example 425 (S)-1-(3-Cyanophenyl)-N-(2-fluoro-6-methyl-5-((3-(2-(piperidin-3-ylamino)pyrimidin-4-yl)pyridin-2-yl)oxy)naphthalen-1-yl)methanesulfonamide hydrochloride Step 1: (S)-tert-Butyl 3-((4-(2-((5-((3-cyanophenyl)methylsulfonamido)-6-fluoro-2-methylnaphthalen-1-yl)oxy)pyridin-3-yl)pyrimidin-2-yl)amino)piperidine-1-carboxylate

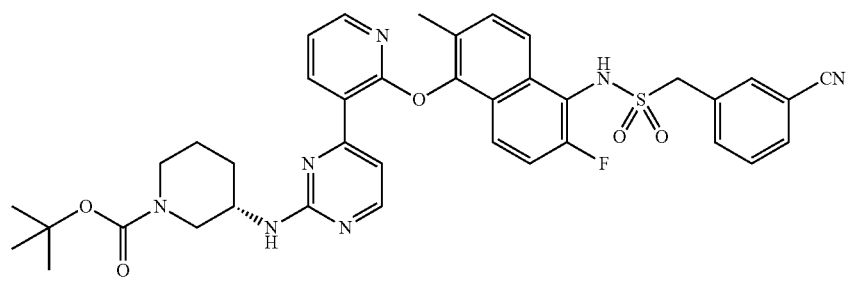 [SMILES: Cc1ccc2c(NS(=O)(=O)Cc3cccc(C#N)c3)c(F)ccc2c1Oc1ncccc1-c1ccnc(N[C@H]2CCCN(C(=O)OC(C)(C)C)C2)n1]

The General Procedure A was followed using (S)-tert-butyl 3-((4-(2-((5-amino-6-fluoro-2-methylnaphthalen-1-yl)oxy)pyridin-3-yl)pyrimidin-2-yl)amino)piperidine-1-carboxylate from Example 275 (60 mg, 0.11 mmol), pyridine (0.09 mL), CH₂Cl₂ (1.5 mL), and (3-cyanophenyl)methanesulfonyl chloride (48 mg, 0.22 mmol). After 18 h, the mixture was concentrated in vacuo. The residue was diluted with EtOAc (50 mL), washed with 1M HCl (2×10 mL), then saturated aqueous NaHCO₃ (10 mL), then saturated aqueous NaCl (10 mL), dried (MgSO₄), filtered and concentrated in vacuo. The crude was purified by C18 reverse phase flash chromatography (0-70% MeCN/10 mM aqueous ammonium formate, pH=3.8). Appropriate fractions combined and lyophilized to provide 54 mg (68% yield) of the title compound. LCMS (ESI) [M+H]⁺=724.3.

Step 2: (S)-1-(3-Cyanophenyl)-N-(2-fluoro-6-methyl-5-((3-(2-(piperidin-3-ylamino)pyrimidin-4-yl)pyridin-2-yl)oxy)naphthalen-1-yl)methanesulfonamide hydrochloride 425

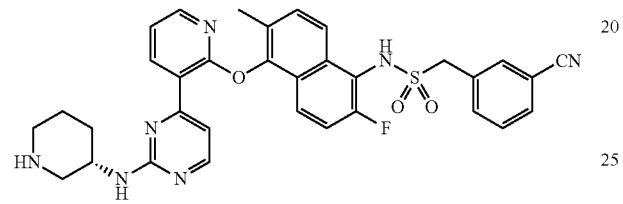

Prepared according to General Procedure B using (S)-tert-butyl 3-((4-(2-((5-((3-cyanophenyl)methylsulfonamido)-6-fluoro-2-methylnaphthalen-1-yl)oxy)pyridin-3-yl)pyrimidin-2-yl)amino)piperidine-1-carboxylate (54 mg, 0.07 mmol), 1,4-dioxane (1.0 mL), and hydrochloric acid (4 M in dioxane, 0.5 mL, 2.0 mmol). After 3 h, the mixture was diluted with MTBE and the resulting solids collected by filtration then dissolved in H₂O and MeCN and lyophilized to provide 41 mg (83% yield) of 425. LCMS (ESI) [M+H]⁺=624.1; ¹H NMR (400 MHz, CD₃OD) δ 8.70 (d, J=7.0 Hz, 1H), 8.47 (d, J=5.5 Hz, 1H), 8.10 (d, J=8.8 Hz, 1H), 8.04 (dd, J=4.8, 1.9 Hz, 1H), 7.88-7.72 (m, 5H), 7.61-7.54 (m, 2H), 7.37 (t, J=9.5 Hz, 1H), 7.27 (dd, J=7.6, 4.9 Hz, 1H), 4.66 (s, 2H), 4.48-4.33 (m, 1H), 3.68-3.60 (m, 1H), 3.40-3.32 (m, 1H), 3.11-3.01 (m, 2H), 2.25 (s, 3H), 2.24-2.17 (m, 1H), 2.17-2.07 (m, 1H), 1.98-1.74 (m, 2H).

Example 426 (S)-1-(4-Cyanophenyl)-N-(2-fluoro-6-methyl-5-((3-(2-(piperidin-3-ylamino)pyrimidin-4-yl)pyridin-2-yl)oxy)naphthalen-1-yl)methanesulfonamide hydrochloride Step 1: (S)-tert-Butyl 3-((4-(2-((5-((4-cyanophenyl)methylsulfonamido)-6-fluoro-2-methylnaphthalen-1-yl)oxy)pyridin-3-yl)pyrimidin-2-yl)amino)piperidine-1-carboxylate

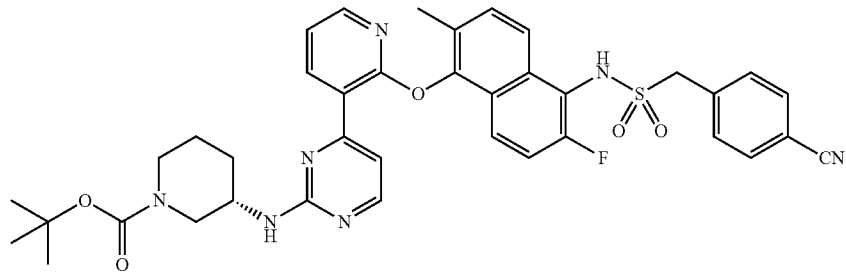 [SMILES: Cc1ccc2c(NS(=O)(=O)Cc3ccc(C#N)cc3)c(F)ccc2c1Oc1ncccc1-c1ccnc(N[C@H]2CCCN(C(=O)OC(C)(C)C)C2)n1]

The General Procedure A was followed using (S)-tert-butyl 3-((4-(2-((5-amino-6-fluoro-2-methylnaphthalen-1-yl)oxy)pyridin-3-yl)pyrimidin-2-yl)amino)piperidine-1-carboxylate from Example 275 (60 mg, 0.11 mmol), pyridine (0.09 mL), CH$_2$Cl$_2$ (1.5 mL), and (4-cyanophenyl)methanesulfonyl chloride (48 mg, 0.22 mmol). After 18 h, the mixture was concentrated in vacuo. The residue was diluted with EtOAc (50 mL), washed with 1M HCl (2×10 mL), then saturated aqueous NaHCO$_3$ (10 mL), then saturated aqueous NaCl (10 mL), dried (MgSO$_4$), filtered and concentrated in vacuo. The crude was purified by C18 reverse phase flash chromatography (0-60% MeCN/10 mM aqueous ammonium bicarbonate, pH=10). Appropriate fractions were combined and lyophilized to provide 47 mg (59% yield) of the title compound. LCMS (ESI) [M+H]$^+$=724.3.

Step 2: (S)-1-(4-Cyanophenyl)-N-(2-fluoro-6-methyl-5-((3-(2-(piperidin-3-ylamino)pyrimidin-4-yl)pyridin-2-yl)oxy)naphthalen-1-yl)methanesulfonamide hydrochloride

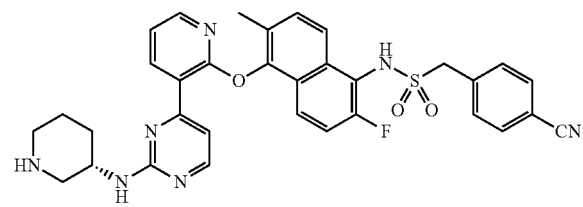 [SMILES: Cc1ccc2c(NS(=O)(=O)Cc3ccc(C#N)cc3)c(F)ccc2c1Oc1ncccc1-c1ccnc(N[C@H]2CCCNC2)n1]

Prepared according to General Procedure B using (S)-tert-butyl 3-((4-(2-((5-((4-cyanophenyl)methylsulfonamido)-6-fluoro-2-methylnaphthalen-1-yl)oxy)pyridin-3-yl)pyrimidin-2-yl)amino)piperidine-1-carboxylate (47 mg, 0.06 mmol), 1,4-dioxane (1.0 mL), and hydrochloric acid (4 M in dioxane, 0.5 mL, 2.0 mmol). After 3 h, the mixture was diluted with MTBE and the resulting solids were collected by filtration then dissolved in H$_2$O and MeCN and lyophilized to provide 32 mg (75% yield) of 426. LCMS (ESI) [M+H]$^+$=624.1; $^1$H NMR (400 MHz, CD$_3$OD) δ 8.71 (d, J=5.4 Hz, 1H), 8.47 (d, J=5.5 Hz, 1H), 8.10 (d, J=8.8 Hz, 1H), 8.04 (dd, J=4.8, 1.9 Hz, 1H), 7.82-7.73 (m, 4H), 7.70-7.65 (m, 2H), 7.57 (d, J=8.8 Hz, 1H), 7.36 (t, J=9.5 Hz, 1H), 7.27 (dd, J=7.6, 4.8 Hz, 1H), 4.67 (s, 2H), 4.48-4.34 (m, 1H), 3.63 (dd, J=12.3, 3.7 Hz, 1H), 3.40-3.33 (m, 1H), 3.12-3.00 (m, 2H), 2.25 (s, 3H), 2.24-2.17 (m, 1H), 2.17-2.07 (m, 1H), 1.98-1.75 (m, 2H).

Example 427 4-[2-[[6-Fluoro-2-methyl-5-[[methyl(2,2,2-trifluoroethyl)sulfamoyl]amino]-1-naphthyl]oxy]-3-pyridyl]-2-[[(3S)-3-piperidyl]amino]pyrimidine hydrochloride Step 1: tert-Butyl (3S)-3-[[4-[2-[[6-fluoro-2-methyl-5-[(2-oxooxazolidin-3-yl)sulfonylamino]-1-naphthyl]oxy]-3-pyridyl]pyrimidin-2-yl]amino]piperidine-1-carboxylate

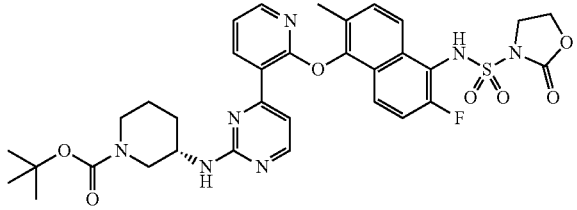 [SMILES: Cc1ccc2c(NS(=O)(=O)N3CCOC3=O)c(F)ccc2c1Oc1ncccc1-c1ccnc(N[C@H]2CCCN(C(=O)OC(C)(C)C)C2)n1]

To a solution of chlorosulfonyl isocyanate (0.12 mL, 1.38 mmol) in CH$_2$Cl$_2$ (0.70 mL) at 0° C. was added 2-bromoethanol (0.1 mL, 1.38 mmol). The reaction mixture was stirred at 0° C. for 1 h. To the reaction mixture was then added tert-butyl (3S)-3-[[4-[2-[(5-amino-6-fluoro-2-methyl-1-naphthyl)oxy]-3-pyridyl]pyrimidin-2-yl]amino]piperidine-1-carboxylate from Example 275 (500 mg, 0.92 mmol) and triethylamine (0.4 mL, 2.85 mmol). The reaction mixture was warmed to rt and stirred overnight. The mixture was then diluted with CH$_2$Cl$_2$ (10 mL) and 1N HCl (5 mL), and the phases were separated. The aqueous phase was extracted again with DCM (10 mL), and the combined organic extracts were dried over Na$_2$SO$_4$, filtered and evaporated. The residue was purified by flash column chromatography through silica gel (0-100% EtOAc/CH$_2$Cl$_2$) to give 469 mg (74% yield) of the title compound. LCMS (ESI) [M+H]$^+$=694.4.

Step 2: tert-Butyl (3S)-3-[[4-[2-[[6-fluoro-2-methyl-5-[[methyl(2,2,2-trifluoroethyl)sulfamoyl]amino]-1-naphthyl]oxy]-3-pyridyl]pyrimidin-2-yl]amino]piperidine-1-carboxylate

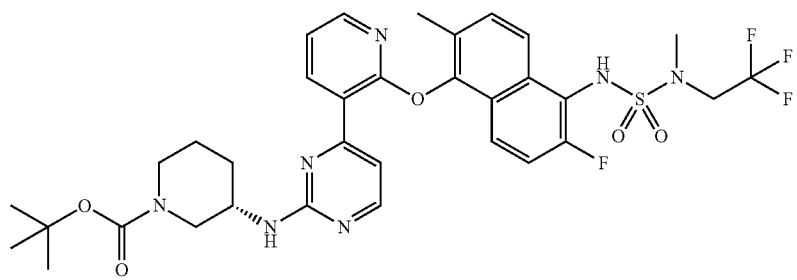 [SMILES: Cc1ccc2c(NS(=O)(=O)N(C)CC(F)(F)F)c(F)ccc2c1Oc1ncccc1-c1ccnc(N[C@H]2CCCN(C(=O)OC(C)(C)C)C2)n1]

Step 3: 4-[2-[[6-Fluoro-2-methyl-5-[[methyl(2,2,2-trifluoroethyl)sulfamoyl]amino]-1-naphthyl]oxy]-3-pyridyl]-2-[[(3S)-3-piperidyl]amino]pyrimidine hydrochloride 427

To a solution of tert-butyl (3S)-3-[[4-[2-[[6-fluoro-2-methyl-5-[(2-oxooxazolidin-3-yl)sulfonylamino]-1-naphthyl]oxy]-3-pyridyl]pyrimidin-2-yl]amino]piperidine-1-carboxylate (75 mg, 0.1 mol) in MeCN (0.40 mL) was added triethylamine (0.08 mL, 0.54 mmol), followed by 2,2,2-trifluoro-N-methyl-ethanamine hydrochloride (65 mg, 0.43 mmol). The reaction mixture was stirred at 85° C. overnight. After 18 h, the volatiles were evaporated and the reaction was diluted with EtOAc (20 mL) and 1N KHSO₄ (10 mL) and the phases were separated. The aqueous phase was extracted again with EtOAc (20 mL), and the combined organic extracts were dried with Na₂SO₄ and evaporated. The residue was purified by flash column chromatography through silica gel (0-4% MeOH/CH₂Cl₂) to give 37 mg (78% yield) of the title compound. LCMS (ESI) [M+H]⁺=720.5.

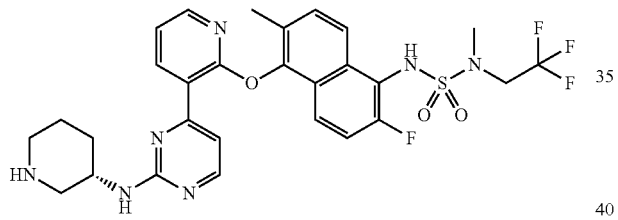

Prepared according to General Procedure B using tert-butyl (3S)-3-[[4-[2-[[6-fluoro-2-methyl-5-[[methyl(2,2,2-trifluoroethyl)sulfamoyl]amino]-1-naphthyl]oxy]-3-pyridyl]pyrimidin-2-yl]amino]piperidine-1-carboxylate (37 mg, 0.05 mmol), 1,4-dioxane (0.2 mL), and hydrochloric acid (4 M in dioxane, 0.49 mL, 2.0 mmol). After 45 min, the mixture was diluted with Et₂O and the resulting solids were collected by filtration then dissolved in H₂O and MeCN and lyophilized to provide 31 mg (90% yield) of 427. LCMS (ESI) [M+H]⁺=620.4; ¹H NMR (400 MHz, DMSO-d₆) 9.94 (s, 1H), 9.14-8.84 (m, 2H), 8.70 (s, 1H), 8.47 (d, J=5.2 Hz, 1H), 8.08 (dd, J=4.8, 2.0 Hz, 1H), 8.05 (d, J=8.8 Hz, 1H), 7.73 (dd, J=9.3, 5.2 Hz, 1H), 7.64 (d, J=8.8 Hz, 1H), 7.57 (d, J=7.2 Hz, 2H), 7.45 (t, J=9.5 Hz, 1H), 7.29 (dd, J=7.6, 4.8 Hz, 1H), 4.27 (s, 1H), 4.02-3.85 (m, 2H), 3.43 (d, J=11.3 Hz, 1H), 3.20 (d, J=12.4 Hz, 1H), 3.00 (s, 3H), 2.94-2.76 (m, 2H), 2.19 (s, J=10.7 Hz, 3H), 2.02 (d, J=12.0 Hz, 1H), 1.91 (d, J=14.3 Hz, 1H), 1.82-1.68 (m, 1H), 1.62 (dd, J=20.6, 10.2 Hz, 1H).

Example 428 N-[2-Fluoro-6-methyl-5-[[3-[2-[[(3S)-3-piperidyl]amino]pyrimidin-4-yl]-2-pyridyl]oxy]-1-naphthyl]pyrrolidine-1-sulfonamide hydrochloride Step 1: tert-Butyl (3S)-3-[[4-[2-[[6-fluoro-2-methyl-5-(pyrrolidin-1-ylsulfonylamino)-1-naphthyl]oxy]-3-pyridyl]pyrimidin-2-yl]amino]piperidine-1-carboxylate

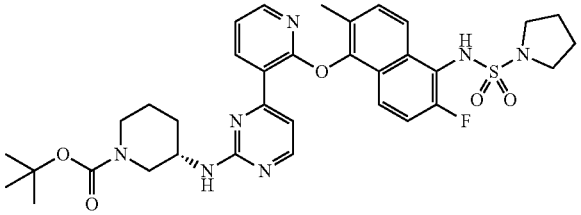 [SMILES: Cc1ccc2c(NS(=O)(=O)N3CCCC3)c(F)ccc2c1Oc1ncccc1-c1ccnc(N[C@H]2CCCN(C(=O)OC(C)(C)C)C2)n1]

To a solution of (S)-tert-butyl 3-((4-(2-((5-amino-6-fluoro-2-methylnaphthalen-1-yl)oxy)pyridin-3-yl)pyrimidin-2-yl)amino)piperidine-1-carboxylate from Example 275 (100 mg, 0.18 mol) in pyridine (1.3 mL) was added pyrrolidine-1-sulfonyl chloride (155 mg, 0.92 mmol) and DMAP (2 mg, 0.02 mmol) and the reaction mixture was stirred at 55° C. overnight. After 16 h, volatiles were evaporated and the reaction was diluted with EtOAc (20 mL) and washed with 1N KHSO₄, dried with Na₂SO₄ and evaporated. The residue was purified by flash column chromatography through silica gel (0-4% MeOH/CH₂Cl₂) to give 25 mg (21% yield) of the title compound. LCMS (ESI) [M+H]⁺=678.5.

Step 2: N-[2-Fluoro-6-methyl-5-[[3-[2-[[(3S)-3-piperidyl]amino]pyrimidin-4-yl]-2-pyridyl]oxy]-1-naphthyl]pyrrolidine-1-sulfonamide hydrochloride 428

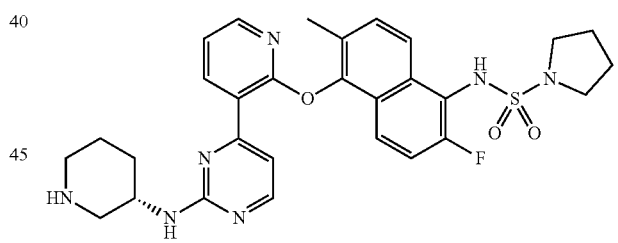

Prepared according to General Procedure B using tert-butyl (3S)-3-[[4-[2-[[6-fluoro-2-methyl-5-(pyrrolidin-1-ylsulfonylamino)-1-naphthyl]oxy]-3-pyridyl]pyrimidin-2-yl]amino]piperidine-1-carboxylate (25 mg, 0.04 mmol), 1,4-dioxane (0.5 mL), and hydrochloric acid (4 M in dioxane, 1.0 mL, 4.0 mmol). After 1 hour, the mixture was diluted with Et₂O and the resulting solids collected by filtration then dissolved in H₂O and MeCN and lyophilized to provide 18 mg (81% yield) of 428. LCMS (ESI) [M+H]⁺=578.4; ¹H NMR (400 MHz, DMSO-d₆) 9.51 (d, J=6.2 Hz, 1H), 9.09-8.82 (m, 2H), 8.68 (s, 1H), 8.47 (d, J=5.2 Hz, 1H), 8.11-8.06 (m, 2H), 7.69 (dd, J=9.3, 5.1 Hz, 1H), 7.62 (d, J=8.8 Hz, 1H), 7.60-7.50 (m, 2H), 7.43 (t, J=9.4 Hz, 1H), 7.29 (dd, J=7.6, 4.8 Hz, 1H), 4.27 (s, 1H), 3.43 (d, J=10.7 Hz, 1H), 3.31-3.14 (m, 5H), 2.94-2.75 (m, 2H), 2.19 (s, 3H), 2.01 (d, J=9.0 Hz, 1H), 1.96-1.83 (m, 5H), 1.82-1.68 (m, 1H), 1.69-1.56 (m, 1H).

Example 429 (S)—N-(2-Fluoro-6-methyl-5-((3-(2-(piperidin-3-ylamino)pyrimidin-4-yl)pyridin-2-yl)oxy)naphthalen-1-yl)-1-(3-methoxyphenyl)methanesulfonamide hydrochloride Step 1: (S)-tert-Butyl 3-((4-(2-((6-fluoro-5-((3-methoxyphenyl)methylsulfonamido)-2-methylnaphthalen-1-yl)oxy)pyridin-3-yl)pyrimidin-2-yl)amino)piperidine-1-carboxylate

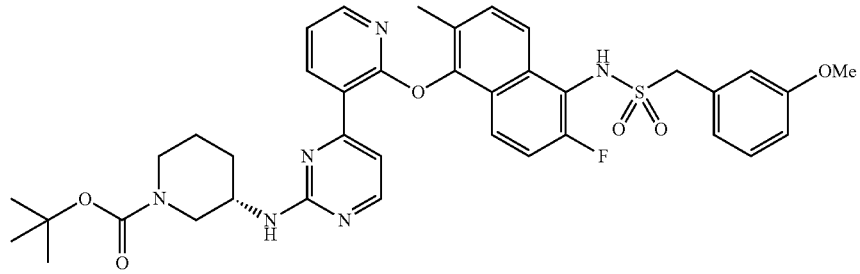 [SMILES: COc1cccc(CS(=O)(=O)Nc2c(F)ccc3c(Oc4ncccc4-c4ccnc(N[C@H]5CCCN(C(=O)OC(C)(C)C)C5)n4)c(C)ccc23)c1]

The General Procedure A was followed using (S)-tert-butyl 3-((4-(2-((5-amino-6-fluoro-2-methylnaphthalen-1-yl)oxy)pyridin-3-yl)pyrimidin-2-yl)amino)piperidine-1-carboxylate from Example 275 (75 mg, 0.14 mmol), pyridine (0.17 mL), CH$_2$Cl$_2$ (0.8 mL), 4-dimethylaminopyridine (1.7 mg, 0.01 mmol) and (3-methoxyphenyl)methanesulfonyl chloride (61 mg, 0.28 mmol). After 2.5 h, the mixture was diluted with CH$_2$Cl$_2$ (50 mL) and washed with 1M KHSO$_4$ (10 mL), dried by passing through a phase cartridge separator and concentrated in vacuo. The crude was purified by flash chromatography through silica gel (10-60% EtOAc/DCM) to provide 46 mg (46% yield) of the title compound. LCMS (ESI) [M+H]$^+$=729.3.

Step 2: (S)—N-(2-Fluoro-6-methyl-5-((3-(2-(piperidin-3-ylamino)pyrimidin-4-yl)pyridin-2-yl)oxy)naphthalen-1-yl)-1-(3-methoxyphenyl)methanesulfonamide hydrochloride 429

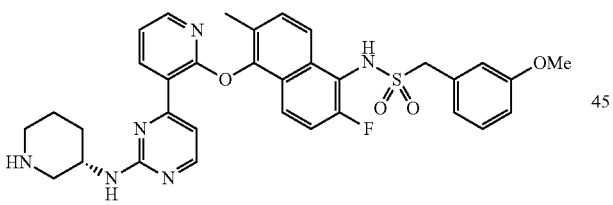

Prepared according to General Procedure B using (S)-tert-butyl 3-((4-(2-((6-fluoro-5-((3-methoxyphenyl)methylsulfonamido)-2-methylnaphthalen-1-yl)oxy)pyridin-3-yl)pyrimidin-2-yl)amino)piperidine-1-carboxylate (46 mg, 0.06 mmol), 1,4-dioxane (0.3 mL), and hydrochloric acid (4 M in dioxane, 0.8 mL, 3.2 mmol). After 60 min, the mixture was diluted with Et$_2$O and the resulting solids were collected by filtration then dissolved in H$_2$O and MeCN and lyophilized to provide 40 mg (95% yield) of 429. LCMS (ESI) [M+H]$^+$=629.2; $^1$H NMR (400 MHz, DMSO-d$_6$) δ 9.79 (s, 1H), 8.83 (bs, 2H), 8.65 (s, 1H), 8.48 (d, J=5.2 Hz, 1H), 8.09 (dd, J=4.8, 2.0 Hz, 1H), 8.00 (d, J=8.7 Hz, 1H), 7.73 (dd, J=9.3, 5.0 Hz, 1H), 7.60 (d, J=8.9 Hz, 1H), 7.58-7.53 (m, 2H), 7.49 (t, J=9.5 Hz, 1H), 7.38-7.22 (m, 2H), 7.08-6.99 (m, 2H), 7.01-6.91 (m, 1H), 4.53 (s, 2H), 4.27 (s, 1H), 3.75 (s, 3H), 3.44 (d, J=12.8 Hz, 1H), 3.21 (d, J=12.5 Hz, 1H), 2.97-2.75 (m, 2H), 2.19 (s, 3H), 2.09-1.97 (m, 1H), 1.97-1.84 (m, 1H), 1.83-1.54 (m, 2H).

Example 430 4-[2-[[5-(3-Methoxypropylamino)-2-methyl-1-naphthyl]oxy]-3-pyridyl]-N-[(3S)-3-piperidyl]pyrimidin-2-amine hydrochloride

Step 1: tert-Butyl (3S)-3-[[4-[2-[[5-(3-methoxypropylamino)-2-methyl-1-naphthyl]oxy]-3-pyridyl]pyrimidin-2-yl]amino]piperidine-1-carboxylate

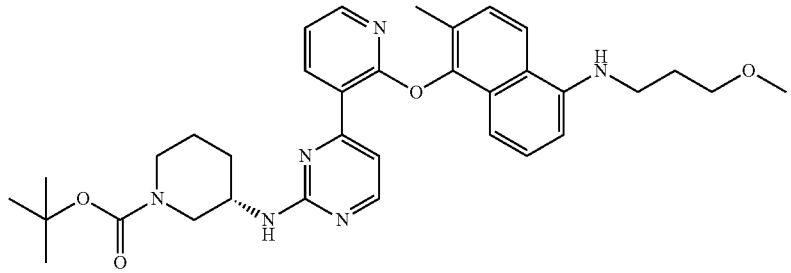 [SMILES: COCCCNc1cccc2c(Oc3ncccc3-c3ccnc(N[C@H]4CCCN(C(=O)OC(C)(C)C)C4)n3)c(C)ccc12]

The General Procedure G was followed using tert-butyl (3S)-3-[[4-[2-[(5-amino-2-methyl-1-naphthyl)oxy]-3-pyridyl]pyrimidin-2-yl]amino]piperidine-1-carboxylate (75 mg, 0.14 mmol), N,N-diisopropylethylamine (0.040 mL, 0.23 mmol), DMF (0.4 mL), and 1-bromo-3-methoxypropane (33 mg, 0.21 mmol). The mixture was stirred overnight at 60° C. After 18 h, a further portion of 1-bromo-3-methoxypropane (33 mg, 0.21 mmol) was added. The reaction was pursued two more days at 60° C. The reaction mixture was then diluted with EtOAc, washed with 1M KHSO$_4$, water, then saturated NaCl, dried (MgSO$_4$), filtered and concentrated in vacuo. The crude was purified by flash chromatography through silica gel (10-70% EtOAc/DCM) to provide 43 mg (50% yield) of the title compound. LCMS (ESI) [M+H]=599.3.

Step 2: 4-[2-[[5-(3-Methoxypropylamino)-2-methyl-1-naphthyl]oxy]-3-pyridyl]-N-[(3S)-3-piperidyl]pyrimidin-2-amine hydrochloride 430

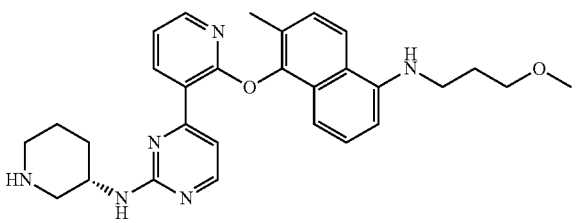 [SMILES: COCCCNc1cccc2c(Oc3ncccc3-c3ccnc(N[C@H]4CCCNC4)n3)c(C)ccc12]

Prepared according to General Procedure B using tert-butyl (3S)-3-[[4-[2-[[5-(3-methoxypropylamino)-2-methyl-1-naphthyl]oxy]-3-pyridyl]pyrimidin-2-yl]amino]piperidine-1-carboxylate (43 mg, 0.072 mmol), 1,4-dioxane (0.3 mL), and hydrochloric acid (4 M in dioxane, 0.92 mL, 3.69 mmol). After 1 h, the mixture was diluted with Et$_2$O and the resulting solids collected by filtration, washed with Et$_2$O, dissolved in H$_2$O and MeCN and lyophilized to provide 34.5 mg (90% yield) of 430. LCMS (ESI) [M+H]$^+$=499.2; 1H NMR (400 MHz, DMSO-d$_6$) δ 9.53-8.95 (m, 1H), 8.78 (s, 1H), 8.49 (d, J=5.4 Hz, 1H), 8.04 (d, J=8.6 Hz, 2H), 7.96-7.51 (m, 2H), 7.43 (d, J=8.6 Hz, 1H), 7.26 (dd, J=7.6, 4.8 Hz, 2H), 7.05 (s, 1H), 6.76 (s, 1H), 4.37 (s, 1H), 3.52-3.38 (m, 3H), 3.35-3.27 (m, 2H), 3.26 (s, 3H), 3.20 (d, J=12.1 Hz, 1H), 2.95-2.74 (m, 2H), 2.20 (s, 3H), 2.09-1.87 (m, 4H), 1.86-1.51 (m, 2H).

Example 431 N-[2-Fluoro-6-methyl-5-[[3-[2-[[(3S,5R)-5-methyl-3-piperidyl]amino]pyrimidin-4-yl]-2-pyridyl]oxy]-1-naphthyl]-2-methoxy-ethanesulfonamide hydrochloride

Step 1: 2-Fluoro-6-methyl-5-((3-(2-(methylthio)pyrimidin-4-yl)pyridin-2-yl)oxy)naphthalen-1-amine

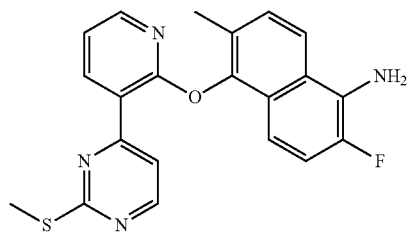 [SMILES: CSc1nccc(-c2cccnc2Oc2c(C)ccc3c(N)c(F)ccc23)n1]

(6-Methyl-5-((3-(2-(methylthio)pyrimidin-4-yl)pyridin-2-yl)oxy)naphthalen-1-amine (13.4 mmol, 5000 mg, 1.0 equiv.) was dissolved in EtOH (35.0 mL) and NMP (35.0 mL). Triethylamine (26.7 mmol, 3.72 mL, 2.0 equiv.) was then added followed by portionwise addition over 1 h of Selectfluor (33.4 mmol, 11.8 g, 2.50 equiv.) and the mixture was stirred at rt. After 16 h, most of the EtOH was evaporated (no heating), the mixture was diluted with EtOAc (75 mL) and 1M KHSO4(aq) (200 mL) and the phases were separated. The aqueous layer was extracted again with EtOAc (75 mL). The combined organic extracts were washed with H$_2$O (100 mL), dried (MgSO4), filtered and concentrated in vacuo. The crude material was purified by flash chromatography through silica gel (0 to 15% EtOAc/CH$_2$Cl$_2$ gradient over 30 min) to provide 1.52 g (29% yield) of the title compound. LCMS (ESI) [M+H]$^+$=393.3. $^1$H NMR (400 MHz, CDCl$_3$) δ 8.73 (dd, J=7.6, 2.0 Hz, 1H), 8.60 (d, J=5.3 Hz, 1H), 8.10 (d, J=4.9 Hz, 1H), 8.09 (dd, J=4.7, 1.9 Hz, 1H), 7.67 (d, J=8.6 Hz, 1H), 7.42 (d, J=8.7 Hz, 1H), 7.16-7.11 (m, 3H), 4.15 (s, 2H), 2.68 (s, 3H), 2.26 (s, 3H).

Step 2: (3S,5R)-Benzyl 3-((4-(2-((5-amino-6-fluoro-2-methylnaphthalen-1-yl)oxy)pyridin-3-yl)pyrimidin-2-yl)amino)-5-methylpiperidine-1-carboxylate

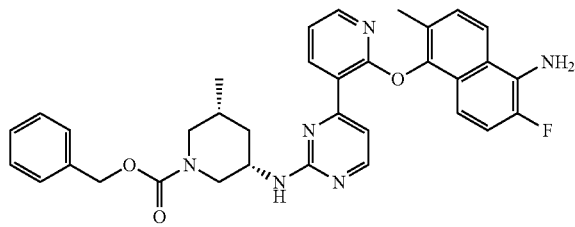 [SMILES: Cc1ccc2c(N)c(F)ccc2c1Oc1ncccc1-c1ccnc(N[C@H]2C[C@@H](C)CN(C(=O)OCc3ccccc3)C2)n1]

2-Fluoro-6-methyl-5-((3-(2-(methylthio)pyrimidin-4-yl)pyridin-2-yl)oxy)naphthalen-1-amine (1.02 mmol, 400 mg, 1.0 equiv.) was dissolved in 1,2-dichloroethane (2.0 mL). To this mixture was then added a solution of mCPBA (1.02 mmol, 225 mg of ~78% pure reagent, 1.0 equiv.) in 1,2-dichloroethane (1.0 mL) and the mixture stirred at rt. After 5 min, LCMS shows complete conversion and the mixture is diluted with $CH_2Cl_2$ (20 mL) and washed with saturated $NaHCO_3$(aq) (10 mL), dried ($MgSO_4$), filtered and concentrated in vacuo to provide crude 2-fluoro-6-methyl-5-((3-(2-(methylsulfinyl)pyrimidin-4-yl)pyridin-2-yl)oxy)naphthalen-1-amine (416 mg, 99% yield) as an orange oil which was used as is without further purification.

Crude 2-fluoro-6-methyl-5-((3-(2-(methylsulfinyl)pyrimidin-4-yl)pyridin-2-yl)oxy)naphthalen-1-amine prepared above (1.02 mmol, 416 mg, 1.0 equiv.) was dissolved in 1,4-dioxane (6.0 mL). To this solution was then added triethylamine (3.06 mmol, 309 mg, 0.42 mL, 3.0 equiv.) followed by addition of (3S,5R)-benzyl 3-amino-5-methylpiperidine-1-carboxylate hydrochloride (1.53 mmol, 435 mg, 1.5 equiv.) and the mixture placed in a 115° C. oil bath sealed overnight. After 16 h, the mixture was cooled to rt and diluted with EtOAc (10 mL) and $H_2O$ (5 mL) and the phases were separated. To the organic extract was then added silica gel and the volatiles were removed on a rotovap to adsorb the crude reaction mixture. Flash chromatography through silica gel (0-100% EtOAc/hexanes) was performed to provide 405 mg (67% yield) of the title compound. LCMS (ESI) [M+H]$^+$=593.6.

Step 3: Benzyl (3S,5R)-3-[[4-[2-[[6-Fluoro-5-(2-methoxyethylsulfonylamino)-2-methyl-1-naphthyl]oxy]-3-pyridyl]pyrimidin-2-yl]amino]-5-methyl-piperidine-1-carboxylate The General Procedure A was followed using benzyl (3S,5R)-3-[[4-[2-[(5-amino-6-fluoro-2-methyl-1-naphthyl)oxy]-3-pyridyl]pyrimidin-2-yl]amino]-5-methyl-piperidine-1-carboxylate (75 mg, 0.13 mmol), pyridine (0.15 mL, 1.90 mmol), $CH_2Cl_2$ (1.0 mL), and 2-methoxyethanesulfonyl chloride (0.21 mL, 0.25 mmol). The mixture was stirred at rt overnight. The reaction was concentrated in vacuo and co-evaporated with toluene. The residue was purified by flash chromatography through silica gel (35% EtOAc/DCM) to provide an inseparable mixture of mono-sulfonylated and bis-sulfonylated products. This mixture was dissolved in THF (1 mL), and treated with a 1M solution of TBAF in THF (1 mL). The mixture was stirred 10 minutes at rt, then THF was removed in vacuo. The residue was dissolved in DCM and passed through a silica pad eluting with 50% EtOAc in DCM. The volatiles were evaporated in vacuo to provide 49 mg (54% yield) of the title compound. LCMS (ESI) [M+H]$^+$=715.5.

Step 4: N-[2-Fluoro-6-methyl-5-[[3-[2-[[(3S,5R)-5-methyl-3-piperidyl]amino]pyrimidin-4-yl]-2-pyridyl]oxy]-1-naphthyl]-2-methoxy-ethanesulfonamide hydrochloride 431

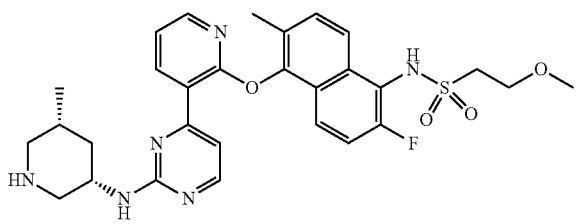

Prepared according to General Procedure H using benzyl (3S,5R)-3-[[4-[2-[[6-fluoro-5-(2-methoxyethylsulfonylamino)-2-methyl-1-naphthyl]oxy]-3-pyridyl]pyrimidin-2-yl]amino]-5-methyl-piperidine-1-carboxylate (49 mg, 0.069 mmol), in MeOH (1 mL), and Pd/C 10% (50 mg). The resulting suspension was cooled to 0° C. for the slow addition of ammonium formate (432 mg, 6.86 mmol), over 30 minutes. The reaction was monitored by LCMS. When complete, the reaction was filtered through a pad of Celite and subsequently washed with EtOAc and MeOH. The volatiles were evaporated in vacuo and the residue was suspended in a mixture of EtOAc (100 mL) and $H_2O$ (50 mL). To this mixture was added a saturated aqueous solution of $Na_2CO_3$ (10 mL). The organic layer was separated, dried ($MgSO_4$), filtered and concentrated in vacuo. The product was dissolved in a mixture of dioxane (1 mL) and MTBE (5 mL). To this solution was added HCl (0.1 mL, 4 M in dioxane). This slurry mixture was stirred at rt for 10 min and the solvent was removed in vacuo. The residue was dissolved in $H_2O$ and MeCN and lyophilized to provide 24 mg (57% yield) of 431. LCMS (ESI) [M+H]$^+$=581.1; 1H NMR (400 MHz, $D_2O$) δ 8.23 (s, 1H), 8.10 (d, J=5.4 Hz, 1H), 7.89 (d, J=8.4 Hz, 1H), 7.77 (s, 1H), 7.55 (s, 1H), 7.44-7.30 (m, 2H), 7.08 (dd, J=16.5, 9.1 Hz, 2H), 4.13 (s, 1H), 3.77 (t, J=5.7 Hz, 2H), 3.57-3.37 (m, 3H), 3.19 (s, 4H), 2.61 (s, 1H), 2.40 (t, J=12.7 Hz, 1H), 2.00 (s, 1H), 1.97 (s, 3H), 1.83-1.62 (m, 1H), 1.11 (d, J=12.8 Hz, 1H), 0.70 (s, 3H).

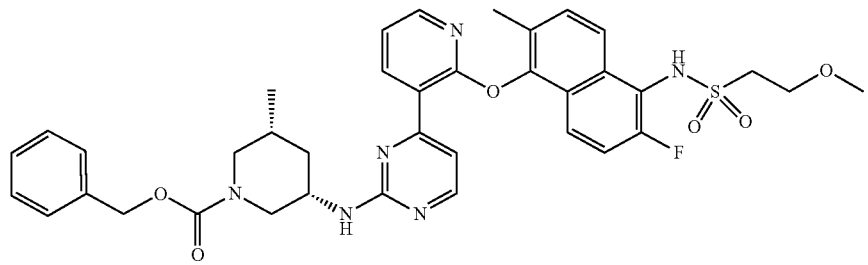 [SMILES: COCCS(=O)(=O)Nc1c(F)ccc2c(Oc3ncccc3-c3ccnc(N[C@H]4C[C@@H](C)CN(C(=O)OCc5ccccc5)C4)n3)c(C)ccc12]

Example 432 3,3,3-Trifluoro-N-(2-fluoro-5-((3-(2-(((3S,5S)-5-fluoropiperidin-3-yl)amino)pyrimidin-4-yl)pyridin-2-yl)oxy)-6-methylnaphthalen-1-yl)propane-1-sulfonamide hydrochloride Step 1: tert-Butyl trans-3-fluoro-5-[[4-[2-[[6-fluoro-2-methyl-5-(3,3,3-trifluoropropylsulfonylamino)-1-naphthyl]oxy]-3-pyridyl]pyrimidin-2-yl]amino]piperidine-1-carboxylate

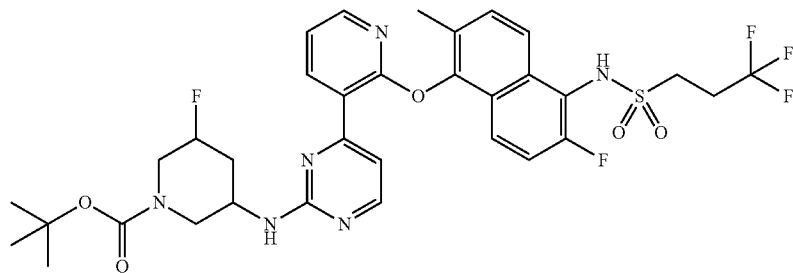 [SMILES: Cc1ccc2c(NS(=O)(=O)CCC(F)(F)F)c(F)ccc2c1Oc1ncccc1-c1ccnc(NC2CC(F)CN(C(=O)OC(C)(C)C)C2)n1]

The General Procedure A was followed using tert-butyl trans-3-[[4-[2-[(5-amino-6-fluoro-2-methyl-1-naphthyl)oxy]-3-pyridyl]pyrimidin-2-yl]amino]-5-fluoro-piperidine-1-carboxylate from Example 322 (250 mg, 0.44 mmol), pyridine (0.54 mL), CH$_2$Cl$_2$ (1.4 mL), 4-dimethylaminopyridine (5 mg) and 3,3,3-trifluoropropane-1-sulfonyl chloride (174 mg, 0.88 mmol). After 18 h, the mixture was diluted with CH$_2$Cl$_2$ (50 mL) and washed with 1M KHSO$_4$ (10 mL), dried by passing through a phase cartridge separator and concentrated in vacuo. The crude was purified by flash chromatography through silica gel (10-50% EtOAc/CH$_2$Cl$_2$) to provide 108 mg (32% yield) of the title compound. LCMS (ESI) [M+H]$^+$=723.4.

Step 2: (3R,5R)-tert-Butyl 3-fluoro-5-((4-(2-((6-fluoro-2-methyl-5-(3,3,3-trifluoropropylsulfonamido)naphthalen-1-yl)oxy)pyridin-3-yl)pyrimidin-2-yl)amino)piperidine-1-carboxylate and (3S,5S)-tert-butyl 3-fluoro-5-((4-(2-((6-fluoro-2-methyl-5-(3,3,3-trifluoropropylsulfonamido)naphthalen-1-yl)oxy)pyridin-3-yl)pyrimidin-2-yl)amino)piperidine-1-carboxylate

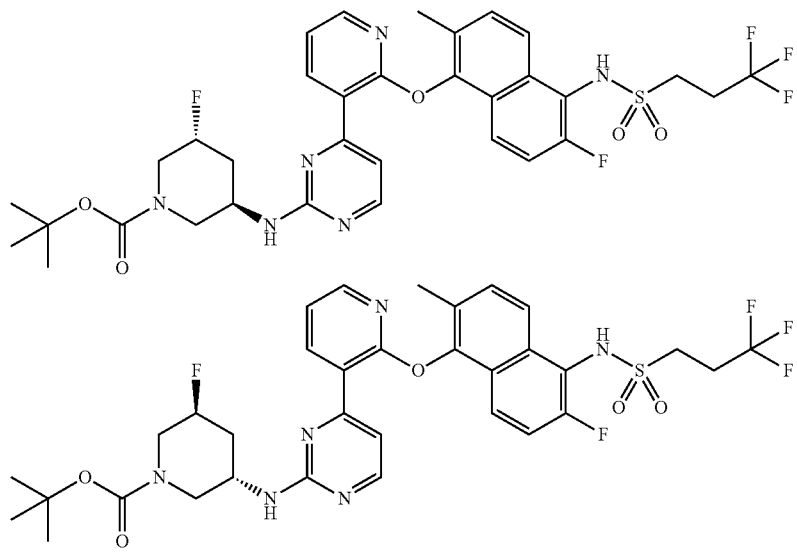

The stereoisomers from Step 1 were subjected to chiral SFC purification (conditions: Lux Cellulose-4, 10×250 mm 5 um, Isocratic 20% MeOH, 10 mL/min, 150 bar.) to provide two trans piperidine enantiomers. Isomer-1: (3R,5R)-tert-butyl 3-fluoro-5-((4-(2-((6-fluoro-2-methyl-5-(3,3,3-trifluoropropylsulfonamido)naphthalen-1-yl)oxy)pyridin-3-yl)pyrimidin-2-yl)amino)piperidine-1-carboxylate, 40 mg (37% yield), white solid, ee=98.8%, LCMS (ESI) [M+H]⁺=723.4; and Isomer-2: (3S,5S)-tert-butyl 3-fluoro-5-((4-(2-((6-fluoro-2-methyl-5-(3,3,3-trifluoropropylsulfonamido)naphthalen-1-yl)oxy)pyridin-3-yl)pyrimidin-2-yl)amino)piperidine-1-carboxylate, 40 mg (37% yield), white solid, ee=95.4%, LCMS (ESI) [M+H]⁺=723.4.

Step 3: 3,3,3-Trifluoro-N-(2-fluoro-5-((3-(2-(((3S,5S)-5-fluoropiperidin-3-yl)amino)pyrimidin-4-yl)pyridin-2-yl)oxy)-6-methylnaphthalen-1-yl)propane-1-sulfonamide hydrochloride (Isomer-2)

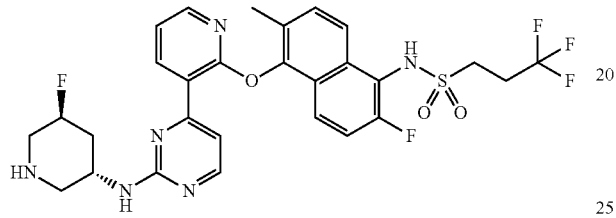

Prepared according to General Procedure B using (3S,5S)-tert-butyl 3-fluoro-5-((4-(2-((6-fluoro-2-methyl-5-(3,3,3-trifluoropropylsulfonamido)naphthalen-1-yl)oxy)pyridin-3-yl)pyrimidin-2-yl)amino)piperidine-1-carboxylate (40 mg, 0.06 mmol), 1,4-dioxane (0.5 mL), and hydrochloric acid (4 M in dioxane, 1 mL, 4.0 mmol). After 1 h, the mixture was diluted with Et₂O and the resulting solids collected by filtration then dissolved in H₂O and MeCN and lyophilized to provide 28 mg (76% yield) of 432. LCMS (ESI) [M+H]⁺=623.3; ¹H NMR (400 MHz, DMSO-d₆) δ 10.12 (s, 1H), 9.63 (d, J=10.3 Hz, 1H), 9.24 (s, 1H), 8.72 (s, 1H), 8.49 (d, J=5.2 Hz, 1H), 8.08 (dd, J=4.8, 1.9 Hz, 1H), 8.05 (d, J=8.7 Hz, 1H), 7.75 (dd, J=9.3, 5.2 Hz, 1H), 7.69-7.55 (m, 3H), 7.48 (t, J=9.5 Hz, 1H), 7.30 (dd, J=7.6, 4.8 Hz, 1H), 5.24 (d, J=45.6 Hz, 1H), 4.52 (s, 1H), 3.58-3.41 (m, 4H), 3.24 (dt, J=24.3, 12.5 Hz, 1H), 3.00-2.74 (m, 3H), 2.42-2.29 (m, 1H), 2.20 (s, 3H), 1.93 (dt, J=25.7, 13.4 Hz, 1H). The absolute stereochemistry was assigned based on the potency in the cellular assay.

Example 433 (S)-1-(3,3-Difluorocyclobutyl)-N-(2-fluoro-6-methyl-5-((3-(2-(piperidin-3-ylamino)pyrimidin-4-yl)pyridin-2-yl)oxy)naphthalen-1-yl)methanesulfonamide Step 1: (S)-tert-Butyl 3-((4-(2-((5-((3,3-difluorocyclobutyl)methylsulfonamido)-6-fluoro-2-methylnaphthalen-1-yl)oxy)pyridin-3-yl)pyrimidin-2-yl)amino)piperidine-1-carboxylate

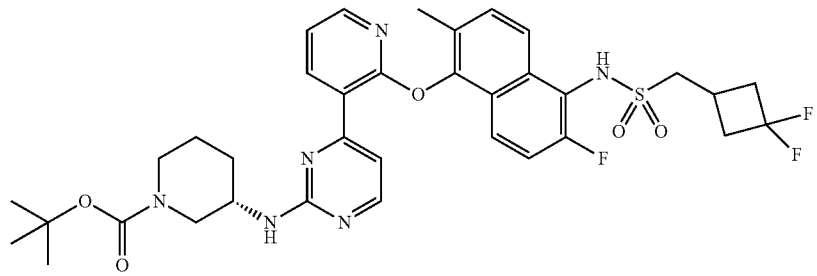 [SMILES: Cc1ccc2c(NS(=O)(=O)CC3CC(F)(F)C3)c(F)ccc2c1Oc1ncccc1-c1ccnc(N[C@H]2CCCN(C(=O)OC(C)(C)C)C2)n1]

The General Procedure A was followed using (S)-tert-butyl 3-((4-(2-((5-amino-6-fluoro-2-methylnaphthalen-1-yl)oxy)pyridin-3-yl)pyrimidin-2-yl)amino)piperidine-1-carboxylate from Example 275 (100 mg, 0.18 mmol), pyridine (0.45 mL), CH$_2$Cl$_2$ (0.5 mL), and (3,3-difluorocyclobutyl)methanesulfonyl chloride (94 mg, 0.46 mmol). After 3 days, the mixture was diluted with CH$_2$Cl$_2$ (50 mL), washed with saturated aqueous NaHCO$_3$ (10 mL), dried (Na$_2$SO$_4$), filtered and concentrated in vacuo. The crude was purified by flash chromatography through silica gel (0-50% EtOAc/CH$_2$Cl$_2$) to provide 79 mg (60% yield) of the title compound. LCMS (ESI) [M+H]$^+$=713.1.

Step 2: (S)-1-(3,3-Difluorocyclobutyl)-N-(2-fluoro-6-methyl-5-((3-(2-(piperidin-3-ylamino)pyrimidin-4-yl)pyridin-2-yl)oxy)naphthalen-1-yl)methanesulfonamide 433

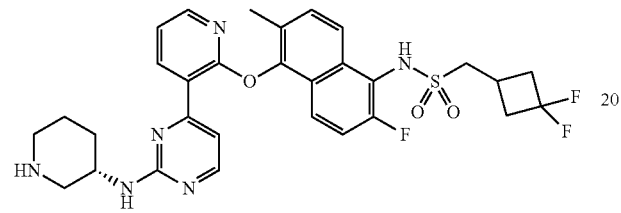

Prepared according to General Procedure B using (S)-tert-butyl 3-((4-(2-((5-((3,3-difluorocyclobutyl)methylsulfonamido)-6-fluoro-2-methylnaphthalen-1-yl)oxy)pyridin-3-yl)pyrimidin-2-yl)amino)piperidine-1-carboxylate (79 mg, 0.11 mmol), EtOAc (4 mL), and hydrochloric acid (4 M in dioxane, 3.0 mL, 12 mmol). After 4 h, the mixture was concentrated in vacuo and purified by C18 reverse phase flash chromatography (10-70% MeCN/10 mM aqueous ammonium formate, pH=3.8). Appropriate fractions were combined and lyophilized to provide 25 mg (37% yield) of 433. LCMS (ESI) [M+H]$^+$=613.1; $^1$H NMR (400 MHz, DMSO-d$_6$) δ 8.60-8.47 (m, 1H), 8.42 (d, J=5.1 Hz, 1H), 8.30 (s, 1H), 8.12-8.01 (m, 2H), 7.68-7.52 (m, 2H), 7.46 (d, J=5.1 Hz, 1H), 7.40 (t, J=9.5 Hz, 1H), 7.27 (dd, J=7.4, 5.1 Hz, 2H), 4.08-3.90 (m, 1H), 3.48-3.38 (m, 5H), 3.23-3.15 (m, 2H), 2.91 (d, J=11.7 Hz, 1H), 2.83-2.69 (m, 2H), 2.61-2.55 (m, 2H), 2.19 (s, 3H), 1.99-1.89 (m, 1H), 1.77-1.66 (m, 1H), 1.59-1.45 (m, 2H).

Example 434 (S)-1-(2-Cyanophenyl)-N-(2-fluoro-6-methyl-5-((3-(2-(piperidin-3-ylamino)pyrimidin-4-yl)pyridin-2-yl)oxy)naphthalen-1-yl)methanesulfonamide hydrochloride Step 1: (S)-tert-Butyl 3-((4-(2-((5-((2-cyanophenyl)methylsulfonamido)-6-fluoro-2-methylnaphthalen-1-yl)oxy)pyridin-3-yl)pyrimidin-2-yl)amino)piperidine-1-carboxylate

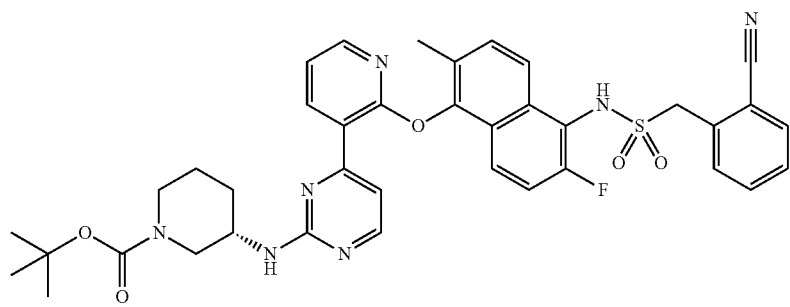 [SMILES: Cc1ccc2c(NS(=O)(=O)Cc3ccccc3C#N)c(F)ccc2c1Oc1ncccc1-c1ccnc(N[C@H]2CCCN(C(=O)OC(C)(C)C)C2)n1]

The General Procedure A was followed using (S)-tert-butyl 3-((4-(2-((5-amino-6-fluoro-2-methylnaphthalen-1-yl)oxy)pyridin-3-yl)pyrimidin-2-yl)amino)piperidine-1-carboxylate from Example 275 (80 mg, 0.15 mmol), pyridine (0.5 mL), CH$_2$Cl$_2$ (1.0 mL), and (2-cyanophenyl)methanesulfonyl chloride (79 mg, 0.37 mmol). After 16 h, the mixture was diluted with CH$_2$Cl$_2$ (50 mL) and washed with saturated aqueous NaHCO$_3$ (10 mL), dried (Na$_2$SO$_4$), filtered and concentrated in vacuo. The crude was purified by flash chromatography through silica gel (0-50% EtOAc/CH$_2$Cl$_2$) to provide 36 mg (34% yield) of the title compound. LCMS (ESI) [M+H]$^+$=724.2.

Step 2: (S)-1-(2-Cyanophenyl)-N-(2-fluoro-6-methyl-5-((3-(2-(piperidin-3-ylamino)pyrimidin-4-yl)pyridin-2-yl)oxy)naphthalen-1-yl)methanesulfonamide hydrochloride

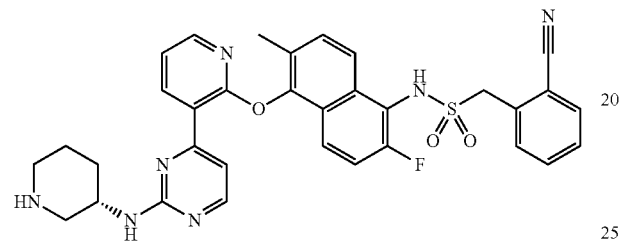

Prepared according to General Procedure B using (S)-tert-butyl 3-((4-(2-((5-((2-cyanophenyl)methylsulfonamido)-6-fluoro-2-methylnaphthalen-1-yl)oxy)pyridin-3-yl)pyrimidin-2-yl)amino)piperidine-1-carboxylate (36 mg, 0.05 mmol), EtOAc (2 mL), and hydrochloric acid (4 M in dioxane, 1.0 mL, 4.0 mmol). After 18 h, the mixture was concentrated in vacuo and the crude residue was washed with EtOAc (3×3 mL) then with MeCN (3×3 mL), dissolved in H$_2$O and MeCN and lyophilized to provide 22 mg (67% yield) of 434. LCMS (ESI) [M+H]$^+$=624.1; $^1$H NMR (400 MHz, DMSO-d$_6$) δ 10.19 (s, 1H), 8.76-8.52 (m, 3H), 8.48 (d, J=5.2 Hz, 1H), 8.09 (dd, J=4.8, 1.9 Hz, 1H), 8.02 (d, J=8.7 Hz, 1H), 7.93 (d, J=7.1 Hz, 1H), 7.82-7.72 (m, 2H), 7.71-7.43 (m, 6H), 7.30 (dd, J=7.5, 4.8 Hz, 1H), 4.80 (s, 2H), 4.33-4.16 (m, 1H), 3.22 (d, J=11.9 Hz, 2H), 2.96-2.77 (m, 2H), 2.19 (s, 3H), 2.07-1.88 (m, 2H), 1.80-1.57 (m, 2H).

Example 435 (S)-4,4,4-Trifluoro-3-hydroxy-N-(6-methyl-5-((3-(2-(((S)-piperidin-3-yl)amino)pyrimidin-4-yl)pyridin-2-yl)oxy)naphthalen-1-yl)butanamide Step 1: tert-Butyl (3S)-3-((4-(2-((2-methyl-5-(4,4,4-trifluoro-3-hydroxybutanamido)naphthalen-1-yl)oxy)pyridin-3-yl)pyrimidin-2-yl)amino)piperidine-1-carboxylate

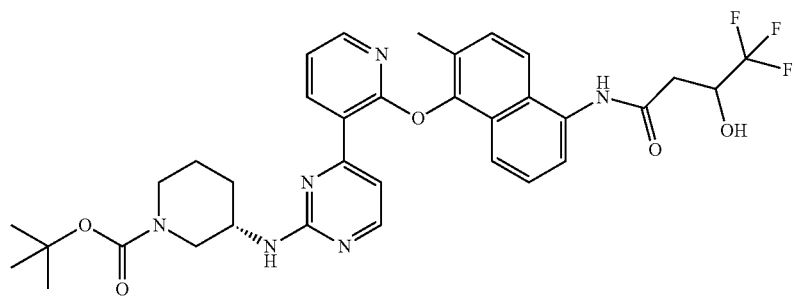 [SMILES: Cc1ccc2c(NC(=O)CC(O)C(F)(F)F)cccc2c1Oc1ncccc1-c1ccnc(N[C@H]2CCCN(C(=O)OC(C)(C)C)C2)n1]

The General Procedure C was followed, using tert-butyl (3S)-3-[[4-[2-[(5-amino-2-methyl-1-naphthyl)oxy]-3-pyridyl]pyrimidin-2-yl]amino]piperidine-1-carboxylate (100 mg, 0.19 mmol), 4,4,4-trifluoro-3-hydroxy-butanoic acid (45.0 mg, 0.28 mmol), HOBt (52.37 mg, 0.38 mmol), EDC HCl (72.81 mg, 0.38 mmol) in DMF (1 mL). The crude product was purified via reverse-phase HPLC, followed by chiral SFC to afford 19.5 mg (15.3% yield) of the (isomer-1, $t_R$=1.084 min) title compound as an off-white solid. LCMS (ESI) [M+H]$^+$=667, and 19.7 mg (15.3% yield) of the (isomer-2, $t_R$=1.309 min) title compound as an off-white solid. LCMS (ESI) [M+H]$^+$=667.

Step 2: 4,4,4-Trifluoro-3-hydroxy-N-(6-methyl-5-((3-(2-(((S)-piperidin-3-yl)amino)pyrimidin-4-yl)pyridin-2-yl)oxy)naphthalen-1-yl)butanamide

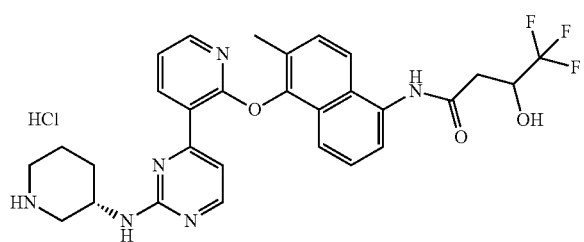 [SMILES: Cc1ccc2c(NC(=O)CC(O)C(F)(F)F)cccc2c1Oc1ncccc1-c1ccnc(N[C@H]2CCCNC2)n1 ; Cl]

The General Procedure B was followed, using tert-butyl (3S)-3-((4-(2-((2-methyl-5-(4,4,4-trifluoro-3-hydroxybutanamido)naphthalen-1-yl)oxy)pyridin-3-yl)pyrimidin-2-yl)amino)piperidine-1-carboxylate (isomer-1, 19.5 mg, 0.03 mmol). The product was lyophilized to yield 17 mg (96.4% yield) of the title compound as a yellow solid HCl salt. LCMS (ESI) [M+H]$^+$=567; $^1$H NMR (400 MHz, DMSO-d$_6$) δ 10.14 (s, 1H), 9.03-8.80 (m, 2H), 8.73-8.54 (m, 2H), 8.48 (d, J=5.2 Hz, 1H), 8.06 (dd, J=4.8, 2.0 Hz, 1H), 7.96 (d, J=8.7 Hz, 1H), 7.65-7.57 (m, 2H), 7.57-7.49 (m, 3H), 7.42 (dd, J=8.5, 7.3 Hz, 1H), 7.27 (dd, J=7.6, 4.8 Hz, 1H), 4.55-4.46 (m, 1H), 4.34-4.23 (m, 1H), 3.49-3.41 (m, 2H), 3.26-3.14 (m, 1H), 2.91-2.78 (m, 4H), 2.22 (s, 3H), 2.06-1.97 (m, 1H), 1.96-1.89 (m, 1H), 1.82-1.59 (m, 2H). The absolute stereochemistry of the alcohol was randomly assigned.

Example 436 (R)-4,4,4-Trifluoro-3-hydroxy-N-(6-methyl-5-((3-(2-(((S)-piperidin-3-yl)amino)pyrimidin-4-yl)pyridin-2-yl)oxy)naphthalen-1-yl) butanamide The General Procedure B was followed, using tert-butyl (3S)-3-((4-(2-((2-methyl-5-(4,4,4-trifluoro-3-hydroxybutanamido)naphthalen-1-yl)oxy)pyridin-3-yl)pyrimidin-2-yl)amino)piperidine-1-carboxylate (isomer-1, 19.7 mg, 0.03 mmol). The product was lyophilized to yield 17 mg (96.4% yield) of the title compound as a yellow solid HCl salt. LCMS (ESI) [M+H]$^+$=567; $^1$H NMR (400 MHz, DMSO-d$_6$) δ 10.15 (s, 1H), 9.07-8.85 (m, 2H), 8.74-8.53 (m, 2H), 8.48 (d, J=5.2 Hz, 1H), 8.06 (dd, J=4.8, 1.9 Hz, 1H), 7.96 (d, J=8.7 Hz, 1H), 7.65-7.55 (m, 3H), 7.52 (d, J=8.8 Hz, 2H), 7.42 (t, J=7.9 Hz, 1H), 7.27 (dd, J=7.6, 4.8 Hz, 1H), 4.55-4.47 (m, 1H), 4.34-4.24 (m, 1H), 3.48-3.41 (m, 2H), 3.21 (d, J=12.4 Hz, 1H), 2.84 (qd, J=15.1, 6.7 Hz, 4H), 2.22 (s, 3H), 2.07-1.98 (m, 1H), 1.96-1.87 (m, 1H), 1.81-1.56 (m, 2H). The absolute stereochemistry of the alcohol was randomly assigned.

Example 437 (S)-1-(3-Chloro-2-methoxyphenyl)-N-(2-fluoro-6-methyl-5-((3-(2-(piperidin-3-ylamino)pyrimidin-4-yl)pyridin-2-yl)oxy)naphthalen-1-yl)methanesulfonamide hydrochloride Step 1: (S)-tert-Butyl 3-((4-(2-((5-((3-chloro-2-methoxyphenyl)methylsulfonamido)-6-fluoro-2-methylnaphthalen-1-yl)oxy)pyridin-3-yl)pyrimidin-2-yl)amino)piperidine-1-carboxylate

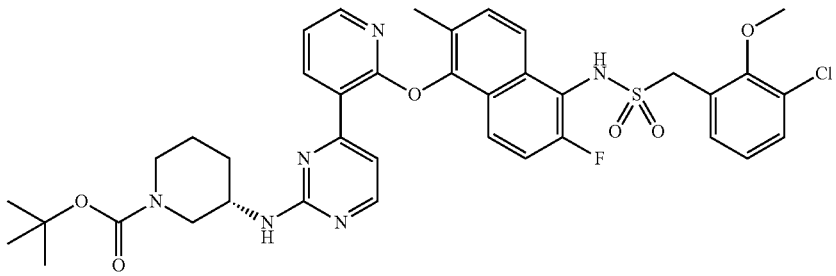 [SMILES: COc1c(Cl)cccc1CS(=O)(=O)Nc1c(F)ccc2c(Oc3ncccc3-c3ccnc(N[C@H]4CCCN(C(=O)OC(C)(C)C)C4)n3)c(C)ccc12]

The General Procedure A was followed using (S)-tert-butyl 3-((4-(2-((5-amino-6-fluoro-2-methylnaphthalen-1-yl)oxy)pyridin-3-yl)pyrimidin-2-yl)amino)piperidine-1-carboxylate from Example 275 (50 mg, 0.09 mmol), pyridine (0.11 mL), CHCl$_3$ (0.65 mL), 4-dimethylaminopyridine (1.1 mg, 0.01 mmol) and (3-chloro-2-methoxyphenyl)methanesulfonyl chloride (35 mg, 0.14 mmol). After 6 days, the mixture was diluted with CH$_2$Cl$_2$ (50 mL) and washed with 1M KHSO$_4$ (10 mL), dried by filtration through a phase cartridge separator and concentrated in vacuo. The crude was purified by flash chromatography through silica gel (0-60% EtOAc/CH$_2$Cl$_2$) to provide 32 mg (46% yield) of the title compound. LCMS (ESI) [M+H]$^+$=763.2.

Step 2: (S)-1-(3-Chloro-2-methoxyphenyl)-N-(2-fluoro-6-methyl-5-((3-(2-(piperidin-3-ylamino)pyrimidin-4-yl)pyridin-2-yl)oxy)naphthalen-1-yl)methanesulfonamide hydrochloride 437

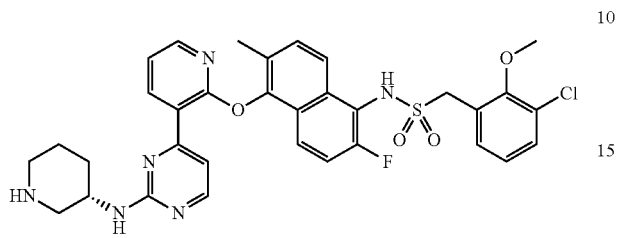

Prepared according to General Procedure B using (S)-tert-butyl 3-((4-(2-((5-(((3-chloro-2-methoxyphenyl)methylsulfonamido)-6-fluoro-2-methylnaphthalen-1-yl)oxy)pyridin-3-yl)pyrimidin-2-yl)amino)piperidine-1-carboxylate (32 mg, 0.04 mmol), 1,4-dioxane (0.22 mL), and hydrochloric acid (4 M in dioxane, 0.5 mL, 2.0 mmol). After 90 min, the mixture was diluted with Et$_2$O and the solids were collected, washed with Et$_2$O, dissolved in H$_2$O and MeCN and lyophilized to provide 28 mg (94% yield) of 437. LCMS (ESI) [M+H]$^+$=663.4; $^1$H NMR (400 MHz, DMSO-d$_6$) δ 9.92 (s, 1H), 8.99-8.58 (m, 3H), 8.48 (d, J=5.2 Hz, 1H), 8.09 (dd, J=4.8, 2.0 Hz, 1H), 8.01 (d, J=8.7 Hz, 1H), 7.73 (dd, J=9.4, 5.1 Hz, 1H), 7.61 (d, J=8.8 Hz, 1H), 7.59-7.44 (m, 3H), 7.44-7.38 (m, 2H), 7.30 (dd, J=7.6, 4.8 Hz, 1H), 7.16-7.05 (m, 1H), 4.60 (s, 2H), 4.25 (s, 1H), 3.79 (s, J=3.9 Hz, 3H), 3.48-3.39 (m, 2H), 3.21 (d, J=12.5 Hz, 1H), 2.93-2.77 (m, 2H), 2.19 (s, 3H), 2.07-1.96 (m, 1H), 1.96-1.87 (m, 1H), 1.81-1.57 (m, 2H).

Example 438 (S)-1-(4-(Difluoromethyl)phenyl)-N-(2-fluoro-6-methyl-5-((3-(2-(piperidin-3-ylamino)pyrimidin-4-yl)pyridin-2-yl)oxy)naphthalen-1-yl)methanesulfonamide hydrochloride Step 1: (S)-tert-Butyl 3-((4-(2-((5-((4-(difluoromethyl)phenyl)methylsulfonamido)-6-fluoro-2-methylnaphthalen-1-yl)oxy)pyridin-3-yl)pyrimidin-2-yl)amino)piperidine-1-carboxylate

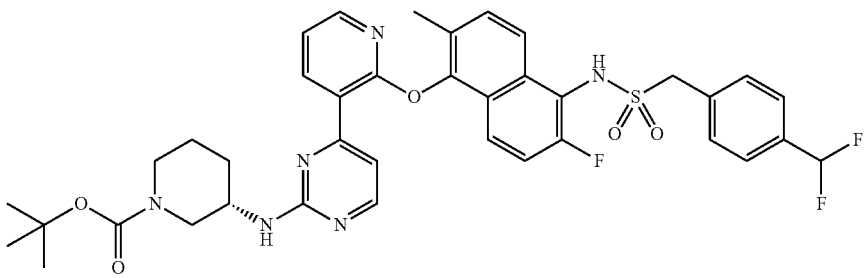 [SMILES: Cc1ccc2c(NS(=O)(=O)Cc3ccc(C(F)F)cc3)c(F)ccc2c1Oc1ncccc1-c1ccnc(N[C@H]2CCCN(C(=O)OC(C)(C)C)C2)n1]

The General Procedure A was followed using (S)-tert-butyl 3-((4-(2-((5-amino-6-fluoro-2-methylnaphthalen-1-yl)oxy)pyridin-3-yl)pyrimidin-2-yl)amino)piperidine-1-carboxylate from Example 275 (75 mg, 0.14 mmol), pyridine (0.17 mL), CH$_2$Cl$_2$ (0.8 mL), 4-dimethylaminopyridine (1.7 mg, 0.01 mmol) and (4-(difluoromethyl)phenyl)methanesulfonyl chloride (50 mg, 0.21 mmol). After 16 h, the mixture was diluted with CH$_2$Cl$_2$ (50 mL) and washed with 1M KHSO$_4$ (10 mL), dried by filtration through a phase cartridge separator and concentrated in vacuo. The crude was purified by flash chromatography through silica gel (10-60% EtOAc/CH$_2$Cl$_2$) to provide 52 mg (50% yield) of the title compound. LCMS (ESI) [M+H]$^+$=749.3.

Step 2: (S)-1-(4-(Difluoromethyl)phenyl)-N-(2-fluoro-6-methyl-5-((3-(2-(piperidin-3-ylamino)pyrimidin-4-yl)pyridin-2-yl)oxy)naphthalen-1-yl)methanesulfonamide hydrochloride 438

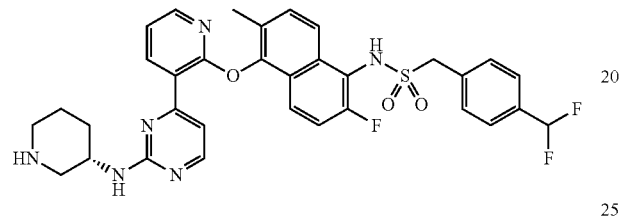

Prepared according to General Procedure B using (S)-tert-Butyl 3-((4-(2-((5-((4-(difluoromethyl)phenyl)methylsulfonamido)-6-fluoro-2-methylnaphthalen-1-yl)oxy)pyridin-3-yl)pyrimidin-2-yl)amino)piperidine-1-carboxylate (51 mg, 0.07 mmol), 1,4-dioxane (0.2 mL), and hydrochloric acid (4 M in dioxane, 0.9 mL, 3.6 mmol). After 90 min, the mixture was diluted with Et$_2$O and the solids were collected, washed with Et$_2$O, dissolved in H$_2$O and MeCN and lyophilized to provide 35 mg (74% yield) of 438. LCMS (ESI) [M+H]$^+$=649.3; $^1$H NMR (400 MHz, DMSO-d$_6$) δ 9.85 (s, 1H), 8.79 (bs, 2H), 8.48 (d, J=5.2 Hz, 1H), 8.09 (dd, J=4.8, 2.0 Hz, 1H), 7.98 (d, J=8.7 Hz, 1H), 7.73 (dd, J=9.4, 5.1 Hz, 1H), 7.61 (s, 4H), 7.60-7.46 (m, 4H), 7.30 (dd, J=7.6, 4.8 Hz, 1H), 7.07 (t, J=55.9 Hz, 1H), 4.65 (s, 2H), 4.26 (s, 1H), 3.50-3.38 (m, 1H), 3.21 (d, J=11.3 Hz, 1H), 2.95-2.76 (m, 2H), 2.19 (s, 3H), 2.08-1.96 (m, 1H), 1.97-1.86 (m, 1H), 1.82-1.53 (m, 2H).

Example 439 (S)-2,2,3,3,3-Pentafluoro-N-(2-fluoro-6-methyl-5-((3-(2-(piperidin-3-ylamino)pyrimidin-4-yl)pyridin-2-yl)oxy)naphthalen-1-yl)propane-1-sulfonamide hydrochloride Step 1: (S)-tert-Butyl 3-((4-(2-((6-fluoro-2-methyl-5-(2,2,3,3,3-pentafluoropropylsulfonamido)naphthalen-1-yl)oxy)pyridin-3-yl)pyrimidin-2-yl)amino)piperidine-1-carboxylate

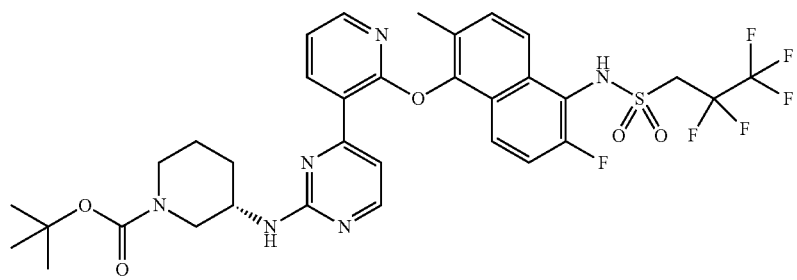 [SMILES: Cc1ccc2c(NS(=O)(=O)CC(F)(F)C(F)(F)F)c(F)ccc2c1Oc1ncccc1-c1ccnc(N[C@H]2CCCN(C(=O)OC(C)(C)C)C2)n1]

The General Procedure A was followed using (S)-tert-butyl 3-((4-(2-((5-amino-6-fluoro-2-methylnaphthalen-1-yl)oxy)pyridin-3-yl)pyrimidin-2-yl)amino)piperidine-1-carboxylate from Example 275 (75 mg, 0.14 mmol), pyridine (0.17 mL), CH$_2$Cl$_2$ (0.8 mL), 4-dimethylaminopyridine (1.7 mg, 0.01 mmol) and 2,2,3,3,3-pentafluoropropane-1-sulfonyl chloride (32 mg, 0.14 mmol). After 1 h, the mixture was diluted with CH$_2$Cl$_2$ (50 mL) and washed with 1M KHSO$_4$ (10 mL), dried by filtration through a phase cartridge separator and concentrated in vacuo. The crude was purified by flash chromatography through silica gel (10-60% EtOAc/CH$_2$Cl$_2$) to provide 62 mg (61% yield) of the title compound. LCMS (ESI) [M+H]$^+$=741.2.

Step 2: (S)-2,2,3,3,3-Pentafluoro-N-(2-fluoro-6-methyl-5-((3-(2-(piperidin-3-ylamino)pyrimidin-4-yl)pyridin-2-yl)oxy)naphthalen-1-yl)propane-1-sulfonamide hydrochloride 439

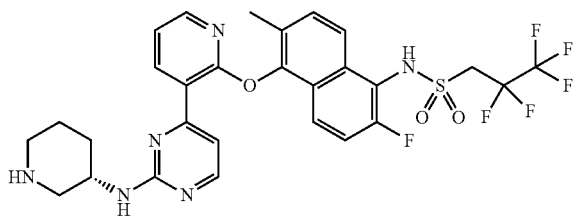 [SMILES: Cc1ccc2c(NS(=O)(=O)CC(F)(F)C(F)(F)F)c(F)ccc2c1Oc1ncccc1-c1ccnc(N[C@H]2CCCNC2)n1]

Prepared according to General Procedure B using (S)-tert-butyl 3-((4-(2-((6-fluoro-2-methyl-5-(2,2,3,3,3-pentafluoropropylsulfonamido)naphthalen-1-yl)oxy)pyridin-3-yl)pyrimidin-2-yl)amino)piperidine-1-carboxylate (62 mg, 0.08 mmol), 1,4-dioxane (0.2 mL), and hydrochloric acid (4 M in dioxane, 0.9 mL, 3.6 mmol). After 60 min, the mixture was diluted with Et$_2$O and the solids were collected, washed with Et$_2$O, dissolved in H$_2$O and MeCN and lyophilized to provide 47 mg (82% yield) of 439. LCMS (ESI) [M+H]$^+$=641.3; $^1$H NMR (400 MHz, DMSO-d$_6$) δ 10.50 (s, 1H), 8.96 (bs, 2H), 8.71 (bs, 1H), 8.48 (d, J=5.2 Hz, 1H), 8.08 (dd, J=4.8, 1.9 Hz, 1H), 8.02 (d, J=8.7 Hz, 1H), 7.77 (dd, J=9.3, 5.2 Hz, 1H), 7.66 (d, J=8.8 Hz, 1H), 7.64-7.54 (m, 2H), 7.49 (t, J=9.5 Hz, 1H), 7.29 (dd, J=7.6, 4.8 Hz, 1H), 4.51 (t, J=17.0 Hz, 2H), 3.51-3.35 (m, 1H), 3.20 (d, J=11.7 Hz, 1H), 2.94-2.75 (m, 2H), 2.20 (s, 3H), 2.06-1.97 (m, 1H), 1.97-1.86 (m, 1H), 1.83-1.53 (m, 2H).

Example 440 4-[2-[[5-[[Cyclopropyl(methyl)sulfamoyl]amino]-6-fluoro-2-methyl-1-naphthyl]oxy]-3-pyridyl]-2-[[(3S)-3-piperidyl]amino]pyrimidine hydrochloride Step 1: tert-Butyl (3S)-3-[[4-[2-[[5-[[cyclopropyl(methyl)sulfamoyl]amino]-6-fluoro-2-methyl-1-naphthyl]oxy]-3-pyridyl]pyrimidin-2-yl]amino]piperidine-1-carboxylate

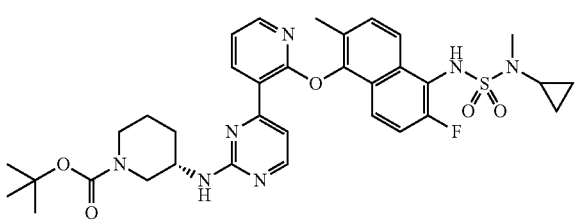 [SMILES: Cc1ccc2c(NS(=O)(=O)N(C)C3CC3)c(F)ccc2c1Oc1ncccc1-c1ccnc(N[C@H]2CCCN(C(=O)OC(C)(C)C)C2)n1]

To a solution of tert-butyl (3S)-3-[[4-[2-[[6-fluoro-2-methyl-5-[(2-oxooxazolidin-3-yl)sulfonylamino]-1-naphthyl]oxy]-3-pyridyl]pyrimidin-2-yl]amino]piperidine-1-carboxylate from Example 427 (75 mg, 0.11 mmol) in MeCN (0.43 mL), was added Et$_3$N (0.075 mL, 0.54 mmol) and N-methylcyclopropanamine (0.036 mL, 0.43 mmol). The reaction mixture was stirred at 85° C. with additional portions of N-methylcyclopropanamine added until conversion reached 85%. The volatiles were evaporated in vacuo. The residue, diluted with 1N KHSO$_4$, was extracted twice with EtOAc, dried (Na$_2$SO$_4$), filtered and concentrated in vacuo. The crude was purified by flash chromatography through silica gel (2-7% MeOH/(90% Hexanes:DCM)) to provide 17 mg (23% yield) of the title compound. LCMS (ESI) [M+H]$^+$=678.5.

Step 2: 4-[2-[[5-[[Cyclopropyl(methyl)sulfamoyl]amino]-6-fluoro-2-methyl-1-naphthyl]oxy]-3-pyridyl]-2-[[(3S)-3-piperidyl]amino]pyrimidine hydrochloride 440

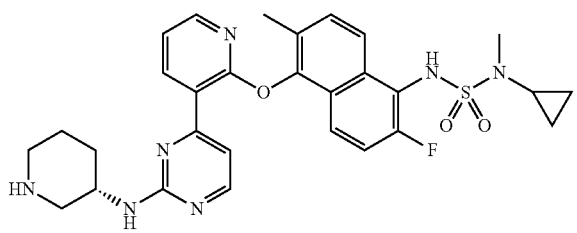 [SMILES: Cc1ccc2c(NS(=O)(=O)N(C)C3CC3)c(F)ccc2c1Oc1ncccc1-c1ccnc(N[C@H]2CCCNC2)n1]

Prepared according to General Procedure B using tert-butyl (3S)-3-[[4-[2-[[5-[[cyclopropyl(methyl)sulfamoyl]amino]-6-fluoro-2-methyl-1-naphthyl]oxy]-3-pyridyl]pyrimidin-2-yl]amino]piperidine-1-carboxylate (17 mg, 0.025 mmol), 1,4-dioxane (0.5 mL), and hydrochloric acid (4 M in dioxane, 1.0 mL, 4.0 mmol). After 1 h, the mixture was diluted with Et$_2$O and the resulting solids were collected by filtration, washed with Et$_2$O, dissolved in H$_2$O and MeCN and lyophilized to provide 16 mg (106% yield) of 440. LCMS (ESI) [M+H]$^+$=578.4; $^1$H 1H NMR (400 MHz, DMSO-d$_6$) δ 9.59 (s, 1H), 8.94-8.73 (m, 2H), 8.71-8.55 (m, 1H), 8.47 (d, J=5.2 Hz, 1H), 8.12-8.09 (m, 1H), 8.09-8.07 (m, 1H), 7.70 (dd, J=9.3, 5.0 Hz, 1H), 7.63 (d, J=8.8 Hz, 1H), 7.56 (d, J=5.1 Hz, 1H), 7.53 (d, J=7.4 Hz, 1H), 7.43 (t, J=9.4 Hz, 1H), 7.29 (dd, J=7.6, 4.8 Hz, 1H), 4.26 (s, 1H), 3.47-3.38 (m, 1H), 3.21 (d, J=11.9 Hz, 1H), 2.93-2.77 (m, 5H), 2.58-2.51 (m, 1H), 2.19 (s, 3H), 2.01 (d, J=9.0 Hz, 1H), 1.91 (d, J=14.5 Hz, 1H), 1.80-1.56 (m, 2H), 0.69-0.56 (m, 4H).

Example 441 4-[2-[[6-Fluoro-2-methyl-5-[[methyl (3,3,3-trifluoropropyl)sulfamoyl]amino]-1-naphthyl] oxy]-3-pyridyl]-2-[[(3S)-3-piperidyl]amino]pyrimidine hydrochloride Step 1: tert-Butyl (3S)-3-[[4-[2-[[6-fluoro-2-methyl-5-[[methyl(3,3,3-trifluoropropyl)sulfamoyl]amino]-1-naphthyl]oxy]-3-pyridyl]pyrimidin-2-yl]amino]piperidine-1-carboxylate

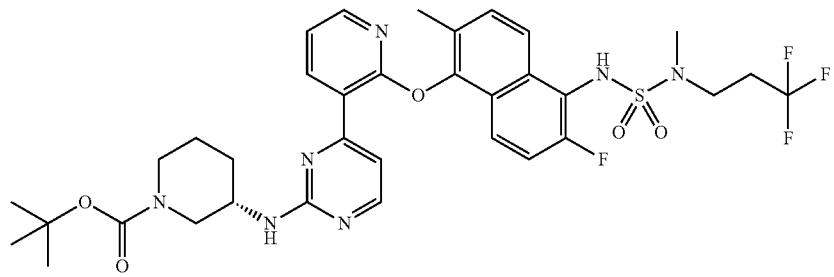 [SMILES: Cc1ccc2c(NS(=O)(=O)N(C)CCC(F)(F)F)c(F)ccc2c1Oc1ncccc1-c1ccnc(N[C@H]2CCCN(C(=O)OC(C)(C)C)C2)n1]

To a solution of tert-butyl (3S)-3-[[4-[2-[[6-fluoro-2-methyl-5-[(2-oxooxazolidin-3-yl)sulfonylamino]-1-naphthyl]oxy]-3-pyridyl]pyrimidin-2-yl]amino]piperidine-1-carboxylate from Example 427 (75 mg, 0.11 mmol), in MeCN (0.43 mL), was added Et₃N (0.075 mL, 0.54 mmol) and 3,3,3-trifluoro-N-methyl-propan-1-amine (55 mg, 0.43 mmol). The reaction mixture was stirred overnight at 85° C. After 18 h, the volatiles were evaporated in vacuo. The residue was diluted with 1N KHSO₄, extracted twice with EtOAc, dried (Na₂SO₄), filtered and concentrated in vacuo. The crude was purified by flash chromatography through silica gel (2-7% MeOH/(75% Hexanes:DCM)) to provide 37 mg (46% yield) of the title compound. LCMS (ESI) [M+H]⁺=734.5.

Step 2: 4-[2-[[6-Fluoro-2-methyl-5-[[methyl(3,3,3-trifluoropropyl)sulfamoyl]amino]-1-naphthyl]oxy]-3-pyridyl]-2-[[(3S)-3-piperidyl]amino]pyrimidine hydrochloride 441

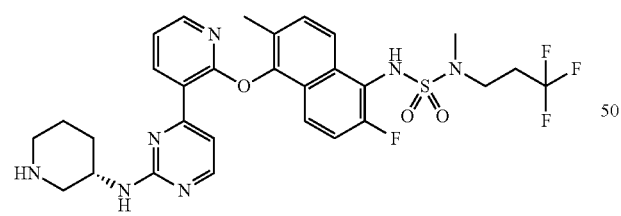

Prepared according to General Procedure B using tert-butyl (3S)-3-[[4-[2-[[6-fluoro-2-methyl-5-[[methyl(3,3,3-trifluoropropyl)sulfamoyl]amino]-1-naphthyl]oxy]-3-pyridyl]pyrimidin-2-yl]amino]piperidine-1-carboxylate (37 mg, 0.050 mmol), 1,4-dioxane (0.5 mL), and hydrochloric acid (4 M in dioxane, 1 mL, 4.0 mmol). After 1 h, the mixture was diluted with Et₂O and the resulting solids were collected by filtration, washed with Et₂O, dissolved in H₂O and MeCN and lyophilized to provide 27 mg (78% yield) of 441. LCMS (ESI) [M+H]⁺=634.4; ¹; ¹H NMR (400 MHz, DMSO-d₆) δ 9.67 (s, 1H), 9.04-8.75 (m, 2H), 8.74-8.57 (m, 1H), 8.47 (d, J=5.2 Hz, 1H), 8.10-8.05 (m, 2H), 7.71 (dd, J=9.3, 5.2 Hz, 1H), 7.64 (d, J=8.8 Hz, 1H), 7.60-7.51 (m, 2H), 7.44 (t, J=9.5 Hz, 1H), 7.29 (dd, J=7.6, 4.8 Hz, 1H), 4.26 (s, 1H), 3.44 (d, J=14.9 Hz, 1H), 3.40-3.32 (m, 2H), 3.21 (d, J=12.8 Hz, 1H), 2.95-2.77 (m, 5H), 2.65-2.53 (m, 2H), 2.19 (s, 3H), 2.01 (d, J=12.5 Hz, 1H), 1.91 (d, J=14.6 Hz, 1H), 1.80-1.56 (m, 2H).

Example 442 (S)-3,3-Difluoro-N-(2-fluoro-6-methyl-5-((3-(2-(piperidin-3-ylamino)pyrimidin-4-yl)pyridin-2-yl)oxy)naphthalen-1-yl)butane-1-sulfonamide hydrochloride Step 1: (S)-tert-Butyl 3-((4-(2-((5-(3,3-difluorobutylsulfonamido)-6-fluoro-2-methylnaphthalen-1-yl)oxy)pyridin-3-yl)pyrimidin-2-yl)amino)piperidine-1-carboxylate

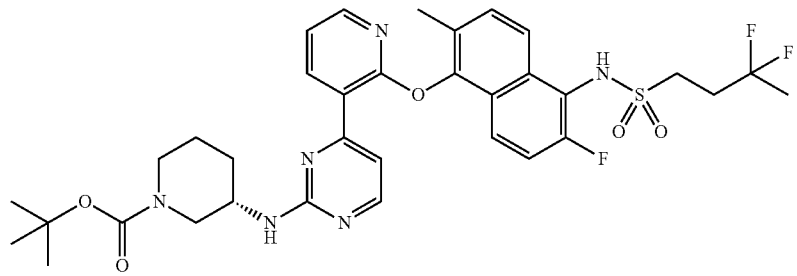 [SMILES: Cc1ccc2c(NS(=O)(=O)CCC(C)(F)F)c(F)ccc2c1Oc1ncccc1-c1ccnc(N[C@H]2CCCN(C(=O)OC(C)(C)C)C2)n1]

The General Procedure A was followed using (S)-tert-butyl 3-((4-(2-((5-amino-6-fluoro-2-methylnaphthalen-1-yl)oxy)pyridin-3-yl)pyrimidin-2-yl)amino)piperidine-1-carboxylate from Example 275 (100 mg, 0.18 mmol), pyridine (0.8 mL), and 3,3-difluorobutane-1-sulfonyl chloride (53 mg, 0.28 mmol). After 72 h, the mixture was neutralized with saturated aqueous sodium bicarbonate (0.1 mL) and the crude was directly purified by C18 reverse phase flash chromatography (30-70% MeCN/10 mM aqueous ammonium bicarbonate, pH=10). Appropriate fractions were combined and lyophilized to provide 60 mg (46% yield) of the title compound. LCMS (ESI) [M+H]$^+$=701.2.

Step 2: (S)-3,3-Difluoro-N-(2-fluoro-6-methyl-5-((3-(2-(piperidin-3-ylamino)pyrimidin-4-yl)pyridin-2-yl)oxy)naphthalen-1-yl)butane-1-sulfonamide hydrochloride 442

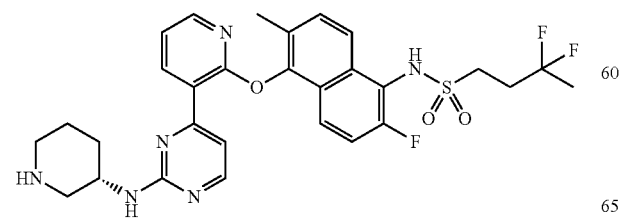

Prepared according to General Procedure B using (S)-tert-butyl 3-((4-(2-((5-(3,3-difluorobutylsulfonamido)-6-fluoro-2-methylnaphthalen-1-yl)oxy)pyridin-3-yl)pyrimidin-2-yl)amino)piperidine-1-carboxylate (60 mg, 0.09 mmol), EtOAc (1.0 mL), and hydrochloric acid (4 M in dioxane, 1.0 mL, 4.0 mmol). After 3 h, the resulting solids were collected by filtration, washed with CH$_2$Cl$_2$, dissolved in H$_2$O and MeCN and lyophilized to provide 45 mg (82% yield) of 442. LCMS (ESI) [M+H]$^+$=601.1; $^1$H NMR (400 MHz, DMSO-d$_6$) δ 9.95 (s, 1H), 9.16 (s, 1H), 9.02 (s, 1H), 8.71 (s, 1H), 8.46 (d, J=5.3 Hz, 1H), 8.06 (dd, J=4.8, 1.9 Hz, 1H), 8.03 (d, J=8.7 Hz, 1H), 7.72 (dd, J=9.3, 5.2 Hz, 1H), 7.63 (d, J=8.8 Hz, 2H), 7.57 (s, 1H), 7.46 (t, J=9.5 Hz, 1H), 7.27 (dd, J=7.6, 4.8 Hz, 1H), 4.29 (s, 1H), 3.41 (d, J=9.6 Hz, 1H), 3.37-3.27 (m, 2H), 3.18 (d, J=12.4 Hz, 1H), 2.90-2.71 (m, 2H), 2.55-2.40 (m, 2H, under the DMSO signal), 2.18 (s, 3H), 2.04-1.94 (m, 1H), 1.94-1.83 (m, 1H), 1.83-1.55 (m, 5H).

Example 443 (S)-1-(Benzo[d]isoxazol-3-yl)-N-(2-fluoro-6-methyl-5-((3-(2-(piperidin-3-ylamino)pyrimidin-4-yl)pyridin-2-yl)oxy)naphthalen-1-yl)methanesulfonamide hydrochloride Step 1: (S)-tert-Butyl 3-((4-(2-((5-(benzo[d]isoxazol-3-ylmethylsulfonamido)-6-fluoro-2-methylnaphthalen-1-yl)oxy)pyridin-3-yl)pyrimidin-2-yl)amino)piperidine-1-carboxylate

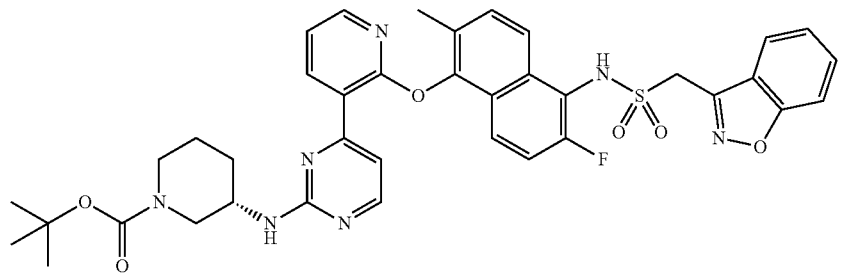 [SMILES: Cc1ccc2c(NS(=O)(=O)Cc3noc4ccccc34)c(F)ccc2c1Oc1ncccc1-c1ccnc(N[C@H]2CCCN(C(=O)OC(C)(C)C)C2)n1]

The General Procedure A was followed using (S)-tert-butyl 3-((4-(2-((5-amino-6-fluoro-2-methylnaphthalen-1-yl)oxy)pyridin-3-yl)pyrimidin-2-yl)amino)piperidine-1-carboxylate from Example 275 (100 mg, 0.18 mmol), pyridine (1.0 mL), CH$_2$Cl$_2$ (1.0 mL), and benzo[d]isoxazol-3-ylmethanesulfonyl chloride (64 mg, 0.28 mmol). After 2 h, the mixture was diluted with CH$_2$Cl$_2$ (50 mL) and washed with saturated aqueous NaHCO$_3$ (10 mL), dried (Na$_2$SO$_4$), filtered and concentrated in vacuo. The crude was purified by flash chromatography through silica gel (0-50% EtOAc/CH$_2$Cl$_2$) to provide 108 mg (79% yield) of the title compound. LCMS (ESI) [M+H]$^+$=740.2.

Step 2: (S)-1-(Benzo[d]isoxazol-3-yl)-N-(2-fluoro-6-methyl-5-((3-(2-(piperidin-3-ylamino)pyrimidin-4-yl)pyridin-2-yl)oxy)naphthalen-1-yl)methanesulfonamide hydrochloride 443

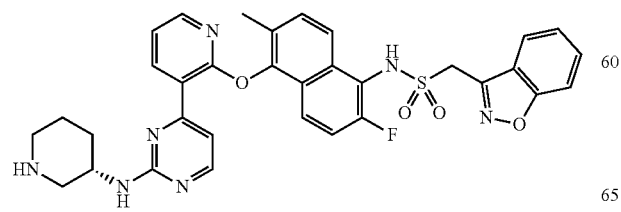

Prepared according to General Procedure B using (S)-tert-butyl 3-((4-(2-((5-(benzo[d]isoxazol-3-ylmethylsulfonamido)-6-fluoro-2-methylnaphthalen-1-yl)oxy)pyridin-3-yl)pyrimidin-2-yl)amino)piperidine-1-carboxylate (108 mg, 0.15 mmol), EtOAc (2 mL), and hydrochloric acid (4 M in dioxane, 2.0 mL, 8.0 mmol). After 90 min, the mixture was concentrated in vacuo and the crude residue was washed with EtOAc (3×3 mL) then with MeCN (3×3 mL), dissolved in $H_2O$ and MeCN and lyophilized to provide 88 mg (88% yield) of 443. LCMS (ESI) $[M+H]^+$=640.2; $^1$H NMR (400 MHz, DMSO-$d_6$) δ 10.19 (s, 1H), 8.88-8.58 (m, 3H), 8.48 (d, J=5.2 Hz, 1H), 8.14-8.05 (m, 2H), 7.98 (d, J=8.0 Hz, 1H), 7.82 (d, J=8.5 Hz, 1H), 7.79-7.67 (m, 2H), 7.63 (d, J=8.8 Hz, 1H), 7.59-7.40 (m, 4H), 7.30 (dd, J=7.6, 4.8 Hz, 1H), 5.17 (s, 2H), 4.35-4.15 (m, 1H), 3.45-3.38 (m, 1H), 3.22 (d, J=11.6 Hz, 1H), 2.94-2.76 (m, 3H), 2.19 (s, 3H), 2.07-1.87 (m, 2H), 1.80-1.54 (m, 2H).

Example 444 2,2,2-Trifluoro-N-(2-fluoro-5-((3-(2-(((3S,5S)-5-fluoropiperidin-3-yl)amino)pyrimidin-4-yl)pyridin-2-yl)oxy)-6-methylnaphthalen-1-yl)ethanesulfonamide hydrochloride Step 1: tert-Butyl trans-3-fluoro-5-[[4-[2-[[6-fluoro-2-methyl-5-(2,2,2-trifluoroethylsulfonylamino)-1-naphthyl]oxy]-3-pyridyl]pyrimidin-2-yl]amino]piperidine-1-carboxylate

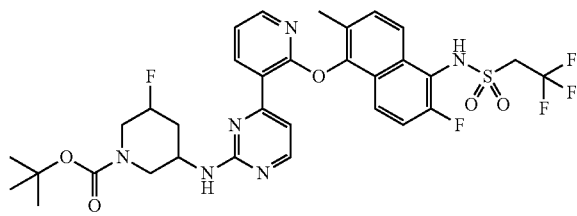 [SMILES: Cc1ccc2c(NS(=O)(=O)CC(F)(F)F)c(F)ccc2c1Oc1ncccc1-c1ccnc(NC2CC(F)CN(C(=O)OC(C)(C)C)C2)n1]

The General Procedure A was followed using tert-butyl trans-3-[[4-[2-[(5-amino-6-fluoro-2-methyl-1-naphthyl)oxy]-3-pyridyl]pyrimidin-2-yl]amino]-5-fluoro-piperidine-1-carboxylate from Example 322 (175 mg, 0.31 mmol), pyridine (0.38 mL), $CH_2Cl_2$ (1.5 mL), 4-dimethylaminopyridine (5 mg) and 2,2,2-trifluoroethanesulfonyl chloride (113 mg, 0.62 mmol). After 3 h, the mixture was diluted with $CH_2Cl_2$ (50 mL) and washed with 1M $KHSO_4$ (10 mL), dried by passing through a phase cartridge separator and concentrated in vacuo. The crude was purified by flash chromatography through silica gel (10-50% EtOAc/$CH_2Cl_2$) to provide 102 mg (46% yield) of the title compound. LCMS (ESI) $[M+H]^+$=709.4

Step 2: (3R,5R)-tert-Butyl 3-fluoro-5-((4-(2-((6-fluoro-2-methyl-5-(2,2,2-trifluoroethylsulfonamido)naphthalen-1-yl)oxy)pyridin-3-yl)pyrimidin-2-yl)amino)piperidine-1-carboxylate and (3S,5S)-tert-butyl 3-fluoro-5-((4-(2-(((6-fluoro-2-methyl-5-(2,2,2-trifluoroethylsulfonamido)naphthalen-1-yl)oxy)pyridin-3-yl)pyrimidin-2-yl)amino)piperidine-1-carboxylate

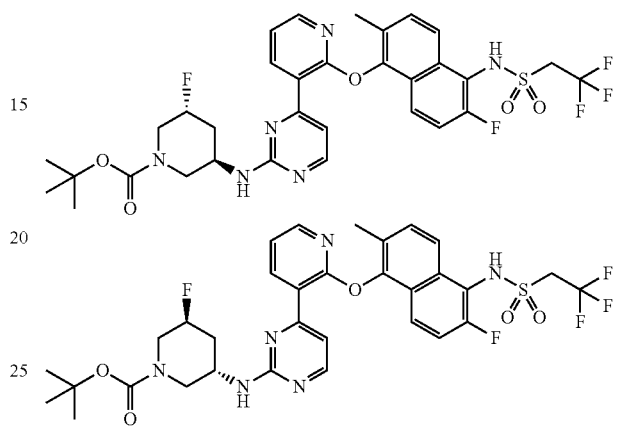

The stereoisomers from Step 1 were subjected to chiral SFC purification (conditions: ID, 10×250 mm 5 um, 30% IPA, 10 mL/min, 100 bar.) to provide two trans piperidine enantiomers. Isomer-1: (3R,5R)-tert-Butyl 3-fluoro-5-((4-(2-(((6-fluoro-2-methyl-5-(2,2,2-trifluoroethylsulfonamido)naphthalen-1-yl)oxy)pyridin-3-yl)pyrimidin-2-yl)amino)piperidine-1-carboxylate, 26 mg (25% yield), white solid, ee=99%, LCMS (ESI) $[M+H]^+$=709.4; and Isomer-2: (3S,5S)-tert-butyl 3-fluoro-5-((4-(2-((6-fluoro-2-methyl-5-(2,2,2-trifluoroethylsulfonamido)naphthalen-1-yl)oxy)pyridin-3-yl)pyrimidin-2-yl)amino)piperidine-1-carboxylate, 32 mg (30% yield), white solid, ee=99%, LCMS (ESI) $[M+H]^+$=709.4.

Step 3: 2,2,2-Trifluoro-N-(2-fluoro-5-((3-(2-(((3S,5S)-5-fluoropiperidin-3-yl)amino)pyrimidin-4-yl)pyridin-2-yl)oxy)-6-methylnaphthalen-1-yl)ethanesulfonamide hydrochloride (Isomer-2)

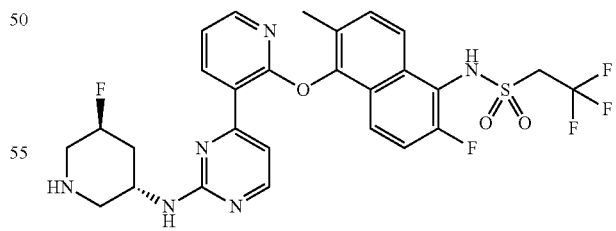

Prepared according to General Procedure B using (3S,5S)-tert-butyl 3-fluoro-5-((4-(2-((6-fluoro-2-methyl-5-(2,2,2-trifluoroethylsulfonamido)naphthalen-1-yl)oxy)pyridin-3-yl)pyrimidin-2-yl)amino)piperidine-1-carboxylate (32 mg, 0.04 mmol), 1,4-dioxane (0.5 mL), and hydrochloric acid (4 M in dioxane, 1 mL, 4.0 mmol). After 1 h, the mixture was diluted with $Et_2O$ and the resulting solids collected by filtration then dissolved in $H_2O$ and MeCN and lyophilized to provide 23 mg (80% yield) of 444. LCMS (ESI) [M+H]⁺=609.3; ¹H NMR (400 MHz, DMSO-d₆) δ 10.44 (s, 1H), 9.47 (d, J=10.0 Hz, 1H), 9.20 (s, 1H), 8.71 (s, 1H), 8.49 (d, J=5.2 Hz, 1H), 8.08 (dd, J=4.8, 1.9 Hz, 1H), 8.02 (d, J=8.8 Hz, 1H), 7.76 (dd, J=9.3, 5.2 Hz, 1H), 7.68-7.56 (m, 3H), 7.48 (t, J=9.4 Hz, 1H), 7.30 (dd, J=7.6, 4.8 Hz, 1H), 5.25 (d, J=45.7 Hz, 1H), 4.67-4.42 (m, 3H), 3.48-3.44 (m, 2H), 3.38-3.12 (m, 1H), 2.83 (q, J=10.5 Hz, 1H), 2.43-2.30 (m, 1H), 2.20 (s, 3H), 1.93 (dt, J=43.6, 12.5 Hz, 1H). The absolute stereochemistry of the fluoropiperidine was assigned based on the potency in the cellular assay.

Example 445 4-(2-((5-(((S)-2-Ethoxy-3,3,3-trifluoropropyl)amino)-2-methylnaphthalen-1-yl)oxy)pyridin-3-yl)-N—((S)-piperidin-3-yl)pyrimidin-2-amine hydrochloride Step 1: (S)-tert-Butyl 3-((4-(2-((2-methyl-5-(((S)-3,3,3-trifluoro-2-hydroxypropyl)amino)naphthalen-1-yl)oxy)pyridin-3-yl)pyrimidin-2-yl)amino)piperidine-1-carboxylate

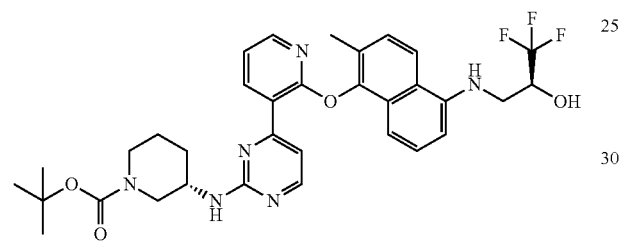

Prepared according to General Procedure F using (S)-tert-butyl 3-((4-(2-((5-amino-2-methylnaphthalen-1-yl)oxy)pyridin-3-yl)pyrimidin-2-yl)amino)piperidine-1-carboxylate (100 mg, 0.19 mmol), acetic acid (0.5 mL) and (2S)-2-(trifluoromethyl)oxirane (0.02 mL, 0.23 mmol). After 2 h, the mixture was concentrated in vacuo. The crude was purified by flash chromatography through silica gel (0-100% EtOAc/CH₂Cl₂) to provide 75 mg (62% yield) of the title compound. LCMS (ESI) [M+H]⁺=639.5.

Step 2: (S)-tert-Butyl 3-((4-(2-((5-(((S)-2-ethoxy-3,3,3-trifluoropropyl)amino)-2-methylnaphthalen-1-yl)oxy)pyridin-3-yl)pyrimidin-2-yl)amino)piperidine-1-carboxylate

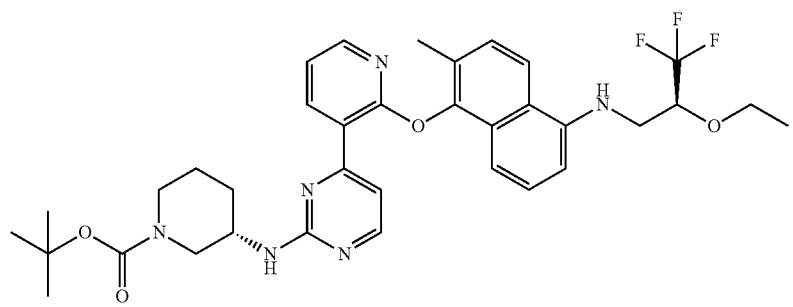 [SMILES: CCO[C@@H](CNc1cccc2c(Oc3ncccc3-c3ccnc(N[C@H]4CCCN(C(=O)OC(C)(C)C)C4)n3)c(C)ccc12)C(F)(F)F]

To a solution of tert-butyl (3S)-3-[[4-[2-[[2-methyl-5-[[(2S)-3,3,3-trifluoro-2-hydroxy-propyl]amino]-1-naphthyl]oxy]-3-pyridyl]pyrimidin-2-yl]amino]piperidine-1-carboxylate (75 mg, 0.12 mmol) in DMF (2 mL) was added cesium carbonate (115 mg, 0.35 mmol) followed by iodoethane (0.01 mL, 0.18 mmol) and the mixture was stirred at 70° C. for 45 min. The reaction mixture was then poured into water (10 mL) and the resulting solids collected by filtration and dissolved in EtOAc (20 mL), dried over MgSO₄ filtered and concentrated in vacuo. The crude was purified by flash chromatography through silica gel (40-100% EtOAc/hexane) to provide 58 mg (74% yield) of the title compound. LCMS (ESI) [M+H]⁺=667.3

Step 3: 4-(2-(((S)-2-Ethoxy-3,3,3-trifluoropropyl)amino)-2-methylnaphthalen-1-yl)oxy)pyridin-3-yl)-N—((S)-piperidin-3-yl)pyrimidin-2-amine hydrochloride 445

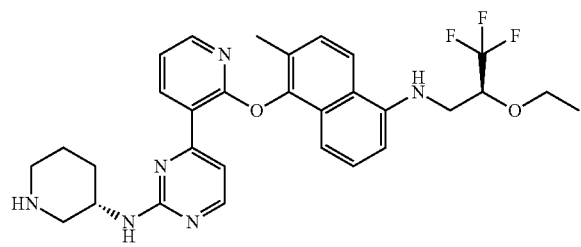 [SMILES: CCO[C@@H](CNc1cccc2c(Oc3ncccc3-c3ccnc(N[C@H]4CCCNC4)n3)c(C)ccc12)C(F)(F)F]

Prepared according to General Procedure B using (S)-tert-butyl 3-((4-(2-((5-(((S)-2-ethoxy-3,3,3-trifluoropropyl)amino)-2-methylnaphthalen-1-yl)oxy)pyridin-3-yl)pyrimidin-2-yl)amino)piperidine-1-carboxylate (58 mg, 0.09 mmol), 1,4-dioxane (1 mL) and hydrochloric acid (4 M in dioxane, 1 mL). After 1 h, the mixture was diluted with MTBE and the resulting solids were collected by filtration then dissolved in H₂O and MeCN and lyophilized to provide 17 mg (32% yield) of 445. LCMS (ESI) [M+H]⁺=567.4, ¹H NMR (400 MHz, DMSO-d₆) δ 9.50-8.99 (m, 2H), 8.47 (d, J=5.3 Hz, 1H), 8.10-8.00 (m, 2H), 7.66 (s, 2H), 7.37 (d, J=8.7 Hz, 1H), 7.29-7.14 (m, 2H), 6.87 (d, J=8.4 Hz, 1H), 6.51 (d, J=7.4 Hz, 1H), 4.30 (s, 1H), 4.27 (s, 1H), 3.66 (dd, J=32.5, 13.0 Hz, 2H), 3.42 (dd, J=13.8, 7.9 Hz, 2H), 3.16 (s, 1H), 2.81 (d, J=9.8 Hz, 2H), 2.00 (s, 1H), 1.88 (s, 1H), 1.79 (s, 1H), 1.64 (s, 1H), 1.05 (s, 3H).

Example 446 (1R,2R)-2-((6-Methyl-5-((3-(2-((S)-piperidin-3-ylamino)pyrimidin-4-yl)pyridin-2-yl)oxy)naphthalen-1-yl)amino)cyclohexanol hydrochloride (Isomer-1) 446

Step 1: (3S)-tert-Butyl 3-((4-(2-((5-((2-hydroxycyclohexyl)amino)-2-methylnaphthalen-1-yl)oxy)pyridin-3-yl)pyrimidin-2-yl)amino)piperidine-1-carboxylate

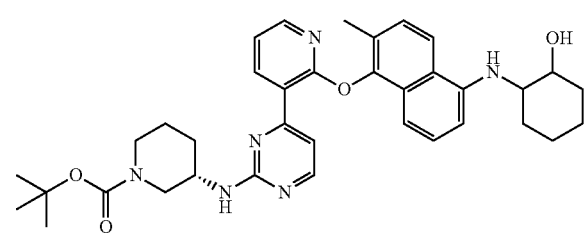 [SMILES: Cc1ccc2c(NC3CCCCC3O)cccc2c1Oc1ncccc1-c1ccnc(N[C@H]2CCCN(C(=O)OC(C)(C)C)C2)n1]

Prepared according to General Procedure F using (S)-tert-butyl 3-((4-(2-((5-amino-2-methylnaphthalen-1-yl)oxy)pyridin-3-yl)pyrimidin-2-yl)amino)piperidine-1-carboxylate (200 mg, 0.38 mmol) and cyclohexene oxide (48 mg, 0.49 mmol), in acetic acid (0.50 mL). The mixture was stirred in a sealed microwave vial at 70° C. for 3 days. AcOH was evaporated in vacuo. The crude was purified by C18 reverse phase flash chromatography (0-65% MeCN/10 mM aqueous ammonium formate, pH=3.8). Appropriate fractions were combined and concentrated in vacuo to provide 115 mg (48% yield) of the title compound. LCMS (ESI) [M+H]⁺=625.4.

Step 2: (S)-tert-Butyl 3-((4-(2-((5-(((1R,2R)-2-hydroxycyclohexyl)amino)-2-methylnaphthalen-1-yl)oxy)pyridin-3-yl)pyrimidin-2-yl)amino)piperidine-1-carboxylate (Isomer-1) and (S)-tert-butyl 3-((4-(2-((5-(((1S,2S)-2-hydroxycyclohexyl)amino)-2-methylnaphthalen-1-yl)oxy)pyridin-3-yl)pyrimidin-2-yl)amino)piperidine-1-carboxylate (Isomer-2)

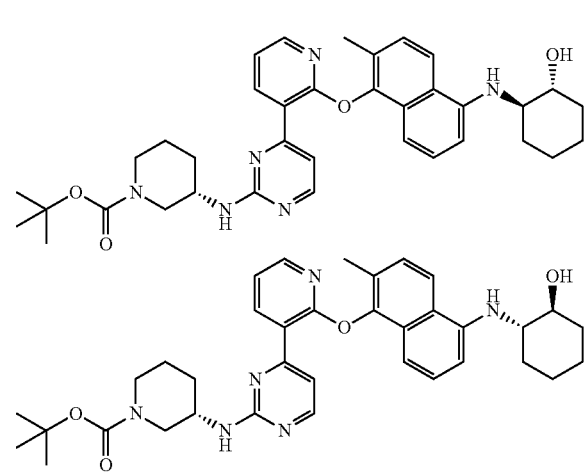

The stereoisomers from Step 1 were subjected to chiral normal phase semi-prep purification (conditions: Chiralpak IA, 5 uM, 20×250 mm, 15 mL/min, 3:7:90 MeOH:DCM:Hexane, 0.5-2.6 mg/inj.) to provide two stereoisomers enantiomeric at the 2-aminocyclohexanol. Isomer-1: (S)-tert-butyl 3-((4-(2-((5-(((1R,2R)-2-hydroxycyclohexyl)amino)-2-methylnaphthalen-1-yl)oxy)pyridin-3-yl)pyrimidin-2-yl)amino)piperidine-1-carboxylate, 36 mg (40% yield), LCMS (ESI) [M+H]⁺=625.3; and Isomer-2: (S)-tert-butyl 3-((4-(2-((5-(((1S,2S)-2-hydroxycyclohexyl)amino)-2-methylnaphthalen-1-yl)oxy)pyridin-3-yl)pyrimidin-2-yl)amino)piperidine-1-carboxylate, 38 mg (42% yield), LCMS (ESI) [M+H]⁺=625.3.

Step 3: (1R,2R)-2-((6-Methyl-5-((3-(2-((S)-piperidin-3-ylamino)pyrimidin-4-yl)pyridin-2-yl)oxy)naphthalen-1-yl)amino)cyclohexanol hydrochloride (Isomer-1) 446

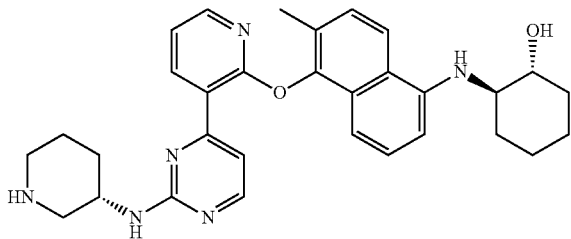

Prepared according to General Procedure B using (S)-tert-butyl 3-((4-(2-((5-(((1R,2R)-2-hydroxycyclohexyl)amino)-2-methylnaphthalen-1-yl)oxy)pyridin-3-yl)pyrimidin-2-yl)amino)piperidine-1-carboxylate (isomer-1) (36 mg, 0.060 mmol), 1,4-dioxane (1 mL) and hydrochloric acid (4 M in dioxane, 0.5 mL, 2 mmol). After 3 hours, the suspension was diluted with MTBE and the precipitate was filtered and washed with MTBE. The collected solids were then dissolved in MeCN and water and lyophilized to provide 32 mg (99% yield) of 446. LCMS (ESI) [M+H]⁺=525.2; ¹H NMR (400 MHz, D₂O) δ 9.53 (s, 1H), 9.29 (s, 1H), 8.83 (s, 1H), 8.49 (d, J=5.3 Hz, 1H), 8.16-8.03 (m, 2H), 7.79 (s, 1H), 7.70-7.60 (m, 1H), 7.58 (d, J=8.7 Hz, 1H), 7.52-7.33 (m, 3H), 7.28 (dd, J=7.5, 4.9 Hz, 1H), 4.17-4.02 (m, 1H), 3.85-3.71 (m, 1H), 3.48-3.33 (m, 1H), 3.30-3.12 (m, 2H), 2.94-2.74 (m, 2H), 2.22 (s, 3H), 2.08-1.97 (m, 2H), 1.96-1.71 (m, 3H), 1.68-1.43 (m, 4H), 1.42-1.01 (m, 3H). The absolute stereochemistry of the alcohol was randomly assigned.

Example 447 (1S,2S)-2-((6-Methyl-5-((3-(2-((S)-piperidin-3-ylamino)pyrimidin-4-yl)pyridin-2-yl)oxy)naphthalen-1-yl)amino)cyclohexanol hydrochloride (Isomer-2)

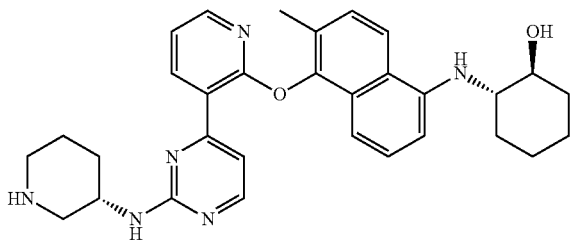 [SMILES: Cc1ccc2c(N[C@H]3CCCC[C@@H]3O)cccc2c1Oc1ncccc1-c1ccnc(N[C@H]2CCCNC2)n1]

Prepared according to General Procedure B using (S)-tert-butyl 3-((4-(2-((5-(((1S,2S)-2-hydroxycyclohexyl)amino)-2-methylnaphthalen-1-yl)oxy)pyridin-3-yl)pyrimidin-2-yl)amino)piperidine-1-carboxylate (isomer-2) (38 mg, 0.061 mmol), 1,4-dioxane (1 mL) and hydrochloric acid (4 M in dioxane, 0.5 mL, 2 mmol). After 3 hours, the suspension was diluted with MTBE and the precipitate was filtered and washed with MTBE. The collected solids were then dissolved in MeCN and water and lyophilized to provide 33 mg (97% yield) of the 447. LCMS (ESI) [M+H]⁺=525.2; ¹H NMR (400 MHz, D₂O) δ 9.44 (s, 1H), 9.22 (s, 1H), 8.81 (s, 1H), 8.48 (d, J=5.3 Hz, 1H), 8.14-8.01 (m, 2H), 7.72 (s, 1H), 7.62 (s, 1H), 7.56 (d, J=8.7 Hz, 1H), 7.48-7.36 (m, 2H), 7.31 (s, 1H), 7.28 (dd, J=7.5, 4.8 Hz, 1H), 3.83-3.64 (m, 2H), 3.49-3.34 (m, 1H), 3.30-3.12 (m, 2H), 2.94-2.74 (m, 2H), 2.21 (s, 3H), 2.07-1.97 (m, 2H), 1.95-1.73 (m, 3H), 1.71-1.56 (m, 3H), 1.49 (s, 1H), 1.41-1.05 (m, 3H). The absolute stereochemistry of the alcohol was randomly assigned.

Example 448 1-(4-Chloro-1-methyl-pyrazol-3-yl)-N-[2-fluoro-6-methyl-5-[[3-[2-[[(3S)-3-piperidyl]amino]pyrimidin-4-yl]-2-pyridyl]oxy]-1-naphthyl]methanesulfonamide hydrochloride Step 1: S-[(1-Methylpyrazol-3-yl)methyl]ethanethioate

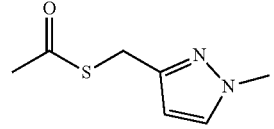

To a solution of 3-(chloromethyl)-1-methyl-pyrazole (300 mg, 2.3 mmol) in DMF (5.7 mL) was added potassium thioacetate (180 mg, 1.58 mmol) and cesium carbonate (482 mg, 1.47 mmol) and the mixture was stirred at rt for 3 h. The reaction was poured in EtOAc (80 mL) and water (25 mL), the phase were separated then the organic phase was washed twice with brine (2×25 mL), dried over MgSO₄, filtered and concentrated to give a pale red oil. The crude product was purified by flash chromatography through silica gel (10-70% EtOAc/hexane) to provide 329 mg (84% yield) of the title compound. LCMS (ESI) [M+H]⁺=171.0.

Step 2: (4-chloro-1-methyl-pyrazol-3-yl)methanesulfonyl chloride

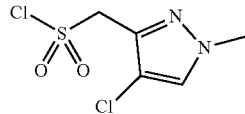

To a solution of 2M HCl (0.11 mL, 0.22 mmol) in MeCN (0.9 mL) was added N-chlorosuccinimide (102 mg, 0.76 mmol). After dissolution, the mixture was cooled to 0° C. and a solution of S-[(1-methylpyrazol-3-yl)methyl] ethanethioate (75 mg, 0.44 mmol) in MeCN (0.9 mL) was added over a period of 2 minutes under nitrogen. The resulting mixture was stirred at 0° C. for 20 min. The reaction mixture was poured in Et₂O then washed with a 12% solution of brine. The organic phase was dried over MgSO₄, filtered and concentrated to afford 76 mg (75% yield) of the title compound. ¹H NMR (400 MHz, CDCl₃) δ 7.46 (s, 1H), 4.93 (s, 2H), 3.94 (s, 3H).

Step 3: tert-Butyl (3S)-3-[[4-[2-[[5-[(4-chloro-1-methyl-pyrazol-3-yl)methylsulfonylamino]-6-fluoro-2-methyl-1-naphthyl]oxy]-3-pyridyl]pyrimidin-2-yl]amino]piperidine-1-carboxylate

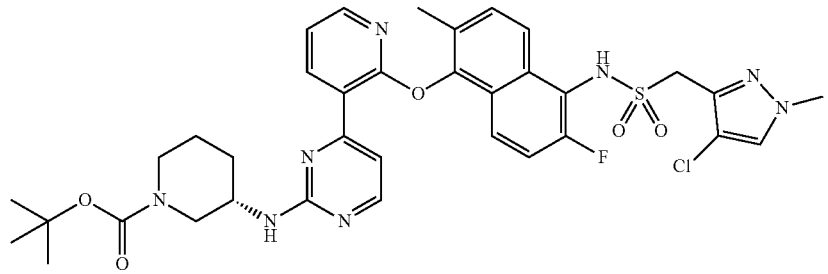 [SMILES: Cc1ccc2c(NS(=O)(=O)Cc3nn(C)cc3Cl)c(F)ccc2c1Oc1ncccc1-c1ccnc(N[C@H]2CCCN(C(=O)OC(C)(C)C)C2)n1]

Prepared according to General Procedure A using tert-butyl (3S)-3-[[4-[2-[(5-amino-6-fluoro-2-methyl-1-naphthyl)oxy]-3-pyridyl]pyrimidin-2-yl]amino]piperidine-1-carboxylate from Example 275 (75 mg, 0.14 mmol) in pyridine (0.17 mL), $CH_2Cl_2$ (0.8 mL), 4-dimethylaminopyridine (1.7 mg, 0.01 mmol) and (4-chloro-1-methyl-pyrazol-3-yl)methanesulfonyl chloride (63 mg, 0.28 mmol). After 2 h, the mixture was diluted with $CH_2Cl_2$ and washed with 1M $KHSO_4$, dried by passing through a phase cartridge separator and concentrated in vacuo. The crude was purified by flash chromatography through silica gel (10-60% EtOAc/$CH_2Cl_2$) to provide 84 mg (83% yield) of the title compound. LCMS (ESI) $[M+H]^+=737.3$.

Step 4: 1-(4-Chloro-1-methyl-pyrazol-3-yl)-N-[2-fluoro-6-methyl-5-[[3-[2-[[(3S)-3-piperidyl]amino]pyrimidin-4-yl]-2-pyridyl]oxy]-1-naphthyl]methanesulfonamide hydrochloride 448

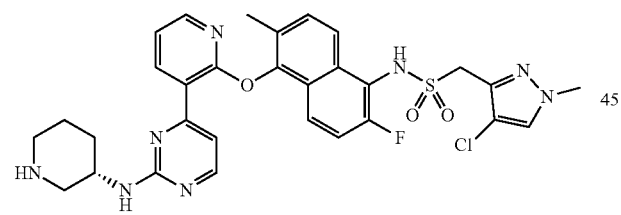

Prepared according to General Procedure B using tert-butyl (3S)-3-[[4-[2-[[5-[[ethyl(methyl)sulfamoyl]amino]-6-fluoro-2-methyl-1-naphthyl]oxy]-3-pyridyl]pyrimidin-2-yl]amino]piperidine-1-carboxylate (82 mg, 0.11 mmol), 1,4-dioxane (0.3 mL), and hydrochloric acid (4 M in dioxane, 0.9 mL, 3.6 mmol). After 90 min, the mixture was diluted with $Et_2O$ and the solids collected, washed with $Et_2O$, dissolved in $H_2O$ and MeCN and lyophilized to provide 57 mg (77% yield) of 448. LCMS (ESI) $[M+H]^+=637.1$; $^1H$ NMR (400 MHz, DMSO-$d_6$) δ 9.94 (s, 1H), 8.94 (bs, 2H), 8.70 (s, 1H), 8.48 (d, J=5.2 Hz, 1H), 8.16-8.05 (m, 2H), 7.99 (s, 1H), 7.73 (dd, J=9.3, 5.1 Hz, 1H), 7.68-7.54 (m, 3H), 7.48 (t, J=9.5 Hz, 1H), 7.29 (dd, J=7.6, 4.8 Hz, 1H), 4.51 (s, 2H), 4.29 (s, 1H), 3.83 (s, 3H), 3.44 (d, J=12.8 Hz, 1H), 3.20 (d, J=11.6 Hz, 1H), 2.95-2.75 (m, 2H), 2.20 (s, 3H), 2.07-1.85 (m, 2H), 1.85-1.49 (m, 2H).

Example 449 N-[2-Fluoro-6-methyl-5-[[3-[2-[[(3S)-3-piperidyl]amino]pyrimidin-4-yl]-2-pyridyl]oxy]-1-naphthyl]-1-(1-methylpyrazol-3-yl)methanesulfonamide hydrochloride Step 1: (1-Methylpyrazol-3-yl)methanesulfonyl chloride

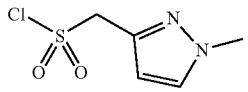

To a solution of 2M HCl (0.29 mL, 0.59 mmol) in MeCN (3.1 mL) was added N-chlorosuccinimide (423 mg, 3.1 mmol). The mixture was cooled to 0° C. and a solution of S-[(1-methylpyrazol-3-yl)methyl] ethanethioate (200 mg, 1.17 mmol) in MeCN (1.5 mL) was added slowly. After 10 min, water and Et$_2$O were added, the phases were separated and the organic phase was washed with a 12% solution of brine. The organic phase was dried over MgSO$_4$, filtered and concentrated. The crude was purified by flash chromatography through silica gel (15-70% EtOAc/hexanes) to provide the title compound. $^1$H NMR (400 MHz, CDCl$_3$) δ 7.42 (d, J=2.3 Hz, 1H), 6.50 (d, J=2.3 Hz, 1H), 4.94 (s, 2H), 3.95 (s, 3H).

Step 2: tert-Butyl (3S)-3-[[4-[2-[[6-fluoro-2-methyl-5-[(1-methylpyrazol-3-yl)methylsulfonylamino]-1-naphthyl]oxy]-3-pyridyl]pyrimidin-2-yl]amino]piperidine-1-carboxylate

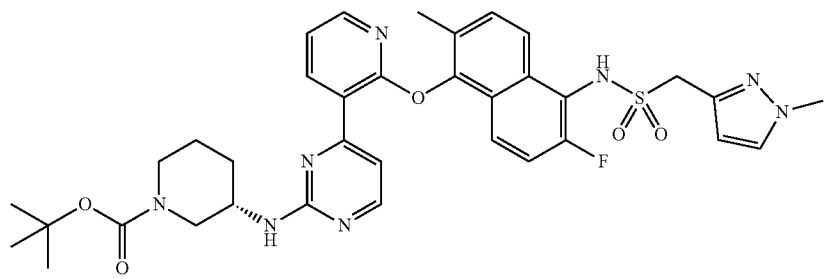 [SMILES: Cc1ccc2c(NS(=O)(=O)Cc3ccn(C)n3)c(F)ccc2c1Oc1ncccc1-c1ccnc(N[C@H]2CCCN(C(=O)OC(C)(C)C)C2)n1]

Prepared according to General Procedure A using tert-butyl (3S)-3-[[4-[2-[(5-amino-6-fluoro-2-methyl-1-naphthyl)oxy]-3-pyridyl]pyrimidin-2-yl]amino]piperidine-1-carboxylate from Example 275 (75 mg, 0.14 mmol) in pyridine (0.17 mL), CH$_2$Cl$_2$ (0.8 mL), 4-dimethylaminopyridine (1.7 mg, 0.01 mmol) and (1-methylpyrazol-3-yl)methanesulfonyl chloride (40 mg, 0.21 mmol). After 16 h, another portion of (1-methylpyrazol-3-yl)methanesulfonyl chloride (21 mg, 0.11 mmol) and stirring was continued for another 5 h. The mixture was then diluted with CH$_2$Cl$_2$ and washed with 1M KHSO$_4$, dried by passing through a phase cartridge separator and concentrated in vacuo. The crude was purified by flash chromatography through silica gel (15-70% EtOAc/CH$_2$Cl$_2$) followed by C18 reverse phase flash chromatography (45-100% MeCN/10 mM aqueous ammonium formate, pH=3.8). Appropriate fractions were combined concentrated to remove MeCN and most of the water then saturated aqueous solution of NaHCO$_3$ and DCM were added and the organic phase was extracted, dried by passing through a phase cartridge separator and concentrated to provide 42 mg (44% yield) of the title compound. LCMS (ESI) [M+H]$^+$=703.3.

Step 3: N-[2-Fluoro-6-methyl-5-[[3-[2-[[(3S)-3-piperidyl]amino]pyrimidin-4-yl]-2-pyridyl]oxy]-1-naphthyl]-1-(1-methylpyrazol-3-yl)methanesulfonamide hydrochloride 449

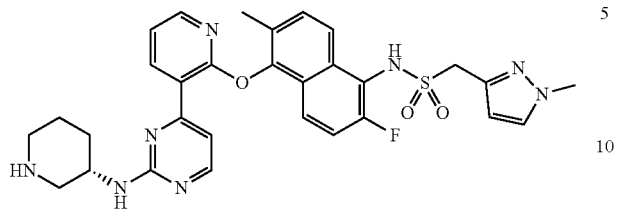

Prepared according to General Procedure B using tert-butyl (3S)-3-[[4-[2-[[6-fluoro-2-methyl-5-[(1-methylpyrazol-3-yl)methylsulfonylamino]-1-naphthyl]oxy]-3-pyridyl]pyrimidin-2-yl]amino]piperidine-1-carboxylate (42 mg, 0.060 mmol), 1,4-dioxane (0.3 mL), and hydrochloric acid (4 M in dioxane, 0.54 mL, 2.1 mmol). After 90 min, the mixture was diluted with Et$_2$O and the solids collected, washed with Et$_2$O, dissolved in H$_2$O and MeCN and lyophilized to provide 32 mg (83% yield) of 449. LCMS (ESI) [M+H]$^+$=603.2; $^1$H NMR (400 MHz, DMSO-d$_6$) δ 9.77 (s, 1H), 9.03-8.53 (m, 1H), 8.48 (d, J=5.2 Hz, 1H), 8.16-7.96 (m, 2H), 7.72 (dd, J=9.4, 5.2 Hz, 1H), 7.68 (d, J=2.2 Hz, 1H), 7.61 (d, J=8.8 Hz, 1H), 7.59-7.51 (m, 2H), 7.47 (t, J=9.5 Hz, 1H), 7.29 (dd, J=7.6, 4.8 Hz, 1H), 6.31 (d, J=2.2 Hz, 1H), 4.49 (s, 2H), 4.37-4.18 (m, 1H), 3.83 (s, 3H), 3.21 (d, J=13.4 Hz, 2H), 2.96-2.77 (m, 2H), 2.19 (s, 3H), 2.07-1.86 (m, 2H), 1.82-1.55 (m, 2H).

Example 450 (S)—N-(2-Fluoro-6-methyl-5-((3-(2-(piperidin-3-ylamino)pyrimidin-4-yl)pyridin-2-yl)oxy)naphthalen-1-yl)-3-methoxypropane-1-sulfonamide hydrochloride Step 1: (S)-tert-Butyl 3-((4-(2-((6-fluoro-5-(3-methoxypropylsulfonamido)-2-methylnaphthalen-1-yl)oxy)pyridin-3-yl)pyrimidin-2-yl)amino)piperidine-1-carboxylate

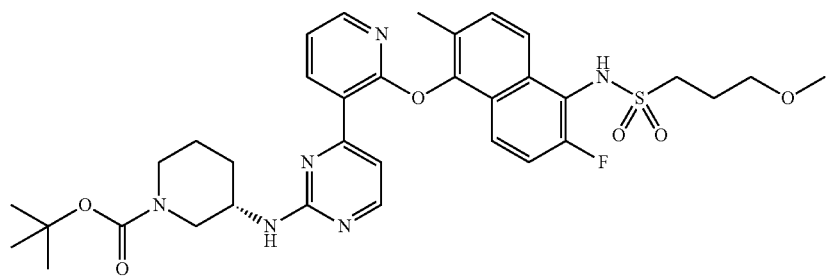 [SMILES: COCCCS(=O)(=O)Nc1c(F)ccc2c(Oc3ncccc3-c3ccnc(N[C@H]4CCCN(C(=O)OC(C)(C)C)C4)n3)c(C)ccc12]

The General Procedure A was followed using (S)-tert-butyl 3-((4-(2-((5-amino-6-fluoro-2-methylnaphthalen-1-yl)oxy)pyridin-3-yl)pyrimidin-2-yl)amino)piperidine-1-carboxylate from Example 275 (90 mg, 0.17 mmol), pyridine (0.2 mL), CH$_2$Cl$_2$ (0.55 mL), 4-dimethylaminopyridine (5 mg, 0.02 mmol) and 3-methoxypropane-1-sulfonyl chloride (57 mg, 0.33 mmol). After 16 h, the mixture was diluted with CH$_2$Cl$_2$ (50 mL) and washed with 1M KHSO$_4$ (10 mL), dried (Na$_2$SO$_4$), filtered and concentrated in vacuo. The crude was purified by flash chromatography through silica gel (0-50% EtOAc/CH$_2$Cl$_2$) to provide 70 mg (62% yield) of the title compound. LCMS (ESI) [M+H]$^+$=681.4.

Step 2: (S)—N-(2-Fluoro-6-methyl-5-((3-(2-(piperidin-3-ylamino)pyrimidin-4-yl)pyridin-2-yl)oxy)naphthalen-1-yl)-3-methoxypropane-1-sulfonamide hydrochloride 450

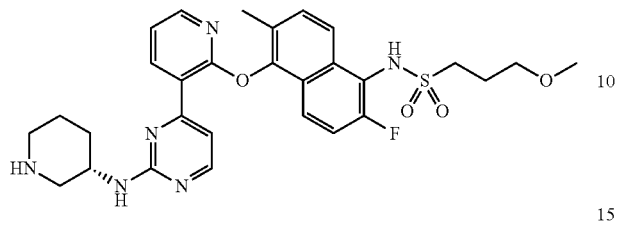

Prepared according to General Procedure B using (S)-tert-butyl 3-((4-(2-((6-fluoro-5-(3-methoxypropylsulfonamido)-2-methylnaphthalen-1-yl)oxy)pyridin-3-yl)pyrimidin-2-yl)amino)piperidine-1-carboxylate (70 mg, 0.10 mmol), 1,4-dioxane (0.5 mL), and hydrochloric acid (4 M in dioxane, 1.0 mL, 4.0 mmol). After 60 min, the mixture was diluted with Et$_2$O and the solids collected, washed with Et$_2$O, dissolved in H$_2$O and MeCN and lyophilized to provide 55 mg (87 yield of 450. LCMS (ESI) [M+H]$^+$=581.4; $^1$H NMR (400 MHz, DMSO-d$_6$) δ 9.77 (s, 1H), 9.19-8.85 (m, 2H), 8.71 (s, 1H), 8.48 (d, J=5.2 Hz, 1H), 8.08 (dd, J=4.8, 2.0 Hz, 1H), 8.06 (d, J=8.7 Hz, 1H), 7.72 (dd, J=9.2, 5.2 Hz, 1H), 7.67-7.55 (m, 3H), 7.46 (t, J=9.4 Hz, 1H), 7.29 (dd, J=7.6, 4.8 Hz, 1H), 4.35-4.18 (m, 1H), 3.48-3.39 (m, 3H), 3.27-3.15 (m, 6H), 2.94-2.77 (m, 2H), 2.19 (s, 3H), 2.11-1.97 (m, 3H), 1.96-1.85 (m, 1H), 1.83-1.56 (m, 2H).

Example 451 (S)-3,3,3-Trifluoro-N-(6-methyl-5-((3-(2-(piperidin-3-ylamino)pyrimidin-4-yl)pyridin-2-yl)oxy)naphthalen-1-yl)propane-1-sulfonamide Step 1: tert-Butyl (S)-3-((4-(2-((2-methyl-5-((3,3,3-trifluoropropyl)sulfonamido)naphthalen-1-yl)oxy)pyridin-3-yl)pyrimidin-2-yl)amino)piperidine-1-carboxylate

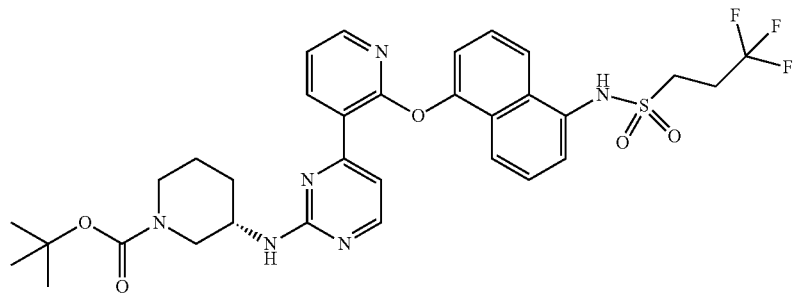 [SMILES: CC(C)(C)OC(=O)N1CCC[C@H](Nc2nccc(-c3cccnc3Oc3cccc4c(NS(=O)(=O)CCC(F)(F)F)cccc34)n2)C1]

The General Procedure A was followed, using tert-butyl (3S)-3-[[4-[2-[(5-amino-1-naphthyl)oxy]-3-pyridyl]pyrimidin-2-yl]amino]piperidine-1-carboxylate (150 mg, 0.29 mmol), 3,3,3-trifluoropropane-1-sulfonyl chloride (115.0 mg, 0.58 mmol) in pyridine (2 mL). The crude product was purified via reverse-phase HPLC to afford 120 mg (60.9% yield) of the title compound as a brown solid. LCMS (ESI) [M+H]$^+$=673.

Step 2: (S)-3,3,3-Trifluoro-N-(6-methyl-5-((3-(2-(piperidin-3-ylamino)pyrimidin-4-yl)pyridin-2-yl)oxy)naphthalen-1-yl)propane-1-sulfonamide

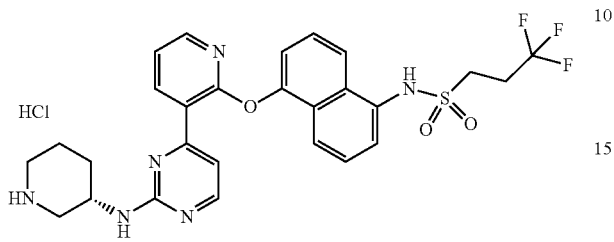

The General Procedure B was followed, using tert-butyl (S)-3-((4-(2-((2-methyl-5-((3,3,3-trifluoropropyl)sulfonamido)naphthalen-1-yl)oxy)pyridin-3-yl)pyrimidin-2-yl)amino)piperidine-1-carboxylate (120 mg, 0.18 mmol). The product was lyophilized to yield 109 mg (100% yield) of the title compound as grayish solid HCl salt. LCMS (ESI) [M+H]$^+$=573; $^1$H NMR (400 MHz, DMSO-d$_6$) δ 10.17 (s, 1H), 8.98-8.80 (m, 2H), 8.62 (s, 2H), 8.45 (d, J=5.2 Hz, 1H), 8.19-8.10 (m, 2H), 7.80-7.73 (m, 1H), 7.65 (dd, J=8.6, 7.5 Hz, 1H), 7.60-7.45 (m, 4H), 7.39 (dd, J=7.6, 1.0 Hz, 1H), 7.32 (dd, J=7.6, 4.8 Hz, 1H), 4.33-4.20 (m, 1H), 3.42-3.37 (m, 4H), 3.20 (d, J=12.4 Hz, 1H), 2.92-2.76 (m, 3H), 2.04-1.96 (m, 1H), 1.95-1.85 (m, 1H), 1.80-1.56 (m, 2H).

Example 452 (S)-1-Phenyl-N-(5-((3-(2-(piperidin-3-ylamino)pyrimidin-4-yl)pyridin-2-yl)oxy)naphthalen-1-yl)methanesulfonamide Step 1: tert-Butyl (S)-3-((4-(2-((5-(((phenylmethyl)sulfonamido)naphthalen-1-yl)oxy)pyridin-3-yl)pyrimidin-2-yl)amino)piperidine-1-carboxylate

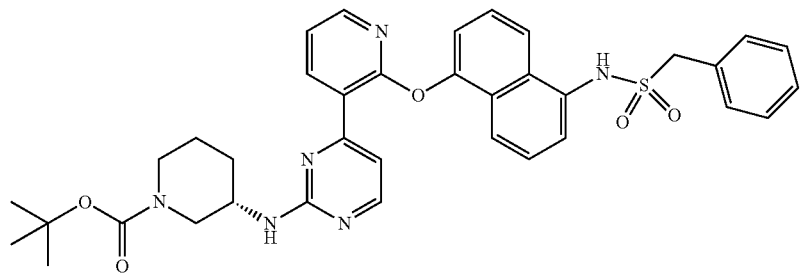 [SMILES: CC(C)(C)OC(=O)N1CCC[C@H](Nc2nccc(-c3cccnc3Oc3cccc4c(NS(=O)(=O)Cc5ccccc5)cccc34)n2)C1]

The General Procedure A was followed, using tert-butyl (3S)-3-[[4-[2-[(5-amino-1-naphthyl)oxy]-3-pyridyl]pyrimidin-2-yl]amino]piperidine-1-carboxylate (150 mg, 0.29 mmol), phenylmethanesulfonyl chloride (111.6 mg, 0.58 mmol) in pyridine (1.5 mL). The crude product was purified via reverse-phase HPLC to afford 105 mg (53.8% yield) of the title compound as a brown solid. LCMS (ESI) [M+H]$^+$=667.

729

Step 2: (S)-1-Phenyl-N-(5-((3-(2-(piperidin-3-ylamino)pyrimidin-4-yl)pyridin-2-yl)oxy)naphthalen-1-yl)methanesulfonamide

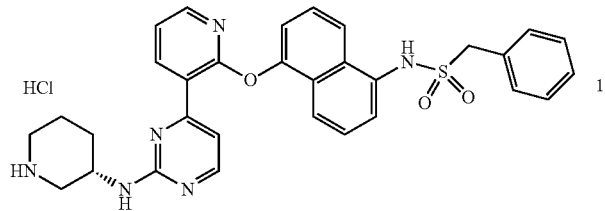

The General Procedure B was followed, using tert-butyl (S)-3-((4-(2-((5-((phenylmethyl)sulfonamido)naphthalen-1-yl)oxy)pyridin-3-yl)pyrimidin-2-yl)amino)piperidine-1-carboxylate (105 mg, 0.16 mmol). The product was lyophilized to yield 91.3 mg (96% yield) of the title compound as a brown solid HCl salt. LCMS (ESI) [M+H]$^+$=567; $^1$H NMR (400 MHz, DMSO-d$_6$) δ 9.94 (s, 1H), 9.00-8.80 (m, 2H), 8.64 (s, 1H), 8.46 (d, J=5.2 Hz, 1H), 8.15-8.08 (m, 2H), 7.71 (dt, J=8.1, 1.1 Hz, 1H), 7.64-7.55 (m, 2H), 7.54-7.43 (m, 3H), 7.41-7.28 (m, 7H), 4.56 (s, 2H), 4.29 (d, J=24.9 Hz, 1H), 3.43 (d, J=12.0 Hz, 1H), 3.20 (d, J=12.0 Hz, 1H), 2.92-2.77 (m, 2H), 2.04-1.96 (m, 1H), 1.95-1.86 (m, 1H), 1.80-1.56 (m, 2H).

Example 453 (S)—N-(2-Fluoro-6-methyl-5-((3-(2-(piperidin-3-ylamino)pyrimidin-4-yl)pyridin-2-yl)oxy)naphthalen-1-yl)-1-(1-fluorocyclopropyl)methanesulfonamide hydrochloride Step 1: (S)-tert-Butyl 3-((4-(2-((6-fluoro-5-((1-fluorocyclopropyl)methylsulfonamido)-2-methylnaphthalen-1-yl)oxy)pyridin-3-yl)pyrimidin-2-yl)amino)piperidine-1-carboxylate

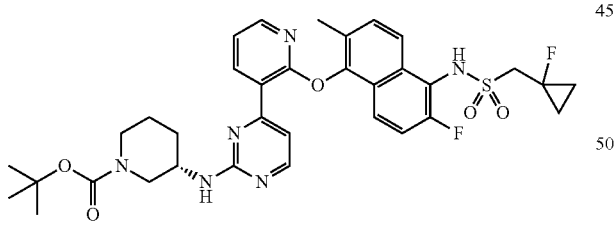

The General Procedure A was followed using (S)-tert-butyl 3-((4-(2-((5-amino-6-fluoro-2-methylnaphthalen-1-yl)oxy)pyridin-3-yl)pyrimidin-2-yl)amino)piperidine-1-carboxylate from Example 275 (90 mg, 0.17 mmol), pyridine (0.2 mL), CH$_2$Cl$_2$ (0.55 mL), 4-dimethylaminopyridine (5 mg, 0.02 mmol) and 3-methoxypropane-1-sulfonyl chloride (57 mg, 0.33 mmol). After 16 h, the mixture was diluted with CH$_2$Cl$_2$ (50 mL) and washed with 1M KHSO$_4$ (10 mL), dried (Na$_2$SO$_4$), filtered and concentrated in vacuo. The crude was purified by flash chromatography through silica gel (5-55% EtOAc/CH$_2$Cl$_2$) to provide 57 mg (51% yield) of the title compound. LCMS (ESI) [M+H]+=681.4.

730

Step 2: (S)—N-(2-Fluoro-6-methyl-5-((3-(2-(piperidin-3-ylamino)pyrimidin-4-yl)pyridin-2-yl)oxy)naphthalen-1-yl)-1-(1-fluorocyclopropyl)methanesulfonamide hydrochloride 453

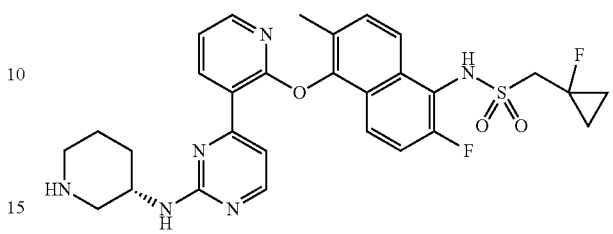

Prepared according to General Procedure B using (S)-tert-butyl 3-((4-(2-((6-fluoro-5-((1-fluorocyclopropyl)methylsulfonamido)-2-methylnaphthalen-1-yl)oxy)pyridin-3-yl)pyrimidin-2-yl)amino)piperidine-1-carboxylate (55 mg, 0.08 mmol), 1,4-dioxane (0.5 mL), and hydrochloric acid (4 M in dioxane, 1.0 mL, 4.0 mmol). After 2 h, the mixture was diluted with Et$_2$O and the solids collected, washed with Et$_2$O, dissolved in H$_2$O and MeCN and lyophilized to provide 42 mg (84% yield) of 453. LCMS (ESI) [M+H]$^+$=581.4; $^1$H NMR (400 MHz, DMSO-d$_6$) δ 9.88 (s, 1H), 9.12-8.83 (m, 2H), 8.69 (s, 1H), 8.47 (d, J=5.2 Hz, 1H), 8.07 (dd, J=5.5, 2.4 Hz, 2H), 7.71 (dd, J=9.2, 5.2 Hz, 1H), 7.64 (d, J=8.7 Hz, 1H), 7.56 (d, J=7.3 Hz, 2H), 7.46 (t, J=9.5 Hz, 1H), 7.29 (dd, J=7.6, 4.8 Hz, 1H), 4.26 (s, 1H), 3.83 (d, J=21.4 Hz, 2H), 3.43 (d, J=9.0 Hz, 1H), 3.20 (d, J=11.4 Hz, 1H), 2.93-2.75 (m, 2H), 2.19 (s, 3H), 2.01 (dd, J=12.6, 2.9 Hz, 1H), 1.96-1.85 (m, 1H), 1.74 (dd, J=22.4, 11.0 Hz, 1H), 1.62 (q, J=10.9 Hz, 1H), 1.14 (dt, J=14.1, 6.9 Hz, 2H), 0.95 (q, J=8.1 Hz, 2H).

Example 454 3,3,3-Trifluoro-N-(2-fluoro-6-methyl-5-((3-(2-((S)-piperidin-3-ylamino)pyrimidin-4-yl)pyridin-2-yl)oxy)naphthalen-1-yl)-2-methylpropane-1-sulfonamide hydrochloride (Isomer-1)

Step 1: S-(3,3,3-Trifluoro-2-methyl-propyl)ethanethioate

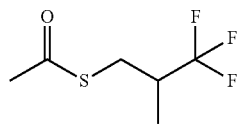

To a solution of (3,3,3-trifluoro-2-methyl-propyl) methanesulfonate (482 mg, 2.34 mmol) in DMF (10 mL) was added cesium carbonate (2.30 g, 7.01 mmol). The mixture was stirred at room temperature for 5 min then thioacetic acid (494 uL, 7.01 mmol) was added. The reaction mixture was stirred for 48 h then poured into water (50 mL) and extracted with Et$_2$O (100 mL). The ether layer was washed twice with brine and dried over MgSO$_4$, filtered and concentrated in vacuo to give 386 mg (89% yield) of the title compound $^1$H NMR (400 MHz, CDCl$_3$) δ 3.25 (dd, J=13.9, 4.6 Hz, 1H), 2.81 (dd, J=13.9, 8.9 Hz, 1H), 2.47-2.36 (m, 1H), 2.36 (s, 3H), 1.17 (d, J=7.0 Hz, 3H).

Step 2: 3,3,3-Trifluoro-2-methylpropane-1-sulfonyl chloride

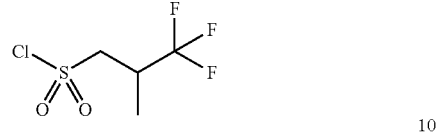

To a solution of 2M HCl (0.47 mL, 0.94 mmol) in MeCN (3.5 mL) at 0° C. was added N-chlorosuccinimide (1.00 g, 7.52 mmol) followed by addition of a solution of S-(3,3,3-trifluoro-2-methyl-propyl) ethanethioate (350 mg, 1.88 mmol) in MeCN (3.5 mL) over a period of 5 minutes under nitrogen. The resulting mixture was stirred at 0° C. for 30 min then increased to rt for 30 min. The reaction mixture was poured into Et$_2$O then washed with a 12% solution of brine. The organic phase was dried over MgSO$_4$, filtered and concentrated in vacuo. The crude was purified by flash chromatography through silica gel (0-100% EtOAc/hexane) to provide 146 mg (37% yield) of the title compound as a clear liquid. $^1$H NMR (400 MHz, CDCl$_3$) δ 4.04 (dd, J=14.4, 2.4 Hz, 1H), 3.63 (dd, J=14.4, 9.7 Hz, 1H), 3.12-3.00 (m, 1H), 1.49-1.45 (m, 3H).

Step 3: (3S)-tert-Butyl 3-((4-(2-((6-fluoro-2-methyl-5-(3,3,3-trifluoro-2-methylpropylsulfonamido)naphthalen-1-yl)oxy)pyridin-3-yl)pyrimidin-2-yl)amino)piperidine-1-carboxylate

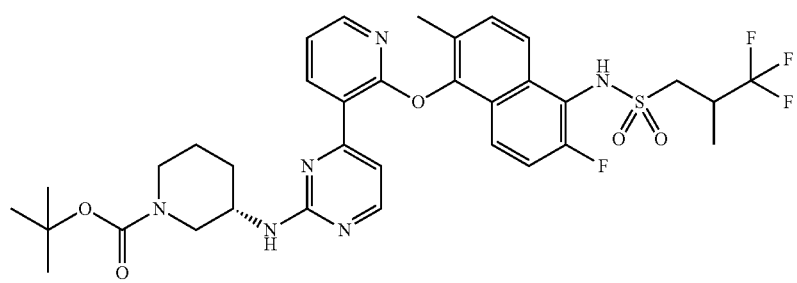 [SMILES: Cc1ccc2c(NS(=O)(=O)CC(C)C(F)(F)F)c(F)ccc2c1Oc1ncccc1-c1ccnc(N[C@H]2CCCN(C(=O)OC(C)(C)C)C2)n1]

The General Procedure A was followed using (S)-tert-butyl 3-((4-(2-((5-amino-6-fluoro-2-methylnaphthalen-1-yl)oxy)pyridin-3-yl)pyrimidin-2-yl)amino)piperidine-1-carboxylate from Example 275 (150 .mg, 0.28 mmol), pyridine (0.67 mL, 8.26 mmol), DCM (1 mL), and 3,3,3-trifluoro-2-methylpropane-1-sulfonyl chloride (145 mg, 0.69 mmol). After 18 h, the mixture was concentrated in vacuo and co-evaporated with toluene. The crude was purified by flash chromatography through silica gel (0-50% EtOAc/CH$_2$Cl$_2$) to provide 110 mg (56% yield) of the title compound. LCMS (ESI) [M+H]$^+$=719.5.

Step 4: (3S)-tert-Butyl 3-((4-(2-((6-fluoro-2-methyl-5-(3,3,3-trifluoro-2-methylpropylsulfonamido)naphthalen-1-yl)oxy)pyridin-3-yl)pyrimidin-2-yl)amino)piperidine-1-carboxylate (Isomer 1) and (3S)-tert-butyl 3-((4-(2-((6-fluoro-2-methyl-5-(3,3,3-trifluoro-2-methylpropylsulfonamido)naphthalen-1-yl)oxy)pyridin-3-yl)pyrimidin-2-yl)amino)piperidine-1-carboxylate (Isomer 2)

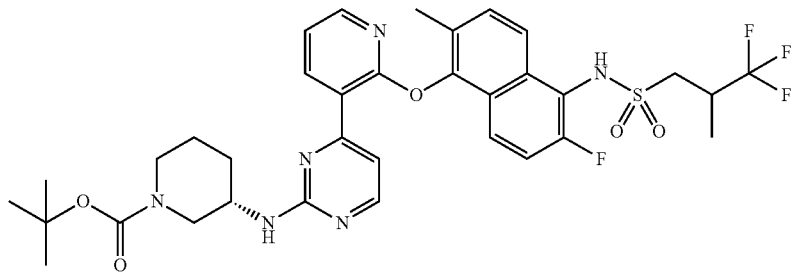 [SMILES: Cc1ccc2c(NS(=O)(=O)CC(C)C(F)(F)F)c(F)ccc2c1Oc1ncccc1-c1ccnc(N[C@H]2CCCN(C(=O)OC(C)(C)C)C2)n1]

The stereoisomers from Step 3 were subjected to chiral SFC purification (IA (250 mm×10 mm, 5 μm); IPA 20%; flow rate (ml/min): 10, 100 bar, 35° C.) to provide two stereoisomers enantiomeric at 2-methylpropane-position. Isomer-1: (3S)-tert-butyl 3-((4-(2-((6-fluoro-2-methyl-5-(3,3,3-trifluoro-2-methylpropylsulfonamido)naphthalen-1-yl)oxy)pyridin-3-yl)pyrimidin-2-yl)amino)piperidine-1-carboxylate, 25 mg (13% yield), ee=99.8%, rt=20.4 min; and Isomer-2: (3S)-tert-butyl 3-((4-(2-((6-fluoro-2-methyl-5-(3,3,3-trifluoro-2-methylpropylsulfonamido)naphthalen-1-yl)oxy)pyridin-3-yl)pyrimidin-2-yl)amino)piperidine-1-carboxylate, 25 mg (13% yield), ee=99.6%, rt=23.1 min.

Step 5: 3,3,3-Trifluoro-N-(2-fluoro-6-methyl-5-((3-(2-((S)-piperidin-3-ylamino)pyrimidin-4-yl)pyridin-2-yl)oxy)naphthalen-1-yl)-2-methylpropane-1-sulfonamide hydrochloride (Isomer 1) 454

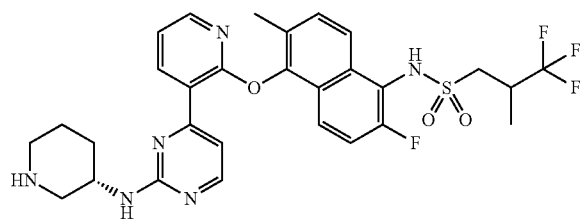 [SMILES: Cc1ccc2c(NS(=O)(=O)CC(C)C(F)(F)F)c(F)ccc2c1Oc1ncccc1-c1ccnc(N[C@H]2CCCNC2)n1]

Prepared according to General Procedure B using (3S)-tert-butyl 3-((4-(2-((6-fluoro-2-methyl-5-(3,3,3-trifluoro-2-methylpropylsulfonamido)naphthalen-1-yl)oxy)pyridin-3-yl)pyrimidin-2-yl)amino)piperidine-1-carboxylate (isomer-1) (25 mg, 0.03 mmol), 1,4-dioxane (0.3 mL) and hydrochloric acid (4 M in dioxane, (0.35 mL, 1.4 mmol). After 90 min, the mixture was diluted with Et$_2$O and the resulting solids were collected by filtration then dissolved in H$_2$O and MeCN and lyophilized to provide 20 mg (87% yield) of 454. LCMS (ESI) [M+H]$^+$=619.1, $^1$H NMR (400 MHz, DMSO-d$_6$) δ 10.11 (s, 1H), 9.08-8.56 (m, 3H), 8.47 (d, J=5.2 Hz, 1H), 8.08 (dd, J=4.8, 1.9 Hz, 1H), 8.04 (d, J=8.7 Hz, 1H), 7.74 (dd, J=9.3, 5.2 Hz, 1H), 7.66 (d, J=8.8 Hz, 1H), 7.62-7.53 (m, 2H), 7.48 (t, J=9.5 Hz, 1H), 7.29 (dd, J=7.6, 4.8 Hz, 1H), 3.59-3.32 (m, 3H), 3.21 (d, J=12.3 Hz, 1H), 3.17-3.01 (m, 1H), 3.00-2.72 (m, 2H), 2.20 (s, 3H), 2.08-1.83 (m, 2H), 1.83-1.51 (m, 2H), 1.35 (d, J=6.9 Hz, 3H).

Example 455 3,3,3-Trifluoro-N-(2-fluoro-6-methyl-5-((3-(2-((S)-piperidin-3-ylamino)pyrimidin-4-yl)pyridin-2-yl)oxy)naphthalen-1-yl)-2-methylpropane-1-sulfonamide hydrochloride (Isomer-2)

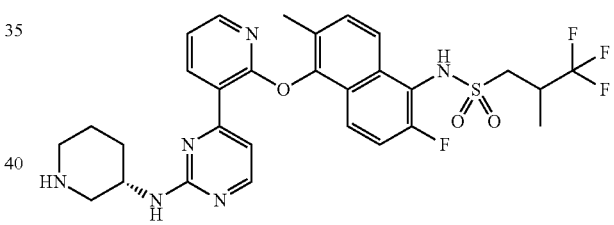

Prepared according to General Procedure B using (3S)-tert-butyl 3-((4-(2-((6-fluoro-2-methyl-5-(3,3,3-trifluoro-2-methylpropylsulfonamido)naphthalen-1-yl)oxy)pyridin-3-yl)pyrimidin-2-yl)amino)piperidine-1-carboxylate (isomer-2) (25 mg, 0.03 mmol), 1,4-dioxane (0.3 mL) and hydrochloric acid (4 M in dioxane, (0.35 mL, 1.4 mmol). After 90 min, the mixture was diluted with Et$_2$O and the resulting solids collected by filtration then dissolved in H$_2$O and MeCN and lyophilized to provide 20 mg (87% yield) of 455. LCMS (ESI) [M+H]$^+$=619.1 $^1$H NMR (400 MHz, DMSO-d$_6$) δ 10.11 (s, 1H), 9.15-8.57 (m, 3H), 8.47 (d, J=5.2 Hz, 1H), 8.08 (dd, J=4.8, 1.9 Hz, 1H), 8.04 (d, J=8.7 Hz, 1H), 7.74 (dd, J=9.3, 5.2 Hz, 1H), 7.66 (d, J=8.8 Hz, 1H), 7.60-7.52 (m, 2H), 7.48 (t, J=9.5 Hz, 1H), 7.29 (dd, J=7.6, 4.8 Hz, 1H), 3.56-3.34 (m, 3H), 3.20 (d, J=12.3 Hz, 1H), 3.15-3.00 (m, 1H), 2.97-2.75 (m, 2H), 2.20 (s, 3H), 2.07-1.86 (m, 2H), 1.82-1.55 (m, 2H), 1.35 (d, J=6.9 Hz, 3H).

Example 456 (S)-2,2-Difluoro-N-(2-fluoro-6-methyl-5-((3-(2-(piperidin-3-ylamino)pyrimidin-4-yl)pyridin-2-yl)oxy)naphthalen-1-yl)butane-1-sulfonamide hydrochloride Step 1: (S)-tert-Butyl 3-((4-(2-((5-(2,2-difluorobutylsulfonamido)-6-fluoro-2-methylnaphthalen-1-yl)oxy)pyridin-3-yl)pyrimidin-2-yl)amino)piperidine-1-carboxylate and (S,Z)-tert-butyl 3-((4-(2-((6-fluoro-5-(2-fluorobut-1-en-1-ylsulfonamido)-2-methylnaphthalen-1-yl)oxy)pyridin-3-yl)pyrimidin-2-yl)amino)piperidine-1-carboxylate

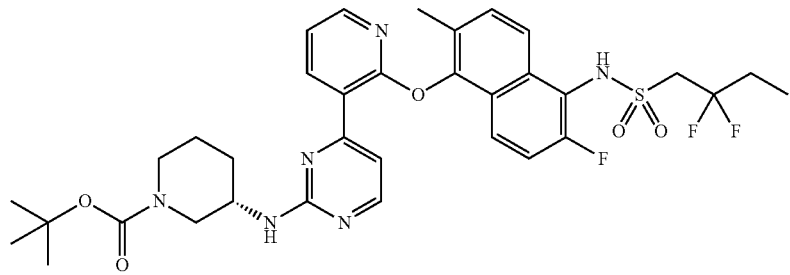

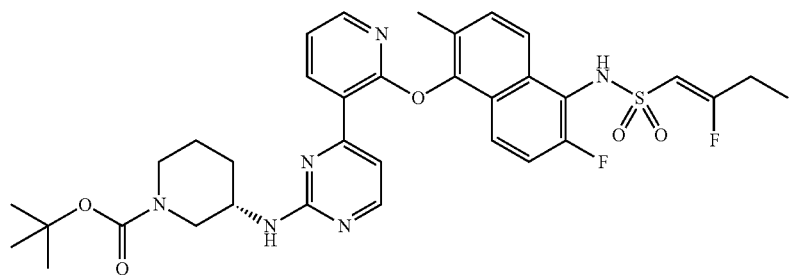

The General Procedure A was followed using (S)-tert-butyl 3-((4-(2-((5-amino-6-fluoro-2-methylnaphthalen-1-yl)oxy)pyridin-3-yl)pyrimidin-2-yl)amino)piperidine-1-carboxylate from Example 275 (90 mg, 0.17 mmol), pyridine (0.2 mL), $CH_2Cl_2$ (0.55 mL), 4-dimethylaminopyridine (5 mg, 0.02 mmol) and 2,2-difluorobutane-1-sulfonyl chloride (64 mg, 0.33 mmol). After 16 h, the mixture was diluted with $CH_2Cl_2$ (50 mL) and washed with 1M $KHSO_4$ (10 mL), dried ($Na_2SO_4$), filtered and concentrated in vacuo. The crude was purified by flash chromatography through silica gel (0-40% EtOAc/$CH_2Cl_2$) to provide a mixture of the two title compounds. This mixture was further purified by flash chromatography through silica gel (3-6% MeOH/10% $CH_2Cl_2$ in hexanes) to provide 59 mg (51% yield) of (S)-tert-Butyl 3-((4-(2-((5-(2,2-difluorobutylsulfonamido)-6-fluoro-2-methylnaphthalen-1-yl)oxy)pyridin-3-yl)pyrimidin-2-yl)amino)piperidine-1-carboxylate (LCMS (ESI) $[M+H]^+$=701.5) and 17 mg (15% yield) of (S,Z)-tert-butyl 3-((4-(2-((6-fluoro-5-(2-fluorobut-1-en-1-ylsulfonamido)-2-methylnaphthalen-1-yl)oxy)pyridin-3-yl)pyrimidin-2-yl)amino)piperidine-1-carboxylate (LCMS (ESI) $[M+H]^+$=681.4).

737

Step 2: (S)-2,2-Difluoro-N-(2-fluoro-6-methyl-5-((3-(2-(piperidin-3-ylamino)pyrimidin-4-yl)pyridin-2-yl)oxy)naphthalen-1-yl)butane-1-sulfonamide hydrochloride 456

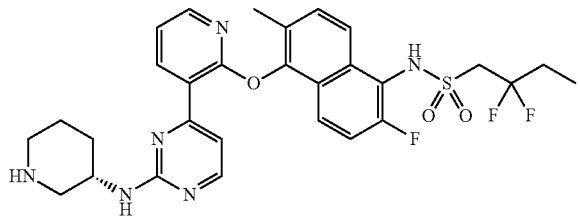 [SMILES: CCC(F)(F)CS(=O)(=O)Nc1c(F)ccc2c(Oc3ncccc3-c3ccnc(N[C@H]4CCCNC4)n3)c(C)ccc12]

Prepared according to General Procedure B using (S)-tert-butyl 3-((4-(2-((5-(2,2-difluorobutylsulfonamido)-6-fluoro-2-methylnaphthalen-1-yl)oxy)pyridin-3-yl)pyrimidin-2-yl)amino)piperidine-1-carboxylate (59 mg, 0.08 mmol), 1,4-dioxane (0.5 mL), and hydrochloric acid (4 M in dioxane, 1.0 mL, 4.0 mmol). After 2 h, the mixture was diluted with Et$_2$O and the solids collected, washed with Et$_2$O, dissolved in H$_2$O and MeCN and lyophilized to provide 49 mg (91% yield) of 456. LCMS (ESI) [M+H]$^+$=601.3; $^1$H NMR (400 MHz, DMSO-d$_6$) δ 10.12 (s, 1H), 9.06-8.79 (m, 2H), 8.69 (s, 1H), 8.48 (d, J=5.2 Hz, 1H), 8.08 (dd, J=4.8, 2.0 Hz, 1H), 8.04 (d, J=8.7 Hz, 1H), 7.74 (dd, J=9.3, 5.1 Hz, 1H), 7.65 (d, J=8.8 Hz, 1H), 7.56 (d, J=7.3 Hz, 2H), 7.48 (t, J=9.5 Hz, 1H), 7.29 (dd, J=7.6, 4.8 Hz, 1H), 4.26 (s, 1H), 4.02 (t, J=13.9 Hz, 2H), 3.44 (d, J=9.8 Hz, 1H), 3.21 (d, J=12.6 Hz, 1H), 2.93-2.77 (m, 2H), 2.20 (s, 3H), 2.11 (ddd, J=25.2, 10.3, 7.5 Hz, 2H), 2.02 (d, J=13.1 Hz, 1H), 1.91 (d, J=14.8 Hz, 1H), 1.83-1.56 (m, 2H), 0.98 (t, J=7.5 Hz, 3H).

738

Example 457 (S,Z)-2-Fluoro-N-(2-fluoro-6-methyl-5-((3-(2-(piperidin-3-ylamino)pyrimidin-4-yl)pyridin-2-yl)oxy)naphthalen-1-yl) but-1-ene-1-sulfonamide hydrochloride

Step 1: (S,Z)-2-Fluoro-N-(2-fluoro-6-methyl-5-((3-(2-(piperidin-3-ylamino)pyrimidin-4-yl)pyridin-2-yl)oxy)naphthalen-1-yl)but-1-ene-1-sulfonamide hydrochloride 457

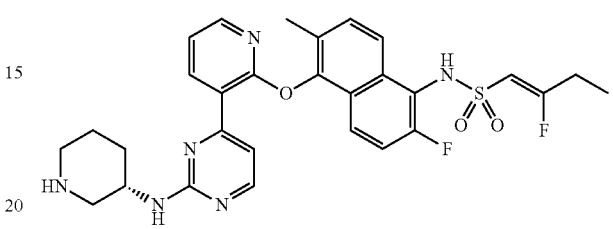

Prepared according to General Procedure B using (S,Z)-tert-butyl 3-((4-(2-((6-fluoro-5-(2-fluorobut-1-en-1-ylsulfonamido)-2-methylnaphthalen-1-yl)oxy)pyridin-3-yl)pyrimidin-2-yl)amino)piperidine-1-carboxylate prepared in Example 456 (17 mg, 0.02 mmol), 1,4-dioxane (0.5 mL), and hydrochloric acid (4 M in dioxane, 1.0 mL, 4.0 mmol). After 90 min, the mixture was diluted with Et$_2$O and the solids were collected, washed with Et$_2$O, dissolved in H$_2$O and MeCN and lyophilized to provide 13 mg (84% yield) of 457. LCMS (ESI) [M+H]$^+$=581.3; $^1$H NMR (400 MHz, DMSO-d$_6$) δ 10.06 (s, 1H), 9.06-8.75 (m, 2H), 8.66 (s, 1H), 8.45 (d, J=5.2 Hz, 1H), 8.05 (dd, J=4.8, 2.0 Hz, 1H), 8.01 (d, J=8.7 Hz, 1H), 7.69 (dd, J=9.3, 5.1 Hz, 1H), 7.59 (d, J=8.8 Hz, 1H), 7.53 (d, J=7.4 Hz, 2H), 7.42 (t, J=9.4 Hz, 1H), 7.27 (dd, J=7.6, 4.8 Hz, 1H), 6.23 (d, J=33.0 Hz, 1H), 4.24 (s, 1H), 3.41 (d, J=12.1 Hz, 1H), 3.18 (d, J=12.5 Hz, 1H), 2.92-2.73 (m, 2H), 2.31 (dq, J=15.0, 7.4 Hz, 2H), 2.16 (s, 3H), 1.99 (d, J=9.7 Hz, 1H), 1.94-1.84 (m, 1H), 1.76-1.52 (m, 2H), 1.00 (t, J=7.5 Hz, 3H).

Example 458 N-[2-Fluoro-6-methyl-5-[[3-[2-[[(3S)-3-piperidyl]amino]pyrimidin-4-yl]-2-pyridyl]oxy]-1-naphthyl]-1-methyl-indole-4-sulfonamide

Step 1: tert-Butyl (3S)-3-[[4-[2-[[6-fluoro-2-methyl-5-[(1-methylindol-4-yl)sulfonylamino]-1-naphthyl]oxy]-3-pyridyl]pyrimidin-2-yl]amino]piperidine-1-carboxylate

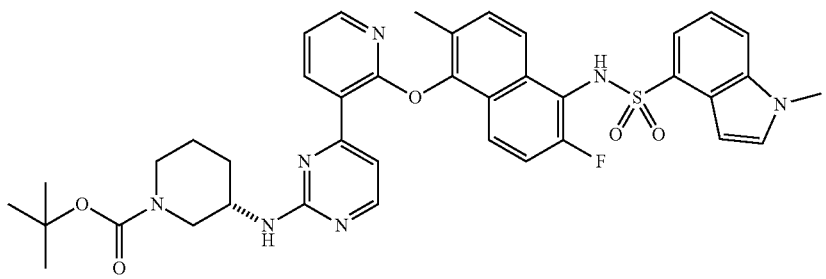 [SMILES: Cc1ccc2c(NS(=O)(=O)c3cccc4c3ccn4C)c(F)ccc2c1Oc1ncccc1-c1ccnc(N[C@H]2CCCN(C(=O)OC(C)(C)C)C2)n1]

739

Prepared according to procedure A using tert-butyl (3S)-3-[[4-[2-[[6-fluoro-2-methyl-5-[(4-phenylphenyl)sulfonylamino]-1-naphthyl]oxy]-3-pyridyl]pyrimidin-2-yl]amino]piperidine-1-carboxylate (50 mg, 0.09 mmol), 1,2-dichloroethane (1.0 mL), DMAP (1 crystal), triethylamine (0.1 mL) and 1-methyl-1H-indole-4-sulfonyl chloride (44 mg, 0.18 mmol). The reaction mixture was stirred at rt for 16 h and then concentrated and transitioned to Step 2. LCMS (5 to 95% acetonitrile in water+0.1% ammonium hydroxide over 2 mins) [M+H]⁺=738.7, rt=1.62 min.

Step 2: N-[2-Fluoro-6-methyl-5-[[3-[2-[[(3S)-3-piperidyl]amino]pyrimidin-4-yl]-2-pyridyl]oxy]-1-naphthyl]-1-methyl-indole-4-sulfonamide

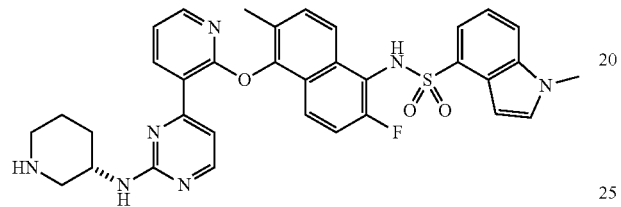

Prepared according to procedure B using tert-butyl (3S)-3-[[4-[2-[[6-fluoro-2-methyl-5-[(1-methylindol-4-yl)sulfonylamino]-1-naphthyl]oxy]-3-pyridyl]pyrimidin-2-yl]amino]piperidine-1-carboxylate (crude residue), methanol (1.4 mL), and hydrochloric acid (4 N in dioxane, 0.25 mL, 1.0 mmol). The reaction was stirred at room temperature for 4 hours. The solution was concentrated, dissolved in DMF (1 mL) and purified by prep-HPLC (basic, 20-60% ACN) affording N-[2-fluoro-6-methyl-5-[[3-[2-[[(3S)-3-piperidyl]amino]pyrimidin-4-yl]-2-pyridyl]oxy]-1-naphthyl]-1-methyl-indole-4-sulfonamide (8.5 mg, 12.7% yield). LCMS (2 to 98% acetonitrile in water+0.1% formic acid over 10 mins) [M+H]⁺=638.7, rt=3.99 min. ¹H NMR (400 MHz, DMSO-d₆) δ 8.49 (s, 1H), 8.45-8.38 (m, 1H), 8.05 (m, 1H), 7.72 (m, 2H), 7.45 (m, 3H), 7.40-7.08 (m, 7H), 6.70 (d, J=3.1 Hz, 1H), 3.86 (s, 3H), 3.21-3.07 (m, 2H), 2.83 (m, 1H), 2.55 (s, 1H), 2.13 (s, 3H), 1.91 (m, 1H), 1.66 (s, 1H), 1.56-1.38 (m, 2H).

Example 459 (S)-1-Cyclopropyl-2-((6-methyl-5-((3-(2-(piperidin-3-ylamino)pyrimidin-4-yl)pyridin-2-yl)oxy)naphthalen-1-yl)amino)ethanone hydrochloride Step 1: tert-Butyl (3S)-3-[[4-[2-[[5-[(2-cyclopropyl-2-oxo-ethyl)amino]-2-methyl-1-naphthyl]oxy]-3-pyridyl]pyrimidin-2-yl]amino]piperidine-1-carboxylate

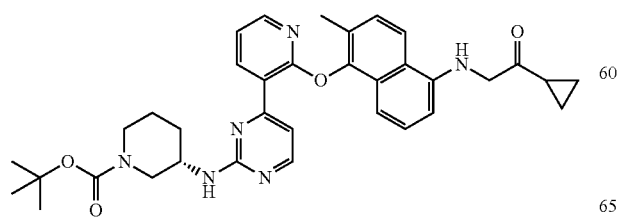

740

To a solution of tert-butyl (3S)-3-[[4-[2-[(5-amino-2-methyl-1-naphthyl)oxy]-3-pyridyl]pyrimidin-2-yl]amino]piperidine-1-carboxylate (527 mg, 1.0 mmol) in DMF (5 mL) was added 2-bromo-1-cyclopropyl-ethanone (500 mg, 3.1 mmol) followed by the addition of potassium carbonate (276 mg, 2.0 mmol). The mixture was stirred at 25° C. for 4 h. Ammonium formate (126 mg, 2 mmol) was added to quench the reaction and the crude was directly purified by C18 reverse phase flash chromatography (50-85% MeCN/10 mM aqueous ammonium formate, pH=3.8). Appropriate fractions combined and lyophilized to provide 415 mg (68% yield) of the title compound. LCMS (ESI) [M+H]⁺=609.2.

Step 2: (S)-1-Cyclopropyl-2-((6-methyl-5-((3-(2-(piperidin-3-ylamino)pyrimidin-4-yl)pyridin-2-yl)oxy)naphthalen-1-yl)amino)ethanone hydrochloride 459

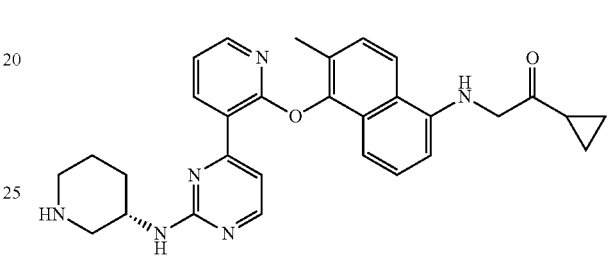

Prepared according to General Procedure B using tert-butyl (3S)-3-[[4-[2-[[5-[(2-cyclopropyl-2-oxo-ethyl)amino]-2-methyl-1-naphthyl]oxy]-3-pyridyl]pyrimidin-2-yl]amino]piperidine-1-carboxylate (35 mg, 0.06 mmol), 1,4-dioxane (0.5 mL), and hydrochloric acid (4 M in dioxane, 1.0 mL, 4.0 mmol). After 1 hour, the mixture was diluted with Et₂O and the resulting solids collected by filtration then dissolved in H₂O and MeCN and lyophilized to provide 26 mg (83% yield) of 459. LCMS (ESI) [M+H]⁺=509.1; ¹H NMR (400 MHz, DMSO-d₆) 9.22 (s, 1H), 9.05 (s, 1H), 8.72 (s, 1H), 8.46 (d, J=5.3 Hz, 1H), 8.03 (dd, J=4.8, 1.9 Hz, 1H), 7.98 (d, J=8.7 Hz, 1H), 7.70 (s, 1H), 7.61 (s, 1H), 7.37 (d, J=8.8 Hz, 1H), 7.23 (dd, J=7.6, 4.8 Hz, 1H), 7.15-7.10 (m, 1H), 6.83 (d, J=8.4 Hz, 1H), 6.20 (d, J=7.3 Hz, 1H), 4.23 (s, 4H), 3.41 (d, J=10.1 Hz, 1H), 3.17 (d, J=11.7 Hz, 1H), 2.90-2.74 (m, 2H), 2.28-2.21 (m, 1H), 2.17 (s, 3H), 2.00 (d, J=9.3 Hz, 1H), 1.90 (dd, J=13.8, 5.2 Hz, 1H), 1.75 (d, J=11.8 Hz, 1H), 1.67-1.55 (m, 1H), 0.87 (ddd, J=7.7, 6.2, 3.3 Hz, 4H).

Example 460 4-[2-[[5-(2,3-Difluoropropylamino)-2-methyl-1-naphthyl]oxy]-3-pyridyl]-N-[(3S)-3-piperidyl]pyrimidin-2-amine hydrochloride Step 1: tert-Butyl (3S)-3-[[4-[2-[[5-[(3,4-dimethoxyphenyl)methylamino]-2-methyl-1-naphthyl]oxy]-3-pyridyl]pyrimidin-2-yl]amino]piperidine-1-carboxylate

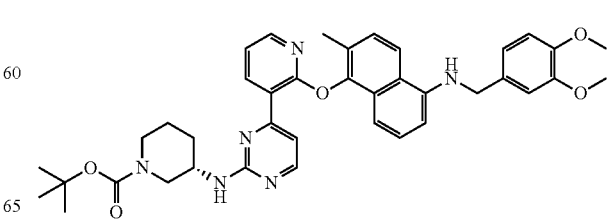

741

To a mixture of tert-butyl (3S)-3-[[4-[2-[(5-amino-2-methyl-1-naphthyl)oxy]-3-pyridyl]pyrimidin-2-yl]amino]piperidine-1-carboxylate (300 mg, 0.57 mmol) and 3,4-dimethoxybenzaldehyde (189 mg, 1.14 mmol), in DCM (2.5 mL), was added acetic acid (0.06 mL, 1.05 mmol) followed by sodium triacetoxyborohydride (180 mg, 0.86 mmol). The resulting mixture was stirred overnight at rt. After 16 h, a further portion of triacetoxyborohydride (180 mg, 0.86 mmol) and AcOH (0.06 mmol) were added. The reaction was pursued 3 hours at rt.

The reaction mixture was then diluted with $H_2O$, extracted twice with EtOAc, dried ($MgSO_4$), filtered and concentrated in vacuo. The crude material was purified by C18 reverse phase flash chromatography (0-70% MeCN/10 mM aqueous ammonium formate, pH=3.8). Appropriate fractions were combined and lyophilized to provide 280 mg (72% yield) of the title compound. LCMS (ESI) $[M+H]^+$=677.3.

Step 2: tert-Butyl (3S)-3-[[4-[2-[[5-[(3,4-dimethoxyphenyl)methyl-(3-fluoro-2-hydroxy-propyl)amino]-2-methyl-1-naphthyl]oxy]-3-pyridyl]pyrimidin-2-yl]amino]piperidine-1-carboxylate

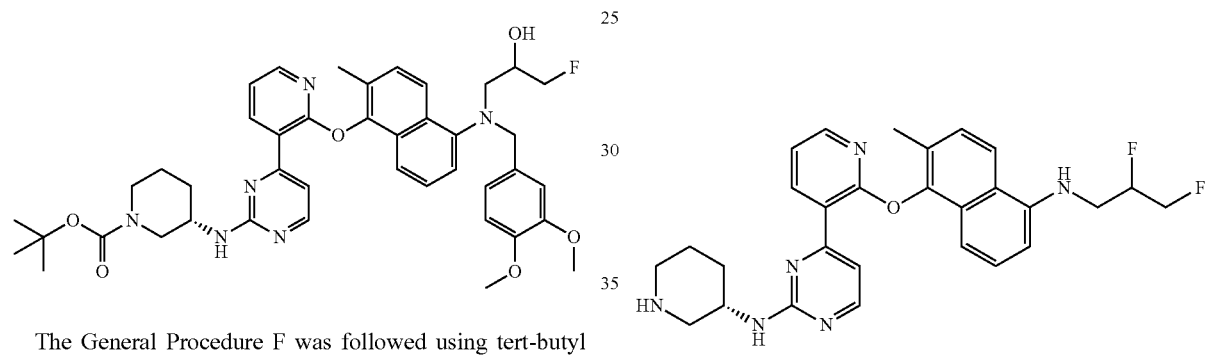

The General Procedure F was followed using tert-butyl (3S)-3-[[4-[2-[[5-[(3,4-dimethoxyphenyl)methylamino]-2-methyl-1-naphthyl]oxy]-3-pyridyl]pyrimidin-2-yl]amino]piperidine-1-carboxylate (270 mg, 0.40 mmol), epifluorohydrin (0.05 mL, 0.70 mmol) and acetic acid (1 mL). The reaction was stirred 3 days at 50° C. AcOH was evaporated in vacuo. The crude material was purified by C18 reverse phase flash chromatography (0-65% MeCN/10 mM aqueous ammonium formate, pH=3.8). Appropriate fractions were combined and lyophilized to provide 119 mg (40% yield) of the title compound. LCMS (ESI) $[M+H]^+$=753.3.

Step 3: tert-Butyl (3S)-3-[[4-[2-[[5-[2,3-difluoropropyl-[(3,4-dimethoxyphenyl)methyl]amino]-2-methyl-1-naphthyl]oxy]-3-pyridyl]pyrimidin-2-yl]amino]piperidine-1-carboxylate

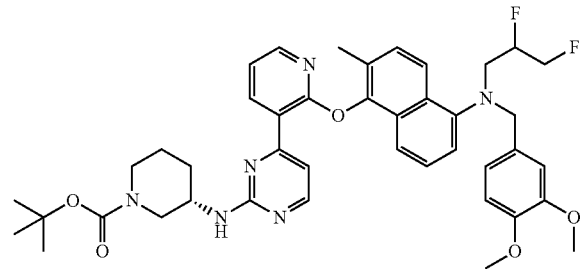 [SMILES: COc1ccc(CN(CC(F)CF)c2cccc3c(Oc4ncccc4-c4ccnc(N[C@H]5CCCN(C(=O)OC(C)(C)C)C5)n4)c(C)ccc23)cc1OC]

742

To a solution of tert-butyl (3S)-3-[[4-[2-[[5-[(3,4-dimethoxyphenyl)methyl-(3-fluoro-2-hydroxy-propyl)amino]-2-methyl-1-naphthyl]oxy]-3-pyridyl]pyrimidin-2-yl]amino]piperidine-1-carboxylate (125 mg, 0.17 mmol), in DCM (2.5 mL), was added Deoxofluor (0.046 mL, 0.25 mmol). The mixture was stirred 2 h at rt then diluted with DCM, washed with a saturated aqueous solution of $NaHCO_3$, then saturated aqueous NaCl, dried ($MgSO_4$), filtered and concentrated in vacuo. The crude was purified by flash chromatography through silica gel (5% EtOAc/DCM) to provide 52 mg (41% yield) of the title compound. LCMS (ESI) $[M+H]^+$=755.3.

Step 4: 4-[2-[[5-(2,3-Difluoropropylamino)-2-methyl-1-naphthyl]oxy]-3-pyridyl]-N-[(3S)-3-piperidyl]pyrimidin-2-amine hydrochloride 460

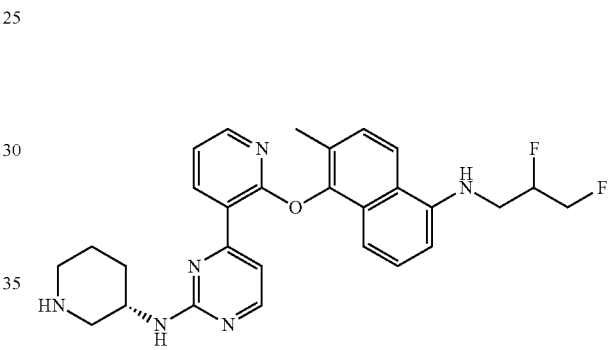

To a solution of tert-butyl (3S)-3-[[4-[2-[[5-[2,3-difluoropropyl-[(3,4-dimethoxyphenyl)methyl]amino]-2-methyl-1-naphthyl]oxy]-3-pyridyl]pyrimidin-2-yl]amino]piperidine-1-carboxylate (50 mg, 0.066 mmol), in DCM (2 mL), was added TFA (0.5 mL, 6.49 mmol). The reaction was stirred overnight at rt. After 18 h, the volatiles were evaporated in vacuo. The crude material was directly purified by C18 reverse phase flash chromatography (0-50% MeCN/10 mM aqueous ammonium formate, pH=3.8). Appropriate fractions were combined. The obtained residue (9 mg, 0.017 mmol) was dissolved in dioxane (1 mL) and a 4M HCl solution in dioxane (0.25 mL, 1.0 mmol) was added. The resulting solution was stirred 1 h at rt, then diluted with MTBE. The solid was filtered, dissolved in a mixture of $ACN/H_2O$ and lyophilized to provide 8 mg (22% yield) of 460 as a mixture of diastereoisomers. LCMS (ESI) $[M+H]^+$=505.1. 1H NMR (400 MHz, $CD_3OD$) δ 8.76 (br s, 1H), 8.51-8.42 (m, 1H), 8.07 (s, 1H), 7.97-7.90 (m, 2H), 7.41 (dd, J=8.7, 3.8 Hz, 1H), 7.32-7.18 (m, 2H), 7.07 (d, J=8.2 Hz, 1H), 6.71 (d, J=7.8 Hz, 1H), 4.85-4.41 (m, 4H), 3.71-3.60 (m, 3H), 3.37 (d, J=12.8 Hz, 1H), 3.16-2.98 (m, 2H), 2.26 (s, 3H), 2.25-2.08 (m, 2H), 2.01-1.76 (m, 2H).

Example 461 3-Methyl-1-((6-methyl-5-((3-(2-((S)-piperidin-3-ylamino)pyrimidin-4-yl)pyridin-2-yl)oxy)naphthalen-1-yl)amino) butan-2-ol (Isomer-1)

Step 1: tert-Butyl (3S)-3-[[4-[2-[[5-[(2-hydroxy-3-methyl-butyl)amino]-2-methyl-1-naphthyl]oxy]-3-pyridyl]pyrimidin-2-yl]amino]piperidine-1-carboxylate

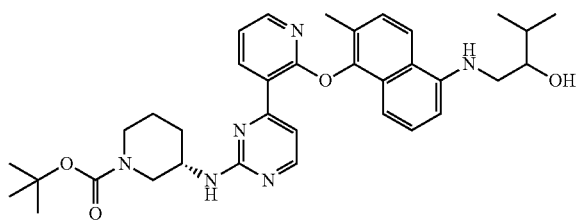 [SMILES: Cc1ccc2c(NCC(O)C(C)C)cccc2c1Oc1ncccc1-c1ccnc(N[C@H]2CCCN(C(=O)OC(C)(C)C)C2)n1]

Prepared according to General Procedure F using tert-butyl (3S)-3-[[4-[2-[(5-amino-2-methyl-1-naphthyl)oxy]-3-pyridyl]pyrimidin-2-yl]amino]piperidine-1-carboxylate (175 mg, 0.33 mmol), 2-isopropyloxirane (0.05 mL, 0.44 mmol), and AcOH (0.5 mL). The reaction was stirred at 70° C. overnight. The crude reaction was concentrated in vacuo and purified by C18 reverse phase flash chromatography (0-65% MeCN/10 mM aqueous ammonium formate, pH=3.8) to provide 72 mg (35% yield) of the title compound. LCMS (ESI) [M+H]$^+$=613.3.

Step 2: (S)-tert-Butyl 3-((4-(2-((5-(((R)-2-hydroxy-3-methylbutyl)amino)-2-methylnaphthalen-1-yl)oxy)pyridin-3-yl)pyrimidin-2-yl)amino)piperidine-1-carboxylate (Isomer-1) and (S)-tert-butyl 3-((4-(2-((5-(((S)-2-hydroxy-3-methylbutyl)amino)-2-methylnaphthalen-1-yl)oxy)pyridin-3-yl)pyrimidin-2-yl)amino)piperidine-1-carboxylate (Isomer-2)

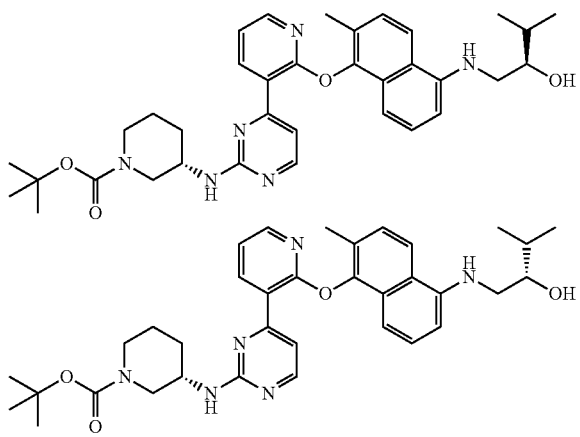

The mixture of stereoisomers from Step 1 were subjected to chiral normal phase semi-prep purification (conditions: Chiralpak IB, 5 uM, 20×250 mm, 9:9:82 MeOH:EtOH:Hexane, 2.5-12 mg/inj.) to provide two stereoisomers enantiomeric at the alcohol position. Isomer-1: (S)-tert-butyl 3-((4-(2-((5-(((R)-2-hydroxy-3-methylbutyl)amino)-2-methylnaphthalen-1-yl)oxy)pyridin-3-yl)pyrimidin-2-yl)amino)piperidine-1-carboxylate, 50 mg (38% yield) white solid, ee=99%, LCMS (ESI) [M+H]$^+$=613.3; and Isomer-2: (S)-tert-butyl 3-((4-(2-((5-(((S)-2-hydroxy-3-methylbutyl)amino)-2-methylnaphthalen-1-yl)oxy)pyridin-3-yl)pyrimidin-2-yl)amino)piperidine-1-carboxylate, 64 mg (49% yield), white solid, ee=99%, LCMS (ESI) [M+H]$^+$=613.3.

Step 3: (R)-3-Methyl-1-((6-methyl-5-((3-(2-((S)-piperidin-3-ylamino)pyrimidin-4-yl)pyridin-2-yl)oxy)naphthalen-1-yl)amino)butan-2-ol hydrochloride (Isomer-1) 461

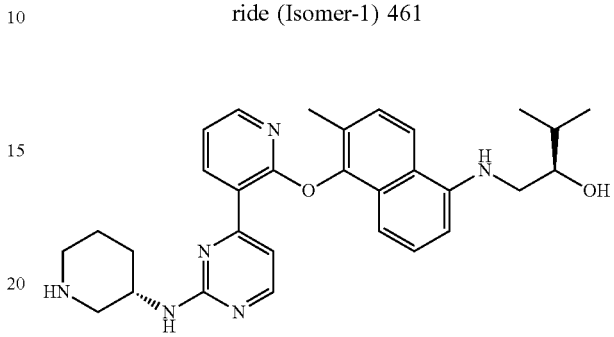

Prepared according to General Procedure B using (S)-tert-butyl 3-((4-(2-((5-(((R)-2-hydroxy-3-methylbutyl)amino)-2-methylnaphthalen-1-yl)oxy)pyridin-3-yl)pyrimidin-2-yl)amino)piperidine-1-carboxylate (64 mg, 0.1 mmol), 1,4-dioxane (1 mL), and hydrochloric acid (4 M in dioxane, 0.5 mL, 2.0 mmol). After 4 h, the mixture was diluted with Et$_2$O and the resulting solids were collected by filtration then dissolved in H$_2$O and MeCN and lyophilized to provide 45 mg (78% yield) of 461. LCMS (ESI) [M+H]$^+$=513.2; $^1$H NMR (400 MHz, CD$_3$OD) 8.83 (s, 1H), 8.49 (d, J=5.6 Hz, 1H), 8.08-7.99 (m, 2H), 7.93 (s, 1H), 7.83 (d, J=8.3 Hz, 1H), 7.71 (d, J=8.8 Hz, 1H), 7.60 (d, J=7.2 Hz, 1H), 7.55-7.47 (m, 1H), 7.32 (dd, J=7.3, 4.9 Hz, 1H), 4.55 (s, 1H), 3.77-3.70 (m, 1H), 3.70-3.60 (m, 2H), 3.44 (d, J=11.3 Hz, 1H), 3.42-3.33 (m, 1H), 3.15-3.01 (m, 2H), 2.31 (s, 3H), 2.28-2.19 (m, 1H), 2.18-2.07 (m, 1H), 2.03-1.80 (m, 2H), 1.77 (dt, J=13.2, 6.6 Hz, 1H), 0.98 (dd, J=21.9, 6.8 Hz, 6H). The absolute stereochemistry of the alcohol was randomly assigned.

Example 462 3-Methyl-1-((6-methyl-5-((3-(2-((S)-piperidin-3-ylamino)pyrimidin-4-yl)pyridin-2-yl)oxy)naphthalen-1-yl)amino) butan-2-ol hydrochloride (Isomer-2)

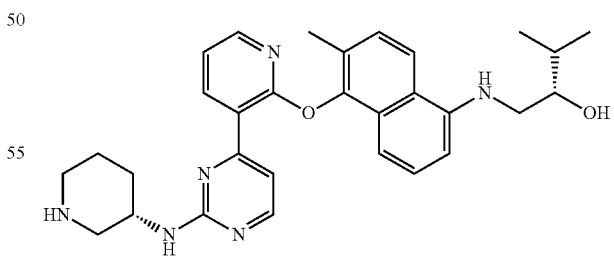

Prepared according to General Procedure B using (S)-tert-butyl 3-((4-(2-((5-(((S)-2-hydroxy-3-methylbutyl)amino)-2-methylnaphthalen-1-yl)oxy)pyridin-3-yl)pyrimidin-2-yl)amino)piperidine-1-carboxylate (50 mg, 0.08 mmol), 1,4-dioxane (1 mL), and hydrochloric acid (4 M in dioxane, 0.5 mL, 2.0 mmol). After 4 h, the mixture was diluted with Et$_2$O and the resulting solids collected by filtration then dissolved in H₂O and MeCN and lyophilized to provide 38 mg (85% yield) of 462. LCMS (ESI) [M+H]⁺=513.2; ¹H NMR (400 MHz, CD₃OD) 8.83 (s, 1H), 8.49 (d, J=5.6 Hz, 1H), 8.08-7.99 (m, 2H), 7.93 (s, 1H), 7.83 (d, J=8.3 Hz, 1H), 7.71 (d, J=8.8 Hz, 1H), 7.60 (d, J=7.2 Hz, 1H), 7.55-7.47 (m, 1H), 7.32 (dd, J=7.3, 4.9 Hz, 1H), 4.55 (s, 1H), 3.77-3.70 (m, 1H), 3.70-3.60 (m, 2H), 3.44 (d, J=11.3 Hz, 1H), 3.42-3.33 (m, 1H), 3.15-3.01 (m, 2H), 2.31 (s, 3H), 2.28-2.19 (m, 1H), 2.18-2.07 (m, 1H), 2.03-1.80 (m, 2H), 1.77 (dt, J=13.2, 6.6 Hz, 1H), 0.98 (dd, J=21.9, 6.8 Hz, 6H). The absolute stereochemistry of the alcohol was randomly assigned.

Example 463 N-(2-Fluoro-5-((3-(2-(((3R,5R)-5-fluoropiperidin-3-yl)amino)pyrimidin-4-yl)pyridin-2-yl)oxy)-6-methylnaphthalen-1-yl)-1-(2-fluorophenyl)methanesulfonamide hydrochloride (Isomer-1)

Step 1: tert-Butyl trans-3-fluoro-5-[[4-[2-[[6-fluoro-5-[(2-fluorophenyl)methylsulfonylamino]-2-methyl-1-naphthyl]oxy]-3-pyridyl]pyrimidin-2-yl]amino] piperidine-1-carboxylate

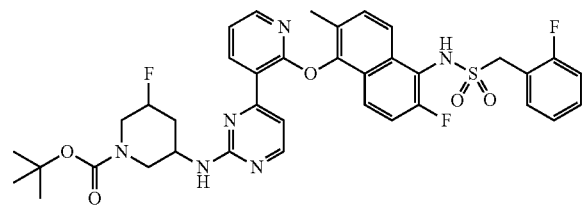 [SMILES: Cc1ccc2c(NS(=O)(=O)Cc3ccccc3F)c(F)ccc2c1Oc1ncccc1-c1ccnc(NC2CC(F)CN(C(=O)OC(C)(C)C)C2)n1]

The General Procedure A was followed using tert-butyl trans-3-[[4-[2-[(5-amino-6-fluoro-2-methyl-1-naphthyl)oxy]-3-pyridyl]pyrimidin-2-yl]amino]-5-fluoro-piperidine-1-carboxylate from Example 322 (250 mg, 0.44 mmol), pyridine (0.54 mL), CH₂Cl₂ (1.4 mL) and (2-fluorophenyl) methanesulfonyl chloride (185 mg, 0.89 mmol). After 18 h, the mixture was diluted with CH₂Cl₂ (50 mL) and washed with 1M KHSO₄ (10 mL), dried by passing through a phase cartridge separator and concentrated in vacuo. The crude was purified by flash chromatography through silica gel (10-50% EtOAc/CH₂Cl₂) to provide 190 mg (58% yield) of the title compound. LCMS (ESI) [M+H]+=735.5.

Step 2: (3R,5R)-tert-Butyl 3-fluoro-5-((4-(2-((6-fluoro-5-((2-fluorophenyl)methylsulfonamido)-2-methylnaphthalen-1-yl)oxy)pyridin-3-yl)pyrimidin-2-yl)amino)piperidine-1-carboxylate (Isomer-1) and (3S,5S)-tert-butyl 3-fluoro-5-((4-(2-((6-fluoro-5-((2-fluorophenyl)methylsulfonamido)-2-methylnaphthalen-1-yl)oxy)pyridin-3-yl)pyrimidin-2-yl)amino) piperidine-1-carboxylate (Isomer-2)

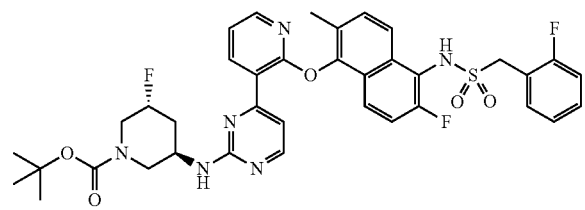

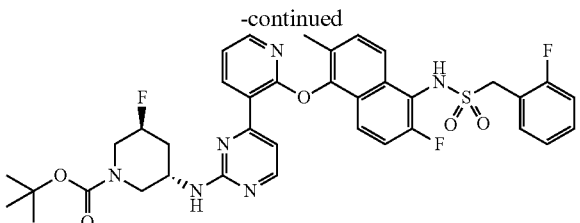

The stereoisomers from Step 1 were subjected to chiral SFC purification (conditions: Lux Cellulose-4, 10×250 mm 5 um, Isocratic 60% MeOH, 10 mL/min, 150 bar.) to provide two trans piperidine enantiomers. Isomer-1: (3R,5R)-tert-butyl 3-fluoro-5-((4-(2-((6-fluoro-5-((2-fluorophenyl)methylsulfonamido)-2-methylnaphthalen-1-yl)oxy)pyridin-3-yl) pyrimidin-2-yl)amino)piperidine-1-carboxylate, 70 mg (37% yield), white solid, ee=99%, LCMS (ESI) [M+H]⁺=735.5; and Isomer-2: (3S,5S)-tert-butyl 3-fluoro-5-((4-(2-((6-fluoro-5-((2-fluorophenyl)methylsulfonamido)-2-methylnaphthalen-1-yl)oxy)pyridin-3-yl)pyrimidin-2-yl)amino)piperidine-1-carboxylate, 65 mg (34% yield), white solid, ee=99%, LCMS (ESI) [M+H]⁺=735.5.

Step 3: N-(2-Fluoro-5-((3-(2-(((3R,5R)-5-fluoropiperidin-3-yl)amino)pyrimidin-4-yl)pyridin-2-yl)oxy)-6-methylnaphthalen-1-yl)-1-(2-fluorophenyl)methanesulfonamide hydrochloride (Isomer-1) 463

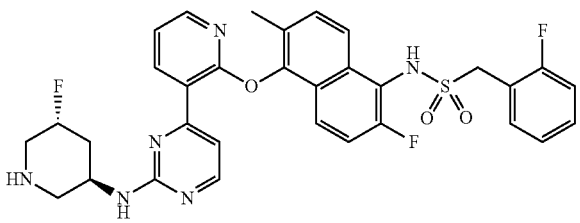 [SMILES: Cc1ccc2c(NS(=O)(=O)Cc3ccccc3F)c(F)ccc2c1Oc1ncccc1-c1ccnc(N[C@H]2CNC[C@H](F)C2)n1]

Prepared according to General Procedure B using (3R, 5R)-tert-butyl 3-fluoro-5-((4-(2-((6-fluoro-5-((2-fluorophenyl)methylsulfonamido)-2-methylnaphthalen-1-yl)oxy) pyridin-3-yl)pyrimidin-2-yl)amino)piperidine-1-carboxylate (70 mg, 0.10 mmol), 1,4-dioxane (0.5 mL), and hydrochloric acid (4 M in dioxane, 1 mL, 4.0 mmol). After 2 h, the mixture was diluted with Et₂O and the resulting solids were collected by filtration then dissolved in H₂O and MeCN and lyophilized to provide 49 mg (76% yield) of 463. LCMS (ESI) [M+H]⁺=635.4; ¹H NMR (400 MHz, DMSO-d₆) δ 9.99 (s, 1H), 9.44 (d, J=12.6 Hz, 1H), 9.19 (s, 1H), 8.79-8.59 (m, 1H), 8.49 (d, J=5.2 Hz, 1H), 8.10 (dd, J=4.8, 1.9 Hz, 1H), 8.01 (d, J=8.7 Hz, 1H), 7.74 (dd, J=9.3, 5.1 Hz, 1H), 7.63 (t, J=9.0 Hz, 3H), 7.55-7.42 (m, 3H), 7.33-7.23 (m, 3H), 5.25 (d, J=44.9 Hz, 1H), 4.63 (s, 2H), 4.51 (s, 1H), 3.58-3.44 (m, 2H), 3.25 (dt, J=24.5, 12.0 Hz, 1H), 2.83 (q, J=11.0 Hz, 1H), 2.43-2.34 (m, 1H), 2.19 (s, 3H), 1.93 (dt, J=24.8, 13.0 Hz, 1H). The absolute stereochemistry was assigned based on the potency in the cellular assay.

Example 464 N-(2-Fluoro-5-((3-(2-(((3S,5S)-5-fluoropiperidin-3-yl)amino)pyrimidin-4-yl)pyridin-2-yl)oxy)-6-methylnaphthalen-1-yl)-1-(2-fluorophenyl)methanesulfonamide hydrochloride (Isomer-2)

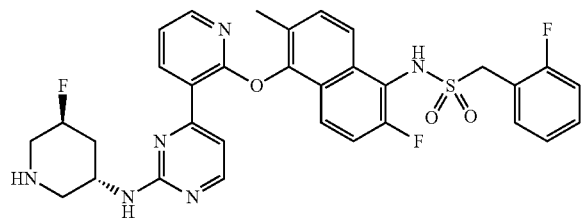 [SMILES: Cc1ccc2c(NS(=O)(=O)Cc3ccccc3F)c(F)ccc2c1Oc1ncccc1-c1ccnc(N[C@@H]2CNC[C@@H](F)C2)n1]

Prepared according to General Procedure B using (3S,5S)-tert-butyl 3-fluoro-5-((4-(2-(((6-fluoro-5-((2-fluorophenyl)methylsulfonamido)-2-methylnaphthalen-1-yl)oxy)pyridin-3-yl)pyrimidin-2-yl)amino)piperidine-1-carboxylate (65 mg, 0.09 mmol), 1,4-dioxane (0.5 mL), and hydrochloric acid (4 M in dioxane, 1 mL, 4.0 mmol). After 2 h, the mixture was diluted with Et$_2$O and the resulting solids collected by filtration then dissolved in H$_2$O and MeCN and lyophilized to provide 49 mg (82% yield) of 464. LCMS (ESI) [M+H]$^+$=635.4; $^1$H NMR (400 MHz, DMSO-d$_6$) δ 10.00 (s, 1H), 9.53 (d, J=11.3 Hz, 1H), 9.22 (s, 1H), 8.72 (s, 1H), 8.49 (d, J=5.2 Hz, 1H), 8.10 (dd, J=4.8, 1.9 Hz, 1H), 8.02 (d, J=8.8 Hz, 1H), 7.74 (dd, J=9.3, 5.1 Hz, 1H), 7.63 (dd, J=10.6, 8.4 Hz, 3H), 7.55-7.41 (m, 3H), 7.32-7.23 (m, 3H), 5.25 (d, J=45.6 Hz, 1H), 4.63 (s, 2H), 4.52 (s, 1H), 3.50 (dd, J=25.7, 14.3 Hz, 2H), 3.25 (dt, J=24.9, 12.2 Hz, 1H), 2.91-2.77 (m, 1H), 2.44-2.34 (m, 1H), 2.19 (s, 3H), 1.93 (dt, J=24.5, 12.6 Hz, 1H). The absolute stereochemistry was assigned based on the potency in the cellular assay.

Example 466 (S)-1-Cyclopentyl-N-(-2-fluoro-6-methyl-5-((3-(2-(piperidin-3-ylamino)pyrimidin-4-yl)pyridin-2-yl)oxy)naphthalen-1-yl)methanesulfonamide 466

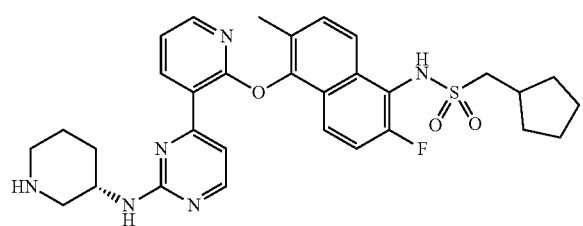 [SMILES: Cc1ccc2c(NS(=O)(=O)CC3CCCC3)c(F)ccc2c1Oc1ncccc1-c1ccnc(N[C@H]2CCCNC2)n1]

Step 1: tert-Butyl (S)-3-((4-(2-((5-((cyclopentylmethyl)sulfonamido)-6-fluoro-2-methylnaphthalen-1-yl)oxy)pyridin-3-yl)pyrimidin-2-yl)amino)piperidine-1-carboxylate

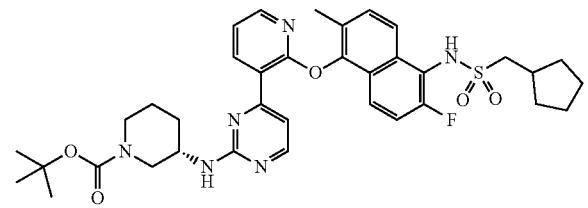 [SMILES: Cc1ccc2c(NS(=O)(=O)CC3CCCC3)c(F)ccc2c1Oc1ncccc1-c1ccnc(N[C@H]2CCCN(C(=O)OC(C)(C)C)C2)n1]

Prepared according to procedure A using tert-butyl (3S)-3-[[4-[2-[(5-amino-6-fluoro-2-methyl-1-naphthyl)oxy]-3-pyridyl]pyrimidin-2-yl]amino]piperidine-1-carboxylate (50 mg, 0.09 mmol), 1,2 dichloroethane (1.0 mL), DMAP (1 crystal), triethylamine (0.1 mL) and cyclopentylmethanesulfonyl chloride (33 mg, 0.18 mmol). The reaction mixture was stirred at rt for 16 h and then concentrated and transitioned to Step 2. LCMS (5 to 95% acetonitrile in water+0.1% ammonium hydroxide over 2 mins) [M+H]$^+$=591.7.

Step 2: (S)-1-Cyclopentyl-N-(-2-fluoro-6-methyl-5-((3-(2-(piperidin-3-ylamino)pyrimidin-4-yl)pyridin-2-yl)oxy)naphthalen-1-yl)methanesulfonamide 466

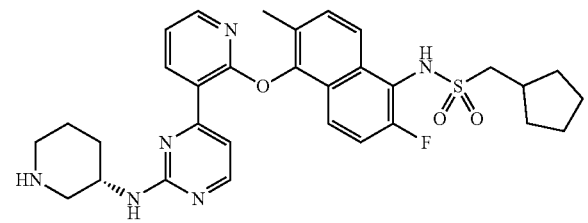 [SMILES: Cc1ccc2c(NS(=O)(=O)CC3CCCC3)c(F)ccc2c1Oc1ncccc1-c1ccnc(N[C@H]2CCCNC2)n1]

Prepared according to procedure B using tert-butyl (S)-3-((4-(2-((5-((cyclopentylmethyl)sulfonamido)-6-fluoro-2-methylnaphthalen-1-yl)oxy)pyridin-3-yl)pyrimidin-2-yl)amino)piperidine-1-carboxylate (crude residue), methanol (1.4 mL), and hydrochloric acid (4 N in dioxane, 0.25 mL, 1.0 mmol). The reaction was stirred at room temperature for 4 hours. The solution was concentrated, dissolved in DMF (1 mL) and purified by prep-HPLC affording 2.6 mg of 466. LCMS (2 to 98% acetonitrile in water+0.1% formic acid over 10 mins) [M+H]$^+$=591.2; $^1$H NMR (400 MHz, DMSO-d$_6$) δ 8.50 (brs, 1H), 8.42-8.38 (m, 1H), 8.15-7.93 (m, 2H), 7.68 (dd, J=9.2, 5.0 Hz, 1H), 7.60 (d, J=8.8 Hz, 1H), 7.50-7.39 (m, 2H), 7.27 (dd, J=7.6, 4.8 Hz, 1H), 7.15 (d, J=7.9 Hz, 1H), 3.92 (brs, 1H), 3.21 (d, J=6.8 Hz, 2H), 3.09-3.20 (m, 2H), 2.80-2.87 (m, 1H), 2.42-2.30 (m, 1H), 2.20 (s, 3H), 2.00-1.75 (m, 3H), 1.72-1.40 (m, 9H), 1.26-1.37 (m, 2H).

Example 467 1-(2,2-Difluorocyclopropyl)-N-(2-fluoro-6-methyl-5-((3-(2-((S)-piperidin-3-ylamino)pyrimidin-4-yl)pyridin-2-yl)oxy)naphthalen-1-yl)methanesulfonamide hydrochloride Step 1: S-((2,2-Difluorocyclopropyl)methyl) ethanethioate

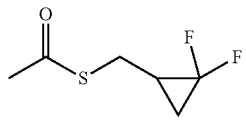

To a solution of (2,2-difluorocyclopropyl)methyl methanesulfonate (861 mg, 4.62 mmol) in DMF (10 mL) was added cesium carbonate (4.55 g, 13.9 mmol). The mixture was stirred at room temperature for 15 min then thioacetic acid (977.8 uL, 13.9 mmol) was added. The reaction mixture was stirred for 2 h then poured into water (50 mL) and extracted with Et$_2$O (100 mL). The ether layer was washed twice with brine and dried over MgSO$_4$, filtered and concentrated in vacuo to give 712 mg, (93% yield) of the title compound. $^1$H NMR (400 MHz, CDCl$_3$) δ 3.06 (dddd, J=14.2, 7.8, 2.7, 1.0 Hz, 1H), 2.95-2.88 (m, 1H), 2.36 (s, 3H), 1.90-1.72 (m, 1H), 1.54-1.40 (m, 1H), 1.14-1.04 (m, 1H).

Step 2: (2,2-Difluorocyclopropyl)methanesulfonyl chloride

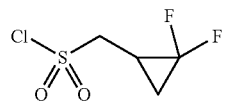

To a mixture of 2M HCl (0.45 mL, 0.90 mmol) in MeCN (3.5 mL) at 0° C. was added N-chlorosuccinimide (964 mg, 7.22 mmol) followed by addition of a solution of S-[(2,2-difluorocyclopropyl)methyl] ethanethioate (300 mg, 1.81 mmol) in MeCN (3.5 mL) over a period of 5 minutes under nitrogen. The resulting mixture was stirred at 0° C. for 30 min. The reaction mixture was poured in Et$_2$O then washed with a 12% solution of brine. The organic phase was dried over MgSO$_4$, filtered and concentrated in vacuo. The crude was purified by flash chromatography through silica gel (0-100% EtOAc/hexane) to provide 245 mg (71% yield) of the title compound as a clear liquid. $^1$H NMR (400 MHz, CDCl$_3$) δ 3.97 (dd, J=14.6, 6.3 Hz, 1H), 3.62 (dddd, J=14.6, 8.6, 2.0, 1.1 Hz, 1H), 2.28-2.10 (m, 1H), 1.85 (tdd, J=11.3, 8.6, 5.8 Hz, 1H), 1.61-1.50 (m, 1H).

Step 3: (3S)-tert-Butyl 3-((4-(2-((5-((2,2-difluorocyclopropyl)methylsulfonamido)-6-fluoro-2-methyl-naphthalen-1-yl)oxy)pyridin-3-yl)pyrimidin-2-yl)amino)piperidine-1-carboxylate

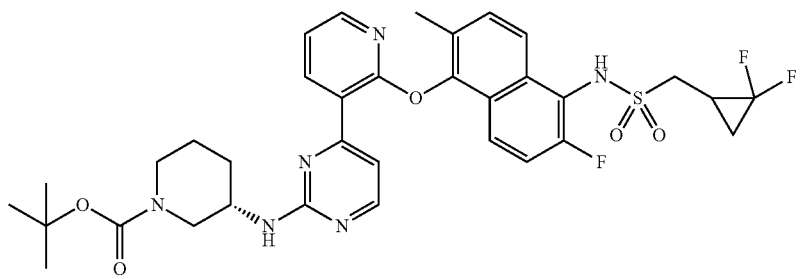 [SMILES: Cc1ccc2c(NS(=O)(=O)CC3CC3(F)F)c(F)ccc2c1Oc1ncccc1-c1ccnc(N[C@H]2CCCN(C(=O)OC(C)(C)C)C2)n1]

The General Procedure A was followed using (S)-tert-butyl 3-((4-(2-((5-amino-6-fluoro-2-methylnaphthalen-1-yl)oxy)pyridin-3-yl)pyrimidin-2-yl)amino)piperidine-1-carboxylate from Example 275 (250 mg, 0.46 mmol), pyridine (1.11 mL, 13.8 mmol) DCM (1 mL) and 2,2-difluorocyclopropyl)methanesulfonyl chloride (175 mg, 0.92 mmol). After 18 h, the mixture was concentrated in vacuo and co-evaporated with toluene. The crude was purified by flash chromatography through silica gel (0-50% EtOAc/CH$_2$Cl$_2$) to provide 210 mg (65% yield) of the title compound. LCMS (ESI) [M+H]$^+$=699.5.

Step 4: 1-(2,2-Difluorocyclopropyl)-N-(2-fluoro-6-methyl-5-((3-(2-((S)-piperidin-3-ylamino)pyrimidin-4-yl)pyridin-2-yl)oxy)naphthalen-1-yl)methanesulfonamide hydrochloride

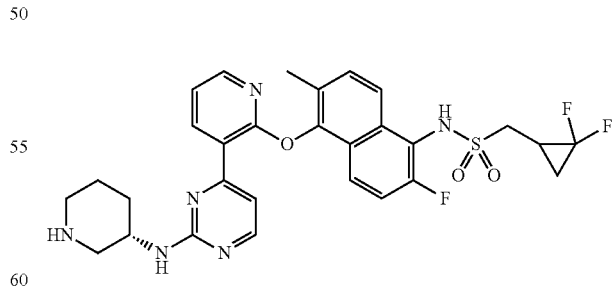

Prepared according to General Procedure B using tert-butyl (3S)-3-[[4-[2-[[5-[(2,2-difluorocyclopropyl)methylsulfonylamino]-6-fluoro-2-methyl-1-naphthyl]oxy]-3-pyridyl]pyrimidin-2-yl]amino]piperidine-1-carboxylate (63 mg, 0.09 mmol) 1,4-dioxane (2 mL) and hydrochloric acid (4 M in dioxane, 2 mL, 8 mmol). After 1 h, the mixture was diluted with MTBE and the resulting solids collected by filtration then dissolved in H$_2$O and MeCN and lyophilized to provide 49 mg (85% yield) of the title compound 467 as a mixture of diastereoisomers. LCMS (ESI) [M+H]$^+$=599.3. $^1$H NMR (400 MHz, DMSO-d$_6$) δ 10.01 (s, 1H), 9.40-9.17 (m, 2H), 8.78 (s, br, 1H), 8.47 (d, J=5.4 Hz, 1H), 8.06 (dd, J=10.8, 6.0 Hz, 2H), 7.81 (s, 1H), 7.72 (dd, J=9.3, 5.1 Hz, 1H), 7.63 (d, J=8.8 Hz, 2H), 7.45 (t, J=9.5 Hz, 1H), 7.28 (dd, J=7.6, 4.8 Hz, 1H), 4.36 (s, 1H), 3.39 (m, 3H), 3.16 (m, 1H), 2.92-2.74 (m, 2H), 2.18 (s, 3H), 2.17-2.08 (m, 1H), 1.99 (s, 1H), 1.94-1.68 (m, 3H), 1.68-1.45 (m, 2H).

Example 468 N-(2-Fluoro-5-((3-(2-(((3S,5S)-5-fluoropiperidin-3-yl)amino)pyrimidin-4-yl)pyridin-2-yl)oxy)-6-methylnaphthalen-1-yl)-1-(5-methylisoxazol-3-yl)methanesulfonamide hydrochloride Step 1: tert-Butyl trans-3-fluoro-5-[[4-[2-[[6-fluoro-2-methyl-5-[(5-methylisoxazol-3-yl)methylsulfonylamino]-1-naphthyl]oxy]-3-pyridyl]pyrimidin-2-yl]amino]piperidine-1-carboxylate

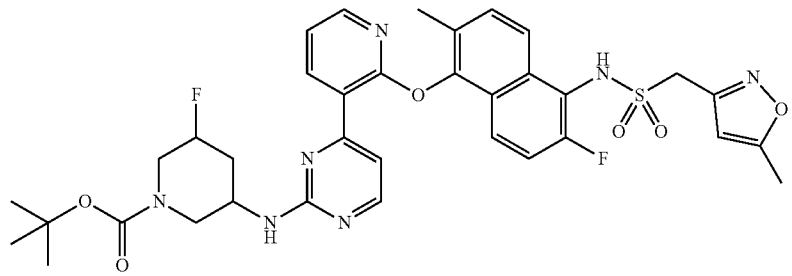 [SMILES: Cc1cc(CS(=O)(=O)Nc2c(F)ccc3c(Oc4ncccc4-c4ccnc(NC5CC(F)CN(C(=O)OC(C)(C)C)C5)n4)c(C)ccc23)no1]

The General Procedure A was followed using tert-butyl trans-3-[[4-[2-[(5-amino-6-fluoro-2-methyl-1-naphthyl)oxy]-3-pyridyl]pyrimidin-2-yl]amino]-5-fluoro-piperidine-1-carboxylate from Example 322 (250 mg, 0.44 mmol), pyridine (0.54 mL), CH$_2$Cl$_2$ (1.4 mL) and (5-methylisoxazol-3-yl)methanesulfonyl chloride (0.12 mL, 0.89 mmol). After 18 h, the mixture was diluted with CH$_2$Cl$_2$ (50 mL) and washed with 1M KHSO$_4$ (10 mL), dried by passing through a phase cartridge separator and concentrated in vacuo. The crude was purified by flash chromatography through silica gel (10-50% EtOAc/CH$_2$Cl$_2$) to provide 155 mg (48% yield) of the title compound. LCMS (ESI) [M+H]$^+$=722.5.

Step 2: (3R,5R)-tert-Butyl 3-fluoro-5-((4-(2-((6-fluoro-2-methyl-5-((5-methylisoxazol-3-yl)methylsulfonamido)naphthalen-1-yl)oxy)pyridin-3-yl)pyrimidin-2-yl)amino)piperidine-1-carboxylate (Isomer-1) and (3S,5S)-tert-butyl 3-fluoro-5-((4-(2-((6-fluoro-2-methyl-5-((5-methylisoxazol-3-yl)methylsulfonamido)naphthalen-1-yl)oxy)pyridin-3-yl)pyrimidin-2-yl)amino)piperidine-1-carboxylate (Isomer-2)

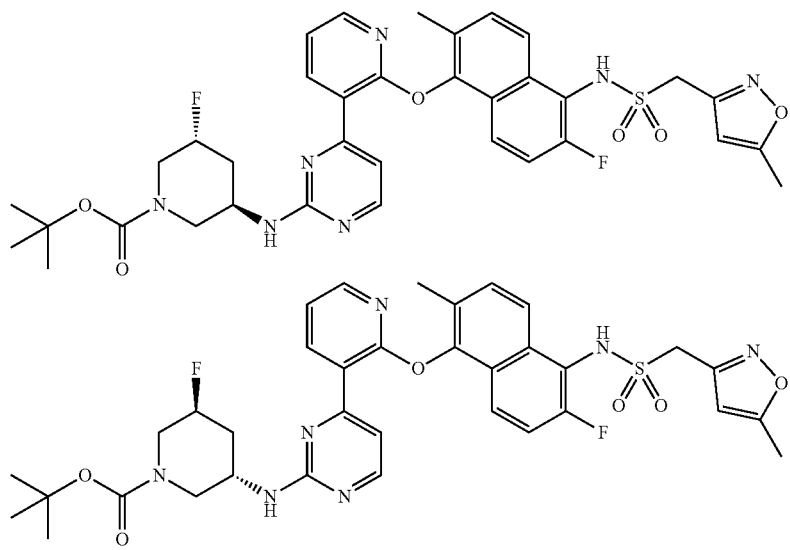

The stereoisomers from Step 1 were subjected to chiral SFC purification (conditions: Lux Cellulose-3, 10×250 mm 5 um, Isocratic 20% MeOH, 10 mL/min, 150 bar.) to provide two trans piperidine enantiomers. Isomer-1: (3R,5R)-tert-butyl 3-fluoro-5-((4-(2-((6-fluoro-2-methyl-5-((5-methylisoxazol-3-yl)methylsulfonamido)naphthalen-1-yl)oxy)pyridin-3-yl)pyrimidin-2-yl)amino)piperidine-1-carboxylate, 75 mg (48% yield), white solid, ee=99.2%, LCMS (ESI) [M+H]$^+$=722.5; and Isomer-2: (3S,5S)-tert-butyl 3-fluoro-5-((4-(2-((6-fluoro-2-methyl-5-((5-methylisoxazol-3-yl)methylsulfonamido)naphthalen-1-yl)oxy)pyridin-3-yl)pyrimidin-2-yl)amino)piperidine-1-carboxylate, 68 mg (44% yield), white solid, ee=98.9%, LCMS (ESI) [M+H]$^+$=722.5.

Step 3: N-(2-Fluoro-5-((3-(2-(((3S,5S)-5-fluoropiperidin-3-yl)amino)pyrimidin-4-yl)pyridin-2-yl)oxy)-6-methylnaphthalen-1-yl)-1-(5-methylisoxazol-3-yl)methanesulfonamide hydrochloride (Isomer-2)

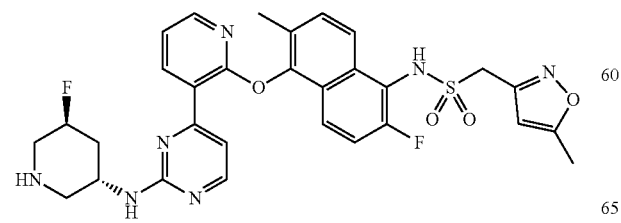

Prepared according to General Procedure B using (3S,5S)-tert-butyl 3-fluoro-5-((4-(2-((6-fluoro-2-methyl-5-((5-methylisoxazol-3-yl)methylsulfonamido)naphthalen-1-yl)oxy)pyridin-3-yl)pyrimidin-2-yl)amino)piperidine-1-carboxylate (68 mg, 0.094 mmol), 1,4-dioxane (0.5 mL), and hydrochloric acid (4 M in dioxane, 1 mL, 4.0 mmol). After 2 h, the mixture was diluted with Et$_2$O and the resulting solids were collected by filtration then dissolved in H$_2$O and MeCN and lyophilized to provide 49 mg (79% yield) of 468. LCMS (ESI) [M+H]$^+$=622.3; $^1$H NMR (400 MHz, DMSO-d$_6$) δ 10.08 (s, 1H), 9.63 (d, J=9.6 Hz, 1H), 9.26 (s, 1H), 8.86-8.60 (m, 1H), 8.49 (d, J=5.2 Hz, 1H), 8.09 (dd, J=4.8, 1.9 Hz, 1H), 8.05 (d, J=8.7 Hz, 1H), 7.74 (dd, J=9.3, 5.1 Hz, 1H), 7.69-7.56 (m, 3H), 7.48 (t, J=9.4 Hz, 1H), 7.30 (dd, J=7.6, 4.8 Hz, 1H), 6.36 (d, J=0.9 Hz, 1H), 5.25 (d, J=44.8 Hz, 1H), 4.65 (s, 2H), 4.52 (s, 1H), 3.49 (dd, J=22.6, 15.2 Hz, 2H), 3.24 (dt, J=24.7, 12.8 Hz, 1H), 2.83 (q, J=10.9 Hz, 1H), 2.43 (d, J=0.8 Hz, 3H), 2.41-2.31 (m, 1H), 2.20 (s, 3H), 1.93 (dt, J=23.9, 13.2 Hz, 1H). The absolute stereochemistry of the fluoropiperidine was assigned based on the potency in the cellular assay.

Example 469 (S)-1,1,1-Trifluoro-3-((5-((3-(2-(((3S,5S)-5-fluoropiperidin-3-yl)amino)pyrimidin-4-yl)pyridin-2-yl)oxy)-6-methylnaphthalen-1-yl)amino)propan-2-ol hydrochloride Step 1: tert-Butyl 3-((4-(2-((5-amino-2-methylnaphthalen-1-yl)oxy)pyridin-3-yl)pyrimidin-2-yl)amino)-5-fluoropiperidine-1-carboxylate

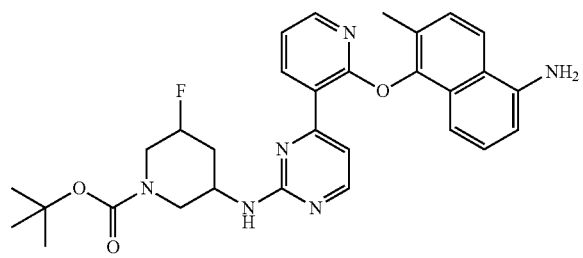 [SMILES: Cc1ccc2c(N)cccc2c1Oc1ncccc1-c1ccnc(NC2CC(F)CN(C(=O)OC(C)(C)C)C2)n1]

To a solution of 6-methyl-5-((3-(2-(methylsulfinyl)pyrimidin-4-yl)pyridin-2-yl)oxy)naphthalen-1-amine (550 mg, 1.41 mmol) in 1,4-dioxane (0.5 mL) was added trans-tert-butyl 3-amino-5-fluoro-piperidine-1-carboxylate (400 mg, 1.83 mmol) and triethylamine (0.78 mL, 570 mg, 5.63 mmol) and the mixture placed in a 120° C. oil bath. After 6 days, the mixture was diluted with EtOAc and washed with saturated aqueous NaHCO$_3$, dried (Na$_2$SO$_4$), filtered and concentrated in vacuo. The crude residue was purified by flash chromatography through silica gel (10-55% EtOAc/DCM) to provide 305 mg (40% yield) of the title compound. LCMS (ESI) [M+H]$^+$=545.4.

Step 2: tert-Butyl 3-fluoro-5-((4-(2-(((S)-3,3,3-trifluoro-2-hydroxypropyl)amino)naphthalen-1-yl)oxy)pyridin-3-yl)pyrimidin-2-yl)amino)piperidine-1-carboxylate

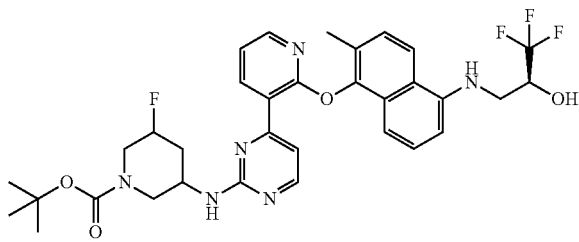 [SMILES: Cc1ccc2c(NC[C@H](O)C(F)(F)F)cccc2c1Oc1ncccc1-c1ccnc(NC2CC(F)CN(C(=O)OC(C)(C)C)C2)n1]

Prepared according to General Procedure F using tert-butyl 3-[[4-[2-[(5-amino-2-methyl-1-naphthyl)oxy]-3-pyridyl]pyrimidin-2-yl]amino]-5-fluoro-piperidine-1-carboxylate (155 mg, 0.28 mmol) and (2S)-2-(trifluoromethyl)oxirane (0.033 mL, 0.43 mmol) in acetic acid (0.57 mL) with stirring at rt for 72 h. Acetic acid was then removed in vacuo and the residue was diluted with ethyl acetate, aqueous saturated sodium bicarbonate was added and the phases were separated. The aqueous phase was extracted with ethyl acetate, the combined organic phase was dried and evaporated. The crude was purified by flash chromatography through silica gel (5-45% EtOAc/DCM) to provide 110 mg (60% yield) of the title compound. LCMS (ESI) [M+H]$^+$=657.5.

Step 3: (3R,5R)-tert-Butyl 3-fluoro-5-((4-(2-((2-methyl-5-(((S)-3,3,3-trifluoro-2-hydroxypropyl)amino)naphthalen-1-yl)oxy)pyridin-3-yl)pyrimidin-2-yl)amino)piperidine-1-carboxylate (Isomer-1) and (3S,5S)-tert-butyl 3-fluoro-5-((4-(2-((2-methyl-5-(((S)-3,3,3-trifluoro-2-hydroxypropyl)amino)naphthalen-1-yl)oxy)pyridin-3-yl)pyrimidin-2-yl)amino)piperidine-1-carboxylate (Isomer-2)

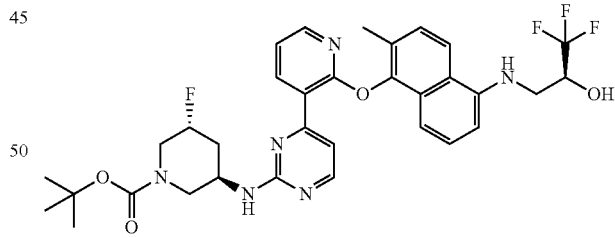

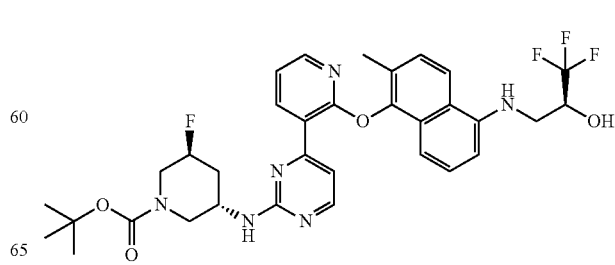

The stereoisomers from Step 1 were subjected to chiral SFC purification (conditions: Lux Cellulose-3 at 40° C., 10×250 mm 5 um, 25% MeOH, 10 mL/min, 150 bar, 9 min/inj.), to provide two trans piperidine enantiomers. Isomer-1: (3R,5R)-tert-butyl 3-fluoro-5-((4-(2-((2-methyl-5-(((S)-3,3,3-trifluoro-2-hydroxypropyl)amino)naphthalen-1-yl)oxy)pyridin-3-yl)pyrimidin-2-yl)amino)piperidine-1-carboxylate, 50 mg (47% yield), ee=99.3%, rt=4.08 min, LCMS (ESI) [M+H]$^+$=657.5; and Isomer-2: (3S,5S)-tert-butyl 3-fluoro-5-((4-(2-((2-methyl-5-(((S)-3,3,3-trifluoro-2-hydroxypropyl)amino)naphthalen-1-yl)oxy)pyridin-3-yl)pyrimidin-2-yl)amino)piperidine-1-carboxylate, 41 mg (37% yield), ee=99.4%, rt=6.34 min, LCMS (ESI) [M+H]$^+$=657.5.

Step 4: (S)-1,1,1-Trifluoro-3-((5-((3-(2-(((3S,5S)-5-fluoropiperidin-3-yl)amino)pyrimidin-4-yl)pyridin-2-yl)oxy)-6-methylnaphthalen-1-yl)amino)propan-2-ol hydrochloride (Isomer-2)

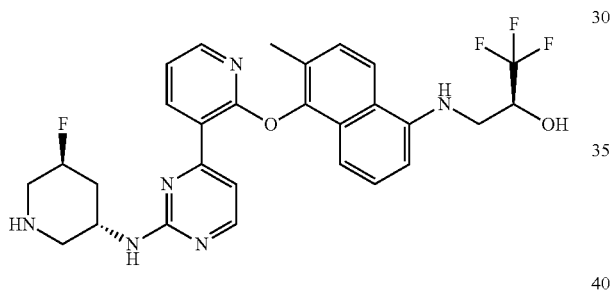

Prepared according to General Procedure B using (3S,5S)-tert-butyl 3-fluoro-5-((4-(2-((2-methyl-5-(((S)-3,3,3-trifluoro-2-hydroxypropyl)amino)naphthalen-1-yl)oxy)pyridin-3-yl)pyrimidin-2-yl)amino)piperidine-1-carboxylate (isomer-2) (41 mg, 0.060 mmol), 1,4-dioxane (0.5 mL), and hydrochloric acid (4 M in dioxane, 1 mL, 4 mmol). After 2 h, the mixture was diluted with Et$_2$O, the solid was filtered and washed with ether. The solid was dissolved with H$_2$O and lyophilized to provide to provide 37 mg (100% yield) of 469. LCMS (ESI) [M+H]$^+$=557.3; 1H NMR (400 MHz, DMSO-d$_6$) δ 9.56 (d, J=11.7 Hz, 1H), 9.36-9.00 (m, 1H), 8.82-8.53 (m, 1H), 8.49 (d, J=5.2 Hz, 1H), 8.07-8.04 (m, 1H), 8.02 (d, J=9.8 Hz, 1H), 7.71-7.52 (m, 2H), 7.38 (d, J=8.8 Hz, 1H), 7.25 (dd, J=7.6, 4.8 Hz, 1H), 7.20 (t, J=8.0 Hz, 1H), 6.86 (d, J=8.4 Hz, 1H), 6.49 (s, 1H), 6.49 (d, J=7.6 Hz, 1H), 5.25 (d, J=46.3 Hz, 1H), 4.52 (s, 1H), 4.38-4.26 (m, 1H), 3.61-3.42 (m, 3H), 3.41-3.13 (m, 2H), 2.93-2.76 (m, 1H), 2.42-2.31 (m, 2H), 2.19 (s, 3H), 1.93 (dt, J=24.2, 12.4 Hz, 1H). The absolute stereochemistry of the fluoropiperidine was assigned based on the potency in the cellular assay.

Example 470 1-((R)-2,2-Difluorocyclobutyl)-N-(2-fluoro-6-methyl-5-((3-(2-((S)-piperidin-3-ylamino)pyrimidin-4-yl)pyridin-2-yl)oxy)naphthalen-1-yl)methanesulfonamide hydrochloride (Isomer 1)

Step 1: (3S)-tert-Butyl 3-((4-(2-((5-((2,2-difluorocyclobutyl)methylsulfonamido)-6-fluoro-2-methylnaphthalen-1-yl)oxy)pyridin-3-yl)pyrimidin-2-yl)amino)piperidine-1-carboxylate

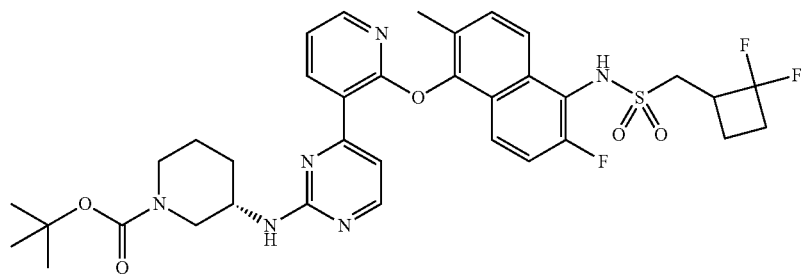 [SMILES: Cc1ccc2c(NS(=O)(=O)CC3CCC3(F)F)c(F)ccc2c1Oc1ncccc1-c1ccnc(N[C@H]2CCCN(C(=O)OC(C)(C)C)C2)n1]

The General Procedure A was followed using tert-butyl (3S)-3-[[4-[2-[(5-amino-6-fluoro-2-methyl-1-naphthyl)oxy]-3-pyridyl]pyrimidin-2-yl]amino]piperidine-1-carboxylate (200 mg, 0.37 mmol) from Example 275, pyridine (0.89 mL, 11.0 mmol), DCM (1 mL) and (2,2-difluorocyclobutyl)methanesulfonyl chloride (188 mg, 0.92 mmol). After 18 h, the mixture was concentrated in vacuo and co-evaporated with toluene. The crude was purified by flash chromatography through silica gel (0-50% EtOAc/CH$_2$Cl$_2$) to provide 148 mg (56% yield) of the title compound. LCMS (ESI) [M+H]$^+$=713.3.

Step 2: (S)-tert-Butyl 3-((4-(2-((5-(((R)-2,2-difluorocyclobutyl)methylsulfonamido)-6-fluoro-2-methylnaphthalen-1-yl)oxy)pyridin-3-yl)pyrimidin-2-yl)amino)piperidine-1-carboxylate (Isomer-1) and (S)-tert-butyl 3-((4-(2-((5-(((S)-2,2-difluorocyclobutyl)methylsulfonamido)-6-fluoro-2-methylnaphthalen-1-yl)oxy)pyridin-3-yl)pyrimidin-2-yl)amino)piperidine-1-carboxylate (Isomer-2)

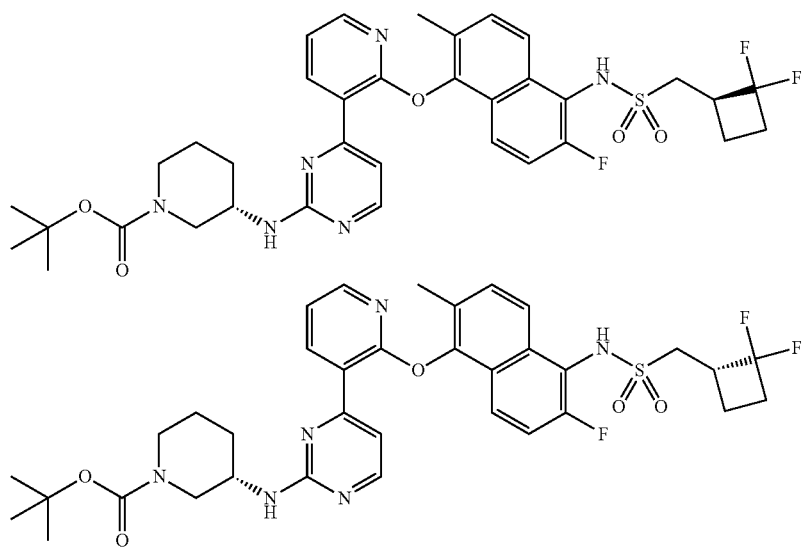

The stereoisomers from Step 1 were subjected to chiral normal phase semi-prep purification (conditions: Chiralpak IB, 5 uM, 20×250 mm, 15 mL/min, 5:5:90 MeOH:EtOH:Hexane, 5-10 mg/inj.) to provide two stereoisomers enantiomeric at 2,2-difluorocyclobutyl position. Isomer 1: (S)-tert-butyl 3-((4-(2-((5-(((R)-2,2-difluorocyclobutyl)methylsulfonamido)-6-fluoro-2-methylnaphthalen-1-yl)oxy)pyridin-3-yl)pyrimidin-2-yl)amino)piperidine-1-carboxylate (62 mg, 24% yield); and isomer-2: (S)-tert-butyl 3-((4-(2-((5-(((S)-2,2-difluorocyclobutyl)methylsulfonamido)-6-fluoro-2-methylnaphthalen-1-yl)oxy)pyridin-3-yl)pyrimidin-2-yl)amino)piperidine-1-carboxylate (62 mg, 24% yield).

Step 3: 1-((R)-2,2-Difluorocyclobutyl)-N-(2-fluoro-6-methyl-5-((3-(2-((S)-piperidin-3-ylamino)pyrimidin-4-yl)pyridin-2-yl)oxy)naphthalen-1-yl)methanesulfonamide hydrochloride (Isomer 1) 470

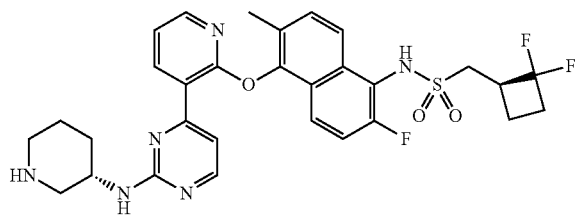 [SMILES: Cc1ccc2c(NS(=O)(=O)C[C@@H]3CCC3(F)F)c(F)ccc2c1Oc1ncccc1-c1ccnc(N[C@H]2CCCNC2)n1]

Prepared according to General Procedure B using (S)-tert-butyl 3-((4-(2-((5-(((R)-2,2-difluorocyclobutyl)methylsulfonamido)-6-fluoro-2-methylnaphthalen-1-yl)oxy)pyridin-3-yl)pyrimidin-2-yl)amino)piperidine-1-carboxylate (62 mg, 0.09 mmol) 1,4-dioxane (1 mL) and hydrochloric acid (4 M in dioxane, 1 mL). After 1 h, the mixture was diluted with MTBE and the resulting solids collected by filtration then dissolved in H$_2$O and MeCN and lyophilized to provide 47 mg (83% yield) of 470. LCMS (ESI) [M+H]$^+$=613.3, $^1$H NMR (400 MHz, DMSO-d$_6$) δ 9.93 (s, 1H), 8.80 (s, 2H), 8.46 (d, J=5.2 Hz, 1H), 8.10-7.99 (m, 2H), 7.71 (dd, J=9.3, 5.1 Hz, 1H), 7.62 (d, J=8.9 Hz, 1H), 7.53 (d, J=7.0 Hz, 2H), 7.46 (t, J=9.5 Hz, 1H), 7.27 (dd, J=7.6, 4.8 Hz, 1H), 3.43 (m, 5H), 3.17 (s, 1H), 2.82 (m, 2H), 2.59 (m, 1H), 2.18 (s, 3H), 1.97 (m, 3H), 1.71-1.62 (m, 3H). The absolute stereochemistry at the cyclobutane was assigned randomly.

Example 471 1-((S)-2,2-Difluorocyclobutyl)-N-(2-fluoro-6-methyl-5-((3-(2-((S)-piperidin-3-ylamino)pyrimidin-4-yl)pyridin-2-yl)oxy)naphthalen-1-yl)methanesulfonamide hydrochloride (Isomer-2)

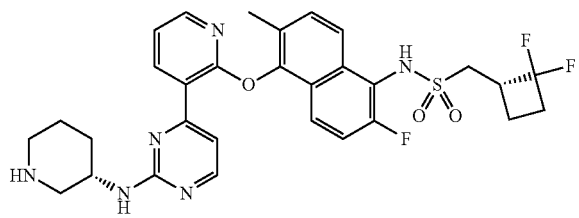 [SMILES: Cc1ccc2c(NS(=O)(=O)C[C@H]3CCC3(F)F)c(F)ccc2c1Oc1ncccc1-c1ccnc(N[C@H]2CCCNC2)n1]

Prepared according to General Procedure B using (S)-tert-butyl 3-((4-(2-((5-(((S)-2,2-difluorocyclobutyl)methylsulfonamido)-6-fluoro-2-methylnaphthalen-1-yl)oxy)pyridin-3-yl)pyrimidin-2-yl)amino)piperidine-1-carboxylate from Example 275 (62 mg, 0.09 mmol) 1,4-dioxane (1 mL) and hydrochloric acid (4 M in dioxane, 1 mL). After 1 h, the mixture was diluted with MTBE and the resulting solids collected by filtration then dissolved in H$_2$O and MeCN and lyophilized to provide 43 mg (76% yield) of 471. LCMS (ESI) [M+H]$^+$=613.3, $^1$H NMR (400 MHz, DMSO) δ 9.94 (s, 1H), 8.96 (s, 2H), 8.46 (d, J=5.2 Hz, 1H), 8.12-7.95 (m, 2H), 7.71 (dd, J=9.3, 5.1 Hz, 1H), 7.67-7.51 (m, 3H), 7.46 (t, J=9.5 Hz, 1H), 7.27 (dd, J=7.6, 4.8 Hz, 1H), 3.43 (m, 4H), 3.16 (m, 1H), 2.81 (m, 2H), 2.67-2.51 (m, 1H), 2.18 (s, 3H), 2.04 (m, 2H), 1.87 (s, 1H), 1.64 (m, 3H). The absolute stereochemistry at the cyclobutane was assigned randomly.

Example 472 3,3-Difluoro-N-(2-fluoro-6-methyl-5-((3-(2-(((3S,5R)-5-methylpiperidin-3-yl)amino)pyrimidin-4-yl)pyridin-2-yl)oxy)naphthalen-1-yl)propane-1-sulfonamide Step 1: Benzyl (3S,5R)-3-((4-(2-((5-((3,3-difluoropropyl)sulfonamido)-6-fluoro-2-methylnaphthalen-1-yl)oxy)pyridin-3-yl)pyrimidin-2-yl)amino)-5-methylpiperidine-1-carboxylate

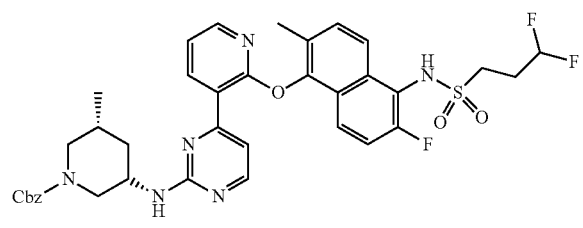

The General Procedure A was followed, using benzyl (3S,5R)-3-[[4-[2-[(5-amino-6-fluoro-2-methyl-1-naphthyl)oxy]-3-pyridyl]pyrimidin-2-yl]amino]-5-methyl-piperidine-1-carboxylate (150 mg, 0.25 mmol), 3,3-difluoropropane-1-sulfonyl chloride (90.39 mg, 0.51 mmol) in pyridine (1.5 mL). The crude product was purified via reverse-phase HPLC to afford 17 mg (9.1% yield) of the title compound as an off-white solid. LCMS (ESI) [M+H]$^+$=735.

Step 2: 3,3-Difluoro-N-(2-fluoro-6-methyl-5-((3-(2-(((3S,5R)-5-methylpiperidin-3-yl)amino)pyrimidin-4-yl)pyridin-2-yl)oxy)naphthalen-1-yl)propane-1-sulfonamide

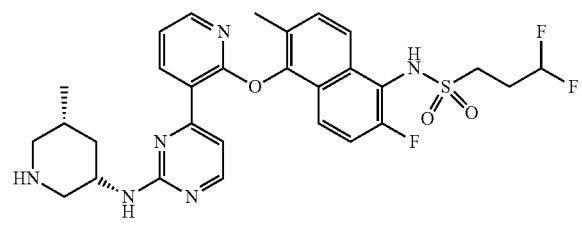

A mixture of benzyl (3S,5R)-3-[[4-[2-[[5-(3,3-difluoropropylsulfonylamino)-6-fluoro-2-methyl-1-naphthyl]oxy]-3-pyridyl]pyrimidin-2-yl]amino]-5-methyl-piperidine-1-carboxylate (17 mg, 0.02 mmol), 10% Pd/C (18 mg), and ammonium formate (43.76 mg, 0.69 mmol) in 2-propanol (1 mL) was heated at 60° C. for 3 hrs. It was filtered through Celite, washed with MeOH (2×1 mL), iPrOAc (2×1 mL), concentrated in vacuo, dried under high vacuum to afford 11 mg (79.1% yield) of the 474 as an off-white solid. LCMS (ESI) [M+H]$^+$=601; $^1$H NMR (400 MHz, DMSO-d$_6$) δ 8.47 (s, 1H), 8.39 (d, J=5.1 Hz, 1H), 8.21 (d, J=8.7 Hz, 1H), 8.04 (dd, J=4.8, 2.0 Hz, 1H), 7.43 (d, J=5.1 Hz, 1H), 7.36 (d, J=8.7 Hz, 1H), 7.26-7.16 (m, 3H), 7.12 (d, J=8.0 Hz, 1H), 6.25 (tt, J=57.1, 4.4 Hz, 1H), 4.33 (d, J=4.2 Hz, 1H), 3.96-3.83 (m, 1H), 3.82-3.72 (m, 1H), 3.22-3.16 (m, 1H), 3.03-2.92 (m, 2H), 2.89-2.82 (m, 1H), 2.38-2.26 (m, 2H), 2.22 (t, J=11.1 Hz, 1H), 2.16 (s, 3H), 2.05-1.95 (m, 2H), 1.58 (qd, J=10.7, 8.5, 4.6 Hz, 1H), 1.04 (d, J=6.1 Hz, 5H), 0.82 (d, J=6.6 Hz, 3H).

Example 473 N-(2-Fluoro-6-methyl-5-((3-(2-((S)-piperidin-3-ylamino)pyrimidin-4-yl)pyridin-2-yl)oxy)naphthalen-1-yl)-1-((R)-spiro[2.2]pentan-1-yl)methanesulfonamide hydrochloride (Isomer-1)

Step 1: (3S)-tert-Butyl 3-((4-(2-((6-fluoro-2-methyl-5-(spiro[2.2]pentan-1-ylmethylsulfonamido)naphthalen-1-yl)oxy)pyridin-3-yl)pyrimidin-2-yl)amino)piperidine-1-carboxylate

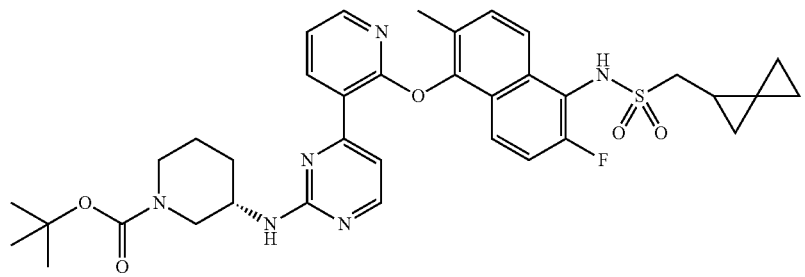 [SMILES: Cc1ccc2c(NS(=O)(=O)CC3CC34CC4)c(F)ccc2c1Oc1ncccc1-c1ccnc(N[C@H]2CCCN(C(=O)OC(C)(C)C)C2)n1]

The General Procedure A was followed using tert-butyl (3S)-3-[[4-[2-[(5-amino-6-fluoro-2-methyl-1-naphthyl)oxy]-3-pyridyl]pyrimidin-2-yl]amino]piperidine-1-carboxylate (250 mg, 0.46 mmol) from Example 275, pyridine (1.1 mL, 13.8 mmol), DCM (1 mL) and spiro[2.2]pentan-2-ylmethanesulfonyl chloride (0.21 mL, 0.92 mmol). After 72 h, the mixture was concentrated in vacuo and co-evaporated with toluene. The crude was purified by flash chromatography through silica gel (0-100% EtOAc/hexane with TEA as additive) to provide 98 mg (31% yield) of the title compound. LCMS (ESI) [M+H]$^+$=689.5.

Step 2: (S)-tert-Butyl 3-((4-(2-((6-fluoro-2-methyl-5-((R)-spiro[2.2]pentan-1-ylmethylsulfonamido) naphthalen-1-yl)oxy)pyridin-3-yl)pyrimidin-2-yl) amino)piperidine-1-carboxylate (Isomer-1) and (S)-tert-butyl 3-((4-(2-((6-fluoro-2-methyl-5-((S)-spiro [2.2]pentan-1-ylmethylsulfonamido)naphthalen-1-yl) oxy)pyridin-3-yl)pyrimidin-2-yl)amino)piperidine-1-carboxylate (Isomer-2)

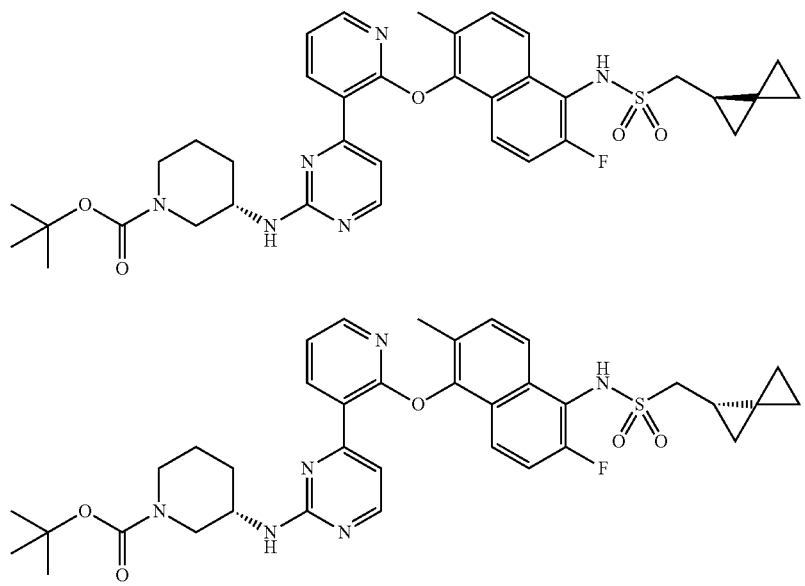

The stereoisomers from Step 1 were subjected to chiral SFC purification (AS (250 mm×10 mm, 5 μm); 25% of 1:1 MeCN+EtOH, flow rate (ml/min): 10, 100 bar, 35° C.) to provide two stereoisomers enantiomeric at spiro[2.2]pentan-1 position. Isomer-1: (S)-tert-butyl 3-((4-(2-((6-fluoro-2-methyl-5-((R)-spiro[2.2]pentan-1-ylmethylsulfonamido) naphthalen-1-yl)oxy)pyridin-3-yl)pyrimidin-2-yl)amino) piperidine-1-carboxylate (29 mg, 21% yield), ee=99.5%; Isomer-2: (S)-tert-butyl 3-((4-(2-((6-fluoro-2-methyl-5-((S)-spiro[2.2]pentan-1-ylmethylsulfonamido)naphthalen-1-yl) oxy)pyridin-3-yl)pyrimidin-2-yl)amino)piperidine-1-carboxylate (27 mg, 20% yield), ee=98.5%.

Step 3: N-(2-Fluoro-6-methyl-5-((3-(2-((S)-piperidin-3-ylamino)pyrimidin-4-yl)pyridin-2-yl)oxy) naphthalen-1-yl)-1-((R)-spiro[2.2]pentan-1-yl)methanesulfonamide hydrochloride (Isomer 1) 473

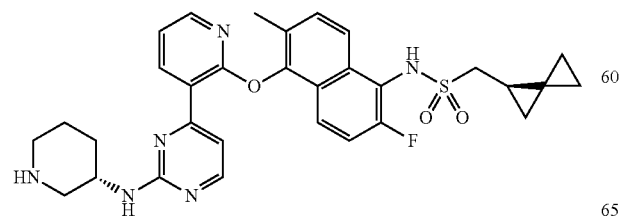

Prepared according to General Procedure B using (S)-tert-butyl 3-((4-(2-((6-fluoro-2-methyl-5-((R)-spiro[2.2]pentan-1-ylmethylsulfonamido)naphthalen-1-yl)oxy)pyridin-3-yl)pyrimidin-2-yl)amino)piperidine-1-carboxylate (29 mg, 0.04 mmol) 1,4-dioxane (1 mL) and hydrochloric acid (4 M in dioxane, (1 mL). After 1 h, the mixture was diluted with MTBE and the resulting solids were collected by filtration then dissolved in H$_2$O and MeCN and lyophilized to provide 23 mg (87% yield) of 473. LCMS (ESI) [M+H]$^+$=589.2, $^1$H NMR (400 MHz, DMSO-d$_6$) δ 9.74 (s, 1H), 9.01 (s, 1H), 8.96 (s, 1H), 8.48 (d, J=5.2 Hz, 1H), 8.12-8.01 (m, 2H), 7.71 (dd, J=9.3, 5.1 Hz, 1H), 7.63 (d, J=8.8 Hz, 1H), 7.59 (s, 1H), 7.45 (t, J=9.5 Hz, 1H), 7.29 (dd, J=7.6, 4.8 Hz, 1H), 3.49-3.38 (m, 1H), 3.27-3.15 (m, 3H), 2.92-2.75 (m, 2H), 2.19 (s, 3H), 2.07-1.97 (m, 1H), 1.96-1.87 (m, 1H), 1.83-1.69 (m, 1H), 1.68-1.53 (m, 2H), 1.15 (dd, J=7.9, 4.3 Hz, 1H), 0.96-0.88 (m, 1H), 0.88-0.77 (m, 3H), 0.72-0.63 (m, 1H). The absolute stereochemistry of the sulfonamide was randomly assigned.

Example 474 N-(2-Fluoro-6-methyl-5-((3-(2-((S)-piperidin-3-ylamino)pyrimidin-4-yl)pyridin-2-yl)oxy)naphthalen-1-yl)-1-((S)-spiro[2.2]pentan-1-yl)methanesulfonamide hydrochloride (Isomer-2)

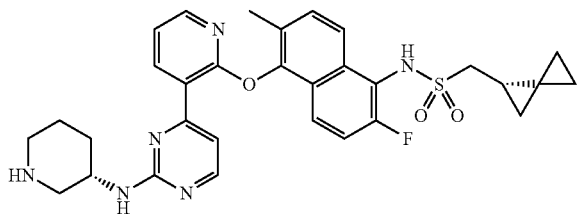 [SMILES: Cc1ccc2c(NS(=O)(=O)C[C@H]3CC34CC4)c(F)ccc2c1Oc1ncccc1-c1ccnc(N[C@H]2CCCNC2)n1]

Prepared according to General Procedure B using (S)-tert-butyl 3-((4-(2-((6-fluoro-2-methyl-5-((S)-spiro[2.2]pentan-1-ylmethylsulfonamido)naphthalen-1-yl)oxy)pyridin-3-yl)pyrimidin-2-yl)amino)piperidine-1-carboxylate (27 mg, 0.04 mmol) 1,4-dioxane (1 mL) and hydrochloric acid (4 M in dioxane, (1 mL). After 1 h, the mixture was diluted with MTBE and the resulting solids were collected by filtration then dissolved in H$_2$O and MeCN and lyophilized to provide 19 mg (77% yield) of 474. LCMS (ESI) [M+H]$^+$=589.2, 1H NMR (400 MHz, DMSO-d$_6$) δ 9.71 (s, 1H), 8.99 (s, 2H), 8.45 (d, J=5.3 Hz, 1H), 8.05 (dd, J=10.4, 5.4 Hz, 2H), 7.72-7.53 (m, 4H), 7.43 (t, J=9.5 Hz, 1H), 7.26 (dd, J=7.6, 4.8 Hz, 1H), 4.29 (s, 1H), 3.39 (s, 1H), 3.19 (dd, J=16.3, 9.5 Hz, 3H), 2.80 (s, 2H), 1.97 (s, 1H), 1.86 (s, 1H), 1.78-1.52 (m, 3H), 1.12 (dd, J=7.7, 4.4 Hz, 1H), 0.92-0.76 (m, 4H), 0.65 (s, 1H). The absolute stereochemistry of the sulfonamide was randomly assigned Example 475 (S)-1,1-Difluoro-3-((6-methyl-5-((3-(2-((S)-piperidin-3-ylamino)pyrimidin-4-yl)pyridin-2-yl)oxy)naphthalen-1-yl)amino)propan-2-ol hydrochloride (Isomer-1)

Step 1: (3S)-tert-Butyl 3-((4-(2-((5-(((3,3-difluoro-2-hydroxypropyl)amino)-2-methylnaphthalen-1-yl)oxy)pyridin-3-yl)pyrimidin-2-yl)amino)piperidine-1-carboxylate

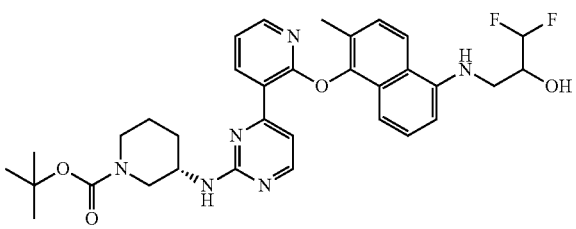 [SMILES: Cc1ccc2c(NCC(O)C(F)F)cccc2c1Oc1ncccc1-c1ccnc(N[C@H]2CCCN(C(=O)OC(C)(C)C)C2)n1]

Prepared according to General Procedure F using tert-butyl (3S)-3-[[4-[2-[(5-amino-2-methyl-1-naphthyl)oxy]-3-pyridyl]pyrimidin-2-yl]amino]piperidine-1-carboxylate (280 mg, 0.53 mmol), acetic acid (0.5 mL) and 2-(difluoromethyl)oxirane (56 mg, 0.62 mmol). After 48 h at rt, the mixture was concentrated in vacuo. The crude product was purified by C18 reverse phase flash chromatography (0-65% MeCN/10 mM aqueous ammonium formate, pH=3.8) to provide 139 mg (42% yield) of the title compound. LCMS (ESI) [M+H]$^+$=621.2.

Step 2: (S)-tert-Butyl 3-((4-(2-((5-(((S)-3,3-difluoro-2-hydroxypropyl)amino)-2-methylnaphthalen-1-yl)oxy)pyridin-3-yl)pyrimidin-2-yl)amino)piperidine-1-carboxylate (Isomer 1) and (S)-tert-butyl 3-((4-(2-((5-(((R)-3,3-difluoro-2-hydroxypropyl)amino)-2-methylnaphthalen-1-yl)oxy)pyridin-3-yl)pyrimidin-2-yl)amino)piperidine-1-carboxylate (Isomer 2)

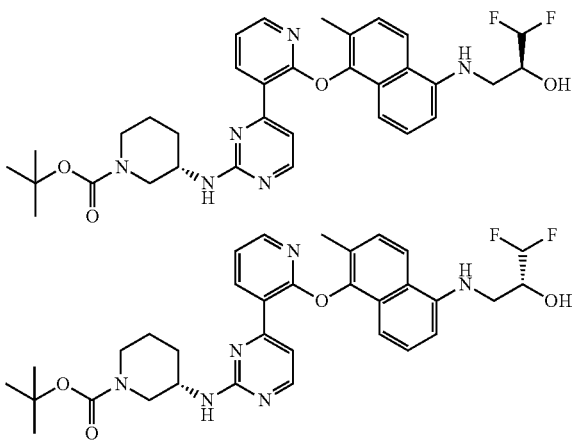

The stereoisomers from Step 1 were subjected to chiral normal phase semi-prep purification (conditions: Chiralpak IB, 5 uM, 20×250 mm, 6:6:88 MeOH:EtOH:Hexane, 12-16 mg/inj.) to provide two stereoisomers enantiomeric at the alcohol position. Isomer 1: (S)-tert-butyl 3-((4-(2-((5-(((S)-

3,3-difluoro-2-hydroxypropyl)amino)-2-methylnaphthalen-1-yl)oxy)pyridin-3-yl)pyrimidin-2-yl)amino)piperidine-1-carboxylate, 46 mg (35% yield), ee=99.6%, LCMS (ESI) [M+H]⁺=621.2; and Isomer 2: (S)-tert-butyl 3-((4-(2-((5-(((R)-3,3-difluoro-2-hydroxypropyl)amino)-2-methylnaphthalen-1-yl)oxy)pyridin-3-yl)pyrimidin-2-yl)amino)piperidine-1-carboxylate, 50 mg (38% yield), ee=98.0%, LCMS (ESI) [M+H]⁺=621.2.

Step 3: (S)-1,1-Difluoro-3-((6-methyl-5-((3-(2-((S)-piperidin-3-ylamino)pyrimidin-4-yl)pyridin-2-yl)oxy)naphthalen-1-yl)amino)propan-2-ol hydrochloride (Isomer-1) 475

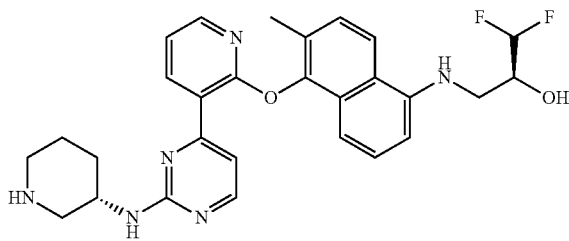 [SMILES: Cc1ccc2c(NC[C@H](O)C(F)F)cccc2c1Oc1ncccc1-c1ccnc(N[C@H]2CCCNC2)n1]

Prepared according to General Procedure B using (S)-tert-butyl 3-((4-(2-((5-(((S)-3,3-difluoro-2-hydroxypropyl)amino)-2-methylnaphthalen-1-yl)oxy)pyridin-3-yl)pyrimidin-2-yl)amino)piperidine-1-carboxylate (46 mg, 0.07 mmol), 1,4-dioxane (1 mL) and hydrochloric acid (4 M in dioxane, 0.5 mL, 2.0 mmol). After 3 h, the mixture was concentrated in vacuo, the residue triturated with MeCN and the resulting solids were collected by filtration then dissolved in H₂O and MeCN and lyophilized to provide 38 mg (92% yield) of the title compound 475. LCMS (ESI) [M+H]⁺=521.0. ¹H NMR (400 MHz, DMSO-d₆) δ 9.23 (s, 1H), 9.07 (s, 1H), 8.76 (s, 1H), 8.48 (d, J=5.3 Hz, 1H), 8.10-7.98 (m, 2H), 7.69 (s, 1H), 7.62 (s, 1H), 7.38 (d, J=8.5 Hz, 1H), 7.29-7.07 (m, 3H), 6.87 (d, J=8.4 Hz, 1H), 6.51 (d, J=7.7 Hz, 1H), 6.03 (td, J=55.3, 2.9 Hz, 1H), 4.46-4.18 (m, 1H), 4.12-3.95 (m, 1H), 3.51-3.34 (m, 2H), 3.32-3.11 (m, 2H), 2.94-2.75 (m, 2H), 2.19 (s, 3H), 2.07-1.86 (m, 2H), 1.84-1.55 (m, 2H). The absolute stereochemistry of the amino alcohol was assigned based on the potency in the cellular assay.

Example 476 (R)-1,1-Difluoro-3-((6-methyl-5-((3-(2-((S)-piperidin-3-ylamino)pyrimidin-4-yl)pyridin-2-yl)oxy)naphthalen-1-yl)amino)propan-2-ol hydrochloride (Isomer-2)

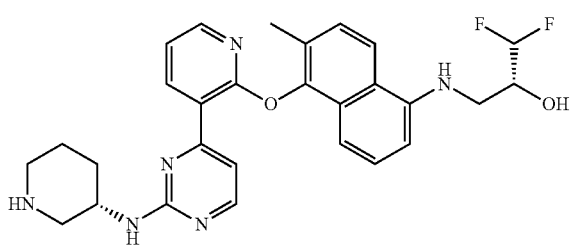 [SMILES: Cc1ccc2c(NC[C@@H](O)C(F)F)cccc2c1Oc1ncccc1-c1ccnc(N[C@H]2CCCNC2)n1]

Prepared according to General Procedure B using (S)-tert-butyl 3-((4-(2-((5-(((R)-3,3-difluoro-2-hydroxypropyl)amino)-2-methylnaphthalen-1-yl)oxy)pyridin-3-yl)pyrimidin-2-yl)amino)piperidine-1-carboxylate (50 mg, 0.08 mmol), 1,4-dioxane (1 mL) and hydrochloric acid (4 M in dioxane, 0.5 mL, 2.0 mmol). After 3 h, the mixture was concentrated in vacuo, the residue triturated with MeCN and the resulting solids collected by filtration then dissolved in H₂O and MeCN and lyophilized to provide 38 mg (92% yield) of the title compound 476. LCMS (ESI) [M+H]⁺=521.0; ¹H NMR (400 MHz, DMSO-d₆) δ 9.32 (s, 1H), 9.13 (s, 1H), 8.75 (s, 1H), 8.49 (d, J=5.4 Hz, 1H), 8.12-7.98 (m, 2H), 7.78 (s, 1H), 7.64 (s, 1H), 7.38 (d, J=8.9 Hz, 1H), 7.30-7.10 (m, 3H), 6.87 (d, J=8.4 Hz, 1H), 6.51 (d, J=7.7 Hz, 1H), 6.04 (td, J=55.3, 2.9 Hz, 1H), 4.49-4.18 (m, 1H), 4.13-3.96 (m, 1H), 3.50-3.36 (m, 2H), 3.32-3.12 (m, 2H), 2.94-2.76 (m, 2H), 2.19 (s, 3H), 2.07-1.85 (m, 2H), 1.85-1.54 (m, 2H). The absolute stereochemistry of the amino alcohol was assigned based on the potency in the cellular assay.

Example 477 N-(2-Fluoro-6-methyl-5-((3-(2-(((3S,5R)-5-methylpiperidin-3-yl)amino)pyrimidin-4-yl)pyridin-2-yl)oxy)naphthalen-1-yl)-1-(2-fluorophenyl)methanesulfonamide Step 1: Benzyl (3S,5R)-3-((4-(2-((6-fluoro-5-(((2-fluorophenyl)methyl)sulfonamido)-2-methylnaphthalen-1-yl)oxy)pyridin-3-yl)pyrimidin-2-yl)amino)-5-methylpiperidine-1-carboxylate

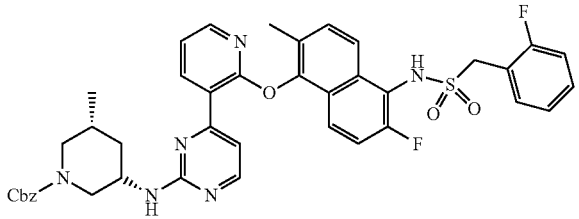

The General Procedure A was followed, using benzyl (3S,5R)-3-[[4-[2-[(5-amino-6-fluoro-2-methyl-1-naphthyl)oxy]-3-pyridyl]pyrimidin-2-yl]amino]-5-methyl-piperidine-1-carboxylate (150 mg, 0.25 mmol), (2-fluorophenyl)methanesulfonyl chloride (105.6 mg, 0.51 mmol) in pyridine (1.5 mL). The crude product was purified via reverse-phase HPLC to afford 30 mg (15.5% yield) of the title compound as an off-white solid. LCMS (ESI) [M+H]⁺=765.

Step 2: N-(2-fluoro-6-methyl-5-((3-(2-(((3S,5R)-5-methylpiperidin-3-yl)amino)pyrimidin-4-yl)pyridin-2-yl)oxy)naphthalen-1-yl)-1-(2-fluorophenyl)methanesulfonamide

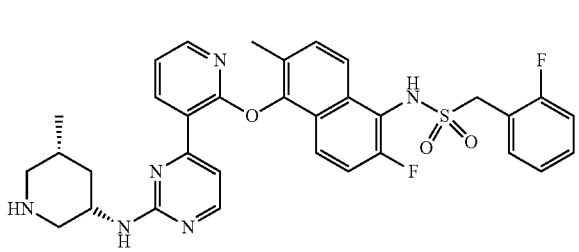

To a mixture of benzyl (3S,5R)-3-[[4-[2-[[6-fluoro-5-[(2-fluorophenyl)methylsulfonylamino]-2-methyl-1-naphthyl]oxy]-3-pyridyl]pyrimidin-2-yl]amino]-5-methyl-piperidine-1-carboxylate (30 mg, 0.04 mmol) in 2-propanoL (1 mL) was added 10% Pd/C (30 mg), followed by ammonium formate (74.20 mg, 1.18 mmol), and the reaction mixture was heated at 60° C. for 3 hrs. The mixture was filtered through Celite, washed with IPA and MeOH, concentrated in vacuo. It was dissolved in dioxane (1 mL), treated with 4N HCl/dioxane (1 mL) for 15 min., concentrated in vacuo. The crude product was purified via reverse-phase HPLC to afford 0.9 mg (3.6% yield) of the title compound as an off-white solid. LCMS (ESI) [M+H]$^+$=631; 1H NMR (400 MHz, DMSO-$d_6$) δ 9.96 (s, 1H), 9.12-9.01 (m, 2H), 8.78-8.65 (m, 2H), 8.47 (d, J=5.2 Hz, 1H), 8.09 (dd, J=4.8, 2.0 Hz, 1H), 8.02 (d, J=8.7 Hz, 1H), 7.74 (dd, J=9.4, 5.1 Hz, 1H), 7.61 (d, J=8.8 Hz, 1H), 7.58-7.41 (m, 5H), 7.32-7.23 (m, 3H), 4.63 (s, 2H), 4.31 (s, 1H), 4.11 (qd, J=7.1, 4.2 Hz, 1H), 3.50 (s, 1H), 3.20 (d, J=11.9 Hz, 1H), 2.62 (d, J=11.6 Hz, 1H), 2.46 (d, J=3.7 Hz, 1H), 2.20 (s, 3H), 2.11-2.03 (m, 1H), 1.99 (d, J=19.8 Hz, 1H), 1.77-1.61 (m, 1H), 1.33-1.19 (m, 2H), 0.93 (d, J=6.6 Hz, 3H).

Example 478 (S)-3,3,3-Trifluoro-N-(3-methyl-4-((3-(2-(piperidin-3-ylamino)pyrimidin-4-yl)pyridin-2-yl)oxy)naphthalen-1-yl)propane-1-sulfonamide 478

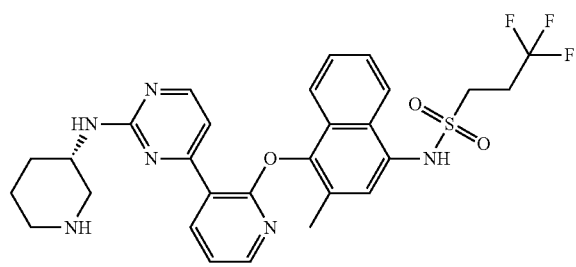 [SMILES: Cc1cc(NS(=O)(=O)CCC(F)(F)F)c2ccccc2c1Oc1ncccc1-c1ccnc(N[C@H]2CCCNC2)n1]

Step 1: tert-Butyl (S)-3-((4-(2-((2-methyl-4-((3,3,3-trifluoropropyl)sulfonamido)naphthalen-1-yl)oxy)pyridin-3-yl)pyrimidin-2-yl)amino)piperidine-1-carboxylate

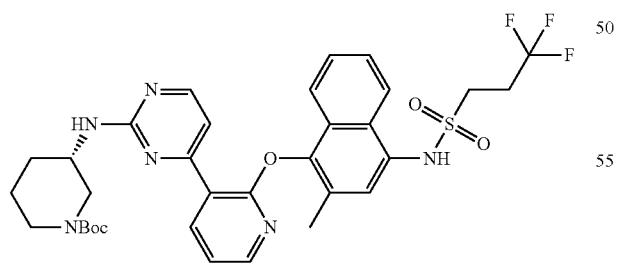

To a mixture of tert-butyl (S)-3-((4-(2-((4-amino-2-methylnaphthalen-1-yl)oxy)pyridin-3-yl)pyrimidin-2-yl)amino)piperidine-1-carboxylate (180 mg, 334 μmol) and N-methylmorpholine (100 μL) in chloroform (2.00 mL) was added 3,3,3-trifluoropropane-1-sulfonyl chloride (66 mg, 334 μmol) in portions at 0° C. The mixture was stirred at 30° C. for 2 hrs. LCMS showed the reaction was complete. The mixture was concentrated. The residue was purified by prep-HPLC to afford 139 mg of the title compound as a yellow solid.

Step 2: (S)-3,3,3-Trifluoro-N-(3-methyl-4-((3-(2-(piperidin-3-ylamino)pyrimidin-4-yl)pyridin-2-yl)oxy)naphthalen-1-yl)propane-1-sulfonamide 478

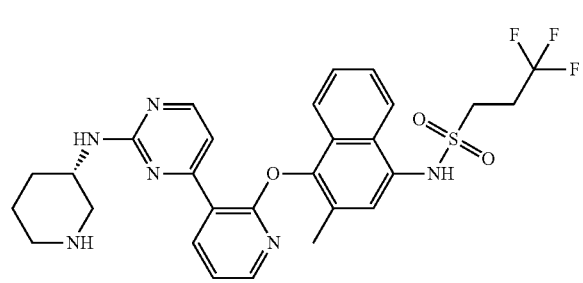 [SMILES: Cc1cc(NS(=O)(=O)CCC(F)(F)F)c2ccccc2c1Oc1ncccc1-c1ccnc(N[C@H]2CCCNC2)n1]

To a solution of tert-butyl (S)-3-((4-(2-((2-methyl-4-((3,3,3-trifluoropropyl)sulfonamido)naphthalen-1-yl)oxy)pyridin-3-yl)pyrimidin-2-yl)amino)piperidine-1-carboxylate (137 mg, 0.199 mmol) in EtOAc (5 mL) and added HCl/EtOAc (5 mL) at 18° C. for 1 hr. The reaction mixture was concentrated in vacuum. The residue was purified by prep-HPLC to afford 2-chloro-N-[2-fluoro-3-methyl-4-[[3-[2-[[(3S)-3-piperidyl]amino]pyrimidin-4-yl]-2-pyridyl]oxy]-1-naphthyl]benzenesulfonamide (32.4 mg, 26% yield) as a yellow solid and as a HCl salt. LCMS (ESI) [M+H]$^+$=587.2; $^1$H NMR (400 MHz, CD$_3$OD) δ 8.90 (br s, 1H), 8.51 (d, J=6.6 Hz, 1H), 8.26 (d, J=8.4 Hz, 1H), 8.16 (br d, J=3.3 Hz, 2H), 7.74 (d, J=8.4 Hz, 1H), 7.61-7.55 (m, 2H), 7.51-7.45 (m, 1H), 7.35 (dd, J=7.5, 4.6, Hz, 1H), 4.68 (br s, 1H), 3.69 (br d, J=10.4 Hz, 1H), 3.45-3.36 (m, 3H), 3.18-3.04 (m, 2H), 2.82-2.70 (m, 2H), 2.29 (s, 4H), 2.19-2.10 (m, 1H), 2.04-1.82 (m, 2H).

Example 479 N-[6-Methyl-5-[[3-[2-[[(3S,5R)-5-methyl-3-piperidyl]amino]pyrimidin-4-yl]-2-pyridyl]oxy]-1-naphthyl]-1-phenyl-methanesulfonamide Step 1: Benzyl (3S,5R)-3-[[4-[2-[(5-amino-2-methyl-1-naphthyl)oxy]-3-pyridyl]pyrimidin-2-yl]amino]-5-methyl-piperidine-1-carboxylate

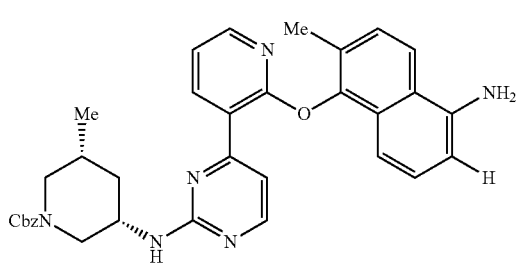 [SMILES: Cc1ccc2c(N)cccc2c1Oc1ncccc1-c1ccnc(N[C@H]2C[C@@H](C)CN(C(=O)OCc3ccccc3)C2)n1]

To a solution of 6-methyl-5-[[3-(2-methylsulfinylpyrimidin-4-yl)-2-pyridyl]oxy]naphthalen-1-amine (200 mg, 0.512 mmol) and benzyl (3S,5R)-3-amino-5-methyl-piperidine-1-carboxylate (190.8 mg, 0.768 mmol) in DMSO (3 mL) was added CsF (77.8 mg, 0.512 mmol) and DIPEA (264 mg, 2.05 mmol, 357.84 μL). The mixture was stirred at 115° C. for 12 hrs. The reaction mixture was purified by prep-TLC to give 150 mg of the crude title as a yellow solid.

Step 2: Benzyl (3R,5S)-3-methyl-5-((4-(2-((2-methyl-5-((phenylmethyl)sulfonamido)naphthalen-1-yl)oxy)pyridin-3-yl)pyrimidin-2-yl)amino)piperidine-1-carboxylate

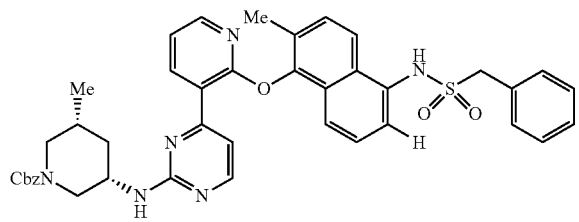 [SMILES: Cc1ccc2c(NS(=O)(=O)Cc3ccccc3)cccc2c1Oc1ncccc1-c1ccnc(N[C@H]2C[C@@H](C)CN(C(=O)OCc3ccccc3)C2)n1]

To a solution of benzyl (3S,5R)-3-[[4-[2-[(5-amino-2-methyl-1-naphthyl)oxy]-3-pyridyl]pyrimidin-2-yl]amino]-5-methyl-piperidine-1-carboxylate (65 mg, 113 μmol) in pyridine (1.00 mL) was added phenylmethanesulfonyl chloride (21.6 mg, 113 μmol). The mixture was stirred at 15° C. for 0.5 hr. LCMS showed no complete conversion. Another 0.5 equivalent of phenylmethanesulfonyl chloride was added to the mixture. The mixture was stirred at 15° C. for 1 additional hr. LCMS showed no complete conversion. Another 0.5 equivalent of phenylmethanesulfonyl chloride was added to the mixture. The mixture was stirred at 15° C. for 1 hr. The mixture was poured into water (2 mL) and extracted with EtOAc (2 mL). The organic layer was separated and concentrated to give 80 mg of the crude title compound as a yellow solid.

Step 3: N-[6-Methyl-5-[[3-[2-[[(3S,5R)-5-methyl-3-piperidyl]amino]pyrimidin-4-yl]-2-pyridyl]oxy]-1-naphthyl]-1-phenyl-methanesulfonamide

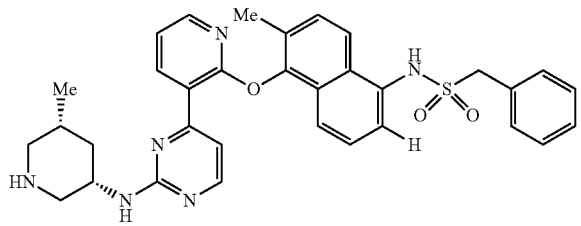 [SMILES: Cc1ccc2c(NS(=O)(=O)Cc3ccccc3)cccc2c1Oc1ncccc1-c1ccnc(N[C@@H]2CNC[C@H](C)C2)n1]

To benzyl (3R,5S)-3-methyl-5-((4-(2-((2-methyl-5-((phenylmethyl)sulfonamido)naphthalen-1-yl)oxy)pyridin-3-yl)pyrimidin-2-yl)amino)piperidine-1-carboxylate (80 mg, 110 μmol) was added HBr/HOAc (2.00 mL) and HBr (400 μL). The mixture was stirred at 45° C. for 0.5 hr. The mixture was concentrated and was then purified by prep-HPLC to provide 49 mg (70% yield) of the title compound as a yellow solid and as a HCl salt. LCMS (ESI) [M+H]$^+$=595.2; $^1$H NMR (400 MHz, CD$_3$OD) δ=9.12-9.10 (m, 1H), 8.92 (br s, 1H), 8.49 (d, J=6.6 Hz, 1H), 8.15 (brd, J=3.5 Hz, 2H), 8.02 (d, J=8.8 Hz, 1H), 7.60 (d, J=8.6 Hz, 1H), 7.53-7.44 (m, 2H), 7.41-7.26 (m, 7H), 4.72 (brs, 1H), 4.47 (s, 2H), 3.76 (brd, J=11.2 Hz, 1H), 3.38 (brd, J=9.9 Hz, 1H), 2.92 (t, J=11.9 Hz, 1H), 2.67 (t, J=12.3 Hz, 1H), 2.28 (s, 4H), 2.12 (brs, 1H), 1.61-1.41 (m, 1H), 1.07 (d, J=6.4 Hz, 3H).

Example 480 (S)—N-(2-Fluoro-3-methyl-4-((3-(2-(piperidin-3-ylamino)pyrimidin-4-yl)pyridin-2-yl)oxy)naphthalen-1-yl)-1-phenylmethanesulfonamide 480

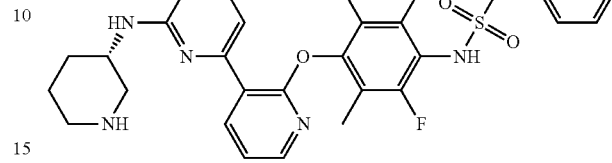

Step 1: tert-Butyl (S)-3-((4-(2-((4-amino-3-fluoro-2-methylnaphthalen-1-yl)oxy)pyridin-3-yl)pyrimidin-2-yl)amino)piperidine-1-carboxylate

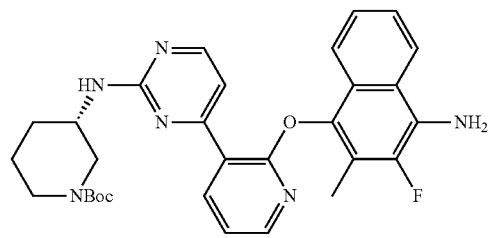 [SMILES: Cc1c(F)c(N)c2ccccc2c1Oc1ncccc1-c1ccnc(N[C@H]2CCCN(C(=O)OC(C)(C)C)C2)n1]

To a mixture of tert-butyl (3S)-3-[[4-[2-[(4-amino-2-methyl-1-naphthyl)oxy]-3-pyridyl]pyrimidin-2-yl]amino]piperidine-1-carboxylate (300 mg, 570 μmol) and triethylamine (158 μL, 1.14 mmol,) in NMP (2 mL)/EtOH (2 mL) was added Selectfluor (504.5 mg, 1.42 mmol) in portions. The mixture was stirred at 15° C. for 12 hrs. This reaction was performed parallel for 7 times. LCMS showed the reaction was complete. H$_2$O (15 mL) was added to the mixture and the mixture was filtered. The filter cake was dried and purified by silica gel chromatography (PE/EtOAc=10/1, 5/1, 3/1, 1/1) to afford 650 mg (30% yield) of the title compound as a black brown solid.

Step 2: tert-Butyl (S)-3-((4-(2-((3-fluoro-2-methyl-4-((phenylmethyl)sulfonamido)naphthalen-1-yl)oxy)pyridin-3-yl)pyrimidin-2-yl)amino)piperidine-1-carboxylate

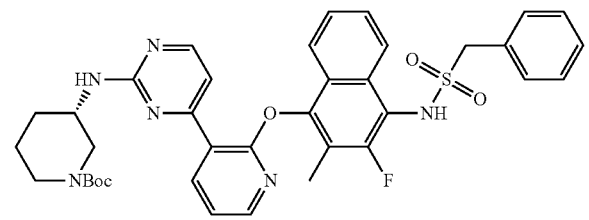 [SMILES: Cc1c(F)c(NS(=O)(=O)Cc2ccccc2)c2ccccc2c1Oc1ncccc1-c1ccnc(N[C@H]2CCCN(C(=O)OC(C)(C)C)C2)n1]

To a solution of tert-butyl (3S)-3-[[4-[2-[(4-amino-3-fluoro-2-methyl-1-naphthyl)oxy]-3-pyridyl]pyrimidin-2-yl]amino]piperidine-1-carboxylate (205 mg, 377 μmol) in pyridine (5 mL) was added benzenesulfonyl chloride (167 mg, 943 µmol) at 0° C. The mixture was stirred at 18° C. for 4 hrs. LCMS showed the reaction was complete. The residue was poured into water (10 mL). The aqueous phase was extracted with ethyl acetate (10 mL*2). The combined organic phase was dried with anhydrous Na$_2$SO$_4$, filtered and concentrated in vacuum. The residue was purified by prep-TLC (silica, petroleum ether:Ethyl acetate=1:1) to afford 150 mg (57% yield) of the title compound as a light yellow solid.

Step 3: (S)—N-(2-Fluoro-3-methyl-4-((3-(2-(piperidin-3-ylamino)pyrimidin-4-yl)pyridin-2-yl)oxy)naphthalen-1-yl)-1-phenylmethanesulfonamide 480

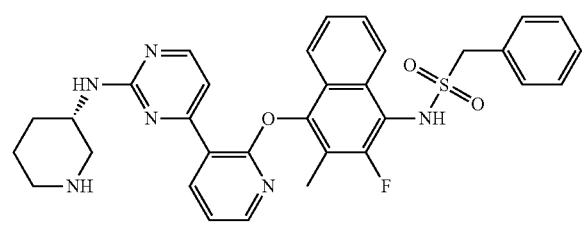 [SMILES: Cc1c(F)c(NS(=O)(=O)Cc2ccccc2)c2ccccc2c1Oc1ncccc1-c1ccnc(N[C@H]2CCCNC2)n1]

To a solution of tert-butyl (S)-3-((4-(2-((3-fluoro-2-methyl-4-((phenylmethyl)sulfonamido)naphthalen-1-yl)oxy)pyridin-3-yl)pyrimidin-2-yl)amino)piperidine-1-carboxylate (201 mg, 0.287 mmol) in EtOAc (5 mL) and added HCl/EtOAc (5 mL) at 18° C. for 1 hr. The reaction mixture was concentrated in vacuum. The residue was purified by prep-HPLC to afford 102 mg (56% yield) of the title compound as a yellow solid and as HCl salt. LCMS (ESI) [M+H]$^+$=599.1; $^1$H NMR (400 MHz, CD$_3$OD) δ 8.87 (br s, 1H), 8.51 (d, J=6.6 Hz, 1H), 8.26 (d, J=8.8 Hz, 1H), 8.16 (br s, 1H), 8.07 (br s, 1H), 7.70 (d, J=8.6 Hz, 1H), 7.56 (t, J=7.9 Hz, 1H), 7.50 (br d, J=4.6 Hz, 2H), 7.43 (br d, J=7.7 Hz, 1H), 7.38 (br s, 4H), 4.59 (s, 3H), 3.67 (br d, J=13.5 Hz, 1H), 3.39 (br d, J=12.6 Hz, 1H), 3.02-3.17 (m, 2H), 2.28 (s, 3H), 2.23-2.26 (m, 1H), 2.12 (br s, 1H), 1.80-2.01 (m, 2H).

Example 481 3,3,3-Trifluoro-N-(6-methyl-5-((3-(2-(((3S,5R)-5-methylpiperidin-3-yl)amino)pyrimidin-4-yl)pyridin-2-yl)oxy)naphthalen-1-yl)propane-1-sulfonamide 481

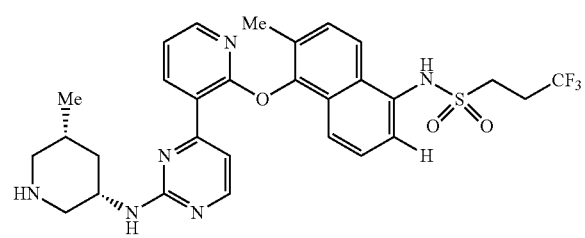 [SMILES: Cc1ccc2c(NS(=O)(=O)CCC(F)(F)F)cccc2c1Oc1ncccc1-c1ccnc(N[C@@H]2CNC[C@H](C)C2)n1]

Step 1: tert-Butyl (3R,5S)-3-methyl-5-((4-(2-((2-methyl-5-((3,3,3-trifluoropropyl)sulfonamido)naphthalen-1-yl)oxy)pyridin-3-yl)pyrimidin-2-yl)amino)piperidine-1-carboxylate

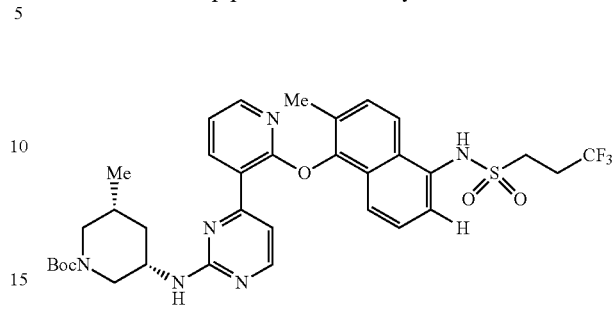

To benzyl (3S,5R)-3-[[4-[2-[(5-amino-2-methyl-1-naphthyl)oxy]-3-pyridyl]pyrimidin-2-yl]amino]-5-methyl-piperidine-1-carboxylate (100 mg, 174 µmol) in CHCl$_3$ (3.00 mL) was added NMM (96 µL, 870 µmol,) and 3,3,3-trifluoropropane-1-sulfonyl chloride (34.2 mg, 174 µmol). The mixture was stirred at 15° C. for 0.5 hr. HPLC showed the reaction worked well. The mixture was poured into water (5 mL), and extracted with EtOAc (5 mL). The organic layer was separated and concentrated to give 125 mg of the crude title compound as a yellow solid.

Step 2: 3,3,3-Trifluoro-N-(6-methyl-5-((3-(2-(((3S,5R)-5-methylpiperidin-3-yl)amino)pyrimidin-4-yl)pyridin-2-yl)oxy)naphthalen-1-yl)propane-1-sulfonamide 481

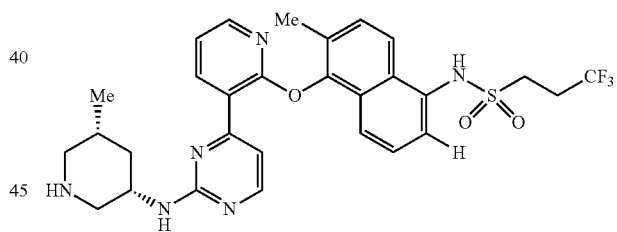

To tert-butyl (3R,5S)-3-methyl-5-((4-(2-((2-methyl-5-((3,3,3-trifluoropropyl)sulfonamido) naphthalen-1-yl)oxy)pyridin-3-yl)pyrimidin-2-yl)amino)piperidine-1-carboxylate (96.7 mg, 138 µmol) was added HBr/HOAc (2.00 mL) and HBr (400 µL). The mixture was stirred at 45° C. for 0.5 hr. The mixture was concentrated and was then purified by prep-HPLC to provide 73 mg (83% yield) of the title compound as a yellow solid and as a HCl salt. LCMS (ESI) [M+H]$^+$=601.2; $^1$H NMR (400 MHz, CD$_3$OD) δ 8.91 (brs, 1H), 8.49 (d, J=6.6 Hz, 1H), 8.14 (brd, J=8.2 Hz, 3H), 7.67 (d, J=8.4 Hz, 1H), 7.61-7.50 (m, 2H), 7.46-7.39 (m, 1H), 7.34 (dd, J=7.6, 5.0 Hz, 1H), 4.71 (brs, 1H), 3.75 (br dd, J=12.1, 3.3 Hz, 1H), 3.44-3.34 (m, 3H), 2.92 (t, J=11.9 Hz, 1H), 2.82-2.56 (m, 3H), 2.36-2.25 (m, 4H), 2.19-1.98 (m, 1H), 1.51 (q, J=12.3 Hz, 1H), 1.07 (d, J=6.6 Hz, 3H).

Example 482 (S)-3,3,3-Trifluoro-N-(2-fluoro-3-methyl-4-((3-(2-(piperidin-3-ylamino)pyrimidin-4-yl)pyridin-2-yl)oxy)naphthalen-1-yl)propane-1-sulfonamide

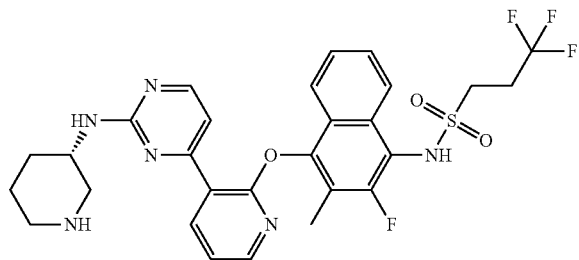 [SMILES: Cc1c(F)c(NS(=O)(=O)CCC(F)(F)F)c2ccccc2c1Oc1ncccc1-c1ccnc(N[C@H]2CCCNC2)n1]

Step 1: tert-Butyl (S)-3-((4-(2-((3-fluoro-2-methyl-4-((3,3,3-trifluoropropyl)sulfonamido)naphthalen-1-yl)oxy)pyridin-3-yl)pyrimidin-2-yl)amino)piperidine-1-carboxylate

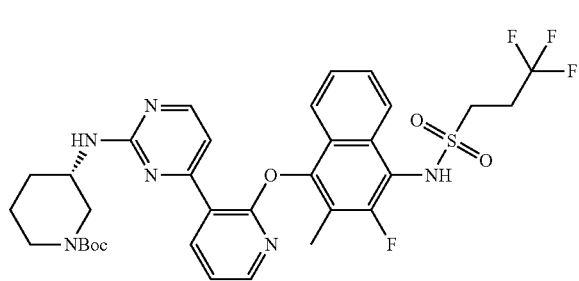 [SMILES: Cc1c(F)c(NS(=O)(=O)CCC(F)(F)F)c2ccccc2c1Oc1ncccc1-c1ccnc(N[C@H]2CCCN(C(=O)OC(C)(C)C)C2)n1]

To a mixture of tert-butyl (3S)-3-[[4-[2-[(4-amino-3-fluoro-2-methyl-1-naphthyl)oxy]-3-pyridyl]pyrimidin-2-yl]amino]piperidine-1-carboxylate (180 mg, 331 µmol) and NMM (109 µL) in CHCl₃ (2 mL) was added 3,3,3-trifluoropropane-1-sulfonyl chloride (65 mg, 331 µmol) in portions at 0° C. The mixture was stirred at 30° C. for 2 hrs. LCMS showed that the reaction was complete. The mixture was concentrated in vacuo. The residue was purified by prep-HPLC to afford tert-butyl (3S)-3-[[4-[2-[[3-fluoro-2-methyl-4-(3,3,3-trifluoropropylsulfonylamino)-1-naphthyl]oxy]-3-pyridyl]pyrimidin-2-yl]amino]piperidine-1-carboxylate (139 mg, 43% yield) as a yellow solid.

Step 2: (S)-3,3,3-Trifluoro-N-(2-fluoro-3-methyl-4-((3-(2-(piperidin-3-ylamino)pyrimidin-4-yl)pyridin-2-yl)oxy)naphthalen-1-yl)propane-1-sulfonamide 482

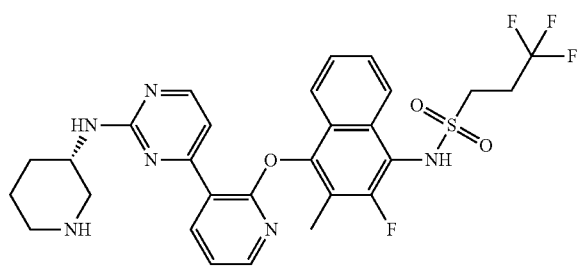 [SMILES: Cc1c(F)c(NS(=O)(=O)CCC(F)(F)F)c2ccccc2c1Oc1ncccc1-c1ccnc(N[C@H]2CCCNC2)n1]

To a solution of tert-butyl (3S)-3-[[4-[2-[[3-fluoro-2-methyl-4-(3,3,3-trifluoropropylsulfonylamino)-1-naphthyl]oxy]-3-pyridyl]pyrimidin-2-yl]amino]piperidine-1-carboxylate (184 mg, 261 µmol) in EtOAc (5 mL) and added HCl/EtOAc (5 mL) at 18° C. for 1 hr. The reaction mixture was concentrated in vacuum and was purified by prep-HPLC to afford 47 mg of the title compound (28% yield) as a yellow solid and as a HCl salt. LCMS (ESI) [M+H]⁺=605.1; ¹H NMR (400 MHz, CD₃OD) δ 8.84 (br s, 1H), 8.52 (d, J=6.2 Hz, 1H), 8.34 (d, J=8.6 Hz, 1H), 8.16 (brs, 1H), 8.01 (br s, 1H), 7.73 (d, J=8.4 Hz, 1H), 7.63 (t, J=7.8 Hz, 1H), 7.43-7.50 (m, 1H), 7.38 (brd, J=6.0 Hz, 1H), 4.59 (br s, 1H), 3.69 (br d, J=12.23 Hz, 1H), 3.49-3.58 (m, 2H), 3.42 (b s, 1H), 3.03-3.20 (m, 2H), 2.84-2.98 (m, 2H), 2.28 (s, 4H), 2.11-2.21 (m, 1H), 1.83-2.01 (m, 2H).

Example 483 N-(4-((3-(2-(((1r,4r)-4-Aminocyclohexyl)amino)pyrimidin-4-yl)pyridin-2-yl)oxy)-2-fluoro-3-methylnaphthalen-1-yl)-3,3,3-trifluoropropane-1-sulfonamide 483

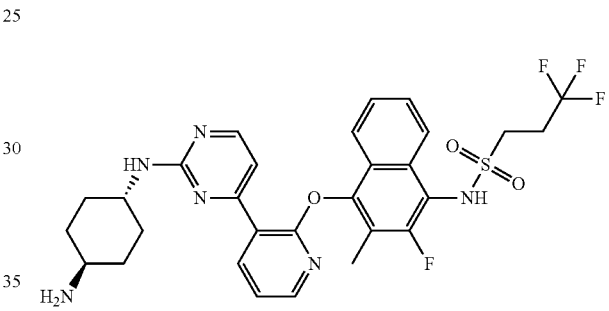

Step 1: tert-Butyl ((1r,4r)-4-((4-(2-((4-amino-3-fluoro-2-methylnaphthalen-1-yl)oxy)pyridin-3-yl)pyrimidin-2-yl)amino)cyclohexyl)carbamate

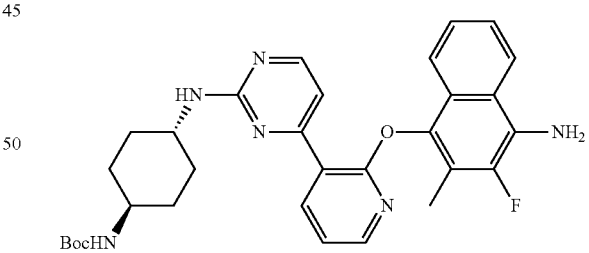

To a mixture of tert-butyl ((1r,4r)-4-((4-(2-((4-amino-2-methylnaphthalen-1-yl)oxy) pyridin-3-yl)pyrimidin-2-yl)amino)cyclohexyl)carbamate (562 mg, 1.039 mmol) and TEA (288 µL, 2.078 mmol) in NMP (5 mL)/EtOH (5 mL) was added selectfluor (970 mg, 2.73 mmol) in portions. The mixture was stirred at 15° C. for 12 hrs. LCMS showed the reaction was complete. H₂O was added to the mixture and the mixture was filtered. The residue was dried and purified by silica gel chromatography (PE/EtOAc=10/1, 5/1, 3/1, 1/1) to afford 180 mg (31% yield) of the title compound as a black brown solid.

Step 2: tert-Butyl ((1r,4r)-4-((4-(2-((3-fluoro-2-methyl-4-((3,3,3-trifluoropropyl) sulfonamido)naphthalen-1-yl)oxy)pyridin-3-yl)pyrimidin-2-yl)amino)cyclohexyl)carbamate

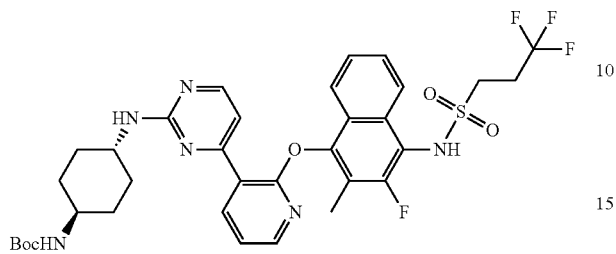

To a mixture of tert-butyl ((1r,4r)-4-((4-(2-((4-amino-3-fluoro-2-methylnaphthalen-1-yl)oxy)pyridin-3-yl)pyrimidin-2-yl)amino)cyclohexyl)carbamate (180 mg, 322 μmol) and NMM (109 μL, 992 μmol) in CHCl$_3$ (2 mL) was added 3,3,3-trifluoropropane-1-sulfonyl chloride (63.3 mg, 322 μmol) in portions at 0° C. The mixture was stirred at 30° C. for 2 hrs. LCMS showed that the reaction was complete. The mixture was concentrated in vacuo. The residue was purified by prep-HPLC to afford 140 mg of the title compound (68% yield) as a brown solid.

Step 3: N-(4-((3-(2-(((1r,4r)-4-Aminocyclohexyl)amino)pyrimidin-4-yl)pyridin-2-yl)oxy)-2-fluoro-3-methylnaphthalen-1-yl)-3,3,3-trifluoropropane-1-sulfonamide 483

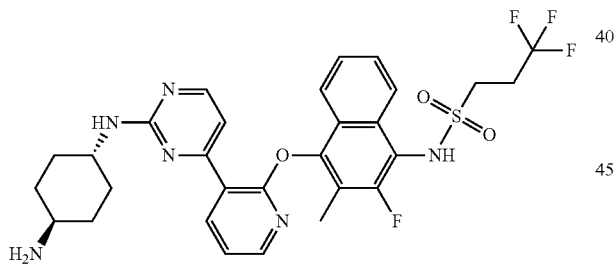

To a solution of tert-butyl ((1r,4r)-4-((4-(2-((3-fluoro-2-methyl-4-((3,3,3-trifluoropropyl) sulfonamido)naphthalen-1-yl)oxy)pyridin-3-yl)pyrimidin-2-yl)amino)cyclohexyl)carbamate (139 mg, 194 μmol,) in EtOAc (5 mL) and added HCl/EtOAc (5 mL) at 18° C. for 1 hr. The reaction mixture was concentrated in vacuum. The residue was purified by prep-HPLC to afford the title compound (33 mg, 26% yield) as a yellow solid and as a HCl salt. LCMS (ESI) [M+H]$^+$=619.2; $^1$H NMR (400 MHz, CD$_3$OD) δ 8.73 (br d, J=7.5 Hz, 1H), 8.44 (br d, J=6.4 Hz, 1H), 8.34 (d, J=8.6 Hz, 1H), 8.17 (br s, 1H), 7.95 (br d, J=6.1 Hz, 1H), 7.76 (br d, J=8.9 Hz, 1H), 7.63 (br t, J=7.6 Hz, 1H), 7.44-7.51 (m, 1H), 7.34-7.40 (m, 1H), 4.16 (br s, 1H), 3.47-3.61 (m, 2H), 3.20 (br s, 1H), 2.83-2.98 (m, 2H), 2.28 (s, 5H), 2.16 (br s, 2H), 1.47-1.71 (m, 4H).

Example 484 1-(4-Cyanophenyl)-N-(2-fluoro-5-((3-(2-(((3S,5S)-5-fluoropiperidin-3-yl)amino)pyrimidin-4-yl)pyridin-2-yl)oxy)-6-methylnaphthalen-1-yl)methanesulfonamide hydrochloride Step 1: tert-Butyl 3-((4-(2-((5-((4-cyanophenyl)methylsulfonamido)-6-fluoro-2-methylnaphthalen-1-yl)oxy)pyridin-3-yl)pyrimidin-2-yl)amino)-5-fluoropiperidine-1-carboxylate

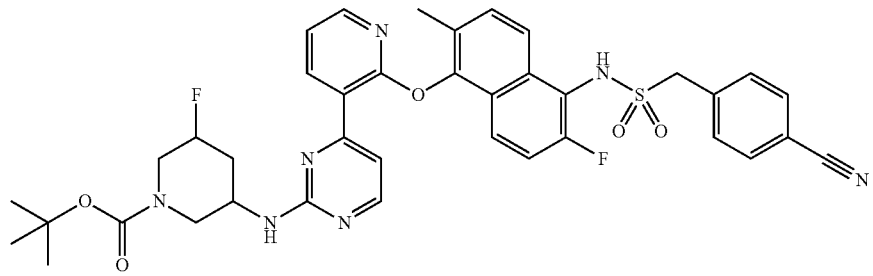 [SMILES: Cc1ccc2c(NS(=O)(=O)Cc3ccc(C#N)cc3)c(F)ccc2c1Oc1ncccc1-c1ccnc(NC2CC(F)CN(C(=O)OC(C)(C)C)C2)n1]

The General Procedure A was followed using tert-butyl trans-3-[[4-[2-[(5-amino-6-fluoro-2-methyl-1-naphthyl)oxy]-3-pyridyl]pyrimidin-2-yl]amino]-5-fluoro-piperidine-1-carboxylate from Example 322 (250 mg, 0.44 mmol), pyridine (0.54 mL), $CH_2Cl_2$ (1.5 mL) and (4-cyanophenyl)methanesulfonyl chloride (192 mg, 0.89 mmol). After 18 h, the mixture was concentrated in vacuo and the crude was purified by flash chromatography through silica gel (0-50% EtOAc/$CH_2Cl_2$) to provide 210 mg (64% yield) of the title compound. LCMS (ESI) $[M+H]^+$=742.4.

Step 2: (3R,5R)-tert-Butyl 3-((4-(2-((5-((4-cyanophenyl)methylsulfonamido)-6-fluoro-2-methylnaphthalen-1-yl)oxy)pyridin-3-yl)pyrimidin-2-yl)amino)-5-fluoropiperidine-1-carboxylate (Isomer-1) and (3S,5S)-tert-butyl 3-((4-(2-((5-((4-cyanophenyl)methylsulfonamido)-6-fluoro-2-methylnaphthalen-1-yl)oxy)pyridin-3-yl)pyrimidin-2-yl)amino)-5-fluoropiperidine-1-carboxylate (Isomer-2)

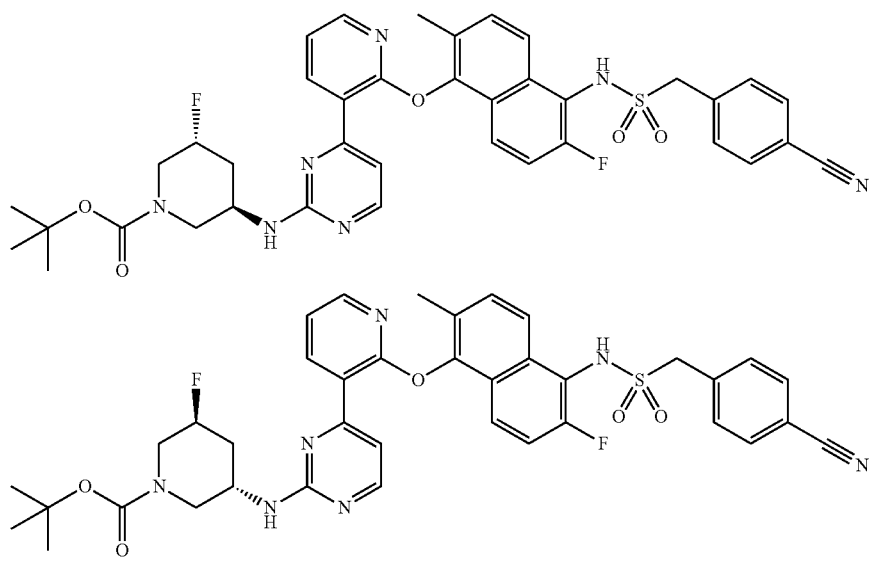

The stereoisomers from Step 1 were subjected to chiral SFC purification (conditions: Lux Cellulose-4, 10×250 mm 5 um, Isocratic 50% MeOH, 10 mL/min, 150 bar.) to provide two trans piperidine enantiomers. Isomer-1: (3R,5R)-tert-butyl 3-((4-(2-((5-((4-cyanophenyl)methylsulfonamido)-6-fluoro-2-methylnaphthalen-1-yl)oxy)pyridin-3-yl)pyrimidin-2-yl)amino)-5-fluoropiperidine-1-carboxylate, 98 mg (47% yield), ee=99.7%; and Isomer-2: (3S,5S)-tert-butyl 3-((4-(2-((5-((4-cyanophenyl)methylsulfonamido)-6-fluoro-2-methylnaphthalen-1-yl)oxy)pyridin-3-yl)pyrimidin-2-yl)amino)-5-fluoropiperidine-1-carboxylate, 98 mg (47% yield), ee=98.8%.

Step 3: 1-(4-Cyanophenyl)-N-(2-fluoro-5-((3-(2-(((3S,5S)-5-fluoropiperidin-3-yl)amino)pyrimidin-4-yl)pyridin-2-yl)oxy)-6-methylnaphthalen-1-yl)methanesulfonamide hydrochloride (Isomer-2)

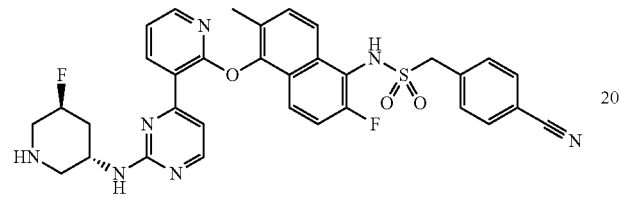

Prepared according to General Procedure B using (3S,5S)-tert-butyl 3-((4-(2-((5-((4-cyanophenyl)methylsulfonamido)-6-fluoro-2-methylnaphthalen-1-yl)oxy)pyridin-3-yl)pyrimidin-2-yl)amino)-5-fluoropiperidine-1-carboxylate (96 mg, 0.13 mmol), 1,4-dioxane (1.5 mL), and hydrochloric acid (4 M in dioxane, 2 mL, 8.0 mmol). After 1 h, the mixture was diluted with MTBE and the resulting solids collected by filtration then dissolved in $H_2O$ and MeCN and lyophilized to provide 83 mg (94% yield) of 484. LCMS (ESI) [M+H]$^+$=642.2; $^1$H NMR (400 MHz, DMSO-$d_6$) δ 9.93 (s, 1H), 9.79 (s, 1H), 8.73 (br, 1H), 8.48 (d, J=5.2 Hz, 1H), 8.07 (d, J=3.0 Hz, 1H), 7.96 (d, J=8.7 Hz, 1H), 7.88 (d, J=8.3 Hz, 2H), 7.67 (ddd, J=32.9, 16.9, 7.0 Hz, 6H), 7.47 (t, J=9.5 Hz, 1H), 7.28 (dd, J=7.5, 4.8 Hz, 1H), 5.22 (d, J=46.5 Hz, 1H), 4.70 (s, 2H), 4.50 (s, 1H), 3.48 (s, 2H), 3.22 (d, J=41.1 Hz, 1H), 2.81 (d, J=10.4 Hz, 1H), 2.34 (s, 1H), 2.17 (s, 3H), 1.92 (dt, J=44.5, 12.0, Hz, 1H). The absolute stereochemistry of the fluoropiperidine was assigned based on the potency in the cellular assay.

Example 485 3,3-Difluoro-N-[2-fluoro-6-methyl-5-[[3-[2-[[(3S,5R)-5-methyl-3-piperidyl]amino]pyrimidin-4-yl]-2-pyridyl]oxy]-1-naphthyl]butane-1-sulfonamide hydrochloride Step 1: Benzyl (3S,5R)-3-[[4-[2-[[5-(3,3-difluorobutylsulfonylamino)-6-fluoro-2-methyl-1-naphthyl]oxy]-3-pyridyl]pyrimidin-2-yl]amino]-5-methyl-piperidine-1-carboxylate

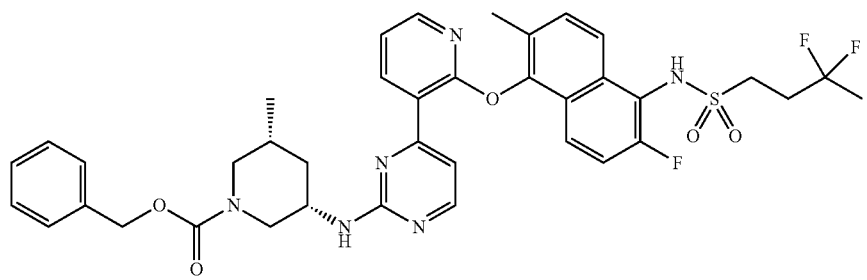 [SMILES: Cc1ccc2c(NS(=O)(=O)CCC(C)(F)F)c(F)ccc2c1Oc1ncccc1-c1ccnc(N[C@H]2C[C@@H](C)CN(C(=O)OCc3ccccc3)C2)n1]

The General Procedure A was followed using benzyl (3S,5R)-3-[[4-[2-[(5-amino-6-fluoro-2-methyl-1-naphthyl)oxy]-3-pyridyl]pyrimidin-2-yl]amino]-5-methyl-piperidine-1-carboxylate from Example 431 (80 mg, 0.13 mmol), pyridine (0.33 mL) and 3,3-difluorobutane-1-sulfonyl chloride (39 mg, 0.20 mmol). After 16 hours, the crude mixture was diluted with MeOH (10 mL) and volatiles were removed in vacuo. The crude was purified by flash chromatography through silica gel (silica gel was pretreated with TEA, 45-100% EtOAc/hexanes) to provide 73 mg (72% yield) of the title compound. LCMS (ESI) [M+H]$^+$=749.3.

Step 2: 3,3-Difluoro-N-[2-fluoro-6-methyl-5-[[3-[2-[[(3S,5R)-5-methyl-3-piperidyl]amino]pyrimidin-4-yl]-2-pyridyl]oxy]-1-naphthyl]butane-1-sulfonamide hydrochloride 485

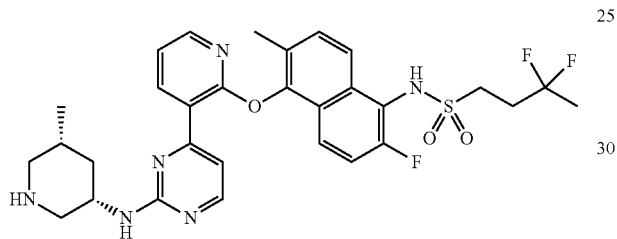

Prepared according to General Procedure H using benzyl (3S,5R)-3-[[4-[2-[[5-(3,3-difluorobutylsulfonylamino)-6-fluoro-2-methyl-1-naphthyl]oxy]-3-pyridyl]pyrimidin-2-yl]amino]-5-methyl-piperidine-1-carboxylate (73 mg, 0.10 mmol), ammonium formate (185 mg, 2.9 mmol), Pd/C (10% on charcoal, 30 mg) and IPA (2.0 mL). After 30 min at 80° C., the reaction was filtered through a pad of Celite and washed with MeOH. The filtrated was concentrated in vacuo and dissolved in a mixture of EtOAc (5 mL) and water (3 mL) and Na$_2$CO$_3$ (saturated, 0.5 mL). The organic layer was separated and the aqueous was extracted with EtOAc (5 mL). The organic extracts were combined, dried over Na$_2$SO$_4$ filtered and concentrated in vacuo. The resulting residue was dissolved in 1,4-dioxane (2 mL) and to the solution was added HCl (4 M in dioxane, 100 uL) and MTBE (5 mL) with stirring. The suspension was filtered and the precipitate was washed with MTBE to provide 25 mg (39%) of 485 after lyophilization. LCMS (ESI) [M+H]$^+$=615.2; $^1$H NMR (400 MHz, DMSO-d$_6$) 9.96 (s, 1H), 8.95 (m, br, 2H), 8.45 (d, J=5.2 Hz, 1H), 8.07-8.00 (m, 2H), 7.72 (dd, J=9.2, 5.0 Hz, 1H), 7.63 (d, J=8.8 Hz, 1H), 7.54 (d, J=7.6 Hz, 2H), 7.46 (t, J=9.5 Hz, 1H), 7.27 (dd, J=7.6, 4.8 Hz, 1H), 4.35-4.15 (m, 1H), 3.33 (d, J=8.7 Hz, 2H), 3.18 (d, J=11.3 Hz, 1H), 2.66-2.54 (m, 1H), 2.18 (s, 3H), 2.08-1.86 (m, 2H), 1.69 (t, J=19.1 Hz, 3H), 1.26 (t, J=12.2 Hz, 1H), 0.86 (br, 3H).

Example 486 2,2-Difluoro-N-[2-fluoro-6-methyl-5-[[3-[2-[[(3S,5R)-5-methyl-3-piperidyl]amino]pyrimidin-4-yl]-2-pyridyl]oxy]-1-naphthyl]butane-1-sulfonamide hydrochloride Step 1: Benzyl (3S,5R)-3-[[4-[2-[[5-(2,2-difluorobutylsulfonylamino)-6-fluoro-2-methyl-1-naphthyl]oxy]-3-pyridyl]pyrimidin-2-yl]amino]-5-methyl-piperidine-1-carboxylate

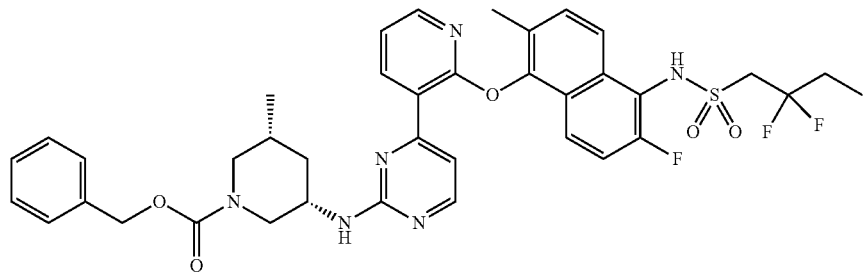 [SMILES: CCC(F)(F)CS(=O)(=O)Nc1c(F)ccc2c(Oc3ncccc3-c3ccnc(N[C@H]4C[C@@H](C)CN(C(=O)OCc5ccccc5)C4)n3)c(C)ccc12]

The General Procedure A was followed using benzyl (3S,5R)-3-[[4-[2-[(5-amino-6-fluoro-2-methyl-1-naphthyl)oxy]-3-pyridyl]pyrimidin-2-yl]amino]-5-methyl-piperidine-1-carboxylate from Example 431 (80 mg, 0.13 mmol), pyridine (0.33 mL) and 2,2-difluorobutane-1-sulfonyl chloride (41 mg, 0.21 mmol). After 16 hours, the crude mixture was diluted with MeOH (10 mL) and the volatiles were removed in vacuo. The crude was purified by flash chromatography through silica gel (silica gel was pretreated with TEA, 45-100% EtOAc/hexanes) to provide 56 mg (52% yield) of the title compound. LCMS (ESI) [M+H]$^+$=749.4.

Step 2: 2,2-Difluoro-N-[2-fluoro-6-methyl-5-[[3-[2-[[(3S,5R)-5-methyl-3-piperidyl]amino]pyrimidin-4-yl]-2-pyridyl]oxy]-1-naphthyl]butane-1-sulfonamide hydrochloride 486

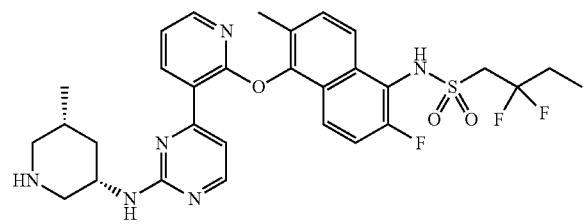 [SMILES: CCC(F)(F)CS(=O)(=O)Nc1c(F)ccc2c(Oc3ncccc3-c3ccnc(N[C@@H]4CNC[C@H](C)C4)n3)c(C)ccc12]

Prepared according to General Procedure H using benzyl (3S,5R)-3-[[4-[2-[[5-(3,3-difluorobutylsulfonylamino)-6-fluoro-2-methyl-1-naphthyl]oxy]-3-pyridyl]pyrimidin-2-yl]amino]-5-methyl-piperidine-1-carboxylate (56 mg, 0.07 mmol), ammonium formate (141 mg, 2.9 mmol), Pd/C (10% on charcoal, 30 mg) and IPA (2.0 mL). After 30 min at 80° C., the reaction was filtered through a pad of Celite and washed with MeOH. The filtrate was concentrated in vacuo and dissolved in a mixture of EtOAc (5 mL) and water (3 mL) and Na$_2$CO$_3$ (saturated, 0.5 mL). The organic layer was separated and the aqueous was extracted with EtOAc (5 mL). The organic extracts were combined and dried over Na2SO$_4$, filtered and concentrated in vacuo. The resulting residue was dissolved in 1,4-dioxane (2 mL) and to the solution was added HCl (4 M in dioxane, 100 uL) and MTBE (5 mL) with stirring. The suspension was filtered and the precipitate was washed with MTBE to provide 27 mg (55% yield) of 486 after lyophilization. LCMS (ESI) [M+H]$^+$=615.2; $^1$H NMR (400 MHz, DMSO-d$_6$) 10.11 (s, 1H), 9.05-8.85 (m, 3H), 8.45 (d, J=5.2 Hz, 1H), 8.10-7.98 (m, 2H), 7.72 (dd, J=9.3, 5.1 Hz, 1H), 7.63 (d, J=8.8 Hz, 1H), 7.53 (d, J=7.4 Hz, 2H), 7.46 (t, J=9.5 Hz, 1H), 7.27 (dd, J=7.6, 4.8 Hz, 1H), 4.26 (s, br, 1H), 4.00 (t, J=14.0 Hz, 2H), 3.17 (s, 1H), 2.18 (s, 3H), 2.14-2.00 (m, 3H), 1.89 (s, 1H), 1.24 (d, J=12.3 Hz, 1H), 0.94 (m, 6H).

Example 487 N-(2-Fluoro-6-methyl-5-((3-(2-(((3S,5R)-5-methylpiperidin-3-yl)amino)pyrimidin-4-yl)pyridin-2-yl)oxy)naphthalen-1-yl)-1-(1-fluorocyclopropyl)methanesulfonamide hydrochloride Step 1: (3S,5R)-Benzyl 3-((4-(2-((6-fluoro-5-((1-fluorocyclopropyl)methylsulfonamido)-2-methylnaphthalen-1-yl)oxy)pyridin-3-yl)pyrimidin-2-yl)amino)-5-methylpiperidine-1-carboxylate

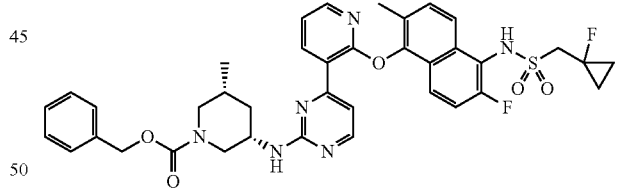

The General Procedure A was followed using benzyl (3S,5R)-3-[[4-[2-[(5-amino-6-fluoro-2-methyl-1-naphthyl)oxy]-3-pyridyl]pyrimidin-2-yl]amino]-5-methyl-piperidine-1-carboxylate from Example 431 (85 mg, 0.14 mmol) pyridine (0.35 mL, 4.3 mmol).), DCM (0.5 mL) and (1-fluorocyclopropyl)methanesulfonyl chloride (37 mg, 0.21 mmol). After 18 h, the mixture was concentrated in vacuo and co-evaporated with MeOH. The crude was purified by flash chromatography through silica gel (0-50% EtOAc/CH$_2$Cl$_2$) to provide 68 mg (65% yield) of the title compound. LCMS (ESI) [M+H]$^+$=729.4

Step 2: N-(2-Fluoro-6-methyl-5-((3-(2-(((3S,5R)-5-methylpiperidin-3-yl)amino)pyrimidin-4-yl)pyridin-2-yl)oxy)naphthalen-1-yl)-1-(1-fluorocyclopropyl)methanesulfonamide hydrochloride 487

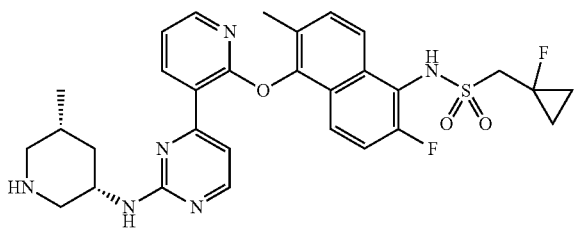

In a flask containing (3S,5R)-benzyl 3-((4-(2-((6-fluoro-5-((1-fluorocyclopropyl)methylsulfonamido)-2-methylnaphthalen-1-yl)oxy)pyridin-3-yl)pyrimidin-2-yl)amino)-5-methylpiperidine-1-carboxylate (68 mg, 0.09 mmol) was added DCM (0.3 mL), MeCN (0.3 mL), dimethyl sulfide (0.27 mL, 3.73 mmol) and boron trifluoride diethyl etherate (0.24 mL, 1.87 mmol) in that order. After 1 h, the mixture was dissolved in ethyl acetate and aqueous saturated sodium bicarbonate solution was added. The phases were separated and the organic phase was washed with brine then dried over magnesium sulfate, filtered and concentrated in vacuo. The residue was dissolved in dioxane (2 mL) and then hydrochloric acid (4 M in dioxane (0.2 mL) was added. After 10 minutes, the reaction was diluted with dioxane (2 mL) and the resulting solids were collected by filtration then dissolved in H$_2$O and MeCN and lyophilized to provide 42 mg (71% yield) of 487. LCMS (ESI) [M+H]$^+$=595.2, $^1$H NMR (400 MHz, DMSO-d$_6$) δ 9.87 (s, 1H), 9.08 (m, br, 2H), 8.45 (d, J=5.2 Hz, 1H), 8.06 (dd, J=5.0, 2.1 Hz, 3H), 7.70 (dd, J=9.2, 5.1 Hz, 1H), 7.62 (d, J=8.8 Hz, 1H), 7.56 (d, J=7.5 Hz, 2H), 7.50-7.40 (m, 2H), 7.27 (dd, J=7.6, 4.8 Hz, 1H), 3.81 (d, J=21.4 Hz, 2H), 3.47 (s, 1H), 3.18 (d, J=11.0 Hz, 1H), 2.62 (d, J=22.7 Hz, 1H), 2.18 (s, 3H), 2.01 (t, J=22.5 Hz, 3H), 1.73-1.51 (m, 1H), 1.31-1.08 (m, 4H), 0.93 (d, J=6.6 Hz, 5H).

Example 488 (S)-1-Cyclopropyl-2-((6-methyl-5-((3-(2-((S)-piperidin-3-ylamino)pyrimidin-4-yl)pyridin-2-yl)oxy)naphthalen-1-yl)amino)ethanol hydrochloride (Isomer-1)

Step 1: (S)-tert-Butyl 3-((4-(2-((5-((2-cyclopropyl-2-oxoethyl)amino)-2-methylnaphthalen-1-yl)oxy)pyridin-3-yl)pyrimidin-2-yl)amino)piperidine-1-carboxylate

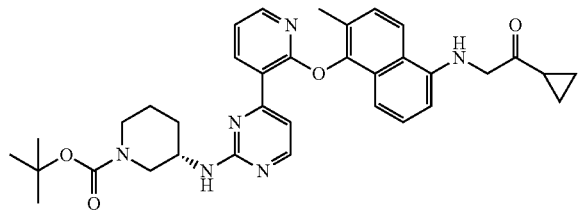 [SMILES: Cc1ccc2c(NCC(=O)C3CC3)cccc2c1Oc1ncccc1-c1ccnc(N[C@H]2CCCN(C(=O)OC(C)(C)C)C2)n1]

A flask was charged with tert-butyl (3S)-3-[[4-[2-[(5-amino-2-methyl-1-naphthyl)oxy]-3-pyridyl]pyrimidin-2-yl]amino]piperidine-1-carboxylate (527 mg, 1.0 mmol), 2-bromo-1-cyclopropyl-ethanone (500 mg, 3.07 mmol), DMF (5 mL), and potassium carbonate (277 mg, 2.0 mmol) in that order. The mixture was stirred at 25° C. for 4 h then 10 mM aqueous ammonium formate (0.12 mL, 1.2 mmol) was added to quench the reaction. The crude mixture was directly purified by C18 reverse phase flash chromatography (50-85% MeCN/10 mM aqueous ammonium formate, pH=3.8). Appropriate fractions were combined and lyophilized to provide 415 mg (46% yield) of the title compound as an orange solid. LCMS (ESI) [M+H]$^+$=609.2.

Step 2: (3S)-tert-Butyl 3-((4-(2-((5-((2-cyclopropyl-2-hydroxyethyl)amino)-2-methylnaphthalen-1-yl)oxy)pyridin-3-yl)pyrimidin-2-yl)amino)piperidine-1-carboxylate

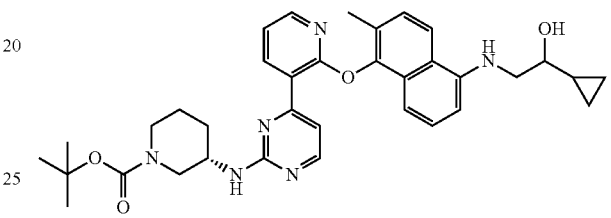

In a flask containing (S)-tert-butyl 3-((4-(2-((5-((2-cyclopropyl-2-oxoethyl)amino)-2-methylnaphthalen-1-yl)oxy)pyridin-3-yl)pyrimidin-2-yl)amino)piperidine-1-carboxylate (363 mg, 0.60 mmol) was added THF (5 mL), water (1 mL) followed by sodium borohydride (345 mg, 9.12 mmol) portionwise at rt. After 30 min, a solution of saturated aqueous ammonium chloride (10 mL) was added slowly, then diluted with EtOAc (50 mL) and the phases were separated. The organic phase was washed with a solution of saturated aqueous ammonium chloride (10 mL), then brine, dried over magnesium sulfate, filtered and concentrated to dryness. MeOH (50 mL) was added and the solution was refluxed for 1 h then concentrated to dryness. The crude product was purified by C18 reverse phase flash chromatography (40-90% MeCN/10 mM aqueous ammonium formate, pH=3.8). Appropriate fractions were combined and lyophilized to provide 169 mg (46% yield) of the title compound as a pale yellow solid. LCMS (ESI) [M+H]$^+$=611.3.

Step 3: (S)-tert-Butyl 3-((4-(2-((5-(((S)-2-cyclopropyl-2-hydroxyethyl)amino)-2-methylnaphthalen-1-yl)oxy)pyridin-3-yl)pyrimidin-2-yl)amino)piperidine-1-carboxylate (Isomer 1) and (S)-tert-butyl 3-((4-(2-((5-(((R)-2-cyclopropyl-2-hydroxyethyl)amino)-2-methylnaphthalen-1-yl)oxy)pyridin-3-yl)pyrimidin-2-yl)amino)piperidine-1-carboxylate (Isomer 2)

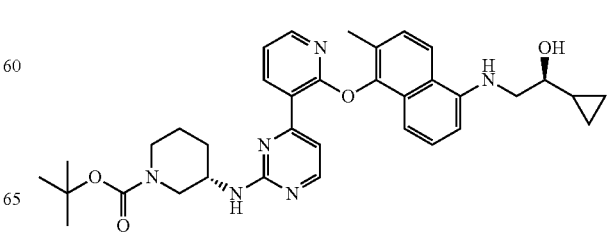

791
-continued

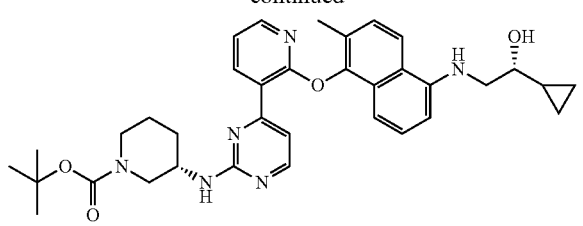

The stereoisomers from Step 2 were subjected to chiral SFC purification (IB (250 mm×10 mm, 5 μm); IPA 40%; flow rate (ml/min): 10, 100 bar, 35° C.) to provide two stereoisomers enantiomeric at the alcohol position. Isomer-1: (S)-tert-butyl 3-((4-(2-((5-(((S)-2-cyclopropyl-2-hydroxyethyl)amino)-2-methylnaphthalen-1-yl)oxy)pyridin-3-yl)pyrimidin-2-yl)amino)piperidine-1-carboxylate, 80 mg (48%), ee=99.1%, LCMS (ESI) [M+H]$^+$=611.2; and Isomer-2: (S)-tert-butyl 3-((4-(2-((5-(((R)-2-cyclopropyl-2-hydroxyethyl)amino)-2-methylnaphthalen-1-yl)oxy)pyridin-3-yl)pyrimidin-2-yl)amino)piperidine-1-carboxylate, 80 mg (48%), ee=99.7%, LCMS (ESI) [M+H]$^+$=611.2.

Step 4: (S)-1-Cyclopropyl-2-((6-methyl-5-((3-(2-((S)-piperidin-3-ylamino)pyrimidin-4-yl)pyridin-2-yl)oxy)naphthalen-1-yl)amino)ethanol hydrochloride (Isomer 1) 488

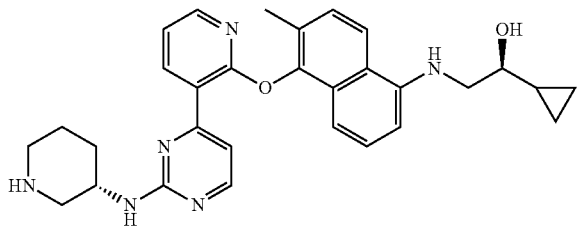

Prepared according to General Procedure B using (S)-tert-butyl 3-((4-(2-((5-(((S)-2-cyclopropyl-2-hydroxyethyl)amino)-2-methylnaphthalen-1-yl)oxy)pyridin-3-yl)pyrimidin-2-yl)amino)piperidine-1-carboxylate (80 mg, 0.13 mmol), EtOAc (1 mL) and hydrochloric acid (4 M in dioxane, 1 mL, 4.0 mmol). After 1 h, the resulting solids were collected by filtration then dissolved in H$_2$O and MeCN and lyophilized to provide 65 mg (91% yield) of 488. LCMS (ESI) [M+H]$^+$=511.2; $^1$H NMR (400 MHz, DMSO-d$_6$) δ 9.56 (s, 1H), 9.26 (s, 1H), 8.86 (s, 1H), 8.51 (d, J=5.4 Hz, 1H), 8.11 (s, 1H), 8.10-8.00 (m, 2H), 7.73 (s, 1H), 7.59 (s, 1H), 7.47 (d, J=8.8 Hz, 2H), 7.33-7.22 (m, 2H), 7.14 (d, J=7.6 Hz, 1H), 6.93 (s, 1H), 4.36 (br m, 1H), 3.51-3.32 (m, 3H), 3.27 (dd, J=11.5, 7.5 Hz, 1H), 3.19 (d, J=11.4 Hz, 1H), 2.92-2.76 (m, 2H), 2.20 (s, 3H), 2.03 (d, J=9.6 Hz, 1H), 1.96-1.87 (m, 1H), 1.80 (s, 1H), 1.66 (s, 1H), 1.00-0.89 (m, 1H), 0.44-0.36 (m, 2H), 0.35-0.29 (m, 1H), 0.29-0.22 (m, 1H). The absolute stereochemistry of the amino alcohol was randomly assigned.

Example 489 (R)-1-Cyclopropyl-2-((6-methyl-5-((3-(2-((S)-piperidin-3-ylamino)pyrimidin-4-yl)pyridin-2-yl)oxy) naphthalen-1-yl)amino)ethanol hydrochloride (Isomer-2)

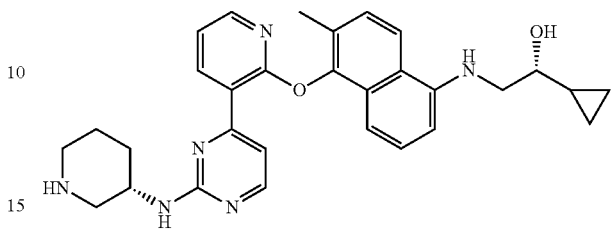

Prepared according General Procedure B using (S)-tert-butyl 3-((4-(2-((5-(((R)-2-cyclopropyl-2-hydroxyethyl)amino)-2-methylnaphthalen-1-yl)oxy)pyridin-3-yl)pyrimidin-2-yl)amino)piperidine-1-carboxylate (80 mg, 0.13 mmol), EtOAc (1 mL) and hydrochloric acid (4 M in dioxane, 1 mL, 4.0 mmol). After 1 h, the resulting solids were collected by filtration and then dissolved in H$_2$O and MeCN. Lyophilization provided 67 mg (93% yield) of the title compound 489. LCMS (ESI) [M+H]$^+$=511.2, $^1$H NMR (400 MHz, DMSO-d$_6$) δ 9.80 (s, 1H), 9.40 (s, 1H), 8.94 (s, 1H), 8.54 (s, 1H), 8.43 (s, 1H), 8.10 (d, J=8.6 Hz, 2H), 7.82 (s, 1H), 7.61 (s, 1H), 7.53 (d, J=8.7 Hz, 2H), 7.39-7.25 (m, 3H), 7.19 (s, 1H), 4.70-4.11 (m, 1H), 3.54-3.36 (m, 3H), 3.36-3.24 (m, 1H), 3.18 (s, 1H), 2.94-2.75 (m, 2H), 2.21 (s, 3H), 2.04 (d, J=9.4 Hz, 1H), 1.90 (s, 1H), 1.85 (s, 1H), 1.68 (s, 1H), 1.00-0.86 (m, 1H), 0.40 (d, J=8.3 Hz, 2H), 0.38-0.30 (m, 1H), 0.28-0.22 (m, 1H). The absolute stereochemistry of the amino alcohol was randomly assigned.

Example 490 N-(2-Fluoro-5-((3-(2-(((3S,5S)-5-fluoropiperidin-3-yl)amino)pyrimidin-4-yl)pyridin-2-yl) oxy)-6-methylnaphthalen-1-yl)-1-(2-methylthiazol-4-yl)methanesulfonamide hydrochloride 490

Step 1: tert-Butyl 3-fluoro-5-[[4-[2-[[6-fluoro-2-methyl-5-[(2-methylthiazol-4-yl)methylsulfonylamino]-1-naphthyl]oxy]-3-pyridyl]pyrimidin-2-yl]amino]piperidine-1-carboxylate

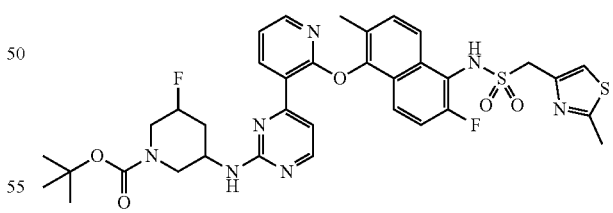

The General Procedure A was followed using tert-butyl trans-3-[[4-[2-[(5-amino-6-fluoro-2-methyl-1-naphthyl) oxy]-3-pyridyl]pyrimidin-2-yl]amino]-5-fluoro-piperidine-1-carboxylate from Example 322 (250 mg, 0.44 mmol), pyridine (0.54 mL), CH$_2$Cl$_2$ (1.5 mL) and (2-methylthiazol-4-yl)methanesulfonyl chloride (0.12 mL, 0.89 mmol). After 18 h, the mixture was diluted with CH$_2$Cl$_2$ (50 mL) and washed with 1M KHSO$_4$ (10 mL), dried by passing through a phase cartridge separator and concentrated in vacuo. The crude was purified by flash chromatography through silica gel (0-50% EtOAc/CH₂Cl₂) to provide 220 mg (67% yield) of the title compound. LCMS (ESI) [M+H]⁺=738.5.

Step 2: (3S,5S)-tert-Butyl 3-fluoro-5-[[4-[2-[[6-fluoro-2-methyl-5-[(2-methylthiazol-4-yl)methyl-sulfonylamino]-1-naphthyl]oxy]-3-pyridyl]pyrimidin-2-yl]amino]piperidine-1-carboxylate (Isomer-1) and (3R,5R)-tert-butyl 3-fluoro-5-[[4-[2-[[6-fluoro-2-methyl-5-[(2-methylthiazol-4-yl)methylsulfonylamino]-1-naphthyl]oxy]-3-pyridyl]pyrimidin-2-yl]amino]piperidine-1-carboxylate (Isomer-2)

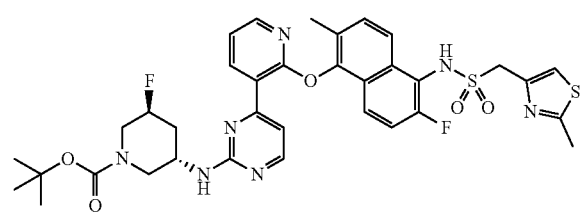 [SMILES: Cc1nc(CS(=O)(=O)Nc2c(F)ccc3c(Oc4ncccc4-c4ccnc(NC5CC(F)CN(C(=O)OC(C)(C)C)C5)n4)c(C)ccc23)cs1]

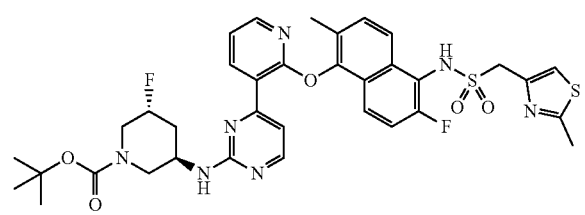

The stereoisomers from Step 1 were subjected to chiral SFC purification (conditions: IA, 10×250 mm 5 um, Isocratic 40% IPA, 10 mL/min, 100 bar.) to provide two trans piperidine enantiomers. Isomer-1): (3S,5S)-tert-butyl 3-fluoro-5-[[4-[2-[[6-fluoro-2-methyl-5-[(2-methylthiazol-4-yl)methylsulfonylamino]-1-naphthyl]oxy]-3-pyridyl]pyrimidin-2-yl]amino]piperidine-1-carboxylate, 70 mg (32% yield), white solid, ee=99%; LCMS (ESI) [M+H]⁺=738.5; and Isomer-2: (3R,5R)-tert-butyl 3-fluoro-5-[[4-[2-[[6-fluoro-2-methyl-5-[(2-methylthiazol-4-yl)methylsulfonylamino]-1-naphthyl]oxy]-3-pyridyl]pyrimidin-2-yl]amino]piperidine-1-carboxylate, 70 mg (32% yield), white solid, ee=99%, LCMS (ESI) [M+H]⁺=738.5.

Step 3: N-(2-Fluoro-5-((3-(2-(((3S,5S)-5-fluoropiperidin-3-yl)amino)pyrimidin-4-yl)pyridin-2-yl)oxy)-6-methylnaphthalen-1-yl)-1-(2-methylthiazol-4-yl)methanesulfonamide hydrochloride 490

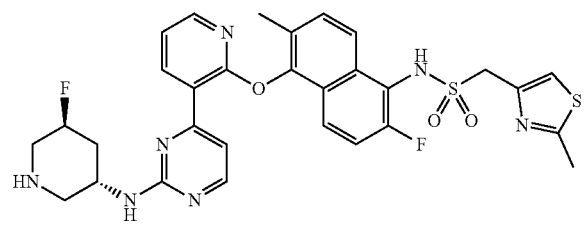 [SMILES: Cc1nc(CS(=O)(=O)Nc2c(F)ccc3c(Oc4ncccc4-c4ccnc(N[C@@H]5CNC[C@@H](F)C5)n4)c(C)ccc23)cs1]

Prepared according to General Procedure B using (3S, 5S)-tert-butyl 3-fluoro-5-[[4-[2-[[6-fluoro-2-methyl-5-[(2-methylthiazol-4-yl)methylsulfonylamino]-1-naphthyl]oxy]-3-pyridyl]pyrimidin-2-yl]amino]piperidine-1-carboxylate (70 mg, 0.095 mmol), 1,4-dioxane (2.0 mL), and hydrochloric acid (4 M in dioxane, 1.5 mL, 6.0 mmol). After 2 h, the mixture was diluted with Et₂O and the resulting solids collected by filtration then dissolved in H₂O and MeCN and lyophilized to provide 63 mg (99% yield) of 490. LCMS (ESI) [M+H]⁺=638.1; ¹H NMR (400 MHz, DMSO-d₆) δ 9.87 (s, 1H), 9.55 (d, J=11.9 Hz, 1H), 9.25 (s, 1H), 8.72 (s, 1H), 8.50 (d, J=5.2 Hz, 1H), 8.09 (dd, J=5.6, 2.7 Hz, 2H), 7.73 (dd, J=9.3, 5.0 Hz, 1H), 7.67 (d, J=7.8 Hz, 1H), 7.62 (d, J=8.8 Hz, 2H), 7.56 (s, 1H), 7.48 (t, J=9.4 Hz, 1H), 7.30 (dd, J=7.6, 4.8 Hz, 1H), 5.25 (d, J=45.7 Hz, 1H), 4.66 (s, 2H), 4.61-4.56 (m, 1H), 3.50 (dd, J=25.5, 13.2 Hz, 2H), 3.25 (dt, J=24.5, 12.8 Hz, 1H), 2.89-2.77 (m, 1H), 2.66 (s, 3H), 2.42-2.29 (m, 1H), 2.19 (s, 3H), 1.93 (dt, J=44.3, 13.1 Hz, 1H). The stereochemistry of the fluoropiperidine was assigned based on the potency in the cellular assay.

Example 491 N-(2-Fluoro-5-((3-(2-(((3R,5R)-5-fluoropiperidin-3-yl)amino)pyrimidin-4-yl)pyridin-2-yl)oxy)-6-methylnaphthalen-1-yl)-1-(2-methylthiazol-4-yl)methanesulfonamide hydrochloride (Isomer-2) 491

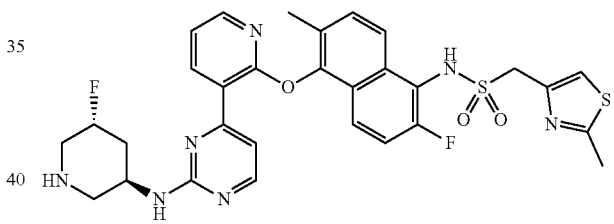

Prepared according to General Procedure B using (3R,5R)-tert-butyl 3-fluoro-5-[[4-[2-[[6-fluoro-2-methyl-5-[(2-methylthiazol-4-yl)methylsulfonylamino]-1-naphthyl]oxy]-3-pyridyl]pyrimidin-2-yl]amino]piperidine-1-carboxylate (70 mg, 0.095 mmol), 1,4-dioxane (2.0 mL), and hydrochloric acid (4 M in dioxane, 1.5 mL, 6.0 mmol). After 2 h, the mixture was diluted with Et₂O and the resulting solids collected by filtration then dissolved in H₂O and MeCN and lyophilized to provide 69 mg (100% yield) of 491. LCMS (ESI) [M+H]⁺=638.2; ¹H NMR (400 MHz, DMSO-d₆) δ 9.85 (s, 1H), 9.60 (d, J=10.0 Hz, 1H), 9.24 (s, 1H), 8.71 (s, 1H), 8.48 (d, J=5.2 Hz, 1H), 8.07 (dd, J=5.6, 2.7 Hz, 2H), 7.71 (dd, J=9.3, 5.1 Hz, 1H), 7.66 (d, J=6.9 Hz, 1H), 7.60 (d, J=8.8 Hz, 2H), 7.54 (s, 1H), 7.46 (t, J=9.4 Hz, 1H), 7.28 (dd, J=7.6, 4.8 Hz, 1H), 5.23 (d, J=45.5 Hz, 1H), 4.64 (s, 2H), 4.50 (s, 1H), 3.59-3.38 (m, 2H), 3.22 (dt, J=40.6, 12.1 Hz, 1H), 2.87-2.74 (m, 1H), 2.64 (s, 3H), 2.41-2.29 (m, 1H), 2.18 (s, 3H), 1.91 (dt, J=24.5, 13.0 Hz, 1H). The stereochemistry of the fluoropiperidine was assigned based on the potency in the cellular assay.

795

Example 492 (3R,5R)—N-(5-Fluoro-3-piperidyl)-4-[2-[[2-methyl-5-[[(2S)-3,3,3-trifluoro-2-methoxy-propyl]amino]-1-naphthyl]oxy]-3-pyridyl]pyrimidin-2-amine hydrochloride (Isomer-1)

Step 1: tert-Butyl 3-fluoro-5-[[4-[2-[[2-methyl-5-[[(2S)-3,3,3-trifluoro-2-hydroxy-propyl]amino]-1-naphthyl]oxy]-3-pyridyl]pyrimidin-2-yl]amino]piperidine-1-carboxylate

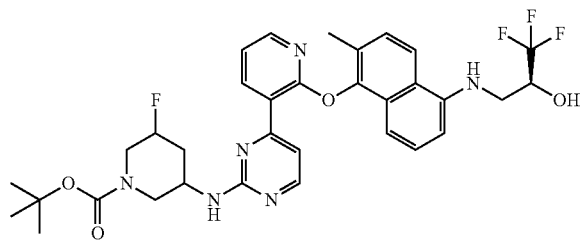 [SMILES: Cc1ccc2c(NC[C@H](O)C(F)(F)F)cccc2c1Oc1ncccc1-c1ccnc(NC2CC(F)CN(C(=O)OC(C)(C)C)C2)n1]

Prepared according to General Procedure F using tert-butyl trans-3-[[4-[2-[(5-amino-6-fluoro-2-methyl-1-naphthyl)oxy]-3-pyridyl]pyrimidin-2-yl]amino]-5-fluoro-piperidine-1-carboxylate from Example 469 (305 mg, 0.56 mmol), (2S)-2-(trifluoromethyl)oxirane (0.07 mL, 0.84 mmol), AcOH (0.5 mL) and the reaction was stirred at rt for 2 days. The crude was concentrated in vacuo and purified by flash chromatography through silica gel (0-50% EtOAc/CH$_2$Cl$_2$) to provide 200 mg (65% yield) of the title compound. LCMS (ESI) [M+H]$^+$=656.3.

Step 2: (3R,5R)-tert-Butyl 3-fluoro-5-((4-(2-((6-fluoro-2-methyl-5-(((S)-3,3,3-trifluoro-2-hydroxypropyl)amino)naphthalen-1-yl)oxy)pyridin-3-yl)pyrimidin-2-yl)amino)piperidine-1-carboxylate (Isomer-1) and (3R,5R)-tert-butyl 3-fluoro-5-((4-(2-((6-fluoro-2-methyl-5-(((S)-3,3,3-trifluoro-2-hydroxypropyl)amino)naphthalen-1-yl)oxy)pyridin-3-yl)pyrimidin-2-yl)amino)piperidine-1-carboxylate (Isomer-2)

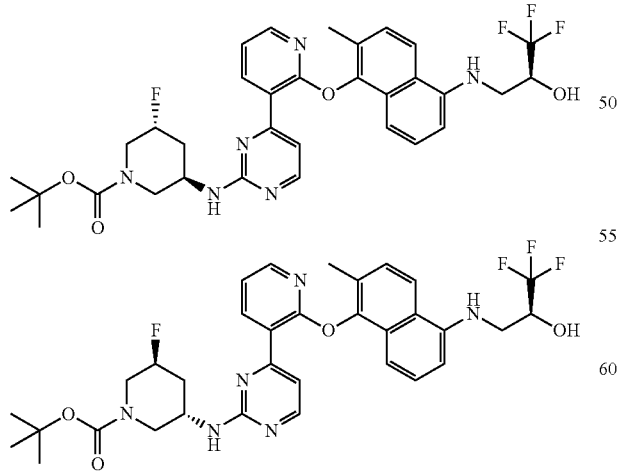

The stereoisomers from Step 1 were subjected to chiral SFC purification (conditions: Lux Cellulose-3, 10×250 mm

796

5 um, Isocratic 25% MeOH, 10 mL/min, 150 bar.) to provide two trans piperidine enantiomers. Isomer-1: (3R,5R)-tert-butyl 3-fluoro-5-((4-(2-((6-fluoro-2-methyl-5-(((S)-3,3,3-trifluoro-2-hydroxypropyl)amino)naphthalen-1-yl)oxy)pyridin-3-yl)pyrimidin-2-yl)amino)piperidine-1-carboxylate, 78 mg (39% yield), white solid, ee=99%, LCMS (ESI) [M+H]$^+$=656.3; and Isomer-2: (3R,5R)-tert-butyl 3-fluoro-5-((4-(2-((6-fluoro-2-methyl-5-(((S)-3,3,3-trifluoro-2-hydroxypropyl)amino)naphthalen-1-yl)oxy)pyridin-3-yl)pyrimidin-2-yl)amino)piperidine-1-carboxylate, 78 mg (39% yield), white solid, ee=99%, LCMS (ESI) [M+H]$^+$=656.3.

Step 3: (3R,5R)-tert-Butyl 3-fluoro-5-((4-(2-((6-fluoro-2-methyl-5-(((S)-3,3,3-trifluoro-2-methoxy-propyl)amino)naphthalen-1-yl)oxy)pyridin-3-yl)pyrimidin-2-yl)amino)piperidine-1-carboxylate (Isomer-1)

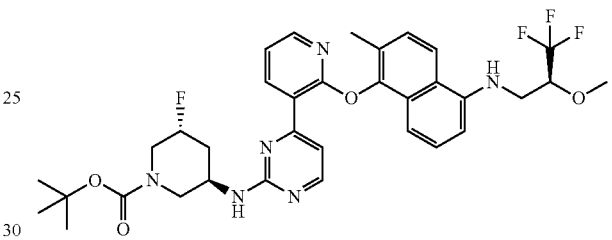

To a solution of (3R,5R)-tert-butyl 3-fluoro-5-((4-(2-((6-fluoro-2-methyl-5-(((S)-3,3,3-trifluoro-2-hydroxypropyl)amino)naphthalen-1-yl)oxy)pyridin-3-yl)pyrimidin-2-yl)amino)piperidine-1-carboxylate (79 mg, 0.12 mmol) in DMF (1 mL) was added cesium carbonate (118 mg, 0.36 mmol) followed by iodomethane (0.01 mL, 0.18 mmol). The reaction is stirred at 75° C. for 30 min then diluted with water (15 mL) and the resulting precipitate was collected by filtration. The solids were dissolved in EtOAc (20 ml) and dried over Na$_2$SO$_4$. The drying reagent was filtered off and the solvent was removed in vacuo to provide 74 mg (91% yield) of the title compound. LCMS (ESI) [M+H]$^+$=671.3.

Step 4: (3R,5R)—N-(5-Fluoro-3-piperidyl)-4-[2-[[2-methyl-5-[[(2S)-3,3,3-trifluoro-2-methoxy-propyl]amino]-1-naphthyl]oxy]-3-pyridyl]pyrimidin-2-amine hydrochloride (Isomer-1) 492

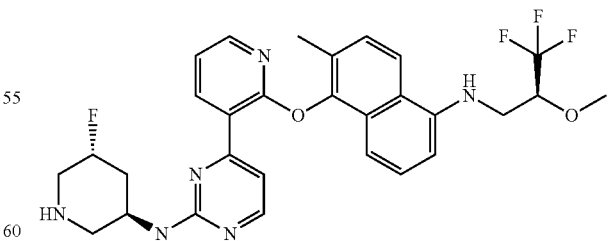

Prepared according to General Procedure B using (3R,5R)-tert-butyl 3-fluoro-5-((4-(2-((6-fluoro-2-methyl-5-(((S)-3,3,3-trifluoro-2-methoxypropyl)amino)naphthalen-1-yl)oxy)pyridin-3-yl)pyrimidin-2-yl)amino)piperidine-1-carboxylate (73 mg, 0.11 mmol), 1,4-dioxane (1.0 mL), and hydrochloric acid (4 M in dioxane, 1.0 mL, 4.0 mmol). After 1 h, the mixture was diluted with Et$_2$O and the resulting solids collected by filtration then dissolved in H$_2$O and MeCN and lyophilized to provide 63 mg (95% yield) of 492. LCMS (ESI) [M+H]$^+$=571.2; $^1$H NMR (400 MHz, DMSO-d$_6$) δ 9.81 (d, J=12.0 Hz, 1H), 8.66-8.78 (m, 2H), 8.47 (d, J=5.3 Hz, 1H), 8.03 (t, J=6.7 Hz, 2H), 7.66 (s, 2H), 7.38 (d, J=8.8 Hz, 1H), 7.28-7.17 (m, 2H), 6.87 (d, J=8.4 Hz, 1H), 6.51 (d, J=7.3 Hz, 1H), 5.23 (d, J=45.4 Hz, 1H), 4.52 (s, 1H), 4.20 (s, 1H), 3.60-3.41 (m, 7H), 3.22 (d, J=40.4 Hz, 1H), 2.81 (d, J=11.3 Hz, 1H), 2.35 (s, 1H), 2.17 (s, 3H), 1.93 (dt, J=44.1, 12.0 Hz, 1H). The stereochemistry of the fluoropiperidine was assigned based on the potency in the cellular assay.

Example 493 (3S,5S)—N-(5-Fluoro-3-piperidyl)-4-[2-[[2-methyl-5-[[(2S)-3,3,3-trifluoro-2-methoxy-propyl]amino]-1-naphthyl]oxy]-3-pyridyl]pyrimidin-2-amine hydrochloride (Isomer-2)

Step 1: (3S,5S)-tert-Butyl 3-fluoro-5-((4-(2-((6-fluoro-2-methyl-5-(((S)-3,3,3-trifluoro-2-methoxy-propyl)amino)naphthalen-1-yl)oxy)pyridin-3-yl)pyrimidin-2-yl)amino)piperidine-1-carboxylate (Isomer-2)

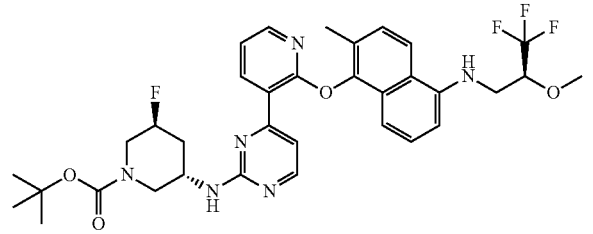 [SMILES: CO[C@@H](CNc1cccc2c(Oc3ncccc3-c3ccnc(N[C@H]4C[C@H](F)CN(C(=O)OC(C)(C)C)C4)n3)c(C)ccc12)C(F)(F)F]

To a solution of (3S,5S)-tert-butyl 3-fluoro-5-((4-(2-((6-fluoro-2-methyl-5-(((S)-3,3,3-trifluoro-2-hydroxypropyl)amino)naphthalen-1-yl)oxy)pyridin-3-yl)pyrimidin-2-yl)amino)piperidine-1-carboxylate (79 mg, 0.12 mmol) in DMF (1 mL) was added cesium carbonate (118 mg, 0.36 mmol) followed by iodomethane (0.01 mL, 0.18 mmol). The reaction was stirred at 75° C. for 30 min then diluted with water (15 mL) and the resulting precipitate was collected by filtration. The solids were dissolved in EtOAc (20 mL) and dried over Na$_2$SO$_4$. The drying reagent was filtered and the solvent was removed in vacuo to provide 72 mg (90% yield) of the title compound. LCMS (ESI) [M+H]$^+$=671.3.

Step 2: (3S,5S)—N-(5-Fluoro-3-piperidyl)-4-[2-[[2-methyl-5-[[(2S)-3,3,3-trifluoro-2-methoxy-propyl]amino]-1-naphthyl]oxy]-3-pyridyl]pyrimidin-2-amine hydrochloride (Isomer-2) 493

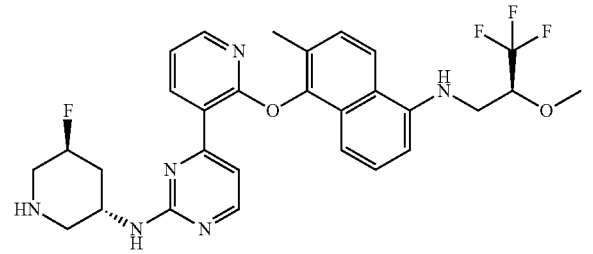 [SMILES: CO[C@@H](CNc1cccc2c(Oc3ncccc3-c3ccnc(N[C@@H]4CNC[C@@H](F)C4)n3)c(C)ccc12)C(F)(F)F]

Prepared according to General Procedure B using (3S,5S)-tert-butyl 3-fluoro-5-((4-(2-((6-fluoro-2-methyl-5-(((S)-3,3,3-trifluoro-2-methoxypropyl)amino)naphthalen-1-yl)oxy)pyridin-3-yl)pyrimidin-2-yl)amino)piperidine-1-carboxylate (72 mg, 0.11 mmol), 1,4-dioxane (1.0 mL), and hydrochloric acid (4 M in dioxane, 1.0 mL, 4.0 mmol). After 1 h, the mixture was diluted with Et$_2$O. The resulting solids were collected by filtration then dissolved in H$_2$O and MeCN and lyophilized to provide 63 mg (97% yield) of 493. LCMS (ESI) [M+H]$^+$=571.2; $^1$H NMR (400 MHz, DMSO-d$_6$) δ 1H NMR (400 MHz, DMSO-d$_6$) 9.81 (d, J=12.0 Hz, 1H), 8.80-8.65 (m, 2H), 8.47 (d, J=5.3 Hz, 1H), 8.03 (t, J=6.7 Hz, 2H), 7.66 (s, 2H), 7.38 (d, J=8.8 Hz, 1H), 7.28-7.17 (m, 2H), 6.87 (d, J=8.4 Hz, 1H), 6.51 (d, J=7.3 Hz, 1H), 5.23 (d, J=45.4 Hz, 1H), 4.52 (s, 1H), 4.20 (s, 1H), 3.60-3.41 (m, 7H), 3.22 (d, J=40.4 Hz, 1H), 2.81 (d, J=11.3 Hz, 1H), 2.35 (s, 1H), 2.17 (s, 3H), 1.93 (dt, J=44.1, 12.0 Hz, 1H). The stereochemistry of the fluoropiperidine was assigned based on the potency in the cellular assay.

Example 494 (S)—N-(2-Fluoro-6-methyl-5-((3-(2-(piperidin-3-ylamino)pyrimidin-4-yl)pyridin-2-yl)oxy)naphthalen-1-yl)-1-(pyridin-2-yl)methanesulfonamide hydrochloride Step 1: (S)-tert-Butyl 3-((4-(2-((6-fluoro-2-methyl-5-(pyridin-2-ylmethylsulfonamido)naphthalen-1-yl)oxy)pyridin-3-yl)pyrimidin-2-yl)amino)piperidine-1-carboxylate

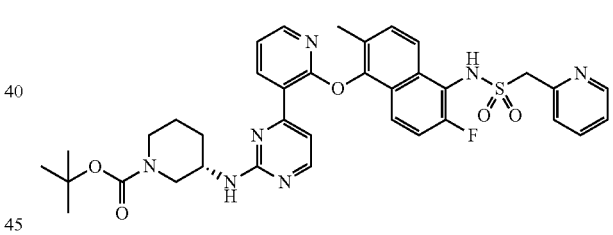

The General Procedure A was followed using (S)-tert-butyl 3-((4-(2-((5-amino-6-fluoro-2-methylnaphthalen-1-yl)oxy)pyridin-3-yl)pyrimidin-2-yl)amino)piperidine-1-carboxylate from Example 275 (100 mg, 0.18 mmol), pyridine (0.44 mL, 5.5 mmol) DCM (1 mL) and 2-pyridylmethanesulfonyl chloride (105 mg, 0.55 mmol). After 18 h, a further portion of 2-pyridylmethanesulfonyl chloride (210 mg, 1.1 mmol) was added and stirred at rt for 3 days. The mixture was diluted with CH$_2$Cl$_2$ and washed with 1M HCl, dried over sodium sulfate, filtered and concentrated in vacuo. The product was purified by prep TLC (1.5% MeOH in DCM, TEA as an additive). Appropriate band was removed and extracted with DCM/MeOH (10:1) for 30 min. The suspension was filtered and the solvent was removed in vacuo to provide 30 mg (23% yield) of the title compound. LCMS (ESI) [M+H]$^+$=700.3.

Step 2: (S)—N-(2-Fluoro-6-methyl-5-((3-(2-(piperidin-3-ylamino)pyrimidin-4-yl)pyridin-2-yl)oxy)naphthalen-1-yl)-1-(pyridin-2-yl)methanesulfonamide hydrochloride

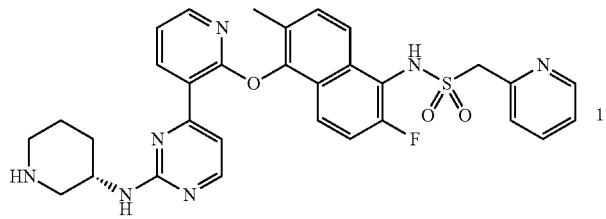

Prepared according to General Procedure B using (S)-tert-butyl 3-((4-(2-((6-fluoro-2-methyl-5-(pyridin-2-ylmethylsulfonamido)naphthalen-1-yl)oxy)pyridin-3-yl)pyrimidin-2-yl)amino)piperidine-1-carboxylate (30 mg, 0.04 mmol) 1,4-dioxane (1 mL) and hydrochloric acid (4 M in dioxane, 1 mL, 4 mmol). After 30 h, the mixture was diluted with MTBE and the resulting solids were collected by filtration, dissolved in H$_2$O and MeCN and lyophilized to provide 25 mg (92% yield) of the title compound 494. LCMS (ESI) [M+H]$^+$=600.2, $^1$H NMR (400 MHz, DMSO-d$_6$) δ 10.06 (s, 1H), 9.08-8.90 (m, 2H), 8.67 (d, J=3.9 Hz, 1H), 8.47 (d, J=5.3 Hz, 1H), 8.07 (dd, J=5.6, 3.7 Hz, 2H), 8.01 (s, 1H), 7.73-7.46 (m, 7H), 7.30-7.26 (m, 1H), 4.80 (s, 2H), 4.40-4.05 (m, 1H), 3.40 (s, 1H), 3.17 (s, 1H), 2.82 (s, 2H), 2.22-2.14 (m, 4H), 2.05-1.96 (m, 1H), 1.96-1.85 (m, 1H), 1.79-1.58 (m, 2H).

Example 495 2,2-Difluoro-N-(2-fluoro-5-((3-(2-(((3R,5R)-5-fluoropiperidin-3-yl)amino)pyrimidin-4-yl)pyridin-2-yl)oxy)-6-methylnaphthalen-1-yl)butane-1-sulfonamide hydrochloride (Isomer-1) 495

Step 1: tert-Butyl 3-((4-(2-((5-(2,2-difluorobutylsulfonamido)-6-fluoro-2-methylnaphthalen-1-yl)oxy)pyridin-3-yl)pyrimidin-2-yl)amino)-5-fluoropiperidine-1-carboxylate

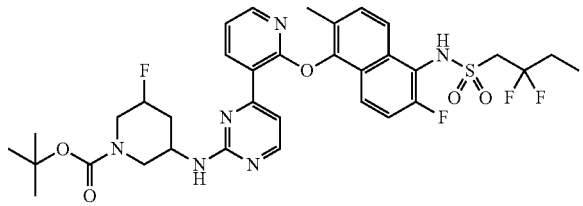 [SMILES: CCC(F)(F)CS(=O)(=O)Nc1c(F)ccc2c(Oc3ncccc3-c3ccnc(NC4CC(F)CN(C(=O)OC(C)(C)C)C4)n3)c(C)ccc12]

The General Procedure A was followed using tert-butyl 3-((4-(2-((5-amino-6-fluoro-2-methylnaphthalen-1-yl)oxy)pyridin-3-yl)pyrimidin-2-yl)amino)-5-fluoropiperidine-1-carboxylate from Example 322 (200 mg, 0.36 mmol), pyridine (0.86 mL, 10.7 mmol), DCM (0.5 mL) and 2,2-difluorobutane-1-sulfonyl chloride (103 mg, 0.53 mmol). After 18 h, the mixture was concentrated in vacuo and co-evaporated with toluene. The crude was purified by flash chromatography through silica gel (0-50% EtOAc/CH$_2$Cl$_2$) to provide 123 mg (48% yield) of the title compound. LCMS (ESI) [M+H]$^+$=719.2.

Step 2: (3R,5R)-tert-Butyl 3-((4-(2-((5-(2,2-difluorobutylsulfonamido)-6-fluoro-2-methylnaphthalen-1-yl)oxy)pyridin-3-yl)pyrimidin-2-yl)amino)-5-fluoropiperidine-1-carboxylate (Isomer-1) and (3S,5S)-tert-Butyl 3-((4-(2-((5-(2,2-difluorobutylsulfonamido)-6-fluoro-2-methylnaphthalen-1-yl)oxy)pyridin-3-yl)pyrimidin-2-yl)amino)-5-fluoropiperidine-1-carboxylate (Isomer-2)

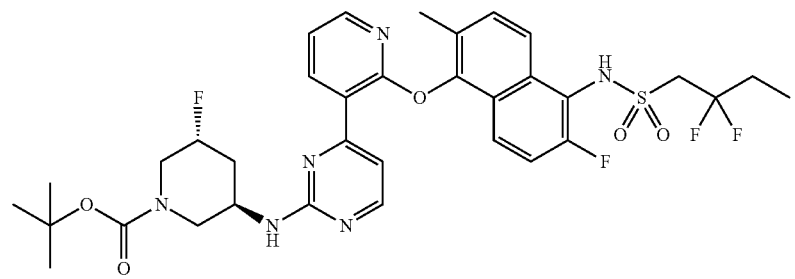

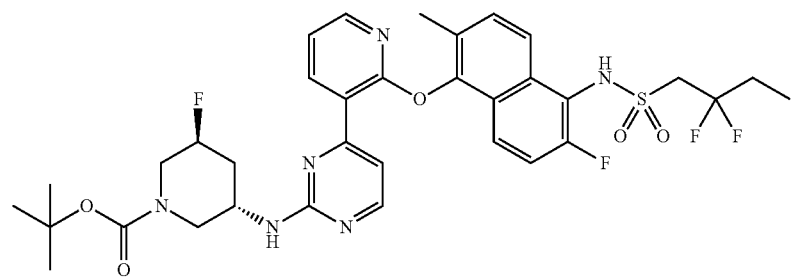

The stereoisomers from Step 1 were subjected to chiral SFC purification (Lux Cellulose-4 (250 mm×10 mm, 5 µm); MeOH 35%; flow rate (mL/min): 10, 150 bar, 40° C.) to provide two trans piperidine enantiomers. Isomer-1: (3R,5R)-tert-butyl 3-((4-(2-((5-(2,2-difluorobutylsulfonamido)-6-fluoro-2-methylnaphthalen-1-yl)oxy)pyridin-3-yl)pyrimidin-2-yl)amino)-5-fluoropiperidine-1-carboxylate, 42 mg (35% yield), ee=99.6%; Isomer-2: (3S,5S)-tert-butyl 3-((4-(2-((5-(2,2-difluorobutylsulfonamido)-6-fluoro-2-methylnaphthalen-1-yl)oxy)pyridin-3-yl)pyrimidin-2-yl)amino)-5-fluoropiperidine-1-carboxylate, 39 mg (32% yield), ee=99.0%.

Step 3: 2,2-Difluoro-N-(2-fluoro-5-((3-(2-(((3R,5R)-5-fluoropiperidin-3-yl)amino)pyrimidin-4-yl)pyridin-2-yl)oxy)-6-methylnaphthalen-1-yl)butane-1-sulfonamide hydrochloride (Isomer-1) 495

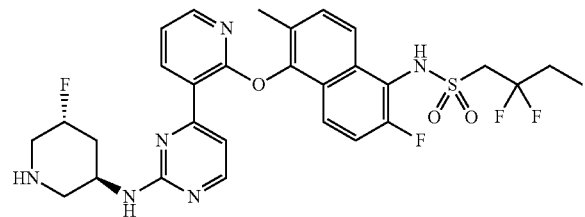 [SMILES: CCC(F)(F)CS(=O)(=O)Nc1c(F)ccc2c(Oc3ncccc3-c3ccnc(N[C@H]4CNC[C@H](F)C4)n3)c(C)ccc12]

Prepared according to General Procedure B using (3R,5R)-tert-butyl 3-((4-(2-((5-(2,2-difluorobutylsulfonamido)-6-fluoro-2-methylnaphthalen-1-yl)oxy)pyridin-3-yl)pyrimidin-2-yl)amino)-5-fluoropiperidine-1-carboxylate (42 mg, 0.06 mmol), 1,4-dioxane (1 mL) and hydrochloric acid (4 M in dioxane, 1 mL, 4 mmol). After 1 h, the mixture was diluted with MTBE and the resulting solids collected by filtration then dissolved in H$_2$O and MeCN and lyophilized to provide 35 mg (91% yield) of 495. LCMS (ESI) [M+H]$^+$=619.1, $^1$H NMR (400 MHz, DMSO-d$_6$) δ 10.11 (s, 1H), 9.50 (s, 1H), 8.47 (d, J=5.2 Hz, 1H), 8.08-7.99 (m, 2H), 7.72 (dd, J=9.4, 5.1 Hz, 1H), 7.62 (dd, J=8.3, 4.4 Hz, 2H), 7.45 (t, J=9.5 Hz, 1H), 7.28-7.22 (m, 1H), 5.23 (d, J=44.9 Hz, 1H), 4.50 (s, 1H), 4.00 (t, J=14.0 Hz, 2H), 2.81 (d, J=9.3 Hz, 1H), 2.31 (s, 1H), 2.18 (s, 3H), 2.09 (td, J=17.7, 7.5 Hz, 2H), 0.96 (t, J=7.5 Hz, 3H). The absolute stereochemistry of the fluoropiperidine was assigned based on the potency in the cellular assay.

Example 496 2,2-Difluoro-N-(2-fluoro-5-((3-(2-(((3S,5S)-5-fluoropiperidin-3-yl)amino)pyrimidin-4-yl)pyridin-2-yl)oxy)-6-methylnaphthalen-1-yl)butane-1-sulfonamide hydrochloride (Isomer-2) 496

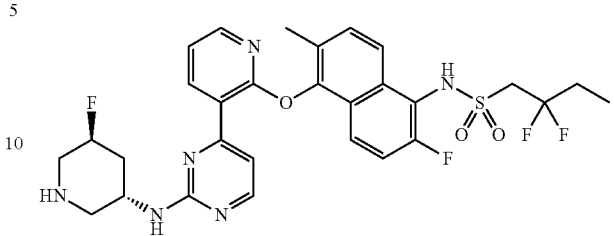

Prepared according to General Procedure B using 3S,5S)-tert-butyl 3-((4-(2-((5-(2,2-difluorobutylsulfonamido)-6-fluoro-2-methylnaphthalen-1-yl)oxy)pyridin-3-yl)pyrimidin-2-yl)amino)-5-fluoropiperidine-1-carboxylate (39 mg, 0.05 mmol), 1,4-dioxane (1 mL) and hydrochloric acid (4 M in dioxane, 1 mL, 4 mmol). After 1 h, the mixture was diluted with MTBE and the resulting solids collected by filtration then dissolved in H$_2$O and MeCN and lyophilized to provide 34 mg (95% yield) of the title compound 496. LCMS (ESI) [M+H]$^+$=619.1, $^1$H NMR (400 MHz, DMSO-d$_6$) δ 10.11 (s, 1H), 9.52 (s, 1H), 8.47 (d, J=5.2 Hz, 1H), 8.09-7.97 (m, 2H), 7.72 (dd, J=9.3, 5.1 Hz, 1H), 7.65-7.61 (m, 2H), 7.45 (t, J=9.4 Hz, 1H), 7.29-7.25 (m, 1H), 5.23 (d, J=43.8 Hz, 1H), 4.50 (s, 1H), 4.00 (t, J=14.0 Hz, 2H), 3.32-3.15 (m, 1H), 2.81 (d, J=8.9 Hz, 1H), 2.31 (s, 1H), 2.18 (s, 3H), 2.14-1.96 (m, 2H), 0.96 (t, J=7.5 Hz, 3H). The absolute stereochemistry of the fluoropiperidine was assigned based on the potency in the cellular assay.

Example 497 3,3-Difluoro-N-(2-fluoro-5-((3-(2-(((3R,5R)-5-fluoropiperidin-3-yl)amino)pyrimidin-4-yl)pyridin-2-yl)oxy)-6-methylnaphthalen-1-yl)butane-1-sulfonamide hydrochloride (Isomer-1)

Step 1: tert-Butyl trans-3-[[4-[2-[[5-(3,3-difluorobutylsulfonylamino)-6-fluoro-2-methyl-1-naphthyl]oxy]-3-pyridyl]pyrimidin-2-yl]amino]-5-fluoro-piperidine-1-carboxylate

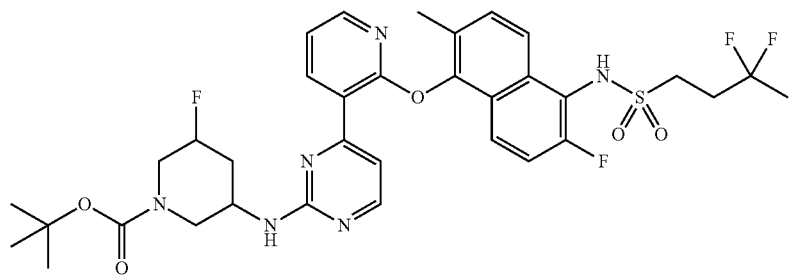 [SMILES: Cc1ccc2c(NS(=O)(=O)CCC(C)(F)F)c(F)ccc2c1Oc1ncccc1-c1ccnc(NC2CC(F)CN(C(=O)OC(C)(C)C)C2)n1]

The General Procedure A was followed using tert-butyl trans-3-[[4-[2-[(5-amino-6-fluoro-2-methyl-1-naphthyl)oxy]-3-pyridyl]pyrimidin-2-yl]amino]-5-fluoro-piperidine-1-carboxylate from Example 322 (200 mg, 0.36 mmol), pyridine (0.86 mL), CH$_2$Cl$_2$ (0.5 mL) and 3,3-difluorobutane-1-sulfonyl chloride (103 mg, 0.53 mmol). After 18 h, the mixture was diluted with toluene (10 mL) and concentrated in vacuo. The crude was purified by flash chromatography through silica gel (0-50% EtOAc/CH$_2$Cl$_2$) to provide 132 mg (51% yield) of the title compound. LCMS (ESI) [M+H]$^+$=719.2.

Step 2: (3R,5R)-tert-Butyl 3-((4-(2-((5-(3,3-difluorobutylsulfonamido)-6-fluoro-2-methylnaphthalen-1-yl)oxy)pyridin-3-yl)pyrimidin-2-yl)amino)-5-fluoropiperidine-1-carboxylate (Isomer-1) and (3S,5S)-tert-butyl 3-((4-(2-((5-(3,3-difluorobutylsulfonamido)-6-fluoro-2-methylnaphthalen-1-yl)oxy)pyridin-3-yl)pyrimidin-2-yl)amino)-5-fluoropiperidine-1-carboxylate (Isomer-2)

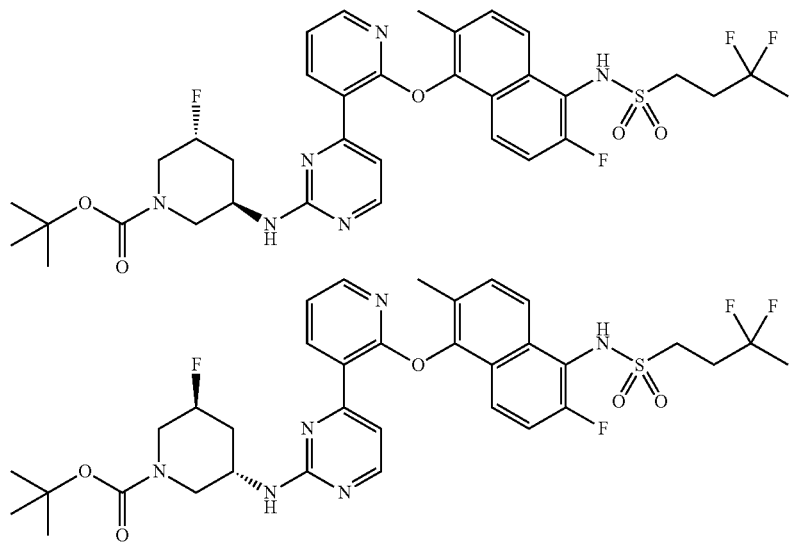

The stereoisomers from Step 1 were subjected to chiral SFC purification (conditions: Lux Cellulose-4, 10×250 mm 5 um, Isocratic 30% MeOH, 10 mL/min, 150 bar.) to provide two trans piperidine enantiomers. Isomer-1: (3R,5R)-tert-Butyl 3-((4-(2-((5-(3,3-difluorobutylsulfonamido)-6-fluoro-2-methylnaphthalen-1-yl)oxy)pyridin-3-yl)pyrimidin-2-yl)amino)-5-fluoropiperidine-1-carboxylate, 48 mg (35% yield), white solid, ee=98.8%; LCMS (ESI) [M+H]$^+$=719.2; and Isomer-2: (3S,5S)-tert-butyl 3-((4-(2-((5-(3,3-difluorobutylsulfonamido)-6-fluoro-2-methylnaphthalen-1-yl)oxy)pyridin-3-yl)pyrimidin-2-yl)amino)-5-fluoropiperidine-1-carboxylate, 46 mg (36% yield), white solid, ee=98.9%, LCMS (ESI) [M+H]$^+$=719.2.

Step 3: 3,3-Difluoro-N-(2-fluoro-5-((3-(2-(((3R,5R)-5-fluoropiperidin-3-yl)amino)pyrimidin-4-yl)pyridin-2-yl)oxy)-6-methylnaphthalen-1-yl)butane-1-sulfonamide hydrochloride (Isomer-1) 497

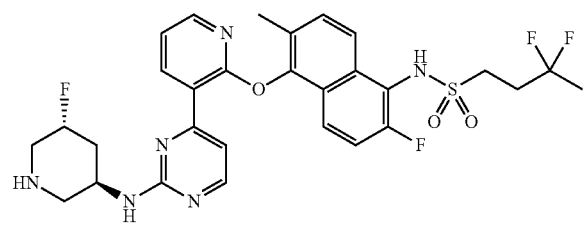 [SMILES: Cc1ccc2c(NS(=O)(=O)CCC(C)(F)F)c(F)ccc2c1Oc1ncccc1-c1ccnc(N[C@H]2CNC[C@H](F)C2)n1]

Prepared according to General Procedure B using (3R, 5R)-tert-butyl 3-((4-(2-((5-(3,3-difluorobutylsulfonamido)-6-fluoro-2-methylnaphthalen-1-yl)oxy)pyridin-3-yl)pyrimidin-2-yl)amino)-5-fluoropiperidine-1-carboxylate (46 mg, 0.064 mmol), 1,4-dioxane (1.0 mL), and hydrochloric acid (4 M in dioxane, 1 mL, 4.0 mmol). After 1 h, the mixture was diluted with Et$_2$O and the resulting solids collected by filtration then dissolved in H$_2$O and MeCN and lyophilized to provide 39 mg (93% yield) of 497. LCMS (ESI) [M+H]$^+$=619.1; $^1$H NMR (400 MHz, DMSO-d$_6$) δ 9.96 (s, 1H), 9.65 (d, J=16.0 Hz, 1H), 9.34-8.60 (m, br, 1H), 8.47 (d, J=5.2 Hz, 1H), 8.08-8.01 (m, 2H), 7.72 (dd, J=9.4, 5.3 Hz, 1H), 7.63 (d, J=8.8 Hz, 3H), 7.45 (t, J=9.5 Hz, 1H), 7.28 (dd, J=7.6, 4.8 Hz, 1H), 5.22 (d, J=45.8 Hz, 1H), 3.49-3.21 (m, 5H), 2.81 (q, J=10.9 Hz, 1H), 2.34 (m, 1H), 2.18 (s, 3H), 2.04-1.80 (m, 1H), 1.69 (t, J=19.1 Hz, 3H). The absolute stereochemistry of the fluoropiperidine was assigned based on the potency in the cellular assay.

Example 498 3,3-Difluoro-N-(2-fluoro-5-((3-(2-(((3S,5S)-5-fluoropiperidin-3-yl)amino)pyrimidin-4-yl)pyridin-2-yl)oxy)-6-methylnaphthalen-1-yl)butane-1-sulfonamide hydrochloride (Isomer-2)

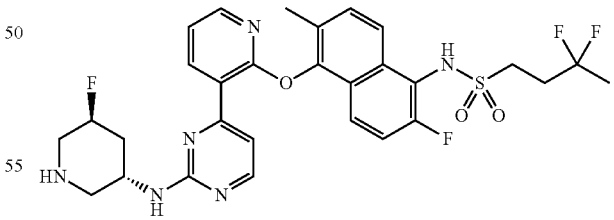

Prepared according to General Procedure B using (3S, 5S)-tert-butyl 3-((4-(2-((5-(3,3-difluorobutylsulfonamido)-6-fluoro-2-methylnaphthalen-1-yl)oxy)pyridin-3-yl)pyrimidin-2-yl)amino)-5-fluoropiperidine-1-carboxylate (48 mg, 0.067 mmol), 1,4-dioxane (1.0 mL), and hydrochloric acid (4 M in dioxane, 1 mL, 4.0 mmol). After 1 h, the mixture was diluted with Et$_2$O. The resulting solids were collected by filtration then dissolved in H$_2$O and MeCN and lyophilized to provide 42 mg (96% yield) of 498. LCMS (ESI)

[M+H]$^+$=619.1; $^1$H NMR (400 MHz, DMSO-d$_6$) δ 9.96 (s, 1H), 9.65 (d, J=16.0 Hz, 1H), 9.34-8.60 (m, 1H), 8.47 (d, J=5.2 Hz, 1H), 8.08-8.01 (m, 2H), 7.72 (dd, J=9.4, 5.3 Hz, 1H), 7.63 (d, J=8.8 Hz, 3H), 7.45 (t, J=9.5 Hz, 1H), 7.28 (dd, J=7.6, 4.8 Hz, 1H), 5.22 (d, J=45.8 Hz, 1H), 3.49-3.21 (m, 5H), 2.81 (q, J=10.9 Hz, 1H), 2.34 (m, 1H), 2.18 (s, 3H), 2.04-1.80 (m, 1H), 1.69 (t, J=19.1 Hz, 3H).

Example 499 (3R,5R)-4-[2-[[6-fluoro-2-methyl-5-[[methyl(2,2,2-trifluoroethyl)sulfamoyl]amino]-1-naphthyl]oxy]-3-pyridyl]-2-[(5-fluoro-3-piperidyl)amino]pyrimidine hydrochloride (Isomer-1)

Step 1: tert-Butyl 3-fluoro-5-[[4-[2-[[6-fluoro-2-methyl-5-[(2-oxooxazolidin-3-yl)sulfonylamino]-1-naphthyl]oxy]-3-pyridyl]pyrimidin-2-yl]amino]piperidine-1-carboxylate

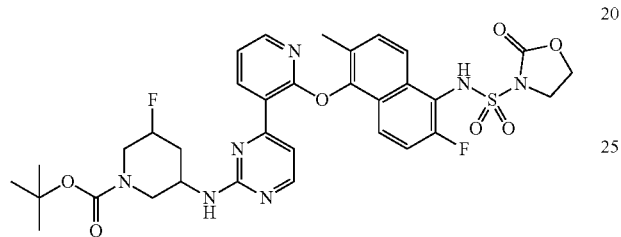

To a solution of chlorosulfonyl isocyanate (0.07 mL, 0.80 mmol) in DCM (0.7 mL) at 0° C. was added 2-bromoethanol (0.06 mL, 0.80 mmol). The reaction mixture was stirred at 0° C. for 1 h. To the reaction mixture was added tert-butyl 3-[[4-[2-[(5-amino-6-fluoro-2-methyl-1-naphthyl)oxy]-3-pyridyl]pyrimidin-2-yl]amino]-5-fluoro-piperidine-1-carboxylate from Example 322 (300 mg, 0.53 mmol) and triethylamine (0.23 mL, 1.65 mmol). The reaction mixture was left to warm up to rt for 18 h. The reaction was diluted with DCM (10 mL) and 1N HCl (5 mL), extracted with DCM (10 mL), dried over Na$_2$SO$_4$ and concentrated in vacuo. The residue was purified by flash column chromatography through silica gel (0-8% MeOH/CH$_2$Cl$_2$) to give 260 mg (69% yield) of the title compound. LCMS (ESI) [M+H]$^+$=712.2.

Step 2: tert-Butyl 3-fluoro-5-((4-(2-((6-fluoro-2-methyl-5-((N-methyl-N-(2,2,2-trifluoroethyl)sulfamoyl)amino)naphthalen-1-yl)oxy)pyridin-3-yl)pyrimidin-2-yl)amino)piperidine-1-carboxylate

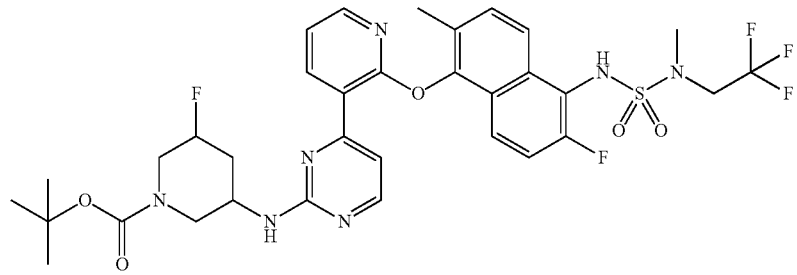

To a solution of tert-butyl 3-fluoro-5-[[4-[2-[[6-fluoro-2-methyl-5-[(2-oxooxazolidin-3-yl)sulfonylamino]-1-naphthyl]oxy]-3-pyridyl]pyrimidin-2-yl]amino]piperidine-1-carboxylate (260 mg, 0.37 mmol) in MeCN (1 mL) was added triethylamine (0.25 mL, 1.83 mmol), followed by 2,2,2-trifluoro-N-methyl-ethanamine hydrochloride (218 mg, 1.46 mmol). The reaction mixture was stirred at 85° C. for 18 h. The volatiles were evaporated and the reaction was diluted with EtOAc (20 mL) and 1N KHSO$_4$ (10 mL), extracted with EtOAc (20 mL), dried with Na$_2$SO$_4$ and evaporated. The residue was purified by flash column chromatography through silica gel (30%-100% EtOAc/Hexanes) to give 156 mg (58% yield) of the title compound. LCMS (ESI) [M+H]$^+$=738.2.

Step 3 (3R,5R)-tert-Butyl 3-fluoro-5-((4-(2-((6-fluoro-2-methyl-5-((N-methyl-N-(2,2,2-trifluoroethyl)sulfamoyl)amino)naphthalen-1-yl)oxy)pyridin-3-yl)pyrimidin-2-yl)amino)piperidine-1-carboxylate (Isomer 1) and (3S,5S)-tert-butyl 3-fluoro-5-((4-(2-((6-fluoro-2-methyl-5-((N-methyl-N-(2,2,2-trifluoroethyl)sulfamoyl)amino)naphthalen-1-yl)oxy)pyridin-3-yl)pyrimidin-2-yl)amino)piperidine-1-carboxylate (Isomer 2)

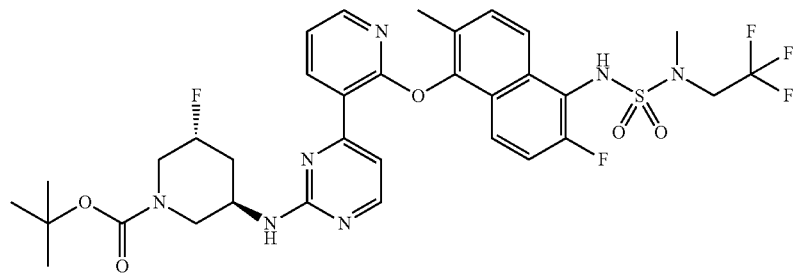

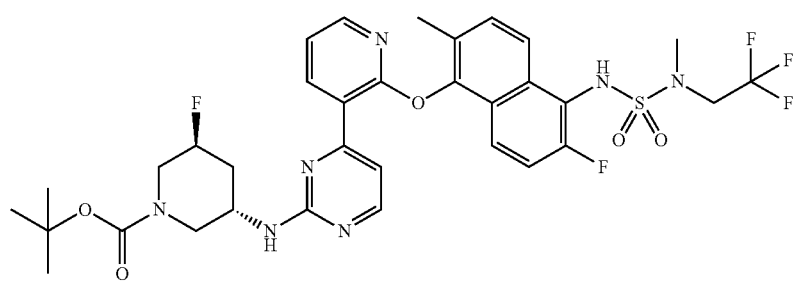

The stereoisomers from Step 2 were subjected to chiral SFC purification (Lux Cellulose-3 (250 mm×10 mm, 5 μm); MeOH 12%; flow rate (ml/min): 10, 150 bar, 40° C.) to provide two trans piperidine enantiomers. Isomer-1: (3R,5R)-tert-butyl 3-fluoro-5-((4-(2-((6-fluoro-2-methyl-5-((N-methyl-N-(2,2,2-trifluoroethyl)sulfamoyl)amino)naphthalen-1-yl)oxy)pyridin-3-yl)pyrimidin-2-yl)amino)piperidine-1-carboxylate, 58 mg (45% yield), ee=99.0%; and Isomer-2: (3S,5S)-tert-butyl 3-fluoro-5-((4-(2-((6-fluoro-2-methyl-5-((N-methyl-N-(2,2,2-trifluoroethyl)sulfamoyl)amino)naphthalen-1-yl)oxy)pyridin-3-yl)pyrimidin-2-yl)amino)piperidine-1-carboxylate, 59 mg (45% yield), ee=99.6%.

Step 4: (3R,5R)-4-[2-[[6-Fluoro-2-methyl-5-[[methyl(2,2,2-trifluoroethyl)sulfamoyl]amino]-1-naphthyl]oxy]-3-pyridyl]-2-[(5-fluoro-3-piperidyl)amino]pyrimidine hydrochloride (Isomer-1) 499

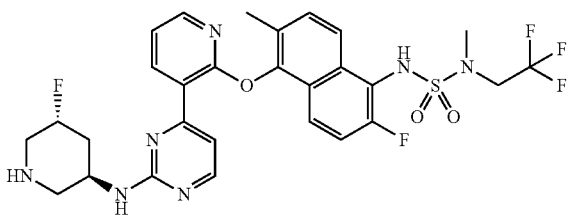 [SMILES: Cc1ccc2c(NS(=O)(=O)N(C)CC(F)(F)F)c(F)ccc2c1Oc1ncccc1-c1ccnc(N[C@H]2CNC[C@H](F)C2)n1]

Prepared according to General Procedure B using (3R,5R)-tert-butyl 3-fluoro-5-((4-(2-((6-fluoro-2-methyl-5-((N-methyl-N-(2,2,2-trifluoroethyl)sulfamoyl)amino)naphthalen-1-yl)oxy)pyridin-3-yl)pyrimidin-2-yl)amino)piperidine-1-carboxylate (56 mg, 0.08 mmol), 1,4-dioxane (1 mL), and hydrochloric acid (4 M in dioxane, 1 mL, 4 mmol). After 1 h, the mixture was diluted with MTBE and the resulting solids collected by filtration then dissolved in H$_2$O and MeCN and lyophilized to provide 49 mg (96% yield) of 499. LCMS (ESI) [M+H]$^+$=638.0, $^1$H NMR (400 MHz, DMSO-d$_6$) δ 9.92 (s, 2H), 9.58 (s, 2H), 9.29-8.63 (m, 3H), 8.47 (d, J=5.2 Hz, 2H), 8.05 (dd, J=12.0, 6.8 Hz, 4H), 7.71 (dd, J=9.2, 5.1 Hz, 2H), 7.62 (d, J=8.7 Hz, 6H), 7.42 (t, J=9.4 Hz, 2H), 7.28 (dd, J=7.6, 4.8 Hz, 2H), 5.23 (d, J=45.4 Hz, 2H), 4.50 (s, 2H), 3.94-3.86 (m, 4H), 3.49 (s, 4H), 3.17 (s, 2H), 2.98 (s, 6H), 2.81 (d, J=10.2 Hz, 2H), 2.31 (s, 2H), 2.17 (s, 6H), 1.91 (d, J=44.0 Hz, 1H). The absolute stereochemistry of the fluoropiperidine was assigned based on the potency in the cellular assay.

Example 500 (3S,5S)-4-[2-[[6-Fluoro-2-methyl-5-[[methyl(2,2,2-trifluoroethyl)sulfamoyl]amino]-1-naphthyl]oxy]-3-pyridyl]-2-[(5-fluoro-3-piperidyl)amino]pyrimidine hydrochloride (Isomer-2)

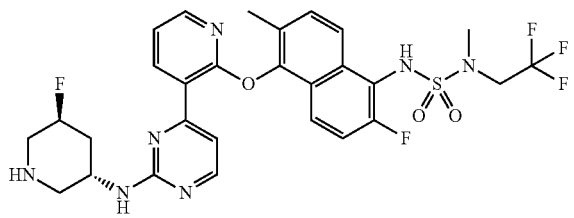 [SMILES: Cc1ccc2c(NS(=O)(=O)N(C)CC(F)(F)F)c(F)ccc2c1Oc1ncccc1-c1ccnc(N[C@@H]2CNC[C@@H](F)C2)n1]

Prepared according to General Procedure B using (3S, 5S)-tert-butyl 3-fluoro-5-((4-(2-((6-fluoro-2-methyl-5-((N-methyl-N-(2,2,2-trifluoroethyl)sulfamoyl)amino)naphthalen-1-yl)oxy)pyridin-3-yl)pyrimidin-2-yl)amino)piperidine-1-carboxylate (56 mg, 0.08 mmol), 1,4-dioxane (1 mL), and hydrochloric acid (4 M in dioxane, 1 mL, 4 mmol). After 1 h, the mixture was diluted with MTBE. The resulting solids collected by filtration then dissolved in H$_2$O and MeCN and lyophilized to provide 48 mg (94% yield) of 500. LCMS (ESI) [M+H]$^+$=638.0, $^1$H NMR (400 MHz, DMSO-d$_6$) δ 9.92 (s, 2H), 9.58 (s, 2H), 9.29-8.63 (m, 3H), 8.47 (d, J=5.2 Hz, 2H), 8.05 (dd, J=12.0, 6.8 Hz, 4H), 7.71 (dd, J=9.2, 5.1 Hz, 2H), 7.62 (d, J=8.7 Hz, 6H), 7.42 (t, J=9.4 Hz, 2H), 7.28 (dd, J=7.6, 4.8 Hz, 2H), 5.23 (d, J=45.4 Hz, 2H), 4.50 (s, 2H), 3.94-3.86 (m, 4H), 3.49 (s, 4H), 3.17 (s, 2H), 2.98 (s, 6H), 2.81 (d, J=10.2 Hz, 2H), 2.31 (s, 2H), 2.17 (s, 6H), 1.91 (d, J=44.0 Hz, 1H). The absolute stereochemistry of the fluoropiperidine was assigned based on the potency in the cellular assay.

Biological Examples

Example 901. IRE1 alpha TR-FRET Competition Binding Assay

To determine the affinity of compound binding to the kinase domain of IRE1 alpha, a Time Resolved Fluorescence Resonance Energy Transfer (TR-FRET) competition assay was used. A His-tagged IRE1 alpha kinase dead construct containing the kinase and RNase domains (KR, AA G547-L977, D688N) was expressed in Sf9 insect cells. The purified protein (final concentration 0.006 µM micromolar) was pre-incubated with anti-His Europium labeled antibody (Life Technologies PV5596, final concentration 0.002 µM micromolar) for one hour at 4° C. in 1×TR-FRET Assay Buffer (50 mM HEPES, pH 7.5, 10 mM MgCl$_2$, 0.083 mM Brij 35, 1 mM DTT, and 0.1% bovine gamma globulin) prior to addition to test compounds. A fluorescent labeled probe based on an ATP competitive inhibitor (Kinase Tracer 236, Life Technologies PV5592) is added to a final concentration of 0.1 µM (micromolar). Reactions were carried out for one hour at room temperature in a final volume of 20 µL (microliter) in 384 well white ProxiPlates (Perkin Elmer 6008289). Binding of the tracer to the IRE1 protein alpha was detected in an Envision instrument (PerkinElmer) equipped with a TRF laser option and a LANCE/Delfia Dual/Bias D400/D630 mirror (Ex 347 nm, 1$^{st}$ Em 665 nm, 2$^{nd}$ Em 615 nm).

Exemplary compound Nos. 101-392 in Table 1 and Nos. 393-491 and 493-500 in Table 2 had activity in the binding assay with an IC$_{50}$ of less than 100 nM.

Example 902. IRE1α RNase Activity Assay

Inhibitors of the RNase activity of IRE1α were assessed by Fluorescence (Forster) resonance energy transfer (FRET) using a mini-XBP-1 stem-loop RNA as a substrate for the IRE1α RNase activity. A 5'-Carboxyfluorescein (FAM)- and 3'-Black Hole Quencher (BHQ)-labeled XBP1 single stem-loop mini-substrate oligonucleotide, TAQMAN® (Roche Molecular Systems) probe (Kutyavin et al (2000) Nucleic Acids Research, 28(2):655-661) is cleaved by IRE1α. When the oligonucleotide is intact, the fluorescence signal is quenched by BHQ. Upon cleavage, the fluorescence is no longer quenched and can be quantified.

An IRE1 alpha construct corresponding to the linker, kinase and RNase domains (LKR, AA Q470-L977) was expressed in Sf9 insect cells. All reagent preparation and procedures are done under RNase free conditions. Test compounds and purified enzyme were combined in RNase Assay Buffer (20 mM HEPES, pH 7.5, 50 mM KAc, 1 mM MgAc, 1 mM DTT, and 0.05% Triton X-100) in a 384 well white ProxiPlate (Perkin Elmer 6008289). Upon addition of the RNA substrate (final assay volume 20 µL, microliter), the plates were placed into a Flexstation 3 instrument (Molecular Devices) for kinetic fluorescence reading at 2 minute intervals (Ex 485, Em 535). The velocity of the reaction, using the first 50 minutes, was used to calculate the RNase activity and inhibition of test compounds.

Exemplary compound Nos. 101-152, 154-215, 217-222, 224-238, 240-249, 251-256, 258-352, and 345-392 in Table 1 and Nos. 393-500 in Table 2 had activity in the IRE1α RNase activity assay with an IC$_{50}$ of less than 10 µmol (micromolar).

Example 903. IRE1 alpha Ribonuclease Luciferase Reporter Assay

HEK293 cells expressing a pBABE.puro HA-2xXBP1delta DBD firefly luciferase reporter (Mendez et al., (2015) "Endoplasmic reticulum stress-independent activation of unfolded protein response kinases by a small molecule ATP-mimic", eLife; 4:e05434) were cultured in DMEM high glucose media containing L-glutamine, 10% fetal bovine serum, 100 units/mL of penicillin and 100 gig/mL (microgram per milliliter) of streptomycin, plus 2 gig/ml puromycin to maintain selective pressure. Upon stimulation of IRE1 and activation of the endogenous RNase activity, a 26 nt intron is removed from XBP1 resulting in a frame shift allowing the transcription of the luciferase.

Cells were seeded without puromycin at 10,000/well in 384 well clear bottom white tissue culture plates (Corning 3707), 25 µL volume. The following morning, test compounds were added and incubated for one hour at 37° C. prior to stimulation of the cells with thapsigargin at 50 µM (micromolar) final concentration for an additional 5 hours. After equilibration to room temperature, 25 µL (microliters) of One-Glo® luciferase detection reagent (Promega cat # E6120) was added, plates sealed and shaken for 5 minutes to lyse cells, then luciferase quantified by luminescence detection using an Envision instrument (PerkinElmer).

Exemplary compound Nos. 101-392 in Table 1 and Nos. 393-500 in Table 2 had activity in the XBP1s-LUC reporter assay with IC$_{50}$ values as shown in Tables 1 and 2.

Further Embodiments

Particular embodiments of the subject matter described herein are as follows:

1. A compound selected from Formula I:

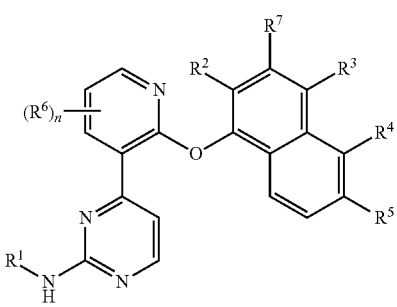

I and stereoisomers, tautomers, or pharmaceutically acceptable salts thereof, wherein:

$R^1$ is selected from $C_3$-$C_{12}$ cycloalkyl, $C_3$-$C_{12}$ heterocyclyl, $C_1$-$C_{12}$ heteroaryl, $C_6$-$C_{20}$ aryl, —($C_1$-$C_6$ alkyldiyl)-($C_3$-$C_{12}$ cycloalkyl), and —($C_1$-$C_6$ alkyldiyl)-($C_3$-$C_{12}$ heterocyclyl);

$R^2$ is selected from H, F, Cl, —CN, —OCH$_3$, —OCH$_2$CH$_3$, and $C_1$-$C_6$ alkyl;

$R^3$ and $R^4$ are independently selected from H, —CN, $C_3$-$C_{12}$ cycloalkyl, $C_3$-$C_{12}$ heterocyclyl, $C_1$-$C_{12}$ heteroaryl, $C_6$-$C_{20}$ aryl, —O—($C_1$-$C_{12}$ heteroaryl), —O—($C_1$-$C_6$ alkyldiyl)-($C_6$-$C_{20}$ aryl), —NR$^8$R$^9$, —NR$^8$C(O)R$^9$, —NR$^8$C(O)R$^9$, —NR$^8$C(O)OR$^9$, —NR$^8$C(O)NHR$^9$, —NR$^8$SO$_2$—($C_1$-$C_6$ alkyl), —NR$^8$SO$_2$—($C_1$-$C_6$ alkenyl), —NR$^8$SO$_2$—($C_1$-$C_{12}$ heteroaryl), —NR$^8$SO$_2$—($C_1$-$C_6$ alkyldiyl)-($C_3$-$C_{12}$ cycloalkyl), —NR$^8$SO$_2$—($C_1$-$C_6$ alkyldiyl)-($C_3$-$C_{12}$ heterocyclyl), —NR$^8$SO$_2$—($C_1$-$C_6$ alkyldiyl)-($C_1$-$C_{12}$ heteroaryl), —NR$^8$SO$_2$—($C_1$-$C_6$ alkyldiyl)-($C_6$-$C_{20}$ aryl), —NR$^8$SO$_2$NR$^8$R$^9$, and —SO$_2$NR$^8$R$^9$;

$R^5$ and $R^7$ are independently selected from H, F, Cl, —CN, —CH$_2$OH, —C(O)NH$_2$, —OH, —OCH$_3$, —OCH$_2$CH$_3$, and $C_1$-$C_6$ alkyl;

$R^6$ are independently selected from H, F, Cl, Br, I, —CN, —NO$_2$, and $C_1$-$C_6$ alkyl;

$R^8$ is independently selected from H, and $C_1$-$C_6$ alkyl;

$R^9$ is independently selected from $C_1$-$C_6$ alkyl, $C_2$-$C_6$ alkenyl, $C_3$-$C_{12}$ cycloalkyl, $C_3$-$C_{12}$ heterocyclyl, $C_1$-$C_{12}$ heteroaryl, $C_6$-$C_{20}$ aryl; —($C_1$-$C_6$ alkyldiyl)-($C_3$-$C_{12}$ cycloalkyl), —($C_1$-$C_6$ alkyldiyl)-($C_3$-$C_{12}$ heterocyclyl), —($C_1$-$C_6$ alkyldiyl)-($C_1$-$C_6$ heteroaryl), —($C_1$-$C_6$ alkyldiyl)-($C_6$-$C_{20}$ aryl), and —($C_1$-$C_6$ alkyldiyl)-O—($C_6$-$C_{20}$ aryl); and n is 0, 1, 2, or 3;

wherein cycloalkyl, heterocyclyl, heteroaryl, aryl, alkyl, alkyldiyl, and alkenyl are optionally and independently substituted with one or more groups selected from F, Cl, Br, I, —CN, —CH$_3$, —CH$_2$CH$_3$, —CH$_2$CH$_2$CH$_3$, —CH(CH$_3$)$_2$, —CH$_2$CH(CH$_3$)$_2$, —CH(CH$_3$)CH$_2$CH$_3$, —CH$_2$C(CH$_3$)$_3$, —CH$_2$OH, —CH$_2$OCH$_3$, —CH$_2$CH$_2$OH, —C(CH$_3$)$_2$OH, —CH(OH)CH(CH$_3$)$_2$, —C(CH$_3$)$_2$CH$_2$OH, —CH$_2$CH$_2$CH$_2$OH, —CH$_2$CH$_2$C(CH$_3$)$_2$OH, —CH$_2$CH$_2$OCH$_3$, —CH$_2$CH(CH$_3$)OCH$_3$, —CH$_2$CH$_2$CH$_2$OCH$_3$, —CH$_2$CH$_2$C(CH$_3$)$_2$OCH$_3$, —CH$_2$CH$_2$SO$_2$CH$_3$, —CH$_2$OP(O)(OH)$_2$, —CH$_2$F, —CHF$_2$, —CH$_2$NH$_2$, —CH$_2$NHSO$_2$CH$_3$, —CH$_2$NHCH$_3$, —CH$_2$N(CH$_3$)$_2$, —CF$_3$, —CH$_2$CF$_3$, —CH$_2$CHF$_2$, —CH$_2$CH$_2$CHF$_2$, —CH$_2$CH$_2$CF$_3$, —CH(CH$_3$)CN, —C(CH$_3$)$_2$CN, —CH$_2$CN, —CO$_2$H, —COCH$_3$, —CO$_2$CH$_3$, —CO$_2$C(CH$_3$)$_3$, —COCH(OH)CH$_3$, —CONH$_2$, —CONHCH$_3$, —CONHCH$_2$CH$_3$, —CONHCH(CH$_3$)$_2$, —CON(CH$_3$)$_2$, —C(CH$_3$)$_2$CONH$_2$, —NH$_2$, —NHCH$_3$, —N(CH$_3$)$_2$, —N(CH$_3$)CH$_2$CH$_3$, —NHCOCH$_3$, —N(CH$_3$)COCH$_3$, —NHS(O)$_2$CH$_3$, —N(CH$_3$)C(CH$_3$)$_2$CONH$_2$, —N(CH$_3$)CH$_2$CH$_2$S(O)$_2$CH$_3$, —NO$_2$, =O, —OH, —OCH$_3$, —OCH$_2$CH$_3$, —OCH$_2$CH$_2$OCH$_3$, —OCH$_2$CH$_2$OH, —OCH$_2$CH$_2$N(CH$_3$)$_2$, —OP(O)(OH)$_2$, —S(O)$_2$N(CH$_3$)$_2$, —SCH$_3$, —S(O)$_2$CH$_3$, —S(O)$_3$H, cyclopropyl, cyclopropylamide, cyclobutyl, oxetanyl, azetidinyl, 1-methylazetidin-3-yl)oxy, N-methyl-N-oxetan-3-ylamino, azetidin-1-ylmethyl, benzyloxyphenyl, pyrrolidin-1-yl, pyrrolidin-1-yl-methanone, phenyl, piperazin-1-yl, piperidin-1-yl, morpholinomethyl, morpholino-methanone, and morpholino.

2. The compound of embodiment 1 having Formula Ia:

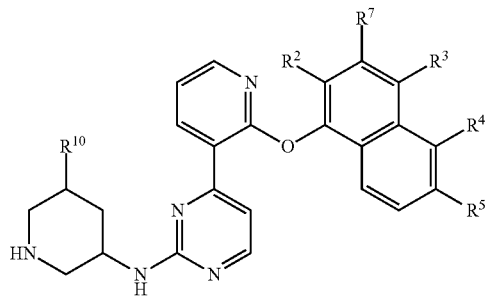

Ia wherein $R^{10}$ is selected from H, F, —CH$_3$, and —NH$_2$.

3. The compound of embodiment 2 having Formula Ib:

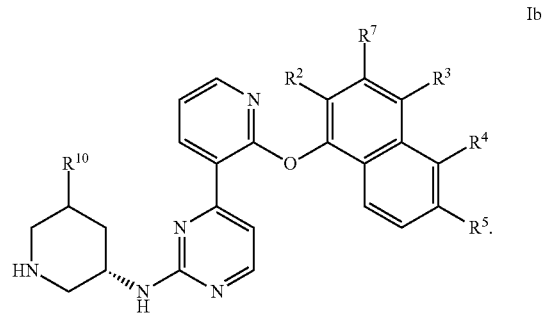

Ib

4. The compound of embodiment 1 having Formula Ic:

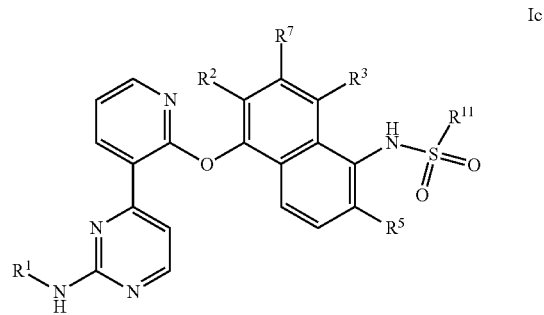

Ic wherein $R^{11}$ is selected from $C_1$-$C_6$ alkyl, $C_1$-$C_6$ alkenyl, $C_1$-$C_{12}$ heteroaryl, ($C_1$-$C_6$ alkyldiyl)-($C_3$-$C_{12}$ heterocyclyl), ($C_1$-$C_6$ alkyldiyl)-($C_1$-$C_{12}$ heteroaryl), ($C_1$-$C_6$ alkyldiyl)-($C_6$-$C_{20}$ aryl), $NR^7$—($C_1$-$C_{12}$ heteroaryl), $NR^7$—($C_1$-$C_6$ alkyl), and $NR^7$—($C_1$-$C_6$ alkyldiyl)-($C_6$-$C_{20}$ aryl).

5. The compound of embodiment 4 wherein $R^{11}$ is selected from benzyl, cyclopropyl, cyclopropylmethyl, cyclobutyl, cyclobutylmethyl, cyclopentanyl, cyclopentanylmethyl, cyclohexyl, cyclohexylmethyl, pyrrolidin-1-yl, piperidin-1-yl, pyridyl, pyridylmethyl, tetrahydrofuranyl, tetrahydrofuranylmethyl, and tetrahydropyranyl, tetrahydropyranylmethyl, thiazolyl, and thiazolylmethyl, optionally and independently substituted with one groups selected from fluoro, chloro, bromo, —$CH_3$, —$CH_2CH_3$, —$CH_2OH$, and —CN.

6. The compound of embodiment 4 wherein $R^{11}$ is selected from —$CH_3$, —$CH_2CH_3$, —CH=$CH_2$, —$CH_2CH_2CH_3$, —$CH(CH_3)_2$, —$CH_2CH(CH_3)_2$, —CH($CH_3$)$CH_2CH_3$, —$CH_2C(CH_3)_3$, —$CH_2CHF_2$, —$CH_2CH_2CHF_2$, —$CH_2CF_3$, —$CH_2CH_2CF_3$, —$CH_2CH_2OCH_3$, —$CH_2CH_2CH_2OCH_3$, —$CH_2CH(CH_3)OCH_3$, —$CH_2F$, —$CH_2Cl$, —$CH_2Br$, —$CH_2CN$, —$NH_2$, —$NHCH_3$, —$N(CH_3)_2$, and —$N(CH_3)CH_2CH_3$.

7. The compound of embodiment 4 having Formula Id:

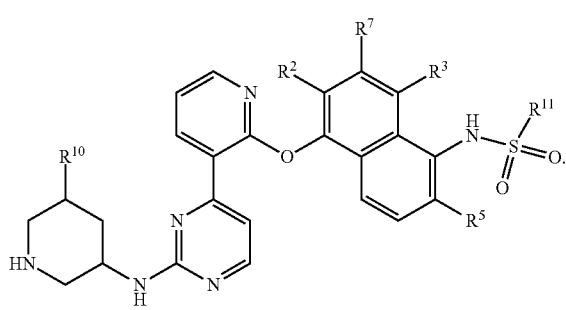

Id

8. The compound of embodiment 7 having Formula Ie:

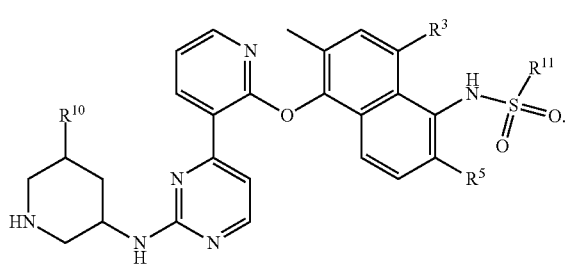

Ie

9. The compound of embodiment 8 having Formula If:

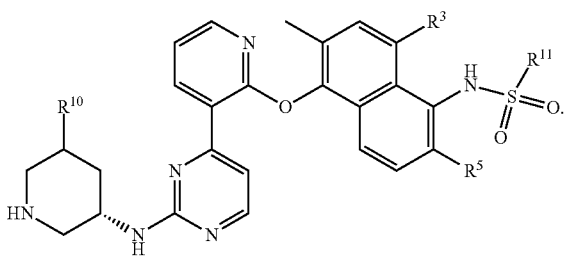

If

10. The compound of embodiment 9 wherein $R^5$ is F.

11. The compound of embodiment 1 wherein $R^1$ is $C_3$-$C_{12}$ cycloalkyl or $C_3$-$C_{12}$ heterocyclyl.

12. The compound of embodiment 11 wherein $R^1$ is cyclohexyl or piperidinyl, optionally substituted with one or more groups selected from F, —$CH_3$, and —$NH_2$.

13. The compound of embodiment 1 wherein $R^2$ is —$CH_3$.

14. The compound of embodiment 1 wherein $R^3$ is selected from —$NR^6R^7$, —$NR^6C(O)R^7$, —$NR^6C(O)R^7$, —$NR^6C(O)OR^7$, —$NR^6C(O)NR^6$, —$NR^6SO_2$—($C_1$-$C_6$ alkyl), —$NR^6SO_2$—($C_1$-$C_6$ alkenyl), —$NR^6SO_2$—($C_1$-$C_{12}$ heteroaryl), —$NR^6SO_2$—($C_1$-$C_6$ alkyldiyl)-($C_3$-$C_{12}$ heterocyclyl), —$NR^6SO_2$—($C_1$-$C_6$ alkyldiyl)-($C_1$-$C_{12}$ heteroaryl), —$NR^6SO_2$—($C_1$-$C_6$ alkyldiyl)-($C_6$-$C_{20}$ aryl), —$NR^6SO_2NR^6$—($C_1$-$C_{12}$ heteroaryl), —$NR^6SO_2NR^6$—($C_1$-$C_6$ alkyl), and —$NR^6SO_2NR^6$—($C_1$-$C_6$ alkyldiyl)-($C_6$-$C_{20}$ aryl).

15. The compound of embodiment 14 wherein $R^6$ is H.

16. The compound of embodiment 1 wherein $R^4$ is selected from —$NR^6R^7$, —$NR^6C(O)R^7$, —$NR^6C(O)R^7$, —$NR^6C(O)OR^7$, —$NR^6C(O)NR^6$, —$NR^6SO_2$—($C_1$-$C_6$ alkyl), —$NR^6SO_2$—($C_1$-$C_6$ alkenyl), —$NR^6SO_2$—($C_1$-$C_{12}$ heteroaryl), —$NR^6SO_2$—($C_1$-$C_6$ alkyldiyl)-($C_3$-$C_{12}$ heterocyclyl), —$NR^6SO_2$—($C_1$-$C_6$ alkyldiyl)-($C_1$-$C_{12}$ heteroaryl), —$NR^6SO_2$—($C_1$-$C_6$ alkyldiyl)-($C_6$-$C_{20}$ aryl), —$NR^6SO_2NR^6$—($C_1$-$C_{12}$ heteroaryl), —$NR^6SO_2NR^6$—($C_1$-$C_6$ alkyl), and —$NR^6SO_2NR^6$—($C_1$-$C_6$ alkyldiyl)-($C_6$-$C_{20}$ aryl).

17. The compound of embodiment 16 wherein $R^6$ is H.

18. The compound of embodiment 1 selected from Table 1.

19. The compound of embodiment 1 selected from Table 2.

20. A pharmaceutical composition comprised of a compound of any of embodiments 1 to 19 and a pharmaceutically acceptable carrier, glidant, diluent, or excipient.

21. A process for making a pharmaceutical composition which comprises combining a compound of any of embodiments 1 to 19 with a pharmaceutically acceptable carrier, glidant, diluent, or excipient.

22. A method of treating an IRE1-related disease or disorder in a patient comprising administering a therapeutically effective amount of the pharmaceutical composition of embodiment 20 to a patient with an IRE1-related disease or condition.

23. The method of embodiment 22 wherein the IRE1-related disease or disorder is cancer selected from squamous cell cancer, small-cell lung cancer, non-small cell lung cancer ("NSCLC"), adenocarcinoma of the lung and squamous carcinoma of the lung, cancer of the peritoneum, hepatocellular cancer, stomach cancer, gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, and head and neck cancer.

24. The method of embodiment 22 wherein the IRE1-related disease or disorder is a hematological malignancy selected from lymphomas, lymphocytic leukemia, myeloma, acute and chronic myelogenous leukemia, myelodysplastic syndrome and myeloproliferative disease.

25. The method of embodiment 24 wherein the cancer is multiple myeloma.

26. The method of embodiment 22 further comprising administering an additional therapeutic agent selected from an anti-inflammatory agent, an immunomodulatory agent, chemotherapeutic agent, an apoptosis-enhancer, a neurotropic factor, an agent for treating cardiovascular disease, an agent for treating liver disease, an anti-viral agent, an agent for treating blood disorders, an agent for treating diabetes, and an agent for treating immunodeficiency disorders.

27. The method of embodiment 26 wherein the additional therapeutic agent is a proteasome inhibitor.

28. The method of embodiment 27 wherein the proteasome inhibitor is selected from carfilzomib, lenalidomide, and bortezomib.

29. A kit for treating a condition mediated by IRE1, comprising:
a) a pharmaceutical composition of embodiment 20; and
b) instructions for use.

We claim:
1. A compound of the Formula I':

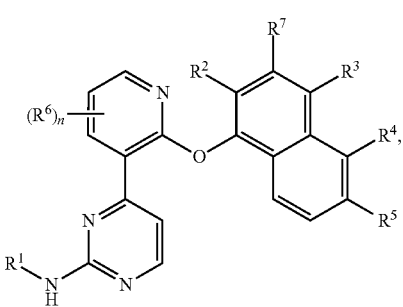

I' or a stereoisomer, tautomer, or pharmaceutically acceptable salt thereof, wherein:

$R^1$ is $C_3$-$C_{12}$ cycloalkyl, $C_3$-$C_{12}$ heterocyclyl, $C_1$-$C_{12}$ heteroaryl, $C_6$-$C_{20}$ aryl, —($C_1$-$C_6$ alkyldiyl)-($C_3$-$C_{12}$ cycloalkyl), or —($C_1$-$C_6$ alkyldiyl)-($C_3$-$C_{12}$ heterocyclyl);

$R^2$ is H, F, Cl, —CN, —OCH$_3$, —OCH$_2$CH$_3$, or $C_1$-$C_6$ alkyl;

$R^3$ is H, —CN, $C_3$-$C_{12}$ cycloalkyl, $C_3$-$C_{12}$ heterocyclyl, $C_1$-$C_{12}$ heteroaryl, $C_6$-$C_{20}$ aryl, —O—($C_1$-$C_{12}$ heteroaryl), —O—($C_1$-$C_6$ alkyldiyl)-($C_6$-$C_{20}$ aryl), —N($R^8$)($C_1$-$C_6$ alkyl), —NR$^8$C(O)R$^9$, —NR$^8$C(O)OR$^9$, —NR$^8$C(O)NHR$^9$, —NR$^8$SO$_2$-($C_1$-$C_6$ alkyl), —NR$^8$SO$_2$-($C_2$-$C_6$ alkenyl), —NR$^8$SO$_2$-($C_3$-$C_{12}$ cycloalkyl), —NR$^8$SO$_2$-($C_1$-$C_{12}$ heteroaryl), —NR$^8$SO$_2$-($C_1$-$C_6$ alkyldiyl)-($C_3$-$C_{12}$ cycloalkyl), —NR$^8$SO$_2$-($C_1$-$C_6$ alkyldiyl)-($C_3$-$C_{12}$ heterocyclyl), —NR$^8$SO$_2$-($C_1$-$C_6$ alkyldiyl)-($C_1$-$C_{12}$ heteroaryl), —NR$^8$SO$_2$-($C_1$-$C_6$ alkyldiyl)-($C_6$-$C_{20}$ aryl), —NR$^8$SO$_2$NR$^8$R$^9$, or —SO$_2$NR$^8$R$^9$;

$R^4$ is H, —CN, $C_3$-$C_2$ cycloalkyl, $C_3$-$C_{12}$ heterocyclyl, $C_1$-$C_{12}$ heteroaryl, $C_6$-$C_{20}$ aryl, —O—($C_1$-$C_{12}$ heteroaryl), —O—($C_1$-$C_6$ alkyldiyl)-($C_6$-$C_{20}$ aryl), —NR$^8$R$^9$, —NR$^8$C(O)R$^9$, —NR$^8$C(O)OR$^9$, —NR$^8$C(O)NHR$^9$, —NR$^8$SO$_2$-($C_1$-$C_6$ alkyl), —NR$^8$SO$_2$-($C_2$-$C_6$ alkenyl), —NR$^8$SO$_2$-($C_1$-$C_{12}$ heteroaryl), —NR$^8$SO$_2$-($C_3$-$C_{12}$ cycloalkyl), —NR$^8$SO$_2$-($C_3$-$C_{12}$ heterocyclyl), —NR$^8$SO$_2$-($C_1$-$C_6$ alkyldiyl)-($C_3$-$C_{12}$ cycloalkyl), —NR$^8$SO$_2$-($C_1$-$C_6$ alkyldiyl)-($C_3$-$C_{12}$ heterocyclyl), —NR$^8$SO$_2$-($C_1$-$C_6$ alkyldiyl)-($C_1$-$C_{12}$ heteroaryl), —NR$^8$SO$_2$-($C_1$-$C_6$ alkyldiyl)-($C_6$-$C_{20}$ aryl), —NR$^8$SO$_2$NR$^8$R$^9$, or —SO$_2$NR$^8$R$^9$;

each $R^5$ and $R^7$ are independently H, F, Cl, —CN, —CH$_2$H, —C(O)NH$_2$, —OH, —OCH$_3$, —OCH$_2$CH$_3$, or $C_1$-$C_6$ alkyl;

n is 0, 1, 2, or 3;

each $R^6$ is independently H, F, Cl, Br, I, —CN, —NO$_2$, —O—($C_1$-$C_6$ alkyl) or $C_1$-$C_6$ alkyl;

each $R^8$ is independently H, or $C_1$-$C_6$ alkyl;

each $R^9$ is independently $C_1$-$C_6$ alkyl, $C_2$-$C_6$ alkenyl, $C_3$-$C_2$ cycloalkyl, $C_3$-$C_{12}$ heterocyclyl, $C_1$-$C_{12}$ heteroaryl, $C_6$-$C_{20}$ aryl; —($C_1$-$C_6$ alkyldiyl)-($C_3$-$C_{12}$ cycloalkyl), —($C_1$-$C_6$ alkyldiyl)-($C_3$-$C_2$ heterocyclyl), —($C_1$-$C_6$ alkyldiyl)-($C_1$-$C_6$ heteroaryl), —($C_1$-$C_6$ alkyldiyl)-($C_6$-$C_{20}$ aryl), or —($C_1$-$C_6$ alkyldiyl)-O—($C_6$-$C_{20}$ aryl); and wherein cycloalkyl, heterocyclyl, heteroaryl, aryl, alkyl, alkyldiyl, and alkenyl are optionally and independently substituted with one or more substituents selected from the group consisting of F, Cl, Br, I, —CN, —CH$_3$, —CH$_2$CH$_3$, —CH$_2$CH$_2$CH$_3$, —CH(CH$_3$)$_2$, —CH$_2$CH(CH$_3$)$_2$, —CH(CH$_3$)CH$_2$CH$_3$, —CH$_2$C(CH$_3$)$_3$, —CH$_2$OH, —CH$_2$OCH$_3$, —CH$_2$CH$_2$OH, —C(CH$_3$)$_2$OH, —CH(OH)CH(CH$_3$)$_2$, —C(CH$_3$)$_2$CH$_2$OH, —CH$_2$CH$_2$CH$_2$OH, —CH$_2$CH$_2$C(CH$_3$)$_2$OH, —CH$_2$CH$_2$OCH$_3$, —CH$_2$CH(CH$_3$)OCH$_3$, —CH$_2$CH$_2$CH$_2$OCH$_3$, —CH$_2$CH$_2$C(CH$_3$)$_2$OCH$_3$, —CH$_2$CH$_2$SO$_2$CH$_3$, —CH$_2$OP(O)(OH)$_2$, —CH$_2$F, —CHF$_2$, —CH$_2$NH$_2$, —CH$_2$NHSO$_2$CH$_3$, —CH$_2$NHCH$_3$, —CH$_2$N(CH$_3$)$_2$, —CF$_3$, —CH$_2$CF$_3$, —CH$_2$CHF$_2$, —CH$_2$CH$_2$CHF$_2$, —CH$_2$CH$_2$CF$_3$, —CH(CH$_3$)CN, —C(CH$_3$)$_2$CN, —CH$_2$CN, —CO$_2$H, —COCH$_3$, —C$_2$CH$_3$, —CO$_2$C(CH$_3$)$_3$, —COCH(OH)CH$_3$, —CONH$_2$, —CONHCH$_3$, —CONHCH$_2$CH$_3$, —CONHCH(CH$_3$)$_2$, —CON(CH$_3$)$_2$, —C(CH$_3$)$_2$CONH$_2$, —NH$_2$, —NHCH$_3$, —N(CH$_3$)$_2$, —N(CH$_3$)CH$_2$CH$_3$, —NHCOCH$_3$, —N(CH$_3$)COCH$_3$, —NHS(O)$_2$CH$_3$, —N(CH$_3$)C(CH$_3$)$_2$CONH$_2$, —N(CH$_3$)CH$_2$CH$_2$S(O)$_2$CH$_3$, —NO$_2$, =O, —OH, —OCH$_3$, —OCH$_2$CH$_3$, —OCH$_2$CH$_2$OCH$_3$, —OCH$_2$CH$_2$OH, —OCH$_2$CH$_2$N(CH$_3$)$_2$, —OP(O)(OH)$_2$, —S(O)$_2$N(CH$_3$)$_2$, —SCH$_3$, —S(O)$_2$CH$_3$, —S(O)$_3$H, cyclopropyl, cyclopropylamide, cyclobutyl, oxetanyl, azetidinyl, 1-methylazetidin-3-yloxy, N-methyl-N-oxetan-3-ylamino, azetidin-1-ylmethyl, benzyloxyphenyl, pyrrolidin-1-yl, pyrrolidin-1-ylmethanone, phenyl, piperazin-1-yl, piperidin-1-yl, morpholinomethyl, morpholino-methanone, and morpholino.

2. The compound of claim 1, or a stereoisomer, tautomer, or pharmaceutically acceptable salt thereof, wherein the compound is of the Formula Ij:

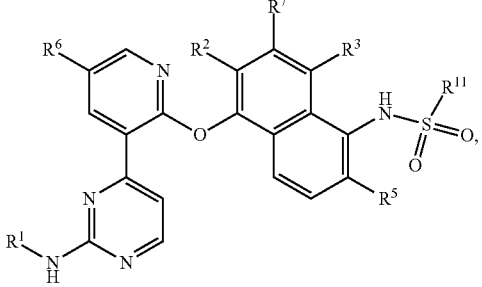

Ij wherein $R^{11}$ is $C_1$-$C_6$ alkyl, $C_2$-$C_6$ alkenyl, $C_1$-$C_{12}$ heteroaryl, $C_3$-$C_{12}$ cycloalkyl, $C_3$-$C_{12}$ heterocyclyl, —($C_1$-$C_6$ alkyldiyl)-($C_3$-$C_{12}$ cycloalkyl), —($C_1$-$C_6$ alkyldiyl)-($C_3$-$C_{12}$ heterocyclyl), —($C_1$-$C_6$ alkyldiyl)-($C_1$-$C_{12}$ heteroaryl), —($C_1$-$C_6$ alkyldiyl)-($C_6$-$C_{20}$ aryl), —$NR^8$—($C_1$-$C_{12}$ heteroaryl), —$NR^8$—($C_1$-$C_6$ alkyl), or —$NR^8$—($C_1$-$C_6$ alkyldiyl)-($C_6$-$C_{20}$ aryl); wherein cycloalkyl, heterocyclyl, heteroaryl, aryl, alkyl, alkyldiyl, and alkenyl are optionally and independently substituted as defined in claim 1.

3. The compound of claim 1, or a stereoisomer, tautomer, or pharmaceutically acceptable salt thereof, wherein $R^1$ is optionally substituted $C_3$-$C_{12}$ cycloalkyl or optionally substituted $C_3$-$C_{12}$ heterocyclyl.

4. The compound of claim 3, or a stereoisomer, tautomer, or pharmaceutically acceptable salt thereof, wherein $R^1$ is cyclohexyl or piperidinyl, optionally substituted with one or more substituents selected from the group consisting of F, —$CH_3$, and —$NH_2$.

5. The compound of claim 3, or a stereoisomer, tautomer, or pharmaceutically acceptable salt thereof, wherein $R^1$ is selected from the group consisting of piperidin-3-yl, 5-fluoropiperidin-3-yl, 5-methylpiperidin-3-yl and 5-fluoro-5-methylpiperidin-3-yl.

6. The compound of claim 1, or a stereoisomer, tautomer, or pharmaceutically acceptable salt thereof, wherein the compound is of the Formula Ih:

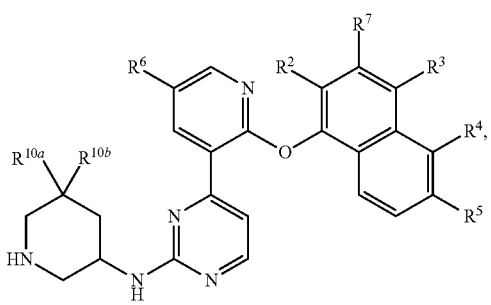

Ih wherein $R^{10a}$ and $R^{10b}$ are independently H, F, —$CH_3$ or —$NH_2$.

7. The compound of claim 2, or a stereoisomer, tautomer, or pharmaceutically acceptable salt thereof, wherein the compound is of the Formula Ik:

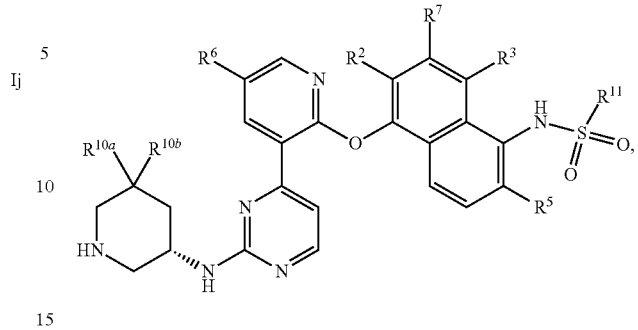

Ik wherein $R^{10a}$ and $R^{10b}$ are independently H, F or —$CH_3$.

8. The compound of claim 1, or a stereoisomer, tautomer, or pharmaceutically acceptable salt thereof, wherein each $R^6$ is independently H, F, Cl, Br, —$OCH_3$, or $C_1$-$C_6$ alkyl.

9. The compound of claim 6, or a stereoisomer, tautomer, or pharmaceutically acceptable salt thereof, wherein the compound is of the Formula Ii:

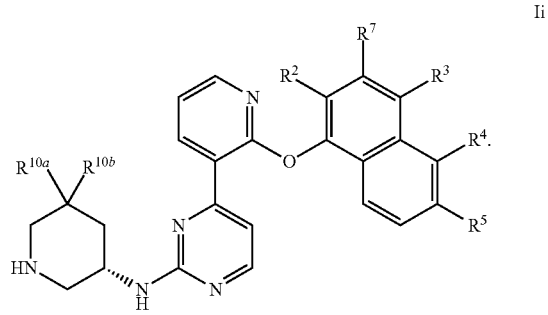

Ii

10. The compound of claim 1, or a stereoisomer, tautomer, or pharmaceutically acceptable salt thereof, wherein $R^2$ is H, F, Cl or $C_1$-$C_6$ alkyl.

11. The compound of claim 10, or a stereoisomer, tautomer, or pharmaceutically acceptable salt thereof, wherein $R^2$ is methyl.

12. The compound of claim 1, or a stereoisomer, tautomer, or pharmaceutically acceptable salt thereof, wherein $R^7$ is hydrogen or fluoro.

13. The compound of claim 1, or a stereoisomer, tautomer, or pharmaceutically acceptable salt thereof, wherein $R^5$ is H, F, Cl or $CH_3$.

14. The compound of claim 1, or a stereoisomer, tautomer, or pharmaceutically acceptable salt thereof, wherein $R^3$ is H.

15. The compound of claim 9, or a stereoisomer, tautomer, or pharmaceutically acceptable salt thereof, wherein the compound is of the Formula Iq:

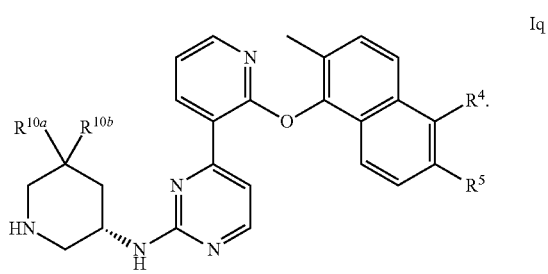

Iq

16. The compound of claim 15, or a stereoisomer, tautomer, or pharmaceutically acceptable salt thereof, wherein $R^4$ is $C_3$-$C_{12}$ heterocyclyl, $C_1$-$C_{12}$ heteroaryl, —$NR^8R^9$, —$NR^8C(O)R^9$, —$NR^8C(O)OR^9$, —$NR^8C(O)NHR^9$ or —$SO_2NR^8R^9$.

17. The compound of claim 15, or a stereoisomer, tautomer, or pharmaceutically acceptable salt thereof, wherein $R^4$ is $C_3$-$C_{12}$ heterocyclyl, $C_1$-$C_{12}$ heteroaryl, —$NR^8R^9$ or —$NR^8C(O)R^9$.

18. The compound of claim 1, or a stereoisomer, tautomer, or pharmaceutically acceptable salt thereof, wherein $R^5$ is H.

19. The compound of claim 7, or a stereoisomer, tautomer, or pharmaceutically acceptable salt thereof, wherein the compound is of the Formula Il:

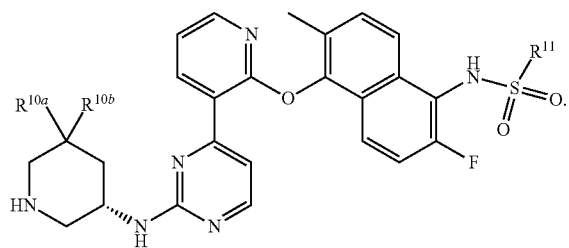

Il

20. The compound of claim 7, or a stereoisomer, tautomer, or pharmaceutically acceptable salt thereof, wherein $R^{11}$ is $C_1$-$C_6$ alkyl, $C_2$-$C_6$ alkenyl, $C_1$-$C_{12}$ heteroaryl, $C_3$-$C_{12}$ cycloalkyl, $C_3$-$C_{12}$ heterocyclyl, —($C_1$-$C_6$ alkyldiyl)-($C_3$-$C_{12}$ cycloalkyl), —($C_1$-$C_6$ alkyldiyl)-($C_3$-$C_{12}$ heterocyclyl), —($C_1$-$C_6$ alkyldiyl)-($C_1$-$C_{12}$ heteroaryl), or —($C_1$-$C_6$ alkyldiyl)-($C_6$-$C_{20}$ aryl); and wherein cycloalkyl, heterocyclyl, heteroaryl, aryl, alkyl, alkyldiyl, and alkenyl are optionally and independently substituted with one or more substituents selected from the group consisting of F, Cl, Br, I, —CN, —$CH_3$, —$CH_2CH_3$, —$CH_2CH_2CH_3$, —$CH_2CH(CH_3)_2$, —$CH(CH_3)CH_2CH_3$, —$CH_2C(CH_3)_3$, —$CH_2OH$, —$CH_2OCH_3$, —$CH_2CH_2OH$, —$C(CH_3)_2OH$, —$CH(OH)CH(CH_3)_2$, —$C(CH_3)_2CH_2OH$, —$CH_2CH_2CH_2OH$, —$CH_2CH_2C(CH_3)_2OH$, —$CH_2CH_2OCH_3$, —$CH_2CH(CH_3)OCH_3$, —$CH_2CH_2CH_2OCH_3$, —$CH_2CH_2C(CH_3)_2OCH_3$, —$CH_2CH_2SO_2CH_3$, —$CH_2OP(O)(OH)_2$, —$CH_2F$, —$CHF_2$, $CH_2NH_2$, —$CH_2NHSO_2CH_3$, —$CH_2NHCH_3$, —$CH_2N(CH_3)_2$, —$CF_3$, —$CH_2CF_3$, —$CH_2CHF_2$, —$CH_2CH_2CHF_2$, —$CH_2CH_2CF_3$, —$CH(CH_3)CN$, —$C(CH_3)_2CN$, —$CH_2CN$, —$CO_2H$, —$COCH_3$, —$CO_2CH_3$, —$CO_2C(CH_3)_3$, —$COCH(OH)CH_3$, —$CONH_2$, —$CONHCH_3$, —$CONHCH_2CH_3$, —$CONHCH(CH_3)_2$, —$CON(CH_3)_2$, —$C(CH_3)_2CONH_2$, —$NH_2$, —$NHCH_3$, —$N(CH_3)_2$, —$N(CH_3)CH_2CH_3$, —$NHCOCH_3$, —$N(CH_3)COCH_3$, —$NHS(O)_2CH_3$, —$N(CH_3)C(CH_3)_2CONH_2$, —$N(CH_3)CH_2CH_2S(O)_2CH_3$, —$NO_2$, =O, —OH, —$OCH_3$, —$OCH_2CH_3$, —$OCH_2CH_2OCH_3$, —$OCH_2CH_2OH$, —$OCH_2CH_2N(CH_3)_2$, —$OP(O)(OH)_2$, —$S(O)_2N(CH_3)_2$, —$SCH_3$, —$S(O)_2CH_3$, —$S(O)_3H$, cyclopropyl, cyclopropylamide, cyclobutyl, oxetanyl, azetidinyl, 1-methylazetidin-3-yloxy, N-methyl-N-oxetan-3-ylamino, azetidine-1-ylmethyl, benzyloxyphenyl, pyrrolidine-1-yl, pyrrolidin-1-yl-methanone, phenyl, piperazin-1-yl, piperidin-1-yl, morpholinomethyl, morpholino-methanone, and morpholino.

21. The compound of claim 7, or a stereoisomer, tautomer, or pharmaceutically acceptable salt thereof, wherein $R^{11}$ is —NR—($C_1$-$C_{12}$ heteroaryl), —$NR^8$—($C_1$-$C_6$ alkyl), or —NR—($C_1$-$C_6$ alkyldiyl)-($C_6$-$C_{20}$ aryl); and $R^8$ is independently H or —$CH_3$; and wherein cycloalkyl, heterocyclyl, heteroaryl, aryl, alkyl, alkyldiyl, and alkenyl are optionally and independently substituted with one or more substituents selected from the group consisting of F, Cl, Br, I, —CN, —$CH_3$, —$CH_2CH_3$, —$CH_2CH_2CH_3$, —$CH(CH_3)_2$, —$CH_2CH(CH_3)_2$, —$CH(CH_3)CH_2CH_3$, —$CH_2C(CH_3)_3$, —$CH_2OH$, —$CH_2OCH_3$, —$CH_2CH_2OH$, —$C(CH_3)_2OH$, —$CH(OH)CH(CH_3)_2$, —$C(CH_3)_2CH_2OH$, —$CH_2CH_2CH_2OH$, —$CH_2CH_2C(CH_3)_2OH$, —$CH_2CH_2OCH_3$, —$CH_2CH(CH_3)OCH_3$, —$CH_2CH_2CH_2OCH_3$, —$CH_2CH_2C(CH_3)_2OCH_3$, —$CH_2CH_2SO_2CH_3$, —$CH_2OP(O)(OH)_2$, —$CH_2F$, —$CHF_2$, $CH_2NH_2$, —$CH_2NHSO_2CH_3$, —$CH_2NHCH_3$, —$CH_2N(CH_3)_2$, —$CF_3$, —$CH_2CF_3$, —$CH_2CHF_2$, —$CH_2CH_2CHF_2$, —$CH_2CH_2CF_3$, —$CH(CH_3)CN$, —$C(CH_3)_2CN$, —$CH_2CN$, —$CO_2H$, —$COCH_3$, —$CO_2CH_3$, —$CO_2C(CH_3)_3$, —$COCH(OH)CH_3$, —$CONH_2$, —$CONHCH_3$, —$CONHCH_2CH_3$, —$CONHCH(CH_3)_2$, —$CON(CH_3)_2$, —$C(CH_3)_2CONH_2$, —$NH_2$, —$NHCH_3$, —$N(CH_3)_2$, —$N(CH_3)CH_2CH_3$, —$NHCOCH_3$, —$N(CH_3)COCH_3$, —$NHS(O)_2CH_3$, —$N(CH_3)C(CH_3)_2CONH_2$, —$N(CH_3)CH_2CH_2S(O)_2CH_3$, —$NO_2$, =O, —OH, —$OCH_3$, —$OCH_2CH_3$, —$OCH_2CH_2OCH_3$, —$OCH_2CH_2OH$, —$OCH_2CH_2N(CH_3)_2$, —$OP(O)(OH)_2$, —$S(O)_2N(CH_3)_2$, —$SCH_3$, —$S(O)_2CH_3$, —$S(O)_3H$, cyclopropyl, cyclopropylamide, cyclobutyl, oxetanyl, azetidinyl, 1-methylazetidin-3-yloxy, N-methyl-N-oxetan-3-ylamino, azetidine-1-ylmethyl, benzyloxyphenyl, pyrrolidine-1-yl, pyrrolidin-1-yl-methanone, phenyl, piperazin-1-yl, piperidin-1-yl, morpholinomethyl, morpholino-methanone, and morpholino.

22. The compound of claim 7, or a stereoisomer, tautomer, or pharmaceutically acceptable salt thereof, wherein $R^{11}$ is selected from the group consisting of benzyl, cyclopropyl, cyclopropylmethyl, cyclobutyl, cyclobutylmethyl, cyclopentanyl, cyclopentanylmethyl, cyclohexyl, cyclohexylmethyl, pyrrolidin-1-yl, piperidin-1-yl, pyridyl, pyridylmethyl, tetrahydrofuranyl, tetrahydrofuranylmethyl, and tetrahydropyranyl, tetrahydropyranylmethyl, thiazolyl, and thiazolylmethyl; each of which is optionally and independently substituted with one or more substituents selected from fluoro, chloro, bromo, —$CH_3$, —$CH_2CH_3$, —$CH_2OH$, and —CN.

23. The compound of claim 7, or a stereoisomer, tautomer, or pharmaceutically acceptable salt thereof, wherein $R^{11}$ is selected from the group consisting of —$CH_3$, —$CH_2CH_3$, —CH=$CH_2$, —$CH_2CH_2CH_3$, —$CH(CH_3)_2$, —$CH_2CH(CH_3)_2$, —$CH(CH_3)CH_2CH_3$, —$CH_2C(CH_3)_3$, —$CH_2CHF_2$, —$CH_2CH_2CHF_2$, —$CH_2CF_3$, —$CH_2CH_2CF_3$, —$CH_2CH_2OCH_3$, —$CH_2CH_2CH_2OCH_3$, —$CH_2CH(CH_3)OCH_3$, —$CH_2F$, —$CH_2Cl$, —$CH_2Br$, —$CH_2CN$, —$NHCH_3$, —$N(CH_3)_2$, and —$N(CH_3)CH_2CH_3$.

24. The compound of claim 6, or a stereoisomer, tautomer, or pharmaceutically acceptable salt thereof, wherein $R^{10a}$ and $R^{10b}$ are H.

25. The compound of claim 6, or a stereoisomer, tautomer, or pharmaceutically acceptable salt thereof, wherein $R^{10a}$ is F and $R^{10b}$ is H.

26. The compound of claim 6, or a stereoisomer, tautomer, or pharmaceutically acceptable salt thereof, wherein $R^{10a}$ is H and $R^{10b}$ is —$CH_3$.

27. The compound of claim 6, or a stereoisomer, tautomer, or pharmaceutically acceptable salt thereof, wherein $R^{10a}$ is F and $R^{10b}$ is —$CH_3$.

28. The compound of claim 1, wherein the compound is selected from the group consisting of
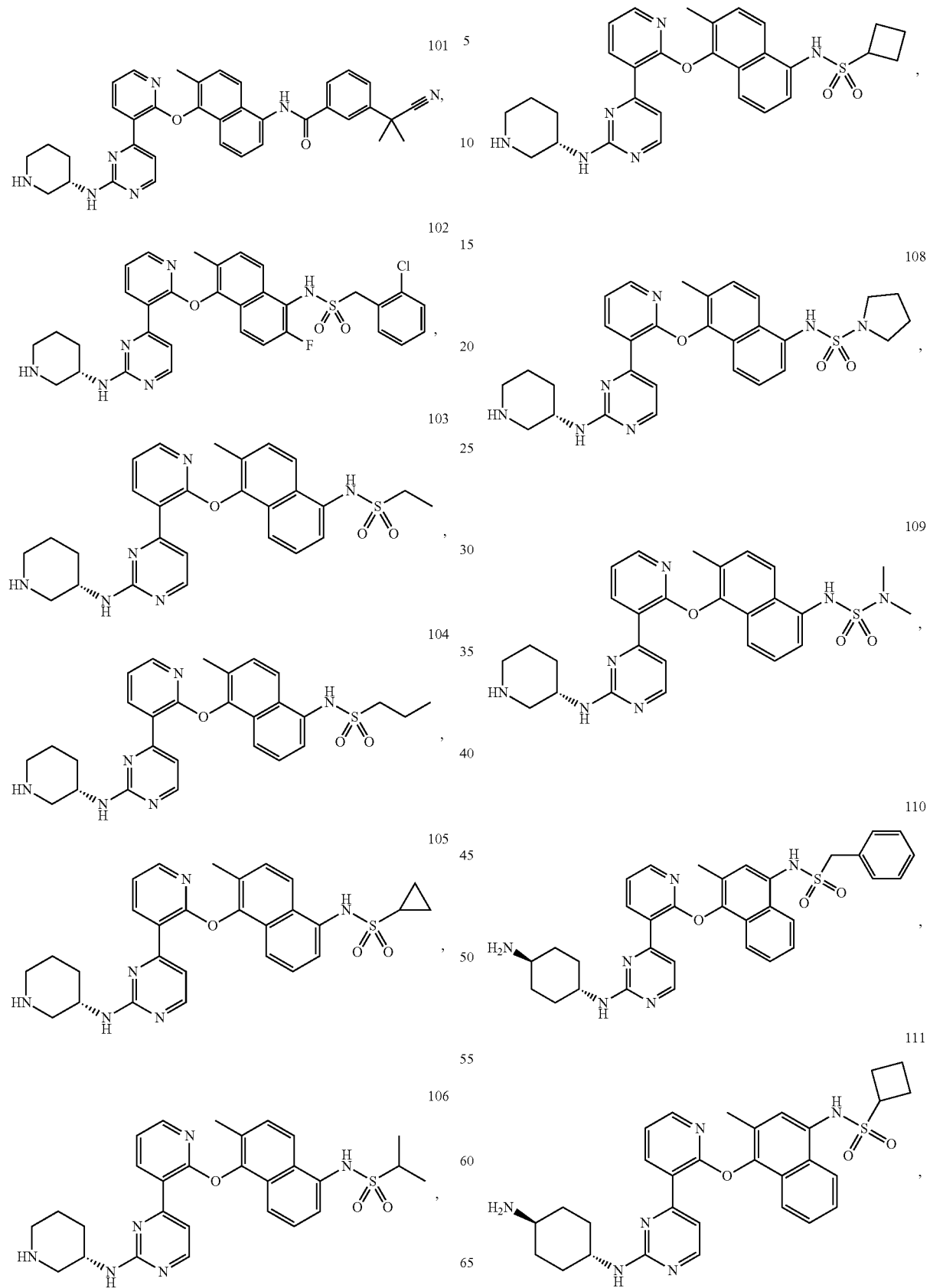

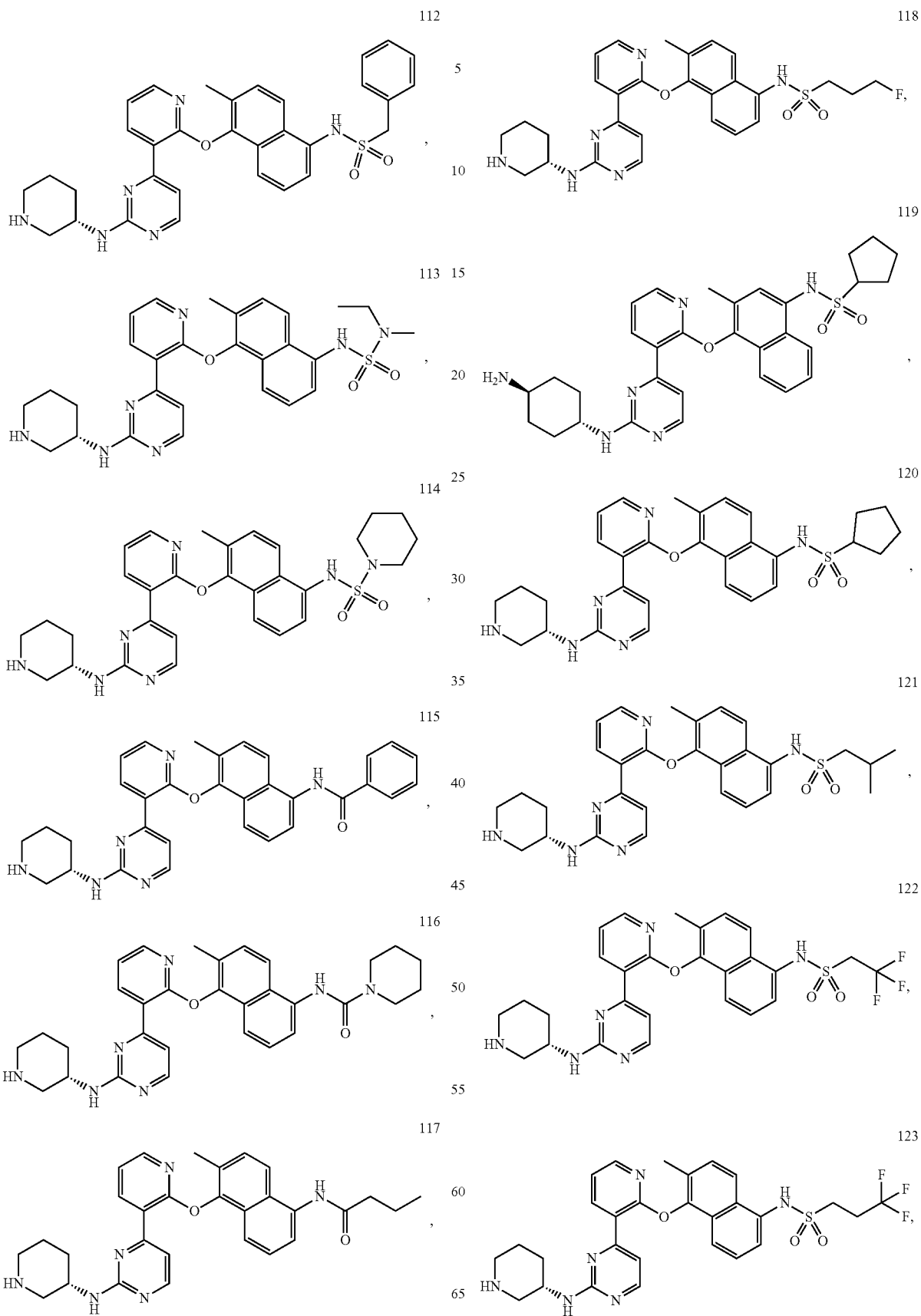

-continued
124
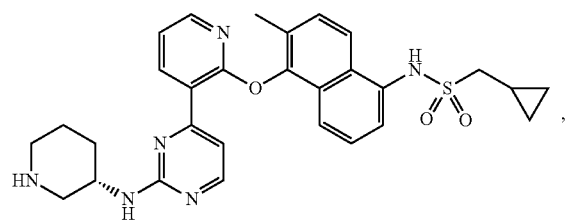
125
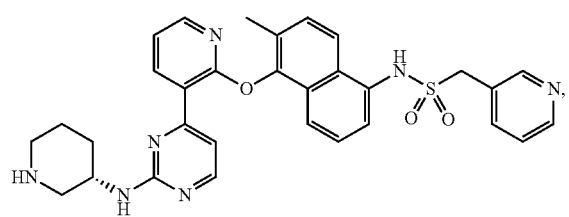
126
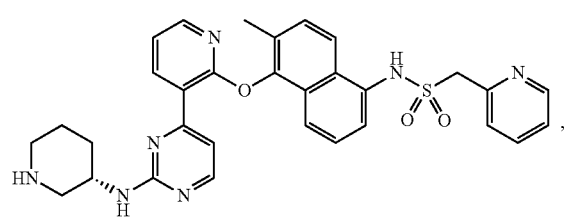
127
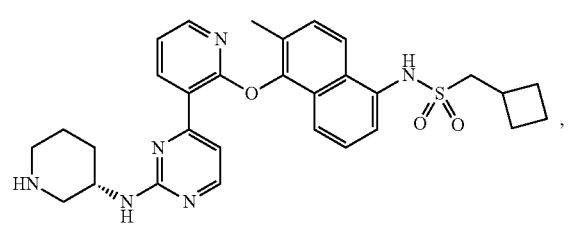
128
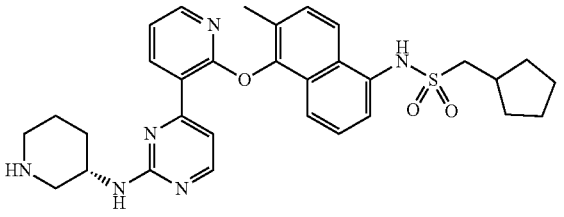
129
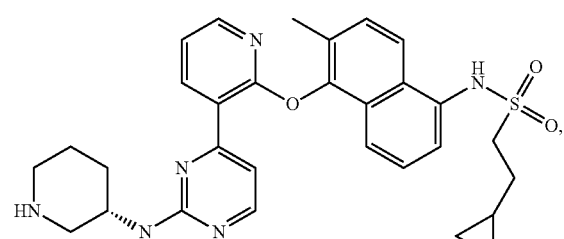
-continued
130
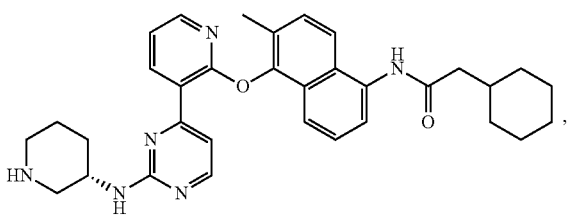
131
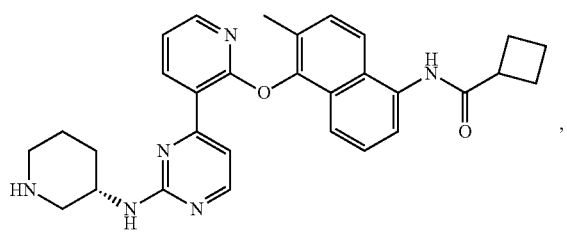
132
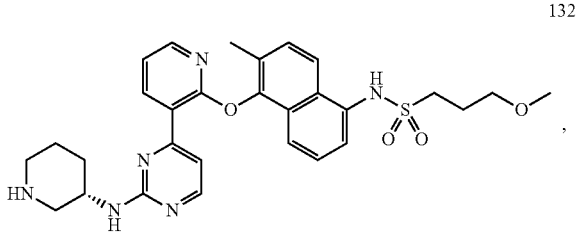
133
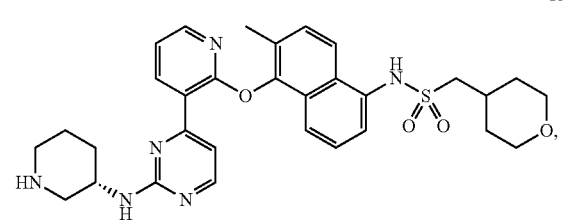
134
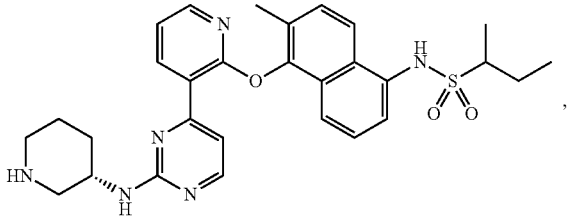
135
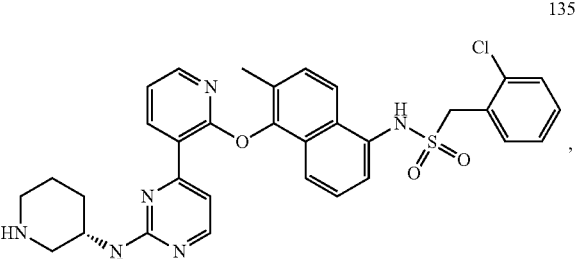

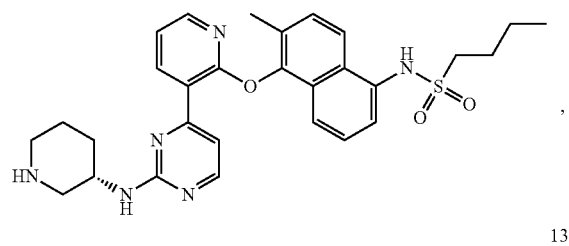
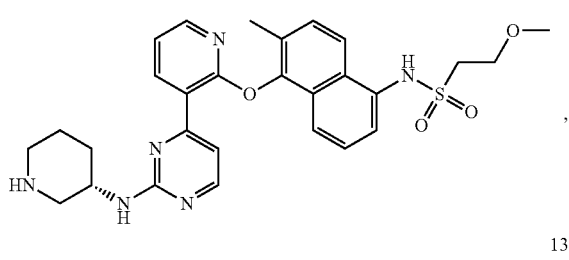
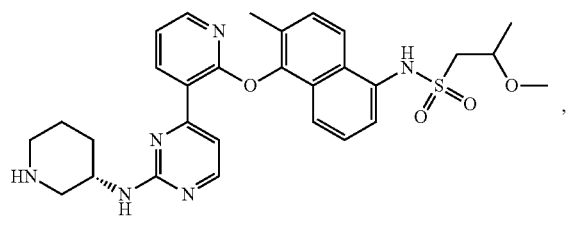
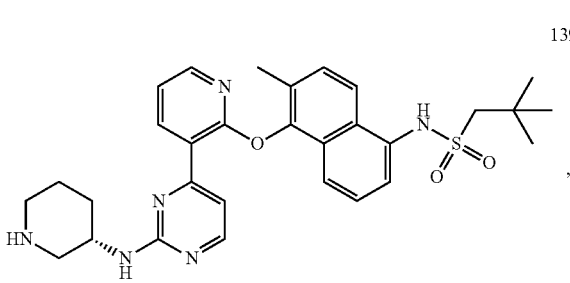

148
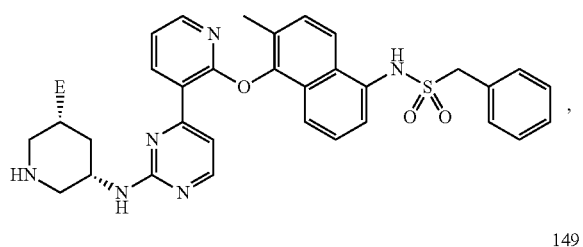
,
149
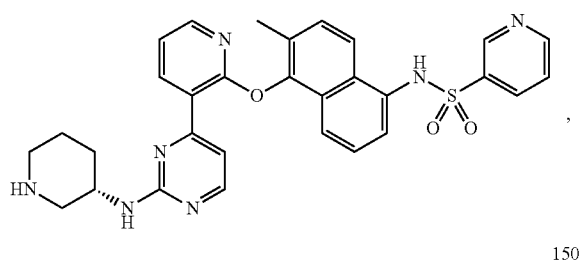
,
150
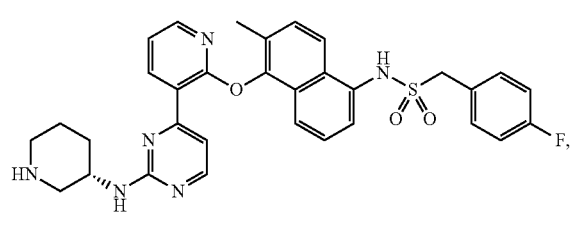
,
151
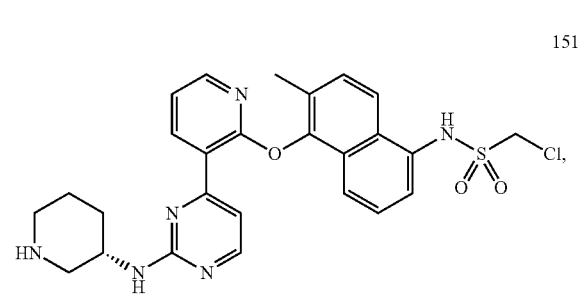
,
152
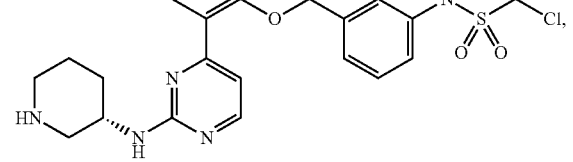
,
153
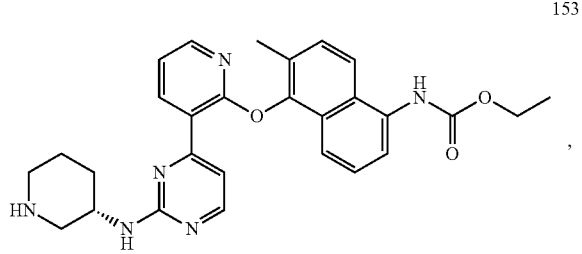
,
154
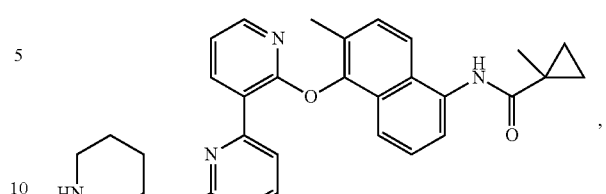
,
155
156
157
158
159

831
-continued
160
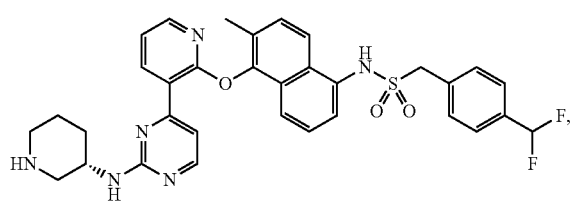
161
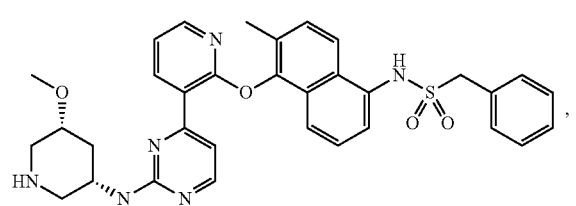
162
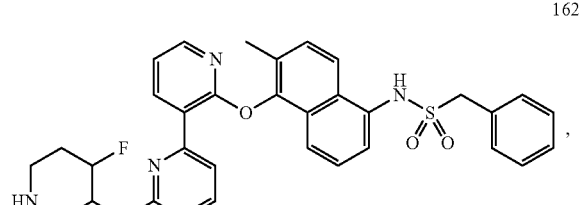
163
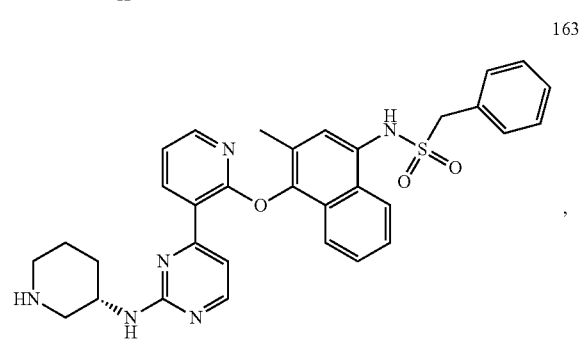
164
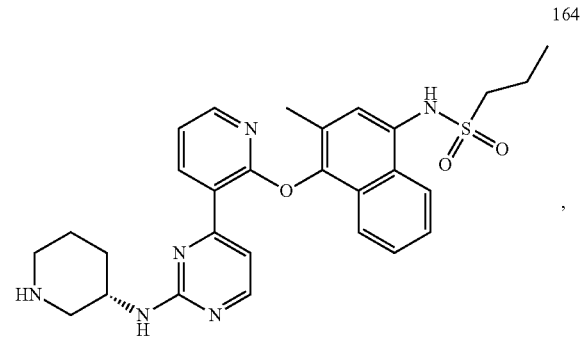
165
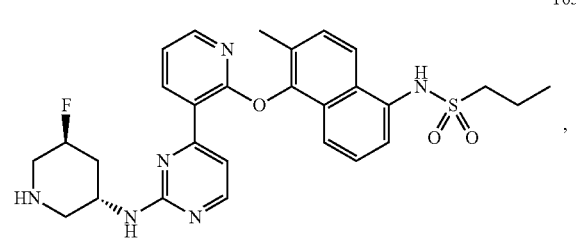
832
-continued
166
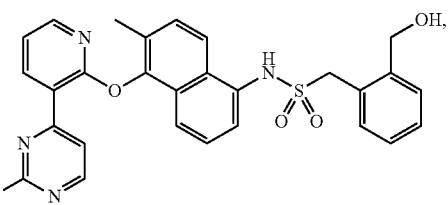
167
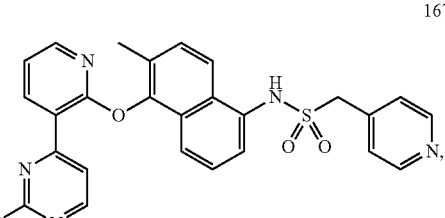
168
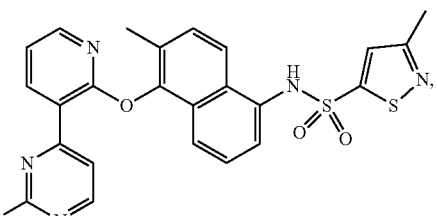
169
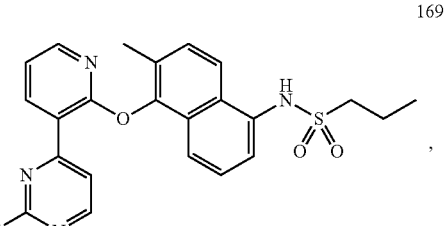
170
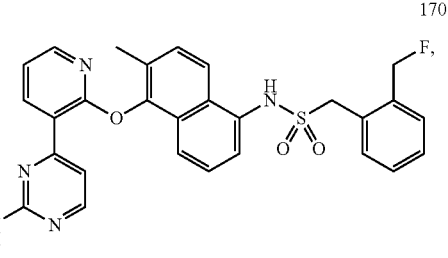
171
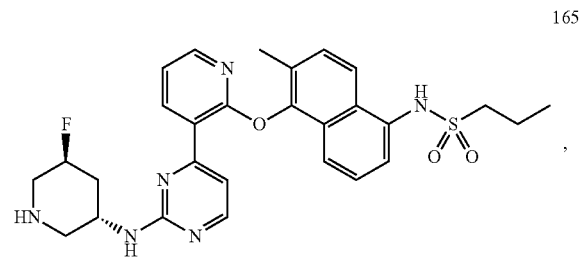

172
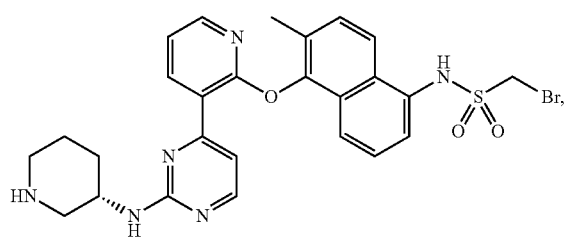
173
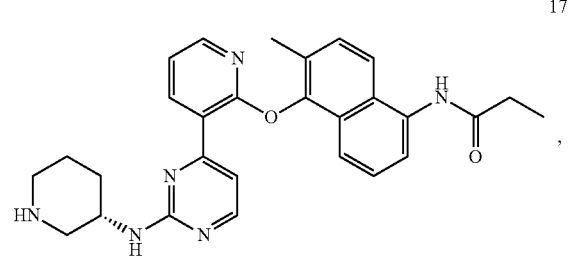
174
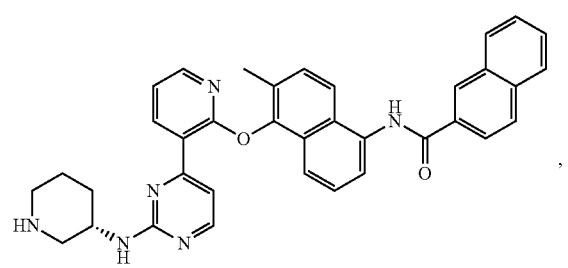
175
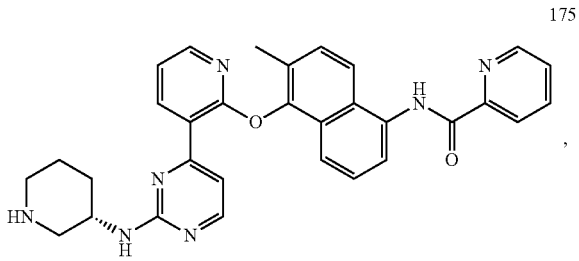
176
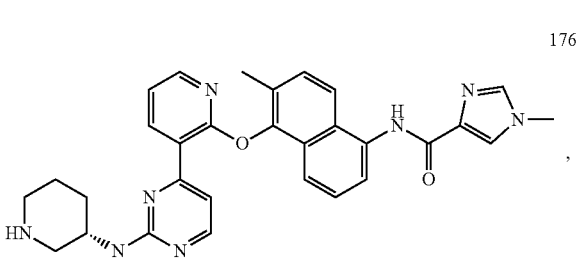
177
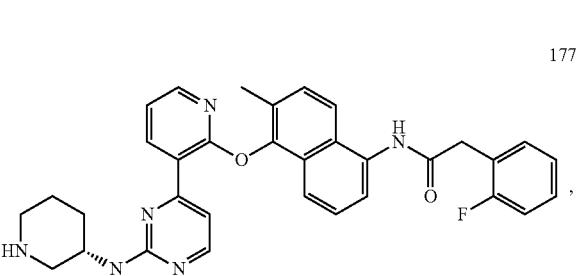
178
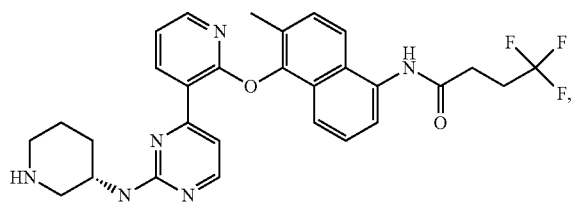
179
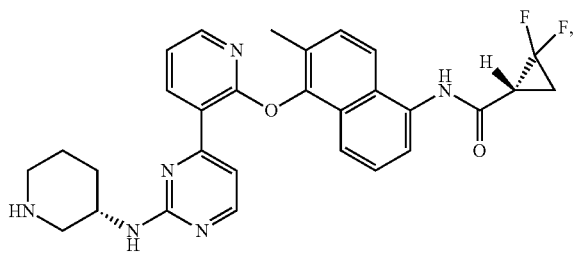
180
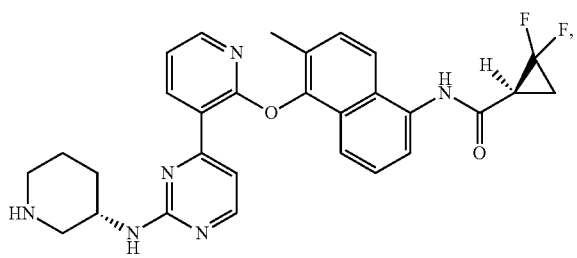
181
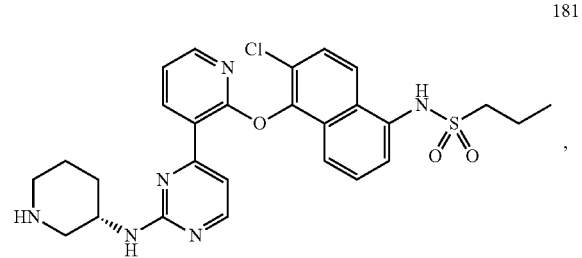
182
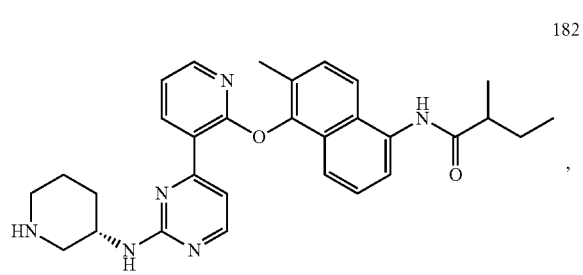
183
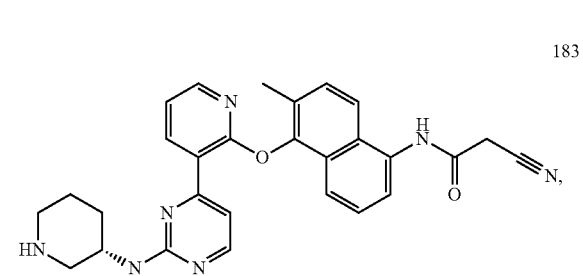

184
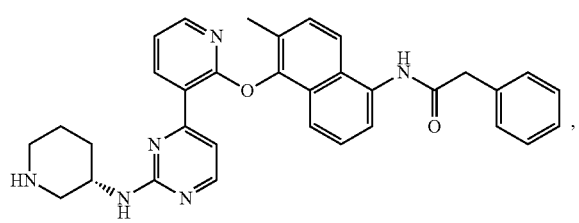
185
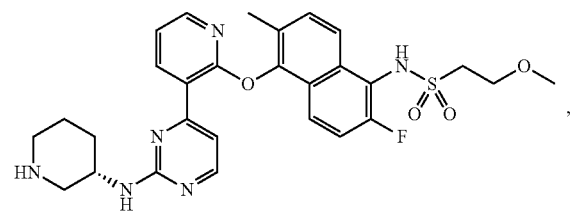
186
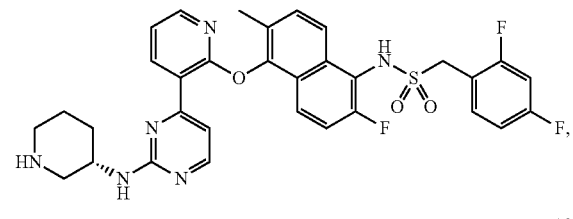
187
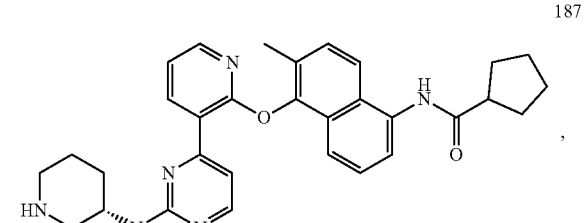
188
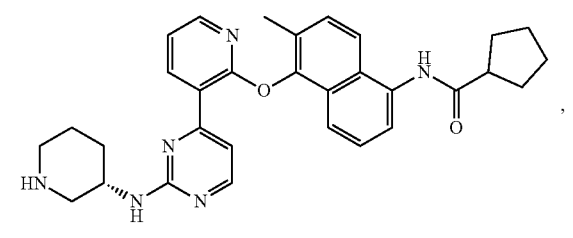
189
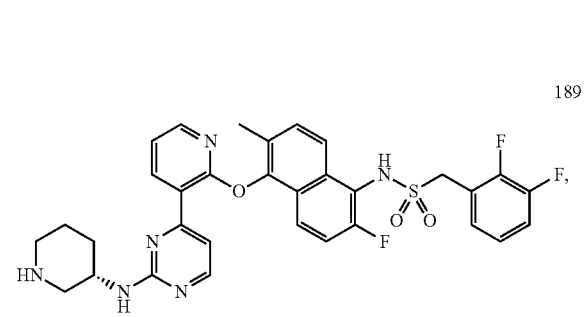
190
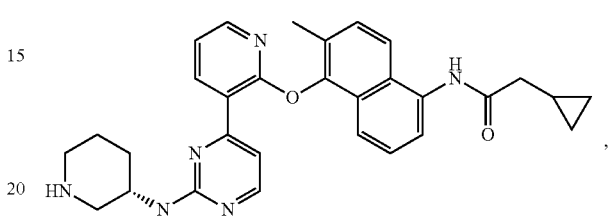
191
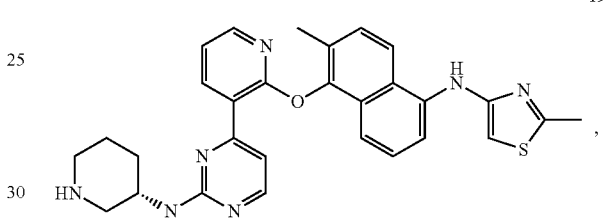
192
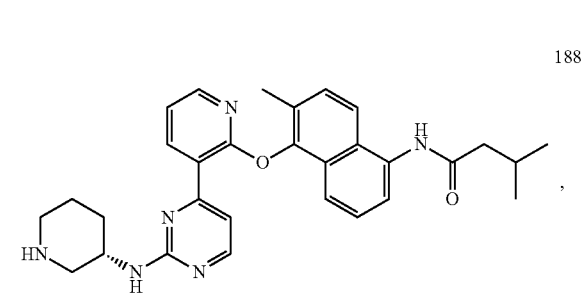
193
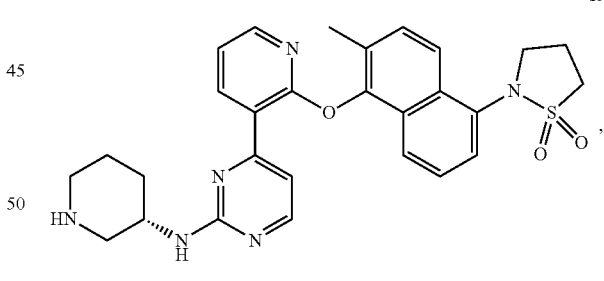
194
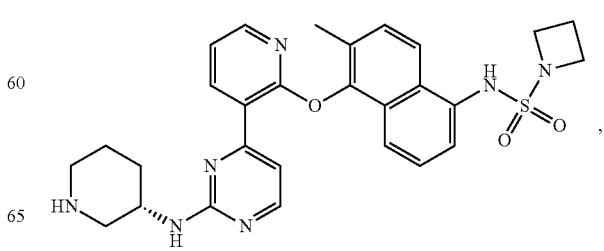
195

196 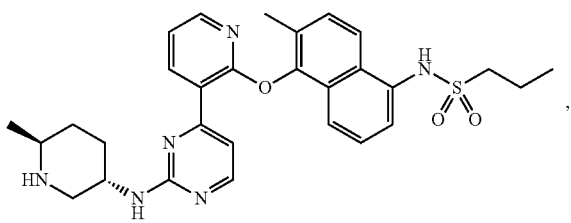,
197 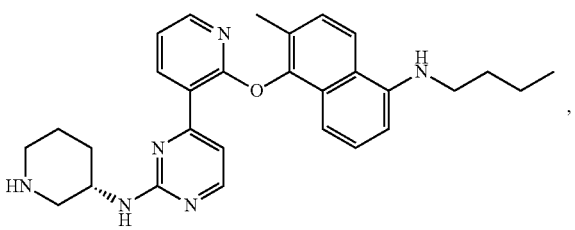,
198 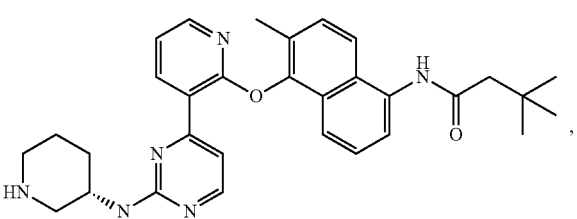,
199 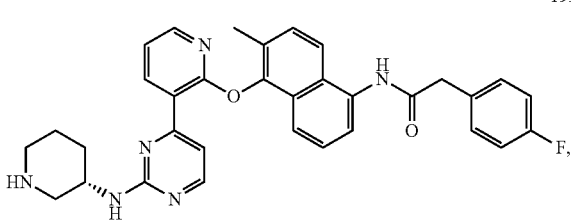,
200 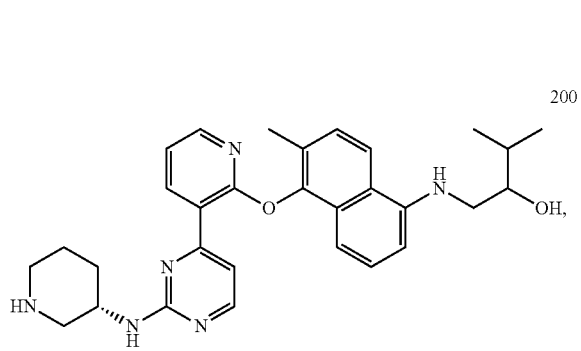,
201 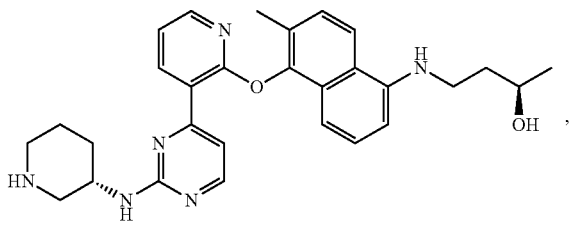,
202 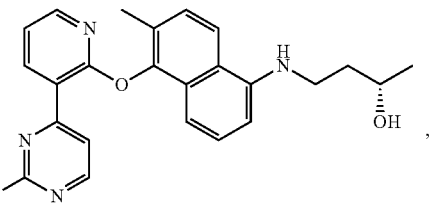,
203 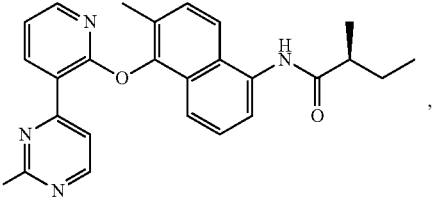,
204 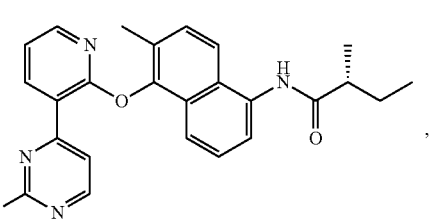,
205 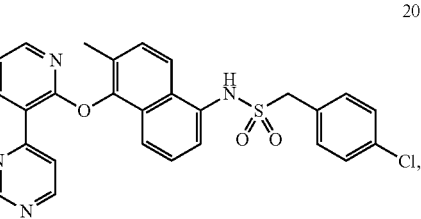,
206 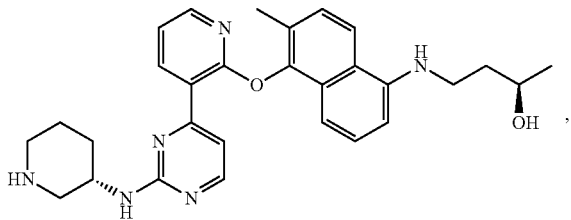,
207 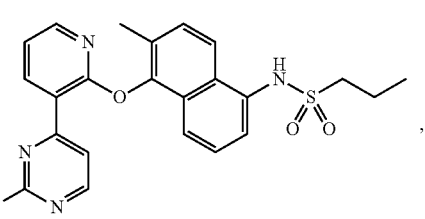, 208
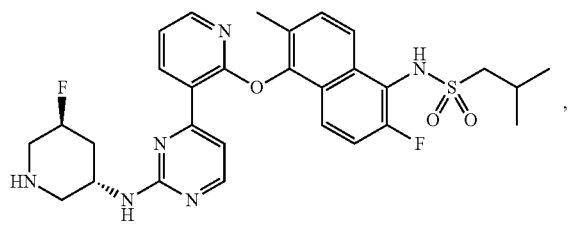
209
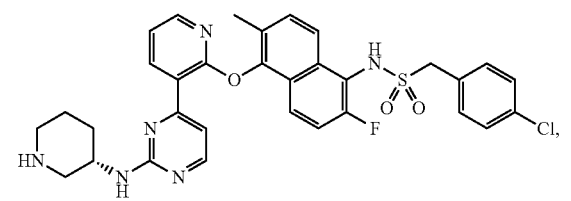
210
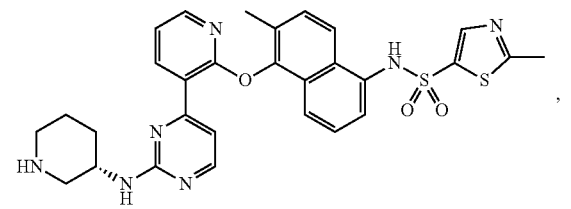
211
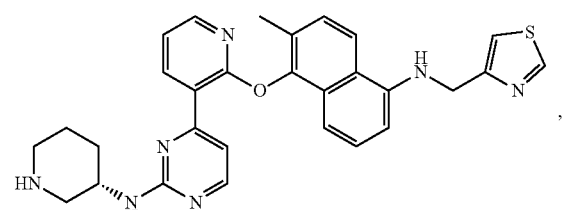
212
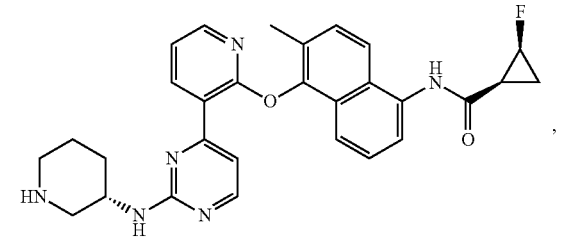
213
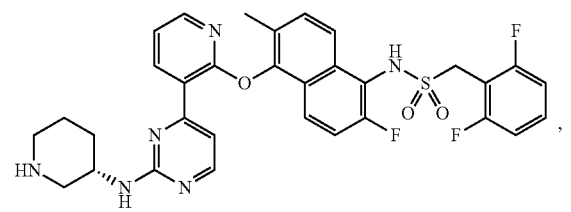
214
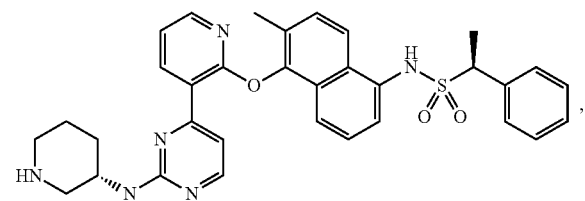
215
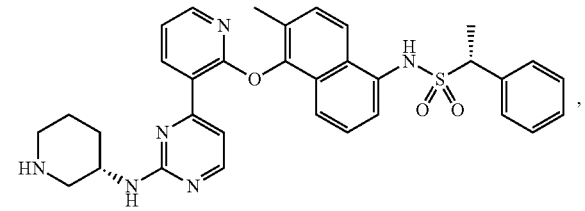
216
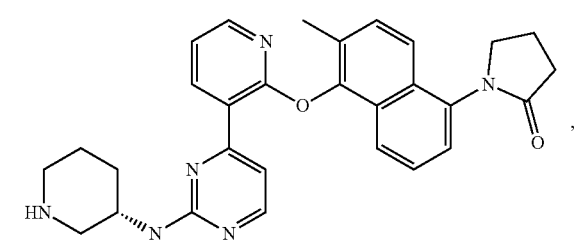
217
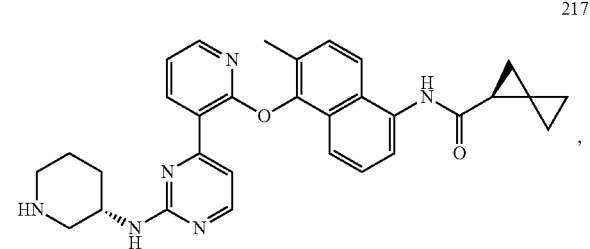
218
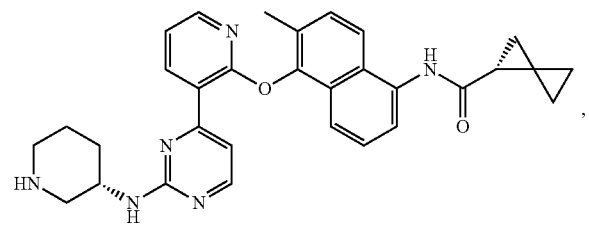
219
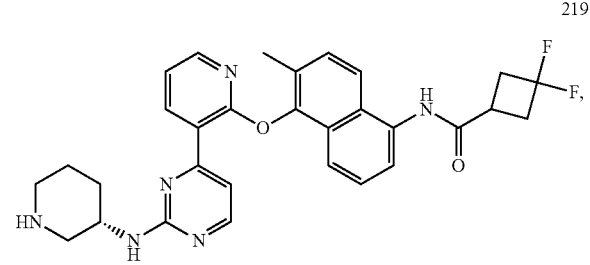

220
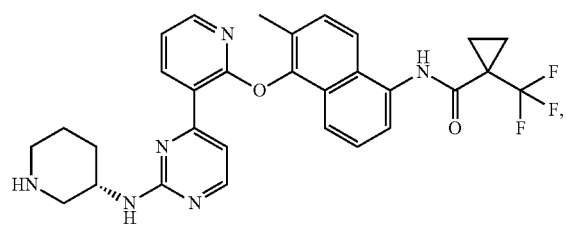
221
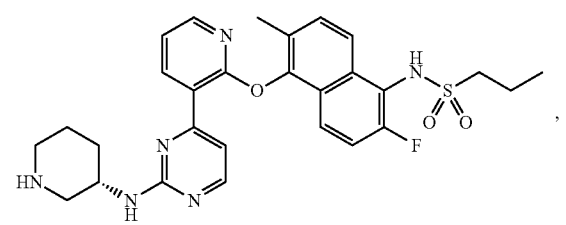
222
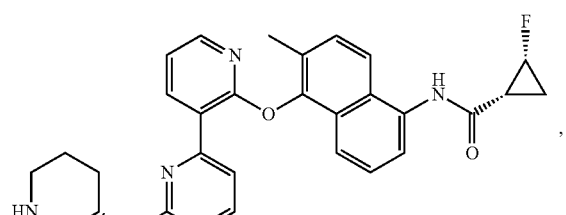
223
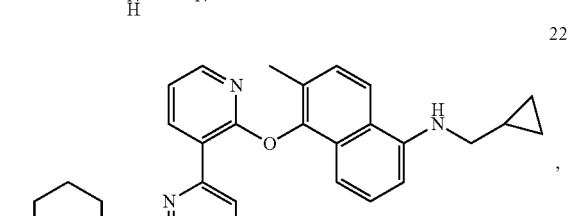
224
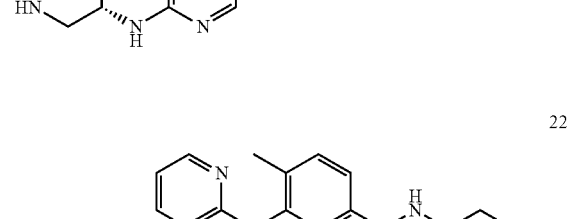
225
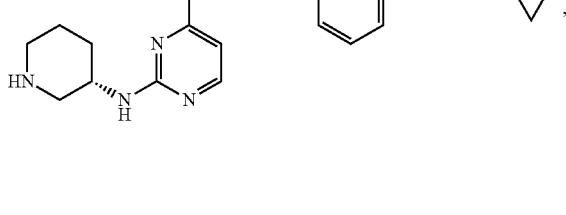
226
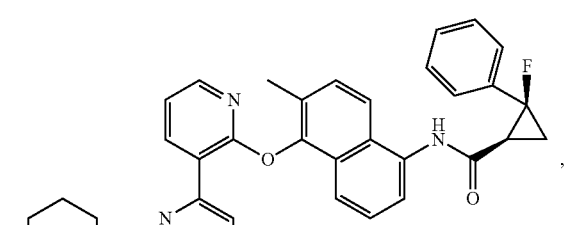
227
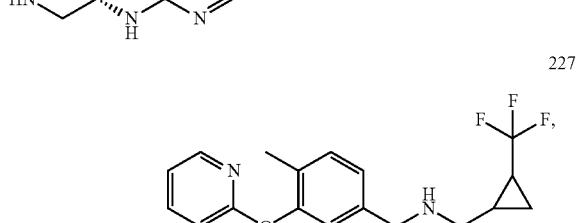
228
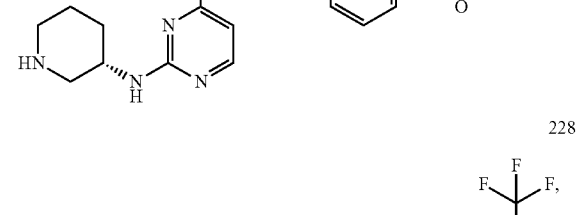
229
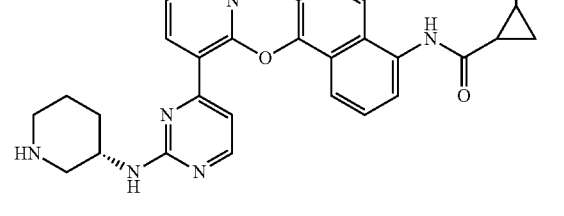
230
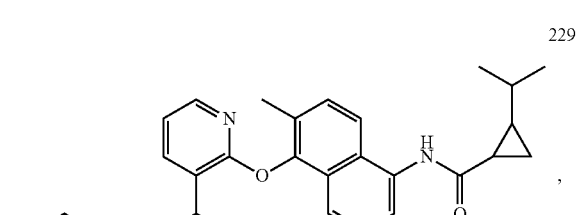

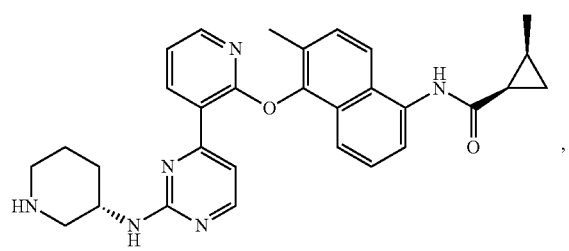
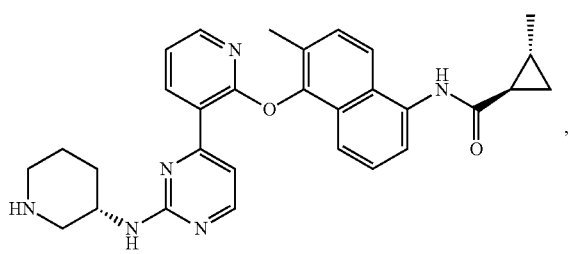
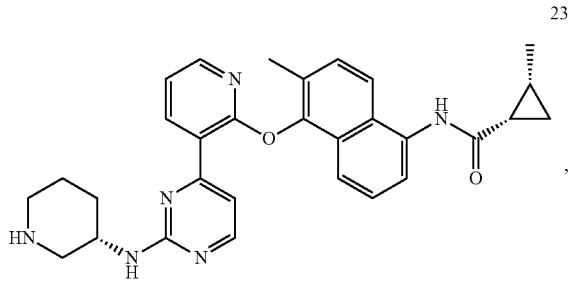
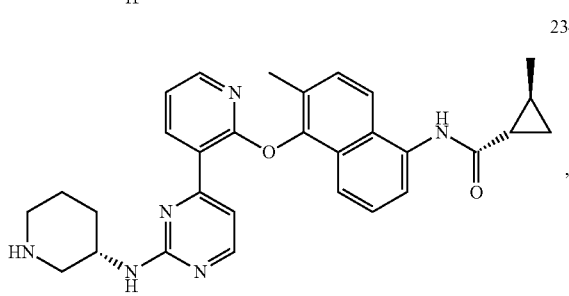
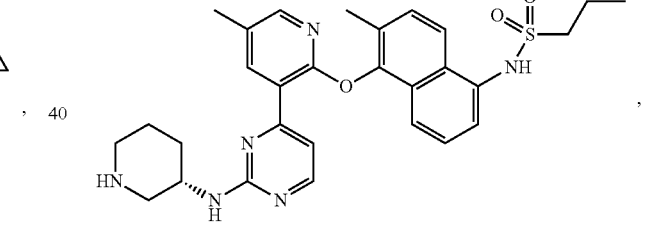
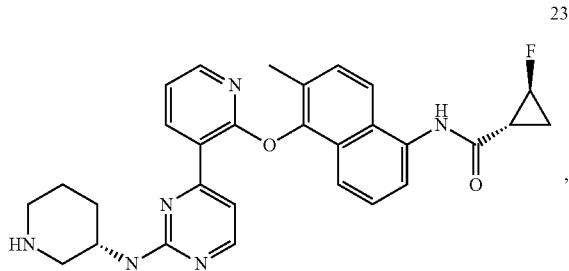
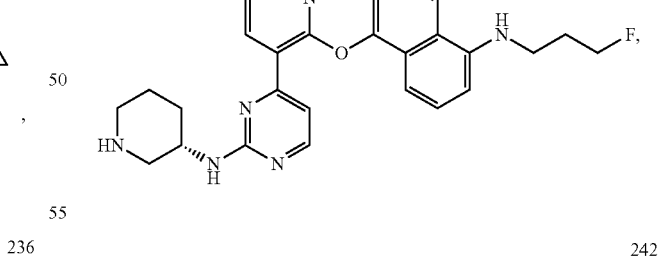
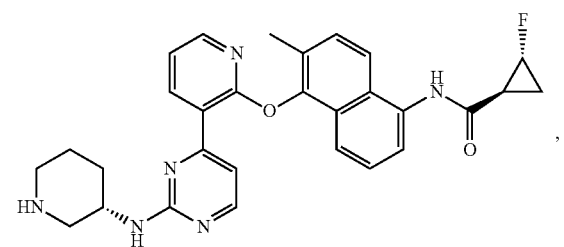
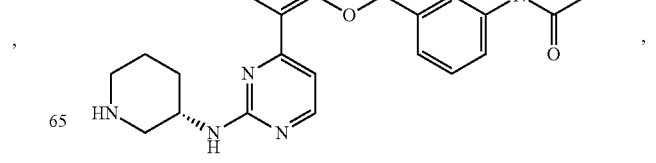

845
-continued
243
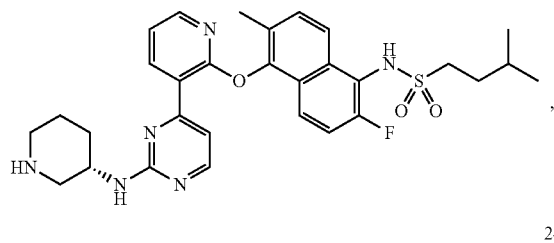
244
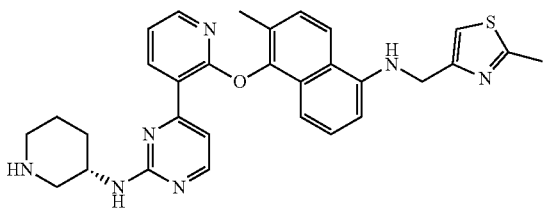
245
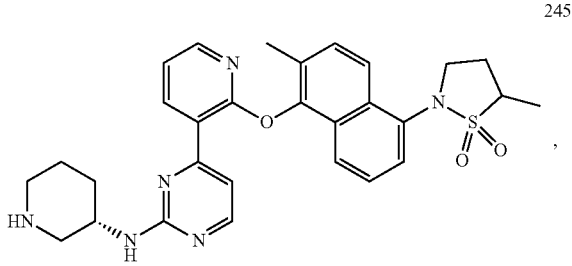
246
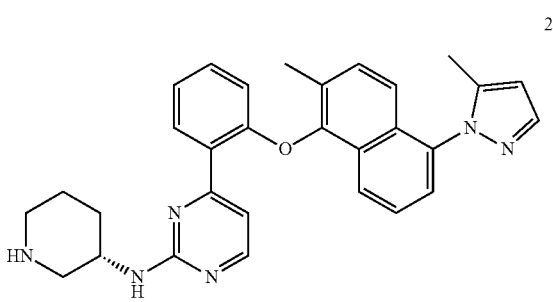
247
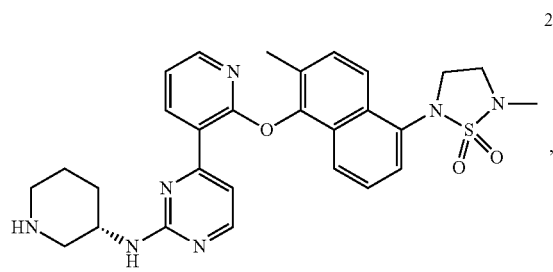
248
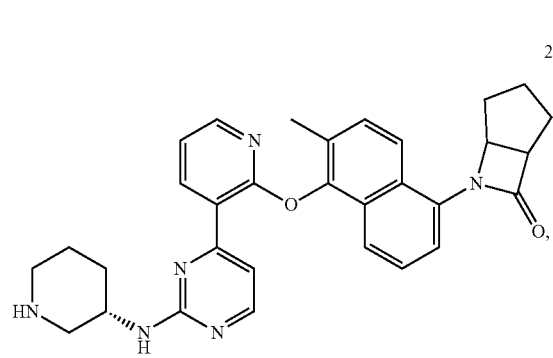
846
-continued
249
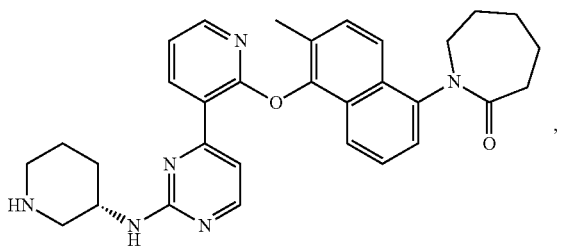
250
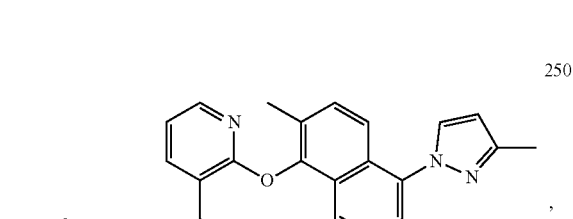
251
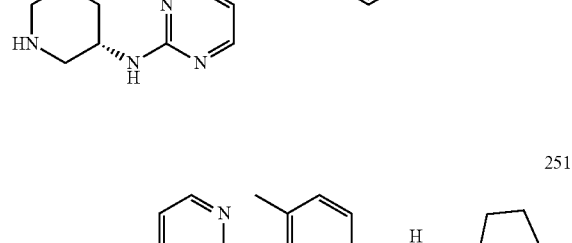
252
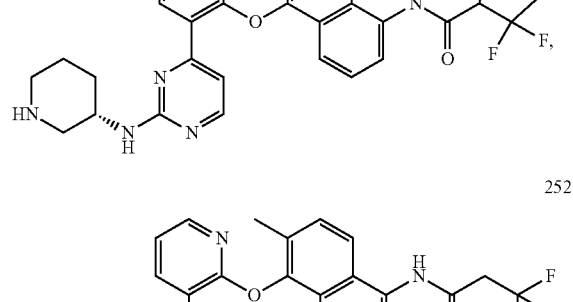
253
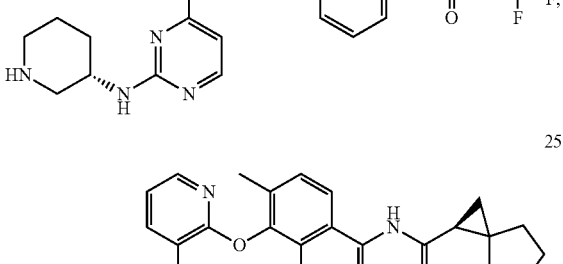
254
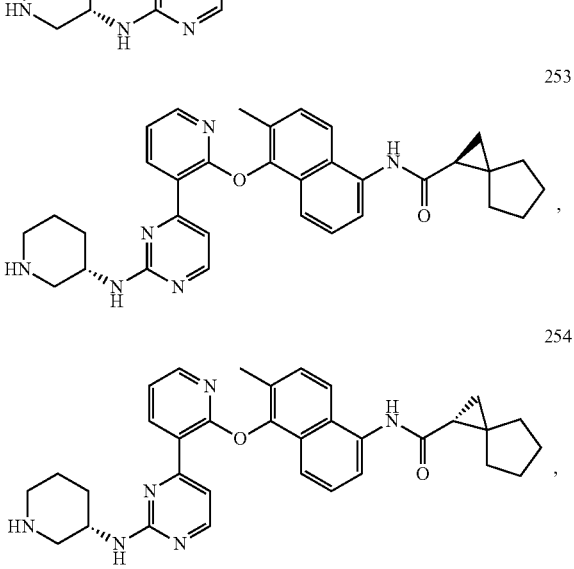

255
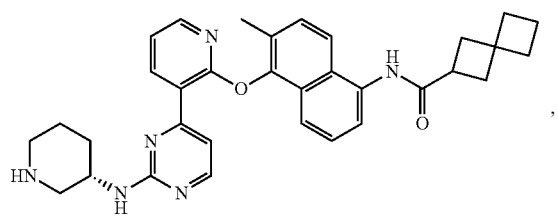
,
256
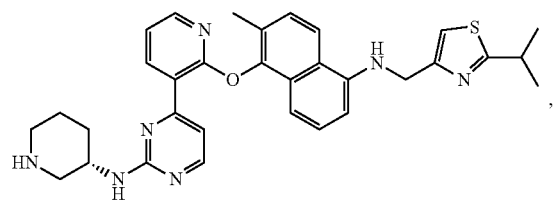
,
257
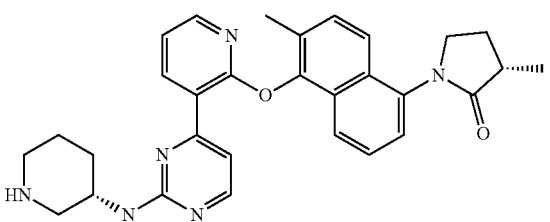
,
258
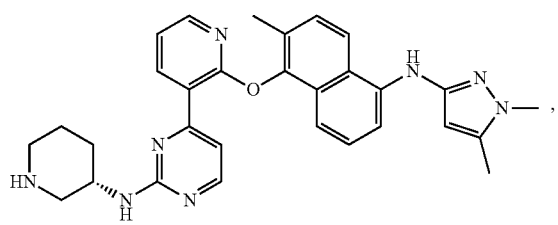
,
259
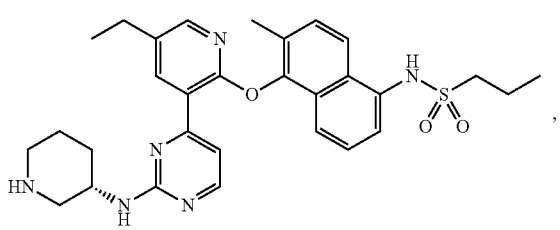
,
260
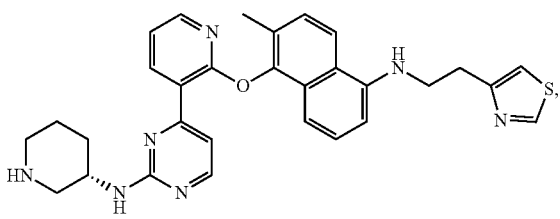
,
261
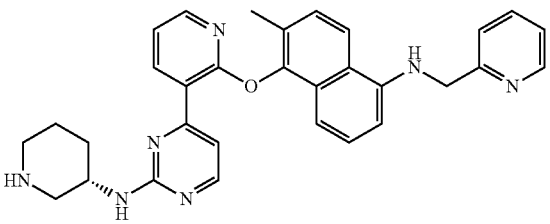
,
262
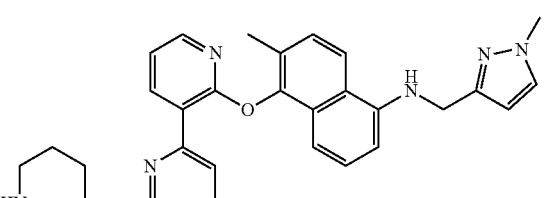
,
263
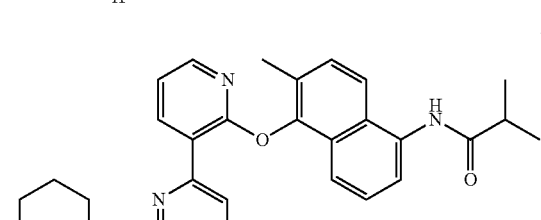
,
264
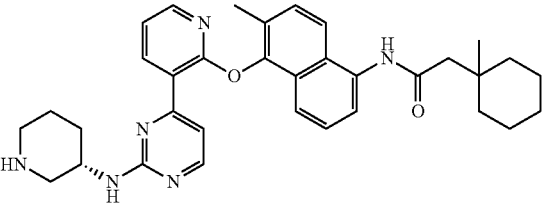
,
265
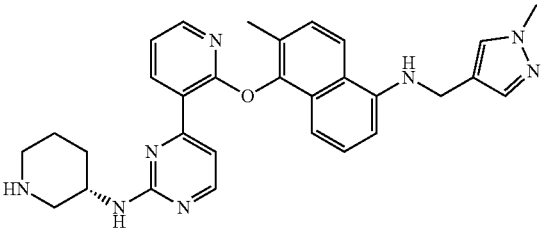
,
266
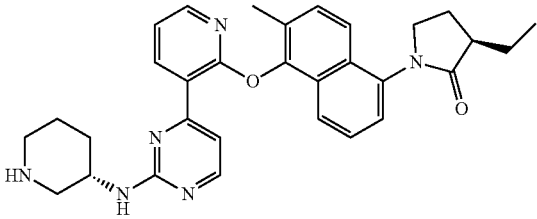
, 849
-continued
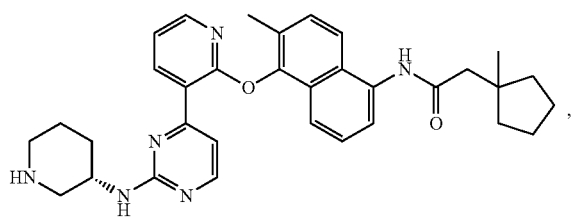
267
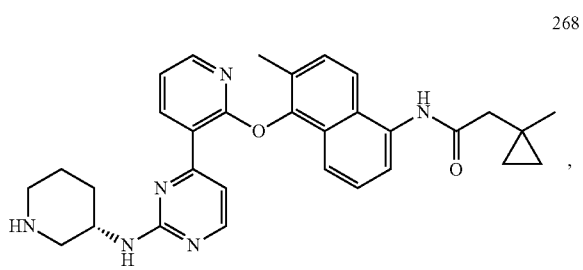
268
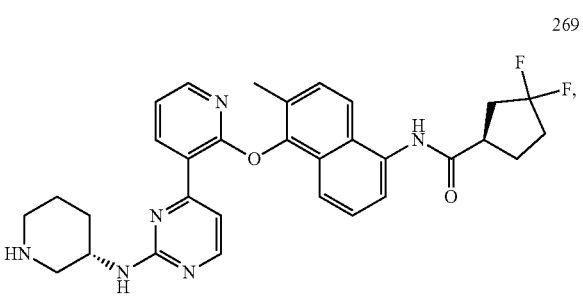
269
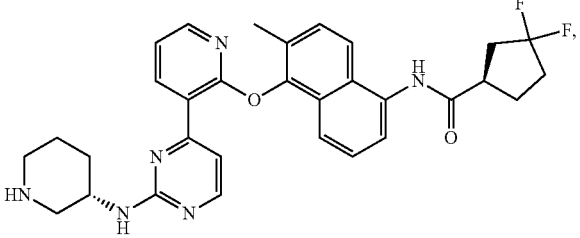
270
271
272
850
-continued
273
274
275
276
277
278
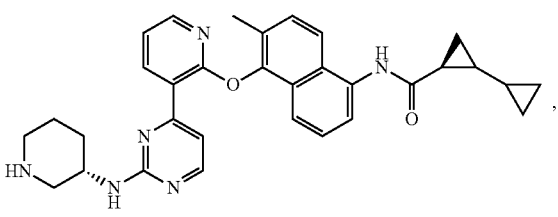

279
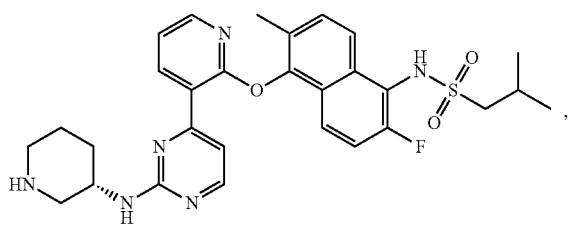
280
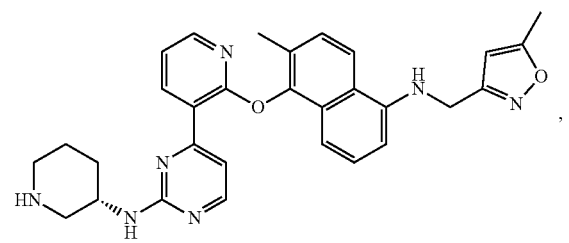
281
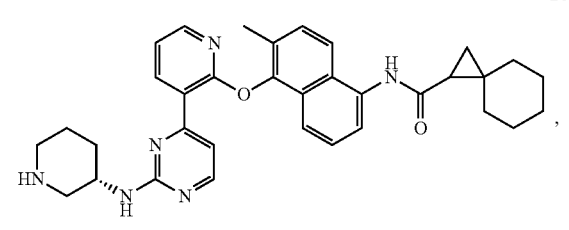
282
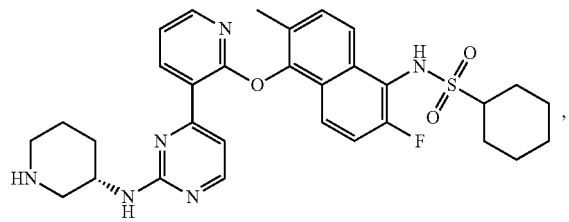
283
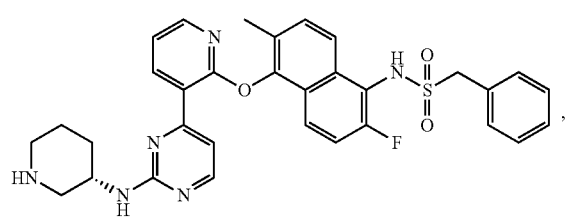
284
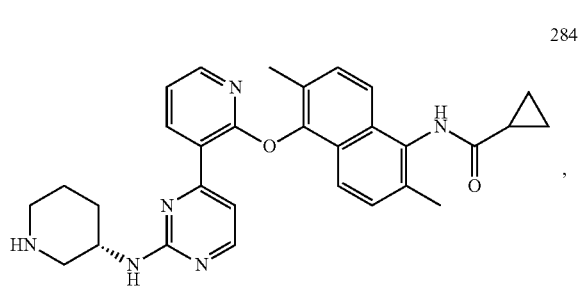
285
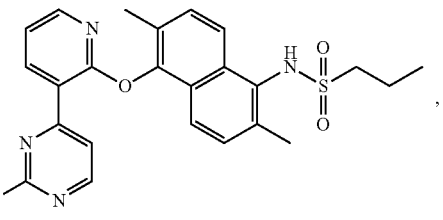
286
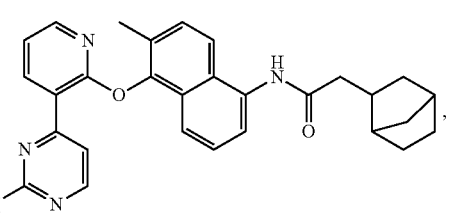
287
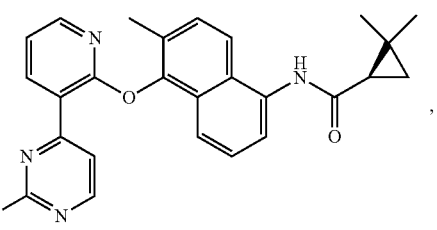
288
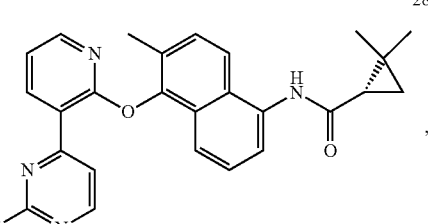
289
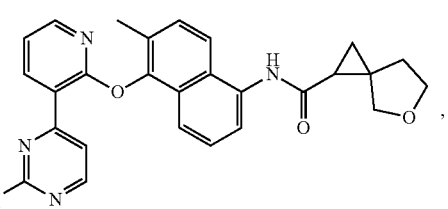
290
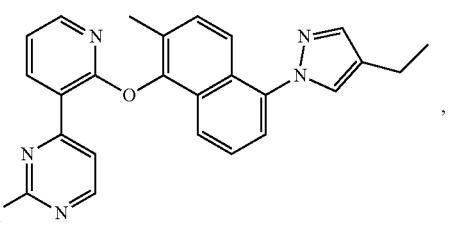

291
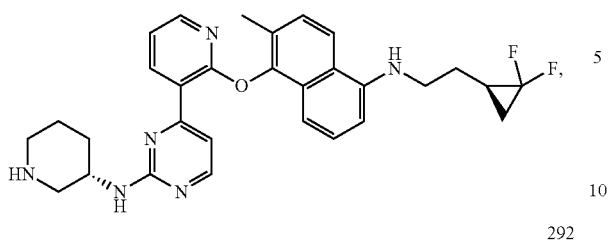
292
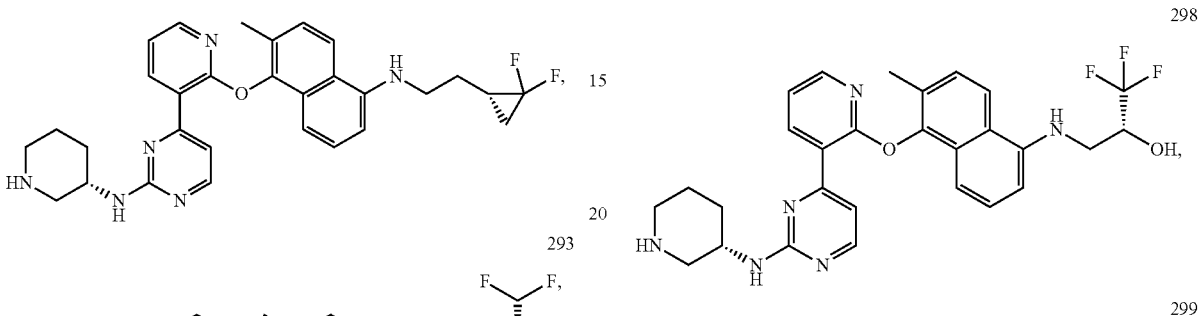
293
294
295
296
297
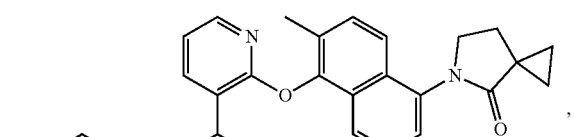
298
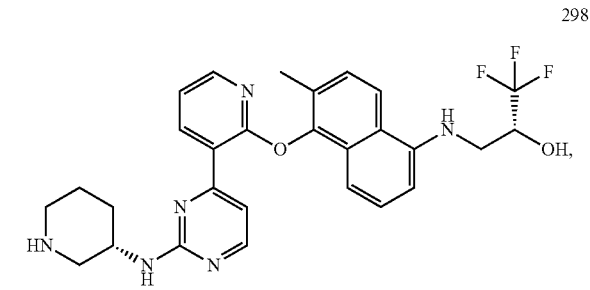
299
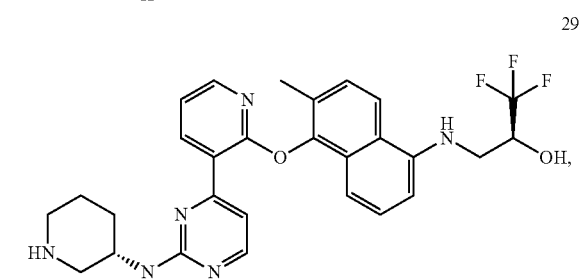
300
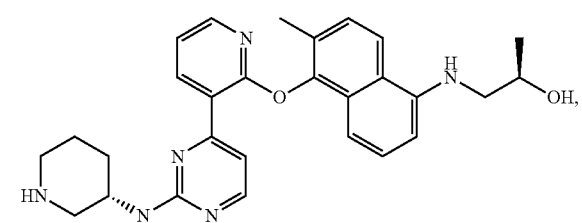
301
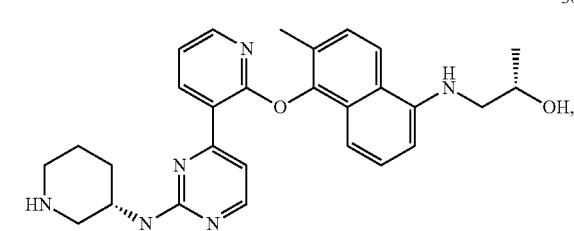
302
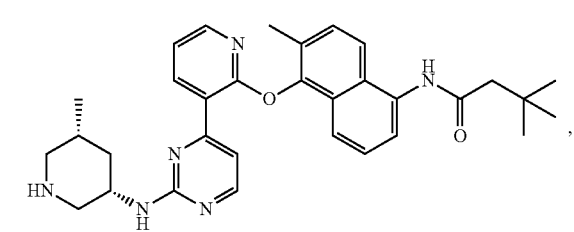

303
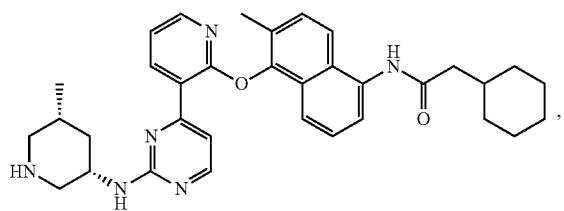
304
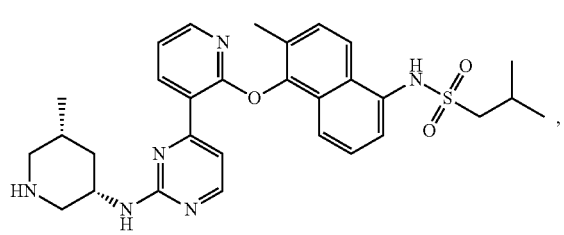
305
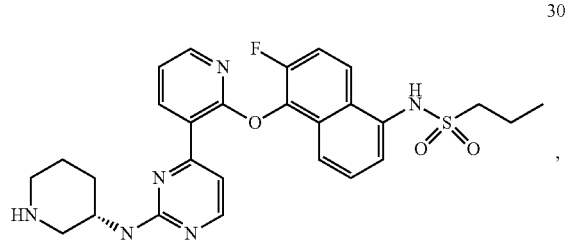
306
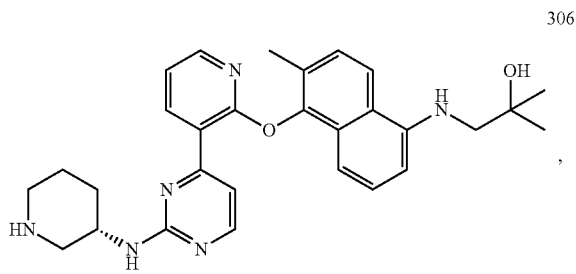
307
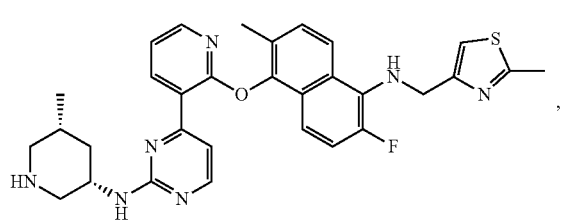
308
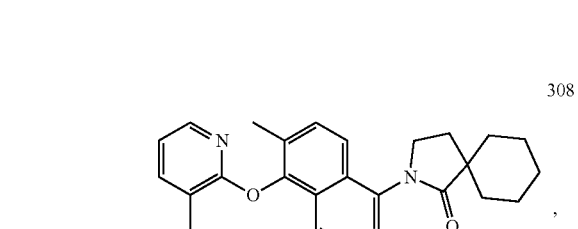
309
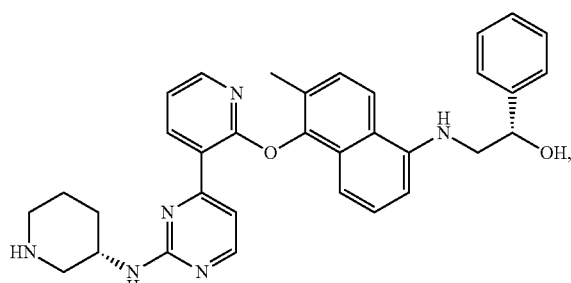
310
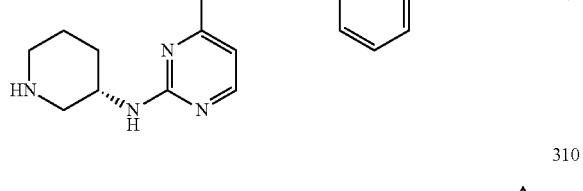
311
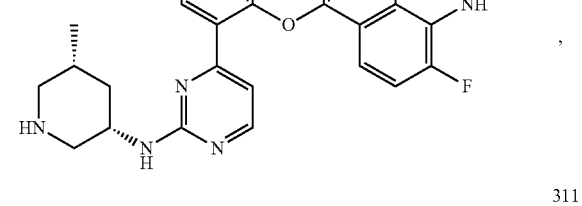
312
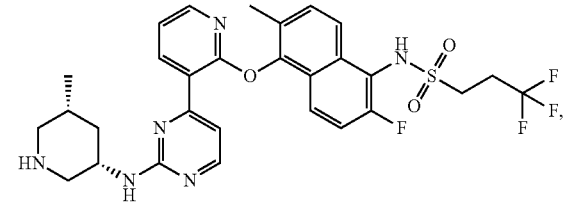
313
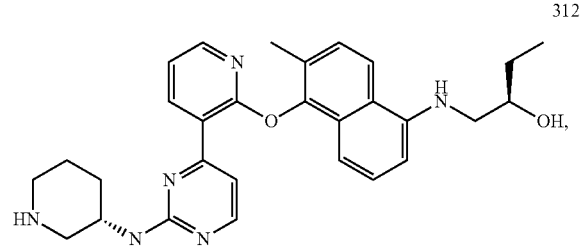
314
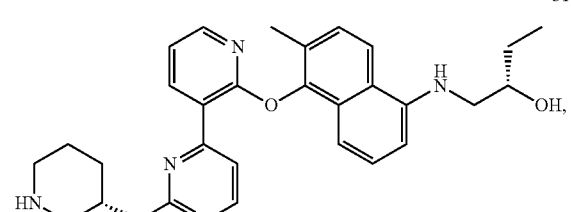
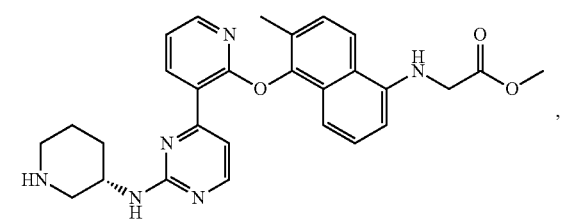

-continued
315
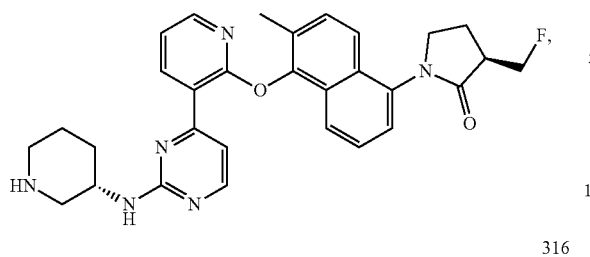
316
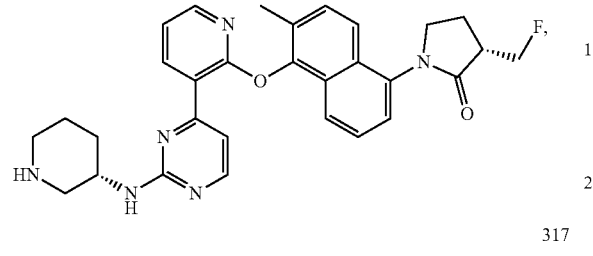
317
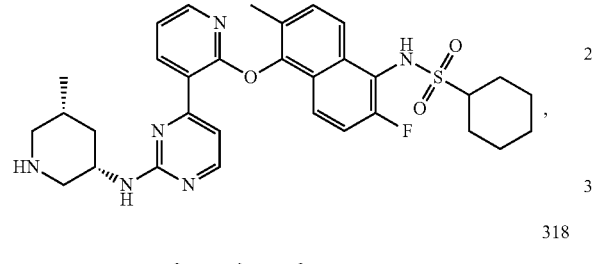
318
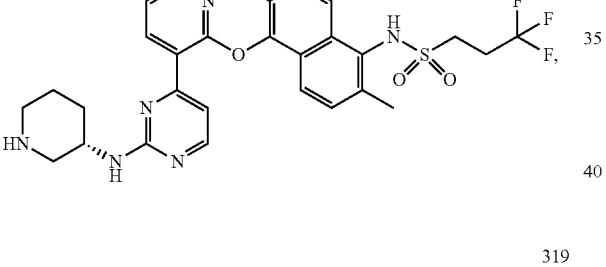
319
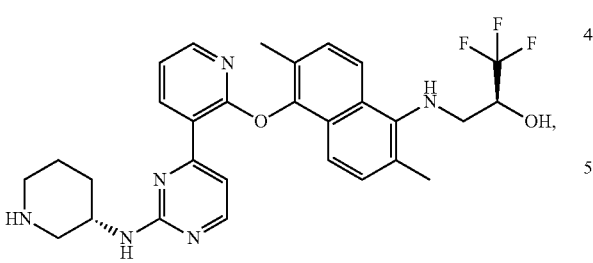
320
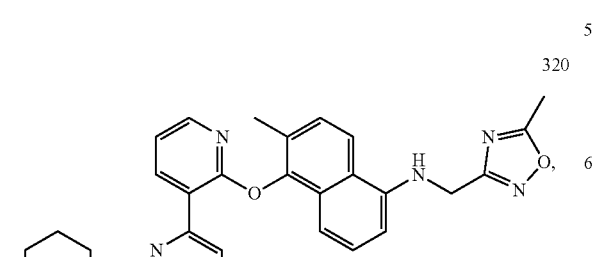
-continued
321
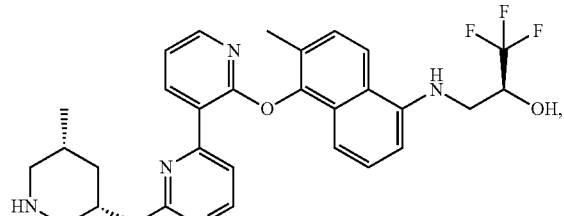
322
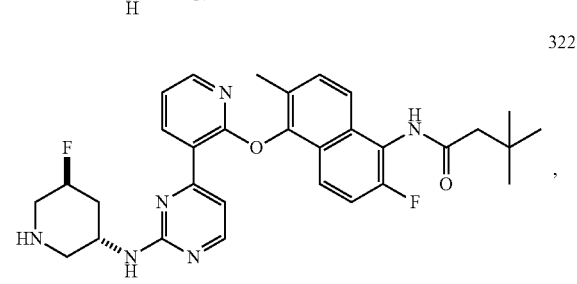
323
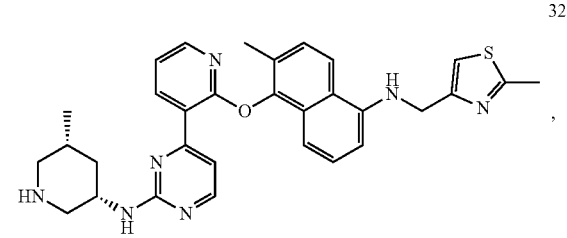
324
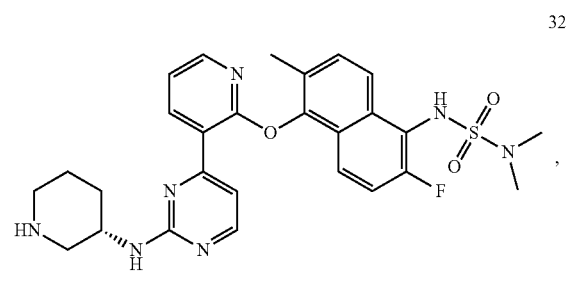
325
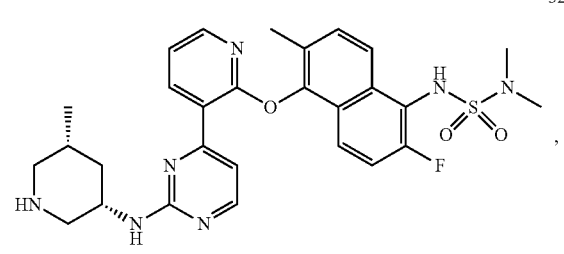
326
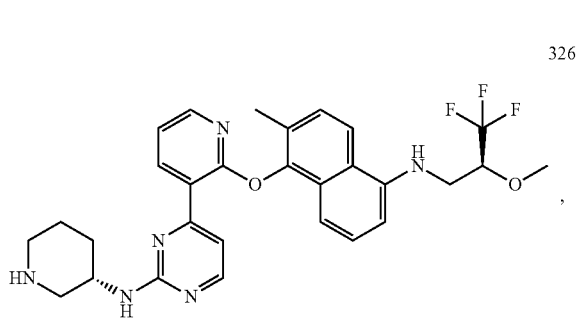

327
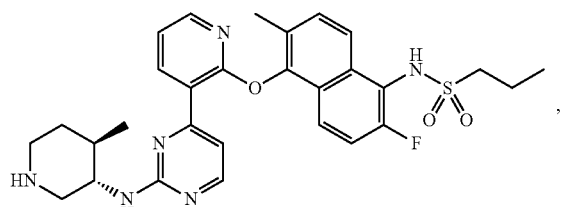
328
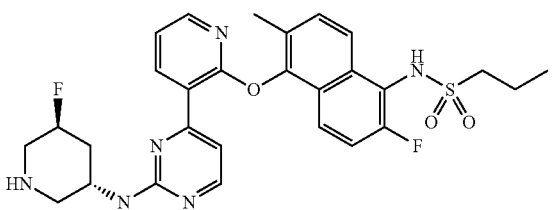
329
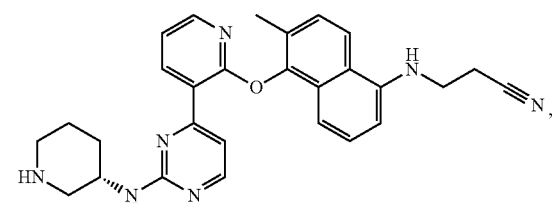
330
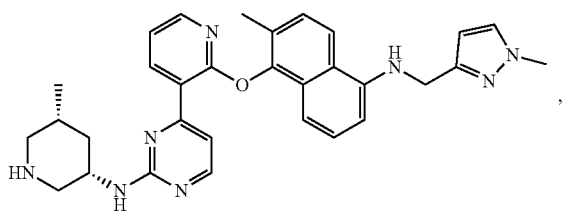
331
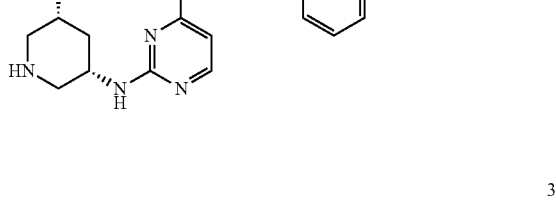
332
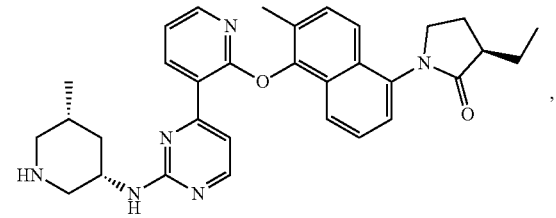
333
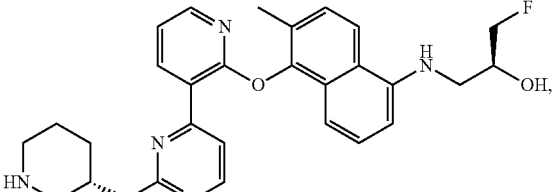
334
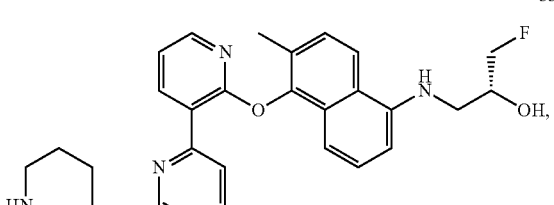
335
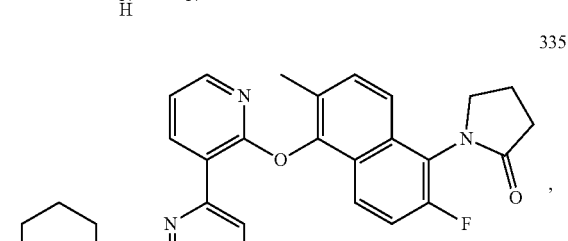
336
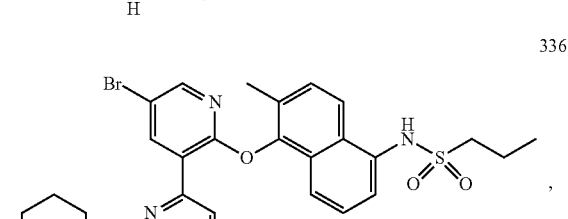
337
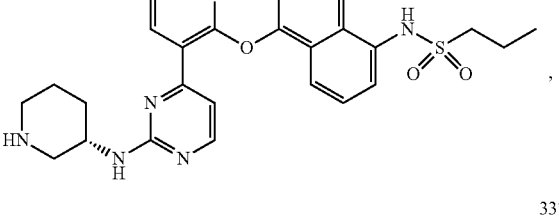
338
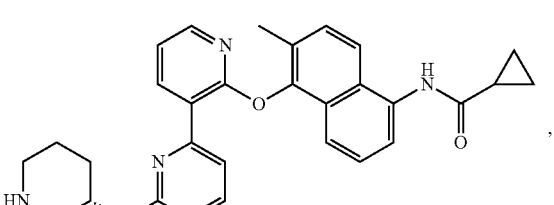

-continued
339
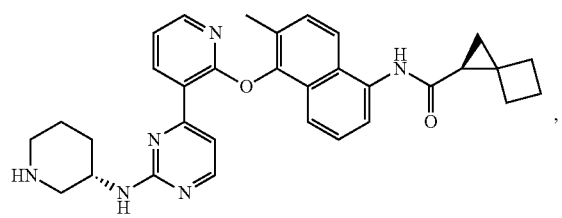
340
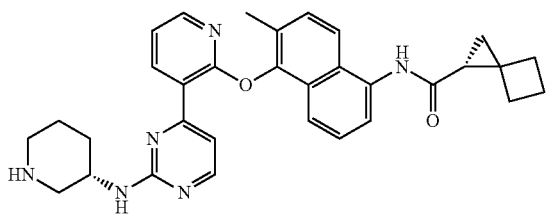
341
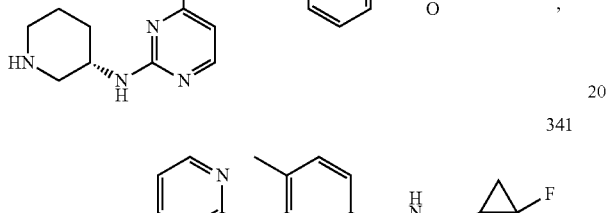
342
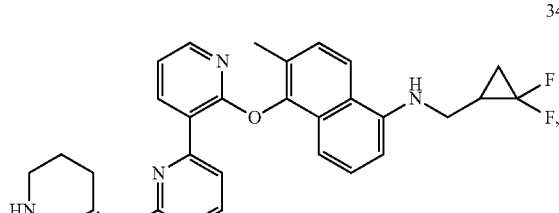
343
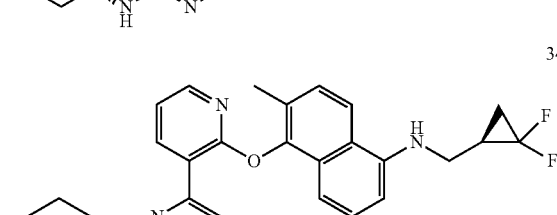
344
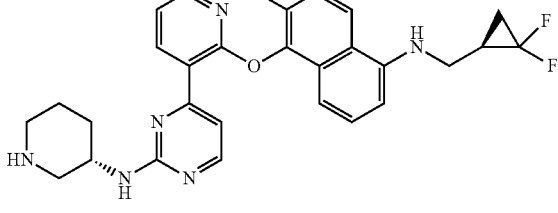
-continued
345
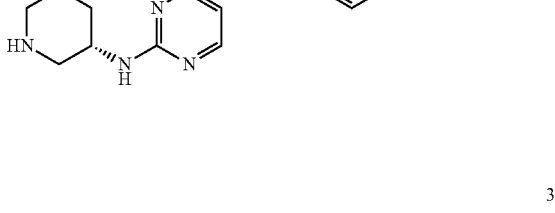
346
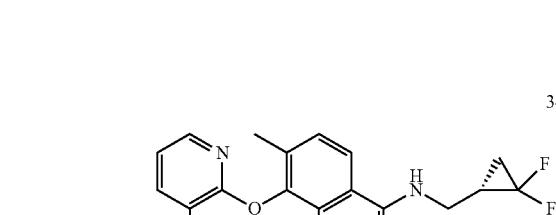
347
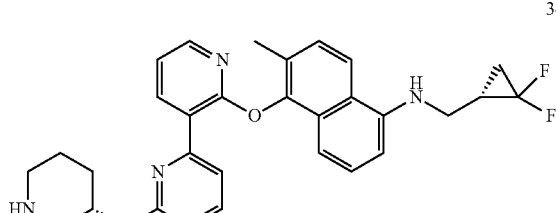
348
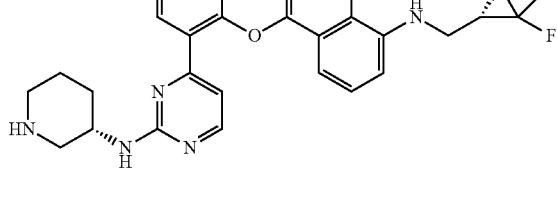
349
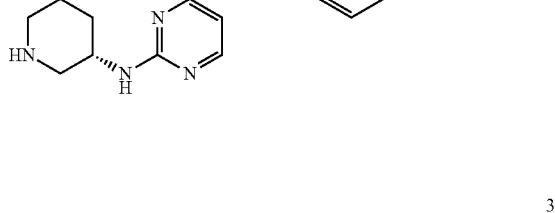
350
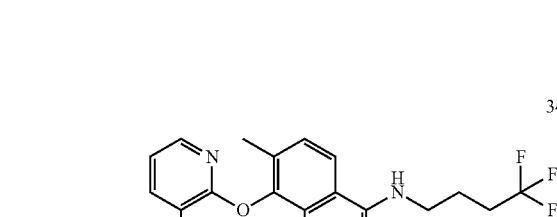

351
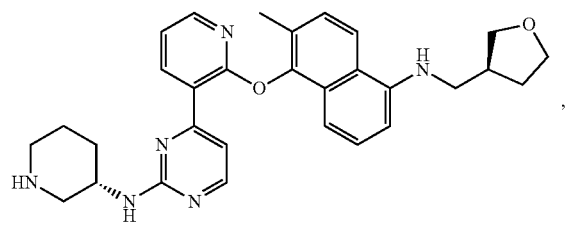
352
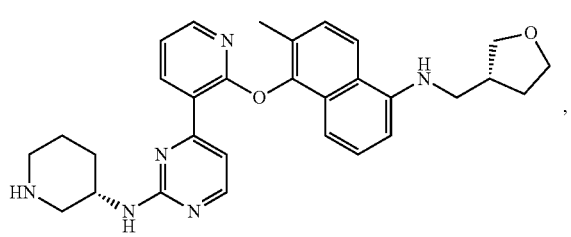
353
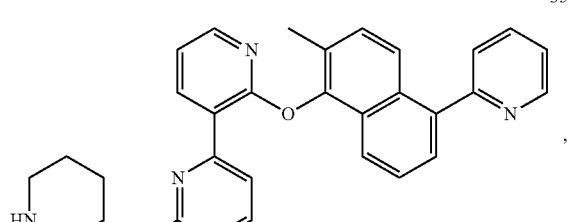
354
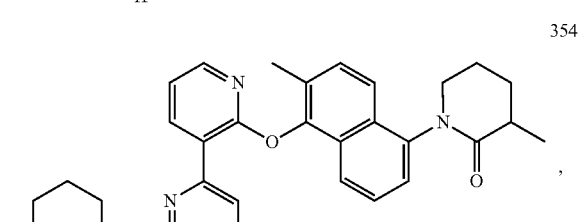
355
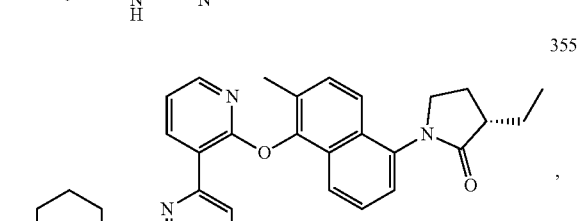
356
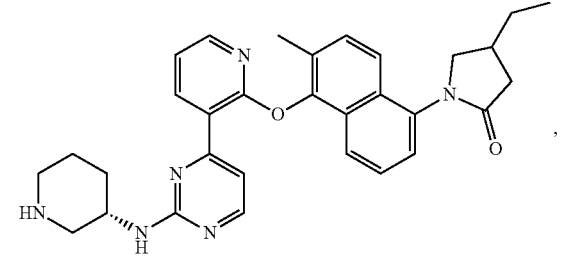
357
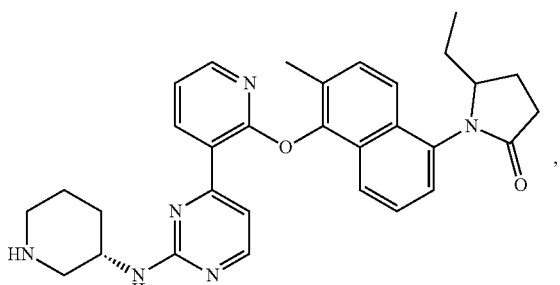
358
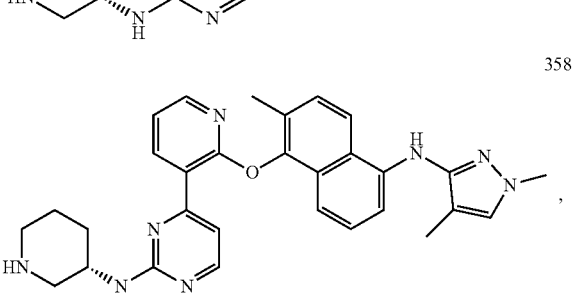
359
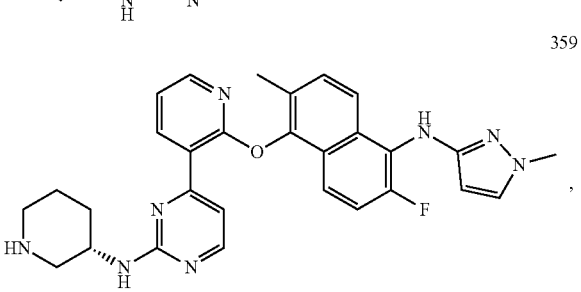
360
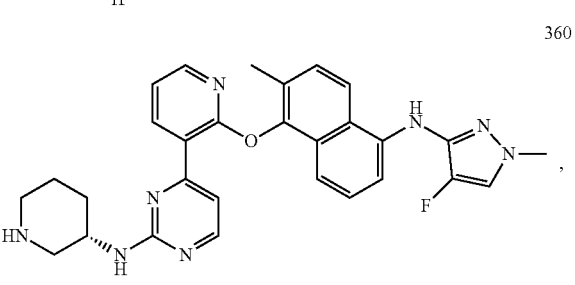
361
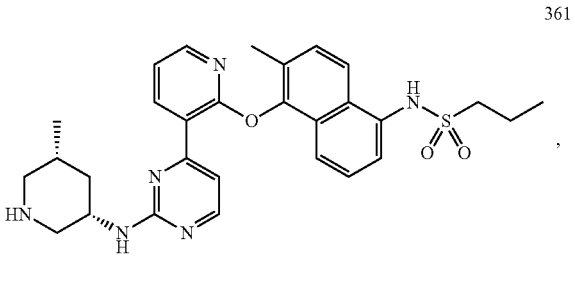
362
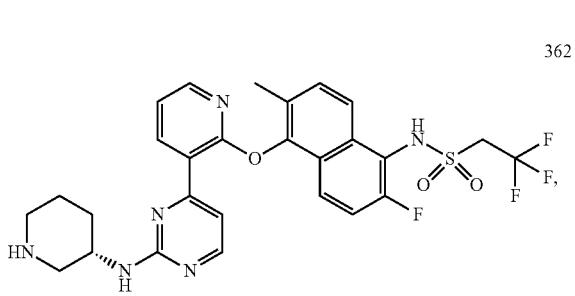

865
-continued
363
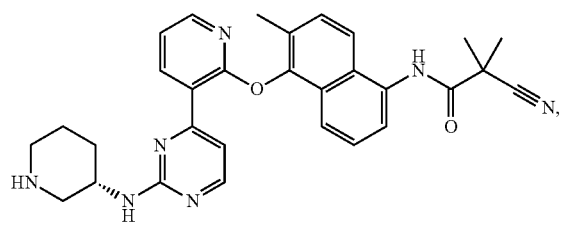
364
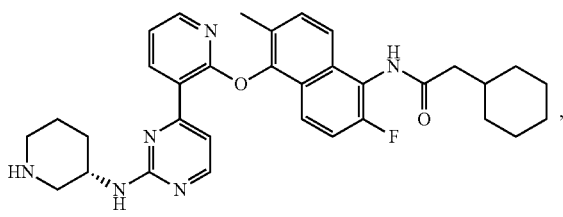
365
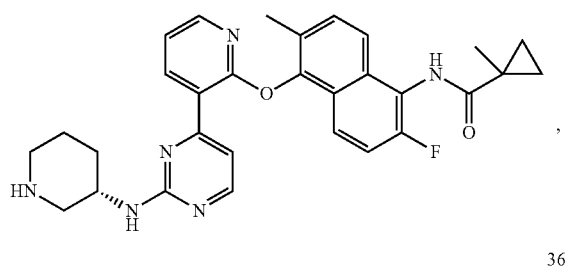
366
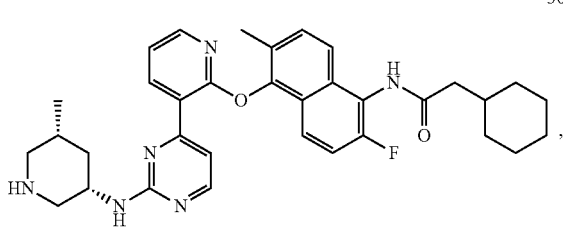
367
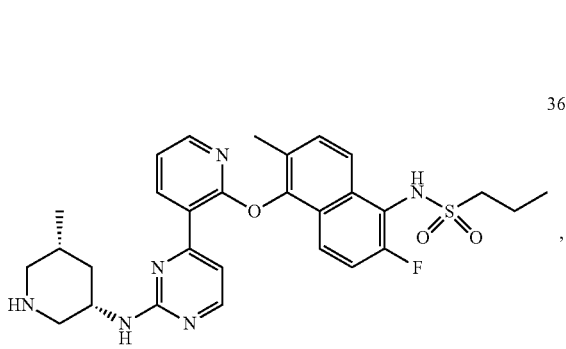
368
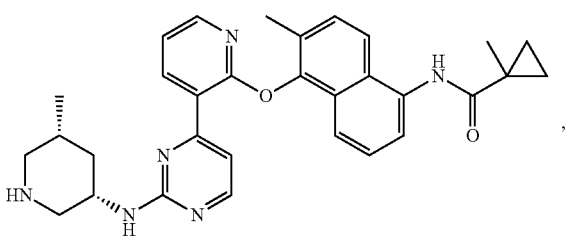
866
-continued
369
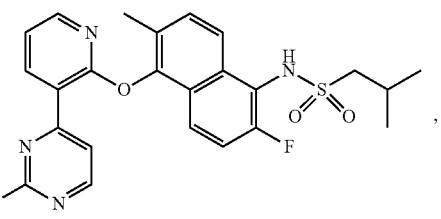
370
371
372
373
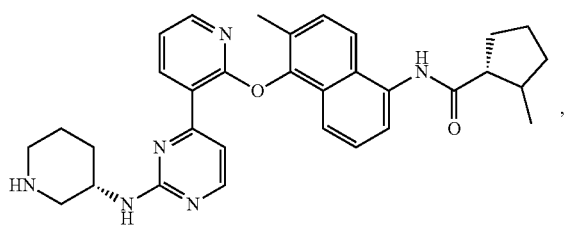
374

375
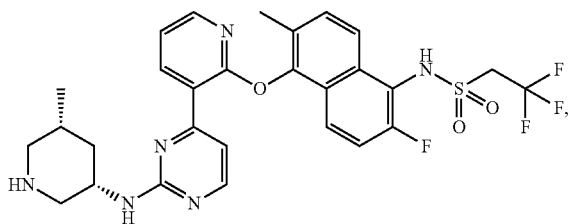
376
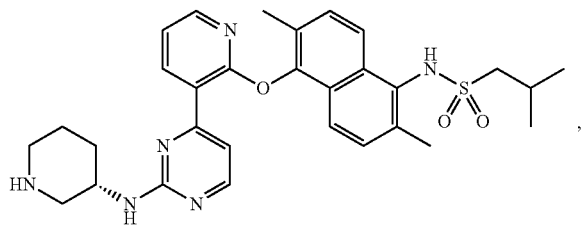
377
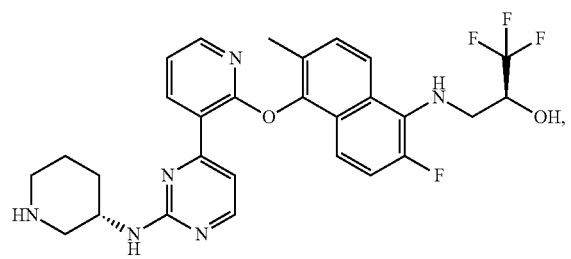
378
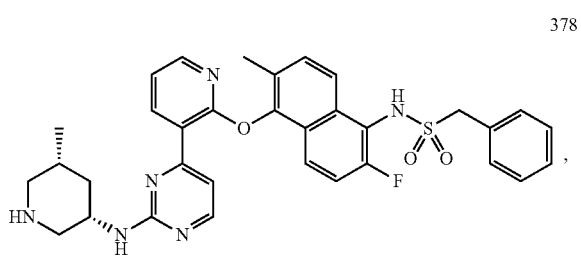
379
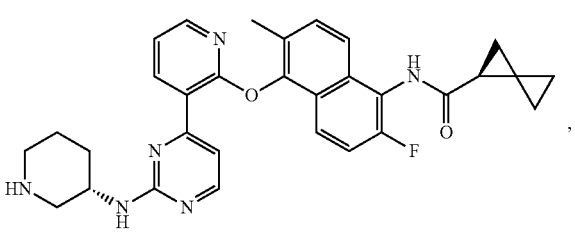
380
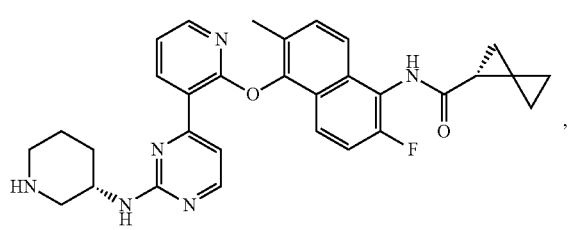
381
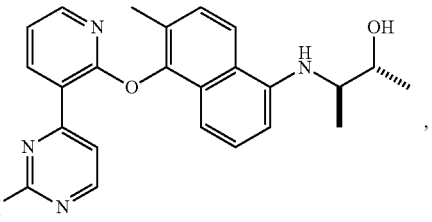
382
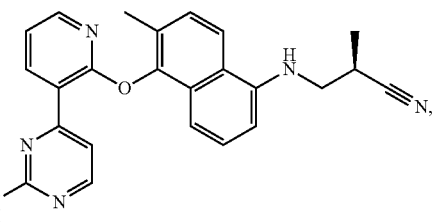
383
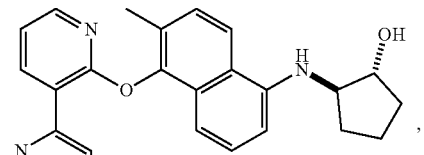
384
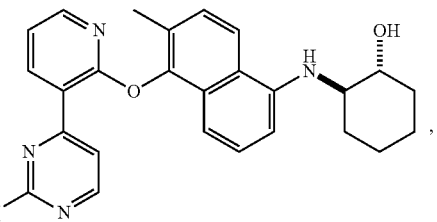
385
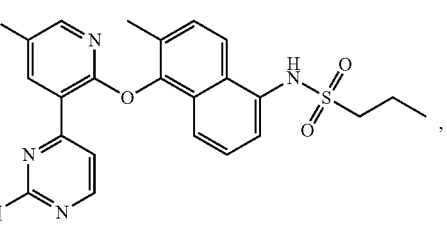
386
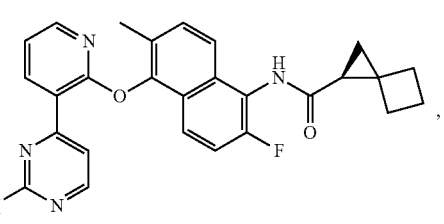

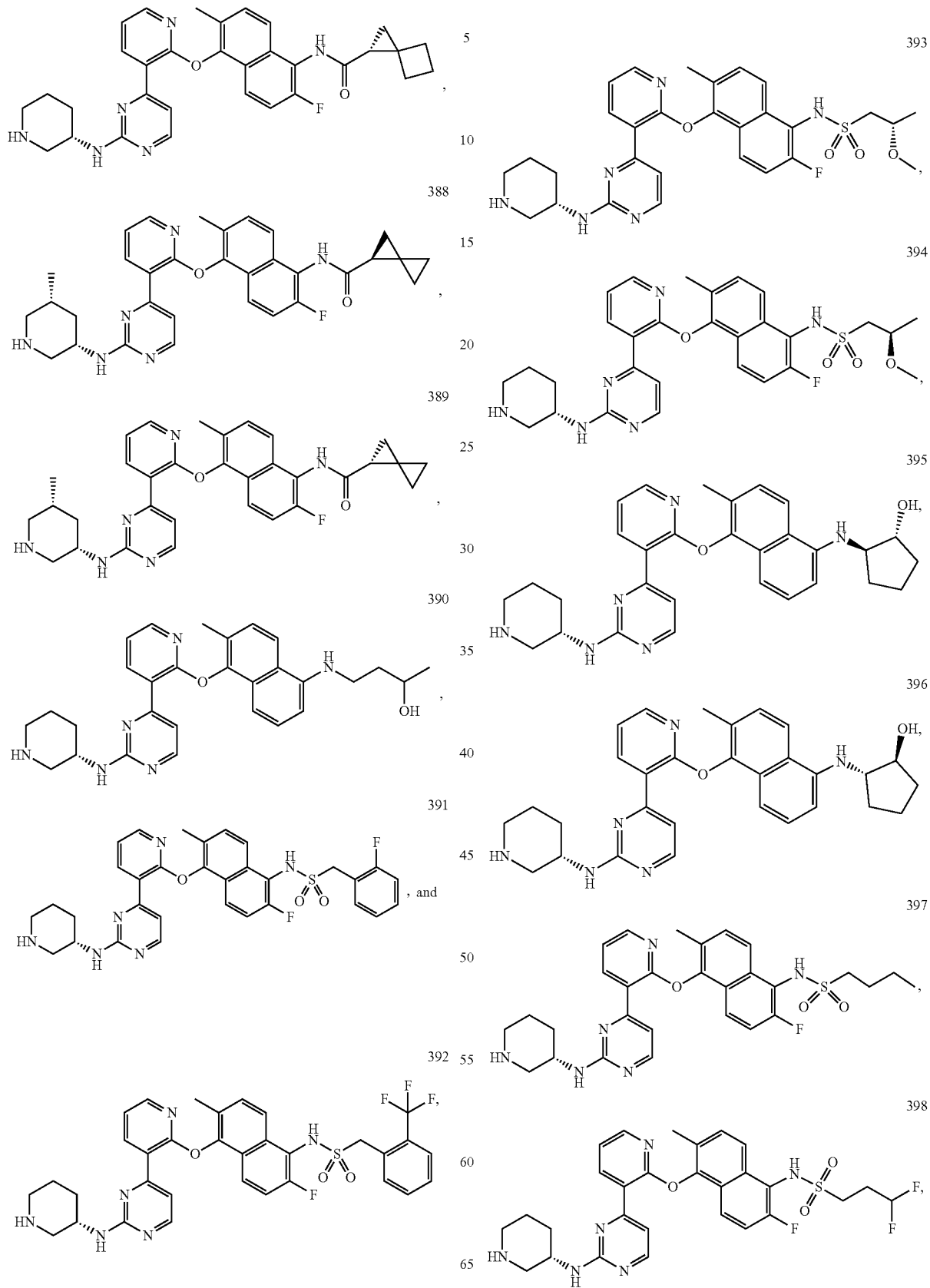
29. The compound of claim 1, wherein the compound is selected from the group consisting of
or a pharmaceutically acceptable salt thereof.

399
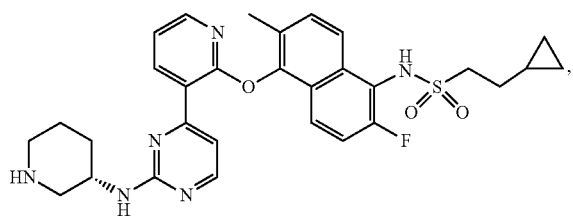
400
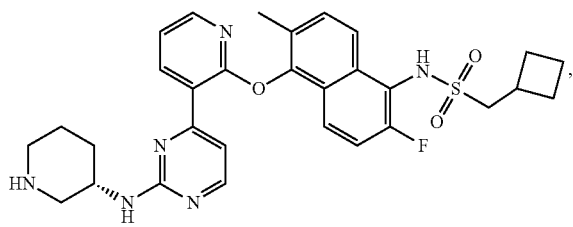
401
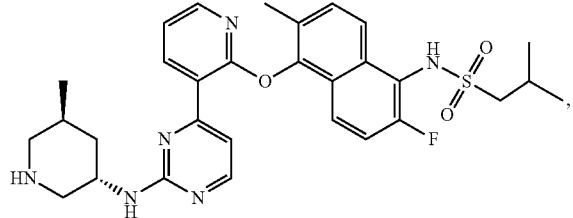
402
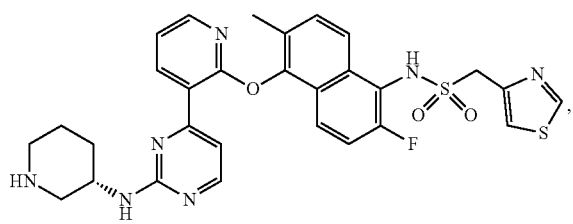
403
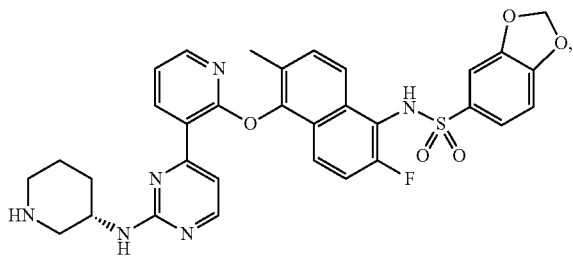
404
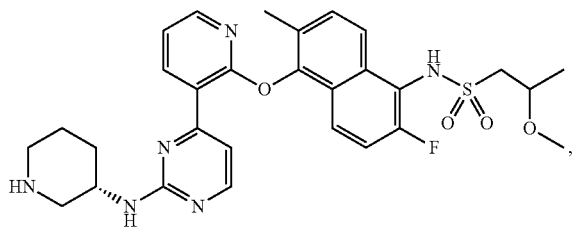
405
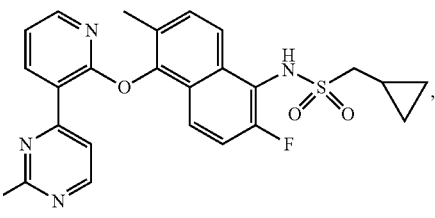
406
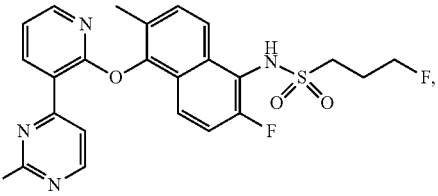
407
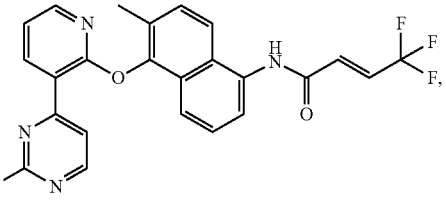
408
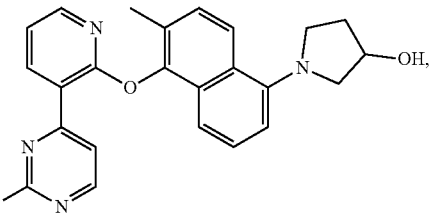
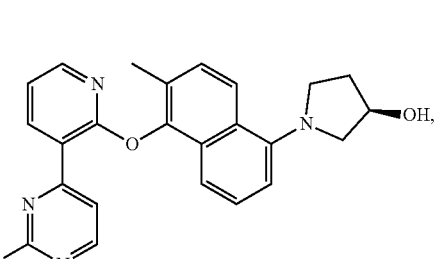
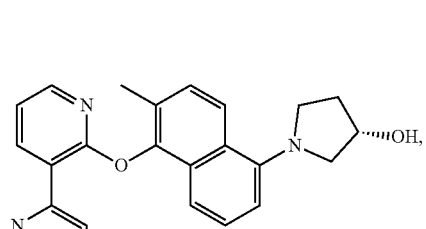

-continued
409
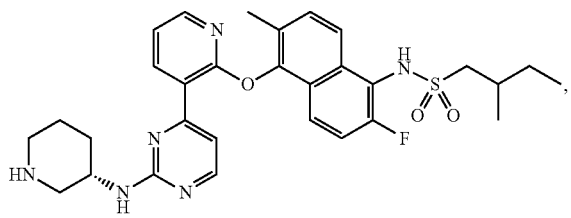
410
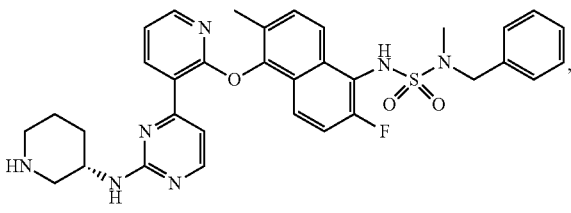
411
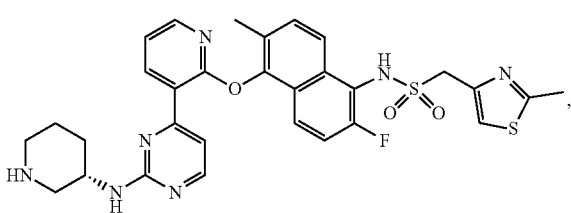
412
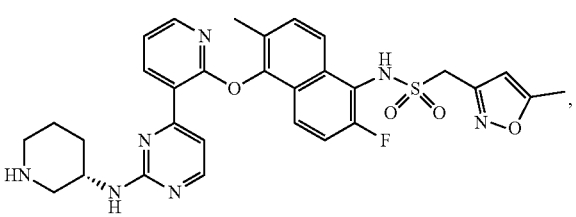
413
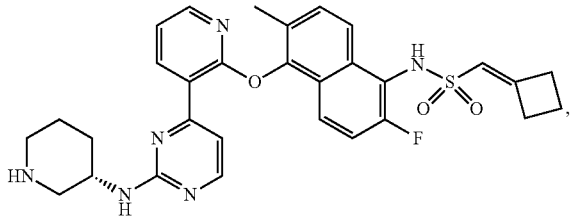
414
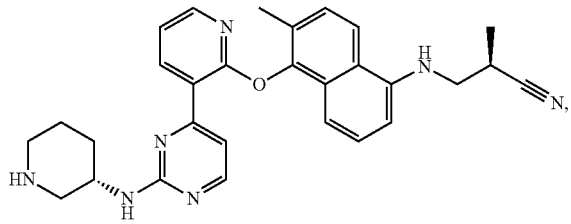
-continued
415
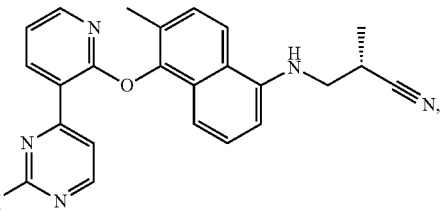
416
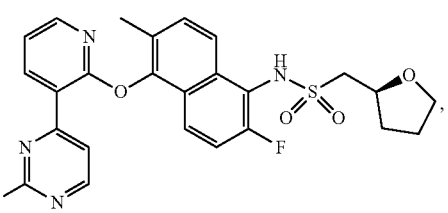
417
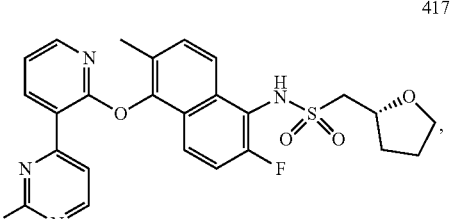
418
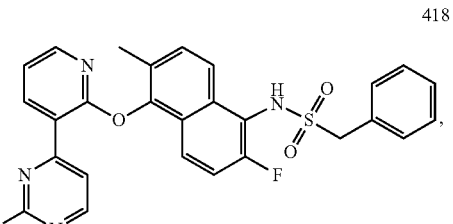
420
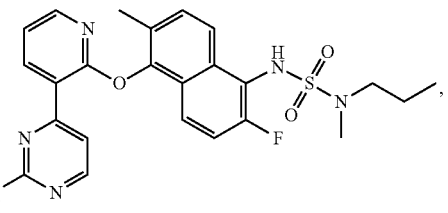
421
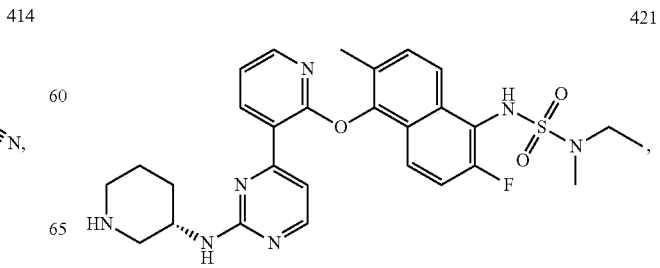

422
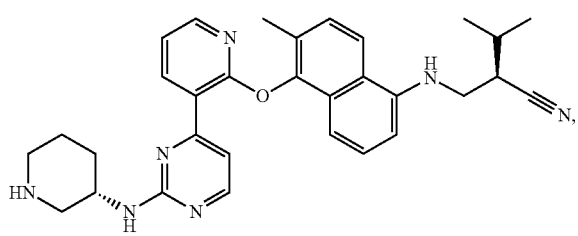
423
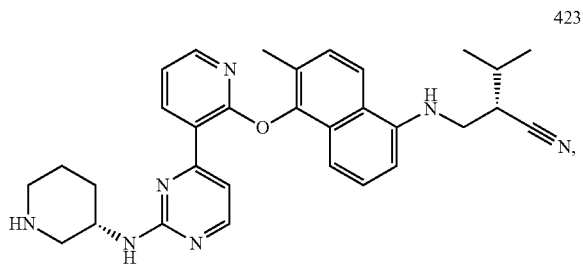
424
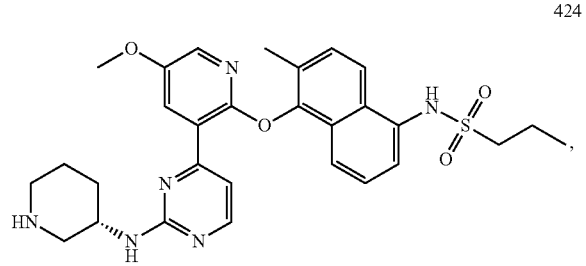
425
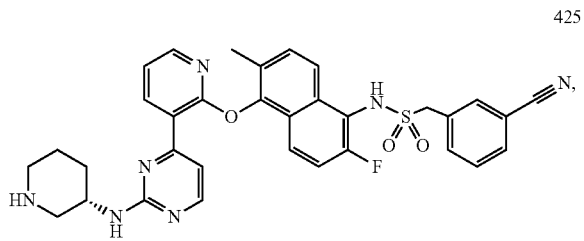
426
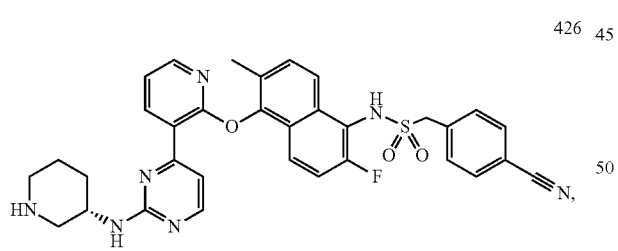
427
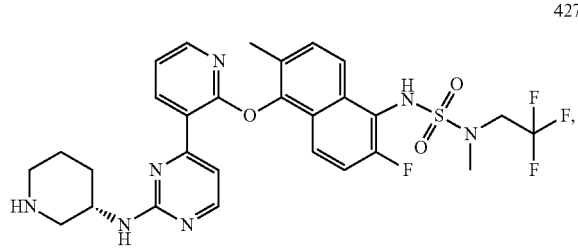
428
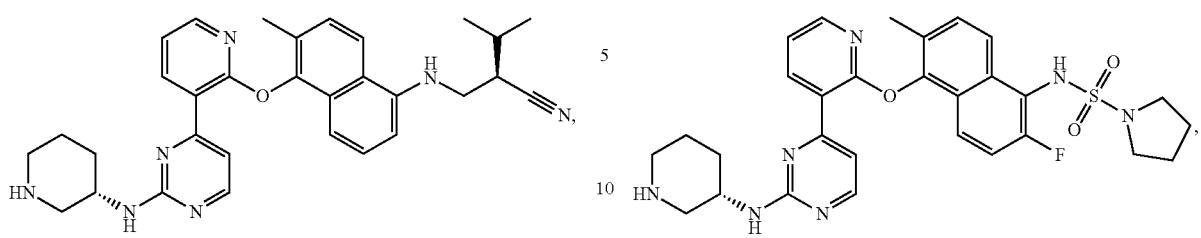
429
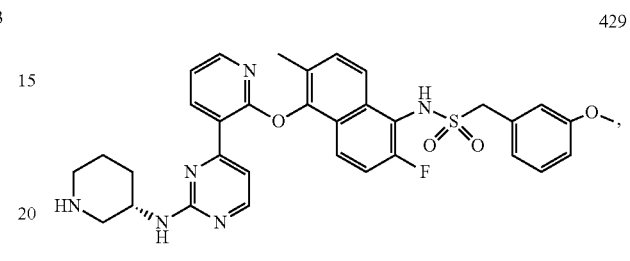
430
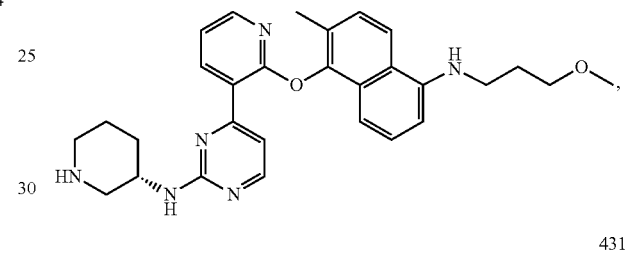
431
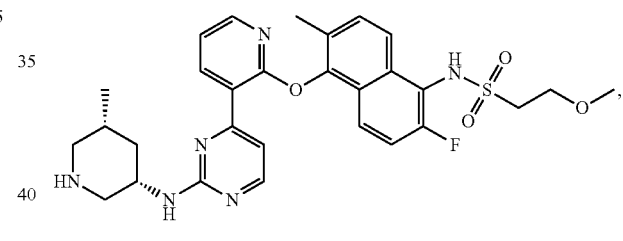
432
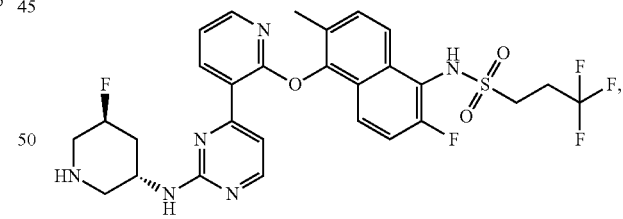
433
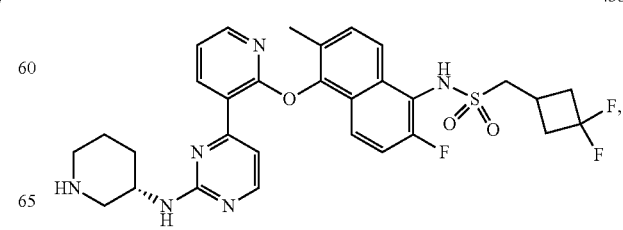

434
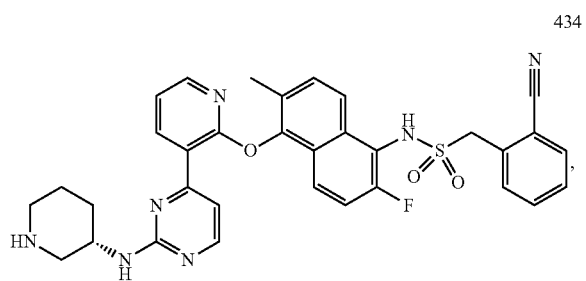
435
436
437
438
439
440
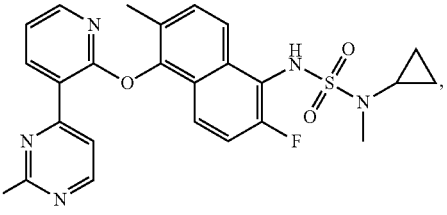
441
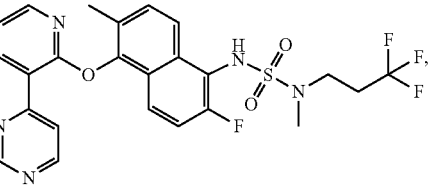
442
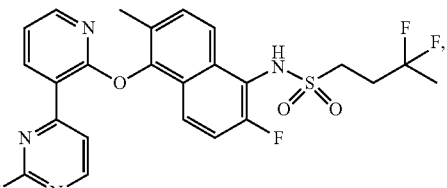
443
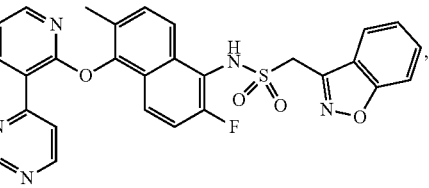
444
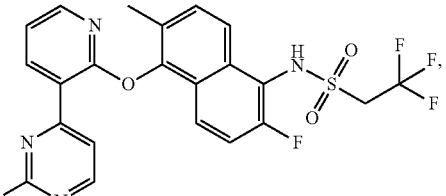
445
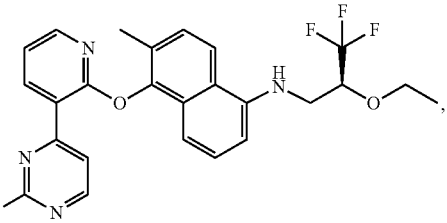

446
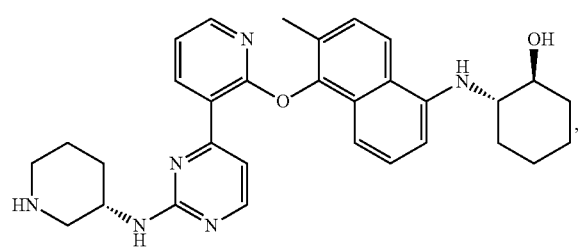
447
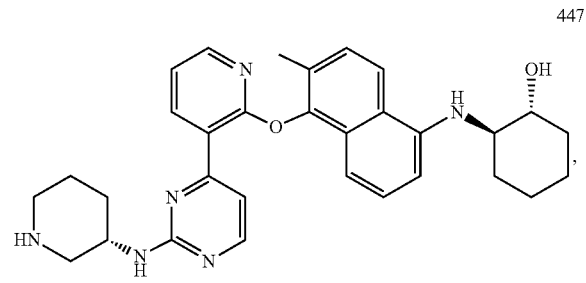
448
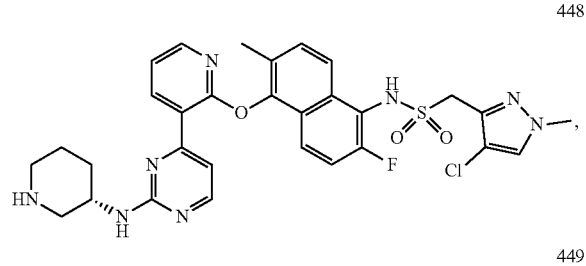
449
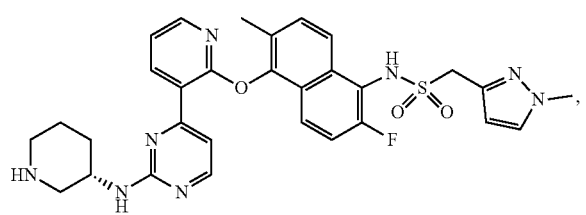
450
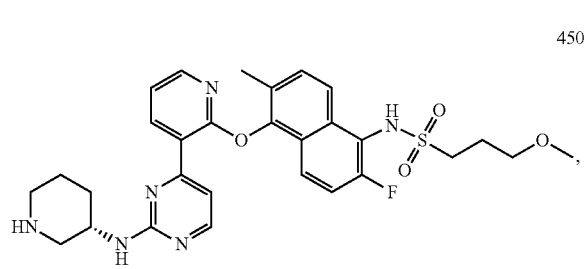
451
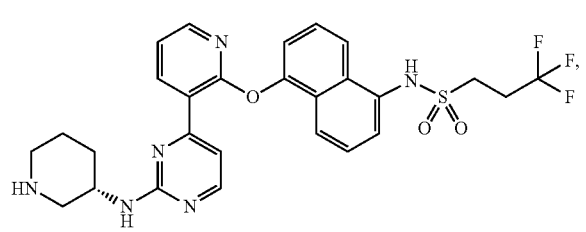
452
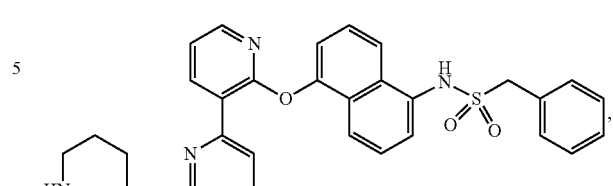
453
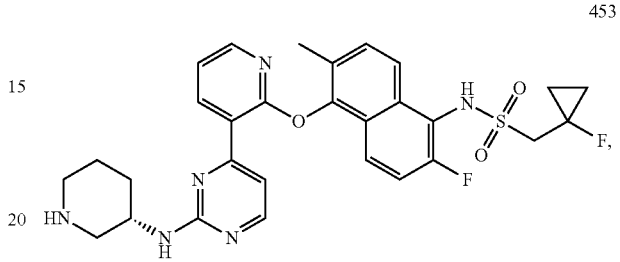
454
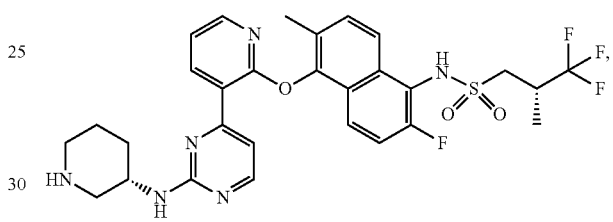
455
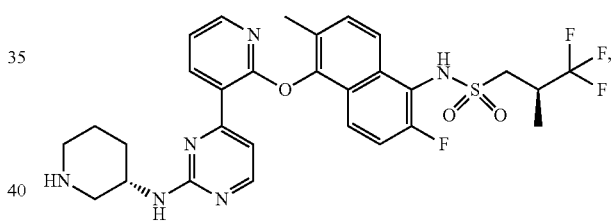
456
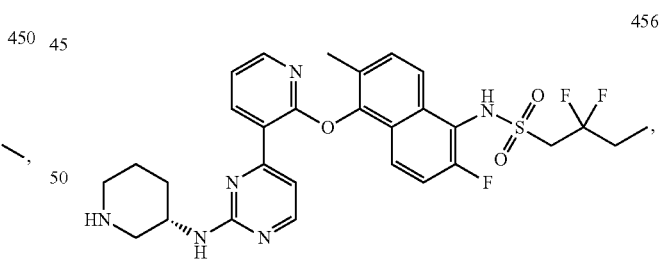
457
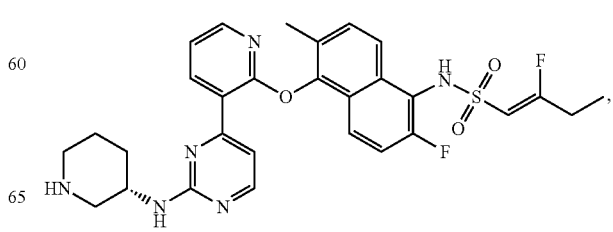

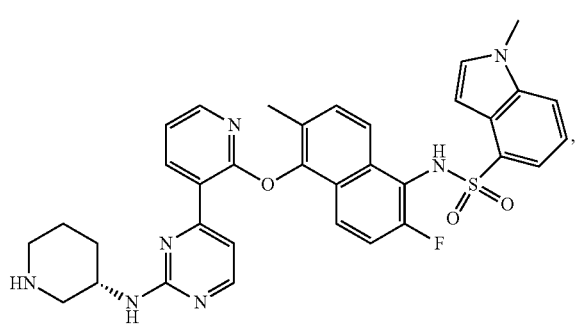
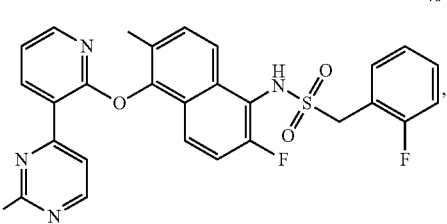
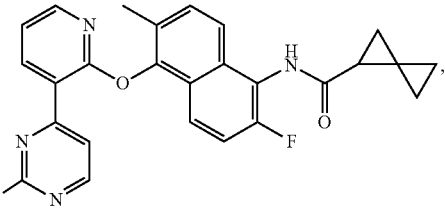
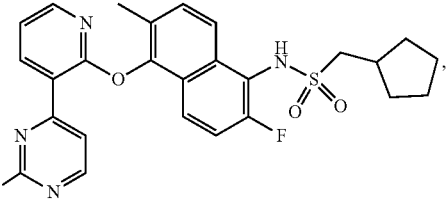
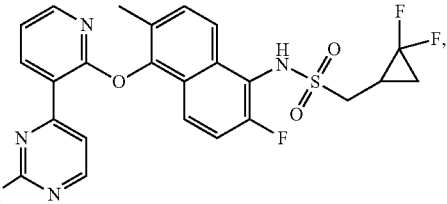
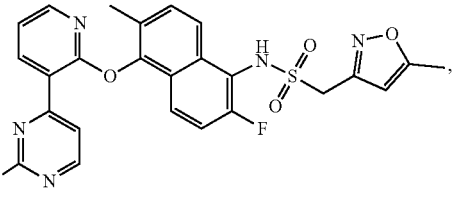
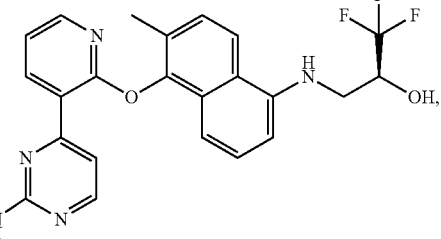

470
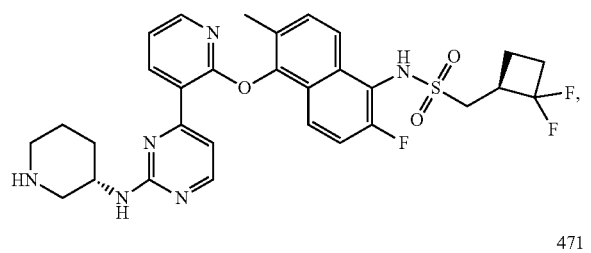
471
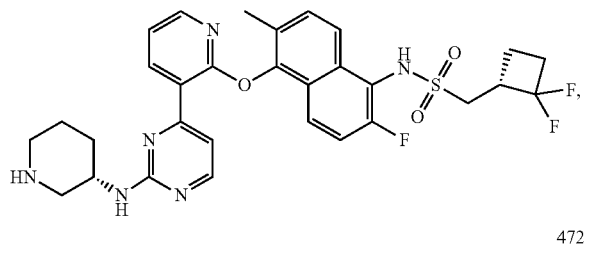
472
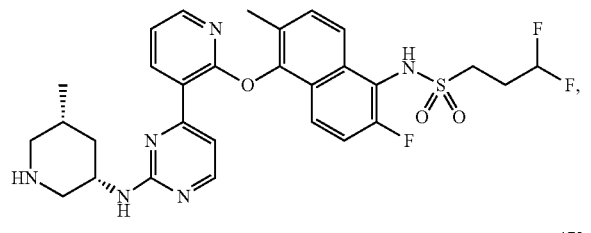
473
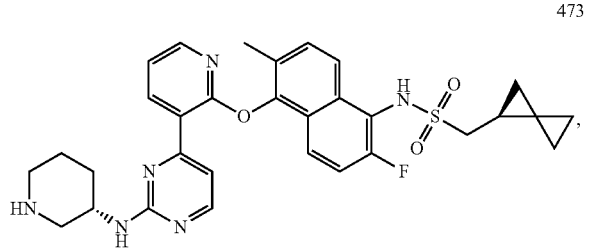
474
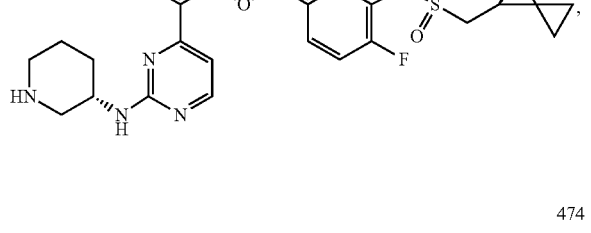
475
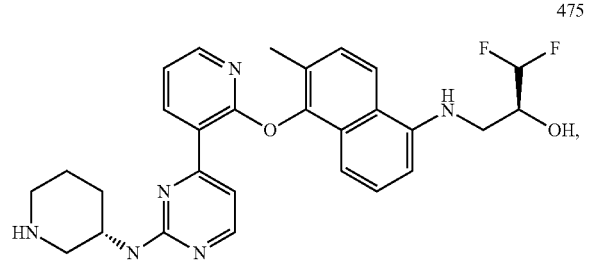
476
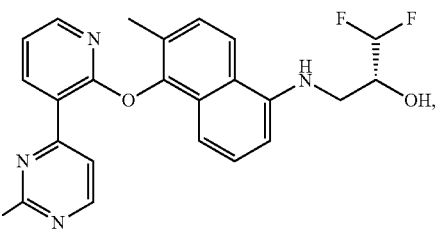
477
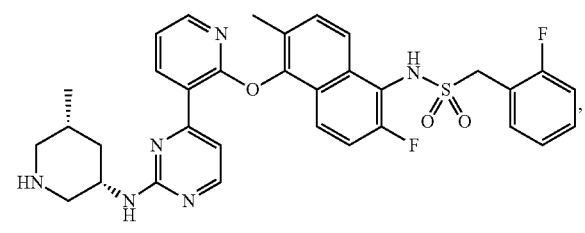
478
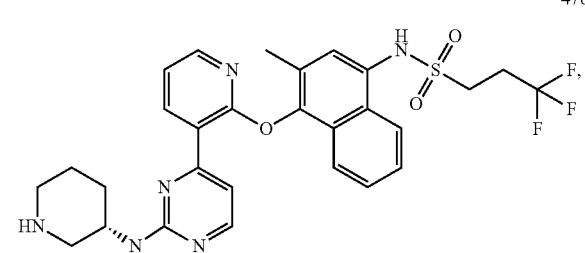
479
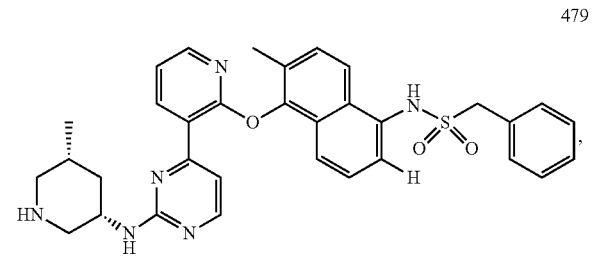
480
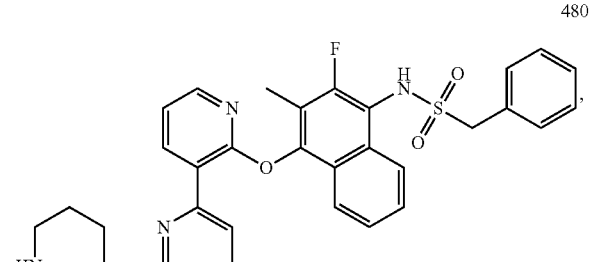
481
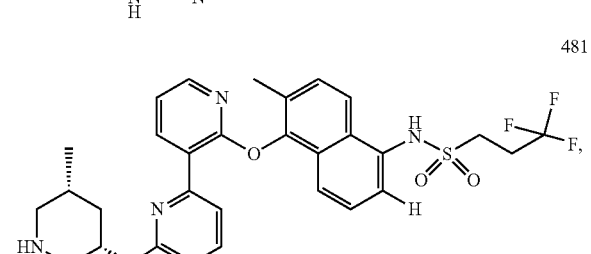

885
-continued
482
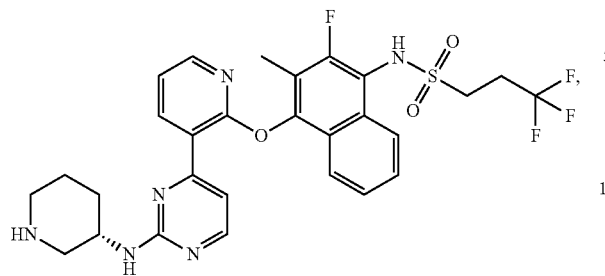
483
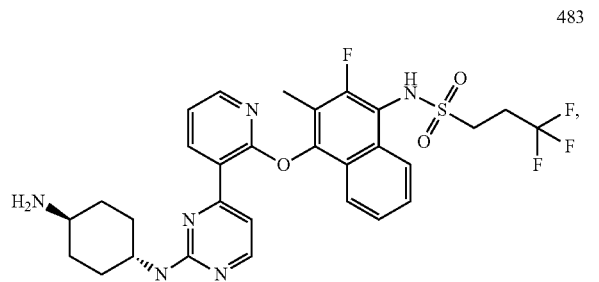
484
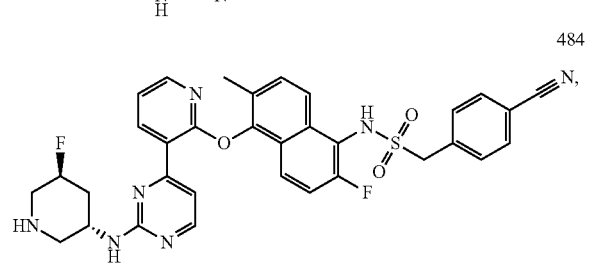
485
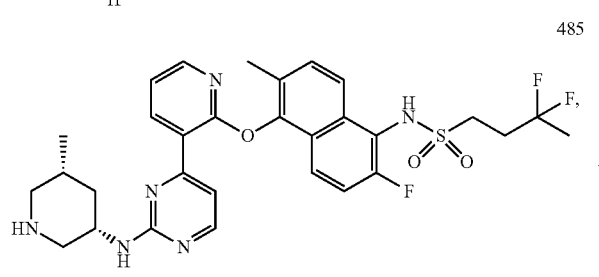
486
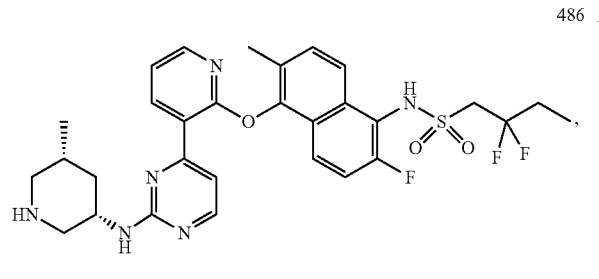
487
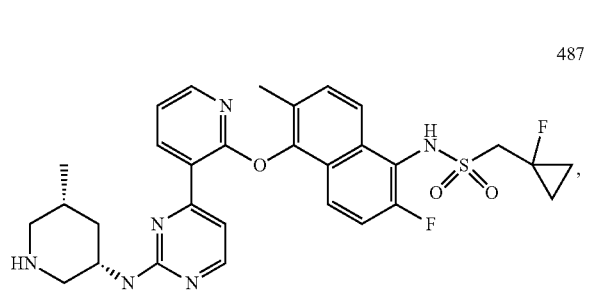
886
-continued
488
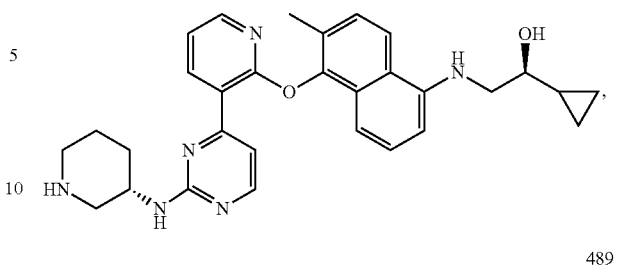
489
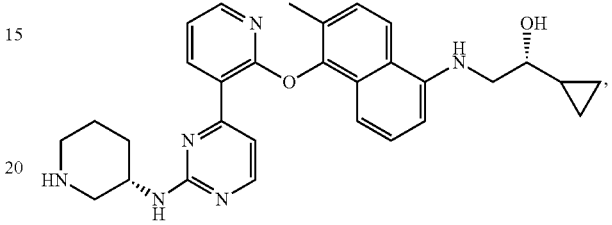
490
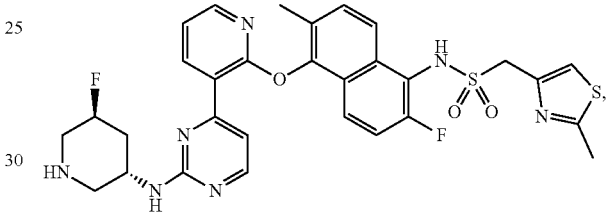
491
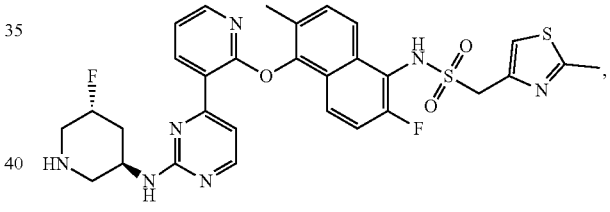
492
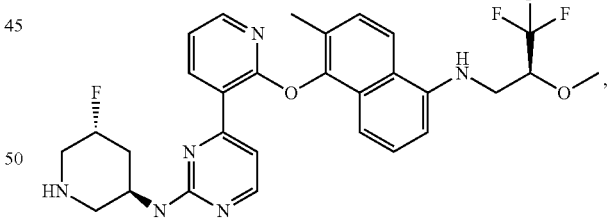
493
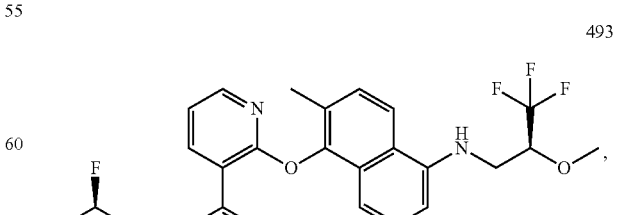

494
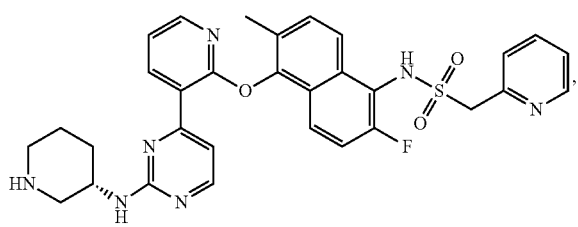
495
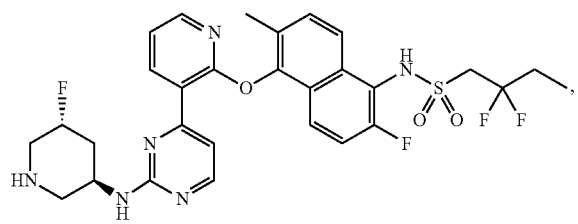
496
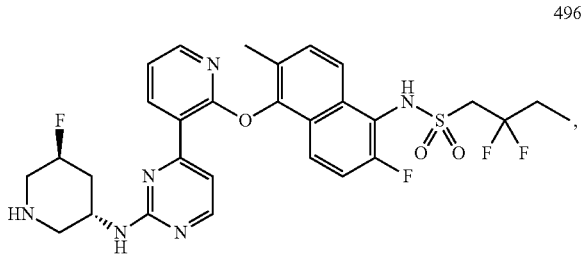
497
498
499
500
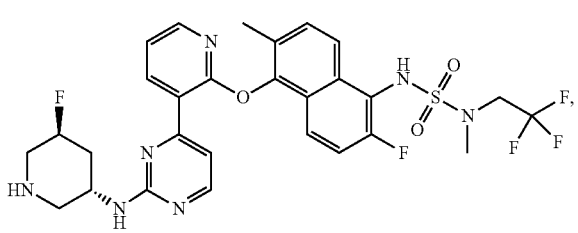
or a pharmaceutically acceptable salt thereof.
30. The compound of claim 1, wherein the compound is selected from the group consisting of
501
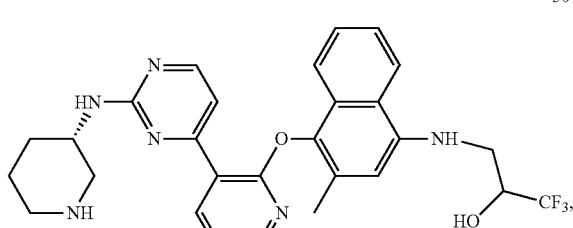
502
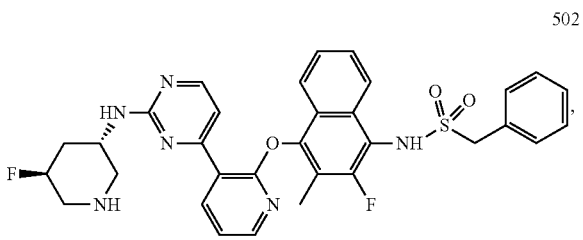
503
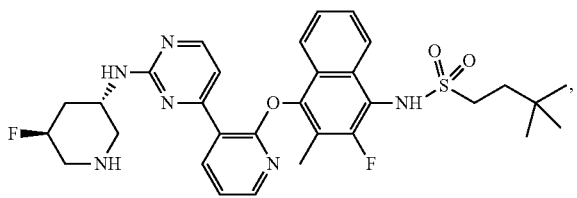
504
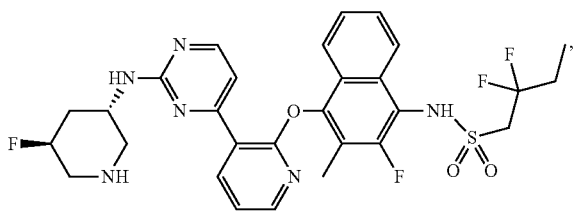
505
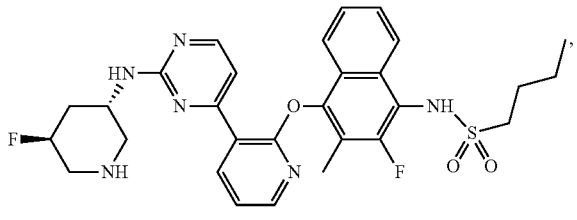

889
-continued
506
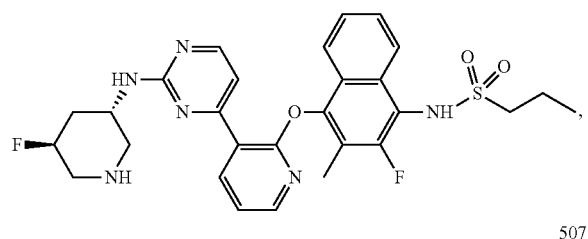
507
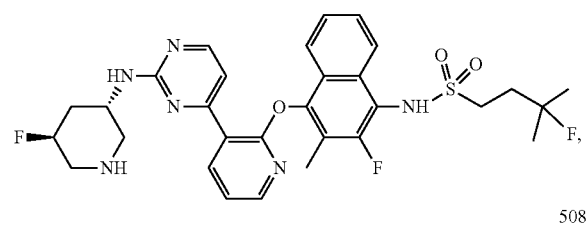
508
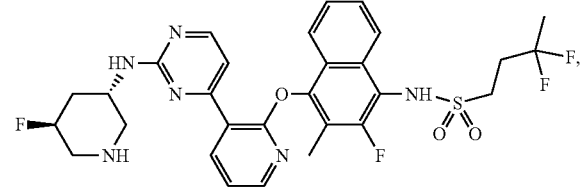
509
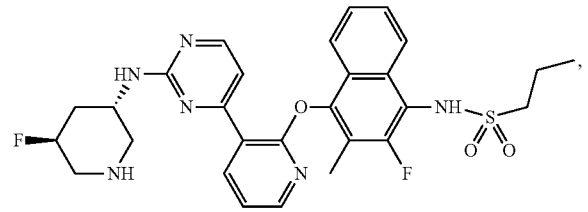
510
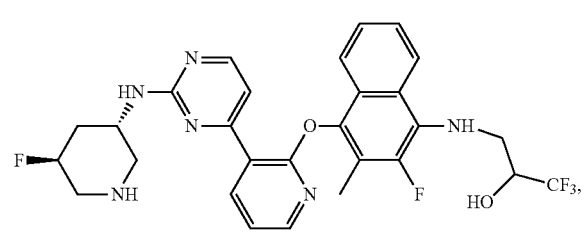
511
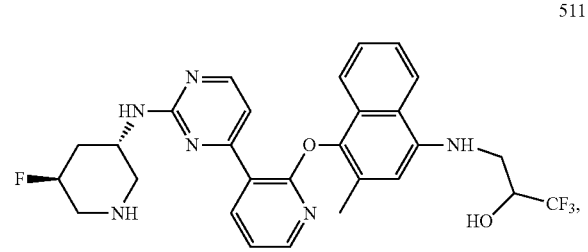
512
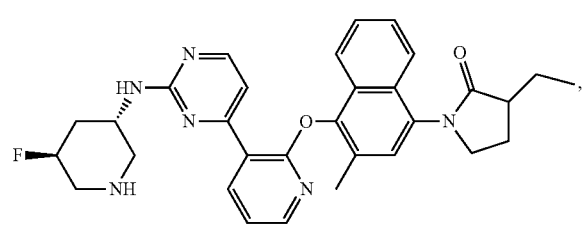
890
-continued
513
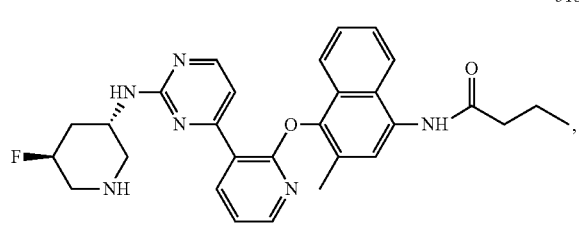
514
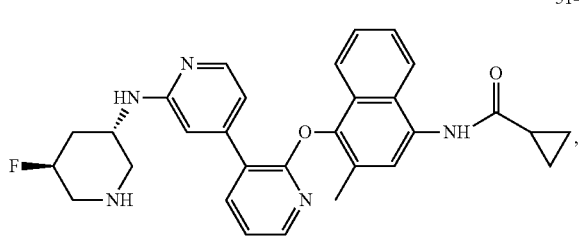
515
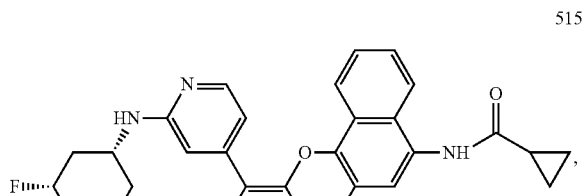
516
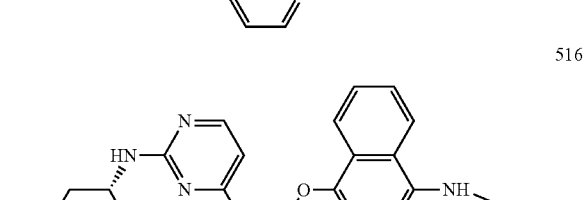
517
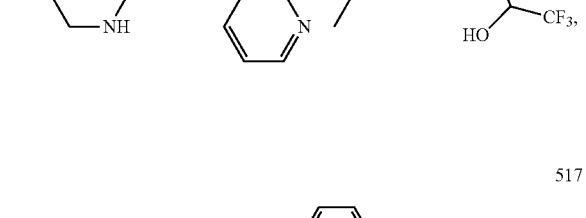
518
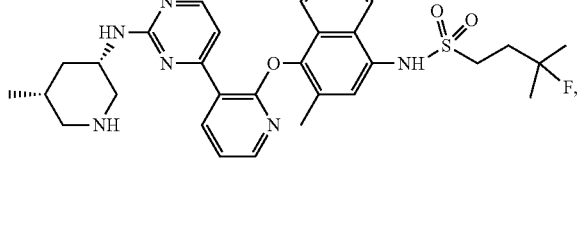

891
-continued
519
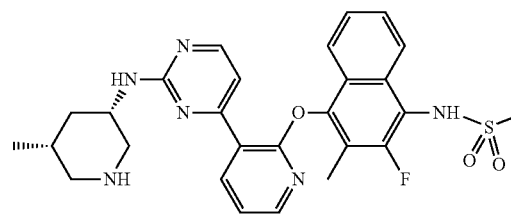
520
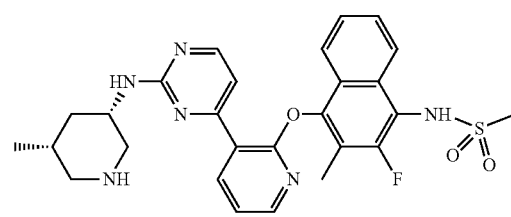
521
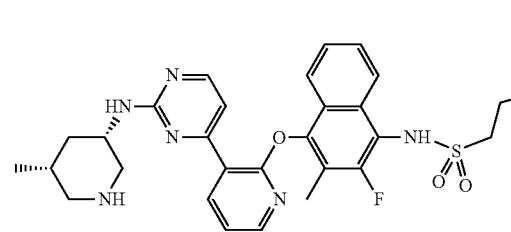
522
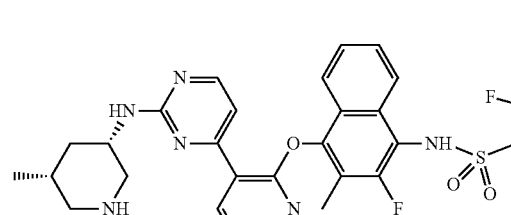
523
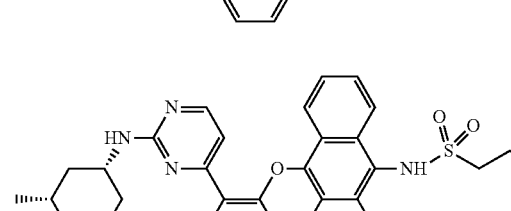
524
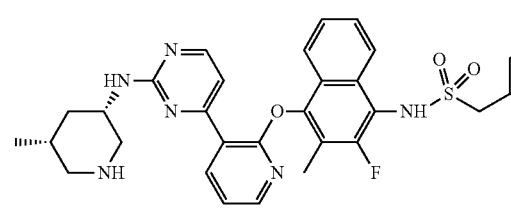
525
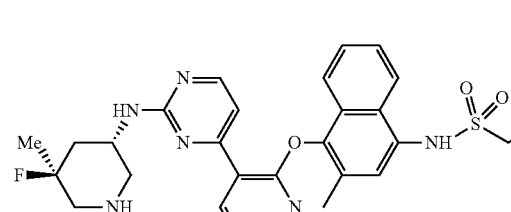
892
-continued
526
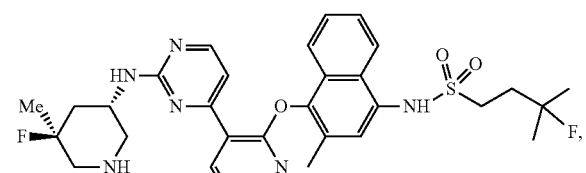
527
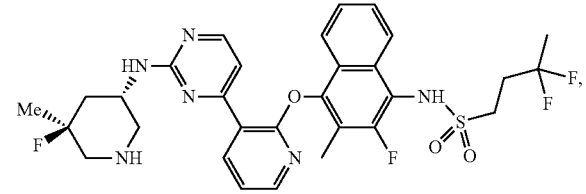
528
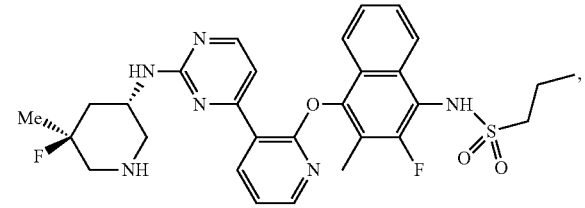
529
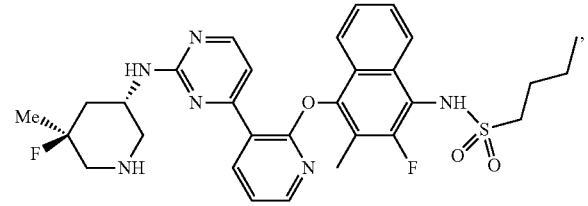
530
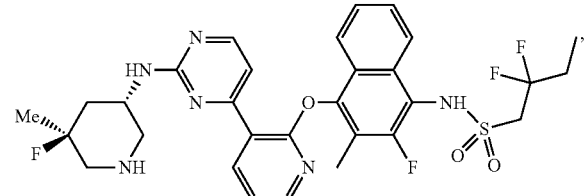
531
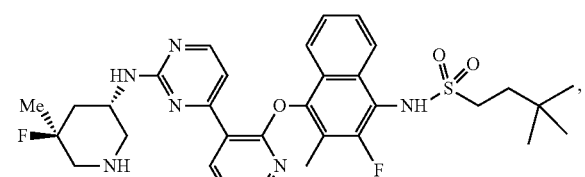
532
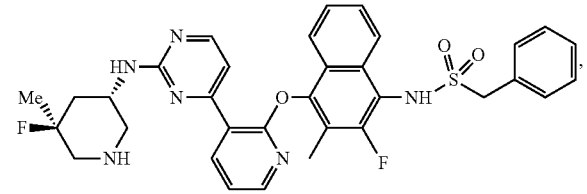

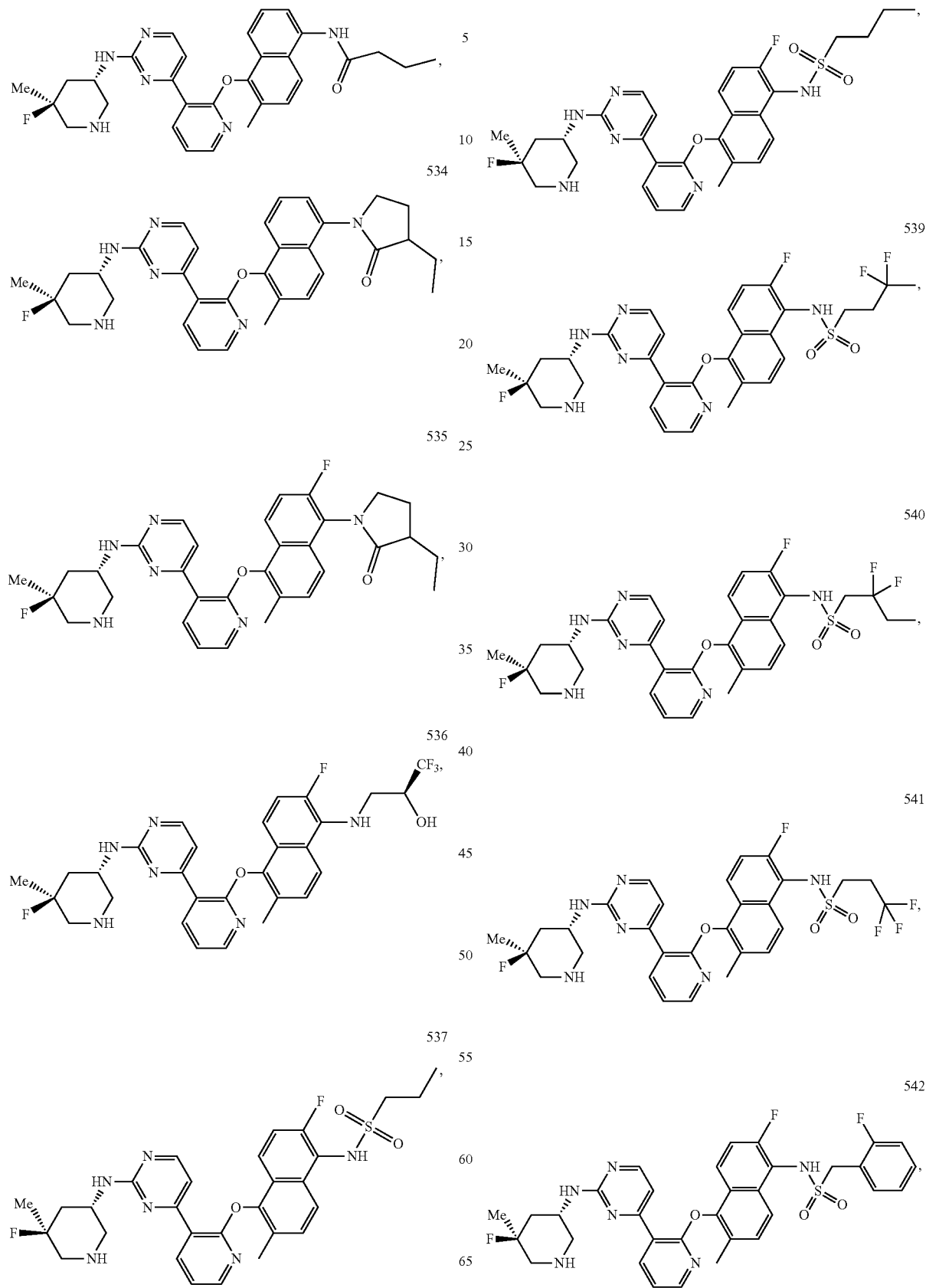

-continued

543

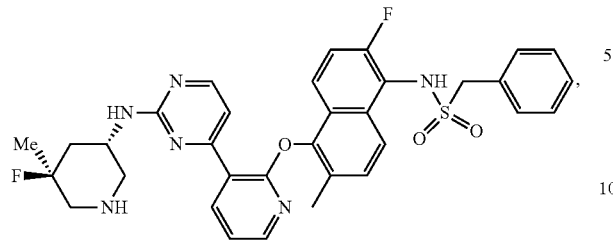

544

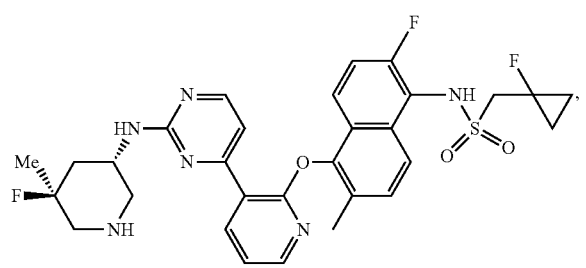

545

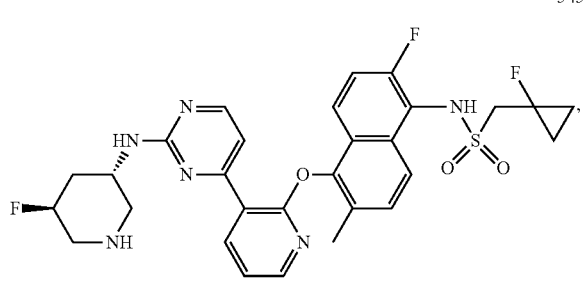

or a pharmaceutically acceptable salt thereof.

31. A compound of the Formula I:

I

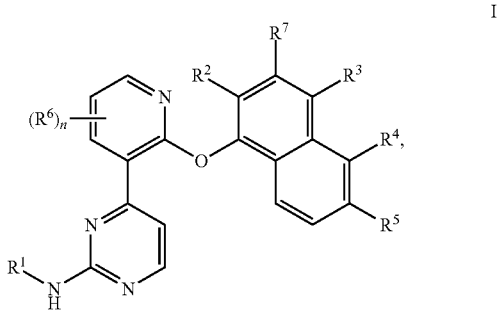

or a stereoisomer, tautomer, or pharmaceutically acceptable salt thereof, wherein:

$R^1$ is selected from $C_3$-$C_{12}$ cycloalkyl, $C_3$-$C_{12}$ heterocyclyl, $C_1$-$C_{12}$ heteroaryl, $C_6$-$C_2$ aryl, —($C_1$-$C_6$ alkyldiyl)-($C_3$-$C_{12}$ cycloalkyl), and —($C_1$-$C_6$ alkyldiyl)-($C_3$-$C_{12}$ heterocyclyl);

$R^2$ is selected from H, F, Cl, —CN, —OCH$_3$, —OCH$_2$CH$_3$, and $C_1$-$C_6$ alkyl;

$R^3$ and $R^4$ are independently selected from H, —CN, $C_3$-$C_{12}$ cycloalkyl, $C_3$-$C_{12}$ heterocyclyl, $C_1$-$C_{12}$ heteroaryl, $C_6$-$C_{20}$ aryl, —O—($C_1$-$C_{12}$ heteroaryl), —O—($C_1$-$C_6$ alkyldiyl)-($C_6$-$C_{20}$ aryl), —NR$^8$R$^9$, —NR$^8$C(O)R$^9$, —NR$^8$C(O)OR$^9$, —NR$^8$C(O)NHR$^9$, —NR$^8$SO$_2$-($C_1$-$C_6$ alkyl), —NR$^8$SO$_2$-($C_2$-$C_6$ alkenyl), —NR$^8$SO$_2$-($C_1$-$C_{12}$ heteroaryl), —NR$^8$SO$_2$-($C_1$-$C_6$ alkyldiyl)-($C_3$-$C_{12}$ cycloalkyl), —NR$^8$SO$_2$-($C_1$-$C_6$ alkyldiyl)-($C_3$-$C_{12}$ heterocyclyl), —NR$^8$SO$_2$-($C_1$-$C_6$ alkyldiyl)-($C_1$-$C_{12}$ heteroaryl), —NR$^8$SO$_2$-($C_1$-$C_6$ alkyldiyl)-($C_6$-$C_{20}$ aryl), —NR$^8$SO$_2$NR$^8$R$^9$, and —SO$_2$NR$^8$R$^9$;

$R^5$ and $R^7$ are independently selected from H, F, Cl, —CN, —CH$_2$OH, —C(O)NH$_2$, —OH, —OCH$_3$, —OCH$_2$CH$_3$, and $C_1$-$C_6$ alkyl;

$R^6$ are independently selected from H, F, Cl, Br, I, —CN, —NO$_2$, and $C_1$-$C_6$ alkyl;

$R^8$ is independently selected from H, and $C_1$-$C_6$ alkyl;

$R^9$ is independently selected from $C_1$-$C_6$ alkyl, $C_2$-$C_6$ alkenyl, $C_3$-$C_{12}$ cycloalkyl, $C_3$-$C_{12}$ heterocyclyl, $C_1$-$C_{12}$ heteroaryl, $C_6$-$C_{20}$ aryl; —($C_1$-$C_6$ alkyldiyl)-($C_3$-$C_{12}$ cycloalkyl), —($C_1$-$C_6$ alkyldiyl)-($C_3$-$C_{12}$ heterocyclyl), —($C_1$-$C_6$ alkyldiyl)-($C_1$-$C_6$ heteroaryl), —($C_1$-$C_6$ alkyldiyl)-($C_6$-$C_{20}$ aryl), and —($C_1$-$C_6$ alkyldiyl)-O—($C_6$-$C_{20}$ aryl); and n is 0, 1, 2, or 3;

wherein cycloalkyl, heterocyclyl, heteroaryl, aryl, alkyl, alkyldiyl, and alkenyl are optionally and independently substituted with one or more groups selected from F, Cl, Br, I, —CN, —CH$_3$, —CH$_2$CH$_3$, —CH$_2$CH$_2$CH$_3$, —CH(CH$_3$)$_2$, —CH$_2$CH(CH$_3$)$_2$, —CH(CH$_3$)CH$_2$CH$_3$, —CH$_2$C(CH$_3$)$_3$, —CH$_2$OH, —CH$_2$OCH$_3$, —CH$_2$CH$_2$OH, —C(CH$_3$)$_2$OH, —CH(OH)CH(CH$_3$)$_2$, —C(CH$_3$)$_2$CH$_2$OH, —CH$_2$CH$_2$CH$_2$OH, —CH$_2$CH$_2$C(CH$_3$)$_2$OH, —CH$_2$CH$_2$OCH$_3$, —CH$_2$CH(CH$_3$)OCH$_3$, —CH$_2$CH$_2$CH$_2$OCH$_3$, —CH$_2$CH$_2$C(CH$_3$)$_2$OCH$_3$, —CH$_2$CH$_2$SO$_2$CH$_3$, —CH$_2$OP(O)(OH)$_2$, —CH$_2$F, —CHF$_2$, —CH$_2$NH$_2$, —CH$_2$NHSO$_2$CH$_3$, —CH$_2$NHCH$_3$, —CH$_2$N(CH$_3$)$_2$, —CF$_3$, —CH$_2$CF$_3$, —CH$_2$CHF$_2$, —CH$_2$CH$_2$CHF$_2$, —CH$_2$CH$_2$CF$_3$, —CH(CH$_3$)CN, —C(CH$_3$)$_2$CN, —CH$_2$CN, —CO$_2$H, —COCH$_3$, —CO$_2$CH$_3$, —CO$_2$C(CH$_3$)$_3$, —COCH(OH)CH$_3$, —CONH$_2$, —CONHCH$_3$, —CONHCH$_2$CH$_3$, —CONHCH(CH$_3$)$_2$, —CON(CH$_3$)$_2$, —C(CH$_3$)$_2$CONH$_2$, —NH$_2$, —NHCH$_3$, —N(CH$_3$)$_2$, —N(CH$_3$)CH$_2$CH$_3$, —NHCOCH$_3$, —N(CH$_3$)COCH$_3$, —NHS(O)$_2$CH$_3$, —N(CH$_3$)C(CH$_3$)$_2$CONH$_2$, —N(CH$_3$)CH$_2$CH$_2$S(O)$_2$CH$_3$, —NO$_2$, =O, —OH, —OCH$_3$, —OCH$_2$CH$_3$, —OCH$_2$CH$_2$OCH$_3$, —OCH$_2$CH$_2$OH, —OCH$_2$CH$_2$N(CH$_3$)$_2$, —OP(O)(OH)$_2$, —S(O)$_2$N(CH$_3$)$_2$, —SCH$_3$, —S(O)$_2$CH$_3$, —S(O)$_3$H, cyclopropyl, cyclopropylamide, cyclobutyl, oxetanyl, azetidinyl, 1-methylazetidin-3-yl)oxy, N-methyl-N-oxetan-3-ylamino, azetidin-1-ylmethyl, benzyloxyphenyl, pyrrolidin-1-yl, pyrrolidin-1-yl-methanone, phenyl, piperazin-1-yl, piperidin-1-yl, morpholinomethyl, morpholino-methanone, and morpholino;

provided that the compound is other than a compound having formula:

1,4-Cyclohexanediamine, N1-[4-[2-[[4-(2-benzoxazolylamino)-2-methyl-1-napthalenyl]oxy]-3-pyridinyl]-2-pyrimidinyl]-, trans-;

1H-Benzimidazol-2-amine, N-[3-methyl-4-[[3-[2-[(3S)-3-piperidinylamino]-4-pyrimidinyl]-2-pyridinyl]oxy]-1-naphthalenyl]-;

1,4-Cyclohexanediamine, N1-[4-[2-[[4-(1H-benzimidazol-2-ylamino)-2-methyl-1-naphthalenyl]oxy]-3-pyridinyl]-2-pyrimidinyl]-, trans-;

1,4-Cyclohexanediamine, N1-[4-[2-[[4-(1H-benzimidazol-2-ylamino)-1-naphthalenyl]oxy]-3-pyridinyl]-2-pyrimidinyl]-, cis-;

1,4-Cyclohexanediamine, N1-[4-[2-[[4-(1H-benzimidazol-2-ylamino)-1-naphthalenyl]oxy]-3-pyridinyl]-2-pyrimidinyl]-, trans-;

1H-Benzimidazol-2-amine, N-[4-[[3-[2-[(3S)-3-piperidinylamino]-4-pyrimidinyl]-2-pyridinyl]oxy]-1-naphthalenyl]-;

1H-Benzimidazol-2-amine, N-[4-[[3-[2-[(3R)-3-piperidinylamino]-4-pyrimidinyl]-2-pyridinyl]oxy]-1-naphthalenyl]-;

1H-Benzimidazol-2-amine, N-[4-[[3-[2-[(1-methyl-3-piperidinyl)amino]-4-pyrimidinyl]-2-pyridinyl]oxy]-1-naphthalenyl]-;

1H-Benzimidazol-2-amine, N-[4-[[3-[2-[[3-(1-piperidinyl)propyl]amino]-4-pyrimidinyl]-2-pyridinyl]oxy]-1-naphthalenyl]-;

1H-Benzimidazol-2-amine, N-[4-[[3-[2-[(1-methyl-4-piperidinyl)amino]-4-pyrimidinyl]-2-pyridinyl]oxy]-1-naphthalenyl]-;

1H-Benzimidazol-2-amine, N-[4-[[3-[2-[[(1-ethyl-4-piperidinyl)methyl]amino]-4-pyrimidinyl]-2-pyridinyl]oxy]-1-naphthalenyl]-;

1H-Benzimidazol-2-amine, N-[4-[[3-[2-[[2-(1-methyl-2-pyrrolidinyl)ethyl]amino]-4-pyrimidinyl]-2-pyridinyl]oxy]-1-naphthalenyl]-;

1H-Benzimidazol-2-amine, N-[4-[[3-[2-[[3-(1-pyrrolidinyl)propyl]amino]-4-pyrimidinyl]-2-pyridinyl]oxy]-1-naphthalenyl]-; or 1H-Benzimidazol-2-amine, N-[4-[[3-[2-[[2-(4-morpholinyl)ethyl]amino]-4-pyrimidinyl]-2-pyridinyl]oxy]-1-naphthalenyl]-; or a pharmaceutically acceptable salt thereof.

32. The compound of claim 31, or a stereoisomer, tautomer, or pharmaceutically acceptable salt thereof, wherein the compound is of the Formula Ic:

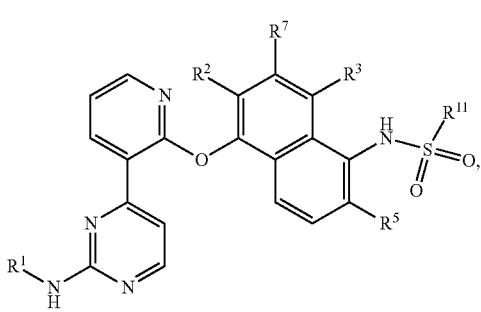

Ic wherein $R^{11}$ is selected from $C_1$-$C_6$ alkyl, $C_2$-$C_6$ alkenyl, $C_1$-$C_{12}$ heteroaryl, ($C_1$-$C_6$ alkyldiyl)-($C_3$-$C_{12}$ heterocyclyl), ($C_1$-$C_6$ alkyldiyl)-($C_1$-$C_{12}$ heteroaryl), ($C_1$-$C_6$ alkyldiyl)-($C_6$-$C_{20}$ aryl), $NR^8$—($C_1$-$C_{12}$ heteroaryl), $NR^8$—($C_1$-$C_6$ alkyl), and $NR^8$—($C_1$-$C_6$ alkyldiyl)-($C_6$-$C_{20}$ aryl).

33. The compound of claim 32, or a stereoisomer, tautomer, or pharmaceutically acceptable salt thereof, wherein the compound is of the Formula If:

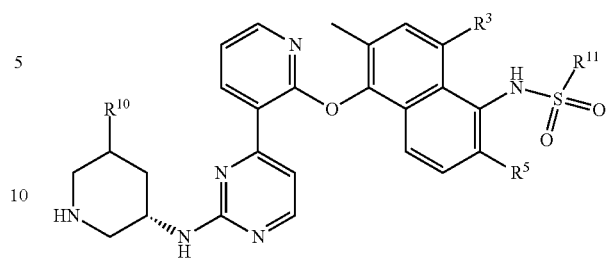

If wherein $R^{10}$ is selected from H, F, —$CH_3$, and —$NH_2$.

34. A pharmaceutical composition comprising a compound of claim 1, or a stereoisomer, tautomer, or pharmaceutically acceptable salt thereof, and a pharmaceutically acceptable carrier, glidant, diluent, or excipient.

35. A process for making a pharmaceutical composition which comprises combining a compound of claim 1, or a stereoisomer, tautomer, or pharmaceutically acceptable salt thereof, with a pharmaceutically acceptable carrier, glidant, diluent, or excipient.

36. A method of treating an IRE1-related disease or disorder in a patient having an IRE1-related disease or condition, the method comprising administering to the patient a therapeutically effective amount of a compound of claim 1, or a stereoisomer, tautomer, or pharmaceutically acceptable salt thereof, wherein the IRE1-related disease or disorder is cancer selected from the group consisting of squamous cell cancer, small-cell lung cancer, non-small cell lung cancer ("NSCLC"), adenocarcinoma of the lung and squamous carcinoma of the lung, cancer of the peritoneum, hepatocellular cancer, stomach cancer, gastrointestinal cancer, esophageal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, and head and neck cancer.

37. A method of treating an IRE1-related disease or disorder in a patient having an IRE1-related disease or condition, the method comprising administering to the patient a therapeutically effective amount of a compound of claim 1, or a stereoisomer, tautomer, or pharmaceutically acceptable salt thereof, wherein the IRE1-related disease or disorder is a hematological malignancy selected from the group consisting of lymphomas, lymphocytic leukemia, myeloma, acute and chronic myelogenous leukemia, myelodysplastic syndrome and myeloproliferative disease.

38. The method of claim 37, wherein the IRE1-related disease or disorder is multiple myeloma.

39. The method of claim 36, wherein the IRE1-related disease or disorder is a triple-negative breast cancer ("TNBC").

40. The method of claim 36, further comprising administering radiotherapy.

41. A pharmaceutical composition comprising a compound of claim 31, or a stereoisomer, tautomer, or pharmaceutically acceptable salt thereof, and a pharmaceutically acceptable carrier, glidant, diluent, or excipient.

* * * * *

UNITED STATES PATENT AND TRADEMARK OFFICE
CERTIFICATE OF CORRECTION

PATENT NO. : 10,968,203 B2  
APPLICATION NO. : 15/989008  
DATED : April 6, 2021  
INVENTOR(S) : Braun et al.

Page 1 of 1

It is certified that error appears in the above-identified patent and that said Letters Patent is hereby corrected as shown below:

In the Claims

Column 816, Line 5 (Approx.), in Claim 1, change "$C_3$-$C_2$ cycloalkyl" to --$C_3$-$C_{12}$ cycloalkyl--.

Column 816, Line 18 (Approx.), in Claim 1, change "—$CH_2H$" to --$CH_2OH$--.

Column 816, Line 27, in Claim 1, change "$C_3$-$C_2$ cycloalkyl" to --$C_3$-$C_{12}$ cycloalkyl--.

Column 816, Line 29, in Claim 1, change "—($C_1$-$C_6$ alkyldiyl)-($C_3$-$C_2$ heterocyclyl)" to -- —($C_1$-$C_6$ alkyldiyl)-($C_3$-$C_{12}$ heterocyclyl)--.

Column 816, Line 50 (Approx.), in Claim 1, change "—$C_2CH_3$" to -- —$CO_2CH_3$--.

Column 819, Line 67, in Claim 21, change "—NR—($C_1$-$C_{12}$ heteroaryl)" to -- —$NR^8$—($C_1$-$C_{12}$ heteroaryl)--.

Column 820, Line 1, in Claim 21, change "—NR—($C_1$-$C_6$ alkyldiyl)-($C_6$-$C_{20}$ aryl)" to -- —$NR^8$—($C_1$-$C_6$ alkyldiyl)-($C_6$-$C_{20}$ aryl)--.

Column 895, Line 57, in Claim 31, change "$C_6$-$C_2$ aryl" to --$C_6$-$C_{20}$ aryl--.

Signed and Sealed this  
Twenty-ninth Day of March, 2022

Drew Hirshfeld  
*Performing the Functions and Duties of the*  
*Under Secretary of Commerce for Intellectual Property and*  
*Director of the United States Patent and Trademark Office*